(12) United States Patent
Leister et al.

(10) Patent No.: US 10,941,189 B2
(45) Date of Patent: *Mar. 9, 2021

(54) CARBOHYDRATE CONTENT OF CTLA4 MOLECULES

(71) Applicant: Bristol-Myers Squibb Company, Princeton, NJ (US)

(72) Inventors: Kirk J. Leister, Fayetteville, NY (US); Eugene J. Schaefer, Westfield, NJ (US); Ronald Charles Bates, Irvine, CA (US); Elizabeth A. Bramhall, Groton, MA (US); David Michael Didio, Syracuse, NY (US); Robert Donaldson, Southborough, MA (US); Alan R. Flesher, Lawrenceville, NJ (US); Helen Gray Haggerty, Manlius, NY (US); David Henry Kirkley, East Syracuse, NY (US); John Malcolm Tabor, Syracuse, NY (US); Lee K. Tay, Princeton Junction, NJ (US); Pallaiah Thammana, Manlius, NY (US); Ajoy Velayudhan, Cary, NC (US); David Edward Smolin, Pennington, NJ (US); Reb J. Russell, Doylestown, PA (US); Thomas James Vanden Boom, Flemington, NJ (US); Dean Woodrow Brownell, Oswego, NY (US); Jeffrey Schrimsher, Hillsborough, NC (US); Joyce Patricia Whitehead, Manlius, NY (US)

(73) Assignee: Bristol-Myers Squibb Company, Princeton, NJ (US)

(*) Notice: Subject to any disclaimer, the term of this patent is extended or adjusted under 35 U.S.C. 154(b) by 76 days.

This patent is subject to a terminal disclaimer.

(21) Appl. No.: 16/042,977

(22) Filed: Jul. 23, 2018

(65) Prior Publication Data
US 2019/0062399 A1 Feb. 28, 2019

Related U.S. Application Data

(62) Division of application No. 12/086,786, filed as application No. PCT/US2006/049074 on Dec. 19, 2006, now Pat. No. 10,508,144.

(60) Provisional application No. 60/752,267, filed on Dec. 20, 2005, provisional application No. 60/752,150, filed on Dec. 20, 2005, provisional application No. 60/849,543, filed on Oct. 5, 2006.

(51) Int. Cl.
| | |
|---|---|
| *A61K 39/395* | (2006.01) |
| *C07K 14/705* | (2006.01) |
| *A61K 38/19* | (2006.01) |
| *C07K 16/28* | (2006.01) |
| *A61K 38/00* | (2006.01) |
| *B01D 15/38* | (2006.01) |

(52) U.S. Cl.
CPC ...... *C07K 14/70521* (2013.01); *A61K 38/195* (2013.01); *C07K 16/2818* (2013.01); *A61K 38/00* (2013.01); *B01D 15/3804* (2013.01); *C07K 2317/73* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,460,694 | A | 7/1984 | Fletcher |
| 4,929,700 | A | 5/1990 | Halenbeck et al. |
| 5,451,660 | A | 9/1995 | Builder et al. |
| 5,456,909 | A | 10/1995 | Marsh, Jr. et al. |
| 5,510,261 | A | 4/1996 | Goochee et al. |
| 5,705,364 | A | 1/1998 | Etcheverry et al. |
| 5,721,121 | A | 2/1998 | Etcheverry et al. |
| 5,739,293 | A | 4/1998 | Eran et al. |
| 5,773,253 | A | 6/1998 | Linsley et al. |
| 5,844,095 | A | 12/1998 | Linsley et al. |
| 5,851,795 | A | 12/1998 | Linsley et al. |
| 5,856,298 | A | 1/1999 | Strickland |
| 5,858,969 | A | 1/1999 | Marsh, Jr. et al. |
| 5,885,579 | A | 3/1999 | Linsley et al. |
| 5,885,796 | A | 3/1999 | Linsley et al. |
| 6,057,131 | A | 5/2000 | Marsh, Jr. et al. |
| 6,090,914 | A | 7/2000 | Linsley et al. |

(Continued)

FOREIGN PATENT DOCUMENTS

| | | |
|---|---|---|
| EP | 1498491 A1 | 1/2005 |
| EP | 1536234 A2 | 6/2005 |

(Continued)

OTHER PUBLICATIONS

Abrams, J. et al., "CTLA4Ig-mediated blockade of T-cell costimulation in patients with psoriasis vulgaris", the Journal of Clinical Investigation, vol. 103(9), pp. 1243-1252 (1999).

(Continued)

*Primary Examiner* — Yunsoo Kim
(74) *Attorney, Agent, or Firm* — Sterne, Kessler, Goldstein & Fox P.L.L.C.

(57) ABSTRACT

The invention provides for mammalian cells capable of producing recombinant CTLA4-Ig and variants thereof. The invention also provides for compositions comprising CTLA4-Ig and formulations thereof. The invention further provides for methods for mass-producing CTLA4-Ig from mammalian cells capable of producing this recombinant protein, and for purifying the CTLA4-Ig.

22 Claims, 116 Drawing Sheets
Specification includes a Sequence Listing.

(56) References Cited

U.S. PATENT DOCUMENTS

| | | | |
|---|---|---|---|
| 6,506,598 B1 | 1/2003 | Andersen et al. | |
| 6,521,419 B1 | 2/2003 | Koduri et al. | |
| 6,528,286 B1 | 3/2003 | Ryll | |
| 6,586,398 B1 | 7/2003 | Kinstler et al. | |
| 6,610,516 B1 | 8/2003 | Andersen et al. | |
| 6,673,575 B1 | 1/2004 | Franze et al. | |
| 6,800,457 B2 | 10/2004 | Koduri et al. | |
| 6,812,330 B2 | 11/2004 | Burton et al. | |
| 6,872,549 B2 | 3/2005 | Van et al. | |
| 6,924,124 B1 | 8/2005 | Singh | |
| 6,953,844 B2 | 10/2005 | Burton et al. | |
| 7,094,874 B2 | 8/2006 | Peach et al. | |
| 7,253,167 B2 | 8/2007 | Lin et al. | |
| 7,304,033 B2 | 12/2007 | Larsen et al. | |
| 7,307,064 B2 | 12/2007 | Rusnak | |
| 7,332,303 B2 | 2/2008 | Schilling et al. | |
| 7,439,230 B2 | 10/2008 | Peach et al. | |
| 7,455,835 B2 | 11/2008 | Cohen et al. | |
| 8,313,913 B2 | 11/2012 | Nakamura et al. | |
| 10,508,144 B2 * | 12/2019 | Leister | A61P 43/00 |
| 2002/0039577 A1 | 4/2002 | Townsend et al. | |
| 2003/0007968 A1 | 1/2003 | Larsen et al. | |
| 2003/0013881 A1 | 1/2003 | Hom et al. | |
| 2003/0077752 A1 | 4/2003 | Cho et al. | |
| 2004/0022787 A1 | 2/2004 | Cohen et al. | |
| 2004/0115768 A1 | 6/2004 | Follstad | |
| 2004/0230051 A1 | 11/2004 | Freeman et al. | |
| 2004/0259205 A1 | 12/2004 | Etcheverry et al. | |
| 2005/0019859 A1 | 1/2005 | Schilling et al. | |
| 2005/0153879 A1 | 7/2005 | Svetina et al. | |
| 2005/0192211 A1 | 9/2005 | Gillies et al. | |
| 2005/0271659 A1 | 12/2005 | Utku et al. | |
| 2009/0252749 A1 | 10/2009 | Leister et al. | |
| 2019/0062399 A1 | 2/2019 | Leister et al. | |
| 2019/0092835 A1 | 3/2019 | Leister et al. | |

FOREIGN PATENT DOCUMENTS

| | | |
|---|---|---|
| EP | 2253644 A1 | 11/2010 |
| WO | WO-9522389 A1 | 8/1995 |
| WO | WO-9534320 A2 | 12/1995 |
| WO | WO-9704801 A1 | 2/1997 |
| WO | WO-9823645 A1 | 6/1998 |
| WO | WO-9833513 A1 | 8/1998 |
| WO | WO-1999062936 A1 | 12/1999 |
| WO | WO-0172769 A2 | 10/2001 |
| WO | WO-0192337 A2 | 12/2001 |
| WO | WO-0195928 A2 | 12/2001 |
| WO | WO-0200717 A2 | 1/2002 |
| WO | WO-0202638 A2 | 1/2002 |
| WO | WO-0205872 A2 | 1/2002 |
| WO | WO-02058729 A2 | 8/2002 |
| WO | WO-02094202 A2 | 11/2002 |
| WO | WO-03085119 A1 | 10/2003 |
| WO | WO-03088991 A1 | 10/2003 |
| WO | WO-03102132 A2 | 12/2003 |
| WO | WO-2004008100 A2 | 1/2004 |
| WO | WO-2004058800 A2 | 7/2004 |
| WO | WO-2004058944 A2 | 7/2004 |
| WO | WO-2004091658 A1 | 10/2004 |
| WO | WO-2005003175 A2 | 1/2005 |
| WO | WO-2005016266 A2 | 2/2005 |
| WO | WO-2005042569 A1 | 5/2005 |
| WO | WO-2006044908 A2 | 4/2006 |
| WO | WO-2007076032 A2 | 7/2007 |
| WO | WO-2007076354 A2 | 7/2007 |
| WO | WO-2008025747 A1 | 3/2008 |
| WO | WO-2008025748 A1 | 3/2008 |

OTHER PUBLICATIONS

Adams, A. et al., "Blockade of the CD40-CD154 Pathway using a chimeric anti-human CD40 monoclonal antibody synergizes with CD28 blockade to prolong islet allograft survival", Transplantation, vol. 78(2),179-180 (2006).

Adams, A. et al., "Calcineurin Inhibitor-Free CD28 Blockade-Based Protocol Protects Allogeneic Islets in Nonhuman Primates", Diabetes, vol. 51, pp. 265-270 (2002).

Adams, A.B., et al., "Development of a Chimeric Anti-CD40 Monoclonal Antibody That Synergizes with LEA29Y to Prolong Islet Allograft Survival," Journal of Immunology, vol. 174(1), pp. 542-550, American Association of Immunologists, United States (2005).

Amersham Biosciences, Antibody Purification Handbook (2002).

Amersham Biosciences, "Gel Filtration Principles and Methods", 2002, Edition AI, 124 pgs.

Anderson, P.J, "Tumor Necrosis Factor Inhibitors: Clinical Implications of Their Different Immunogenicity Profiles," Seminars in Arthritis and Rheumatism, vol. 34(5 Suppl1), pp. 19-22, W.B. Saunders, United States (Apr. 2005 ).

Anumula, K.R., et al., "Rapid Characterization of Asparagine-linked Oligosaccharides Isolated From Glycoproteins Using a Carbohydrate Analyzer," European Journal of Biochemistry, vol. 195(1), pp. 269-280, Springer, England (Jan. 1991).

Arden, N. et al., "Life and death in mammalian cell culture: strategies for apoptosis inhibition", Trends in Biotechnology, vol. 22(4), pp. 174-180—2004.

Bajorath, J. et al., "Molecular Modeling of Immunoglobulin Superfamily Proteins: CTLA-4 (CD152)—Comparison of a Predicted and Experimentally Determined Three-Dimensional Structure", Journal of Molecular Modeling, vol. 3, pp. 287-293 (1997).

Baldari, C., et al., "A Novel Leader Peptide Which Allows Efficient Secretion of a Fragment of Human Interleukin 1 Beta in Saccharomyces Cerevisiae," the EMBO Journal, vol. 6(1), pp. 229-234, Wiley Blackwell, England (Jan. 1987).

Balzano, C., et al., "CTLA-4 and CD28: Similar Proteins, Neighbouring Genes," International Journal of Cancer, vol. Supplement 7, pp. 28-32, Alan R. Liss, Inc, United States (1992).

Barnes, L.M., et al., "Stability of Protein Production from Recombinant Mammalian Cells," Biotechnology and Bioengineering, vol. 81(6), pp. 631-639, Wiley, United States (2003).

Batty, Jr., D. Scott, et al., "Development of LEA29Y and the Clinical Potential of Co-stimulation Blockade in Solid Organ Transplantation", Abstract SA22.

Bollati-Fogolin, M., et al., "Temperature Reduction in Cultures of Hgm-CSF-Expressing CHO Cells: Effect on Productivity and Product Quality," Biotechnology Progress, vol. 21(1), pp. 17-21, Wiley-Blackwell, United States (2005).

Bonnerjea, J., "Purification of Therapeutic Proteins", Methods in Molecular Biology, vol. 244, pp. 455-462 (2004).

Brady, Jamie L., et al., "Additive Efficacy of Ctla41g and Ox401g Secreted by Genetically Modified Grafts1", Transplantation, vol. 69(5); pp. 724-230 (2000).

Broach, J.R, "Construction of High Copy Yeast Vectors Using 2-microns Circle Sequences," Methods in Enzymology, vol. 101, pp. 307-325, Academic Press, United States (1983).

Brorson, Kurt, et al., "Defining Your Product Profile and Maintaining Control over It, Part 4 Product-Related Impurities: Tackling Aggregates", BioProcess International p. 50-54 (Nov. 2005).

Broudy, V. et al., "Recombinant Human Erythropoietin: Purification and Analysis of Carbohydrate Linkage", Archives of Biochemistry and Biophysics, vol. 265(2), pp. 329-336 (1988).

Brunet, J. et al., "A Differential Molecular Biology Search for Genes Preferentially Expressed in Functional T Lymphocytes: The CLTA Genes", Immunological Reviews, vol. 103, pp. 21-35 (1988).

Brunet, J. et al., "A new member of the immunoglobulin superfamily-CTLA-4", Nature, vol. 328, pp. 267-270 (1987).

Bruno, D. et al., "Challenges in therapeutic strategies for transplantation: Where now from here?", Transplant Immunology, vol. 1S, pp. 149-155 (2005).

Butler, M., "Animal Cell Cultures: Recent Achievements and Perspectives in the Production of Biopharmaceuticals," Applied Microbiology and Biotechnology, vol. 68(3), pp. 283-291, Springer International, Germany (2005).

(56) References Cited

OTHER PUBLICATIONS

Chamow, Steven M., et al., "Antibody Fusion Proteins", WileyLiss, 1999, 7 pgs.

Chamow, Steven M., et al., "Immunoadhesins: principles and applications", Tibtech, Feb. 1996, vol. 14, 9 pgs.

Chang, C. et al., "Crystallization and preliminary X-ray analysis of CTLA-4 (CD1S2) membrane-external domain", Acta Crystallographica D, vol. S6, pp. 1468-1469 (2000).

Che, X., et al., "Monocyte chemoattractant protein-1 expressed in neurons and astrocytes during focal ischemia in mice", Brain Research, vol. 902, pp. 171-177 (2001).

Chee Furng Wong, D., et al., "Impact of Dynamic Online Fed-batch Strategies on Metabolism, Productivity and N-glycosylation Quality in CHO Cell Cultures," Biotechnology & Bioengineering, vol. 89(2), pp. 164-177, Wiley, United States (Jan. 2005).

Choy, E.H and Panayi, G.S, "Cytokine Pathways and Joint Inflammation in Rheumatoid Arthritis," the New England Journal of Medicine, vol. 344(12), pp. 907-916, Massachusetts Medical Society, United States (Mar. 2001).

Chu, L. and Robinson, D.K., "Industrial Choices for Protein Production by Large-scale Cell Culture," Current Opinion in Biotechnology, vol. 12(2), pp. 180-187, Elsevier, England (Apr. 2001).

Chun, T. et al., "Two different forms of human CTLA-4 proteins following peripheral T cell activation", Immunology letters, vol. 91, pp. 213-220 (2004).

Churms, S., "Recent developments in the chromatographic analysis of carbohydrates", Journal of Chromatography, vol. 500, pp. 555-583 (1990).

Clark, K. et al., "Temperature Effects on Product-Quality-Related Enzymes in Batch CHO Cell Cultures Producing Recombinant tPA", Biotechnol. Progress, vol. 20, pp. 1888-1892 (2004).

Clarke, L., et al., "Selection Procedure for Isolation of Centromere DNAs from *Saccharomyces cerevisiae*," Methods in Enzymology, vol. 101, pp. 300-307, Academic Press, United States (1983).

Cleveland, W.L., et al., "Routine Large-scale Production of Monoclonal Antibodies in a Protein-free Culture Medium," Journal of Immunological Methods 56(2):221-234, Elsevier, Netherlands (Jan. 1983).

Colbere-Garapin, F., et al., "A New Dominant Hybrid Selective Marker for Higher Eukaryotic Cells," Journal of Molecular Biology, vol. 150(1), pp. 1-14, Elsevier, England (Jul. 1981).

Cox, G. et al., Refolding and Characterization of Recombinant Human Soluble CTLA-4 Expressed in *Escherichia coif*, Protein Expression and Purification, vol. 17, pp. 26-32 (1999).

Cron, R., "A Signal Achievement in the Treatment of Arthritis", Arthritis & Rheumatism, vol. 52(8), pp. 2229-2232 (2005).

Crouse, G.F., et al., "Expression and Amplification of Engineered Mouse Dihydrofolate Reductase Minigenes," Molecular and Cellular Biology, vol. 3(2), 257-266, American Society for Microbiology, United States (1983).

Dahl, A. et al., "Demonstration of Multiple Novel Glycoforms of the Stem Cell Survival Factor CCg", Journal of Neuroscience Research, vol. 77, pp. 9-14 (2004).

Damle, N. et al., "Costimulation of T Lymphocytes with Integrin Ligands Intercellular Adhesion Molecule-1 or Vascular Cell Adhesion Molecule-1 Induces Functional Expression of CTLA-4, a Second Receptor for BT", Journal of Immunology, vol. 152, pp. 2686-2697 (1994).

Dariavach, P, et al., "Human Ig superfamily CTLA-4 gene: chromosomal localization and identity of protein sequence between murine and human CTLA-4 cytoplasmic domains", European Journal of Immunology, vol. 18, pp. 1901-1905 (1988).

Darlington, P. et al., "Hierarchical Regulation of CTLA-4 Dimer-Based• Lattice Formation and Its Biological Relevance for T Cell Inactivation", the Journal of Immunology, vol. 175, pp. 996-1004 (2005).

Database: GenBank: MK13084 gi: 13128929, Feb. 27, 2001.

Database: GenBank:CAA49866 gi: 33069, Mar. 15, 2001.

Dionex, "Direct Determination of Sialic Acids in Glycoprotein Hydrolyzates by HPAE-PAD", Application Update 180, Thermo Scientific, p. 1-9.

Dionex, UHPLC Determination of Sialic Acids with Fluorescence Detection, Application Note 278, Thermo Scientific, p. 1-10.

Dumont, F., "Technology evaluation: Abatacept, Bristol-Myers Squibb" Current Opinion in Molecular Therapeutics, vol. 6(3), pp. 318-330 (2004).

Egen, J. et al., "CTLA-4: new insights into its biological function and use in• tumor immunotherapy", Nature Immunology, vol. 3(7), pp. 611-618 (2002).

Ellis, J. et al., "Interactions of CD80 and CD86 with CD28 and CTLA4", the Journal of Immunology, vol. 56, pp. 2700-2709 (1996).

Emery, P. et al., "A Multi-center, randomized, double blind, placebo controlled study to evaluate multiple doses of CTLA41g and LEA29Y administered intravenously to subjects with rheumatoid arthritis", Abstract W103-A056—2001.

EPO Mise—Observation letter by a third party. Letter attached.

Fahrner, R.L., et al., "Industrial Purification of Pharmaceutical Antibodies: Development, Operation, and Validation of Chromatography Processes," Biotechnology and Genetic Engineering Reviews, vol. 18, pp. 301-327, Taylor and Francis, England (2001).

Fairman, R. et al., "Molecular Weights of CTLA-4 and CD80 by Sedimentation Equilibrium Ultracentrifugation", Analytical Biochemistry, vol. 270, pp. 286-295 (1999).

Fiers, W., et al., "Complete Nucleotide Sequence of SV40 DNA," Nature, vol. 273, pp. 113-120 (May 1978).

Figueroa, B, Jr., et al., "Comparison of Bcl-2 to a Bcl-2 Deletion Mutant for Mammalian Cells Exposed to Culture Insults," Biotechnology and Bioengineering, vol. 73(3), pp. 211-222, Wiley, United States (May 2001).

Finck, B. et al., "Treatment of Murine Lupus with CTLA41g" Science, vol. 265(5176), pp. 1225-1227 (1994).

Freireich, E.J., et al., "Quantitative Comparison of Toxicity of Anticancer Agents in Mouse, Rat, Hamster, Dog, Monkey, and Man," Cancer Chemotherapy Reports, vol. 50(4), pp. 219-244, National Cancer Institute, United States (May 1966).

Gen Genetic Engineering & Biotechnology News, "Addressing Stability of Biological Drugs Forced Degradation Studies Predict Effects on Bioproducts in Drug Development and Manufacture", Mar. 15, 2005, vol. 25, No. 6, p. 1-6.

Generic Pharmaceutical Association (GphA), "Biopharmaceuticals ("Follow-On" Protein Products): Scientific Considerations for an Abbreviated Approval Pathway", Dec. 8, 2004, p. 1-29.

Genovese, M.C., et al., "Abatacept for Rheumatoid Arthritis Refractory to Tumor Necrosis Factor Alpha Inhibition," the New England Journal of Medicine, vol. 353(11), pp. 1114-1123, Massachusetts Medical Society, United States (2005).

Gluzman, Y., "SV40-transformed Simian Cells Support the Replication of Early SV40 Mutants," Cell, vol. 23(1); pp. 175-182, Cell Press, United States (Jan. 1981).

Grace VYDAC Enhancing the Science of Separations, "The Handbook of Analysis and Purification of Peptides and Proteins by Reversed-Phase HPLC", Third Edition, 2002, 36 pgs.

Graham, F.L., et al., "Characteristics of a Human Cell Line Transformed by DNA from Human Adenovirus Type 5," the Journal of General Virology, vol. 36(1), pp. 59-74, Society for General Microbiology, England (Jul. 1977).

Graser, E. et al., "Synergism of CTLA4-IG and Anti-CD4 Monoclonal Antibody Treatment in a Rat Kidney Transplant Model", Transplantation Proceedings, vol. 29, pp. 1307-1309 (1997).

Greene, J. et al., "Covalent Dimerization of CD2B/CTLA-4 and Oligomerization of CDBO/CDB6 Regulate T Cell Costimulatory Interactions", the Journal of Biological Chemistry, vol. 271(43), pp. 26762-26771 (1996).

Greene, J. L., et al., "Covalent Dimerization of CD28/CTLA-4 and Oligomerization of CD80/CD86 Regulate T Cell Costimulatory Interactions", the Journal of Biological Chemistry, vol. 271(43), pp. 26762-26771 (Oct. 1996).

(56) References Cited

OTHER PUBLICATIONS

Greve, K. et al., "Capillary electrophoretic examination of underivatized oligosaccharide mixtures released from immunoglobulin G antibodies and CTLA4Ig fusion protein", Journal of Chromatography, vol. 749, pp. 237-245 (1996).

Greve, K. et al., "Liquid chromatographic and capillary electrophoretic examination of intact and degraded fusion protein CTLA4Ig and kinetics of conformational transition", Journal of Chromatography A., vol. 723, pp. 273-284 (1996).

Griggs, N. et al., "The Relative Contribution of the CD2B and gp39 Costimulatory Pathways in the Clonal Expansion and Pathogenic Acquisition of Self-reactive T Cells", Journal of Experimental Medicine, vol. 183, pp. 801-810 (2005).

Grinyo, A. et al., "Belatacept (LEA29Y) as part of a CNI-free regimen in recipients of renal allografts with higher risk of poor long-term function and graft loss: comparison with cyclosporine", Abstract #946.

Gu, Long, et al., In vivo properties of monocyte chemoattractant protein-1, Journal of Leukocyte Biology, vol. 62, p. 577-580 (1997).

Haffar, O. et al., "Costimulation of T-cell activation and virus production by B7 antigen on activated CD4+ T cells from human immunodeficiency virus type 1-infected donors", Proceeding of the National Academy of Sciences USA, vol. 90, pp. 11094-11098 (1993).

Haraoui, B., et al., "Anti-infliximab Antibodies in Patients With Rheumatoid Arthritis Who Require Higher Doses of Infliximab to Achieve or Maintain a Clinical Response," the Journal of Rheumatology, vol. 33(1), pp. 31-36, Journal of Rheumatology Publishing Co, Canada (Jan. 2006).

Hardy, L.A., et al., "Examination of MCP-1 (CCL2) partitioning and presentation during transendothelialleukocyte migration", Laboratory Investigation, vol. 84, p. 81-90 (2004).

Harper, K., et al., "CTLA-4 and CD28 Activated Lymphocyte Molecules are Closely Related in Both Mouse and Human as to Sequence, Message Expression, Gene Structure, and Chromosomal Location," Journal of Immunology vol. 147(3), pp. 1037-1044, American Association of Immunologists, United States (Aug. 1991).

Haselbeck, A., et al., "Description and Application of an Immunological Detection System for Analyzing Glycoproteins on Blots," Glycoconjugate Journal, vol. 7(1), pp. 63-74, Kluwer Academic (Jan. 1990).

Hermeling, Suzanne, et al., "Structure-Immunogenicity Relationships of Therapeutic Proteins", Pharmaceutical Research, vol. 21(6), pp. 897-903 (Jun. 2004).

Hess, B., et al., "Cooperation of Glycolytic Enzymes," Advances in Enzyme Regulation, vol. 7, pp. 149-167, Pergamon Press, England (1969).

Hirose, K. et al., "Treatment of Kidney transplant patients with the novel costimulatory blocker LEA29Y (BMS-224818) and Anti-IL2 Receptor antibody does not impede the development of regulatory T cells", Abstract #1036.

Holland, M.J. and Holland, J.P., "Isolation and Identification of Yeast Messenger Ribonucleic Acids Coding for Enolase, Glyceraldehyde-3-phosphate Dehydrogenase, and Phosphoglycerate Kinase," Biochemistry, vol. 17(23), pp. 4900-4907, American Chemical Society, United States (Nov. 1978).

Hu, Y. et al., "An improved, inexpensive procedure for the large-scale purification of recombinant human erythropoietin", Biotechnology and Applied Biochemistry, vol. 40, pp. 89-94 (2004).

Hubbard, S.C and Ivatt, R,J., "Synthesis and Processing of Asparagine-linked Oligosaccharides," Annual Review of Biochemistry, vol. 50, pp. 555-583, Annual Reviews, United States (1981).

Hurum, D.C., et al., "Determination of sialic acids in infant formula by chromatographic methods: A comparison of high-performance anionexchange chromatography with pulsed amperometric detection and ultrahigh-performance liquid chromatography methods", Journal of Dairy Science, vol. 95, pp. 1152-1161 (2011).

Hutton, S. et al., "Development and application of cytotoxic T lymphocyte associated antigen 4 as a protein scaffold for the generation of novel binding ligands", FEBS Letters, vol. 475, pp. 225-231 (2000).

International Conference on Harmonisation of Technical Requirements for Registration of Pharmaceuticals for Human Use, Specifications: Test Procedures and Acceptance Criteria for Biotechnological / Biological Products Q6B, Mar. 10, 1999.

Itoh, S., et al., "Simultaneous Microanalysis of N-linked Oligosaccharides in a Glycoprotein Using Microbore Graphitized Carbon Column Liquid Chromatography-mass Spectrometry," Journal of Chromatography A, vol. 968(1-2), pp. 89-100, Elsevier, Netherlands (Aug. 2002).

Janeway, Jr., C.A., et al., "Immune Biology of the Immune System in Health and Disease", Immunobiology, 5th Edition 2001, pp. 304-305, Fig. 8.12.

Javeed, M. et al., "Emerging immunomodulatory therapies targeting the costimulatory pathways for the prevention of transplant rejection", I Drugs, vol. 6(10), pp. 964-969 (2003).

Judge, T. et al., "The in Vivo Mechanism of Action of CTLA4Ig", the Journal of Immunology, vol. 156, pp. 2294-2299 (1996).

Kaplan, H.A., et al., "Oiigosaccharyl transferase: the central enzyme in the pathway of glycoprotein assembly", Biochimica et Biophysica Acta, 1987, vol. 906, pp. 161-173.

Karin, M., et al., "Human Metallothionein Genes—primary Structure of the Metallothionein-II Gene and a Related Processed Gene," Nature, vol. 299(5886): pp. 797-802, Nature Publishing Group, England (Oct. 1982).

Keler, T. et al., "Activity and Safety of CTLA-4 Blockade combined with Vaccines in Cynomolgus Macaques", the Journal of Immunology, vol. 171, pp. 6251-6259 (2003).

Kiener, P. et al., "Stimulation of CD40 with Purified Soluble gp39 Induces Proinflammatory responses in human monocytes", the Journal of Immunology, vol. 155, pp. 4917-4925 (1995).

Kim, N.S and Lee, G,M., "Response of Recombinant Chinese Hamster Ovary Cells to Hyperosmotic Pressure: Effect of Bcl-2 Overexpression," Journal of Biotechnology, vol. 95(3), pp. 237-248, Elsevier Science Publishers, Netherlands (May 2002).

Koduri, R.K., et al., "An Efficient Homologous Recombination Vector PTV(I) Contains a Hot Spot for Increased Recombinant Protein Expression in Chinese Hamster Ovary Cells," Gene, vol. 280(1-2), pp. 87-95, Elsevier/North-Holland, Netherlands (Dec. 2001).

Kokko, K. et al., "Enhanced immunosuppression induced by targeted mutation of cytotoxic T lymphocyte antigen 4-immunoglobulin", Current Opinion in Organ Transplantation, vol. 10, pp. 265-269 (2005).

Kolhekar, A.S., et al., "Peptidylglycine Alpha-hydroxylating Monooxygenase: Active Site Residues, Disulfide Linkages, and a Two-domain Model of the Catalytic Core," Biochemistry, vol. 36(36), pp. 10901-10909, American Chemical Society, United States (Sep. 1997).

Kremer, J. et al., "Treatment of Rheumatoid Arthritis by selective inhibition of T-Cell Activation with Fusion Protein CTLA4Ig", the New England Journal of Medicine, vol. 349, pp. 1907-1915 (2003).

Kremer, J. et al., "Treatment of Rheumatoid Arthritis with the selective costimulation modulator abatacept", Arthritis & Rheumatism, vol. 52(8), pp. 2263-2271 (2005).

Kretzmer, G., "Industrial processes with animal cells", Applied Microbiology and Biotechnology, vol. 59, pp. 135-142 (2002).

Kuiper, H. et al., "Activated T Cells can induce high levels of CTLA-4 expression on B cells", the Journal of Immunology, vol. 155, pp. 1776-1783—1995.

Kurjan, J. and Herskowitz, I., "Structure of a Yeast Pheromone Gene (MF Alpha): A Putative Alpha-factor Precursor Contains Four Tandem Mature Alpha-factor," Cell, vol. 30(3), pp. 933-943, Cell Press, United States (Oct. 1982).

Lafage-Pochitaloff, M. et al., "Human CD28 and CTLA-4 Ig superfamily genes are located on chromosome 2 at bands q33-q34", Immunogenetics, vol. 31, pp. 198-201 (1990).

Larsen, C. et al., "Calcineurin inhibitor-free immunosuppression with belatacept (LEA29Y) in renal transplant: Phase II 12-month results", Abstract #535.

(56) References Cited

OTHER PUBLICATIONS

Larsen, C. et al., "Rational Development of LEA29Y (belatacept), a High-Affinity Variant of CTLA4-Ig with Potent Immunosuppressive Properties", American J. of Transplantation, vol. 5, pp. 443-453 (2005).

Lee, Y. et al., "Administration of CTLA4-Ig enhances the incidence of hamster-to-rat xenogeneic bone marrow engraftment and alters the presentation of graft-vs-host disease", Transplantation Proceedings, vol. 32, pp. 1032-1033 (2000).

Lenschow, D. et al., "Long-Term Survival of Xenogeneic Pancreatic Islet Grafts Induced by CTLA4Ig", Science, vol. 257, pp. 789-792 (1992).

Leung, H. et al., "Cytotoxic T Lymphocyte-associated Molecule-4, a high avidity receptor for CD80 and CD86, Contains an Intracellular Localization Motif in Its Cytoplasmic Tail", the Journal of Biological Chemistry, vol. 270(42), pp. 25107-25114 (1995).

Li, F., et al., "Current Therapeutic Antibody Production and Process Optimization," BioProcessing Journal, vol. 4(5), pp. 23-30, (2005).

Lindsten, T. et al., "Characterization of CTLA-4 Structure and Expression on Human T Cells", the Journal of Immunology, vol. 151(7), pp. 3489-3499 (1993).

Linsley, P. et al., "Binding Stoichiometry of the Cytotoxic T Lymphocyte Associated Molecule-4 (CTLA-4)", the Journal of Biological Chemistry, vol. 270(25), pp, 15417-15424 (1995).

Linsley, P. et al., "CD28 Engagement by 87/BB-1 Induces Transient Down-Regulation of CD28 Synthesis and Prolonged Unresponsiveness to CD28 Signaling", the Journal of Immunology, vol. 150(8), pp. 3161-3169 (1993).

Linsley, P. et al., "CD28/CTLA-4 receptor structure, binding stoichiometry and aggregation during T-cell activation", Research in Immunology, vol. 146(3), pp. 130-140 (1995).

Linsley, P. et al., "Coexpression and Functional Cooperation of CTLA-4 and CD28 on Activated T Lymphocytes", Journal of Experimental Medicine, vol. 176, pp. 1595-1604, the Rockefeller University Press, United States (1992).

Linsley, P. et al., "Human B7-1 (CD80) and 87-2 (CD86) Bind with Similar Avidities but Distinct Kinetics to CD28 and CTLA-4 Receptors", Immunity, vol. 1, pp. 793-801 (1994).

Linsley, P. et al., "Immunosuppression in Vivo by a Soluble Form of the CTLA-4 T Cell Activation Molecule", Science, vol. 257, pp. 792-795 (1992).

Linsley, P. et al., "Intracellular Trafficking of CTLA-4 and Focal Localization towards Sites of TCR Engagement", Immunity, vol. 4, pp. 535-543 (1996).

Linsley, P.S., et al., "CTLA-4 is a Second Receptor for the B Cell Activation Antigen B7," Journal of Experimental Medicine, vol. 174(3), pp. 561-569, the Rockefeller University Press, United States (Sep. 1991).

Lnobe, M. et al., "Identification of an Alternatively spliced form of the murine homologue of BT," Biochemical and Biophysical Research Communications, vol. 200(1), pp. 443-449 (1994).

Lowy, I., et al., "Isolation of Transforming DNA: Cloning the Hamster aprt Gene," Cell, vol. 22(3), pp. 817-823, Cell Press, United States (Dec. 1980).

Lu, P. et al., "Requirement of CTLA-4 Counter Receptors for IL-4 but not IL-10 Elevations during a Primary Systemic in Vivo Immune Response", the Journal of Immunology, vol. 154, pp. 1078-1087 (1995).

Lucklow, V.A., et al., "High Level Expression of Nonfused Foreign Genes With Autographa Californica Nuclear Polyhedrosis Virus Expression Vectors," Virology, vol. 170(1), pp. 31-39 (1989).

Mach, H., et al., "Statistical Determination of the Average Values of the Extinction Coefficients of Tryptophan and Tyrosine in Native Proteins," Analytical Biochemistry, vol. 200(1), pp. 74-80, Elsevier, United States (Jan. 1992).

Magistrelli, G. et al., "A soluble form of CTLA-4 generated by alternative splicing is expressed by nonstimulated human T cells", European Journal of Immunology, vol. 29, pp. 3596-3602 (1999).

Malik, N., et al., "Molecular Cloning, Sequence Analysis, and Functional Expression of a Novel Growth Regulator, Oncostatin M," Molecular and Cellular Biology, vol. 9(7), pp. 2847-2853, American Society for Microbiology, United States (Jul. 1989).

Mastrangelo, A.J., et al., "Part I. Bcl-2 and Bcl-x(L) Limit Apoptosis upon Infection with Alphavirus Vectors," Biotechnology and Bioengineering, vol. 67(5), pp. 544-554, Wiley, United States (Mar. 2000).

Mather, J.P., "Establishment and Characterization of Two Distinct Mouse Testicular Epithelial Cell Lines," Biology of Reproduction, vol. 23(1), pp. 243-252, Society for the Study of Reproduction, United States (Aug. 1980).

Mather, J.P., et al., "Culture of Testicular Cells in Hormone-Supplemented Serum-Free Medium," Annals of the New York Academy of Sciences, vol. 383, pp. 44-68,Blackwell, United States (1982).

Matthews, J. et al., "Clinical Trials of Transplant Tolerance: Slow but steady Progress", American Journal of Transplantation, vol. 3, pp. 794-803 (2003).

Metzler, W.J., et al., "Solution Structure of Human CTLA-4 and Delineation of a CD80/CD86 Binding Site Conserved in CD28," Nature Structural Biology, vol. 4(7), pp. 527-531, Nature Publishing Co., United States (Jul. 1997).

Moreland, L. et al., "A Multi-Center, Randomized, Double-blind, placebo controlled study to evaluate the safety and preliminary clinical activity of multiple doses of CTLA4Ig and LEA29Y administered intravenously to subjects with rheumatoid arthritis", Abstract 1327.

Moreland, L. et al., "Costimulatory Blockade in Patients with Rheumatoid Arthritis", Arthritis and Rheumatology, vol. 46(6), pp. 1470-1479 (2002).

Morgan, R.A. and Anderson, W.F., "Human Gene Therapy," Annual Review of Biochemistry, vol. 62, pp. 191-217, Annual Reviews, United States (1993).

Mulligan, R., "The Basic Science of Gene Therapy", Science, vol. 260, pp. 926-932 (1993).

Mulligan, R.C. and Berg, P., "Selection for Animal Cells that Express the *Escherichia coli* Gene Coding for Xanthine-guanine Phosphoribosyltransferase," Proceedings of the National Academy of Sciences USA, vol. 78(4), pp. 2072-2076, National Academy of Sciences, United States (Apr. 1981).

Nashan, B. et al., "Co-Stimulation blockade with LEA29Y in renal transplant: Improved renal function •and CV/Metabolic Profile at 6 months compared with Cyclosporine", Abstract #1035.

Nelson, A et al., "Medullary Thymic Epithelium a Ligand for cTLA4 in Situ and in Vivo", the Journal of Immunology, vol. 151(5), pp. 2453-2461 (1993).

Oaks, M. et al., "A Native Soluble form of CTLA-4", Cellular Immunology, vol. 201, pp. 144-153 (2000).

Ogawa, H.K., et al., "Determination of N-acetylneuraminic Acid and N-glycolylneuraminic Acid in Glycoproteins by High-performance Liquid Chromatography Without Derivatization," Journal of Chromatography, vol. 612(1), pp. 145-149, Elsevier, Netherlands (Jan. 1993).

O'Hare, K., et al., "Transformation of Mouse Fibroblasts to Methotrexate Resistance by a Recombinant Plasmid Expressing a Prokaryotic Dihydrofolate Reductase," Proceedings of the National Academy of Sciences USA, vol. 78(3), pp. 1527-1531, National Academy of Sciences, United States (Mar. 1981).

EPO Opposition Division, Preliminary and non-binding opinion, Application No. 06 848 052.4, Aug. 11, 2015, 6 pages.

Ostrov, D. et al., "Structure of Murine CTLA:-4 and its role in modulating T Cell Responsiveness", Science, vol. 290, pp. 816-819 (2000).

Peach, R. et al., "Both Extracellular Immunoglobin-like Domains of CD80 Contains residues Critical for Binding T Cell Surface Receptors CTLA-4 and CD28", the Journal of Biological Chemistry, vol. 270(36), pp. 21181-21187 (1995).

Peach, R.J., et al., "Complementarity Determining Region 1 (CDR1)- and CDR3-Analogous Regions in CTLA-4 and CD28 Determine the Binding to B7-1," Journal of Experimental Medicine, vol. 180(6), pp. 2049-2058, Rockefeller University Press, United States (Dec. 1994).

(56) References Cited

OTHER PUBLICATIONS

Peach, Robert J., et al., "CTLA4Ig: A Novel Immunoglobulin Chimera with Immunosuppressive Properties", Methods: A Companion to Methods in Enzymology, vol. 8, pp. 116-123 (1995).
Pistillo, M. et al., "Molecular characterization and applications of recombinant scFv antibodies to CD152 co-stimulatory molecule", Tissue Antigens, vol. 55, pp. 229-238 (2000).
Prodjosudjadi, W., et al., "Production and cytokine-mediated regulation of monocyte chemoattractant protein-1 by human proximal tubular epithelial cells", Kidney International, vol. 48, p. 1477-1486 (1995).
Reichmann, G. et al., "The CD28/B7 Interaction is not required for Resistance to Toxoplasma gondii in the Brain but Contributes to the Development of Immunopathology", the Journal of Immunology, vol. 163, pp. 3354-3362 (1999).
Reitstotter, Kinzebach & Partner; letter dated Jul. 28, 2010 to EPO, RE: EP Application No. 06848052.4-2405, 9 pgs.
Reitstotter, Kinzebach & Partner; letter dated Nov. 6, 2009 to EPO, RE: EP Application No. 06848052.4-2405, 6 pgs.
Rosenberg, Amy S., et al., "A Risk-Based Approach to Immunogenicity Concerns of Therapeutic Protein Products, Part 2: Considering Host- Specific and Product-Specific Factors Impacting Immunogenicity", BioPharm International, vol. 17(12), pp. 1-6 (2004).
Rudd, C. et al., "Unifying Concepts in CD28, ICOS and CTLA4 Co-Receptor Signalling", Nature Reviews/Immunology, vol. 3, pp. 544-556 (2003).
Ruderman, E. et al., "The evolving clinical profile of abatacept (CTLA4-Ig): a novel co-stimulatory modulator for the treatment of rheumatoid arthritis", Arthritis Research & Therapy, vol. 7(Suppl 2), pp. S21-S25 (2005).
Saha, B. et al., "Toxic Shock Syndrome Toxin-1-Induced Death is Prevented by CTLA41g", the Journal of Immunology, vol. 157, pp. 3869-3875 (1996).
Santerre, R.F., et al., "Expression of Prokaryotic Genes for Hygromycin B and G418 Resistance as Dominant-selection Markers in Mouse L Cells," Gene, vol. 30(1-3), pp. 147-156, Elsevier/North-Holland, Netherlands (Oct. 1984).
Sauerwald, T.M., et al., "Inhibiting Apoptosis in Mammalian Cell Culture using the Caspase Inhibitor XIAP and Deletion Mutants," Biotechnology and Bioengineering, vol. 77(6), pp. 704-716, Wiley, United States (Mar. 2002).
Sauerwald, T.M., et al., "Study of Caspase Inhibitors for Limiting Death in Mammalian Cell Culture," Biotechnology and Bioengineering, vol. 81(3), pp. 329-340, Wiley, United States (Feb. 2003).
Schiff, L., "Review: Production, Characterization, and Testing of Banked Mammalian Cell Substrates used to Produce Biological Products", in Vitro Cellular & Developmental Biology, vol. 41, pp. 65-70 (2005).
Schultz, L.D., et al., "Expression and Secretion in Yeast of a 400-kDa Envelope Glycoprotein Derived From Epstein-Barr Virus," Gene, vol. 54(1), pp. 113-123, Elsevier/North-Holland, Netherlands (1987).
Schwartz, J. et al., "Structural basis for co-stimulation by the human CTLA-4/B7-2 complex", Nature, vol. 410, pp. 604-608 (2001).
Seed, B., "An LFA-3 cDNA Encodes a Phospholipid-linked Membrane Protein Homologous to its Receptor CD2," Nature, vol. 329(6142), pp. 840-842, Nature Publishing Group, England (Oct. 1987).
Senger, R. et al., "Effect of Shear Stress on Intrinsic CHO Culture State and Glycosylation of Recombinant Tissue-Type Plasminogen Activator Protein", Biotechnology Progress, vol. 19, pp. 1199-1209 (2003).
Shapiro, A.M. James, et al., "Strategic Opportunities in Clinical Islet Transplantation", Transplantation, vol. 79(10), pp. 1304-1307 (2005).
Shi, W.X., et al., "Linkage-specific Action of Endogenous Sialic Acid O-acetyltransferase in Chinese Hamster Ovary Cells," Journal of Biological Chemistry, vol. 271(25), pp. 15130-15138, American Society for Biochemistry and Molecular Biology, United States (Jun. 1996).

Shukla, A.A., et al., "Downstream Processing of Monoclonal Antibodies—Application of Platform Approaches," Journal of Chromatography B, vol. 848(1), pp. 28-39, Elsevier, Netherlands (2007).
Smith, G.E., et al., "Production of Human Beta Interferon in Insect Cells Infected With a Baculovirus Expression Vector," Molecular and Cellular Biology, vol. 3(12), pp. 2156-2165, American Society for Microbiology, United States (Dec. 1983).
Smith, R., "Therapies for rheumatoid arthritis: hope springs eternal", Drug Discovery Today, vol. 10(23/24), pp. 1598-1606 (2005).
Srinivas, N.R., et al., "A Pharmacokinetic Study of Intravenous CTLA4Ig, a Novel Immunosuppressive Agent, in Mice", Journal of Pharmaceutical Sciences, vol. 85(3), pp. 296-298 (1996).
Stamper, C.C., et al., "Crystal Structure of the B7-1/CTLA-4 Complex that Inhibits Human Immune Responses," Nature, vol. 410(6828), pp. 608-611, Nature Publishing Group, England (2001).
Stinchcomb, D.T., et al., "Isolation and Characterisation of a Yeast Chromosomal Replicator," Nature, vol. 282(5734), pp. 39-43, Nature Publishing Group, England (Nov. 1979).
EPO Summons to Attend Oral Proceedings Pursuant to Rule 115(1) EPC, Application No. 06 848 052.4-1410/1969007, Aug. 11, 2015, 1 page.
Szybalska, E.H. and Szybalski, W., "Genetics of Human Cess Line IV DNA-mediated Heritable Transformation of a Biochemical Trait," Proceedings of the National Academy of Sciences USA, vol. 48, pp. 2026-2034, National Academy of Sciences, United States (Dec. 1962).
Szymkowski, D., "Timely lessons for target-based discovery of antiinflammatory drugs", Drug Discovery Today, vol. 10(1), pp. 14-17 (2005).
Tan, P. et al., "Induction of Alloantigen-specific Hyporesponsiveness in Human T Lymphocytes by Blocking Interaction of CD28 with its Natural Ligand B7/BB1"; Journal of Experimental Medicine, vol. 177, pp. 165-173 (1993).
Teng, G.G., et al, "Abatacept: a costimulatory inhibitor for treatment of rheumatoid arthritis", Expert Opinion on Biological Therapy, vol. 5(9), pp. 1245-1254 (2005).
Tolstoshev, P., "Gene Therapy, Concepts, Current Trials and Future Directions," Annual Review of Pharmacology and Toxicology, vol. 33, pp. 573-596, Annual Reviews, United States (1993).
Tschumper, G. and Carbon, J., "Sequence of a Yeast DNA Fragment Containing a Chromosomal Replicator and the TRP1 Gene," Gene, vol. 10(2), pp. 157-166, Elsevier/North-Holland, Netherlands (Jul. 1980).
Urlaub, G. and Chasin, L.A., "Isolation of Chinese Hamster Cell Mutants Deficient in Dihydrofolate Reductase Activity," Proceedings of the National Academy of Sciences USA, vol. 77(7), pp. 4216-4220, National Academy of Sciences, United States (Jul. 1980).
Urlaub, G., et al., "Deletion of the Diploid Dihydrofolate Reductase Locus from Cultured Mammalian Cells," Cell, vol. 33(2), pp. 405-412, Cell Press, United States (Jun. 1983).
Urlaub, G., et al., "Effect of gamma Rays at the Dihydrofolate Reductase Locus: Deletions and Inversions," Somatic Cell and Molecular Genetics, vol. 12(6), pp. 555-566, Kluwer Academic/Plenum Publishers, United States (Nov. 1986).
Van Der Merwe, P.A., et al., "CD80 (B7-1) Binds Both CD28 and CTLA-4 With a Low Affinity and Very Fast Kinetics," Journal of Experimental Medicine, vol. 185(3), pp. 393-403, Rockefeller University Press, United States (Feb. 1997).
Vincenti, F. et al., "Co-Stimulation Blockade with LEA29Y in a Calcineurin Inhibitor Free Maintenance Regimen in Renal Transplant: 6-Month Efficacy and Safety", Abstract #1037.
Vincenti, F., "Protein therapies and antiproliferatives: a new paradigm in immunosuppression", Transplantation Reviews, vol. 19, pp. 179-185 (2005).
Vincenti, F., "The Role of Newer Monoclonal Antibodies in Renal Transplantation", Transplantation Proceedings, vol. 33, pp. 1000-1001 (2001).
Vincenti, F., "What's in the Pipeline? New Immunosuppressive Drugs in Transplantation", American Journal of Transplantation, vol. 2, pp. 898-903 (2002).

(56) References Cited

OTHER PUBLICATIONS

Wallace, P. et al., "Induction and Reversal of Long-Lived Specific Unresponsiveness to at T-Dependent Antigen following CTLA4lg Treatment", the Journal of Immunology, vol. 154, pp. 5885-5895 (1995).
Walsh, G., "Biopharmaceutical benchmarks—2003: Since 2000, over a quarter of all new drugs approved have been biopharmaceuticals", Nature Biotechnology, vol. 21(8), pp. 865-870 (2003).
Walunas, T. et al., "CTLA-4 can function as a Negative Regulator bf T Cell Activation", Immunity, Vol.1, pp. 405-413 (1994).
Wang, G. et al., "Purification and Characterization of Hypoxia-inducible Factor 1", the Journal of Biological Chemistry, vol. 270(3), pp. 1230-1237 (1995).
Warner, TG., "Enhancing therapeutic glycoprotein production in Chinese hamster ovary cells by metabolic engineering endogenous gene control with antisense DNA and gene targeting" Glycobiology, vol. 9(9) pp. 841-850 (1999).
Warren, L, "The Thiobarbituric Acid Assay of Sialic Acids," Journal of Biological Chemistry 234(8), pp. 1971-1975, American Society for Biochemistry and Molecular Biology, United States (Aug. 1959).
Weikert, S., et al., "Engineering Chinese Hamster Ovary Cells to Maximize Sialic Acid Content of Recombinant Glycoproteins," Nature Biotechnology, vol. 17(11), pp. 1116-1121, (1999).
Wigler, M. et al., "Transfer of Purified Herpes Virus Thymidine Kinase Gene to Cultured Mouse Cells", Cell, vol. 11, pp. 223-232 (1977).
Wigler, M., et al., "Transformation of Mammalian Cells with an Amplifiable Dominant-Acting Gene," Proceedings of the National Academy of Sciences USA, vol. 77(6), pp. 3567-3570, National Academy of Sciences, United States (Jun. 1980).
Williams, A. et al., "The Immunoglobulin Superfamily-Domains for cell surface recognition", Annual Review of Immunology, vol. 6, pp. 381-405 (1988).
Winkler, Marjorie E., et al., "Validation studies to support the lenercept recovery process", Abstract, 216th ACS National Meeting, 1998, 1 pg.
Wu, G.Y. and Wu, C.H., "Delivery Systems for Gene Therapy," Biotherapy, vol. 3(1), pp. 87-95, Kluwer Academic Publishers, Netherlands (1991).
Wurm, F.M., "Production of Recombinant Protein Therapeutics in Cultivated Mammalian Cells," Nature Biotechnology, vol. 22(11), pp. 1393-1398, Nature America Publishing, United States (Nov. 2004).
Yao, K., et al., "Direct Determination of Bound Sialic Acids in Sialoglycoproteins by Acidic Ninhydrin Reaction," Analytical Biochemistry, vol. 179(2), pp. 332-335, Elsevier, United States (Jun. 1989).
Yoon, S. K. et al., "Effect of Culture pH on Erythropoietin Production by Chinese Hamster Ovary Cells grown in Suspension at 32.5 and 37.0° C.", Biotechnology and Bioengineering, vol. 89(3), pp. 345-356 (2005).
Yoon, S.K. et al., "Effect of Simultaneous Application of Stressful Culture Conditions on Specific Productivity and Heterogeneity of Erythropoietin in Chinese Hamster Ovary Cells", Biotechnology Progress, vol. 20, pp. 1293-1296 (2004).
Yoon, S.K.et al., "Effect of Low Culture Temperature on Specific Productivity, Transcription Level, and Heterogeneity of Erythropoietin in Chinese Hamster Ovary Cells", Biotechnology and Bioengineering, vol. 82, pp. 289-298 (2003).
Yuk, I. et al., "Changes in the overall extent of protein glycosylation by Chinese hamster ovary cells over the course of batch culture", Biotechnology & Applied Biochemistry, vol. 36, pp. 133-140 (2002).
Zambrowicz, B. et al., "Predicting drug efficacy: knockouts model pipeline drugs of the pharmaceutical industry", Current Opinion in Pharmacology, vol. 3, pp. 563-570 (2003).
Zanette, D. et al., "Evaluation of phenylboronate agarose for industrial-scale purification of erythropoietin from mammalian cell cultures", Journal of Biotechnology, vol. 101, pp. 275-287 (2003).
Zhang, X. et al., "Crystallization and preliminary X-ray analysis of the complex between human CTLA-4 and B7-2", Acta Crystallographica D, vol. 57, pp. 898-899 (2001).
Zhang, X. et al., "Expression, Refolding, Purification, Molecular Characterization, Crystallization, and Preliminary X-ray analysis of the Receptor binding domain of Human B7-2", Protein Expression and Purification, vol. 25, pp. 105-113 (2002).
Co-pending U.S. Appl. No. 16/044,217 inventors Leister, Kirk J., et al., filed Jul. 24, 2018 (Not Published).
Co-pending U.S. Appl. No. 16/044,252, inventors Leister, Kirk J., et al., filed Jul. 24, 2018 (Not Published).
Ashkenzai, A., et al., "Immunoadhesins: An Alternative to Human Monoclonal Antibodies," Methods: A Comparison to Methods in Enzymology 8:104-115, Academic Press, United States (Oct. 1995).
Bristol-Myers Squibb, "Graphical Representation of the results in [01389] of EP 1969007B," Cited as D57 in European Patent EP1969007B, submitted Jun. 23, 2017, 2 pages.
Cromwell, M.E.M., et al., "Protein Aggregation and Bioprocessing," AAPS 8(3):e572-e579, Springer Journal, United States (Sep. 2006).
Liu, H., et al., "In vitro and in vivo modifications of recombinant and human IgG antibodies," MAbs 6(5):1145-1154, Taylor & Francis, United States (Oct. 2014).
Wikipedia.org, "Parts-per notation," retrieved Jun. 18, 2014, retrieved from http://en.wikipedia.org/wiki/Parts-per_notation, 8 pages.
Scopes, Springer Advanced Text in Chemistry; Protein Purification, Principles and Practice, 3ed. Cantor, C.R., 4 pages, Nov. 19, 1993.
Zoon, K.C., "Points to Consider in the Manufacture and Testing of Monoclonal Antibody Products for Human Use," Center for Biologics and Evaluation: 14 pages, FDA, United States (Feb. 1997).
Affidavit of Ronald Bates, filed in European Patent Application No. 2,253,644 B1, dated Feb. 9, 2018, 15 pages.
Nebija, D., et al., "Charge Heterogeneity study of a Fc-Fusion Protein, abatacept, using two-dimensional gen electrophoresis," Pharmazie 70:527-534, Govi-Verlag, Germany (Aug. 2015).
Notice of Opposition, filed by D. Young & Co. LLP., against EP1969007, 37 pages, dated May 27, 2014.
Notice of Opposition, filed by Potter Clarkson LLP., against EP1969007, 18 pages, dated May 23, 2014.
Decision of the Opposition Division and Instructions , European Patent Office., in EP1969007, 1 page, dated Oct. 6, 2017.
Grounds for the Decision (Annexure), European Patent Office., in EP1969007, 18 pages, dated Oct. 6, 2017.
Notice of Appeal, Bristol-Myers Squibb Company, in EP1969007, dated Nov. 13, 2017, 3 pages.
Statement of Grounds of Appeal, Dorries Frank-Molnia & Pohlman, in EP1969007, dated Feb. 16, 2018, 31 pages.
Statement of Grounds of Appeal, Potter Clarkson LLP, in EP1969007, Dorries Frank-Molnia & Pohlman, dated Feb. 14, 2018, 24 pages.
Reply to Appeal, Bristol-Myers Squibb Company, in EP1969007, dated Jul. 4, 2018, 31 pages.
Reply to Appeal, Dorries Frank-Molnia & Pohlman, in EP1969007, dated Jul. 2, 2018, 7 pages.
Reply to Appeal, Potter Clarkson LLP, in EP1969007, dated Jun. 28, 2018, 4 pages.
Notice of Opposition, filed by Potter Clarkson LLP., against EP2253644, 16 pages, dated Jul. 16, 2014.
Notice of Opposition, filed by Potter Clarkson LLP., against EP2253644, 37 pages, dated Jul. 15, 2014.
Decision of the Opposition Division and Instruction, and Grounds of the Decision, European Patent Office, EP2253644, 24 pages, Sep. 29, 2017.
Notice of Appeal, filed by Bristol-Myers Squibb Company, in EP2253644, 1 page, dated Dec. 8, 2017.
Statement of Grounds of Appeal, filed by Bristol-Myers Squibb Company, in EP2253644, 12 pages, dated Feb. 9, 2018.
Reply to Appeal, filed by Dorries Frank-Molnia & Pohlman, in EP2253644, 23 pages, dated Jun. 25, 2018.
Reply to Appeal, filed by Potter Clarkson LLP, in EP2253644, 21 pages, dated Jun. 25, 2018.
Reply from the Opponent to the Submission of the Proprietor, filed by Dorries Frank-Molnia & Pohlman, in EP2253644, 19 pages, dated Jul. 13, 2015.

(56) References Cited

OTHER PUBLICATIONS

Reply of the Patent Proprietor to the notice of the Opposition, filed by Bristol-Myers Squibb Company, in EP2253644, 24 pages, dated Mar. 2, 2015.
Office action dated May 29, 2019, in U.S. Appl. No. 16/044,217, inventor Leister, K.J., et al., filed Jul. 24, 2018, 7 pages.
Office action dated Oct. 24, 2019, in U.S. Appl. No. 16/044,217, inventor Leister, K.J., et al., filed Jul. 24, 2018, 7 pages.
Office action dated Jul. 8, 2019, in U.S. Appl. No. 16/044,252, inventor Leister, K.J., et al., filed Jul. 24, 2018, 7 pages.
Momenta, Momenta and Mylan Report Initial Results from Phase 1 Clinical Trial for M834, a Proposed Biosimilar of Orencia (Abatacept), Nov. 1, 2017, 2 pages.
Office action dated Jul. 17, 2018, in U.S. Appl. No. 12/086,786, inventor Leister, K.J., et al., filed Jan. 27, 2009, 6 pages.
Office action dated Apr. 24, 2017, in U.S. Appl. No. 12/086,786, inventor Leister, K.J., et al., filed Jan. 27, 2009, 5 pages.
Office action dated Nov. 9, 2016, in U.S. Appl. No. 12/086,786, inventor Leister, K.J., et al., filed Jan. 27, 2009, 24 pages.
Office action dated Mar. 16, 2016, in U.S. Appl. No. 12/086,786, inventor Leister, K.J., et al., filed Jan. 27, 2009, 8 pages.
Office action dated Jul. 9, 2015, in U.S. Appl. No. 12/086,786, inventor Leister, K.J., et al., filed Jan. 27, 2009, 8 pages.
Office action dated Oct. 9, 2014, in U.S. Appl. No. 12/086,786, inventor Leister, K.J., et al., filed Jan. 27, 2009, 7 pages.
Office action dated Feb. 10, 2014, in U.S. Appl. No. 12/086,786, inventor Leister, K.J., et al., filed Jan. 27, 2009, 7 pages.
Office action dated Apr. 18, 2012, in U.S. Appl. No. 12/086,786, inventor Leister, K.J., et al., filed Jan. 27, 2009, 7 pages.
Office action dated Aug. 16, 2011, in U.S. Appl. No. 12/086,786, inventor Leister, K.J., et al., filed Jan. 27, 2009, 2 pages.
Office action dated Aug. 16, 2011, in U.S. Appl. No. 12/086,786, inventor Leister, K.J., et al., filed Jan. 27, 2009, 5 pages.
Office action dated Dec. 18, 2019, in U.S. Appl. No. 16/044,252, inventor Leister, K.J., et al., filed Jul. 24, 2018, 6 pages.

\* cited by examiner

```
  1  AGCTTCACCA ATG GGT GTA CTG CTC ACA CAG AGG ACG CTG
                M   G   V   L   L   T   Q   R   T   L
                └──▶ Oncostatin M Signal Sequence ─▶

41  CTC AGT CTG GTC CTT GCA CTC CTG TTT CCA AGC ATG GCG
      L   S   L   V   L   A   L   L   F   P   S   M   A

80  AGC ATG GCA ATG CAC GTG GCC CAG CCT GCT GTG GTA CTG
      S   M   A  M   H   V   A   Q   P   A   V   V   L
                 └──▶ Human CTLA4 ─▶

119  GCC AGC AGC CGA GGC ATC GCC AGC TTT GTG TGT GAG TAT
      A   S   S   R   G   I   A   S   F   V   C   E   Y

158  GCA TCT CCA GGC AAA GCC ACT GAG GTC CGG GTG ACA GTG
      A   S   P   G   K   A   T   E   V   R   V   T   V

197  CTT CGG CAG GCT GAC AGC CAG GTG ACT GAA GTC TGT GCG
      L   R   Q   A   D   S   Q   V   T   E   V   C   A

236  GCA ACC TAC ATG ATG GGG AAT GAG TTG ACC TTC CTA GAT
      A   T   Y   M   M   G   N   E   L   T   F   L   D

275  GAT TCC ATC TGC ACG GGC ACC TCC AGT GGA AAT CAA GTG
      D   S   I   C   T   G   T   S   S   G   N   Q   V

314  AAC CTC ACT ATC CAA GGA CTG AGG GCC ATG GAC ACG GGA
      N   L   T   I   Q   G   L   R   A   M   D   T   G

353  CTC TAC ATC TGC AAG GTG GAG CTC ATG TAC CCA CCG CCA
      L   Y   I   C   K   V   E   L   M   Y   P   P   P

392  TAC TAC CTG GGC ATA GGC AAC GGA ACC CAG ATT TAT GTA
      Y   Y   L   G   I   G   N   G   T   Q   I   Y   V

431  ATT GAT CCA GAA CCG TGC CCA GAT TCT GAT CAG GAG CCC
      I   D   P   E   P   C   P   D   S   D   Q  E   P
                                               └──▶

470  AAA TCT TCT GAC AAA ACT CAC ACA TCC CCA CCG TCC CCA
      K   S   S*  D   K   T   H   T   S*  P   P   S*  P
     Human IgG₁ Hinge ─▶

509  GCA CCT GAA CTC CTG GGG GGA TCG TCA GTC TTC CTC TTC
     │A   P   E   L   L   G   G   S*  S   V   F   L   F
     └──▶ Human IgG₁ C_H2 Domain ─▶

548  CCC CCA AAA CCC AAG GAC ACC CTC ATG ATC TCC CGG ACC
      P   P   K   P   K   D   T   L   M   I   S   R   T
```

FIG. 1A

```
ATGGGTGTACTGCTCACACAGAGGACGCTGCTCAGTCTGGTCCTTGCACTCCTGTTTCCA        -19
M--G--V--L--L--T--Q--R--T--L--L--S--L--V--L--A--L--L--F--P--        -7

AGCATGGCCAGCATGGCAATGCACGTGGCCCAGCCTGCTGTGGTACTGGCCAGCAGCCGA        +42
S--M--A--S--M--A--M--H--V--A--Q--P--A--V--V--L--A--S--S--R--        +14
                +1

GGCATCGCTAGCTTTGTGTGTGAGTATGCATCTCCAGGCAAATATACTGAGGTCCGGGTG        +102
G--I--A--S--F--V--C--E--Y--A--S--P--G--K--Y--T--E--V--R--V--        +34

ACAGTGCTTCGGCAGGCTGACAGCCAGGTGACTGAAGTCTGTGCGGCAACCTACATGATG        +162
T--V--L--R--Q--A--D--S--Q--V--T--E--V--C--A--A--T--Y--M--M--        +54

GGGAATGAGTTGACCTTCCTAGATGATTCCATCTGCACGGGCACCTCCAGTGGAAATCAA        +222
G--N--E--L--T--F--L--D--D--S--I--C--T--G--T--S--S--G--N--Q--        +74

GTGAACCTCACTATCCAAGGACTGAGGGCCATGGACACGGGACTCTACATCTGCAAGGTG        +282
V--N--L--T--I--Q--G--L--R--A--M--D--T--G--L--Y--I--C--K--V--        +94

GAGCTCATGTACCCACCGCCATACTACGAGGGCATAGGCAACGGAACCCAGATTTATGTA        +342
E--L--M--Y--P--P--P--Y--Y--E--G--I--G--N--G--T--Q--I--Y--V--        +114

ATTGATCCAGAACCGTGCCCAGATTCTGATCAGGAGCCCAAATCTTCTGACAAAACTCAC        +402
I--D--P--E--P--C--P--D--S--D--Q--E--P--K--S--S--D--K--T--H--        +134

ACATCCCCACCGTCCCCAGCACCTGAACTCCTGGGGGGATCGTCAGTCTTCCTCTTCCCC        +462
T--S--P--P--S--P--A--P--E--L--L--G--G--S--S--V--F--L--F--P--        +154

CCAAAACCCAAGGACACCCTCATGATCTCCCGGACCCCTGAGGTCACATGCGTGGTGGTG        +522
P--K--P--K--D--T--L--M--I--S--R--T--P--E--V--T--C--V--V--V--        +174

GACGTGAGCCACGAAGACCCTGAGGTCAAGTTCAACTGGTACGTGGACGGCGTGGAGGTG        +582
D--V--S--H--E--D--P--E--V--K--F--N--W--Y--V--D--G--V--E--V--        +194

CATAATGCCAAGACAAAGCCGCGGGAGGAGCAGTACAACAGCACGTACCGTGTGGTCAGC        +642
H--N--A--K--T--K--P--R--E--E--Q--Y--N--S--T--Y--R--V--V--S--        +214

GTCCTCACCGTCCTGCACCAGGACTGGCTGAATGGCAAGGAGTACAAGTGCAAGGTCTCC        +702
V--L--T--V--L--H--Q--D--W--L--N--G--K--E--Y--K--C--K--V--S--        +234

AACAAAGCCCTCCCAGCCCCCATCGAGAAAACCATCTCCAAAGCCAAAGGGCAGCCCCGA        +762
N--K--A--L--P--A--P--I--E--K--T--I--S--K--A--K--G--Q--P--R--        +254

GAACCACAGGTGTACACCCTGCCCCCATCCCGGGATGAGCTGACCAAGAACCAGGTCAGC        +822
E--P--Q--V--Y--T--L--P--P--S--R--D--E--L--T--K--N--Q--V--S--        +274

CTGACCTGCCTGGTCAAAGGCTTCTATCCCAGCGACATCGCCGTGGAGTGGGAGAGCAAT        +882
L--T--C--L--V--K--G--F--Y--P--S--D--I--A--V--E--W--E--S--N--        +294

GGGCAGCCGGAGAACAACTACAAGACCACGCCTCCCGTGCTGGACTCCGACGGCTCCTTC        +942
G--Q--P--E--N--N--Y--K--T--T--P--P--V--L--D--S--D--G--S--F--        +314

TTCCTCTACAGCAAGCTCACCGTGGACAAGAGCAGGTGGCAGCAGGGGAACGTCTTCTCA        +1002
F--L--Y--S--K--L--T--V--D--K--S--R--W--Q--Q--G--N--V--F--S--        +334

TGCTCCGTGATGCATGAGGCTCTGCACAACCACTACACGCAGAAGAGCCTCTCCCTGTCT        +1062
C--S--V--M--H--E--A--L--H--N--H--Y--T--Q--K--S--L--S--L--S--        +354

CCGGGTAAATGA
P--G--K--*
```

FIG. 2

*MGVLLTQRTLLSLVLALLFPSMASMA*

MHVAQPAVVLASSRGIASFVCEYASPGKYTEVRVTVLRQADSQVTEVCAA 50

TYMMGNELTFLDDSICTGTSSGNQVNLTIQGLRAMDTGLYICKVELMYPP 100

PYYEGIGNGTQIYVIDPEPCCPDSDQEPKSSDKTHTSPPSPAPELLGGSSV 150

FLFPPKPKDTLMISRTPEVTCVVVDVSHEDPEVKFNWYVDGVEVHNAKTK 200

PREEQYNSTYRVVSVLTVLHQDWLNGKEYKCKVSNKALPAPIEKTISKAK 250

GQPREPQVYTLPPSRDELTKNQVSLTCLVKGFYPSDIAVEWESNGQPENN 300

YKTTPPVLDSDGSFFLYSKLTVDKSRWQQGNVFSCSVMHEALHNHYTQKS 350

LSLSPGK

*Pro-sequence*

FIG. 3

*MGVLLTQRTLLSLVLALLFPSMASMA*\*

M\*\*HVAQPAVVLASSRGIASFVCEYASPGKYTEVRVTVLRQADSQVTEVCAA⁵⁰

TYMMGNELTFLDDSICTGTSSGNQVṈLTIQGLRAMDTGLYICKVELMYPP¹⁰⁰

PYYLGIGNGTQIYVIDPEPC̱PDSDQEPKSSDKTHTSPPSPAPELLGGSSV¹⁵⁰

FLFPPKPKDTLMISRTPEVTCVVVDVSHEDPEVKFNWYVDGVEVHNAKTK²⁰⁰

PREEQYN̲STYRVVSVLTVLHQDWLNGKEYKCKVSNKALPAPIEKTISKAK²⁵⁰

GQPREPQVYTLPPSRDELTKNQVSLTC̱LVKGFYPSDIAVEWESNGQPENN³⁰⁰

YKTTPPVLDSDGSFFLYSKLTVDKSRWQQGNVFSCSVMHEALHNHYTQKS³⁵⁰

LSLSPGK\*\*\*

G\*\*\*\*

Key:
*Pro-sequence*
CTLA-4 domain with two amino acid substitutions (L104E and A29Y)
Human IgG Fc fragment
Amino Acid Substitution
N̲-linked Glycosylation Site
C̱-120, Inter-chain disulfide bond

| | Structure | Expected Mass (Daltons) | Observed Mass (Daltons) |
|---|---|---|---|
| *Asialylated* | | | |
| P2100 | 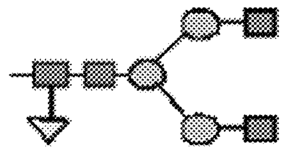 | 1463 | 1576 [M-H]⁻ • TFA |
| P2110 | 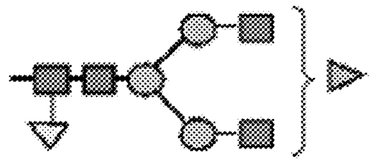 | 1625 | 1738 [M-H]⁻ • TFA |
| P2120 | 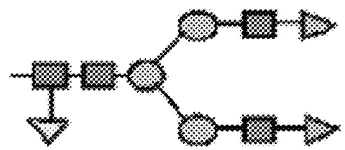 | 1787 | 1900 [M-H]⁻ • TFA |

Legend: ★ NANA, △ Galactose, ■ GlcNAc, ● Mannose, ▷ Fucose

FIG. 88A

| Structure | Expected Mass (Daltons) | Observed Mass (Daltons) |
|---|---|---|
| *Mono-sialylated* | | |
| P2111 | 1916 | 1915 [M-H]⁻ |
| P2121 | 2078 | 2077 [M-H]⁻ |
| P3131 | 2443 | 1279 [M-2H]²⁻ |
| P2122 | 2369 | 1184 [M-2H]²⁻ |
| P3132 | 2734 | 1367 [M-2H]²⁻ |
| P4142 | 3099 | 1549 [M-2H]²⁻ |

Legend: NANA, Galactose, GlcNAc, Mannose, Fucose

| Glycopeptide | Expected Mass In Daltons | Observed Mass In Daltons |
|---|---|---|
| Unmodified T8 | 435 | 436.2 [M+H]$^+$ |
| T8 (NANA-Hexose-HexNAc) | 1092 | 1092.2 [M+H]$^+$ |

FIG. 96

CARBOHYDRATE CONTENT OF CTLA4 MOLECULES

RELATED APPLICATIONS

The present patent application is a divisional of U.S. application Ser. No. 12/086,786 with 371(c) date of Jan. 27, 2009, which is the national phase application of International Application No. PCT/US2006/049074, filed Dec. 19, 2006, which claims the priority of U.S. Ser. No. 60/752,267, filed on Dec. 20, 2005, U.S. Ser. No. 60/849,543, filed on Oct. 5, 2006, and U.S. Ser. No. 60/752,150, filed on Dec. 20, 2005, all of which are hereby incorporated by reference in their entireties. This application also incorporates by reference in its entirety International Application No. PCT/US2006/062297 entitled "Stable Protein Formulations" filed on Dec. 19, 2006.

REFERENCE TO SEQUENCE LISTING SUBMITTED ELECTRONICALLY VIA EFS-WEB

The content of the electronically submitted sequence listing (Name: 3338.1350004_Sequence_listing_ST25.txt; Size: 83,616 bytes; and Date of Creation: Jul. 22, 2018) filed with the application is incorporated herein by reference in its entirety.

All patents, patent applications and publications cited herein are hereby incorporated by reference in their entirety.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Cytotoxic T lymphocyte antigen 4 (CTLA4), a member of the immunoglobulin superfamily, is a molecule expressed by activated T cells. CTLA4 is similar to the T-cell co-stimulatory molecule CD28, and both molecules bind to B7-1 (CD80) and B7-2 (CD86) on antigen-presenting cells (APCs). However, CTLA4 transmits an inhibitory signal to T cells, whereas CD28 transmits a stimulatory signal.

CTLA4-Ig molecules are fusion proteins of the ligand-binding domain of cytotoxic T lymphocyte antigen 4 (CTLA4) and an immunoglobulin (Ig) heavy chain constant region. This soluble molecule exerts its physiological effects by binding to B7 antigens (CD80 and CD86) on the surface of various antigen-presenting cells (APC), thus blocking the functional interaction of B7-1 and B7-2 with CD28 on the surface of T-cells. This blockade results in the suppression of T-cell activation, and hence, the suppression of the immune response. CTLA4-Ig molecules can therefore provide a method for inhibiting tissue and/or solid organ transplant rejections, as well as a therapeutic use for diseases or disorders that relate to disregulated immune responses in general, including autoimmunity. For example, CTLA4-Ig molecules can suppress the production of anti-dsDNA antibodies and decrease nephritis in lupus prone mice; can reduce proteinuria and prolong survival in mice with advanced nephriti; and can improve clinical outcomes for psoriasis and rheumatoid arthritis.

To improve the therapeutic usefulness of CTLA4-Ig molecules, it is important to determine molecular alterations that can be made to enhance the efficacy of the molecule as an inhibitor of T cell stimulation, for example, by increasing the avidity and potency of the molecule for B7 antigens. An increase in the avidity and potency of CTLA4-Ig molecules may allow for administration of a decreased amount of CTLA4-Ig molecules to a patient to achieve a desired therapeutic effect (i.e., administration of a lower dose). An increase in the avidity and potency of CTLA4-Ig molecules may also decrease the number of doses or the frequency of doses that are administered to a patient to achieve a desired therapeutic effect.

SUMMARY OF THE INVENTION

The present invention relates to improved compositions and methods for producing CTLA4-Ig compositions. The invention is directed to CTLA4-Ig molecules, improved compositions comprising CTLA4-Ig molecules, and improved methods for producing (including mass-producing) CTLA4-Ig molecules and other recombinant proteins.

The invention includes any permutations and/or combinations of any of the elements and characteristics described herein, whether described singly or in certain combinations or permutations.

Cells:

The invention provides for a clonal Chinese Hamster Ovary cell population capable of producing CTLA4-Ig. The invention provides for a clonal Chinese Hamster Ovary cell population capable of producing CTLA4-Ig, each cell comprising 30 or more copies of a CTLA4-Ig expression cassette. The invention also provides for a clonal Chinese Hamster Ovary cell population capable of producing CTLA4-Ig, each cell comprising 30 or more copies of a CTLA4-Ig expression cassette, wherein the 30 or more copies are integrated at a single site in the genome of each cell. The invention provides for a clonal Chinese Hamster Ovary cell population capable of producing CTLA4-Ig, wherein a CTLA4-Ig expression cassette is stable over about 105 passages. In one embodiment, the CTLA4-Ig is encoded by an expression cassette comprising a nucleic acid sequence described by Koduri R., et al. (*Gene*, 2001, 280: 87-95) and in U.S. Pat. Nos. 6,800,457 and 6,521,419, which are hereby incorporated by reference in their entireties. In another embodiment, the CTLA4-Ig is encoded by an expression cassette integrated into a cell genome from the cell population at a specific locus described by Koduri R., et al. (*Gene*, 2001, 280:87-95) and in U.S. Pat. Nos. 6,800,457 and 6,521,419, which are hereby incorporated by reference in their entireties. In one embodiment, the population comprises a sub-population of cells comprising 33 or more copies of the CTLA4-Ig expression cassette, wherein the 33 or more copies are integrated at a single site in the genome of each cell of the subpopulation.

The invention provides for a clonal Chinese Hamster Ovary cell population capable of producing CTLA4-Ig, wherein at least 75% of the population of cells has 30 or more copies of a CTLA4-Ig expression cassette, wherein the 30 or more copies are integrated at a single site in the genome of each cell of the 75% of the population. The invention provides for a clonal Chinese Hamster Ovary cell population capable of producing CTLA4-Ig, wherein at least 85% of the population of cells has 30 or more copies of a CTLA4-Ig expression cassette, wherein the 30 or more copies are integrated at a single site in the genome of each cell of the 85% of the population. The invention provides for a clonal Chinese Hamster Ovary cell population capable of producing CTLA4-Ig, wherein at least 95% of the population of cells has 30 or more copies of a CTLA4-Ig expression cassette, wherein the 30 or more copies are integrated at a single site in the genome of each cell of the 95% of the population. In one embodiment, the cell population is capable of producing greater than 0.5 or more grams of CTLA4-Ig protein per liter of liquid culture, and wherein the CTLA4-Ig exhibits acceptable carbohydrate characteristics, where the molar ratio of sialic acid to CTLA4-Ig is from about 6 to about 14 at a culture scale of 1,000 L or more. In another embodiment, the cell population has been adapted to serum-free, chemically defined medium. In another embodiment, CTLA4-Ig produced from culture of the cell population has an extinction coefficient of 1.00±0.05 AU mL cm-1 mg-1. In another embodiment, the cell population, when grown in culture, is capable of producing CTLA4-Ig polypeptides, wherein: (a) about 90% of the CTLA4-Ig polypeptides comprise an amino acid sequence of SEQ ID NO:2 beginning with the methionine at residue 27; (b) about 10% of the CTLA4-Ig polypeptides comprise the amino acid sequence of SEQ ID NO:2 beginning with the alanine at residue number 26; (c) about 4% of the CTLA4-Ig polypeptides comprise the amino acid sequence of SEQ ID NO:2 ending with the lysine at residue number 383, (d) about 96% of the CTLA4-Ig polypeptides comprise the amino acid sequence of SEQ ID NO:2 ending with the glycine at residue number 382; and optionally, (e) about less than 1% of the CTLA4-Ig polypeptides comprise the amino acid sequence of SEQ ID NO:2 beginning with the methionine at residue number 25.

The invention provides for a progeny cell of the clonal cell, wherein the progeny cell produces CTLA4-Ig. In one embodiment, the progeny cell is obtained from culturing the clonal parental cell over at least 5 generations. In another embodiment, the progeny cell is obtained from culturing a cell over at least 10 generations, over at least 20 generations, over at least 40 generations, over at least 50 generations, over at least 75 generations, or over at least 100 generations. The invention provides for a cell line produced from the clonal cell. In one embodiment, the cell line is clonal. The invention provides for a cell line capable of producing: (a) a CTLA4-Ig fusion protein having an amino acid sequence of SEQ ID NO:10 (methionine at amino acid position 27 and glycine at amino acid position 382; FIGS. 1A and 1B); (b) a CTLA4-Ig fusion protein having an amino acid sequence of SEQ ID NO: 7 (methionine at amino acid position 27 and lysine at amino acid position 383; FIGS. 1A and 1B); (c) a CTLA4-Ig fusion protein having an amino acid sequence of SEQ ID NO: 9 (alanine at amino acid position 26 and glycine at amino acid position 382; FIGS. 1A and 1B); (d) a CTLA4-Ig fusion protein having an amino acid sequence of SEQ ID NO: 6 (alanine at amino acid position 26 and lysine at amino acid position 383; FIGS. 1A and 1B); (e) a CTLA4-Ig fusion protein having an amino acid sequence of SEQ ID NO:8 (methionine at amino acid position 25 and glycine at amino acid position 382; FIGS. 1A and 1B); or (f) a CTLA4-Ig fusion protein having an amino acid sequence of SEQ ID NO:5 (methionine at amino acid position 25 and lysine at amino acid position 383; FIGS. 1A and 1B). In another embodiment, the cell line is capable of producing CTLA4-Ig fusion proteins, wherein: (a) about 90% of the CTLA4-Ig polypeptides comprise an amino acid sequence of SEQ ID NO:2 beginning with the methionine at residue 27; (b) about 10% of the CTLA4-Ig polypeptides comprise the amino acid sequence of SEQ ID NO:2 beginning with the alanine at residue number 26; (c) about 4% of the CTLA4-Ig polypeptides comprise the amino acid sequence of SEQ ID NO:2 ending with the lysine at residue number 383, (d) about 96% of the CTLA4-Ig polypeptides comprise the amino acid sequence of SEQ ID NO:2 ending with the glycine at residue number 382; and optionally, (e) about less than 1% of the CTLA4-Ig polypeptides comprise the amino acid sequence of SEQ ID NO:2 beginning with the methionine at residue number 25.

In one embodiment, the CTLA4-Ig fusion proteins, which are produced from culturing the cell line, have an extinction coefficient of 1.00±0.05 AU mL cm-1 mg-1. The invention provides for a cell population derived from the clonal cell line. In an embodiment, the cell population consists of at least one additional genetic change as compared to the original clonal cell line and wherein the derived cell population is capable of producing CTLA4-Ig. In another embodiment, the cell population consists of at least 2, at least 3, at least 4, at least 5, at least 6, at least 7, at least 8, at least 10, at least 15, or at least 20 additional genetic changes as compared to the parental cell, and wherein the derived cell population is capable of producing CTLA4-Ig. In one embodiment, the genetic change comprises at least one non-conservative mutation in the cellular genome or in the recombinant expression cassette encoding CTLA4-Ig. In another embodiment, the genetic change comprises at least one additional recombinant nucleic acid within the cell. In a further embodiment, the change comprises a mutation of the cellular genome. In another embodiment, the change comprises the addition of a nucleic acid to either the cell genome or as a trans nucleic acid, which encodes an anti-apoptotic polypeptide. In another embodiment, the anti-apoptotic polypeptide relates to glycosylation. In another embodiment, genetic change comprises at least one mutation of the cellular genome or of the recombinant expression cassette encoding CTLA4-Ig.

Compositions:

The invention provides for a population of CTLA4-Ig molecules having an average molar ratio of sialic acid groups to CTLA4-Ig dimer or molecule of from about 6 to about 18. The invention provides for a population of CTLA4-Ig molecules having an average molar ratio of sialic acid groups to CTLA4-Ig dimer or molecule of from about 8 to about 18. The invention provides for a population of CTLA4-Ig molecules having an average molar ratio of sialic acid groups to CTLA4-Ig dimer or molecule of from about 11 to about 18. The invention provides for a population of CTLA4-Ig molecules having an average molar ratio of sialic acid groups to CTLA4-Ig dimer or molecule of from about 12 to about 18. The invention provides for a population of CTLA4-Ig molecules having an average molar ratio of sialic acid groups to CTLA4-Ig dimer or molecule of from about 13 to about 18. The invention provides for a population of CTLA4-Ig molecules having an average molar ratio of sialic acid groups to CTLA4-Ig dimer or molecule of from about 14 to about 18. The invention provides for a population of CTLA4-Ig molecules having an average molar ratio of sialic acid groups to CTLA4-Ig dimer or molecule of from about 15 to about 17. The invention provides for a population of CTLA4-Ig molecules having an average molar ratio of sialic acid groups to CTLA4-Ig dimer or molecule of about 16. The invention provides for a population of CTLA4-Ig molecules, wherein greater than 95% of the molecules are CTLA4-Ig dimers. In one embodiment, greater than 98% of the molecules are CTLA4-Ig dimers. In another embodiment, greater than 99% of the molecules are CTLA4-Ig dimers. In another embodiment, greater than 99.5% of the molecules are CTLA4-Ig dimers. In another embodiment, from about 95% to about 99.5% of the molecules are CTLA4-Ig dimers and about 0.5% to about 5% of the molecules are CTLA4-Ig tetramers or high molecular weight species. In another embodiment, about 98.6% of the molecules are CTLA4-Ig dimers and about 1.2% of the molecules are CTLA4-Ig tetramers or high molecular weight species and about less than 0.7% of the molecules are CTLA4-Ig monomers. The invention provides for a population consisting of CTLA4-Ig dimers. The invention provides for a population of CTLA4-Ig molecules, wherein the population is substantially free of CTLA4-Ig monomer. The invention provides for a population of CTLA4-Ig molecules, wherein the population is substantially free of CTLA4-Ig tetramer. The invention provides for a population of CTLA4-Ig monomer molecules substantially free of CTLA4-Ig dimer and tetramer. In one embodiment, each monomer of each CTLA4-Ig dimer has at least 3 sialic acid groups. In another embodiment, each monomer of each CTLA4-Ig dimer has from at least 3 sialic acid groups to at least 8 sialic acid groups. The invention provides for a purified population of CTLA4-Ig tetramer molecules, the population being substantially free of CTLA4-Ig dimer, and optionally wherein the population comprises an amount that is greater than about 100 grams. The invention provides for a purified population of CTLA4-Ig tetramer molecules, the population being substantially free of CTLA4-Ig monomer, and optionally wherein the population comprises an amount that is greater than about 100 grams. In one embodiment, each tetramer molecule comprises two pairs of CTLA4-Ig polypeptides, wherein each polypeptide has an amino acid sequence selected from the group consisting of SEQ ID NOS: 5-10, and wherein each member of the pair of polypeptides is covalently linked to the other member, and wherein the two pairs of polypeptides are non-covalently associated with one another. In another embodiment, each tetramer molecule is capable of binding to a CD80 or CD86. In a further embodiment, each tetramer molecule has at least a 2-fold greater avidity for CD80 or CD86 as compared to a CTLA4-Ig dimer molecule. In another embodiment, each tetramer molecule has at least a 2-fold greater inhibition of T cell proliferation or activation as compared to a CTLA4-Ig dimer molecule. The invention provides for a composition comprising CTLA4-Ig molecules, wherein the composition comprises dominant isoforms visualizable on an isoelectric focusing gel of CTLA4-Ig which have an isoelectric point, pI, less than or equal to 5.1 as determined by isoelectric focusing. In one embodiment, the invention provides for a composition comprising CTLA4-Ig molecules, wherein the composition comprises dominant isoforms visualizable on an isoelectric focusing gel of CTLA4-Ig which have an isoelectric point, pI, less than or equal to 5.8 as determined by isoelectric focusing. In one embodiment, the pI increases after neuraminidase treatment. In one embodiment, the composition comprises dominant isoforms visualizable on an isoelectric focusing gel of CTLA4-Ig which have an isoelectric point, pI, less than or equal to 5.7, 5.6, 5.5, 5.4, 5.3, 5.2, 5.1, 5.0, 4.9, 4.8, 4.7, 4.6, or 4.5 as determined by isoelectric focusing. In another embodiment, at least 40% of the CTLA4-Ig molecules exhibit an isoelectric point less than or equal to about 5.1 as determined by isoelectric focusing. In another embodiment, at least 70% of the CTLA4-Ig molecules exhibit an isoelectric point less than or equal to about 5.1 as determined by isoelectric focusing. In another embodiment, at least 90% of the CTLA4-Ig molecules exhibit an isoelectric point less than or equal to about 2.5 as determined by isoelectric focusing. The invention provides for a population of CTLA4-Ig molecules having a pI of from about 2.0±0.2 to about 5.0±0.2. The invention provides for a population of CTLA4-Ig molecules having a pI of from about 4.0±0.2 to about 5.0±0.2. The invention provides for a population of CTLA4-Ig molecules having a pI from about 4.3±0.2 to about 5.0±0.2. The invention provides for a population of CTLA4-Ig molecules having a pI of about 3.3±0.2 to about 4.7±0.2. The invention provides for a method for preparing a composition, the composition comprising a CTLA4-Ig molecule with a pI of from about 2.0±0.2 to about 5.0±0.2, the method comprising: (a) subjecting a mixture of CTLA4-Ig molecules to isoelectric focusing gel electrophoresis, wherein a single band on the gel represents a population of CTLA4-Ig molecules with a particular pI, and (b) isolating the population of CTLA4-Ig molecules having a pI of from about 2.0±0.2 to about 5.0±0.2 so as to prepare the composition.

The invention provides for a composition comprising CTLA4-Ig molecules, wherein the CTLA4-Ig molecules are characterized by an average molar ratio of GlcNAc per mole of CTLA4-Ig dimer or to CTLA4-Ig molecule of from about 15 to about 35. The invention provides for a composition comprising CTLA4-Ig molecules, wherein the CTLA4-Ig molecules are characterized by an average molar ratio of GalNAc per mole of CTLA4-Ig dimer or to CTLA4-Ig molecule of from about 1.7 to about 3.6. The invention provides for a composition comprising CTLA4-Ig molecules, wherein the CTLA4-Ig molecules are characterized by an average molar ratio of galcatose per mole of CTLA4-Ig dimer or to CTLA4-Ig molecule of from about 8 to about 17. The invention provides for a composition comprising CTLA4-Ig molecules, wherein the CTLA4-Ig molecules are characterized by an average molar ratio of fucose per mole of CTLA4-Ig dimer or to CTLA4-Ig molecule of from about 3.5 to about 8.3. The invention provides for a composition comprising CTLA4-Ig molecules, wherein the CTLA4-Ig molecules are characterized by an average molar ratio of mannose per mole of CTLA4-Ig dimer or to CTLA4-Ig molecule of from about 7.2 to about 22. The invention provides for a composition comprising CTLA4-Ig molecules, wherein the CTLA4-Ig molecules are characterized by an average molar ratio of sialic acid per mole of CTLA4-Ig dimer or to CTLA4-Ig molecule of from about 6 to about 12.

The invention provides for a composition comprising CTLA4-Ig molecules characterized by: (a) an average molar ratio of GlcNAc per mole of CTLA4-Ig dimer or CTLA4-Ig molecule from about 15 to about 35; and (b) an average molar ratio of sialic acid per mole of CTLA4-Ig dimer or CTLA4-Ig molecule from about 6 to about 12. The invention provides for a composition comprising CTLA4-Ig molecules characterized by: (a) an average molar ratio of GlcNAc per mole of CTLA4-Ig dimer or CTLA4-Ig molecule from about 15 to about 35; (b) an average molar ratio of GalNAc per mole CTLA4-Ig dimer or CTLA4-Ig molecule from about 1.7 to about 3.6; and (c) an average molar ratio of sialic acid per mole of CTLA4-Ig dimer or CTLA4-Ig molecule from about 6 to about 12. The invention provides for a composition comprising CTLA4-Ig molecules characterized by: (a) an average molar ratio of GlcNAc per mole of CTLA4-Ig dimer or CTLA4-Ig molecule from about 15 to about 35; (b) an average molar ratio of GalNAc per mole CTLA4-Ig dimer or CTLA4-Ig molecule from about 1.7 to about 3.6; (c) an average molar ratio of galcatose per mole CTLA4-Ig dimer or CTLA4-Ig molecule from about 8 to about 17; and (d) an average molar ratio of sialic acid per mole of CTLA4-Ig dimer or CTLA4-Ig molecule from about 6 to about 12. The invention provides for a composition comprising CTLA4-Ig molecules characterized by: (a) an average molar ratio of GlcNAc per mole of CTLA4-Ig dimer or CTLA4-Ig molecule from about 15 to about 35; (b) an average molar ratio of GalNAc per mole CTLA4-Ig dimer or CTLA4-Ig molecule from about 1.7 to about 3.6; (c) an average molar ratio of galcatose per mole CTLA4-Ig dimer or CTLA4-Ig molecule from about 8 to about 17; (d) an average molar ratio of fucose per mole CTLA4-Ig dimer or CTLA4-Ig molecule from about 3.5 to about 8.3; and (e) an average molar ratio of sialic acid per mole of CTLA4-Ig dimer or CTLA4-Ig molecule from about 6 to about 12. The invention provides for a composition comprising CTLA4-Ig molecules characterized by: (a) an average molar ratio of GlcNAc per mole of CTLA4-Ig dimer or CTLA4-Ig molecule from about 15 to about 35; (b) an average molar ratio of GalNAc per mole CTLA4-Ig dimer or molecule from about 1.7 to about 3.6; (c) an average molar ratio of galcatose per mole CTLA4-Ig dimer or molecule from about 8 to about 17; (d) an average molar ratio of fucose per mole CTLA4-Ig dimer or molecule from about 3.5 to about 8.3; (e) an average molar ratio of mannose per mole CTLA4-Ig dimer or molecule from about 7.2 to about 22; and (f) an average molar ratio of sialic acid per mole of CTLA4-Ig dimer or CTLA4-Ig molecule from about 6 to about 12. The invention provides for a composition comprising CTLA4-Ig molecules, wherein composition exhibits an NGNA chromatogram peak of about 9.589+/−0.3 and an NANA chromatogram peak of about 10.543+/−0.3. The invention provides for a composition comprising CTLA4-Ig molecules, wherein the CTLA-Ig molecules exhibit a carbohydrate profile as shown in FIG. 67. The invention provides for a composition comprising CTLA4-Ig molecules, wherein the CTLA4-Ig molecules exhibit a carbohydrate profile of Domains I-V (e.g., I-IV), wherein Domain I comprises peaks which represent a-sialylated oligosaccharides, Domain II comprises peaks which represent mono-sialylated oligosaccharides, Domain III comprises peaks which represent di-sialylated oligosaccharides, and Domain IV comprises peaks which represent tri-sialylated oligosaccharides. Domain V comprises peaks that represent tetra-sialyated oligosaccharides. In one embodiment, the difference in retention times of N-linked oligosaccharides between a first peak in Domain I and a main peak in Domain II is from about 22 to about 28 minutes. The invention provides for a composition comprising CTLA4-Ig dimer molecules, wherein at least 0.5% of the CTLA4-Ig dimer molecules are cysteinylated. In one embodiment, at least 1.0% of the CTLA4-Ig dimer molecules are cysteinylated. The invention provides for a population of CTLA4-Ig molecules, wherein the population exhibits a mass spectrometry profile as shown in FIGS. 8A and 8B. The invention provides for a population of CTLA4-Ig molecules, wherein the population exhibits a capillary electrophoresis profile as shown in FIGS. 19 and 20. The invention provides for a composition of CTLA4-Ig molecules having an average molar ratio of sialic acid groups to CTLA4-Ig dimer of from about 6 to about 18. The invention provides for a CTLA4-Ig composition obtained by any of the methods described herein. The invention provides for a population of CTLA4-Ig molecules, wherein the molecules are glycosylated at an aparagine amino acid residue at position 102 of SEQ ID NO:2, an aparagine amino acid residue at position 134 of SEQ ID NO:2, an aparagine amino acid residue at position 233 of SEQ ID NO:2, a serine amino acid residue at position 155 of SEQ ID NO:2, or a serine amino acid residue at position 165 of SEQ ID NO:2.

The invention provides for a population of CTLA4-Ig molecules, wherein the population of molecules is characterized by: (a) an average molar ratio of GlcNAc per mole of CTLA4-Ig dimer or CTLA4-Ig molecule from about 15 to about 35; (b) an average molar ratio of GalNAc per mole CTLA4-Ig dimer or molecule from about 1.7 to about 3.6; (c) an average molar ratio of galcatose per mole CTLA4-Ig dimer or molecule from about 8 to about 17; (d) an average molar ratio of fucose per mole CTLA4-Ig dimer or molecule from about 3.5 to about 8.3; (e) an average molar ratio of mannose per mole CTLA4-Ig dimer or molecule from about 7.2 to about 22; (f) an average molar ratio of sialic acid per mole of CTLA4-Ig dimer or molecule from about 6 to about 12; (g) a pI as determined from visualization on an isoelectric focusing gel in a range from about 2.4±0.2 to about 5.0±0.2; (h) MCP-1 of less than or equal to 5 ppm; (i) less than 3.0% tetramer (e.g., 2.5% high molecular weight species or tetramer, 2.0% high molecular weigh species or tetramer; (j) less than 0.5% monomer; (k) CTLA4-Ig polypeptides of the population having an amino acid at least 95% identical to any of SEQ ID NOS: 2-8; (l) wherein CTLA4-Ig molecules within the population is capable of binding to CD80 and CD86.

Compositions:

The invention provides for a composition comprising an effective amount of the CTLA4-Ig molecules of the invention and a pharmaceutically acceptable carrier. The invention provides for a composition comprising excipients as described in U.S. Application No. 60/752,150, filed Dec. 20, 2005. In one embodiment, the composition includes CTLA4-Ig. In one embodiment, the composition further comprises a pharmaceutically acceptable diluent, adjuvant or carrier. In another embodiment, the composition further comprises maltose, sodium phosphate monobasic monohydrate, sodium chloride, sodium hydroxide, and sterile water. In another embodiment, the composition comprises sucrose, poloxamer, sodium phosphate monobasic monohydrate, sodium phosphate dibasic anhydrous, sodium chloride, sodium hydroxide, and sterile water.

Formulations and Kits:

The invention provides for a lyophilized CTLA4-Ig mixture comprising at least 95% CTLA4-Ig dimer, and not more than 5% CTLA4-Ig tetramer. In one embodiment, the mixture comprises at least 98% CTLA4-Ig dimer and no more than 2% CTLA4-Ig high molecular weight species or tetramer. In another embodiment, the mixture comprises at least 99% CTLA4-Ig dimer and no more than 1% CTLA4-Ig high molecular weight species or tetramer. In another embodiment, the mixture comprises at least 8.0 moles of sialic acid per mole of CTLA4-Ig dimer or molecule. In another embodiment, the mixture comprises from about 15.7 to about 31 moles of GlcNAc per mole of CTLA4-Ig dimer or molecule. In another embodiment, the mixture comprises from about 1.6 to about 3.2 moles of GalNAc per mole of CTLA4-Ig dimer or molecule. In another embodiment, the mixture comprises from about 9.3 to about 15.5 moles of galactose per mole of CTLA4-Ig dimer or molecule. In one embodiment, the mixture comprises from about 3.6 to about 7.9 moles of fucose per mole of CTLA4-Ig dimer or molecule. In one embodiment, the mixture comprises from about 9.7 moles of mannose per mole of CTLA4-Ig dimer or molecule. The invention also provides for a pharmaceutical kit comprising: (a) a container containing a lyophilized CTLA4-Ig mixture of the invention; and (b) instructions for reconstituting the lyophilized CTLA4-Ig mixture into solution for injection.

Illustrative Methods of Treatment:

The invention provides for a method for inhibiting T cell proliferation (or activation), the method comprising contacting a T cell with an effective amount of a CTLA4-Ig composition of the invention. The invention provides for a method for inhibiting an immune response in a subject, the method comprising administering to a subject in need thereof an effective amount of a CTLA4-Ig composition of the invention. The invention provides for a method for inducing immune tolerance to an antigen in a subject, the method comprising administering to a subject in need thereof an effective amount of a CTLA4-Ig composition of the invention. The invention provides for a method for treating inflammation in a subject, the method comprising administering to a subject in need thereof an effective amount of a CTLA4-Ig composition of the invention. The invention provides for a method for treating rheumatoid arthritis comprising administering to a subject in need thereof an effective amount of a CTLA4-Ig composition of the invention. The invention provides for a method for treating psoriasis in a subject, the method comprising administering to a subject in need thereof an effective amount of a CTLA4-Ig composition of the invention. The invention provides for a method for treating lupus in a subject, the method comprising administering to a subject in need thereof an effective amount of a CTLA4-Ig composition of the invention. The invention provides for a method for treating or preventing an allergy in a subject, the method comprising administering to a subject in need thereof an effective amount of a CTLA4-Ig composition of the invention. The invention provides for a method for treating or preventing graft vs host disease in a subject, the method comprising administering to a subject in need thereof an effective amount of a CTLA4-Ig composition of the invention. The invention provides for a method for treating or preventing rejection of a transplanted organ in a subject, the method comprising administering to a subject in need thereof an effective amount of a CTLA4-Ig composition of the invention. The invention provides for a method for treating multiple sclerosis in a subject, the method comprising administering to a subject in need thereof an effective amount of a CTLA4-Ig composition of the invention. The invention provides for a method for treating Crohn's Disease in a subject, the method comprising administering to a subject in need thereof an effective amount of a CTLA4-Ig composition of the invention. The invention provides a method for treating type I diabetes in a subject, the method comprising administering to a subject in need thereof an effective amount of a CTLA4-Ig composition of the invention. The invention provides a method for treating inflammatory bowel disease in a subject, the method comprising administering to a subject in need thereof an effective amount of a CTLA4-Ig composition of the invention. The invention provides a method for treating oophoritis in a subject, the method comprising administering to a subject in need thereof an effective amount of a CTLA4-Ig composition of the invention. The invention provides a method for treating glomerulonephritis in a subject, the method comprising administering to a subject in need thereof an effective amount of a CTLA4-Ig composition of the invention. The invention provides a method for treating allergic encephalomyelitis in a subject, the method comprising administering to a subject in need thereof an effective amount of a CTLA4-Ig composition of the invention. The invention provides a method for treating myasthenia gravis in a subject, the method comprising administering to a subject in need thereof an effective amount of a CTLA4-Ig composition of the invention.

The invention provides for the use of a population of CTLA4-Ig molecules having an average molar ratio of sialic acid groups to CTLA4-Ig dimer or molecule of from about 6 to about 18 in the manufacture of a medicament for the therapeutic and/or prophylactic treatment of an immune disorder. The invention provides for the use of a population of CTLA4-Ig molecules having an average molar ratio of sialic acid groups to CTLA4-Ig dimer or molecule of from about 6 to about 18 in the manufacture of an anti-rheumatoid arthritis agent in a package together with instructions for its use in the treatment of rheumatoid arthritis.

Illustrative Combination Therapies:

The invention provides for a method for inhibiting T cell proliferation (or activation), the method comprising contacting a T cell with an effective amount of a CTLA4-Ig composition of the invention in combination with methotrexate. The invention provides a method for inhibiting an immune response in a subject, the method comprising administering to a subject in need thereof an effective amount of a CTLA4-Ig composition of the invention in combination with methotrexate. The invention provides a method for inducing immune tolerance to an antigen in a subject, the method comprising administering to a subject in need thereof an effective amount of a CTLA4-Ig composition of the invention in combination with methotrexate.

Methods for Producing CTLA4-Ig:

The invention provides a method for producing a recombinant protein, the method comprising: (a) expanding mammalian cells that secrete a recombinant protein, wherein the expanding is from a seed culture to a liquid culture, wherein the recombinant protein concentration is at least 0.5 grams/L of liquid culture; and (b) isolating the recombinant protein from the liquid culture. The liquid culture can be at least 1,000 L, at least 5,000 L, at least 10,000 L, at least 15,000 L, at least 20,000 L, at least 25,000 L, at least 30,000 L, at least 40,000 L. In one embodiment, the expanding of step (a) comprises: (i) culturing the cells in a serum-free, chemically defined medium with at least four passages so as to obtain a cell density of at least about $1.0 \times 10^5$ viable cells per mL, wherein each seed stage starts at about $2 \times 10^5$ per ml and goes to 1-2 mil cells per ml; (ii) maintaining the cells in culture for a time sufficient to produce from the culture at least about 0.5 g/L. In one embodiment, the protein is a glycoprotein. In one embodiment, the protein is a CTLA4-Ig protein. In one embodiment, the mammalian cells are progeny of a CHO clonal cell line capable of producing CTLA4-Ig fusion protein, wherein the CHO cells have stably integrated in their genome at least 30 copies of a CTLA4-Ig expression cassette. In one embodiment, the time sufficient is a time by which the cells' viability does not fall below 30%. In another embodiment, the time sufficient is a time by which the cells' viability does not fall below 40%. In another embodiment, the time sufficient is a time by which the cells' viability does not fall below 50%. In another embodiment, the time sufficient is a time by which the cells' viability does not fall below 60%. In another embodiment, the time sufficient is a time by which the cells' viability does not fall below 70%, or 80% or 90% or 95%.

In a further embodiment, the at least four passages comprises: (i) growing the cells in a culture volume of at least 50 mL until a cell density of from about 1 million to about 2.5 mill cels per ml is reached, (ii) growing the cells in a culture volume of at least 10 L until a cell density of about 1 million to about 2.5 million cels per ml is reached; (iii) growing the cells in a culture volume of at least 100 L until a cell density of about 1 million to about 2.5 million cels per ml is reached; and (iv) growing the cells in a culture volume of 200 L until a cell density of about 1 million to about 2.5 million cels per ml is reached. In one embodiment, galactose is added to the serum-free, chemically defined medium. In one embodiment, the maintaining comprises (i) lowering the temperature of the culture from 37±2° C. to 34±2° C.; and (ii) lowering the temperature of the culture from 34±2° C. to 32±2° C. In another embodiment, the temperature is kept within the range of 32±2° C. for at least 5 days. In another embodiment, the temperature is kept within the range of 32±2° C. for at least 6 days. In another embodiment, the temperature is kept within the range of 32±2° C. for at least 7 days. In another embodiment, the temperature is kept within the range of 32±2° C. for at least 8 days. In another embodiment, the temperature is kept within the range of 32±2° C. for at least 9 days. In another embodiment, the temperature is kept within the range of 32±2° C. for at least 10 days. In another embodiment, the temperature is kept within the range of 32±2° C. for at least 11 days. In another embodiment, the temperature is kept within the range of 32±2° C. for at least 12 days. In another embodiment, the temperature is kept within the range of 32±2° C. for at least 13 days. In another embodiment, the temperature is kept within the range of 32±2° C. for at least 14 days. In another embodiment, the temperature is kept within the range of 32±2° C. for at least 15 days. In another embodiment, the temperature is kept within the range of 32±2° C. for at least 16 days. In another embodiment, the temperature is kept within the range of 32±2° C. for at least 17 days. In another embodiment, the temperature is kept within the range of 32±2° C. for at least 18 days. In another embodiment, the temperature is kept within the range of 32±2° C. for up to 18 days. In another embodiment, the temperature is kept within the range of 32±2° C. until the cell density of the culture is from about $30 \times 10^5$ to about $79 \times 10^5$ cells per mL of liquid culture.

The invention provides for a method for producing a recombinant protein, the method comprising: (a) expanding mammalian cells that secrete a recombinant protein from a seed culture to a liquid culture so that the recombinant protein concentration is at least 0.5 grams/L of liquid culture; and (b) isolating the recombinant protein from the liquid culture, wherein the isolating occurs only when the liquid culture contains greater than or equal to about 6.0 moles of NANA per mole of CTLA4-Ig protein or dimer. The invention provides for a method for producing a recombinant protein, the method comprising: (a) expanding mammalian cells that secrete a recombinant protein from a seed culture to a liquid culture of so that the recombinant protein concentration is at least 0.5 grams/L of liquid culture; and (b) isolating the recombinant protein from the liquid culture, wherein the isolating occurs only when the liquid culture has a cell density of from about $33 \times 10^5$ to about $79 \times 10^5$ cells per mL. The invention provides for a method for producing a recombinant protein, the method comprising: (a) expanding mammalian cells that secrete a recombinant protein from a seed culture to a liquid culture so that the recombinant protein concentration is at least 0.5 grams/L of liquid culture; and (b) isolating the recombinant protein from the liquid culture, wherein the isolating occurs when cell viability in the liquid culture has not fallen below about 20%, or about 30%, or about 38%. The invention provides for a method for producing a recombinant protein, the method comprising: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the liquid culture, wherein the isolating occurs only when endotoxin is less than or equal to about 76.8 EU per mL of liquid culture. The invention provides for a method for producing a recombinant protein, the method comprising: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the at least 10,000 L liquid culture, wherein the isolating occurs only when bioburden is less than 1 colony forming unit per mL of liquid culture. The liquid culture of the invention can be of a volume of at least 5,000 L, at least 10,000 L, at least 15,000 L, at least 20,000 L, at least 25,000 L, at least 30,000 L, at least 40,000 L, at least 50,000 L, at least 60,000 L.

The invention provides a method for producing a recombinant protein, the method comprising: (a) expanding mammalian cells that secrete a recombinant protein from a seed culture to a liquid culture so that the recombinant protein concentration is at least 0.5 grams/L of liquid culture; and (b) isolating the recombinant protein from the liquid culture, wherein the isolating occurs only if at least two of the following conditions are met: (i) the liquid culture contains greater than or equal to about 6.0 moles of NANA per mole of protein, (ii) the liquid culture has a cell density of from about $33 \times 10^5$ to about $79 \times 10^5$ cells per mL, (iii) cell viability in the liquid culture has not fallen below about 20%, or about 38%, or (iv) amount of CTLA4-Ig in the culture is greater than 0.5 g/L. In one embodiment, the isolating comprises: (i) obtaining a cell culture supernatent; (ii) subjecting the supernatant to anion exchange chromatography to obtain an eluted protein product; (iii) subjecting the eluted protein product of step (ii) to hydrophobic interaction chromatography so as to obtain an enriched protein product; (iv) subjecting the enriched protein product to affinity chromatography to obtain an eluted and enriched protein product; and (v) subjecting the eluted and enriched protein product of (iv) to anion exchange chromatography. In another embodiment, the enriched protein product obtained in step (iii) is characterized in that a percentage of any high molecular weight contaminant is less than 25% by weight. In another embodiment, the anion exchange chromatography of step (ii) is carried out using a wash buffer comprising about 75 mM HEPES, and about 360 mM NaCl, and having a pH of about 8.0. In another embodiment, the anion exchange chromatography of step (ii) is carried out using an elution buffer comprising about 25 mM HEPES, and about 325 mM NaCl, and having a pH of about 7.0. In another embodiment, the hydrophobic interaction chromatography of step (iii) is carried out using a single wash buffer comprising about 25 mM HEPES, and about 850 mM NaCl, and having a pH of about 7.0. In another embodiment, the affinity chromatography of step (iv) is carried out using a wash buffer comprising about 25 mM Tris, and about 250 mM NaCl, and having a pH of about 8.0. In another embodiment, the affinity chromatography of step (iv) is carried out using an elution buffer comprising about 100 mM Glycine and having a pH of about 3.5. In another embodiment, the anion exchange chromatography of step (v) is carried out using a wash buffer comprising about 25 mM HEPES, and from about 120 mM NaCl to about 130 mM NaCl, and having a pH of about 8.0. In another embodiment, the anion exchange chromatography of step (v) is carried out using an elution buffer comprising about 25 mM HEPES, and about 200 mM NaCl, and having a pH of about 8.0. In another embodiment, the anion exchange chromatography of step (ii) is carried out using a column having an anion exchange resin having a primary, secondary, tertiary, or quartenary amine functional group. In another embodiment, the resin has a quartenary amine functional group. In another embodiment, the hydrophobic interaction chromatography of step (iii) is carried out using a hydrophobic interaction resin having a phenyl, an octyl, a propyl, an alkoxy, a butyl, or an isoamyl functional group. In another embodiment, the functional group is a phenyl functional group. In another embodiment, the affinity chromatography of step (iv) is carried out using a column containing Protein A.

The invention provides for a method for preparing CTLA4-Ig, the method comprising purifying CTLA4-Ig from a liquid cell culture so that the purified CTLA4-Ig (a) has about 38 ng of MCP-1 per mg of CTLA4-Ig dimer, and (b) comprises less than 2.5% of CTLA4-Ig high molecular weight species (e.g., tetramer) by weight. The invention provides for a method for producing CTLA4-Ig, the method comprising: (a) expanding progeny cells or CHO cells that are capable of producing CTLA4-Ig, wherein the expanding is from a seed culture to a liquid culture of at least 10,000 L, wherein the CTLA4-Ig concentration is at least 0.5 grams/L of liquid culture; and (b) isolating CTLA4-Ig from the at least 10,000 L liquid culture, wherein the chromotagraphy is on a column with hydrophobic interaction resin with at least a phenyl functional group, wherein the isolating comprises a step of hydrophobic interaction chromatography carried out using a single wash buffer comprising about 25 mM HEPES, and about 850 mM NaCl, and having a pH of about 7.0.

CTLA4-Ig molecules include beta polypeptide molecules. CTLA4$^{A29YL104E}$-Ig is a beta polypeptide molecule. The present invention relates to methods for producing (including mass-producing) beta polypeptide compositions or beta polypeptide molecule compositions, and improved compositions. The invention is directed to beta polypeptide molecules, improved compositions comprising beta polypeptide molecules, and improved methods for producing (including mass-producing) beta polypeptide molecules and other recombinant glycoproteins.

Methods for Producing Beta Polypeptides and Other Glycoproteins:

The invention provides for a method for producing a recombinant glycoprotein, the method comprising: (a) expanding mammalian cells that secrete a recombinant glycoprotein, wherein the expanding is from a seed culture to a liquid culture of at least about 10,000 L, wherein the recombinant protein concentration is at least about 0.5 g/L of liquid culture, wherein the expanding comprises: (i) culturing the cells in a serum-free, chemically defined medium with at least four passages so as to obtain a cell density of at least about $1.0 \times 10^5$ viable cells per mL, wherein each seed stage starts at about $2 \times 10^5$ per ml and goes to about 1-2 million cells per ml, wherein the culturing comprises: (1) culturing the cells in a serum-free, chemically-defined inoculum medium for from about 15 days to about 25 days; then (2) culturing the cells in a serum-free, chemically-defined basal medium until a cell density of about at least 4 million cells per mL is reached; and (ii) maintaining the cells in culture for a time sufficient to produce the recombinant protein from the culture at least about 0.5 g/L; and (b) isolating the recombinant protein from the at least about 10,000 L liquid culture.

The invention provides for a method for producing a recombinant glycoprotein, the method comprising: (a) expanding mammalian cells that secrete a recombinant glycoprotein, wherein the expanding is from a seed culture to a liquid culture of at least about 10,000 L, wherein the recombinant protein concentration is at least about 0.5 g/L of liquid culture, wherein the expanding comprises: (i) culturing the cells in a serum-free, chemically defined medium with at least four passages so as to obtain a cell density of at least about $1.0 \times 10^5$ viable cells per mL, wherein each seed stage starts at about $2 \times 10^5$ per ml and goes to about 1-2 million cells per ml; and (ii) maintaining the cells in culture for a time sufficient to produce the recombinant protein from the culture at least about 0.5 g/L, wherein the maintaining comprises: (1) lowering the temperature of the culture from $37 \pm 2°$ C. to $34 \pm 2°$ C.; and (2) adding a polyanionic compound to the culture; and (b) isolating the recombinant protein from the at least about 10,000 L liquid culture.

The invention provides for a method for producing a recombinant glycoprotein, the method comprising: (a) expanding mammalian cells that secrete a recombinant glycoprotein, wherein the expanding is from a seed culture to a liquid culture of at least about 10,000 L, wherein the recombinant protein concentration is at least about 0.5 g/L of liquid culture; and (b) isolating the recombinant protein from the at least about 10,000 L liquid culture, wherein the isolating comprises: (i) obtaining a soluble fraction of the culture of step (a); (ii) subjecting the soluble fraction to affinity chromatagraphy to obtain an eluted protein product; (iii) subjecting the eluted protein product of step (ii) to anion exchange chromatography so as to obtain an eluted and enriched protein product; and (iv) subjecting the enriched protein product to hydrophobic interaction chromatography to obtain an enriched protein product.

In one embodiment of the invention, the protein comprises a CTLA4-Ig. In another embodiment, the protein comprises a beta polypeptide or beta polypeptide molecules. In another embodiment, the protein comprises beta polypeptides having SEQ ID NO: 11, 12, 13, 14, 15, or 16.

In one embodiment of the invention, the at least four passages comprises: (i) growing the cells in a culture volume of at least 50 mL until a cell density of from about 1 million to about 2.5 million cells per ml is reached; (ii) growing the cells in a culture volume of at least 10 L until a cell density of about 1 million to about 2.5 million cells per ml is reached; (iii) growing the cells in a culture volume of at least 100 L until a cell density of about 1 million to about 2.5 million cells per ml is reached; and (iv) growing the cells in a culture volume of 200 L until a cell density of about 1 million to about 2.5 million cells per ml is reached.

In one embodiment of the invention, the isolating comprises: (i) obtaining a soluble fraction of the culture of step (a); (ii) subjecting the soluble fraction to affinity chromotagraphy to obtain an eluted protein product; (iii) subjecting the eluted protein product of step (ii) to anion exchange chromatography so as to obtain an eluted and enriched protein product; and (iv) subjecting the enriched protein product to hydrophobic interaction chromatography to obtain an enriched protein product.

In one embodiment, the enriched protein product obtained in step (iv) is characterized in that a percentage of any high molecular weight multimer is less than 25% by weight. In another embodiment, the anion exchange chromatography of step (iii) is carried out using a wash buffer comprising about 50 mM HEPES, and about 135 mM NaCl, and having a pH of about 7. In another embodiment, the anion exchange chromatography of step (iii) is carried out using an elution buffer comprising about 50 mM HEPES, and about 200 mM NaCl, and having a pH of about 7. In another embodiment, the hydrophobic interaction chromatography of step (iv) is carried out using a wash buffer comprising about 50 mM HEPES, and about 1.2 M $(NH_4)_2SO_4$, and having a pH of about 7. In another embodiment, the affinity chromatography of step (ii) is carried out using a wash buffer comprising about 25 mM $NaH_2PO_4$, and about 150 mM NaCl, and having a pH of about 7.5. In another embodiment, the affinity chromatography of step (ii) is carried out using an elution buffer comprising about 250 mM Glycine and having a pH of about 3. In another embodiment, the anion exchange chromatography of step (iii) is carried out using a column having an anion exchange resin having a primary, secondary, tertiary, or quarternary amine functional group. In another embodiment, the resin has a quarternary amine functional group. In another embodiment, the hydrophobic interaction chromatography of step (iii) is carried out using a hydrophobic interaction resin having a phenyl, an octyl, a propyl, an alkoxy, a butyl, or an isoamyl functional group. In another embodiment, the functional group is a phenyl functional group. In another embodiment, the affinity chromatography of step (ii) is carried out using a column containing Protein A.

In another embodiment, the expanding comprises: (i) culturing the cells in a serum-free, chemically defined medium with at least four passages so as to obtain a cell density of at least about $1.0 \times 10^5$ viable cells per mL, wherein each seed stage starts at about $2 \times 10^5$ per ml and goes to about 1-2 million cells per ml; and (ii) maintaining the cells in culture for a time sufficient to produce the recombinant protein from the culture at least about 0.5 g/L. In another embodiment, the culturing comprises: (i) culturing the cells in a serum-free, chemically-defined inoculum medium for from about 15 days to about 25 days; then (ii) culturing the cells in a serum-free, chemically-defined basal medium until a cell density of about at least 4 million cells per mL is reached.

In another embodiment, the maintaining comprises (i) lowering the temperature of the culture from $37 \pm 2°$ C. to $34 \pm 2°$ C.; and (ii) adding a polyanionic compound to the culture. In one embodiment, the polyanionic compound is dextran sulfate and wherein the dextran sulfate is added to the culture at a final concentration of about 50 mg/ml. In another embodiment, the temperature is kept within the range of $34 \pm 2°$ C. for at least 5 days. In another embodiment, the temperature is kept within the range of $34 \pm 2°$ C. for at least 6 days. In another embodiment, the temperature is kept within the range of $34 \pm 2°$ C. for at least 7 days. In another embodiment, the temperature is kept within the range of $34 \pm 2°$ C. for at least 8 days. In another embodiment, the temperature is kept within the range of $34 \pm 2°$ C. for at least 9 days. In another embodiment, the temperature is kept within the range of $34 \pm 2°$ C. for at least 10 days. In another embodiment, the temperature is kept within the range of $34 \pm 2°$ C. for at least 11 days. In another embodiment, the temperature is kept within the range of $34 \pm 2°$ C. for at least 12 days. In another embodiment, the temperature is kept within the range of $34 \pm 2°$ C. for at least 13 days. In another embodiment, the temperature is kept within the range of $34 \pm 2°$ C. for at least 14 days. In another embodiment, the temperature is kept within the range of $34 \pm 2°$ C. for at least 15 days. In another embodiment, the temperature is kept within the range of $34 \pm 2°$ C. for at least 16 days. In another embodiment, the temperature is kept within the range of $34 \pm 2°$ C. for at least 17 days. In another embodiment, the temperature is kept within the range of $34 \pm 2°$ C. for at least 18 days. In another embodiment, the temperature is kept within the range of $34 \pm 2°$ C. for at least 19 days. In another embodiment, the temperature is kept within the range of $34 \pm 2°$ C. for at least 20 days. In another embodiment, the temperature is kept within the range of $34 \pm 2°$ C. for at least 21 days. In another embodiment, the temperature is kept within the range of $34 \pm 2°$ C. for at least 22 days. In another embodiment, the temperature is kept within the range of $34 \pm 2°$ C. for at least 23 days. In another embodiment, the temperature is kept within the range of $34 \pm 2°$ C. for at least 24 days. In another embodiment, the temperature is kept within the range of $34 \pm 2°$ C. for at least 25 days. In another embodiment, the temperature is kept within the range of $34 \pm 2°$ C. for at least 26 days. In another embodiment, the temperature is kept within the range of $34 \pm 2°$ C. for at least 27 days. In another embodiment, the temperature is kept within the range of $34 \pm 2°$ C. for at least 28 days. In another embodiment, the temperature is kept within the range of $34 \pm 2°$ C. for up to 28 days. In another embodiment, the temperature is kept within the range of $34 \pm 2°$ C. until the cell density of the culture is from about $30 \times 10^5$ to about $79 \times 10^5$ cells per mL of liquid culture.

In one embodiment, the time sufficient is a time by which the cells' viability does not fall below 30%. In another embodiment, the time sufficient is a time by which the cells' viability does not fall below 40%. In another embodiment, the time sufficient is a time by which the cells' viability does not fall below 50%. In another embodiment, the time sufficient is a time by which the cells' viability does not fall below 60%. In another embodiment, the time sufficient is a time by which the cells' viability does not fall below 70%, or 80% or 90% or 95%.

In one embodiment, galactose is added to the serum-free, chemically defined medium. In another embodiment, isolating occurs when the liquid culture contains greater than or equal to about 6 moles of sialic acid per mole of protein. In another embodiment, isolating occurs when the liquid culture contains from about 5.2 to about 7.6 moles of sialic acid per mole of protein. In another embodiment, the isolating occurs when the liquid culture has a cell density of from about $33 \times 10^5$ to about $79 \times 10^5$ cells per mL. In another embodiment, the isolating occurs when cell viability in the liquid culture has not fallen below about 37%. In another embodiment, the isolating occurs when endotoxin is less than or equal to about 4.8 EU per mL of liquid culture. In another embodiment, the isolating occurs when bioburden is less than about 1 colony forming unit per mL (cfu/ml) of liquid culture. In another embodiment, the isolating occurs if at least two of the following conditions are met: (i) the liquid culture contains greater than or equal to about 6 moles of sialic acid per mole of protein, (ii) the liquid culture has a cell density of from about $33 \times 10^5$ to about $79 \times 10^5$ cells per mL, (iii) cell viability in the liquid culture has not fallen below about 37%, or (iv) the amount of glycoprotein in the culture is from about 0.46 g/L to about 0.71 g/L.

In one embodiment, the mammalian cells are progeny of a Chinese Hamster Ovary clonal cell line that produces any combination of beta polypeptides or beta polypeptide molecules, wherein each polypeptide comprises SEQ ID NO: 11, 12, 13, 14, 15, or 16, wherein the Chinese Hamster Ovary cells each have stably integrated in their genome at least 30 copies of an expression cassette comprising SEQ ID NO:3. In one embodiment, the liquid culture comprises a cell of or a progeny cell of a cell a production cell line of the invention.

The invention provides for a beta polypeptide comprising SEQ ID NO: 11, 12, 13, 14, 15, or 16 obtained by a method provided by the invention. The invention provides for a composition comprising beta polypeptides or beta polypeptide molecules, wherein each polypeptide comprises SEQ ID NO: 11, 12, 13, 14, 15, or 16 obtained by a method provided by the invention. The invention provides for a beta polypeptide obtained by a method provided by the invention.

Cells:

The invention provides for a clonal Chinese Hamster Ovary cell comprising a nucleic acid encoding a beta polypeptide or a beta polypeptide molecule. The invention provides for a clonal Chinese Hamster Ovary cell population that produces beta polypeptides or beta polypeptide molecules. In one embodiment, the beta polypeptide comprises SEQ ID NO: 11, 12, 13, 14, 15, or 16. The invention provides for a clonal Chinese Hamster Ovary cell comprising a nucleic acid comprising an expression cassette encoding the amino acid sequence of SEQ ID NO: 11, 12, 13, 14, 15, or 16. In one embodiment, the expression cassette comprises SEQ ID NO:3. The invention provides for a clonal Chinese Hamster Ovary cell population that produces a beta polypeptide or beta polypeptide molecule, wherein the beta polypeptide is expressed from a nucleotide sequence derived from a plasmid having ATCC Accession No. PTA-2104 deposited under the provisions of the Budapest Treaty on Jun. 19, 2000 with the American Type Culture Collection (ATCC), 10801 University Blvd., Manassas, Va., 20110.

The invention provides for a clonal Chinese Hamster Ovary cell population that produces a beta polypeptide or beta polypeptide molecules, each cell comprising 30 or more copies of a beta polypeptide expression cassette. The invention provides for a clonal Chinese Hamster Ovary cell population that produces a beta polypeptide or beta polypeptide molecules, each cell comprising 30 or more copies of a beta polypeptide expression cassette, wherein the 30 or more copies are integrated at a single site in the genome of each cell. The invention provides for a clonal Chinese Hamster Ovary cell population that produces a beta polypeptide or beta polypeptide molecules, wherein a beta polypeptide expression cassette is stable over about 105 passages. In one embodiment, the beta polypeptide is encoded by an expression cassette integrated into a cell genome.

The invention provides for a clonal Chinese Hamster Ovary cell population that produces a beta polypeptide, wherein at least 75% of the population of cells has 30 or more copies of a beta polypeptide expression cassette per cell, wherein the 30 or more copies are integrated at a single site in the genome of each cell of the 75% of the population. The invention provides for a clonal Chinese Hamster Ovary cell population that produces a beta polypeptide, wherein at least 85% of the population of cells has 30 or more copies of a beta polypeptide expression cassette per cell, wherein the 30 or more copies are integrated at a single site in the genome of each cell of the 85% of the population. The invention provides for a clonal Chinese Hamster Ovary cell population that produces a beta polypeptide, wherein at least 95% of the population of cells has 30 or more copies of a beta polypeptide expression cassette per cell, wherein the 30 or more copies are integrated at a single site in the genome of each cell of the 95% of the population. In one embodiment, the expression cassette is derived from a plasmid deposited as ATCC Accession No. PTA-2104. In another embodiment, the expression cassette comprises a nucleic acid having the sequence of SEQ ID NO:3. In one embodiment, the cell population produces at least about 0.5 grams of the beta polypeptide per liter of liquid culture, and wherein the beta polypeptide has a molar ratio of sialic acid to beta polypeptide dimer or beta polypeptide molecule of from about 5.5 to about 8.5 at a culture scale of 1,000 L or more. In another embodiment, the cell population produces at least 5, at least 10 or at least 20 grams of the beta polypeptide per liter of liquid culture. In another embodiment, the beta polypeptide has a molar ratio of sialic acid to beta polypeptide dimer or beta polypeptide molecule of from about 5 to about 10 at a culture scale of 1,000 L or more. In another embodiment, the cell population has been adapted to a serum-free, chemically defined medium. In another embodiment, a beta polypeptide produced from culture of the cell population has an extinction coefficient of 1.0±0.05 AU mL cm$^{-1}$ mg$^{-1}$. In another embodiment, the cell population, when grown in culture, produces beta polypeptides, wherein: (a) about 90% or about 80% of the beta polypeptides comprise an amino acid sequence of SEQ ID NO:4 beginning with the methionine at residue 27; (b) about 10% or about 20% of the beta polypeptides comprise the amino acid sequence of SEQ ID NO:4 beginning with the alanine at residue number 26; (c) from about 4% to about 8% of the beta polypeptides comprise the amino acid sequence of SEQ ID NO:4 ending with the lysine at residue number 383; (d) from about 92% to about 96% of the beta polypeptides comprise the amino acid sequence of SEQ ID NO:4 ending with the glycine at residue number 382; and optionally, (e) about less than 1% of the beta polypeptides comprise the amino acid sequence of SEQ ID NO:4 beginning with the methionine at residue number 25.

The invention provides for a progeny cell of a cell population of the invention, wherein the progeny cell produces a beta polypeptide. In one embodiment, the progeny cell is obtained from culturing a cell over at least 5, at least 10, at least 20, at least 40, at least 50, at least 75 generations. In another embodiment, the progeny cell is obtained from culturing a cell for 27 generations.

The invention provides for a cell line produced from any cell provided by the invention. In one embodiment, the cell line is clonal. In one embodiment, the cell line produces: (a) a beta polypeptide having an amino acid sequence of SEQ ID NO:16 (methionine at amino acid position 27 and glycine at amino acid position 382 of SEQ ID NO:4); (b) a beta polypeptide having an amino acid sequence of SEQ ID NO:13 (methionine at amino acid position 27 and lysine at amino acid position 383 of SEQ ID NO:4); (c) a beta polypeptide having an amino acid sequence of SEQ ID NO: 15 (alanine at amino acid position 26 and glycine at amino acid position 382 of SEQ ID NO:4); (d) a beta polypeptide having an amino acid sequence of SEQ ID NO: 12 (alanine at amino acid position 26 and lysine at amino acid position 383 of SEQ ID NO:4); (e) a beta polypeptide having an amino acid sequence of SEQ ID NO: 11 (methionine at amino acid position 25 and lysine at amino acid position 383 of SEQ ID NO:4); (f) a beta polypeptide having an amino acid sequence of SEQ ID NO: 14 (methionine at amino acid position 25 and glycine at amino acid position 382 of SEQ ID NO:4); or (g) any combination thereof. In one embodiment, the cell line produces beta polypeptides or beta polypeptide molecules, wherein: (a) about 90% or about 80% of the beta polypeptides comprise an amino acid sequence of SEQ ID NO:4 beginning with the methionine at residue 27; (b) about 10% or about 20% of the beta polypeptides comprise the amino acid sequence of SEQ ID NO:4 beginning with the alanine at residue number 26; (c) from about 4% to about 8% of the beta polypeptides comprise the amino acid sequence of SEQ ID NO:4 ending with the lysine at residue number 383; (d) from about 92% to about 96% of the beta polypeptides comprise the amino acid sequence of SEQ ID NO:4 ending with the glycine at residue number 382; and optionally, (e) about less than 1% of the beta polypeptides comprise the amino acid sequence of SEQ ID NO:2 beginning with the methionine at residue number 25. In one embodiment, wherein the beta polypeptides, which are produced from culturing the cell line, have an extinction coefficient of 1.0±0.05 AU mL cm-1 mg-1.

The invention provides for a cell population derived from a cell of the invention. In one embodiment, the cells of the population contain at least one additional genetic change as compared to the cell of the invention from which the population was derived, and wherein the cells produce a beta polypeptide. In another embodiment, the cells of the population contain at least 2, at least 3, at least 4, at least 5, at least 6, at least 7, at least 8, at least 9, at least 10, or at least 20 additional genetic change as compared to the cell of the invention from which the population was derived, and wherein the cells produce a beta polypeptide. In one embodiment, the genetic change comprises at least one non-conservative mutation in the cellular genome or in the expression cassette encoding the beta polypeptide. In another embodiment, the genetic change comprises at least one additional recombinant nucleic acid within the cell. In another embodiment, the genetic change comprises a mutation of the cellular genome. In another embodiment, the genetic change comprises addition of a nucleic acid to the cell genome or as a trans nucleic acid, and wherein the nucleic acid encodes an anti-apoptotic polypeptide. In another embodiment, the anti-apoptotic polypeptide relates to glycosylation. In another embodiment, the genetic change comprises at least one mutation of the cellular genome or of the expression cassette encoding a beta polypeptide. In another embodiment, the cell population, when grown in culture, produces: (a) a beta polypeptide having an amino acid sequence of SEQ ID NO:16 (methionine at amino acid position 27 and glycine at amino acid position 382 of SEQ ID NO:4); (b) a beta polypeptide having an amino acid sequence of SEQ ID NO:7 (methionine at amino acid position 27 and lysine at amino acid position 383 of SEQ ID NO:4); (c) a beta polypeptide having an amino acid sequence of SEQ ID NO:15 (alanine at amino acid position 26 and glycine at amino acid position 382 of SEQ ID NO:4); (d) a beta polypeptide having an amino acid sequence of SEQ ID NO:12 (alanine at amino acid position 26 and lysine at amino acid position 383 of SEQ ID NO:4); (e) a beta polypeptide having an amino acid sequence of SEQ ID NO:11 (methionine at amino acid position 25 and lysine at amino acid position 383 of SEQ ID NO:4); (f) a beta polypeptide having an amino acid sequence of SEQ ID NO:14 (methionine at amino acid position 25 and glycine at amino acid position 382 of SEQ ID NO:4); or (g) any combination thereof.

Compositions:

The invention provides for an isolated population of beta polypeptides or beta polypeptide molecules, wherein each polypeptide comprises the sequence of SEQ ID NO: 11, 12, 13, 14, 15, or 16, having an average molar ratio of sialic acid groups to beta polypeptide dimer or beta polypeptide molecule of from about 5 to about 10. In one embodiment, the average molar ratio of sialic acid groups to beta polypeptide dimer or beta polypeptide molecule of from about 5.5 to about 8.5. In one embodiment, average molar ratio of sialic acid groups to beta polypeptide dimer or beta polypeptide molecule of from about 5.2 to about 7.6. The invention provides for an isolated population of beta polypeptides, wherein each polypeptide comprises the sequence of SEQ ID NO: 11, 12, 13, 14, 15, or 16, having an average molar ratio of sialic acid groups to beta polypeptide dimer or beta polypeptide molecule of about 6. The invention provides for an isolated population of beta polypeptides, wherein each polypeptide comprises the sequence of SEQ ID NO11, 12, 13, 14, 15, or 16, and wherein greater than 95% of the polypeptides are formed into dimers. In one greater than 98%, greater than 99%, or greater than 99.5% of the polypeptides are formed into dimers. In another embodiment, from about 95% to about 99.5% of the polypeptides are formed into dimers and about 0.5% to about 5% of the polypeptides are formed into tetramers or high molecular weight species. In another embodiment, about 98.6% of the polypeptides are formed into dimers and about 1.2% of the polypeptides are formed into tetramers or high molecular weight species and about less than 0.7% of the polypeptides are monomers. In another embodiment, about 95% of the polypeptides are formed into dimers and about 4% of the polypeptides are formed into tetramers or high molecular weight species and about 1% of the polypeptides are isolated population of beta polypeptide dimers, wherein each polypeptide monomer comprises the sequence of SEQ ID NO: 11, 12, 13, 14, 15, or 16. In one embodiment, the population is substantially free of beta polypeptide monomer. In another embodiment, the population is substantially free of beta polypeptide tetramer. The invention provides for an isolated population of beta polypeptide monomers substantially free of beta polypeptide dimer and tetramer. In one embodiment, each monomer of each beta polypeptide dimer comprises the sequence of SEQ ID NO: 11, 12, 13, 14, 15, or 16 and has at least 2.5 sialic acid groups.

The invention provides for an isolated population of beta polypeptides, wherein each polypeptide comprises the sequence of SEQ ID NO: 11, 12, 13, 14, 15, or 16, having a potency of from about 70% to about 130% in a B7 binding assay, compared to a CTLA4-Ig standard, wherein the assay comprises measuring surface plasmon resonance. The invention provides for an isolated population of beta polypeptides, wherein each polypeptide comprises the sequence of SEQ ID NO: 11, 12, 13, 14, 15, or 16, having a potency of from about 50% to about 150% in a human cell IL-2 inhibition assay, compared to a standard. The invention provides for a purified population of beta polypeptide tetramers or high molecular weight species, wherein each polypeptide monomer comprises the sequence of SEQ ID NO: 11, 12, 13, 14, 15, or 16, the population being substantially free of beta polypeptide dimers, and optionally wherein the population comprises an amount that is greater than about 100 grams. The invention provides for a purified population of beta polypeptide tetramers or high molecular weight species, wherein each polypeptide monomer comprises the sequence of SEQ ID NO: 11, 12, 13, 14, 15, or 16, the population being substantially free of beta polypeptide monomer, and optionally wherein the population comprises an amount that is greater than about 100 grams. In one embodiment, each tetramer molecule comprises two pairs of beta polypeptides, wherein each polypeptide monomer comprises the sequence of SEQ ID NO: 11, 12, 13, 14, 15, or 16, and wherein each member of the pair of polypeptides is covalently linked to the other member, and wherein the two pairs of polypeptides are non-covalently associated with one another. In one embodiment, each tetramer molecule is capable of binding to a CD80 or CD86. In one embodiment, each tetramer molecule has at least a 2-fold greater avidity for CD80 or CD86 as compared to a beta polypeptide dimer, wherein each polypeptide monomer of the dimer comprises the sequence of SEQ ID NO: 11, 12, 13, 14, 15, or 16. In another embodiment, each tetramer molecule has at least a 2-fold greater avidity for CD80 or CD86 as compared to a CTLA4-Ig tetramer molecule comprising the sequence of SEQ ID NO:2. In another embodiment, each tetramer molecule has at least a 2-fold greater inhibition of T cell proliferation or activation as compared to a beta polypeptide dimer, wherein each polypeptide monomer of the dimer comprises the sequence of SEQ ID NO: 11, 12, 13, 14, 15, or 16. In another embodiment, each tetramer molecule has at least a 2-fold greater inhibition of T cell proliferation or activation as compared to a CTLA4-Ig tetramer molecule comprising the sequence of SEQ ID NO:2.

The invention provides for an isolated composition comprising beta polypeptides or beta polypeptide molecules, wherein each polypeptide comprises the sequence of SEQ ID NO: 11, 12, 13, 14, 15, or 16, and wherein the composition comprises dominant isoforms visualizable on an isoelectric focusing gel which have an isoelectric point, pI, less than or equal to 5.5 as determined by isoelectric focusing. In one embodiment, the pI increases after neuraminidase treatment. In one embodiment, at least 40% of the beta polypeptides or beta polypeptide molecules exhibit an isoelectric point less than or equal to about 5.3 as determined by isoelectric focusing. In one embodiment, at least 70% of the beta polypeptides or beta polypeptide molecules exhibit an isoelectric point less than or equal to about 5.3 as determined by isoelectric focusing. In one embodiment, at least 90% of the beta polypeptides or beta polypeptide molecules exhibit an isoelectric point less than or equal to about 5.3 as determined by isoelectric focusing. The invention provides for an isolated population of beta polypeptides or beta polypeptide molecules having a pI of from about 2.0±0.2 to about 5.2±0.2. The invention provides for an isolated population of beta polypeptides or beta polypeptide molecules having a pI from about 4.5±0.2 to about 5.2±0.2. The invention provides for an isolated population of beta polypeptides or beta polypeptide molecules having a pI of about 4.7±0.2 to about 5.1±0.2. The invention provides for a method for preparing a composition, the composition comprising beta polypeptides or beta polypeptide molecules with a pI of from about 2.0±0.2 to about 5.2±0.2, wherein each polypeptide comprises the sequence of SEQ ID NO: 11, 12, 13, 14, 15, or 16, the method comprising: (a) subjecting a mixture of beta polypeptides to isoelectric focusing gel electrophoresis, wherein a single band on the gel represents a population of beta polypeptides or beta polypeptide molecules with a particular pI, and (b) isolating the population of beta polypeptides or beta polypeptide molecules having a pI of from about 2.0±0.2 to about 5.2±0.2 so as to prepare the composition.

The invention provides for an isolated composition comprising beta polypeptides or beta polypeptide molecules, wherein each polypeptide comprises the sequence of SEQ ID NO: 11, 12, 13, 14, 15, or 16, and wherein the polypeptides are characterized by an average molar ratio of GlcNAc per mole of beta polypeptide dimer or beta polypeptide molecule of from about 24 to about 28. The invention provides for an isolated composition comprising beta polypeptides, wherein each polypeptide comprises the sequence of SEQ ID NO: 11, 12, 13, 14, 15, or 16, and wherein the polypeptides are characterized by an average molar ratio of GalNAc per mole of beta polypeptide dimer or beta polypeptide molecule of from about 2.7 to about 3.6. The invention provides for an isolated composition comprising beta polypeptides, wherein each polypeptide comprises the sequence of SEQ ID NO: 11, 12, 13, 14, 15, or 16, and wherein the polypeptides are characterized by an average molar ratio of galactose per mole of beta polypeptide dimer or beta polypeptide molecule of from about 11 to about 13. The invention provides for an isolated composition comprising beta polypeptides, wherein each polypeptide comprises the sequence of SEQ ID NO: 11, 12, 13, 14, 15, or 16, and wherein the polypeptides are characterized by an average molar ratio of fucose per mole of beta polypeptide dimer or beta polypeptide molecule of from about 6.4 to about 7.0. The invention provides for an isolated composition comprising beta polypeptides, wherein each polypeptide comprises the sequence of SEQ ID NO: 11, 12, 13, 14, 15, or 16, and wherein the polypeptides are characterized by an average molar ratio of mannose per mole of beta polypeptide dimer or beta polypeptide molecule of from about 14 to about 16. The invention provides for an isolated composition comprising beta polypeptides, wherein each polypeptide comprises the sequence of SEQ ID NO: 11, 12, 13, 14, 15, or 16, and wherein the molecules are characterized by an average molar ratio of sialic acid per mole of beta polypeptide dimer or beta polypeptide molecule of from about 5.5 to about 8.5. The invention provides for an isolated composition comprising beta polypeptides, wherein each polypeptide comprises the sequence of SEQ ID NO: 11, 12, 13, 14, 15, or 16, and wherein the molecules are characterized by an average molar ratio of sialic acid per mole of beta polypeptide dimer or beta polypeptide molecule of from about 5 to about 10. The invention provides for an isolated composition comprising beta polypeptides, wherein each polypeptide comprises the sequence of SEQ ID NO: 11, 12, 13, 14, 15, or 16, and wherein the polypeptides are characterized by: (a) an average molar ratio of GlcNAc per mole of beta polypeptide dimer or beta polypeptide molecule from about 24 to about 28; and (b) an average molar ratio of sialic acid per mole of beta polypeptide dimer or beta polypeptide molecule from about 5.5 to about 8.5. The invention provides for an isolated composition comprising beta polypeptides, wherein each polypeptide comprises the sequence of SEQ ID NO: 11, 12, 13, 14, 15, or 16, and wherein the molecules are characterized by: (a) an average molar ratio of GlcNAc per mole of beta polypeptide dimer or beta polypeptide molecule from about 24 to about 28; (b) an average molar ratio of GalNAc per mole of beta polypeptide dimer or beta polypeptide molecule from about 2.7 to about 3.6; and (c) an average molar ratio of sialic acid per mole of beta polypeptide dimer or beta polypeptide molecule from about 5.5 to about 8.5. The invention provides for an isolated composition comprising beta polypeptides, wherein each polypeptide comprises the sequence of SEQ ID NO: 11, 12, 13, 14, 15, or 16, and wherein the molecules are characterized by: (a) an average molar ratio of GlcNAc per mole of beta polypeptide dimer or beta polypeptide molecule from about 24 to about 28; (b) an average molar ratio of GalNAc per mole of beta polypeptide dimer or beta polypeptide molecule from about 2.7 to about 3.6; (c) an average molar ratio of galactose per mole of beta polypeptide dimer or beta polypeptide molecule from about 11 to about 13; and (d) an average molar ratio of sialic acid per mole of beta polypeptide dimer or beta polypeptide molecule from about 5.5 to about 8.5. The invention provides for an isolated composition comprising beta polypeptides, wherein each polypeptide comprises the sequence of SEQ ID NO: 11, 12, 13, 14, 15, or 16, and wherein the polypeptides are characterized by: (a) an average molar ratio of GlcNAc per mole of beta polypeptide dimer or beta polypeptide molecule from about 24 to about 28; (b) an average molar ratio of GalNAc per mole of beta polypeptide dimer or beta polypeptide molecule from about 2.7 to about 3.6; (c) an average molar ratio of galactose per mole of beta polypeptide dimer or beta polypeptide molecule from about 11 to about 13; (d) an average molar ratio of fucose per mole of beta polypeptide dimer or beta polypeptide molecule from about 6.4 to about 7.0; and (e) an average molar ratio of sialic acid per mole of beta polypeptide dimer or beta polypeptide molecule from about 5.5 to about 8.5. The invention provides for an isolated composition comprising beta polypeptides, wherein each polypeptide comprises the sequence of SEQ ID NO: 11, 12, 13, 14, 15, or 16, and wherein the polypeptides are characterized by: (a) an average molar ratio of GlcNAc per mole of beta polypeptide dimer or beta polypeptide molecule from about 24 to about 28; (b) an average molar ratio of GalNAc per mole of beta polypeptide dimer or beta polypeptide molecule from about 2.7 to about 3.6; (c) an average molar ratio of galactose per mole of beta polypeptide dimer or beta polypeptide molecule from about 11 to about 13; (d) an average molar ratio of fucose per mole of beta polypeptide dimer or beta polypeptide molecule from about 6.4 to about 7.0; (e) an average molar ratio of mannose per mole of beta polypeptide dimer or beta polypeptide molecule from about 14 to about 16; and (f) an average molar ratio of sialic acid per mole of beta polypeptide dimer or beta polypeptide molecule from about 5.5 to about 8.5. The invention provides for an isolated composition comprising beta polypeptides, wherein each polypeptide comprises the sequence of SEQ ID NO: 11, 12, 13, 14, 15, or 16, and wherein the polypeptides are characterized by: (a) an average molar ratio of galactose per mole of beta polypeptide dimer or beta polypeptide molecule from about 8 to about 17; (b) an average molar ratio of sialic acid per mole of beta polypeptide dimer or beta polypeptide molecule from about 5.5 to about 8.5; and (c) a carbohydrate profile substantially the same as FIG. 8. The invention provides for an isolated composition comprising beta polypeptides or beta polypeptide molecules, wherein each polypeptide comprises the sequence of SEQ ID NO: 11, 12, 13, 14, 15, or 16, and wherein the polypeptides are characterized by: (a) an average molar ratio of galactose per mole of beta polypeptide dimer or beta polypeptide molecule from about 8 to about 17; (b) an average molar ratio of sialic acid per mole of beta polypeptide dimer or beta polypeptide molecule from about 5.5 to about 8.5; (c) a carbohydrate profile substantially the same as FIG. 8; and (d) a beta polypeptide tetramer content less than about 5%. The invention provides for an isolated composition comprising beta polypeptides or beta polypeptide molecules, wherein each polypeptide comprises the sequence of SEQ ID NO: 11, 12, 13, 14, 15, or 16, and wherein the polypeptides are characterized by: (a) an average molar ratio of galactose per mole of beta polypeptide dimer or beta polypeptide molecule from about 11 to about 13; and (b) an average molar ratio of sialic acid per mole of beta polypeptide dimer or beta polypeptide molecule from about 5.5 to about 8.5. The invention provides for an isolated composition comprising beta polypeptides, wherein each polypeptide comprises the sequence of SEQ ID NO: 11, 12, 13, 14, 15, or 16, and wherein the polypeptides are characterized by: (a) an average molar ratio of galactose per mole of beta polypeptide dimer or beta polypeptide molecule from about 11 to about 13; (b) an average molar ratio of sialic acid per mole of beta polypeptide dimer or beta polypeptide molecule from about 5.5 to about 8.5; and (c) a beta polypeptide tetramer content less than about 5%. The invention provides for an isolated composition comprising beta polypeptides, wherein each polypeptide comprises the sequence of SEQ ID NO: 11, 12, 13, 14, 15, or 16, and wherein polypeptides are characterized by: (a) an average molar ratio of sialic acid per mole of beta polypeptide dimer or beta polypeptide molecule from about 5.5 to about 8.5; and (b) a carbohydrate profile substantially the same as FIG. 8. The invention provides for an isolated composition comprising beta polypeptides, wherein each polypeptide comprises the sequence of SEQ ID NO: 11, 12, 13, 14, 15, or 16, and wherein the polypeptides are characterized by: (a) an average molar ratio of galactose per mole of beta polypeptide dimer or beta polypeptide molecule from about 11 to about 13; and (b) a carbohydrate profile substantially the same as FIG. 8. The invention provides for an isolated composition comprising beta polypeptides, wherein each polypeptide comprises the sequence of SEQ ID NO: 11, 12, 13, 14, 15, or 16, and wherein polypeptides are characterized by: (a) an average molar ratio of sialic acid per mole of beta polypeptide dimer or beta polypeptide molecule from about 5.5 to about 8.5; and (b) a beta polypeptide tetramer or high molecular weight species content less than about 5%. The invention provides for an isolated composition comprising beta polypeptides or beta polypeptide molecules, wherein each polypeptide comprises the sequence of SEQ ID NO: 11, 12, 13, 14, 15, or 16, and wherein the polypeptides are characterized by: (a) an average molar ratio of galactose per mole of beta polypeptide dimer or beta polypeptide molecule from about 11 to about 13; and (b) a beta polypeptide tetramer or high molecular weight species content less than about 5%.

The invention provides for an isolated composition comprising beta polypeptides or beta polypeptide molecules, wherein each polypeptide comprises the sequence of SEQ ID NO: 11, 12, 13, 14, 15, or 16, and wherein the polypeptides exhibit a carbohydrate profile substantially the same as FIG. 8. The invention provides for an isolated composition comprising beta polypeptides, wherein each polypeptide comprises the sequence of SEQ ID NO: 11, 12, 13, 14, 15, or 16, and wherein the polypeptides exhibit a carbohydrate profile of Domains I-IV, wherein Domain I comprises peaks which represent a-sialylated oligosaccharides, Domain II comprises peaks which represent mono-sialylated oligosaccharides, Domain III comprises peaks which represent di-sialylated oligosaccharides, and Domain IV comprises peaks which represent tri-sialylated oligosaccharides. In one embodiment, the difference in retention times of N-linked oligosaccharides between a first peak in Domain I and a main peak in Domain II is from about 11 to about 13 minutes. In one embodiment, the sum of Domains III and IV comprises from about 25% to about 36% of the total carbohydrate profile.

The invention provides for an isolated composition comprising beta polypeptide dimers or beta polypeptide molecules, wherein each polypeptide monomer comprises the sequence of SEQ ID NO: 11, 12, 13, 14, 15, or 16, and wherein at least about 0.5% of the molecules are cysteinylated. The invention provides for an isolated population of beta polypeptides, wherein each polypeptide comprises the sequence of SEQ ID NO: 11, 12, 13, 14, 15, or 16, and wherein the population exhibits a mass spectrometry profile as shown in FIG. 10. The invention provides for an isolated population of beta polypeptides or beta polypeptide molecules, wherein each polypeptide comprises the sequence of SEQ ID NO: 11, 12, 13, 14, 15, or 16, having an average molar ratio of sialic acid groups to beta polypeptide dimer or beta polypeptide molecule of from about 5.5 to about 8.5, wherein the beta polypeptide dimer or beta polypeptide molecules is produced from cells of a production cell line. The invention provides for an isolated composition comprising beta polypeptides, wherein each polypeptide comprises the sequence of SEQ ID NO: 11, 12, 13, 14, 15, or 16, wherein the polypeptides are glycosylated at an asparagine amino acid residue at position 102 of SEQ ID NO:4, an asparagine amino acid residue at position 134 of SEQ ID NO:4, an asparagine amino acid residue at position 233 of SEQ ID NO:4. The invention provides for an isolated composition comprising beta polypeptides, wherein each polypeptide comprises the sequence of SEQ ID NO: 11, 12, 13, 14, 15, or 16, and wherein the molecules are characterized by: (a) an average molar ratio of GlcNAc per mole of beta polypeptide dimer or beta polypeptide molecule from about 24 to about 28; (b) an average molar ratio of GalNAc per mole of beta polypeptide dimer or beta polypeptide molecule from about 2.7 to about 3.6; (c) an average molar ratio of galactose per mole of beta polypeptide dimer or beta polypeptide molecule from about 11 to about 13; (d) an average molar ratio of fucose per mole of beta polypeptide dimer or beta polypeptide molecule from about 6.4 to about 7.0; (e) an average molar ratio of mannose per mole of beta polypeptide dimer or beta polypeptide molecule from about 14 to about 16; (f) an average molar ratio of sialic acid per mole of beta polypeptide dimer or beta polypeptide molecule from about 5.5 to about 8.5; (g) a pI as determined from visualization on an isoelectric focusing gel in a range from about 2.4±0.2 to about 5.2±0.2; (h) MCP-1 of less than or equal to 5 ppm; (i) less than 5% tetramer or high molecular weight species; (j) less than beta polypeptide 1% monomer; and (k) beta polypeptides or beta polypeptide molecules of the population having an amino acid at least 95% identical to any of SEQ ID NOS:4, 11, 12, 13, 14, 15, or 16, wherein the beta polypeptides within the population are capable of binding to CD80 and CD86. The invention provides for an isolated population of beta polypeptides, wherein each polypeptide comprises the sequence of SEQ ID NO: 11, 12, 13, 14, 15, or 16, and wherein the population of molecules is characterized by: (a) an average molar ratio of GlcNAc per mole of beta polypeptide dimer or beta polypeptide molecule from about 24 to about 28; (b) an average molar ratio of GalNAc per mole of beta polypeptide dimer or beta polypeptide molecule from about 2.7 to about 3.6; (c) an average molar ratio of galactose per mole of beta polypeptide dimer or beta polypeptide molecule from about 11 to about 13; (d) an average molar ratio of fucose per mole of beta polypeptide dimer or beta polypeptide molecule from about 6.4 to about 7.0; (e) an average molar ratio of mannose per mole of beta polypeptide dimer or beta polypeptide molecule from about 14 to about 16; (f) an average molar ratio of sialic acid per mole of beta polypeptide dimer or beta polypeptide molecule from about 5.5 to about 8.5; (g) a pI as determined from visualization on an isoelectric focusing gel in a range from about 2.4±0.2 to about 5.2±0.2; (h) MCP-1 of less than or equal to 5 ppm; (i) less than 5% beta polypeptide tetramer or high molecular weight; (j) less than 1% monomer; and (k) beta polypeptides of the population having an amino acid at least 95% identical to any of SEQ ID NOS:4, 11, 12, 13, 14, 15, or 16, wherein beta polypeptide molecules within the population are capable of binding to CD80 and CD86; or pharmaceutical equivalents thereof.

The invention provides for a composition comprising an effective amount of the beta polypeptide of the invention and a pharmaceutically acceptable carrier. The invention provides for a composition comprising excipients as described in U.S. Application No. 60/752,150; filed Dec. 20, 2005. In one embodiment, the composition includes beta polypeptide molecules. In one embodiment, the composition further comprises a pharmaceutically acceptable diluent, adjuvant or carrier. In one embodiment, the composition further comprises sucrose, sodium phosphate monobasic monohydrate, sodium chloride, sodium hydroxide, hydrochloric acid, and sterile water. In another embodiment, the composition comprises sucrose, poloxamer, sodium phosphate monobasic monohydrate, sodium phosphate dibasic anhydrous, sodium chloride, sodium hydroxide, and sterile water.

In one embodiment, the composition is lyophilized. The invention provides for a lyophilized composition comprising an effective amount of the beta polypeptides of the invention, sucrose, sodium phosphate monobasic monohydrate, sodium chloride, sodium hydroxide, and hydrochloric acid.

Formulations and Kits:

The invention provides for lyophilized beta polypeptide mixture, wherein each polypeptide comprises the sequence of SEQ ID NO: 11, 12, 13, 14, 15, or 16, comprising at least 95% beta polypeptide dimer, and not more than 5% beta polypeptide tetramer (high molecular weight species). In one embodiment, the mixture comprises at least 98% beta polypeptide dimer and no more than 2% beta polypeptide tetramer (high molecular weight species). In one embodiment, the mixture comprises at least 99% beta polypeptide dimer and no more than 1% beta polypeptide tetramer (high molecular weight species). In one embodiment, the mixture comprises at least 5 moles of sialic acid per mole of beta polypeptide dimer or beta polypeptide molecule. In one embodiment, the mixture comprises from about 24 to about 28 moles of GlcNAc per mole of beta polypeptide dimer (high molecular weight species). In one embodiment, the mixture comprises from about 2.7 to about 3.6 moles of GalNAc per mole of beta polypeptide dimer or beta polypeptide molecule. In one embodiment, the mixture comprises from about 11 to about 13 moles of galactose per mole of beta polypeptide dimer or beta polypeptide molecule. In one embodiment, the mixture comprises from about 6.4 to about 7.0 moles of fucose per mole of beta polypeptide dimer or beta polypeptide molecule. In one embodiment, the mixture comprises from about 14 to about 16 moles of mannose per mole of beta polypeptide dimer or beta polypeptide molecule. The invention also provides for a pharmaceutical kit comprising: (a) a container containing a lyophilized beta polypeptide mixture of the invention and (b) instructions for reconstituting the lyophilized beta polypeptide mixture into solution for injection.

Illustrative Methods of Treatment:

A method for inhibiting T cell proliferation, activation or both, the method comprising contacting a T cell with an effective amount of a beta polypeptide composition of the invention. The invention provides for a method for inhibiting an immune response in a subject, the method comprising administering to a subject in need thereof an effective amount of a beta polypeptide composition of the invention. The invention provides for a method for treating an immune disorder in a subject, the method comprising administering to a subject in need thereof an effective amount of a beta polypeptide composition of the invention. The invention provides for a method for inducing immune tolerance to an antigen in a subject, the method comprising administering to a subject in need thereof an effective amount of a beta polypeptide composition of the invention. The method provides for a method for treating inflammation in a subject, the method comprising administering to a subject in need thereof an effective amount of a beta polypeptide composition of the invention. The method provides for a method for treating rheumatoid arthritis comprising administering to a subject in need thereof an effective amount of a beta polypeptide composition of the invention. The invention provides for a method for treating psoriasis in a subject, the method comprising administering to a subject in need thereof an effective amount of a beta polypeptide composition of the invention. The invention provides for a method for treating lupus in a subject, the method comprising administering to a subject in need thereof an effective amount of a beta polypeptide composition of the invention.

The invention provides for a method for treating or preventing an allergy in a subject, the method comprising administering to a subject in need thereof an effective amount of a beta polypeptide composition of the invention. The invention provides for a method for treating or preventing graft versus host disease in a subject, the method comprising administering to a subject in need thereof an effective amount of a beta polypeptide composition of the invention. The invention provides for a method for treating or preventing rejection of a transplanted organ in a subject, the method comprising administering to a subject in need thereof an effective amount of a beta polypeptide composition of the invention. The invention provides for a method for treating or preventing rejection of transplanted tissue in a subject, the method comprising administering to a subject in need thereof an effective amount of the composition a beta polypeptide composition of the invention. The invention provides for a method for treating or preventing rejection of a transplanted cell in a subject, the method comprising administering to a subject in need thereof an effective amount of a beta polypeptide composition of the invention. In one embodiment, the transplanted cell is a bone marrow cell. In another embodiment, the transplanted cell is an islet cell. In another embodiment, the transplanted cell is an insulin-producing pancreatic islet cell. The invention provides for a method for treating multiple sclerosis in a subject, the method comprising administering to a subject in need thereof an effective amount of a beta polypeptide composition of the invention. The invention provides for a method for treating Crohn's Disease in a subject, the method comprising administering to a subject in need thereof an effective amount of a beta polypeptide composition of the invention. The invention provides for a method for treating type I diabetes in a subject, the method comprising administering to a subject in need thereof an effective amount of a beta polypeptide composition of the invention. The invention provides for a method for treating inflammatory bowel disease in a subject, the method comprising administering to a subject in need thereof an effective amount of a beta polypeptide composition of the invention. The invention provides for a method for treating oophoritis in a subject, the method comprising administering to a subject in need thereof an effective amount of a beta polypeptide composition of the invention. The invention provides for a method for treating glomerulonephritis in a subject, the method comprising administering to a subject in need thereof an effective amount of a beta polypeptide composition of the invention. The invention provides for a method for treating allergic encephalomyelitis in a subject, the method comprising administering to a subject in need thereof an effective amount of a beta polypeptide composition of the invention. The invention provides for a method for treating myasthenia gravis in a subject, the method comprising administering to a subject in need thereof an effective amount of a beta polypeptide composition of the invention.

The invention provides for the use of a population of beta polypeptides or beta polypeptide molecules, wherein each polypeptide comprises the sequence of SEQ ID NO: 11, 12, 13, 14, 15, or 16, and wherein the population has an average molar ratio of sialic acid groups to beta polypeptide dimer or beta polypeptide molecule of from about 5 to about 10 in the manufacture of a medicament for the therapeutic and/or prophylactic treatment of an immune disorder. The invention provides for the use of a population of beta polypeptides or beta polypeptide molecules, wherein each polypeptide comprises the sequence of SEQ ID NO11, 12, 13, 14, 15, or 16, and wherein the population has an average molar ratio of sialic acid groups to beta polypeptide dimer or beta polypeptide molecule of from about 5 to about 10 in the manufacture of an anti-rheumatoid arthritis agent in a package together with instructions for its use in the treatment of rheumatoid arthritis. In one embodiment, the population has an average molar ratio of sialic acid groups to beta polypeptide dimer or beta polypeptide molecule of from about 5.5 to about 8.5.

Illustrative Combination Therapies:

The invention provides for a method for inhibiting T cell proliferation, activation or both, the method comprising contacting a T cell with an effective amount of a beta polypeptide composition of the invention in combination with methotrexate. The invention provides for a method for inhibiting an immune response in a subject, the method comprising administering to a subject in need thereof an effective amount of a beta polypeptide composition of the invention in combination with methotrexate. The invention provides for a method for inducing immune tolerance to an antigen in a subject, the method comprising administering to a subject in need thereof an effective amount of a beta polypeptide composition of the invention in combination with methotrexate.

BRIEF DESCRIPTION OF THE DRAWINGS

FIGS. 1A-1B presents the nucleotide sequence (SEQ ID NO:1) of a portion of an expression cassette for a CTLA4-Ig molecule. Also shown is the amino acid sequence (SEQ ID NO:2) encoded by the nucleic acid. CTLA4-Ig molecules that can be produced from this expression cassette include molecules having the amino acid sequence of residues: (i) 26-383 of SEQ ID NO:2, (ii) 26-382 of SEQ ID NO:2, (iii) 27-383 of SEQ ID NO:2, (iv) 26-382 of SEQ ID NO:2, (v) 25-382 of SEQ ID NO:2, and (vi) 25-383 of SEQ ID NO:2. The expression cassette comprises the following regions: (a) an Oncostatin M signal sequence (nucleotides 11-88 of SEQ ID NO:1; amino acids 1-26 of SEQ ID NO:2); (b) an extracellular domain of human CTLA4 (nucleotides 89-463 of SEQ ID NO:1; amino acids 27-151 of SEQ ID NO:2); (c) a modified portion of the human IgG1 constant region (nucleotides 464-1159 of SEQ ID NO:1; amino acids 152-383 of SEQ ID NO:2), including a modified hinge region (nucleotides 464-508 of SEQ ID NO:1; amino acids 152-166 of SEQ ID NO:2), a modified human IgG1 $C_H2$ domain (nucleotides 509-838 of SEQ ID NO:1; amino acids 167-276 of SEQ ID NO:2), and a human IgG1 $C_H3$ domain (nucleotides 839-1159 of SEQ ID NO:1; amino acids 277-383 of SEQ ID NO:2).

FIG. 2 presents the nucleic acid (top row) and amino acid (bottom row) sequences corresponding to $CTLA4^{A29YL104E}$-Ig. The amino acid sequence contains an amino acid change from the sequence shown in FIG. 1, wherein the changes are at position 29 (A to Y) and at position 104 (L to E) compared to that of SEQ ID NO: 2, wherein numbering of amino acid residues begins at Methionine (M) marked by "+1." The nucleotide sequence of $CTLA4^{A29YL104E}$-Ig is shown in this figure starting from the A at position 79 (i.e., the position marked by the "+1" below the M) through the A at nucleotide position 1149 (SEQ ID NO:3). In particular, the nucleotide sequence encoding $CTLA4^{A29YL104E}$-Ig is from the nucleotide at position 79 to the nucleotide at position 1149, designated SEQ ID NO:3. The full nucleotide sequence shown in FIG. 2 is designated SEQ ID NO:23 and includes the nucleic acid sequence encoding the Oncostatin M signal peptide.

FIG. 3 presents the amino acid sequence (SEQ ID NO:4) of CTLA4$^{A29YL104E}$-Ig molecule including an Oncostatin M prosequence (see bold italics). Polypeptides that can be produced that are CTLA4$^{A29YL104E}$-Ig molecules include molecules having the amino acid sequence of residues: (i) 26-383 of SEQ ID NO:4, (ii) 26-382 of SEQ ID NO:4, (iii) 27-383 of SEQ ID NO:4, (iv) 26-382 of SEQ ID NO:4, (v) 25-382 of SEQ ID NO:4, and (vi) 25-383 of SEQ ID NO:4.

FIG. 5 represents the theoretical cDNA-derived amino acid sequence of a CTLA4$^{A29YL104E}$-Ig (SEQ ID NO:4). Two amino acid substitutions were made in the CTLA-4 extracellular domain (L104E and A29Y) to generate CTLA4$^{A29YL104E}$-Ig. The sequence identifies the signal peptide (pro-sequence) of oncostatin M along with the N-linked glycosylation sites.

FIG. 26A shows the single chain peptide spectrum illustrating cysteinylation modification. FIG. 26B shows the spectrum of the single-chain peptide following reduction and demonstrates that the modification occurs at Cys$^{146}$. FIG. 26C shows alkylation of the reduced single-chain peptide, which demonstrates that the cysteinylation occurs at Cys$^{146}$.

FIG. 60A is from an analysis of CTLA4-Ig produced in a culture method without galactose added, and FIG. 60B is from an analysis where galactose was added to the culture at day 14. This trace of from an analysis of CTLA4-Ig produced in a culture method without additional galactose added to the culture. The percentages of N-linked carbohydrates in each Domain is shown in the inset table.

FIG. 68 depicts an isoelectric focusing gel of CTLA4-Ig. The bands are characterized by:

| Lane | Description | Protein Load (micrograms) | Band No. | Cumulative % Band Intensity | Relative Band Percent (%) |
|---|---|---|---|---|---|
| 1 | IEF Markers | NA | NA | NA | NA |
| 2 | CTLA4-Ig material | 20 | 16 | 100 | NA |
| 3 | CTLA4-Ig Drug Substance | 20 | 16 | 100 | 100 |
| 4 | Staining Control | 1 | NA | NA | NA |

Figure 69:
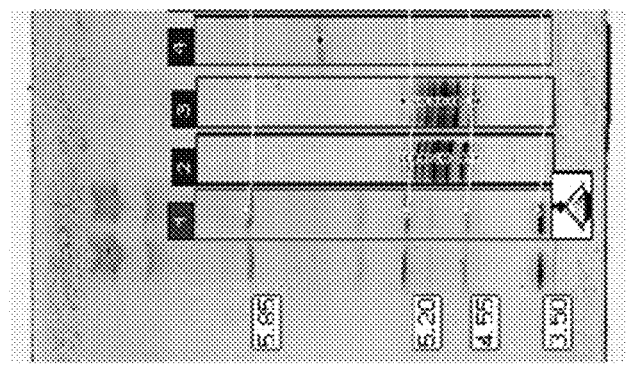

FIG. 69 depicts a representative isoelectric focusing gel quantitative analysis report of CTLA4-Ig. The quantitation of the gel was performed and the data is as follows:

| IEF Marker | | | Lot 188667-2003-015 | | | BQC060082 (DS ABC04014) | | | Staining Control | | |
|---|---|---|---|---|---|---|---|---|---|---|---|
| Lane 1 Band | Lane 1 Band % | Lane 1 pI | Lane 2 Band | Lane 2 Band % | Lane 2 pI | Lane 3 Band | Lane 3 Band % | Lane 3 pI | Lane 4 Band | Lane 4 Band % | Lane 4 pI |
| 1 | 20.95 | 5.85 | 1 | 0.51 | 5.28 | 1 | 1.34 | 5.26 | 1 | 100 | 5.68 |
| 2 | 22.39 | 5.2 | 2 | 0.17 | 5.25 | 2 | 2.34 | 5.19 | | | |
| 3 | 9.62 | 4.55 | 3 | 0.71 | 5.23 | 3 | 0.99 | 5.17 | | | |
| 4 | 47.04 | 3.5 | 4 | 1.61 | 5.2 | 4 | 3.2 | 5.14 | | | |
| | | | 5 | 1.15 | 5.18 | 5 | 3.23 | 5.11 | | | |
| | | | 6 | 7.44 | 5.15 | 6 | 3.41 | 5.08 | | | |
| | | | 7 | 10.96 | 5.09 | 7 | 10.29 | 5.03 | | | |
| | | | 8 | 9.32 | 5.02 | 8 | 5.95 | 5.01 | | | |
| | | | 9 | 18.22 | 4.94 | 9 | 5.66 | 4.97 | | | |
| | | | 10 | 5.52 | 4.91 | 10 | 13.4 | 4.91 | | | |
| | | | 11 | 4.19 | 4.88 | 11 | 17.11 | 4.85 | | | |
| | | | 12 | 22.58 | 4.82 | 12 | 7.39 | 4.8 | | | |
| | | | 13 | 3.8 | 4.67 | 13 | 16.03 | 4.72 | | | |
| | | | 14 | 10.02 | 4.63 | 14 | 3.88 | 4.56 | | | |
| | | | 15 | 3.44 | 4.55 | 15 | 4.97 | 4.52 | | | |
| | | | 16 | 0.35 | 4.48 | 16 | 0.8 | 4.45 | | | |
| | | | Bands (4.3-5.6) | 16 | | Bands (4.3-5.6) | 16 | | | | |
| | | | % Bands (4.3-5.3) | 100 | | % Bands (4.3-5.3) | 100 | | | | |
| | | | Sample Relative Percent (%) | | | | 100 | | | | |

Sample Relative Percent (%) = (Sample % Band Intensity/Ref % Band Intensity) × 100
NOTE:
For the pI range of 4.3 to 5.3

| | Peak Name | RT | Area | % Area |
|---|---|---|---|---|
| 1 | Domain I | 19.413 | 47807873 | 31.3 |
| 2 | Domain II | 29.076 | 50746179 | 33.2 |
| 3 | Domain III | 42.819 | 36640805 | 24.0 |
| 4 | Domain V | 67.546 | 3421324 | 2.2 |
| 5 | Domain IV | 55.899 | 14331509 | 9.4 |
| 6 | Peak 1A | 19.413 | 11115168 | 7.3 |
| 7 | Peak 1B | 20.290 | 16331761 | 10.7 |
| 8 | Peak 1C | 21.032 | 13507144 | 8.8 |
| 9 | Peak 2 | 21.925 | 4285962 | 2.8 |
| 10 | | 22.685 | 2567838 | 1.7 |
| 11 | | 29.076 | 2808537 | 1.8 |
| 12 | | 30.763 | 27989176 | 18.3 |
| 13 | | 31.577 | 19948466 | 13.0 |
| 14 | | 42.819 | 4555254 | 3.0 |
| 15 | Peak 3 | 43.823 | 22213064 | 14.5 |
| 16 | | 46.626 | 9872487 | 6.5 |
| 17 | | 55.899 | 3898179 | 2.5 |
| 18 | Peak 4 | 57.368 | 6789516 | 4.4 |
| 19 | | 60.333 | 3643813 | 2.4 |
| 20 | | 67.546 | 3421324 | 2.2 |

Figure 70A:
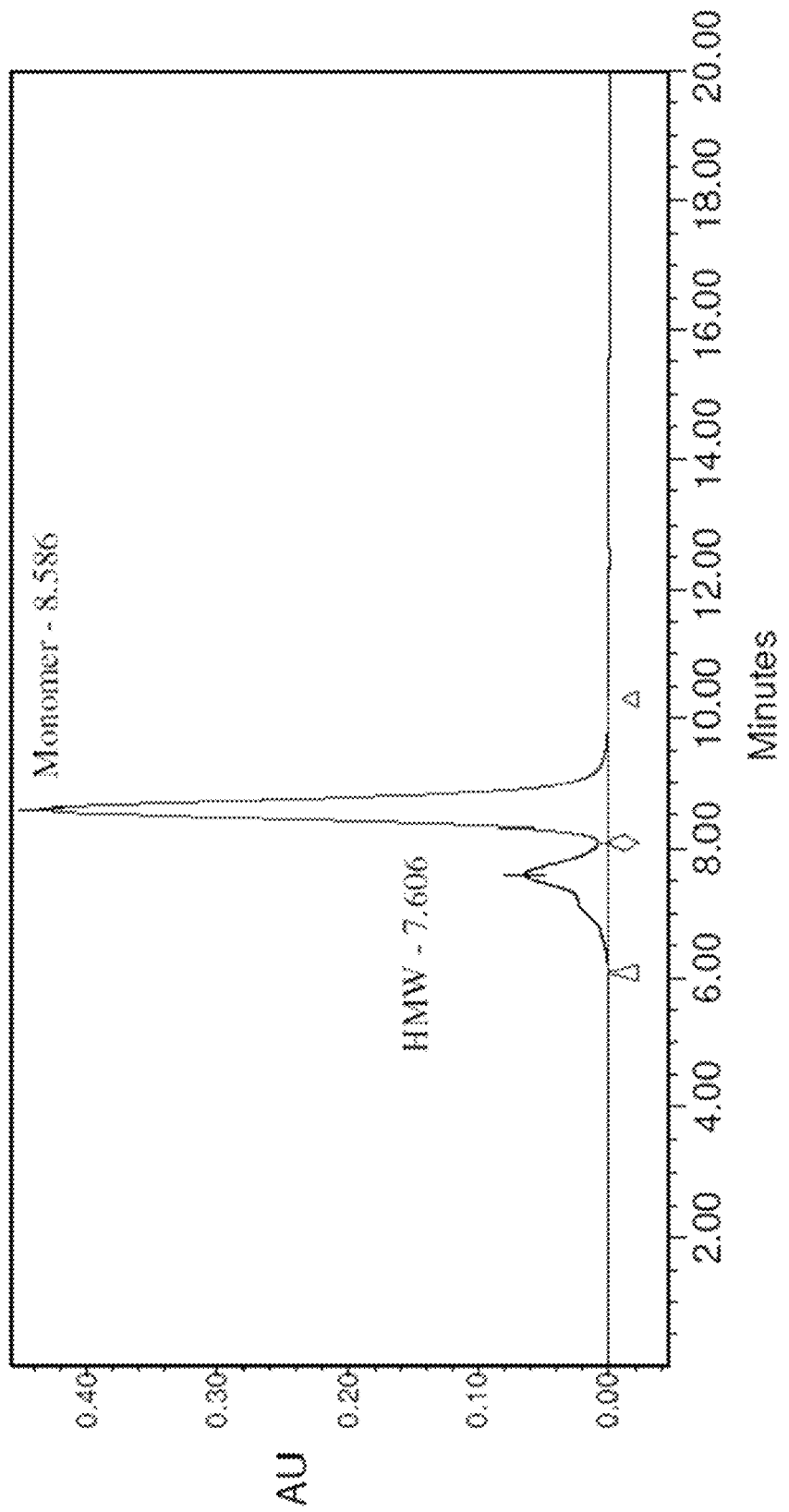
Figure 70B:
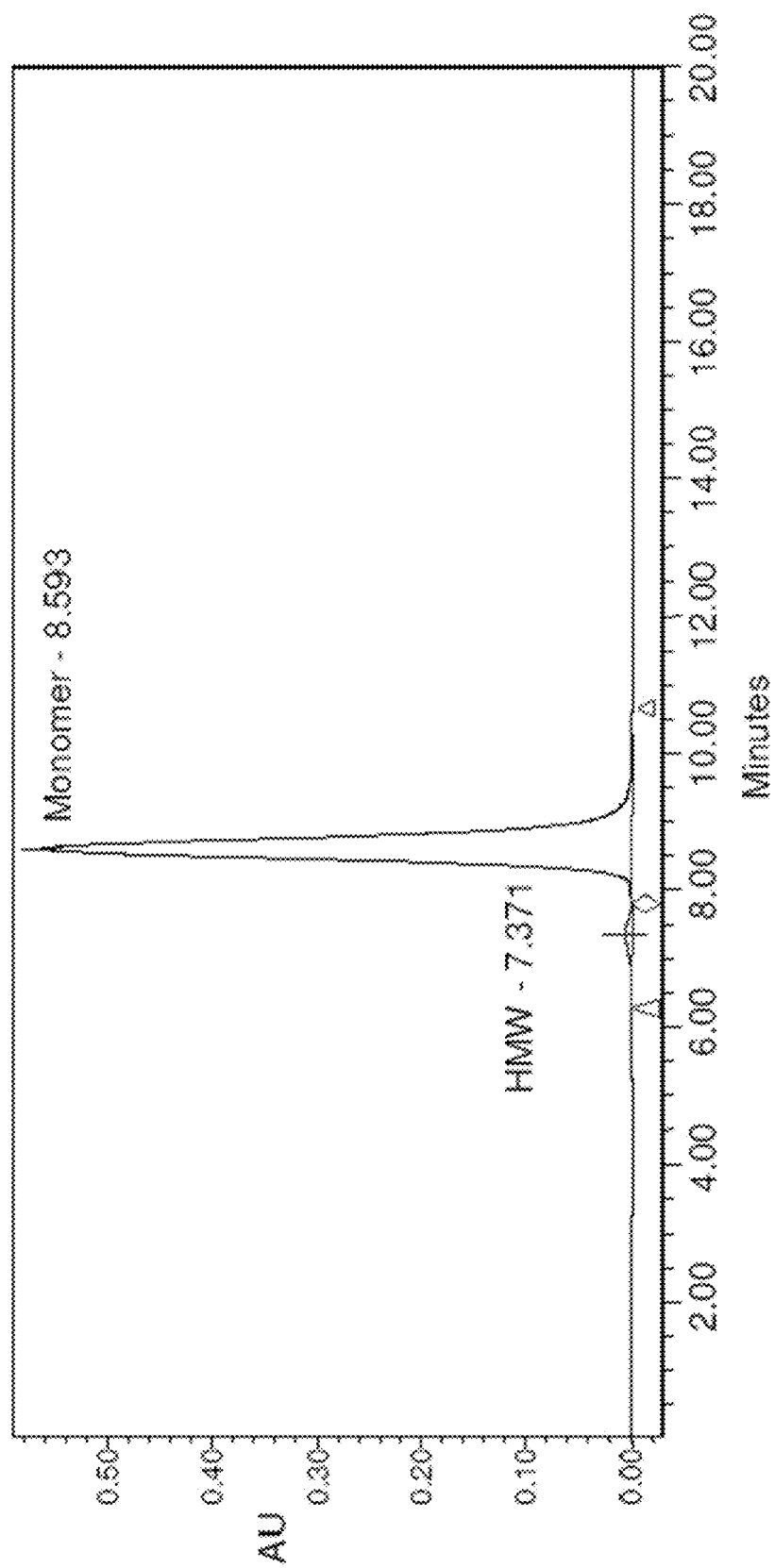

FIGS. 70A-70B. FIG. 70A depicts Typical 20 μL Injection of System Suitability Standard on TOSO HAAS 3000 SWXL Column Equipped with a Guard Column. FIG. 70B depicts a 20 μL Injection of CTLA4-Ig Reference Material on TOSO HAAS 3000 SWXL Column Equipped with a Guard Column.

Figure 71:
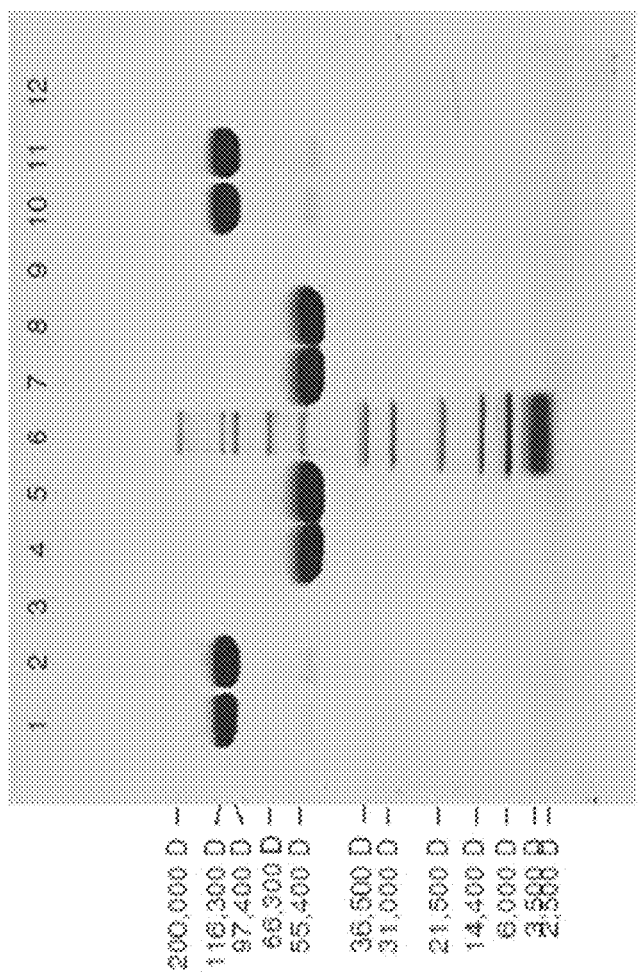

FIG. 71—Example of digitally acquired image of SDS-PAGE Analysis of CTLA4-Ig by Coomassie Blue stained Polyacrylamide (4-20) Gel Electrophoresis

| Lane | Description | Protein Load (micrograms) | Non-Reduced (NR)/Reduced (R) Condition | Percent (%) Band Intensity |
|---|---|---|---|---|
| 1 | CTLA4-Ig drug substance | 10 | NR | 100 |
| 2 | CTLA4-Ig material | 10 | NR | 99 |
| 3 | Blank | NA | NR | NA |
| 4 | CTLA4-Ig drug substance | 10 | R | 100 |
| 5 | CTLA4-Ig material | 10 | R | 100 |
| 6 | Molecular Weight Marker | NA | NA | NA |
| 7 | CTLA4-Ig drug product | 10 | NR | 99 |

-continued

| Lane | Description | Protein Load (micrograms) | Non-Reduced (NR)/Reduced (R) Condition | Percent (%) Band Intensity |
|---|---|---|---|---|
| 8 | CTLA4-Ig material | 10 | NR | 100 |
| 9 | Blank | NA | NR | NA |
| 10 | CTLA4-Ig drug product | 10 | R | 99 |
| 11 | CTLA4-Ig material | 10 | R | 99 |
| 12 | Trypsin Inhibitor Staining Control | NA | NA | NA |

Figure 72:
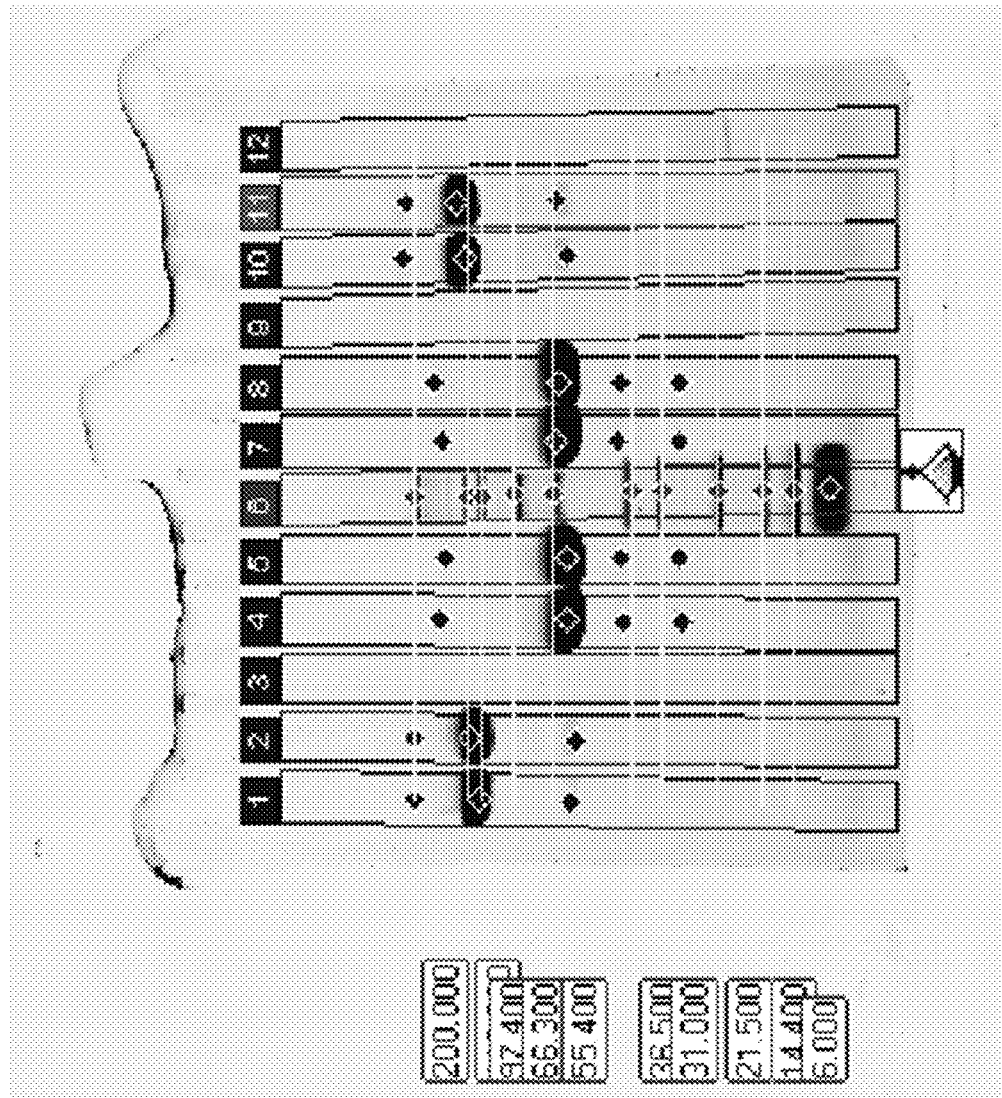

FIG. 72 depicts an example of quantitative analysis report for Coomassie Blue stained SDS-PAGE.

Figure 73:
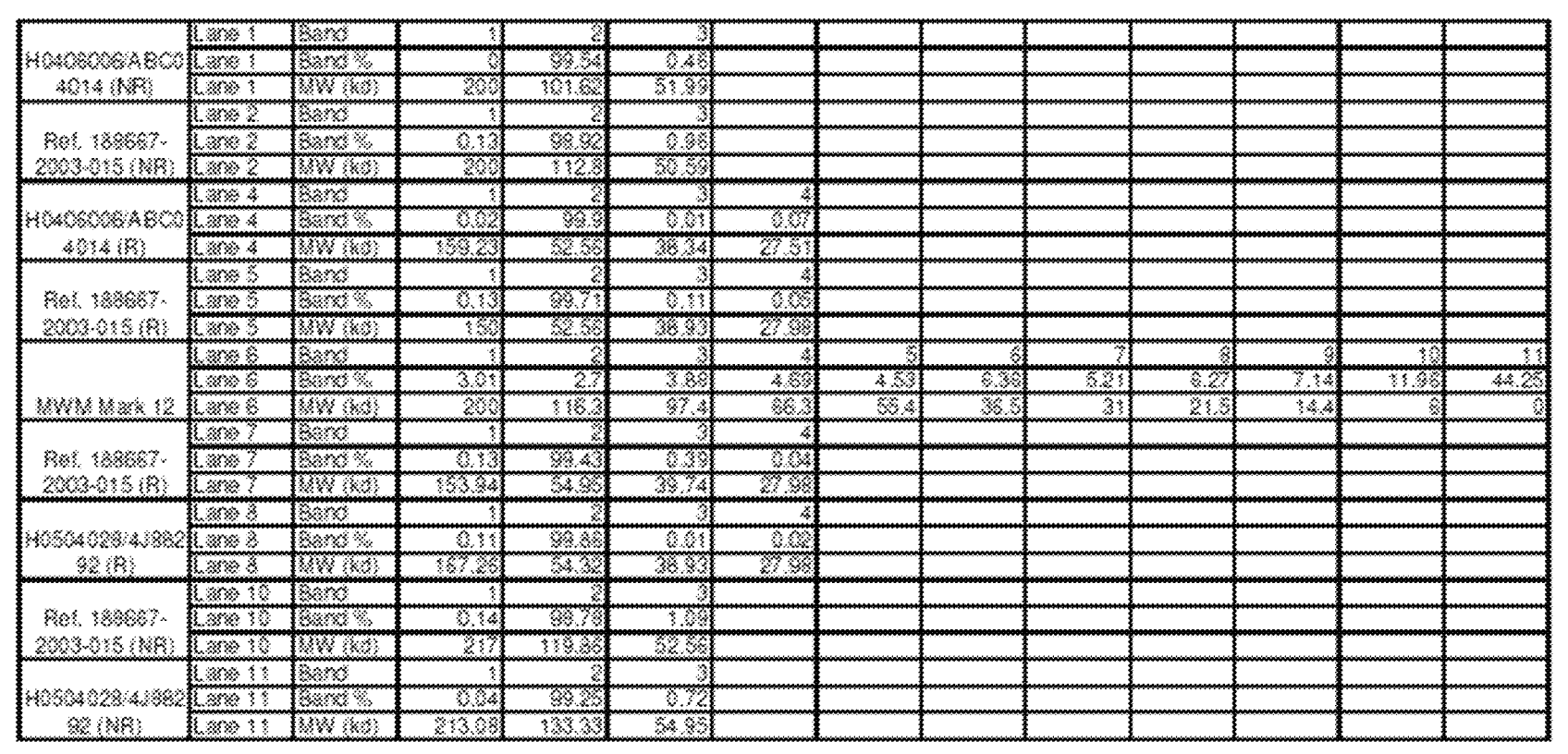

FIG. 73 shows a table setting out the quantitative analysis of the stained SDS-PAGE gel in FIG. 72.

Figure 74:
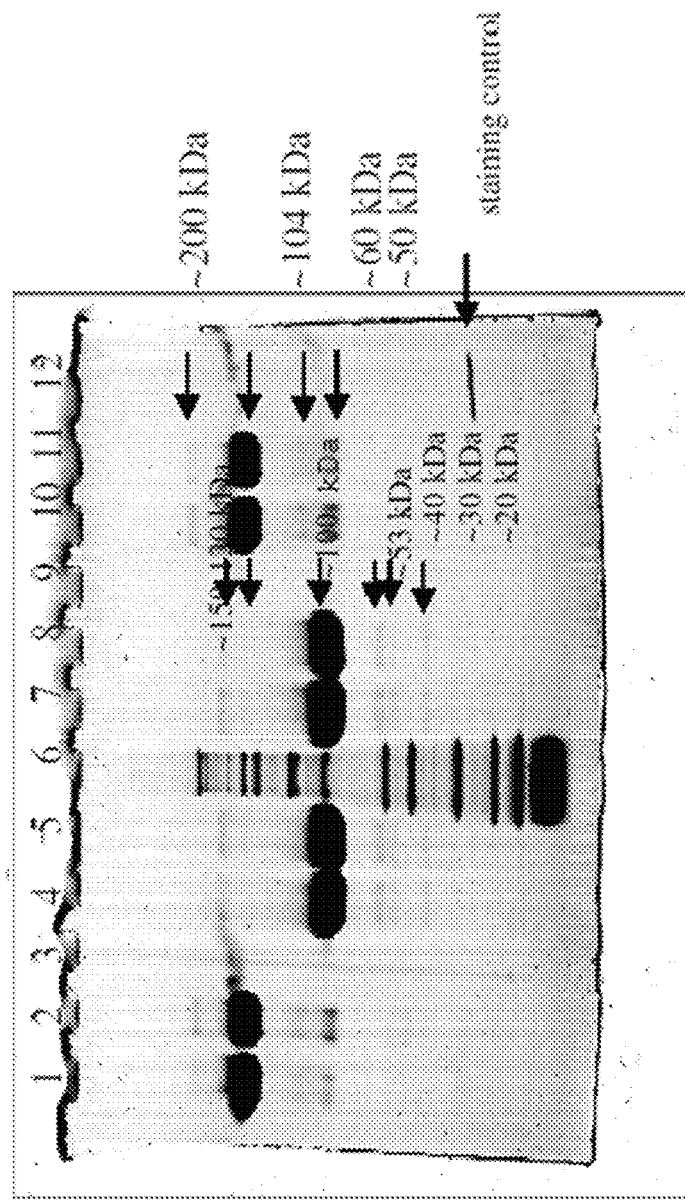

FIG. 74 depicts example of an enhanced image of SDS-PAGE Analysis of CTLA4-Ig Coomassie Blue Stained Gel for illustrating the migrating positions of the major and expected minor bands relative to the Molecular Weight Markers.

Figure 75:
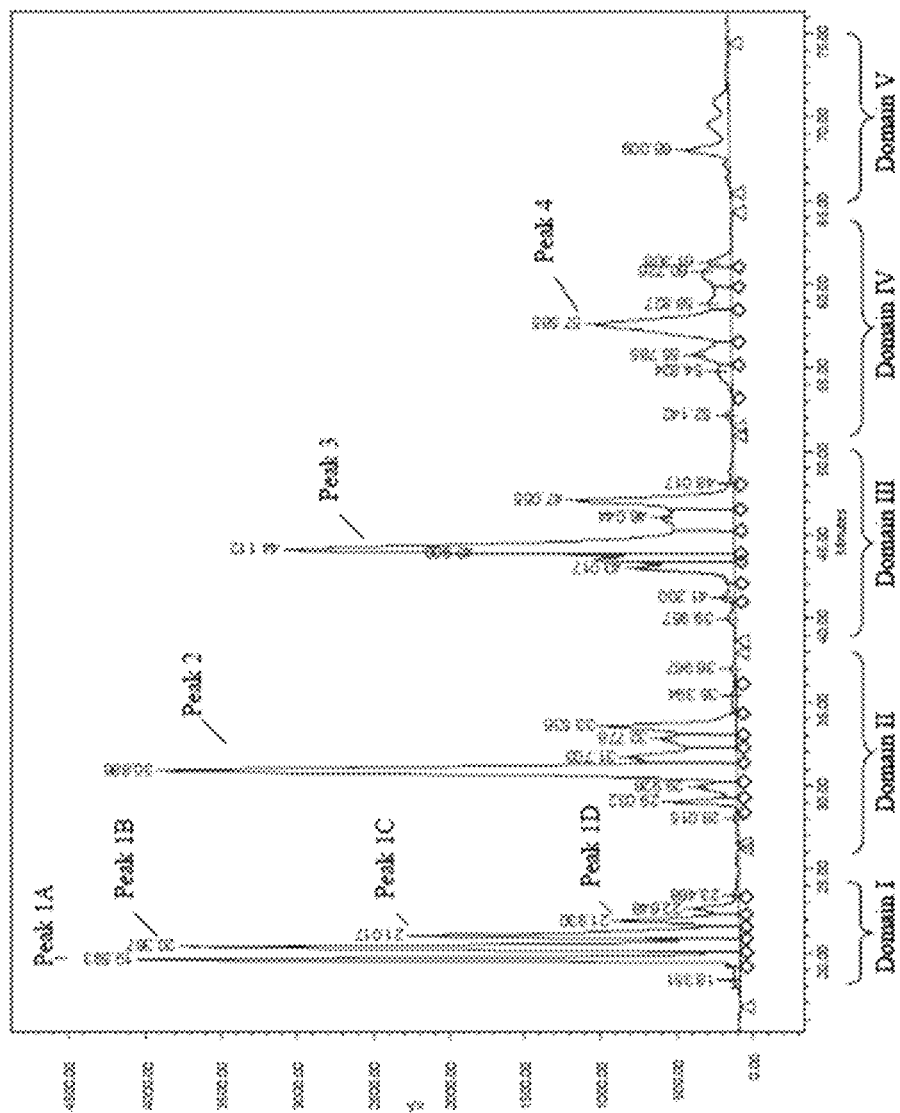

FIG. 75 is a depiction of a representative N-Linked Carbohydrate Profile of CTLA4-Ig reference/standard material. This is a representative carbohydrate profile of run on the Waters system. Retention times are system dependent.

Figure 76:
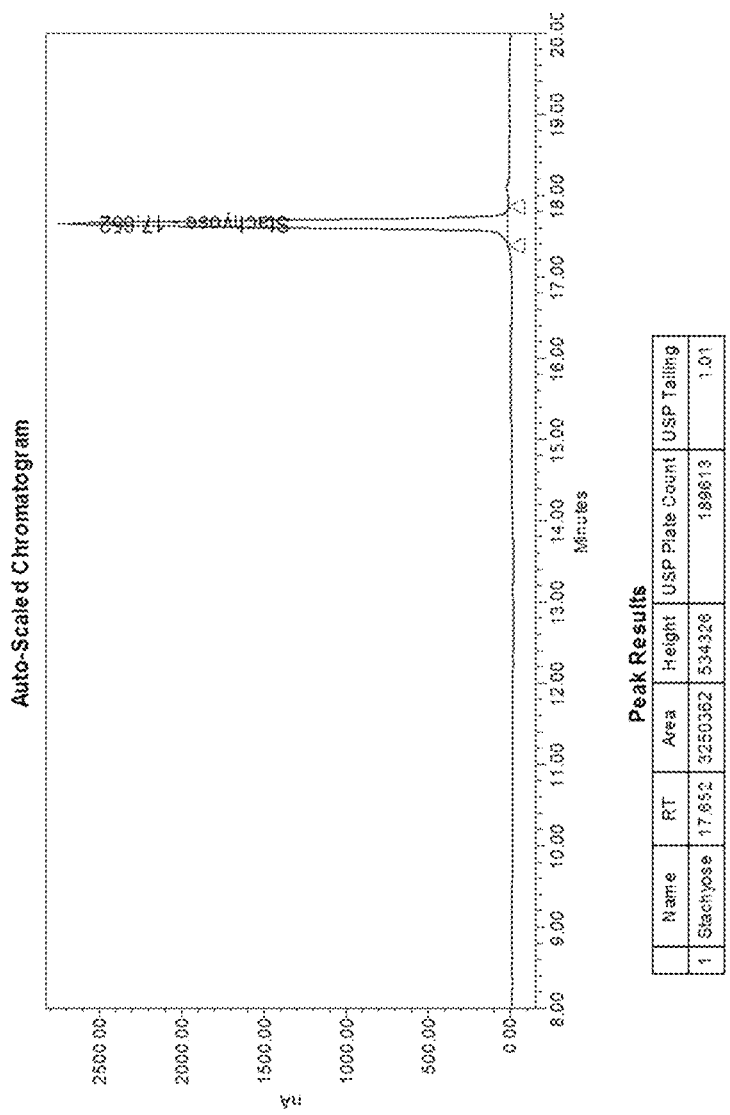

FIG. 76 is a depiction of a representative Stachyose System Suitability Chromatogram.

Figure 77:
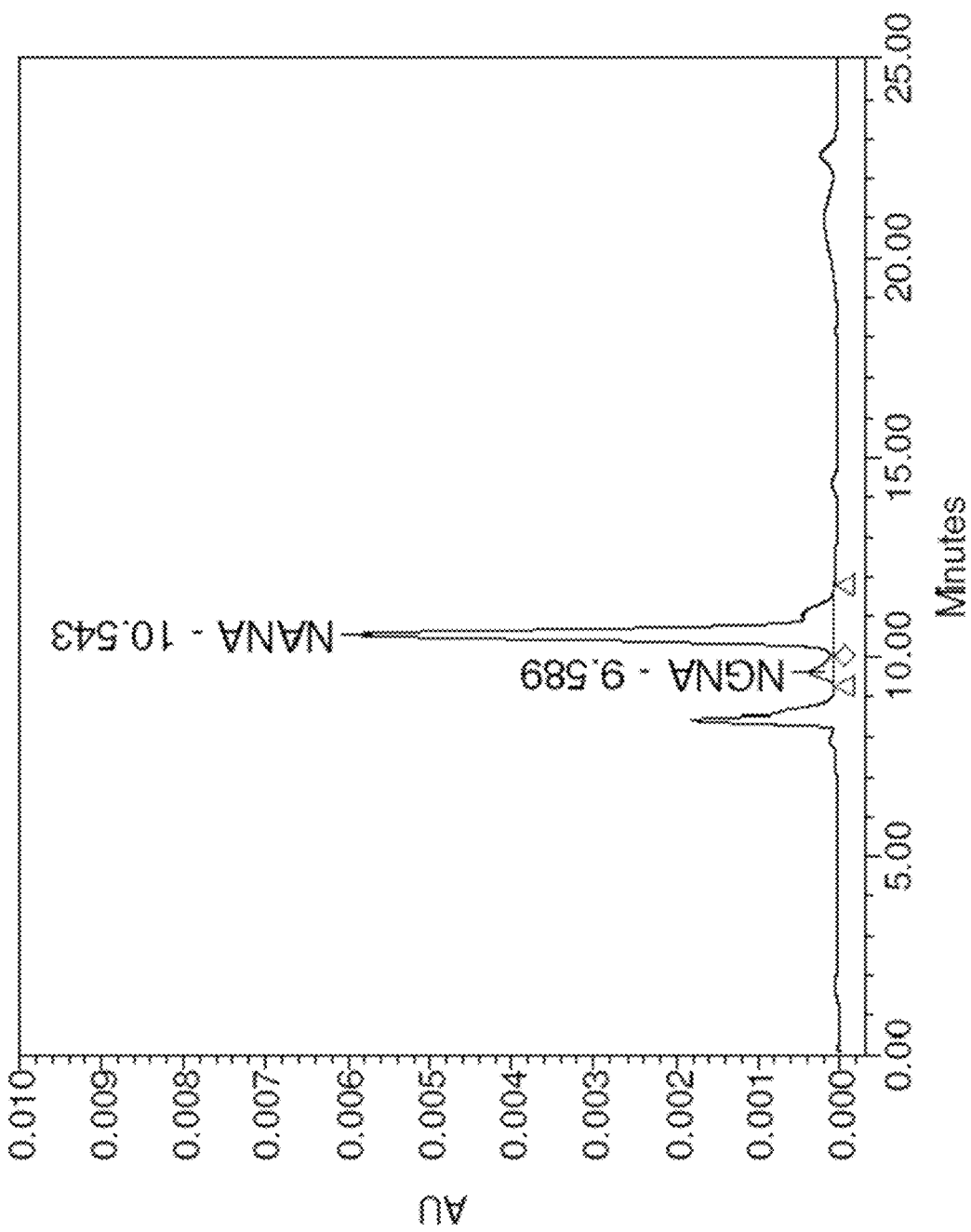

FIG. 77 is a trace of a Representative Chromatogram of Hydrolyzed CTLA4-Ig Material.

Figure 78:
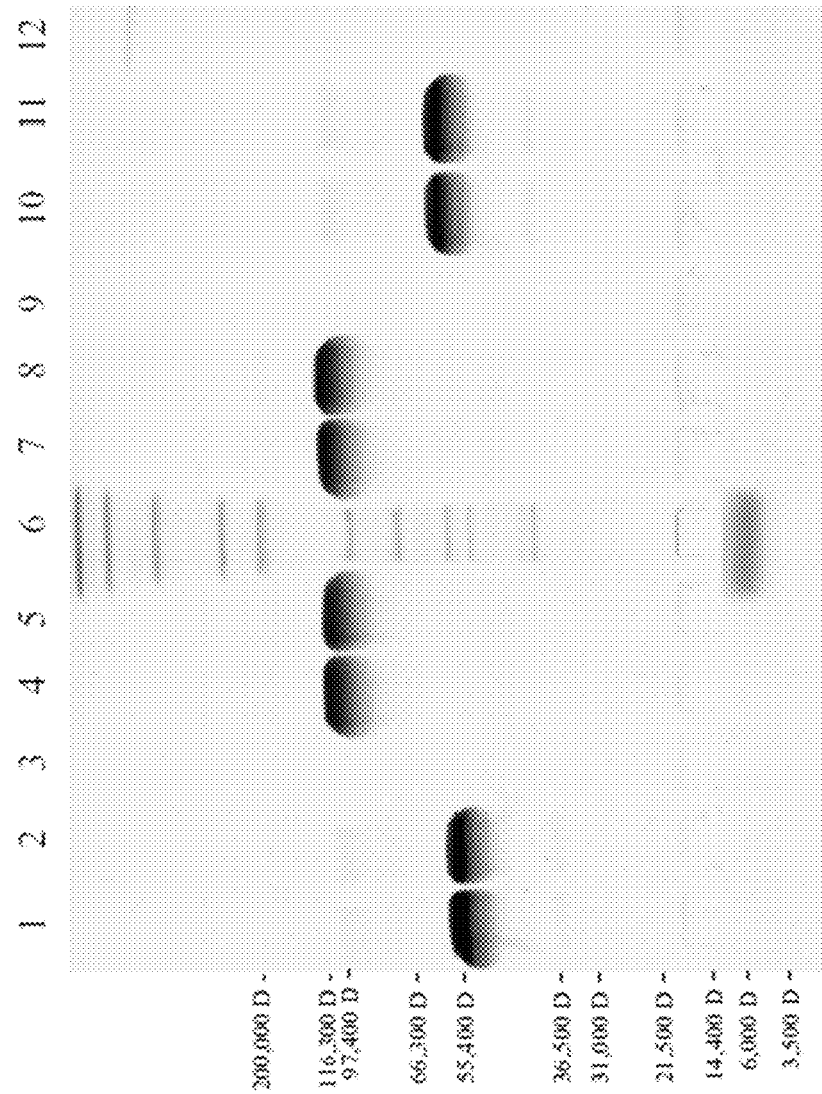

FIG. 78 depicts a canned gel image of SDS-PAGE Analysis of CTLA4$^{A29YL104E}$-Ig Coomassie Blue Stained Polyacrylamide (4-20%) Gel Electrophoresis Coomassie Blue Staining.

| Lane# | Description | Protein Load (μg) | Condition R/NR | % Purity (%) |
|---|---|---|---|---|
| 1 | CTLA4$^{A29YL104E}$-Ig Drug Substance | 10 | NR | 99 |
| 2 | CTLA4$^{A29YL104E}$-Ig Reference Material | 10 | NR | 99 |
| 3 | Blank | NA | NR | NA |
| 4 | CTLA4$^{A29YL104E}$-Ig Drug Substance | 10 | R | 100 |
| 5 | CTLA4$^{A29YL104E}$-Ig Reference Material | 10 | R | 100 |
| 6 | Molecular Weight Marker | NA | R | NA |
| 7 | CTLA4$^{A29YL104E}$-Ig Reference Material | 10 | R | 99 |
| 8 | CTLA4$^{A29YL104E}$-Ig Drug Product | 10 | R | 99 |
| 9 | Blank | 0 | NR | 0 |
| 10 | CTLA4$^{A29YL104E}$-Ig Reference Material | 10 | NR | 100 |
| 11 | CTLA4$^{A29YL104E}$-Ig Drug Product | 10 | NR | 100 |
| 12 | Staining control | 0.1 | NR | 100 |

Figure 79:
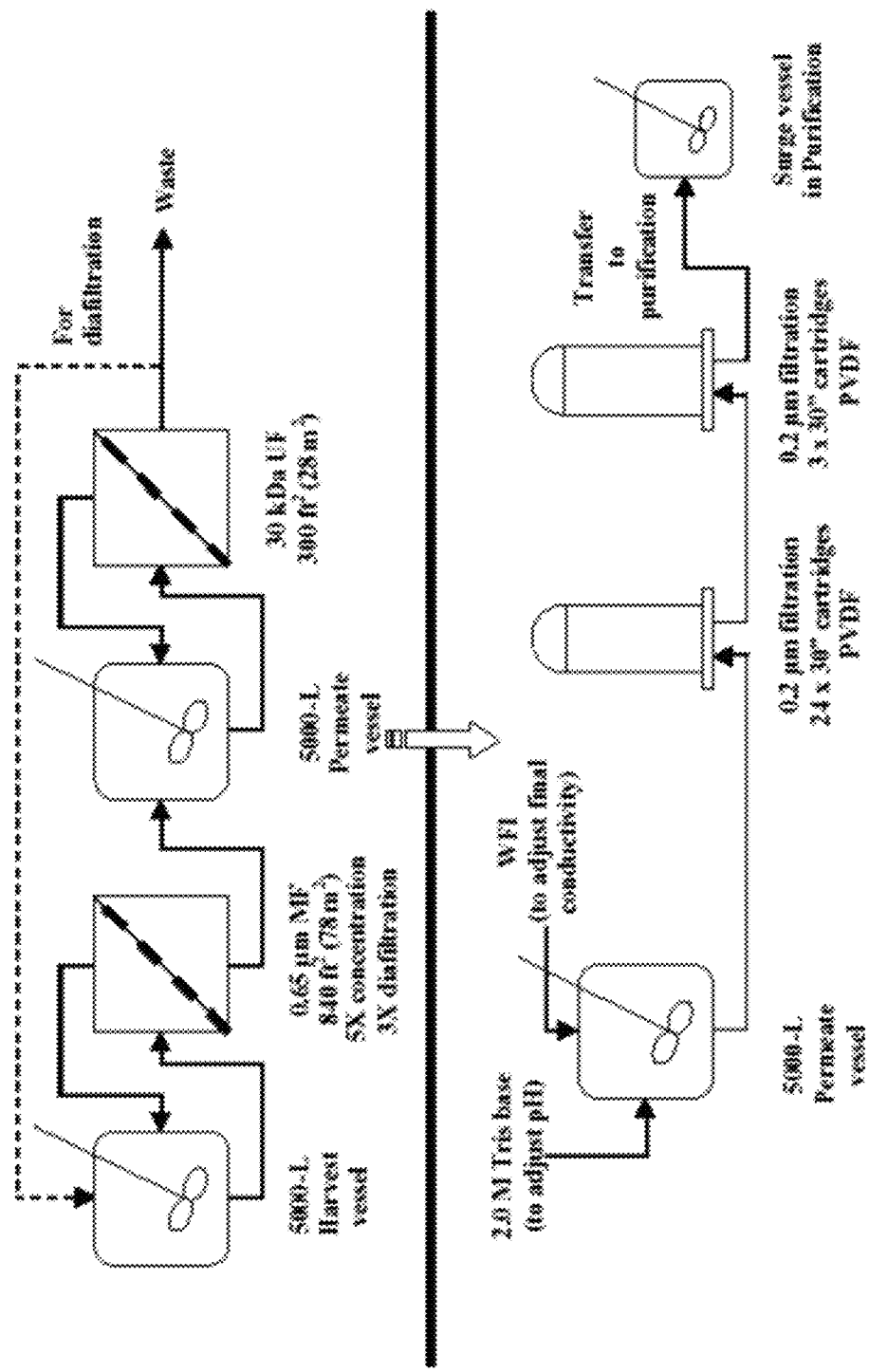

FIG. 79 depicts a flow diagram of the harvest steps, see Example 28.

Figure 80:
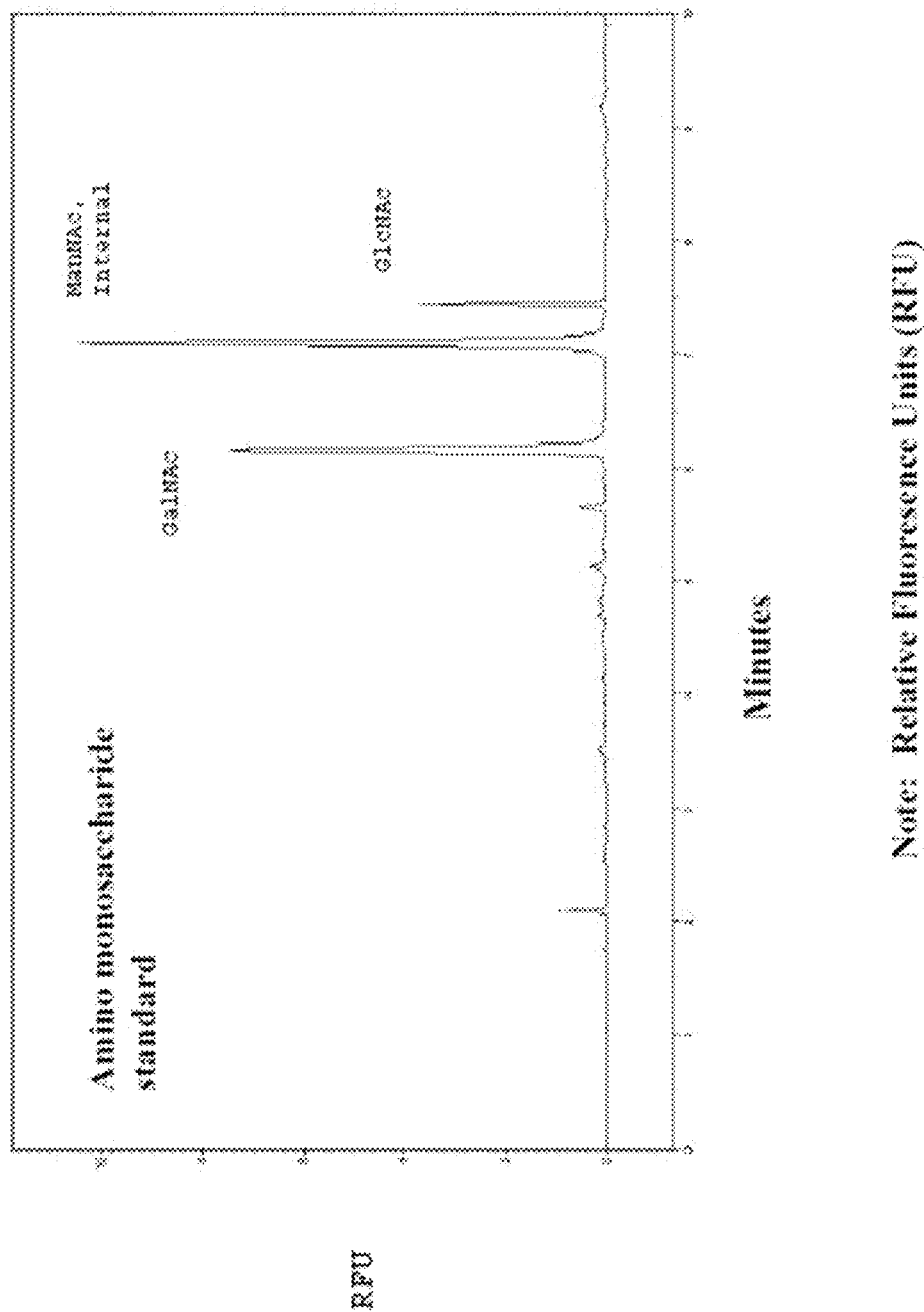

FIG. 80 depicts an electropherogram of system suitability of amino monosaccharides. See Example 16.

Figure 81:
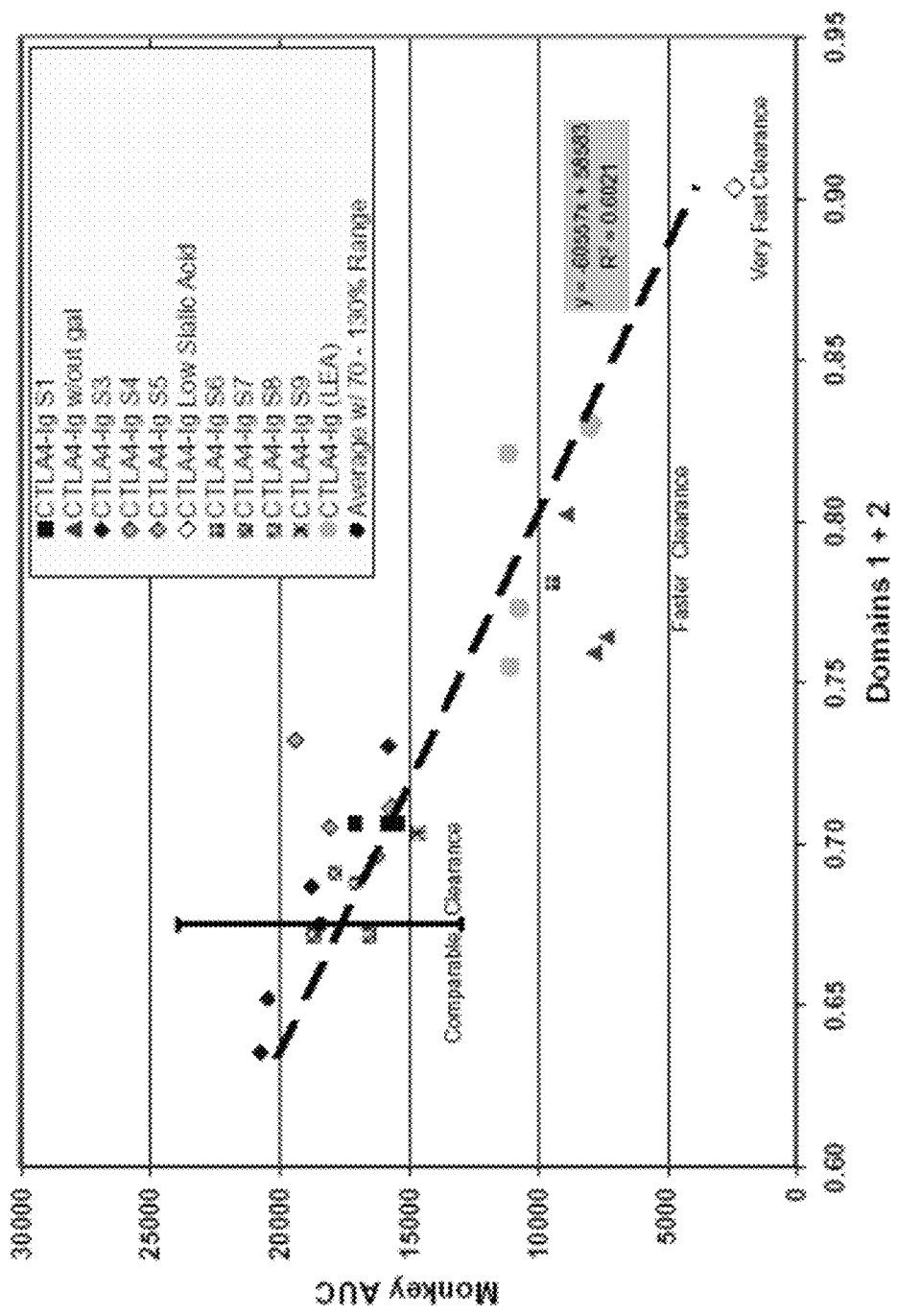

FIG. 81 depicts a graph of pharmacokinetic data showing monkey AUC on the Y axis and percent of N-linked glycosylation as shown in Domains I and II from a carbohydrate profile on the X axis. See methods of determining the N-linked carbohydrate profile in, for example, Examples 3, 44, 22 and 37. As the percentage of Domains I and II increases (and the percentage of Domains III, IV and V decreases), AUC increases. Note that the negative control, the CTLA4-Ig with low sialic acid is cleared very rapidly. Note that the mutant CTLA4-Ig molecules, CTLA4-Ig$^{A29YL104E}$-Ig (designated LEA) is included in this graph.

Figure 82:
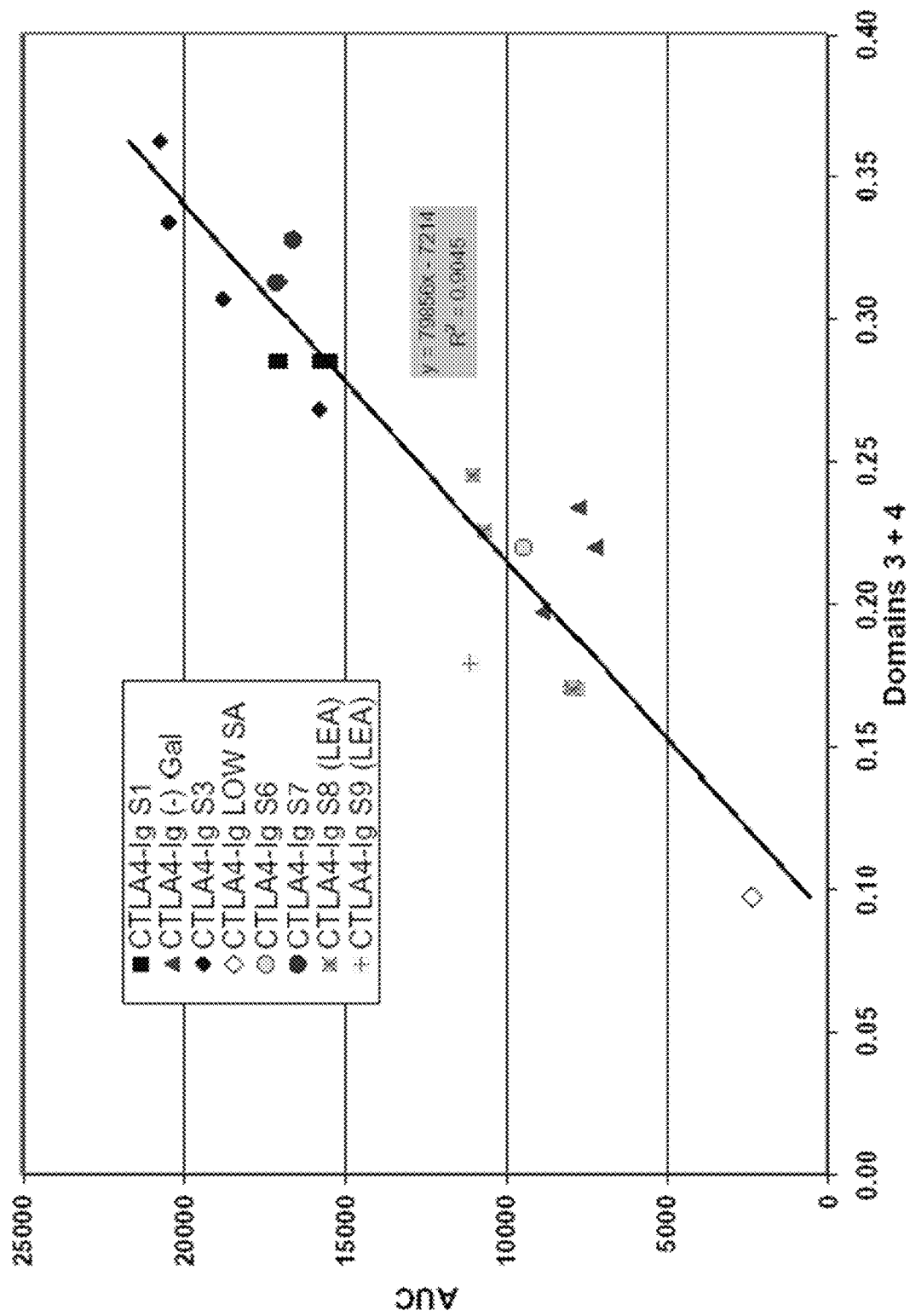

FIG. 82 depicts a graph of pharmacokinetic data showing AUC on the Y axis and percent of N-linked glycosylation as shown in Domains III and IV (as determined from an N-linked carbohydrate profile) on the X-axis. As the percentage of Domains III and IV increase, the AUC increases. Note that the negative control, the CTLA4-Ig with low sialic acid is cleared very rapidly. See methods of determining the N-linked carbohydrate profile in, for example, Examples 3, 44, 22 and 37. Note that the mutant CTLA4-Ig molecules, CTLA4-Ig$^{A29YL104E}$-Ig (designated LEA) is included in this graph.

Figure 83:
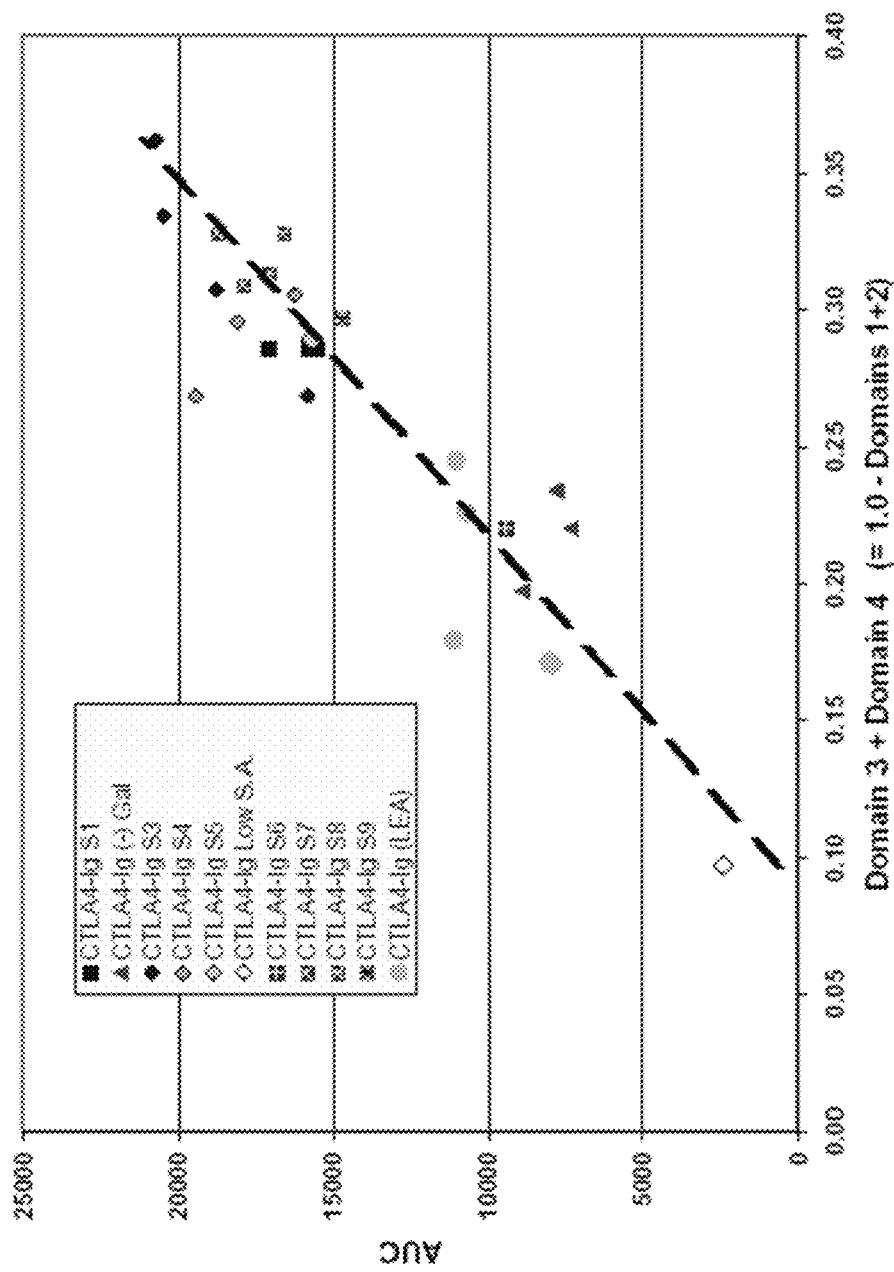

FIG. 83 depicts another graph of pharmacokinetic data showing AUC on the Y axis and percent of N-linked glycosylation as shown in Domains III and IV from a carbohydrate profile on the X-axis. As the percentage of Domains III and IV increase, the AUC increases. Note that the negative control, the CTLA4-Ig with low sialic acid is cleared very rapidly. See methods of determining the N-linked carbohydrate profile in, for example, Examples 3, 44, 22 and 37. Note that the mutant CTLA4-Ig molecules, CTLA4-Ig$^{A29YL104E}$-Ig (designated LEA) is included in this graph.

Figure 84:
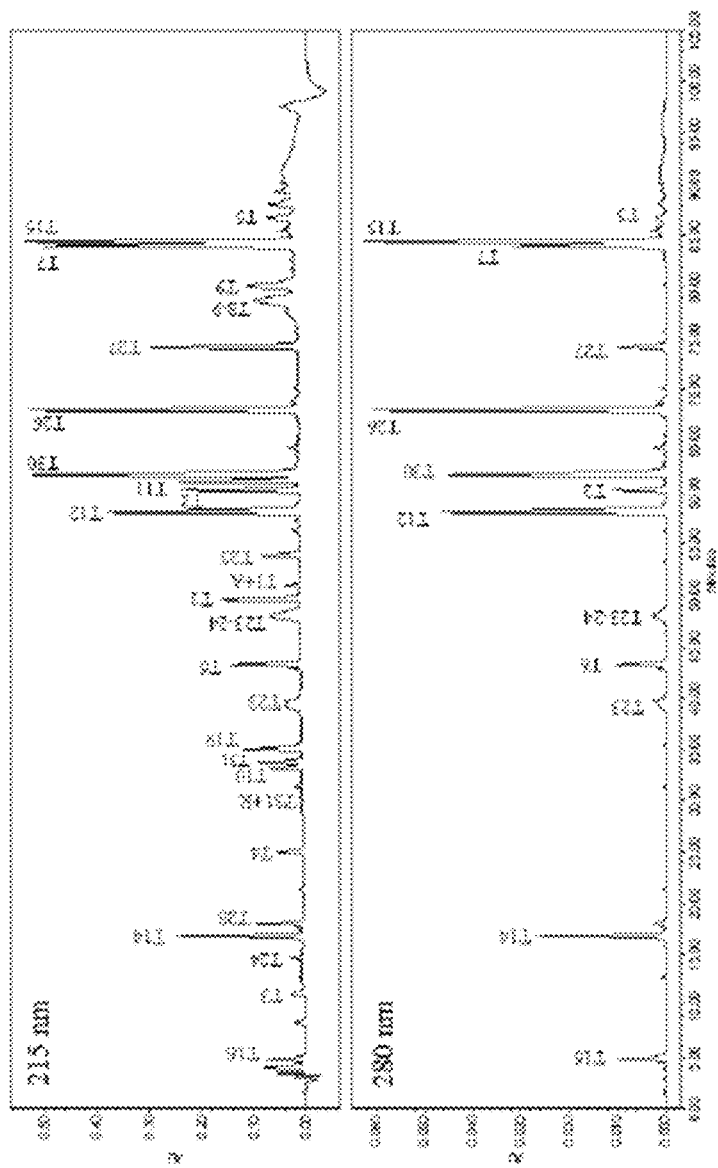

FIG. 84 depicts a tryptic Map of CTLA4-Ig standard see Table at end of Example 65 for peak assignments. The small peak labeled T1+A is the T1 tryptic peptide extended by an N-terminal alanine residue. The small peak labeled T31+K is the T31 tryptic peptide extended by a C-terminal lysine residue.

Figure 85:
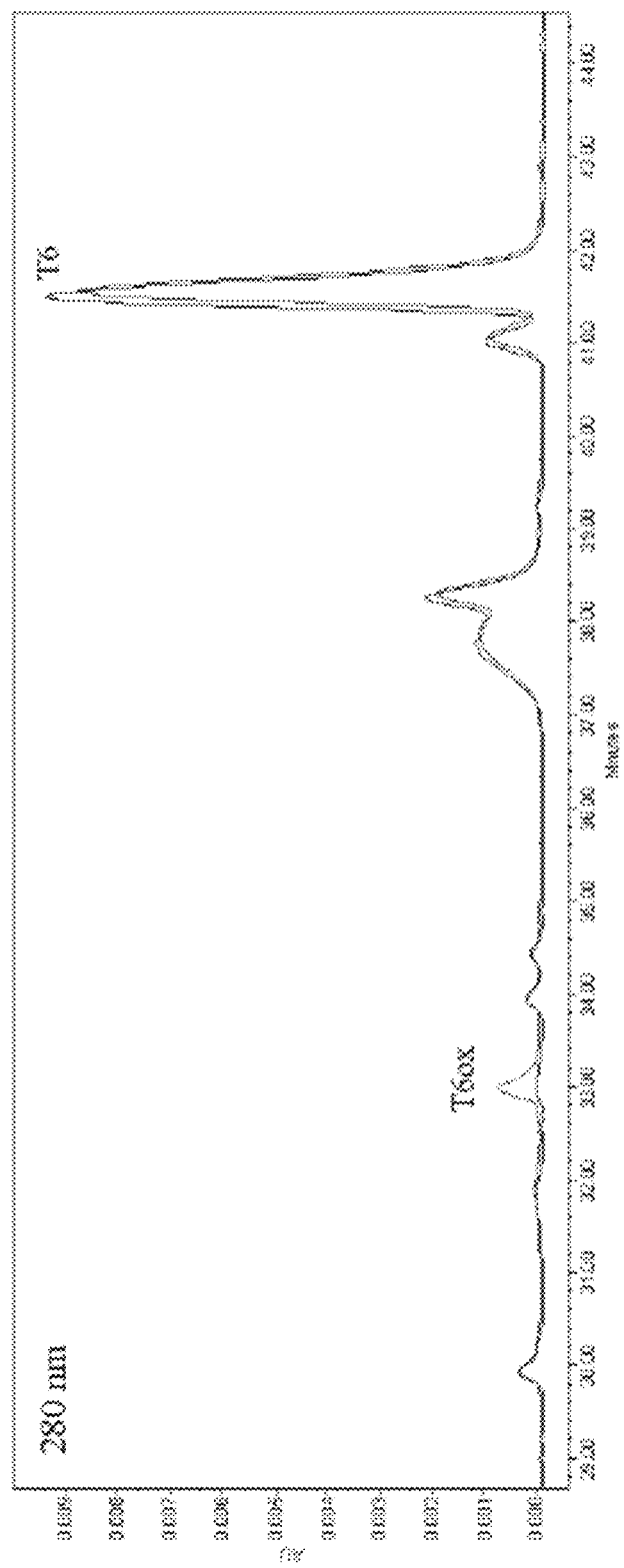

FIG. 85 depicts an overlay of 280 nm Data for Tryptic Map of CTLA4-Ig Standard Plus Same Spiked with 5 mole % of T6ox Indicator Peptide, Met(O) 85 (84-93). See Example 65.

Figure 86:
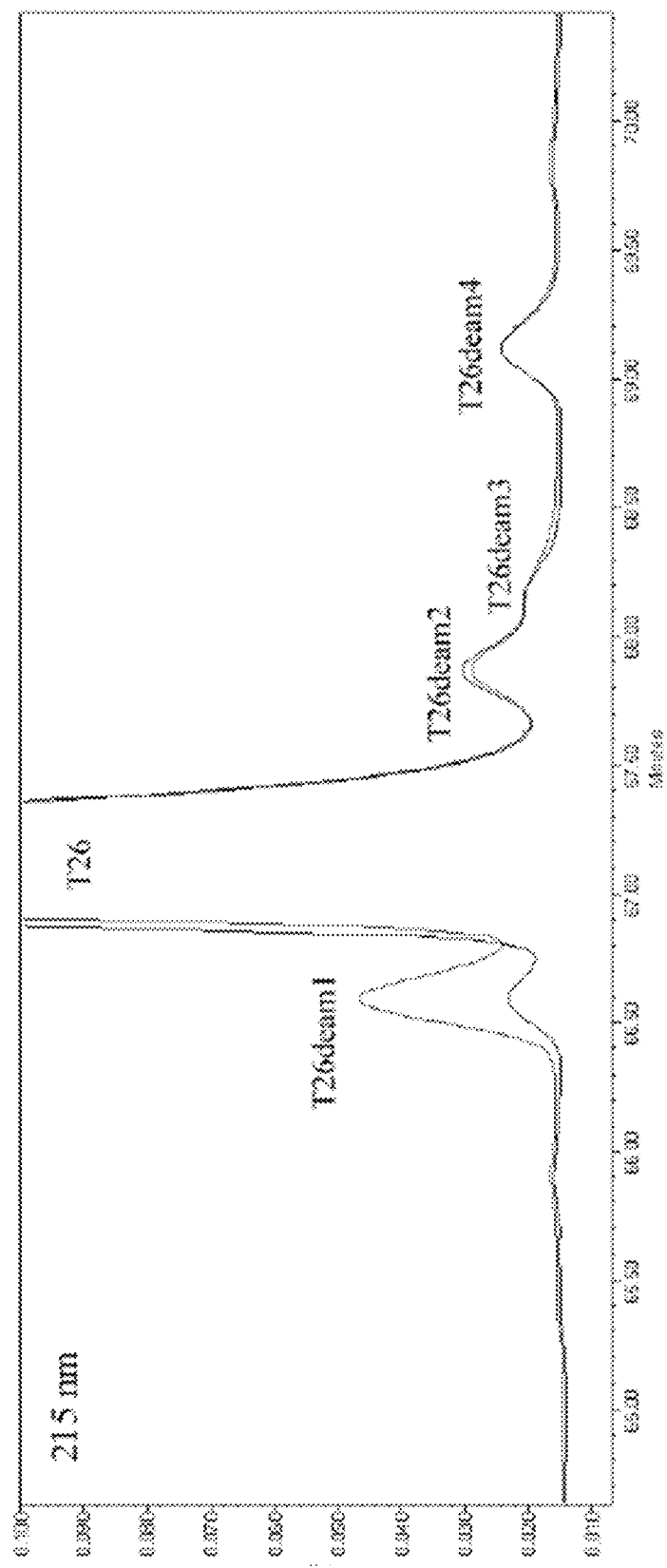

FIG. 86 depicts an expanded View of 215 nm Data for Tryptic Map of CTLA4-Ig Standard Plus Same Spiked with 5 mole % of T26deam1 Indicator Peptide, isoAsp294(281-302). See Example 65.

Figure 87:
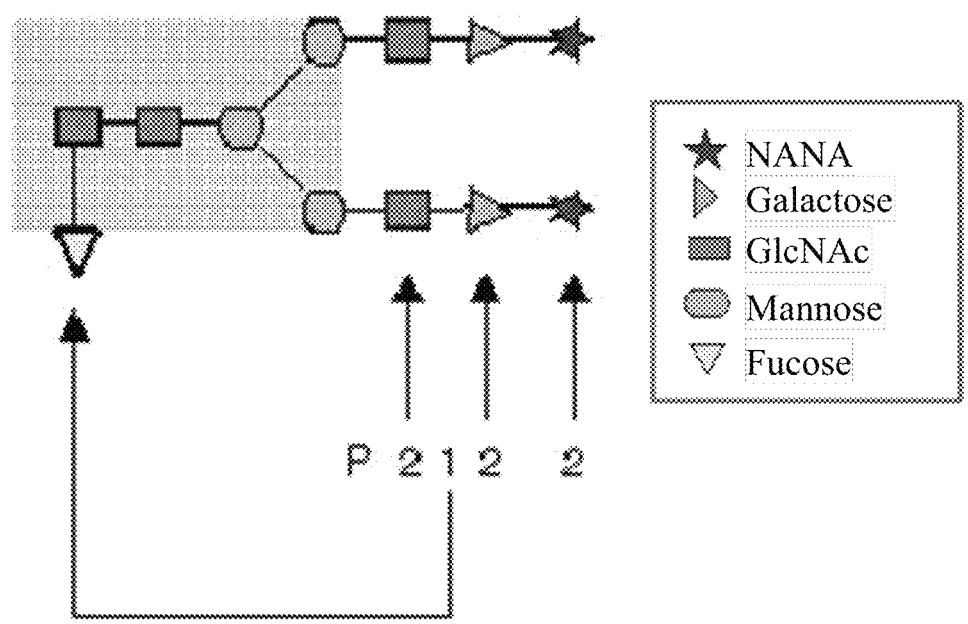

FIG. 87 provides the legend for naming the oligosaccharides in FIG. 88. The grey shaded area shows the N-linked oligosaccharide core structure, where P stands for PNGase F digestion, and the subsequent digits describe the number of Mannose (circle), Fucose (downwards pointing triangle), Galactose (right pointing triangle), and sialic acid residues (star), respectively. N-acetyl glucosamine (GlcNAc) is represented by a square.

Figure 88C:
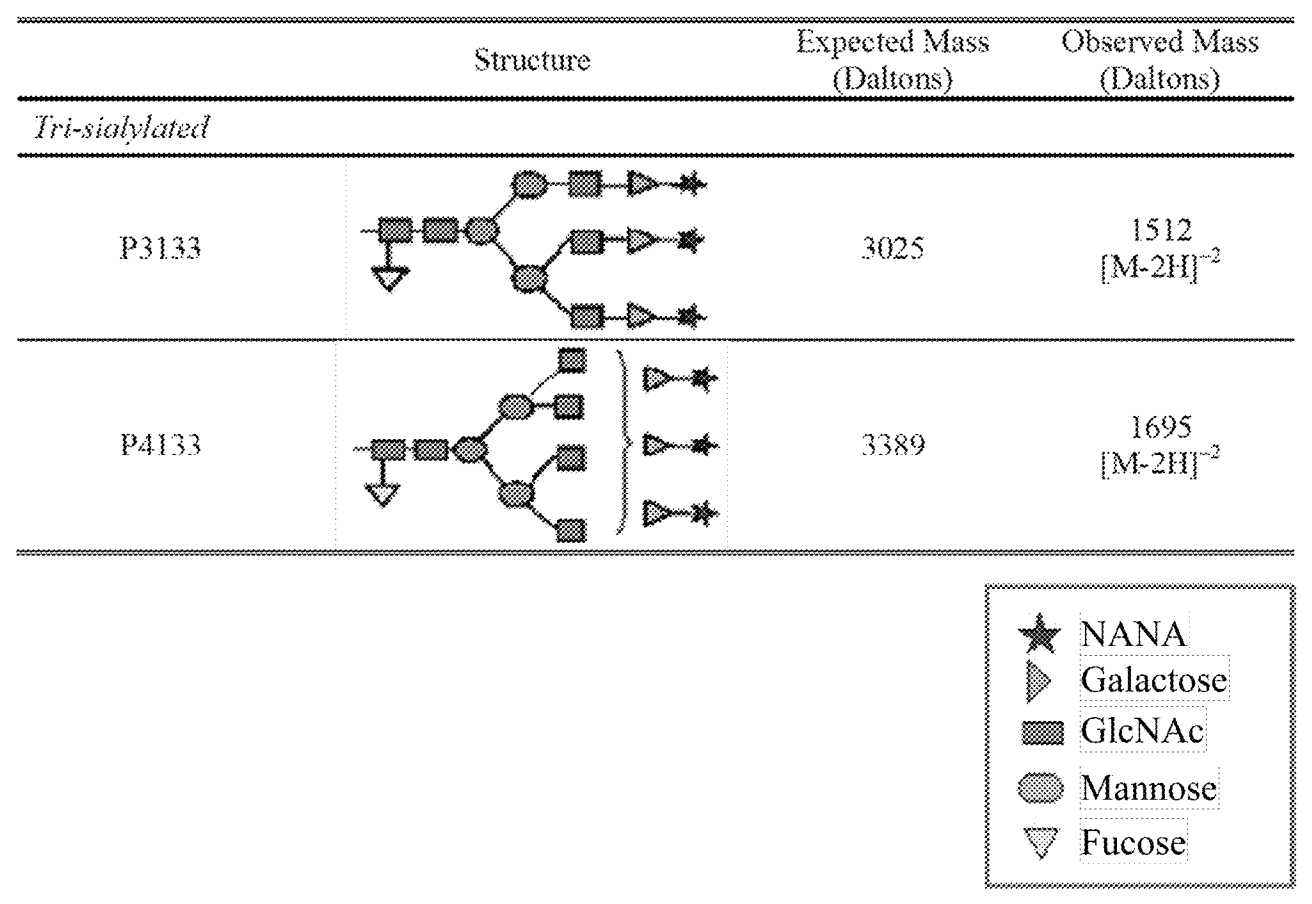

FIG. 88A-88C shows the N-linked oligosaccharide structures and masses detected in CTLA4-Ig.

Figure 89:
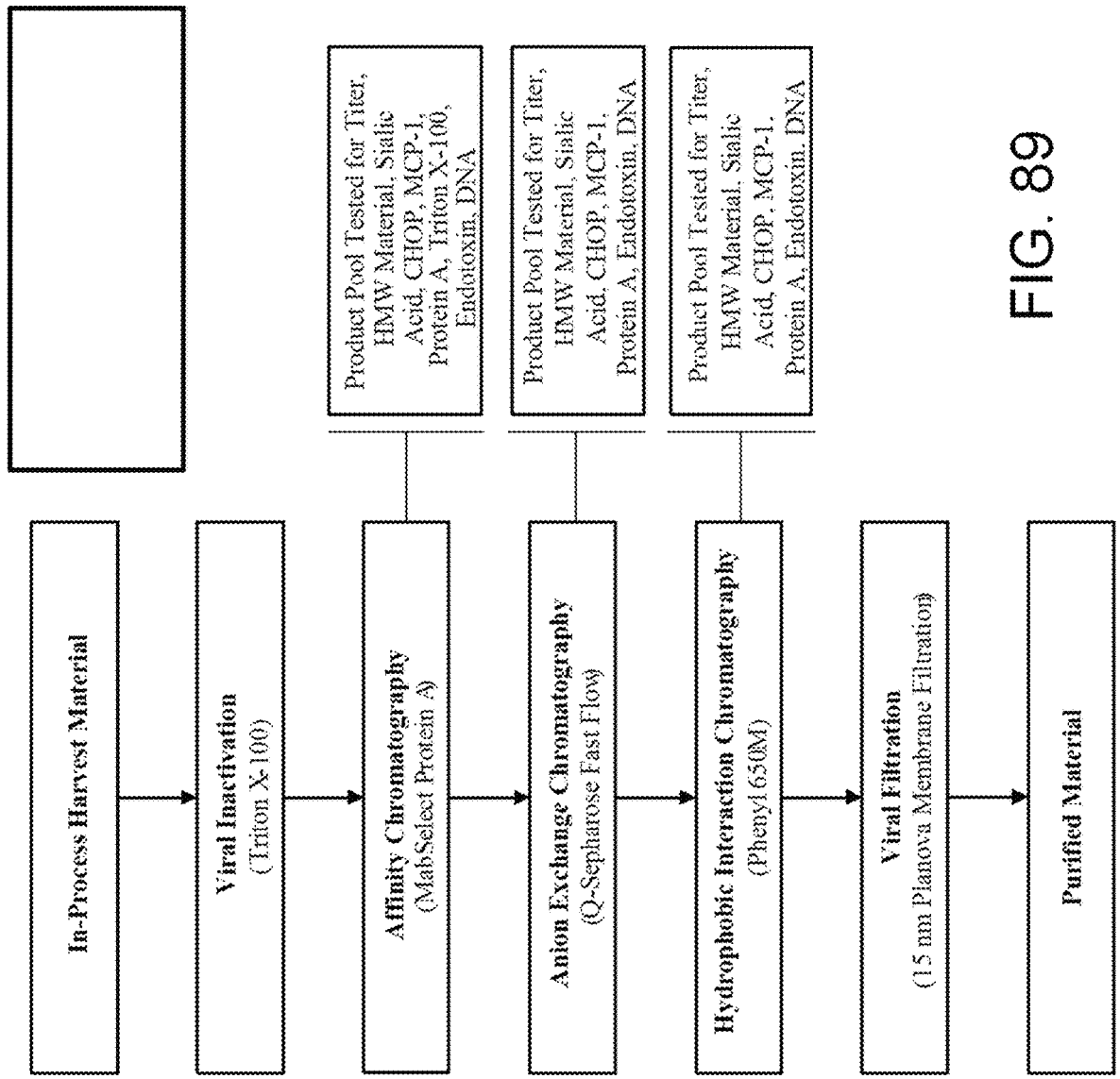

FIG. 89 is a flow diagram showing an example of a purification process of CTLA4$^{A29YL104E}$.

Figure 90:
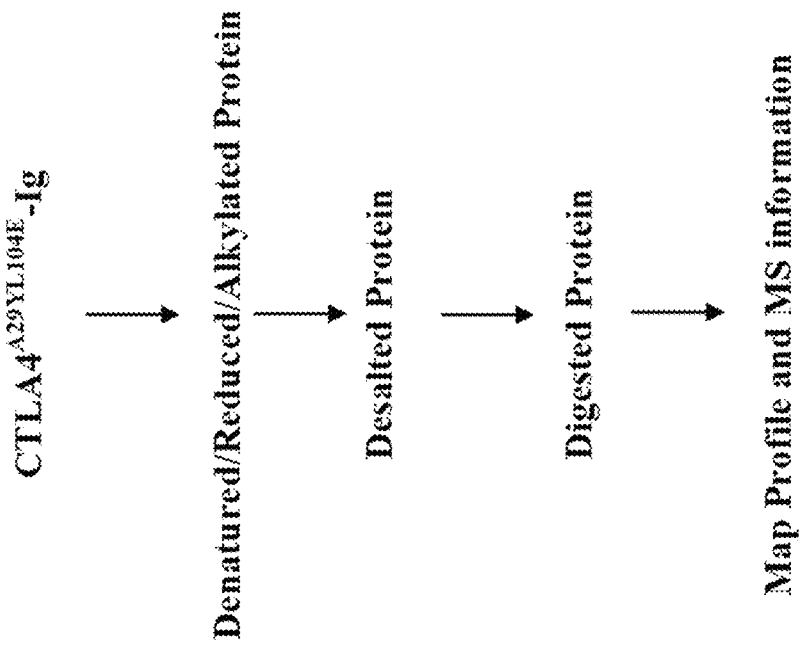

FIG. 90 is a flow diagram showing an overview of the procedure for carbohydrate content analysis of a CTLA$^{A29YL104E}$-Ig composition, tryptic peptide mapping and IEF.

Figure 91:
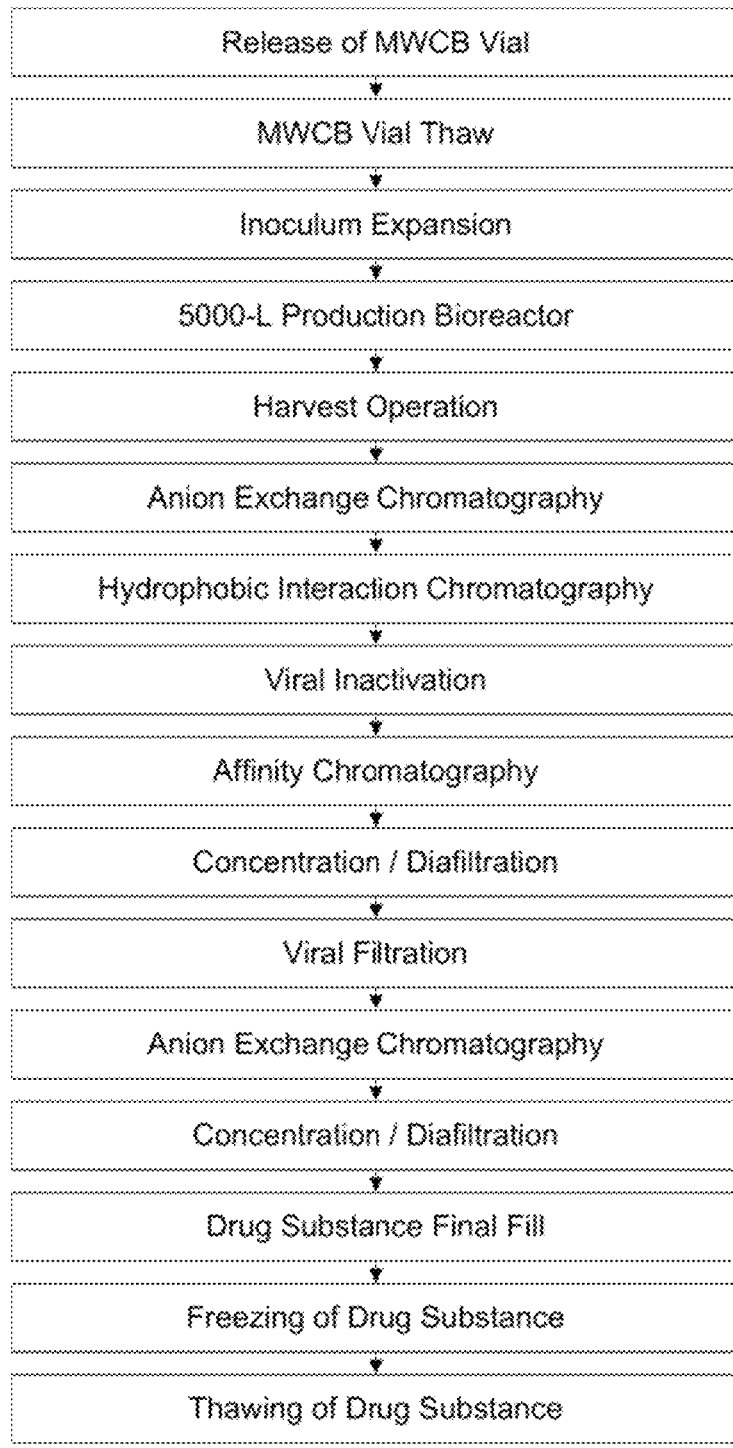

FIG. 91 is a flow diagram for the CTLA4-Ig production process.

Figure 92:
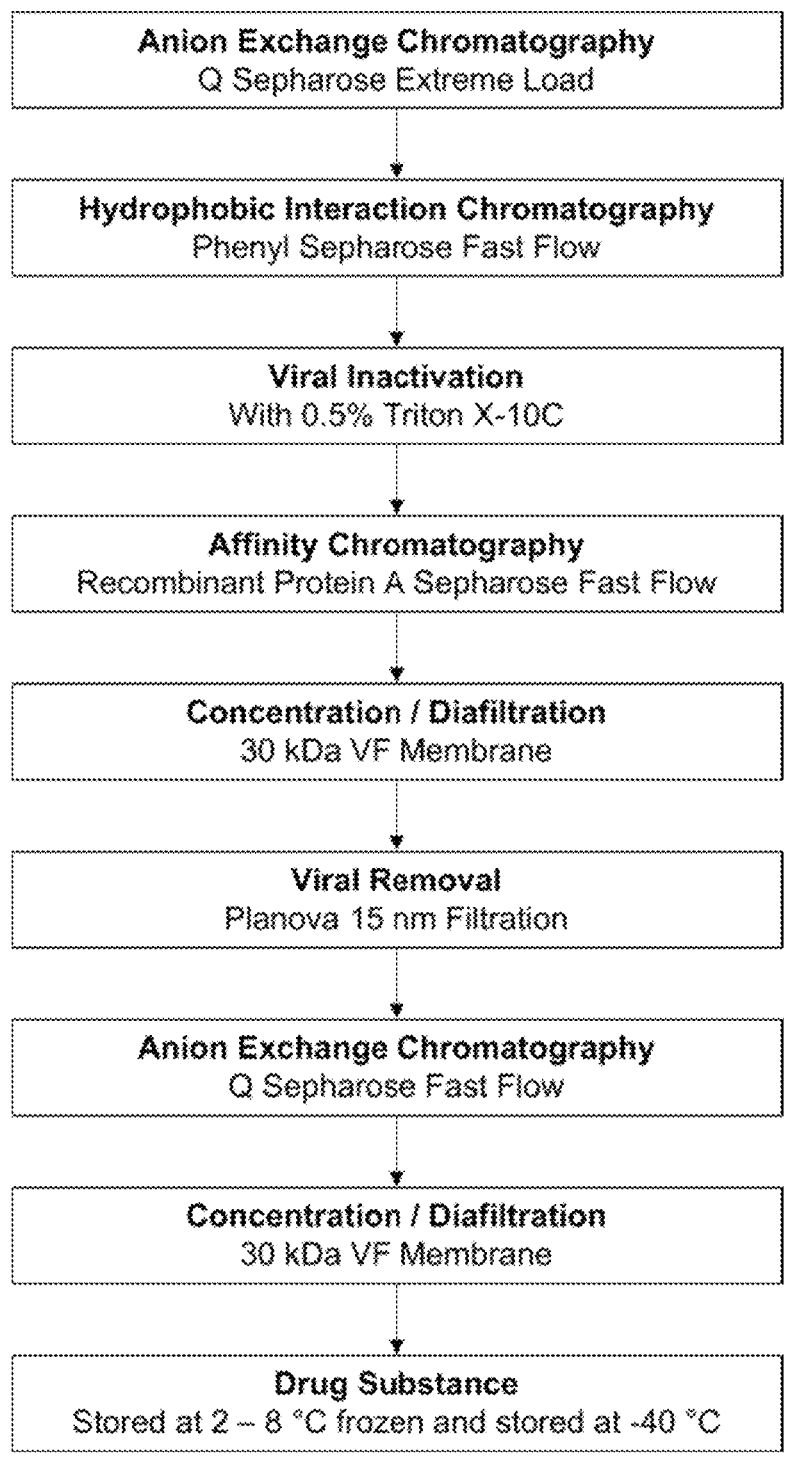

FIG. 92 is a flow diagram for the downstream steps of CTLA4-Ig production process.

Figure 93:
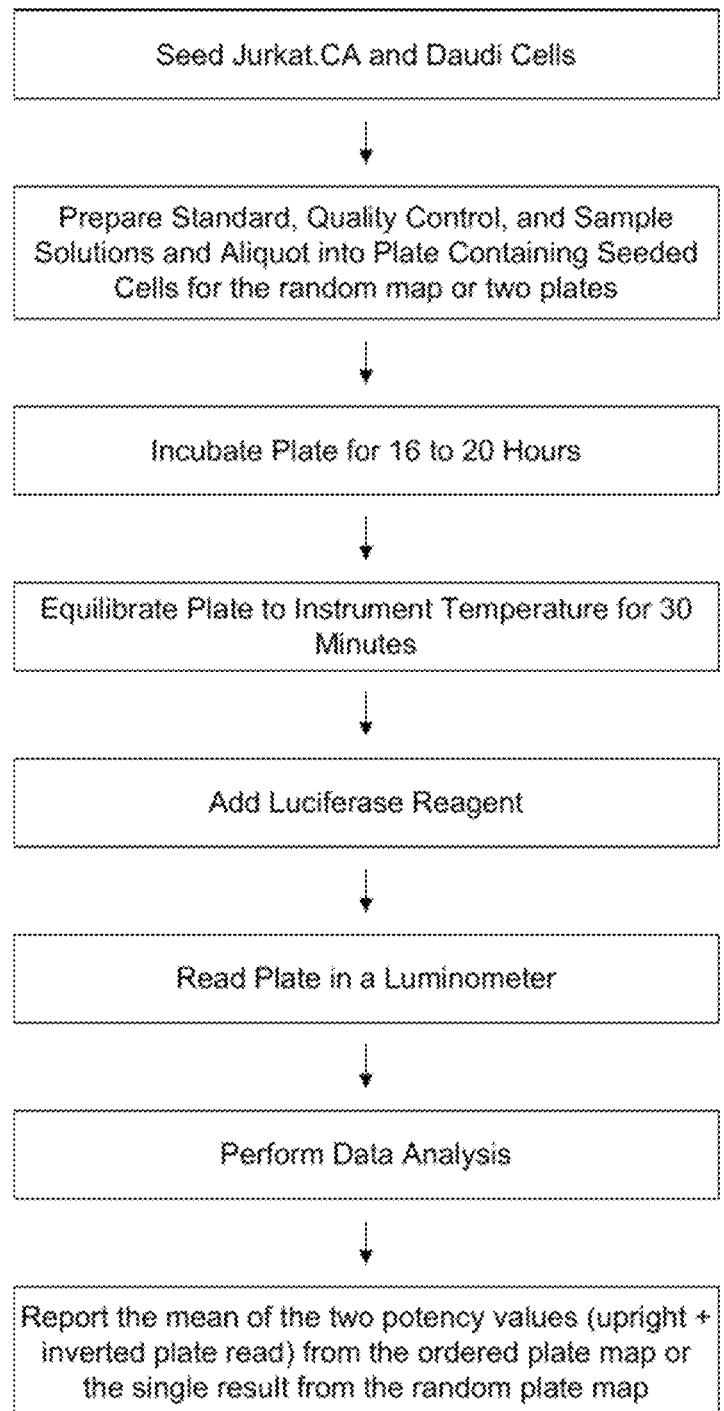

FIG. 93 is a flow diagram of the procedure for an in-vitro cell based bioassay for CTLA4$^{A29YL104E}$-Ig.

Figure 94:
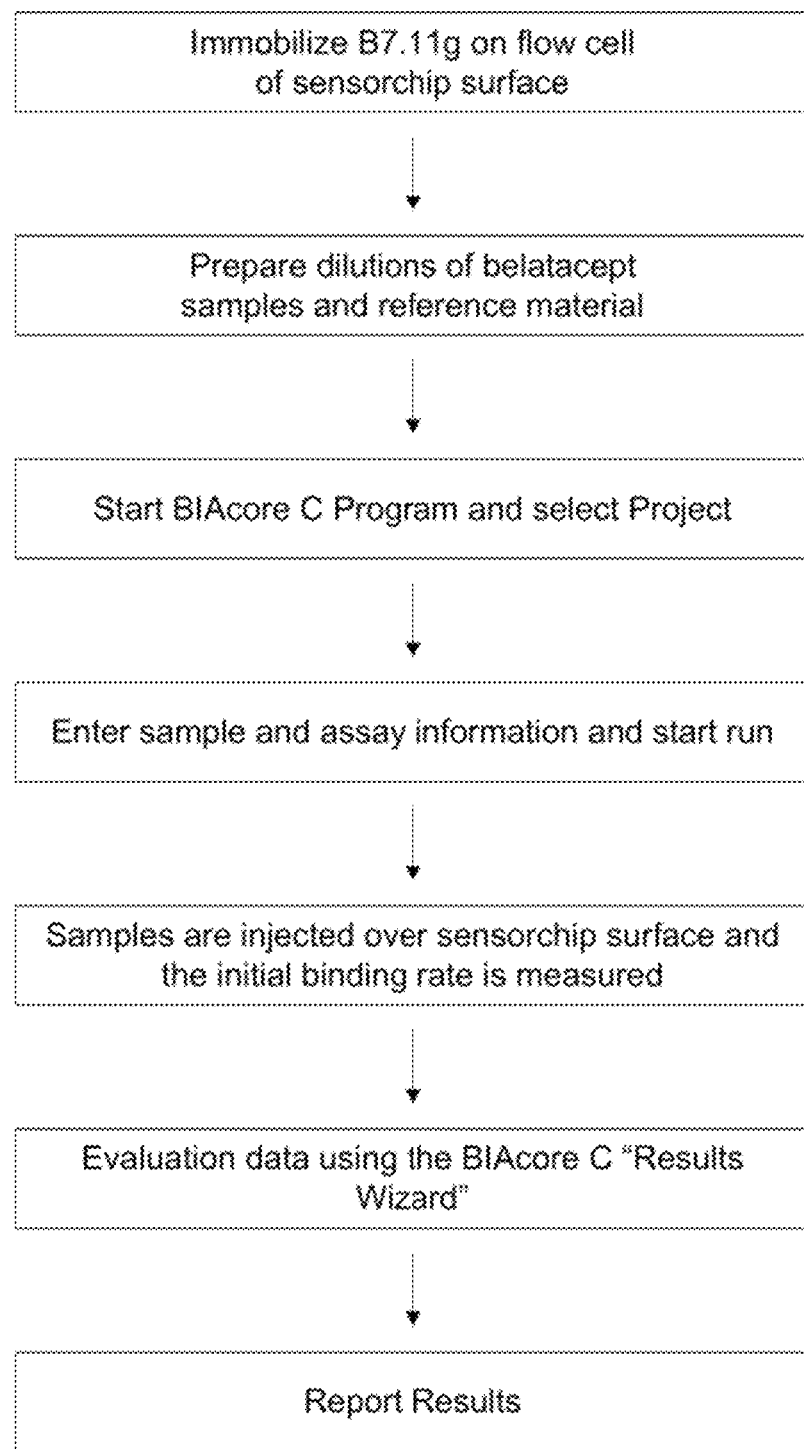

FIG. 94 is an outline for a method for determination of bio-specific binding of CTLA4$^{A29YL104E}$-Ig to the B7.1-Ig receptor by surface plasmon resonance (BIAcore).

Figure 95:
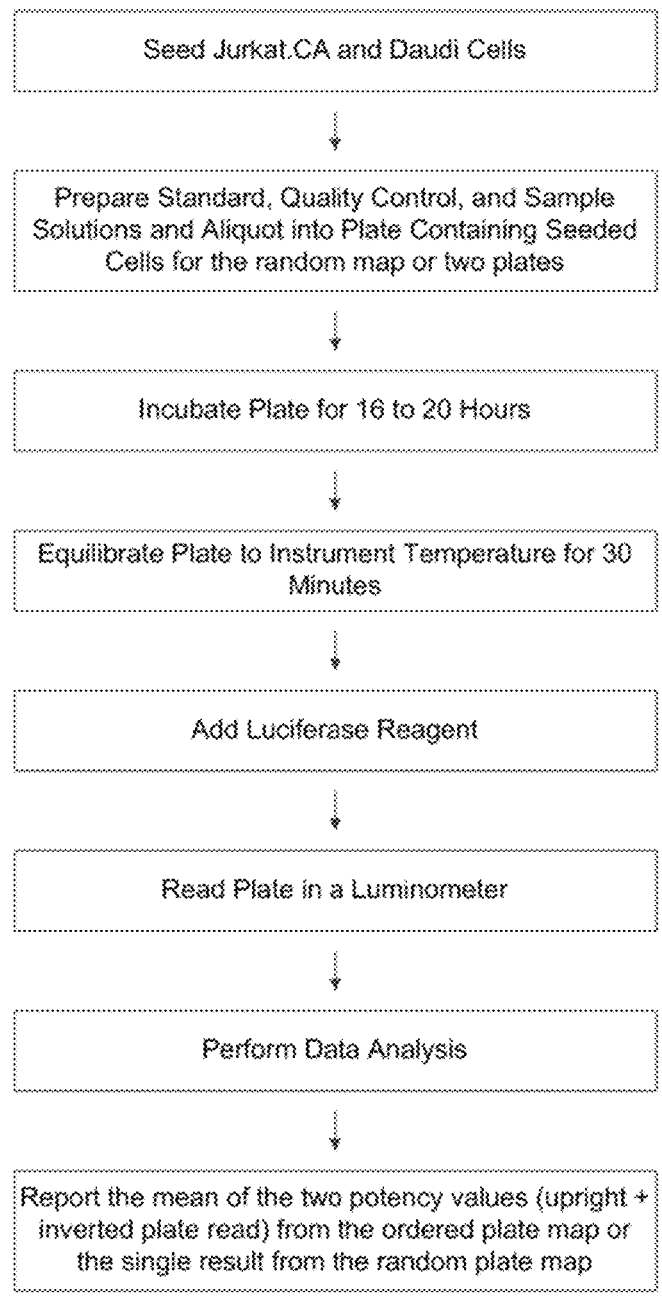

FIG. 95 is a flow diagram of the procedure for an in-vitro cell based bioassay for CTLA4$^{A29YL104E}$-Ig.

FIG. 96 shows oligosaccharide structures of Peptide T8.

Figure 97:
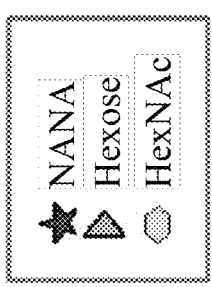

FIG. 97 shows oligosaccharide structures of Peptide T9.

Figure 98:
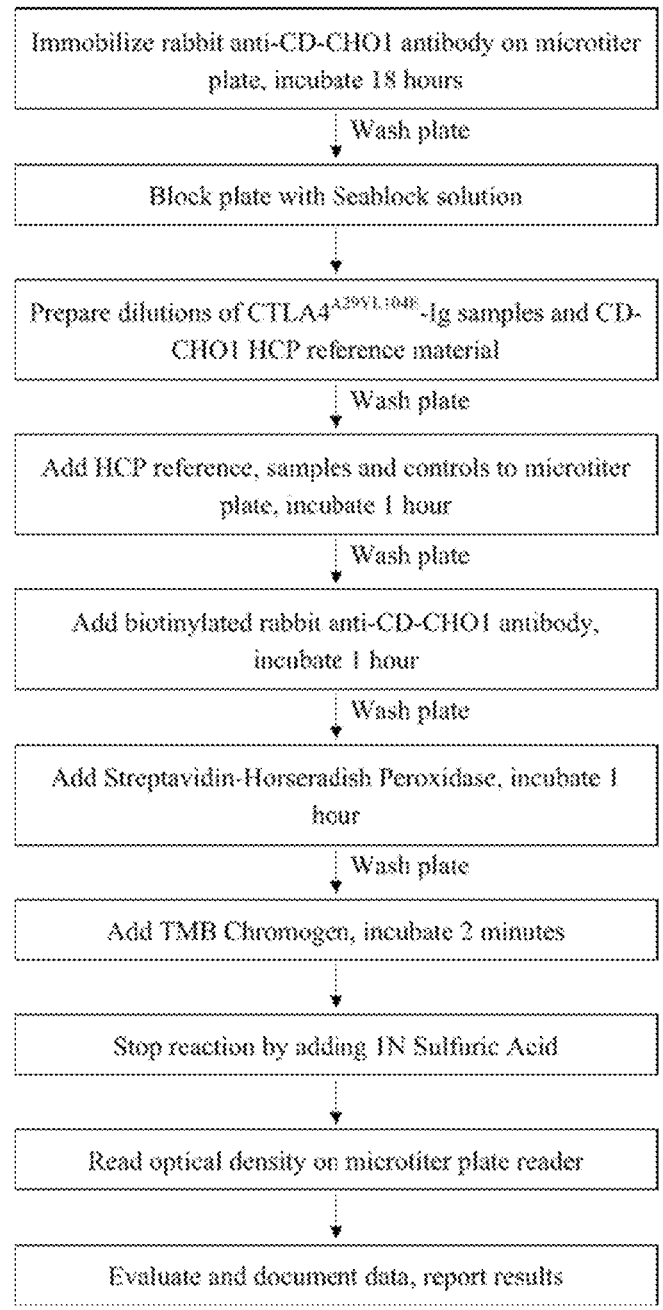

FIG. 98 is a method outline for determination of Chinese hamster ovary (CHO) host cell protein impurities in CTLA4$^{A29YL104E}$-Ig drug substance by ELISA.

Figure 99:
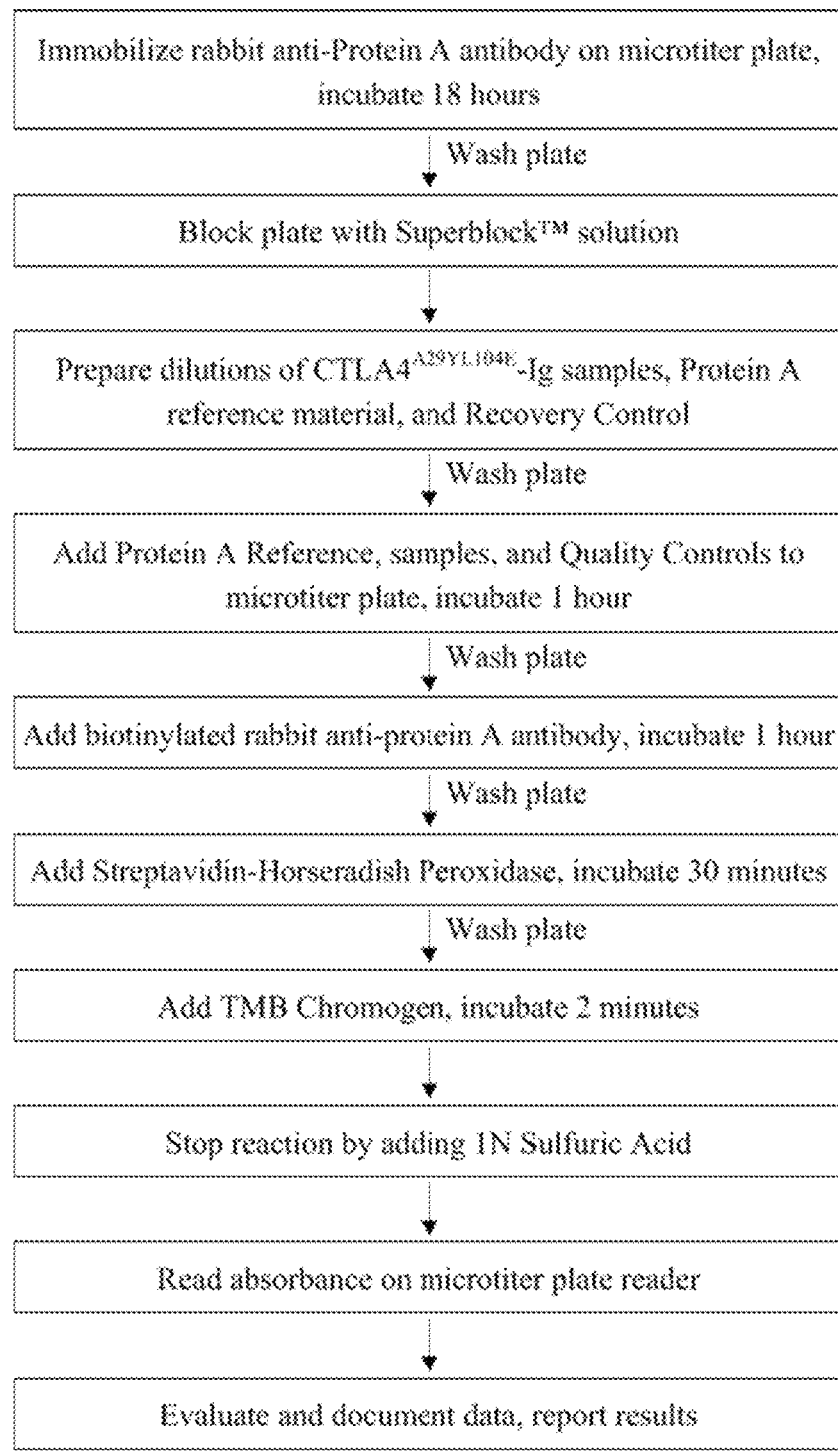

FIG. 99 is a method outline for determination of Protein A levels in CTLA4$^{A29YL104E}$-Ig by ELISA.

DETAILED DESCRIPTION OF THE INVENTION

CTLA4-Ig molecules can be used to treat a variety of disorders, including disorders relating to aberrant immunoproliferative and immunoreactive phemonena such as autoimmunity and allergy. The invention provides CTLA4-Ig compositions that comprise, for example, populations of CTLA4-Ig molecules having particular glycosylation modifications, having particular carbohydrate profiles or characteristics, having particular multimeric structures, and/or having particular avidity strengths. Documents that are hereby incorporated by reference in their entirety that also describe CTLA4-Ig molecules, uses and methods thereof, include U.S. Pat. Nos. 5,434,131; 5,851,795; 5,885,796; 5,885,579; and 7,094,874.

The invention also provides cell lines that are capable of producing large amounts of CTLA4-Ig molecules via the mass-production and culturing methods provided herein. One particular cell line of the invention is a clonal cell line that can be used to mass-produce CTLA4-Ig molecules such that it has a particular glycosylation and carbohydrate profile. As compared to the heterogeneous and non-clonal cell population having ATCC Accession No. 68629 (see U.S. Pat. No. 5,434,131, which is hereby incorporated by reference in its entirety), the clonal cell lines of the invention can secrete a population of CTLA4-Ig molecules having a more consistent or more uniform glycosylation or carbohydrate profile. Further, as compared to the heterogeneous and non-clonal cell population having ATCC Accession No. 68629, the clonal cell lines of the invention can secrete a greater amount of CTLA4-Ig molecules, in part because the present clonal cell lines are selected to have a high-copy number of CTLA4-Ig expression cassettes integrated into a single site in the genome of the cell.

The invention provides for the discovery that the avidity and potency of CTLA4-Ig (SEQ ID NO:2) can be increased by making two amino acid substitutions in the B7 binding region of the CTLA-4 binding domain: (i) alanine at position 29 of SEQ ID NO:2 is substituted by tyrosine (A29Y), and (ii) lysine at position 10 µL of SEQ ID NO:2 is substituted by glutamate (L104E). The invention provides a subgenus of CTLA4-Ig molecules, called "beta polypeptide molecules," which comprise beta polypeptides which have B7 binding activity and may comprise the amino acid sequence in SEQ ID NO: 24 (CTLA4 extracellular domain with A29Y and L104E mutations), linked to an immunoglobulin constant region, or portion thereof.

[SEQ ID NO: 24]
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSD

A CTLA4 extracellular domain

[SEQ ID NO: 18]
MHVAQPAVVLASSRGIASFVCEYASPGKATEVRVTVLRQADSQVTEVCAA

TYMMGNELTFLDDSICTGTSSGNQVNLTIQGLRAMDTGLYICKVELMYPP

PYYLGIGNGTQIYVIDPEPCPDSD

Terms

As used herein, the term "clonal" refers to a cell population that is expanded from a single cell. With respect to a clonal cell line or clonal cell population capable of expressing a CTLA4-Ig molecule, the clonal cell line or population is expanded from a single cell that was isolated from a population of cells that were transfected with an expression vector encoding the CTLA4-Ig molecule. The transfected population of cells can be a heterogeneous population. A clonal cell line or population can be considered to be homogeneous in the sense that all of the cells in the population came from a single transfectant.

As used herein, the term "B7-1" refers to CD80; the term "B7-2" refers CD86; and the term "B7" refers to either or both of B7-1 and B7-2 (CD80 and CD86). The term "B7-1-Ig" or "B7-1Ig" refers to CD80-Ig; the term "B7-2-Ig" or "B7-2Ig" refers CD86-Ig.

Figure 1B:
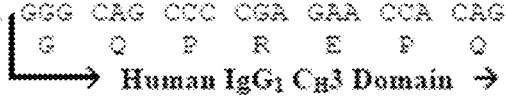

As used herein, the terms "CTLA4-Ig" or "CTLA4-Ig molecule" or "CTLA4Ig molecule" or "CTLA4-Ig protein" or "CTLA4Ig protein" are used interchangeably, and refer to a protein molecule that comprises at least a CTLA4-Ig polypeptide having a CTLA4 extracellular domain and an immunoglobulin constant region or portion thereof. In some embodiments, for example, a CTLA4-Ig polypeptide comprises at least the amino acid sequence of SEQ ID NO:18. In certain embodiments, the CTLA4 extracellular domain and the immunoglobulin constant region or portion thereof can be wild-type, or mutant or modified. A mutant CTLA4-Ig polypeptide is a CTLA4-Ig polypeptide comprising a mutant CTLA4 extracellular domain. A mutant CTLA4Ig molecule comprises at least a mutant CTLA4-Ig polypeptide. In some embodiments, the CTLA4 extracellular domain and the immunoglobulin constant region or portion thereof can be mammalian, including human or mouse. In some embodiments, a mutant CTLA4 extracellular domain can have an amino acid sequence that is at least 75%, 80%, 85%, 90%, 95%, 96%, 97%, 98%, or 99% identical to the CTLA4 extracellular domain shown in FIG. 1 or SEQ ID NO:18. In some embodiments, a mutant immunoglobulin constant region or portion thereof can have an amino acid sequence that is at least 75%, 80%, 85%, 90%, 95%, 96%, 97%, 98%, or 99% identical to the immunoglobulin (g) constant region as shown in FIG. 1. The polypeptide can further comprise additional protein domains. A CTLA4-Ig molecule can refer to a monomer of the CTLA4-Ig polypeptide, and also can refer to multimer forms of the polypeptide, such as dimers, tetramers, and hexamers, etc. (or other high molecular weight species). CTLA4-Ig molecules are also capable of binding to CD80 and/or CD86. CTLA4-Ig molecules include mutant CTLA4Ig molecules, such as "beta polypeptides molecules," e.g., CTLA4$^{A29YL104E}$-Ig. For example, CTLA4-Ig comprises CTLA4-Ig molecules, and CTLA4$^{A29YL104E}$-Ig comprises beta polypeptides molecules (an example of mutant CTLA4-Ig molecules).

As used herein, the term "CTLA4 extracellular domain" refers to a protein domain comprising all or a portion of the amino acid sequence shown in SEQ ID NO:18, that binds to B7-1 (CD80) and/or B7-2 (CD86). In some embodiments, a CTLA4 extracellular domain can comprise a polypeptide having an amino acid sequence that is at least 75%, 80%, 85%, 90%, 95%, 96%, 97%, 98%, or 99% identical to amino acids 27-150 of SEQ ID NO:2, which are the same as amino acids shown SEQ ID NO:18. The amino acid 151 of SEQ ID NO:2 is a junction amino acid.

As used herein, the term "beta polypeptide" refers to a mutant CTLA4-Ig polypeptide that (1) comprises the amino acid sequence of SEQ ID NO:18 wherein the amino acid at position 29 is mutated to tyrosine and the amino acid at position 10 μL is mutated to glutamate, optionally with various additional mutations, and an immunoglobulin constant region, or a portion thereof; and (2) is capable of binding to CD80 and/or CD86. In some embodiments, for example, a beta polypeptide comprises at least the amino acid sequence of the extracellular domain of $CTLA4^{A29YL104E}$-Ig (as shown in SEQ ID NO:24). Non-limiting examples of beta polypeptides include belatacept and SEQ ID NOS: 4 and 11-16. In certain embodiments, the immunoglobulin constant region or portion thereof can be wild-type, or mutant or modified. In certain embodiments, the immunoglobulin constant region or portion thereof can be mammalian, including human or mouse. Additional non-limiting examples of beta polypeptides include a beta polypeptide comprising one or more amino acid mutations in the immunoglobulin constant region or portion thereof (for example, substitution of cysteine 120 of SEQ ID NO:4), and a beta polypeptide comprising further mutations at one or more of amino acid position 25, 30, 93, 96, 103 or 105 of SEQ ID NO:18. A beta polypeptide molecule comprises a beta polypeptide. A beta polypeptide molecule can refer to a monomer of the beta polypeptide and smultimer forms of the beta polypeptide, such as dimers, tetramers and hexamers, etc. For example, belatacept comprises beta polypeptide molecules. Beta polypeptide molecules are further described in U.S. Provisional Application No. 60/849,543 filed on Oct. 5, 2006, which is hereby incorporated by reference in its entirety.

As used herein, the terms "glutamate" and "glutamic acid" are used interchangeably.

Figure 4:
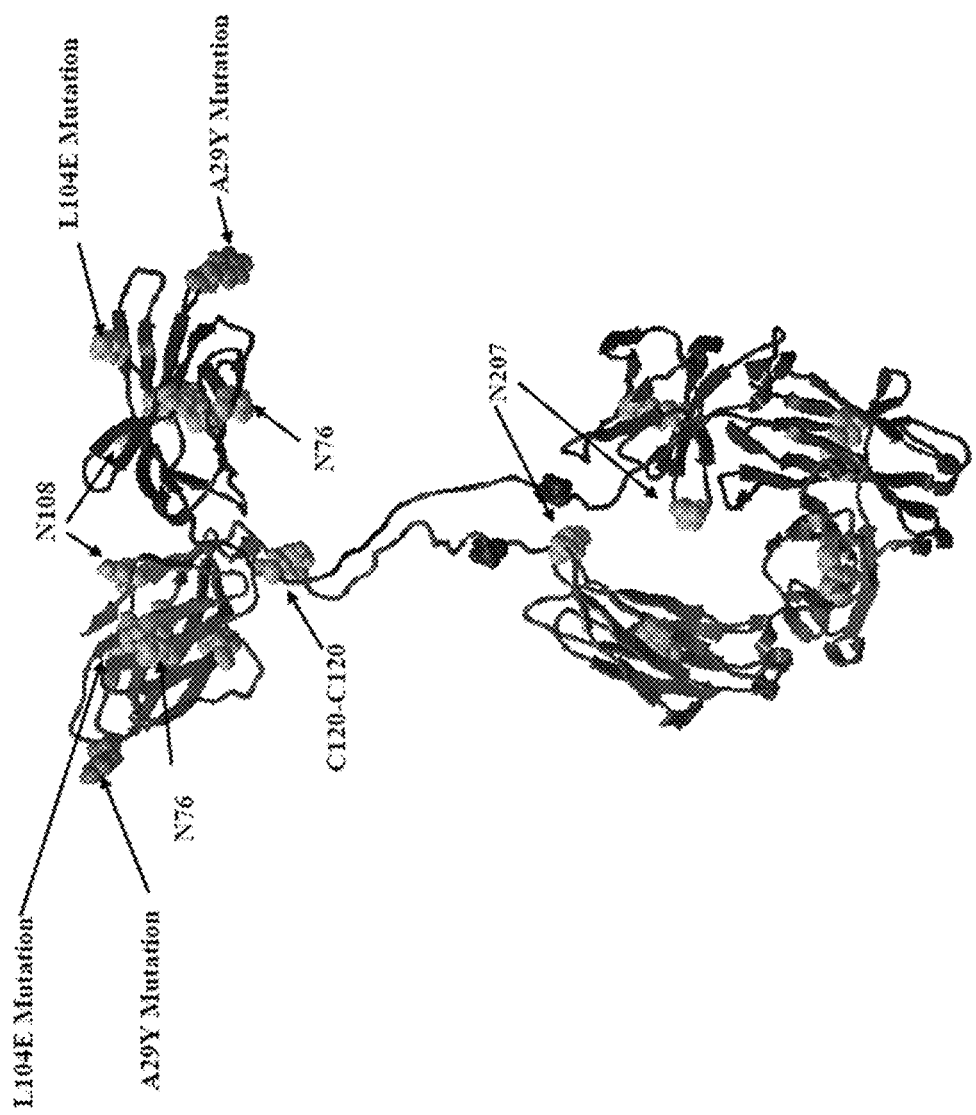
FIG. 4 is a model of a CTLA4$^{A29YL104E}$-Ig shown with the N-linked glycosylation sites (N76, N108, and N207), the C120-C120 disulfide bond, and the two amino acid substitutions made in the CTLA-4 domain (L104E and A29Y).

As used herein, the term "dimer" refers to a CTLA4-Ig protein or CTLA4-Ig molecule composed of two CTLA4-Ig polypeptides or monomers linked or joined together. The linkage between monomers of a dimer can be a non-covalent linkage or interaction, a covalent linkage or interaction, or both. An example of a CTLA4-Ig dimer is shown in FIG. 4. A CTLA4-Ig protein or CTLA4-Ig molecule composed of two identical monomers is a homodimer. A CTLA4-Ig homodimer also encompasses a molecule comprising two monomers that may differ slightly in sequence. A homodimer encompasses a dimer where the monomers joined together have substantially the same sequence. The monomers comprising a homodimer share considerable structural homology. For example, the differences in sequence may be due to N-termal processing modifications of the monomer.

As used herein, "conservative mutation" refers to a change in a nucleic acid sequence that substitutes one amino acid for another of the same class (e.g., substitution of one nonpolar amino acid for another, such as isoleucine, valine, leucine, or methionine; or substitution of one polar amino acid for another, such as substitution of arginine for lysine, glutamic acid for aspartic acid or glutamine for asparagine).

As used herein, "non-conservative mutation" refers to a change in a nucleic acid sequence that substitutes one amino acid for another of a different class (e.g., substitution of one basic amino acid, such as lysine, arginine or histidine, with an acidic amino acid, such as aspartic acid or glutamic acid). For example, an amino acid can be biochemically dissimilar from another amino acid based on size, charge, polarity, reactivity or other such characteristics of amino acids.

As used herein, "isolated" refers to a molecule that is taken out of its native environment and is in an environment different from that in which the molecule naturally occurs, or a substance (e.g., a protein) that is partially or completely recovered or separated from other components of its environment such that the substance (e.g., protein) is the predominant species (e.g., protein species) present in the resultant composition, mixture, or collection of components (for example, on a molar basis it is more abundant than any other individual species in the composition). For example, a preparation may consist of more than about 70, 71, 72, 73, 74, 75, 76, 77, 78, 79, 80, 81, 82, 83, 84, 85, 86, 87, 88, 89, 90, 91, 92, 93, 94 or or 95%, of isolated CTLA4-Ig. "Isolated" does not exclude mixtures of CTLA4-Ig molecules with other CTLA4-Ig molecules from the environment in which the molecule naturally occurs. "Isolated" does not exclude pharmaceutically acceptable excipients combined with CTLA4-Ig, wherein the CTLA4-Ig has been recovered from its environment, such as a cell culture, a batch culture, or a bioreactor, etc. As used herein, "isolating" refers to carrying out a process or method to obtain an isolated CTLA4-Ig molecule.

As used herein, the term "soluble CTLA4" means a molecule that can circulate in vivo or CTLA4 which is not bound to a cell membrane. For example, the soluble CTLA4 can include CTLA4-Ig which includes the extracellular region of CTLA4, linked to an Ig.

As used herein, the term "soluble fraction of a cell culture" refers to the liquid portion of a cell culture other than, or which is substantially free of, insoluble, particulate or solid components of the cell culture, such as cells, cell membranes and nuclei. The soluble fraction may be, for example, the resulting supernatant following centrifugation of the cell culture, or the resulting filtrate following filtration of the cell culture.

As used herein, the term "expression cassette" refers to a nucleic acid having at least a 5' regulatory region (e.g., promoter) operably linked to a nucleotide sequence that encodes a polypeptide, and optionally an untranslated 3' termination region (e.g., stop codon and polyadenylation sequence). Under appropriate conditions, a polypeptide encoded by an expression cassette is produced by the expression cassette. An expression cassette may also have one or more nucleotide sequences that target integration of the expression cassette into a specific site in the genome of a host cell (for example, see Koduri et al., (2001) Gene 280:87-95). For example, a $CTLA4^{A29YL104E}$-Ig polypeptide expression cassette derived from a plasmid deposited as ATCC Accession No. PTA-2104, is one example of an expression cassette encoding a $CTLA4^{A29YL104E}$-Ig.

As used herein, the term "substantially purified" refers to a composition comprising a CTLA4-Ig molecule or a selected population of CTLA4-Ig molecules that is removed from its natural environment (e.g., is isolated) and is at least 90% free, 91% free, 92% free, 93% free, 94% free, 95% free, 96% free, 97% free, 98% free, 99% free, 99.5% free, or 99.9% free from other components, such as cellular material or culture medium, with which it is naturally associated. For example, with respect to a recombinantly produced CTLA4-Ig protein molecule, the term "substantially purified" can also refer to a composition comprising a CTLA4-Ig protein molecule that is removed from the production environment such that the protein molecule is at least 90% free, 91% free, 92% free, 93% free, 94% free, 95% free, 96% free, 97% free, 98% free, 99% free, 99.5% free, or 99.9% free from protein molecules which are not polypeptides of SEQ ID NO: 2 or mutant polypeptides of SEQ ID NO: 2 which are of interest. "Substantially purified" does not exclude mixtures of CTLA4-Ig molecules (such as dimers) with other CTLA4-Ig molecules (such as tetramer). "Substantially purified" does not exclude pharmaceutically acceptable excipients or carriers combined with CTLA4-Ig molecules, wherein the CTLA4-Ig molecules have been taken out of their native environment.

As used herein, the term "large-scale process" is used interchangeably with the term "industrial-scale process". The term "culture vessel" is used interchangeably with "bioreactor", "reactor" and "tank".

A "liquid culture" refers to cells (for example, bacteria, plant, insect, yeast, or animal cells) grown on supports, or growing suspended in a liquid nutrient medium.

A "seed culture" refers to a cell culture grown in order to be used to inoculate larger volumes of culture medium. The seed culture can be used to inoculate larger volumes of media in order to expand the number of cells growing in the culture (for example, cells grown in suspension).

As used herein, "culturing" refers to growing one or more cells in vitro under defined or controlled conditions. Examples of culturing conditions which can be defined include temperature, gas mixture, time, and medium formulation As used herein, "expanding" refers to culturing one or more cells in vitro for the purpose of obtaining a larger number of cells in the culture.

As used herein, "population" refers to a group of two or more molecules ("population of molecules") or cells ("population of cells") that are characterized by the presence or absence of one or more measurable or detectable properties. In a homogeneous population, the molecules or cells in the population are characterized by the same or substantially the same properties (for example, the cells of a clonal cell line). In a heterogeneous population, the molecules or cells in the population are characterized by at least one property that is the same or substantially the same, where the cells or molecules may also exhibit properties that are not the same (for example, a population of CTLA4-Ig molecules having a substantially similar average sialic content, but having non-similar mannose content).

As used herein, "high molecular weight aggregate" is used interchangeably with "high molecular weight species" to refer to a CTLA4-Ig molecule comprising at least three CTLA4-Ig monomers. For example, a high molecular weight aggregate may be a tetramer, a pentamer or a hexamer.

"Percent (%) yield" refers to the actual yield divided by the theoretical yield, and that value multiplied by 100. The actual yield can be given as the weight in gram or in mol (for example, a molar yield). The theoretical yield can be given as the ideal or mathematically calculated yield.

As used herein, an "amount of MCP-1" refers to (1) an amount of MCP-1 (Monocyte chemotactic protein-1, especially, hamster MCP-1) alone, or (2) an amount of "MCP-1 like" protein, wherein "MCP-1 like" protein includes MCP-1, together with proteins homologous to MCP-1, fragments of MCP-1, and/or fragments of proteins homologous to MCP-1 (for example, in each of the aforementioned instances, as may be cross-reactive with an antibody (e.g., polyclonal ELISA) assay for the detection of MCP-1). The absence of MCP-1 (and/or proteins homologous to MCP-1, fragments of MCP-1, and/or fragments of proteins homologous to MCP-1) is contemplated where no lower limit is provided with regard to a range of amounts of MCP-1.

As used herein, "glycosylation content" refers to an amount of N-linked or 0-linked sugar residues covalently attached to a protein molecule, such as a glycoprotein like a CTLA4-Ig molecule.

As used herein, the term "molar ratio of sialic acids to protein" is calculated and given as number of moles of sialic acid molecules per moles of protein (CTLA4-Ig molecules) or dimer.

As used herein, the term "glycoprotein" refers to a protein that is modified by the addition of one or more carbohydrates, including the addition of one or more sugar residues.

As used herein, the term "sialylation" refers to the addition of a sialic acid residue to a protein, including a glycoprotein.

As used herein, the term "glycoprotein isoform" refers to a molecule characterized by its carbohydrate and sialic acid content as determined by isoelectric focusing (IEF) gel electrophoresis or other suitable methods for distinguishing different proteins in a mixture by their molecular weight, charge, and/or other characteristics. For example, each distinct band observed on an IEF gel represents molecules that have a particular isoelectric point (pI) and thus the same net overall charge. A glycoprotein isoform can be a distinct band observed on an IEF gel where each band can be a population of molecules that have a particular pI.

"Immune tolerance" refers to a state of unresponsiveness to a specific antigen or group of antigens to which a person is normally responsive (for example, a state in which a T cell can no longer respond to antigen).

"Potency" refers to a measure of the response as a function of ligand concentration. For example, agonist potency is quantified as the concentration of ligand that produces half the maximal effect ($EC_{50}$). A non-limiting pharmacological definition of potency includes components of affinity and efficacy, where, efficacy is the ability of a drug to evoke a response once bound. Potency is related to affinity, but potency and affinity are different measures of drug action.

As used herein, "pharmaceutically acceptable carrier" refers to a vehicle for a pharmacologically active agent. The carrier facilitates delivery of the active agent to the target site without terminating the function of the agent. Non-limiting examples of suitable forms of the carrier include solutions, creams, gels, gel emulsions, jellies, pastes, lotions, salves, sprays, ointments, powders, solid admixtures, aerosols, emulsions (e.g., water in oil or oil in water), gel aqueous solutions, aqueous solutions, suspensions, liniments, tinctures, and patches suitable for topical administration.

As used herein, the phrase "pharmaceutically acceptable composition" (or "pharmaceutical composition") refers to a composition that is acceptable for pharmaceutical administration, such as to a human being. Such a composition can include substances that are impurities at a level not exceeding an acceptable level for pharmaceutical administration (such level including an absence of such impurities), and can include pharmaceutically acceptable excipients, vehicles, carriers and other inactive ingredients, for example, to formulate such composition for ease of administration, in addition to any active agent(s). For example, a pharmaceutically acceptable CTLA4-Ig composition can include MCP-1 or DNA, so long as those substances are at a level acceptable for administration to humans.

"Drug substance" is the active pharmaceutical ingredient contained in a pharmaceutical composition. The term "drug substance" includes an active pharmaceutical ingredient in solution and/or in buffered form. "Drug product" is a pharmaceutical composition containing drug substance formulated for pharmaceutical administration. For purposes of the assays contained in the Examples and elsewhere herein, which may refer to drug substance and/or drug product, exemplary drug substances and drug products that may be assayed are as follows.

Exemplary drug substance for CTLA4-Ig molecules comprising SEQ ID NO:s 2, 5, 6, 7, 8, 9, 10 or 18 is CLTA4-Ig protein at a concentration of 50 mg/ml, in a buffered aqueous solution (25 mM sodium phosphate, 50 mM sodium chloride, pH of 7.5).

Exemplary drug product for CTLA4-Ig molecules comprising SEQ ID NOs: 2, 5, 6, 7, 8, 9, 10 or 18 is, 250 mg lyophilized CTLA4-Ig protein, 500 mg maltose, 17.2 mg monobasic sodium phosphate, and 14.6 mg sodium chloride, pH 7.0-8.0; or

| Composition of lyophilized CTLA4-Ig protein (250 mg/vial) drug product | |
|---|---|
| Component | Amount (mg/vial)$^a$ |
| CTLA4-Ig protein | 262.5 |
| Maltose monohydrate | 525 |
| Sodium phosphate monobasic, monohydrate$^b$ | 18.1 |
| Sodium chloride$^b$ | 15.3 |
| Hydrochloric Acid | Adjust to pH 7.5 |
| Sodium hydroxide | Adjust to pH 7.5 | buffered aqueous solution (25 mM sodium phosphate, 10 mM sodium chloride, pH of 7.5).

Exemplary drug product for CTLA4Ig molecules comprising SEQ ID NOs: 4, 11, 12, 13, 14, 15, 16, or 24:

| Composition of lyophilized CLTA4$^{A29YL104E}$-Ig 100 mg/vial drug product | |
|---|---|
| Component | Amount/Vial (mg) |
| CLTA4$^{A29YL104E}$-Ig | 110 |
| Sucrose | 220 |
| Sodium Phosphate Monobasic Monohydrate | 15.18 |
| Sodium Chloride | 2.55 |
| 1N Sodium Hydroxide | Adjust to pH 7.5 |
| 1N Hydrochloric Acid | Adjust to pH 7.5 |

As used herein, the terms "culture medium" and "cell culture medium" and "feed medium" and "fermentation medium" refer to a nutrient solutions used for growing and or maintaining cells, especially mammalian cells. Without limitation, these solutions ordinarily provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range. The nutrient solution can be supplemented electively with one or more components from any of the following categories: (1) hormones and other growth factors such as, serum, insulin, transferrin, and epidermal growth factor; (2) salts, for example, magnesium, calcium, and phosphate; (3) buffers, such as HEPES; (4) nucleosides and bases such as, adenosine, thymidine, and hypoxanthine; (5) protein and tissue hydrolysates, for example peptone or peptone mixtures which can be obtained from purified gelatin, plant material, or animal byproducts; (6) antibiotics, such as gentamycin; (7) cell protective agents, for example pluronic polyol; and (8) galactose.

The term "inoculation" as used herein refers to the addition of cells to culture medium to start the culture.

The term "growth phase" of the cell culture as used herein refers to the period of exponential cell growth (for example, the log phase) where cells are primarily dividing rapidly. During this phase, the rate of increase in the density of viable cells is higher than at any other time point.

As used herein, the term "production phase" of the cell culture refers to the period of time during which cell growth is stationary or is maintained at a near constant level. The density of viable cells remains approximately constant over a given period of time. Logarithmic cell growth has terminated and protein production is the primary activity during the production phase. The medium at this time is generally supplemented to support continued protein production and to achieve the desired glycoprotein product.

As used herein, the terms "expression" or "expresses" are used to refer to transcription and translation occurring within a cell. The level of expression of a product gene in a host cell can be determined on the basis of either the amount of corresponding mRNA that is present in the cell or the amount of the protein encoded by the product gene that is produced by the cell, or both.

As used herein, "glycosylation" refers to the addition of complex oligosaccharide structures to a protein at specific sites within the polypeptide chain. Glycosylation of proteins and the subsequent processing of the added carbohydrates can affect protein folding and structure, protein stability, including protein half life, and functional properties of a protein. Protein glycosylation can be divided into two classes by virtue of the sequence context where the modification occurs, O-linked glycosylation and N-linked glycosylation. O-linked polysaccharides are linked to a hydroxyl group, usually to the hydroxyl group of either a serine or a threonine residue. O-glycans are not added to every serine and threonine residue. O-linked oligosaccharides are usually mono or biantennary, i.e. they comprise one or at most two branches (antennas), and comprise from one to four different kinds of sugar residues, which are added one by one. N-linked polysaccharides are attached to the amide nitrogen of an asparagine. Only asparagines that are part of one of two tripeptide sequences, either asparagine-X-serine or asparagine-X-threonine (where X is any amino acid except proline), are targets for glycosylation. N-linked oligosaccharides can have from one to four branches referred to as mono-, bi-, tri-tetraantennary. The structures of and sugar residues found in N- and O-linked oligosaccharides are different. Despite that difference, the terminal residue on each branch of both N- and O-linked polysaccharide can be modified by a sialic acid molecule a modification referred as sialic acids capping. Sialic acid is a common name for a family of unique nine-carbon monosaccharides, which can be linked to other oligosaccharides. Two family members are N-acetyl neuraminic acid, abbreviated as Neu5Ac or NANA, and N-glycolyl neuraminic acid, abbreviated as Neu5Gc or NGNA. The most common form of sialic acid in humans is NANA. N-acetylneuraminic acid (NANA) is the primary sialic acid species present in CTLA4-Ig molecules. However, it should be noted that minor but detectable levels of N glycolylneuraminic acid (NGNA) are also present in CTLA4-Ig molecules. Furthermore, the method described herein can be used to determine the number of moles of sialic acids for both NANA and NGNA, and therefore levels of both NANA and NGNA are determined and reported for CTLA4-Ig molecules. N- and O-linked oligosaccharides have different number of branches, which provide different number of positions to which sialic acid molecules can be attached. N-linked ologosaccharides can provide up to four attachment positions for sialic acids, while O-linked oligosaccharides can provide two sites for sialic acid attachment.

As used herein, the term "large-scale process" can be used interchangeably with the term "industrial-scale process". Furthermore, the term "culture vessel" can be used interchangeably with "bioreactor", "reactor" and "tank".

As used herein, the phrase "working solution(s)" refers to solutions that are used in a method. Non-limiting examples of working solutions include buffers.

As used herein, "reference material" refers to a material that is used as a standard in a method. For example, a reference material can be used as a standard to which experimental samples will be compared.

The absence of a substance is contemplated where no lower limit is provided with regard to a range of amounts of such substance.

As used herein, recited temperatures in reference to cell culture refers to the temperature setting on the instrument that regulates the temperature of the bioreactor. Of course, the temperature of the liquid culture itself will adopt the temperature set on the instrument regulating the temperature for the bioreactor. Where the temperature refers to a cell culture that is maintained on a shelf in an incubator, the temperature then refers to the shelf temperature of the incubator.

Non-Limiting Embodiments of the Invention

The invention provides for compositions of CTLA4-Ig molecules and compositions of mutant CTLA4-Ig molecules, such as CTLA4$^{A29YL104E}$Ig. The invention provides for compositions with certain characteristics, such as certain amounts of bacterial endotoxin, bioburden, a pI within a certain range (or certain IEF bands within a pI of a certain range), a certain amount of monomer (single chain), dimer or high molecular weight species (such as tetramer), a certain tryptic peptide profile, a certain set of major bands on SDS-PAGE, a certain DNA content, an amount of MCP-1 not exceeding a certain maximum, an amount of cell protein not exceeding a certain maximum, an amount of Triton X-100 not exceeding a certain maximum, an amount of Protein A not exceeding a certain maximum, a certain profile of N-linked carbohydrates, a certain amino monosaccharide composition (GlcNac, GalNAc), a certain neutral monosaccharide composition (galactose, fucose, mannose), a certain amount of B7 binding, a certain amount of activity in a IL-2 inhibition cell assay, and/or a certain sialic acid composition (NANA, NGNA), in each case where said certain amounts can be a range or ranges. The invention provides compositions with any one of the aforementioned characteristics, or more than one of the aforementioned characteristics, up to an including all of the aforementioned characteristics in any and all possible permutations or combinations. The invention includes all the compositions of the invention in isolated or substantially purified form, or not in isolated or substantially purified form. The invention provides for compositions which are pharmaceutical compositions.

In one aspect, the invention is directed to a method for obtaining a composition comprising an isolated population of CTLA4-Ig molecules from a liquid culture medium, the medium comprising an initial population of CTLA4-Ig molecules, wherein (1) CTLA4-Ig molecules of the initial population have one or more sialic acid residues, (2) the number of sialic acid residues per CTLA4-Ig molecule varies within the initial population, and (3) the initial population comprises CTLA4-Ig dimer and high molecular weight aggregate, and the method comprises (a) harvesting the liquid culture medium from a culture of mammalian cells expressing CTLA4-Ig molecules; (b) separating the CTLA4-Ig molecules from cellular components; (c) separating CTLA4-Ig dimers from CTLA4-Ig high molecular weight aggregates; and (d) separating the CTLA4-Ig molecules into two or more fractions, wherein at least one fraction has a greater molar ratio of sialic acid to CTLA4-Ig molecules compared to at least one other fraction, and wherein steps (b), (c) and (d) are carried out simultaneously or in any order, so as to obtain said composition.

In one embodiment of the method of the invention, the harvesting in step (a) comprises obtaining a soluble fraction of the liquid culture. In another embodiment, steps (c) and (d) of the method comprise the use of column chromatography so as to obtain fractions of CTLA4-Ig molecules having different sialic acid contents. In yet another embodiment, the method further comprises use of column chromatography to reduce MCP-1 content in the composition.

In some embodiments of the method of the invention, the CTLA4-Ig molecules comprise one or more polypeptides having SEQ ID NO:2, 5, 6, 7, 8, 9, or 10. In other embodiments, the CTLA4-Ig molecules comprise one or more polypeptides having SEQ ID NO:4, 11, 12, 13, 14, 15 or 16.

In some embodiment of the method of the invention, the fraction in (d) having the greater molar ratio of sialic acid to CTLA4-Ig molecules exhibits an average molar ratio of sialic acid to CTLA4-Ig molecules from about 8 to about 14. In specific embodiments, the average molar ratio is from about 8 to about 11, from about 8 to about 10, or from about 8 to about 9.

The invention provides for a method for isolating CTLA4-Ig molecules, the method comprising: (i) obtaining a soluble fraction of a liquid culture comprising mammalian cells that produce composition comprising CTLA4-Ig molecules; (ii) subjecting the soluble fraction to anion exchange chromatography to obtain an eluted composition comprising CTLA4-Ig molecules; (iii) subjecting the composition of step (ii) to hydrophobic interaction chromatography so as to obtain an enriched composition comprising CTLA4-Ig molecules; (iv) subjecting the composition of (iii) to affinity chromatography to obtain a further enriched composition comprising CTLA4-Ig molecules; and (v) subjecting the composition of (iv) to anion exchange chromatography. In one embodiment, the composition obtained in step (ii) is characterized by: (a) an average of 6.0-10.1 moles of NANA per mole of CTLA4Ig molecule; and (b) less than or equal to 25.7 area percent CTLA4-Ig high molecular weight species as determined by size exclusion chromatography and spectrophotometric detection. In another embodiment, the composition obtained in step (iii) is characterized by: (a) an average of 6.8-11.4 moles of NANA per mole of CTLA4Ig molecule; and (b) less than or equal to 2.5 area percent of CTLA4-Ig high molecular weight species as determined by size exclusion chromatography and spectrophotometric detection. In a further embodiment, the composition obtained in step (iv) is characterized by: (a) an average of 8.0-11.0 moles of NANA per mole of CTLA4-Ig molecule; and (b) less than or equal to 2.5 area percent of CTLA4-Ig high molecular weight species. In another embodiment, the composition obtained in step (v) is characterized by: (a) an average of 8.0-11.9 moles of NANA per mole of CTLA4-Ig molecule; and (b) less than or equal to 2.0 area percent being CTLA4-Ig high molecular weight species as determined by size exclusion chromatography and spectrophotometric detection (SPD). In one embodiment, an example of SPD can be at A 280 nm.

The present invention also provides a method for isolating a composition of CTLA4-Ig molecules comprising: (i) obtaining a soluble fraction of a liquid culture comprising mammalian cells that produce CTLA4-Ig molecules, and, in any order, (ii) subjecting the soluble fraction to anion exchange chromatography so as to obtain an enriched and eluted composition comprising CTLA4-Ig molecules; (iii) subjecting the soluble fraction to hydrophobic interaction chromatography so as to obtain an enriched and eluted composition comprising CTLA4-Ig molecules; (iv) subjecting the soluble fraction to affinity chromatography so as to obtain an enriched and eluted composition comprising CTLA4-Ig molecules; and (v) subjecting the soluble fraction to anion exchange chromatography so as to obtain an eriched and eluted composition comprising CTLA4-Ig molecules. In another aspect, the present invention provides a method for isolating a composition comprising CTLA4-Ig molecules, the method comprising: (i) obtaining a soluble fraction of a liquid culture comprising mammalian cells that produce CTLA4-Ig molecules; (ii) subjecting the soluble fraction to anion exchange chromatography to obtain an eluted composition comprising CTLA4-Ig molecules; (iii) subjecting the protein product of step (ii) to hydrophobic interaction chromatography so as to obtain an enriched composition comprising CTLA4-Ig molecules; (iv) subjecting the protein product of (iii) to affinity chromatography to obtain a further enriched composition comprising CTLA4-Ig molecules; and (v) subjecting the protein product of (iv) to anion exchange chromatography, so as to isolate a composition comprising CTLA4-Ig molecules.

In one embodiment, the composition comprising CTLA4-Ig molecules obtained in step (ii) of the method is characterized by: (a) an average molar ratio of NANA to CTLA4Ig molecules of from 6.0 to 10.1, and (b) less than or equal to 2.5 area percent CTLA4-Ig high molecular weight species as determined by size exclusion chromatography and spectrophotometric detection. In another embodiment, the composition comprising CTLA4-Ig molecules obtained in step (iii) of the method is characterized in that in that (a) CTLA4-Ig high molecular weight species is less than about 2.5 area % as determined by size exclusion chromatography and spectrophotometric detection, (b) cellular protein is less than about 95 ng/ml, and (c) MCP-1 is less than about 5 ppm. In an additional embodiment, the composition comprising CTLA4-Ig molecules obtained in step (iii) of the method is characterized by: (a) an average molar ratio of NANA to CTLA4-Ig molecules of from 6.8 to 11.4, and (b) less than or equal to 2.5 area percent CTLA4-Ig high molecular weight species as determined by size exclusion chromatography and spectrophotometric detection. In a further embodiment, the composition comprising CTLA4-Ig molecules obtained in step (iv) of the method is characterized by: (a) an average molar ratio of NANA to CTLA4-Ig molecules of from 8.0 to 11.0, and (b) less than or equal to 2.5 area percent CTLA4-Ig high molecular weight species as determined by size exclusion chromatography and spectrophotometric detection. In still another embodiment, the composition obtained in step (iii) of the invention is characterized in that CTLA4-Ig high molecular weight species is less than 2.5% area percent as determined by size exclusion chromatography and spectrophotometric detection. In yet another embodiment, the protein composition comprising CTLA4-Ig molecules in step (v) of the method is characterized by: (a) an average molar ratio of NANA to CTLA4-Ig molecules of from 8.0 to 11.9, and (b) less than or equal to 2.0 area percent CTLA4-Ig high molecular weight species as determined by size exclusion chromatography and spectrophotometric detection.

The invention also provides, in another aspect, a method for isolating a composition of CTLA4-Ig molecules, comprising: (i) obtaining a soluble fraction of a liquid culture comprising mammalian cells that produce CTLA4-Ig molecules, and, in any order, (ii) subjecting the soluble fraction to anion exchange chromatography so as to obtain an enriched and eluted composition comprising CTLA4-Ig molecules; (iii) subjecting the soluble fraction to hydrophobic interaction chromatography so as to obtain an enriched and eluted composition comprising CTLA4-Ig molecules; (iv) subjecting the soluble fraction to affinity chromatography so as to obtain an enriched and eluted composition comprising CTLA4-Ig molecules; and (v) subjecting the soluble fraction to anion exchange chromatography so as to obtain an enriched and eluted composition comprising CTLA4-Ig molecules, wherein the composition obtained in step (iii) is characterized in that the percentage of CTLA4-Ig high molecular weight species is less than about 2.5 area %, cellular protein is less than 95 ng/ml, and MCP-1 is less than about 5 ppm.

In still another aspect, the invention provides a method for isolating a composition of CTLA4-Ig molecules, the method comprising: (i) obtaining a soluble fraction of a liquid culture comprising mammalian cells that produce CTLA4-Ig molecules, and, in any order, (ii) subjecting the soluble fraction to anion exchange chromatography so as to obtain an enriched and eluted composition comprising CTLA4-Ig molecules; (iii) subjecting the soluble fraction to hydrophobic interaction chromatography so as to obtain an enriched and eluted composition comprising CTLA4-Ig molecules; (iv) subjecting the soluble fraction to affinity chromatography so as to obtain an enriched and eluted composition comprising CTLA4-Ig molecules; and (v) subjecting the soluble fraction to anion exchange chromatography so as to obtain an enriched and eluted composition comprising CTLA4-Ig molecules, wherein the composition obtained in step (iii) is characterized in that the percentage of CTLA4-Ig high molecular weight species is less than about 2.5 area %, cellular protein is less than 95 ng/ml, MCP-1 is less than about 5 ppm, and the average molar ratio of NANA to CTLA4-Ig molecules is of from about 8.0 to about 12.

In one embodiment, the anion exchange chromatography of step (ii) of the method is carried out using a wash buffer comprising about 75 mM HEPES, and about 360 mM NaCl, and having a pH of about 8.0. In another embodiment, the anion exchange chromatography of step (ii) of the invention is carried out using an elution buffer comprising about 25 mM HEPES, and about 850 mM NaCl, and having a pH of about 7.0. In an additional embodiment, the hydrophobic interaction chromatography of step (iii) of the method is carried out using a single wash buffer comprising about 25 mM HEPES, and about 850 mM NaCl, and having a pH of about 7.0. In a further embodiment, the affinity chromatography of step (iv) of the method is carried out using a wash buffer comprising about 25 mM Tris, and about 250 mM NaCl, and having a pH of about 8.0. In still another embodiment, the affinity chromatography of step (iv) of the method is carried out using an elution buffer comprising about 100 mM glycine and having a pH of about 3.5. In yet another embodiment, the anion exchange chromatography of step (v) of the method is carried out using a wash buffer comprising about 25 mM HEPES, and from about 120 mM NaCl to about 130 mM NaCl, and having a pH of about 8.0.

In still another embodiment, the anion exchange chromatography of step (v) of the method is carried out using an elution buffer comprising about 25 mM HEPES, and about 200 mM NaCl, and having a pH of about 8.0. In yet another embodiment, the anion exchange chromatography of step (ii) of the method is carried out using a column having an anion exchange resin comprising a primary, secondary, tertiary, or quarternary amine functional group. In a specific embodiment, the resin comprises a quarternary amine functional group. In still another embodiment, the hydrophobic interaction chromatography of step (iii) of the method is carried out using a hydrophobic interaction resin comprising a phenyl, an octyl, a propyl, an alkoxy, a butyl, or an isoamyl functional group. In a specific embodiment, the functional group comprises a phenyl functional group. In still another embodiment, the affinity chromatography of step (iv) of the method is carried out using an affinity chromatography resin comprising Protein A.

In yet another aspect, the invention provides a method for preparing a composition comprising CTLA4-Ig molecules, comprising purifying CTLA4-Ig molecules from a liquid cell culture, wherein the purified CTLA4-Ig composition comprises (a) a pharmaceutically acceptable amount of MCP-1 per mg of CTLA4-Ig molecules, and (b) less than 2.5 area % of CTLA4-Ig high molecular weight species as determined by size exclusion chromatography and spectrophotometric detection. In one embodiment, the pharmaceutically acceptable amount of MCP-1 comprises from about 40 to about 0.5 ng/mg of CTLA4-Ig molecules. In another embodiment, the pharmaceutically acceptable amount of MCP-1 comprises from about 35 to about 0.5 ng/mg of CTLA4-Ig molecules. In an additional embodiment, the pharmaceutically acceptable amount of MCP-1 comprises from about 10 to about 0.5 ng/mg of CTLA4-Ig molecules. In a further embodiment, the affinity chromatography of step (iv) of the method is carried out using a column comprising a resin capable of reducing MCP-1 in the eluted protein product. In still another embodiment, the hydrophobic interaction chromatography of step (iii) of the method is carried out using a hydrophobic interaction resin, wherein the resin is capable of (a) separating CTLA4-Ig dimers from CTLA4-Ig high molecular weight species; (b) increasing sialic acid content of the eluted CTLA4-Ig molecules; or (c) both (a) and (b). In yet another embodiment, the anion exchange chromatography of step (ii) or step (iv), or both, is carried out using an anion exchange resin, wherein the resin is capable of (a) decreasing the CTLA4-Ig high molecular weight aggregate content of the eluted composition; (b) increasing the sialic content of the eluted composition; or (c) both (a) and (b).

In another aspect, the invention provides a method for isolating a composition comprising CTLA4-Ig molecules, the method comprising: (i) obtaining a soluble fraction of a liquid culture comprising mammalian cells that produce CTLA4-Ig molecules, and in any order; (ii) subjecting the soluble fraction to affinity chromatography so as to obtain an eluted composition comprising CTLA4-Ig molecules; (iii) subjecting the soluble fraction to anion exchange chromatography so as to obtain an eluted and enriched composition comprising CTLA4-Ig molecules; and (iv) subjecting the soluble fraction to hydrophobic interaction chromatography so as to obtain an eluted and enriched composition comprising CTLA4-Ig molecules. In one embodiment, the affinity chromatography step is performed first. In another embodiment, the affinity chromatography of step (ii) of the method is carried out using a resin comprising Protein A. In an additional embodiment, the affinity chromatography of step (ii) is carried out using an elution buffer comprising guanidine. In a further embodiment, the affinity chromatography of step (ii) is carried out using an elution buffer comprising urea. In yet another embodiment, the affinity chromatography of step (ii) results in an increase in CTLA4-Ig dimers in the eluted composition comprising CTLA4-Ig molecules.

In yet another aspect, the invention provides a method for isolating composition comprising CTLA4-Ig molecules from liquid harvested from a mammalian cell culture, wherein the cells produce CTLA4-Ig molecules, the method comprising: (i) obtaining a soluble fraction of the harvested liquid; (ii) subjecting the soluble fraction to affinity chromatography to obtain an eluted composition comprising CTLA4-Ig molecules; (iii) subjecting the composition of step (ii) to anion exchange chromatography so as to obtain an eluted and enriched composition comprising CTLA4-Ig molecules; and (iv) subjecting the composition from step (iii) to hydrophobic interaction chromatography to obtain a further enriched composition comprising CTLA4-Ig molecules. In one embodiment, the composition obtained in step (iv) of the method is characterized in that the percentage of high molecular weight species is less than about 2.5 area % as determined by size exclusion chromatography and spectrophotometric detection, and the percentage of cellular protein is less than about 95 ng/ml, and the percentage of MCP-1 is less than about 5 ppm. In another embodiment, the anion exchange chromatography of step (iii) is carried out using a wash buffer comprising about 50 mM HEPES, and about 135 mM NaCl, and having a pH of about 7. In an additional embodiment, the anion exchange chromatography of step (iii) is carried out using an elution buffer comprising about 50 mM HEPES, and about 200 mM NaCl, and having a pH of about 7. In a specific embodiment, the hydrophobic interaction chromatography of step (iii) is carried out using a hydrophobic interaction resin comprising a phenyl, an octyl, a propyl, an alkoxy, a butyl, or an isoamyl functional group. In a further embodiment, the hydrophobic interaction chromatography of step (iv) is carried out using a wash buffer comprising about 50 mM HEPES, and about 1.2 M $(NH_4)_2SO_4$, and having a pH of about 7. In still another embodiment, the affinity chromatography of step (ii) is carried out using a wash buffer comprising about 25 mM $NaH_2PO_4$, and about 150 mM NaCl, and having a pH of about 7.5. In yet another embodiment, the affinity chromatography of step (ii) is carried out using an elution buffer comprising about 250 mM glycine and having a pH of about 3. In another embodiment, the anion exchange chromatography of step (iii) is carried out using a column having an anion exchange resin comprising a primary, secondary, tertiary, or quarternary amine functional group. In a specific embodiment, the resin comprises a quarternary amine functional group.

In one embodiment, the hydrophobic interaction chromatography of step (iii) is carried out using a hydrophobic interaction resin comprising a phenyl, an octyl, a propyl, an alkoxy, a butyl, or an isoamyl functional group. In one embodiment, the functional group comprises a phenyl functional group. In one embodiment, the affinity chromatography of step (ii) is carried out using a resin comprising Protein A. The invention provides for a composition comprising CTLA4-Ig molecules obtained by any of the methods of the invention. In one embodiment, the composition comprises one or more polypeptides having SEQ ID NO:2, 5, 6, 7, 8, 9 or 10. In one embodiment, the composition comprises one or more polypeptides having SEQ ID NO:4, 11, 12, 13, 14, 15 or 16. The invention provides for a CTLA4-Ig expression plasmid having the nucleic acid sequence of SEQ ID NO:17. The invention provides for a substantially purified composition comprising CTLA4-Ig molecules, wherein the CTLA4-Ig molecules have an average molar ratio of sialic acid to CTLA4-Ig protein of from about 5.5 to about 18. The invention provides for a substantially purified composition comprising CTLA4-Ig molecules, wherein the CTLA4-Ig molecules have an average molar ratio of sialic acid to CTLA4-Ig molecules of from about 5.5 to about 9.5.

The invention provides for a substantially purified composition comprising CTLA4-Ig molecules, wherein the CTLA4-Ig molecules have an average molar ratio of sialic acid to CTLA4-Ig molecules of from about 5 to about 10. The invention provides for a substantially purified composition comprising CTLA4-Ig molecules, wherein the CTLA4-Ig molecules have an average molar ratio of sialic acid to CTLA4-Ig molecules of from about 6 to about 18. The invention provides for a substantially purified composition comprising CTLA4-Ig molecules, wherein the CTLA4-Ig molecules have an average molar ratio of sialic acid to CTLA4-Ig molecules of from about 8 to about 18.

The invention provides for a substantially purified composition comprising CTLA4-Ig molecules, wherein the CTLA4-Ig molecules have an average molar ratio of sialic acid to CTLA4-Ig molecules of from about 8 to about 12. The invention provides for a substantially purified composition comprising CTLA4-Ig molecules, wherein the CTLA4-Ig molecules have an average molar ratio of sialic acid to CTLA4-Ig molecules of from about 8 to about 11. The invention provides for a substantially purified composition comprising CTLA4-Ig molecules, wherein the CTLA4-Ig molecules have an average molar ratio of sialic acid to CTLA4-Ig molecules of from about 7 to about 12.

The invention provides for a substantially purified composition comprising CTLA4-Ig molecules, wherein the CTLA4-Ig molecules have an average molar ratio of sialic acid to CTLA4-Ig molecules of from about 7 to about 11. The invention provides for a substantially purified composition comprising CTLA4-Ig molecules, wherein the CTLA4-Ig molecules have an average molar ratio of sialic acid to CTLA4-Ig molecules of from about 11 to about 18. The invention provides for a substantially purified composition comprising CTLA4-Ig molecules, wherein the CTLA4-Ig molecules have an average molar ratio of sialic acid to CTLA4-Ig molecules of from about 12 to about 18.

The invention provides for a substantially purified composition comprising CTLA4-Ig molecules, wherein the CTLA4-Ig molecules have an average molar ratio of sialic acid to CTLA4-Ig molecules of from about 13 to about 18. The invention provides for a substantially purified composition comprising CTLA4-Ig molecules, wherein the CTLA4-Ig molecules have an average molar ratio of sialic acid to CTLA4-Ig molecules of from about 14 to about 18. The invention provides for a substantially purified composition comprising CTLA4-Ig molecules, wherein the CTLA4-Ig molecules have an average molar ratio of sialic acid to CTLA4-Ig molecules of from about 15 to about 17.

The invention provides for a substantially purified composition comprising CTLA4-Ig molecules, wherein the CTLA4-Ig molecules have an average molar ratio of sialic acid to CTLA4-Ig molecules of about 16. The invention provides for a substantially purified composition comprising CTLA4-Ig molecules, wherein the CTLA4-Ig molecules have an average molar ratio of sialic acid to CTLA4-Ig molecules of about 10. The invention provides for a substantially purified composition comprising CTLA4-Ig molecules, wherein the CTLA4-Ig molecules have an average molar ratio of sialic acid to CTLA4-Ig molecules of about 6. In one embodiment, the sialic acid is N-acetyl neuraminic acid (NANA). The invention provides for a substantially purified composition comprising CTLA4-Ig molecules, wherein the CTLA4-Ig molecules have an average molar ratio of NANA to CTLA4-Ig molecules of from about 8 to about 12. The invention provides for a substantially purified composition comprising CTLA4-Ig molecules, wherein the CTLA4-Ig molecules have an average molar ratio of N-glycolyl neuraminic acid (NGNA) to CTLA4-Ig molecules of less than or equal to about 1.5.

The invention provides for a substantially purified composition comprising CTLA4-Ig molecules, wherein the CTLA4-Ig molecules have an average molar ratio of NGNA to CTLA4-Ig molecules of from about 0.5 to about 1.5. The invention provides for a substantially purified composition comprising CTLA4-Ig molecules, wherein the CTLA4-Ig molecules have an average molar ratio of NGNA to CTLA4-Ig molecules of from about 1.0 to about 1.5. The invention provides for a substantially purified composition comprising CTLA4-Ig molecules, wherein the CTLA4-Ig molecules have an average molar ratio of sialic acid to CTLA4-Ig molecules of from about 6 to about 18.

The invention provides for a substantially purified composition comprising CTLA4-Ig molecules, wherein the CTLA4-Ig molecules are characterized by an average molar ratio of sialic acid per mole of CTLA4-Ig molecules of from about 6 to about 12.

The invention provides for a substantially purified composition comprising CTLA4-Ig molecules, wherein each polypeptide of the molecule comprises the sequence of SEQ ID NO:11, 12, 13, 14, 15 or 16, and wherein the CTLA4-Ig molecules are characterized by an average molar ratio of sialic acid per mole of CTLA4-Ig molecules of from about 5.5 to about 9.5. In one embodiment, the molar ratio of sialic acid per mole of CTLA4-Ig molecules is determined by acid hydrolysis and HPLC. In one embodiment, the CTLA4-Ig molecules comprise one or more polypeptides having SEQ ID NO:2, 5, 6, 7, 8, 9 or 10.

In one embodiment, the CTLA4-Ig molecules comprise one or more polypeptides having SEQ ID NO:4, 11, 12, 13, 14, 15 or 16. The invention provides for a substantially purified composition comprising CTLA4-Ig molecules, wherein greater than or equal to 95% of the CTLA4-Ig molecules are CTLA4-Ig dimers. In one embodiment, greater than or equal to 98% of the CTLA4-Ig molecules are CTLA4-Ig dimers. In one embodiment, greater than or equal to 99% of the CTLA4-Ig molecules are CTLA4-Ig dimers.

In one embodiment, greater than or equal to 99.5% of the CTLA4-Ig molecules are CTLA4-Ig dimers. In one embodiment, from about 95% to about 99.5% of the CTLA4-Ig molecules are CTLA4-Ig dimers and about 0.5 area percent to about 5 area percent of the molecules are CTLA4-Ig high molecular weight species as determined by size exclusion chromatography and spectrophotometric detection. In one embodiment, about 98.6% of the molecules are CTLA4-Ig dimers and about 1.2 area percent of the molecules are CTLA4-Ig high molecular weight species and about less than 0.7 area percent of the molecules are CTLA4-Ig monomers as determined by size exclusion chromatography and spectrophotometric detection. In one embodiment, about less then about 0.3% of the molecules are multimers comprising five or more CTLA4-Ig monomers. The invention provides for a composition consisting essentially of CTLA4-Ig dimers. The invention provides for a composition consisting essentially of CTLA4-Ig molecules, wherein the population is substantially free of CTLA4-Ig monomers. The invention provides for a composition consisting essentially of CTLA4-Ig molecules, wherein the population is substantially free of CTLA4-Ig high molecular weight species. The invention provides for a composition consisting essentially of CTLA4-Ig monomers substantially free of CTLA4-Ig dimers and high molecular weight species. In one embodiment, each monomer of each CTLA4-Ig dimer has at least 3 sialic acid groups. In one embodiment, each monomer of each CTLA4-Ig dimer has at least 2.5 sialic acid groups. In one embodiment, each monomer of each CTLA4-Ig dimer has from at least 3 sialic acid groups to at least 8 sialic acid groups.

In one embodiment, each monomer of each CTLA4-Ig dimer has from at least 2.5 sialic acid groups to at least 5 sialic acid groups. In one embodiment, each dimer comprises two CTLA4-Ig polypeptides, wherein each polypeptide has an amino acid sequence selected from the group consisting of SEQ ID NOS:5-16. In one embodiment, the composition comprises one or more polypeptides having SEQ ID NO:2, 5, 6, 7, 8, 9 or 10. In one embodiment, the composition comprises one or more polypeptides having SEQ ID NO:4, 11, 12, 13, 14, 15 or 16. The invention provides for an isolated composition comprising CTLA4-Ig tetramers, which is substantially free of CTLA4-Ig dimers. The invention provides for an isolated composition comprising CTLA4-Ig tetramers which is substantially free of CTLA4-Ig monomers. In one embodiment, the composition exists as an amount that is greater than about 100 grams. In one embodiment, each tetramer comprises two pairs of CTLA4-Ig polypeptides, wherein each polypeptide has an amino acid sequence selected from the group consisting of SEQ ID NOS:5-10. In one embodiment, each tetramer comprises two pairs of CTLA4-Ig polypeptides, wherein each polypeptide has an amino acid sequence selected from the group consisting of SEQ ID NOS:11-16. In one embodiment, each tetramer is capable of binding to a CD80 or CD86. The invention provides for a pharmaceutically acceptable composition comprising CTLA4-Ig molecules, wherein the composition is substantially free of MCP-1. The invention provides for a pharmaceutically acceptable composition comprising CTLA4-Ig molecules, wherein the composition comprises no more than about 25 ppm MCP-1. In one embodiment, the composition comprises no more than 10 ppm MCP-1. In one embodiment, the composition comprises from about 0.2 ng/ml MCP-1 to about 10 ng/ml of MCP-1. In one embodiment, the invention provides for a pharmaceutically acceptable composition comprising CTLA4-Ig molecules, wherein the composition comprises (a) from about 0.2 ng/ml MCP-1 to about 10 ng/ml of MCP-1 and (b) no more than 25 ng/ml of CHO protein or no more than 10 ng/ml of CHO protein. In one embodiment, the composition comprises no more than about 20 pg/ml of DNA.

The invention provides for an isolated composition comprising CTLA4-Ig molecules, wherein, when administered to a subject at an intravenous dose of about 10 mg/kg, the CTLA4-Ig molecules are capable of exhibiting: an area under the curve (AUC) of about 44400 μg.h/ml; a volume of distribution of about 0.09 L/kg; a peak concentration (Cmax) of about 292 μg/ml; and a clearance rate of about 0.23 ml/h/kg. The invention provides for an isolated composition comprising CTLA4-Ig molecules, wherein the composition comprises dominant isoforms of CTLA4-Ig molecules visualizable on an isoelectric focusing gel which have an isoelectric point, pI, less than or equal to 5.1±0.2 as determined by isoelectric focusing. In one embodiment, the average pI of the composition increases after neuraminidase treatment. In one embodiment, at least 40% of the CTLA4-Ig molecules exhibit an isoelectric point less than or equal to about 5.1±0.2 as determined by isoelectric focusing. In one embodiment, at least 70% of the CTLA4-Ig molecules exhibit an isoelectric point less than or equal to about 5.1±0.2 as determined by isoelectric focusing. In one embodiment, at least 90% of the CTLA4-Ig molecules exhibit an isoelectric point less than or equal to about 5.1±0.2 as determined by isoelectric focusing. The invention provides for an isolated composition comprising CTLA4-Ig molecules having a pI of from about 3.0±0.2 to about 5.0±0.2. The invention provides for an isolated composition comprising CTLA4-Ig molecules having a pI from about 4.3±0.2 to about 5.0±0.2.

The invention provides for an isolated composition comprising CTLA4-Ig molecules having a pI of about 3.3±0.2 to about 4.7±0.2. In one embodiment, the composition is substantially purified. The invention provides for a method for preparing a composition, the composition comprising a CTLA4-Ig molecule with a pI of from about 3.0±0.2 to about 5.0±0.2, the method comprising: (a) subjecting a mixture of CTLA4-Ig molecules to isoelectric focusing gel electrophoresis, wherein a single band on the gel represents a population of CTLA4-Ig molecules with a particular pI, and (b) isolating the population of CTLA4-Ig molecules having a pI of from about 3.0±0.2 to about 5.0±0.2 so as to prepare the composition. The invention provides for an isolated composition comprising CTLA4-Ig molecules, wherein the composition comprises dominant isoforms visualizable on an isoelectric focusing gel which have an isoelectric point, pI, less than or equal to 5.5±0.2 as determined by isoelectric focusing. In one embodiment, the average pI of the composition increases after neuraminidase treatment. In one embodiment, at least 40% of the CTLA4-Ig molecules exhibit an isoelectric point less than or equal to about 5.3±0.2 as determined by isoelectric focusing. In one embodiment, at least 70% of the CTLA4-Ig molecules exhibit an isoelectric point less than or equal to about 5.3±0.2 as determined by isoelectric focusing. In one embodiment, at least 90% of the CTLA4-Ig molecules exhibit an isoelectric point less than or equal to about 5.3±0.2 as determined by isoelectric focusing. The invention provides for an isolated composition comprising CTLA4-Ig molecules having a pI of from about 3.0±0.2 to about 5.2±0.2.

The invention provides for an isolated composition comprising CTLA4-Ig molecules having a pI from about 4.5±0.2 to about 5.2±0.2. The invention provides for an isolated composition comprising CTLA4-Ig molecules having a pI of about 4.7±0.2 to about 5.1±0.2. In one embodiment, the composition is substantially purified.

The invention provides for a method for preparing a composition, the composition comprising CTLA4-Ig molecules with a pI of from about 2.0±0.2 to about 5.2±0.2, the method comprising: (a) subjecting a mixture of CTLA4-Ig molecules to isoelectric focusing gel electrophoresis, wherein a single band on the gel represents a population of CTLA4-Ig molecules with a particular pI, and (b) isolating the population of CTLA4-Ig molecules having a pI of from about 3.0±0.2 to about 5.2±0.2 so as to prepare the composition. The invention provides for a composition comprising CTLA4-Ig molecules, wherein the CTLA4-Ig molecules are characterized by an average molar ratio of GlcNAc to CTLA4-Ig molecules of from about 17 to about 28. The invention provides for a composition comprising CTLA4-Ig molecules, wherein the CTLA4-Ig molecules are characterized by an average molar ratio of GlcNAc to CTLA4-Ig molecules of from about 17 to about 25. The invention provides for a composition comprising CTLA4-Ig molecules, wherein the CTLA4-Ig molecules are characterized by an average molar ratio of GlcNAc to CTLA4-Ig molecules of from about 15 to about 35.

The invention provides for a composition comprising CTLA4-Ig molecules, wherein each polypeptide of the molecule comprises the sequence of SEQ ID NO:11, 12, 13, 14, 15 or 16, and wherein the CTLA4-Ig molecules are characterized by an average molar ratio of GlcNAc to CTLA4-Ig molecules of from about 24 to about 28. The invention provides for a composition comprising CTLA4-Ig molecules, wherein the CTLA4-Ig molecules are characterized by an average molar ratio of GalNAc to CTLA4-Ig molecules of from about 1.7 to about 3.6. The invention provides for a composition comprising CTLA4-Ig molecules, wherein each polypeptide of the molecule comprises the sequence of SEQ ID NO:11, 12, 13, 14, 15 or 16, and wherein the CTLA4-Ig molecules are characterized by an average molar ratio of GalNAc to CTLA4-Ig molecules of from about 2.7 to about 3.6.

The invention provides for a composition comprising CTLA4-Ig molecules, wherein the CTLA4-Ig molecules are characterized by an average molar ratio of galactose to CTLA4-Ig molecules of from about 8 to about 17. The invention provides for a composition comprising CTLA4-Ig molecules, wherein each polypeptide of the molecule comprises the sequence of SEQ ID NO:11, 12, 13, 14, 15 or 16, and wherein the CTLA4-Ig molecules are characterized by an average molar ratio of galactose to CTLA4-Ig molecules of from about 11 to about 13. The invention provides for a composition comprising CTLA4-Ig molecules, wherein the CTLA4-Ig molecules are characterized by an average molar ratio of fucose to CTLA4-Ig molecules of from about 3.5 to about 8.3.

The invention provides for a composition comprising CTLA4-Ig molecules, wherein each polypeptide of the molecule comprises the sequence of SEQ ID NO:11, 12, 13, 14, 15 or 16, and wherein the CTLA4-Ig molecules are characterized by an average molar ratio of fucose to CTLA4-Ig molecules of from about 6.4 to about 7.0. The invention provides for a composition comprising CTLA4-Ig molecules, wherein the CTLA4-Ig molecules are characterized by an average molar ratio of mannose to CTLA4-Ig molecules of from about 7.7 to about 22. The invention provides for a composition comprising CTLA4-Ig molecules, wherein each polypeptide of the molecule comprises the sequence of SEQ ID NO:11, 12, 13, 14, 15 or 16, and wherein the CTLA4-Ig molecules are characterized by an average molar ratio of mannose to CTLA4-Ig molecules of from about 14 to about 16.

In one embodiment, the molar ratio of GlcNAc to CTLA4-Ig molecules is determined by capillary electrophoresis. In one embodiment, the molar ratio of GalNAc to CTLA4-Ig molecules is determined by capillary electrophoresis. In one embodiment, the molar ratio of galactose to CTLA4-Ig molecules is determined by capillary electrophoresis.

In one embodiment, the molar ratio of fucose to CTLA4-Ig molecules is determined by capillary electrophoresis. In one embodiment, the molar ratio of mannose to CTLA4-Ig molecules is determined by capillary electrophoresis. In one embodiment, the CTLA4-Ig molecules are obtained by enzymatic attachment of one or more carbohydrates to the molecule. The invention provides for a composition comprising CTLA4-Ig molecules, wherein the molecules comprise carbohydrate residues attached to the molecules enzymatically in vitro. The invention provides for a composition comprising CTLA4-Ig molecules characterized by: (a) an average molar ratio of GlcNAc to CTLA4-Ig molecules from about 15 to about 35; and (b) an average molar ratio of sialic acid to CTLA4-Ig molecules from about 6 to about 12. The invention provides for a composition comprising CTLA4-Ig molecules characterized by: (a) an average molar ratio of GlcNAc to CTLA4-Ig molecules from about 15 to about 35; (b) an average molar ratio of GalNAc to CTLA4-Ig molecules from about 1.7 to about 3.6; and (c) an average molar ratio of sialic acid to CTLA4-Ig molecules from about 6 to about 12. The invention provides for a composition comprising CTLA4-Ig molecules characterized by: (a) an average molar ratio of GlcNAc to CTLA4-Ig molecules from about 15 to about 35; (b) an average molar ratio of GalNAc to CTLA4-Ig molecules from about 1.7 to about 3.6; (c) an average molar ratio of galactose to CTLA4-Ig molecules from about 8 to about 17; and (d) an average molar ratio of sialic acid to CTLA4-Ig molecules from about 6 to about 12. The invention provides for a composition comprising CTLA4-Ig molecules characterized by: (a) an average molar ratio of GlcNAc to CTLA4-Ig molecules from about 15 to about 35; (b) an average molar ratio of GalNAc to CTLA4-Ig molecules from about 1.7 to about 3.6; (c) an average molar ratio of galactose to CTLA4-Ig molecules from about 8 to about 17; (d) an average molar ratio of fucose to CTLA4-Ig molecules from about 3.5 to about 8.3; and (e) an average molar ratio of sialic acid to CTLA4-Ig molecules from about 6 to about 12. The invention provides for a composition comprising CTLA4-Ig molecules characterized by: (a) an average molar ratio of GlcNAc to CTLA4-Ig molecules from about 15 to about 35; (b) an average molar ratio of GalNAc to CTLA4-Ig molecules from about 1.7 to about 3.6; (c) an average molar ratio of galactose to CTLA4-Ig molecules from about 8 to about 17; (d) an average molar ratio of fucose to CTLA4-Ig molecules from about 3.5 to about 8.3; (e) an average molar ratio of mannose to CTLA4-Ig molecules from about 7.2 to about 22; and (f) an average molar ratio of sialic acid to CTLA4-Ig molecules from about 6 to about 12. The invention provides for a composition comprising CTLA4-Ig molecules characterized by: (a) an average molar ratio of GlcNAc to CTLA4-Ig molecules from about 24 to about 28; and (b) an average molar ratio of sialic acid to CTLA4-Ig molecules from about 5.5 to about 9.5. The invention provides for a composition comprising CTLA4-Ig molecules characterized by: (a) an average molar ratio of GlcNAc to CTLA4-Ig molecules from about 24 to about 28; (b) an average molar ratio of GalNAc to CTLA4-Ig molecules from about 2.7 to about 3.6; and (c) an average molar ratio of sialic acid to CTLA4-Ig molecules from about 5.5 to about 9.5. The invention provides for a composition comprising CTLA4-Ig molecules characterized by: (a) an average molar ratio of GlcNAc to CTLA4-Ig molecules from about 24 to about 28; (b) an average molar ratio of GalNAc to CTLA4-Ig molecules from about 2.7 to about 3.6; (c) an average molar ratio of galactose to CTLA4-Ig molecules from about 11 to about 13; and (d) an average molar ratio of sialic acid to CTLA4-Ig molecules from about 5.5 to about 9.5. The invention provides for a composition comprising CTLA4-Ig molecules characterized by: (a) an average molar ratio of GlcNAc to CTLA4-Ig molecules from about 24 to about 28; (b) an average molar ratio of GalNAc to CTLA4-Ig molecules from about 2.7 to about 3.6; (c) an average molar ratio of galactose to CTLA4-Ig molecules from about 11 to about 13; (d) an average molar ratio of fucose to CTLA4-Ig molecules from about 6.4 to about 7.0; and (e) an average molar ratio of sialic acid to CTLA4-Ig molecules from about 5.5 to about 9.5. The invention provides for a composition comprising CTLA4-Ig molecules characterized by: (a) an average molar ratio of GlcNAc to CTLA4-Ig molecules from about 24 to about 28; (b) an average molar ratio of GalNAc to CTLA4-Ig molecules from about 2.7 to about 3.6; (c) an average molar ratio of galactose to CTLA4-Ig molecules from about 11 to about 13; (d) an average molar ratio of fucose to CTLA4-Ig molecules from about 6.4 to about 7.0; (e) an average molar ratio of mannose to CTLA4-Ig protein from about 14 to about 16; and (f) an average molar ratio of sialic acid to CTLA4-Ig protein from about 5.5 to about 9.5.

The invention provides for a composition comprising CTLA4-Ig molecules, wherein the CTLA4-Ig molecules are glycosylated at an asparagine amino acid residue at position 102 of SEQ ID N0:2 or 4, an asparagine amino acid residue at position 134 of SEQ ID N0:2 or 4, an asparagine amino acid residue at position 233 of SEQ ID N0:2 or 4, a serine amino acid residue at position 155 of SEQ ID N0:2 or 4, or a serine amino acid residue at position 165 of SEQ ID N0:2 or 4. The invention provides for a composition comprising CTLA4-Ig molecules, wherein the CTLA4-Ig molecules are glycosylated, and wherein at least about 2% of total mass of glycosylation is O-linked glycosylation.

Figure 67:
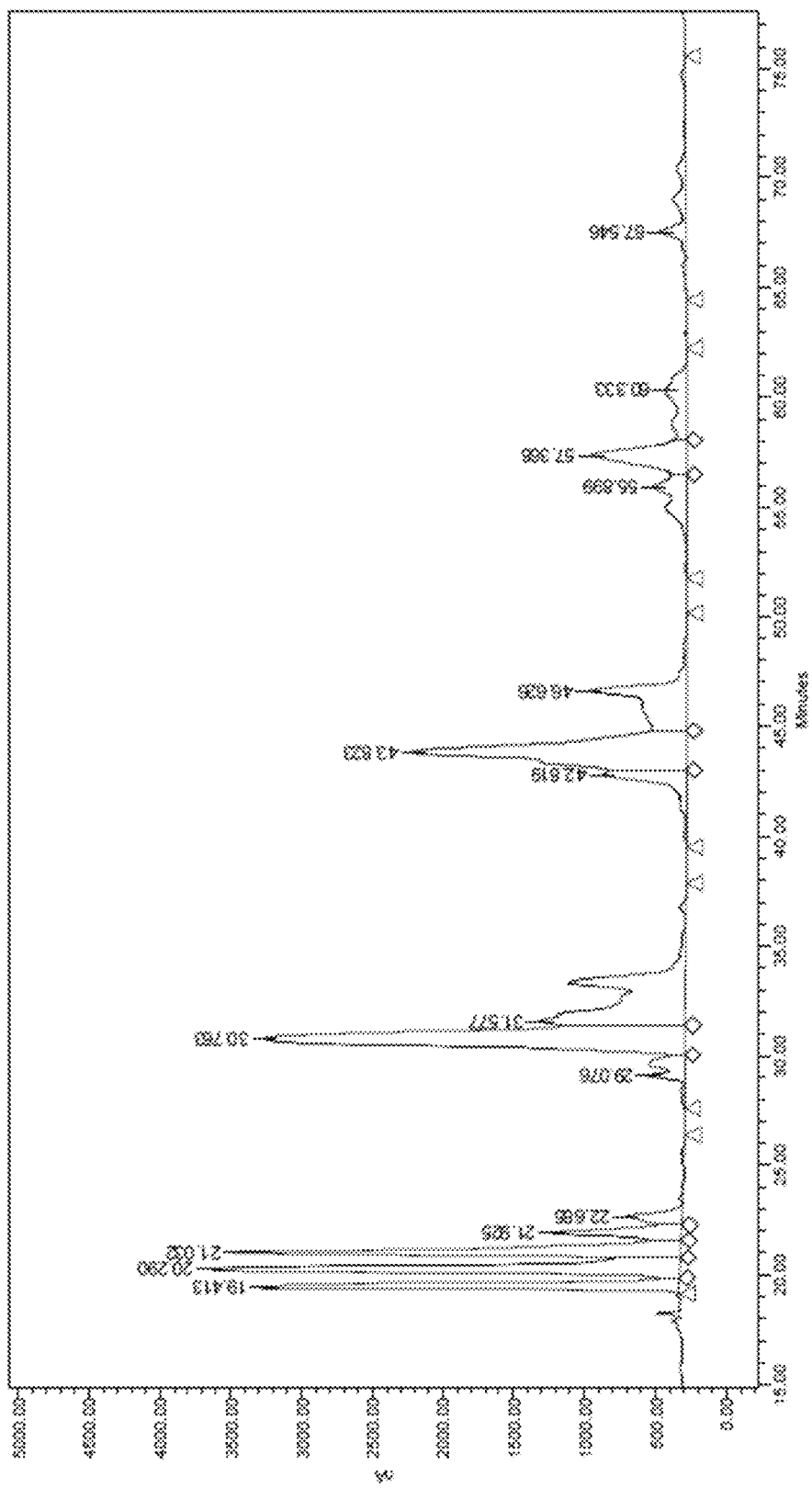
FIG. 67 depicts a typical N-Linked Oligosaccharide Profile (Domains I, II, III, IV and V, and Peaks 1A and 1B within 5% of Lot averages). Peaks 1A, 1B and 1C represent the asialo N-linked oligosaccharide structures of G0, G1 and G2. The data for the profile is in the table directly below. See Example 44.
Figure 68:
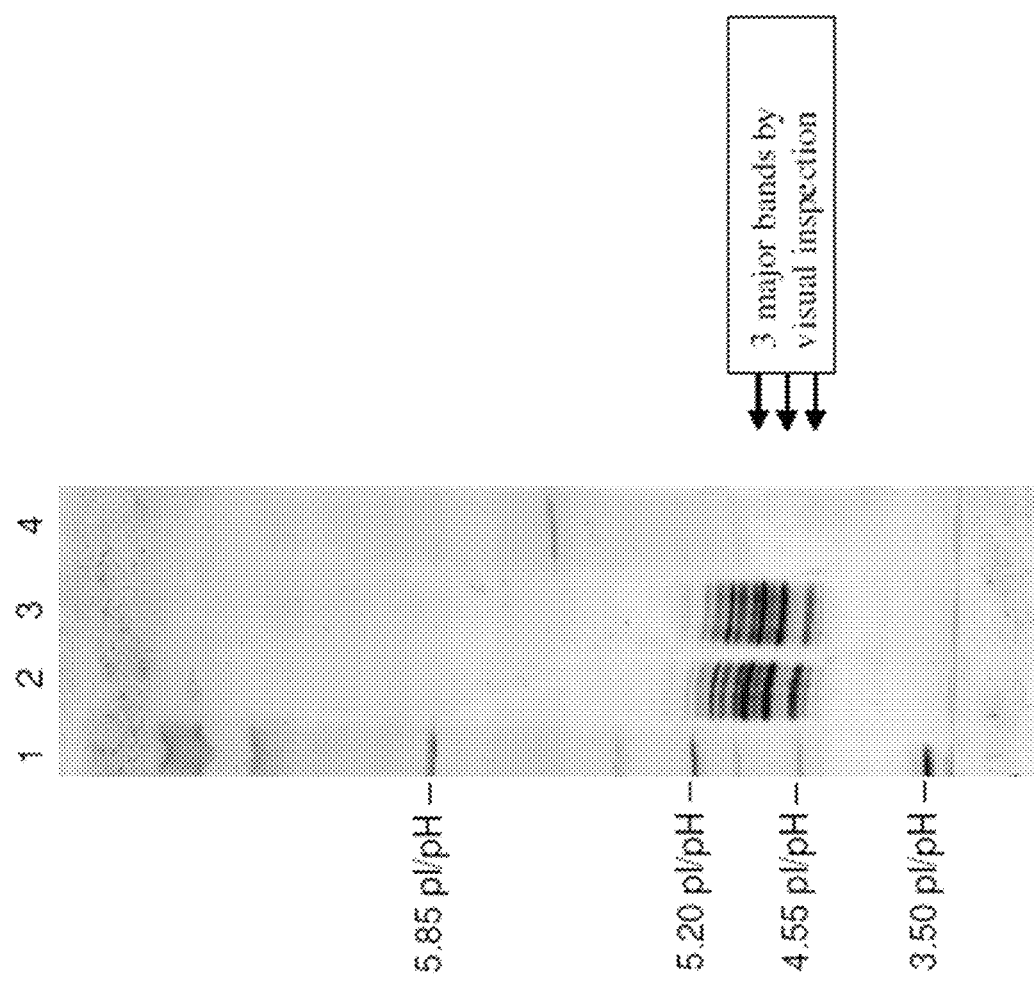

The invention provides for a composition comprising CTLA4-Ig molecules, wherein the composition exhibits an NGNA chromatogram peak of about 9.6±0.3 and an NANA chromatogram peak of about 10.5±0.3. The invention provides for a composition comprising CTLA4-Ig molecules, wherein the CTLA4-Ig molecules exhibit a carbohydrate profile substantially the same as FIG. 67. The invention provides for a composition comprising CTLA4-Ig molecules, wherein the CTLA-Ig molecules exhibit a carbohydrate profile as shown in FIG. 67. The invention provides for a composition consisting essentially of CTLA4-Ig molecules, wherein the CTLA4-Ig molecules exhibit a carbohydrate profile of Domains I-IV, wherein Domain I comprises peaks which represent a-sialylated oligosaccharides, Domain II comprises peaks which represent mono-sialylated oligosaccharides, Domain III comprises peaks which represent di-sialylated oligosaccharides, Domain IV comprises peaks which represent tri-sialylated oligosaccharides, and Domain V comprises peaks which represent tetra-sialyated oligosaccharides, and wherein the profile is a chromatogram of oligosaccharides released from CTLA4-Ig. In one embodiment, the difference in retention times of N-linked oligosaccharides between a first peak in Domain I and a main peak in Domain II is from about 10 to about 12 minutes. In one embodiment, the difference in retention times of N-linked oligosaccharides between a first peak in Domain I and a main peak in Domain II is from about 11 to about 13 minutes. In one embodiment, glycosylation of Domains III and IV comprises about 25% to about 36% of N-linked glycosylation as measured by HPAEC. In one embodiment, glycosylation of Domain I comprises about 24.5% to about 35.2% of N-linked glycosylation as measured by HPAEC. In one embodiment, glycosylation of Domain II comprises about 26.3% to about 34.1% of N-linked glycosylation as measured by HPAEC. In one embodiment, glycosylation of Domain III comprises about 21.9% to about 31.5% of N-linked glycosylation as measured by HPAEC. In one embodiment, glycosylation of Domain IV and Domain V comprises about 7.9% to about 18.6% of N-linked glycosylation as measured by HPAEC.

In one embodiment: (a) Domain I exhibits an area percentage of at least about 31; (b) Domain II exhibits an area percentage of at least about 33; (c) Domain III exhibits an area percentage of at least about 24; (iv) Domain IV exhibits an area percentage of at least about 9.4, (v) Domain V exhibits an area percentage of at least about 67; or wherein the area is measured from a chromatogram of oligosaccharides released from CTLA4-Ig.

In one embodiment: (a) Domain I exhibits at least about 5 peaks; (b) Domain II exhibits at least about 5 peaks; (c) Domain III exhibits at least about 5 peaks; (d) Domain IV exhibits at least about 6 peaks, or (e) Domain V exhibits at least about 6 peaks, and wherein the peaks are exhibited on a chromatogram. A composition wherein Domain I exhibits at least two peaks, wherein a first peak has a minimum area of about 4.5% and a maximum area of about 11.2%, and wherein a second peak has a minimum area of about 8.7% and a maximum of about 11.8%.

In one embodiment, Domain III and IV exhibit an area percentage of about 25% to about 36% as measured by HPAEC. In one embodiment, Domain I exhibits an area percentage of about 24.5% to about 35.2% as measured by HPAEC. In one embodiment, Domain II exhibits an area percentage of about 26.3% to about 34.1% as measured by HPAEC. In one embodiment, Domain III exhibits an area percentage of about 21.9% to about 31.5% as measured by HPAEC. In one embodiment, Domain IV exhibits an area percentage of about 7.9% to about 18.6% as measured by HPAEC.

The invention provides for a composition comprising CTLA4-Ig polypeptides, wherein: (a) about 80% of the polypeptides have biantennary N-linked glycosylation; (b) about 14% of the polypeptides have triantennary N-linked glycosylation; and (c) about 6% of the polypeptides have tetraantennary N-linked glycosylation. In one embodiment, the N-linked glycosylation is determined by high pH anion exchange chromatography with pulsed amperometric detection (HPEAC-PAD). The invention provides for a composition comprising CTLA4-Ig molecules characterized by: (a) an average molar ratio of galactose to CTLA4-Ig molecules of from about 8 to about 17; and (b) an average molar ratio of NANA to CTLA4-Ig molecules of from about 6 to about 12. The invention provides for a composition comprising CTLA4-Ig molecules characterized by:

(a) an average molar ratio of galactose to CTLA4-Ig molecules of from about 8 to about 17; (b) an average molar ratio of NANA to CTLA4-Ig molecules of from about 6 to about 12; and (c) a CTLA4-Ig high molecular weight species area percent of less than about 3% as determined by size exclusion chromatography and spectrophotometric detection. The invention provides for a composition comprising CTLA4-Ig molecules characterized by: (a) an average molar ratio of galactose to CTLA4-Ig molecules of from about 8 to about 17; (b) an average molar ratio of NANA to CTLA4-Ig molecules of from about 6 to about 12; and (c) an average molar ratio of NGNA to CTLA4-Ig molecules of less than or equal to about 1.5.

The invention provides for a composition comprising CTLA4-Ig molecules characterized by: (a) an average molar ratio of galactose to CTLA4-Ig molecules of from about 8 to about 17; (b) an average molar ratio of NANA to CTLA4-Ig molecules of from about 6 to about 12; (c) a CTLA4-Ig high molecular weight aggregate content less than about 3 area percent as determined by size exclusion chromatography and spectrophotometric detection; and (d) a carbohydrate profile substantially the same as that of FIG. 67. The invention provides for a composition comprising CTLA4-Ig molecules characterized by: (a) an average molar ratio of galactose to CTLA4-Ig molecules of from about 8 to about 17; (b) an average molar ratio of NANA to CTLA4-Ig molecules of from about 6 to about 12; (c) a CTLA4-Ig high molecular weight aggregate content less than about 3 area percent as determined by size exclusion chromatography and spectrophotometric detection; and (d) a glycosylation content in Domains III, IV and V of at least about 29.8% to about 50.1% of N-linked glycosylation as determined by HPAEC. The invention provides for a composition comprising CTLA4-Ig molecules characterized by: (a) an average molar ratio of galactose to CTLA4-Ig molecules of from about 8 to about 17; (b) an average molar ratio of NANA to CTLA4-Ig molecules of from about 6 to about 12; and (c) a CTLA4-Ig high molecular weight species of less than about 3 area percent as determined by size exclusion chromatography and spectrophotometric detection. In one embodiment, the molecules are further characterized by an average molar ratio of NANA to CTLA4-Ig molecules from about 8 to about 12.

In one embodiment, the molecules are further characterized by: (a) about 80% biantennary N-linked glycosylation; (b) about 14% triantennary N-linked glycosylation; and (c) about 6% tetraantennary N-linked glycosylation. In one embodiment, the molecules further comprise any combination of one or more of: (a) the amino acid sequence of SEQ ID NO:10 (methionine at amino acid position 27 and glycine at amino acid position 382 of SEQ ID NO:2); (b) the amino acid sequence of SEQ ID NO:7 (methionine at amino acid position 27 and lysine at amino acid position 383 of SEQ ID NO:2); (c) the amino acid sequence of SEQ ID NO:9 (alanine at amino acid position 26 and glycine at amino acid position 382 of SEQ ID NO:2); and (d) the amino acid sequence of SEQ ID NO:6 (alanine at amino acid position 26 and lysine at amino acid position 383 of SEQ ID NO:2). In one embodiment, (a) about 90% of the molecules comprise the amino acid sequence of SEQ ID NO:2 beginning with the methionine at residue 27; (b) about 10% of the molecules comprise the amino acid sequence of SEQ ID NO:2 beginning with the alanine at residue number 26; (c) about 4% of the molecules comprise the amino acid sequence of SEQ ID NO:2 ending with the lysine at residue number 383; and (d) about 96% of the molecules comprise the amino acid sequence of SEQ ID NO:2 ending with the glycine at residue number 382. The invention provides for a composition comprising CTLA4-Ig polypeptides, wherein: (a) about 80% of the polypeptides have biantennary N-linked glycosylation; (b) about 14% of the polypeptides have triantennary N-linked glycosylation; (c) about 6% of the polypeptides have tetraantennary N-linked glycosylation; and (d) an average molar ratio of NGNA to CTLA4-Ig molecules of less than or equal to 1.5. The invention provides for a composition comprising CTLA4-Ig polypeptides, wherein: (a) about 80% of the polypeptides have biantennary N-linked glycosylation; (b) about 14% of the polypeptides have triantennary N-linked glycosylation; (c) about 6% of the polypeptides have tetraantennary N-linked glycosylation; and (d) an average molar ratio of GlcNAc to CTLA4-Ig molecules of from about 15 to about 35. The invention provides for a composition comprising CTLA4-Ig polypeptides, wherein: (a) about 80% of the polypeptides have biantennary N-linked glycosylation; (b) about 14% of the polypeptides have triantennary N-linked glycosylation; (c) about 6% of the polypeptides have tetraantennary N-linked glycosylation; and (d) an average molar ratio of GalNAc to CTLA4-Ig molecules of from about 1.7 to about 3.6. The invention provides for a composition comprising CTLA4-Ig molecules characterized by: (a) an average molar ratio of galactose to CTLA4-Ig molecules of from about 11 to about 13; and (b) an average molar ratio of sialic to CTLA4-Ig molecules of from about 5.5 to about 9.5.

The invention provides for a composition comprising CTLA4-Ig molecules characterized by: (a) an average molar ratio of galactose to CTLA4-Ig molecules of from about 11 to about 13; (b) an average molar ratio of sialic acid to CTLA4-Ig molecules of from about 5.5 to about 9.5; and (c) a CTLA4-Ig high molecular weight species of less than about 5 area percent as determined by size exclusion chromatography and spectrophotometric detection. The invention provides for a composition comprising CTLA4-Ig molecules characterized by: (a) an average molar ratio of galactose to CTLA4-Ig molecules of from about 11 to about 13;

(b) an average molar ratio of sialic acid to CTLA4-Ig molecules of from about 5.5 to about 9.5; (c) a CTLA4-Ig high molecular weight species content less than about 5 area percent as determined by size exclusion chromatography and spectrophotometric detection; and (d) a carbohydrate profile substantially the same as that of FIG. 67. The invention provides for a composition comprising CTLA4-Ig molecules characterized by: (a) an average molar ratio of galactose to CTLA4-Ig molecules of from about 11 to about 13; (b) an average molar ratio of sialic acid to CTLA4-Ig molecules of from 5.5 to about 9.5; (c) a CTLA4-Ig high molecular weight species content less than about 5 area percent as determined by size exclusion chromatography and spectrophotometric detection; and (d) a glycosylation content in Domains III, IV and V of at least about 29.8% to about 50.1% of N-linked glycosylation as determined by HPAEC.

The invention provides for a composition comprising CTLA4-Ig molecules characterized by: (a) an average molar ratio of galactose to CTLA4-Ig molecules of from about 11 to about 13; (b) an average molar ratio of sialic acid to CTLA4-Ig molecules of from about 5.5 to about 9.5; and (c) a CTLA4-Ig high molecular weight species content less than about 5 area percent as determined by size exclusion chromatography and spectrophotometric detection. In one embodiment, the molecules are further characterized by: (a) about 80% biantennary N-linked glycosylation; (b) about 14% triantennary N-linked glycosylation; and (c) about 6% tetraantennary N-linked glycosylation. In another embodiment, the molecules further comprise any combination of one or more of: (a) the amino acid sequence of SEQ ID NO:16 (methionine at amino acid position 27 and glycine at amino acid position 382 of SEQ ID NO:4); (b) the amino acid sequence of SEQ ID NO:13 (methionine at amino acid position 27 and lysine at amino acid position 383 of SEQ ID NO:4); (c) the amino acid sequence of SEQ ID NO:15 (alanine at amino acid position 26 and glycine at amino acid position 382 of SEQ ID NO:4); and (d) the amino acid sequence of SEQ ID NO:12 (alanine at amino acid position 26 and lysine at amino acid position 383 of SEQ ID NO:4). In another embodiment, (a) about 90% of the molecules comprise the amino acid sequence of SEQ ID NO:4 beginning with the methionine at residue 27; (b) about 10% of the molecules comprise the amino acid sequence of SEQ ID NO:4 beginning with the alanine at residue number 26; (c) about 4% of the molecules comprise the amino acid sequence of SEQ ID NO:4 ending with the lysine at residue number 383; and (d) about 96% of the molecules comprise the amino acid sequence of SEQ ID NO:4 ending with the glycine at residue number 382. The invention provides for a composition comprising CTLA4-Ig polypeptides, wherein:

(a) about 80% of the polypeptides have biantennary N-linked glycosylation; (b) about 14% of the polypeptides have triantennary N-linked glycosylation; (c) about 6% of the polypeptides have tetraantennary N-linked glycosylation; and(d) an average molar ratio of GlcNAc per mole of CTLA4-Ig protein of from about 24 to about 28. The invention provides for a composition comprising CTLA4-Ig polypeptides, wherein: (a) about 80% of the polypeptides have biantennary N-linked glycosylation; (b) about 14% of the polypeptides have triantennary N-linked glycosylation; (c) about 6% of the polypeptides have tetraantennary N-linked glycosylation; and(d) an average molar ratio of GalNAc to CTLA4-Ig molecules of from about 2.7 to about 3.6. In another embodiment, the composition is a substantially purified composition. The invention provides for a composition comprising CTLA4-Ig molecules, wherein less than or equal to about 2.5% of the CTLA4-Ig molecules are oxidized. The invention provides for a composition comprising CTLA4-Ig molecules, wherein less than or equal to about 2.0% of the CTLA4-Ig molecules are deamidated. The invention provides for a composition comprising CTLA4-Ig dimer molecules, wherein at least 0.5% of the CTLA4-Ig dimer molecules are cysteinylated. In one embodiment, at least 1.0% of the CTLA4-Ig dimer molecules are cysteinylated. The invention provides for a population of CTLA4-Ig molecules, wherein the population exhibits a mass spectrometry profile substantially the same as FIG. 63, 64 or 66. The invention provides for a population of CTLA4-Ig molecules, wherein the population exhibits a capillary electrophoresis profile substantially the same as FIG. 47.

The invention provides for a composition comprising CTLA4-Ig molecules, wherein the composition is characterized by: (a) an average molar ratio of GlcNAc to CTLA4-Ig molecules from about 15 to about 35; (b) an average molar ratio of GalNAc to CTLA4-Ig molecules from about 1.7 to about 3.6; (c) an average molar ratio of galcatose to CTLA4-Ig molecules from about 8 to about 17; (d) an average molar ratio of fucose to CTLA4-Ig molecules from about 3.5 to about 8.3; (e) an average molar ratio of mannose to CTLA4-Ig molecules from about 7.2 to about 22; (f) an average molar ratio of sialic acid to CTLA4-Ig molecules from about 6 to about 12; (g) a pI as determined from visualization on an isoelectric focusing gel in a range from about 2.4±0.2 to about 5.0±0.2; (h) MCP-1 of less than or equal to 3 ppm; (i) less than 2.5 area percent of high molecular weight species as determined by size exclusion chromatography and spectrophotometric detection; (j) less than 0.5 area percent of monomer as determined by size exclusion chromatography and spectrophotometric detection; (k) CTLA4-Ig polypeptides having an amino acid at least 95% identical to any of SEQ ID NOS:5-10; (l) CTLA4-Ig molecules capable of binding to CD80 and CD86. The invention provides for a composition comprising CTLA4-Ig molecules, wherein the population of molecules is characterized by: (a) an average molar ratio of GlcNAc to CTLA4-Ig molecules from about 15 to about 35; (b) an average molar ratio of GalNAc to CTLA4-Ig molecules from about 1.7 to about 3.6; (c) an average molar ratio of galcatose to CTLA4-Ig molecules from about 8 to about 17; (d) an average molar ratio of fucose to CTLA4-Ig molecules from about 3.5 to about 8.3; (e) an average molar ratio of mannose to CTLA4-Ig molecules from about 7.2 to about 22; (f) an average molar ratio of sialic acid to CTLA4-Ig molecules from about 6 to about 12; (g) a pI as determined from visualization on an isoelectric focusing gel in a range from about 3.4±0.2 to about 5.0±0.2; (h) MCP-1 of less than or equal to 5 ppm; (i) less than 2.5 area percent of high molecular weight species as determined by size exclusion chromatography and spectrophotometric detection; (j) less than 0.5 area percent of monomer as determined by size exclusion chromatography and spectrophotometric detection; (k) CTLA4-Ig polypeptides having an amino acid at least 95% identical to any of SEQ ID NOS:5-10; (l) CTLA4-Ig molecules capable of binding to CD80 and CD86; or pharmaceutical equivalents thereof.

The invention provides for an isolated composition comprising CTLA4-Ig molecules having an incidence of immunogenicity of less than or equal to 7.4%. In one embodiment, the incidence of immunogenicity is from about 2.1% to about 7.4%. In one embodiment, the incidence of immunogenicity is less than or equal to 3.7%. In one embodiment, the incidence of immunogenicity is less than or equal to 3.0%. In one embodiment, the incidence of immunogenicity is from about 2.8% to about 3.0%. The invention provides for an isolated composition comprising CTLA4-Ig molecules, wherein, following administration of the composition to humans, production of antibodies that bind to the CTLA4-Ig molecules occurs at an incidence in the humans of less than or equal to 7.4%. In one embodiment, the incidence is from about 2.1% to about 7.4%. In one embodiment, the incidence is less than or equal to 3.7%. In one embodiment, the incidence is less than or equal to 3.0%. In one embodiment, the incidence is from about 2.8% to about 3.0%. The invention provides for an isolated composition comprising CTLA4-Ig molecules, wherein, following administration of the composition to humans, production of antibodies that bind to the CTLA4 portions of the CTLA4-Ig molecules occurs in the humans at an incidence of less than or equal to 4.9%. In one embodiment, the incidence is from about 0.5% to about 4.9%. In one embodiment, the incidence is less than or equal to 1.2%. In one embodiment, the incidence is less than or equal to 1.0%. In one embodiment, the incidence is from about 0.9% to about 1.0%. In one embodiment, the incidence is measured in an enzyme-lined immunosorbent assay (ELISA). In one embodiment, wherein the incidence is measured in an an electrochemoluminescence assay (ECL).

The invention provides for an isolated composition comprising CTLA4-Ig molecules, wherein, following administration of the composition to humans, production of antibodies that neutralize the CTLA4-Ig molecules occurs at an incidence of less than or equal to 75% of the humans having antibodies that bind to the CTLA4 portion of the CTLA4-Ig molecule. In one embodiment, the incidence is 40-75%. In one embodiment, the incidence is less than or equal to 40%. In one embodiment, the incidence is measured in a cell-based luciferase reporter assay.

The invention provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when the liquid culture exhibits greater than or equal to about 6.0 moles of NANA per mole of CTLA4-Ig dimer or to CTLA4-Ig molecule, as determined by assessing an aliquot of the liquid culture. The method also provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when the liquid culture exhibits from about 5.2 to about 7.6 moles of sialic acid per mole of CTLA4-Ig dimer or to CTLA4-Ig molecule, as determined by assessing an aliquot of the liquid culture. The method also provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when the liquid culture has a cell density of from about $33 \times 10^5$ viable cells per mL of liquid culture to about $79 \times 10^5$ cells per mL of liquid culture. The invention also provides a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when cell viability in the liquid culture is not less than about 38%. The invention also provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when cell viability in the liquid culture is not less than about 37%. The method also provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when endotoxin is less than or equal to about 76.8 EU per mL of liquid culture, as determined by assessing an aliquot of the liquid culture. The method also provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when endotoxin is less than or equal to about 4.8 EU per mL of liquid culture, as determined by assessing an aliquot of the liquid culture. The invention also provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs only when bioburden is less than 1 colony forming unit per mL of liquid culture, as determined by assessing an aliquot of the liquid culture. The invention also provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when at least two of the following conditions are met: (i) the liquid culture contains greater than or equal to about 6.0 moles of NANA per mole of CTLA4-Ig dimer or to CTLA4-Ig molecule; (ii) the liquid culture has a cell density of from about $33 \times 10^5$ viable cells per mL of liquid culture to about $79 \times 10^5$ viable cells per mL of liquid culture; (iii) the cell viability in the liquid culture is not less than about 38%; or (iv) the yield of CTLA4-Ig protein is greater than about 0.5 grams of CTLA4-Ig protein per liter of liquid culture, wherein NANA concentration in (i) and yield in (iv) are determined by assessing an aliquot of the liquid culture. The invention also provides for a method for producing CTLA4-Ig protein, the method comprising: (a) expanding mammalian cells that produce CTLA4-Ig protein, wherein the expanding is from a seed culture to a liquid culture of at least 10,000 L until the CTLA4-Ig protein is produced at a yield of at least about 0.5 grams of CTLA4-Ig protein per liter of liquid culture, as determined by assessing an aliquot of the liquid culture; and (b) isolating the CTLA4-Ig protein from the at least 10,000 L liquid culture, wherein the isolating occurs when at least two of the following conditions are met: (i) the liquid culture contains from about 5.2 to about 7.6 moles of sialic acid per mole of CTLA4-Ig dimer or to CTLA4-Ig molecule; (ii) the cell viability in the liquid culture is not less than about 37%; or (iii) the yield of CTLA4-Ig protein is greater than about 0.5 grams of CTLA4-Ig protein per liter of liquid culture, wherein the sialic acid content in (i) and yield in (iii) are determined by assessing an aliquot of the liquid culture.

Sequences:
SEQ ID NO:1 [CTLA4-Ig nucleotide sequence, See FIG. 1]
SEQ ID NO:2 [CTLA4-Ig amino acid sequence, See FIG. 1]
SEQ ID NO:3 [CTLA4$^{A29YL104E}$-Ig nucleotide sequence comprises nucleotides 79 to 1149 of the nucleic acid sequence shown in FIG. 2]
SEQ ID NO: 23 is the full nucleotide sequence shown in FIG. 2. This nucleotide sequence includes the coding sequence for the prosequence.
SEQ ID NO:4 [CTLA4$^{A29YL104E}$-Ig amino acid sequence, FIG. 3, without the pro-sequence]

[amino acids 25-383 of SEQ ID NO: 2]
SEQ ID NO: 5
MAMHVAQPAVVLASSRGIASFVCEYASPGKATEVRVTVLRQADSQVTEVCAATYMMGNELTF
LDDSICTGTSSGNQVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

[amino acids 26-383 of SEQ ID NO: 2]
SEQ ID NO: 6
AMHVAQPAVVLASSRGIASFVCEYASPGKATEVRVTVLRQADSQVTEVCAATYMMGNELTFL
DDSICTGTSSGNQVNLTIQGLRAMDTGLYICKVELMYPPPYYLGIGNGTQIYVIDPEPCPDS
DQEPKSSDKTHTSPPSPAPELLGGSSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

[amino acids 27-383 of SEQ ID NO: 2]
SEQ ID NO: 7
MHVAQPAVVLASSRGIASFVCEYASPGKATEVRVTVLRQADSQVTEVCAATYMMGNELTFLD
DSICTGTSSGNQVNLTIQGLRAMDTGLYICKVELMYPPPYYLGIGNGTQIYVIDPEPCPDSD
QEPKSSDKTHTSPPSPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

[amino acids 25-382 of SEQ ID NO: 2]
SEQ ID NO: 8
MAMHVAQPAVVLASSRGIASFVCEYASPGKATEVRVTVLRQADSQVTEVCAATYMMGNELTF
LDDSICTGTSSGNQVNLTIQGLRAMDTGLYICKVELMYPPPYYLGIGNGTQIYVIDPEPCPD
SDQEPKSSDKTHTSPPSPAPELLGGSSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG

[amino acids 26-382 of SEQ ID NO: 2]
SEQ ID NO: 9
AMHVAQPAVVLASSRGIASFVCEYASPGKATEVRVTVLRQADSQVTEVCAATYMMGNELTFL
DDSICTGTSSGNQVNLTIQGLRAMDTGLYICKVELMYPPPYYLGIGNGTQIYVIDPEPCPDS
DQEPKSSDKTHTSPPSPAPELLGGSSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG

[amino acids 27-382 of SEQ ID NO: 2]
SEQ ID NO: 10
MHVAQPAVVLASSRGIASFVCEYASPGKATEVRVTVLRQADSQVTEVCAATYMMGNELTFLD
DSICTGTSSGNQVNLTIQGLRAMDTGLYICKVELMYPPPYYLGIGNGTQIYVIDPEPCPDSD
QEPKSSDKTHTSPPSPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISK

```
AKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

[amino acids 25-383 of SEQ ID NO: 4]
                                                   SEQ ID NO: 11
MAMHVAQPAVVLASSRGIASFVCEYASPGKYTEVRVTVLRQADSQVTEVCAATYMMGNELTF

LDDSICTGTSSGNQVNLTIQGLRAMDTGLYICKVELMYPPPYYEGIGNGTQIYVIDPEPCPD

SDQEPKSSDKTHTSPPSPAPELLGGSSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

[amino acids 26-383 of SEQ ID NO: 4]
                                                   SEQ ID NO: 12
AMHVAQPAVVLASSRGIASFVCEYASPGKYTEVRVTVLRQADSQVTEVCAATYMMGNELTFL

DDSICTGTSSGNQVNLTIQGLRAMDTGLYICKVELMYPPPYYEGIGNGTQIYVIDPEPCPDS

DQEPKSSDKTHTSPPSPAPELLGGSSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

[amino acids 27-383 of SEQ ID NO: 4]
                                                   SEQ ID NO: 13
MHVAQPAVVLASSRGIASFVCEYASPGKYTEVRVTVLRQADSQVTEVCAATYMMGNELTFLD

DSICTGTSSGNQVNLTIQGLRAMDTGLYICKVELMYPPPYYEGIGNGTQIYVIDPEPCPDSD

QEPKSSDKTHTSPPSPAPELLGGSSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

[amino acids 25-382 of SEQ ID NO: 4]
                                                   SEQ ID NO: 14
MAMHVAQPAVVLASSRGIASFVCEYASPGKYTEVRVTVLRQADSQVTEVCAATYMMGNELTF

LDDSICTGTSSGNQVNLTIQGLRAMDTGLYICKVELMYPPPYYEGIGNGTQIYVIDPEPCPD

SDQEPKSSDKTHTSPPSPAPELLGGSSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

[amino acids 26-382 of SEQ ID NO: 4]
                                                   SEQ ID NO: 15
AMHVAQPAVVLASSRGIASFVCEYASPGKYTEVRVTVLRQADSQVTEVCAATYMMGNELTFL

DDSICTGTSSGNQVNLTIQGLRAMDTGLYICKVELMYPPPYYEGIGNGTQIYVIDPEPCPDS

DQEPKSSDKTHTSPPSPAPELLGGSSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

[amino acids 27-382 of SEQ ID NO: 4]
                                                   SEQ ID NO: 16
MHVAQPAVVLASSRGIASFVCEYASPGKYTEVRVTVLRQADSQVTEVCAATYMMGNELTFLD

DSICTGTSSGNQVNLTIQGLRAMDTGLYICKVELMYPPPYYEGIGNGTQIYVIDPEPCPDSD
```

```
                             -continued
QEPKSSDKTHTSPPSPAPELLGGSSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

SEQ ID NO: 17
[CTLA4 extracellular domain sequence]
                                                        SEQ ID NO: 18
MHVAQPAVVLASSRGIASFVCEYASPGKATEVRVTVLRQADSQVTEVCAATYMMGNELTFLD

DSICTGTSSGNQVNLTIQGLRAMDTGLYICKVELMYPPPYYLGIGNGTQIYVIDPEPCPD

SD

SEQ ID NO: 19
5'-AGAAAAGGGGCTGGAGAGATGGCTCAGTGGTTAAGAGCA-3'

SEQ ID NOS: 20-22

SEQ ID NO: 20
--5'-GTACTCAGG

SEQ ID NO: 21
--AGTCAGAGAC

SEQ ID NO: 22
--CGGCAGATCTCTGTGAGTTTGAGGCCAGCCTGGTCTACAAAGCAAGTT-
3'
```

CTLA4-Ig Monomers and Multimers

In certain embodiments, the invention provides cell lines having an expression cassette that comprises SEQ ID NO:1 (FIG. 1A). Such an expression cassette when expressed in mammalian cells, including CHO cells, can result in the production of N- and C-terminal variants, such that the proteins produced from the expression cassette can have the amino acid sequence of residues: (i) 26-383 of SEQ ID NO:2, (ii) 26-382 of SEQ ID NO:2; (iii) 27-383 of SEQ ID NO:2, or (iv) 27-382 of SEQ ID NO:2, or optionally (v) 25-382 of SEQ ID NO:2, or (vi) 25-383 of SEQ ID NO:2 (FIG. 1A). These proteins can be referred to herein as "SEQ ID NO:2 monomers," or monomers "having a SEQ ID NO:2 sequence." These SEQ ID NO:2 monomers can dimerize, such that dimer combinations can include, for example: (i) and (i); (i) and (ii); (i) and (iii); (i) and (iv); (i) and (v); (i) and (vi); (ii) and (ii); (ii) and (iii); (ii) and (iv); (ii) and (v); (ii) and (vi); (iii) and (iii); (iii) and (iv); (iii) and (v); (iii) and (vi); (iv) and (iv); (iv) and (v); (iv) and (vi); (v) and (v); (v) and (vi); and, (vi) and (vi). These different dimer combinations can also associate with each other to form tetramer CTLA4-Ig molecules. These monomers, dimers, teramers, and other multimers can be referred to herein as "SEQ ID NO:2 proteins" or proteins "having a SEQ ID NO:2 sequence." While the cell lines can produce these variants immediately upon translation, the variants can more typically be a product of post-translational actions in the cells. The cell line also secretes CTLA4-Ig molecules. Abatacept refers to SEQ ID NO:2 proteins.

CTLA4-Ig molecules can include, for example, CTLA4-Ig proteins in monomer, dimer, trimer, tetramer, pentamer, hexamer, or other multimeric forms. CTLA4-Ig molecules can comprise a protein fusion with at least an extracellular domain of CTLA4 and an immunoglobulin constant region. CTLA4-Ig molecules can have wild-type or mutant sequences, for example, with respect to the CTLA4 extracellular domain and immunoglobulin constant region sequences. CTLA4-Ig monomers, alone, or in dimer, tetramer or other multimer form, can be glycosylated.

In some embodiments, the invention provides populations of CTLA4-Ig molecules that have at least a certain percentage of dimer or other multimer molecules. For example, the invention provides CTLA4-Ig molecule populations that are greater than 90%, 95%, 96%, 97%, 98%, 99%, or 99.5% CTLA4-Ig dimers. In one embodiment, the invention provides a CTLA4-Ig molecule population that comprises from about 95% to about 99.5% CTLA4-Ig dimer and from about 0.5% to about 5% of CTLA4-Ig tetramer. In another embodiment, the CTLA4-Ig molecule population comprises about 98% CTLA4-Ig dimer, about 1.5% CTLA4-Ig tetramer and about 0.5% CTLA4-Ig monomer.

In one embodiment, the invention provides a population of CTLA4-Ig molecules wherein the population is substantially free of CTLA4-Ig monomer molecules. Substantially free of CTLA4-Ig monomer molecules can refer to a population of CTLA4-Ig molecules that have less than 1%, 0.5%, or 0.1% of monomers.

In one embodiment, the invention provides a population of CTLA4-Ig molecules wherein the population is substantially free of CTLA4-Ig multimers that are larger than dimers, such as tetramers, hexamers, etc. (e.g., high molecular weight species). Substantially free of CTLA4-Ig multimer molecules larger than dimers can refer to a population of CTLA4-Ig molecules that have less than 6%, 5%, 4%, 3%, 2%, 1%, 0.5%, or 0.1% of CTLA4-Ig multimers (e.g., high molecular weight species) larger than dimeric form.

A CTLA4-Ig monomer molecule can have, for example, the amino acid sequence of: (i) 26-383 of SEQ ID NO:2, (ii) 26-382 of SEQ ID NO:2 (iii) 27-383 of SEQ ID NO:2, or (iv) 27-382 of SEQ ID NO:2, or optionally (v) 25-382 of SEQ ID NO:2, or (vi) 25-383 of SEQ ID NO:2. When an expression cassette comprising the nucleic acid sequence of SEQ ID NO:1 is expressed in CHO cells, the predominant monomer form expressed has the N-terminus amino acid residue of methionine (residue 27 of SEQ ID NO:2), which corresponds to the N-terminus amino acid residue of wild-type human CTLA4. However, because SEQ ID NO:1 also includes the coding sequence for an Oncostatin M Signal Sequence (nucleotides 11-88 of SEQ ID NO:1), the expressed protein from SEQ ID NO:1 contains an Oncostatin M Signal Sequence. The signal sequence is cleaved from the expressed protein during the process of protein export from the cytoplasm, or secretion out of the cell. But cleavage can result in N-terminal variants, such as cleavage between amino acid residues 25 and 26 of SEQ ID NO. 2 (resulting in an N-terminus of residue 26, i.e., the "Ala variant"), or between amino acid residues 24 and 25 of SEQ ID NO. 2 (resulting in an N-terminus of residue 25, i.e., the "Met-Ala variant"), as opposed to cleavage between amino acid residues 26 and 27 of SEQ ID NO. 2 (resulting in an N-terminus of residue 27). For example, the Met-Ala variant can be present in a mixture of CTLA4-Ig molecules at about 1%, and the Ala variant can be present in a mixture of CTLA4-Ig molecules at about 8-10%. In addition, the expressed protein from SEQ ID NO:1 can have C-terminus variants due to incomplete processing. The predominant C-terminus is the glycine at residue 382 of SEQ ID NO:2. In a mixture of CTLA4-Ig molecules, monomers having lysine at the C-terminus (residue 383 of SEQ ID NO:2) can be present, for example, at about 4-5%.

In one embodiment, a CTLA4-Ig molecule has the amino acid sequence of SEQ ID NO: 5 as follows (which is the same as amino acids 25-383 of SEQ ID NO:2):

[SEQ ID NO: 5]
MAMHVAQPAVVLASSRGIASFVCEYASPGKATEVRVTLRQADSQVTEVC

AATYMMGNELTFLDDSICTGTSSGNQVNLTIQGLRAMDTGLYICKVELMY

PPPYYLGIGNGTQIYVIDPEPCPDSDQEPKSSDKTHTSPPSPAPELLGGS

SVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQ

KSLSLSPGK;

In another embodiment, a CTLA4-Ig molecule has the amino acid sequence of SEQ ID NO: 6 as follows (which is the same as amino acids 26-383 of SEQ ID NO:2):

[SEQ ID NO: 6]
AMHVAQPAVVLASSRGIASFVCEYASPGKATEVRVTLRQADSQVTEVCA

ATYMMGNELTFLDDSICTGTSSGNQVNLTIQGLRAMDTGLYICKVELMYP

PPYYLGIGNGTQIYVIDPEPCPDSDQEPKSSDKTHTSPPSPAPELLGGSS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPGK;

In another embodiment, a CTLA4-Ig molecule has the amino acid sequence of SEQ ID NO: 7 as follows (which is the same as amino acids 27-383 of SEQ ID NO:2):

[SEQ ID NO: 7]
MHVAQPAVVLASSRGIASFVCEYASPGKATEVRVTVLRQADSQVTEVCAA

TYMMGNELTFLDDSICTGTSSGNQVNLTIQGLRAMDTGLYICKVELMYPP

PYYLGIGNGTQIYVIDPEPCPDSDQEPKSSDKTHTSPPSPAPELLGGSSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPGK;

In another embodiment, a CTLA4-Ig molecule has the amino acid sequence of SEQ ID NO: 8 as follows (which is the same as amino acids 25-382 of SEQ ID NO:2):

[SEQ ID NO: 8]
MAMHVAQPAVVLASSRGIASFVCEYASPGKATEVRVTLRQADSQVTEVC

AATYMMGNELTFLDDSICTGTSSGNQVNLTIQGLRAMDTGLYICKVELMY

PPPYYLGIGNGTQIYVIDPEPCPDSDQEPKSSDKTHTSPPSPAPELLGGS

SVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQ

KSLSLSPG;

In one embodiment, a CTLA4-Ig molecule has the amino acid sequence of SEQ ID NO: 9 as follows (which is the same as amino acids 26-382 of SEQ ID NO:2):

[SEQ ID NO: 9]
AMHVAQPAVVLASSRGIASFVCEYASPGKATEVRVTLRQADSQVTEVCA

ATYMMGNELTFLDDSICTGTSSGNQVNLTIQGLRAMDTGLYICKVELMYP

PPYYLGIGNGTQIYVIDPEPCPDSDQEPKSSDKTHTSPPSPAPELLGGSS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPG;

In one embodiment, a CTLA4-Ig molecule has the amino acid sequence of SEQ ID NO: 10 as follows (which is the same as amino acids 27-382 of SEQ ID NO:2):

[SEQ ID NO: 10]
MHVAQPAVVLASSRGIASFVCEYASPGKATEVRVTLRQADSQVTEVCAA

TYMMGNELTFLDDSICTGTSSGNQVNLTIQGLRAMDTGLYICKVELMYPP

PYYLGIGNGTQIYVIDPEPCPDSDQEPKSSDKTHTSPPSPAPELLGGSSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENN

-continued

YKTTPPVLDSDGSFFLYSKLTVDKSRWQQGNVFSCSVMHEALHNHYTQKS
LSLSPG.

A CTLA4-Ig monomer molecule can comprise an extracellular domain of human CTLA4. In one embodiment, the extracellular domain can comprise the nucleotide sequence of nucleotides 89-463 of SEQ ID NO:1 that code for amino acids 27-151 of SEQ ID NO:2. In another embodiment, the extracellular domain can comprise mutant sequences of human CTLA4. In another embodiment, the extracellular domain can comprise nucleotide changes to nucleotides 89-463 of SEQ ID NO:1 such that conservative amino acid changes are made. In another embodiment, the extracellular domain can comprise a nucleotide sequence that is at least 75%, 80%, 85%, 90%, 95%, 96%, 97%, 98%, or 99% identical to nucleotides 89-463 of SEQ ID NO:1.

A CTLA4-Ig monomer molecule can comprise a constant region of a human immunoglobulin. This constant region can be a portion of a constant region; this constant region can have a wild-type or mutant sequence. The constant region can be from human IgG1, IgG2, IgG3, IgG4, IgM, IgA1, IgA2, IgD or IgE. The constant region can be from a light chain or a heavy chain of an immunoglobulin. Where the constant region is from an IgG, IgD, or IgA molecule, the constant region can comprise one or more of the following constant region domains: CL, CH1, hinge, CH2, or CH3. Where the constant region is from IgM or IgE, the constant region can comprise one or more of the following constant region domains: $C_L$, $C_H1$, $C_H2$, $C_H3$, or $C_H4$. In one embodiment, the constant region can comprise on or more constant region domains from IgG, IgD, IgA, IgM or IgE.

In one embodiment, CTLA4-Ig dimers are comprised of two monomers, wherein each monomer can have the same or different amino acid sequence, and where the sequence can be the amino acid sequence of: (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, and (vi) 25-383 of SEQ ID NO:2. Such CTLA4-Ig monomers can dimerize through the extracellular domain of the human CTLA4 sequence via a cysteine amino acid residue at position 146 of SEQ ID NO:2.

A CTLA4-Ig molecule can multimerize through the interaction of IgM or IgA constant region domains with a J chain protein. IgM and IgA are usually produced as multimers in association with an additional polypeptide chain, the J chain. In pentameric IgM, the monomers are crosslinked by disulfide bonds to each other in the CH3 domain and to the J chain through the CH4 domain. IgM can also form hexamers that lack a J chain where multimerization is achieved through disulfide bonds to each. In dimeric IgA, the monomers have disulfide bonds to the J chain via their CH3 domain and not each other. Thus, in one embodiment, the invention provides CTLA4-Ig multimers, including dimers, pentamers, and hexamers, wherein the Ig portion comprises an IgM constant region or portion thereof or an IgA constant region or portion thereof. Such CTLA4-Ig multimers based on IgM or IgA can include the J chain.

In one embodiment, a CTLA4-Ig monomer molecule (CTLA4 GenBank Accession No. I13253) comprises a modified human IgG1 hinge region (nucleotides 464-508 of SEQ ID NO:1; amino acids 152-166 of SEQ ID NO:2) wherein the serines at amino acid residues 156, 162, and 165 of SEQ ID NO:2 have been engineered from cysteines present in the wild-type sequence.

In one embodiment, a CTLA4-Ig monomer molecule comprises a modified human IgG1 CH2 region and a wild-type CH3 region (the modified human IgG1 $C_H2$ domain having nucleotides 509-838 of SEQ ID NO:1 and amino acids 167-276 of SEQ ID NO:2; the human IgG1 $C_H3$ domain having nucleotides 839-1159 of SEQ ID NO:1 and amino acids 277-383 of SEQ ID NO:2).

Figure 7:
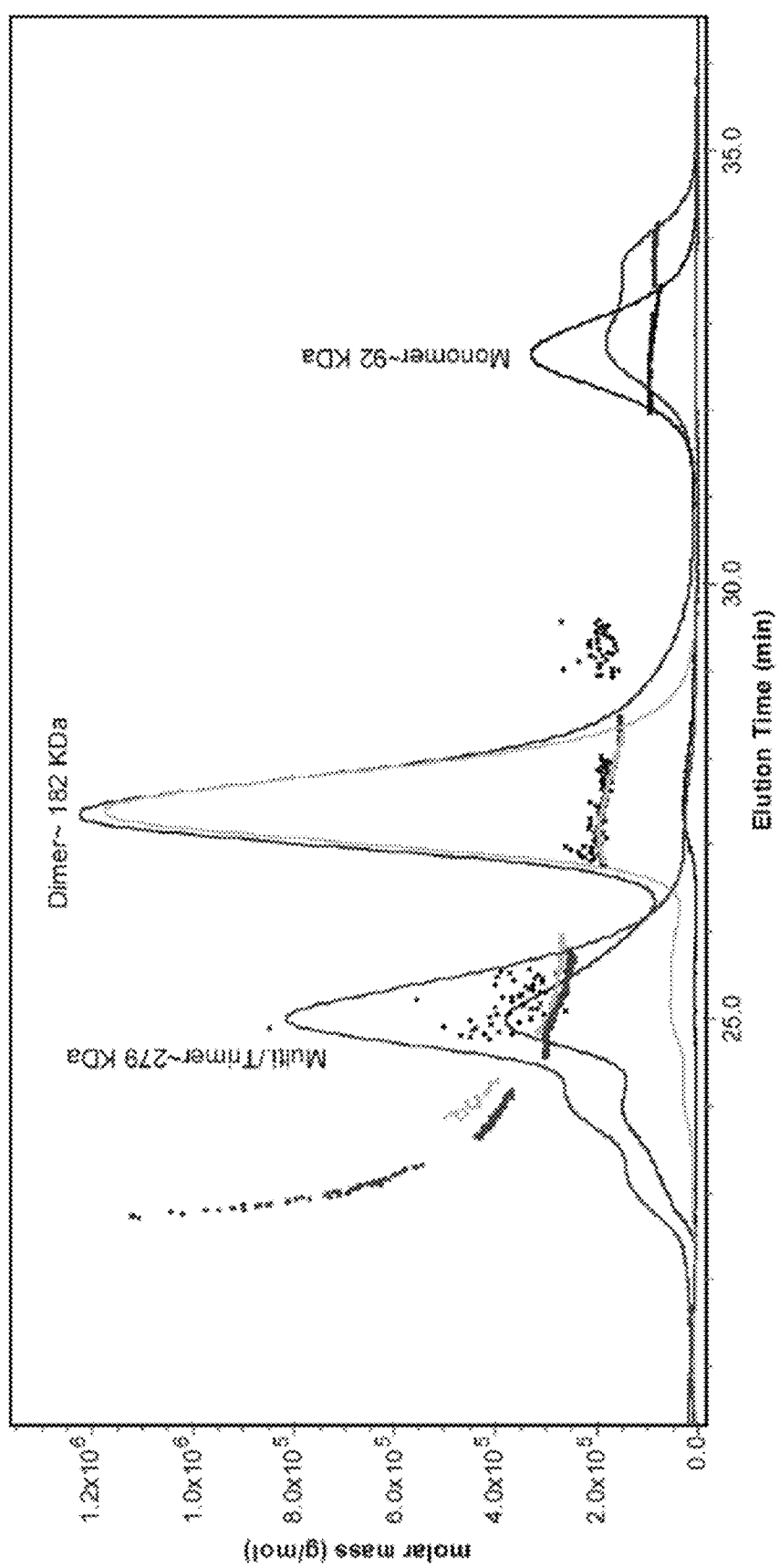
FIG. 7 is a graph that shows the apparent molecular weights which correspond to multimer, tetramer, and dimer fractions of a CTLA4-Ig HIC cleaning peak as determined by an overlay of two-column SEC with dynamic light scattering detection (DSL) and retention time on SEC.
Figure 8B:
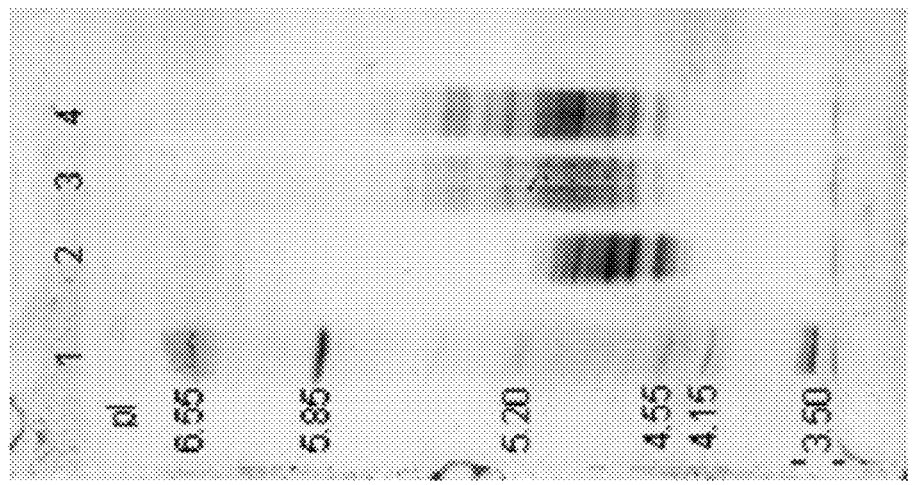
FIG. 8A (left) and 8B (right) show representative IEF gels of fractions of glycosylated CTLA4-Ig molecules (comprising SEQ ID NO:2 monomers) isolated and purified from HIC cleaning peak. The loading order for the gel in FIG. 8A is: lane 1, pI markers (Amersham); lane 2, CLTA4-Ig dimer standard; lane 3, Protein A eluate; lane 4, Multimer; lane 5, tetramer; lane 6, dimer. The loading order for the gel in FIG. 8B is: lane 1, pI marker (Amersham); lane 2, lane 2, CLTA4-Ig dimer standard; lane 3, tetramer; lane 4, dissociated tetramer. The panels show that the tetramer is less sialylated than the dimer.
Figure 8A:
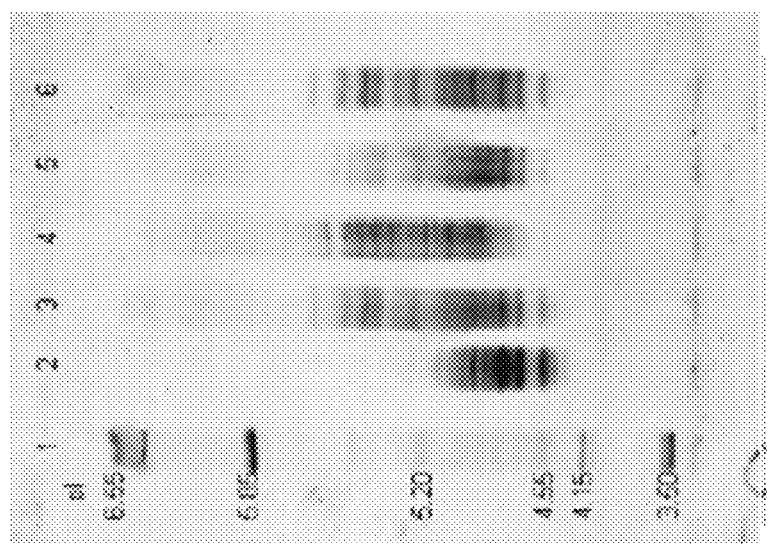
Figure 9:
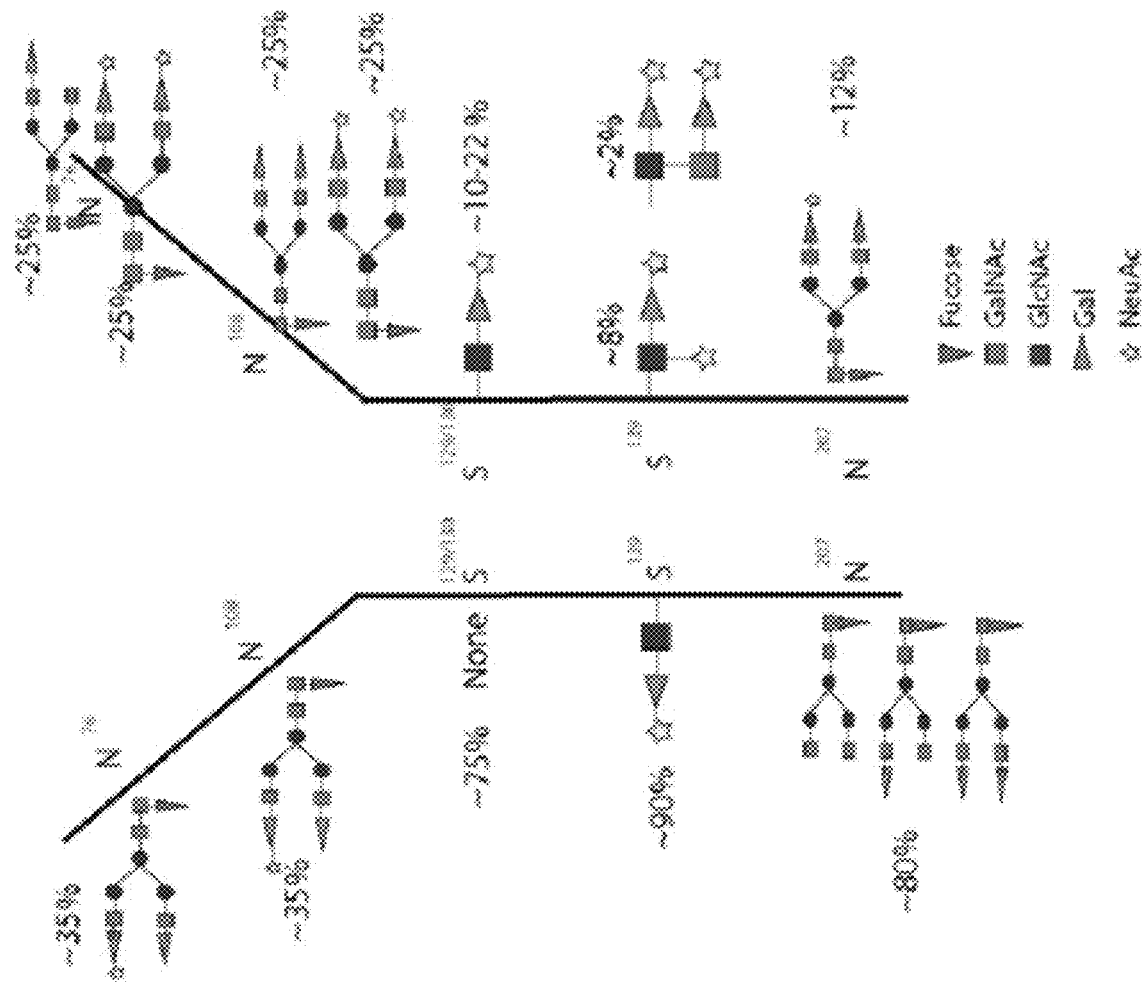
FIG. 9 shows the predominant carbohydrate structures and relative amounts of carbohydrates observed on a CTLA4-Ig dimer comprising monomers of SEQ ID NO:2. The amino acid residue numbering in the figure is not consistent with SEQ ID NO:2. For the amino acid residue numbering in the figure to be consistent with SEQ ID NO:2, the numeration needs to increase by 26, i.e., N$^{76}$ is N$^{102}$.

In one embodiment, a CTLA4-Ig molecule population comprises monomers having a sequence shown in any one or more of FIG. 7, 8, or 9 of the U.S. patent application published as Publication No. US 2002/0182211 A1, and in U.S. patent applications published as Publication Nos. US20030083246 and US20040022787, each of which is hereby incorporated by reference in its entirety.

In one embodiment, a CTLA4-Ig tetramer molecule comprises two pairs or two dimers of CTLA4-Ig polypeptides, wherein each polypeptide has one of the following amino acid sequences: (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, and (vi) 25-383 of SEQ ID NO:2. Each member of the pair of polypeptides or dimer is covalently linked to the other member, and the two pairs of polypeptides are non-covalently associated with one another thereby forming a tetramer. Such tetramer molecules are capable of binding to CD80 or CD86. In another embodiment, such tetramer molecules can bind to CD80 or CD86 with an avidity that is at least 2-fold greater than the binding avidity of a CTLA4-Ig dimer (whose monomers have one of the above amino acid sequences) to CD80 or CD86. In another embodiment, such tetramer molecules can bind to CD80 or CD86 with an avidity that is at least 2-fold greater than the binding affinity or avidity of wild-type CTLA4 to CD80 or CD86. Such greater avidity can contribute to higher efficacy in treating immune disorders and other diseases as described below, as well as in inhibiting tissue and/or solid organ transplant rejections. In addition, greater or improved avidity can produce the result of higher potency of a drug. For example, a therapeutic composition comprising CTLA4-Ig tetramer would have a higher avidity and therefore higher potency than the same amount of a therapeutic composition having CTLA4-Ig monomer. In another embodiment, such tetramer molecules can have at least a 2-fold greater inhibition on T cell proliferation as compared to a CTLA4-Ig dimer (whose monomers have one of the above amino acid sequences). In another embodiment, such tetramer molecules can have at least a 2-fold greater inhibition on T cell proliferation as compared to a wild-type CTLA4 molecule.

CTLA4$^{A29YL104E}$-Ig Monomers, Dimers, and Multimers

CTLA4$^{A29YL104E}$-Ig are modified forms of CTLA4-Ig (FIG. 1A; SEQ ID NOS: 1-2). The modification consists of point mutations that result in two amino acid substitutions (L104E and A29Y) as shown in FIG. 2 (corresponding to amino acid positions 55 and 130 in FIG. 3; SEQ ID NO: 4). Relative to CTLA4-Ig, CTLA4$^{A29YL104E}$-Ig (for example, SEQ ID NOS:5-10) bind CD80 (B7-1) with approximately 2-fold increased avidity, and binds CD86 (B7-2) with approximately 4-fold increased avidity. CTLA4$^{A29YL104E}$-Ig are approximately 10-fold more effective than CTLA4-Ig at inhibiting T cell proliferation, cytokine production, and CD28-dependent killing of target cells by natural killer cells. CTLA4$^{A29YL104E}$-Ig cause modest inhibition of B7-1 mediated T cell proliferation but are markedly more potent than CTLA4-Ig at blocking B7-2 mediated T cell proliferation. The increased potency is comparable, whether blocking B7-2 alone or blocking both B7-1 and B7-2, suggesting that the enhanced immunomodulatory activity of CTLA4$^{A29YL104E}$-Ig can most likely be attributed to the enhanced potency for blocking B7-2.

CTLA4$^{A29YL104E}$-Ig is a genetically engineered fusion protein, which consists of the functional binding domain of modified human CTLA-4 and the Fc domain of human immunoglobulin of the IgG1 class (FIG. 3A-3B). Two amino acid substitutions were made in the B7 binding region of the CTLA-4 domain (L104E and A29Y) to generate a CTLA4$^{A29YL104E}$-Ig molecule. A CTLA4$^{A29YL104E}$-Ig dimer is comprised of two glycosylated CTLA4$^{A29YL104E}$-Ig chains. It exists as a covalent dimer linked through an inter-chain disulfide bond. A molecular model of a CTLA4$^{A29YL104E}$-Ig molecule is shown in FIG. 4. A CTLA4$^{A29YL104E}$-Ig molecule has an average mass of approximately 91,800 Da as determined by matrix-assisted laser desorption-ionization time-of-flight (MALDI-TOF) mass spectrometry.

In certain embodiments, the invention provides cell lines having an expression cassette that comprises SEQ ID NO:3. Such an expression cassette when expressed in mammalian cells, for example CHO cells, can result in the production of N- and C-terminal variants, such that the polypeptides produced from the expression cassette can have the amino acid sequence of residues: (i) 26-383 of SEQ ID NO:4, (ii) 26-382 of SEQ ID NO:4; (iii) 27-383 of SEQ ID NO:4, or (iv) 27-382 of SEQ ID NO:4, or optionally (v) 25-382 of SEQ ID NO:4, or (vi) 25-383 of SEQ ID NO:4. These polypeptides can be referred to herein as "SEQ ID NO:4 monomers," or monomers "having a SEQ ID NO:4 sequence."

These SEQ ID NO:4 monomers can dimerize, such that dimer combinations can include, for example: (i) and (i); (i) and (ii); (i) and (iii); (i) and (iv); (i) and (v); (i) and (vi); (ii) and (ii); (ii) and (iii); (ii) and (iv); (ii) and (v); (ii) and (vi); (iii) and (iii); (iii) and (iv); (iii) and (v); (iii) and (vi); (iv) and (iv); (iv) and (v); (iv) and (vi); (v) and (v); (v) and (vi); and, (vi) and (vi). These different dimer combinations can also associate with each other to form tetramer CTLA4$^{A29YL104E}$-Ig molecules. These monomers, dimers, teramers, and other multimers can be referred to herein as "SEQ ID NO:4 polypeptides" or polypeptides "having a SEQ ID NO:4 sequence." While the cell lines can produce these variants immediately upon translation, the variants can more typically be a product of post-translational actions in the cells. Dimers can be covalently joined together, non-covalently joined together, or both. The invention provides for compositions that consist essentially of dimers that are covalently bound together. For example, the invention provides for compositions where at least 50% of the CTLA4-Ig dimers are made up of monomers joined covalently. The invention also provides for compositions where at least 60%, 70%, 80%, 85%, 90%, 95%, 96%, 97%, 98%, 99% or 100% of the CTLA4-Ig dimers are made up of monomers joined covalently. The invention also provides for compositions of CTLA4-Ig molecules, wherein the molecules are predominantly in dimer form, and the dimers are predominantly formed by covalent linkages. For example, the invention provides for a composition wherein the majority of the CTAL4-Ig dimers are joined covalently. It is possible that some fraction of the CTLA4-Ig dimers in the composition are joined non-covalently.

CTLA4$^{A29YL104E}$-Ig molecules can include, for example, CTLA4$^{A29YL104E}$-Ig in monomer, dimer, trimer, tetramer, pentamer, hexamer, or other multimeric forms. CTLA4$^{A29YL104E}$-Ig molecules can comprise a protein fusion with at least an extracellular domain of modified CTLA4 (SEQ ID NO:18) and an immunoglobulin constant region. CTLA4$^{A29YL104E}$-Ig molecules can have mutant sequences, for example, with respect to the modified CTLA4 extracellular domain and immunoglobulin constant region sequences. CTLA4$^{A29YL104E}$-Ig monomers, alone, or in dimer, tetramer or other multimer form, can be glycosylated.

In some embodiments, the invention provides populations of CTLA4$^{A29YL104E}$-Ig molecules that have at least a certain percentage of dimer or other multimer molecules. For example, the invention provides CTLA4$^{A29YL104E}$-Ig molecule populations that are greater than 90%, 95%, 96%, 97%, 98%, 99%, or 99.5% of CTLA4$^{A29YL104E}$-Ig dimers. In one embodiment, the invention provides a CTLA4$^{A29YL104E}$-Ig molecule population that comprises from about 95% to about 99.5% of CTLA4$^{A29YL104E}$-Ig dimer and from about 0.5% to about 5% of CTLA4$^{A29YL104E}$-Ig tetramer. In a further embodiment, the invention provides a CTLA4$^{A29YL104E}$-Ig molecule population that comprises from about 95% to about 99.5% of CTLA4$^{A29YL104EA}$-Ig dimer, from about 0.5% to about 2.5% of CTLA4$^{A29YL104EA}$-Ig monomer, and from about 0.5% to about 5% of CTLA4$^{A29YL104E}$-Ig tetramer. In another embodiment, the CTLA4$^{A29YL104E}$-Ig molecule population comprises about 96% of CTLA4$^{A29YL104E}$-Ig dimer, about 2.5% of CTLA4$^{A29YL104EA}$-Ig tetramer, and about 0.5% of CTLA4$^{A29YL104E}$-Ig monomer.

In one embodiment, the invention provides a population of CTLA4$^{A29YL104E}$-Ig molecules wherein the population is substantially free of CTLA4$^{A29YL104E}$-Ig monomers. Substantially free of CTLA4$^{A29YL104E}$-Ig monomers can refer to a population of CTLA4$^{A29YL104E}$-Ig molecules that have less than 1%, 0.5%, or 0.1% of monomers.

In another embodiment, the invention provides a population of CTLA4$^{A29YL104E}$-Ig molecules wherein the population is substantially free of CTLA4$^{A29YL104E}$-Ig multimers that are larger than dimers, such as tetramers, hexamers, etc. Substantially free of CTLA4$^{A29YL104EA}$-Ig multimers larger than dimers can refer to a population of CTLA4$^{A29YL104E}$-Ig molecules that have less than 6%, 5%, 4%, 3%, 2%, 1%, 0.5%, or 0.1% of CTLA4$^{A29YL104E}$-Ig multimers larger than dimers.

A CTLA4$^{A29YL104E}$-Ig monomer can have, for example, the amino acid sequence of: (i) 26-383 of SEQ ID NO:4, (ii) 26-382 of SEQ ID NO:4 (iii) 27-383 of SEQ ID NO:4, or (iv) 27-382 of SEQ ID NO:4, or optionally (v) 25-382 of SEQ ID NO:4, or (vi) 25-383 of SEQ ID NO:4. When an expression cassette comprising the nucleic acid sequence of SEQ ID NO:3 or 23 is expressed in CHO cells, the predominant monomer form expressed has the N-terminus amino acid residue of methionine (residue 27 of SEQ ID NO:4), which corresponds to the N-terminus amino acid residue of human CTLA4. However, because SEQ ID NO:23 also includes the coding sequence for an Oncostatin M Signal Sequence (nucleotides 11-88 of SEQ ID NO:23), the expressed protein from SEQ ID NO:23 contains an Oncostatin M Signal Sequence.

The signal sequence is cleaved from the expressed protein during the process of protein export from the cytoplasm, or secretion out of the cell. But cleavage can result in N-terminal variants, such as cleavage between amino acid residues 25 and 26 of SEQ ID NO:4 (resulting in an N-terminus of residue 26, i.e., the "Ala variant"), or between amino acid residues 24 and 25 SEQ ID NO:4 (resulting in an N-terminus of residue 25, i.e., the "Met-Ala variant"), as opposed to cleavage between amino acid residues 26 and 27 SEQ ID NO:4 (resulting in an N-terminus beginning with the Met residue at amino acid position 27). For example, the Met-Ala variant can be present in a mixture of CTLA4$^{A29YL104E}$-

Ig molecules at about 1%, and the Ala variant can be present in a mixture of CTLA4$^{A29YL104E}$-Ig molecules at about 10-20%.

In addition, the expressed protein from a nucleic acid comprising SEQ ID NO:3 can have C-terminus variants due to incomplete processing. The predominant C-terminus is the glycine at residue 382 of SEQ ID NO:4. In a mixture of CTLA4$^{A29YL104E}$-Ig molecules, monomers having lysine at the C-terminus (residue 383 of SEQ ID NO:4) can be present, for example, at about 4-8%

In one embodiment, a CTLA4$^{A29YL104E}$-Ig molecule comprises the amino acid sequence of SEQ ID NO: 11 as follows (which is the same as amino acids 25-383 of SEQ ID NO:4):

[SEQ ID NO: 11]
MAMHVAQPAVVLASSRGIASFVCEYASPGKYTEVRVTVLRQADSQVTEVC

AATYMMGNELTFLDDSICTGTSSGNQVNLTIQGLRAMDTGLYICKVELMY

PPPYYEGIGNGTQIYVIDPEPCPDSDQEPKSSDKTHTSPPSPAPELLGGS

SVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQ

KSLSLSPGK.

In another embodiment, a CTLA4$^{A29YL104E}$-Ig molecule comprises the amino acid sequence of SEQ ID NO: 12 as follows (which is the same as amino acids 26-383 of SEQ ID NO:4):

[SEQ ID NO: 12]
AMHVAQPAVVLASSRGIASFVCEYASPGKYTEVRVTVLRQADSQVTEVCA

ATYMMGNELTFLDDSICTGTSSGNQVNLTIQGLRAMDTGLYICKVELMYP

PPYYEGIGNGTQIYVIDPEPCPDSDQEPKSSDKTHTSPPSPAPELLGGSS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPGK.

In a further embodiment, a CTLA4$^{A29YL104E}$-Ig molecule comprises the amino acid sequence of SEQ ID NO: 13 as follows (which is the same as amino acids 27-383 of SEQ ID NO:4):

[SEQ ID NO: 13]
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSDQEPKSSDKTHTSPPSPAPELLGGSSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPGK.

In another embodiment, a CTLA4$^{A29YL104E}$-Ig molecule comprises the amino acid sequence of SEQ ID NO: 14 as follows (which is the same as amino acids 25-382 of SEQ ID NO:4):

[SEQ ID NO: 14]
MAMHVAQPAVVLASSRGIASFVCEYASPGKYTEVRVTVLRQADSQVTEVC

AATYMMGNELTFLDDSICTGTSSGNQVNLTIQGLRAMDTGLYICKVELMY

PPPYYEGIGNGTQIYVIDPEPCPDSDQEPKSSDKTHTSPPSPAPELLGGS

SVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQ

KSLSLSPG.

In one embodiment, a CTLA4$^{A29YL104E}$-Ig molecule has the amino acid sequence of SEQ ID NO: 15 as follows (which is the same as amino acids 26-382 of SEQ ID NO:4):

[SEQ ID NO: 15]
AMHVAQPAVVLASSRGIASFVCEYASPGKYTEVRVTVLRQADSQVTEVCA

ATYMMGNELTFLDDSICTGTSSGNQVNLTIQGLRAMDTGLYICKVELMYP

PPYYEGIGNGTQIYVIDPEPCPDSDQEPKSSDKTHTSPPSPAPELLGGSS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPG.

In a further embodiment, a CTLA4$^{A29YL104E}$-Ig molecule has the amino acid sequence of SEQ ID NO: 16 as follows (which is the same as amino acids 27-382 of SEQ ID NO:4):

[SEQ ID NO: 16]
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSDQEPKSSDKTHTSPPSPAPELLGGSSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPG.

A CTLA4$^{A29YL104E}$-Ig monomer comprises an extracellular domain of human CTLA4, wherein two amino acid substitutions were made in the CTLA-4 domain (L104E and A29Y) (FIG. 5). In one embodiment, the extracellular domain can comprise the nucleotide sequence of nucleotides 89-463 of SEQ ID NO:23 that code for amino acids 27-151 of SEQ ID NO:4. In another embodiment, the extracellular domain can comprise mutant sequences of human CTLA4 (such as single, double, and triple site mutants in amino acids 27-151 of SEQ ID NO:4). In another embodiment, the extracellular domain can comprise nucleotide changes to nucleotides 89-463 of SEQ ID NO:23 such that conservative amino acid changes are made. In a further embodiment, the extracellular domain can comprise nucleotide changes to nucleotides 89-463 of SEQ ID NO:23 such that non-conservative amino acid changes are made. In another embodiment, the extracellular domain can comprise a nucleotide sequence that is at least 75%, 80%, 85%, 90%, 95%, 96%, 97%, 98%, or 99% identical to nucleotides 89-463 of SEQ ID NO:23.

A CTLA4$^{A29YL104E}$-Ig monomer can comprise a constant region of a human immunoglobulin. This constant region can be a portion of a constant region. This constant region also can have a wild-type or mutant sequence. The constant region can be from human IgG$_1$, IgG$_2$, IgG$_3$, IgG$_4$, IgM, IgA$_1$, IgA$_2$, IgD or IgE. The constant region can be from a light chain or a heavy chain of an immunoglobulin. Where the constant region is from an IgG, IgD, or IgA molecule, the constant region can comprise one or more of the following constant region domains: $C_L$, $C_H1$, hinge, $C_H2$, or $C_H3$. Where the constant region is from IgM or IgE, the constant region can comprise one or more of the following constant region domains: $C_L$, $C_H1$, $C_H2$, $C_H3$, or $C_H4$. In one embodiment, the constant region can comprise on or more constant region domains from IgG, IgD, IgA, IgM or IgE.

In one embodiment, CTLA4$^{A29YL104E}$-Ig dimers are comprised of two monomers, wherein each monomer can have the same or different amino acid sequence, and where the sequence can be the amino acid sequence of: (i) 26-383 of SEQ ID NO:4, (ii) 26-382 of SEQ ID NO:4, (iii) 27-383 of SEQ ID NO:4, (iv) 27-382 of SEQ ID NO:4, (v) 25-382 of SEQ ID NO:4, and (vi) 25-383 of SEQ ID NO:4. Such CTLA4$^{A29YL104E}$-Ig monomers can dimerize through the extracellular domain of the human CTLA4 sequence via a cysteine amino acid residue at position 146 of SEQ ID NO:4 (or cysteine amino acid residue at position 120 of FIG. 5).

A CTLA4$^{A29YL104E}$-Ig molecule can multimerize through the interaction of IgM or IgA constant region domains with a J chain protein. IgM and IgA are usually produced as multimers in association with an additional polypeptide chain, the J chain. In pentameric IgM, the monomers are crosslinked by disulfide bonds to each other in the $C_H3$ domain and to the J chain through the $C_H4$ domain. IgM can also form hexamers that lack a J chain where multimerization is achieved through disulfide bonds to each. In dimeric IgA, the monomers have disulfide bonds to the J chain via their $C_H3$ domain and not each other. Thus, in one embodiment, the invention provides CTLA4$^{A29YL104E}$-Ig multimers, including dimers, pentamers, and hexamers, wherein the Ig portion comprises an IgM constant region or portion thereof or an IgA constant region or portion thereof. Such CTLA4$^{A29YL104E}$-Ig multimers based on IgM or IgA can include the J chain.

In one embodiment, a CTLA4$^{A29YL104E}$-Ig monomer comprises a modified human IgG1 hinge region (nucleotides 464-508 of SEQ ID NO:23; amino acids 152-166 of SEQ ID NO:4) wherein the serine residues at positions 156, 162, and 165 of SEQ ID NO:4 have been engineered from cysteine residues present in the wild-type sequence.

In one embodiment, a CTLA4$^{A29YL104E}$-Ig monomer comprises a modified human IgG1 CH2 region and a wild-type CH3 region (the modified human IgG1 CH2 domain having nucleotides 509-838 of SEQ ID NO:1 and amino acids 167-276 of SEQ ID NO:2; the human IgG1 $C_H3$ domain having nucleotides 839-1159 of SEQ ID NO:1 and amino acids 277-383 of SEQ ID NO:2).

In one embodiment, a CTLA4$^{A29YL104E}$-Ig molecule population comprises monomers having a sequence shown U.S. Patent Application Publication Nos. U.S. 2002/0039577, U.S. 2003/0007968, U.S. 2004/0022787, U.S. 2005/0019859 and U.S. 2005/0084933, and U.S. Pat. No. 7,094,874, each of which is hereby incorporated by reference in its entirety.

In one embodiment, a CTLA4$^{A29YL104E}$-Ig tetramer comprises two pairs or two dimers of CTLA4$^{A29YL104E}$-Ig molecules, wherein each polypeptide has one of the following amino acid sequences: (i) 26-383 of SEQ ID NO:4, (ii) 26-382 of SEQ ID NO:4, (iii) 27-383 of SEQ ID NO:4, (iv) 27-382 of SEQ ID NO:4, (v) 25-382 of SEQ ID NO:4, and (vi) 25-383 of SEQ ID NO:4. Each member of the pair of polypeptides or dimer is covalently linked to the other member, and the two pairs of polypeptides are non-covalently associated with one another thereby forming a tetramer. Such tetramer molecules are capable of binding to CD80 or CD86. In another embodiment, such tetramer molecules can bind to CD80 or CD86 with an avidity that is at least 2-fold greater than the binding avidity of a CTLA4$^{A29YL104E}$-Ig dimer (whose monomers have one of the above amino acid sequences) to CD80 or CD86.

Such greater avidity can contribute to higher efficacy in treating immune disorders and other diseases as described below, as well as in inhibiting tissue and/or solid organ transplant rejections. In addition, greater or improved avidity can produce the result of higher potency of a drug. For example, a therapeutic composition comprising CTLA4$^{A29YL104E}$-Ig tetramer would have a higher avidity and therefore higher potency than the same amount of a therapeutic composition having CTLA4$^{A29YL104E}$-Ig monomer. In another embodiment, such tetramer molecules can have at least a 2-fold greater inhibition on T cell proliferation as compared to a CTLA4$^{A29YL104E}$-Ig dimer (whose monomers have one of the above amino acid sequences). In another embodiment, such tetramer molecules can have at least a 2-fold greater inhibition on T cell proliferation as compared to a CTLA4-Ig tetramer molecule.

Characterization of CTLA4-Ig and CTLA4$^{A29YL104E}$-Ig Molecules

T cell proliferation can be measured using standard assays known in the art. For example, one of the most common ways to assess T cell proliferation is to stimulate T cells via antigen or agonistic antibodies to TCR and to measure, for example, the incorporation of tritiated thymidine ($^3$H-TdR) in proliferating T cells or the amount of cytokines released by proliferating T cells into culture. The inhibitory effect of CTLA4-Ig or CTLA4$^{A29YL104E}$-Ig molecules upon T cell activation or proliferation can thereby be measured.

The affinity of a CTLA4-Ig molecule is the strength of binding of the molecule to a single ligand, including CD80, CD86, or CD80Ig or CD86Ig fusion proteins. The affinity of CTLA4-Ig or CTLA4$^{A29YL104E}$-Ig to ligands can be measured, for example, by using binding interaction analysis (BIA) based on surface plasmon technique. Aside from measuring binding strength, it permits real time determination of binding kinetics, such as association and dissociation rate constants. A sensor chip, consisting of a glass slide coated with a thin metal film, to which a surface matrix is covalently attached, is coated with one of the interactants, i.e, CTLA4-Ig, CTLA4$^{A29YL104E}$-Ig, or one of the ligands. A solution containing the other interactant is allowed to flow over its surface. A continuous light beam is directed against the other side of the surface, and its reflection angle is measured. On binding of CTLA4-Ig or CTLA4$^{A29YL104E}$-Ig to the ligand, the resonance angle of the light beam changes (as it depends on the refractive index of the medium close to the reactive side of the sensor, which in turn is directly correlated to the concentration of dissolved material in the medium). It is subsequently analyzed with the aid of a computer.

In one embodiment, CTLA4-Ig binding experiments can be performed by surface plasmon resonance (SPR) on a BIAcore instrument (BIAcore AG, Uppsala, Sweden). CTLA4-Ig can be covalently coupled by primary amine groups to a carboxymethylated dextran matrix on a BIAcore sensor chip, thereby immobilizing CTLA4-Ig to the sensor chip. Alternatively, an anti-constant region antibody can be used to immobilize CTLA4-Ig indirectly to the sensor surface via the Ig fragment. Thereafter, ligands are added to the chip to measure CTLA4-Ig binding to the ligands. Affinity measurements can be performed, for example, as described in van der Merwe, P. et al., *J. Exp. Med.* (1997) 185 (3):393-404, which is hereby incorporated by reference in its entirety. In another embodiment, CTLA4$^{A29YL104E}$-Ig binding experiments can be performed using surface plasmon resonance (SPR) technology as described above (FIG. 6; see EXAMPLE 21).

The avidity of CTLA4-Ig or CTLA4$^{A29YL104E}$-Ig molecules can also be measured. Avidity can be defines as the sum total of the strength of of binding of two molecules or cells to one another at multiple sites. Avidity is distinct from affinity, which is the strength of binding one site on a molecule to its ligand. Without being bound by theory, higher avidity of CTLA4-Ig or CTLA4$^{A29YL104E}$-Ig molecules can lead to increased potency of inhibition by CTLA4-Ig or CTLA4$^{A29YL104E}$-Ig molecules on T-cell proliferation and activation. Avidity can be measured, for example, by two categories of solid phase assays: a) competitive inhibition assays, and b) elution assays. In both of them the ligand is attached to a solid support. In the competitive inhibition assay, CTLA4-Ig or CTLA4$^{A29YL104E}$-Ig molecules are then added in solution at a fixed concentration, together with free ligand in different concentrations, and the amount of ligand, which inhibits solid phase binding by 50%, is determined. The less ligand needed, the stronger the avidity. In elution assays, the ligand is added in solution. After obtaining a state of equilibrium, a chaotrope or denaturant agent (e.g. isothiocyanate, urea, or diethylamine) is added in different concentrations to disrupt CTLA4-Ig/ligand interactions or CTLA4$^{A29YL104E}$-Ig/ligand interactions. The amount of CTLA4-Ig or CTLA4$^{A29YL104E}$-Ig resisting elution is determined thereafter with an ELISA. The higher the avidity, the more chaotropic agent is needed to elute a certain amount of CTLA4-Ig or CTLA4$^{A29YL104E}$-Ig. The relative avidity of a heterogeneous mixture of CTLA4-Ig molecules or CTLA4$^{A29YL104E}$-Ig can be expressed as the avidity index (AI), equal to the concentration of eluting agent needed to elute 50% of the bound CTLA4-Ig or CTLA4$^{A29YL104E}$-Ig molecules. Refined analysis of data can be performed by determining percentages of eluted CTLA4-Ig or CTLA4$^{A29YL104E}$-Ig at different concentrations of the eluting agent.

A Phenyl Sepharose 4 Fast Flow column chromatography, Hydrophobic Interaction Chromatography (HIC), process can be used to reduce the amount of CTLA4-Ig high molecular weight species eluted in a HIC purification step (see Example 15). Therefore, the cleaning peak from the HIC column is enriched in CTLA4-Ig HMW species. For example, preparative single or tandem column SEC HPLC can be employed to purify dimer, tetramer and multimer subpopulations from HIC cleaning peak material. In one embodiment, the purified components are CTLA4-Ig dimer, tetramer, and hexamer. Characterization of high molecular weight components of CTLA4-Ig present in the HIC cleaning peak can be done by static and dynamic light scattering techniques. Samples taken at the hydrophobic interaction chromatography (HIC) process step chase revealed the presence of dimer, tetramer, and multimers at various sampling points. Hexamer species can be detected only in samples corresponding to the "start of the cleaning peak" and "cleaning peak maximum OD". Decamer species were detected in the "cleaning peak maximum OD" only. Molar mass and hydrodynamic radius formation can be determined by fractionation via size exclusion chromatography (SEC) employing MultiAngle light scattering (MALS) coupled with quasi elastic light scatter (QELS) detection.

With respect to CTLA4-Ig molecules produced from the cell line, SEC shows the Protein A eluate is a mixture of multimer, tetramer, and dimer components. Fractionation of this mixture on preparative tandem SEC column enables isolation of quantities of multimer, tetramer and dimer species. The area percent recovery for each component in SEC analysis of the isolated fractions results in 93-98% homogeneity for each fraction. In one aspect, purification of the individual components enables comparison of the physicochemical properties of components of CTLA4-Ig HMW material to those of CTLA4-Ig dimer. FIG. 7 shows the apparent molecular weights, which correspond to multimer, tetramer, and dimer fractions of CTLA4-Ig HIC cleaning peak, as determined by SEC with dynamic light scattering detection (DSL) and retention time on SEC. In one embodiment, the biospecific binding activity of purified components from the HIC cleaning peak is comparable to the binding activity of determined by the BIAcore based immobilized B7-1Ig binding assay. In another aspect, sialic acid molar ratio for components isolated from HIC cleaning peak are in the range of 4.9 to 7.6 whereas the sialic acid molar ratio of CTLA4-Ig molecules or dimer (not in the HIC cleaning peak) is in the range of 8-10. Analysis by IEF gel indicates reduced mobility CTLA4-Ig isoforms purified from HIC cleaning peak compared to the migration of CTLA4-Ig dimer. This is consistent with lower sialic acid molar ratios observed for the CTLA4-Ig HIC cleaning peak fractions (FIG. 8).

The choice of cell culture conditions can influence the formation of single chain (i.e., monomer) and high molecular weight species (i.e, dimers, tetramers, etc.) of a recombinant protein product. Growth conditions, also including but not limited to media composition, are factors that can affect the formation of single chain, and the level of cysteinylation. This is likely the result of presence of agents that lead to disulfide bond reduction. The supplementation of cysteine directly or cysteine containing media to cells secreting CTLA4-Ig or CTLA4$^{A29YL104E}$-Ig can result in a rapid formation of single chain and high molecular weight species. The rate is proportional to amount of cysteine added. In another embodiment, the supplementation of iodoacetamide, a compound that reacts with free sulfhydryls, blocks the formation of high molecular weight species of CTLA4-Ig or CTLA4$^{A29YL104E}$-Ig that are dependent upon disulfide bonds.

For example, the iodoacetamide sensitive and non-sensitive high molecular weight pathway highlight two major and distinctly different mechanisms by which high molecular weight species can form in CTLA4-Ig. The supplementation of high salt concentrations (0.5M) to CTLA4-Ig solutions results in a sustained, rapid rate of high molecular weight formation. EDTA, ConAcidSol II, and yeastolates modestly increase single chain formation (see Example 5).

In certain embodiments, the invention provides methods for generating high molecular weight CTLA4-Ig populations, wherein mixtures containing predominantly monomers or dimers of CTLA4-Ig are supplemented with high salt such that the mixture has a salt concentration greater than about 0.3, 0.4, 0.45, 0.5, or 0.6M. In one embodiment, such methods generate a mixture comprising a CTLA4-Ig population that has at least 50%, 55%, 60%, 65%, 70%, 75%, 80%, 85%, 90%, or 95% CTLA4-Ig tetramer molecules.

In one embodiment, the invention provides a population of CTLA4-Ig single chain species containing a modification on $Cys^{146}$ such that it is cysteinylated (see Example 4). Cysteinlyation is a posttranslational modification wherein a cysteine within a polypeptide chain is modified by the attachment of another cysteine via a disulfide bond. Cysteinylation of proteins have been implicated in modifying protein bioactivity including immunogenicity and antigenicity of MHC Class-I restricted viral determinants. In one embodiment, the invention provides a composition that comprises at least 1, 5, 10, 15, 20, 25, 50, 75, 90, or 95% of cysteinylated single chain CTLA4-Ig molecules. In another embodiment of the invention, a CTLA4-Ig population has no more than about 1% CTLA4-Ig monomer molecules, or in another embodiment, less than 0.6% CTLA4-Ig monomer.

The present invention provides a composition comprising CTLA4-Ig molecules, wherein the CTLA4-Ig molecules have an average molar ratio of sialic acid to CTLA4-Ig molecules of from about 5 to about 18. In some embodiments the average molar ratio of sialic acid to CTLA4-Ig molecules is between from about X to about Y, inclusive of X and Y, where X is about 4, 5, 6, 7, 8, 9, 10, 11, 12, 13, 14, 15, 16, or 17, and Y is about 5, 6, 7, 8, 9, 10, 11, 12, 13, 14, 15, 16, 17 or 18. In other embodiments the average molar ratio of sialic acid to CTLA4-Ig molecules is between from about X to about Y, inclusive of X and Y, where X is about 4.0, 4.5, 5.0, 5.5 or 6.0, and Y is about 8.0, 8.5, 9.0, 9.5, or 10.0. In other embodiments the average molar ratio of sialic acid to CTLA4-Ig molecules is between from about X to about Y, inclusive of X and Y, where X is about 6.0, 6.5, 7.0, 7.5, 8.0, 8.5 or 9.0 and Y is about 11.0, 11.5, 12.0, 12.5 or 13.0. In other embodiments the average molar ratio of sialic acid to CTLA4-Ig molecules is from about 6 to about 14, from about 7 to about 13, from about 8 to about 12, or from about 9 to about 11. In other embodiments the average molar ratio of sialic acid to CTLA4-Ig molecules is from about 5 to about 9, from about 5.5 to about 9.5, from about 6 to about 9, from about 6 to about 10, or from about 7 to about 10. In other embodiments the average molar ratio of sialic acid to CTLA4-Ig molecules is greater than or equal to 5, or greater than or equal to 8. In certain embodiments, the sialic acid is N-acetyl neuraminic acid (NANA).

The present invention provides a composition comprising CTLA4-Ig molecules, wherein the CTLA4-Ig molecules have an average molar ratio of N-glycolyl neuraminic acid (NGNA) to CTLA4-Ig molecules of less than or equal to 2.5, less than or equal to 2.0, less than or equal to 1.5, less than or equal to 1.0, or less than or equal to 0.5.

The present invention provides a composition comprising CTLA4-Ig molecules, wherein the CTLA4-Ig molecules are greater than or equal to 93.0 area percent, greater than or equal to 93.5 area percent, greater than or equal to 94.0 area percent, greater than or equal to 94.5 area percent, greater than or equal to 95.0 area percent, greater than or equal to 95.5 area percent, greater than or equal to 96.0 area percent, greater than or equal to 96.5 area percent, or greater than or equal to 97.0 area percent CTLA4-Ig dimers as determined by size exclusion chromatography and spectrophotometric detection. In some embodiments, the composition comprises CTLA4-Ig molecules, wherein the CTLA4-Ig molecules are greater than or equal to 95.0 area percent CTLA4-Ig dimers, and less than or equal to 4.0 area percent high molecular weight species as determined by size exclusion chromatography and spectrophotometric detection. In some embodiments, the composition comprises CTLA4-Ig molecules, wherein the CTLA4-Ig molecules are greater than or equal to 95.0 area percent CTLA4-Ig dimers, and less than or equal to 5.0 area percent high molecular weight species as determined by size exclusion chromatography and spectrophotometric detection.

The present invention provides a composition comprising CTLA4-Ig molecules, wherein the CTLA4-Ig molecules are of less than or equal to 2.0 area percent, less than or equal to 1.5 area percent, less than or equal to 1.0 area percent, or less than or equal to 0.5 area percent area percent CTLA4-Ig monomers (i.e., single chain) as determined by size exclusion chromatography and spectrophotometric detection.

The present invention provides a composition comprising CTLA4-Ig molecules, wherein the CTLA4-Ig molecules are of less than or equal to 5.0 area percent, less than or equal to 4.5 area percent, less than or equal to 4.0 area percent, less than or equal to 3.5 area percent, less than or equal to 3.0 area percent, less than or equal to 2.5 area percent, less than or equal to 2.0 area percent, less than or equal to 1.5 area percent, less than or equal to 1.0 area percent, or less than or equal to 0.5 area percent CTLA4-Ig high molecular weight species (e.g., tetramer) as determined by size exclusion chromatography and spectrophotometric detection. In some embodiments, especially those involving concentrated compositions comprising CTLA4-Ig molecules, (such as, for example, those for subcutaneous administration) the CTLA4-Ig molecules are of less than or equal to 10 area percent, less than or equal to 9 area percent, less than or equal to 8 area percent, less than or equal to 7 area percent, less than or equal to 6 area percent CTLA4-Ig high molecular weight species as determined by size exclusion chromatography and spectrophotometric detection.

The present invention provides a composition comprising CTLA4-Ig molecules, wherein the composition comprises an amount of MCP-1 or MCP-1-like material less than or equal to 50 ppm, less than or equal to 40 ppm, less than or equal to 38 ppm, less than or equal to 30 ppm less than or equal to 20 ppm, less than or equal to 10 ppm, 5 ppm, less than or equal to 4 ppm, less than or equal to less than or equal to 3 ppm, less than or equal to 2 ppm or less than or equal to 1 ppm. The present invention provides a composition comprising CTLA4-Ig molecules, wherein the composition comprises MCP-1 or MCP-1-like material at less than or equal to 50 ng/mg CTLA4-Ig molecules, less than or equal to 40 ng/mg CTLA4-Ig molecules, less than or equal to 38 ng/mg CTLA4-Ig molecules, less than or equal to 30 ng/mg CTLA4-Ig molecules, less than or equal to 20 ng/mg CTLA4-Ig molecules, less than or equal to 10 ng/mg CTLA4-Ig molecules, less than or equal to 5 ng/mg, less than or equal to 4 ng/mg CTLA4-Ig molecules, less than or equal to 3 ng/mg CTLA4-Ig molecules, less than or equal to 2 ng/mg CTLA4-Ig molecules or less than or equal to 1 ng/mg CTLA4-Ig molecules. The present invention provides a composition comprising CTLA4-Ig molecules and an amount of MCP-1 (including the absence of MCP-1) wherein said composition is a pharmaceutically acceptable composition.

The present invention provides a composition comprising CTLA4-Ig molecules, wherein the CTLA4-Ig molecules have an average molar ratio of galactose to CTLA4-Ig molecules of from about 6 to about 19. In some embodiments the average molar ratio of sialic acid to CTLA4-Ig molecules is from about X to about Y, where X is about 6, 7, 8, 9, 10, 11, 12, 13, 14, 15, 16, 17 or 18, and Y is about 7, 8, 9, 10, 11, 12, 13, 14, 15, 16, 17, 18 or 19. In other embodiments the average molar ratio of galactose to CTLA4-Ig molecules is between from about X to Y, inclusive of X and Y, where X is about 6.0, 6.5, 7.0, 7.5, 8.0, 8.5, 9.0, 9.5, or 10.0 and Y is about 12.0, 12.5, 13.0, 13.5, 14.0, 14.5, 15.0, 15.5, or 16.0. In other embodiments the average molar ratio of galactose to CTLA4-Ig molecules is between from about X to about Y, inclusive of X and Y, wherein X is about 6.0, 6.5, 7.0, 7.5 or 8.0 and Y is about 15.0, 15.5, 16.0, 16.5, 17.0, 17.5, 18.0, 18.5, or 19.0. In other embodiments the average molar ratio of galactose to CTLA4-Ig molecules is from about from about 7 to about 15, from about 8 to about 14, from about 9 to about 13, from about 10 to about 12. In other embodiments the average molar ratio of galactose to CTLA4-Ig molecules is from about 7 to about 18, from about 8 to about 17, from about 9 to about 17, from about 9 to about 16, or from about 10 to about 15. In other embodiments the average molar ratio of galactose to CTLA4-Ig molecules is greater than or equal to 8.

The present invention provides a composition comprising CTLA4-Ig molecules, wherein the CTLA4-Ig molecules have an average molar ratio of fucose to CTLA4-Ig molecules of from about 0.5 to about 12. In some embodiments the average molar ratio of sialic acid to CTLA4-Ig molecules is between from about X to about Y, inclusive of X and Y, where X is about 0.5, 1.0, 1.5, 2.0, 2.5, 3.0, 3.5 or 4.5, and Y is about 7.0, 7.5, 8.0, 8.5, 9.0, 9.5, 10.0 or 10.5. In other embodiments the average molar ratio of fucose to CTLA4-Ig molecules is between from about X to about Y, inclusive of X and Y, where X is about 2.9, 3.1, 3.3, 3.5, 3.7, 3.9, or 4.1 and Y is about 7.9, 8.1, 8.3, 8.5, 8.7, 8.9, or 9.1. In other embodiments the average molar ratio of fucose to CTLA4-Ig molecules is between from about X to about Y, inclusive of X and Y, wherein X is about 1.0, 1.5, 1.7, 1.9, 2.1, 2.3, or 2.5, and Y is about 8.7, 8.9, 9.1, 9.3, 9.6, 9.9, 10.1, 10.3 or 10.5. In other embodiments the average molar ratio of fucose to CTLA4-Ig molecules is from about from about 3.3 to about 8.5, from about 3.5 to about 8.3, from about 3.7 to about 8.1, from about 3.9 to about 7.9. In other embodiments the average molar ratio of fucose to CTLA4-Ig molecules is from about 1.5 to about 9.5, from about 1.7 to about 9.3, from about 1.9 to about 9.1, or from about 2.1 to about 8.9. In other embodiments the average molar ratio of fucose to CTLA4-Ig molecules is greater than or equal to 1.7.

The present invention provides a composition comprising CTLA4-Ig molecules, wherein the CTLA4-Ig molecules have an average molar ratio of mannose to CTLA4-Ig molecules of from about 5 to about 25. In some embodiments the average molar ratio of sialic acid to CTLA4-Ig molecules is between from about X to about Y, inclusive of X and Y, where X is about 5, 6, 7, 8, 9, 10, 11, 12, 13, 14, 15, 16, 17, 18, 19, 20 or 21, and Y is about 6, 7, 8, 9, 10, 11, 12, 13, 14, 15, 16, 17, 18, 19, 20, 21, 22, 23 or 24. In other embodiments the average molar ratio of mannose to CTLA4-Ig molecules is between from about X to about Y, inclusive of X and Y, where X is about 6.5, 7.0, 7.5, 7.7, 7.9, 8.1, 8.3, 8.5, 9.0, 9.5, 10.0, 10.5, 11.0, 11.5 or 12.0 and Y is about 17.0, 17.5, 18.0, 18.5, 19.0, 19.5, 20.0, 20.5, 21.0, 21.5, 22.0, 22.5, 23, 23.5 or 24.0. In other embodiments the average molar ratio of mannose to CTLA4-Ig molecules is between from about X to Y, inclusive of X and Y, where X is about 8, 8.5, 9.0, 9.5 10.0 or 11.0 and Y is about 17.0, 17.5, 18.0, 18.5, 19.0, 19.5 or 20.0. In other embodiments the average molar ratio of mannose to CTLA4-Ig molecules is from about from about 6 to about 23, from about 7 to about 22, from about 7.7 to about 22, from about 8 to about 21, from about 9 to about 20, from about 10 to about 19, from about 11 to about 19, and from about 11 to about 17. In other embodiments the average molar ratio of mannose to CTLA4-Ig molecules is from about 8 to about 19, from about 9 to about 18, from about 10 to about 17, or from about 11 to about 16. In other embodiments the average molar ratio of mannose to CTLA4-Ig molecules is greater than or equal to 7.

The present invention provides a composition comprising CTLA4-Ig molecules, wherein the CTLA4-Ig molecules are of less than or equal to 5.0 area percent, less than or equal to 4.5 area percent, less than or equal to 4.0 area percent, less than or equal to 3.5 area percent, less than or equal to 3.0 area percent, less than or equal to 2.5 area percent, less than or equal to 2.0 area percent, less than or equal to 1.5 area percent, less than or equal to 1.0 area percent, or less than or equal to 0.5 area percent oxidized species. The present invention provides a composition comprising CTLA4-Ig molecules, wherein the CTLA4-Ig molecules are less than or equal to 5.0 area percent, less than or equal to 4.5 area percent, less than or equal to 4.0 area percent, less than or equal to 3.5 area percent, less than or equal to 3.0 area percent, less than or equal to 2.5 area percent, less than or equal to 2.0 area percent, less than or equal to 1.5 area percent, less than or equal to 1.0 area percent, or less than or equal to 0.5 area percent deamidated species. In some embodiments the composition comprises CTLA4-Ig molecules, wherein the CTLA4-Ig molecules are less than or equal to 3.5 area percent oxidized species and less than or equal to 2.5 area percent deamidated species.

The present invention provides a composition comprising CTLA4-Ig molecules, wherein the composition comprises bacterial endotoxins LAL at less than or equal to 0.7 EU/mg CTLA4-Ig molecules, less than or equal to 0.6 EU/mg CTLA4-Ig molecules, less than or equal to 0.5 EU/mg CTLA4-Ig molecules, less than or equal to 0.42 EU/mg CTLA4-Ig molecules, less than or equal to 0.4 EU/mg CTLA4-Ig molecules, less than or equal to 0.35 EU/mg CTLA4-Ig molecules, less than or equal to 0.3 EU/mg CTLA4-Ig molecules, less than or equal to 0.25 EU/mg CTLA4-Ig molecules, less than or equal to 0.20 EU/mg CTLA4-Ig molecules, less than or equal to 0.15 EU/mg CTLA4-Ig molecules, or less than or equal to 0.05 EU/mg CTLA4-Ig molecules.

The present invention provides a composition comprising CTLA4-Ig molecules, wherein the composition comprises bioburden at less than or equal to 2 CFU/10 mL, less than or equal to 1.5 CFU/10 mL, less than or equal to 1 CFU/10 mL, or less than or equal to 0.5 CFU/10 mL.

The present invention provides a composition comprising CTLA4-Ig molecules, wherein the composition comprises DNA at less than or equal to 25 pg/mg CTLA4-Ig molecules, less than or equal to 20 pg/mg CTLA4-Ig molecules, less than or equal to 15 pg/mg CTLA4-Ig molecules, less than or equal to 10 pg/mg CTLA4-Ig molecules, less than or equal to 5.0 pg/mg CTLA4-Ig molecules, less than or equal to 4.0 pg/mg CTLA4-Ig molecules, less than or equal to 3.5 pg/mg CTLA4-Ig molecules, less than or equal to 3.0 pg/mg CTLA4-Ig molecules, less than or equal to 2.5 pg/mg CTLA4-Ig molecules, less than or equal to 1.5 pg/mg CTLA4-Ig molecules, less than or equal to 1.0 pg/mg CTLA4-Ig molecules, or less than or equal to 0.5 pg/mg CTLA4-Ig molecules, or less than or equal to 0.20 pg/ml CTLA4-Ig molecules.

The present invention provides a composition comprising CTLA4-Ig molecules, wherein the composition comprises cellular protein (e.g., CHO protein or CHOP) at less than or equal to 200 ng/mg CTLA4-Ig molecules, less than or equal to 150 ng/mg CTLA4-Ig molecules, less than or equal to 125 ng/mg CTLA4-Ig molecules, less than or equal to 100 ng/mg CTLA4-Ig molecules, less than or equal to 90 ng/mg CTLA4-Ig molecules, less than or equal to 80 ng/mg CTLA4-Ig molecules, 70 ng/mg CTLA4-Ig molecules, less than or equal to 60 ng/mg CTLA4-Ig molecules, less than or equal to 50 ng/mg CTLA4-Ig molecules, less than or equal to 40 ng/mg CTLA4-Ig molecules, less than or equal to 30 ng/mg CTLA4-Ig molecules, less than or equal to 25 ng/mg CTLA4-Ig molecules, less than or equal to 20 ng/mg CTLA4-Ig molecules, less than or equal to 15 ng/mg CTLA4-Ig molecules, less than or equal to 10 ng/mg CTLA4-Ig molecules, or less than or equal to 5 ng/mg CTLA4-Ig molecules. The present invention provides a composition comprising CTLA4-Ig molecules, wherein the composition comprises cellular protein at less than or equal to 200 ppm, less than or equal to 150 ppm, less than or equal to 125 ppm, less than or equal to 100 ppm, less than or equal to 90 ppm, less than or equal to 80 ppm, 70 ppm, less than or equal to 60 ppm, less than or equal to 50 ppm, less than or equal to 40 ppm, less than or equal to 30 ppm, less than or equal to 25 ppm, less than or equal to 20 ppm, less than or equal to 15 ppm, less than or equal to 10 ppm, or less than or equal to 5 ppm.

The present invention provides a composition comprising CTLA4-Ig molecules, wherein the composition comprises Triton-X (e.g., Triton X-100) at less than or equal to 4.0 ng/mg CTLA4-Ig molecules, less than or equal to 3.5 ng/mg CTLA4-Ig molecules, less than or equal to 3.0 ng/mg CTLA4-Ig molecules, less than or equal to 2.5 ng/mg CTLA4-Ig molecules, less than or equal to 2.0 ng/mg CTLA4-Ig molecules, less than or equal to 1.5 ng/mg CTLA4-Ig molecules, less than or equal to 1.0 ng/mg CTLA4-Ig molecules, or less than or equal to 0.5 ng/mg CTLA4-Ig molecules. The present invention provides a composition comprising CTLA4-Ig molecules, wherein the composition comprises Triton-X at less than or equal to 4.0 ppm, less than or equal to 3.5 ppm, less than or equal to 3.0 ppm, less than or equal to 2.5 ppm, less than or equal to 2.0 ppm, less than or equal to 1.5 ppm, less than or equal to 1.0 ppm, or less than or equal to 0.5 ppm.

The present invention provides a composition comprising CTLA4-Ig molecules, wherein the composition comprises Protein A at less than or equal to 8.0 ng/mg CTLA4-Ig molecules, less than or equal to 7.5 ng/mg CTLA4-Ig molecules, less than or equal to 7.0 ng/mg CTLA4-Ig molecules, less than or equal to 6.5 ng/mg CTLA4-Ig molecules, less than or equal to 6.0 ng/mg CTLA4-Ig molecules, less than or equal to 5.5 ng/mg CTLA4-Ig molecules, less than or equal to 5.0 ng/mg CTLA4-Ig molecules, less than or equal to 4.5 ng/mg CTLA4-Ig molecules, less than or equal to 4.0 ng/mg CTLA4-Ig molecules, less than or equal to 3.5 ng/mg CTLA4-Ig molecules, less than or equal to 3.0 ng/mg CTLA4-Ig molecules, less than or equal to 2.5 ng/mg CTLA4-Ig molecules, less than or equal to 2.0 ng/mg CTLA4-Ig molecules, less than or equal to 1.5 ng/mg CTLA4-Ig molecules, less than or equal to 1.0 ng/mg CTLA4-Ig molecules, or less than or equal to 0.5 ng/mg CTLA4-Ig molecules. The present invention provides a composition comprising CTLA4-Ig molecules, wherein the composition comprises Protein A at less than or equal to 8.0 ppm, less than or equal to 7.5 ppm, less than or equal to 7.0 ppm, less than or equal to 6.5 ppm, less than or equal to 6.0 ppm, less than or equal to 5.5 ppm, less than or equal to 5.0 ppm, less than or equal to 4.5 ppm, less than or equal to 4.0 ppm, less than or equal to 3.5 ppm, less than or equal to 3.0 ppm, less than or equal to 2.5 ppm, less than or equal to 2.0 ppm, less than or equal to 1.5 ppm, less than or equal to 1.0 ppm, or less than or equal to 0.5 ppm.

The present invention provides a composition comprising CTLA4-Ig molecules, wherein the CTLA4-Ig molecules have an average molar ratio of GlcNAc to CTLA4-Ig molecules of from about 10 to about 40. In some embodiments the average molar ratio of GlcNAc to CTLA4-Ig molecules is between from about X to about Y, inclusive of X and Y, where X is any whole number between 10 and 39 and Y is any whole number between 11 and 40. In other embodiments the average molar ratio of GlcNAc to CTLA4-Ig molecules is between from about X to Y, inclusive of X and Y, where X is about 12, 14, 14, 15, 16 or 17, and Y is about 32, 33, 34, 35, 36 or 37. In other embodiments the average molar ratio of GlcNAc to CTLA4-Ig molecules is from about 12 to about 35, from about 13 to about 35, from about 14 to about 35, from about 15 to about 35.

The present invention provides a composition comprising CTLA4-Ig molecules, wherein the CTLA4-Ig molecules have an average molar ratio of GalNAc to CTLA4-Ig molecules of from about 0.5 to about 7.0. In some embodiments the average molar ratio of GalNAc to CTLA4-Ig molecules is between from about X to about Y, inclusive of X and Y, where X is 0.5, 0.6, 0.7, 0.8, 0.9, 1.0, 1.1, 1.2, 1.3, 1.4, 1.5, 1.6, 1.7, 1.8, 1.9, or 2.0, and Y is 3.0, 3.1, 3.2, 3.3, 3.4, 3.5, 3.6, 3.7, 3.8, 3.9, 4.0, 4.1, 4.2, 4.3, 4.4, 4.5, 0.46, 4.7, 4.8, 4.9, 5.0, 6.0, 7.0 or 8.0. In other embodiments the average molar ratio of GalNAc to CTLA4-Ig molecules is between from about X to Y, inclusive of X and Y, where X is about 0.6, 0.7, 0.8, 0.9, or 1.0, and Y is about 3.4, 3.5, 3.6, 3.7, 3.8, 3.9, 4.0, 4.1 or 4.2. In other embodiments the average molar ratio of GalNAc to CTLA4-Ig molecules is from about 0.7 to about 4.1, from about 0.8 to about 4.0, from about 0.9 to about 3.9, or about 1.0 to about 3.8, or about 1.1 to about 3.7. In other embodiments the average molar ratio of GalNAc to CTLA4-Ig molecules is from about 1.6 to about 3.7, from about 1.7 to about 3.6, from about 1.8 to about 3.5, or 1.9 to about 3.4.

The invention provides for a composition comprising CTLA4-Ig molecules, wherein the CTLA4-Ig composition exhibits bands in pI ranges as determined on an isoelectric focusing gel (IEF gel) as follows: from about 10 to about 22 bands in the pI range of from about 4.3 to about 5.6; cumulative bands intensity of from about 90% to about 110% in a pI range from about 4.3 to about 5.3 and about 3 major bands in a pI range from about 4.5 to about 5.2. In one embodiment, the bands in the range of from about 4.3 to about 5.6 is from about 5 to about 30, from about 6 to about 29, from about 7 to about 28, from about 8 to about 27, from about 9 to about 26, from about 10 to about 25, from about 11 to about 24, from about 12 to about 23, from about 13 to about 22, from about 14 to about 21, from about 15 to about 20, from about 16 to about 19, from about 17 to about 20, from about 18 to about 19.

Glycosylated CTLA4-Ig and CTLA4$^{A29YL104E}$-Ig Molecules and Populations Thereof Without limitation, glycosylation can refer to the addition of complex oligosaccharide structures to a protein at specific sites within the polypeptide chain. Glycosylation of proteins and the subsequent processing of the added carbohydrates can affect protein folding and structure, protein stability, including protein half life, and functional properties of a protein. Protein glycosylation can be divided into two classes by virtue of the sequence context where the modification occurs, O-linked glycosylation and N-linked glycosylation. O-linked polysaccharides are linked to a hydroxyl group, usually to the hydroxyl group of either a serine or a threonine residue. O-glycans are not added to every serine and threonine residue. O-linked oligosaccharides are usually mono or biantennary, i.e. they comprise one or at most two branches (antennas), and comprise from one to four different kinds of sugar residues, which are added one by one.

N-linked polysaccharides are attached to the amide nitrogen of an asparagine. Only asparagines that are part of one of two tripeptide sequences, either asparagine-X-serine or asparagine-X-threonine (where X is any amino acid except proline), are targets for glycosylation. N-linked oligosaccharides can have from one to four branches referred to as mono-, bi-, tri-tetraantennary. The structures of and sugar residues found in N- and O-linked oligosaccharides are different. Despite that difference, the terminal residue on each branch of both N- and O-linked polysaccharide can be modified by a sialic acid molecule a modification referred as sialic acids capping. Sialic acid is a common name for a family of unique nine-carbon monosaccharides, which can be linked to other oligosaccharides. Two family members are N-acetyl neuraminic acid, abbreviated as Neu5Ac or NANA, and N-glycolyl neuraminic acid, abbreviated as Neu5Gc or NGNA.

The most common form of sialic acid in humans is NANA. N-acetylneuraminic acid (NANA) is the primary sialic acid species present in CTLA4-Ig molecules. However, it should be noted that minor but detectable levels of N-glycolylneuraminic acid (NGNA) are also present in CTLA4-Ig molecules. Furthermore, the method described herein can be used to determine the number of moles of sialic acids for both NANA and NGNA, and therefore levels of both NANA and NGNA are determined and reported for CTLA4-Ig molecules. N- and O-linked oligosaccharides have different number of branches, which provide different number of positions to which sialic acid molecules can be attached. N-linked ologosaccharides can provide up to four attachment positions for sialic acids, while O-linked oligosaccharides can provide two sites for sialic acid attachment.

Glycosylated proteins (glycoproteins), many of which have been produced by recombinant DNA technology methods, are of great interest as diagnostic and therapeutic agents. Many eukaryotic transmembrane proteins destined for the cell surface and secreted proteins are post-translationally modified to incorporate N-linked and O-linked carbohydrate groups. N-linked oligosaccharides are attached to asparagine residues when they are part of the peptide motif Asn-X-Ser/Thr, where X can be any amino acid except proline. O-linked oligosaccharides are attached to serine or threonine residues. The structures of N-linked and O-linked oligosaccharides as well as the sugar residues found in each can be different. One type of sugar that is commonly found on both is N-acetylneuraminic acid (NANA; hereafter referred to as sialic acid). Usually, sialic acid is the terminal residue of both N-linked and O-linked oligosaccharides. The glycoprotein, because of its negative charge, can exhibit acidic properties.

Glycosylated proteins are purported to play roles in augmenting protein folding, regulating cell sorting and trafficking, preventing protein aggregation, mediating cell-cell adhesion, and increasing resistance to proteolysis. In eukaryotic organisms, the nature and extent of glycosylation can have a profound impact on the circulating half-life and bioactivity of glycoprotein therapeutics by processes which involve receptor mediated endocytosis and clearance. Receptor-mediated systems are thought to play a major role in clearing serum glycoproteins by recognizing the various sugar components of the oligosaccharide. A glycoprotein's terminal sialic acid group can affect absorption, half-life, and serum clearance. Thus, glycoprotein production strategies, which maintain the terminal sialic acid component of the glycosylated protein, can better increase the protein's bioavailability and serum half-life. Several production process parameters have been investigated pertaining to recombinant glycoprotein synthesis, especially the effect of media composition and temperature shifts in various production strategies.

CTLA4-Ig dimers composed of monomers having the amino acid sequence of residues (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, or (vi) 25-383 of SEQ ID NO:2, can have a predicted theoretical MW of about 78,000 to about 79,000 Daltons. However, the MW for such dimers obtained by MALDI-TOF is approximately 91,000 Daltons. This difference in MW of approximately 13,000-14,000 Daltons is due at least in part to glycosylation, which in one embodiment, accounts for approximately 15% of the mass of this particular CTLA4-Ig monomer molecule. The above specified monomers have three N-linked glycosylation sites that have been confirmed by peptide mapping to occur at asparagines at residues 102, 134, and 233 of SEQ ID N0:2. Carbohydrate molecules that are linked through asparagine can be cleaved selectively using the enzyme Peptide-N Glycosidase F (PN-Gase F). In one instance, treatment of the monomer having the sequence 27-383 of SEQ ID N0:2 with PNGase F resulted in a species with a MW of approximately 80,200 Daltons, and because the theoretical MW of this monomer is about 80,200, the treatment suggested that the unaccounted 1,400 Daltons (80,200−78,800=1,400) can be due to O-linked glycosylation. Although there are numerous serine and threonine residues that have the potential of being glycosylation sites, only two O-linked sites were identified: Ser$^{155}$ and Ser$^{165}$ of SEQ ID NO:2. In one embodiment, the predominant glycan attached to these two sites is HexNAc-Hex-NeuAc.

For example, FIG. 9 presents an overall view of the N-linked and O-linked carbohydrate structures on CTLA4-Ig molecules comprised of monomers having a sequence from SEQ ID NO:2 (i.e, a monomer having one of the following sequences: (i) 26-383 of SEQ ID NO:2, (ii) 26-382 of SEQ ID NO:2, (iii) 27-383 of SEQ ID NO:2, (iv) 27-382 of SEQ ID NO:2), (v) 25-382 of SEQ ID NO:2, or (vi) 25-383 of SEQ ID NO:2 wherein in one embodiment such molecules with the shown carbohydrate characteristics are produced by the cell-line of the invention or progeny thereof according to the method of production described in Examples 14-15. The major structures listed for each site are based on the orthogonal techniques (see herein). For each structure there is an estimated percentage of that structure observed during these experiments. These percentages represent best estimates from the orthogonal techniques.

CTLA4$^{A29YL104E}$-Ig dimers composed of monomers having the amino acid sequence of residues (i) 26-383 of SEQ ID NO:4, (ii) 26-382 of SEQ ID NO:4, (iii) 27-383 of SEQ ID NO:4, (iv) 27-382 of SEQ ID NO:4, (v) 25-382 of SEQ ID NO:4, or (vi) 25-383 of SEQ ID NO:4, can have a predicted theoretical MW of about 78,000 to about 79,000 Daltons. However, the MW for such dimers obtained by MALDI-TOF is approximately 91,500 Daltons. This difference in MW of approximately 12,000-13,000 Daltons is due at least in part to glycosylation. The above specified monomers have three N-linked glycosylation sites that have been confirmed by peptide mapping to occur at asparagines at residues 102, 134, and 233 of SEQ ID N0:4 (N76, N108, and N207 of FIG. 4). Carbohydrate molecules that are linked through asparagine can be cleaved selectively using the enzyme Peptide-N Glycosidase F (PNGase F). Although there are numerous serine and threonine residues that have the potential of being glycosylation sites, only three O-linked sites were identified: Ser149, Ser155, and Ser165 of SEQ ID NO:4 (See Table 25 in EXAMPLE 22) In one embodiment, the predominant glycan attached to these sites is HexNAc-Hex-NeuAc.

In certain embodiments, CTLA4-Ig or CTLA4$^{A29YL104E}$-Ig molecules are glycoproteins that can be produced by the culture methods of the invention. In one embodiment, CTLA4-Ig glycoproteins are modified with oligosaccharides that represent approximately 15% (w/w) of the molecule. These oligosaccharides can play an important role in the pharmacokinetic (PK) parameters of a CTLA4-Ig or CTLA4$^{A29YL104E}$-Ig glycoprotein. In addition, different oligosaccharide profiles can influence the stability and degradation of proteins. For example, O-linked oligosaccharides may enhance the stability of CTLA4$^{A29YL104E}$-Ig molecules by preventing autolysis in the hinge region of the immunoglobulin constant region.

The oligosaccharide distribution on a population of CTLA4-Ig or CTLA4$^{A29YL104E}$-Ig molecules can be heterogeneous in nature due to the complexity of cell culture and processes. The heterogeneity can be present due to glycosylation sites being completely occupied to unoccupied, and the fact that any specific site can be populated with many different oligosaccharide structures, which can further display variation in the pattern of sialic acid modification.

In one embodiment, the primary sialic acid moiety on CTLA4-Ig or CTLA4$^{A29YL104E}$-Ig molecules is N-acetyl neuraminic acid (NeuAc, NANA), and the secondary sialic acid moiety is N-glycolyl neuraminic acid (NGNA). The charged nature of sialic acid and the complex sialic acid-containing structures can result in multiple isoforms of CTLA4-Ig or CTLA4$^{A29YL104E}$-Ig, respectively, where such isoforms can be evident in an isoelectric focusing (IEF) profile. For example, see FIG. 10 and Example 3 for IEF profile of CTLA4-Ig. Additionally, see FIG. 11 and EXAMPLE 22 for IEF profile of CTLA4$^{A29YL104E}$-Ig.

Figure 11:
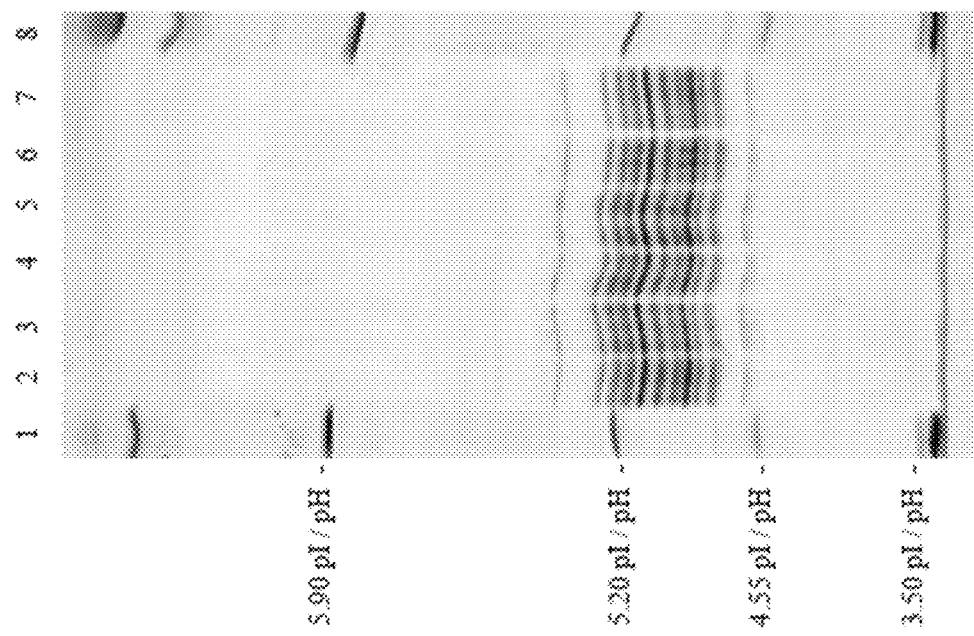
FIG. 11 shows a representative IEF gel (pH 4.0 to 6.5) of a CTLA4$^{A29YL104E}$-Ig dimer comprising SEQ ID NO:4 monomers. Lanes 1 and 8 show a calibration standard, lane 2-7 each show 10 µg/µl of CTLA4$^{A29YL104E}$-Ig dimer.

In one embodiment, the invention provides a population of CTLA4-Ig molecules that have a dominant CTLA4-Ig isoform having an isoelectric point (pI) that is less than or equal to 5.1 or 5.0, which can be determined for example by IEF. In another embodiment, a population of CTLA4$^{A29YL104E}$-Ig molecules is provided that has dominant CTLA4$^{A29YL104E}$-Ig isoforms having an isoelectric point (pI) that is less than or equal to 5.5, which can be determined for example by IEF (FIG. 11).

In one embodiment, the invention provides a population of CTLA4-Ig molecules that have a pI of from about 4.2 to about 5.7, from about 4.25 to about 5.5, from about 4.3 to about 5.3, or from about 4.5 to about 5.2. In another embodiment, the invention provides a population of CTLA4-Ig molecules that have a pI of from about 4.45 to about 5.30. In a further embodiment, the invention provides a population of CTLA4-Ig molecules that have a pI of from about 4.3 to about 5.1. In a particular embodiment, the invention provides a population of CTLA4-Ig molecules that have a pI of from about 4.45 to about 5.0. In one embodiment, the invention provides a population of CTLA4-Ig molecules where at least 40%, 50%, 60%, 70%, 80%, 90%, or 95% of the molecules in the population exhibit an isoelectric point less than or equal to about 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, or 2.1 as determined by IEF (these values can have a Standard Deviation of ±0.2). In one embodiment, the invention provides a method for preparing a population of CTLA4-Ig molecules having a pI of from about 4.45 to about 5.30, or from about 4.45 to about 5.1, or from about 4.45 to about 5.0, wherein the methods involves subjecting a population of CTLA4-Ig molecules to IEF gel electrophoresis, wherein a single band on the gel represents a sub-population of CTLA4-Ig molecules having a particular pI, and isolating the sub-population of CTLA4-Ig molecules having the particular pI by excising the band from the gel and subsequent purification of the proteins from the excised gel band.

In further embodiments, the invention provides a population of CTLA4$^{A29YL104E}$-Ig molecules that have a pI of from about 4.5 to about 5.2. In other embodiments, the invention provides a population of CTLA4$^{A29YL104E}$-Ig molecules that have a pI of from about 4.7 to about 5.1. In another embodiment, the invention provides a population of CTLA4$^{A29YL104E}$-Ig molecules that have a pI of from about 2.0 to about 5.2. In one embodiment, the invention provides a population of CTLA4$^{A29YL104E}$-Ig molecules where at least 40%, 50%, 60%, 70%, 80%, 90%, or 95% of the molecules in the population exhibit an isoelectric point less than or equal to about 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, or 3.0 as determined by IEF (these values can have a Standard Deviation of ±0.2). In one embodiment, the invention provides a method for preparing a population of CTLA4$^{A29YL104E}$-Ig molecules having a pI of from about 4.5 to about 5.2; from about 4.7 to about 5.1; from about 2.0 to about 5.2, wherein the method involves subjecting a population of CTLA4$^{A29YL104E}$-Ig molecules to IEF gel electrophoresis, wherein a single band on the gel represents a sub-population of CTLA4$^{A29YL104E}$-Ig molecules having a particular pI, and isolating the sub-population of CTLA4$^{A29YL104E}$-Ig molecules having the particular pI by excising the band from the gel and subsequent purification of the proteins from the excised gel band.

In certain embodiments, the invention provides populations of CTLA4-Ig molecules having an average molar ratio of moles sialic acid groups to moles CTLA4-Ig molecules of from: about 6 to about 32, about 8 to about 32, about 11 to about 30, about 12 to about 20, about 13 to about 19, about 14 to about 18, about 15 to about 17, about 6 to about 16, about 8 to about 16, about 8 to about 14, about 8 to about 12.

In some embodiments, a maximum allowable CHO host cell protein of ≤25 ppm to ≤10 ng/mg characterizes the composition of CTLA4-Ig molecules. In another embodiment, the composition of CTLA4-Ig molecules is characterized by host cell DNA at a level of ≤2.5 pg/mg to ≤1.0 pg/mg. In another embodiment, the composition of CTLA4-

Ig molecules is characterized by Triton X-100 at a level of ≤1.0 ng/mg or ≤1.0 ppm. The concentration of Triton X-100 can be determined by extraction of the Triton X-100 using Waters OASIS-HLB solid-phase extraction followed by washing with water to remove residual protein. The bound Triton X-100 is removed by elution with acetonitrile. The acetonitrile eluate is analyzed by reversed-phase chromatography using a SAS Hypersil 5 µm column and a mobile phase consisting of acetonitrile:water (80:20). Detection is by UV absorbance at 225 nm. In one embodiment, the composition of CTLA4-Ig molecules is characterized by ≤2.5 area % oxidation and ≤2.0 area % deamidation. In another embodiment, the composition of CTLA4-Ig molecules is characterized by ≤3.0 area % oxidation and ≤2.5 area % deamidation. The tryptic peptide mapping method was used for quantitation of oxidation and deamidation. The percent oxidation data was determined by the use of an RP-HPLC tryptic mapping assay that quantitates the area percent oxidation of Met85 in the CTLA4-Ig protein to methionine sulfoxide. Percent oxidation in the method is obtained by measuring UV peak areas in the RP-HPLC tryptic map for the T6 tryptic peptide, comprised of residues 84-93 containing Met85, and the corresponding oxidized tryptic peptide, T6ox, containing Met(O)85. The area percent oxidation of Met85 to Met(O)85 is proportional to the area percent of the T6ox peak: Percent Oxidation=100*AT6ox/(AT6ox+AT6), where, AT6=peak area for T6 tryptic peptide, (84-93). AT6ox=peak area for T6ox tryptic peptide, Met(O)85(84-93). The percent deamidation data, acquired by using a RP-HPLC tryptic mapping assay that quantitates the area percent oxidation and deamidation, is obtained by measuring UV peak areas in the RP-HPLC tryptic map for the T26 tryptic peptide, comprised of residues 281-302 containing Asn294, and the corresponding deamidated tryptic peptide, T26deam1, containing isoAsp294. The area percent deamidation of Asn294 to isoAsp294, then, is proportional to the area percent of the T26deam1 peak: where, AT26=peak area for T26, (281-302), AT26deam1=peak area for T26deam1, isoAsp294 (281-302). AT26deam2=peak area for T26deam2, Asp299 (281-302). AT26deam3=peak area for T26deam3, Asp294 (281-302). AT26deam4=peak area for T26deam4, Asu294 (281-302).

In another embodiment, the composition of CTLA4-Ig molecules is characterized by N-Acetylglucosamine (GlcNAc) of from 15 to 35 Moles:Mole CTLA4-Ig Protein, or N-Acetylgalactosamine (GalNAc) of from 1.7 to 3.6 Moles:Mole CTLA4-Ig Protein. The amino monosaccharides are quantitated by capillary electrophoresis (CE) following release from the protein by acid hydrolysis. The released amino monosaccharides are re-acetylated, and fluorescently labeled with aminopyrene trisulfonic acid (APTS) to facilitate their detection and quantitation. N-Acetylmannosamine is added to a sample and amino monosaccharide standards to serve as an internal standard. The peak areas of the amino monosaccharides in the samples are normalized using the internal standard and quantified by comparing with their respective normalized amino monosaccharides peak areas in the standard. The molar ratio of each monosaccharide relative to the CTLA4-Ig molecule is then calculated.

In one embodiment, the composition of CTLA4-Ig molecules is characterized by the following N-linked oligosaccharide profile specifications:

| N-Linked Oligosaccharide Profile Specifications | | | |
|---|---|---|---|
| | % Difference Domain I | % Difference Domain II | % Difference Domain III |
| % Difference | 19-31 | 7-19 | −6--18 |
| Standard Deviation (% Difference from above specification) | ±29 | ±27 | ±25 |

In one embodiment, the composition of CTLA4-Ig molecules is characterized by neutral monosaccharide where the composition has ratios of about:
Galactose: 8.0 to 17 Moles:Mole CTLA4-Ig Protein
Fucose: 3.5 to 8.3 Moles:Mole CTLA4-Ig Protein
Mannose: 7.7 to 22 Moles:Mole CTLA4-Ig Protein, or
Galactose: 9.0 to 17 Moles:Mole CTLA4-Ig Protein
Mannose: 11 to 19 Moles:Mole CTLA4-Ig Protein.

| Illustrative Neutral Monosaccharide Composition: Moles:Mole Protein of Galactose, Fucose and Mannose | | | | |
|---|---|---|---|---|
| | Process W (n = 34) | | Process CD-CHO1 (n = 109) | |
| Neutral Monosaccharide | Mean (SD) | Min, Max | Mean (SD) | Min, Max |
| Galactose | 13.9 (1.1) | 12.0, 16.0 | 12.6 (1.0) | 10.0, 16.0 |
| Fucose | 5.8 (1.0) | 4.2, 7.7 | 5.6 (0.7) | 4.5, 7.6 |
| Mannose | 15.3 (1.0) | 13.0, 17.0 | 15.4 (1.0) | 13.0, 18.0 |

| Illustrative Sialic Acid (NANA:Mole Protein) | | | | |
|---|---|---|---|---|
| | Process W (n = 34) | | Process CD-CHO1 (n = 109) | |
| Sialic Acid | Mean (SD) | Min, Max | Mean (SD) | Min, Max |
| NANA | 10.2 (0.6) | 9.3, 11.6 | 9.7 (0.6) | 8.2, 11.5 |

In another embodiment, the monosaccharide molar ratio range for a CTLA4$^{A29YL104E}$-Ig composition is as follows: mannose from about 10-20 moles/mole protein; fucose from about 4.2-7.0 moles/mole protein; and galactose from about 9.2-17 moles/mole protein. In another embodiment, the CTLA4$^{A29YL104E}$-Ig composition is characterized by a NANA molar ratio of from about 5.0-10.0 mole of NANA/mole protein. In another embodiment, the CTLA4$^{A29YL104E}$-Ig composition is characterized by a NGNA molar ratio of <1.5 mole NGNA/mole protein. In some embodiment, the % deviation of molar ratio for sialic acids is ≤15% or ≤20% or ≤30%.

In one embodiment, a population of CTLA4-Ig molecules can comprise CTLA4-Ig monomers that each have at least 3 sialic acid groups. In another embodiment a population of CTLA4-Ig molecules comprises CTLA4-Ig monomers that each have from 3 to 8 sialic acid groups.

In one embodiment, the invention provides a population of CTLA4-Ig molecules where at least 40%, 50%, 60%, 70%, 80%, 90%, or 95% of the molecules in the population exhibit an isoelectric point less than or equal to about 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, or 3.0.

In some embodiments, the invention provides populations of CTLA4-Ig molecules having an average molar ratio of moles NANA to moles CTLA4-Ig molecules or dimer of from: about 6 to about 16, about 6 to about 14, about 6 to about 12, about 8 to about 12, about 8 to about 14, about 8 to about 16.

In other embodiments, the invention provides populations of CTLA4-Ig molecules having an average molar ratio of moles NGNA to moles CTLA4-Ig molecules or dimer of less than or equal to about 2, 1.8, 1.6, 1.5, 1.4, 1.0, 0.8, or 0.5

In particular embodiments, the invention provides populations of CTLA4$^{A29YL104E}$-Ig molecules having an average molar ratio of moles sialic acid groups to moles CTLA4$^{A29YL104E}$-Ig molecules or dimer of from about 5.5 to about 8.5. In another embodiment, the invention provides populations of CTLA4$^{A29YL104E}$-Ig molecules having an average molar ratio of moles sialic acid groups to moles CTLA4$^{A29YL104E}$-Ig molecules or dimer of from about 5 to about 10.

In one embodiment, a population of CTLA4$^{A29YL104E}$-Ig molecules can comprise CTLA4$^{A29YL104E}$-Ig monomers that each have at least 2.5 sialic acid groups. In another embodiment a population of CTLA4$^{A29YL104E}$-Ig molecules comprises CTLA4$^{A29YL104E}$-Ig monomers that each have from 2.5 to 5 sialic acid groups.

In other embodiments, the invention provides populations of CTLA4-Ig molecules that are distinguished by the population's average molar ratio of moles amino monosaccharides and/or neutral monosaccharides and/or sialic acids to moles CTLA4-Ig molecules or dimer. In particular embodiments, the invention provides populations of CTLA4$^{A29YL104E}$-Ig molecules that are distinguished by the population's average molar ratio of moles amino monosaccharides and/or neutral monosaccharides and/or sialic acids to moles CTLA4$^{A29YL104E}$-Ig molecules or dimer. Amino monosaccharides include N-acetyl galactosamine (GalNAc) and N-acetyl glucosamine (GlcNAc). Neutral monosaccharides include mannose, fucose, and galactose. Sialic acids include N-acetyl neuraminic acid (NANA) and N-glycolyl neuraminic acid (NGNA).

In one embodiment, the invention provides a population of CTLA4-Ig molecules that are characterized by an average molar ratio of moles GlcNAc per mole of CTLA4-Ig dimer or to CTLA4-Ig molecule that is from about 10 to about 40, from about 15 to about 35, from about 15 to about 25, or from about 15 to about 20. In another embodiment, the invention provides a population of CTLA4-Ig molecules where at least 40%, 50%, 60%, 70%, 80%, 90%, or 95% of the molecules in the population are characterized by an average molar ratio of moles GlcNAc per mole of CTLA4-Ig dimer or to CTLA4-Ig molecule that is less than or equal to about 40, 38, 35, 30, 25, 20, 18, or 15.

In another embodiment, the invention provides a population of CTLA4-Ig molecules that are characterized by an average molar ratio of moles GalNAc per mole of CTLA4-Ig dimer or to CTLA4-Ig molecule that is from about 1.5 to about 8.5, from about 1.7 to about 3.0, from about 1.7 to about 4.0, from about 1.7 to about 5.0, from about 1.7 to about 6.0, from about 1.7 to about 7.0, from about 1.7 to about 8.0, or from about 1.7 to about 8.3. In another embodiment, the invention provides a population of CTLA4-Ig molecules where at least 40%, 50%, 60%, 70%, 80%, 90%, or 95% of the molecules in the population are characterized by an average molar ratio of moles GalNAc per mole of CTLA4-Ig dimer or to CTLA4-Ig molecule that is less than or equal to about 8.5, 8, 7.5, 7, 6.5, 6, 5.5, 5, 4.5, 4.0, 3.8, 3.6, 3.5, 3.0, 2.5, 2.0, 1.7, or 1.5.

In a further embodiment, the invention provides a population of CTLA4-Ig molecules that are characterized by an average molar ratio of moles galactose per mole of CTLA4-Ig dimer or to CTLA4-Ig molecule that is from about 7.5 to about 20.0, from about 8.0 to about 19.0, from about 8 to about 18.0, from about 8.0 to about 17.0, from about 8.5 to about 17.0, or from about 9.0 to about 17.0. In another embodiment, the invention provides a population of CTLA4-Ig molecules where at least 40%, 50%, 60%, 70%, 80%, 90%, or 95% of the molecules in the population characterized by an average molar ratio of moles galactose per mole of CTLA4-Ig dimer or to CTLA4-Ig molecule that is less than or equal to about 20.0, 19.0, 18.0, 17.0, 16.0, 15.0, 14.0, 13.0, 12.0, 11.0, 10.0, 9.0, 8.5, 8.0, or 7.5.

In a further embodiment, the invention provides a population of CTLA4-Ig molecules that are characterized by an average molar ratio of moles fucose per mole of CTLA4-Ig dimer or to CTLA4-Ig molecule that is from about 3 to about 8.5, from about 3.5 to about 8.5, from about 3.5 to about 8.3, from about 3.5 to about 8.0, from about 3.5 to about 7.5, or from about 3.5 to about 7.0. In another embodiment, the invention provides a population of CTLA4-Ig molecules where at least 40%, 50%, 60%, 70%, 80%, 90%, or 95% of the molecules in the population characterized by an average molar ratio of moles fucose per mole of CTLA4-Ig dimer or to CTLA4-Ig molecule that is less than or equal to about 8.5, 8.3, 8.0, 7.5, 7.0, 6.5, 6.0, 5.5, 5.0, 4.5, 4.0, 3.5, 3.2, or 3.0.

In a further embodiment, the invention provides a population of CTLA4-Ig molecules that are characterized by an average molar ratio of moles mannose per mole of CTLA4-Ig dimer or to CTLA4-Ig molecule that is from about 7 to about 23, from about 7.5 to about 23, from about 7.7 to about 23, from about 7.7 to about 22.5, from about 7.7 to about 22, from about 7.7 to about 20, from about 7.7 to about 18, from about 7.7 to about 16, from about 8.0 to about 16.0, from about 9.0 to about 17.0, from about 10 to about 19.0, or from about 11 to about 19.0. In another embodiment, the invention provides a population of CTLA4-Ig molecules where at least 40%, 50%, 60%, 70%, 80%, 90%, or 95% of the molecules in the population characterized by an average molar ratio of moles mannose per mole of CTLA4-Ig molecules or dimer or to CTLA4-Ig molecule that is less than or equal to about 23, 22.5, 22, 21, 20, 19, 18, 17, 16, 15, 14, 13, 12, 11, 10, 9.5, 9, 8.5, 8, 7.7, 7.5, 7.3, or 7.

In one embodiment, the invention provides a glycosylated CTLA4-Ig population that exhibits increased PK values, such as increased exposure as measured by area under the curve (AUC), such as resulting from or as demonstrated by decreased clearance from the serum while retaining bioactivity. In another embodiment, the invention provides a glycosylated CTLA4$^{A29YL104E}$-Ig population that exhibits increased pharmacokinetic (PK) values as demonstrated by decreased clearance from the serum while retaining bioactivity.

In some embodiments, the invention provides analogs of soluble CTLA4-Ig molecules, which have additional glycosylation sites. In other embodiments, the invention provides analogs of soluble CTLA4$^{A29YL104E}$-Ig molecules, which have additional glycosylation sites. Additional glycosylation sites provide attachment points for additional carbohydrate structures that can be sialylated. Increased sialic content can be lead to increased PK values, and/or increased glycoprotein stability. Higher sialic acid content is beneficial. In vitro post-purification methods that use enzymes to add more sialic acids can be performed to produce further embodiments of the CTLA4-Ig or CTLA4$^{A29YL104E}$-Ig molecules of the invention.

The embodiments of the invention include any one range disclosed herein in combination with any one or more ranges disclosed herein. The embodiments of the invention include any one characteristic or property of CTLA4-Ig disclosed herein in combination with any one or more characteristics or properties of CTLA4-Ig disclosed herein.

Methods for Analyzing and Isolating CTLA4-Ig and CTLA4$^{A29YL104E}$-Ig Glycoproteins The following methods described herein can be used to distinguish, identify, or isolate particular CTLA4-Ig or CTLA4$^{A29YL104E}$-Ig molecule populations on the basis of various sugar profiles, including but not limited to a population's average molar ratio of moles amino monosaccharides and/or neutral monosaccharides and/or sialic acids per mole CTLA4-Ig or CTLA4$^{A29YL104E}$-Ig molecules or dimer.

A glycoprotein that is secreted from cultured cells can be isolated from the culture medium or supernatant. The glycoprotein produced by the cells is collected, recovered, isolated, and/or purified, or substantially purified, as desired, at the end of the total cell culture period using isolation and purification methods as known and practiced in the art or as described herein. In one embodiment, a glycoprotein of the invention, which is expressed by the cell but not secreted by the cell, can still be recovered from the cells, e.g., via making cell lysates and isolating the glycoprotein, and/or using methods that are known and practiced in the art, and as further described below.

The glycoprotein produced by the cell culture processes of this invention comprises complex carbohydrates that can be analyzed by various techniques of carbohydrate analysis. For example, techniques such as lectin blotting, well-known in the art, reveal proportions of terminal mannose, or other sugars such as galactose. Termination of mono-, bi-, tri-, or tetra-antennary oligosaccharide by sialic acids can be confirmed by release of sugars from the protein using anhydrous hydrazine or enzymatic methods and fractionation of oligosaccharides by ion-exchange chromatography, size exclusion chromatography, or other methods that are known in the art.

There are two main types of glycosidic linkages found in glycoprotiens, N- and O-linked. N-glycosylations are created by a covalent link of the glycan to the amide nitrogen of an asparagine residue. O-glycosidic linkages are created by the covalent linkage of the hydroxyl group of serine, threonine, hydroxylysine or hydroxyproline to the glycan. The carbohydrate moieties of glycoproteins are involved in numerous molecular recognition phenomena, including host-pathogen interactions, clearance from serum and targeting of different tissues. With respect to CTLA4-Ig and CTLA4$^{A29YL104E}$-Ig molecules, carbohydrate moieties can at least affect binding between CTLA4-Ig molecules and CD80 or CD86, or between CTLA4$^{A29YL104E}$-Ig molecules and CD80 or CD86.

Carbohydrate structures typically occur on the expressed protein as N-linked or 0-linked carbohydrates. The N-linked and O-linked carbohydrates differ primarily in their core structures. N-linked glycosylation refers to the attachment of the carbohydrate moiety via GlcNAc to an asparagine residue in the peptide chain. In one embodiment, the N-linked carbohydrates all contain a common Man1-6(Man1-3)Man$_\beta$1-4Glc-NAc$_\beta$1-4GlcNAc$_\beta$—R core structure, where R in this core structure represents an asparagine residue. The peptide sequence of the protein produced will contain an asparagine-X-serine, asparagine-X-threonine, and asparagine-X-cysteine, wherein X is any amino acid except proline.

In contrast, O-linked carbohydrates are characterized by a common core structure, which contains GalNAc attached to the hydroxyl group of a threonine or serine. Of the N-linked and O-linked carbohydrates, the most important are the complex N- and O-linked carbohydrates. Such complex carbohydrates contain several antennary structures. The mono-, bi-, tri, -, and tetra-, antennary structures are important for the addition of terminal sialic acids. Such outer chain structures provide for additional sites for the specific sugars and linkages that comprise the carbohydrates of the protein products.

Therapeutic glycoproteins are often produced using recombinant DNA cell culture techniques. Protein glycosylation distributions in cell culture can be affected by variations in pH, cell density, nutrient concentrations, and metabolite concentrations. The sensitivity of glycan distributions to environmental effects makes it necessary to carefully monitor the glycan distribution during product development and production in order to ensure that a reproducible product is manufactured.

The development of recombinant-derived glycoproteins for therapeutic use has led to an increasing demand for methods to characterize and profile their carbohydrate structures. Oligosaccharide mapping has been used during initial characterization of recombinant proteins for comparison to the native protein, to identify oligosaccharide structures present, to monitor consistency of oligosaccharide composition, to evaluate changes that can result from alteration in cell culture or production process, and to identify changes in glycosylation that occur as a result of expression in different cell lines.

A variety of techniques are available to evaluate carbohydrate structural distributions. These include gel-filtration, chromatographic and electrophoretic separation techniques coupled with a wide range of detection techniques. If sample amounts are limited, the glycoproteins are often derivatized with fluorescence reagents such as 2-aminobenzoic acid and 2-aminopyridine in order to improve detection. However, derivatization and purification of the derivatives can be time consuming. When sample size is not an issue, direct evaluation of carbohydrate structural distributions is possible.

Analysis of Oligosaccharide Content of a Glycoprotein

A particular glycoprotein can display heterogeneity of carbohydrates. Heterogeneity can be seen at several levels: glycosylation sites can vary from completely occupied to unoccupied, and any specific site can be populated with many different oligosaccharide structures, wherein each structure can be modified by sialic acid molecules, such as NANA or NGNA.

The carbohydrate content of the protein of the present invention can be analyzed by methods known in the art, including methods described in the Examples herein. Several methods are known in the art for glycosylation analysis and are useful in the context of the present invention. These methods provide information regarding the identity and the composition of the oligosaccharide attached to the produced peptide. Methods for carbohydrate analysis useful in connection with the present invention include, but are not limited to, lectin chromatography; high performance anion-exchange chromatography combined with pulsed amperometric detection (HPAEC-PAD), which uses high pH anion exchange chromatography to separate oligosaccharides based on charge; NMR; Mass spectrometry; HPLC; porous graphitized carbon (GPC) chromatography.

Methods for releasing oligosaccharides are known. These methods include 1) enzymatic methods, which are commonly performed using peptide-N-glycosidase F/endo-α-galactosidase; 2) β-elimination methods, using a harsh alkaline environment to release mainly O-linked structures; and 3) chemical methods using anhydrous hydrazine to release both N- and O-linked oligosaccharides. Methods for analysis can comprise the following steps: 1. Dialysis of the sample against deionized water to remove all buffer salts, followed by lyophilization. 2. Release of intact oligosaccharide chains with anhydrous hydrazine. 3. Treatment of the intact oligosaccharide chains with anhydrous methanolic HCl to liberate individual monosaccharides as O-methyl derivatives. 4. N-acetylation of any primary amino groups. 5. Derivatization to yield per-O-trimethylsilyl methyl glycosides. 6. Separation of these derivatives by capillary gas-liquid chromatography (GLC) on a CP-SIL8 column. 7. Identification of individual glycoside derivatives by retention time from the GLC and mass spectroscopy, compared to known standards. 8. Quantification of individual derivatives by FID with an internal standard (13-O-methyl-D-glucose).

The presence of neutral and amino sugars can be determined by using high performance anion-exchange chromatography combined with pulsed amperometric detection (HPAEC-PAD Carbohydrate System; Dionex Corp.). For instance, sugars can be released by hydrolysis in 20% (v/v) trifluoroacetic acid at 100° C. for 6 hours. Hydrolysates are then dried by lyophilization or with a Speed-Vac (Savant Instruments). Residues are then dissolved in 1% sodium acetate trihydrate solution and analyzed on an HPLC-AS6 column (as described by Anumula et al., 1991, *Anal. Biochem.*, 195:269-280).

Alternatively, immunoblot carbohydrate analysis can be performed. In this procedure protein-bound carbohydrates are detected using a commercial glycan detection system (Boehringer), which is based on the oxidative immunoblot procedure described by Haselbeck et al. (1993, *Glycoconjugate J.*, 7:63). The staining protocol recommended by the manufacturer is followed except that the protein is transferred to a polyvinylidene difluoride membrane instead of a nitrocellulose membrane and the blocking buffers contain 5% bovine serum albumin in 10 mM Tris buffer, pH 7.4, with 0.9% sodium chloride. Detection is carried out with anti-digoxigenin antibodies linked with an alkaline phosphate conjugate (Boehringer), 1:1000 dilution in Tris buffered saline using the phosphatase substrates, 4-nitroblue tetrazolium chloride, 0.03% (w/v) and 5-bromo-4 chloro-3-indoyl-phosphate 0.03% (w/v) in 100 mM Tris buffer, pH 9.5, containing 100 mM sodium chloride and 50 mM magnesium chloride. The protein bands containing carbohydrate are usually visualized in about 10 to 15 minutes.

Carbohydrates associated with protein can also be cleaved by digestion with peptide-N-glycosidase F. According to this procedure the residue is suspended in 14 µL of a buffer containing 0.18% SDS, 18 mM beta-mercaptoethanol, 90 mM phosphate, 3.6 mM EDTA, at pH 8.6, and heated at 100° C. for 3 minutes. After cooling to room temperature, the reaction mixture is divided into two approximately equal parts. One part, which is not treated further, serves as a control. The other part is adjusted to about 1% NP-40 detergent followed by the addition of 0.2 units of peptide-N-glycosidase F (Boehringer). Both parts are warmed at 37° C. for 2 hours and then analyzed by SDS-polyacrylamide gel electrophoresis.

Glycan mapping of glycoproteins is becoming increasingly accepted. The methodology described herein allows for rapid characterization of oligosaccharides in terms of glycan type, extent of sialylation and number of branches on the non-reducing end of the carbohydrates. Thus, in certain embodiments, the invention provides CTLA4-Ig populations characterized by particular oligosaccharide profiles. Oligosaccharide profiling is typically done by chromatographic separation of oligosaccharides followed by detection and relative quantitation. An alternative to chromatographic profiling is the direct analysis of oligosaccharides by ESI infusion after online desalting.

Oligosaccharide profiling by PGC can be been used to characterize the N-linked oligosaccharides from CTLA4-Ig molecules. There are 31 structural classes of oligosaccharides identified from CTLA4-Ig molecules (SEQ ID NO:2), including a structural class containing O-acetylated sialic acid groups. Structural class verification is achieved through the use of MS/MS and positive ion mode MS. Relative quantitation of structural classes is possible through integration of the UV trace at 206 nm. Comparison of the subpopulation profiles from individual N-link sites is known, revealing significant population differences between N-link sites. Oligosaccharide profiling using PGC provides a convenient information rich alternative to the more traditional profiling methods such as HPAEC.

N-Linked Structures in CTLA4-Ig Molecules Comprising Monomers of SEQ ID NO:2

There are three N-linked glycosylation sites per chain (i.e., per monomer) on a CTLA4-Ig multimer or dimer, wherein the monomer has a sequence from SEQ ID NO:2, for example: (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, or (vi) 25-383 of SEQ ID NO:2). The variations in glycosylation by site are analyzed by isolating peptide fragments containing N-linked glycans from a tryptic digest of the protein. The N-linked glycosylation sites on the protein are located at $Asn^{102}$, $Asn^{134}$ and $Asn^{233}$, contained in tryptic fragments 5, 7, and 14, respectively. Enzymatic release of N-linked oligosaccharides from the isolated peptide fragments, followed by PGC profiling of the released oligosaccharides results in the profiles shown in FIG. 12. It is clear from the profile of the glycans released from $Asn^{233}$ (Tryptic fragment 14, T14) that the oligosaccharide population is enriched in the asialo structures (structures have no sialic acids). Oligosaccharide profiles from the glycans attached at $Asn^{102}$ and $Asn^{134}$ (T5 and T7) contain the bulk of the sialylated structures Isolated oligosaccharides released from glycoprotein are directly injected into the porous graphitized carbon LC/UV/MS system. FIGS. 13 and 14 show the TIC and UV chromatograms of a typical PGC profiles generated by acetonitrile gradients containing acidic and basic additives. In most cases, the mass spectra from a single chromatographic peak contain mass peaks for a single oligosaccharide. Thirty oligosaccharide structural classes are identified from the TFA containing elution profile. Only sixteen oligosaccharide structural classes are identified from the $NH_4OH$ containing elution profile. Within each structural class there are variant structures containing substitution of N-glycolylneuraminic acid (NGNA) in place of N-acetylneuraminic acid (NANA) as well as differing degrees of sialic acid acetylation. Although only qualitatative information can be gained from comparison of the ion counts for the oligosaccharide classes, it is apparent that the major structural classes within each of the four domains are P2100, P2111, P2122, and P3133. This is consistent with the integration values obtained from the UV trace at 206 nm. Further structural verification can be obtained from the positive ion mass spectrogram. Positive ion mode ionization promotes in source fragmentation of oligosaccharides, mainly at the glycosidic bonds. Because there is good separation of oligosaccharides, as determined by the negative ion mass spectra, the fragmented spectra from the positive ion mode mimic the positive ion MS/MS spectra. Domain III (di-sialylated structures) contains a significant amount of the O-acetylated structure P2122-Ac. Positive ion m/s data supports O-acetylation of one of the sialic acids on the structure. The most common O-acetylation site of sialic acid residues are at the C-7 and C-9 positions (Shi W X, Chammas R., Varki A., *J. Biol. Chem.* 271 (1996) 15130-15188). At physiologic extracellular pH, O-acetyl esters at C-7 spontaneously migrate to C-9. The most likely O-acetylation site is therefore C-9.

Analysis of N-Linked Oligosaccharide Content:

The analytical techniques can comprise cleavage and isolation of N-linked oligosaccharides by column chromatography, which in a non-limiting embodiment uses a Hypercarb column. Glycans subjected to Hypercarb chromatography are isolated and can be analyzed by HPAEC-PAD which analysis determines the types of carbohydrates that modify a particular glycoprotein. Analytical characterization of the N-linked oligosaccharides can also be achieved by Liquid Chromatography/Mass Spectrometry (LC/MS) using a Porous Graphitized Carbon (PGC). Carbohydrate analysis can also include trypsin, Asp-N, and Trypsin/Chymotrypsin peptide mapping to determine the peptides, which comprise carbohydrate structures.

N-linked oligosaccharide structures can be analyzed using a series of orthogonal mass spectrometry and HPAEC-PAD techniques (see Examples). These techniques include several endopeptidase cleavages followed by LC/MS/MS analysis. With respect to CTLA4-Ig monomers having a sequence from SEQ ID NO:2, the three major sites of N-linked glycosylation were characterized using LC/MS and LC/MS/MS electrospray ionization and the major structures at each N-link site were determined. These data are summarized in FIG. 9. There are at least three major attachment points for N-linked oligosaccharides at $Asn^{102}$, $Asn^{134}$, and $Asn^{233}$. In addition, $Asn^{233}$ is found to contain a population of N-linked structures that contained no sialic acid groups occurring about 80% of the time.

N-Linked Oligosaccharide Structures of CTLA4-Ig Determined by LC/MS of the Glycopeptides, LC/MS of the Oligosaccharides, and HPAEC-PAD:

The N-linked carbohydrates are associated with a consensus sequence motif of Asn-X-Ser/Thr. This sequence appears three times on CTLA4-Ig monomer chains having one of the following sequences: (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, and (vi) 25-383 of SEQ ID NO:2. The consensus sequence motif appears in SEQ ID NO:2 at: $Asn^{102}$ $Leu^{103}$ $Thr^{104}$; $Asn^{134}$ $Gly^{135}$ $Thr^{136}$; and $Asn^{233}$ $Ser^{134}$ $Thr^{235}$. Based on the consensus sequence, there are six N-linked carbohydrate sites per dimer molecule that is formed of any one or two of the following monomer sequences: (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, and (vi) 25-383 of SEQ ID NO:2.

N-linked carbohydrates can be of three general varieties: high-mannose, hybrid and/or complex. A LC/MS technique for the glycopeptide analysis was developed. Trypsin endoproteolytic cleavage of monomers (having one of the sequences (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, and (vi) 25-383 of SEQ ID NO:2) result in three peptides that contain N-linked glycosylation. All three N-linked sites are populated with carbohydrate structures. Tryptic fragment T5 corresponding to amino acids 65-109 of SEQ ID NO:2 contains a glycosylation on $Asn^{102}$. Tryptic fragment T7 corresponding to amino acids 120-154 of SEQ ID NO:2 contains a glycosylation on $Asn^{134}$. Tryptic fragment T14 corresponding to amino acids 229-237 of SEQ ID NO:2 contains a glycosylation on $Asn^{233}$.

Figure 12:
FIG. 12 shows the N-linked carbohydrate profile of a CTLA4-Ig molecule population comprising monomers of SEQ ID NO:2. The carbohydrates were collected from glycopeptides and separated using the LC/MS PGC N-linked Oligosaccharide technique. The chromatograms provide the population profile for each N-link attachment site. A) The Asn$^{76}$ (Asn$^{102}$ of SEQ ID NO:2) carbohydrates from the T5 peptide and B) the Asn$^{108}$ (Asn$^{134}$ of SEQ ID NO:2) carbohydrates from the T7 peptide both show distributions among mono- and multi-sialylated species. C) The Asn$^{207}$ (Asn$^{233}$ of SEQ ID NO:2) carbohydrates from the T14 peptide consist of predominantly asialylated species. D) The distribution of N-linked carbohydrates for CTLA4-Ig molecules is shown. E) A selected raw spectrum from the T5 peptide shows a major peak corresponding to the bi-antennary monosialylated structure depicted. F) A selected raw spectrum from the T14 shows a major peak corresponding to the bi-antennary asialo structure. G) A selected raw spectrum consists of a minor species which coelutes with the peak at 64.23 minutes, which corresponds to the tri-antennary di-sialylated structure. H) A selected raw spectrum reveals the major species in the peak at 64.23 minutes, which corresponds to the bi-antennary di-sialylated structure.
Figure 13A:
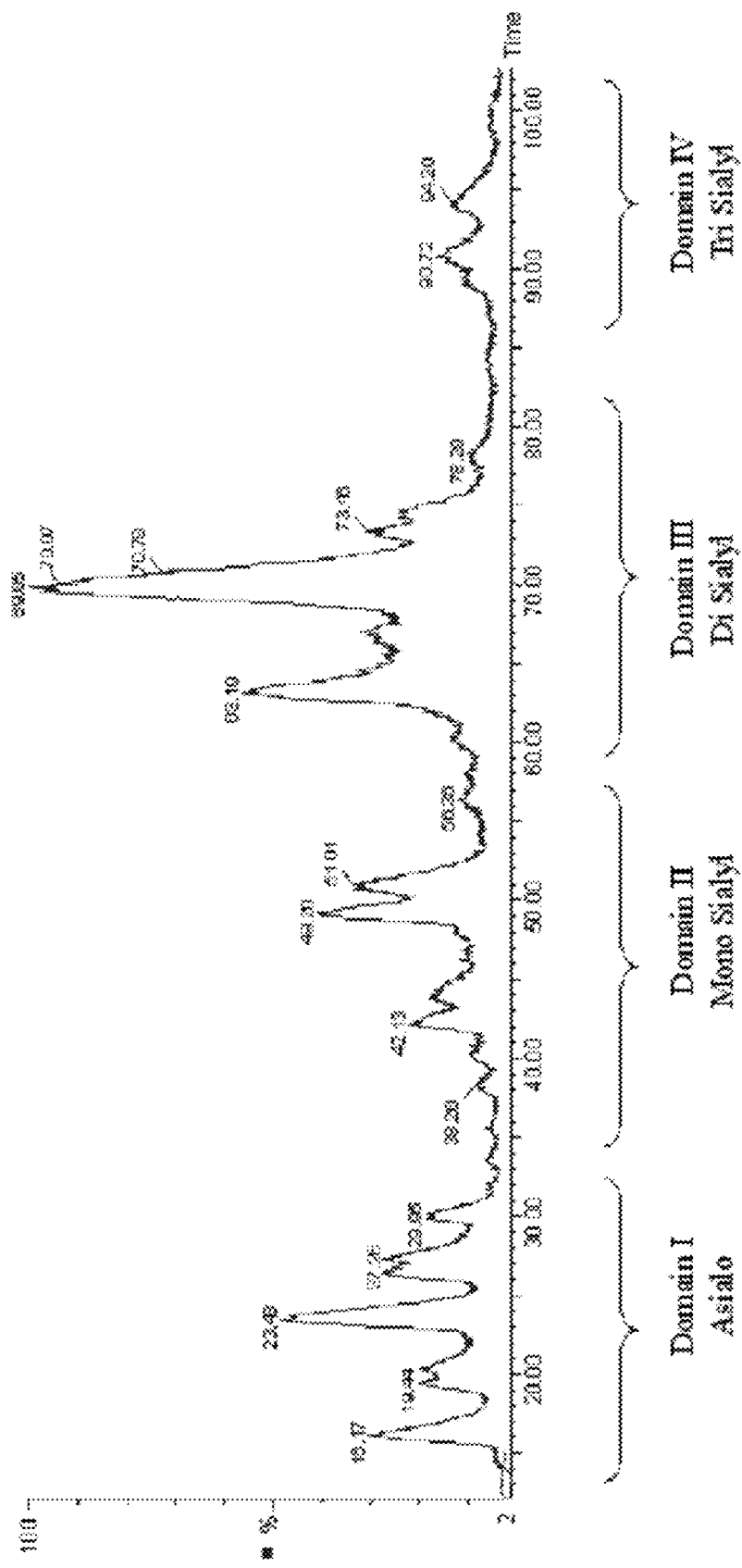
FIG. 13 A-13B shows a UV and TIC trace of an N-linked oligosaccharide profile of a CTLA4-Ig SEQ ID NO:2 monomer from PGC chromatography under acidic elution conditions (0.05% TFA). The trace of FIG. 13A shows negative ion total count (TIC) for PGC chromatograpm under acidic elution conditions (0.05% TFA). The trace of FIG. 13B shows UV trace at 206 nm for PGC chromatogram under acidic elutions (0.05% TFA).
Figure 13B:
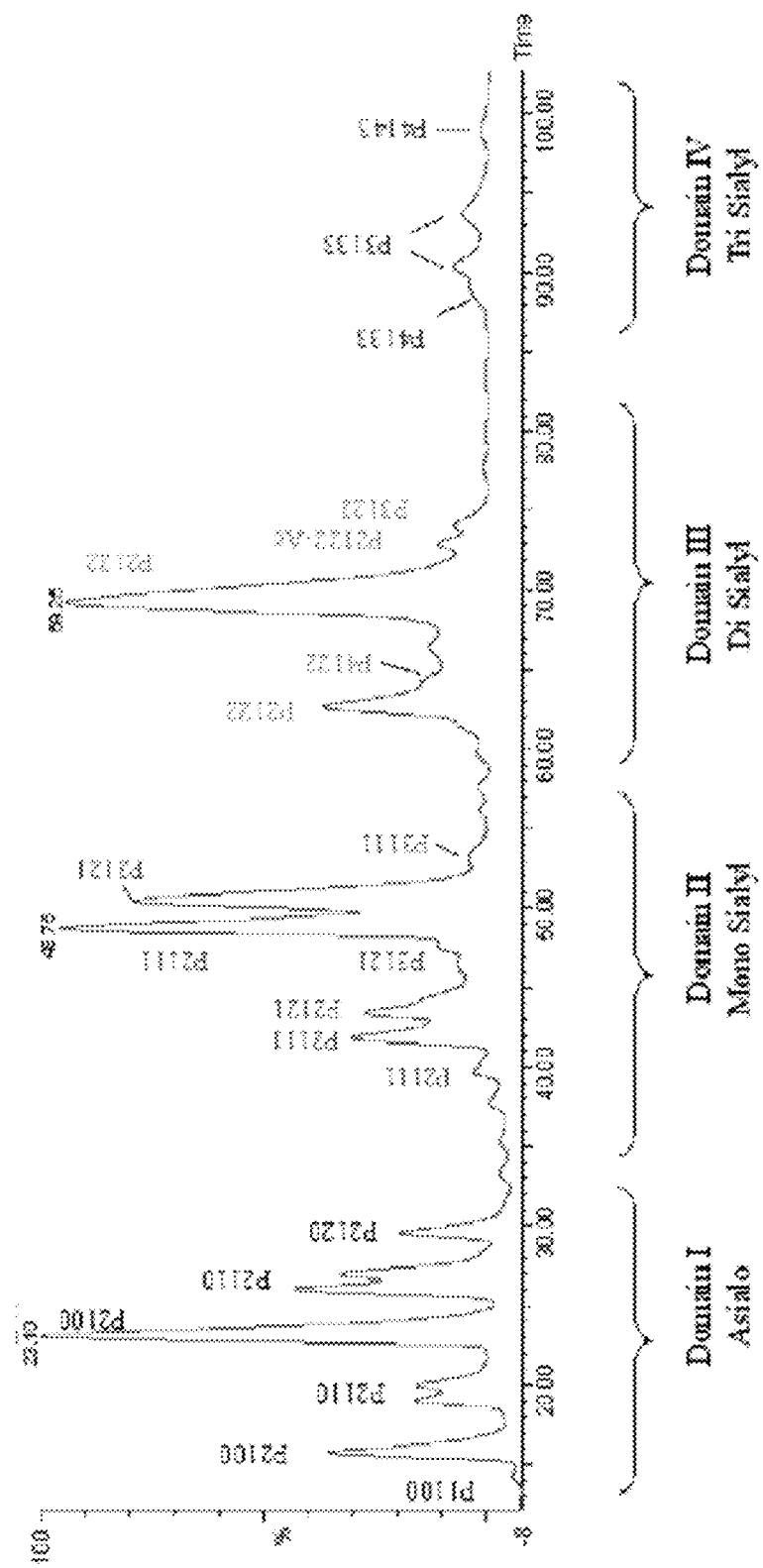

In order to determine the specific types of glycosylation on each site, carbohydrates were obtained from each specific site by increasing the scale of protein digestion and separation followed by collection of the T5, T7, and T14 peptides. The tryptic peptide peaks of interest were treated with PNGase F and processed for analysis by LC/MS on a Hypercarb column. Results showed that a heterogeneous population of complex bi-, tri-, and tetra-antennary structures at each site. These can be seen in FIG. 12 where the chromatography separates the sugars into five domains: asialo, mono-sialo, di-sialo, tri-sialo, and tetra-sialo structures (referred to as Domains I, II, III, IV, and V, respectively). A chromatogram (FIG. 12 panel A) for the $Asn^{102}$ (T5) carbohydrates illustrates a series of mono- and di-sialo structures at the site. A chromatogram (FIG. 12 panel B) for $Asn^{134}$ (T7) illustrates two main di-sialo structures with a population of mono-sialo structures. A chromatogram (FIG. 12 panel C) for $Asn^{233}$ (T14) illustrates little sialylation. For each of the N-linked carbohydrate sites, a MS spectrum and corresponding structure is shown for the major peak in each chromatogram (see FIG. 12, panels E, F, H). In FIG. 12, panel D, the total N-linked carbohydrate profile of CTLA4-Ig is shown in the chromatogram. The mass and structures of selected peaks are listed in Table 1. The oligosaccharide LC/MS data were supported by in-depth analysis of the peptide map. $Asn^{102}$ (T5 peptide) has the greatest degree of carbohydrate heterogeneity ranging from bi-antennary, non-sialylated structures to tetra-antennary, tetra-sialylated structures. $Asn^{134}$ (T7 peptide) contains primarily bi-antennary structures. This site contains much less heterogeneity than the $Asn^{102}$ site. The $Asn^{233}$ (T14 peptide) site contains little sialylation. A third analytical technique, HPAEC-PAD, was also employed to support the two orthogonal LC/MS findings.

TABLE 1

The major N-linked structures and selected minor complex structures observed using LC/MS methods

| Structure | Theoretical Mass | Actual Deconvoluted Mass |
|---|---|---|
| $(GlcNAc)_4$ (Fuc)1 $(Man)_3$ | 1462 | 1575* |
| $(GlcNAc)_4$ (Fuc)1 $(Man)_3$ $(Gal)_1$ | 1624 | 1737* |
| $(GlcNAc)_4$ (Fuc)1 $(Man)_3$ $(Gal)_2$ | 1786 | 1899* |
| $(GlcNAc)_4$ (Fuc)1 $(Man)_3$ $(Gal)_1$ $(NeuAc)_1$ | 1916 | 1916 |
| $(GlcNAc)_4$ (Fuc)1 $(Man)_3$ $(Gal)_2$ $(NeuAc)_1$ | 2077 | 2077 |
| $(GlcNAc)5$ (Fuc)1 $(Man)_3$ $(Gal)_3$ $(NeuAc)_1$ | 2443 | 2442 |
| $(GlcNAc)_4$ (Fuc)1 $(Man)_3$ $(Gal)_2$ $(NeuAc)_2$ | 2369 | 2368 |
| $(GlcNAc)_5$ (Fuc)1 $(Man)_3$ $(Gal)_3$ $(NeuAc)_2$ | 2734 | 2734 |
| $(GlcNAc)_5$ (Fuc)1 $(Man)_3$ $(Gal)_3$ $(NeuAc)_3$ | 3025 | 3025 |
| $(GlcNAc)_6$ (Fuc)1 $(Man)_3$ $(Gal)_3$ $(NeuAc)_3$ | 3388 | 3388 |
| $(GlcNAc)_6$ (Fuc)1 $(Man)_3$ $(Gal)_3$ $(NeuAc)_4$ | 3680 | 3680 |

*The asialo species are detected as TFA adducts.

The population of total N-linked carbohydrates was analyzed using HPAEC-PAD. The data obtained by this method are listed in Tables 2 and 3. In Table 2, the relative area percentages of asialo to tri-sialo domains are listed within each site ($Asn^{102}$, $Asn^{134}$, and $Asn^{233}$ of SEQ ID NO:2). In Table 3, the oligosaccharide domain area percentages are listed as a fraction of the entire population of oligosaccharides.

TABLE 2

The area percentages for each domain observed by the HPAEC-PAD

| N linked | Asialo | Mono | Di | Tri |
|---|---|---|---|---|
| $N^{102}$ | 27 | 37 | 25 | 11 |
| $N^{134}$ | 25 | 38 | 28 | 8 |
| $N^{233}$ | 82 | 12 | 5 | 1 |

TABLE 3

The area percentages for each domain expressed as weighted average on Table 2 data set.

| N linked | Asialo | Mono | Di | Tri |
|---|---|---|---|---|
| $N^{102}$ | 9 | 12 | 8 | 4 |
| $N^{134}$ | 8 | 13 | 9 | 3 |
| $N^{233}$ | 28 | 4 | 2 | 0 |
| Total/Molecule | 45 | 29 | 19 | 7 |

Assuming full glycosylation.

N-Linked Oligosaccharide Structures of CTLA4$^{A29A104E}$-Ig Molecules Determined by LC/MS of the Glycopeptides, LC/MS of the Oligosaccharides, and HPAEC-PAD:

The N-linked carbohydrates are associated with a consensus sequence motif of Asn-X-Ser/Thr. This sequence appears three times on CTLA4$^{A29YL104E}$-Ig monomer chains having one of the following sequences: (i) 26-383 of SEQ ID NO:4, (ii) 26-382 of SEQ ID NO:4, (iii) 27-383 of SEQ ID NO:4, (iv) 27-382 of SEQ ID NO:4, (v) 25-382 of SEQ ID NO:4, and (vi) 25-383 of SEQ ID NO:4. The consensus sequence motif appears in SEQ ID NO:4 at: Asn$^{102}$ Leu$^{103}$ Thr$^{104}$; Asn$^{134}$ Gly$^{135}$ Thr$^{136}$; and Asn$^{233}$ Ser$^{234}$ Thr$^{235}$. Based on the consensus sequence, there are six N-linked carbohydrate sites per dimer molecule that is formed of any one or two of the following monomer sequences: (i) 26-383 of SEQ ID NO:4, (ii) 26-382 of SEQ ID NO:4, (iii) 27-383 of SEQ ID NO:4, (iv) 27-382 of SEQ ID NO:4, (v) 25-382 of SEQ ID NO:4, and (vi) 25-383 of SEQ ID NO:4.

N-linked carbohydrates can be of three general varieties: high-mannose, hybrid and/or complex. A LC/MS technique for the glycopeptide analysis was developed. Trypsin endoproteolytic cleavage of monomers (having one of the sequences (i) 26-383 of SEQ ID NO:4, (ii) 26-382 of SEQ ID NO:4, (iii) 27-383 of SEQ ID NO:4, (iv) 27-382 of SEQ ID NO:4, (v) 25-382 of SEQ ID NO:4, and (vi) 25-383 of SEQ ID NO:4) result in three peptides that contain N-linked glycosylation (See Table 25 in EXAMPLE 22). All three N-linked sites are populated with carbohydrate structures. Tryptic fragment T5 corresponding to amino acids 65-109 of SEQ ID NO:4 contains a glycosylation on Asn$^{102}$. Tryptic fragment T7 corresponding to amino acids 120-154 of SEQ ID NO:4 contains a glycosylation on Asn$^{134}$. Tryptic fragment T14 corresponding to amino acids 229-237 of SEQ ID NO:4 contains a glycosylation on Asn$^{233}$ (See Table 25 in EXAMPLE 22).

Figure 15:
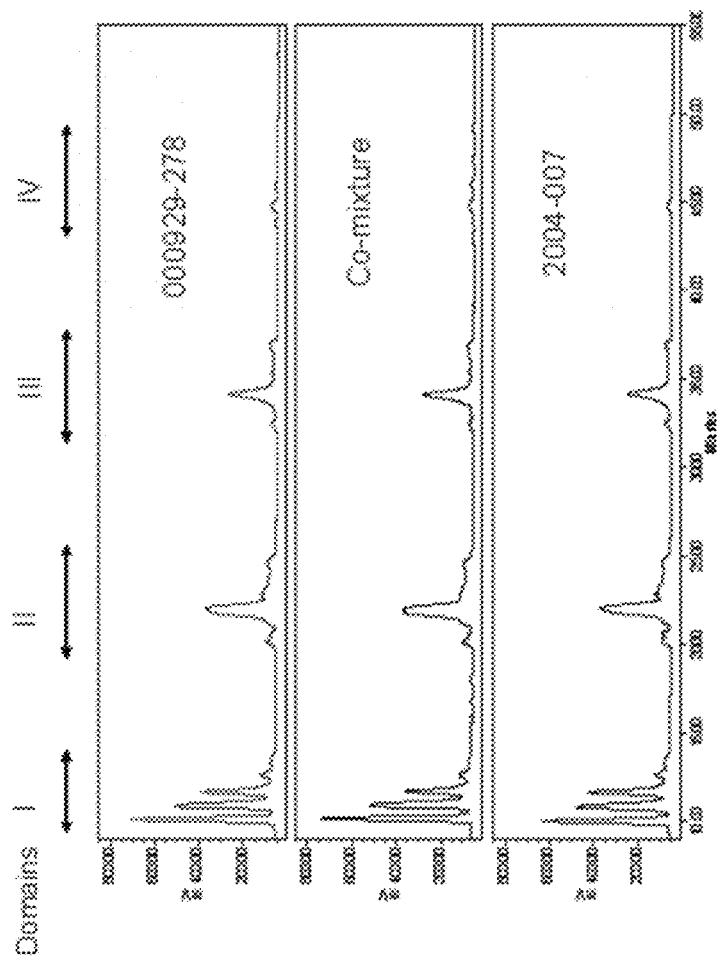
FIG. 15 represents the comparative N-linked oligosaccharide carbohydrate profiles for CTLA4$^{A29YL104E}$-Ig molecules comprising SEQ ID NO:4. Four oligosaccharide domains are observed: Domain I contains non-sialylated species, while Domains II, III, and IV contain mono-sialylated, di-sialylated and tri-sialylated species, respectively. Isolating the oligosaccharides chromatographically and analyzing them by mass spectroscopy determined the domains.

In order to determine the specific types of glycosylation on each site, carbohydrates were obtained from each specific site by increasing the scale of protein digestion and separation followed by collection of the T5, T7, and T14 peptides. The tryptic peptide peaks of interest were treated with PNGase F and processed for analysis by LC/MS on a Hypercarb column. Results showed that a heterogeneous population of complex bi-, tri-, and tetra-antennary structures at each site. These can be seen in FIG. 15 where the chromatography separates the sugars into four domains: asialo, mono-sialo, di-sialo, and tri-sialo structures (referred to as Domains I, II, III, and IV respectively). The characteristics of a carbohydrate profile that can be analyzed and compared between glycosylated molecules, or populations or compositions comprising glycosylated molecules include peak area percent, domain area percent, valley-to-valley distance, or peak-to-peak distance.

LC/MS Characterization of CTLA4-Ig N-Linked Oligosaccharides

LC/MS porous graphitic carbon (PGC) chromatography is a method for profiling N-linked oligosaccharides can provide several advantages over the High pH Anion Exchange Chromatography (HPAEC). Some of these advantages include: Direct profiling from digest mixtures which minimizes sample loss and degradation; direct MS interface provides a method for rapid characterization and analysis of oligosaccharides; increased resolution through PGC chromatography permits both the inter-domain comparisons as well as more subtle intra-domain analysis.

The LC/MS PGC method allows for rapid profiling and characterization of oligosaccharides in terms of glycan type, and determining the extent of sialylation and branching on the non-reducing end of the carbohydrates. Then negative ion mode MS spectra produce data that is simple to interpret, with minimal oligosaccharide fragmentation, while positive mode ionization allows for structural class verification. The method described here can be applied to whole digest mixtures of glycoproteins, as well as to previously isolated oligosaccharide samples without the need for derivatization. The chromatographic mobile phases used allow for collection of peaks from the profiles and concentration to dryness, without further manipulation for more detailed characterization. In one embodiment the method is used to characterize CTLA4-Ig N-linked oligosaccharides. Using the LC/MS PGC method, thirty-one distinct classes of oligosaccharides can be identified on CTLA4-Ig molecules comprised of monomers having sequences from SEQ ID NO:2, e.g., SEQ ID NO: 5, 6, 7, 8, 9, or 10.

Figure 16:
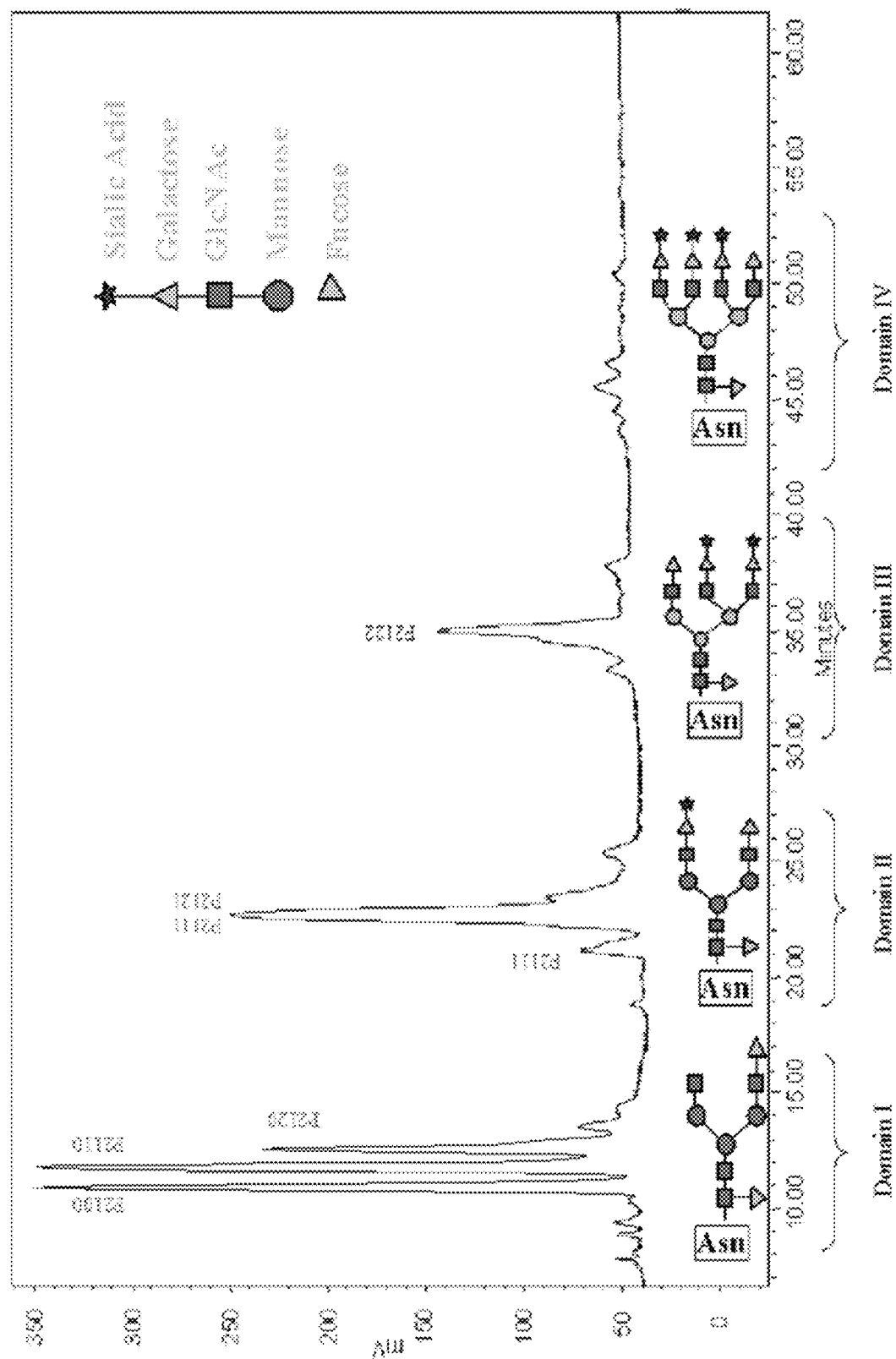
FIG. 16 shows an HPAEC-PAD profile of N-linked oligosaccharides of CTLA4-Ig molecules comprising SEQ ID NO:2 monomers. Domains are shown in order of increasing sialic acid content for oligosaccharides. Domains I, II, III an IV contain oligosaccharide structures having 0, 1, 2, and 3 sialic acids respectively. Peak labels represent oligosaccharide structures assigned by HPAEC-PAD profiling of peaks collected from PGC profiling. The structural identification of carbohydrate structure is consistent with previous determinations.

High pH anion exchange chromatography (HPAEC) has been used extensively to profile oligosaccharides released from glycoproteins without the need for derivatization. The high resolution of HPAEC and the fact that the separation is influenced by the type of sugar residue present, type of linkage and the size of the glycan are reasons for the widespread use of the technique. The dominating factor in separation is charge, highly charged oligosaccharides eluting later than less charged glycans. Chromatographic profiles are often divided into domains defined by the number of charged species, typically sialic acid residues, on the glycans (FIG. 16).

To obtain more information about the structure of the unknown oligosaccharides the HPAEC peaks can be collected, desalted and characterized by MS and/or NMR. One consideration to HPAEC-PAD profiling of oligosaccharide distributions is the variability inherent to the detection mode. Electrochemical cell aging and electrode surface fouling result in profile variability. It has also been reported that oligosaccharide structures and the degree of sialylation can cause variability among detection cells when using HPAEC with pulsed amperometric detection (HPAEC-PAD). This variability can affect quantitative and relatively quantitative results used to evaluate the effect of process changes or determine batch to batch consistency. Because of its speed and specificity, mass spectrometry (MS) has gained popularity as a technique for assessment of oligosaccharide profiling of glycoprotiens. Although MS profiles cannot be used to directly determine anomeric configuration or branching patterns, MS data can be used to identify structural classes and detect qualitative changes in glycoform distributions.

The porous graphitized carbon (PGC) chromatographic profiling method for enzymatically released N-linked oligosaccharides uses both ultraviolet (UV) and mass spectroscopic (MS) detection to profile and characterize N-linked oligosaccharides, either directly from enzymatic digest mixtures or from isolated oligosaccharides. This method can be used to profile and characterize oligosaccharide released from CTLA4-Ig glycoproteins. The LC/MS PGC method can evaluate the consistency of the oligosaccharide distributions resulting from the production process, as well as any changes in the oligosaccharide distributions resulting from process modifications. In a chromatographic microanalysis of N-linked oligosaccharides of CTLA4-Ig molecules, enzymatically released N-linked oligosaccharides can be readily separated by the PGC column in order of increasing sialylation and increasing size. The range of structures present and the relative amounts of each class of structure are determined through a combination of MS and UV analysis (Example 3).

To optimize the LC/MS PGC method, optimization of mass spectral conditions can be useful. Optimization can include a set of surface mapping experiments in order to evaluate the effects of solvent composition and MS ionization parameters on oligosaccharide detection. Solvent composition parameters for evaluation comprise percentage acetonitrile (by volume) and eluent additives (trifluoroacetic acid and ammonium hydroxide). MS ionization parameters evaluated for evaluation include the desolvation temperature, capillary voltage and cone voltage settings for the electrospray source.

The ionization parameters can play a significant role in signal response. The model resulting from the surface mapping determination was used to set ionization parameters during the chromatographic determination. Higher values for both desolvation temperature and cone voltage result in greater response. The capillary voltage optimum varies depending on the eluent additive, the TFA containing solvent system having a slightly higher optimal capillary voltage. The factor with the largest effect is the volume percentage of acetonitrile, higher acetonitrile content resulting in higher responses.

Porous Graphitized Carbon Chromatography

Figure 14A:
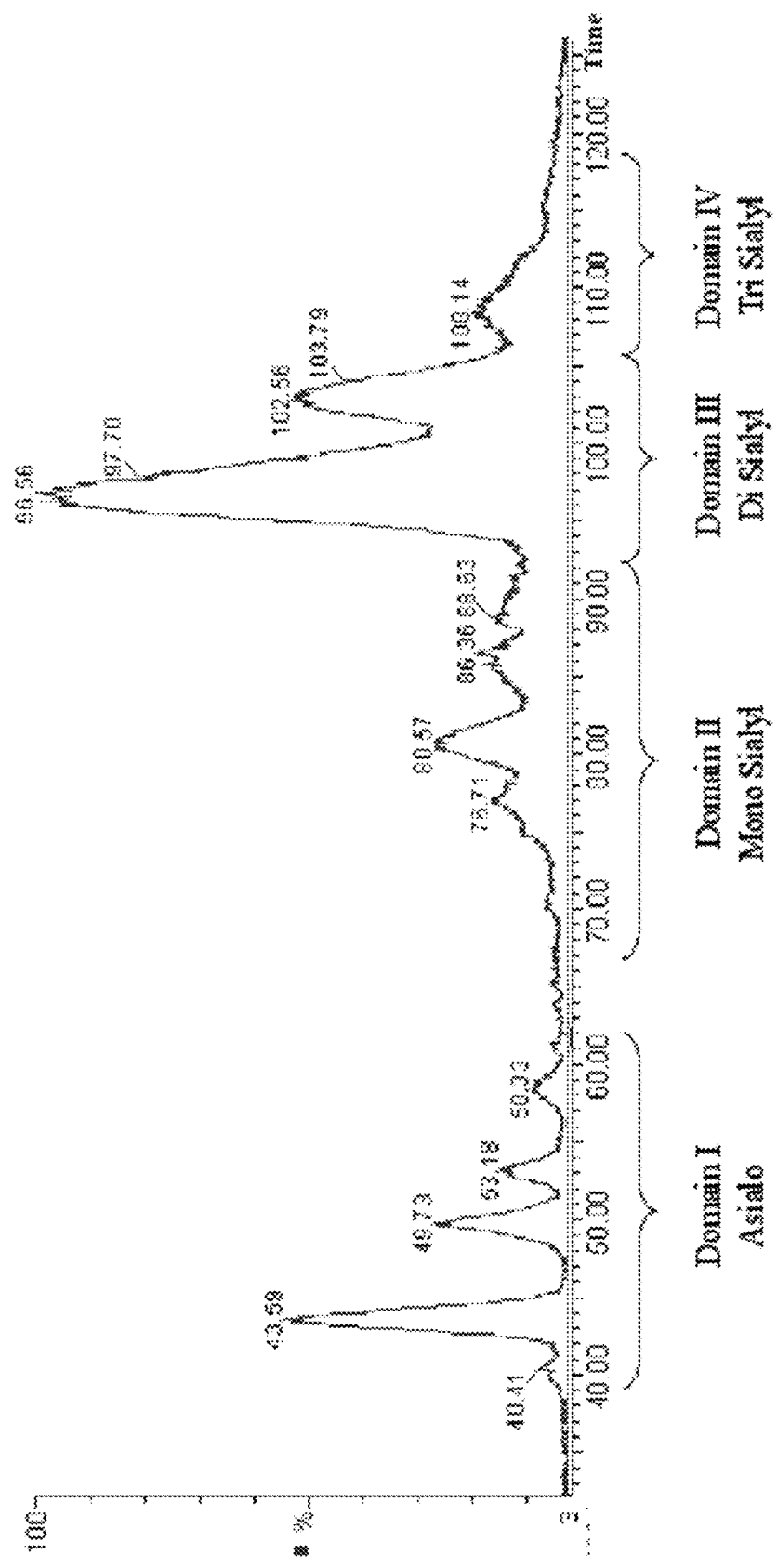
FIG. 14A-14B show a UV and TIC trace of an N-linked oligosaccharide profile of a CTLA4-Ig SEQ ID N0:2 monomer from PGC chromatography under basic elution conditions (0.4% NH$_4$OH). The trace of FIG. 14A shows negative ion total count (TIC) for PGC chromatograpm under basic elution conditions (0.4% NH$_4$OH). The trace of FIG. 14B shows UV trace at 206 nm for PGC chromatogram under basic elutions (0.4% NH$_4$OH).
Figure 14B:
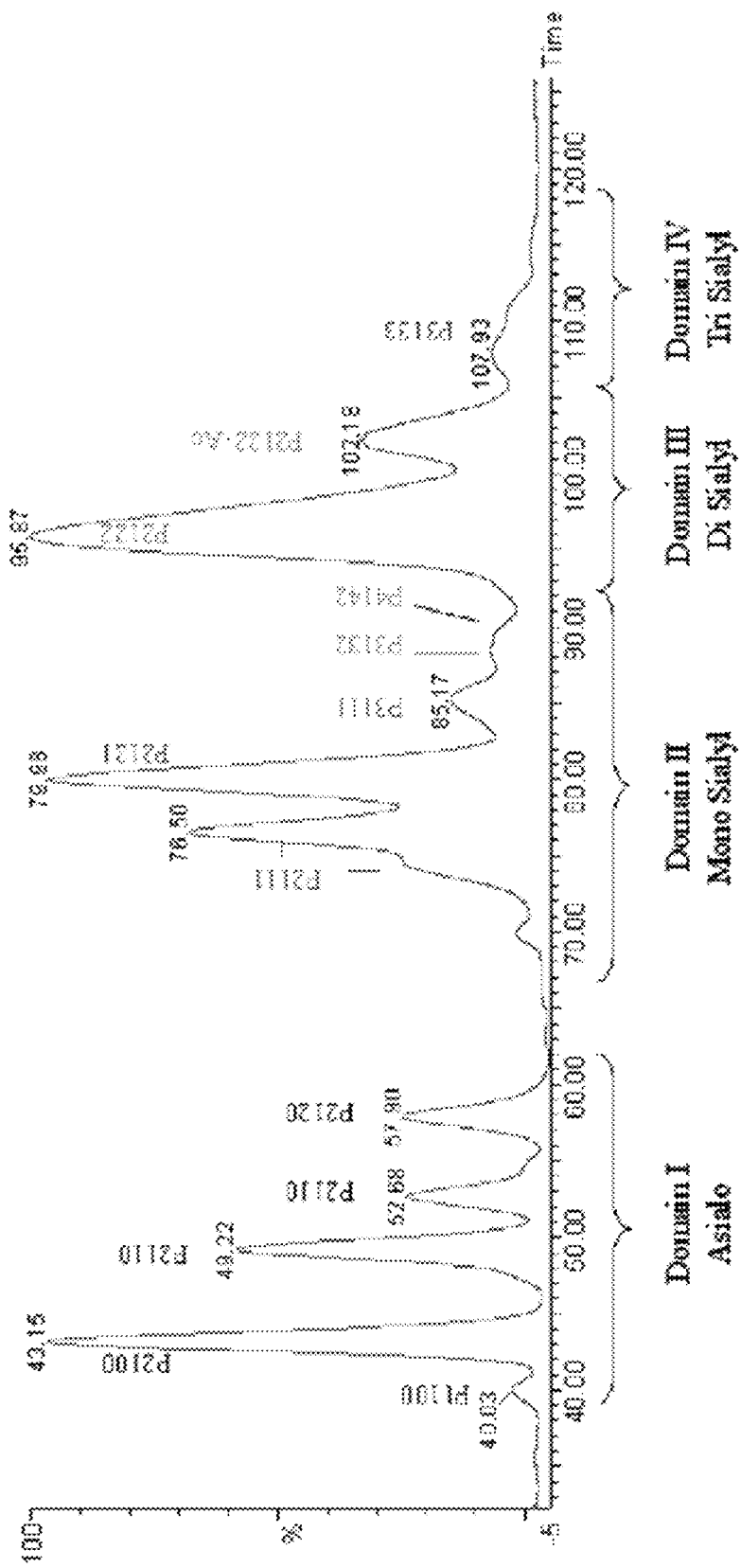

Porous graphitized carbon (PGC) has been used for solid phase extraction desalting of oligosaccharides. PGC has also been known as an effective chromatographic media for oligosaccharide separation under both acidic and basic elution conditions. Chromatography conditions for both acidic and basic profiling of enzymatically released oligosaccharides from CTLA4-Ig molecules having monomer sequences from SEQ ID NO:2 are developed. Each condition is compatible with both UV and MS detection. As was observed in the infusion experiments, the acidic elution conditions result in higher MS sensitivity than the basic conditions. The MS response for neutral oligosaccharides eluted under acidic conditions, detected as TFA adducts, are five to nine times the intensity of the corresponding peak eluted under basic conditions. The difference in signal response is less dramatic for the acidic oligosaccharides, averaging three times the signal response for monosialylated glycans and equal signal response for di-sialylated glycans. The increased number of peaks in the TFA eluted chromatogram (FIGS. 13A-13B) compared to the NH$_4$OH eluted chromatogram (FIG. 14A-14B) is a result of separation of anomeric forms of oligosaccharides. Collection and concentration of individual peaks eluted from the TFA gradient result in splitting of the single peak into two peaks of identical mass upon re-injection. Basic elution of the oligosaccharides from the PGC column results in a simpler profile (FIG. 14A-14B). The basic elution conditions do not result in complete anomeric separation, however significant peak broadening is observed. The peaks resolution can be increased by increasing the column temperature, which will accelerate the interchange of anomeric forms (Itoh S., et al., *J. Chromatogr. A.* 2002 968(1-2), 89-100). However, the sensitivity (ion count) for the detected oligosaccharides remains reduced compared to the acidic elution conditions. It has been reported that addition of salts such as ammonium acetate can increase sensitivity. (Churms S C, *J. Chromatogr. A.* 500 (1990) 555-583.)

Addition of ammonium acetate, ammonium trifluoroacetate or ammonium formate results in increased response but also results in asymmetric peak broadening. The resulting peak broadening and potential interference of the added salt with UV detection made salt addition an unattractive option. An alternative means of eliminating anomeric separation is to reduce the oligosaccharides to the corresponding alditols.

Higher sensitivity and chromatographic resolution make the acidic elution conditions useful for oligosaccharide profiling. A particular profiling system consists of a Luna C18 column coupled through two dual-position six port valves to the Hypercarb 5 µM column (100×4.6 mm). The Hypercarb column is coupled to a UV detector (Waters 2996 PDA) in series with a Q-ToF Micro (Micromass) with a standard ESI probe. Through appropriate switch control, prepurified CTLA4-Ig samples can be profiled using the Hypercarb column alone, or digest mixtures can be profiled by direct injection of the digest mixture onto the Luna C18 in series with the Hypercarb column. Typically, profiles are obtained from the N-linked oligosaccharides released from 10 to 20 nmoles of protein.

Figure 17A:
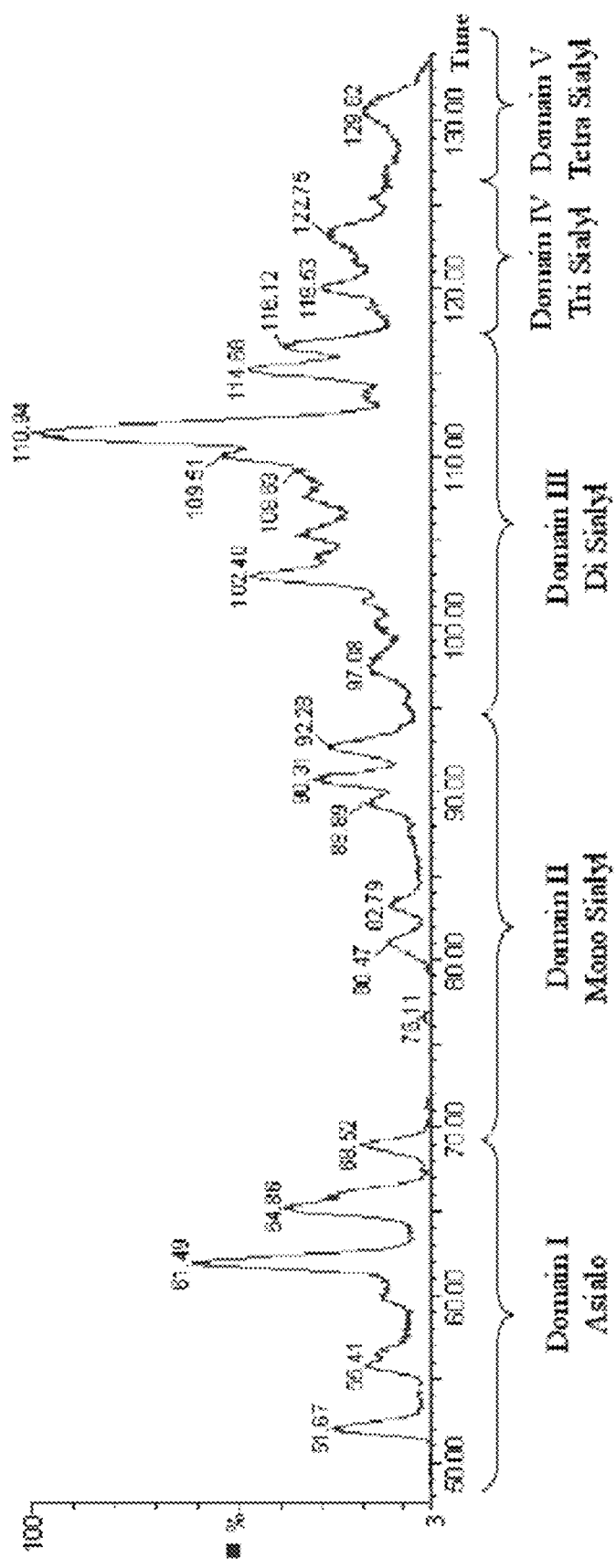
FIG. 17A-17B shows a PGC profile of CTLA4-Ig molecules comprising monomers of SEQ ID N0:2. The profile is obtained from direct injection of carbohydrate digest mixture prepared as described in Example 3. Direct injection results in detection of structure P4144 eluting at 130 minutes. The tetra-sialylated structure P4144 is not observed in profiles of oligosaccharides which are isolated prior to injection.
Figure 17B:
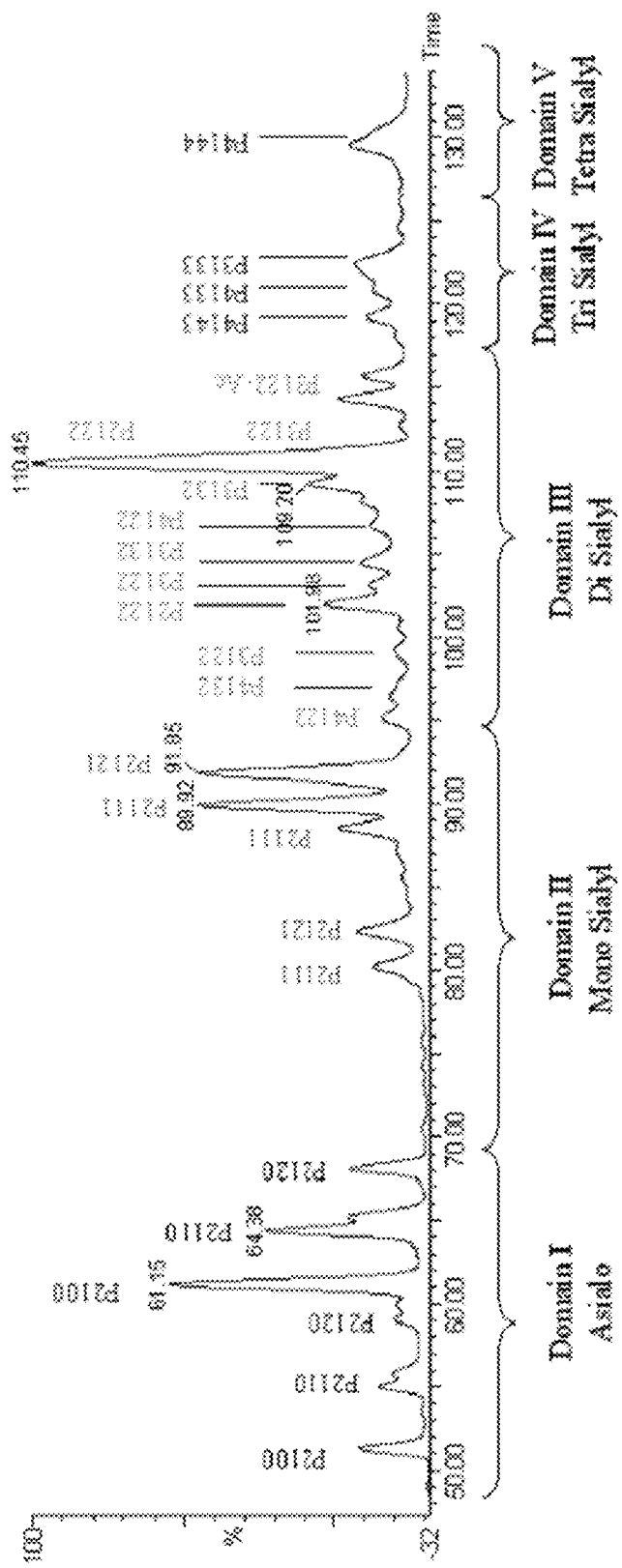

In certain embodiments, the invention provides a population of CTLA4-Ig molecules that have a chromatogram according to any one or more of the chromatograms having representative peaks. Representative oligosaccharide profile chromatograms for CTLA4-Ig molecules having monomers with sequences from SEQ ID NO:2 are shown in FIG. 12, FIGS. 13A-13B, FIGS. 14A-14B (PGC), FIG. 16 (HPAEC/PAD), and FIGS. 17A-17B. Both of these chromatographic profiles can be broken down into four distinct domains containing oligosaccharide structures with increasing degrees of sialylation in the later eluting domains. The PGC chromatographic system allows for direct interface with a mass detector. The mass resolution and signal to noise ratios are acceptable even for oligosaccharides which are present in low percentages. Chromatographic resolution of individual oligosaccharide structures appears greater in the PGC chromatographic separation as compared to the HPAEC.

Collecting peaks from the HPAEC method requires desalting and the high pH employed introduces the possibility of peeling reactions that could interfere with accurate structural identification of peaks. Because the chromatographic conditions used with PGC chromatography are free of salts, the eluted oligosaccharide peaks can be collected and concentrated with minimal manipulation. This allows for the collection and concentration of eluted peaks, followed by injection of the collected oligosaccharides onto the HPAEC system. Re-injection of the collected oligosaccharides onto a HPAEC-PAD system allows for structural assignment of some of the peaks present in the HPAEC profile (FIG. 16). Due to incomplete peak resolution on the anion exchange column, not all of the isolated peaks could be mapped to the HPAEC profile.

The profiles resulting from direct injection of digest mixtures and those for isolated oligosaccharides from the same protein sample are not identical. The profiles resulting from direct injection (FIGS. 17A-17B) have different anomer ratios suggesting that the concentration of collected oligosaccharides is resulting in increased anomerization. More importantly, the profile resulting from direct injection contains a peak, which corresponds to a tetra-sialylated structure. This structure is not identified in the profile of the collected and isolated oligosaccharides. In addition to shortened assay time, profiling directly from digest mixtures can result in a more accurate representation of the oligosaccharide distribution, by avoiding glycan degradation during collection and concentration.

Relative Quantitation

The surface mapping performed on infusion samples indicates that the volume percentage of acetonitrile has a significant effect on the ionization efficiency of eluting oligosaccharides. The dependence of signal intensity on acetonitrile content in the mobile phase makes relative quantitation of oligosaccharides by MS dependent on the retention time of the eluting peak. Variations in column condition can effect elution times on PGC columns. For this reason, it would be difficult to obtain consistent relative quantitation from the ion chromatogram elution profile. The UV trace at 206 nm should not be affected by the solvent composition to the same extent as the ion trace. The relative quantitation was performed using the UV trace, the ion trace was used for characterization and qualitative comparisons only. Replicate injections for oligosaccharides isolated from a single glycoprotein lot resulted in percent relative standard deviations (% RSD) of less than 4% for each of the four oligosaccharide domains quantified.

O-Linked Structures in CTLA4-Ig Molecules Comprising Monomers of SEQ ID NO:2

In addition to the N-linked carbohydrates, CTLA4-Ig molecules can contain 0-linked carbohydrates. The O-linked oligosaccharide structures can be analyzed using a series of orthogonal mass spectrometry techniques. These techniques include several endopeptidase cleavages followed by LC/MS/MS analysis.

With respect to CTLA4-Ig molecules formed of monomers having a sequence from SEQ ID NO: 5, 6, 7, 8, 9, or 10, the two major sites of O-linked glycosylation were characterized using exact mass electrospray ionization and the major structures at each 0-link site were determined.

These data are summarized in FIG. 9. Data are consistent with there being three major O-linked structures: $(GalNAc)_1$ $(Gal)_1$ $(NeuAc)_1$; $(GalNAc)_1$ $(Gal)_1$ $(NeuAc)_2$; $(GalNAc)_1$ $(GlcNac)_1$ $(Gal)_2$ $(NeuAc)_2$. Each structure is observed in differing amounts on each site. These amounts are relatively quantitative and represent data obtained from multiple analyses. The O-linked oligosaccharides contribute a substantial amount of sialic acid to CTLA4-Ig. There are two major O-linked oligosaccharide attachment points per chain. The primary site of occurrence for O-linked oligosaccharides is $Ser^{165}$, which is occupied in about 95% of the time. The secondary site of occurrence for O-linked oligosaccharides is $Ser^{155/156}$ which is occupied=25% of the time. The orthogonal data presented herein provides an overview of the predominant carbohydrate structures present on such CTLA4-Ig molecules and is summarized in FIG. 9.

In general, the O-linked carbohydrates have far greater heterogeneity of structure than are present in N-linked carbohydrates. In addition, there is no consensus sequence for O-link attachment. Thus, a series of orthogonal techniques were developed for use in the structural characterization of the O-linked oligosaccharides: LC/MS intact analysis and LC/MS glycopeptide analysis.

Based on Edman degradation and MALDI, an O-link site was reported to be $Ser^{165}$ (with respect to SEQ ID NO:2). To obtain direct data for the presence of $Ser^{165}$ glycosylation, MS/MS sequencing using b' and y" ion series on the T9 peptide (see Table 4 and Table 5) was performed. Table 4 lists the ion series for the T9 peptide in four different states of glycosylation. In all four states, the b' ion series, b1 . . . b6 ions are in agreement. However, the b' ion series, b7 . . . $b_{max}$ vary by the different glycosylation states at b7 ($Ser^{165}$). As a confirmation, the corresponding y" ion series is reported. In all four y" ion series, the y1 . . . y19 ions are in complete agreement. However, the y" ion series, y20 . . . ymax vary by the different glycosylation states at y20 ($Ser^{139}$). The b' and y" ion series taken together support the implication of Edman sequencing that $Ser^{139}$ is the primary site of O-linked glycosylation on the T9 peptide. T9 is a peptide that contains several serine and threonine residues.

Table 4 presents LC/MS/MS b' and y" ions for the T9 peptide with and without the O-linked ladder of $(GalNAc)_1$ $(Gal)_1$ $(NeuAc)_1$. The b' ion series are identical for all spectra until b7 where the spectrum then differs by the O-linked carbohydrate structure listed above each series. The y' ion series are identical for all spectra until y19 where the spectrum then differs by the O-linked carbohydrate structure listed above each series.

TABLE 4

| LC/MS/MS b' and y" ions for the T9 peptide. | | | | | | | | |
|---|---|---|---|---|---|---|---|---|
| T9-GalNAc-Gal-NeuAc | | T9-GalNac-Gal | | T9-GalNac | | T9 | | |
| b' | y" | b' | y" | b' | y" | b' | y" |
| 1 Thr 26 | 102.1 | — | 1 Thr 26 | 102.1 | — | 1 Thr 26 | 102.1 | — | 1 Thr 26 | 102.1 | — |
| 2 His 25 | 239.1 | 3243.6 | 2 His 25 | 239.1 | 2952.5 | 2 His 25 | 239.1 | 2790.5 | 2 His 25 | 239.1 | 2587.4 |
| 3 Thr 24 | 340.2 | 3106.6 | 3 Thr 24 | 340.2 | 28152.5 | 3 Thr 24 | 340.2 | 2653.4 | 3 Thr 24 | 340.2 | 2450.3 |
| 4 Ser 23 | 427.2 | 3005.5 | 4 Ser 23 | 427.2 | 2714.4 | 4 Ser 23 | 427.2 | 2552.4 | 4 Ser 23 | 427.2 | 2349.3 |
| 5 Pro 22 | 524.2 | 2918.5 | 5 Pro 22 | 524.2 | 2627.4 | 5 Pro 22 | 524.2 | 2465.3 | 5 Pro 22 | 524.2 | 2262.3 |
| 6 Pro 21 | 621.3 | 2821.4 | 6 Pro 21 | 621.3 | 2530.3 | 6 Pro 21 | 621.3 | 2368.3 | 6 Pro 21 | 621.3 | 2165.2 |

TABLE 4-continued

LC/MS/MS b' and y" ions for the T9 peptide.

| T9-GalNAc-Gal-NeuAc | | T9-GalNac-Gal | | T9-GalNac | | T9 | |
|---|---|---|---|---|---|---|---|
| b' | y" | b' | y" | b' | y" | b' | y" |
| 7 Olk 20  1364.6 | 2724.4 | 7 Oln 20  1073.52 | 2433.3 | 7 Oli 20  911.4 | 2271.2 | 7 Ser 20  708.3 | 2068.1 |
| 8 Pro 19  1461.6 | 1981.1 | 8 Pro 19  1170.5 | 1981.1 | 8 Pro 19  1008.5 | 1981.1 | 8 Pro 19  605.4 | 1981.1 |
| 9 Ala 18  1532.6 | 1884.1 | 9 Ala 18  1241.6 | 1884.1 | 9 Ala 18  1079.5 | 1884.1 | 9 Ala 18  876.4 | 1884.1 |
| 10 Pro 17  1629.7 | 1813.0 | 10 Pro 17  1338.6 | 1813.0 | 10 Pro 17  1176.6 | 1813.0 | 10 Pro 17  973.5 | 1813.0 |
| 11 Glu 16  1758.7 | 1716.0 | 11 Glu 16  1467.6 | 1716.0 | 11 Glu 16  1305.6 | 1716.0 | 11 Glu 16  1102.5 | 1716.0 |
| 12 Leu 15  1871.8 | 1586.9 | 12 Leu 15  1580.7 | 1586.9 | 12 Leu 15  1418.7 | 1586.9 | 12 Leu 15  1215.6 | 1586.9 |
| 13 Leu 14  1984.9 | 1473.8 | 13 Leu 14  1693.8 | 1473.8 | 13 Leu 14  1531.8 | 1473.8 | 13 Leu 14  1328.7 | 1473.8 |
| 14 Gly 13  2041.9 | 1360.8 | 14 Gly 13  1750.8 | 1360.8 | 14 Gly 13  1588.8 | 1360.8 | 14 Gly 13  1385.7 | 1360.8 |
| 15 Gly 12  2099.0 | 1303.7 | 15 Gly 12  18070.9 | 1303.7 | 15 Gly 12  1645.8 | 1303.7 | 15 Gly 12  1442.7 | 1303.7 |
| 16 Ser 11  2186.0 | 1246.7 | 16 Ser 11  1894.9 | 1246.7 | 16 Ser 11  1732.8 | 1246.7 | 16 Ser 11  1529.8 | 1246.7 |
| 17 Ser 10  2273.0 | 1159.7 | 17 Ser 10  1981.9 | 1159.7 | 17 Ser 10  1819.9 | 1159.7 | 17 Ser 10  1616.8 | 1159.7 |

TABLE 5

O-linked glycopeptide fragments with the corresponding sequence numbers, amino acid sequences and theoretical masses

| Enzyme | Enzyme Fragment | Amino Acid Sequence Fragment | Sequence (SEQ ID NO: 2) | Unmodified Mass |
|---|---|---|---|---|
| Trypsin | T9 | 159-184 | THTSPPSPAPELLGGSS VFLFPPKPK | 2688.44 |
| AspN | D8 | 150-156 | DQEPKSS | 790.36 |
| Tryp/ chrmo | N/A | 159-171 | THTSPPSPAPELL | 1345.7 |

Figure 18:
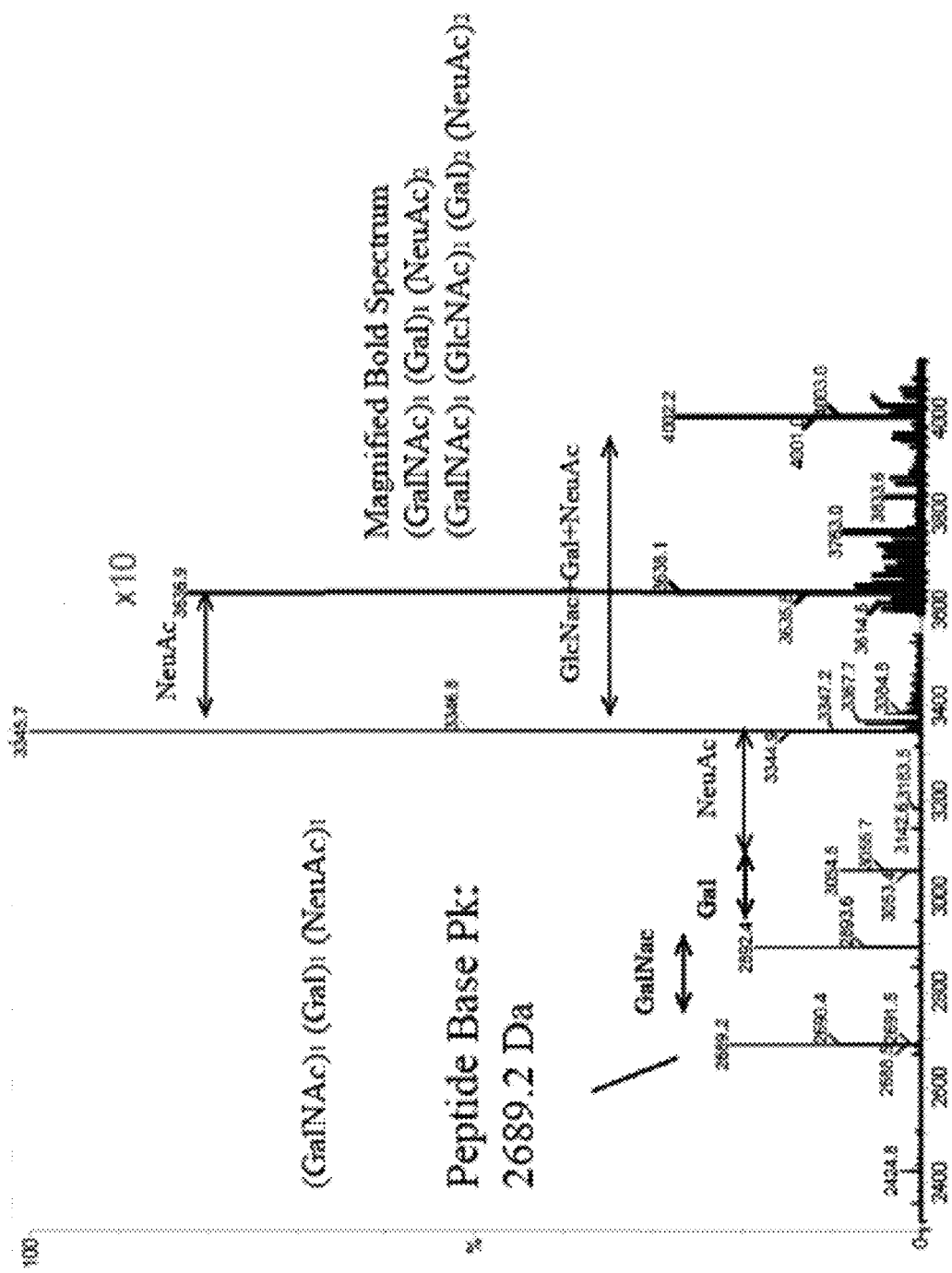
FIG. 18 presents a LC/MS deconvoluted positive electrospray spectrum for the T9 fragment of a SEQ ID N0:2 monomer. The spectrum illustrates three major O-linked structures. The spectrum illustrates the base peptide with sugar ladder consistent with the 0-linked structure (GalNAc)$_1$ (Gal)$_1$(NeuAc)$_1$. The bold portion of the spectrum has been enhanced 10-fold with respect to the non-bold portion of the spectrum and illustrates two additional O-linked structures with (GalNAc)$_1$(Gal)$_1$(NeuAc)$_2$ and (GalNAc)$_1$(GlcNAc)$_1$(Gal)$_2$(NeuAc)$_2$.

The O-linked carbohydrate structures at $Ser^{165}$ represent a heterogeneous population of three major species. In FIG. 18, the T9 glycopeptide is observed in the deconvoluted spectrum. There is a base peak at 2689.2 amu which is in agreement with the theoretical mass for this peptide of 2689.11 amu. The spectrum illustrates three major O-linked structures. The spectrum illustrates the base peptide with a sugar ladder consistent with the O-linked structure (GalNAc)$_1$ (Gal)$_1$ (NeuAc)$_1$. The magnified bold portion of the spectrum has been enhanced 10-fold and identifies two additional O-linked structures consistent with (GalNAc)$_1$ (Gal)$_1$ (NeuAc)$_2$ and (GalNAc)$_1$ (GlcNAc)$_1$ (Gal)$_2$ (NeuAc)$_2$.

Mass spectrometry was used to assess the relative abundance of each O-linked species. In FIG. 18, the (GalNAc)$_1$ (Gal)$_1$ (NeuAc)$_1$ glycan is observed in a 10:1 ratio with the (GalNAc)$_1$ (Gal)$_1$ (NeuAc)$_2$ glycan and in a 30:1 ratio with the (GalNAc)$_1$ (GlcNAc)$_1$ (Gal)$_2$ (NeuAc)$_2$ glycan. In one embodiment therefore, the invention provides a population comprising CTLA4-Ig molecules that have a 10:1 ratio of (GalNAc)$_1$ (Gal)$_1$ (NeuAc)$_1$ glycan to (GalNAc)$_1$ (Gal)$_1$ (NeuAc)$_2$ glycan. In another embodiment, the invention provides a population comprising CTLA4-Ig molecules that have a 30:1 ratio of (GalNAc)$_1$ (Gal)$_1$ (NeuAc)$_1$ glycan to (GalNAc)$_1$ (GlcNAc)$_1$ (Gal)$_2$ (NeuAc)$_2$ glycan. The (GalNAc)$_1$ (Gal)$_1$ (NeuAc)$_2$ glycan is observed in a ratio of 20:1 with the (HexNAc)$_2$ (Gal)$_2$ (NeuAc)$_2$ glycan. In another embodiment, the invention provides a population comprising CTLA4-Ig molecules that have a 20:1 ratio of the (GalNAc)$_1$ (Gal)$_1$ (NeuAc)$_2$ glycan to (HexNAc)$_2$ (Gal)$_2$ (NeuAc)$_2$ glycan. In another embodiment, the invention provides a population of CTLA4-Ig molecules that comprise all of the said ratios in this paragraph. In addition, a negative ion electrospray spectrum confirms these three predominant structures; the relative abundance of each is shown in FIG. 9.

With respect to CTLA4-Ig molecules comprising monomers of SEQ ID NO:2, in addition to the $Ser^{165}$ site, a second O-link site is observed at $Ser^{155}$ or $Ser^{156}$. This site is referred to as $Ser^{155/156}$. The D8 peptide containing $Ser^{155/156}$ was generated from an AspN digestion and corresponds to amino acids 150-156 of SEQ ID NO:2. The peptide is separated and detected by LC/MS. The spectrum (not shown herein) for the D8 O-linked glycopeptide shows a base peak of 790.2 amu that is in agreement with the theoretical mass of 790.8 amu. The spectrum illustrates the peptide ion and a series of ions which are consistent with the structure, (GalNAc)$_1$ (Gal)$_1$ (NeuAc)$_1$. The peptide is predominantly non-glycosylated; the glycosylated (GalNAc)$_1$ (Gal)$_1$ (NeuAc)$_1$ species constitutes approximately 22% peak area.

The O-linked oligosaccharide structures of the CTLA4-Ig single chain were characterized using a series of orthogonal mass spectrometry techniques. These techniques include endopeptidase cleavages with LC/MS analysis of the two predominant sites of O-linked glycosylation with the use of electrospray ionization to determine the predominant structures at each O-link site. These data are summarized in FIG. 19. There can be four predominant O-linked structures: $(GalNAc)_1(Gal)_1(NeuAc)_1$; $(GalNAc)_1(Gal)_1 (NeuAc)_2$; $(HexNAc)_2(Gal)_2(NeuAc)_2$; $(HexNAc)_2(Gal)_2, (NeuAc)_3$. These structures are detected in differing amounts on each site. Greater than 95% of the CTLA4-Ig single chain has at least $(HexNAc)_2 (Gal)_2 (NeuAc)_2$.

Another assay was developed to confirm the O-linked carbohydrates and look for less prevalent structures. This technique utilized trypsin and chymotrypsin co-digestion to produce a peptide confirmed by MS/MS to be THTSPPSPA-PELL (amino acids 159-171 of SEQ ID NO:2). This peptide allowed for the identification of one monosialylated, two di-sialylated and one tri-sialylated O-linked species. A definitive structure has not been elucidated for the tri-sialylated species, however two possibilities are proposed: a peptide containing a core 2 structure with 3 sialic acids or two core 1 structures present on two different amino acid residues.

A complementary technique, intact analysis by MS, was used to confirm the presence of heterogeneous O-link glycosylations of CTLA4-Ig molecules. CTLA4-Ig dimers and CTLA4-Ig single chain were treated with PNGase F to remove the N-linked oligosaccharides. The molecule was then detected by the mass spectrometer and the corresponding ions were deconvoluted into the spectrum. In the single chain material, the predominant glycan composition is (HexNAc)2(Hex)2(NeuAc)2, while the reference is predominantly (HexNAc)1(Hex)1(NeuAc)1. The glycosylation compositions are in agreement with those observed during the LC/MS peptide analysis. In addition to a change in the O-linked glycosylation pattern, a second major modification was observed. A mass shift of 113±4 u is observed between the single chain non-reduced species and the reduced CTLA4Ig standard. The mass shift of 113±4 u disappeared upon reduction with DTT. In the dimer material, the resulting ion envelope was deconvoluted into a spectrum (not shown herein) with a major peak at 79944 amu, which corresponds to the presence of two $(GalNAc)_1 (Gal)_1 (NeuAc)_1$ structures. The next largest peak, at 80600 amu, corresponds to three 0-link structures or a combination of at most one branched 0-link structure. The third largest peak corresponds to either four O-linked structures or a combination containing at most two branched 0-link structures.

Determination of Sialic Acid Content

Another aspect of glycoprotein characterization is determination of sialic acid. Sialic acid content can be a signature characteristic of glycoprotein. Sialic acid content of a glycoprotein of the present invention can be assessed by conventional methods. For example, sialic acid can be separately determined by a direct colorimetric method (Yao et al., 1989, *Anal. Biochem.*, 179:332-335), using at least triplicate samples. Another method of sialic acid determination involves the use of thiobarbaturic acid (TBA), as described by Warren et al., 1959, *J. Biol. Chem.*, 234:1971-1975. Yet another method involves high performance chromatography, such as described by H. K. Ogawa et al., 1993, *J. Chromatography*, 612:145-149.

In one embodiment, a method to determine the amount of N-Acetyl Neuraminic Acid (NANA) and N-Glycolyl Neuraminic Acid (NGNA) is through acid hydrolysis treatment of the glycoprotein of interest (for example, see Example 3). In this method, NANA and NGNA are cleaved from the protein by acid hydrolysis. In one embodiment the glycoprotein is substantially purified by methods suitable for its purification. The released NANA and NGNA are separated by HPLC on a Rezex Monosaccharide RHM column and detected by UV absorbance (206 nm). NANA and NGNA are quantitated based on the response factors of concurrently run NANA and NGNA standards. The results can be reported as molar ratios (MR) of NANA and NGNA respectively, to protein.

The purpose of the acid hydrolysis method of measuring sialic acid content is to measure the amount of total sialic acid (NANA and NGNA) to protein in CTLA4-Ig or $CTLA4^{A29YL104E}$-Ig samples (molar ratios). It is important to note, however, that these sialic acid molar ratios include both bound and free NANA and NGNA. Molar ratio results are obtained based on the peak area comparison of NANA and NGNA from hydrolyzed CTLA4-Ig or $CTLA4^{A29YL104E}$-Ig samples versus non-hydrolyzed NANA and NGNA standards. Hydrolyzed standards of NANA and NGNA can also be used.

For example, molar ratios were obtained for CTLA4-Ig molecules having SEQ ID NO:2 amino acid sequences. Without hydrolysis, the peak of interest in chromatograms of NANA and NGNA standards appears as a single peak. When the NANA standard and CTLA4-Ig samples are hydrolyzed, the resulting chromatograms show NANA as a major peak followed closely by a small shoulder peak (<10% of the major peak area; referred to as "degraded NANA"); the same concentration of NANA standards with and without hydrolysis resulted in very close peak areas, including the degradant. No peak is clearly seen in the chromatograms for a degraded NGNA species, although the area counts of the NGNA peak in a hydrolyzed NGNA standard were seen to decrease approximately 8-9%. Mass spectrometry (MS) experiments demonstrated that the "NANA degradant" in both the hydrolyzed NANA standard and the hydrolyzed CTLA4-Ig samples results from loss of 18 Daltons (water) from NANA. Therefore, the method appropriately includes the small shoulder peak in the integration of NANA peak in hydrolyzed CTLA4-Ig. It was also demonstrated by MS experiments that NGNA degraded upon hydrolysis with a loss of 18 Daltons. The NGNA degradant eluted between NANA and NANA degradant so that UV did not detect it. In CTLA4-Ig material, NGNA content is roughly 5% of NANA content and, as a result, co-elution of the NGNA degradant causes less than 0.5% change of the NANA peak area, which is within the variability range of the NANA peak area. The method cannot include the area of degraded NGNA in the NGNA result; therefore the NGNA result can be low by <10%, also within the variability of the method.

Because NGNA is thought to be more immunogenic than NANA, there is a clinical preference for a recombinant therapeutic that contains a low NGNA molar ratio. In one embodiment of the invention, the preponderance of sialic acid in a population of CTLA4-Ig molecules is NANA and not NGNA, wherein in this population the molar ratio of moles sialic acid per mole CTLA4-Ig molecules or dimer is from about 5 to about 18. In another embodiment, the preponderance of sialic acid in a population of $CTLA4^{A29YL104E}$-Ig molecules is NANA and not NGNA, wherein in this population the molar ratio of moles sialic acid per mole $CTLA4^{A29YL104E}$-Ig molecules or dimer is from about 5.5 to about 8.5.

CTLA4-Ig and CTLA4$^{A29YL104E}$-Ig Expression Cassettes

The invention provides for a nucleic acid encoding a CTLA4-Ig molecule, which is an expression cassette in one embodiment. The invention also provides for a nucleic acid encoding a CTLA4$^{A29YL104E}$-Ig molecule. In one embodiment, the nucleic acid encoding CTLA4-Ig molecule is contained within an expression cassette. In another embodiment, the nucleic acid encoding the CTLA4-Ig molecule is contained within an expression cassette derived from a plasmid having the nucleotide sequence of SEQ ID NO:17. In further embodiments, the nucleic acid encoding the CTLA4$^{A29YL104E}$-Ig molecule is contained within an expression cassette. In certain embodiments, the nucleic acid encoding the CTLA4$^{A29YL104E}$-Ig molecule is contained within an expression cassette derived from a plasmid deposited as ATCC Accession No. PTA-2104.

The nucleic acids of the invention can be a cDNA, cDNA-like, DNA or RNA nucleic acid molecule of interest in an expressible format, such as an expression cassette, which can be expressed from the natural promoter or a derivative thereof or an entirely heterologous promoter. Alternatively, the nucleic acid of interest can encode an anti-sense RNA. The nucleic acid of interest can encode a protein (for example a glycoprotein, such as CTLA4-Ig or CTLA4$^{A29YL104E}$-Ig glycoprotein), and may or may not include introns.

In one embodiment, the nucleic acid encoding a peptide having CTLA4 activity can be obtained from T cell genomic DNA or from mRNA present in activated T lymphocytes. In another embodiment, the nucleic acid encoding a CTLA4$^{A29YL104E}$-Ig also can be obtained from T cell genomic DNA or from mRNA present in activated T lymphocytes. In another embodiment of the invention, the gene encoding a protein of interest, for example CTLA4 or CTLA4$^{A29YL104E}$-Ig, can be cloned from either a genomic library or a cDNA according to standard protocols that one skilled in the art practices. A cDNA, for example encoding CTLA4 or CTLA4$^{A29YL104E}$-Ig, can be obtained by isolating total mRNA from a suitable cell line. Using methods known in the art, double stranded cDNAs can be prepared from the total mRNA and subsequently can be inserted into a suitable bacteriophage vector or plasmid. Genes can also be cloned using PCR techniques well established in the art. In one embodiment, a gene that encodes CTLA4 or CTLA4$^{A29YL104E}$-Ig can be cloned via PCR in accordance with the nucleotide sequence information provided by this invention.

In another embodiment, a DNA vector containing a CTLA4 or CTLA4$^{A29YL104E}$-Ig cDNA can act as a template in PCR reactions wherein oligonucleotide primers designed to amplify a region of interest can be used as to obtain an isolated DNA fragment encompassing that region. In a particular embodiment of the invention, the region of interest targeted in CTLA4 cDNA can be the extracellular domain of CTLA4, including the extracellular domain of human CTLA4. In certain embodiments, the region of interest targeted in a CTLA4$^{A29YL104E}$-Ig cDNA can be the extracellular domain of CTLA4 with amino acid changes at amino acid positions 55 and 130 of SEQ ID NO:2, (for example, see SEQ ID NO: 18) including the extracellular domain of human CTLA4 harboring the amino acid changes described above.

To express a fusion protein in the context of this invention, the chimeric gene fusion in one embodiment (for example a gene encoding a CTLA4-immunoglobulin (CTLA4-Ig) fusion protein or CTLA4$^{A29YL104E}$-Ig fusion protein) includes a nucleotide sequence, which encodes a signal sequence whereby upon transcription and translation of the chimeric gene, directs the newly synthesized fusion protein for secretion. In one embodiment, a native CTLA4 signal sequence (e.g., the human CTLA4 signal sequence described in Harper, K., et al. (1991, J. Immunol. 147, 1037-1044) can be used. In an alternative embodiment of the invention, a heterologous signal sequence can be used to direct CTLA4-Ig or CTLA4$^{A29YL104E}$-Ig secretion (for example, the oncostatin-M signal sequence (Malik N., et al., 1989, Mol Cell Biol 9(7), 2847-2853) or an immunoglobulin signal sequence). One skilled in the art understands that the nucleotide sequence corresponding to the signal sequence can be inserted into the chimeric gene fusion by standard recombinant DNA techniques, such as by performing an in-frame ligation of the signal sequence at the 5' end of a nucleic acid sequence encoding CTLA4.

Under the provisions of the Budapest Treaty, DNA encoding the amino acid sequence corresponding to a CTLA4-Ig fusion protein has been deposited with the American Type Culture Collection (ATCC), 10801 University Blvd., Manassas, Va., 20110, on May 31, 1991. It has been assigned ATCC Accession No. 68629. Additionally, an expression plasmid comprising a nucleic acid sequence encoding the amino acid sequence corresponding to a CTLA4$^{A29YL104E}$-Ig was deposited under the provisions of the Budapest Treaty on Jun. 19, 2000 with the ATCC. The deposited plasmid has been assigned ATCC Accession No. PTA-2104. The deposited plasmid is also referred to as pD16 LEA29Y and pD16 L104EA29Y. CTLA4$^{A29YL104E}$-Ig s are further described in U.S. Pat. No. 7,094,874 and co-pending U.S. patent application Ser. Nos. 09/579,927, 60/287,576, and 60/214,065, and in International Patent Publication No. WO 01/923337 A2, all of which are incorporated by reference in this application in their entireties.

An expression vector of the invention can be used to transfect cells, either eukaryotic (for example, yeast, mammalian, or insect cells) or prokaryotic in order to produce proteins (for example, fusion proteins such as CTLA4-Ig, CTLA4$^{A29YL104E}$-Ig molecules, and the like) encoded by nucleotide sequences of the vector. One skilled in the art understands that expression of desired protein products in prokaryotes is most often carried out in E. coli with vectors that contain constitutive or inducible promoters. Some E. coli expression vectors (also known in the art as fusion-vectors) are designed to add a number of amino acid residues, usually to the N-terminus of the expressed recombinant protein. Said fusion vectors can serve three functions: 1) to increase the solubility of the desired recombinant protein; 2) to increase expression of the recombinant protein of interest; and 3) to aid in recombinant protein purification by acting as a ligand in affinity purification. Some examples of fusion expression vectors include, but are not limited to: a) pGEX (Amrad Corp., Melbourne, Australia) which fuse glutathione S-tranferase to desired protein; b) pcD-NATM3.1/V5-His A B & C (Invitrogen Corp, Carlsbad, Calif.) which fuse 6x-His to the recombinant proteins of interest; and c) pMAL (New England Biolabs, Beverly, Mass.) which fuse maltose E binding protein to the target recombinant protein.

The cells suitable for culturing according to the processes and methods of the present invention can harbor introduced expression vectors (constructs), such as plasmids and the like. The expression vector constructs can be introduced via transfection, lipofection, transformation, injection, electroporation, or infection. The expression vectors can contain coding sequences, or portions thereof, encoding the proteins for expression and production in the culturing process. Such expression vectors can include the required components for the transcription and translation of the inserted coding sequence. Expression vectors containing sequences encoding the produced proteins and polypeptides, as well as the appropriate transcriptional and translational control elements, can be generated using methods well known to and practiced by those skilled in the art. These methods include in vitro recombinant DNA techniques, synthetic techniques, and in vivo genetic recombination which are described in J. Sambrook et al., 1989, Molecular Cloning, A Laboratory Manual, Cold Spring Harbor Press, Plainview, N.Y. and in F. M. Ausubel et al., 1989, Current Protocols in Molecular Biology, John Wiley & Sons, New York, N.Y.

A selectable marker can be used in a recombinant expression vector (for example, a plasmid), wherein the vector is stably integrated into the genome of the cell, to confer resistance to the cells harboring the vector. This allows for their selection in an appropriate selection medium. A number of selection systems can be used, including but not limited to, the hypoxanthine-guanine phosphoribosyltransferase (HGPRT), the Herpes Simplex Virus thymidine kinase (HSV TK), (Wigler et al., 1977, *Cell*, 11:223), (Szybalska and Szybalski, 1992, *Proc. Natl. Acad. Sci. USA*, 48:202), and adenine phosphoribosyltransferase (APRT), (Lowy et al., 1980, *Cell*, 22:817) genes, which can be employed in hgprt-, tk-, or aprt-cells, respectively.

The following non-limiting examples of marker genes, which can be contained within an expression vector, can also be used as the basis of selection for anti-metabolite resistance: gpt, which confers resistance to mycophenolic acid (Mulligan and Berg, 1981, *Proc. Natl. Acad. Sci. USA*, 78:2072); dhfr, which confers resistance to methotrexate (Wigler et al., 1980, *Proc. Natl. Acad. Sci. USA*, 77:357; and O'Hare et al., 1981, *Proc. Natl. Acad. Sci. USA*, 78:1527); hygro, which confers resistance to hygromycin (Santerre et al., 1984, *Gene*, 30:147); and neo, which confers resistance to the aminoglycoside G418 (*Clinical Pharmacy*, 12:488-505; Wu and Wu, 1991, *Biotherapy*, 3:87-95; Tolstoshev, 1993, *Ann. Rev. Pharmacol. Toxicol.*, 32:573-596; Mulligan, 1993, *Science*, 260:926-932; Anderson, 1993, *Ann. Rev. Biochem.*, 62:191-21; May, 1993, *TIB Tech*, 11 (5):155-215). Recombinant DNA techniques commonly known in the art can be routinely applied to elect the desired recombinant cell clones. Such techniques are described, for example, in Ausubel et al. (eds.), Current Protocols in Molecular Biology, John Wiley & Sons, N Y (1993); Kriegler, 1990, Gene Transfer and Expression, A Laboratory Manual, Stockton Press, NY; in Chapters 12 and 13, Dracopoli et al. (eds), Current Protocols in Human Genetics, John Wiley & Sons, N Y (1994); Colberre-Garapin et al., 1981. *J. Mol. Biol.*, 150:1, which are incorporated by reference herein in their entireties.

The expression levels of an expressed protein molecule can be increased via amplification of the expression vector (for a review, see Bebbington and Hentschel, "The use of vectors based on gene amplification for the expression of cloned genes in mammalian cells in DNA cloning", Vol. 3, Academic Press, New York, 1987). An increase in the level of an inhibitor present in the culture medium of a host cell will increase the number of copies of the marker gene when a marker in the expression vector system expressing a protein of interest is amplifiable. Since the amplified region is associated with the protein-encoding gene, protein production will concomitantly increase (Crouse et al., 1983, *Mol. Cell. Biol.*, 3:257). Vectors that harbor the nucleic acid sequences that encode for the selectable markers glutamine synthase (GS) or dihydrofolate reductase (DHFR) can be amplified in the presence of the drugs methionine sulphoximine or methotrexate, respectively. An advantage of such vectors is the availability of cell lines, for example the murine myeloma cell line, NS0 and the Chinese Hamster Ovary, CHO, cell line DG44, which are glutamine synthase negative and dihydrofolate reductase negative, respectively.

In one embodiment of the present invention, a nucleic acid sequence encoding a soluble CTLA4 or CTLA4$^{429YL104E}$-Ig fusion protein molecule can be inserted into an expression vector designed for expressing foreign sequences in a eukaryotic host. The regulatory components of the vector can vary according to the eukaryotic host chosen for use. Vectors used to express soluble CTLA4 or CTLA4$^{429YL104E}$-Ig in eukaryotic host cells can include enhancer sequences for optimization of protein expression.

Mammalian cells (such as BHK cells, VERO cells, CHO cells and the like) can harbor an expression vector (for example, one that contains a gene encoding the CTLA4-Ig fusion protein or the CTLA4$^{429YL104E}$-Ig fusion protein) via introducing the expression vector into an appropriate host cell. Accordingly, the invention encompasses expression vectors containing a nucleic acid sequence that encodes a CTLA4-Ig or CTLA4$^{429YL104E}$-Ig fusion protein and encompasses host cells into which such expression vectors can be introduced via methods known in the art. As described herein, an expression vector of the invention can include nucleotide sequences that encode a CTLA4-Ig or CTLA4$^{429YL104E}$-Ig fusion protein linked to at least one regulatory sequence in a manner that allows expression of the nucleotide sequence in a host cell. To those skilled in the art, regulatory sequences are well known and can be selected to direct the expression of a protein of interest in an appropriate host cell as described in Goeddel, Gene Expression Technology: Methods in Enzymology 185, Academic Press, San Diego, Calif. (1990). Regulatory sequences can comprise the following: enhancers, promoters, polyadenylation signals, and other expression control elements. Practitioners in the art understand that designing an expression vector can depend on factors, such as the choice of host cell to be transfected and/or the type and/or amount of desired protein to be expressed.

Cloning and expression plasmids (for example, pcSD and piLN) are constructed as described in Examples 11. In one embodiment of this invention, an isolated DNA fragment from plasmid pSV2dhfr– is ligated to the pcDNA3 vector backbone generating the expression vector pcSD. Vector pcSD is comprised of the following features: a cytomegalovirus (CMV) promoter followed by a multiple cloning site (MCS); a bovine growth hormone (BGH) polyadenylation signal and transcriptional termination sequence; a mouse dhfr cDNA sequence for selection and amplification; an ampicillin resistance gene; and a pUC origin of replication for selection and maintenance in *Escherichia coli*. Vector piLN is constructed containing cDNAs encoding portions of the amino acid sequence corresponding to a fragment of the extracellular domain of the human CTLA4 receptor Example 11, where the cDNA encoding a first amino acid sequence is joined to DNA encoding a second amino acid sequence, which corresponds to an IgC region that permits the expression of the CTLA4 receptor gene by altering the solubility of the expressed CTLA4 protein (see FIG. 1 and brief description for FIG. 1 for residues corresponding to CTLA4 extracellular portion and IgG1 constant region). In one embodiment, an oncostatin M signal peptide sequence can be fused to the amino acid sequence corresponding to the extracellular domain of CTLA4 which subsequently is fused to a second amino acid sequence corresponding to an Ig domain (for example, the human IgC$_{\gamma1}$ domain) as previously described in FIG. 1. The oncostatin M signal sequence allows for soluble forms of the CTLA4 gene (for example CTLA4-Ig) protein product to be generated.

To construct a pcSD expression vector containing a gene encoding the CTLA4-immunoglobulin fusion protein, methods known in the art (for example, restriction site subcloning) can be used. The starting material for one embodiment of the invention can be a digested and excised DNA fragment from the cloning vector piLN described in Example 11. In another embodiment, the excised DNA fragment from said vector contains the amino acid sequence of the oncostatin M signal sequence and CTL4Ig fusion protein, wherein said DNA fragment is ligated to the digested pcSD vector. The oncostatin M-CTLA4-Ig DNA fragment can be inserted between the CMV promoter and a cassette containing the BGH polyadenylation signal and transcriptional termination sequence. This would place a CTLA4-Ig gene product under the control of the CMV promoter in the plasmid designated pcSDhuCTLA4-Ig (FIG. 20; SEQ ID NO: 17).

Figure 21:
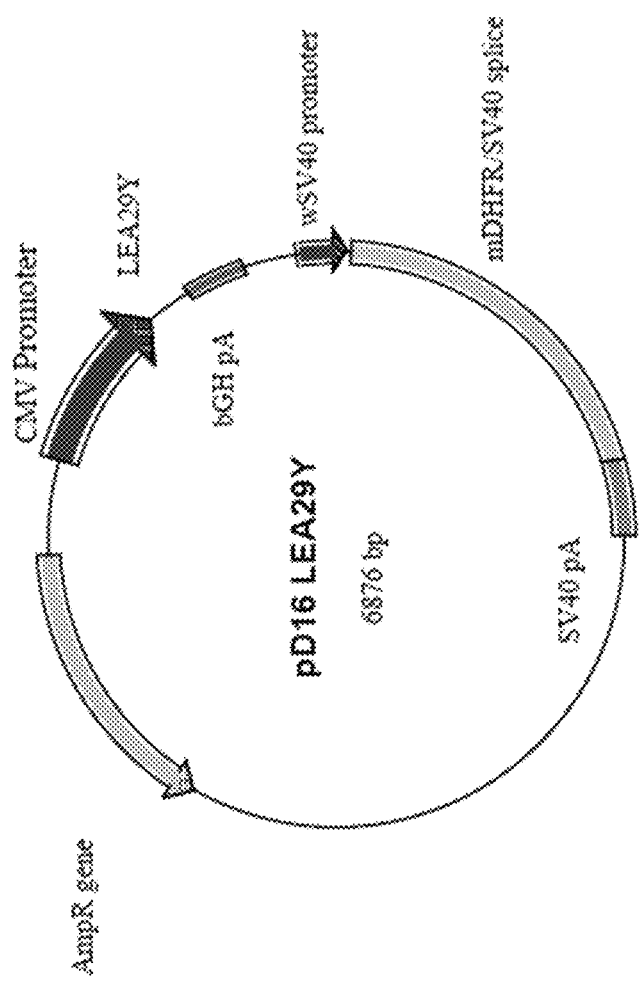
FIG. 21 depicts a map of the plasmid pD16LEA29Y. This plasmid comprises a sequence that can encode a human CTLA4$^{A29YL104E}$-Ig molecule (i.e., SEQ ID NO:4).

Additionally, cloning and expression plasmids (for example, pD16LEA29Y) can be derived from the Invitrogen plasmid pcDNA3. Vector pD16LEA29Y (FIG. 21) comprises the following features: the neomycin resistance gene from pcDNA3 was replaced with the murine dihydrofolate reductase (DHFR) gene under control of the enhancerless (weakened) SV40 promoter; the gene encoding a CTLA4$^{A29YL104E}$-Ig is expressed from the CMV promoter, and the poly adenylation signal is from the bovine growth hormone gene; the expression cassette for the gene of interest is flanked by transcription termination sequences, i.e., 5' to the promoter and 3' to the poly A site; the vectors contain two distinct restriction site polylinkers, one 3' to the promoter for cloning the gene of interest, and one 5' to the promoter for vector linearization prior to transfection; the vector contains an ampicillin resistance gene and the ColE1 origin of replication for plasmid propagation in *E. coli*; the CTLA4$^{A29YL104E}$-Ig sequence (SEQ ID NO:3) is preceded by the Oncostatin M signal peptide and assembled in the expression vector known as vector pD16LEA29Y.

The vector is constructed containing cDNAs encoding portions of the amino acid sequence corresponding to a fragment of the extracellular domain of the human CTLA4 receptor (SEQ ID NO:2), wherein the amino acid Ala at position 55 is replaced by the amino acid Tyr and the amino acid Leu at position 130 is replaced by the amino acid Glu (FIG. 3). These amino acid changes are depicted in the CTLA4$^{A29YL104E}$-Ig amino acid sequence having SEQ ID NO: 4. The cDNA encoding a first amino acid sequence (for example, the sequence that encodes a CTLA4$^{A29YL104E}$-Ig) is joined to DNA encoding a second amino acid sequence, which corresponds to an IgC region that permits the expression of the CTLA4$^{A29YL104E}$-Ig receptor gene by altering the solubility of the expressed CTLA4$^{A29YL104E}$-Ig protein (see FIG. 3 and the brief description for FIG. 3 for residues corresponding to the modified CTLA4 extracellular portion and IgG1 constant region) having SEQ ID NO: 3.

In one embodiment, an oncostatin M signal peptide sequence can be fused to the amino acid sequence corresponding to the extracellular domain of CTLA4 which subsequently is fused to a second amino acid sequence corresponding to an Ig domain (for example, the human IgC$_{\gamma1}$ domain) as previously described in FIG. 3. The oncostatin M signal sequence allows for soluble forms of the CTLA4 gene (for example a CTLA4$^{A29YL104E}$-Ig) protein product to be generated.

Stable Transfection to Generate Cell Line

Vectors that contain DNA encoding a protein of interest (for example, fusion constructs, glycoproteins, and the like) can be transformed into suitable host cells (for example bacterial cells) in order to produce large quantities of cloned DNA. Some non-limiting examples of bacterial cells for transformation include the bacterial cell line *E. coli* strains DH5a or MC1061/p3 (Invitrogen Corp., San Diego, Calif.), which can be transformed using standard procedures practiced in the art, and colonies can then be screened for the appropriate plasmid expression.

Expression vectors for eukaryotic cells, such as mammalian cells, can include promoters and control sequences compatible with mammalian cells. In one embodiment of the invention, these regulatory elements can be, for example, a CMV promoter found in the pcSD or pD16LEA29Y vector, or the avian sarcoma virus (ASV) located in the piLN vector. Other commonly used early and late promoters include, but are not limited to, those from Simian Virus 40 (SV 40) (Fiers, et al., 1973, *Nature* 273:113), or other viral promoters such as those derived from bovine papilloma, polyoma, and Adenovirus 2 virus. The regulatable promoter, hMTII (Karin, et al., 1982, *Nature* 299:797-802) can also be used, in addition to others known in the art. For recombinant protein expression in cultured insect cells (for example, SF 9 cells), some baculovirus vectors available include the pVL series (Lucklow, V. A., and Summers, M. D., 1989, *Virology* 170:31-39) and the pAc series (Smith et al., 1983, *Mol. Cell Biol.* 3:2156-2165). A practitioner skilled in the art also understands that enhancer regions (those sequences found upstream or downstream of the promoter region in non-coding DNA regions) are also important in optimizing expression. Origins of replication can be employed, if needed, from viral sources, for example if utilizing a prokaryotic host for introduction of plasmid DNA. However, chromosome integration is a common mechanism for DNA replication in eukaryotic organisms.

Although in an embodiment of this invention mammalian host cells (such as CHO cells) are employed for expression of desired protein (for example, fusion proteins, glycoproteins, and the like), other eukaryotic organisms also may be used as hosts. Laboratory strains of the budding yeast *Saccharomyces cerevisiae* (also known as Baker's yeast or Brewer's yeast) can be used as well other yeast strains, such as the fission yeast *Schizosaccharomyces pombe*. Yeast vectors harboring DNA encoding a protein of interest (for example fusion constructs, glycoproteins, and the like such as CTLA4-Ig or CTLA4$^{A29YL104E}$-Ig), can utilize the 2μ origin of replication of Broach, *Meth. Enz.* 101:307 (1983), or other origins of replications compatible with yeast (for example, Stinchcomb et al., 1979, *Nature* 282:39; Tschempe et al., 1980, *Gene* 10:157; and Clarke et al., 1983, *Meth. Enz.* 101:300). A regulatory element contained within yeast vectors can be a promoter for the synthesis of glycolytic enzymes (Hess et al., 1968, *J. Adv. Enzyme Reg.* 7:149; Holland et al., 1978, *Biochemistry* 17:4900).

One skilled in the art can also utilize other promoters wherein growth conditions can regulate transcription of said regulatable gene, and can include the following non-limiting examples: isocytochrome C, alcohol dehydrogenase 2, enzymes responsible for maltose and galactose utilization, acid phosphatase, and degradative enzymes associated with nitrogen metabolism. Similar to mammalian expression systems, terminator sequences in yeast expression vectors are also desirable at the 3' end of the coding sequences and are found in the 3' untranslated region following the open reading frame in yeast-derived genes. Some non-limiting examples of yeast vectors suitable for recombinant protein expression in yeast (for example, in *S. cerevisiae*) include pMFa (Kurjan and Herskowitz, (1982) *Cell* 30:933-943), pJRY88 (Schultz et al., 1987, *Gene* 54:113-123), pYepSec1 (Baldari, et al., 1987, *Embo J.* 6:229-234), pYES2 (Invitrogen Corporation, San Diego, Calif.), as well as those belonging to the pRS family of yeast vectors.

Clones, for example bacterial clones, which contain DNA encoding a protein of interest (for example, fusion constructs, glycoproteins, and the like), obtained as described above may then transfected into suitable host cells, such as mammalian cells, for expression of the desired product. Transfection techniques are carried out using standard techniques established in the art appropriate to said host cells, wherein the transfection technique depends on the host cell used. For example, mammalian cell transfection can be accomplished using lipofection, protoplast fusion, DEAE-dextran mediated transfection, $CaPO_4$ co-precipitation, electroporation, direct microinjection, as well as other methods known in the art which can comprise: scraping, direct uptake, osmotic or sucrose shock, lysozyme fusion or erythrocyte fusion, indirect microinjection such as via erythrocyte-mediated techniques, and/or by subjecting host cells to electric currents. As other techniques for introducing genetic information into host cells will be developed, the above-mentioned list of transfection methods is not considered to be exhaustive.

Expression of DNA encoding a protein of interest (for example, fusion constructs, glycoproteins, and the like) in eukaryotic host cells derived from multicellular organisms (for example, mammalian in origin) is particularly utilized in the context of this invention (Tissue Cultures, Academic Press, Cruz and Patterson, Eds. (1973)). Host cells derived from multicellular organisms have the ability to splice out introns and thus can be used directly to express genomic DNA fragments. As stated earlier, useful host cell lines include, but are not limited to, Chinese hamster ovary (CHO), BHK cells, monkey kidney (COS), VERO and HeLa cells. In the present invention, cell lines stably expressing the protein of interest (for example, fusion constructs, glycoproteins, and the like) are used. In one embodiment, a mammalian cell line, (such as a CHO cell line) is transfected (for example by electroporation) with an expression vector (for example, pcSDhuCTLA4-Ig, pD16LEA29Y, and the like) containing a DNA sequence encoding a glycoprotein of interest. In one embodiment, the glycoprotein of interest can be a CTLA4-Ig protein, including the CTLA4-Ig protein(s) having an amino acid sequence contained in SEQ ID NO:2, encoded by a portion of the nucleotide sequence in SEQ ID NO:1. In another embodiment, the glycoprotein of interest can be a $CTLA4^{A29YL104E}$-Ig, including the $CTLA4^{A29YL104E}$-Ig having an amino acid sequence contained in SEQ ID NO:4, encoded by a portion of the nucleotide sequence in SEQ ID NO:23.

A recombinant protein, such as CTLA4-Ig or $CTLA4^{A29YL104E}$-Ig, can be expressed in eukaryotic host cells, such as mammalian cells (for example, CHO, BHK, VERO, or NSO cells), insect cells (for example, using a baculovirus vector), or yeast cells. Those skilled in the art can use other suitable host cells, such as those described earlier, in the context of this invention. In one embodiment, eukaryotic, rather than prokaryotic, expression of a recombinant fusion protein, (such as CTLA4-Ig or $CTLA4^{A29YL104E}$-Ig) is employed. Expression of eukaryotic recombinant proteins, such as human CTLA4-Ig or $CTLA4^{A29YL104E}$-Ig, in eukaryotic cells, such as CHO cells, can lead to partial and/or complete glycosylation, as well as the formation of intra- or inter-chain disulfide bonds. For transient amplification and expression of a desired protein, a vector harboring DNA encoding a protein of interest (for example fusion constructs, glycoproteins, and the like such as CTLA4-Ig or $CTLA4^{A29YL104E}$-Ig), is delivered into eukaryotic cells by a transfection method known in the art but not integrated into the cell's genome. Expression of transfected genes can be measured within 16-96 hours. Mammalian cells (such as COS cells) can be used in conjunction with vectors such as pCDM8 to transiently express a desired protein (Gluzman, Y., 1981, *Cell* 23:175-182; Seed, B., 1987, *Nature* 329:840).

It is understood in the art that for stable transfection of mammalian cells, a small fraction of cells can integrate DNA into their genomes and successful integration can depend on the expression vector and transfection method utilized. For stable amplification and expression of a desired protein, a vector harboring DNA encoding a protein of interest (for example fusion constructs, glycoproteins, and the like such as CTLA4-Ig or $CTLA4^{A29YL104E}$-Ig) is stably integrated into the genome of eukaryotic cells (such as mammalian cells), resulting in the stable expression of transfected genes. In order to identify and select clones stably expressing a gene that encodes a protein of interest, a gene that encodes a selectable marker (for example, resistance to antibiotics) can be introduced into the host cells along with the gene of interest. Selectable markers used by one skilled in the art can be those that confer resistance to drugs, such as G418 and hygromycin. The gene encoding a selectable marker can be introduced into a host cell on a separate plasmid or can be introduced on the same plasmid as the gene of interest. Cells containing the gene of interest can be identified by drug selection wherein cells that have incorporated the selectable marker gene will survive in the presence of said drug, while cells that have not incorporated the selectable marker gene die. Surviving cells can then be screened for the production of the desired protein (for example, a CTLA4-Ig protein or $CTLA4^{A29YL104E}$-Ig).

As described earlier, CHO cells deficient in expression of the dihydrofolate reductase (dhfr) gene can survive only with the addition of nucleosides. When said cells are stably transfected with a DNA vector harboring the dhfr gene, cells are then capable of producing the necessary nucleosides. By using dhfr as the selectable marker, one skilled in the art understands that in the presence of the anti-metabolite, methotrexate, gene amplification of dhfr as well as the transfected gene of interest (for example, CTLA4-Ig or $CTLA4^{A29YL104E}$-Ig) readily occurs. In one embodiment of this invention, mammalian cells, such as CHO dhfr– cells, are transfected with an expression vector, such as pcSDhuCTLA4-Ig (Examples 11-13) or pD16LEA29Y, to generate a population of cells that can be stably amplified and that can stably express a desired protein product, (such as CTLA4-Ig or beta p $CTLA4^{A29YL104E}$-Ig olypeptide, respectively). In another embodiment, the dhfr– negative cell line DG44 (Invitrogen Corp. Carlsbad, Calif.) can be employed for stable transfection. In another embodiment of this invention, transfection can occur via electroporation.

As is readily practiced in the art, transfected mammalian cells (for example dhfr– negative CHO cells) are maintained in non-selective medium containing serum for 1-2 days post-transfection. Cells then are treated with trypsin and re-plated in serum-containing medium, in the presence of a selective pressure (for example, a drug such as methotrexate). Cells are cultured in selective serum-containing medium for 2-3 weeks, with frequent changes of selective medium in order to eliminate debris and dead cells, until distinct colonies can be visualized. Individual colonies can then be trypsinized and placed into multi-well plates for further propagation and amplification in the presence of selective medium in order to identify producers that express a high level of the desired protein (for example, fusion constructs, glycoproteins, and the like) via methods established in the art such as ELISAs or immunoprecipitation. In one embodiment of this invention, the method described above was carried out for transfecting dhfr– negative CHO cells (for example DG44 cells) in order to establish a stable cell line expressing a recombinant protein of interest (for example, a CTLA4-Ig protein) (see for example, Examples 12-13). In another embodiment, a stable cell line expressing a CTLA4$^{A29YL104E}$-Ig was established (see EXAMPLE 23).

A stable CHO line of the invention stably expresses CTLA4-Ig protein molecules as CTLA4-Ig monomers having the sequence (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, and (vi) 25-383 of SEQ ID NO:2. This cell line can secrete a population of CTLA4-Ig molecules that can exist as multimeric forms (such as dimers, tetramers, and the like), wherein the multimeric form can have different monomer sequences of SEQ ID NO:2. The expression cassette integrated into this cell line comprises SEQ ID NO:1, and is contained within pcSDhuCTLA4-Ig.

The invention also provides a stable CHO line, which stably expresses a CTLA4$^{A29YL104E}$-Ig. In one embodiment, the cell line expresses CTLA4$^{A29YL104E}$-Ig monomers having the sequence (i) 26-383 of SEQ ID NO:4, (ii) 26-382 of SEQ ID NO:4, (iii) 27-383 of SEQ ID NO:4, (iv) 27-382 of SEQ ID NO:4, (v) 25-382 of SEQ ID NO:4, and (vi) 25-383 of SEQ ID NO:4. In another embodiment, the cell line can secrete a population of CTLA4$^{A29YL104E}$-Ig molecules that can exist as multimeric forms (such as dimers, tetramers, and the like), wherein the multimeric form can have different monomer sequences of SEQ ID NO:4. The expression cassette integrated into this cell line comprises SEQ ID NO:3, and is contained within pD16LEA29Y.

Subcloning to Generate a Clonal Population of Cells

Cells identified as being producers of a desired protein (for example, fusion constructs, glycoproteins, and the like) are isolated from cell culture and subsequently amplified under production-equivalent conditions wherein culture medium can contain serum. Subcloning methods known in the art, such as, but not limited to, soft-agar cloning, can be employed. The stable recombinant cell clones obtained can then be further multiplied under serum- and animal product-free conditions. According to the present invention, a stable cell clone expressing the desired protein product (for example CTLA4-Ig, a CTLA4$^{A29YL104E}$-Ig, and the like) is achieved via obtaining a recombinant cell clone from a cell culture that is obtained after culturing a recombinant original cell clone in serum-containing medium and re-adapting the cells to serum- and animal product-free medium. In one embodiment, the cell clones expressing CTLA4-Ig can be continued to be cultured in serum- and animal product-free medium through at least 50 generations. In another embodiment of the invention, the cell clones can be continued to be cultured as described above through at least 75 generations. According to the invention, cell clones can also be continued to be cultured in serum- and animal product-free medium through at least 100 generations.

In a further embodiment, the cell clones expressing a CTLA4$^{A29YL104E}$-Ig can be continued to be cultured in serum- and animal product-free medium through at least 27 generations. In another embodiment, the cell clones can continue to be cultured as described above through at least 75 generations. Additionally, cell clones can be cultured in serum- and animal product-free medium through at least 100 generations.

In one embodiment, the invention provides a cell line that produces CTLA4-Ig molecules comprising SEQ ID NO:2 monomers, wherein the cell line is stable for over 100 generations, and wherein cell line stability comprises: (1) doubling time at generation 100 is less than about 24.5±2.6 hours; (2) cell viability at generation 100 is greater than 95%, (3) production titer for CTLA4-Ig in 5-L bioreactors is greater than 1.69 mg/mL at generation 100; (4) sialic acid molar ratio to protein is about 9.3 to about 11.0 at generation 105.

The stable recombinant cell clone of this invention is present in isolated form wherein isolation can occur according to methods practiced in the art (for example, soft-agar cloning or limited dilution cloning or the like). In this invention, the stable recombinant cell clone is derived from a recombinant mammalian cell (for example, a CHO cell) that contains DNA sequences encoding a recombinant protein of interest (for example, fusion constructs, glycoproteins, and the like, such as CTLA4-Ig or CTLA4$^{A29YL104E}$-Ig), which can grow in suspension or adherently. A recombinant protein expressed by the cell line of this invention can be a therapeutic glycoprotein, such as CTLA4-Ig or CTLA4$^{A29YL104E}$-Ig. According to the present invention, stable recombinant cell clones derived from eukaryotic cells (such as mammalian CHO cells, DG44 cells, or dhfr– negative CHO cells), which contain a DNA sequence encoding a recombinant glycoprotein, such as CTLA4-Ig or CTLA4$^{A29YL104E}$-Ig, and which are capable of stably expressing the recombinant glycoprotein over several generations is useful.

In one embodiment of the invention, a population of mammalian host cells stably expressing a protein of interest (for example, fusion constructs, glycoproteins, and the like, such as CTLA4-Ig or CTLA4$^{A29YL104E}$-Ig) is obtained under serum- and animal product-free conditions via amplifying the stably transfected cells. According to the invention, a recombinant cell clone can then be characterized in that it is stable in serum-free and animal product-free culturing medium through at least 105 generations, for example.

In one embodiment of the invention, the clonal population of cells produces CTLA4-Ig molecules. Some of the specific characteristics of this population of CTLA4-Ig molecules are listed below in Table 6. A population of CTLA4-Ig molecules can at least includes CTLA4-Ig dimer molecules that comprise two monomer molecules that each can have one of the following sequences: (i) 26-383 of SEQ ID NO:2, (ii) 26-382 of SEQ ID NO:2, (iii) 27-383 of SEQ ID NO:2, (iv) 27-382 of SEQ ID NO:2, (v) 25-382 of SEQ ID NO:2, and (vi) 25-383 of SEQ ID NO:2. Thus, the population of CTLA4-Ig molecules can include predominantly homodimers or heterodimers. The population can include both homodimers and heterodimers. In one embodiment, the invention provides for a population of CTLA4-Ig molecules having the characteristics shown in Table 6 or a pharmaceutical equivalent thereof. As used herein, a pharmaceutical equivalent is where a population of molecules has a safety and efficacy profile equivalent to the original population (standard population) for treating a patient, as would be understood by a governmental agency, such as the FDA. For example, the CTLA4-Ig population of this invention can have the characteristics shown in Table 6. In another embodiment, the population of CTLA4-Ig molecules of the invention can have the characteristics shown in Table 6 or equivalents thereof singly or in any combination or permutaion thereof.

In another embodiment, the clone of interest can also be characterized according to the recombinant product expressed and its biochemical characteristics (for example, CTLA4-Ig having a particular extinction coefficient value). An extinction coefficient value (also referred to as an absorptivity value ($a_s$)) can be derived theoretically or experimentally. At 280 nm, the absorptivity value ($a_s$) of CTLA4-Ig was determined to be 1.01 mL mg$^{-1}$ cm$^{-1}$ using the method of Mach, et al. (Analytical Biochemistry, Vol. 200, pp. 74-80, 1992) as detailed below.

Equation 1 was used to determine the molar absorptivity ($\epsilon$).

$$\epsilon=[(\text{Number of disulfide bonds}\times134)+(\text{Number of Tryptophan residues}\times5,540)+(\text{Number of Tyrosine residues}\times1,480)] \quad \text{Equation 1:}$$

CTLA4-Ig has 9 disulfide bonds, 8 tryptophan residues and 32 tyrosine residues to give a molar absorptivity ($\epsilon$) of 92,886 M$^{-1}$cm$^{-1}$ as shown in Equation 2.

$$\epsilon=(9\times134)+(8\times5,540)+(32\times1,480)]=92,886 \text{ M}^{-1}\text{cm}^{-1} \quad \text{Equation 2:}$$

The absorptivity constant ($a_s$) was calculated by dividing the molar absorptivity ($\epsilon$) by the molecular weight where the molecular weight was determined by MALDI-TOF as shown in Equation 3:

$$a_s=\epsilon/\text{Molecular Weight}=92,886 \text{ M}^{-1}\text{cm}^{-1}/92,278 \text{ Da}=1.01 \text{ mL mg}^{-1}\text{cm}^{-1} \quad \text{Equation 3:}$$

A comparison of the theoretically derived absorptivity value to the experimentally determined absorptivity values on two lots of CTLA4-Ig (comprising SEQ ID NO:2) material was carried out using amino acid analysis. The average experimentally determined absorptivity constant is 1.00±0.05 mL mg$^{-1}$ cm$^{-1}$. The experimental value confirms the theoretical value of 1.01 mL mg$^{-1}$ cm$^{-1}$ within the error of the experimental determination. Thus, in one embodiment, the invention provides a cell line that produces CTLA4-Ig molecules that have an absorptivity value or extinction coefficient of about 1.00±0.05 mL mg$^{-1}$ cm$^{-1}$.

Figure 22:
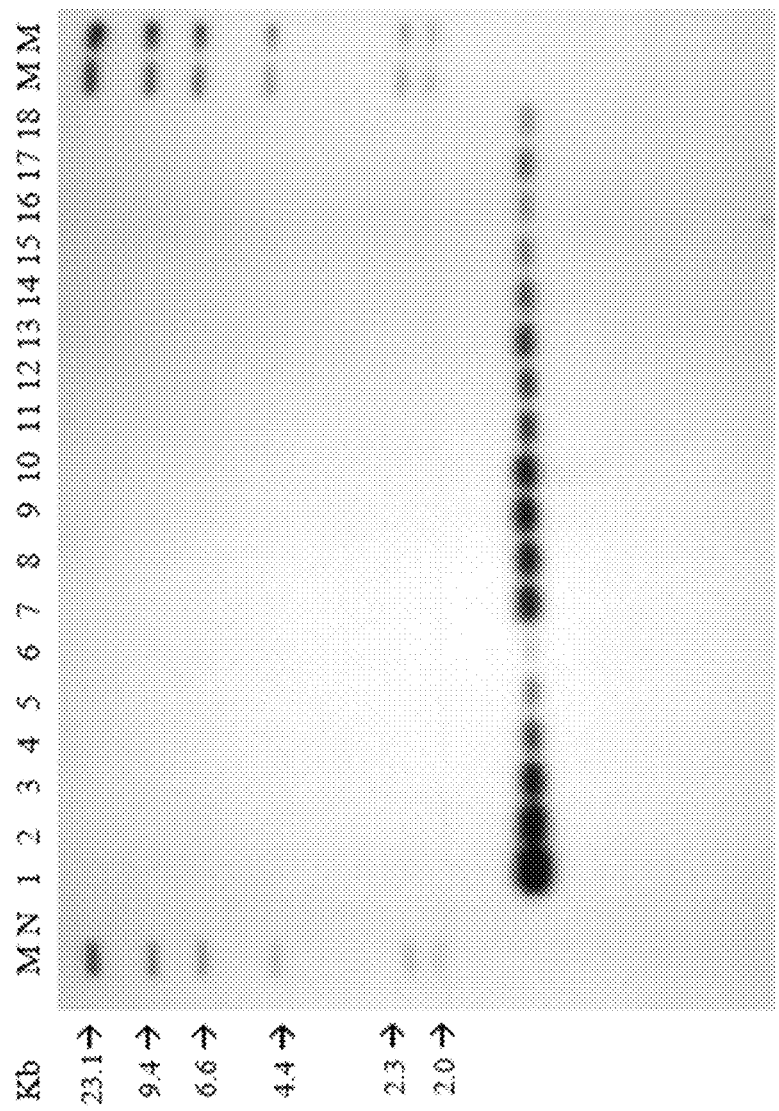
FIG. 22 is a photograph of a Southern blot of DNA extracted from CHO cells expressing the CTLA4-Ig expression cassette derived from 1D5-100A1 (for example, clone 17). The lanes for the gel from left to right are: lane M, DNA molecular weight marker; lane N, EcoRI/XbaI digested untransfected CHO DNA (5 mg); lane 1, EcoRI/XbaI digested untransfected CHO DNA (2.5 µg)+1 ng pcSDhuCTLA4-Ig; lane 2, EcoRI/XbaI digested untransfected CHO DNA (2.5 µg)+0.5 ng pcSDhuCTLA4-Ig; lane 3, EcoRI/XbaI digested untransfected CHO DNA (2.5 µg)+0.25 ng pcSDhuCTLA4-Ig; lane 4, EcoRI/XbaI digested untransfected CHO DNA (2.5 µg)+0.125 ng pcSDhuCTLA4-Ig; lane 5, EcoRI/XbaI digested untransfected CHO DNA (2.5 µg)+0.0625 ng pcSDhuCTLA4-Ig; lane 6, EcoRI/XbaI digested untransfected CHO DNA (2.5 µg)+0.03125 ng pcSDhuCTLA4-Ig; lane 7, EcoRI/XbaI digested DNA: MCB (5.0 µg); lane 8, EcoRI/XbaI digested DNA: EPCB Lot Number C20030618A-01 (5.0 µg); lane 9, EcoRI/XbaI digested DNA: EPCB Lot Number C20030712A-01 (5.0 µg); lane 10, EcoRI/XbaI digested DNA: EPCB Lot Number C20030801A-01 (5.0 µg); lane 11, EcoRI/XbaI digested DNA: MCB (2.5 µg); lane 12, EcoRI/XbaI digested DNA: EPCB Lot Number C20030618A-01 (2.5 µg); lane 13, EcoRI/XbaI digested DNA: EPCB Lot Number C20030712A-01 (2.5 µg); lane 14, EcoRI/XbaI digested DNA: EPCB Lot Number C20030801A-01 (2.5 µg); lane 15, EcoRI/XbaI digested DNA: MCB (1.25 µg); lane 16, EcoRI/XbaI digested DNA: EPCB Lot Number C20030618A-01 (1.25 µg); lane 17, EcoRI/XbaI digested DNA: EPCB Lot Number C20030712A-01 (1.25 µg); lane 18, EcoRI/XbaI digested DNA: EPCB Lot Number C20030801A-01 (1.25 µg).

According to this invention, the recombinant clone of interest can also be characterized according to the number of sites a DNA sequence that encodes a protein of interest (for example, fusion constructs, glycoproteins, and the like, such as CTLA4-Ig) is integrated into the host cell genome. One skilled in the art understands that standard Southern hybridization techniques will allow for such an analysis. In one embodiment of the invention, a single hybridizing fragment of approximately 1.2 kb was detected in each of the EcoRI, and XbaI restriction digests of genomic DNA prepared from the recombinant cell clone of the invention, consistent with the expected size of the CTLA4-Ig gene (Southern hybrid; FIG. 22). The figure depiction is consistent with a single integration site of the plasmid as well as there being no insertions or deletions in the CTLA4-Ig gene being detectable by Southern hybridization analysis.

In one embodiment, the invention provides CHO cell populations capable of producing CTLA4-Ig molecules, wherein each cell of the population comprises at least 30 copies of a nucleic acid that codes for a CTLA4-Ig protein, wherein the 30 or more copies are integrated in tandem at a single site in the genome of the cell, and wherein the population of cells are clonal. In other embodiments, the CHO cell populations capable of producing CTLA4-Ig molecules comprise a population wherein at least 75%, 80%, 85%, 90%, 95%, or 99% of the cells in the populations comprises at least 30 copies of a nucleic acid that codes for a CTLA4-Ig protein.

In another embodiments, the invention provides a cell line that when cultured in conditions according to Example 14, produces CTLA4-Ig molecules comprised of SEQ ID NO:2 in an amount that is least 1.0, 1.3, 1.6, 1.8, 2.0, or 2.5 grams of CTLA4-Ig molecules per liter cell culture at the production stage.

According to the invention, a mammalian cell line (for example a dhfr negative CHO cell line) is generated which expresses a desired protein (for example a CTLA4-Ig protein) that when grown in a suspended culture can produce a population of molecules that is secreted into the culture supernatant. This population of molecules can have, for example, one or more or all of the following characteristics listed in TABLE 6.

TABLE 6

Illustrative CTLA4-Ig Characteristics

| | Characteristic | |
|---|---|---|
| 1 | N-terminal Sequence | aa 26 (Ala) of SEQ ID NO: 2 |
| | | aa 27 (Met) of SEQ ID NO: 2 |
| 2 | C-terminal Sequence | aa 382 (Gly) of SEQ ID NO: 2 |
| | | aa 383 (Lys) of SEQ ID NO: 2 |
| 3 | B7 Binding | 70-130% |
| 4 | pI | 4.3-5.6 |
| 5 | Sialic Acid Ratio | ≥8.0 moles per mole CTLA4-Ig molecules |
| | NANA | 8.0-12.0 moles per mole CTLA4-Ig molecules |
| | NGNA | ≤1.5 moles per mole CTLA4-Ig molecules |
| 6 | dimer | ≥95% |
| 7 | HMW Species (e.g. tetramer) | ≤4.0% |
| 8 | Low Molecular Weight Species (e.g. monomer) | ≥0.5% |
| 9 | Exctinction Coefficient | 1.0 ± 0.05 ml/mg · cm |
| 10 | Free Sulfhydryl Groups | ≤0.24 free thiols per molecule |
| 11 | Amino Monosaccharide Composition: GlcNAc | 15-35 moles per mole CTLA4-Ig molecules |
| 12 | Amino Monosaccharide Composition: GalNAc | 1.7-8.3 moles per mole CTLA4-Ig molecules |
| 13 | Neutral Monosaccharide Composition: Galactose | 8-17 moles per mole CTLA4-Ig molecules |
| 14 | Neutral Monosaccharide Composition: Fucose | 3.5-8.3 moles per mole CTLA4-Ig molecules |
| 15 | Neutral Monosaccharide Composition: Mannose | 7.7-22 moles per mole CTLA4-Ig molecules |

According to Table 6, the percent of CTLA4-Ig dimer, percent of HMW species (for example CTLA4-Ig multimers such as a tetramer), and percent of LMW species (for example CTLA4-Ig monomer) are with respect to a population of CTLA4-Ig molecules. The moles of sugars and the moles of sialic acid described in Table 6 are with respect to mole of CTLA4-Ig molecules or dimer. The percent of B7 binding found in Table 6 is in reference to CTLA4-Ig binding experiments performed by surface plasmon resonance (SPR) on a BIAcore instrument described earlier wherein the percentage is a comparison to B7 binding to a CTLA4-Ig control.

In one embodiment, a mammalian cell line (such as, a dhfr negative CHO cell line) generates a population of CTLA4-Ig molecules displaying characteristic attributes numbers 1-5 from Table 6. In another embodiment of the invention, a mammalian cell line generates a population of CTLA4-Ig molecules having characteristic attributes numbers 1-10 from Table 6. In other embodiments, a mammalian cell line generates a population of CTLA4-Ig molecules displaying characteristic attributes numbers 1-15 from Table 6. In a further embodiment, the amount of free sulfhydryl groups on CTLA4-Ig is about ≤0.20 free thiols per molecule.

Upon purification of the cell culture supernatant that contains the desired protein (for example a CTLA4-Ig protein) secreted by a population of transfected mammalian cells (for example a dhfr negative CHO cell), the population of molecules can have further characteristics. In addition to those characteristics listed in Table 6, this population of molecules can have, for example, one or more or all of the following characteristics: a pH range from about 7.0-8.0; ability to inhibit human cell IL-2 activity by 50-150%; Monocyte Chemotactic Protein (MCP-1) present in the final purified product at ≤5 ng/mg CTLA4-Ig dimer or CTLA4-Ig molecules; concentration of DNA present in the final purified product at ≤2.5 pg/mg CTLA4-Ig dimer; CHO host cell protein present in the final purified product at ≤50 ng/mg CTLA4-Ig dimer; concentration of Triton X-100 in the final purified product at ≤1.0 ppm; amount of Protein A at ≤5 ng/mg CTLA4-Ig dimer; amount of bacterial endotoxins in the final purified product at ≤0.3 EU/mg CTLA4-Ig dimer; amount of Bioburden in the final purified product at ≤3.0 CFU/10 ml.

In one embodiment, Monocyte Chemotactic Protein (MCP-1) is present in the final purified product at ≤3 ng/mg CTLA4-Ig dimer or CTLA4-Ig molecules; the concentration of DNA present in the final purified product at 0.0 pg/mg CTLA4-Ig dimer; CHO host cell protein present in the final purified product at 10 ng/mg CTLA4-Ig dimer; amount of Protein A at ≤1 ng/mg CTLA4-Ig dimer; amount of bacterial endotoxins in the final purified product at ≤0.15 EU/mg CTLA4-Ig dimer; and amount of Bioburden in the final purified product at ≤1.0 CFU/10 ml; a pH range from about 7.2-7.8. In a particular embodiment, Monocyte Chemotactic Protein (MCP-1) is present in the final purified product at ≤1 ng/mg CTLA4-Ig dimer or CTLA4-Ig molecules. In a further embodiment, CTLA4-Ig molecules inhibit human cell IL-2 activity by 60-140%.

In another embodiment of the invention, the clonal population of cells produces CTLA4$^{A29YL104E}$-Ig molecules. Some of the specific characteristics of this population of CTLA4$^{A29YL104E}$-Ig molecules are listed in Table 7. A population of CTLA4$^{A29YL104E}$-Ig molecules can at least includes CTLA4$^{A29YL104E}$-Ig dimer molecules that comprise two monomer molecules that each can have one of the following sequences: (i) 26-383 of SEQ ID NO:4, (ii) 26-382 of SEQ ID NO:4, (iii) 27-383 of SEQ ID NO:4, (iv) 27-382 of SEQ ID NO:4, (v) 25-382 of SEQ ID NO:4, and (vi) 25-383 of SEQ ID NO:4. Thus, the population of CTLA4$^{A29YL104E}$-Ig molecules can include predominantly homodimers or heterodimers, or any mixture thereof. In one embodiment, the invention provides for a population of CTLA4$^{A29YL104E}$-Ig molecules having the characteristics shown in Table 7 or a pharmaceutical equivalent thereof. As used herein, a pharmaceutical equivalent is where a population of molecules has a safety and efficacy profile equivalent to the original population (standard population) for treating a patient, as would be understood by a governmental agency, such as the FDA. For example, the CTLA4$^{A29YL104E}$-Ig population of this invention can have the characteristics shown in Table 7. In another embodiment, the population of CTLA4$^{A29YL104E}$-Ig molecules of the invention can have the characteristics shown in Table 7 or equivalents thereof singly or in any combination or permutation thereof.

In one embodiment, the invention provides CHO cell populations capable of producing CTLA4$^{A29YL104E}$-Ig molecules, wherein each cell of the population comprises at least 30 copies of a nucleic acid that codes for a CTLA4$^{A29YL104E}$-Ig protein, wherein the 30 or more copies are integrated in tandem at a single site in the genome of the cell, and wherein the population of cells are clonal. In other embodiments, the CHO cell populations capable of producing CTLA4$^{A29YL104E}$-Ig molecules comprise a population wherein at least 75%, 80%, 85%, 90%, 95%, or 99% of the cells in the populations comprises at least 30 copies of a nucleic acid that codes for a CTLA4$^{A29YL104E}$-Ig.

Figure 23:
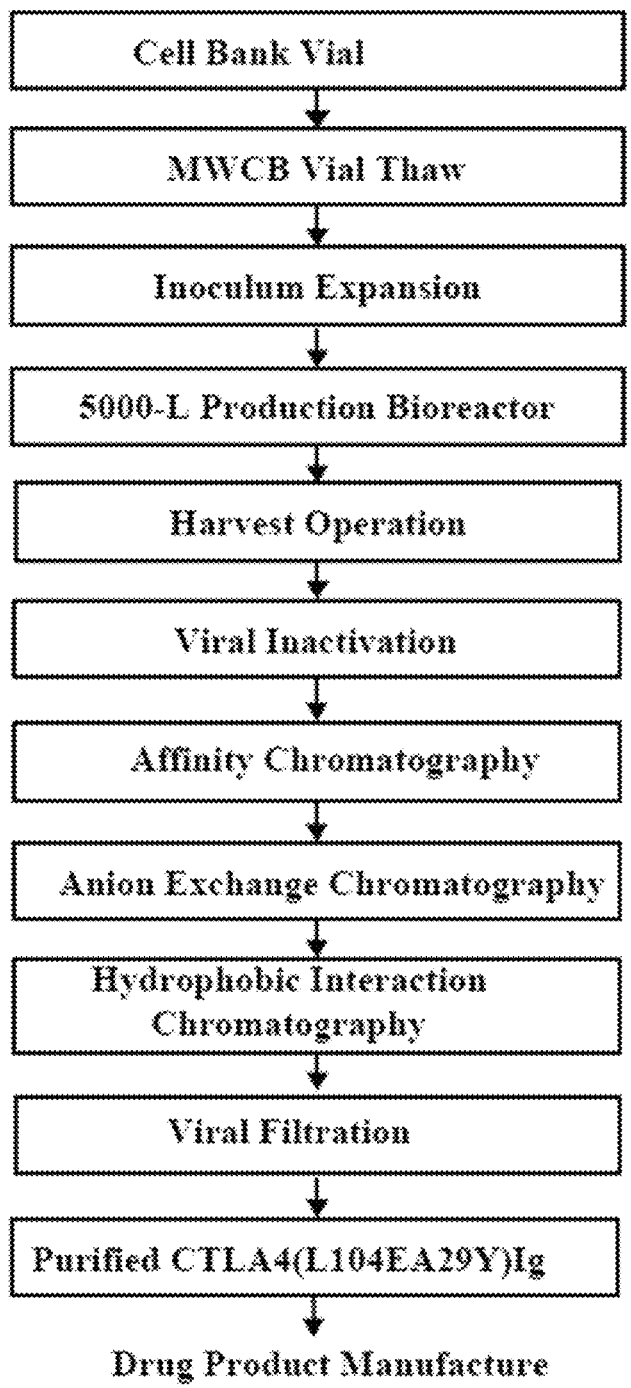
FIG. 23 depicts a flow diagram of a production-scale culturing process. This process allows for the mass-production of recombinant proteins in a 25,000-L production bioreactor.

In another embodiments, the invention provides a cell line that when cultured in conditions according to FIG. 23 or Examples 19-20, produces CTLA4$^{A29YL104E}$-Ig molecules comprised of SEQ ID NO:4 in an amount that is least 22, 22.5, 23, 27.5, or 28 grams of CTLA4$^{A29YL104E}$-Ig molecules per liter cell culture at the production stage.

According to the invention, a mammalian cell line (for example a dhfr negative CHO cell line) is generated which expresses a desired protein (for example a CTLA4$^{A29YL104E}$-Ig) that when grown in a suspended culture can produce a population of molecules that is secreted into the culture supernatant. This population of molecules can have, for example, one or more or all of the following characteristics listed in TABLE 7.

TABLE 7

Illustrative Characteristics of a CTLA4$^{A29YL104E}$-Ig

| | Characteristic | |
|---|---|---|
| 1 | N-terminal Sequence | aa 26 (Ala) of SEQ ID NO: 4 |
| | | aa 27 (Met) of SEQ ID NO: 4 |
| 2 | C-terminal Sequence | aa 382 (Gly) of SEQ ID NO: 4 |
| | | aa 383 (Lys) of SEQ ID NO: 4 |
| 3 | B7 Binding | 70-130% |
| 4 | pI | 4.5-5.5 |
| 5 | Sialic Acid Ratio | ≥5.0 moles per mole Total CTLA4-Ig protein |
| 6 | Dimer | ≥95% |
| 7 | HMW Species (e.g., tetramer) | ≤4% |
| 8 | LMW species (e.g., monomer) | ≤1% |
| 9 | Amino Monosaccharide Composition: GlcNAc | 24-28 moles per mole Total CTLA4-Ig protein |
| 10 | Amino Monosaccharide Composition: GalNAc | 2.7-3.6 moles per mole Total CTLA4-Ig protein |
| 11 | Neutral Monosaccharide Composition: Galactose | 11-13 moles per mole Total CTLA4-Ig protein |
| 12 | Neutral Monosaccharide Composition: Fucose | 6.4-7.0 moles per mole Total CTLA4-Ig protein |
| 13 | Neutral Monosaccharide Composition: Mannose | 14-16 moles per mole Total CTLA4-Ig protein |

According to Table 7, the percent of CTLA4$^{A29YL104E}$-Ig dimer, percent of HMW species (for example CTLA4$^{A29YL104E}$-Ig multimers such as a tetramer), and percent of LMW species (for example CTLA4$^{A29YL104E}$-Ig monomer) are with respect to a population of CTLA4$^{A29YL104E}$-Ig molecules. The moles of sugars and the moles of sialic acid described in Table 7 are with respect to mole of CTLA4$^{A29YL104E}$-Ig molecules or dimer. The percent of B7 binding found in Table 7 is in reference to CTLA4$^{A29YL104E}$-Ig binding experiments performed by surface plasmon resonance (SPR) on a BIAcore instrument described earlier wherein the percentage is a comparison to B7 binding to a CTLA4$^{A29YL104E}$-Ig control.

In one embodiment, a mammalian cell line (such as, a dhfr negative CHO cell line) generates a population of CTLA4$^{A29YL104E}$-Ig molecules displaying characteristic attributes numbers 1-5 from Table 7. In another embodiment of the invention, a mammalian cell line generates a population of CTLA4$^{A29YL104E}$-Ig molecules having characteristic attributes numbers 1-10 from Table 7. In other embodiments, a mammalian cell line generates a population of CTLA4$^{A29YL104E}$-Ig molecules displaying characteristic attributes numbers 1-13 from Table 7.

Upon purification of the cell culture supernatant that contains the desired protein (for example a CTLA4$^{A29YL104E}$-Ig) secreted by a population of transfected mammalian cells (for example a dhfr negative CHO cell), the population of molecules can have further characteristics. In addition to those characteristics listed in Table 7, this population of molecules can have, for example, one or more or all of the following characteristics: Monocyte Chemotactic Protein (MCP-1) present in the final purified product at ≤5 ng/mg CTLA4$^{A29YL104E}$-Ig dimer; concentration of DNA present in the final purified product at ≤2.5 pg/mg CTLA4$^{A29YL104E}$-Ig dimer; and CHO host cell protein present in the final purified product at ≤50 ng/mg CTLA4$^{A29YL104E}$-Ig dimer.

General Culturing of Cell Lines

According to this invention, mammalian cells are cultured to produce a desired protein, including a glycoprotein, as conventionally known by one skilled in the art. The mammalian cells expressing a glycoprotein of interest should express or be manipulated to express the appropriate enzymes such that under satisfactory conditions, post-translational modifications most pertinent to glycosylation occur in vivo. The enzymes include those necessary for the addition and completion of N- and O-linked carbohydrates, such as those described in Hubbard and Ivatt, *Ann. Rev. Biochem.*, 50:555-583(1981) for N-linked oligosaccharides. The enzymes optionally include oligosaccharyltransferase, alpha-glucosidase I, alpha-glucosidase II, ER alpha(1,2) mannosidase, Golgi alpha-mannodase I, N-acetylyglucosaminyltransferase I, Golgi alpha-mannodase II, N-acetylyglucosaminyltransferase II, alpha(1,6)fucosyltransferase, beta (1,4)galactosyltransferase, and an appropriate sialyltransferase.

A delay in apoptosis (programmed cell death) can have an effect of increasing cell viability during a cell culturing processes. A decrease in apoptosis, and in turn, an increase in the lifetime of a particular cell can increase protein production from a cell culture. Apoptotic events can be inhibited in a cell by introducing into a cell (such as a mammalian cell, an insect cell, or a yeast cell) one or more anti-apoptotic proteins, which inhibit apoptosis in cells at precise points along the apoptotic pathway. Another method to inhibit apoptosis is to inhibit release of pro-apoptotic molecules from the mitochondria in the cell. Variants of pro-apoptotic proteins known in the art, such as a dominant-negative form of caspase-9, can be used as an inhibitor of apoptosis in a cell. Such a variant protein can be introduced into a cell in order to delay programmed cell death. Inhibition of apoptosis of a cell, in turn, prolongs the time during which a particular cell produces protein, resulting in an overall increase in the production of a desired protein by a particular cell. Several genes that encode caspase inhibitors (such as X-linked inhibitor of apoptosis (XIAP) or variants thereof) or anti-apoptotic genes (for example, Bcl-2 and Bcl-x$_L$ or variants thereof), can be transfected into genetically engineered mammalian cells (such as, CHO cells, VERO cells, BHK cells, and the like) (Sauerwald, T. et al., 2003, *Biotechnol Bioeng.* 81:329-340; Sauerwald, T. et al., 2002, *Biotechnol Bioeng.* 77:704-716; Mastrangelo, A., et al., 2000, *Biotechnol Bioeng.* 67:544-564; Kim, N., et al., 2002, *J Biotechnol.* 95:237-248; Figueroa, B., et al., 2001, *Biotechnol Bioeng.* 73:211-222).

In one embodiment, mammalian cells, which produce a recombinant protein, can be transfected with a vector containing an anti-apoptotic gene (such as bcl-2). In another embodiment, recombinant mammalian cells can be transfected with a plasmid that contains a gene encoding for a caspase inhibitor, or a gene that encodes a variant of a pro-apoptotic molecule as described above, a gene that encodes a protein that is known to an individual skilled in the art to possess anti-apoptotic activity, or any combination thereof.

In another embodiment, the overall product quality (for example enhanced glycosylation) of a desired recombinant protein (such as a therapeutic protein) can be enhanced. To increase glycosylation of a recombinant protein, mammalian cells (for example CHO cells, VERO cells, BHK cells, and the like) can be transfected with nucleic acids encoding one or more enzymes that are involved in glycosylation (such as α2,3-sialyltransferase, β1,4-galactosyltransferase, and the like) of proteins (Weikert et al., 1999, *Nature Biotechnol* 17:1116-21). In one embodiment, a plasmid that encodes β1,4-galactosyltransferase can be introduced into mammalian cells expressing a protein of interest. In another embodiment, a plasmid that encodes α2,3-sialyltransferase can be introduced into mammalian cells expressing a protein of interest.

Various culturing parameters can be used with respect to the host cell being cultured. Appropriate culture conditions for mammalian cells are well known in the art (Cleveland et al., *J. Immunol. Methods*, 56: 221-234 (1983)) or can be determined by the skilled artisan (see, for example, Animal Cell Culture: A Practical Approach 2nd Ed., Rickwood, D. and Hames, B. D., eds. (Oxford University Press: New York, 1992)), and vary according to the particular host cell selected.

Without limitation, cell culture medium (such as inoculum medium, feed medium, basal medium, and the like) can refer to a nutrient solution used for growing and or maintaining cells, especially mammalian cells. These solutions ordinarily provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range. The nutrient solution can be supplemented electively with one or more components from any of the following categories: (1) hormones and other growth factors such as, serum, insulin, transferrin, and epidermal growth factor; (2) salts, for example, magnesium, calcium, and phosphate; (3) buffers, such as HEPES; (4) nucleosides and bases such as, adenosine, thymidine, and hypoxanthine; (5) protein and tissue hydrolysates, for example peptone or peptone mixtures which can be obtained from purified gelatin, plant material, or animal byproducts; (6) antibiotics, such as gentamycin; (7) cell protective agents, for example pluronic polyol; and (8) galactose. An example of basal medium can be Cell Growth Basal Medium. An example of incoculum medium can be Inoculum Cell Growth Basal Medium. An example of feed medium can be Production Bioreactor Feed Medium.

Commercially available media can be utilized and include, for example, Minimal Essential Medium (MEM, Sigma, St. Louis, Mo.); Dulbecco's Modified Eagles Medium (DMEM, Sigma); Ham's F10 Medium (Sigma); HyClone cell culture medium (HyClone, Logan, Utah); RPMI-1640 Medium (Sigma); and chemically-defined (CD) media, which are formulated for particular cell types, e.g., CD-CHO Medium (Invitrogen, Carlsbad, Calif.). Any of these media can be supplemented as necessary with the previously defined supplementary components or ingredients, including optional components, in appropriate concentrations or amounts, as necessary or desired. The mammalian cell culture that can be used with the present invention is prepared in a medium suitable for the particular cell being cultured. In one embodiment, the cell culture medium can be one of the aforementioned that is generally free of serum from any mammalian source (for example, fetal bovine serum (FBS)). In another embodiment of this invention, the mammalian cell culture can be grown in the commercially available chemically defined (CD)-CHO Medium, supplemented with additional components specified in Table 15. In a further embodiment, the mammalian cell culture can be grown in CD-CHO Medium, supplemented with additional components specified in Table 20 or 21.

The methods of the present invention include the culturing of numerous cell types. In one embodiment of the invention, the cells are animal or mammalian. In another embodiment, the cells can express and secrete large quantities of a desired protein. In another embodiment of the invention, cells can express and secrete large quantities of a glycoprotein of interest into the culture medium. The animal or mammalian cells can also be molecularly modified to express and secrete a protein of interest. The protein produced by the host cell can be endogenous or homologous to the host cell. The protein also can be heterologous (for example, foreign), to the host cell whereby genetic information coding for the protein of interest is introduced into the host cell via methods standard in the art (for example by electroporation, transfection, and the like). In one embodiment, a mammalian glycoprotein can be produced and secreted by a Chinese hamster ovary (CHO) host cell into the culture medium.

In some embodiments, the invention provides populations of CTLA4-Ig molecules produced by the methods of production discussed herein, including the method of mass-production that is described in Example 14. The process can result in the production of CTLA4-Ig molecules of high molecular weight (HMW) (for example, see Examples 14 and 15). In another embodiment, populations of CTLA4$^{A29YL104E}$-Ig molecules are provided that are produced by the production methods discussed herein, such as the method of mass-production that is described in EXAMPLES 19 and 20, and shown in FIG. 23. The process can result in the production of CTLA4$^{A29YL104E}$-Ig molecules of high molecular weight (HMW) (for example, see EXAMPLES 19 and 20). In some embodiments, the HMW species can be about 15-25% of the molecules or dimer produced by a method for production, including a chemically defined (CD)-CHO1 fermentation process. In other embodiments, the present invention provides methods for isolation, purification and characterization of CTLA4-Ig or CTLA4$^{A29YL104E}$-Ig HMW components produced by a CD-CHO1 fermentation process. CTLA4-Ig or CTLA4$^{A29YL104E}$-Ig HMW components are multimers (i.e, tetramers, hexamers, etc.), which have a higher molecular weight than CTLA4-Ig or CTLA4$^{A29YL104E}$-Ig dimers.

Animal or mammalian host cells capable of harboring, expressing, and secreting large quantities of a glycoprotein of interest into the culture medium for subsequent isolation and/or purification include, but are not limited to, Chinese hamster ovary cells (CHO), such as CHO-K1 (ATCC CCL-61), DG44 (Chasin et al., 1986, *Som. Cell Molec. Genet*, 12:555-556; Kolkekar et al., 1997, *Biochemistry*, 36:10901-10909; and WO 01/92337 A2), dihydrofolate reductase negative CHO cells (CHO/dhfr−, Urlaub and Chasin, 1980, Proc. Natl. Acad. Sci. USA, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293 cells subcloned for growth in suspension culture, Graham et al., 1977, *J. Gen. Virol.*, 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals NY Acad. Sci.*, 383:44-68); MCR 5 cells; FS4 cells. In one aspect of this invention, CHO cells are utilized, particularly, CHO/dhfr− and CHO DG44 cells.

Examples of mammalian glycoproteins that can be produced by the methods of this invention include, without limitation, cytokines, cytokine receptors, growth factors (e.g., EGF, HER-2, FGF-α, FGF-β, TGF-α, TGF-β, PDGF, IGF-1, IGF-2, NGF, NGF-β); growth factor receptors, including fusion or chimeric proteins. Other examples include, but are not limited to growth hormones (e.g., human growth hormone, bovine growth hormone); insulin (e.g., insulin A chain and insulin B chain), proinsulin; erythropoietin (EPO); colony stimulating factors (e.g., G-CSF, GM-CSF, M-CSF); interleukins (e.g., IL-1 through IL-12); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; follicle stimulating hormone (FSH); luteinizing hormone (LH); calcitonin; CD proteins (e.g., CD3, CD4, CD8, CD28, CD19, etc.); CTLA proteins (e.g., CTLA4); T-cell and B-cell receptor proteins; bone morphogenic proteins (BNPs, e.g., BMP-1, BMP-2, BMP-3, etc.); neurotrophic factors, e.g., bone derived neurotrophic factor (BDNF); neurotrophins, e.g., 3-6; renin; rheumatoid factor; RANTES; albumin; relaxin; macrophage inhibitory protein (e.g., MIP-1, MIP-2); viral proteins or antigens; surface membrane proteins; ion channel proteins; enzymes; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), as well as others known in the art. Suitable proteins, polypeptides, and peptides that can be produced by the methods of the present invention include, but are not limited to, fusion proteins, polypeptides, chimeric proteins, as well as fragments or portions, or mutants, variants, or analogs of any of the aforementioned proteins and polypeptides.

The methods of the invention can also be used to produce CTLA4-Ig molecules which are variants of SEQ ID NO: 5, 6, 7, 8, 9, or 10. In one embodiment, a CTLA4-Ig molecule can comprise a monomer having one or more changes in residues 55 (A55Y) and 130 (L130E) (residues referred to are from SEQ ID NO:2). See the descriptions of variants and mutants of CTLA4-Ig described in U.S. Publication No. US 2002/0182211 A1, which is hereby incorporated by reference in its entirety. In another embodiment, a CTLA4-Ig variant can comprise a CTLA4-Ig molecule having a mutation within the CTLA-4 region or a mutation in the Ig region, or any combination thereof. In one embodiment, a CTLA4-Ig variant molecule comprises a CTLA4-Ig molecule having an amino acid sequence that is at least about 70%, about 75%, about 80%, about 85%, about 90%, about 95%, or about 99% identical to SEQ ID NOS: 5, 6, 7, 8, 9, or 10. In one embodiment, the CTLA4-Ig variant molecule is capable of binding to CD80 or CD86. In another embodiment, the variant is able to form a dimer. In a further embodiment, the variant exhibits a carbohydrate profile similar to that exhibited by a non-mutated CTLA4-Ig molecule population. In one embodiment, the CTLA4-Ig variant molecules have the same potential N-linked and O-linked glycosylation sites present in SEQ ID NO:2. In another embodiment, a CTLA4-Ig variant molecule has the same N-linked and O-linked glycosylation sites present in SEQ ID NO:2, and has additional glycosylation sites. The mutations can include, but are not limited to, nucleotide deletions, insertions, additions; amino acid deletions, substations, additions; nucleic acid frameshifts; the substitutions can be either non-conservative (e.g., a glycine substituted with a tryptophan) or conservative substitutions (e.g., a leucine substituted for an isoleucine).

CTLA4-Ig variant molecules include, but are not limited to, CTLA4-L104EA29YIg (using the residue numbering system according to SEQ ID NO:2, CTLA4-L104EA29YIg herein is referred to as CTLA4-L130EA55YIg), as well as those CTLA4-Ig variant molecules described in U.S. patent application Ser. No. 09/865,321 (U.S. Pub. No. US2002/0182211), 60/214,065 and 60/287,576; in WO 01/92337 A2; in U.S. Pat. Nos. 6,090,914, 5,844,095 and 5,773,253; and as described in R. J. Peach et al., 1994, *J Exp Med*, 180:2049-2058. In one embodiment, CTLA4-Ig variant molecules produced in the present methods can be secreted from a cell that comprises an expression vector coding for a CTLA4-Ig variant protein.

A CTLA4-Ig variant, L130EA55Yig, is a genetically engineered fusion protein similar in structure to CTAL4-Ig molecule. L130EA55Y-Ig has the functional extracellular binding domain of modified human CTLA-4 and the Fc domain of human immunoglobulin of the IgG1 class. Two amino acid modifications, leucine to glutamic acid at position 104 (L104E) of an L104EA29Y variant, which corresponds to position 130 of SEQ ID NO:2, and alanine to tyrosine at position 29 (A29Y) of an L104EA29Y variant, which corresponds to position 55 of SEQ ID NO:2, were made in the B7 binding region of the CTLA-4 domain to generate L130EA55Y. L130EA55Y-Ig can comprise two homologous glycosylated polypeptide chains of approximately 45,700 Daltons each, which are held together by one inter-chain disulfide bond and non-covalent interactions. DNA encoding L130EA55Y-Ig was deposited as DNA encoding L104EA29Y-Ig on Jun. 20, 2000, with the American Type Culture Collection (ATCC) under the provisions of the Budapest Treaty. It has been accorded ATCC accession number PTA-2104. L104EA29Y-Ig (corresponding to L130EA55Y-Ig in this application) is further described in co-pending U.S. patent application Ser. Nos. 09/579,927, 60/287,576 and 60/214,065, and Ser. No. 09/865,321 and in WO/01/923337 A2, all of which are incorporated by reference in this application in their entireties.

Since the recombinant protein L130EA55Y-Ig is different at only 2 amino acids (Tyr at amino acid position 55 and Glu at amino acid position 130) compared to CTLA4-Ig monomers having an Ala at amino acid position 55 and Leu at amino acid position 130 of SEQ ID NO:2, and because these 2 mutations do not affect N- or O-linked glycosylation, CTLA4-Ig variant molecule populations comprising L130EA55Y-Ig may have the same profile or a very similar glycosylation profile as do populations comprising wild type CTLA4-Ig. Further, because the recombinant protein L130EA55Y-Ig is different at only 2 amino acids (Tyr at amino acid position 55 and Glu at amino acid position 130) compared to CTLA4-Ig monomers having an Ala at amino acid position 55 and Leu at amino acid position 130 of SEQ ID NO:2, the present methods of this invention should be able to produce L130EA55Y-Ig with similar characteristic attributes as described in Table 6.

The methods of the invention can also be used to produce CTLA4$^{A29YL104E}$-Ig molecules, which are variants of SEQ ID NOS: 11, 12, 13, 14, 15, or 16. In one embodiment, a CTLA4$^{A29YL104E}$-Ig can comprise a monomer having one or more changes in SEQ ID NO:3. For example, descriptions of other CTLA4$^{A29YL104E}$-Ig molecules are described in U.S. Patent Application Publication Nos. U.S. 2002/0039577, U.S. 2003/0007968, U.S. 2004/0022787, U.S. 2005/0019859, and U.S. 2005/0084933, and U.S. Pat. No. 7,094,874, which are hereby incorporated by reference in their entirety.

In one embodiment, CTLA4$^{A29YL104E}$-Ig comprises one or more mutations within the CTLA-4 region (SEQ ID NO:18), or a mutation in the Ig region, or any combination thereof. In other embodiments, a CTLA4$^{A29YL104E}$-Ig molecule comprises a CTLA4$^{A29YL104E}$-Ig having an amino acid sequence that is at least about 70%, about 75%, about 80%, about 85%, about 90%, about 95%, or about 99% identical to SEQ ID NOS: 11, 12, 13, 14, 15, or 16. In a further embodiment, a CTLA4$^{A29YL104E}$-Ig molecule as described above is capable of binding to CD80 or CD86. In another embodiment, the CTLA4$^{A29YL104E}$-Ig is able to form a dimer. In a further embodiment, the CTLA4$^{A29YL104E}$-Ig exhibits a carbohydrate profile similar to that exhibited by a non-mutated CTLA4$^{A29YL104E}$-Ig molecule population. In yet other embodiments, the CTLA4$^{A29YL104E}$-Ig molecules have the same potential N-linked and O-linked glycosylation sites present in SEQ ID NO:4. In another embodiment, a CTLA4$^{A29YL104E}$-Ig has the same N-linked and O-linked glycosylation sites present in SEQ ID NO:4, and has additional glycosylation sites. The mutations can include, but are not limited to, nucleotide deletions, insertions, additions; amino acid deletions, substitutions, additions; nucleic acid frameshifts; the substitutions can be either non-conservative (e.g., a glycine substituted with a tryptophan) or conservative substitutions (e.g., a leucine substituted for an isoleucine).

In one embodiment of the invention, a population of CTLA4-Ig variant molecules can be produced by mammalian cells (for example dhfr negative CHO cells), which express a gene encoding the desired protein (for example a L130EA55Y-Ig protein or the like), grown in suspension according to the mass-production method of this invention.

According to this invention, a recombinant CTLA4-Ig variant protein produced by mammalian cells can be recovered according to the harvesting parameters described herein. In other embodiments, a recombinant CTLA4-Ig variant protein produced by mammalian cells can be purified according to the purification scheme described in this invention (Example 15).

In one embodiment of the invention, a population of CTLA4$^{A29YL104E}$-Ig molecules can be produced by mammalian cells (for example dhfr negative CHO cells), which express a gene encoding the desired protein (for example a CTLA4$^{A29YL104E}$-Ig), grown in suspension according to the mass-production method of this invention. According to this invention, a recombinant CTLA4$^{A29YL104E}$-Ig produced by mammalian cells can be recovered according to the harvesting parameters described herein. In other embodiments, a recombinant CTLA4$^{A29YL104E}$-Ig produced by mammalian cells can be purified according to the purification scheme described in this invention (EXAMPLES 19-20).

Types of Cell Cultures and General Culturing Processes

A protein of interest, for example a glycoprotein, a fusion protein and the like, can be produced by growing cells expressing the desired protein product under a variety of cell culture conditions. A practitioner skilled in the art understands that cell cultures and culturing runs for protein production can include, but are not limited to, three general types: continuous culture, batch culture, and fed-batch culture. In a continuous culture process, a fresh culture medium supplement (for example, feeding medium) is supplied to cells during the culturing period while old culture medium is removed. The product produced during a continuous culture can also be harvested, for example, on a daily basis or continuously. As long as the cells remain alive, and the environmental and culturing conditions are maintained, cells can remain in culture as long as is desired in a continuous culturing process.

In a batch culture process, cells are initially cultured in medium and this culturing medium is neither replaced, nor removed, nor supplemented. The cells are not "fed" with new medium during or before the end of the culturing run thus culturing continues until nutrients are exhausted. The protein product is harvested at the end of the culturing run.

For fed-batch culture processes, the culturing run time can be increased by supplementing the culture medium one or more times daily (or continuously) with fresh medium during the run. In this process, the cells are supplied with fresh medium, a "feeding medium", during the culturing period. Fed-batch cultures can include the various feeding schedules described previously, for example, daily, every two days, every other day, etc.; more than once per day, or less than once per day, and so on. Fed-batch cultures also can be fed continuously with feeding medium. At the end of the culturing/production run, the protein product of interest is then harvested.

Cell culture systems for the small- or large-scale production of proteins, including glycoproteins, produced by mammalian host cells are useful within the context of this invention. Those having skill in the art understand that tissue culture dishes, spinner flasks, and T-flasks are typically used for culturing methods on a laboratory scale. The processes that can be used for culturing on a larger scale (e.g., 500 L, 5000 L, 10,000 L, 20,000 L and the like) include, but are not limited to, a hollow fiber bioreactor, a fluidized bed bioreactor, a stirred tank bioreactor system, or a roller bottle culture. The later two processes can be utilized with or without microcarriers.

The systems can be operated in a batch, fed-batch, or continuous mode. For production-scale culturing, the stirred-tank bioreactor is the system of choice because of its flexibility. These reactors can maintain cells in suspension by agitation through mechanical stirring with gas bubble sparging or an impeller. The stirred-tank bioreactors can be scaled up to large production-scale volumes (for example, 20,000 liters) and can be operated in different feed modes. These systems provide a large surface area for cell growth and the efficient transfer of metabolic wastes, oxygen, and nutrients, as well as maintain a homogenous environment throughout the reactor by preventing cells from settling to the bottom via continuous stirring or mixing of the components within the reactors. For the production of a desired glycoprotein, the present invention embodies large-scale, fed-batch cell cultures maintained in a stirred-tank bioreactor, fed daily with feeding medium containing D-galactose. In another embodiment, fed-batch cell cultures can also be maintained in a stirred-tank bioreactor, fed daily with feeding medium that contains suitable concentrations of the limiting cell culture nutrients important for protein glycosylation, such as glucose and glutamine (Chee et al., 2005, *Biotechnol. Bioeng.* 89:164-177).

The cells of the culture producing a protein of interest can be propagated according to any scheme or routine that is most suitable for the particular mammalian host cell and the particular production plan contemplated. Cell culture conditions can be developed to enhance expansion or growth of a population of mammalian host cells in the growth phase of the cell culture for a period of time that is maximized for such expansion and growth. The growth phase of the cell culture comprises the period of exponential cell growth (for example, the log phase) where cells are primarily dividing rapidly. During this phase, the rate of increase in the density of viable cells is higher than at any other time point.

Also, cell culture conditions can be developed to enhance protein production during the production phase of the cell culture for a period of time. The production phase of the cell culture comprises the period of time during which cell growth is stationary or is maintained at a near constant level. The density of viable cells remains approximately constant over a given period of time. Logarithmic cell growth has terminated and protein production is the primary activity during the production phase. The medium at this time is generally supplemented to support continued protein production and to achieve the desired glycoprotein product.

Culture conditions, such as temperature, pH, dissolved oxygen ($DO_2$), and the like, are those used in culturing mammalian host cells that are understood by the individual skilled in the art. An appropriate temperature range for culturing mammalian host cells, such as CHO cells, is between 30 to 40° C., and in one embodiment about 37° C. The pH generally is adjusted to a level between about 6.5 and 7.5 using either an acid or base. A suitable $DO_2$ is between 5-90% of air saturation. These culture conditions can be used to facilitate the culturing of mammalian cells that produce a desired protein or glycoprotein product.

A mammalian host cell population can be expanded and grown in a growth phase culture wherein cells, possibly removed from storage, are inoculated into a culturing medium acceptable for promoting growth and high viability. The cells can then be maintained in a production phase for a suitable period of time by the addition of fresh culturing medium to the host cell culture. During the production phase, cells can be subjected to various shifts in temperature to enhance protein production. Multiple temperature shift culturing processes are described in patent application U.S.

Ser. No. 10/742,564, filed Dec. 18, 2003, and U.S. Ser. No. 10/740,645, filed on Dec. 18, 2003. The contents from these applications are incorporated by reference herein in their entirety. In this invention, the two or more temperature shifts comprising the cell culture processes can result in an increased number of viable cells that survive in culture until the end of the process or production run. During the production phase of the culture, the greater the number of cells that survive can result in a greater amount of protein or glycoprotein product produced, increasing the amount of protein product at the end of the process.

A particular aspect of this invention embodies a fed-batch, large-scale (for example 500 L, 5000 L, 10000 L, and the like), mammalian cell culture, that is fed daily or with feeding medium described in Tables 14, 15, comprising D-galactose in order for cells to produce a glycoprotein of interest. To increase the quality of the protein produced in this embodiment, two or more temperature shifts can be employed during the culture period to extend the protein production phase beyond that which occurs when no temperature shift is used, or when only one temperature shift is used. In another embodiment, the invention entails a fed-batch, large-scale (for example 500 L, 5000 L, 10000 L, and the like), mammalian cell culture, that is fed 1 or more times daily with feeding medium described in Table 22, which comprise D-galactose in order for cells to produce a glycoprotein of interest (for example, CTLA4$^{A29YL104E}$-Ig). One or more temperature shifts also can be employed during the culture period to extend the protein production phase beyond that which occurs when no temperature shift is used in order to increase the quality of the glycoprotein. Alternatively, dextran sulfate can be added to the culture with a concomitant temperature shift.

Mass-Production of Recombinant Protein in Bioreactors

The present invention provides methods for conventional stirred tank bioreactor cultivation of eukaryotic cells (for example, a 20000 L cell culture volume), particularly to produce large-scale or industrial amounts of desired protein products that are expressed by such cells. The cultivation process is a fed-batch culturing process of eukaryotic cells grown in suspension, with harvesting of culture supernatant, wherein eukaryotic cells, for example mammalian cells, expressing a protein of interest, secrete desired protein product into the culture medium.

Methods for large-scale cultivation of mammalian cells, particularly to produce large amounts of desired protein products that are expressed by such cells, are embodied in the present invention. The methods can be carried out by steps comprising:

(i) inoculating cells into a seed culture vessel (for example, a T-175 flask) containing serum-free culture medium and propagating the seed culture (for example, a starter culture that used to inoculate a larger volume) at least until the cells reach a minimal cross-seeding density whereby the density is a pre-determined value needed for sufficient propagation of cells in the subsequent culturing volume;

(ii) transferring the propagated seed culture to a larger culture vessel (for example, roller bottles or cell bags) containing culture medium lacking animal-derived components in order to expand the culture;

(iii) transferring the expanded seed culture to a large-scale culture vessel containing serum-free culture medium to further propagate to the cell culture; and (iv) maintaining the large-scale culture in medium lacking animal-derived components, at least until said cells reach a target density or display a specific biochemical characteristic.

In some embodiments, the method can comprise the step of (iv) harvesting of the culture medium and replacing that medium with fresh medium.

In other embodiments, methods for large-scale cultivation of mammalian cells can be carried out by steps comprising:

(i) inoculating cells into a seed culture vessel (for example, a T-175 flask) containing serum-free culture medium (for example, inoculoum medium) and propagating the seed culture (for example, a starter culture that used to inoculate a larger volume) at least until the cells reach a minimal cross-seeding density whereby the density is a pre-determined value needed for sufficient propagation of cells in the subsequent culturing volume;

(ii) transferring the propagated seed culture to a larger culture vessel (for example, roller bottles or cell bags) containing culture medium lacking animal-derived components (for example, inoculum medium) in order to expand the culture;

(iii) transferring the expanded seed culture to a large-scale culture vessel (such as 1000-L bioreactors) containing serum-free culture medium (for example, basal medium) to further propagate to the cell culture; and (iv) maintaining the large-scale culture in medium lacking animal-derived components (for example, feed medium), at least until said cells reach a target density or display a specific biochemical characteristic.

In some embodiments of the invention, the method can comprise the step of:

(v) harvesting of the culture medium and replacing the spent medium with fresh medium.

The present invention is applicable to any cell type in any formulation of medium lacking animal-derived components in order to produce large-scale quantities of desired protein products, and can utilize either of the following two processes, or variations thereof: a) microcarrier processes, or b) suspension cell processes. Culturing of cells, for example mammalian cells, can utilize either process, operated in two distinct phases, a growth phase and a production phase. In another embodiment of the invention, any formulation of medium which contains animal-derived components (some non-limiting examples being Bovine-Serum Albumin (BSA) or FBS) can be employed as well for the production of large-scale protein quantities as described above.

One skilled in the art understands that a microcarrier process, not limited to a standard microcarrier-process or a perfusion microcarrier process, can be used for cell culturing wherein cells are attached to and/or immobilized in a macroporous carrier. In a standard microcarrier-process, cells are inoculated into a seed culture vessel containing serum-free culture medium and propagated until the cells reach a minimum seeding density. Subsequently, the propagated seed culture is transferred to a large-scale culture vessel containing serum-free culture medium and microcarriers. In this growth phase, the cells are grown on microcarriers until the carriers are fully colonized, for example by cells migrating into the carriers in the case of a process using macroporous carriers.

Medium exchange can occur when microcarriers settle to the bottom of the culture vessel, after which a predetermined percentage of the tank volume is removed and a corresponding percentage tank volume of fresh medium is added to the vessel. Microcarriers are then re-suspended in the culturing medium. A skilled artisan understands that the process of medium removal and replacement can be repeated at a predetermined interval, for example every 24 hours whereby the amount of replaced medium is dependent on cell density and can typically be from 25% to 80% of the tank volume. 60-95% of the tank medium in the tank can be changed every 24 hours when the cell density reaches a pre-determined value suitable for protein expression. Those having skill in the art often use the aforementioned medium exchange % value throughout the production phase as well.

During the production phase, culture medium can be exchanged by allowing the microcarriers to settle to the bottom of the tank, after which the selected % of the tank volume is removed and a corresponding % tank volume, for example 60-95% as described earlier, of fresh culturing medium is added to the vessel. Microcarriers are then re-suspended in the culturing medium and the medium removal and replacement process can be repeated daily.

The microcarrier perfusion process resembles the standard microcarrier process and also is operated in the growth/expansion and production phases. The main difference between the two processes is the method employed to change the culture medium. A defined amount of the tank volume, for example 60-95% of the total tank volume, is changed all at once in the standard microcarrier process, whereas in the perfusion process the medium is added continuously. Essentially, a % tank volume medium is changed gradually over a predetermined length of time while the microcarriers are kept in the vessel by using a separation device (or perfusion device) that allows the medium to leave the vessel but retains the microcarriers within the tank. The growth phase in this process is as described for a standard microcarrier process except for the gradual medium exchange.

Two non-limiting options for a suspension cell process include a suspension cell perfusion process and a suspension cell batch process. In the perfusion process, cells in a culturing medium are freely suspended without being immobilized in carriers and, and like the microcarrier processes, can be operated in two distinct phases (for example, a growth phase and a production phase). During the growth phase of a suspension cell-perfusion process, cells are inoculated into a seed culture vessel containing serum-free culture medium and propagated until cells reach a target cross-seeding density. The propagated seed culture can then be transferred to a large-scale culture vessel, which contains culturing medium lacking animal-derived components, and propagated until a pre-determined cell density value suitable for protein expression is reached. A continuous perfusion of the culture vessel with fresh culture medium is performed to execute the medium exchange process.

In the suspension cell batch process, cell culturing can be carried out via the following non-limiting formats: a) simple batch process or b) fed-batch process. Cells are inoculated into a seed culture vessel containing culture medium lacking animal-derived components in a simple batch process and propagated until the cells reach a pre-determined cross-seeding density. Subsequently, the propagated seed culture is transferred to a large-scale culture vessel containing serum-free culture medium and the culturing vessel is operated until the nutrients in the culture medium have been exhausted. In a fed-batch process, feeding a concentrated solution of nutrients (for example a feed medium) to the tank can extend the nutrient supply in the medium of this culturing process, thus extending the process time and ultimately leading to an increase in the production of the desired protein within the culture vessel. The method of adding the feed medium can vary. It can be added either as a single pulse bolus (once, twice, three times etc., a day) or can be fed gradually throughout a 24-hour period. This feed allows cells to be propagated in a large-scale culture vessel and the medium, which can contains the secreted protein product of interest, to be harvested at the end of the run before any of the nutrients become exhausted. Instead of removing all of the contents from the vessel, one skilled in the art would remove only a portion of the tank volume (can be about 80%).

An optional aspect of the fed-batch process is the use of temperature shifts. In this process, temperatures employed as the operating temperatures during the production phase are lower than the temperature used during the growth phase. Said temperature ranges for a fed batch process, for example the process used in this invention, could consist of an initial growth phase at a temperature suitable for growth of the particular cell line in use followed by a decrease in the operating temperature at a pre-determined cell density.

In one embodiment, a process for a large-scale fed-batch culture process comprises the following: (i) inoculating cells into a seed culture vessel (for example, a T-175 flask) containing serum-free culture medium and propagating the seed culture at least until the cells reach a pre-determined cross-seeding density at a temperature suitable for growth; (ii) transferring the propagated seed culture to a larger culture vessel (for example, roller bottles or cell bags) containing culture medium lacking animal-derived components in order to expand the culture at a suitable temperature suitable; (iii) transferring the expanded seed culture to a large-scale culture vessel containing serum-free culture medium to further propagate to the cell culture at a suitable temperature; and (iv) maintaining the large-scale culture at a decreased temperature suitable for protein expression, in medium lacking animal-derived components, with daily replacements by fresh feed medium, at least until said cells reach a target density or critical length of time.

The step of replacement with fresh feed medium in (iv) can entail removing a predetermined volume, for example 80%, of the tank volume and replacing it with the same volume of fresh feed medium.

In a further embodiment, a process for a large-scale fed-batch culture process comprises the following: (i) inoculating cells into a seed culture vessel (for example, a T-175 flask) containing serum-free culture medium and propagating the seed culture at least until the cells reach a pre-determined cross-seeding density at a temperature suitable for growth; (ii) transferring the propagated seed culture to a larger culture vessel (for example, roller bottles or cell bags) containing culture medium lacking animal-derived components in order to expand the culture at a suitable temperature suitable; (iii) transferring the expanded seed culture to a large-scale culture vessel (for example, a 1000-L bioreactor) containing serum-free culture medium to further propagate to the cell culture at a suitable temperature; and (iv) maintaining the large-scale culture at a decreased temperature suitable for protein expression, in medium lacking animal-derived components, with daily replacements by fresh feed medium, at least until said cells reach a target density or critical length of time.

The step of replacement with fresh feed medium in (iv) can entail removing a predetermined volume, for example about 80% of the tank volume, and replacing it with the same volume of fresh feed medium.

In one embodiment of this invention, the cells cultured in a fed-batch process are mammalian cells, for example CHO cells, which express a desired protein product. Mammalian cells are inoculated into a seed culture vessel (for example, a T-175 flask) containing serum-free culture medium, for example CD-CHO medium (Example 13), and propagated at a temperature suitable for growth, for example at about 35-39° C., for 3-4 days until the cells reach a pre-determined cross-seeding density (for example, having ≥6.0×10$^6$ viable cells, or wherein the final culture viability ≥80%). The propagated seed culture is then transferred to a large culture vessel (for example, roller bottles) containing culture medium lacking animal-derived components for expansion at a suitable temperature (for example at about 35-39° C.) for approximately 3-4 days. The cell culture is further expanded in a larger culture vessel (for example, a 20 L cell bag, a 100 L cell bag, and the like) containing serum free medium, for example CD-CHO medium, at a temperature suitable for growth, for example at about 35-39° C., for 3-4 days until the cells reach a target seeding density (for example, having ≥1-2×10$^6$ viable cells/ml, or wherein the final culture viability ≥80%). In one embodiment, the inoculum expansion involves a minimum of 4 passages. In another embodiment of the invention, inoculum expansion entails no more than 20 passages.

The expanded seed culture can then used to inoculate a large-scale culturing tank (for example, a 1000 L, a 4000 L bioreactor and the like), containing serum-free culture medium (for example CD-CHO medium) to further propagate the cell culture at a suitable temperature, for example at about 35-39° C., for 3-6 days, until the cells reach a target seeding density (for example, having ≥1-2×10$^6$ viable cells/ml, or wherein the final cell culture viability ≥80%). A large-scale culture (for example a 10,000 L, 15,000 L, 20,000 L culture in a bioreactor and the like) is subsequently maintained in serum-free culture medium, wherein the medium is a feed medium (for example eRDF medium, Example 14), at a temperature lower than the growth temperature (for example at or about 33-35° C. for 3-4 days, and at or about 31-33° C. for 6-8 days), suitable for protein expression and production of the secreted protein product. The feed medium is replaced daily with fresh feed medium, whereby the tank's replacement with fresh feed medium entails removal of a predetermined volume, for example 80% of the tank volume, and replacing the tank with the same volume of fresh feed medium. The commercial scale culture is maintained until said cells reach a target value of production parameters that can be, but are not limited to, a length of time, a target cell density, or biochemical protein characteristic (such as a NANA molar ratio as previously described) wherein the viable cell density can be 3.0-8.0×10$^6$ cells/ml; a NANA molar ratio can be ≥6.0; a final cell culture viability can be ≥30%; and a final protein product titer can be ≥0.5 g/L).

In a particular embodiment of this invention, the cells cultured in a fed-batch process are mammalian cells, for example CHO cells, which express a desired protein product (for example, a CTLA4-Ig molecule). CHO cells are inoculated into a seed culture vessel (for example, a T-175 flask) containing serum-free culture medium, for example CD-CHO medium, and propagated at a temperature suitable for growth, for example at about 37° C., for 3-4 days until the cells reach a pre-determined cross-seeding density (for example, having ≥10.0×10$^6$ viable cells, or wherein the final culture viability ≥84%). The propagated seed culture is then transferred to a large culture vessel (for example, roller bottles) containing culture medium lacking animal-derived components for expansion at a suitable temperature (approximately 37° C.) for about 4 days. The cell culture is further expanded in a larger culture vessel (for example, a 20 L cell bag, a 100 L cell bag, and the like) containing serum-free medium, for example CD-CHO medium, for 4 days at a temperature suitable for growth (for example at about 37° C.) until the cells reach a target seeding density (for example, having ≥1-2×10$^6$ viable cells/ml, or wherein the final culture viability ≥91%). The inoculum expansion can involve a minimum of 7 passages.

The expanded seed culture is then used to inoculate a large-scale culturing tank (for example, a 4000 L bioreactor and the like), containing serum-free culture medium (for example CD-CHO medium) to further propagate the cell culture at a suitable temperature, for example at about 37° C., for 5-6 days, until the cells reach a target seeding density (for example, having ≥1-2×10$^6$ viable cells/ml, or wherein the final cell culture viability ≥86%). A commercial-scale culture (for example a 20,000 L culture in a bioreactor) is subsequently maintained in serum-free culture medium, wherein the medium is a feed medium (for example eRDF medium), at a temperature lower than the growth temperature, which is suitable for protein expression and production of the secreted protein product (for example, CTLA4-Ig). The commercial-scale culture is first lowered from about 37° C. to about 34° C. for 4 days, and then subjected to a second temperature shift by lowering the temperature from about 34° C. to about 32° C. for 8 days. The feed medium is replaced daily with fresh feed medium, whereby replacing the feed medium in the bioreactor tank entails removal of a predetermined volume, for example 80% of the tank volume, and replacing it with the same volume of fresh feed medium. The commercial scale is maintained until said CHO cells and/or secreted protein product reach a target value of the following non-limiting production parameters: a viable cell density of 4.0-7.0×10$^6$ cells/ml; a NANA molar ratio ≥8.0; a final cell culture viability ≥38%; and a final protein product titer of ≥0.6 g/L.

In another embodiment of this invention, the cells cultured in a fed-batch process are mammalian cells, for example CHO cells, which express a desired protein product. Mammalian cells are inoculated into a seed culture vessel (for example, a T-175 flask) containing serum-free culture medium, for example CD-CHO medium (EXAMPLE 19), and propagated at a temperature suitable for growth, for example from about 35° C. to about 39° C., for about 3-4 days; or from about 36° C. to about 38° C., for about up to about 4 days until the cells reach a pre-determined cross-seeding density (for example, having a cell density of greater than or equal to 1.5×10$^6$, or wherein the final culture viability is greater than or equal to about 80%). The propagated seed culture is then transferred to a large culture vessel (for example, roller bottles) containing culture medium lacking animal-derived components for expansion at a suitable temperature (for example, from about 35° C. to about 39° C., or from about 36° C. to about 38° C.) for about 3-4 days or up to about 4 days. The cell culture is further expanded in a larger culture vessel (for example, a 20 L cell bag, a 100 L cell bag, and the like) containing serum free medium, for example CD-CHO medium, at a temperature suitable for growth, for example from about 35° C. to about 39° C., or from about 36° C. to about 38° C., for about 3-4 days or up to about 4 days until the cells reach a target seeding density (for example, having at least about 1.5×10$^6$ viable cells/ml, or wherein the final culture viability is greater than or equal to 80%). In one embodiment, the inoculum expansion involves a minimum of 4 passages. In another embodiment of the invention, inoculum expansion entails no more than 20 passages. In some embodiments, the CD-CHO medium is a CD-CHO inoculum medium.

The expanded seed culture can then be used to inoculate a large-scale culturing tank (for example, a 1000 L, a 4000 L bioreactor, and the like), containing serum-free culture medium (for example CD-CHO medium, such as CD-CHO inoculum medium and/or CD-CHO basal medium) to further propagate the cell culture at a suitable temperature, for example from about 35° C. to about 39° C., or from about 36° C. to about 38° C. for from about 3 to about 6 days, or for from about 4 to about 5 days, or for about 4.7 days, or for less than or equal to about 113 hours, until the cells reach a target seeding density (for example, having about $2.3 \times 10^6$ viable cells/ml, or wherein the final cell culture viability is at least about 88%).

A commercial-scale culture (for example a 10,000 L, 15,000 L, 20,000 L, 30,000 L culture in a bioreactor and the like) is subsequently maintained in serum-free culture medium, wherein the medium is a feed medium (for example, eRDF medium, EXAMPLE 19), at a temperature of from about 35° C. to about 39° C. for from about 3 to about 6 days, or from about 4 to about 5 days, suitable for protein expression and production of the secreted protein product. Alternatively, a polyanionic compound (for example, such as dextran sulfate) can be added to a culture maintained in serum-free culture medium, wherein the medium is a feed medium (for example, eRDF medium, EXAMPLE 19) as described below and in U.S. Pat. App. Publication No. 2005/0019859, which is hereby incorporated by reference in its entirety. The culture can be concomitantly subjected to a single step temperature lowering (for example, at or about 32° C. to at or about 36° C. for from about 3 to about 14 days, or for from about 10 to about 13 days, or for from about 234 to about 304 hours.

In one embodiment of the invention, the culture can also be concomitantly subjected to a multi-step temperature lowering (for example, at or about 33° C. to at or about 35° C. for about 3-6 days, and at or about 31° C. to at or about 33° C. for about 6-8 days). The above described processed are suitable for protein expression and production of the secreted protein product.

The feed medium in the instances described above can be replaced daily (1, 2, 3, etc. times daily) or every few days with fresh feed medium. The tank's replacement with fresh feed medium entails removal of a predetermined volume, for example 80% of the tank volume, and replacing the tank with the same volume of fresh feed medium. The commercial scale culture is maintained until said cells reach a target value of production parameters that can be, but are not limited to, a length of time, a target cell density, or biochemical protein characteristic (such as a NANA molar ratio as previously described) wherein the viable cell density can be $3.0-8.0 \times 10^6$ cells/ml; a NANA molar ratio can be $\geq 5.0$, or about 6, or from about 5.2 to about 7.6; a final cell culture viability can be greater than or equal to about 30% or greater than or equal to about 37%; and a final protein product titer can be from about 0.46 to about 0.71 g/L, greater than or equal to 0.5 g/L, or greater than or equal to 20 g/L.

In accordance with the present invention, a cell culture process involving the delayed addition of polyanionic compound is provided. The process comprises adding polyanionic compound to a cell culture at a time after inoculation (for example, during the growth phase or during the production phase of the culturing process). The delayed addition of polyanionic compound achieves increased cell viability. In one embodiment, the invention is directed to a cell culturing process that comprises culturing host cells, which express a protein of interest, and adding polyanionic compound to the cell culture at a time after inoculation.

Polyanionic compounds include, but are not limited to, dextran sulfate (available from Sigma-Aldrich, St. Louis, Mo.), heparin (available from Sigma-Aldrich), heparan sulfate (available from Sigma-Aldrich), mannan sulfate, chondroitin sulfate (available from Sigma-Aldrich), dermatan sulfate (available from Sigma-Aldrich), keratan sulfate (available from Sigma-Aldrich), hyaluronate (available from Sigma-Aldrich), poly(vinyl sulfate) (available from Sigma-Aldrich), kappa-carrageenan (available from Sigma-Aldrich), and suramin (available from Sigma-Aldrich). The compounds are readily available from the listed sources, or readily obtainable through means known to one of skill in the art. These compounds are frequently available in the form of a salt, including but not limited to sodium salt, but may also be used in non-salt forms. A polyanionic compound includes all forms thereof, including but not limited to salt forms, such as sodium salts.

Particularly useful, non-limiting examples of polyanionic compounds of the invention include poysulfated compounds: dextran sulfate, heparin, heparan sulfate, mannan sulfate, chondroitin sulfate, dermatan sulfate, keratan sulfate, poly(vinyl sulfate), kappa-carrageenan, and suramin. In one embodiment, the polyanionic compound is dextran sulfate. Dextran sulfate may have an average molecular weight of 5,000 to 500,000 Da. In another embodiment of the invention, dextran sulfate having a molecular weight of 5,000 Da is used.

According to methods of the invention, polyanionic compound may be added to the cell culture one time, two times, three times, or any number of times during the specified cell culture period (for example, at a time after inoculation, such as during the growth phase or the production phase). One or more polyanionic compounds may be used in conjunction. For example, any given single addition of a polyanionic compound may include the addition of one or more other polyanionic compounds. Similarly, if there is more than one addition of a polyanionic compound, different polyanionic compounds may be added at the different additions. Additional compounds and substances, including polyanionic compounds, may be added to the culture before, with, or after the addition of polyanionic compound, either during or not during the specified time period. In a particular embodiment, there is a single, for example one time, addition of polyanionic compound. In another embodiment, one polyanionic compound is added.

Polyanionic compound may be added to the cell culture by any means. Means of adding polyanionic compound include, but are not limited to, dissolved in water, dissolved in culture medium, dissolved in feed medium, dissolved in a suitable medium, and in the form in which it is obtained. In particular, polyanionic compound is added dissolved in water. In accordance with the invention, polyanionic compound is added to bring the concentration in the culture to an appropriate level. As non-limiting examples, polyanionic compound is added to a concentration of 1-1000 mg/L, 1-200 mg/L, 1-100 mg/L, or 25-75 mg/L. Particularly useful concentrations of polyanionic compound added to the cell culture include, but are not limited to, about 25-200 mg/L; about 25-100 mg/L; and about 50-100 mg/L. In one embodiment of the invention, the concentration of polyanionic compound added to the culture is about 50 mg/L. In another embodiment, the concentration of polyanionic compound added to the culture is about 100 mg/L.

Methods of the invention provide that the culture may be run for any length of time after addition of polyanionic compound. The culture run time may be determined by one of skill in the art, based on relevant factors such as the quantity and quality of recoverable protein, and the level of contaminating cellular species (e.g. proteins and DNA) in the supernatant resulting from cell lysis, which will complicate recovery of the protein of interest. In some embodiments of the cell culturing process, polyanionic compound is added at a time after inoculation (for example, during the growth phase of the cell culture process or during the production phase of the cell culture process). Polyanionic compound is added at a time after inoculation that is during on or about the end of the growth phase. In particular, polyanionic compound is added at a time after inoculation that is during the production phase, for example, at the onset of the production phase.

In a particular embodiment of this invention, the cells cultured in a fed-batch process are mammalian cells, for example CHO cells, which express a desired protein product (for example, a $CTLA4^{A29YL104E}$-Ig molecule). CHO cells are inoculated into a seed culture vessel (for example, a T-175 flask) containing serum-free culture medium, for example CD-CHO medium (such as CD-CHO inoculum medium), and propagated at a temperature suitable for growth, for example at about 37° C., for about 3-4 days until the cells reach a pre-determined cross-seeding density (for example, having $\geq 1.5 \times 10^6$ viable cells, or wherein the final culture viability $\geq 80\%$). The propagated seed culture is then transferred to a large culture vessel (for example, roller bottles) containing culture medium lacking animal-derived components for expansion at a suitable temperature (at about 37° C.) for about 4 days. The cell culture is further expanded in a larger culture vessel (for example, a 20 L cell bag, a 100 L cell bag, and the like) containing serum-free medium, for example CD-CHO medium (such as CD-CHO inoculum medium), for about 4 days at a temperature suitable for growth (for example, at about 37° C.) until the cells reach a target seeding density (for example, having $\geq 1.5 \times 10^6$ viable cells, or wherein the final culture viability $\geq 80\%$). The inoculum expansion can involve a minimum of 7 passages.

The expanded seed culture is then used to inoculate a large-scale culturing tank (for example, a 1000-L, a 4000-L bioreactor, and the like), containing serum-free culture medium (for example CD-CHO medium, such as CD-CHO basal medium) to further propagate the cell culture at a suitable temperature, for example at about 37° C., for about 5-6 days, until the cells reach a target seeding density (for example, having about $2.3 \times 10^6$ viable cells/ml, or wherein the final cell culture viability $\geq 88\%$). A commercial-scale culture (for example a 10,000 L, 15,0000 L, or 20,000 L culture and the like in a bioreactor) is subsequently maintained in serum-free culture medium, wherein the medium is a feed medium (for example eRDF medium), at a temperature lower than the growth temperature, which is suitable for protein expression and production of the secreted protein product (for example, a $CTLA4^{A29YL104E}$-Ig).

The commercial-scale culture is lowered, for example, from about 37° C. to about 34° C. for about 4 days. Polyanionic compound may be added concomitantly to the culture when the temperature is lowered. Alternatively, the commercial-scale culture is lowered from about 35° C.-37° C. to about 32° C.-36° C. for about 12 days and polyanionic compound is concomitantly added to the culture as the temperature is lowered.

The feed medium in the instances described above can be replaced daily (1, 2, 3, etc. times daily) or every few days with fresh feed medium. The tank's replacement with fresh feed medium entails removal of a predetermined volume, for example 80% of the tank volume, and replacing the tank with the same volume of fresh feed medium. In one embodiment, the feed medium is added daily for about 2 to 3 days until, for example, the glucose concentration falls to 1 g/L. In another embodiment, the feed medium is added every 8 hours, for example, once the glucose concentration has reached 1 g/L. The commercial scale is maintained until said CHO cells and/or secreted protein product reach a target value of the following non-limiting production parameters: a NANA molar ratio of about 6.0, or from about 5.2 to about 7.6; a final cell culture viability $\geq 37\%$; and a final protein product titer of from about 0.46 to about 0.71 g/L.

In an embodiment of the present invention, the cells being cultivated can be mammalian cells, or an established mammalian cell line, including, without limitation, CHO (e.g., ATCC CCL 61), HEK293 (e.g., ATCC CRL 1573; Graham et al., *J. Gen. Virol.* 36:59-72, 1977), COS-1 (e.g., ATCC CRL 1650), DG44 (CHO cell line) (*Cell,* 33: 405, 1983, and *Somatic Cell and Molecular Genetics* 12: 555, 1986), and baby hamster kidney (BHK) cell lines. Other useful non-limiting examples are myelomas, 3T3 cells, Namalwa cells, and fusions of myelomas with other cells. In some embodiments, the cells can be mutant or recombinant cells, such as, for example, cells that express a different spectrum of enzymes that catalyze post-translational modification of proteins (e.g., processing enzymes such as propeptides or glycosylation enzymes such as glycosyl transferases and/or glycosidases) than the cell type from which they were derived. In one particular aspect of this invention, CHO/dhfr– cells particularly are utilized.

The culturing vessels used for expanding the cell culture can be, but are not limited to, Erlenmyer flasks, T-175 flasks, roller bottles, and cell bags. The large-scale culture vessels can be, for example airlift reactors where agitation is obtained by means of introducing air from the bottom of the vessel or conventional stirred tank reactors (CSTR), where agitation is obtained by means of conventional impeller types. Among the parameters controlled within specified limits are temperature, pH, and dissolved oxygen tension (DOT). The temperature-control medium in this system is water, and can be heated or cooled as necessary. The water can be passed through a piping coil immersed in the cell culture medium or through a jacket surrounding the vessel. The pH, for example, can be regulated by addition of base to the cell culture medium when required or by varying the $CO_2$ concentration in the head-space gas. DOT can be maintained by sparging with pure oxygen or air or mixtures thereof.

The invention therefore provides a method for producing a recombinant protein, the method comprising at least two steps: (a) expanding mammalian cells that secrete a recombinant protein (i.e., a protein that the mammalian cells do not normally express or over-express, where the recombinant protein is expressed in the cells via an expression vector or construct that has been transfected into the cells or the parents of the cells) from a seed culture to a liquid culture of at least 10,000 L, and (b) isolating the recombinant protein from the at least 10,000 L liquid culture. In one embodiment, this method can be used such that the recombinant protein is produced at a concentration of at least 0.5 grams per liter of liquid culture prior to purification of the protein from the liquid culture. In another embodiment, the method according to the invention can be used to produce a recombinant protein at a concentration of at least from about 0.46 to about 0.71 grams per liter of liquid culture prior to purification of the protein from the liquid culture.

In one embodiment, the expansion step can involve (i) culturing the cells in a serum-free medium with at least four passages so as to obtain a cell density of at least about 1.0×10⁵ viable cells per mL, and (ii) maintaining the cells in culture for a time sufficient to produce at least about 0.5 of the recombinant protein. In one embodiment, the number of passages does not exceed 36 passages. In another embodiment, the number of passages can exceed 36 passages where the cells are stable over generations with respect to copy number of the nucleic acid coding for the recombinant protein, cell viability, and doubling time.

The time sufficient to produce at least about 0.5 to about 1.3 g/L of the recombinant protein can be any amount of time as long as the cell viability does not fall below 5%, 10%, 25%, 30%, 50%, 60%, 70%, 80%, 90%, 95%, 98% and/or as long as the number of cell generations does not exceed 50, 75, 100, 105, or 125 generations. The maintaining step can also comprise temperature shift steps, such as lowering the temperature of the culture first from 37±2° C. to 34±2° C. and at a later time from 34±2° C. to 32±2° C. The temperature of 32±2° C. can be maintained for at least 5, 6, 7, 8, 9, 10, 11, 12, 13, 14, 15, 16, 17, 18, 20, 30, 50, or 100 days. The temperature of 32±2° C. can be maintained for at least 20, 50, 75, or 100 cell generations. The temperature of 32±2° C. can be maintained until the cell density of the culture is from about 30 to about 100×10⁵ cells per mL of liquid culture.

In other embodiments, the invention provides methods for producing a recombinant protein, the method comprising at least the steps of: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the at least 10,000 L liquid culture when the liquid culture: (i) contains greater than or equal to about 6.0 moles of NANA per mole of protein (glycoprotein in this case); (ii) has a cell density of from about 33 to about 79×10⁵ cells per mL; (iii) cell viability in the liquid culture is not less than about 38% or is greater than or equal to about 38%; (iv) endotoxin is less than or equal to about 76.8 EU per mL of liquid culture; and/or (v) bioburden is less than 1 colony forming unit per mL of liquid culture.

In a further embodiment, the expansion step can involve (i) culturing the cells in a serum-free medium with at least four passages so as to obtain a cell density of at least about 1.0×10⁶ viable cells per mL, and (ii) maintaining the cells in culture for a time sufficient to produce at least from about 0.46 to about 0.71 grams of the recombinant protein per liter of liquid culture. In one embodiment, the number of passages does not exceed 36 passages. In another embodiment, the number of passages can exceed 36 passages where the cells are stable over generations with respect to copy number of the nucleic acid coding for the recombinant protein, cell viability, and doubling time.

The time sufficient to produce at from about 0.46 to about 0.71 g/L of the recombinant protein can be any amount of time as long as the cell viability does not fall below 5%, 10%, 25%, 30%, 50%, 60%, 70%, 80%, 90%, 95%, 98% and/or as long as the number of cell generations does not exceed 27, 50, 75, 100, 105, or 125 generations. The maintaining step can also comprise temperature shift steps, such as lowering the temperature of the culture first from 37±2° C. to 34±2° C. The temperature of 34±2° C. can be maintained for at least 5, 6, 7, 8, 9, 10, 11, 12, 13, 14, 15, 16, 17, 18, 20, 30, 50, or 100 days. Alternatively, the maintaining step can a temperature shift step, such as lowering the temperature of the culture from 37±2° C. to 34±2° C.

Polyanionic compound can be added to the cultures as temperature lowering commences. The concentration of polyanionic compound added to the culture can be about 1 mg/L, 5 mg/L, 10 mg/L, 12.5 mg/L, 15 mg/L, 25 mg/L, 50 mg/L, 75 mg/L, 100 mg/L, 200 mg/L, 250 mg/L, 500 mg/L, 750 mg/L, or 1000 mg/L. The temperature of 32±2° C. can be maintained for at least 5, 6, 7, 8, 9, 10, 11, 12, 13, 14, 15, 16, 17, 18, 20, 30, 50, or 100 days. The temperature of 34±2° C. can be maintained for at least 20, 27, 50, 75, or 100 cell generations.

In further embodiments, the invention provides methods for producing a recombinant protein, the method comprising at least the steps of: (a) expanding mammalian cells that secrete a recombinant protein from a seed culture to a liquid culture of at least 10,000 L so that the recombinant protein concentration is at least from about 0.46 to about 0.71 grams per liter of liquid culture; and (b) isolating the recombinant protein from the culture of at least 10,000 L liquid culture when the liquid culture: (i) contains about 6 moles of NANA per mole of protein (glycoprotein in this case); (ii) cell viability in the liquid culture is not less than about 37%; (iii) endotoxin is less than or equal to about 4.8 EU per mL of liquid culture; and/or (iv) bioburden is less than 1 colony forming unit per mL of liquid culture.

The recombinant protein produced by these methods of the invention can be a secreted protein, a glycoprotein, a cytokine, a hormone, a CTLA4-Ig protein, or a CTLA4$^{A29YL104E}$-Ig protein. In one embodiment, the mammalian cells are progeny or subclones of cells provided by the invention. In another embodiment, the mammalian cells are progeny or subclones of cells derived from the cell line of the invention. In a further embodiment, the mammalian cells are a clonal population from cells transfected with an expression cassette comprising SEQ ID NO:1. In a particular embodiment, the mammalian cells are a clonal population from cells transfected with an expression cassette comprising SEQ ID NO:3.

General Techniques for the Purification of Recombinant Protein from Culture

Following the protein production phase of the cell culture process, the protein of interest, for example a glycoprotein, is recovered from the cell culture medium using techniques understood by one skilled in the art. In particular, the protein of interest is recovered from the culture medium as a secreted polypeptide, although it also can be recovered from host cell lysates. The culture medium or lysate is initially centrifuged to remove cellular debris and particulates. The desired protein subsequently is purified from contaminant DNA, soluble proteins, and polypeptides, with the following non-limiting purification procedures well-established in the art: SDS-PAGE; ammonium sulfate precipitation; ethanol precipitation; fractionation on immunoaffinity or ion-exchange columns; reverse phase HPLC; chromatography on silica or on an anion-exchange resin such as QAE or DEAE; chromatofocusing; gel filtration using, for example, Sephadex G75™ column; and protein A Sepharose™ columns to remove contaminants such as IgG. Addition of a protease inhibitor, such as phenyl methyl sulfonyl fluoride (PMSF), or a protease inhibitor cocktail mix also can be useful to inhibit proteolytic degradation during purification. A person skilled in the art will recognize that purification methods suitable for a protein of interest, for example a glycoprotein, can require alterations to account for changes in the character of the protein upon expression in recombinant cell culture.

Purification techniques and methods that select for the carbohydrate groups of the glycoprotein are also of utility within the context of the present invention. For example, such techniques include, HPLC or ion-exchange chromatography using cation- or anion-exchange resins, wherein the more basic or more acidic fraction is collected, depending on which carbohydrate is being selected for. Use of such techniques also can result in the concomitant removal of contaminants.

In the present invention, CHO cells capable of producing CTLA4-Ig or CTLA4$^{429YL104E}$-Ig fusion proteins are grown as a suspension in a CHO specific medium to a predetermined cell density. CHO cells grown in suspension in the serum-free expression medium subsequently produce CTLA4-Ig or CTLA4$^{429YL104E}$-Ig molecules, which are secreted by the CHO cells into the culture medium. The cell suspension can be cleared via centrifugation and CTLA4-Ig molecules can then be separated from the cleared culture supernatant by standard purification techniques. Non-limiting examples of suitable purification procedures for obtaining greater purity and homogeneity of CTLA4-Ig or CTLA4$^{429YL104E}$-Ig, either individually or in combination, are: affinity chromatography on sepharose; fractionation on anion-exchange columns (AEC); and hydrophobic interaction chromatography (HIC).

In some embodiments, isolating CTLA4-Ig molecules or other proteins (including glycoproteins) from the methods of production described herein can at least include the following steps: (i) obtaining a cell culture supernatant; (ii) subjecting the supernatant to anion exchange chromatography to obtain an eluted protein product; (iii) subjecting the eluted protein product of step (ii) to hydrophobic interaction chromatography so as to obtain an enriched protein product; (iv) subjecting the enriched protein product to affinity chromatography to obtain an eluted and enriched protein product; and (v) subjecting the eluted and enriched protein product of (iv) to anion exchange chromatography. The enriched protein product obtained in step (iii) can be charactertized, for example, in that its percentage of any HMW protein or contaminant is less than 5, 10, 15 or 25%. The anion exchange chromatography of step (ii) can be carried out, for example, by using a wash buffer comprising about 25-100 mM HEPES and about 300-900 mM NaCl and having a pH of about 7.0-8.0. The hydrophobic interaction chromatography of step (iii) can be carried out, for example, by using a single wash buffer having a pH of about 7.0 and comprising about 25 mM HEPES and about 850 mM NaCl; or a wash buffer having a pH of about 8.0 and comprising about 25 mM Tris and about 250 mM NaCl. The affinity chromatography of step (iv) can be carried out, for example, by using an elution buffer having a pH of about 3.5 and comprising about 100 mM glycine. The affinity chromatography of step (v) can be carried out, for example, by using a wash buffer having a pH of about 8.0 and comprising about 25 mM HEPES and from about 120 mM NaCl to about 130 mM NaCl, or a wash buffer having a pH of about 8.0 and comprising about 25 mM HEPES and about 200 mM NaCl. The anion exchange chromatography of step (ii) can be carried out using a column having an anion exchange resin having a primary, secondary, tertiary, or quartenary amine functional group. The hydrophobic interaction column of step (iii) can be carried out using a hydrophobic interaction resin having a phenyl, an octyl, a propyl, an alkoxy, a butyl, or an isoamyl functional group.

In other embodiments, isolating CTLA4$^{429YL104E}$-Ig molecules or other proteins (including glycoproteins) from the methods of production described herein can at least include the following steps: (i) obtaining a cell culture supernatant; (ii) subjecting the supernatant to affinity chromatography to obtain an eluted protein product; (iii) subjecting the eluted protein product of step (ii) to anion exchange chromatography so as to obtain an enriched protein product; and (iv) subjecting the enriched protein product to hydrophobic interaction chromatography to obtain an eluted and enriched protein product with reduced high molecular weight (HMW) protein complexes. The enriched protein product obtained in step (iv) can be characterized, for example, in that its percentage of any HMW protein or contaminant is less than 5, 10, 15 or 25%. The affinity chromatography of step (ii) can be carried out, for example, by using an elution buffer having a pH of about 3.0 and comprising about 250 mM glycine. The affinity chromatography of step (ii) can be carried out, for example, by using a wash buffer having a pH of about 7.5 and comprising about 25 mM NaH$_2$PO$_4$ and about 150 mM NaCl. The anion exchange chromatography of step (iii) can be carried out, for example, by using a wash buffer comprising about 50 mM HEPES and about 135 mM NaCl and having a pH of about 7.0. The anion exchange chromatography of step (iii) can be carried out, for example, by using an elution buffer comprising about 50 mM HEPES and about 200 mM NaCl and having a pH of about 7.0. The hydrophobic interaction chromatography of step (iv) can be carried out, for example, by using a wash buffer having a pH of about 7.0 and comprising about 50 mM HEPES and about 1.2 M (NH$_4$)$_2$SO$_4$. The anion exchange chromatography of step (iii) can be carried out using a column having an anion exchange resin having a primary, secondary, tertiary, or quartenary amine functional group. The hydrophobic interaction column of step (iv) can be carried out using a hydrophobic interaction resin having a phenyl, an octyl, a propyl, an alkoxy, a butyl, or an isoamyl functional group.

In one embodiment, the invention provides a method for purifying CTLA4-Ig molecules from a liquid cell culture so that the purified CTLA4-Ig is substantially free of Monocyte Chemotactic Protein-1 (MCP-1). In one embodiment, the invention provides for a pharmaceutically acceptable composition of CTLA4-Ig molecules, wherein the composition comprises no more than 0.5 ppm MCP-1, 1 ppm MCP-1, 2 ppm MCP-1, 3 ppm MCP-1, 4 ppm MCP-1, 5 ppm MCP-1, 6 ppm MCP-1, 7 ppm MCP-1, 8 ppm MCP-1, 9 ppm MCP-1 or 10 ppm MCP-1. In another embodiment, in the composition, the amount of MCP-1 cannot exceed 1%, 0.5%, or 0.1% of the weight of purified CTLA4-Ig. In another embodiment, the composition of CTLA4-Ig molecules is substantially free of MCP-1 where there is less than 50, 45, 40, 38, 35, 30, 25, 20, 15, 10, 9, 8, 7, 6, 5, 4, 3, 2, or 1 ng/mL of MCP-1 in the QFF eluate liquid. In another embodiment, the invention provides a method for purifying CTLA4-Ig molecules from a liquid cell culture so that the purified CTLA4-Ig is substantially free of MCP-1 and comprises less than 2.5% of CTLA4-Ig tetramer.

The amount of Monocyte chemotactic protein 1 (MCP-1) in the composition can be quantified using an ELISA method. The coating antibody is a goat anti-mouse MCP-1 IgG antibody. The secondary antibody is a rabbit anti-rat MCP-1 IgG antibody. Detection is accomplished using horseradish peroxidase conjugated goat anti-rabbit IgG antibody and the substrate TMB. The horseradish peroxidase reagent produces a colorimetric reaction that develops in proportion to the amount of protein captured. The ELISA quantifies the MCP-1 level relative to a material standard curve. In one embodiment, MCP-1 was quantified in the composition and the MCP-1 levels were in ranges from 0-0.097 ng/mg and 0.014 ng/mg.

In another embodiment, the invention provides a method for purifying CTLA4$^{429YL104E}$-Ig molecules from a liquid cell culture so that the purified CTLA4$^{A29YL104E}$-Ig is substantially free of Monocyte Chemotactic Protein-1 (MCP-1). In one embodiment, the amount of MCP-1 cannot exceed 1%, 0.5%, or 0.1% of the weight of purified CTLA4$^{A29YL104E}$-Ig. In another embodiment, CTLA4$^{A29YL104E}$-Ig is substantially free of MCP-1 where there is less than 50, 45, 40, 38, 35, or 30 ng/mL of MCP-1 in the HIC eluate liquid. In a further embodiment, the invention provides a method for purifying CTLA4$^{A29YL104E}$-Ig molecules from a liquid cell culture so that the purified CTLA4$^{A29YL104E}$-Ig is substantially free of MCP-1 and comprises less than 2.5% of CTLA4$^{A29YL104E}$-Ig tetramer.

Glycoprotein Recovery from the Cell Culture and Purification

The present invention describes a series of steps for the separation of a glycoprotein (for example, CTLA4-Ig or CTLA4$^{A29YL104E}$-Ig) from an impure, cell-culture supernatant, protein pool that contains the glycoprotein of interest (such as CTLA4-Ig or CTLA4$^{A29YL104E}$-Ig) and undesirable contaminants. The impure, cell-culture supernatant can be used as the starting material for the purification of the CTLA4-Ig or CTLA4$^{A29YL104E}$-Ig glycoprotein.

In one embodiment of the present invention, the impure, cell-culture supernatant that contains CTLA4-Ig glycoprotein and undesirable contaminants is applied to an anion-exchange medium. The CTLA4-Ig glycoprotein present in the impure, cell-culture supernatant binds to the anion-exchange medium. The anion-exchange medium is then washed to remove any unbound material from the anion-exchange medium. CTLA4-Ig glycoprotein is eluted after the unbound material is removed, and the eluate is collected.

In one embodiment of the present invention, the impure, cell-culture supernatant that contains CTLA4$^{A29YL104E}$-Ig glycoprotein and undesirable contaminants is applied to an affinity chromatography medium. The CTLA4$^{A29YL104E}$-Ig glycoprotein present in the impure, cell-culture supernatant binds to the affinity chromatography medium. The affinity chromatography medium is then washed to remove any unbound material from the anion-exchange medium. CTLA4$^{A29YL104E}$-Ig glycoprotein is eluted after the unbound material is removed, and the eluate is collected.

In a particular embodiment of this invention, Q-Sepharose Anion-Exchange Chromatography (AEC), for example using a Q-Sepharose XL column (GE Healthcare), is employed to separate CTLA4-Ig glycoprotein from the harvest material, as well as for decreasing bulk contaminants. This column can be used as an early step in the purification of CTLA4-Ig glycoprotein from a mammalian cell culture, for fractionation of the harvested cell culture medium. In another embodiment, Q-Sepharose Anion-Exchange Chromatography, for example Q-Sepharose Fast Flow (GE Healthcare), can be used after an affinity chromatography purification step. The very high flow property of the anion exchange columns allows the large volume of CTLA4-Ig glycoprotein or harvested cell culture medium to be readily concentrated before subsequent chromatography steps, such as SP-Sepharose or HIC, by adjusting conditions so that the CTLA4-Ig glycoprotein binds the column. For a wash buffer of pH from about pH 5 to 9, in particular about 8, 75 mM HEPES and 360 mM NaCl concentrations are useful. Typically, for an elution buffer of pH from about pH 5 to 8, in particular about 7, 25 mM HEPES and 325 mM NaCl concentrations are useful.

Suitable resins for separating CTLA4-Ig glycoprotein from the harvested culture medium were those having immobilized amine functional groups. Most useful are the quarternary amine functional group resins, for example those on Q-Sepharose Fast Flow resins from GE Healthcare, where a quarternary ammonium ligand is bound to high-porosity, cross-linked agarose. Also useful are the primary, secondary and tertiary amine functional group resins, for example those on DEAE Sepharose Fast Flow resins from GE Healthcare, where a tertiary diethylaminoethyl ligand is bound to high-porosity, cross-linked agarose.

In another embodiment of the present invention, the CTLA4-Ig glycoprotein-containing eluate from the anion-exchange medium is collected and then contacted with a hydrophobic interaction resin. As described below, the CTLA4-Ig glycoprotein-containing volume passes through the HIC column and the collected pool, which can be further purified, is then bound to an anion-exchange resin.

HIC is useful for the separation of desired CTLA4-Ig glycoprotein dimers from high molecular weight material and other protein impurities from the mammalian cell culture. For example, CTLA4-Ig-expressing-CHO cell culture contains high molecular weight aggregates of CTLA4-Ig glycoprotein. Also found in the mammalian cell culture medium are CHO cell protein impurities. These undesirable products could generate an unwanted antigenic response in a patient and contribute to poor product quality or activity. HIC effectively separates hydrophobic variants, CTLA4-Ig glycoprotein dimers from CTLA4-Ig glycoprotein HMW complexes and CHO protein impurities via the latter products binding to the HIC resin and the CTLA4-Ig glycoprotein dimers passing through the column. Thus, a CTLA4-Ig glycoprotein pool could be obtained that is substantially free of these species, and that is particularly suited for another chromatographic step, such as anion-exchange chromatography. A source of CTLA4-Ig glycoprotein mixtures for use with HIC is mammalian cell culture, for example a CHO cell culture. In particular, the culture can be subjected to at least one prior purification step as discussed previously.

In another embodiment of this invention, the HIC method can be modified to collect a pool of other glycoproteins (for example, CTLA4-Ig HMW complexes). HMW aggregates can bind to the HIC resin (for example, comprising CTLA4-Ig tetramer and the like). These HMW complexes have a higher avidity and bind more efficaciously in vivo than CTLA4-Ig dimer alone. Thus, one skilled in the art can obtain a pool of CTLA4-Ig HMW aggregates by eluting the CTLA4-Ig pool off of the HIC.

The most useful HIC resins for separating CTLA4-Ig glycoprotein forms are those having immobilized phenyl functional groups. Of the phenyl-HIC resins, Phenyl Sepharose Fast Flow High Sub (high substitution) by GE Healthcare is most useful. Phenyl Toyopearl media by TosoHaas and TSK Phenyl 5PW are non-limiting examples of other phenyl-HIC resins that can be used. Other HIC functional groups include, but are not limited to, the propyl, octyl, alkoxyl, butyl, and isoamyl moieties.

For example, a Phenyl Sepharose 4 Fast Flow column chromatography, Hydrophobic Interaction Chromatography (HIC), process can be used to reduce the amount of CTLA4-Ig or CTLA4$^{A29YL104E}$-Ig high molecular weight species eluted in a HIC purification step (see Example 15 and EXAMPLE 20). Therefore, the cleaning peak from the HIC column is enriched in CTLA4-Ig or CTLA4$^{A29YL104E}$-Ig HMW species.

The unbound fraction containing CTLA4-Ig glycoprotein from the HIC purification step can be subjected to an additional purification method, such as affinity chromatography, and the resulting eluate can then be applied to an anion-exchange medium. The CTLA4-Ig glycoprotein binds to the anion-exchange resin, which can be subsequently washed to remove unbound proteins. After the unbound proteins are removed, CTLA4-Ig glycoprotein is eluted from the second anion-exchange resin. The eluate is collected and can be further concentrated.

In another embodiment of this invention, affinity chromatography, for example rProtein A Sepharose Fast Flow (GE Healthcare), is employed to further enrich CTLA4-Ig glycoprotein, which can be further followed by an anion-exchange chromatography step, for example Q-Sepharose Fast Flow (GE Healthcare). The affinity chromatography step can also reduce the levels of CHO proteins and Monocyte Chemotactic Protein (MCP-1, a chemokine) impurities. Affinity chromatography involves adsorptive separation, where a molecule of interest to be purified, for example CTLA4-Ig glycoprotein, binds specifically and reversibly to a ligand immobilized on some matrix or resin. Some non-limiting examples of affinity purification columns include lectin; affinity tag (for example, a GST column or 6x-His column); Streptavidin; heparin; or antibody (for example, a Protein A column or a Protein G column). In particular, this invention utilizes a protein A resin for binding the CTLA4-Ig glycoprotein. For a wash buffer of pH from about 5 to 9, more effective at about 8, 25 mM Tris and 250 mM NaCl concentrations are useful. For an elution buffer of pH from about 2 to 5, more effective at about 3.5, 100 mM glycine concentration is useful. The affinity chromatography eluate can then be neutralized and loaded onto an anion exchange chromatography column, Q-Sepharose Fast Flow being most useful.

To further reduce the levels of protein A, DNA, and non-desired CTLA4-Ig glycoprotein species in the product after the foregoing recovery/initial purification steps, another ion-exchange step can be incorporated into the purification procedure. This invention can employ commercially available ion-exchange columns, such as a Q-Sepharose Fast Flow column from GE Healthcare, or a DEAE Sepharose Fast Flow column, also from GE Healthcare. As determined herein, the most suitable resins for separating CTLA4-Ig glycoprotein from the harvested culture medium were those having immobilized amine functional groups. Other useful groups are the quarternary amine functional group resins, for example those in a Q-Sepharose Fast Flow column from GE Healthcare, where a quarternary ammonium ligand is bound to high-porosity, cross-linked agarose. Also useful are the primary, secondary and tertiary amine functional group resins, for example those in a DEAE Sepharose Fast Flow column from GE Healthcare, where a tertiary diethylaminoethyl ligand is bound to high-porosity, cross-linked agarose. In a particular embodiment of the invention, a column that utilizes a strong anion exchanger, such as a Q-Sepharose Fast Flow column, is utilized.

In one embodiment of the invention, a CTLA4-Ig glycoprotein eluate is loaded onto an anion exchange column, for example Q-Sepharose Fast Flow. The column is washed and CTLA4-Ig glycoprotein is subsequently eluted from the anion exchange column. For a wash buffer of pH from about 5 to 9, in one embodiment, pH 8, 25 mM HEPES and 100-140 mM NaCl concentrations are useful. For an elution buffer of pH from about 5 to 9, or in another embodiment, pH 8, 25 mM HEPES and 200 mM NaCl concentrations are useful. CTLA4-Ig glycoprotein eluted from the anion-exchange medium is recovered, concentrated and washed, by diafiltration or other suitable method known to one skilled in the art, to provide a final purified CTLA4-Ig glycoprotein product. The CTLA4-Ig glycoprotein product prepared in accordance with the process of the present invention is of high purity, for example containing ≥95% of the CTLA4-Ig dimer, containing ≤5% of the CTLA4-Ig HMW product, and containing ≤1% of CTLA4-Ig monomer.

The purification method can further comprise additional steps that inactivate and/or remove viruses and/or retroviruses that might potentially be present in the cell culture medium of mammalian cell lines. A significant number of viral clearance steps are available, including but not limited to, treating with chaotropes such as urea or guanidine, detergents, additional ultrafiltration/diafiltration steps, conventional separation, such as ion-exchange or size exclusion chromatography, pH extremes, heat, proteases, organic solvents or any combination thereof.

In another embodiment of this invention, affinity chromatography, for example MabSelect Protein A Sepharose resin (GE Healthcare), is employed to capture $CTLA4^{A29YL104E}$-Ig glycoprotein, which can be further followed by an anion-exchange chromatography step, for example Q-Sepharose Fast Flow (GE Healthcare). The affinity chromatography step can also reduce the levels of CHO proteins and Monocyte Chemotactic Protein (MCP-1, a chemokine) impurities. Affinity chromatography involves adsorptive separation, where a molecule of interest to be purified, for example $CTLA4^{A29YL104E}$-Ig glycoprotein, binds specifically and reversibly to a ligand immobilized on some matrix or resin. Some non-limiting examples of affinity purification columns include lectin; affinity tag (for example, a GST column or 6x-His column); Streptavidin; heparin; or antibody (for example, a Protein A column or a Protein G column). In particular, this invention utilizes a protein A resin for binding the $CTLA4^{A29YL104E}$-Ig glycoprotein. For a wash buffer of pH from about 5 to 9, more effective at about 7.5, 25 mM Tris, 25 mM $NaH_2PO_4$, and 250 mM NaCl concentrations are useful. For an elution buffer of pH from about 2 to 5, more effective at about 3.5, 100-300 mM glycine concentration is useful. The affinity chromatography eluate can then be neutralized and loaded onto an anion exchange chromatography column, Q-Sepharose Fast Flow being most useful.

To further reduce the levels of protein A, DNA, and non-desired $CTLA4^{A29YL104E}$-Ig glycoprotein species in the product after the foregoing recovery/initial purification steps, an ion-exchange step can be incorporated into the purification procedure. This invention can employ commercially available ion-exchange columns, such as a Q-Sepharose Fast Flow column from GE Healthcare, Q-Sepharose XL column (GE Healthcare), or a DEAE Sepharose Fast Flow column, also from GE Healthcare. The most suitable resins for separating $CTLA4^{A29YL104E}$-Ig glycoprotein are those having immobilized amine functional groups. Other useful groups are the quarternary amine functional group resins, for example those in a Q-Sepharose Fast Flow column from GE Healthcare, where a quarternary ammonium ligand is bound to high-porosity, cross-linked agarose. Also useful are the primary, secondary and tertiary amine functional group resins, for example those in a DEAE Sepharose Fast Flow column from GE Healthcare, where a tertiary diethylaminoethyl ligand is bound to high-porosity, cross-linked agarose. In a particular embodiment of the invention, a column that utilizes a strong anion exchanger, such as a Q-Sepharose Fast Flow column, is utilized.

In one embodiment of the invention, a $CTLA4^{A29YL104E}$-Ig glycoprotein eluate is loaded onto an anion exchange column, for example Q-Sepharose Fast Flow. The column is washed and $CTLA4^{A29YL104E}$-Ig glycoprotein is subsequently eluted from the anion exchange column. For a wash buffer of pH from about 5 to 9, in one embodiment, pH 7, 25-55 mM HEPES and 100-140 mM NaCl concentrations are useful. For an elution buffer of pH from about 5 to 9, or in another embodiment, pH 7, 25-50 mM HEPES and 200 mM NaCl concentrations are useful.

In another embodiment of the present invention, the CTLA4$^{A29YL104E}$-Ig glycoprotein-containing eluate from the anion-exchange medium is collected and then contacted with a hydrophobic interaction resin. HIC is useful for the separation of desired CTLA4$^{A29YL104E}$-Ig glycoprotein dimers from high molecular weight material and other protein impurities from the mammalian cell culture. For example, CTLA4$^{A29YL104E}$-Ig expressing-CHO cell culture contains high molecular weight aggregates of CTLA4$^{A29YL104E}$-IG glycoprotein. Also found in the mammalian cell culture medium are CHO cell protein impurities. These undesirable products could generate an unwanted antigenic response in a patient and contribute to poor product quality or activity.

HIC effectively separates hydrophobic variants, CTLA4$^{A29YL104E}$-Ig glycoprotein dimers from CTLA4$^{A29YL104E}$-Ig glycoprotein HMW complexes and CHO protein impurities via the latter products binding to the HIC resin and the CTLA4$^{A29YL104E}$-Ig glycoprotein dimers passing through the column. Thus, a CTLA4$^{A29YL104E}$-Ig glycoprotein pool could be obtained that is substantially free of these species. A source of CTLA4$^{A29YL104E}$-Ig glycoprotein mixtures for use with HIC is mammalian cell culture, for example a CHO cell culture. In particular, the culture can be subjected to at least one prior purification step as discussed previously.

In another embodiment of this invention, the HIC method can be modified to collect a pool of other glycoproteins (for example, CTLA4$^{A29YL104E}$-Ig HMW complexes). HMW aggregates can bind to the HIC resin (for example, comprising CTLA4$^{A29YL104E}$-Ig tetramer and the like). These HMW complexes have a higher avidity and bind more efficaciously in vivo than CTLA4$^{A29YL104E}$-Ig dimer alone. Thus, one skilled in the art can obtain a pool of CTLA4$^{A29YL104E}$-Ig HMW aggregates by eluting the CTLA4$^{A29YL104E}$-Ig pool off of the HIC.

CTLA4$^{A29YL104E}$-Ig glycoprotein eluted from the HIC medium is recovered, concentrated and washed, by diafiltration or other suitable method known to one skilled in the art, to provide a final purified CTLA4$^{A29YL104E}$-Ig glycoprotein product. The CTLA4$^{A29YL104E}$-Ig glycoprotein product prepared in accordance with the process of the present invention is of high purity, for example containing ≥95% of the CTLA4$^{A29YL104E}$-Ig dimer, containing ≤5% of the CTLA4$^{A29YL104E}$-Ig HMW product, and containing ≤1% of CTLA4$^{A29YL104E}$-Ig monomer.

The most useful HIC resins for separating CTLA4$^{A29YL104E}$-Ig glycoprotein forms are those having immobilized phenyl functional groups. Of the phenyl-HIC resins, Phenyl Sepharose Fast Flow High Sub (high substitution) by GE Healthcare is most useful. Phenyl Toyopearl media by TosoHaas and TSK Phenyl 5PW are non-limiting examples of other phenyl-HIC resins that can be used. Other HIC functional groups include, but are not limited to, the propyl, octyl, alkoxyl, butyl, and isoamyl moieties.

The purification method can further comprise additional steps that inactivate and/or remove viruses and/or retroviruses that might potentially be present in the cell culture medium of mammalian cell lines. A significant number of viral clearance steps are available, including but not limited to, treating with chaotropes such as urea or guanidine, detergents, additional ultrafiltration/diafiltration steps, conventional separation, such as ion-exchange or size exclusion chromatography, pH extremes, heat, proteases, organic solvents or any combination thereof.

In one aspect, purified CTLA4-Ig molecules which have been concentrated and subjected to diafiltration step can be filled into 2-L BIOTAINER® bottles, 50-L bioprocess bag or any other suitable vessel. CTLA4-Ig molecules in such vessels can be stored for about 60 days at 2° to 8° C. prior to freezing. Extended storage of purified CTLA4-Ig at 2° to 8° C. may lead to an increase in the proportion of CLTA4-Ig tetramer. Therefore, for long-term storage, CTLA4-Ig molecules can be frozen at about −70° C. prior to storage and stored at a temperate of about −40° C. The freezing temperature can vary from about −50° C. to about −90° C. The freezing time can vary and largely depends on the volume of the vessel that contains CTLA4-Ig molecules, and the number of vessels that are loaded in the freezer. For example, in one embodiment, CTLA4-Ig molecules are in 2-L BIOTAINER® bottles. Loading of less than four 2-L BIOTAINER® bottles in the freezer may require from about 14 to at least 18 hours of freezing time. Loading of at least four bottles may require from about 18 to at least 24 hours of freezing time. Vessels with frozen CTLA4-Ig molecules are stored at a temperature from about −35° C. to about −55° C.

The storage time at a temperature of about −35° C. to about −55° C. can vary and can be as short as 18 hours. The frozen CTLA4-Ig molecules can be thawed in a control manner. Thawing of frozen CTLA4-Ig molecules is controlled and can be done in an incubator at a temperature from about 20° C. to about 24° C. The duration of the thawing steps depends on the loading of the incubator wherein loading of less than four 2-L BIOTAINER bottles may require less than about 24 hours of thawing time. Loading of four 2-L BIOTAINER® bottles may require about 18 hours. Thawed solution comprising CTLA4-Ig molecules can be mixed to avoid potential concentration gradients. Therefore, thawing can be done in a controlled-temperature incubator, which also allows for shaking of the vessels, which contain CTLA4-Ig. The speed of shaking can be from about 40 to about 80 rpm. Thawed CTLA4-Ig molecules can be further mixed for additional 5-10 min at a rotational rate of about 3 rpm. Thawed CTLA4-Ig molecules can be stored at 2° to 8° C., alequated and lyophilized during the production of pharmaceutical compositions comprising CTLA4-Ig.

The present invention can be further applied to the purification of other, non-limiting examples, of therapeutic glycoproteins produced in large scale. The process of this invention can be applicable to the production of other glycoproteins having more than one glycosylated variant in mammalian cell cultures. One skilled in the art will understand the modifications that might become necessary in the course of the adaptation of the exemplified method to the production of different glycoproteins.

Formulations & Kits

The invention also provides any of the described CTLA4-Ig molecules as a lyophilized mixture. Formulations comprising CTLA4-Ig to be lyophilized can further comprise three basic components: (1) an additional active ingredient(s) including other recombinant proteins or small molecules (such as immunosuppressants), (2) an excipient(s) and (3) a solvent(s). Excipients include pharmaceutically acceptable reagents to provide good lyophilized cake properties (bulking agents) as well as to provide lyoprotection and/or cryoprotection of proteins ("stabilizer"), maintenance of pH (buffering agents), and proper conformation of the protein during storage so that substantial retention of biological activity (including active ingredient stability, such as protein stability) is maintained. With respect to excipients, an example of a formulation can include one or more of a buffering agent(s), a bulking agent(s), a protein stabilizer(s) and an antimicrobial(s). Sugars or polyols can be used as nonspecific protein stabilizers in solution and during freeze-thawing and freeze-drying. Polymers can be used to stabilize proteins in solution and during freeze-thawing and freeze-drying. One popular polymer is serum albumin, which has been used both as a cryoprotectant and lyoprotectant. In one embodiment, the invention provides formulations that are albumin free. Various salts can be used as bulking agents. Illustrative salt bulking agents include, for example, NaCl, $MgCl_2$ and $CaCl_2$). Certain amino acids can be used as cryoprotectants and/or lyoprotectants and/or bulking agents. Amino acids that can be used include, but are not limited to, glycine, proline, 4-hydroxyproline, L-serine, sodium glutamate, alanine, arginine and lysine hydrochloride. Many buffering agents covering a wide pH range are available for selection in formulations. Buffering agents include, for example, acetate, citrate, glycine, histidine, phosphate (sodium or potassium), diethanolamine and Tris. Buffering agents encompasses those agents which maintain the solution pH in an acceptable range prior to lyophilization. Formulations have previously been described in U.S. Patent Application No. 60/752,150, filed Dec. 20, 2005, which is hereby incorporated by reference in its entirety.

In one embodiment, the invention provides a lyophilized CTLA4-Ig mixture comprising at least 90%, 95%, 99%, or 99.5% CTLA4-Ig dimer. In one embodiment, the invention provides a lyophilized CTLA4-Ig mixture comprising at least 90%, 95%, 99%, or 99.5% CTLA4-Ig dimer and not more than 5%, 4%, 3%, 2%, or 1% CTLA4-Ig tetramer. In another embodiment, the invention provides a lyophilized CTLA4-Ig mixture comprising at least 90%, 95%, 99%, or 99.5% CTLA4-Ig dimer, and not more than 5%, 4%, 3%, 2%, or 1% CTLA4-Ig tetramer, and not more than 2%, 1.5%, 1.0%, 0.8%, 0.5%, or 0.3% CTLA4-Ig monomer. In a further embodiment, the invention provides a lyophilized CTLA4-Ig mixture comprising at least 8.0 moles of sialic acid per mole of CTLA4-Ig dimer or to CTLA4-Ig molecule. In another embodiment, the invention provides a lyophilized CTLA4-Ig mixture comprising: from about 15 to about 35 moles of GlcNac per mole of CTLAIg molecules or dimer; from about 1 to about 5 moles of GalNac per mole of CTLA4-Ig dimer or to CTLA4-Ig molecule; from about 5 moles to about 20 moles of galactose per mole of CTLA4-Ig dimer or to CTLA4-Ig molecule; from about 2 to about 10 moles of fucose per mole of CTLA4-Ig dimer or to CTLA4-Ig molecule; and/or from about 5-15 moles of mannose per mole of CTLA4-Ig dimer or to CTLA4-Ig molecule A $CTLA4^{A29YL104E}$-Ig drug substance is available as an aqueous solution at approximately 25 mg/mL (22.5-27.5 mg/mL) concentration in 25 mM sodium phosphate and 10 mM sodium chloride buffer at pH ~7.5. $CTLA4^{A29YL104E}$-Ig has a tendency to form high molecular weight species in aqueous solution. Therefore, a freeze-dried product was developed in order to minimize the levels of high molecular weight species that may form in the drug product. Various excipients such as maltose, sucrose, and amino acids such as L-arginine hydrochloride were screened as potential lyoprotectants during freeze drying of $CTLA4^{A29YL104E}$-Ig. Sucrose was found to be the most effective lyoprotectant. It was further observed that increasing the sucrose to protein ratio improved protein stability. A sucrose:protein ratio of 2:1 (wt.:wt.) was chosen for the protein solution to be freeze dried. The freeze-dried drug product has adequate stability and satisfactory constitution behavior.

Methods of Treatment

According to this invention, a disease mediated by T cell interactions with B7 positive cells can be treated by receiving a pharmaceutically acceptable formulation of CTLA4-Ig or $CTLA4^{A29YL104E}$-Ig. The CTLA4-Ig or $CTLA4^{A29YL104E}$-Ig molecules secreted by an engineered mammalian cell line (for example, a dhfr– negative Chinese Hamster Ovary cell line that harbors DNA encoding CTLA4-Ig or $CTLA4^{A29YL104E}$-Ig) can be a population of molecules having a particular glycosylation profile. As stated herein, a particular glycoyslation profile can affect CTLA4-Ig or $CTLA4^{A29YL104E}$-Ig binding to CD80 and/or CD86 such that CTLA4-Ig or $CTLA4^{A29YL104E}$-Ig molecules can provide a greater inhibition on T cell activation and/or proliferation. As stated herein, a particular glycosylation profile can be affected by the cell line and the method of production. Thus, in certain embodiments of the invention, the invention provides CTLA4-Ig or $CTLA4^{A29YL104E}$-Ig molecules produced by a cell line in a production method described herein in order to treat T-cell related diseases or disorders, that include but are not limited to, generally any T-cell dependent lymphoproliferative disease or disorder and any T-cell dependent autoimmune disease or disorder, and more specifically: T cell lymphoma, T cell acute lymphoblastic leukemia, testicular angiocentric T cell lymphoma, benign lymphocytic angiitis, graft versus host disease (GVHD), immune disorders associated with graft transplantation rejection, psoriasis, inflammation, allergy, oophoritis, inflammatory bowel disease, glomerulonephritis, encephalomyelitis, Hashimoto's thyroiditis, Graves' disease, Addison's disease, Crohn's disease, Sjogren's syndrome, lupus erythematosus, primary myxedema, pernicious anemia, autoimmune atrophic gastritis, rheumatoid arthritis, insulin dependent diabetes mellitus, good pasture's syndrome, myasthenia gravis, pemphigus, multiple sclerosis, sympathetic ophthalmia, autoimmune uveitis, autoimmune hemolytic anemia, idiopathic thrombocytopenia, primary biliary cirrhosis, chronic action hepatitis, ulceratis colitis, scleroderma, polymyositis, and mixed connective tissue disease.

The invention provides the use of any of the disclosed CTLA4-Ig or $CTLA4^{A29YL104E}$-Ig molecules in methods for inhibiting T cell proliferation or activation, inhibiting an immune response in a subject or in vitro, and for treating an immune disorder in a subject or inducing immune tolerance to an antigen in a subject. Immune tolerance is a type of immunological response in which there develops a specific nonreactivity of the lymphoid tissues towards a specific antigen, where in the absence of tolerance, the antigen is able to induce an immune response. In one embodiment, the CTLA4-Ig or $CTLA4^{A29YL104E}$-Ig molecules and compositions of the invention can be used to treat a subject who has received a transplant in order to induce tolerance, and reduce the possibility of rejection. In another embodiment, the transplant is an organ transplant, a tissue transplant or a cell transplant. In another embodiment, the cell transplant comprises bone marrow cells or islet cells.

The invention provides the use of any of the disclosed CTLA4-Ig or $CTLA4^{A29YL104E}$-Ig molecules in the manufacture of a medicament for treating any of the above stated diseases or disorders. The invention also provides the use of any of the disclosed CTLA4-Ig or $CTLA4^{A29YL104E}$-Ig molecules in a coadministration with another agent for the treatment of the above-mentioned diseases or disorders. The CTLA4-Ig or $CTLA4^{A29YL104E}$-Ig molecules of the invention can be administered to a subject, for example, intravenously, subcutaneously, and/or by inhalation. CTLA4-Ig or CTLA4$^{A29YL104E}$-Ig formulations applicable for intravenous or subcutaneous administration are described in U.S. Ser. No. 60/752,150, filed on Dec. 20, 2005, which is hereby incorporated by reference in its entirety. CTLA4-Ig or CTLA4$^{A29YL104E}$-Ig formulations can also include liposome-based formulations wherein the liposomes can deliver CTLA4-Ig or CTLA4$^{A29YL104E}$-Ig molecules to target cells or tissues. CTLA4-Ig or CTLA4$^{A29YL104E}$-Ig molecules can also be delivered to target cells or tissues by administration of a virus vector that comprises a CTLA4-Ig or CTLA4$^{A29YL104E}$-Ig gene expression cassette. Administration and dosages of a CTLA4-Ig or CTLA4$^{A29YL104E}$-Ig population of molecules are described in U.S. Patent applications published as US20030083246 and US20040022787, as well as the pending U.S. patent application Ser. No. 60/668,774, filed on Apr. 6, 2005, all of which are hereby incorporated by reference in their entireties.

The CTLA4-Ig or CTLA4$^{A29YL104E}$-Ig molecules described herein may be in a variety of dosage forms which include, but are not limited to, liquid solutions or suspensions, tablets, pills, powders, suppositories, polymeric microcapsules or microvesicles, liposomes, and injectable or infusible solutions. The form depends upon the mode of administration and the therapeutic application. An effective mode of administration and dosage regimen for the molecules of the present invention depends upon the severity and course of the disease, the subject's health and response to treatment and the judgment of the treating physician. Accordingly, the dosages of the molecules should be titrated to the individual subject. The interrelationship of dosages for animals of various sizes and species and humans based on mg/m$^2$ of surface area is described by Freireich, E. J., et al. (Quantitative Comparison of Toxicity of Anticancer Agents in Mouse, Rat, Hamster, Dog, Monkey and Man. *Cancer Chemother, Rep.,* 50, No. 4, 219-244, May 1966). Adjustments in the dosage regimen may be made to optimize the growth inhibiting response.

Doses may be divided and administered on a daily basis or the dose may be reduced proportionally depending upon the situation. For example, several divided doses may be administered daily or monthly or the dose may be proportionally reduced as indicated by the specific therapeutic situation. In one embodiment, the administration is monthly, quarterly, daily, twice a day, about every 10 hours, about every 6 hours, about every 4 hours, about every 2 hours, about once an hour. In accordance with the practice of the invention an effective amount for treating a subject may be between about 0.1 and about 10 mg/kg body weight of subject. Also, the effective amount may be an amount between about 1 and about 10 mg/kg body weight of subject. The CTLA4-Ig or CTLA4$^{A29YL104E}$-Ig molecules of the invention also have in vivo clinical application. They can be used for the enumeration of B7 positive cells in the diagnosis or prognosis of some conditions of immunodeficiency, the phenotyping of leukemias and lymphomas, and the monitoring of immunological change following organ transplantation.

The delivery of the compositions described herein may be achieved via injection, oral delivery, inhalation of a spray or other particular dispersion, subcutaneous injection, intravenous delivery, topical delivery, suppository, ocular delivery, nasal or oral delivery. The composition can be delivered via encapsulation in a liposome or other membrane-like delivery vehicle. The composition can be delivered via blood or other fluids that are previously treated with the composition and then subsequently transfused into a subject.

```
SEQUENCE LISTINGS
SEQ ID NO: 17 is the nucleotide sequence encoding the
pcSDhuCTLA4Ig:
GATCTCCCGA TCCCCTATGG TCGACTCTCA GTACAATCTG CTCTGATGCC GCATAGTTAA

GCCAGTATCT GCTCCCTGCT TGTGTGTTGG AGGTCGCTGA GTAGTGCGCG AGCAAAATTT

AAGCTACAAC AAGGCAAGGC TTGACCGACA ATTGCATGAA GAATCTGCTT AGGGTTAGGC

GTTTTGCGCT GCTTCGCGAT GTACGGGCCA GATATACGCG TTGACATTGA TTATTGACTA

GTTATTAATA GTAATCAATT ACGGGGTCAT TAGTTCATAG CCCATATATG GAGTTCCGCG

TTACATAACT TACGGTAAAT GGCCCGCCTG GCTGACCGCC CAACGACCCC CGCCCATTGA

CGTCAATAAT GACGTATGTT CCCATAGTAA CGCCAATAGG GACTTTCCAT TGACGTCAAT

GGGTGGACTA TTTACGGTAA ACTGCCCACT TGGCAGTACA TCAAGTGTAT CATATGCCAA

GTACGCCCCC TATTGACGTC AATGACGGTA AATGGCCCGC CTGGCATTAT GCCCAGTACA

TGACCTTATG GGACTTTCCT ACTTGGCAGT ACATCTACGT ATTAGTCATC GCTATTACCA

TGGTGATGCG GTTTTGGCAG TACATCAATG GGCGTGGATA GCGGTTTGAC TCACGGGGAT

TTCCAAGTCT CCACCCCATT GACGTCAATG GGAGTTTGTT TTGGCACCAA AATCAACGGG

ACTTTCCAAA ATGTCGTAAC AACTCCGCCC CATTGACGCA AATGGGCGGT AGGCGTGTAC

GGTGGGAGGT CTATATAAGC AGAGCTCTCT GGCTAACTAG AGAACCCACT GCTTACTGGC

TTATCGAAAT TAATACGACT CACTATAGGG AGACCCAAGC TTGGTACCGA GCTCGGATCC

ACTAGTAACG GCCGCCAGTG TGCTGGAATT CTGCAGATAG CTTCACCAAT GGGTGTACTG

CTCACACAGA GGACGCTGCT CAGTCTGGTC CTTGCACTCC TGTTTCCAAG CATGGCGAGC

ATGGCAATGC ACGTGGCCCA GCCTGCTGTG GTACTGGCCA GCAGCCGAGG CATCGCCAGC
```

-continued

```
TTTGTGTGTG AGTATGCATC TCCAGGCAAA GCCACTGAGG TCCGGGTGAC AGTGCTTCGG

CAGGCTGACA GCCAGGTGAC TGAAGTCTGT GCGGCAACCT ACATGATGGG GAATGAGTTG

ACCTTCCTAG ATGATTCCAT CTGCACGGGC ACCTCCAGTG GAAATCAAGT GAACCTCACT

ATCCAAGGAC TGAGGGCCAT GGACACGGGA CTCTACATCT GCAAGGTGGA GCTCATGTAC

CCACCGCCAT ACTACCTGGG CATAGGCAAC GGAACCCAGA TTTATGTAAT TGATCCAGAA

CCGTGCCCAG ATTCTGATCA GGAGCCCAAA TCTTCTGACA AAACTCACAC ATCCCCACCG

TCCCCAGCAC CTGAACTCCT GGGGGGATCG TCAGTCTTCC TCTTCCCCCC AAAACCCAAG

GACACCCTCA TGATCTCCCG GACCCCTGAG GTCACATGCG TGGTGGTGGA CGTGAGCCAC

GAAGACCCTG AGGTCAAGTT CAACTGGTAC GTGGACGGCG TGGAGGTGCA TAATGCCAAG

ACAAAGCCGC GGGAGGAGCA GTACAACAGC ACGTACCGTG TGGTCAGCGT CCTCACCGTC

CTGCACCAGG ACTGGCTGAA TGGCAAGGAG TACAAGTGCA AGGTCTCCAA CAAAGCCCTC

CCAGCCCCCA TCGAGAAAAC CATCTCCAAA GCCAAAGGGC AGCCCCGAGA ACCACAGGTG

TACACCCTGC CCCCATCCCG GGATGAGCTG ACCAAGAACC AGGTCAGCCT GACCTGCCTG

GTCAAAGGCT TCTATCCCAG CGACATCGCC GTGGAGTGGG AGAGCAATGG GCAGCCGGAG

AACAACTACA AGACCACGCC TCCCGTGCTG GACTCCGACG GCTCCTTCTT CCTCTACAGC

AAGCTCACCG TGGACAAGAG CAGGTGGCAG CAGGGGAACG TCTTCTCATG CTCCGTGATG

CATGAGGCTC TGCACAACCA CTACACGCAG AAGAGCCTCT CCCTGTCTCC GGGTAAATGA

GTGCGACGGC CGGCAAGCCC CCGCTCCCCG GGCTCTCGCG GTCGCACGAG GATGCTTCTA

GAGGGCCCTA TTCTATAGTG TCACCTAAAT GCTAGAGCTC GCTGATCAGC CTCGACTGTG

CCTTCTAGTT GCCAGCCATC TGTTGTTTGC CCCTCCCCCG TGCCTTCCTT GACCCTGGAA

GGTGCCACTC CCACTGTCCT TTCCTAATAA AATGAGGAAA TTGCATCGCA TTGTCTGAGT

AGGTGTCATT CTATTCTGGG GGGTGGGGTG GGGCAGGACA GCAAGGGGGA GGATTGGGAA

GACAATAGCA GGCATGCTGG GGATGCGGTG GGCTCTATGG CTTCTGAGGC GGAAAGAACC

AGCTGGGGCT CTAGGGGGTA TCCCCACGCG CCCTGTAGCG GCGCATTAAG CGCGGCGGGT

GTGGTGGTTA CGCGCAGCGT GACCGCTACA CTTGCCAGCG CCCTAGCGCC CGCTCCTTTC

GCTTTCTTCC CTTCCTTTCT CGCCACGTTC GCCCTGTGGA ATGTGTGTCA GTTAGGGTGT

GGAAAGTCCC CAGGCTCCCC AGCAGGCAGA AGTATGCAAA GCATGCATCT CAATTAGTCA

GCAACCAGGT GTGGAAAGTC CCCAGGCTCC CCAGCAGGCA GAAGTATGCA AGCATGCAT

CTCAATTAGT CAGCAACCAT AGTCCCGCCC CTAACTCCGC CCATCCCGCC CTAACTCCG

CCCAGTTCCG CCCATTCTCC GCCCCATGGC TGACTAATTT TTTTTATTTA TGCAGAGGCC

GAGGCCGCCT CGGCCTCTGA GCTATTCCAG AAGTAGTGAG GAGGCTTTTT TGGAGGCCTA

GGCTTTTGCA AAAAGCTTGG ACAGCTGAGG GCTGCGATTT CGCGCCAAAC TTGACGGCAA

TCCTAGCGTG AAGGCTGGTA GGATTTTATC CCCGCTGCCA TCATGGTTCG ACCATTGAAC

TGCATCGTCG CCGTGTCCCA AGATATGGGG ATTGGCAAGA ACGGAGACCT ACCCTGGCCT

CCGCTCAGGA ACGAGTTCAA GTACTTCCAA AGAATGACCA CAACCTCTTC AGTGGAAGGT

AAACAGAATC TGGTGATTAT GGGTAGGAAA ACCTGGTTCT CCATTCCTGA GAAGAATCGA

CCTTTAAAGG ACAGAATTAA TATAGTTCTC AGTAGAGAAC TCAAAGAACC ACCACGAGGA

GCTCATTTTC TTGCCAAAAG TTTGGATGAT GCCTTAAGAC TTATTGAACA ACCGGAATTG

GCAAGTAAAG TAGACATGGT TTGGATAGTC GGAGGCAGTT CTGTTTACCA GGAAGCCATG

AATCAACCAG GCCACCTCAG ACTCTTTGTG ACAAGGATCA TGCAGGAATT TGAAAGTGAC
```

-continued

```
ACGTTTTCC CAGAAATTGA TTTGGGGAAA TATAAACTTC TCCCAGAATA CCCAGGCGTC

CTCTCTGAGG TCCAGGAGGA AAAAGGCATC AAGTATAAGT TGAAGTCTA CGAGAAGAAA

GACTAACAGG AAGATGCTTT CAAGTTCTCT GCTCCCCTCC TAAAGCTATG CATTTTTATA

AGACCATGGG ACTTTTGCTG GCTTTAGATC TTTGTGAAGG AACCTTACTT CTGTGGTGTG

ACATAATTGG ACAAACTACC TACAGAGATT TAAAGCTCTA AGGTAAATAT AAAATTTTTA

AGTGTATAAT GTGTTAAACT ACTGATTCTA ATTGTTTGTG TATTTTAGAT TCCAACCTAT

GGAACTGATG AATGGGAGCA GTGGTGGAAT GCCTTTAATG AGGAAAACCT GTTTTGCTCA

GAAGAAATGC CATCTAGTGA TGATGAGGCT ACTGCTGACT CTCAACATTC TACTCCTCCA

AAAAAGAAGA GAAAGGTAGA AGACCCCAAG GACTTTCCTT CAGAATTGCT AAGTTTTTTG

AGTCATGCTG TGTTTAGTAA TAGAACTCTT GCTTGCTTTG CTATTTACAC CACAAAGGAA

AAAGCTGCAC TGCTATACAA GAAAATTATG GAAAAATATT CTGTAACCTT TATAAGTAGG

CATAACAGTT ATAATCATAA CATACTGTTT TTTCTTACTC CACACAGGCA TAGAGTGTCT

GCTATTAATA ACTATGCTCA AAAATTGTGT ACCTTTAGCT TTTTAATTTG TAAAGGGGTT

AATAAGGAAT ATTTGATGTA TAGTGCCTTG ACTAGAGATC ATAATCAGCC ATACCACATT

TGTAGAGGTT TTACTTGCTT TAAAAAACCT CCCACACCTC CCCCTGAACC TGAAACATAA

AATGAATGCA ATTGTTGTTG TTAACTTGTT TATTGCAGCT TATAATGGTT ACAAATAAAG

CAATAGCATC ACAAATTTCA CAAATAAAGC ATTTTTTTCA CTGCATTCTA GTTGTGGTTT

GTCCAAACTC ATCAATGTAT CTTATCATGT CTGGATCGGC TGGATGATCC TCCAGCGCGG

GGATCTCATG CTGGAGTTCT TCGCCCACCC CAACTTGTTT ATTGCAGCTT ATAATGGTTA

CAAATAAAGC AATAGCATCA CAAATTTCAC AAATAAAGCA TTTTTTTCAC TGCATTCTAG

TTGTGGTTTG TCCAAACTCA TCAATGTATC TTATCATGTC TGTATACCGT CGACCTCTAG

CTAGAGCTTG GCGTAATCAT GGTCATAGCT GTTTCCTGTG TGAAATTGTT ATCCGCTCAC

AATTCCACAC AACATACGAG CCGGAAGCAT AAAGTGTAAA GCCTGGGGTG CCTAATGAGT

GAGCTAACTC ACATTAATTG CGTTGCGCTC ACTGCCCGCT TTCCAGTCGG GAAACCTGTC

GTGCCAGCTG CATTAATGAA TCGGCCAACG CGCGGGGAGA GGCGGTTTGC GTATTGGGCG

CTCTTCCGCT TCCTCGCTCA CTGACTCGCT GCGCTCGGTC GTTCGGCTGC GGCGAGCGGT

ATCAGCTCAC TCAAAGGCGG TAATACGGTT ATCCACAGAA TCAGGGGATA ACGCAGGAAA

GAACATGTGA GCAAAAGGCC AGCAAAAGGC CAGGAACCGT AAAAAGGCCG CGTTGCTGGC

GTTTTTCCAT AGGCTCCGCC CCCCTGACGA GCATCACAAA AATCGACGCT CAAGTCAGAG

GTGGCGAAAC CCGACAGGAC TATAAAGATA CCAGGCGTTT CCCCCTGGAA GCTCCCTCGT

GCGCTCTCCT GTTCCGACCC TGCCGCTTAC CGGATACCTG TCCGCCTTTC TCCCTTCGGG

AAGCGTGGCG CTTTCTCAAT GCTCACGCTG TAGGTATCTC AGTTCGGTGT AGGTCGTTCG

CTCCAAGCTG GGCTGTGTGC ACGAACCCCC CGTTCAGCCC GACCGCTGCG CCTTATCCGG

TAACTATCGT CTTGAGTCCA ACCCGGTAAG ACACGACTTA TCGCCACTGG CAGCAGCCAC

TGGTAACAGG ATTAGCAGAG CGAGGTATGT AGGCGGTGCT ACAGAGTTCT TGAAGTGGTG

GCCTAACTAC GGCTACACTA GAAGGACAGT ATTTGGTATC TGCGCTCTGC TGAAGCCAGT

TACCTTCGGA AAAAGAGTTG GTAGCTCTTG ATCCGGCAAA CAAACCACCG CTGGTAGCGG

TGGTTTTTTT GTTTGCAAGC AGCAGATTAC GCGCAGAAAA AAGGATCTC AAGAAGATCC

TTTGATCTTT TCTACGGGGT CTGACGCTCA GTGGAACGAA AACTCACGTT AAGGGATTTT

GGTCATGAGA TTATCAAAAA GGATCTTCAC CTAGATCCTT TTAAATTAAA AATGAAGTTT

TAAATCAATC TAAAGTATAT ATGAGTAAAC TTGGTCTGAC AGTTACCAAT GCTTAATCAG
```

```
TGAGGCACCT ATCTCAGCGA TCTGTCTATT TCGTTCATCC ATAGTTGCCT GACTCCCCGT

CGTGTAGATA ACTACGATAC GGGAGGGCTT ACCATCTGGC CCCAGTGCTG CAATGATACC

GCGAGACCCA CGCTCACCGG CTCCAGATTT ATCAGCAATA AACCAGCCAG CCGGAAGGGC

CGAGCGCAGA AGTGGTCCTG CAACTTTATC CGCCTCCATC CAGTCTATTA ATTGTTGCCG

GGAAGCTAGA GTAAGTAGTT CGCCAGTTAA TAGTTTGCGC AACGTTGTTG CCATTGCTAC

AGGCATCGTG GTGTCACGCT CGTCGTTTGG TATGGCTTCA TTCAGCTCCG GTTCCCAACG

TCAAGGCGA GTTACATGAT CCCCCATGTT GTGCAAAAAA GCGGTTAGCT CCTTCGGTCC

CCGATCGTT GTCAGAAGTA AGTTGGCCGC AGTGTTATCA CTCATGGTTA TGGCAGCACT

CATAATTCT CTTACTGTCA TGCCATCCGT AAGATGCTTT TCTGTGACTG GTGAGTACTC

AACCAAGTCA TTCTGAGAAT AGTGTATGCG GCGACCGAGT TGCTCTTGCC CGGCGTCAAT

ACGGGATAAT ACCGCGCCAC ATAGCAGAAC TTTAAAAGTG CTCATCATTG GAAAACGTTC

TTCGGGGCGA AAACTCTCAA GGATCTTACC GCTGTTGAGA TCCAGTTCGA TGTAACCCAC

TCGTGCACCC AACTGATCTT CAGCATCTTT TACTTTCACC AGCGTTTCTG GGTGAGCAAA

AACAGGAAGG CAAAATGCCG CAAAAAAGGG AATAAGGGCG ACACGGAAAT GTTGAATACT

CATACTCTTC CTTTTTCAAT ATTATTGAAG CATTTATCAG GGTTATTGTC TCATGAGCGG

ATACATATTT GAATGTATTT AGAAAAATAA ACAAATAGGG GTTCCGCGCA CATTTCCCCG

AAAAGTGCCA CCTGACGTCG ACGGATCGGG A
```

SEQ ID NO: 18 is the amino acid sequence of the extracellular domain of human CTLA4.
MHVAQPAVVLASSRGIASFVCEYASPGKATEVRVTVLRQADSQVTEVCAATYMMGNELTFLD

DSICTGTSSGNQVNLTIQGLRAMDTGLYICKVELMYPPPYYLGIGNGTQIYVIDPEPCPDSD

Further Non-Limiting Embodiments

The invention provides for a clonal Chinese Hamster Ovary cell population capable of producing CTLA4-Ig. In one embodiment, the cell population is capable of producing greater than 0.5 or more grams of CTLA4-Ig protein per liter of liquid culture, and wherein the CTLA4-Ig exhibits a molar ratio of sialic acid to CTLA4-Ig dimer is from about 6 to about 14 at a culture scale of 1,000 L or more. In one embodiment, the cell population has been adapted to serum-free, chemically defined medium. In another embodiment, CTLA4-Ig produced from culture of the cell population has an extinction coefficient of $1.00 \pm 0.05$ AU mL cm$^{-1}$ mg$^{-1}$. In a further embodiment, the cell population, when grown in culture, is capable of producing CTLA4-Ig polypeptides, wherein: (a) about 90% of the CTLA4-Ig polypeptides comprise an amino acid sequence of SEQ ID NO:2 beginning with the methionine at residue 27; (b) about 10% of the CTLA4-Ig polypeptides comprise the amino acid sequence of SEQ ID NO:2 beginning with the alanine at residue number 26; (c) about 4% of the CTLA4-Ig polypeptides comprise the amino acid sequence of SEQ ID NO:2 ending with the lysine at residue number 383; (d) about 96% of the CTLA4-Ig polypeptides comprise the amino acid sequence of SEQ ID NO:2 ending with the glycine at residue number 382; and optionally, (e) about less than 1% of the CTLA4-Ig polypeptides comprise the amino acid sequence of SEQ ID NO:2 beginning with the methionine at residue number 25.

The invention provides for a progeny cell of the cells described above, wherein the progeny cell produces CTLA4-Ig. In one embodiment, the progeny cell is obtained from culturing a cell over at least 5 generations. In another embodiment, the progeny cell is obtained from culturing a cell over at least 10 generations. In another embodiment, the progeny cell is obtained from culturing a cell over at least 20 generations. In another embodiment, the progeny cell is obtained from culturing a cell over at least 40 generations. In another embodiment, the progeny cell is obtained from culturing a cell over at least 50 generations. In another embodiment, the progeny cell is obtained from culturing a cell over at least 75 generations. In another embodiment, the progeny cell is obtained from culturing a cell over at least 100 generations.

The invention provides for a cell line produced from any of the cells described above. In one embodiment, the cell line is clonal. In another embodiment, the cell line is capable of producing: (a) a CTLA4-Ig fusion protein having an amino acid sequence of SEQ ID NO:8 (methionine at amino acid position 27 and glycine at amino acid position 382 of SEQ ID NO:2); (b) a CTLA4-Ig fusion protein having an amino acid sequence of SEQ ID NO:5 (methionine at amino acid position 27 and lysine at amino acid position 383 of SEQ ID NO:2); (c) a CTLA4-Ig fusion protein having an amino acid sequence of SEQ ID NO:7 (alanine at amino acid position 26 and glycine at amino acid position 382 of SEQ ID NO:2); (d) a CTLA4-Ig fusion protein having an amino acid sequence of SEQ ID NO: 4 (alanine at amino acid position 26 and lysine at amino acid position 383 of SEQ ID NO:2); (e) a CTLA4-Ig fusion protein having an amino acid sequence of SEQ ID NO:4 (methionine at amino acid position 25 and lysine at amino acid position 383 of SEQ ID NO:2); or (f) a CTLA4-Ig fusion protein having an amino acid sequence of SEQ ID NO:6 (methionine at amino acid position 25 and glycine at amino acid position 382 of SEQ ID NO:2).

In another embodiment, the cell line is capable of producing CTLA4-Ig fusion proteins, wherein: (a) about 90% of the CTLA4-Ig polypeptides comprise an amino acid sequence of SEQ ID NO:2 beginning with the methionine at residue 27; (b) about 10% of the CTLA4-Ig polypeptides comprise the amino acid sequence of SEQ ID NO:2 beginning with the alanine at residue number 26; (c) about 4% of the CTLA4-Ig polypeptides comprise the amino acid sequence of SEQ ID NO:2 ending with the lysine at residue number 383; (d) about 96% of the CTLA4-Ig polypeptides comprise the amino acid sequence of SEQ ID NO:2 ending with the glycine at residue number 382; and optionally, (e) about less than 1% of the CTLA4-Ig polypeptides comprise the amino acid sequence of SEQ ID NO:2 beginning with the methionine at residue number 25.

In one embodiment, the CTLA4-Ig fusion proteins, which are produced from culturing the cell line, have an extinction coefficient of 1.00±0.05 AU mL cm-1 mg-1. In one embodiment, the invention provides for a cell population derived from a cell of the invention. In one embodiment, the cell population consists of at least one additional genetic change as compared to the originally transfected cell and wherein the derived cell population is capable of producing CTLA4-Ig. In other embodiments, the cell population consists of at least 2, 3, 4, 5, 6, 7, 8, 9, 10, 11, 12, 13, 14, 15, 16, 17, 18, 19, 20, 21, 22, 23, 24, 25, 26 additional genetic changes as compared to the originally transfected cell and wherein the derived cell population is capable of producing CTLA4-Ig. In one embodiment, the genetic change comprises at least one non-conservative mutation in the cellular genome or in the recombinant expression cassette encoding CTLA4-Ig.

In one embodiment, the genetic change comprises at least one additional recombinant nucleic acid within the cell. In one embodiment, the change comprises a mutation of the cellular genome. In one embodiment, the change comprises the addition of a nucleic acid to either the cell genome or as a trans nucleic acid, which encodes an anti-apoptotic polypeptide. In one embodiment, the anti-apoptotic polypeptide relates to glycosylation.

In one embodiment, genetic change comprises at least one mutation of the cellular genome or of the recombinant expression cassette encoding CTLA4-Ig. In one embodiment, the cell population, when grown in culture, is capable of producing: (a) a CTLA4-Ig fusion protein having an amino acid sequence of SEQ ID NO:8 (methionine at amino acid position 27 and glycine at amino acid position 382 of SEQ ID NO:2); (b) a CTLA4-Ig fusion protein having an amino acid sequence of SEQ ID NO:5 (methionine at amino acid position 27 and lysine at amino acid position 383 of SEQ ID NO:2); (c) a CTLA4-Ig fusion protein having an amino acid sequence of SEQ ID NO:7 (alanine at amino acid position 26 and glycine at amino acid position 382 of SEQ ID NO:2); (d) a CTLA4-Ig fusion protein having an amino acid sequence of SEQ ID NO: 4 (alanine at amino acid position 26 and lysine at amino acid position 383 of SEQ ID NO:2); (e) a CTLA4-Ig fusion protein having an amino acid sequence of SEQ ID NO:4 (methionine at amino acid position 25 and lysine at amino acid position 383 of SEQ ID NO:2); or (f) a CTLA4-Ig fusion protein having an amino acid sequence of SEQ ID NO:6 (methionine at amino acid position 25 and glycine at amino acid position 382 of SEQ ID NO:2).

The invention provides for a population of CTLA4-Ig molecules having an average molar ratio of sialic acid groups to CTLA4-Ig dimer of from about 6 to about 18. The invention provides for a population of CTLA4-Ig molecules having an average molar ratio of sialic acid groups to CTLA4-Ig dimer of from about 8 to about 18. The invention provides for a population of CTLA4-Ig molecules having an average molar ratio of sialic acid groups to CTLA4-Ig dimer of from about 11 to about 18. The invention provides for a population of CTLA4-Ig molecules having an average molar ratio of sialic acid groups to CTLA4-Ig dimer of from about 12 to about 18. The invention provides for a population of CTLA4-Ig molecules having an average molar ratio of sialic acid groups to CTLA4-Ig dimer of from about 13 to about 18. The invention provides for a population of CTLA4-Ig molecules having an average molar ratio of sialic acid groups to CTLA4-Ig dimer of from about 14 to about 18. The invention provides for a population of CTLA4-Ig molecules having an average molar ratio of sialic acid groups to CTLA4-Ig dimer of from about 15 to about 17. The invention provides for a population of CTLA4-Ig molecules having an average molar ratio of sialic acid groups to CTLA4-Ig dimer of about 16.

The invention provides for a population of CTLA4-Ig molecules, wherein greater than 95% of the molecules are CTLA4-Ig dimers. In one embodiment, greater than 98% of the molecules are CTLA4-Ig dimers. In one embodiment, greater than 99% of the molecules are CTLA4-Ig dimers. In one embodiment, greater than 99.5% of the molecules are CTLA4-Ig dimers. In one embodiment, from about 95% to about 99.5% of the molecules are CTLA4-Ig dimers and about 0.5% to about 5% of the molecules are CTLA4-Ig tetramers. In one embodiment, about 98.6% of the molecules are CTLA4-Ig dimers and about 1.2% of the molecules are CTLA4-Ig tetramers and about less than 0.7% of the molecules are CTLA4-Ig monomers. The invention provides for a population consisting of CTLA4-Ig dimers. The invention provides for a population of CTLA4-Ig molecules, wherein the population is substantially free of CTLA4-Ig monomer. The invention provides for a population of CTLA4-Ig molecules, wherein the population is substantially free of CTLA4-Ig tetramer. The invention provides for a population of CTLA4-Ig monomer molecules substantially free of CTLA4-Ig dimer and tetramer. In one embodiment, each monomer of each CTLA4-Ig dimer has at least 3 sialic acid groups.

In one embodiment, each monomer of each CTLA4-Ig dimer has from at least 3 sialic acid groups to at least 8 sialic acid groups. The invention provides for a purified population of CTLA4-Ig tetramer molecules, the population being substantially free of CTLA4-Ig dimer, and optionally wherein the population comprises an amount that is greater than about 100 grams. The invention provides for a purified population of CTLA4-Ig tetramer molecules, the population being substantially free of CTLA4-Ig monomer, and optionally wherein the population comprises an amount that is greater than about 100 grams. In one embodiment, each tetramer molecule comprises two pairs of CTLA4-Ig polypeptides, wherein each polypeptide has an amino acid sequence selected from the group consisting of SEQ ID NOS: 3-8, and wherein each member of the pair of polypeptides is covalently linked to the other member, and wherein the two pairs of polypeptides are non-covalently associated with one another. In one embodiment, each tetramer molecule is capable of binding to a CD80 or CD86. In one embodiment, each tetramer molecule has at least a 2-fold greater avidity for CD80 or CD86 as compared to a CTLA4-Ig dimer molecule. In one embodiment, each tetramer molecule has at least a 2-fold greater inhibition of T cell proliferation or activation as compared to a CTLA4-Ig dimer molecule.

The invention provides for a composition comprising CTLA4-Ig molecules, wherein the composition comprises dominant isoforms visualizable on an isoelectric focusing gel of CTLA4-Ig which have an isoelectric point, pI, less than or equal to 5.1 as determined by isoelectric focusing. In one embodiment, the pI increases after neuraminidase treatment. In one embodiment, at least 40% of the CTLA4-Ig molecules exhibit an isoelectric point less than or equal to about 5.1 as determined by isoelectric focusing. In one embodiment, at least 70% of the CTLA4-Ig molecules exhibit an isoelectric point less than or equal to about 5.1 as determined by isoelectric focusing. In one embodiment, at least 90% of the CTLA4-Ig molecules exhibit an isoelectric point less than or equal to about 2.5 as determined by isoelectric focusing. The invention provides for a population of CTLA4-Ig molecules having a pI of from about 2.0±0.2 to about 5.0±0.2. The invention provides for a population of CTLA4-Ig molecules having a pI from about 4.3±0.2 to about 5.0±0.2. The invention provides for a population of CTLA4-Ig molecules having a pI of about 3.3±0.2 to about 4.7±0.2. The invention provides for a method for preparing a composition, the composition comprising a CTLA4-Ig molecule with a pI of from about 2.0±0.2 to about 5.0±0.2, the method comprising: (a) subjecting a mixture of CTLA4-Ig molecules to isoelectric focusing gel electrophoresis, wherein a single band on the gel represents a population of CTLA4-Ig molecules with a particular pI, and (b) isolating the population of CTLA4-Ig molecules having a pI of from about 2.0±0.2 to about 5.0±0.2 so as to prepare the composition. The invention provides for a composition comprising CTLA4-Ig molecules, wherein the CTLA4-Ig molecules are characterized by an average molar ratio of GlcNAc per mole of CTLA4-Ig dimer of from about 17 to about 25. The invention provides for a composition comprising CTLA4-Ig molecules, wherein the CTLA4-Ig molecules are characterized by an average molar ratio of GlcNAc per mole of CTLA4-Ig dimer of from about 15 to about 35. The invention provides for a composition comprising CTLA4-Ig molecules, wherein the CTLA4-Ig molecules are characterized by an average molar ratio of GalNAc per mole of CTLA4-Ig dimer of from about 1.7 to about 3.6. The invention provides for a composition comprising CTLA4-Ig molecules, wherein the CTLA4-Ig molecules are characterized by an average molar ratio of galcatose per mole of CTLA4-Ig dimer of from about 8 to about 17. The invention provides for a composition comprising CTLA4-Ig molecules, wherein the CTLA4-Ig molecules are characterized by an average molar ratio of fucose per mole of CTLA4-Ig dimer of from about 3.5 to about 8.3. The invention provides for a composition comprising CTLA4-Ig molecules, wherein the CTLA4-Ig molecules are characterized by an average molar ratio of mannose per mole of CTLA4-Ig dimer of from about 7.2 to about 22. The invention provides for a composition comprising CTLA4-Ig molecules, wherein the CTLA4-Ig molecules are characterized by an average molar ratio of sialic acid per mole of CTLA4-Ig dimer of from about 6 to about 12. The invention provides for a composition comprising CTLA4-Ig molecules characterized by: (a) an average molar ratio of GlcNAc per mole of CTLA4-Ig dimer from about 15 to about 35; and (b) an average molar ratio of sialic acid per mole of CTLA4-Ig dimer from about 6 to about 12. The invention provides for a composition comprising CTLA4-Ig molecules characterized by: (a) an average molar ratio of GlcNAc per mole of CTLA4-Ig dimer from about 15 to about 35; (b) an average molar ratio of GalNAc per mole CTLA4-Ig dimer from about 1.7 to about 3.6; and (c) an average molar ratio of sialic acid per mole of CTLA4-Ig dimer from about 6 to about 12. The invention provides for a composition comprising CTLA4-Ig molecules characterized by: (a) an average molar ratio of GlcNAc per mole of CTLA4-Ig dimer from about 15 to about 35; (b) an average molar ratio of GalNAc per mole CTLA4-Ig dimer from about 1.7 to about 3.6; (c) an average molar ratio of galcatose per mole CTLA4-Ig dimer from about 8 to about 17; and (d) an average molar ratio of sialic acid per mole of CTLA4-Ig dimer from about 6 to about 12. The invention provides for a composition comprising CTLA4-Ig molecules characterized by: (a) an average molar ratio of GlcNAc per mole of CTLA4-Ig dimer from about 15 to about 35; (b) an average molar ratio of GalNAc per mole CTLA4-Ig dimer from about 1.7 to about 3.6; (c) an average molar ratio of galcatose per mole CTLA4-Ig dimer from about 8 to about 17; (d) an average molar ratio of fucose per mole CTLA4-Ig dimer from about 3.5 to about 8.3; and (e) an average molar ratio of sialic acid per mole of CTLA4-Ig dimer from about 6 to about 12. The invention provides for a composition comprising CTLA4-Ig molecules characterized by: (a) an average molar ratio of GlcNAc per mole of CTLA4-Ig dimer from about 15 to about 35; (b) an average molar ratio of GalNAc per mole CTLA4-Ig dimer from about 1.7 to about 3.6; (c) an average molar ratio of galcatose per mole CTLA4-Ig dimer from about 8 to about 17; (d) an average molar ratio of fucose per mole CTLA4-Ig dimer from about 3.5 to about 8.3; (e) an average molar ratio of mannose per mole CTLA4-Ig dimer from about 7.2 to about 22; and (f) an average molar ratio of sialic acid per mole of CTLA4-Ig dimer from about 6 to about 12.

Figure 19:
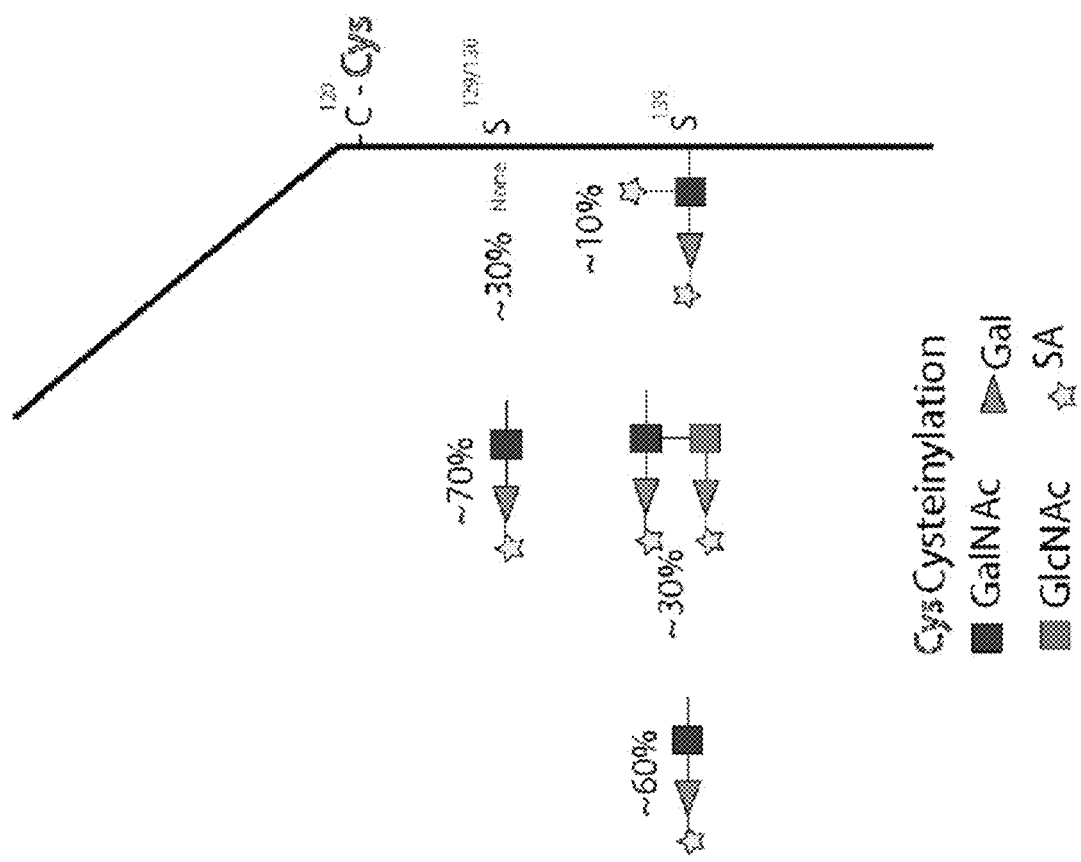
FIG. 19 shows the attachment points and relative populations of O-linked carbohydrate structures of a CTLA4-Ig single chain having a SEQ ID NO:2 monomer sequence. The relative amounts at each site show data generated by two or more orthogonal techniques and are subject to variability. The location of the covalent cysteinylation is also depicted.
Figure 20:
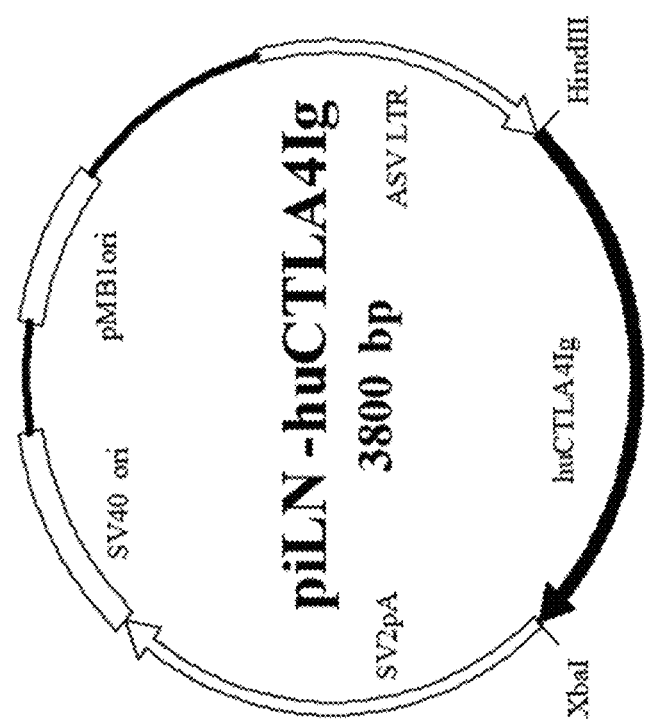
FIG. 20 depicts a map of the intermediate plasmid piLN-huCTLA4-Ig. This plasmid has comprises a sequence that can encode a human CTLA4-Ig molecule (huCTLA4-Ig) (i.e., SEQ ID NO:1) flanked by the restriction enzyme sites HindIII and XbaI.

The invention provides for a composition comprising CTLA4-Ig molecules, wherein composition exhibits an NGNA chromatogram peak of about 9.589+/−0.3 and an NANA chromatogram peak of about 10.543+/−0.3. The invention provides for a composition comprising CTLA4-Ig molecules, wherein the CTLA-Ig molecules exhibit a carbohydrate profile as shown in FIG. 7. The invention provides for a composition comprising CTLA4-Ig molecules, wherein the CTLA4-Ig molecules exhibit a carbohydrate profile of Domains I-IV, wherein Domain I comprises peaks which represent a-sialylated oligosaccharides, Domain II comprises peaks which represent mono-sialylated oligosaccharides, Domain III comprises peaks which represent di-sialylated oligosaccharides, and Domain IV comprises peaks which represent tri-sialylated oligosaccharides. In one embodiment, the difference in retention times of N-linked oligosaccharides between a first peak in Domain I and a main peak in Domain II is from about 22 to about 28 minutes. The invention provides for a composition comprising CTLA4-Ig dimer molecules, wherein at least 0.5% of the CTLA4-Ig dimer molecules are cysteinylated. In another embodiment, at least 1.0% of the CTLA4-Ig dimer molecules are cysteinylated. The invention provides for a population of CTLA4-Ig molecules, wherein the population exhibits a mass spectrometry profile as shown in FIG. 8. The invention provides for a population of CTLA4-Ig molecules, wherein the population exhibits a capillary electrophoresis profile as shown in FIGS. 19 and 20. The invention provides for a composition of CTLA4-Ig molecules having an average molar ratio of sialic acid groups to CTLA4-Ig dimer of from about 6 to about 18, wherein the CTLA4-Ig dimer is produced from cells of a commercial cell line. The invention provides for a CTLA4-Ig composition obtained by any method of the invention. The invention provides for a population of CTLA4-Ig molecules, wherein the molecules are glycosylated at an aparagine amino acid residue at position 102 of SEQ ID NO:2, an aparagine amino acid residue at position 134 of SEQ ID NO:2, an aparagine amino acid residue at position 233 of SEQ ID NO:2, a serine amino acid residue at position 155 of SEQ ID NO:2, a serine amino acid residue at position 165 of SEQ ID NO:2. The invention provides for a population of CTLA4-Ig molecules, wherein the population of molecules is characterized by: (a) an average molar ratio of GlcNAc per mole of CTLA4-Ig dimer from about 15 to about 35; (b) an average molar ratio of GalNAc per mole CTLA4-Ig dimer from about 1.7 to about 3.6; (c) an average molar ratio of galcatose per mole CTLA4-Ig dimer from about 8 to about 17; (d) an average molar ratio of fucose per mole CTLA4-Ig dimer from about 3.5 to about 8.3; (e) an average molar ratio of mannose per mole CTLA4-Ig dimer from about 7.2 to about 22; (f) an average molar ratio of sialic acid per mole of CTLA4-Ig dimer from about 6 to about 12; (g) a pI as determined from visualization on an isoelectric focusing gel in a range from about 2.4±0.2 to about 5.0±0.2; (h) MCP-1 of less than or equal to 5 ppm; (i) less than 2.5% tetramer; (j) less than 0.5% monomer; (k) CTLA4-Ig polypeptides of the population having an amino acid at least 95% identical to any of SEQ ID NOS: 2-8; (l) wherein CTLA4-Ig molecules within the population is capable of binding to CD80 and CD86. The invention provides for a population of CTLA4-Ig molecules, wherein the population of molecules is characterized by: (a) an average molar ratio of GlcNAc per mole of CTLA4-Ig dimer from about 15 to about 35; (b) an average molar ratio of GalNAc per mole CTLA4-Ig dimer from about 1.7 to about 3.6; (c) an average molar ratio of galcatose per mole CTLA4-Ig dimer from about 8 to about 17; (d) an average molar ratio of fucose per mole CTLA4-Ig dimer from about 3.5 to about 8.3; (e) an average molar ratio of mannose per mole CTLA4-Ig dimer from about 7.2 to about 22; (f) an average molar ratio of sialic acid per mole of CTLA4-Ig dimer from about 6 to about 12; (g) a pI as determined from visualization on an isoelectric focusing gel in a range from about 2.4±0.2 to about 5.0±0.2; (h) MCP-1 of less than or equal to 5 ppm; (i) less than 2.5% tetramer; (j) less than 0.5% monomer; (k) CTLA4-Ig polypeptides of the population having an amino acid at least 95% identical to any of SEQ ID NOS: 2-8; (l) wherein CTLA4-Ig molecules within the population is capable of binding to CD80 and CD86; or pharmaceutical equivalents thereof. The invention provides for a composition comprising an effective amount of the CTLA4-Ig molecules and a pharmaceutically acceptable carrier. The invention provides for a composition comprising an effective amount of the CTLA4-Ig molecules, wherein the composition further comprises an amount of maltose monohydrate. In one embodiment, the composition further comprises a pharmaceutically acceptable diluent, adjuvant or carrier. In one embodiment, the composition further comprises maltose, sodium phosphate monobasic monohydrate, sodium chloride, sodium hydroxide, and sterile water. In one embodiment, the composition further comprises sucrose, poloxamer, sodium phosphate monobasic monohydrate, sodium phosphate dibasic anhydrous, sodium chloride, sodium hydroxide, and sterile water.

The invention provides for a lyophilized CTLA4-Ig mixture comprising at least 95% CTLA4-Ig dimer, and not more than 5% CTLA4-Ig tetramer. In one embodiment, the mixture comprises at least 98% CTLA4-Ig dimer and no more than 2% CTLA4-Ig tetramer. In one embodiment, the mixture comprises at least 99% CTLA4-Ig dimer and no more than 1% CTLA4-Ig tetramer. In one embodiment, the mixture comprises at least 8.0 moles of sialic acid per mole of CTLA4-Ig dimer. In one embodiment, the mixture comprises from about 15.7 to about 31 moles of GlcNAc per mole of CTLA4-Ig dimer. In one embodiment, the mixture comprises from about 1.6 to about 3.2 moles of GalNAc per mole of CTLA4-Ig dimer. In one embodiment, the mixture comprises from about 9.3 to about 15.5 moles of galactose per mole of CTLA4-Ig dimer. In one embodiment, the mixture comprises from about 3.6 to about 7.9 moles of fucose per mole of CTLA4-Ig dimer. In one embodiment, the mixture comprises from about 9.7 moles of mannose per mole of CTLA4-Ig dimer. The invention provides for a pharmaceutical kit comprising: (a) a container containing a lyophilized CTLA4-Ig mixture of claim 1; and (b) instructions for reconstituting the lyophilized CTLA4-Ig mixture into solution for injection.

The invention provides for a method for inhibiting T cell proliferation (or activation), the method comprising contacting a T cell with an effective amount of the CTLA4-Ig composition. The invention provides for a method for inhibiting an immune response in a subject, the method comprising administering to a subject in need thereof an effective amount of the composition. The invention provides methods for inducing immune tolerance to an antigen in a subject, treating inflammation in a subject, treating rheumatoid arthritis, treating psoriasis in a subject, treating lupus in a subject, treating or preventing an allergy in a subject, treating or preventing graft vs host disease in a subject, treating or preventing rejection of a transplanted organ in a subject, treating multiple sclerosis in a subject, treating type I diabetes in a subject, treating inflammatory bowel disease in a subject, treating oophoritis in a subject, treating glomerulonephritis in a subject, treating allergic encephalomyelitis in a subject, or treating myasthenia gravis in a subject by administering a composition of the invention in an amount to a subject to treat the disease or disorder. The composition may be combined with a pharmaceutically acceptable carrier. The invention provides for the use of a population of CTLA4-Ig molecules having an average molar ratio of sialic acid groups to CTLA4-Ig dimer of from about 6 to about 18 in the manufacture of a medicament for the therapeutic and/or prophylactic treatment of an immune disorder. The invention provides for the use of a population of CTLA4-Ig molecules having an average molar ratio of sialic acid groups to CTLA4-Ig dimer of from about 6 to about 18 in the manufacture of an anti-rheumatoid arthritis agent in a package together with instructions for its use in the treatment of rheumatoid arthritis. The invention provides for a method for inhibiting T cell proliferation (or activation), the method comprising contacting a T cell with an effective amount of the composition of the invention in combination with methotrexate. The invention provides for a method for inhibiting an immune response in a subject, the method comprising administering to a subject in need thereof an effective amount of the composition of the invention in combination with methotrexate. The invention provides for a method for inducing immune tolerance to an antigen in a subject, the method comprising administering to a subject in need thereof an effective amount of the composition of any of claims 1-64 in combination with methotrexate. The invention provides for a method for producing a recombinant protein, the method comprising: (a) expanding mammalian cells that secrete a recombinant protein, wherein the expanding is from a seed culture to a liquid culture of at least 10,000 L, wherein the recombinant protein concentration is at least 0.5 grams/L of liquid culture; and (b) isolating the recombinant protein from the at least 10,000 L liquid culture. In one embodiment, the expanding of step (a) comprises: (i) culturing the cells in a serum-free, chemically defined medium with at least four passages so as to obtain a cell density of at least about $1.0 \times 10^5$ viable cells per mL, wherein each seed stage starts at about $2 \times 10^5$ per ml and goes to 1-2 mil cells per ml; (ii) maintaining the cells in culture for a time sufficient to produce from the culture at least about 0.5 g/L. In one embodiment, the protein is a glycoprotein. In one embodiment, the protein is a CTLA4-Ig protein. In one embodiment, the mammalian cells are progeny cells. In one embodiment, the mammalian cells are progeny of a CHO clonal cell line capable of producing CTLA4-Ig fusion protein, wherein the CHO cells have stably integrated in their genome at least 30 copies of a CTLA4-Ig expression cassette. In one embodiment, the time sufficient is a time by which the cells' viability does not fall below 30%. In one embodiment, the time sufficient is a time by which the cells' viability does not fall below 40%. In one embodiment, the time sufficient is a time by which the cells' viability does not fall below 50%. In one embodiment, the time sufficient is a time by which the cells' viability does not fall below 60%. In one embodiment, the time sufficient is a time by which the cells' viability does not fall below 70%, or 80% or 90% or 95%. In one embodiment, the at least four passages comprises: (i) growing the cells in a culture volume of at least 50 mL until a cell density of from about 1 million to about 2.5 mill cels per ml is reached, (ii) growing the cells in a culture volume of at least 10 L until a cell density of about 1 million to about 2.5 million cels per ml is reached; (iii) growing the cells in a culture volume of at least 100 L until a cell density of about 1 million to about 2.5 million cels per ml is reached; and (iv) growing the cells in a culture volume of 200 L until a cell density of about 1 million to about 2.5 million cels per ml is reached. In one embodiment, galactose is added to the serum-free, chemically defined medium. In one embodiment, the maintaining comprises (i) lowering the temperature of the culture from $37\pm2°$ C. to $34\pm2°$ C.; and (ii) lowering the temperature of the culture from $34\pm2°$ C. to $32\pm2°$ C. In one embodiment, the temperature is kept within the range of $32\pm2°$ C. for at least 5 days. In one embodiment, the temperature is kept within the range of $32\pm2°$ C. for at least 6 days. In one embodiment, the temperature is kept within the range of $32\pm2°$ C. for at least 7 days. In one embodiment, the temperature is kept within the range of $32\pm2°$ C. for at least 8 days. In one embodiment, the temperature is kept within the range of $32\pm2°$ C. for at least 9 days. In one embodiment, the temperature is kept within the range of $32\pm2°$ C. for at least 10 days. In one embodiment, the temperature is kept within the range of $32\pm2°$ C. for at least 11 days. In one embodiment, the temperature is kept within the range of $32\pm2°$ C. for at least 12 days. In one embodiment, the temperature is kept within the range of $32\pm2°$ C. for at least 13 days. In one embodiment, the temperature is kept within the range of $32\pm2°$ C. for at least 14 days. In one embodiment, the temperature is kept within the range of $32\pm2°$ C. for at least 15 days. In one embodiment, the temperature is kept within the range of $32\pm2°$ C. for at least 16 days. In one embodiment, the temperature is kept within the range of $32\pm2°$ C. for at least 17 days. In one embodiment, the temperature is kept within the range of $32\pm2°$ C. for at least 18 days. In one embodiment, the temperature is kept within the range of $32\pm2°$ C. for up to 18 days. In one embodiment, the temperature is kept within the range of $32\pm2°$ C. until the cell density of the culture is from about $30 \times 10^5$ to about $79 \times 10^5$ cells per mL of liquid culture. The invention provides for a method for producing a recombinant protein, the method comprising: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the at least 10,000 L liquid culture, wherein the isolating occurs only when the liquid culture contains greater than or equal to about 6.0 moles of NANA per mole of protein. The invention provides for a method for producing a recombinant protein, the method comprising: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the at least 10,000 L liquid culture, wherein the isolating occurs only when the liquid culture has a cell density of from about $33 \times 10^5$ to about $79 \times 10^5$ cells per mL.

The invention provides for a method for producing a recombinant protein, the method comprising: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the at least 10,000 L liquid culture, wherein the isolating occurs when cell viability in the liquid culture has not fallen below about 20%, or about 30%, or about 38%. The invention provides for a method for producing a recombinant protein, the method comprising: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the at least 10,000 L liquid culture, wherein the isolating occurs only when endotoxin is less than or equal to about 76.8 EU per mL of liquid culture. The invention provides for a method for producing a recombinant protein, the method comprising: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the at least 10,000 L liquid culture, wherein the isolating occurs only when bioburden is less than 1 colony forming unit per mL of liquid culture. The invention provides for a method for producing a recombinant protein, the method comprising: (a) expanding mammalian cells that secrete a recombinant protein from a seed culture to a liquid culture of at least 10,000 L so that the recombinant protein concentration is at least 0.5 grams/L of liquid culture; and (b) isolating the recombinant protein from the at least 10,000 L liquid culture, wherein the isolating occurs only if at least two of the following conditions are met: (i) the liquid culture contains greater than or equal to about 6.0 moles of NANA per mole of protein, (ii) the liquid culture has a cell density of from about $33 \times 10^5$ to about $79 \times 10^5$ cells per mL, (iii) cell viability in the liquid culture has not fallen below about 20%, or about 38%, or (iv) amount of CTLA4-Ig in the culture is greater than 0.5 g/L. In one embodiment, the isolating comprises: (i) obtaining a cell culture supernatent; (ii) subjecting the supernatant to anion exchange chromotagraphy to obtain an eluted protein product; (iii) subjecting the eluted protein product of step (ii) to hydrophobic interaction chromatography so as to obtain an enriched protein product; (iv) subjecting the enriched protein product to affinity chromatography to obtain an eluted and enriched protein product; and (v) subjecting the eluted and enriched protein product of (iv) to anion exchange chromatography. In one embodiment, the enriched protein product obtained in step (iii) is characterized in that a percentage of any high molecular weight multimer is less than 25% by weight. In one embodiment, the anion exchange chromatography of step (ii) is carried out using a wash buffer comprising about 75 mM HEPES, and about 360 mM NaCl, and having a pH of about 8.0. In one embodiment, the anion exchange chromatography of step (ii) is carried out using an elution buffer comprising about 25 mM HEPES, and about 325 mM NaCl, and having a pH of about 7.0. In one embodiment, the hydrophobic interaction chromatography of step (iii) is carried out using a single wash buffer comprising about 25 mM HEPES, and about 850 mM NaCl, and having a pH of about 7.0. In one embodiment, the affinity chromatography of step (iv) is carried out using a wash buffer comprising about 25 mM Tris, and about 250 mM NaCl, and having a pH of about 8.0. In one embodiment, the affinity chromatography of step (iv) is carried out using an elution buffer comprising about 100 mM Glycine and having a pH of about 3.5. In one embodiment, the anion exchange chromatography of step (v) is carried out using a wash buffer comprising about 25 mM HEPES, and from about 120 mM NaCl to about 130 mM NaCl, and having a pH of about 8.0. In one embodiment, the anion exchange chromatography of step (v) is carried out using an elution buffer comprising about 25 mM HEPES, and about 200 mM NaCl, and having a pH of about 8.0. In one embodiment, the anion exchange chromatography of step (ii) is carried out using a column having an anion exchange resin having a primary, secondary, tertiary, or quartenary amine functional group. In one embodiment, the resin has a quartenary amine functional group. In one embodiment, the hydrophobic interaction chromatography of step (iii) is carried out using a hydrophobic interaction resin having a phenyl, an octyl, a propyl, an alkoxy, a butyl, or an isoamyl functional group. In one embodiment, the functional group is a phenyl functional group. In one embodiment, the affinity chromatography of step (iv) is carried out using a column containing Protein A. In one embodiment, method for preparing CTLA4-Ig, the method comprising purifying CTLA4-Ig from a liquid cell culture so that the purified CTLA4-Ig (a) has about 38 ng of MCP-1 per mg of CTLA4-Ig dimer, and (b) comprises less than 2.5% of CTLA4-Ig tetramer by weight.

In one embodiment, the liquid cell culture comprises a cell of or a progeny cell of the invention. The invention provides a method for producing CTLA4-Ig, the method comprising: (a) expanding progeny cells of any of commercial cell line or CHO cells that are capable of producing CTLA4-Ig, wherein the expanding is from a seed culture to a liquid culture of at least 10,000 L, wherein the CTLA4-Ig concentration is at least 0.5 grams/L of liquid culture; and (b) isolating CTLA4-Ig from the at least 10,000 L liquid culture, wherein the chromotagraphy is on a column with hydrophobic interaction resin with at least a phenyl functional group, wherein the isolating comprises a step of hydrophobic interaction chromatography carried out using a single wash buffer comprising about 25 mM HEPES, and about 850 mM NaCl, and having a pH of about 7.0.

EXAMPLES OF THE INVENTION

A number of Examples are provided below to facilitate a more complete understanding of the present invention. The following examples illustrate the exemplary modes of making and practicing the present invention. However, the scope of the invention is not limited to specific embodiments disclosed in these Examples, which are for purposes of illustration only, since alternative methods may be utilized to obtain similar results.

The following Examples refer to CTLA4-Ig molecules that comprise sequences of one or more of SEQ ID NOS: 2, 4, 5, 6, 7, 8, 9, 10, 11, 12, 13, 14, 15 or 16. These Examples are not meant to be limiting, and one skilled in the art understands that the Examples can be expanded and adapted to, for example, other CTLA4-Ig molecules, other glycoproteins, and other proteins related to or comprising portions of an Ig-superfamily protein.

The following table sets out examples that relate to CTLA4-Ig and to CTLA4$^{A29YL104E}$-Ig.

| CTLA4-Ig Protein Characteristics | Exemplary CTLA4-Ig Protein No. 1 - CTLA4-Ig having SEQ ID NO: 1, 2, 5, 6, 7, 8, 9, or 10 | Exemplary CTLA4-Ig Protein No. 2 - CTLA4$^{A29YL104E}$-Ig having SEQ ID NO: 3 or 4 or 11-16 |
|---|---|---|
| Binding to B7-1; on/off rates; potency, valency | Example 6 | |
| Bioburden | Example 49 | |
| Capillary Electrophoresis | | Example 38 |
| Carbohydrate content, N-linked | Example 3 Example 44 | Example 22 |
| HPEAC profile, Domains | | Example 37 |
| Cell line transfection | Example 12 | Example 23 |
| CHO DNA | Example 58 | Example 55 |
| CHO Host cell protein | Example 60 | Example 52 |
| Genetic Characterization | | Example 24 |
| Disaggregation | Example 5 Example 33 | |
| Endotoxin | Example 48 | Example 48 |
| Final fill | Example 30 | |
| Formulations | Example 2 | Example 27 |
| GalNAc, GlcNAc molar ratios | Example 17, Example 63 | Example 36 |
| IEF | Example 50 | Example 22 |
| IL-2 bioassay | Example 45 | Example 40 |
| Immunogenicity | Example 31 | |
| Single dose healthy PK | Example 66 | |
| MALDI-TOF | Example 8 | |
| Mannose, fucose, galactose molar ratios | Example 18 Example 64 | Example 35 |
| Mass Spec | Example 7 | |
| MCP-1 | Example 59 | Example 54 |
| Media/culturing | Example 9 | |
| Monkey PK | Example 32 | |
| Monomer | Example 4 | |
| NANA, NGNA molar ratios | Example 3, Example 16 | Example 39 |
| O-linked | Example 46 | |
| Oxidation and Deamidation | Example 47 | |
| PK Correlations | Example 42 | |
| Plasmid | Example 1, Example 11, Example 67 | |
| Production | Example 14 Example 28 | Example 19 |
| Protein A Purification | Example 62 Example 15 Example 29 | Example 53 Example 20 |
| Multiple Dose RA PK | Example 34 | |
| SDS-PAGE | Example 51 | Example 26 Example 56 |
| SEC - HMW, dimer, monomer, size homogeneity | Example 10 | Example 25 |
| SPR - binding to B7.1 (BIAcore) | Example 21 | Example 41 |
| Sub-cloning of cell lines | Example 13 | Example 24 |

| CTLA4-Ig Protein Characteristics | Exemplary CTLA4-Ig Protein No. 1 - CTLA4-Ig having SEQ ID NO: 1, 2, 5, 6, 7, 8, 9, or 10 | Exemplary CTLA4-Ig Protein No. 2 - CTLA4$^{A29YL104E}$-Ig having SEQ ID NO: 3 or 4 or 11-16 |
|---|---|---|
| Triton-X 100 | Example 61 | Example 57 |
| Trypic mappings | Example 3, Example 47, Example 65 | Example 22 |

Abbreviations 15N 15 Nanometer
$A_{280}$ Absorbance at 280 nm
CTLA4-Ig Cytotoxic T-Lymphocyte Antigen-4 Immunoglobulin; CTLA-4 Ig
API Active Pharmaceutical Ingredient
AU Absorbance Units
B7 CTLA-4 Receptor Ligand
cfu Colony Forming Unit
CHO Chinese Hamster Ovary
CHOP Chinese Hamster Ovary Host Cell Proteins
CV Column Volume
Drug Substance Fill Drug Substance Concentration/Diafiltration and Fill Step
ELISA Enzyme Linked Immunosorbent Assay
EU Endotoxin Units
Fc The constant region of antibodies
GalNAc N-Acetyl-galactosamine
GlcNAc N-Acetyl-glucosamine
HEPES 4-(2-Hydroxyethyl)piperazine-1-ethanesulfonic Acid
HIC Hydrophobic Interaction Chromatography; Phenyl Sepharose™ Fast Flow
HMW High Molecular Weight
HPLC High Performance Liquid Chromatography
IgG1 Immunoglobulin in Class G1
IPC In-Process Control
LAL Limulus Amebocyte Lysate
MBR(s) Master Batch Record(s)
MCP-1 Monocyte Chemotactic Protein 1
MTX Methotrexate
MW Molecular Weight
N/A Not Applicable
NANA N-acetylneuraminic Acid; Sialic Acid; SA
NMWC Nominal Molecular Weight Cutoff
OD Optical Density
PAR Proven Acceptable Range
Planova Viral removal filters, pore size 15 nm
PP(s) Process Parameter(s)
PQ Performance Qualification
psi Pounds per Square Inch
psid Pounds per Square Inch, Differential
psig Pounds per Square Inch; Gauge
QFF Q Sepharose™ Fast Flow
QXL Q Sepharose Extreme Load
rPA Recombinant Protein A Sepharose Fast Flow
SA Sialic Acid; N-acetylneuraminic Acid; NANA
SDS-PAGE Sodium Dodecylsulfate Polyacrylamide Gel Electrophoresis
SOP Standard Operating Procedure
Tris Tris (Hydroxymethyl) Aminomethane
Triton X-100 t-Octylphenoxypolyethoxyethanol; Polyethylene glycol tert-octylphenyl ether
UF Ultrafiltration
UV Ultraviolet
v/v Volume per Volume
VF Viral Filtration; Nanometer Filtration
VI Viral Inactivation Example 1: Confirmation of the CTLA4-Ig Coding Sequence in Plasmid pcSDhuCTLA4-Ig The annotated nucleic acid sequence of the CTLA4-Ig gene present in pcSDhuCTLA4-Ig and the corresponding deduced amino acid sequence of CTLA4-Ig are shown in FIG. 1. The pcSDhuCTLA4-Ig nucleic acid was transfected into CHO cells in order to generate stable transfectants that could express CTLA4-Ig molecules (see Example 12). The transfectants were screened and certain transfectants were subcloned or expanded to generate clonal cell lines.

Analysis of the DNA sequence data confirmed that the junctions created during the plasmid construction were as designed and that the synthetic oligonucleotide primers used in the polymerase chain reaction generated the correct oncostatin M signal sequence upstream of the CTLA4-Ig sequence. The desired cysteine to serine changes (at positions 156, 162 and 165 of SEQ ID NO:2) in the hinge region of the fusion protein were confirmed. These amino acid residues are designated in bold with an asterisk in FIG. 1. An additional amino acid change of proline to serine at position 174 of SEQ ID NO:2 was also detected. This change was introduced during the $IgG_1$ cDNA synthesis by the polymerase chain reaction. This amino acid residue is also designated in bold with an asterisk in FIG. 1.

The analysis of the DNA sequence data identified one additional difference when compared to the published nucleotide sequences of the human CTLA4 and human $IgG_1$ constant region. The codon at amino acid 110 of the CTLA4 coding region was identified as ACC (threonine) rather than GCC (alanine).

Example 2: CTLA4-Ig Formulation

CTLA4-Ig composition for Injection, 250 mg/vial, is a sterile, non-pyrogenic lyophile for intravenous (IV) administration. The population of CTLA4-Ig molecules is packaged in 15-cc Type I flint tubing glass vials. Each vial is stoppered with a 20-mm Daikyo gray butyl D-21-7-S/B2-TR fluoro-resin coated stopper and sealed with a 20-mm aluminum, white, flip-off seal.

Each single-use vial contains 250 mg of CTLA4-Ig composition which is constituted with Sterile Water for Injection, USP and further diluted with 0.9% Sodium Chloride Injection, USP, at the time of use. The composition of CTLA4-Ig for Injection, 250 mg/vial, and the function of each component is listed in the Table below.

TABLE 8

Composition of CTLA4-Ig

| Component | Function | mg per Vial |
|---|---|---|
| CTLA4-Ig | Active Ingredient | 262.5 |
| Maltose Monohydrate | Bulking Agent/ Stabilizer | 525 |
| Sodium Phosphate, Monobasic, Monohydrate$^b$ | Buffering Agent | 18.1 |
| Sodium Chloride$^b$ | Ionic Strength Adjustment | 15.3 |

TABLE 8-continued

Composition of CTLA4-Ig

| Component | Function | mg per Vial |
|---|---|---|
| Hydrochloric Acid | pH Adjustment | adjust pH to ~7.5 |
| Sodium Hydroxide | pH Adjustment | |

[b]These components are present in the CTLA4-Ig composition solution

CTLA4-Ig composition contains approximately 50 mg/mL CTLA4-Ig in 25 mM sodium phosphate buffer and 50 mM sodium chloride at pH 7.5. During early development, this buffer system was selected based on the evaluation of the physical and chemical stability of CTLA4-Ig as a function of pH, buffer type, buffer concentration and sodium chloride concentration. The stability of CTLA4-Ig solutions was investigated in the pH range of 5 to 9. The results indicated that the formation of high molecular weight species was pH dependent and the pH range of maximum stability was between 7 and 8. In a separate determination, the effect of buffer type and concentration was evaluated, where the CTLA4-Ig composition was found to be equally stable in sodium phosphate or tris buffer at pH 8. Additionally, the buffer concentrations between 10 to 100 mM concentration did not have any impact on the stability of the CTLA4-Ig composition at 2°–8° C. Similarly, the presence of sodium chloride between 30 to 500 mM concentration had no effect on the solution-state stability of the CTLA4-Ig composition stored at 2°–8° C.

Based on these results, the CTLA4-Ig composition at 10 mg/mL in 25 mM sodium phosphate buffer and 50 mM sodium chloride at pH 7.5 was selected for formulation at 50 mg/vial strength. The CTLA4-Ig concentration was later changed to 50 mg/mL in the same buffer composition to allow for the development of the CTLA4-Ig compositions with 200- and 250 mg/vial strengths.

CTLA4-Ig for injection is formulated with maltose in addition to sodium phosphate buffer and sodium chloride. The function of excipients used in this product is listed in the Table above.

The presence of inorganic salts, such as sodium chloride and sodium phosphate buffer components reduce the glass transition temperature (Tg') of the frozen system. Moreover, dibasic sodium phosphate, which is formed in situ at pH 7.5 undergoes preferential crystallization during freezing, which reduces the micro-environmental pH of the frozen solution. Based on these reasons, the minimum amounts of sodium chloride and sodium phosphate buffer were selected to minimize their impact on the lyophilization process. Maltose is added as a stabilizer which acts as a cryo- and lyo-protectant during lyophilization and upon subsequent storage of the drug product, respectively. CTLA4-Ig composition for Injection, 250 mg/vial, is a sterile, single use vial without antimicrobial preservatives.

Example 3: Carbohydrate Content Analysis of a CTLA4-Ig Composition

The purpose of the method is to provide chromatographic profiles of CTLA4-Ig N-linked oligosaccharides. This procedure can be used to obtain the molar ratio of N-Acetyl Neuraminic Acid (NANA) and N-Glycolyl Neuraminic Acid (NGNA) to protein in CTLA4-Ig samples (total bound plus free). NANA and NGNA are two forms of sialic acid. The glycosylation on the CTLA4-Ig protein contains N-linked oligosaccharides. For example, these oligosaccharides can be liberated by enzymatic hydrolysis with PNGase F over the course of 22 hours. The free oligosaccharides are profiled using high pH anion exchange chromatography employing electrochemical detection. Carbohydrate profiles for the N-linked oligosaccharides were evaluated using High pH Anion Exchange Chromatography with Pulsed Amperometric Detection (HPAEC-PAD). These profiles were confirmed and structural information was obtained using Porous Graphitized Carbon (PGC) chromatography coupled with MS. Both techniques and results are described in this section. This procedure is exemplary for CTLA4-Ig of SEQ ID NO:

N-Linked Oligosaccharide Isolation:

Cleavage of asparagine-linked (N-linked) oligosaccharides from CTLA4-Ig was performed by enzymatic hydrolysis using PNGase F. To perform the deglycosylation, CTLA4-Ig was first reduced and denatured: 1-2 mg of CTLA4-Ig in 176 μL of 5 mM sodium phosphate buffer containing 0.5% SDS and 1% beta-mercaptoethanol was heated at 100° C. for 2 minutes, then allowed to cool to ambient temperature. To the cooled mixture, 16 μL of 10% NP-40 were added. The sample was mixed well and 40 μL of PNGase F (50,000 U/mL, in 50 mM sodium phosphate buffer) were added. The sample was mixed well and incubated at 38° C. for 24 hrs. The enzymatically-released oligosaccharides (glycans) were purified by reversed phase high performance liquid chromatography (HPLC) using a Phenomenex Luna C18 column (4.6×150 mm; 5 μL) coupled with a Thermo HyperCarb column (4.6×100 mm; 5 μL) at a flow rate of 1.0 mL/minute; the chromatograph used for the isolation was a Waters Alliance 2695 equipped with a Waters 2996 detector. The columns were first equilibrated with 0.05% triflouroacetic acid (TFA). After injection of a sample, a gradient of acetonitrile was initiated, terminating at 15 minutes with a solvent composition of 0.05% TFA in 12% acetonitrile. The glycans were then eluted from the HyperCarb column with a step gradient to 0.05% TFA in 60% acetonitrile. The glycans were collected while monitoring by UV absorbance at 206 nm and were concentrated to dryness under vacuum. Prior to subsequent injections the Luna C18 column was cleaned with 0.05% TFA in 40% acetonitrile, 40% isopropanol, 20% water.

Preparation of NANA Stock Solution (N-Acetyl Neuraminic Acid) (1 mg/mL). Important: Prior to weighing, allow the NANA standard to warm to room temperature. Failure to do so will result in water condensation in the standard. Open only long enough to obtain desired amount, then reseal bottle tightly and return to freezer, storing with desiccant. Accurately weigh between 3 and 10 mg of the N-Acetyl Neuraminic Acid. Record to the nearest 0.1 mg. Transfer to an appropriate size container if weighing is done using weighing paper/boat. Add sufficient amount of HPLC grade water to yield a concentration of 1 mg/mL solution. Mix with a stirring bar or by vortexing until dissolved. Store between 2 and 8° C. for up to 3 months in a polypropylene tube.

Preparation of NGNA Stock Solution (N-Glycolyl Neuraminic Acid) (1 mg/mL) Important: Prior to weighing, allow the NGNA standard to warm to room temperature. Failure to do so will result in water condensation in stock. Open only long enough to obtain desired amount then reseal bottle tightly and return to freezer, storing with desiccant. Accurately weigh between 3 and 10 mg (record to the nearest 0.1 mg of Nglycolyl Neuraminic Acid. Record to the nearest 0.1 mg. Transfer to an appropriate size container if weighing is done using weighing paper/boat. Add an appropriate volume of HPLC grade water to yield a target concentration of 1 mg/mL solution. Mix with a stirring bar or by vortexing until dissolved. Store between 2 and 8° C. for up to 3 months in a polypropylene tube.

System Suitability Solution. Add 0.050 mL each of 1 mg/mL of NANA and NGNA stock solutions to 0.900 mL HPLC grade water in an appropriate container. Mix by vortexing. Store between 2 and 8° C. for up to 3 months. N-Acetyl Neuraminic Acid Working Solution (0.050 mg/mL). Accurately measure 0.050 mL of 1 mg/mL NANA stock solution and add to 0.950 mL of HPLC grade water. Mix by vortexing. Prepare in duplicate at the time of use. N-Glycolyl Neuraminic Acid Working Solution (0.050 mg/mL). Accurately measure 0.050 mL of 1 mg/mL NGNA stock solution and add to 0.950 mL of HPLC grade water. Mix by vortexing. Prepare in duplicate at the time of use.

Preparation of Samples and Hydrolysis Blank. Obtain the protein concentration for CTLA4-Ig material from the Certificate of Analysis (COA). Prepare a single sample of Hydrolysis Blank by adding 0.190 mL of HPLC grade water to 1.5 mL micro centrifuge tube. Prepare two 1 mg/mL solutions of samples and CTLA4-Ig Reference Material using HPLC grade water. Mix by vortexing.

Hydrolysis of Samples, CTLA4-Ig Reference Material, and Hydrolysis Blank. Perform the hydrolysis on duplicate preparations of reference material and samples in 1.5 mL micro centrifuge tubes. Note: It is important to use micro centrifuge tubes which will fit completely into the heating block. Add 0.010 mL of 1 M H2SO4 to 0.190 mL of 1 mg/mL dilutions of samples and CTLA4-Ig reference material, and hydrolysis blank. Mix by vortexing and secure lid by lid-lock or tape. Place the micro centrifuge tubes in 80° C.±2° C. heating block for 1 hour ±2 min. After incubation, remove tubes from heating block, place tubes in micro centrifuge and spin to force sample to the bottom of the tube. Aliquot hydrolyzed solutions into autosample vials and place in autosampler for injection.

Instrument Conditions. Prepare the High Performance Liquid Chromatography (HPLC) system. Set up the following conditions. Equilibrate the column for at least one hour at the flow rate of 0.6 mL/min and a temperature of 40° C.

| Mobile Phase(s) | A: 5 mM H₂SO₄ B: HPLC Grade Water (Column Wash) |
| --- | --- |
| Flow Rate | 0.6 mL/min |
| Run Time | 25 minutes |
| Detector Wavelength | 206 nm |
| Column Temperature | 40° C. |
| Autosampler | |
| Temperature | 4° C. |
| Injection Volume | 5 µL |
| Retention Times | |
| NGNA | 9.8 ± 1 minutes (system dependent) |
| NANA | 10.8 ± 1 minutes (system dependent) |
| Gradient conditions | Isocratic |

System Suitability. Start analysis with an injection of mobile phase as the Instrument Blank to evaluate system baseline, which should be flat and stable. If the baseline is not flat and stable, additional blank injections should be made. Note: A shift of the baseline should not exceed 0.25 AU. Perform six replicate injections of system suitability solution. Calculate Resolution (R) and Theoretical Plates (N).

Using the first system suitability injection, calculate the number of theoretical plates (N) using the following equation:

$$\text{Number of Theoretical Plates} \rightarrow N = 16\left(\frac{t}{W}\right)^2$$

Where:
N=Theoretical Plate Count
t=Retention time of NANA peak, in minutes
W=NANA Peak width at baseline, in minute Calculate the moles of NANA and NGNA in the CTLA4-Ig Reference Material and samples. NANA and NGNA standards are injected at the beginning and end of each run. Average the area counts for the replicate injections of NANA and NGNA. Use this area in the following equation:

moles of NANA or NGNA in $$\text{abatacept reference material or sample} = \frac{(X)(Y)}{(Z)}$$

X=Moles of NANA or NGNA in Working Solutions calculated in Section 7.3.1
Y=Area counts of NANA or NGNA in abatacept reference material or sample for each preparation (Note: see Section 7.2 and FIG. 3 for peaks to integrate for NANA)
Z=Averaged area of the replicate NANA or NGNA in Working Solutions In one embodiment, the resolution between the NGNA and NANA peaks must be >1.3. The theoretical plate count must be > or = to 4000. The system suitability injection reproducibility evaluated as % RSD of the area counts of NANA peak must be 3%. The theoretical plate count must be ≥4000. The system suitability injection reproducibility evaluated as % RSD of the area counts of NANA peak must be 3%.

N-Linked Oligosaccharide Profiling by High pH Anion Exchange Chromatography with Pulsed Amperometric Detection (HPAEC-PAD):

HPAEC of isolated oligosaccharides was performed on a chromatography system consisting of a Waters Alliance equipped with a Waters 464 electrochemical detector utilizing a Dionex CarboPack PA1 (4×250 mm) anion exchange column and a Dionex CarboPack guard column. The oligosaccharide samples were eluted using a sodium acetate gradient in 200 mM sodium hydroxide (increasing sodium acetate concentration from 0 mM at the time of injection to 225 mM at 60 minutes). The electrochemical detector was run under pulse mode with pulse potentials E1=0.05V (t1=0.4 sec), S=0.75V (t₂=0.2 sec), E3=−0.15V (t₃=0.4 sec). The detection cell was composed of a gold working electrode, a stainless steel counter electrode and a silver/silver chloride reference electrode.

This method describes the procedure to determine the HPAEC (High pH Anion Exchange Chromatography) oligosaccharide profile of N-linked oligosaccharides released from protein in CTLA4-Ig samples. The purpose of the method is to provide chromatographic profiles of CTLA4-Ig, such as CTLA4-Ig drug substance N-linked oligosaccharides which can be used for comparative analysis between different compositions of CTLA4-Ig molecules. The glycosylation on the CTLA4-Ig protein contains N-linked oligosaccharides. These oligosaccharides are liberated by enzymatic hydrolysis with PNGase F (Peptide: N-Glycosidase F) over the course of 22 hours. The free oligosaccharides are profiled using high pH anion exchange chromatography employing electrochemical detection.

| | |
|---|---|
| CTLA4-Ig Bulk Drug Substance | CTLA4-Ig in 25 mM Sodium Phosphate, 10 mM NaCl, pH = 7.5 |
| Waters Total Recovery Vials with bonded PTFE/silicone septa | Waters Corporation, Catalog No. 186000234 |
| RapiGest SF | Waters Corporation, Catalog No. 186001861 |
| Alliance HPLC system equipped with: Autosampler (refrigerated), Eluent Degas Module Model 2465 Electrochemical Detector | Waters Corporation |
| Column: CarboPac PA-1 4 × 250 mm | Dionex Corporation, Catalog No. 35391 |
| Guard Column: CarboPac PA-1 4 × 50 mm | Dionex Corporation, Catalog No. 43096 |
| Empower Data Collection system | |

Oligosaccharide profiles of drug substance are evaluated against concurrently run samples of reference material. Results are reported as percent deviation of selected domains and peaks from the same peaks in the reference standards.

Chromatography Conditions for Oligosaccharide Profile by Anion-Exchange Chromatography

| | |
|---|---|
| Column Temperature | 29° C. |
| Flow Rate | 1 mL/min |
| Mobile Phases and Gradient | Gradient Program |

| Conditions | | | |
|---|---|---|---|
| 1: 500 mM NaOAc 2: 400 mM NaOH 3: HPLC Grade Water | | | |
| Time (min) | % 1 | % 2 | % 3 |
| Initial | 0 | 30 | 70 |
| 0.0 | 0 | 30 | 70 |
| 11.0 | 0 | 30 | 70 |
| 12.0 | 4 | 30 | 66 |
| 20.0 | 10 | 30 | 60 |
| 80.0 | 45 | 30 | 25 |
| 81.0 | 0 | 30 | 70 |
| 100 | 0 | 30 | 70 |

| | |
|---|---|
| Waters 2465 settings Mode Empower settings | Pulse Range = 5 µA E1 = +0.05 V E2 = +0.75 V E3 = −0.15 V t1 = 400 msec t2 = 200 msec t3 = 400 msec Sampling time(ts) = 100 msec Time constant(filter)t = 0.1 sec Range offset = 5% Polarity + Temperature = 29° C. |

NOTE:
Equilibrate the column and detector with the initial mobile phase at the analysis flow rate for approximately 2 hours, or until baseline is stable before making injections.

| | |
|---|---|
| Autosampler Temperature set to: | 4° C. |
| Injection Volume | 60 µL |
| Run Time | 100 minutes |
| Approximate Retention Times (RT; minutes) of dominant peaks in each Domain (see FIG. 1); values may vary depending on RT of System Suitability (SS) Standard | |
| | Approximate RTs (min) |
| SS: | 18.5 |
| Peak 1A: | 20.0 |

-continued

| | |
|---|---|
| Peak 1B: | 20.8 |
| Peak 1C: | 21.4 |
| Peak 1D: | 22.4 |
| Peak 1E: | 23.1 |
| Peak 2 | 31.5 |
| Peak 3: | 44.8 |
| Peak 4: | 58.5 |

Preparation of Mobile Phases for HPAEC Oligosaccharide Carbohydrate Profiling

HPAEC Eluent 1: 500 mM Sodium Acetate (NaOAc). Weigh 20.51±0.05 g of Sodium Acetate (anhydrous) into a 500 mL graduated cylinder containing 400 mL of HPLC grade water. Bring volume to 500 mL with HPLC grade water and stir for 5 minutes using a plastic serological pipette until completely mixed. Filter the solution through a 0.2 µm nylon filter. Transfer to a 1 L eluent bottle. Cap the bottle loosely and sparge with helium for 20 minutes. Tighten cap and pressurize the bottle with helium. Store solution at room temperature under helium for up to three weeks.

HPAEC Eluent 2: 400 mM Sodium Hydroxide (NaOH). Using a 1 L graduated cylinder, measure 960 mL of HPLC grade water and transfer to a clean 1 L eluent bottle. Using a serological plastic pipet, add 40.0 mL of 10 N NaOH directly into the eluent bottle and mix the eluent by swirling. Cap the bottle loosely and sparge with helium for 20 minutes. Tighten cap and pressurize the bottle with helium. Store solution at room temperature under helium for up to three weeks.

HPAEC Eluent 3: HPLC grade Water. Fill a 1 L eluent bottle with approximately 1 L of HPLC grade water. Place eluent bottle on system, cap loosely, and sparge for approximately 20 minutes. Tighten cap and pressurize the bottle with helium. Store solution at room temperature under helium for up to three weeks.

50 mM Sodium Phosphate Buffer, 0.02% Sodium Azide, pH=7.5.

| | |
|---|---|
| $NaH_2PO_4 \cdot H_2O$ | 6.9 g |
| $NaN_3$ | 0.2 g |
| $H_2O$ | 1.0 liter final volume |

Weigh out 6.9 g±0.1 g of $NaH_2PO_4 \cdot H_2O$ and 0.2 g $NaN_3$ and dissolve in 800 mL of HPLC grade $H_2O$ in a 1 L reagent bottle using continuous mixing with a magnetic stirring bar.

Using a pH meter, adjust the pH of the solution to 7.5 using 10M NaOH. Bring the final volume to 1.0 liter using a 1 L graduated cylinder. Store solution at room temperature for up to six months.

PNGase F Enzyme Working Stock in 50 mM Sodium Phosphate Buffer, 0.02% Sodium Azide, pH=7.5.

| 50 mM Sodium Phosphate Buffer | |
|---|---|
| 0.02% Sodium Azide, pH = 7.5. | 1.8 mL |
| PNGase F from Kit, Catalog No. P0704L | 0.2 mL |

Pipette 1.8 mL of 50 mM Sodium Phosphate Buffer, 0.02% Sodium Azide, pH 7.5 into a 1.8 mL cryogenic vial. Add 0.2 mL of PNGase F from kit and mix thoroughly. Store solution at −20° C. or less for up to six months. The solution may be aliquoted prior to freezing.

External System Suitability Standard. Stachyose Stock Solution (1.25 mg/mL). Weigh 0.125 g of Stachyose onto a weighing paper. Using an analytical balance and transfer to a 100 mL volumetric flask. Fill to mark with HPLC grade water and mix thoroughly. Aliquot in 2 mL portions into Nalgene cryovials. Store solution at −20° C. or less for up to six months.

Stachyose System Suitability Standard (12.5 µg/mL). Pipet 1 mL of the 1.25 mg/mL stock into a 100 mL volumetric flask. Fill to mark with HPLC grade water and mix thoroughly. Aliquot in 200 µL portions into 0.65 mL microfuge tubes. Place tubes in appropriately labeled storage box. Store system suitability solution at −20° C. or less for up to six months.

Standard and Sample Preparation

Reference Material Preparation. To a vial containing 1 mg of lyophilized RapiGest SF, add 625 µL of 50 mM NaPhosphate buffer containing 0.02% NaAzide, pH 7.5. To a 0.65 mL Eppendorf tube add 120 µL of the RapiGest SF containing buffer. Add 40 of Reference Material (~50 mg/mL). The final RapiGest SF concentration should be 0.12% w/v. Add 40 µL of the PNGase F working stock, mix thoroughly, spin down the sample, and place at 38±2° C. for 22±2 hours (water bath or the Alliance autosampler compartment). Pipet sample into a microcon YM-10 centrifugal filter and centrifuge at 13,000 g for 30 minutes. Place 200 µL of HPLC water in the filter and rinse into the filtrate by centrifuging for an additional 30 minutes at 13,000 g. Vortex the combined filtrate for 15 seconds and centrifuge the sample for 10 seconds. Using a pipette transfer the resulting solution (~380 µL) to an HPLC total recovery autosampler vial (item 1.15).

Sample Preparation. To a 0.65 mL Eppendorf tube add 120 µL of the RapiGest SF containing buffer. Add 40 µL of protein sample (this volume should equate to between 1 and 2 mg of CTLA4-Ig). The final RapiGest SF concentration should be 0.12% w/v. Add 40 µL of the PNGase F working stock mix thoroughly by vortexing for 10 seconds. Spin down the sample, and place at 38±2° C. for 22±2 hours (water bath or the Alliance autosampler compartment). Pipet sample into a microcon YM-10 centrifugal filter and centrifuge at 13,000 g for 30 minutes. Place 200 µL of HPLC water in the filter and rinse into the filtrate by centrifuging for an additional 30 minutes at 13,000 g. Vortex the combined filtrate for 15 seconds and centrifuge the sample for 10 seconds. Transfer the resulting solution (~380 uL) to a total recovery HPLC autosampler vial (item 1.15).

System Suitability

Electrochemical Detector Cell Stabilization. Inject 30 µL of the external stachyose system suitability standard (12.5 µg/mL). Ensure the peak height for stachyose is 800 nA. Ensure there is no excessive electrical noise from the cell and the baseline is flat. A representative system suitability chromatogram is shown in FIG. 2. If the stachyose sensitivity or the baseline is unacceptable, check the buffer composition, clean the electrode or replace the electrode. If excessive noise is present, check cell to ensure removal of all air bubbles. Restabilize the cell and re-inject stachyose standard.

Theoretical Plates (N). Determine the number of Theoretical Plates (N) based on the Stachyose peak using the formula below. This is done through the Empower data analysis system or may also be done manually. $N=16(t/W)^2$ WHERE t: retention time measured from time of injection to peak elution time at maximum height W: width of peak by extrapolation of sides to baseline.

N must be ≥6000. If the plate count is less than 6000, adjust the run gradient or replace column.

Tailing Factor (T). Determine column Tailing Factor (T) based on the Stachyose peak using the formula below. This is done through the Empower data analysis system or may also be done manually. $T=(W_{0.05}/2f)$, WHERE:

$W_{0.05}$: width of peak at 5% of height (0.05h).

f: the measurement (width) from front edge of peak at $W_{0.05}$ to the apex of the peak.

T must be ≤1.2. If the tailing factor is greater than 1.2, check buffer composition, replace the column or clean the column as indicated in and re-inject system suitability standard.

Stachyose System Suitability Standard Retention Time Verification. The retention time is system dependent. The stachyose system suitability standard should exhibit a retention time of 18.5±2.0 minutes. CTLA4-Ig Standard Material. Observe the carbohydrate profile from the first bracketing reference material injected prior to injection of samples. The carbohydrate profile should be similar to that shown in FIG. 1. Absolute retention times are system dependent. Ensure that the difference in retention times between the first peak in Domain I (Peak 1A) and the main peak in Domain III (Peak 3) is between 22 minutes and 28 minutes. If delineation of peaks does not resemble that obtained in FIG. 1 take appropriate actions (e.g. check instrument function, clean column, check/replace buffers, replace column) and re-evaluate. The following procedure may be used to clean the column: turn off the cell and clean the column with 80% Eluent 1, 20% Eluent 2 for 5 minutes followed by 50% Eluent 1, 50% Eluent 2 for 10 minutes. Re-equilibrate the column and cell (with cell turned on) at initial conditions and re-evaluate.

Injection Sequence

Set up the injection sequence of isolated oligosaccharides as follows:

Stachyose Standard (30 µL)
Reference Material (60 µL)
Sample(s) (60 µL)
Reference Material (60 µL)
It is recommended that ≤ five samples be run between bracketing reference material injections.

Data Analysis

Process the Chromatograms. Process the chromatograms for the Reference Material and samples in Empower. Set integration parameters so that peak delineation and the baseline is similar to that shown in FIG. 75, integration lines may need to be placed manually. Perform calculations for relative Domain areas and relative peak areas shown. Determine the average values for these parameters for the CTLA4-Ig Material and for each sample if replicate injections were made. For the Reference Material, determine relative deviation for Domains I, II, III, Peaks 1A and 1B for each replicate with respect to the average of all replicates.

Comparison of Profiles of Sample to Reference Material Profiles. Visual Comparison. Determine if both samples and Reference Material have the same number of Domains and primary peaks. Primary peaks are those peaks labeled in FIG. 75 (Peaks 1A, 1B, 1C, 1D, 2, 3 and 4). Relative Quantitation Comparison. Compare the relative areas of samples (Domains I, II, and III and Peaks 1A, and 1B; if replicate injections were made of samples use their average values) with the average relative areas from the bracketing CTLA4-Ig injections. Determine the relative difference of these areas from the average CTLA4-Ig Material values. Calculations-% Domain Area (Relative Domain Area). Calculate the % Domain area for the Domains of the profiles for the Reference Material and samples. Refer to FIG. 75 for pattern of Domain areas. Following the example in FIG. 75, calculate the Domain percent ratios by using the following information and formula (retention times are system dependent and reflect result in FIG. 75):

Domain I: Sum of the peak areas at approximate retention times 18-24 minutes (Peaks 1A-1E)
Domain II: Sum of the peaks from 26-38 minutes
Domain III: Sum of the peaks from 39-50 minutes
Domain IV: Sum of the peaks from 51-64 minutes
Domain V Sum of the peaks from 65-75 minutes
NOTE: Retention time windows for Domains will shift according to variations in daily chromatographic performance. Adjust times accordingly.

$$\text{Domain Area \%} = \frac{\text{Individiual Domain Area}}{\text{Sum of all Domain Areas}} \times 100\%$$

For Domains I-III also calculate the average values in the bracketing reference material injections, as well as in samples if replicate injections are made.

% Peak Area (Relative Peak Area). Calculate the % peak area for Peaks 1A, 1B, 1C, and 3 of the profiles for the Reference Material and samples. Refer to FIG. 1 for pattern of peak areas; retention times are system dependent. Calculate the peak percent ratios by using the following information and formula:

$$\text{Individual Peak Area \%} = \frac{\text{Individual Peak Area}}{\text{Sum of the all Domain Areas}} \times 100\%$$

For each of Peaks 1A and 1B, also calculate the average values in the bracketing reference material injections, as well as in samples if replicate injections are made. Calculation of the Percent Difference from Average Reference Material Values. Use the following formula to calculate percent differences in average relative areas of Domains I-III, Peaks 1A and 1B of samples compared to Reference Material:

% Diff=|$RM$–$S$|/$RM$×100

WHERE:
RM=average relative area value of interest for Reference Material
S=average relative area value of interest for a sample
| |=absolute value Exemplary Values. For a run to be acceptable the exemplary values must be met and all injections relevant to the sample must have successfully occurred. Additionally, for each of the bracketing Reference Material injections, the % Domain Areas for Domain I, II and III and % Peak Areas for Peak 1A and 1B must be within 15% of their average values.

Analysis by HPAEC-PAD:

N-linked oligosaccharides were cleaved from CTLA4-Ig molecules and analyzed by HPAEC-PAD. Oligosaccharides elute into four domains based on the amount of sialic acid present. Domains were established based on the migration of oligosaccharide standards and were confirmed by MS. Domain I represents asialylated species. Domains II, III, and IV represent mono-, di-, and tri-sialylated species, respectively. In order to characterize the structure of the oligosaccharides at the three N-linked sites, peptides T5, T7 and T14 were individually isolated (refer to Table 59 for identity of these peptides). This was performed using tryptic digestion of CTLA4-Ig and manually collecting peaks corresponding to these three peptides.

The isolated peptides were treated with PNGase F to release the oligosaccharides, which were subsequently purified and analyzed by HPAEC-PAD. Peptide T5 did not produce a good profile since it is difficult to purify due to its extreme hydrophobicity. Quantities of cleaved oligosaccharides are low due to low recovery of this peptide from the reversed phase chromatography step after tryptic digestion.

TABLE 59

Theoretically Expected and Observed Masses of CTLA4-Ig

| Fragment No. | Residue No. | Expected Mass (Daltons) | Observed Mass (Daltons) | Peptide Sequence |
| --- | --- | --- | --- | --- |
| T1 + A | -1-14 | 1536.8 | 1536.8 | AMHVAQPAVVLASSR |
| T1 | 1-14 | 1465.8 | 1465.7 | MHVAQPAVVLASSR |
| T2 | 15-28 | 1485.7 | 1485.6 | GIASFVCEYASPG K |
| T3 | 29-33 | 574.6 | 574.2 | ATEVR |
| T4 | 34-38 | 586.7 | 586.3 | VTVLR |
| T5$^a$ | 39-83 | 4900.4 | c | QADSQVTEVCAATYMMGNELTFLD DSICTGTSSGNQVNLTIQGLR |
| T6 | 84-93 | 1171.4 | 1171.4 | AMDTGLYICK |

TABLE 59-continued

Theoretically Expected and Observed Masses of CTLA4-Ig

| Fragment No. | Residue No. | Expected Mass (Daltons) | Observed Mass (Daltons) | Peptide Sequence |
|---|---|---|---|---|
| T7[a] | 94-128 | 3997.5 | c | VELMYPPPYYLGIGNGTQIYVIDPEPCPDSDQEPK |
| T8[b] | 129-132 | 435.2 | ND | SSDK |
| T9[b] | 133-158 | 3345.7 | c | THTSPPSPAPELLGGSSVFLFPPKPK |
| T10 | 159-165 | 834.9 | 834.4 | DTLMISR |
| T11 | 166-184 | 2139.3 | 2138.6 | TPEVTCVVVDVSHEDPEVK |
| T12 | 185-198 | 1677.8 | 1677.2 | FNWYVDGVEVHNAK |
| T13 | 199-202 | 500.6 | 500.3 | TKPR |
| T14a | 203-211 | 1189.2 | c | EEQYNSTYR |
| T15 | 212-227 | 1808.1 | 1807.4 | VVSVLTVLHQDWLNGK |
| T16 | 228-230 | 438.5 | 438.1 | EYK |
| T17 | 231-232 | 307.4 | ND | CK |
| T18 | 233-236 | 446.5 | ND | VSNK |
| T19 | 237-244 | 838.0 | 837.4 | ALPAPIEK |
| T20 | 245-248 | 447.5 | 447.2 | TISK |
| T21 | 249-250 | 217.2 | ND | AK |
| T22 | 251-254 | 456.2 | 456.2 | GQPR |
| T23 | 255-265 | 1286.4 | 1286.6 | EPQVYTLPPSR |
| T24 | 266-270 | 604.7 | 604.3 | DELTK |
| T25 | 271-280 | 1161.4 | 1160.5 | NQVSLTCLVK |
| T26 | 281-302 | 2544.7 | 2545.6 | GFYPSDIAVEWESNGQPENNYK |
| T27 | 303-319 | 1874.1 | 1873.2 | TTPPVLDSDGSFFLYSK |
| T28 | 320-324 | 574.7 | 574.2 | LTVDK |
| T29 | 325-326 | 261.3 | ND | SR |
| T30 | 327-349 | 2803.1 | 2800.8 | WQQGNVFSCSVMHEALHNHYTQK |
| T31 | 350-356 | 659.7 | 659.1 | SLSLSPG |
| T31 + K | 350-357 | 787.9 | 787.0 | SLSLSPGK |
| T2 clip | 15-23 | NE | 1045.3 | GIASFVCEY |
| T12 clip | 185-195 | NE | 1364.7 | FNWYVDGVEVH |
| T27 clip | 303-317 | NE | 1658.5 | TTPPVLDSDGSFFLY |
| T30 clip | 327-335 | NE | 1125.3 | WQQGNVFSC |
| T30 clip | 327-333 | NE | 878.3 | WQQGNVF |

ND not detected
NE not expected from trypsin digestion (these masses were not expected from the digest, non-specific cleavage).
[a] Tryptic peptides T5, T7, and T14 have N-linked glycosylation. The mass listed is that of the peptide without glycosylation.
[b] Tryptic peptides T8 and T9 have O-linked glycosylation. The mass listed is that of the peptide without glycosylation.
c Several different masses corresponding to different glycoforms of glycosylated peptides were observed.

The HPAEC-PAD profiles for all N-linked carbohydrates from CTLA4-Ig and the three peptides are shown in FIGS. 54A-54D. Panel A shows the N-linked oligosaccharide profile of the CTLA4-Ig molecule, while panels B, C and D show the profiles for the T5, T7 and T14, respectively. The amount of oligosaccharides injected for each of the peptides is different due to the preparation processes. The majority of oligosaccharides detected on peptide T5 consist of the mono- and di-sialylated oligosaccharides. The profile of T7 contains primarily mono-, di-, and some a- and tri sialylated glycan species. Only a small amount of the tri-sialylated structures can be detected on T5. Peptide T14 consists of predominantly asialylated oligosaccharides and a small amount of mono- and di-sialylated oligosaccharides The results obtained by HPAEC-PAD provide information on site-specific N-linked glycosylation. N-linked oligosaccharides from the CTLA4 region of CTLA4-Ig contain a greater proportion of sialylated species than those from the Fc region of CTLA4-Ig.

Trypsin, Asp-N, and Trypsin/Chymotrypsin Peptide Mapping of CTLA4-Ig:

CTLA4-Ig was denatured and reduced in 50 mM Tris buffer (pH 8.0) containing 6 M Guanidine and 5 mM dithiothreitol (DTT). After a 20 minute incubation at 50° C., iodoacetamide (IAA) was added to a final concentration of 10 mM to alkylate free thiols, and the incubation was continued for an additional 20 minutes at 50° C. in the dark. The reduced and alkylated mixture was loaded onto a desalting column (Amersham NAP-5), then eluted into the void volume with either 50 mM Tris, 10 mM CaCl2, pH 8.0 or 50 mM sodium phosphate buffer, pH 7.5. Following desalting, reduced/alkylated CTLA4-Ig was digested using two different proteases: trypsin or Asp-N. For trypsin plus chymotrypsin digestion CTLA4-Ig is neither reduced nor alkylated.

For trypsin digestion, sequence grade trypsin (Roche, 2%, w/w, enzyme/protein) was added and incubated for 4 hours at 37° C. For Asp-N digestion, sequence grade Asp-N (Roche, 4%, w/w, enzyme/protein) was added and incubated for 16 hours at 37° C. For the trypsin/chymotrypsin digestion, sequence grade trypsin (Promega, 4%, w/w, enzyme/protein) was added and incubated for 4 hours at 37° C., then a-chymotrypsin was added (Sigma, 4%, w/w, enzyme/protein) and incubated for 16 hours at 37° C. All samples were placed in a freezer after the digestion.

The resulting peptide mixtures were separated by gradient elution from a Waters Atlantis™ dC18 column (2.1×250 mm) on a Waters Alliance HPLC Workstation at 0.120 mL/minute. The column was directly connected to the Waters Micromass Q-Tof Micro™ mass spectrometer equipped with an ion-spray source for collection of mass spectra. Peptide mixtures were also separated on a Varian Polaris C18 column (4.6×250 mm) at 0.7 mL/minute using the same HPLC workstation. The columns were equilibrated with solvent A (0.02% TFA in water) and peptides were eluted by increasing concentration of solvent B (95% acetonitrile/0.02% TFA in water). A post-column splitter valve was used to direct 15% of the flow to the Q-Tof workstation, which was run in the positive TOF mode (m/z 100–2000). The typical ion spray voltage used was 3000 V.

CTLA4-Ig Analysis by MS:

CTLA4-Ig was diluted with 100 mM Tris, 25 mM NaCl, pH 8 to a final concentration of 0.7 mg/mL. PNGase F (New England Biolabs) was diluted 30-fold with 100 mM Tris, 25 mM NaCl, pH 8 to a final concentration of 17 U/μL. Equal volumes (60 μL each) of diluted purified fermentation sample and diluted glycosidase solution were mixed and incubated at 37° C. for 4 hours.

The resulting deglycosylated CTLA4-Ig (2 μg) was loaded onto a polymeric-based (copolymer of polystyrene and poly N-vinyl-2-pyrrolidinone) Waters Oasis® reversed phase extraction cartridge column (2.1×20 mm). The loaded column was washed with 5% solvent B (solvent A: 1% formic acid in water, solvent B: 1% formic acid in acetonitrile) at a flow rate of 0.2 mL/minute for five minutes to desalt, with the eluent diverted to waste. At the end of 5 minutes, a fast gradient (5% solvent B to 95% solvent B in 10 minutes) began the elution of CTLA4-Ig off the column; here the eluent was directed into the mass spectrometer (Waters Micromass Q-Tof Micro™) at 45 μL/min after flow splitting (chromatography system used was a Waters Alliance 2695 equipped with a Waters 2996 detector).

The capillary voltage for the Q-Tof Micro™ was set at 3 kV and the sample cone voltage at 40 V. The scans in every 0.9 second were averaged into one scan; the inter-scan time was 0.1 second. The Q-Tof analyzer scans from m/z 800 to 2500. Spectra corresponding to the portion higher than half the maximum peak height (in TIC chromatogram) are combined using Waters MassLynx' software. The combined spectrum was subjected to Waters MaxEnt1 deconvolution. The resolution was set at 1 Da/Channel, and the uniform Gaussian damage model was selected with width at half height set between 0.5-1 Da. Minimum intensity ratios for the left peak and the right peak were both set at 50%.

N-Linked Oligosaccharide Analysis by Liquid Chromatography/Mass Spectrometry (LC/MS) Using a Porous Graphitized Carbon (PGC):

Isolated oligosaccharides were separated on a porous graphitized column (Thermo Hypercarb; 4.6×100 mm) using a Waters Alliance 2695 HPLC system equipped with a Waters 2996 photodiode array detector. Oligosaccharide separation was achieved using a two-stage gradient of increasing proportions of acetonitrile in 0.05% TFA. In the first stage of the gradient, the acetonitrile percentage ranged from 9.6% at the time of injection to 24% at 80 minutes. In the second stage of the gradient, the acetonitrile percentage ranged from 24% at 80 minutes to 60% at 110 minutes. A flow rate of 0.2 mL/minute was used throughout. The elution stream was monitored at by UV detection at 206 nm and analyzed by mass spectrometry using a Waters MicroMass Q-Tof Micro™ for mass identification.

Carbohydrate Analysis by LC/MS PGC Method:

Oligosaccharide isolation by deglycosylation of the protein was performed by enzymatic hydrolysis using PNGase F (New England Biolabs, Beverly, Mass.). For the deglycosylation, between 1 and 2 mg glycoprotein in 160 μL of 50 mM sodium phosphate buffer containing 0.15% (w/v) Rapigest SF (Waters Corporation) was denatured by heating at 100° C. for 2 minutes. The cooled solution was mixed and 40 μL of PNGase F (50,000 U/mL, in 50 mM sodium phosphate buffer, pH 7.5) was added. The sample was vortexed followed by incubation at 38° C. for 24 hours. The enzymatically-released oligosaccharides were purified by high performance liquid chromatography. Reversed phase liquid chromatography was performed on a Phenomenex Luna 5 μL C18 column (4.6×150 mm, Phenomenex, Torrance, Calif.) coupled with a Thermo HyperCarb 5 (4.6×100 mm, Phenomenex, Torrance, Calif.) at a flow rate of 1.0 mL/min. The columns were equilibrated with 0.05% tri-flouroacetic acid (TFA) prior to injection. After sample injection (150 μL of the digest mixture), a gradient of acetonitrile was initiated terminating at 15 minutes and a solvent composition of 0.05% TFA in 12% acetonitrile. The glycans were then eluted from the HyperCarb column by washing with 0.05% TFA in 60% acetonitrile. The glycans were detected by UV absorbance at 206 nm. Peaks eluted from the Hypercarb wash were collected and concentrated to dryness under vacuum. Prior to subsequent injections the Luna C18 column was cleaned with 0.05% TFA in 40% acetonitrile, 40% isopropanol, 20% water.

Profiling of Isolated Oligosaccharides with PGC

The system used for PGC chromatography of isolated oligosaccharides consisted of a Waters Alliance equipped with a Waters 2996 photodiode array detector utilizing a Hypercarb column (2.1×100 mm). The oligosaccharide samples were eluted using an acetonitrile gradient.

Acidic Mobile Phase Elution: Acetonitrile gradient in 0.05% triflouroacetic acid (TFA). A two-stage gradient of increasing acetonitrile was used for the chromatographic separation of oligosaccharides. The initial linear gradient of increasing acetonitrile volume percentage from 9.6% at the time of injection to 24% at 80 minutes is followed by a second gradient of increasing acetonitrile volume percentage from 24% at 80 minutes to 60% acetonitrile at 110 minutes. A flow rate of 0.15 ml/min was used throughout the gradient. The elution stream was monitored at 206 nm with a Waters UV detector, followed by a Micromass Q-Tof Micro for mass identification. The ionization parameters for the ESI probe were set as follows: Capillary voltage=3 kV, Cone voltage=45 V, Source temperature 80° C., and desolvation temperature of 175° C.

Basic Mobile Phase Elution: An acetonitrile gradient in 0.4% ammonium hydroxide ($NH_4OH$) was used for the chromatographic separation of oligosaccharides. A linear gradient of increasing acetonitrile volume percentage from 10.4% at the time of injection to 28% at 150 minutes at a flow rate of 0.15 mL/min was used to produce the profile. The elution stream was monitored at 206 nm with a Waters UV detector, followed by a Micromass Q-Tof Micro for mass identification. The ionization parameters for the ESI probe were set as follows: Capillary voltage =3 kV, Cone voltage =45 V, Source temperature 80° C., and desolvation temperature of 175° C.

Direct profiling of oligosaccharide digest mixtures with PGC: The system used for PGC chromatography of oligosaccharide digest mixtures consisted of a Waters Alliance fitted with both a Luna C18 and a Hypercarb porous graphite column (4.6×100 mm, Thermo). The system was interfaced with a Waters 2996 photodiode array detector and a Q-ToF Micro (Micromass). Deglycosylation of protein was performed by enzymatic hydrolysis using PNGase F. For the deglycosylation, between 1 and 2 mg glycoprotein in 160 μL of 50 mM sodium phosphate buffer containing 0.15% by weight Rapigest SF (Waters Corporation), was denatured by heating at 100° C. for 2 minutes. The cooled solution was mixed well and 40 μL of PNGase F (50,000 U/mL, in 50 mM sodium phosphate buffer, pH 7.5) was added. The sample was mixed and then incubated at 38° C. for 24 hrs. The enzymatically-released oligosaccharides were profiled by high performance liquid chromatography. Reversed phase liquid chromatography was performed on a Phenomenex Luna 5|u C18 column (4.6×150 mm) coupled to a Thermo HyperCarb column 5 μL (4.6×100 mm) at a flow rate of 1.0 mL/min. The columns were equilibrated with 0.05% triflouroacetic acid (TFA). After sample injection (150 |iL of digest mixture) a gradient of acetonitrile was initiated, terminating at 11 minutes and a solvent composition of 0.05% TFA in 9% acetonitrile. A column switch was used to isolate the hypercarb column and the glycans are then eluted from the HyperCarb column with a linear gradient of increasing acetonitrile percentage. An initial gradient of increasing acetonitrile percentage from 9% at the time of injection to 36% at 160 minutes was used. The second gradient involved increasing acetonitrile volume percentage from 36% at 160 minutes to 60% acetonitrile at 170 minutes. A flow rate of 0.15 mL/min was used throughout the elution gradients. The glycans were detected by UV absorbance at 206 nm, and by MS scanning the mass range from 400-3000 m/z. MS parameters were set to the following values: Capillary 3 kV, Cone 45 V. Prior to subsequent injections the Luna C18 column was cleaned with 0.05% TFA in 40% acetonitrile, 40% isopropanol, 20% water.

Figure 55:
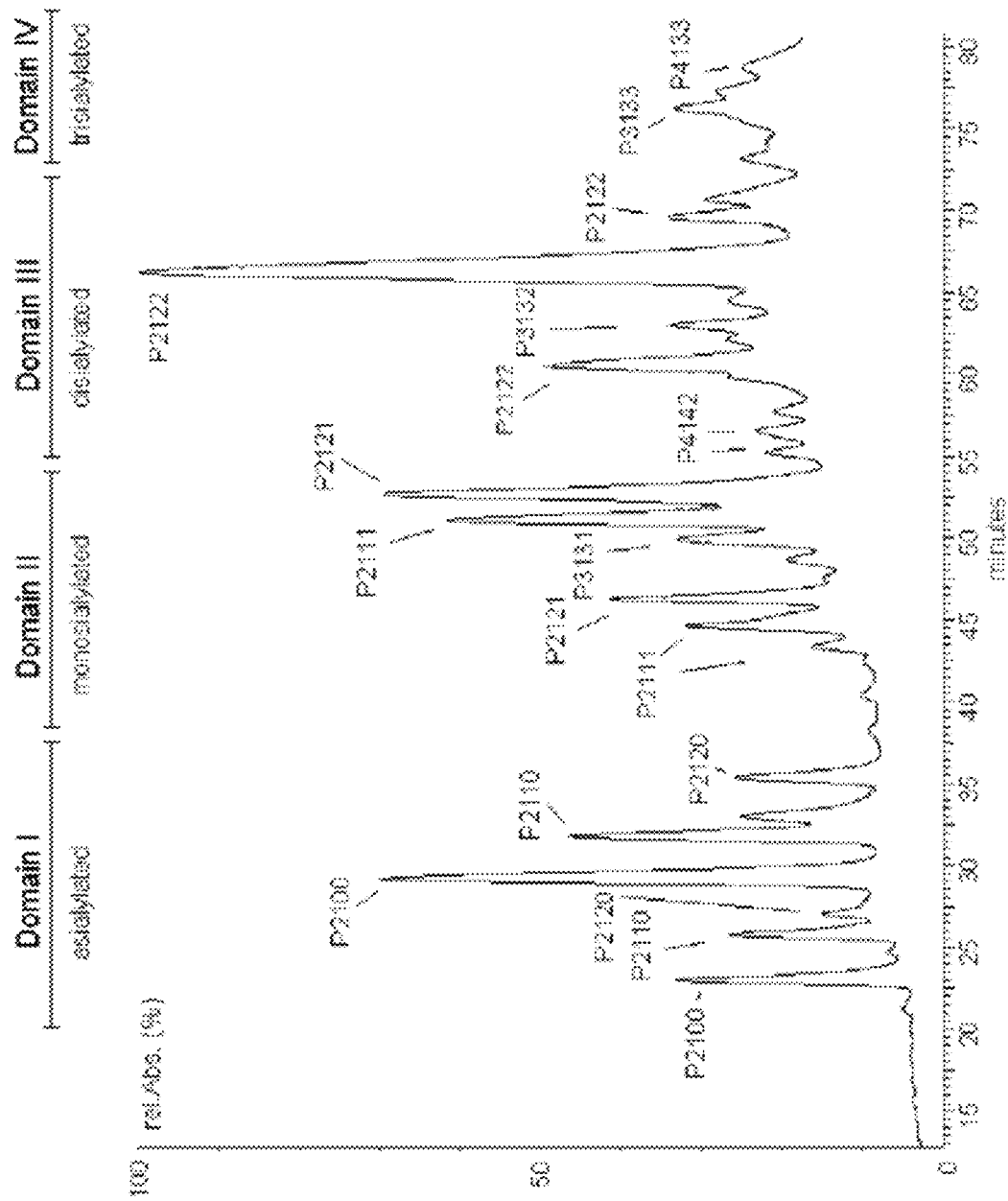
FIG. 55 is a graph depicting the labeled oligosaccharide profile of CTLA4-Ig obtained from PGC (Hypercarb) Column.

Analysis by Porous Graphitized Carbon Chromatography:

The structures of the oligosaccharides from Domains I-IV were investigated using Porous Graphitized Carbon chromatography (PGC) coupled to MS. N-linked oligosaccharides were isolated from CTLA4-Ig and purified as described in the previous HPAEC-PAD section. The oligosaccharides were analyzed using a Hypercarb (PGC) column with a UV detector followed by Q-TOF ESI/MS. The PGC profile for the N-linked oligosaccharides released from CTLA4-Ig by PNGase F digestion is shown in FIG. 55 with domains noted. The order of elution is the same as that observed in HPAEC-PAD. The structures obtained are shown in FIG. 88A-88C with the nomenclature for the oligosaccharides shown in FIG. 87.

In Domain I, six peaks were identified, corresponding to three asialylated oligosaccharides (structures P2100, P2110, P2120). The 113 Dalton mass difference between the predicted structure and observed mass is due to detection of a trifluoroacetic acid (TFA) adduct. Different peaks with the same mass of 1,463 corresponding to P2100, indicates they are likely different anomers.

In Domain II, six peaks were identified, corresponding to three biantennary and triantennary oligosaccharides (structures P2111, P2121, and P3131, respectively), each containing one sialic acid residue (N-acetylneuraminic acid, NANA).

In Domain III, six peaks were identified, corresponding to three biantennary, triantennary and tetraantennary oligosaccharides (structures P2122, P3132, and P4142, respectively), each containing two sialic acid residues (NANA).

In Domain IV, two peaks were identified, corresponding to two triantennary and tetraantennary oligosaccharides (structures P3133 and P4133), each containing three sialic acid residues (NANA).

Measurement of Molar Ratio of Moles Sialic Acid to Moles CTLA4-Ig Molecules or Dimer by Acid Hydrolysis Treatment of CTLA4-Ig Molecules (See FIGS. 24 and 25):

In this method, NANA and NGNA are cleaved from the protein by acid hydrolysis. The released NANA and NGNA are separated by HPLC on a Rezex Monosaccharide RHM column and detected by UV absorbance (206 nm). NANA and NGNA are quantitated based on the response factors of concurrently run NANA and NGNA standards. The test results are reported as molar ratios (MR) of NANA and NGNA respectively, to protein. This assay determines the total number of moles, bound and unbound, of sialic acid.

Reagent, instrumentation and chromatographic conditions used in the assay: 1M sulphuric acid $H_2SO_4$ (stock) and 5 mM $H_2SO_4$ mobile phase running buffer; NANA standard solution of 1 mg/ml; NGNA standard solution of 1 mg/ml. Alliance chromatographic system-Waters Corporation 2695 Separations Module with integrated autosampler; Rezex monosaccharide RHM column-8 micrometer, 7.8×300 mm, Phenomenex, equipped with 7.8×50 mm guard column, Phenomenex; Detector—Waters Corporation 996 photodiode array detector or Waters Corporation 2487 dual wavelength absorbance detector. Chromatographic parameters: Flow—0.600 mL/min; Mobile phase—5 mM $H_2SO_4$; Injection volume—5microL; Target concentration—1 mg/ml; Run time—25 min; Column temperature—40° C.; Autosampler temperature—4° C.; Wavelength—206 nm; Retention time NANA (system dependent)—10.8 min (+ or −1 min), Retention time NGNA (system dependent)–9.8 min (+ or −1 min.).

System Suitability Standard: Add 50 µL each of 1 mg/mL of NANA and NGNA to 900 µL $H_2O$ in an appropriate container. Store at 4° C. for up to 3 months; N-Acetyl Neuraminic Acid Working Standard (0.05 mg/mL); N-Glycolyl Neuraminic Acid Working Standard (0.05 mg/mL).

Hydrolysis of Samples and CTLA4-Ig standard material: Samples and CTLA4-Ig standard material are diluted to 1 mg/mL in $H_2O$ for hydrolysis. CTLA4-Ig samples and CTLA4-Ig standard material are hydrolyzed by adding 10 µL 1 M $H_2SO_4$ to 190 µL of 1 mg/mL diluted samples and CTLA4-Ig. Hydrolysis is performed in duplicate in 1.5 mL micro centrifuge tubes. Lids are secured by lid-lock or tape. Tubes are mixed by vortexing and placed in 80° C. heating block for 1 h. After incubation, tubes are removed from the heating block, cooled down at room temperature for 3 min, and placed in centrifuge for a quick spin to collect sample to the bottom of the tube. From the tubes, 50 µL are aliquoted of the hydrolyzed solution into sample vial, which is placed in cooled autosampler for injection. A hydrolysis blank is made as a single preparation by adding 10 µL 1 M $H_2SO_4$ to 190 µL water in 1.5 mL micro centrifuge tubes. The blank is processed as the samples.

System Suitability: To check the system suitability six replicate injections of the system suitability standard (5 µL each) were injected followed by one injection of the hydrolysis blank (5 µL). Using the last system suitability standard injection, Resolution (R), acceptable values are higher than 1.3, and Theoretical Plates (N), acceptable theoretical plate count must be at least 4000, were calculate respectively. Using the last five system suitability replicates, reproducibility of NANA counts were calculated, and the hydrolysis blank was evaluated.

Figure 24:
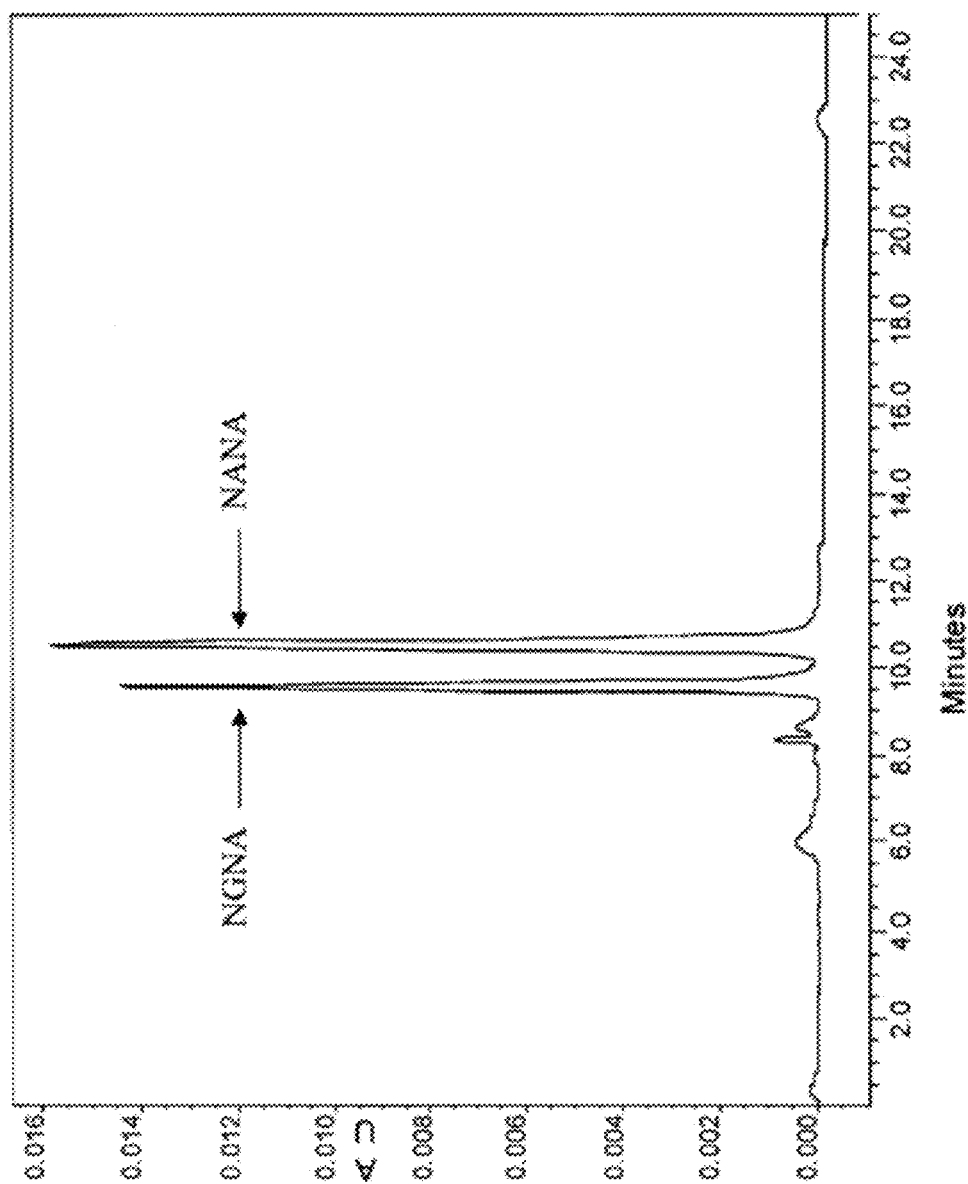
FIG. 24 shows a representative chromatogram of NGNA and NANA system suitability standard. The peak at ~9.7 min is NGNA, and the peak at ~10.7 min is NANA.
Figure 25:
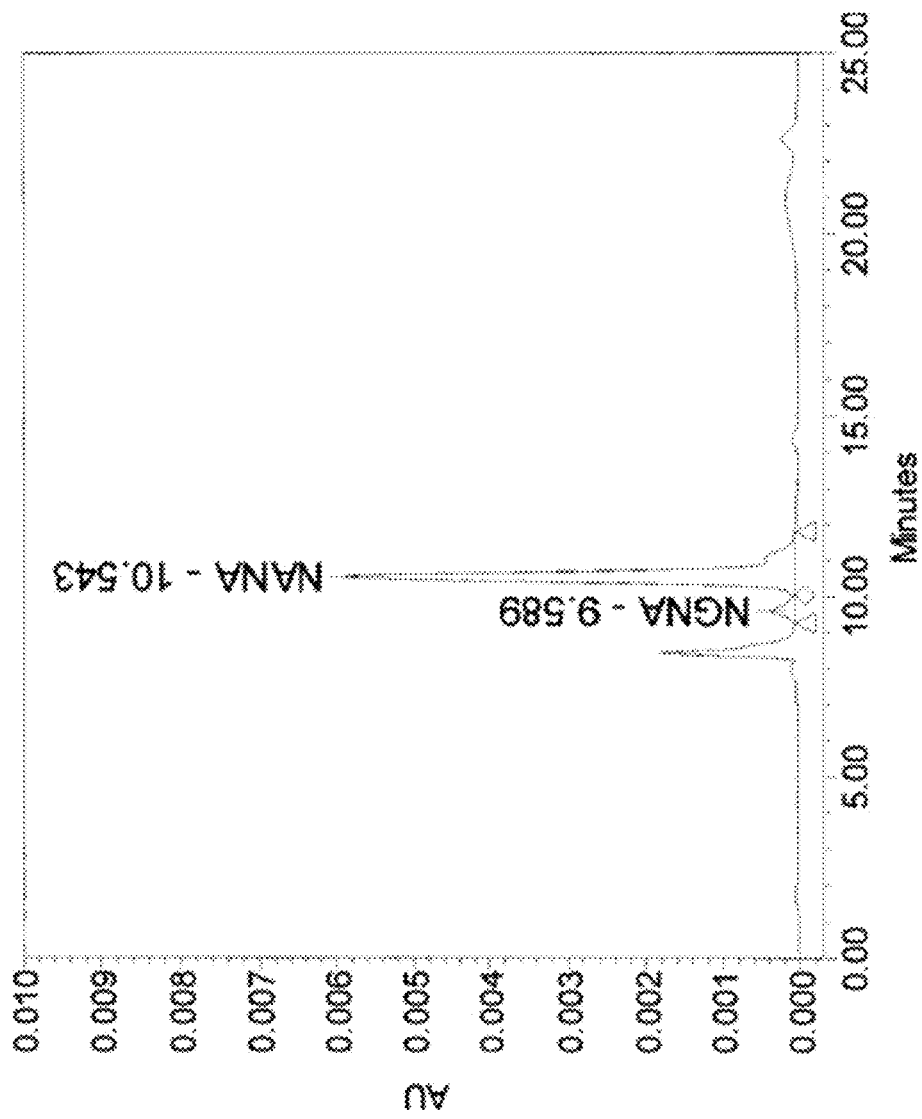
FIG. 25 shows a representative chromatogram of hydrolyzed CTLA4-Ig molecules comprising SEQ ID NO:2 monomers. The peak at ~8.4 min is the solvent peak. The peak at ~9.6 min is NGNA. The peak at ~10.5 min is NANA. The peak at ~11.3 min is degraded NANA, resulting from the hydrolysis conditions. The area counts of NANA and degraded NANA are combined for calculations of the NANA molar ratio.

Resolution: Using the last system suitability standard injection, peak Resolution was calculated using the following equation: $R=2(T2-T1)/(W2+W1)$, where R is resolution, T2 is the retention time of the NANA peak (peak 2), T1 is the retention time of the NGNA peak (peak 1), W2 is the width at the baseline of lines drawn tangent to the sides of peak 2, W1 is the width at the baseline of lines drawn tangent to the sides of peak 1. FIG. 24 depicts a typical system suitability injection.

Theoretical plates (N): Using the last system suitability standard injection, the theoretical plate count (N) was calculated using the following equation: $N=16(RT^2/W)$, where N is the theoretical plate count, RT is the retention time of the NANA peak in minutes, W is the width at the baseline of lines drawn tangent to the sides of the NANA peak.

The last five injections of the system suitability standard were used to calculate the average area counts and their standard deviation for NANA. The relative standard deviation was equal or less than 3%. The hydrolysis blank was free of any significant peaks with the retention time of NANA and NGNA.

Injection sequence: One injection each of the NANA and NGNA working standards was injected, followed by the hydrolyzed CTLA4-Ig sample material (duplicate samples), followed by the hydrolyzed CTLA4-Ig material. After the CTLA4-Ig runs were completed, one injection each of the NANA and NGNA working standards was injected.

To determine the moles of NANA or NGNA injected in the working standard the following equation is used: mole NANA or NGNA=(C)(P)(I)/MW, where C is the concentration of NANA and NGNA in the working standard, P is the purity of the standard, I is the injection volume, MW is the molecular weight (309.2 g/mole for NANA, and 325.3 g/mole for NGNA).

To determine the moles of NANA and NGNA in the CTLA4-Ig samples, the following equation is used: moles NANA or NGNA in sample=(X)(Y)/Z, where X is the number of moles in the working standard of NANA and NGNA, Y is the average counts of NANA and NGNA in the CTLA4-Ig sample, Z is the averaged area of the duplicate NANA and NGNA in Working Standards. From the duplicate injections of the standards, the area counts of the NANA and NGNA standard must have less than 10% RSD.

To determine the amount injected in each sample, the following equation is used: moles protein=(C)(D)(I)/MW, where C is the concentration of CTLA4-Ig dimer in g/ml (obtained from UV analysis), D is the dilution for hydrolysis (0.95), I is the injection volume (0.005 ml) and MW is the molecular weight of CTLA4-Ig dimer as determined from mass spectrometry (92,439 g/mol).

Molar ratio (MR) of NANA or NGNA to CTLA4-Ig protein is calculated by the following equation: MR=A/B, where A is the number of moles of NANA or NGNA, and B is the number of moles of CTLA4-Ig molecules or dimer.

Molar ratio (MR) of sialic acid, NANA and NGNA, to CTLA4-Ig protein is calculated by the following equation: MR=(A+B)/C, where A is the number of moles of NANA, B is the number of moles of NGNA, and C is the number of moles of CTLA4-Ig molecules or dimer. Duplicates of CTLA4-Ig samples and CTLA4-Ig standard material must have less than 10% RSD in molar ratios for NANA.

Linearity of Responses Determined by Hydrolysis Method of Measuring Sialic Acid Content:

NANA responses were demonstrated to be linear to with respect to NANA standard concentrations in the range from 0.5 µg/mL (~0.1% nominal NANA standard=NANA~QL) to 98.7 µg/mL (~200% nominal NANA standard). NGNA responses were demonstrated to be linear to NGNA standard concentrations in the range from 5.0 µg/mL (~10% nominal NGNA standard) to 82.0 µg/mL (~160% nominal NGNA standard).

Responses of NANA from hydrolyzed CTLA4-Ig material are linear with respect to protein concentrations in the range from 0.25 mg/mL (25% nominal CTLA4-Ig load) to 2.0 mg/mL CTLA4-Ig (200% nominal CTLA4-Ig load). Responses of NGNA from hydrolyzed CTLA4-Ig material are linear to protein concentrations in the range from 0.25 mg/mL (25% nominal CTLA4-Ig load) to 2.0 mg/mL CTLA4-Ig 200% nominal CTLA4-Ig load).

Accuracy of the hydrolysis method of measuring sialic acid content: Accuracy was demonstrated for CTLA4-Ig material (1 mg/mL) spiked with NANA or NGNA standards.

Precision of the hydrolysis method of measuring sialic acid content: Validation experiments demonstrated instrument precision (% RSD<3%), repeatability for sample preparations (% RSD<4%) and reproducibility across different sample preparations, different days, different instruments and different analysts (% RSD<6% for NANA, % RSD<12% for NGNA). NANA and NGNA molar ratios were considered to be precise within a range of 10% and 20%, respectively, of the reported results.

Range of the hydrolysis method of measuring sialic acid content: The working range for this assay was shown to be from 0.49 mg/mL to 3.87 mg/mL CTLA4-Ig material.

Detection Limit (DL) of the hydrolysis method of measuring sialic acid content: The individual DL values for NANA and NGNA standards using a photodiode array detector (PDA; HPLC System 1) were 0.464 µg/mL and 0.402 µg/mL, respectively; the individual DL values for NANA and NGNA using dual wavelength detector (HPLC system 2) were 0.131 µg/mL and 0.111 µg/mL, respectively. The method DL, for both sialic species and based on use of the least sensitive detector, was 0.5 µg/mL for NANA and NGNA.

Quantitation Limit (QL) of the hydrolysis method of measuring sialic acid content: The individual QL values for NANA and NGNA standards using a photodiode array detector (PDA; HPLC System 1) were 1.68 µg/mL and 1.52 µg/mL, respectively; the QL values for NANA and NGNA using a dual wavelength detector (HPLC System 2) were 0.48 µg/mL and 0.41 µg/mL, respectively. The method QL, for both sialic acid species and based on use of the least sensitive detector, was 1.7 µg/mL for NANA and NGNA.

Ruggedness/Robustness: The method was demonstrated to be robust with respect to the sample 48 hours refrigerated solution stability, the use of difference columns, the use of different NANA and NGNA lots and the use of mobile phases with ±5% alteration of concentration.

Figure 10:
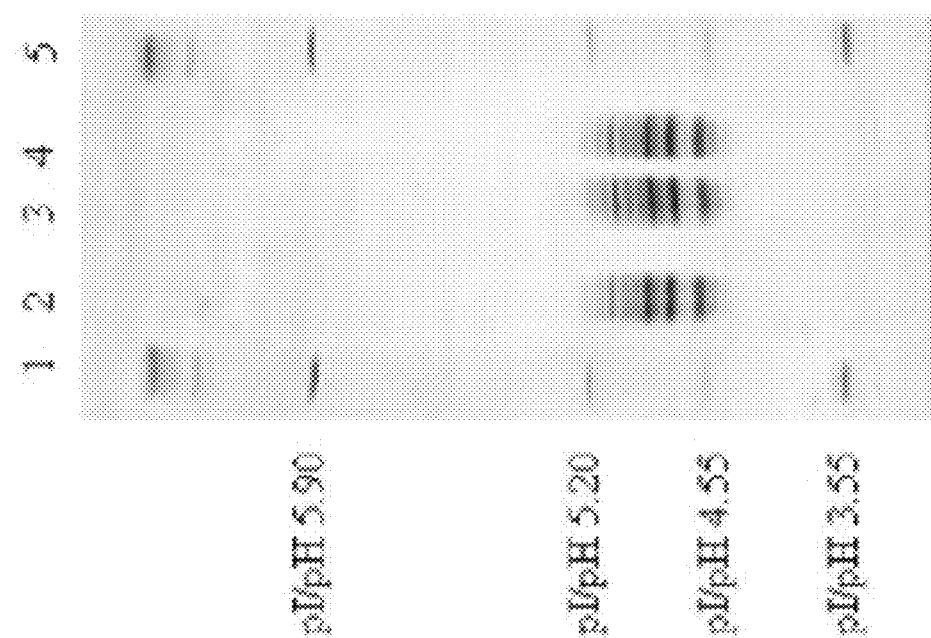
FIG. 10 shows a representative IEF gel (pH 4.0 to 6.5) of a CTLA4-Ig dimer comprising SEQ ID NO:2 monomers. Lanes 1 and 5 show a calibration standard, lane 2, 3, 4 each show 20 µg/µl of CLTA4-Ig dimer.

IEF Gel Electrophoresis:

The pI of the glycoprotein can also be measured, before and after treatment with neuraminidase, to remove sialic acids. An increase in pI following neuraminidase treatment indicates the presence of sialic acids on the glycoprotein. An IEF gel can be use to determine the isolecetrc point, the numer of isoforms of CTLA4-Ig. A suitable system for running IEF gel is the Multiphore II Electrophoresis System, and an IEF gel of pH 4.0 to 6.5 (Amersham Biosciences). The anode buffer has the following composition: 0.1M Glutamic Acid in 0.5M Phosphoric acid. The cathode buffer has the following composition: 0.1M beta-Alanine. The IEF was gel is prefocused under constant power (25watts) and current (25 mAmps) until the voltage reaches ≥300V. IEF calibration standards and samples of the appropriate concentration were loaded and the gel was run under constant power (25watts) and current (25mAmps) with maximum of 2000V for 2.5 hours. After fixing and Coomassie blue staining of the IEF gel, protein bands are visualized by densitometer. A typical IEF gel of CTLA4-Ig dimer preparation is shown in FIG. 10.

Example 4: Isolation and Characterization of Single Chain (Monomer) of CTLA4-Ig

Preparation of native single chain CTLA4-Ig: Samples of CTLA4-Ig recombinant protein prepared by the methods of the invention was separated by non-denaturing SEC using a 2695 Alliance HPLC (Waters, Milford, Mass.) on two 21.5× 300 mm TSK Gel® G3000SW$_{XL}$ preparative columns (Tosoh Bioscience, Montgomery, Pa.) in tandem. Thirty injections (1.0 mL each) of the sample at ~50 mg/mL were separated under isocratic conditions using a mobile phase consisting of 0.2 M NaH$_2$PO$_4$, 0.9% NaCl, pH 7.0, at a flow rate of 1.0 mL/min. Samples were monitored at an absorbance of 280 nm using Water's 2996 PDA detector. Analysis was performed using Waters Millennium 4.0™ and Empower Pro© Software. Fractions were collected (1.0 mL each) on a Foxy 200 automated fraction collector from 90 to 150 minutes. Fractions 16 to 39 (starting at 105 mL and ending at 129 mL) were pooled and concentrated using centricon concentrators with a cutoff of 3500 MW.

The sample (2.0 mL at ~4 mg/mL) was further chromatographed under denaturing conditions using a HiLoad 26/60 Superdex 200 prep grade column (Amersham Biosciences, Piscataway, N.J.) at an isocratic flow rate of 2.0 mL/min using 200 mM NaH$_2$PO4, 6.0 M guanidine hydrochloride at pH 6.0 as mobile phase on an ÄKTAexplorer™ (Amersham Biosciences). Fractions 12-16 were collected, pooled, buffer-exchanged into 200 mM NaH$_2$PO$_4$, pH 6.0 using a HiPrep 26/10 desalting column (Amersham Biosciences), and finally concentrated.

Preparation of induced single chain CTLA4-Ig: Induced single chain CTLA4-Ig was prepared through denaturation, reduction, and alkylation of CTLA4-Ig recombinant protein prepared by the methods of the invention. Guanidine hydrochloride (0.684 g) was weighed into a 1.5 mL Eppendorf centrifuge tube, and 512 µL of 200 mM NaH$_2$PO$_4$, pH 6.0 was added and vortexed until the guanidine hydrochloride was completely dissolved. CTLA4-Ig recombinant protein was denatured by adding 238 µL of CTLA4-Ig material (concentration: 50 mg/mL) into the above tube and vortexed, resulting in a CTLA4-Ig final concentration of ~10.0 mg/mL in 6.0 M guanidine hydrochloride. The denatured protein was reduced by adding 2.6 µL of 1.0 M DTT and incubating at 37° C. for 90 minutes. The reduced protein was then alkylated by the addition of 0.047 g iodoacetamide solid into the sample mixture, followed by vortexing, and incubation at 37° C. for 60 minutes in the dark. The sample (2.0 mL at ~4.0 mg/mL for each injection) was chromatographed under denaturing conditions using a HiLoad 26/60 Superdex 200 prep grade column at an isocratic flow rate of 2.0 mL/min using 200 mM NaH$_2$PO$_4$, 6.0 M guanidine hydrochloride at pH 6.0 on an AKTAexplorer™. The resulting single chain fractions (9-12) were collected, pooled, buffer-exchanged into 200 mM NaH$_2$PO4, pH 6.0 on a HiPrep 26/10 desalting column, and concentrated.

MALDI-TOF Mass Spectrometry Analysis of Naive and Induced Single Chain CTLA4-Ig:

The single chain samples (20 µL) were desalted and concentrated with C4 ZipTips (Millipore, Billerica, Mass.), then eluted with 20 µL of 80% acetonitrile with 0.1% TFA saturated with sinnapinic acid. The mixture (1.0 µL) was spotted onto a well of the MALDI sample plate and allowed to air dry before being placed in the mass spectrometer. The MALDI-MS spectra were acquired on an OmniFlex mass spectrometer (Bruker Daltonics, Mass.) using a nitrogen laser (337 nm). Samples were analyzed in the reflective, positive-ion mode by delayed extraction using an accelerating voltage of 20 kV and a delay time of 200 ns. A total of 250 single-shot spectra were summed for each sample. External calibration was achieved using a mixture of Trypsinogen (23982 m/z), Protein A (44613 m/z), and Bovine Albumin (66431 m/z).

Single Chain Analysis Using Denaturing (Guanidine HCl) Size Exclusion Chromatography:

CTLA4-Ig supernatant from cell culture growth collected at different points during the time course are prepared for HPLC analysis. The samples are prepared by weighing 0.114 g guanidine hydrochloride (Mallinckrodt Baker Inc.) in a 0.65 mL Eppendorf microcentrifuge tube; adding 125 uL of time course CTLA4-Ig sample, and vortexing to completely dissolve the guanidine HCl. Then immediately adding 1.8 uL of 250 mM iodoacetamide and mix, and incubating at 37° C. for 30 minutes.

A tandem TSK-GEL®G3000SW$_{XL}$ size exclusion column (7.8 mm ID×30 cm) with a TSK column guard (SW$_{XL}$, 6.0 mm ID×4.0 cm) is used for the single chain SEC analysis performed on the Waters 2695 separations module with a 2996 photodiode array detector. 25 μL of each sample is injected onto the column equilibrated with 200 mM sodium phosphate, 6.0 M guanidine hydrochloride pH 6.0 as mobile phase. The proteins are separated on the column with a flow rate of 0.5 mL/min, and the resulting chromatogram is collected over a 60 minutes window. The integration and quantitation of individual peaks (monomer, single chain, etc.) are performed using the Empower Pro software. To ensure the HPLC system is working properly, injections are also made on the mobile phase, the protein sample buffer, the system suitability standard, and the current CTLA4-Ig material before and after the sample injections. The peak resolution and plate count on the system suitability standard chromatogram are calculated.

Analysis of Cysteinylation of CTLA4-Ig Single Chain by LC/MS Peptide Analysis:

CTLA4-Ig was denatured and reduced in 50 mM Tris buffer (pH 8.0) containing 6 M Guanidine and 5 mM dithiothreitol (DTT). After a 20 minute incubation at 50° C., iodoacetamide (IAM) was added to a final concentration of 10 mM to alkylate free thiols and the incubation was continued for an additional 20 minutes at 50° C. in the dark. The reduced and alkylated mixture was loaded onto a desalting column (Amersham, NAP-5), then eluted into the void volume with either 50 mM Tris, 10 mM CaCl2, pH 8.0 or 50 mM sodium phosphate buffer, pH 7.5. Following desalting, reduced/alkylated CTLA4-Ig was digested using two different proteases: trypsin or Asp-N. CTLA4-Ig material was also subjected to trypsin/chymotrypsin digestion without reduction and alkylation.

For trypsin digestion, sequence grade trypsin (Promega, 2%, w/w, enzyme/protein) was added and the mixture was incubated for 4 hours at 37° C. For Asp-N digestion, sequence grade Asp-N(Roche, 2%, w/w, enzyme/protein) was added and the mixture was incubated for 16 hours at 37° C. For the trypsin/chymotrypsin digestion, sequence grade trypsin (Promega, 4%, w/w, enzyme/protein) was added and the mixture was incubated for 4 hours at 37° C., then a-chymotrypsin was added (Sigma, 4%, w/w, enzyme/protein) and the mixture was incubated for 16 hours at 37° C. All samples were frozen (−20° C.) after the digestion.

The resulting peptide mixtures were separated by gradient elution from a Waters Atlantis™ dC18 column (2.1×250 mm) on a Waters Alliance HPLC Workstation at 0.12 mL/minute. The column was directly connected to the Waters Micromass Q-Tof Micro™ mass spectrometer equipped with an ion-spray source for collection of mass spectra. Peptide mixtures were also separated on a Varian Polaris C18 column (4.6×250 mm) at 0.70 mL/minute using the same HPLC workstation. The columns were equilibrated with solvent A (0.02% TFA in water) and peptides were eluted by increasing concentration of solvent B (95% acetonitrile/0.02% TFA in water). A post-column splitter valve was used to direct 15% of the flow to the Q-Tof workstation, which was run in the positive TOF (time of flight) mode (m/z 100-2000). The typical ion spray voltage used was 3000 V.

The loss of 113±4 u upon reduction suggests that there is a covalent disulfide modification to the protein. The predicted shift for cysteinylation is 119.14 u. However, an actual mass loss of 111.14 u is expected upon reduction of the single chain species. Loss of 119.14 u results from the removal of a cysteine and a gain of 8 u results from the addition of 8 protons upon reduction of the eight intra chain cysteines ($Cys^{47, 74, 92, 118, 197, 157, 303, 361}$ of SEQ ID NO:2).

Thus, the additional 113±4 u on the intact mass corresponds to cysteinylation with a cysteine amino acid. The cysteine most likely to be modified is $Cys^{146}$ since the interchain disulfide linkage is absent in the single chain species based on the intact MALDI data. Using LC/MS peptide analysis to examine the peptides, which contain $Cys^{146}$, it is found that reduced and non-reduced material display different retention times and masses than the single chain material. To confirm cysteinylation, the single chain peptide containing $Cys^{146}$ was collected and analyzed using MALDI.

Figure 26A:
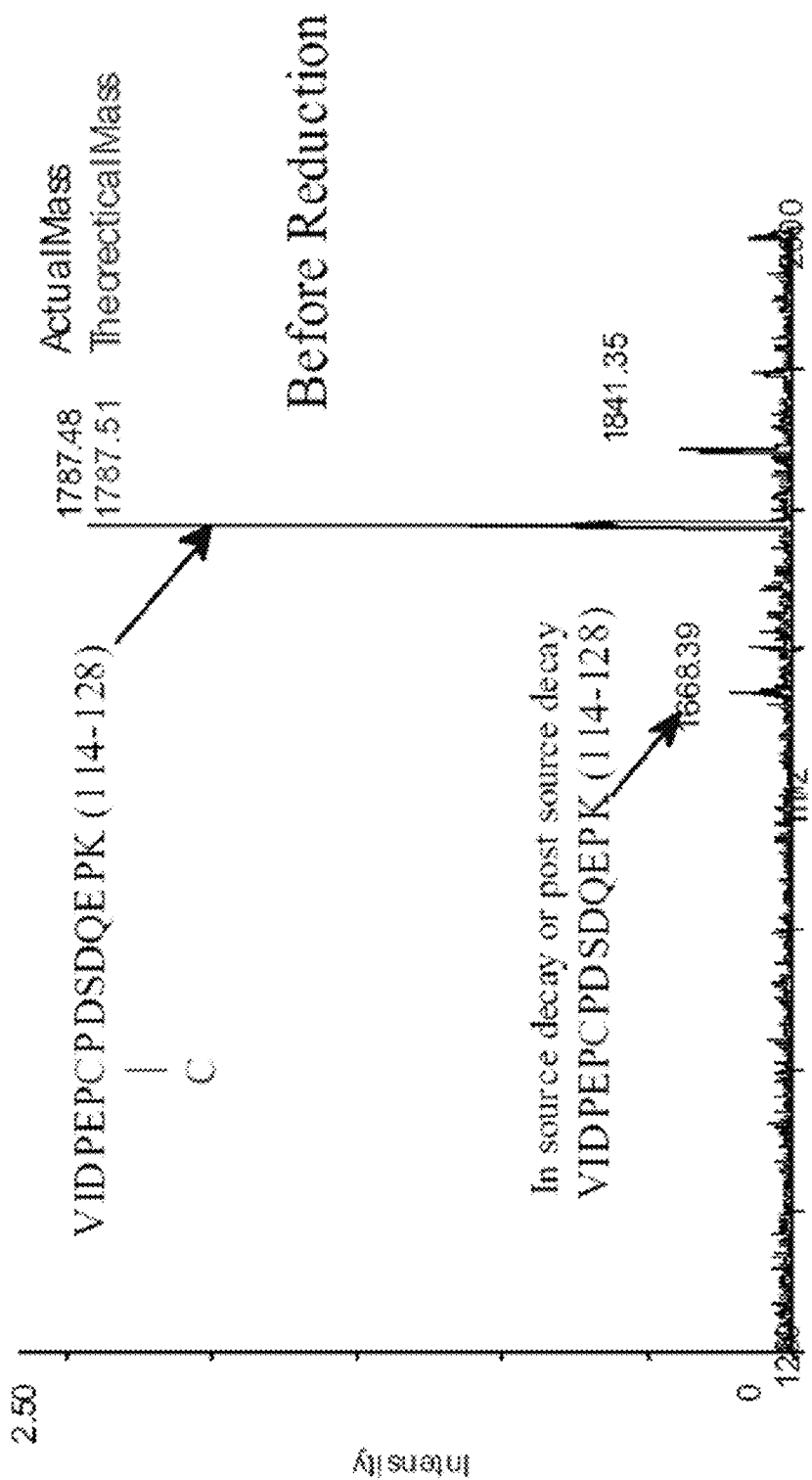
FIGS. 26A, 26B, and 26C show the MALDI spectra of CTLA4-Ig cysteinylated peptide. The MALDI spectra were obtained for CTLA4-Ig trypsin/chymotrypsin fragment containing Cys$^{146}$ of SEQ ID NO:2.
Figure 26B:
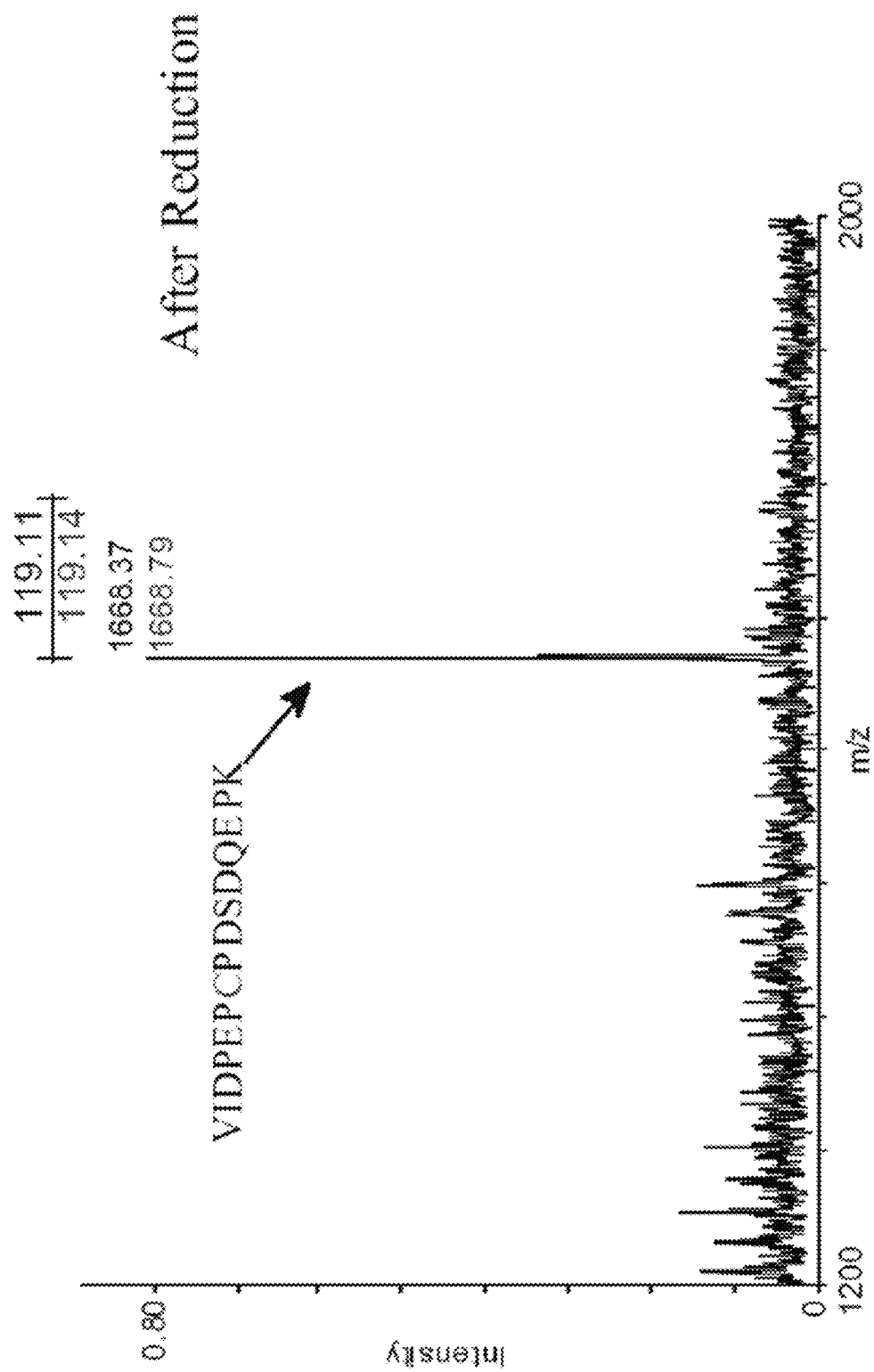
Figure 26C:
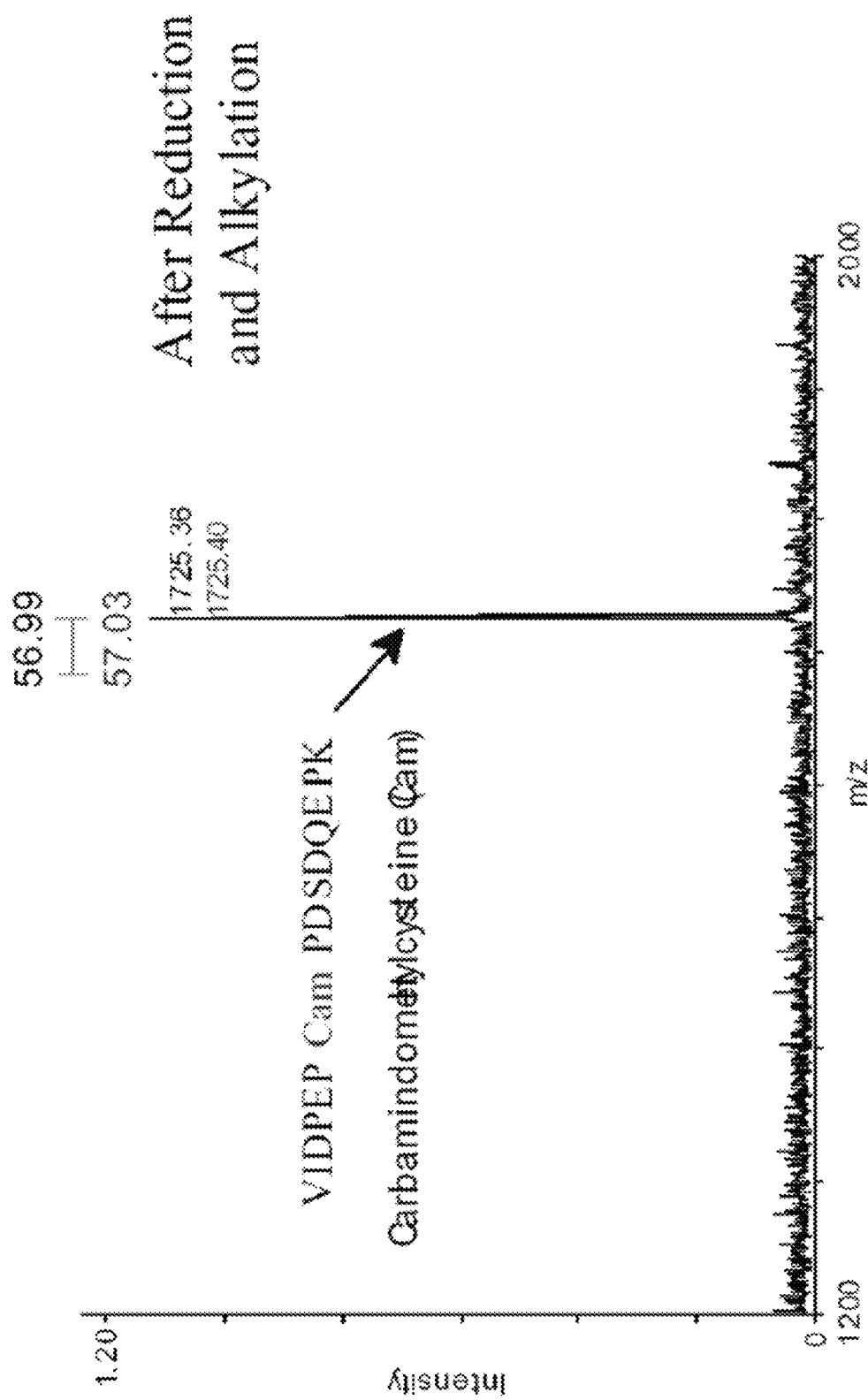

The collected peak containing $Cys^{146}$ has a mass of 1787.48 u, in agreement with the predicted mass of 1787.51 u for the peptide with a cysteinylation of $Cys^{146}$ (FIG. 26, panel A). This peptide, after being subjected to reduction, loses 119.11 u in agreement with a predicted loss of 119.14 u; the loss of cysteine (FIG. 26, panel B). The material is then further manipulated with iodoacetamide producing a shift of 56.99 u in agreement with a predicted mass gain of 57.03 u (FIG. 26, panel C).

Example 5: Manipulating Monomer or Multimer CTLA4-Ig Formation

Agonistic Effects of Media and Media Components on Single Chain Formation:

The agonistic affects of different media and media components are determined for single chain formation. CTLA4-Ig molecules can be incubated at 37° C. with various media and individual media constituents over a period of 60 hours and analyzed for single chain formation by tandem column denaturing SEC. An overwhelming agonist response for single chain formation is found upon the addition of 10 mM cysteine to formulation buffer. There is a rapid rise in single chain formation which peaks around six hours following the addition of cysteine. This response gradually decreases over the remaining 56 hours. In addition, the +30% gal feed affected a more gradual but still relatively rapid increase in single chain formation. The +30% gal feed is a composition of galactose and 117E. This mixture is added every day to feed the cells. While in this experiment, cysteine was introduced at artificially large quantities independent of 117E, there is a need to determine which of the 117E components can be involved in single chain formation.

Specific components of 117E and other media are incubated with CTLA4 Ig over a period of 60 hours and analyzed for single chain formation by tandem column denaturing SEC. Investigation into this medium centers around possible disulfide reducing components and/or inhibitors, which would effect single chain formation based on previous experiments showing the interchain disulfide is not present. The constituents of 117E which are known to have some reducing affects on disulfides were tested; lipoic acid, cystine, cysteine, methionine, and glutathione. Again, an overwhelming agonist response for single chain formation is found upon the addition of cysteine to formulation buffer. There is a rapid response in single chain formation, which peaks at around six hours, following the addition of cysteine. This response gradually decreases over the remaining 56 hours. The major single chain formation occurs with cysteine containing media: cysteine, yeastolates and fermentation media. The other sulfur containing components such as methionine, and glutathione have no to very little affect on single chain formation. There are no affects of ammonium chloride observed.

The present invention therefore encompasses a method for providing a ratio of single chain:dimer form of a protein, such protein capable of existing in dimer as well as in single chain form, comprising the steps of (1) providing and/or maintaining (such as during step (2)) a liquid cell culture medium for the culture of cells expressing said protein, in which the concentration of an agent capable of reducing or inhibiting dimer formation (such as cysteine) is selected to provide said ratio, and (2) culturing said cells to express said protein. Adding and/or increasing the concentration of such an agent (for example, cysteine) in a liquid cell culture medium provides a higher ratio of single chain:dimer form of such protein, while removing, decreasing or eliminating the concentration of such an agent (for example, cysteine) in a liquid cell culture medium decreases the ratio of single chain:dimer form of said protein.

One particular embodiment of this method is where said protein is a glycoprotein capable of dimer formation through the formation of an interchain disulfide bond, such as the CTLA4-Ig molecules of the present invention.

Agonistic Effects of High Salt on High Molecular Weight Formation:

During the purification process, CTLA4-Ig is exposed to high salt concentrations for varying amounts of time. The affects of high salt concentrations are determined for high molecular weight formation. CTLA4-Ig (at ~50 mg/mL) is incubated in the presence of 500 mM sodium phosphate, pH=6.0, 37° C. There is an agonistic affect at high concentrations of sodium phosphate; a sustained, rapid increase in high molecular weight forms, mostly tetramer, is observed over a period of 100 hours.

The present invention therefore encompasses a method for reducing the ratio of aggregate:dimer form of a protein, such protein capable of existing in aggregate as well as in dimer form, during processing (such as during purification) of such protein, comprising the use of one or more liquids which are non-aggregate salt solutions. A "non-aggregate salt solution" refers to a liquid containing a concentration of salt dissolved therein which is, relative to the same liquid containing a higher concentration of such salt, less agonistic in the formation of aggregate.

One particular embodiment of this method is where said protein is a glycoprotein capable of dimer formation through the formation of an interchain disulfide bond, such as the CTLA4-Ig molecules of the present invention.

Antagonistic Effects on Single Chain Formation:

The previous modeling experiments demonstrated a large and rapid affect on single chain formation by the addition of cysteine containing components. Cysteine is an amino acid which contains a free sulfhydryl. If the sulfhydryl is involved in the formation of single chain it should be blocked through the use of antagonistic compounds. One such compound is iodoacetamide. Iodoacetamide is a water-soluble compound that reacts in a rapid fashion with any free sulfhydryl to form an irreversible thioether bond. CTLA4-Ig is incubated at 37° C. with various medias, cysteine, and iodoacetamide over a period of 60 hours and analyzed for single chain formation by tandem column denaturing SEC and HMW by tandem column non-denaturing SEC. Iodoacetimide not only blocks single chain formation but also blocks aggregate formation in both a CTLA4-Ig composition and high salt. Iodoacetamide does not block the aggregate formation in low sialic acid monomer. However, the amount of aggregate formed in low sialic acid material is comparable to the amount formed in CTLA4-Ig composition.

The model provides insight to a mechanism that has not previously been well understood. It appears that there are at least two major pathways of aggregate formation in the CTLA4-Ig process that have been identified. The first pathway, which produces the large amount of aggregate, free sulfhydryl cysteine acts as an agonist for the formation of single chain species. The agonistic affect of cysteine can be blocked by the addition of iodoacetamide. Surprisingly, iodoacetamide is not only an antagonist for single chain formation but also high molecular weight formation. It should be noted that the process is designed to produce a composition that contains an increased amount of sialic acid as compared to fermentation during the downstream purification. In a second path, which produces much less aggregate, a subspecies which contains low amounts of sialic acid is not affected by iodoacetamide for the formation of single chain or aggregate.

The present invention therefore encompasses a method for decreasing the ratio of single chain:dimer form of a protein, such protein capable of existing in dimer as well as in single chain form, comprising the steps of (1) providing and/or maintaining (such as during step (2)) a liquid cell culture medium for the culture of cells expressing said protein, such medium containing an agent antagonistic to single chain formation (such as iodoacetamide), and (2) culturing said cells to express said protein.

The present invention also encompasses a method for decreasing the ratio of aggregate:dimer form of a protein, such protein capable of existing in aggregate as well as in dimer form, comprising the steps of (1) providing and/or maintaining (such as during step (2)) a liquid cell culture medium for the culture of cells expressing said protein, such medium containing an agent antagonistic to aggregate chain formation and/or antagonistic to single chain formation (such as iodoacetamide), and (2) culturing said cells to express said protein.

One particular embodiment of this method is where said protein is a glycoprotein capable of dimer formation through the formation of an interchain disulfide bond, such as the CTLA4-Ig molecules of the present invention.

Based on these data, it is not difficult to imagine at least two pathways to aggregate formation are induced in CTLA4-Ig. In the major pathway, single chain is involved in the formation of aggregate through a yet not completely clear mechanism. A second minor pathway, which is independent of single chain formation, is involved in the formation of aggregate. These pathways can help to explain why there are at least three forms of high molecular weight species that can be chromatographically separated. These are models and must be tested during the actual fermentation process in order to determine the actual affects if any and magnitude of the affects. Based on this data consideration should be given to testing not only the current fermentation process but also fermentation devoid of cysteine.

Example 6: CTLA4-Ig Dimer and Tetramer

CTLA4-Ig Dimer and Tetramer Binding to B7-1 Ig

The invention provides methods for evaluation of CTLA4-Ig dimer and tetramer binding to B7-1Ig. Physical characteristics (e.g. diffusion coefficient, molecular weight, binding valency) and instrument operational parameters (e.g. flow rate, chip density) can influence the Biacore assay results. Under mass transfer limitation; the binding rate of tetramer is approximately 20% slower than dimer for the same molar concentration. At a specified flow rate, it is possible that tetramer molecules penetrated the matrix less efficiently compared to the dimer. Under a high density B7-1Ig immobilized chip, competitive binding of tetramer and dimer exhibits comparable inhibition curves. This indicates that the theoretical valency of tetramer (four) versus dimer (two) has no influence on binding to B7-1Ig. Molar concentrations of tetramer can be calculated based on a dimer standard curve. Using this approach, the binding of tetramer to B7-1Ig was found to have equivalent dose dependent response compared to dimer.

Comparison of the binding potency of a tetramer and a dimer is influenced by the unit of measurement used for the preparation of standards and samples. Tetramer and dimer samples can be compared at a concentration of 2000 ng/mL. On a mass basis (ng/mL), each species shows a binding potency of approximately 100% using a standard curve of the same species. However, the binding potency of tetramer was halved when determined on a dimer standard curve, and the binding potency of a dimer was more than doubled when determined on a tetramer standard curve. Since the Biacore instrument detects molecular interactions based on mass, the signal resonance units (RU) from identical concentrations (ng/mL) of tetramer and dimer should be the same. Although the detection system is a function of mass, the interaction between molecules occurs on a molar basis. Therefore, the molar concentrations of CTLA4-Ig dimer and CTLA4-Ig tetramer are 21.6 nM and 10.8 nM, respectively, at 2000 ng/mL. Using the molar concentration, both CTLA4-Ig dimer and CTLA4-Ig tetramer samples show comparable binding potency on a dimer standard curve. Using the same molar concentration approach on a CTLA4-Ig tetramer standard curve, the CTLA4-Ig dimer sample shows an additional 30% increase in binding potency compared to the tetramer sample. This observation is due to a decrease in the slope of the tetramer standard curve at high concentrations, resulting in a higher calculated concentration for a given initial binding rate. One explanation for this observation is the effect of mass transfer.

Mass transfer limitation experiment indicates that the initial binding rate of the CTLA4-Ig tetramer is approximately 20% slower than the CTLA4-Ig dimer for the same number of molecules (i.e. the binding rate of the tetramer differs from dimer by a factor of 0.8). This observed difference is due to the molecular weight of the two species and its effect on diffusion of the molecules to the surface of the chip. The diffusion coefficient of a molecule is inversely proportional to the cube-root of the molecular weight. A lower diffusion coefficient would indicate slower movement of the molecules. Based on respective molecular weights, the calculated diffusion coefficient of CTLA4-Ig tetramer is 0.8 times that of the CTLA4-Ig dimer, or conversely the dimer is 1.25 times that of the tetramer. Experimental data are consistent with this observation where the CTLA4-Ig dimer shows a potency of 133% as calculated from a CTLA4-Ig tetramer standard curve using molar concentrations. Mass transfer limitations on high-density chips are more pronounced at lower flow rates and lower analyte concentrations. As the flow rate increases, the dimer shows faster initial binding rates compared to tetramer. Therefore, the increased molecular weight and lower diffusion coefficient of the tetramer contribute to initial binding rate differences compared to dimer.

Competitive binding of CTLA4-Ig tetramer and dimer to B71Ig indicates that tetramer and dimer show similar binding valency under mass transfer limited conditions. The effects of additional tetramer onto a B7-1Ig chip initially bound with either dimer or tetramer indicate low binding potential. This observation is not due to limited binding site availability because additional dimer could bind to B7-1Ig chips initially bound with CTLA4-Ig dimer or CTLA4-Ig teramer. Limited penetration into the matrix can explain the observed decrease in tetramer binding.

The nature in which molecules bind on the Biacore affects the interpretation of the results. The tetramer and dimer molecules diffuse at different rates due to their differences in molecular size under the condition of mass transfer limitation. In addition, steric hindrance on the surface of a high density chip affects penetration of subsequent molecules to the matrix.

Physical characteristics such as the molecular weight, diffusion coefficient, and binding of each species need to be considered when performing concentration analyses on the Biacore. Standards used for comparison to the analyte of interest should be of the same material. However, tetramer can still be analyzed against dimer standards if both the standards and samples are expressed on a molar basis where molecular size is taken into consideration. The data presented indicate that the binding of CTLA4-Ig dimer and CTLA4-Ig tetramer to B7-1Ig is comparable.

Both CTLA4-Ig dimer and tetramer show similar association rates ($k_{on}$). However, the tetramer shows a slower dissociation rate ($k_{off}$) which is attributed to avidity due to the increase in the number of binding sites.

Binding kinetic analysis between two proteins such as a ligand and receptor can be performed on the Biacore using a chip immobilized with a low density of ligand of approximately 600-800 RUs such that the maximum binding capacity ($R_{max}$) is in the range of 50-150 RU. The purpose of a low-density chip is to minimize the effects of avidity and mass transport. Avidity is observed when multivalent analytes remain bound to the surface of the chip due to close proximity of ligands available as dissociation of individual binding sites occurs. Mass transport is observed when there is a significant difference in the analyte concentrations between the surface of the chip and the bulk solution.

In one embodiment, the CTLA4-Ig molecule is a dimer consisting of two single-chain molecules linked by a single interchain-disulfide bond, and contains two binding sites for B7 molecules. In another embodiment, formation of CTLA4-Ig tetramer, as confirmed by light-scattering, SEC and SDS-PAGE, results in a molecule with potentially four binding sites. The binding kinetics of purified monomer and dimer are statistically compared to CTLA4-Ig dimer material. There are no significant differences in the $k_{on}$ rates (p values >0.05). The $k_{off}$ rate of tetramer is significantly different from the $k_{off}$ rate of the dimer. The $k_{off}$ rate of the dimer purified from the HIC cleaning peak is not significantly different from the $k_{off}$ rate of the CTLA4-Ig dimer material. Therefore, the tetramer dissociates slower than the dimer, indicating an avidity effect due to the increased number of binding sites per molecule.

Tetramer can be unfolded and dissociated into dimer by guanidine treatment. This guanidine-treated CTLA4-Ig dimer was analyzed and the results indicate that its binding kinetic characteristics were similar to those of the CTLA4-Ig dimer formed under physiological conditions. This observation supports the hypothesis that the observed difference in the $k_{off}$ rate between dimer and tetramer is related to binding valency of the molecules and the inherent nature of the specific Biacore method where avidity plays a role in the binding kinetics.

Affinity Purification of CTLA4-Ig Material from HIC Cleaning Peak:

Protein A-Sepharose affinity chromatography: 500 mL of HIC cleaning peak was filtered through a 0.22 micron 1L filter system (Corning, Corning, N.Y., Part no. 430517) and loaded onto a rProtein A-Sepharose column (5 cm×15 cm), which was pre-equilibrated with phosphate buffered saline (Sigma, St. Louis, Mo., P-4417) at pH 7.4. The column was washed with 700 mL PBS, pH 7.4 and eluted with 100 mM glycine, pH 3.5. Fractions of 50 mL each were neutralized during collection by the addition of 0.5 mL of 2.0 M tris, pH 10 to the collection tubes. Fractions were assayed at 280 nm absorbance, pooled and concentrated using a centriprep YM-3 cartridge (Millipore Corporation, Bedford, Mass., Part no. 4203). The purified protein solution was stored at −70° C.

PROSEP-rA (recombinant Protein A) affinity chromatography: 500 mL of HIC cleaning peak was filtered through a 0.22 micron 1L filter system (Corning, Corning, N.Y., Part no. 430517) and loaded at a flow rate of 25 mL/minute on a PROSEP-rA High Capacity (Millipore Corporation, Bedford, Mass.) column (25 mm×28 cm), which was pre-equilibrated with 25 mM Tris, pH 8.0 containing 250 mM sodium chloride. Waters PrepLC system equipped with Waters 2767 Sample Manager and Waters 2996 Photodiode Array Detector was used for this chromatography. The column was washed with 25 equilibration buffer for 30 minutes at a flow rate of 25 mL/minute and eluted with 100 mM acetate, pH 3.0 at a flow rate of 25 mL/minute for 30 minutes. Fractions of 10 mL each were neutralized during elution by collecting over 50 ul of 2.0 M tris, pH 10, which was previously added to the tubes. Fractions having high absorbance at 280 nm were pooled and concentrated using a centriprep YM-3 cartridge (Millopore Corporation, Bedford, Mass., Part No. 4203). The purified protein solution was stored at −70° C.

Size Exclusion Chromatography: Size exclusion chromatography was performed on a Waters Alliance 2695 separations module equipped with a Waters 2996 Photodiode Array Detector (Milford, Mass.), and a Foxy 200 fraction collector controlled by Millennium[32] version 3.20 or Empower software. Tandem TOSOH BIOSCIENCE (Montgomery, Pa.) TSK G3000 SW (21.5 mm×300 mm) and tandem TSK G3000 SW×L (7.8 mm×300 mm) columns were used for preparative and analytical SEC, respectively. Eluted proteins were monitored by UV absorbance at 280 nm.

Preparative isolation of dimer, tetramer and multimer was achieved by SEC of Protein A purified HIC cleaning peak material. Thirteen samples (~10 mg each) of Protein A eluate were injected onto a preparative tandem SEC column using a mobile phase of 100 mM monobasic sodium phosphate buffer pH 7.0 containing 0.9% sodium chloride at a flow rate of 1 mL/min. Fractions were collected at every minute from 90-160 minutes for each of the thirteen injections. The run time for a single injection was 180 minutes.

Each fraction was examined by tandem column analytical size exclusion HPLC. Fractions 13-15 (containing multimer), fractions 22 and 23 (containing teramer), and fractions 43-49 (containing dimer) were pooled. Purified multimer, tetramer and dimer fractions were examined on analytical two column SEC with dynamic light scattering detection (DSL).

Biospecific Binding Analysis of CTLA4-Ig Component of the HIC Cleaning Peak and Purified Components to Immobilized B7-1 Ig:

The biospecific binding of CTLA4-Ig to immobilized B7-1Ig (on a CM5 chip) was measured using a SPR based BIAcore C biosensor (BIAcore, AB, Piscataway N.J.). CTLA4-Ig material was used to generate the standard curve. B7-1Ig was immobilized at a density of 5000 to 10,000 resonance units (RU's) on an activated CM5 sensor chip. CTLA4-Ig reference standards, quality controls, and samples were injected at a flow rate of 20 μL/min. over the B7-1Ig sensor chip surface to generate sensorgrams. The initial binding rate (RU/s) of CTLA4-Ig onto immobilized B7-1Ig was measured under diffusion-limited conditions on a high density B7-1Ig surface, and this correlates directly to the active concentration of CTLA4-Ig in the samples. Standard, quality control sample, and unknown sample concentrations were interpolated from the standard curve generated by plotting the RU's versus CTLA4-Ig concentrations in the nominal range of 125-8000 ng/mL. The final results were expressed as percent binding (Mean Concentration of unknown/sample/2000)×100.

Determination of Molar Mass and Hydrodynamic Radius:

The SEC separation was performed with a TSK3000 SWXL column and corresponding guard column. The mobile phase consisted of 25 mM HEPES, 850 mM NaCl, pH 7.0, using isocratic conditions for elution at 0.8 mL/min. HPLC analyses were performed at ambient temperatures and samples maintained at 4° C. during analysis. Molar mass determination incorporated the Wyatt Dawn EOS utilizing 15 distinct scattering angles to measure the angular variation of light scatter for each species. A Zimm plotting formalism was used for molar mass determination where slices for each species were averaged for molar mass. The specific refractive index increment (dn/dc) value used to calculate absolute molar mass was 0.189 obtained using a) and an Optilab DSP Interferometer (RI. Hydrodynamic radius (Rh) determination was performed in-line with a Photon Correlator QELS detector positioned at an angle approximately 90° to the flow cell. The translational diffusion constant is measured from this signal and $R_h$ is calculated using the Einstein-Stokes relationship. Data analysis was accomplished using Astra software version 4.90 from Wyatt Technology.

The molecular weight and hydrodynamic radius values for dimer and tetramer species were found to be 86-91 kDa and 172-199 kDa, respectively. The cleaning peak samples were observed to contain additional HMW species corresponding to hexamer and decamer by molecular weight. The range of the hydrodynamic radii for the dimer species is 3.8-4.7 nm. The ranges of the hydrodynamic radii of the heterogeneous tetramer species were 5.7 nm to 6.2-6.3 nm.

Binding of CTLA4-Ig Dimer and Tetramer to B7-1Ig Using Surface Plasmon Resonance:

Concentration Analyses: Concentration analyses of the various CTLA4-Ig species to B7-1Ig were performed on a Biacore 3000 instrument (Biacore, Piscataway, N.J.) according to Method 7441-4[2] with minor modifications. Modifications include the following: Biacore 3000 was used instead of Biacore C. The flow rate was 10 μL/min instead of 20 μL/min. Sample was injected for 60 seconds as opposed to 15 seconds. The sensor chip surface was regenerated at 30 μL/min by three short 30-second (15 μL) pulses of 10 mM sodium citrate, pH 4.0, containing 100 mM NaCl (regeneration buffer), followed by one 30-second pulse of water.

A CMS sensor chip was immobilized with B7-1Ig at a concentration of 20 μg/mL in acetate buffer, pH 5.0, aiming for a target density of 6000-12000 resonance unit (RU). Standards were prepared by serially diluting CTLA4-Ig material to concentrations of 62.5-8000 ng/mL (0.675-86.3 nM) and dimer to concentrations of 125-16000 ng/mL (0.675-86.3 nM) in HBS-EP buffer. Test samples, consisting of either monomer or dimer, were diluted to a target concentration of ~2000 ng/mL and analyzed on the Biacore. Concentrations were determined by the BIAevaluation software (version 4.0.1) using standard curves of either CTLA4-Ig material (>98% monomer) or purified dimer. The binding potency is calculated as the percentage of the concentration determined on the Biacore divided by the concentration determined by A280 nm.

The binding rate of a molecule to a given surface is a function of concentration, which allows for the determination of unknown concentrations. CTLA4-Ig dimer exhibits a higher binding rate as a function of concentration (ng/mL) as compared to CTLA4-Ig tetramer.

The binding potencies of CTLA4-Ig dimer and tetramer are summarized in Table 7. Based on ng/mL, the binding potency of a dimer sample is calculated from a dimer standard curve and found to be 99.5%; whereas, an equivalent concentration of a tetramer sample is 47.2%. Conversely, the binding potency of a dimer sample is calculated from a tetramer standard curve and found to be 266%; whereas, an equivalent concentration of a tetramer sample is 103%. However, when dimer and tetramer are expressed as molar concentrations (nM), the binding potencies of both species are comparable. The binding potency of dimer and tetramer samples calculated from a dimer standard curve are 99.4% and 94.3%, respectively. On a tetramer standard curve, it is 133% and 103%, respectively. Standard curves of dimer and tetramer are comparable based on molar concentrations.

TABLE 9

Binding Potencies of CTLA4-Ig Dimer and Tetramer.

| Sample | Dimer Standard Curve | | Tetramer Standard Curve | |
| --- | --- | --- | --- | --- |
| | ng/mL | nM | ng/mL | nM |
| Dimer | 99.5% | 99.4% | 266% | 133% |
| Tetramer | 47.2% | 94.3% | 103% | 103% |

Binding Valency:

CTLA4-Ig dimer (25-1600 nM) or tetramer (25-400 nM) was pre-mixed at various molar ratios with B7-1Ig for three minutes before 30 μL of the mixture was injected at a flow rate of 10 μL/min over a B7-1Ig chip immobilized with a density of 9392 RU. The chip was regenerated after each injection by three 30-second pulses of regeneration buffer followed by one 30-second pulse of water. The RU's obtained at the end of each injection were compared.

Theoretically, the binding valency of the dimer molecule is two; each single chain consists of one binding site. A tetramer molecule consists of two dimer molecules, and thus has a binding valency of four. To determine the apparent binding valency of dimer and teramer, a competitive assay was designed and conducted on the Biacore 3000. In the experiment, analytes were pre-mixed with B7-1Ig at various molar ratios for three minutes before the mixture was injected onto a B7-1Ig chip (9392 RU) at a flow rate of 10 μL/min for one minute. Table 10 shows the percentage of either dimer or tetramer that was competitively inhibited with increasing molar amounts of B7-1Ig. At a molar ratio of 1.25 (B7-1Ig) to 1 (dimer or tetramer), a significant difference was observed in competitive inhibition with monomer at 96.1% and dimer at 84.9%. However, dimer and tetramer exhibit similar inhibition curves, this suggests that the valencies are approximately equal. In addition, both dimer and teramer also showed similar inhibition profiles using lower density chips.

TABLE 10

Inhibition of Dimer and Tetramer with B7-1Ig.

| B7-1Ig | Dimer (% Inhibition) | | | Tetramer (% Inhibition) | | |
| --- | --- | --- | --- | --- | --- | --- |
| Molar Ratio | N | Avg | S.D. | N | Avg | S.D. |
| 0.02 to 1 | 1 | 1.5 | n/a | 1 | 3.4 | n/a |
| 0.04 to 1 | 2 | 1.2 | 0.2 | 2 | 5.1 | 0.3 |
| 0.08 to 1 | 3 | 2.9 | 1.1 | 3 | 7.4 | 0.8 |
| 0.16 to 1 | 4 | 5.5 | 0.7 | 4 | 12.6 | 0.9 |
| 0.32 to 1 | 5 | 14.7 | 3.3 | 5 | 20.9 | 2.2 |
| 0.64 to 1 | 5 | 38.1 | 6.1 | 4 | 40.8 | 3.5 |
| 1.25 to 1 | 5 | 96.1 | 2.6 | 3 | 84.9 | 4.6 |
| 2.5 to 1 | 4 | 99.7 | 0.1 | 2 | 97.5 | 0.5 |
| 5.0 to 1 | 3 | 99.9 | 0.1 | 1 | 99.4 | n/a |
| 10.0 to 1 | 2 | 100.0 | 0.0 | n/a | n/a | n/a |
| 20.0 to 1 | 1 | 100.0 | n/a | n/a | n/a | n/a |

Saturation of B7-1Ig Chip: CTLA4-Ig dimer or tetramer (200, 1000, or 8000 ng/mL) was initially injected at 10 μL/min for one minute over a high density B7-1Ig chip (6738 RU) followed by a series of seven 1-minute injections with either monomer or dimer (200, 1000, or 8000 ng/mL). The chip was regenerated after each condition by four 25 μL injections of regeneration buffer followed by 25 μL injection of water. The RU's obtained at the end of each injection were compared.

Either dimer or tetramer was repeatedly injected over a B7-1Ig surface pre-coated with either dimer or tetramer without surface regeneration. Initial binding with tetramer does not impede subsequent injections of dimer from binding, however, additional tetramer injections result in a significantly decreased rate of binding as compared to dimer injection. Initial binding with dimer followed by subsequent injections of dimer results in an increased binding towards saturation. Subsequent injection of tetramer to the dimer pre-coated chip shows a gradual decrease in binding, indicating a dissociation of molecules from the chip and a lack of tetramer penetration into the matrix. Similar results are observed with initial injection of either 200 ng/mL or 8000 ng/mL of CTLA4-Ig molecules.

CTLA4-Ig Tetramer has Higher Avidity to the B7-1Ig Receptor:

CTLA4-Ig species, including, the discarded portions of purification columns such as the cleaning peaks of HIC and QFF columns were purified and their binding kinetics were analyzed on the Biacore.

CTLA4-Ig Species from HIC Cleaning Peak: The HIC column is used in the CTLA4-Ig process to remove high molecular weight species such as DNA. CTLA4-Ig species from the cleaning peak from the HIC column can be used for subsequent purification and kinetic analysis. The HIC cleaning peak was passed through a Protein A column to capture all CTLA4-Ig species and to remove other impurities that can be present. The eluate from the Protein A column, which consisted of a mixture of all CTLA4-Ig species (i.e., dimer, tetramer, hexamer multimer), showed apparent $k_{on}$ and $k_{off}$ rates which were comparable to the CTLA4-Ig dimer standard. Separation of the Protein A eluate by 2-column SEC resulted in three CTLA4-Ig species: dimer, tetramer, and hexamer/multimer, with $k_{on}$ and $k_{off}$ rates as summarized in Table 11. Sialic acid content of the purified dimer from the HIC cleaning peak was low compared to CTLA4-Ig dimer.

In Table 11, sample concentrations of 75-200 nM were tested on B7-1Ig chip (694 RU). CTLA4-Ig species purified from the HIC cleaning peak showed lower binding compared to CTLA4-Ig reference. Tetramer which was disaggregated gave comparable $k_{on}$ and $k_{off}$ rates to CTLA4-Ig reference.

TABLE 11

Kinetic Analysis of CTLA4-Ig Species from HIC Cleaning Peak

| Species | $k_{on} \times 10^5$ (1/Ms) | $k_{off} \times 10^3$ (1/s) | $K_A \times 10^7$ (1/M) | $K_D$ (nM) |
|---|---|---|---|---|
| CLTA4-Ig dimer standard | 4.03 | 9.65 | 4.18 | 23.9 |
| Protein A Eluate | 3.77 | 9.73 | 3.87 | 25.8 |
| Dimer | 1.52 | 5.88 | 2.59 | 38.7 |
| Tetramer | 1.65 | 8.07 | 2.04 | 48.9 |
| Hexamer | 1.54 | 12.3 | 1.25 | 79.9 |
| Dimerized Tetramer | 3.12 | 9.88 | 3.16 | 31.7 |

Statistical analysis of the data was performed using the Student's T-test based on 7 observations of the CTLA4-Ig dimer standard and 14 observations of purified dimer and tetramer. There was no difference in the $k_{on}$ rates comparing the CTLA4-Ig dimer standard with either purified dimer or tetramer. However, the $k_{off}$ rate and $K_D$ were statistically significant when the reference was compared with purified tetramer (Table 12). Comparing the purified tetramer to purified dimer, both the $k_{on}$ and $k_{off}$ rates as well as the $K_D$ were statistically different. It should be pointed out that although the data were grouped into dimer and tetramer, individual classifications of samples (i.e., frontal, backside, etc.) can have slightly different characteristics that can affect their binding kinetics. For the dimer, the $k_{on}$ and $k_{off}$ rates averaged $3.3 \pm 1.0 \times 10^5$ M-1s-$^1$ and $8.8 \pm 3.5 \times 10^{-3}$ s-$^1$, respectively. The the $k_{on}$ and $k_{off}$ rates of the tetramer were $2.6 \pm 0.8 \times 10^5$ M-1s-$^1$ and $3.1 \pm 1.4 \times 10^{-3}$ s$^{-1}$, respectively.

In Table 12, Dimer (n=14) and tetramer (n=14) and CTLA4-Ig dimer standard (n=7) were analyzed.

TABLE 12

Statistical Analysis of CLTA4-Ig Species.

| Student's T-test | p-values | | |
|---|---|---|---|
| | $k_{on}$ | $k_{off}$ | $K_D$ |
| Dimer standard vs. Dimer | 0.9118 | 0.8678 | 0.7893 |
| Dimer standard vs. Tetramer | 0.1044 | 0.0000002 | 0.0002 |
| Dimer vs. Tetramer | 0.0372 | 0.000006 | 0.0004 |

CTLA4-Ig Species from QFF Cleaning Peak:

The QFF column is the last purification column used to clean up residual impurities from the product. CTLA4-Ig species were isolated from the cleaning peak of the QFF column using the 2-column SEC method and analyzed on the Biacore 3000. The data showed that the binding kinetics of this "QFF cleaning peak" sample was similar to the CTLA4-Ig dimer standard. In addition, both dimer and tetramer purified from the QFF cleaning peak gave similar binding kinetics compared to those purified from the composition. Furthermore, sialic acid contents of the purified monomer fractions were greater than that of CTLA4-Ig dimer standard.

Guanidine Treatment (Dimerization of the Tetramer):

The tetramer can be converted to dimer by treatment with guanidine followed by dialysis into phosphate buffer and confirmed to exist as a dimer by analytical SEC. Kinetic analysis of the "dimerized" tetramer from the HIC cleaning peak showed that its $k_{on}$ and $T_{off}$ rates were similar to those of CTLA4-Ig dimer.

Example 7: Intact Analysis by MS Electrospray Ionization (ESI)

CTLA4-Ig was diluted with 100 mM Tris, 25 mM NaCl, pH 8 to a final concentration of 0.7 mg/mL. PNGase F (New England Biolabs) was diluted 30-fold with 100 mM Tris, 25 mM NaCl, pH 8 to a final concentration of 17 units/4. Equal volumes (60 4 each) of diluted sample and diluted glycosidase solution were mixed and incubated at 37° C. for 4 hours.

The resulting deglycosylated CTLA4-Ig (2 4) was loaded onto a Waters Oasis® reversed phase extraction cartridge column (2.1×20 mm). The loaded column was washed with 5% solvent B (solvent A:1% formic acid in water, solvent B: 1% formic acid in acetonitrile) at a flow rate of 0.2 mL/minute for five minutes to desalt, with the eluant diverted to waste. At the end of 5 minutes, a fast gradient (5% solvent B to 95% solvent B in 10 minutes) began the elution of CTLA4-Ig off the column; here the eluant was directed into the mass spectrometer (Waters Micromass Q-Tof Micro™) at 45 µL/min after flow splitting (chromatography system used was a Waters Alliance 2695 equipped with a Waters 2996 detector).

The capillary voltage for the Q-Tof Micro™ was set at 3 kV and the sample cone voltage at 40 V. The scans (every 0.9 second) were averaged into one scan; the inter-scan time was 0.1 second. The Q-Tof analyzer scans from m/z 800 to 2500. Spectra corresponding to the portion higher than half the maximum peak height (in TIC chromatogram) were combined using Waters MassLynx™ software. The combined spectra were subjected to Waters MaxEnt1 deconvolution. The resolution was set at 1 Da/Channel, and the uniform Gaussian damage model was selected with width at half height set between 0.5-1 Da. Minimum intensity ratios for the left peak and the right peak were both set at 50%.

Example 8: Matrix Assisted Laser Desorption Ionization-Time of Flight (MALDI-TOF)

MALDI-MS spectra were acquired on an OmniFlex™ (Bruker Daltonics, Mass.) using a nitrogen laser (337 nm). Protein samples were used without desalting or desalted using solid phase extraction in the form of C4 ZipTip® pipette tips (Millipore, Bedford Mass.). The pipette tips were wetted with acetonitrile-water (1:1 v/v) and equilibrated with 0.1% trifluoroacetic acid (TFA) prior to use. The pipette tips were then loaded by drawing and expelling 10 µL of sample from the pipette three times. The loaded sample was washed three times with 10 µL of 0.1% TFA. Desalted protein samples were eluted from the pipette with 10 µL of acetonitrile to water (1:1 v/v). Samples were spotted by mixing a 1 µL sample (either desalted or buffer containing) with 1 µL of matrix solution and placing 1 µL of the mixture on the stainless steel target. The matrix solution was a saturated solution of sinapic acid in 1:1 water to acetonitrile (v/v) containing 0.1% TFA. The mixture was spotted onto the MALDI sample plate and allowed to air dry before being placed in the mass spectrometer. All protein samples were analyzed in the linear, positive-ion mode by delayed extraction using an accelerating voltage of 20 kV and a delay time of 200 nanoseconds. A total of 400 single-shot spectra were accumulated from each sample. External calibration was achieved using a mixture of standard proteins containing trypsinogen (23982 m/z), Protein A (44613 m/z), and bovine albumin (66431 m/z).

MALDI-TOF MS Analysis of Peptides

Peptide mixture was separated by reversed phase chromatography and fractions from chromatographic peaks were collected and evaporated to dryness. Sample was reconstituted in 50 µL of 25 mM phosphate buffer pH 7.5. DTT was added to a final concentration of 5 mM and the fractions were incubated at 50° C. for 20 minutes. After reduction, IAM was added to a 10 mM final concentration and incubated in darkness at 50° C. for an additional 20 minutes.

MALDI-MS spectra were acquired on an OmniFlex (Bruker Daltonics, Mass.) using a nitrogen laser (337 nm). Samples were prepared by mixing a 1 µL sample with 1 of matrix solution. The matrix solution was a saturated solution of a-cyano-4-hydroxycinnamic acid in 1 to 1 water: acetonitrile with 0.1% TFA. The mixture was spotted onto a well of the MALDI sample plate and allowed to air dry before being placed in the mass spectrometer. All peptides were analyzed in the reflective, positive-ion mode by delayed extraction using an accelerating voltage of 20 kV and a delay time of 200 nanoseconds. A total of 100 single-shot spectra were accumulated from each sample. External calibration was achieved using a mixture of standard peptides containing angiotensin II (1046.54 m/z), angiotensin I (1296.68 m/z), substance P (1347.74 m/z), bombesin (1619.82 m/z), ACTH clip 1-17 (2093.09 m/z), ACTH clip 18-39 (2465.20 m/z), and somatostatin (3147.47 m/z).

Example 9: Analysis of Media and Media Constituents Effects on CTLA4-Ig Single Chain and Multimer Species CTLA4-Ig dimer, a low sialic acid sub-fraction, a high sialic acid sub-fraction, monomer frontal, and monomer species of CTLA4-Ig are prepared and purified. These samples are used in a series of modeling experiments designed to determine the affects of media and media constituents on single chain and high molecular weight formation over times between zero to at least 60 hours. The affects of formulation buffer, iodoacetamide, sodium phosphate, ammonium chloride, basal medium, fermentation broth, medium 177e, medium Concentrated Acid Solution I, medium concentrated acid solution II, insulin, EDTA, cysteine, lipoic acid, glutathione, methionine, and yeastolates alone and in combinations are tested.

Example 10: Analyzing CTLA4-Ig Molecules by Size

A method of size exclusion chromatography (SEC) which uses denaturing conditions can be employed for the quantitation of protein species of different size. In one embodiment tandem SEC method using denaturing conditions can be employed for the quantitation of CTLA4-Ig single chain species. Single chain CTLA4-Ig can be a species lacking the inter-chain disulfide bridge. Single chain CTLA4-Ig species isolated during the purification process is referred to as native single chain CTLA4-Ig. Purified single chain produced by reduction and alkylation of CTLA4-Ig dimer is referred as induced single chain. Native and induced single chain CTLA4-Ig have the same characteristics.

Materials:
Potassium Phosphate Monobasic ($KH_2PO_4$) ACS grade
Potassium Hydroxide (KOH) 45% w/w Solution ACS grade
Sodium Chloride (NaCl) ACS grade
Calibrated Adjustable Single Pipettor, 100_L
Rainin, (Catalog No. P-100)
Water ($H_2O$) HPLC grade
2.0 mL Cryogenic Vials Nalgene, (Catalog No. 5000-0020)
Concentrated HydrochloricAcid (HCl) Fisher (Catalog No. A144-212)
Sodium Hydroxide, (NaOH) 10N Solution
J. T. Baker, (Catalog No. 5674-02)
1000 mL Filter Unit 0.22 mm Corning, (Catalog No. 430517)
Polypropylene 15 mL test tube Falcon, (Catalog No. 352097)
Sodium Azide (NaN3) ACS grade
Sodium Phosphate Monobasic, Monohydrate (NaH2PO4.H2O)
Potassium Hydroxide (KOH) Pellets Instrumentation and Conditions
HPLC System Waters 2695 Separations Module
Column Toso Haas 5 µTSK 3000 SWXL, 300 mm×7.8 mm I.D. (Part No. 08541)
Guard Column Toso Haas 5 µTSK 3000 SWXL, 40 mm×6.0 mm I.D. (Part No. 08543)
Detector Waters 2487 Dual Wavelength Detector Wavelength 280 nm Flow Rate 1 mL/min
Integration System Empower
Injection Volume 20
Assay Target Conc. 10 mg/mL
Mobile Phase 0.2 M KH2PO4, 0.9% NaCl, pH 6.8 with KOH
Assay Run Time 20 min
Column Temperature Ambient
Sample Temperature 4° C.
Retention Time Monomer 8.7 min±1.0 min, HMW species at 7.5 min±1.0 min, if
present MW species will elute after the Monomer peak.

Reagents
4N Potassium Hydroxide (4N KOH) (100 mL)
Use one of the following preparations as described:
Add 40 mL of HPLC grade water and 11.6 mL of 45% w/w solution of KOH to a 100 mL volumetric flask. Bring volume up to 100 mL with HPLC grade water.
In a 100 mL volumetric flask add 80 mL of HPLC grade water, weigh 22.4 grams of KOH pellets, and stir magnetically until completely dissolved. Bring to volume of 100 mL with HPLC grade water.
Transfer solution into a 250 mL glass reagent bottle. Mix well by invertion. Store at room temperature for up to 1 year.
Mobile Phase (0.2 M $KH_2PO_4$, 0.9% NaCl, pH 6.8)
Weigh out 27.2 grams of $KH_2PO_4$ and 9.0 grams of NaCl into a 1000 mL beaker. Dissolve the solids in 800 mL of HPLC grade water using continuous mixing with a magnetic stirring bar.
Using a pH meter, adjust the pH of the solution to 6.8 using 4N KOH solution. If the pH exceeds 6.8, adjust it with concentrated HCl.
Bring the final volume to 1 liter using a 1000 mL graduated cylinder. Filter the solution through a 0.22 µm filter unit.
Transfer into a 1000 mL glass reagent bottle and sonicate while vacuum degassing for 5+/−1 minute. Degas before each use.
Store at room temperature for up to 1 month.

2N Sodium Hydroxide (2N NaOH)
Transfer 20 mL of 10N NaOH into a 100 mL glass graduated cylinder.
Bring volume up to 100 mL with HPLC water.
Transfer solution into a 250 mL glass reagent bottle. Mix well by invention. Store at room temperature for up to 1 year.
Weigh 3.45 grams of $NaH_2PO_4.H_2O$ and 2.92 grams of NaCl and dissolve with mixing with a stir bar in 900 mL of HPLC grade water. Using a pH meter, adjust the pH of the solution to 7.4 with 2N NaOH. If the pH exceeds 7.4, adjust it with concentrated HCl.
Bring the final volume to 1 liter using a 1000 mL graduated cylinder. Filter the solution through a 0.22 μm filter unit.
Store at 2°–8° C. for up to 6 months.
Column Storage Buffer (0.05% w/v NaN3 in Water)
Weigh 50±5 mg of Sodium Azide and add it to a 1000 mL beaker with a magnetic stir bar.
Add 500 mL of HPLC grade water to the beaker and stir until completely dissolved. Bring the volume to 1 L with water. Filter the solution through a 0.22 μm filter unit and pour into a 1000 mL HPLC reagent bottle.
Store at room temperature for up to 6 months.

Preparation of High Molecular Weight Species and System Suitability Standard

This will provide for a three-fold dilution of heated to unheated CTLA4-Ig reference material and a 15%-30% High Molecular Weight Species area percent amount. In a 15 mL Falcon test tube, prepare approximately 3 mL of reference material at 10.0±1.0 mg/mL using CTLA4-Ig dilution buffer. The initial concentration of CTLA4-Ig is from the COA. Make the 10.0±1.0 mg/mL dilution from that value. Transfer 1.0 mL of the diluted reference material, made in into a 2.0 mL cryovial using a 1 mL pipettor, and heat it in a water bath at 67±2° C. for 45±2 minutes. Transfer the heated reference material made in back into the 15 mL test tube using a 1 mL pipettor. Gently pipet up and down a 1 mL volume of the contents of the test tube for a total of 10 times. This is the system suitability standard. Storage conditions: Prepare 150 μL aliquots of the system suitability standard in 2.0 mL cryovials for storage at −80±5° C. for up to 1 year. Obtain the initial concentration of Reference Material, and make the 10.0±1.0 mg/mL dilution from that value. Use a minimum of 100 μl of reference material and an appropriate amount of the dilution buffer to achieve a final concentration of 10.0±1.0 mg/mL. Refer to the following equation for dilutions Dilution Buffer to Add =

$$\frac{(\text{Aliquot Volume} \times \text{Starting Concentration})}{\text{Target Concentration}} - \text{Aliquot volume}$$

For CTLA4-Ig Drug Substance make the 10.0±1.0 mg/mL dilution from the protein concentration using a minimum of a 100 μL aliquot of sample and an appropriate amount of the dilution buffer to achieve a final concentration of 10.0±1.0 mg/mL. Refer to the following equation for dilutions:

$$\frac{(0.1 \text{ mL} \times 50 \text{ mg/mL})}{10 \text{ mg/mL}} - 0.1 \text{ mL} = 0.4 \text{ mL dilution buffer}$$

Once diluted to 10.0±1.0 mg/mL, the samples can be stored at 2°-8° C. for up to 24 hours. For CTLA4-Ig Drug Product make the 10.0±1.0 mg/mL dilution from the protein concentration using a minimum of a 200 μL aliquot of sample, and an appropriate amount of the dilution buffer to achieve a final concentration of 10.0±1.0 mg/mL. Refer to the following equation for dilutions:

$$\frac{(0.2 \text{ mL} \times 25 \text{ mg/mL})}{10 \text{ mg/mL}} - 0.2 \text{ mL} = 0.3 \text{ mL dilution buffer}$$

Place the Mobile Phase in one solvent reservoir and HPLC grade water in another. Sonicate and vacuum degas prior to run. Turn on detector and allow 15 minutes to warm up prior to the run. Before a new or current column is used for analysis, flush the column with HPLC grade water for at least 20 minutes followed by mobile phase buffer equilibration for at least 20 minutes. Use a flow rate of 1.0 mL/min. Thaw a 150 μL aliquot of system suitability standard, add it to an autosampler vial and place the vial in the autosampler. Inject 20 μL of the standard under the conditions.

Determine the percentage of High Molecular Weight Species eluting at approximately 7.5 minutes according to the following formula: (In the formula below, Monomer actually refers to dimer.)

$$\text{Area \% High Molecular Weight Species} = \frac{(A)}{(A) + (B)} \times 100$$

Where:
A=Peak area of High Molecular Weight Species
B=Peak area of Monomer

The Area Percent High Molecular Weight Species should not be less than 15%. If it is less than 15%, add additional concentrated High Molecular Weight Species to the system suitability standard above. Resolution (R) Determination and Retention Time Evaluation. Inject 20 μL of system suitability standard. Calculate the resolution between the High Molecular Weight Species (retention time approximately 7.5 minutes) and the Monomer peak (retention time approximately 8.7 minutes) using the following equation: (In the formula below, "monomer" actually refers to dimer.)

$$\text{Resolution } (R) = \frac{2(t_2 - t_1)}{W_2 + W_1}$$

Where:
$t_1$=Retention time of the high molecular weight species
$t_2$=Retention of time of Monomer
$W_1$=Peak width of high molecular weight species
$W_2$=Peak width of Monomer Peak width is measured in minutes at the base of the peak after extrapolating the relatively straight sides of the peak to the baseline. Retention time and peak width are measured in the same units. In one embodiment, (R) must be and the retention time for the peak should be 8.7±1.0 minutes.

Number of Theoretical Plates Determination (N)

From the system suitability standard chromatogram, determine the efficiency of the column by calculating the number of theoretical plates (N) according to the following equation:

$$N = 16\left(\frac{t}{w}\right)^2$$

Where:

t=is the retention time of Monomer (in minutes)

w=is the width (in minutes) at baseline of the Monomer obtained by extrapolating the sides of the peak to the base line.

A total of six (6) injections of CTLA4-Ig material will be made. Aliquot 200 µL of 10 mg/mL reference material into an autosampler vial, and place the vial in the autosampler and inject six times. Process the chromatograms, and calculate the dimer peak area for each chromatograph. Sum the dimer peak areas from the six chromatographs and calculate the average, standard deviation and % RSD according to the following equations:

$$\frac{X_1 + X_2 + X_3 \ldots X_n}{n_x}$$

Where:

$X_{1, 2, 3 \ldots}$ =a specific value in a set of data $n_x$=a set of values (x)

5.4.4.2 Calculate the standard deviation as follows:

$$\sqrt{\frac{n\sum x^2 - (\sum x)^2}{n(n-1)}}$$

Where:

n=number of values (x) in a set of data x=one value in a set of data 5.4.4.3 Calculate the % Relative Standard Deviation (RSD) as follows:

$$\% \ RSD = \frac{\text{Standard Deviation}}{\text{Mean}} \times 100$$

Example of an Injection Sequence:

| SAMPLE | INJECTION |
| --- | --- |
| Dilution Buffer Blank | 1 Injection |
| Systeme Suitability | 1 Injection |
| Reference Material | 6 Injections |
| Sample #1 | 2 Injections |
| Sample #2 | 2 Injections |
| Sample #3 | 2 Injections |
| Reference Material | 1 Injection |
| Dilution Buffer Blank | 1 Injection |

Integration of Peaks

Integrate all peak areas in the chromatogram from 5.5 to 11.8 minutes. Enlarge baseline of chromatogram to ensure total area of all LMW and HMW species are included in the integration. Disregard peaks in the sample that correspond to peaks in the control. The inclusion volume peak (11.8-13.5 minutes) and peaks after are not considered in this calculation. However, if the area at the inclusion volume is 0.1% or greater of the total area, it should be noted. The dimer peak elutes at 8.7±1.0 minutes, the high molecular weight species peak elutes at 7.5±1.0 minutes, and the low molecular weight species (e.g., monomer, if present) will elute after the dimer peak. Any peak other than the high molecular weight species, dimer or low molecular weight species that has 280 nm absorbance in excess of 0.1 area % of the total peak area should be noted. Calculate the area percentages as follows: (The reference to "Abatacept Monomer" in this example refers to CTLA4-Ig dimer.)

$$\text{Area \% High Molecular Weight Species} = \frac{(B)}{(A) + (B) + (C)} \times 100 \quad 7.2.1$$

$$\text{Area \% Low Molecular Weight Species} = \frac{(C)}{(A) + (B) + (C)} \times 100 \quad 7.2.2$$

Area % Monomer = 100 − (Area % HMW + Area % LMW)

Where:

A=Abatacept Monomer peak area

B=Total area of all peaks with retention times less than Abatacept Monomer

C=Total area of all peaks with retention times greater than Abatacept Monomer peak (excluding inclusion volume).

Samples were separated by size exclusion chromatography using a Water's ALLIANCE® 2695 (Milford, Mass.) on two 7.8×300 mm TSK Gel G3000SWXL™ columns (Tosoh Biosep, Montgomery, Pa.) placed in series employing a 6.0×40 mm guard column. 25 microliters of each purified sample was injected and separated under isocratic conditions using 0.1M $Na_2HPO_4$, 0.1M $Na_2SO_4$, pH 6.8 at 1.0 mL/min. Samples were detected at 280 nm using a 996 PDA (photodiode array) detector (Waters, Milford, Mass.) and analyzed using MILLENNIUM 4.0™ chromatography software (Waters, Milford, Mass.).

The overlaid chromatograms of native and induced single chain material from the denaturing analytical tandem size exclusion chromatography show an average retention time (6 replicates) of 27.96±0.02 and 27.99±0.02, respectively. The average peak area for native single chain was found to be 495525.0±9589.6 and for induced single chain to be 463311.8±7997.2 (Table 13). The overlaid MALDI-TOF spectra of native and induced single chain material have peaks that are quite broad with a baseline width of about 15000 mass units. This is expected due to the heterogeneity of the glycosylation in both samples. The apex point of the single chain peak in each mass spectrum was used to calculate the average mass. The average masses for native and induced CTLA4-Ig single chain are 45694.426±297.735 and 45333.086±264.778 mass units respectively based on the analysis of six replicates (Table 14). The native single chain mass is expected to be higher than that of induced single chain, because on the native single chain there is an extra cysteine (residue mass 103 dalton) on $Cys^{146}$ of SEQ ID NO:2, whereas the induced single chain is a result of selectively reducing a single interchain disulfide bridge followed by alkylation that adds an acetyl group (mass 58 dalton).

These data show that the native and induced materials produce equivalent results by the tandem denaturing SEC chromatography and MALDI-TOF analyses. These results demonstrate comparability between the native and induced CTLA4-Ig single chain materials.

TABLE 13

HPLC SEC Data of Native and Induced Single Chain

| | Induced | | Native | |
|---|---|---|---|---|
| Replicates | Retention Time (min) | Peak Area (\|xV * sec) | Retention Time (min) | Peak Area (\|xV * sec) |
| 1 | 27.985 | 470199 | 27.968 | 505576 |
| 2 | 27.979 | 464424 | 27.941 | 499800 |
| 3 | 27.977 | 469509 | 27.934 | 505708 |
| 4 | 27.998 | 469081 | 27.954 | 482472 |
| 5 | 28.027 | 453103 | 27.991 | 490434 |
| 6 | 28.016 | 453555 | 27.985 | 489160 |
| Average | 27.997 | 463311.8 | 27.962 | 495525.0 |
| Stdev | 0.021 | 7997.2 | 0.023 | 9589.6 |
| % RSD | 0.074 | 1.726 | 0.083 | 1.935 |

TABLE 14

MALDI-TOF Mass Spectrometry Data of Native and Induced Single Chain

| Replicates | Induced SC mass | Native SC mass |
|---|---|---|
| 1 | 45397.896 | 45597.475 |
| 2 | 45432.199 | 45621.300 |
| 3 | 45256.929 | 45543.839 |
| 4 | 45433.849 | 45555.893 |
| 5 | 45381.812 | 45634.620 |
| 6 | 45348.376 | 45340.712 |
| Average | 45375.177 | 45548.973 |
| Stdev | 66.265 | 108.043 |
| % RSD | 0.15 | 0.24 |

The presence of cysteines within a polypepetide chain permits formation of disulphide bonds, which can be intramolecular or intermolecular leading to formation of dimer or multimer protein complexes. CTLA4-Ig exists as a dimer (wherein the dimer is made up of two monomers having any one of the following sequences: (i) 26-383 of SEQ ID N0:2, (ii) 26-382 of SEQ ID N0:2; (iii) 27-383 of SEQ ID N0:2, (iv) 26-382 of SEQ ID N0:2), (v) 25-382 of SEQ ID N0:2, and (vi) 25-383 of SEQ ID N0:2 held together by one disulfide bond between $C^{146}$ on each chain. The reduction of this disulfide bond can result in the formation of two equivalent protein chains held together by non-covalent electrostatic forces. When subjected to denaturing conditions that overwhelm or outweigh the attracting electrostatic forces, such CTLA4-Ig can completely dissociate resulting in two identical protein structures of approximately 46 kDa. The resulting structure is referred to as single chain or monomer. The presence of the single chain can be monitored by tandem column size exclusion chromatography run under denaturing conditions.

A subpopulation of CTLA4-Ig molecules contains a modification on $Cys^{146}$: the disulfide linkage present in the majority population is changed to a free cysteine amino acid (referred to as a cysteinylation). CTLA4-Ig dimer is predominantly a protein with a molecular weight of approximately 92,000. It is comprised of two glycosylated polypeptide chains which are held together by one inter-chain disulfide bond at Cys' and non-covalent interactions (also referred to as CTLA4-Ig "dimer"). The purified protein exists as a heterogeneous population and contains modifications such as glycosylations and variations at the N- and C-termini.

A distinct population of CTLA4-Ig molecules exists, which lacks the interchain disulfide bond linkage. This non-covalently linked population exists within the frontal dimer peak generated by size exclusion chromatography. The frontal dimer was found to lack the interchain disulfide bond. The CTLA4-Ig species which lack the interchain disulphide link are modified by cysteinylation at $Cys^{146}$, which modification occurs on >99% of the single chain species based on the ESI-MS intact data. $Cys^{146}$ cysteinylation and the enrichment of O-linked carbohydrates are the two major modifications on the CTLA4-Ig single chain species. The frontal dimer is subjected to denaturing size exclusion chromatography resulting in isolation of the CTLA4-Ig single chain peak. The purified frontal monomer material was compared to CTLA4-Ig with and without solid phase extraction (SPE) and analyzed on MALDI. The purified frontal monomer contains two dominant species: a major species at either 47005 u for SPE-treated or 46897 u for non-treated; a minor species at either 95070 u for SPE-treated or 96172 u for non-treated. The CTLA4-Ig material also contains two dominant species: a major species at either 91518 u for SPE-treated or 91143 u for non-treated; a minor species at either 45660 u for SPE-treated or 46014 u for non-treated.

| | 1 example | 2 example |
|---|---|---|
| Size Homogeneity (HPLC) Dimer | ≥95.5 Area % | ≥95.5 Area % |
| | ≥97.0% Area % | ≥97.0% Area % |
| Size Homogeneity (HPLC) High MW Species | ≤3.0 Area %. | ≤3.0 Area %. |
| | ≤2.0 Area %. | ≤2.0 Area %. |
| Size Homogeneity (HPLC) Low MW Species (monomer) | ≤0.5 Area % | ≤0.5 Area % |

The CTLA4-Ig composition, in one embodiment, have the following characteristics as to Size Homogeneity (HPLC) analysis of dimer, High MW Species, and Low MW Species (monomer, single chain):
≥97.0% Dimer
≤2.0% HMW species
≤0.5% LMW species (e.g., monomer, single chain)
In another embodiment, the CTLA4-Ig composition has the following characteristic amounts of each species:
≥95.5% dimer
≤3.0% HMW species
≤0.5% LMW species (e.g., monomer, single chain)

| Summary of SE-HPLC Analysis of Process CD-CHO1 Batches | | |
|---|---|---|
| | Process CD-CHO1 n = 109 | |
| | dimer | HMW |
| Average (%) | 99.4 | 0.6 |
| % CV | 0.3% | 45.7% |
| Minimum (%) | 98.4 | 0.2 |
| Maximum (%) | 99.8 | 1.6 |
| 95% Tolerance Interval | ≥98.7 | ≤1.3 |

The percent monomer ranged from 98.4 to 99.8% with an average value of 99.4% for drug substance manufactured using Process CD-CHO1. The percentage HMW species varied from 0.2 to 1.6%. The average value was 0.6% with a CV of 45.7%. The 95% tolerance interval was ≥98.7% for the dimer and ≤1.3% for the HMW species. The percent HMW species of the batches varied from a minimum value of 0.4% to a maximum value of 2.1%. The average percent HMW species was 0.8% with a % CV of 40%. In all cases, the LMW or monomer species were below the detection limit (DL=0.1%). The 95% tolerance interval (to provide coverage for 99 area % of the population) for CTLA4-Ig manufactured by Process CD-CHO1 were ≤1.3 and ≤1.8% respectively for the HMW species. The 95% tolerance intervals for the dimer in drug substance from Process CD-CHO1 were 98.7% and 96.5% respectively.

| Summary of combined data for CTLA4-Ig | | |
|---|---|---|
| | dimer (n = 143) | HMW (n = 141)$^a$ |
| Average (%) | 99.3 | 0.6 |
| % CV | 0.5 | 46.9 |
| Minimum (%) | 94.8 | 0.2 |
| Maximum (%) | 99.8 | 2.1 |
| 95% Tolerance Interval | ≥97.3 | ≤1.8 |
| % CV (between-site) | 0.3% | 26.4% |
| % CV (within-site) | 0.5% | 44.2% |
| % CV (total-site) | 0.6% | 51.4% |

The above Table shows that the percent HMW species ranged from 0.2 to 2.1% with an average of 0.6%. The dimer ranged from 94.8% to 99.8% with an average value of 99.3% and a precision of 0.3%. The variation between-site, within-site and total-site variation for the dimer was within 0.3 to 0.5%. The between site variation for the HMW was 26.4%. The within-site and total-site variation was for the percent HMW species 44.2 and 51.4% respectively. The 95% tolerance interval for the dimer (97.3%) and the HMW species (1.8%) were within the specification.

Example 11: Vector Construction

Figure 27:
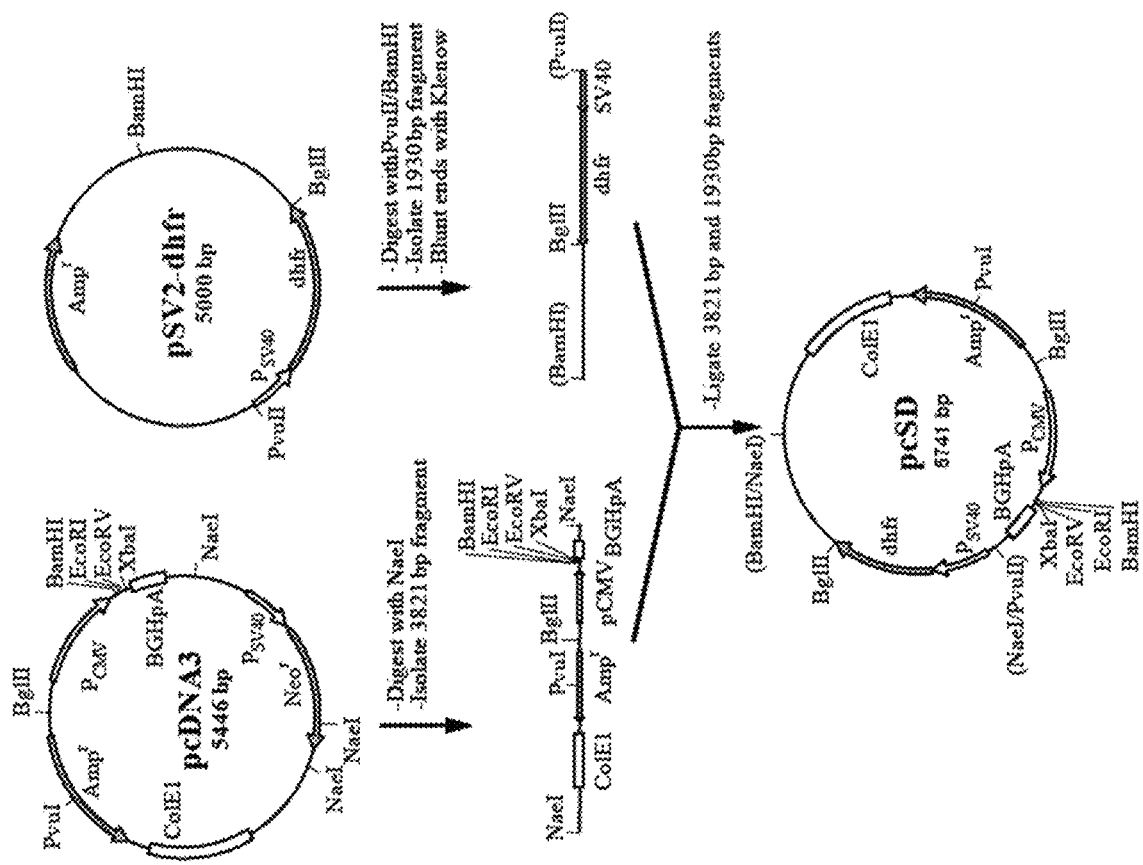
FIG. 27 presents a cloning scheme useful for generating the vector pcSD. pcDNA3 was digested with the restriction enzyme NaeI in order to isolate a 3.821 Kb fragment that contains the CMV promoter, an ampicillin resistance gene, and an origin of replication for E. coli. pSV2-dhfr was digested with the restriction enzymes PvuII and BamHI in order to isolate a 1.93 Kb fragment, which contains the SV40 promoter and the dhfr gene, and was subsequently blunt-ended. To generate pcSD, both fragments were ligated. The map of plasmid pcSD is shown at the bottom of the figure.

Construction of the pcSD Expression Vector:

The expression vector, pcSD was constructed from the commercially available pcDNA3 vector (Invitrogen, Carlsbad, Calif.) as shown in FIG. 27. The neomycin resistance gene cassette was removed from plasmid pcDNA3 by digestion with restriction endonuclease Nae I. The restriction endonuclease Nae I creates blunt ends. The DNA fragments were separated by agarose gel electrophoresis and the 3.821 kb pcDNA3 vector backbone was purified from the gel. The DNA fragment containing the gene coding for mouse dihydrofolate reductase (dhfr) and an SV40 promoter was isolated from plasmid pSV2-dhfr by digestion of the plasmid with restriction endonucleases Pvu II and BamH I. The 1.93 kb fragment corresponding to the dhfr gene cassette was separated and purified by agarose gel electrophoresis. The 3-prime recessed ends generated by BamH I digestion were filled in using the Klenow fragment of DNA polymerase I to generate blunt ends. This isolated fragment was ligated to the blunt-ended 3.8 kb pcDNA3 vector backbone to create the expression vector pcSD. This expression vector has the following features: a cytomegalovirus (CMV) promoter followed by a multiple cloning site, a bovine growth hormone (BGH) polyadenylation signal and transcriptional termination sequence, a mouse dhfr cDNA sequence for selection and amplification, and an ampicillin resistance gene and pUC origin of replication for selection and maintenance in *Escherichia coli*.

Construction of the pcSDhuCTLA4-Ig Expression Vector:

A 1.2 kilobase (kb) DNA fragment containing a sequence encoding a CTLA4-Ig protein was isolated from plasmid pCDM8-CTLA4-Ig by digestion with the restriction enzymes Hind III and Xba I. The 1.2-kb Hind III/Xba I fragment was ligated into vector piLN previously digested with the restriction enzymes Hind III and Xba I. The resulting plasmid construct, designated piLN-huCTLA4-Ig, is shown in FIG. 20. The piLN-huCTLA4-Ig plasmid was used as the source of the CTLA4-Ig coding sequence used in the construction of the final expression vector pcSDhuCTLA4-Ig.

Figure 28:
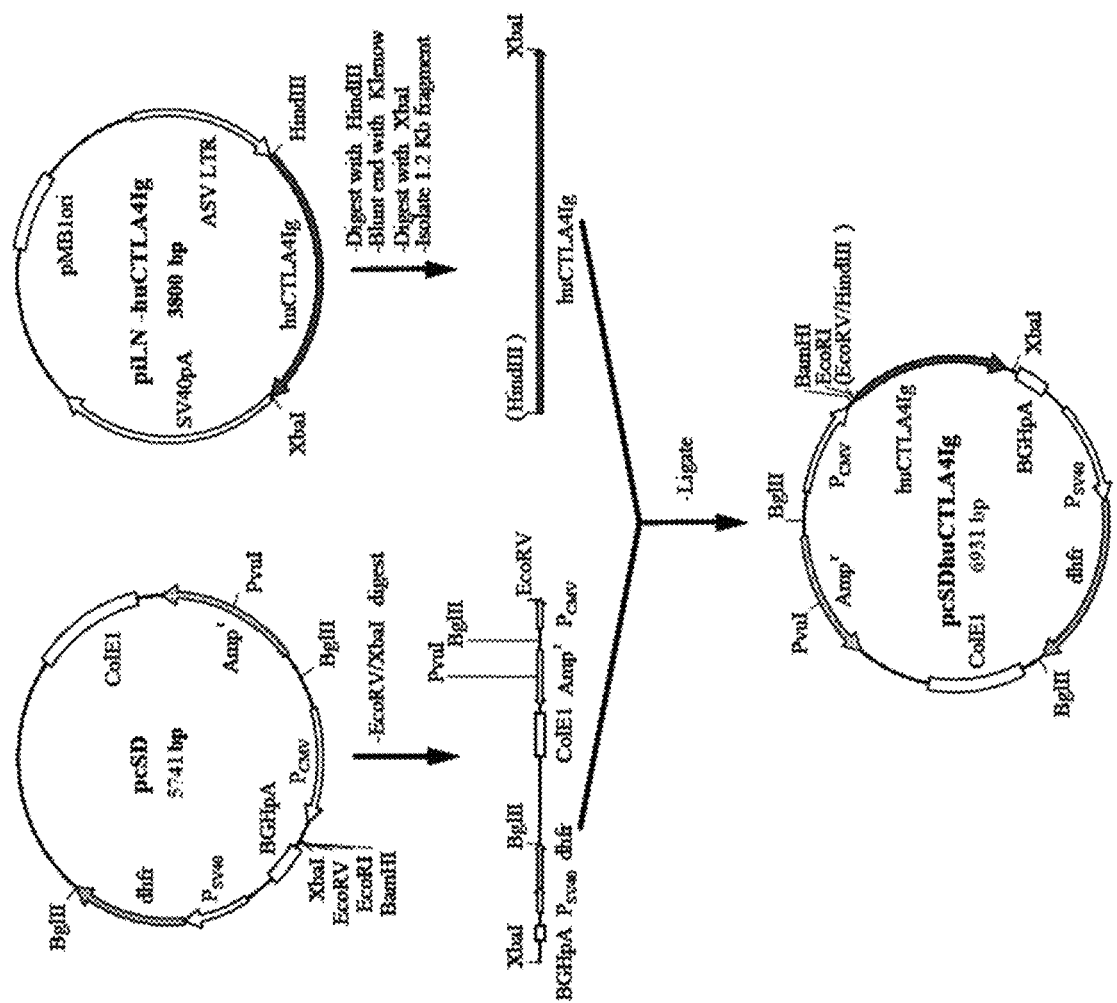
FIG. 28 presents a cloning scheme useful for generating the expression vector pcSDhuCTLA4-Ig. pcSD was digested with the restriction enzymes EcoRV and XbaI. piLN-huCTLA4-Ig was digested with the restriction enzyme HindIII, blunt-ended, and then digested with the restriction enzyme XbaI in order to isolate the 1.2 Kb huCTLA4-Ig fragment. To generate pcSDhuCTLA4-Ig, the CTLA4-Ig fragment was ligated to the digested pcSD vector. The map of plasmid pcSDhuCTLA4-Ig is shown at the bottom of the figure. This plasmid was linearized and transfected into CHO cells that do not have a functional dhfr gene. As the plasmid contains a functional dhfr gene, stable transfectants can be selected on the basis of cell survival. The pcSDhuCTLA4-Ig has the expression cassette comprising the CMV promoter, a sequence that can encode a human CTLA4-Ig molecule (huCTLA4-Ig) (i.e., SEQ ID NO:1) and a poly(A) tail sequence from BGH.

The final vector for expression of the CTLA4-Ig gene was constructed as shown in FIG. 28. A 1.2 kb DNA fragment containing the CTLA4-Ig gene was isolated from plasmid piLN-huCTLA4-Ig by a two step restriction digest procedure. Plasmid piLN-huCTLA4-Ig was first digested with restriction enzyme Hind III. The resulting 3-prime recessed ends were filled in by treatment with the Klenow fragment of DNA polymerase I. The plasmid was then digested with the restriction enzyme Xba I to release the 1.2 kb fragment containing the CTLA4-Ig gene. This fragment was purified and ligated to the EcoR V and Xba I fragment isolated from the restriction digestion of pcSD. The EcoR V and Xba I restriction sites are located in the multiple cloning site of pcSD between the CMV promoter and a cassette containing the bovine growth hormone polyadenylation signal and transcriptional termination sequence. This placed the CTLA4-Ig gene fragment under the control of the CMV promoter. This plasmid is designated pcSDhuCTLA4-Ig, and comprises SEQ ID NO:1.

Example 12: Transfection of CTLA4-Ig Expression Vector to Obtain Stable Cell Lines This Example and Example 13 describe a newly transfected population of cells from which individual clones were selected and expanded, and thus the expanded clones are different than the cells deposited with the ATCC as Accession No. CRL-10762. The previous CHO cell line harboring an expression vector containing DNA encoding the amino acid sequence corresponding to CTLA4-Ig (DNA having ATCC Accession Number 68629) is described in U.S. Pat. No. 5,434,131. Briefly, an expression plasmid (for example, pCDM8) containing cDNA that was deposited under ATCC Accession No. 68629, was transfected by lipofection using standard procedures into dhfr negative-CHO cells to obtain cell lines that stably express CTLA4-Ig. Screening B7 positive CHO cell lines for B7 binding activity in the medium using immunostaining resulted in a stable transfectant that expressed CTLA4-Ig. This heterogenous population of transfected cells was designated Chinese Hamster Ovary Cell Line, CTLA4-Ig-24 and was deposited with the ATCC under the Budapest Treaty on May 31, 1991 having ATCC Accession Number CRL-10762.

The Chinese hamster ovary cell line, DG44, contains a deletion of the gene coding for the enzyme dihydrofolate reductase. The expression plasmid pcSDhuCTLA4-Ig contains a copy of the dihydrofolate reductase gene (dhfr). Insertion of plasmid pcSDhuCTLA4-Ig into the DG44 genome results in functional complementation of the dhfr deletion. This functional complementation can be used for selection of transfectants in the presence of methotrexate (MTX) and amplification of dhfr and adjacent genes.

The human CTLA4-Ig-secreting cell line 1D5 was constructed by transfection of cell line DG44 with the pcSDhuCTLA4-Ig expression plasmid as shown in FIG. 28. The plasmid DNA was introduced into DG44 cells by electroporation using standard procedures known in the art. Transfectants were selected using a minimal essential medium (MEM; JRH Biosciences, Inc., Kansas) supplemented with 5% (v/v) dialyzed Fetal Bovine Serum. Culture supernatants from the transfectants were screened for human IgG production using a sandwich ELISA method. An Fc-specific goat anti-human IgG was used as the capture antibody. Goat anti-human IgG antibody conjugated to horseradish peroxidase was used to detect human IgG. Transfectants expressing higher levels of the human CTLA4-Ig gene were selected for further amplification.

Gene amplification of the selected transfectants was accomplished by addition of MTX to the culture medium at a final concentration of 100 nM. MTX is a folic acid analogue that acts as a competitive inhibitor of dihydrofolate reductase. Addition of MTX to the medium allowed selection of transfectants containing multiple copies of the dhfr gene and elevated levels of dihydrofolate reductase. Transfectants also containing multiple copies of the adjacent CTLA4-Ig gene were identified using the human IgG specific ELISA method. A CTLA4-Ig-producing clone, designated 1D5, was selected for further development, in part described in Example 13.

Example 13: Subcloning of Stably Transfected Cells

Cell line 1D5 was subjected to soft agar cloning. Subclones derived from the soft agar cloning were analyzed for human IgG production using the ELISA method. Selected subclones were evaluated for CTLA4-Ig production and growth properties. The lead subclone, designated 1D5-100A1, was selected.

The 1D5-100A1 cell line was adapted from DE medium (JRH Biosciences, Inc., Kansas, which contains animal-sourced raw materials, to a chemically defined medium designated CD-CHO (Table 15). CD-CHO medium is a proprietary, animal component-free medium manufactured by Invitrogen Corporation, Carlsbad, Calif.

TABLE 15

Composition of Process Y Medium

| Component | Concentration |
|---|---|
| CD-CHO 25x Acid Solubles I | 40.0 mL/L |
| CD-CHO 25x Acid Solubles II | 40.0 mL/L |
| CD-CHO 25x Salts I | 40.0 mL/L |
| CD-CHO 25x Salts II | 40.0 mL/L |
| L-Glutamine | 0.585 g/L |
| r-human Insulin (10 mg/mL solution) | 0.1 mL/L |
| Methotrexate (20 mM solution) | 5 µL/L |
| Sodium Bicarbonate | 2.22 g/L |
| Water | As required |
| 1N HCl Solution | 0-5 mL/L to adjust pH |
| 10N NaOH Solution | 0-10 mL/L to adjust pH |

Cell line 1D5-100A1 was cultured and passaged in DE medium according to standard tissue culture protocol. The cells were then transferred to a medium composed of 50% DE medium and 50% CD-CHO medium. After several passages in this medium, the cells were transferred to T-flasks containing 100% CD-CHO medium. The cells were grown in 100% CD-CHO medium for several passages. The adapted cells were then subjected to cloning by limiting dilution.

Cells from the CD-CHO-adapted 1D5-100A1 cell line were cloned by limiting dilution using serum-free media. The 1D5-100A1 cells were seeded at a target of 1 cell/well into 96-well microtiter plates containing supplemented MCDB medium. MCDB is a chemically defined medium formulation distributed by Sigma-Aldrich, St. Louis, Mo. The MCDB medium was supplemented with 4 mM glutamine, 500 µg/mL recombinant human insulin, 100 nM MTX and 10% conditioned medium. The conditioned medium was a filter-sterilized supernatant from a culture of the CD-CHO adapted 1D5-100A1 cell line grown in MCDB medium.

Wells containing a single colony were identified and the clones evaluated for CTLA4-Ig production using the ELISA method. Selected clones were expanded from 96-well microtiter plates to 6-well cell culture plates. The cultures were further expanded into 25 cm$^2$ T-flasks and then roller bottles.

The roller bottle cultures were evaluated for CTLA4-Ig titer, CTLA4-Ig sialic acid content, and growth. Three clones were selected for further evaluation in bioreactors and further characterization. A frozen vial research stock of clonal cell line 1D5-100A1.17 stored at −80° C. was used to generate a cell bank.

Example 14: Production of CTLA4-Ig in Bioreactors Via a Fed-Batch Process

Commercial Scale Culturing of Suspension Mammalian Cells Expressing CTLA4-Ig:

This Example describes the production of CTLA4-Ig molecules comprising SEQ ID NO:2 monomers, from suspension cultured dhfr− negative CHO cells. The methods described in this Example can be adapted and extended for the production of other recombinant proteins, including but not limited to, secreted proteins such as cytokines and other hormones, secreted proteins that are members of the Ig superfamily or comprise a portion of an Ig superfamily protein, and generally any protein expressed in CHO cells.

The culture flasks (for example, T-175 and Erlenmyer flasks), roller bottles, and cell bags were used for the inoculum expansion steps of the CTLA4-Ig culturing process to serially propagate cells from a frozen vial to provide a sufficient number of viable cells to inoculate a 20,000-L bioreactor.

A single vial of cells is removed from the vapor phase of a liquid nitrogen storage freezer and thawed in a water bath at 37° C. The entire contents of the vial are aseptically transferred into a sterile 15-mL conical centrifuge tube. CD-CHO medium is added to bring the final volume to 10 mL. The cell suspension is centrifuged, the supernatant discarded and the cell pellet resuspended in 10 mL of CD-CHO cell culture medium. The resuspended cells are transferred to a T-175 flask containing 10 mL of CD-CHO medium. The viable cell density and the percent viability of the culture in the T-175 flask is determined. A criterion for the percent viability at this step of 84% was established. CD-CHO medium is added to the T-175 flask to achieve a target viable cell density of 1.7-2.6×10$^5$ cells/mL.

The T-175 flask is incubated at 37° C. in an atmosphere of 6% carbon dioxide for a maximum of four days to achieve a target final cell number of ≥6×10$^6$ viable cells. Following the T-175 flask step, the culture is expanded using a series of shaker flasks, 1-L, and 2-L Roller Bottles. At each passage, the cells are seeded at a target density of 2.0×10$^5$ viable cells/mL, wherein cultures targeted at having a final culture cell viability ≥80%. The cultures are incubated in CD-CHO medium at 37° C. in an atmosphere of 6% carbon dioxide for a maximum of four days.

Expansion of the culture occurs in a series of cell bags (20-L, 100-L, and 200-L) in order to further inoculate a 1000-L bioreactor. Cell culture material from the 2-L roller bottles inoculum expansion step is pooled to inoculate a 20-L cell bag at a target seeding density of 2.0×10⁵ viable cells/mL. A condition for the final viable cell density at the 2-L roller bottle inoculum expansion step of 1.0 to 2.0×10⁶ cells/mL and a minimum percent cell viability of ≥80% were established. Upon inoculation, the 20-L cell bag culture is incubated in CD-CHO medium at 37° C. in an atmosphere of 6% carbon dioxide for a maximum of four days. For each subsequent passage (100-L and 200-L cell bags), the cells are seeded at a target density of 2.0×10⁵ viable cells/mL, wherein cultures targeted at having a final culture cell viability ≥80%. The cultures are incubated in CD-CHO medium at 37° C. in an atmosphere of 6% carbon dioxide for a maximum of four days. Exemplary values for the final viable cell density at the 20-L, 100-L, and 200-L cell bag inoculum expansion step of 1.0 to 2.0×10⁶ cells/mL and a minimum percent cell viability of ≥80% were established. These exemplary values ensure that a sufficient number of viable cells is used to inoculate the 1000-L bioreactor.

The objective of the 1000-L and 4000-L seed bioreactor inoculum expansion steps of the CTLA4-Ig process is to provide a sufficient number of viable cells to inoculate the 20,000-L production bioreactor.

The seed bioreactors are operated in batch mode using CD-CHO cell culture medium. Temperature, pH, dissolved oxygen, pressure, agitation and gas flow rates for air, oxygen, and carbon dioxide are controlled by a distributed control system (DCS) and provide conditions for optimal growth of the culture in the seed bioreactors. The seed bioreactors are operated at 37° C. Culture samples are removed from the seed bioreactors for the determination of viable cell density, percent viability, and metabolite concentrations.

The 1000-L seed bioreactor is inoculated with inoculum from the 200-L cell bag expansion step to a target initial viable cell density of 1.0 to 3.0×10⁵ viable cells/mL. The culture is incubated in CD-CHO medium at 37° C. for a maximum of 5 days. Exemplary values for the final viable cell density at the 1000-L seed bioreactor inoculum expansion step is 1.0 to 2.0×10⁶ cells/mL and a minimum percent cell viability is 80%.

The 4000-L seed bioreactor is inoculated with inoculum from the 1000-L seed bioreactor expansion step to a target initial viable cell density of 1.0 to 3.0×10⁵ viable cells/mL. The culture is incubated in CD-CHO medium at 37° C. for a maximum of 6 days. Exemplary values for the final viable cell density at the 4000-L seed bioreactor inoculum expansion step is 1.0 to 2.0×10⁶ cells/mL and a minimum percent cell viability is 80%. These exemplary values ensure that a sufficient number of viable cells is used to inoculate the 20,000-L production bioreactor.

The 20,000-L seed bioreactor is inoculated with inoculum from the 4000-L seed bioreactor expansion step to a target initial viable cell density of 1.0 to 1.8×10⁵ viable cells/mL. The culture is incubated in CD-CHO medium at 37° C. for a maximum of 6 days. Exemplary values for the final viable cell density at the 20,000-L seed bioreactor inoculum expansion step is 1.0 to 2.0×10⁶ cells/mL and a minimum percent cell viability is 80%. These exemplary values ensure that a sufficient number of viable cells is used prior to initiating the production phase in the 20,000-L production bioreactor.

Commercial Scale Production of CTLA4-Ig:

The production phase of this invention occurring in a 20,000-L production bioreactor produces both high quantity and high quality CTLA4-Ig protein, which involves culture runs having a two-step temperature shift. The 20,000 L culture that is incubated in CD-CHO medium at 37° C. for a maximum of 6 days (as described above) is subjected to a temperature shift (T-shift) from 37° C. to 34° C. on day 6 (the end of logarithmic growth phase). Twelve hours after the 37° C. to 34° C. temperature-shift, CD-CHO medium is supplemented with a modified eRDF feed medium (Invitrogen Corp., Carlsbad, Calif.; Tables 16, 17), and this feed is provided daily to the production reactor as a bolus (1% w/w).

TABLE 16

Composition of eRDF Feed Medium

| Component | Concentration |
|---|---|
| eRDF-1 Medium (Invitrogen Corp.) | 16.47 g/kg |
| Dextrose | 30.29 g/kg |
| D-Galactose | 12.38 g/kg |
| L-Glutamine | 4.02 g/kg |
| r-human Insulin (10 mg/mL solution) | 0.98 mL/kg |
| TC Yeastolate | 4.90 g/kg |
| Water | As required |
| 1N HCl Solution | 0-5 mL/kg to adjust pH |
| 10N NaOH Solution | 0-2 mL/kg to adjust pH |

TABLE 17

Composition of eRDF-1 Medium

| Component | Concentration (mg/L) |
|---|---|
| Cupric Sulfate 5H$_2$O | 0.0008 |
| Ferrous Sulfate 7H$_2$O | 0.220 |
| Magnesium Sulfate (MgSO$_4$) | 66.20 |
| Zinc Sulfate 7H$_2$O | 0.230 |
| Sodium Pyruvate | 110.0 |
| DL-Lipoic Acid Thioctic | 0.050 |
| Linoleic Acid | 0.021 |
| L-Alanine | 6.68 |
| L-Arginine | 581.44 |
| L-Asparagine | 94.59 |
| L-Aspartic Acid | 39.93 |
| L-Cystine 2HCl | 105.38 |
| L-Glutamic Acid | 39.7 |
| Glycine | 42.8 |
| L-Histidine HCl—H$_2$O | 75.47 |
| L-Isoleucine | 157.40 |
| L-Leucine | 165.30 |
| L-Lysine HCl | 197.26 |
| L-Methionine | 49.24 |
| L-Phenylalanine | 74.30 |
| L-Proline | 55.3 |
| L-Hydroxyproline | 31.5 |
| L-Serine | 85.10 |
| L-Threonine | 110.8 |
| L-Tryptophan | 18.40 |
| L-Tyrosine 2Na 2H$_2$O | 108.10 |
| L-Valine | 108.9 |
| Para Amino Benzoic Acid | 0.51 |
| Vitamin B12 | 0.339 |
| Biotin | 1.00 |
| D-Ca Pantothenate | 1.29 |
| Choline Chloride | 12.29 |
| Folic Acid | 1.96 |
| i-Inositol | 46.84 |
| Niacinamide | 1.47 |
| Pyridoxal HCl | 1.00 |
| Pyridoxine HCl | 0.420 |
| Riboflavin | 0.21 |
| Thiamine HCl | 1.59 |
| Putrescine 2HCl | 0.020 |

The 20,000 L culture is incubated in CD-CHO medium supplemented daily with eRDF feed medium at 34° C. for a maximum of 4 days. On day 10, the 20,000 L culture is subjected to a second T-shift from 34° C. to 32° C. The 20,000 L production culture in the production bioreactor was maintained at 32° C. for a maximum of 8 days. On day 18, a culture sample was analyzed for the following exemplary values: viable cell density at the 20,000-L seed bioreactor production step is 3.0 to 8.0×10$^6$ cells/mL; minimum percent cell viability is ≥38%; final sialic acid molar ratio (described elsewhere) is ≥6; and final CTLA4-Ig protein product titer is 0.5 to 1.3 g/L. These exemplary values ensure that a protein product of sufficient quality and quantity is being produced by the recombinant CHO cell line and that the 20,000-L mammalian cell culture is ready to be harvested.

The culture in the bioreactor during the production phase is given a daily bolus feed using modified eRDF medium (Table 16, 17), as follows: starting 12 hours after the initial temperature shift (37° C. to 34° C.), a minimum of 1% culture volume was added as feeding medium; if the glucose level fell below 3 g/L, a calculated volume is added to bring the glucose level back to 3 g/L.

The production phase had duration of 18 days at the 20,000 L scale. Samples were taken on a daily basis from the production bioreactor for analysis. For example, a sample used for cell counting was stained with trypan blue (Sigma, St. Louis, Mo.). Cell count and cell viability determination was performed using a hemocytometer to count viable stained cells under the microscope. For analysis of metabolites, an additional sample aliquot was centrifuged for 20 minutes at 2000 rpm (4° C.) to pellet the cells. The supernatant was analyzed for protein titer, sialic acid, glucose, lactate, glutamine, glutamate, pH, $pO_2$, $pCO_2$, ammonia, and LDH, using techniques and protocols conventionally practiced in the art.

Example 15: Purification of Recombinant CTLA4-Ig

QXL Anion Exchange Chromatography for CTLA4-Ig Purification:

The anion exchange chromatography step in the CTLA4-Ig process uses Q Sepharose Extreme Load (QXL) anion exchange chromatography resin. This resin is supplied by GE Healthcare, Waukesha, Wis. (formerly Amersham Biosciences). The QXL chromatography step is to capture and concentrate the CTLA4-Ig dimer from the in-process material from the harvest operation steps for further downstream processing.

A 1.0-2.0 m inner diameter column is packed with QXL resin to a height of 17 to 30 cm, representing a volume of about 643 L to 1018 L. The column is qualified for use by determining the height equivalent to a theoretical plate (HETP) and asymmetry ($A_s$) of the packed column. A HETP of 0.02 to 0.08 cm and an $A_s$ of 0.8 to 1.2 are employed for qualification of the QXL column.

The QXL column operation is carried out at ambient temperature. The clarified cell culture broth is loaded onto an equilibrated QXL column. The QXL chromatography step is performed using a maximum flow rate of 99.4 L/min. The column inlet pressure is maintained below 35 psig. The maximum CTLA4-Ig protein load for the QXL column is 28 grams of CTLA4-Ig per liter of resin.

The QXL chromatography column is first sanitized with a 1 N sodium hydroxide solution. The sanitization is performed using 2 to 4 column volumes (CV) of the 1 N sodium hydroxide solution. The sanitization is complete when the conductivity of the column effluent equals 169±33 mS/cm and the column is held for 60 to 120 minutes.

After the sanitization step, the column is equilibrated with a 75 mM HEPES, 360 mM sodium chloride, pH 8.0 buffer. The equilibration is complete when a minimum of 3 CV of equilibration buffer have been passed through the column and the pH of the effluent is 8.0±0.2 and the conductivity of the effluent is 13.4±1.0 mS/cm.

The in-process material from the harvest operation step is loaded onto the QXL column. The column is washed with a minimum of 10 CV of wash buffer (75 mM HEPES, 360 mM NaCl, pH 8.0), and the absorbance at 280 nm (A280) of the column effluent is measured at the end of the wash step. CTLA4-Ig is then eluted from the column with a 25 mM HEPES, 325 mM NaCl or 850 mM NaCl, pH 7.0 buffer. The eluate is diverted into a collection vessel when the A280 increases to ≥0.02 absorbance units (AU) above the AU value at the end of the wash step. The eluate is collected until the A280 of the trailing edge of the elution peak decreases to a value of ≤1.0 AU.

A CTLA4-Ig dimer product with a molar ratio of moles sialic acid to moles CTLA4-Ig protein that is ≥8 is collected, and a pool of CTLA4-Ig high molecular weight material is present at ≤25.7%. The CTLA4-Ig high molecular weight material, which includes tetramers, can then be further purified for use as a separate substance for the methods of treatment described herein.

Phenyl Sepharose FF HIC for CTLA4-Ig Purification:

The hydrophobic interaction chromatography (HIC) step uses Phenyl Sepharose Fast Flow resin (GE Healthcare, Waukesha, Wis. (formerly Amersham Biosciences)). The HIC step reduces the level of CTLA4-Ig high molecular weight material present in the QXL product pool. The CTLA4-Ig dimer does not bind to the HIC resin under the loading conditions used for the HIC step.

A 1.0 to 2.0 m inner diameter column is packed with Phenyl Sepharose Fast Flow resin to a height of 18 to 22 cm, representing a volume of about 680 to 852 L. The column is qualified for use by determining the HETP and $A_s$ of the packed column. A HETP of 0.02 to 0.08 cm and an $A_s$ of 0.8 to 1.2 are employed for qualification of the HIC column.

The HIC column operation is carried out at ambient temperature. The eluate pool from the QXL column step is loaded without further treatment onto the equilibrated HIC column. The HIC step is operated at a maximum flow rate of 65.4 L/min and at a operating pressure of ≤13 psig. The maximum CTLA4-Ig protein load applied to the HIC column is 10.0 g of CTLA4-Ig protein per liter of resin. Multiple cycles of the HIC step can be employed based on the amount of CTLA4-Ig protein present in the QXL eluate pool.

The HIC column is first sanitized with a 1 N sodium hydroxide solution. The sanitization is complete when 2 to 4 CV of the 1 N sodium hydroxide solution have been passed through the column. The column is then held for 60 to 120 minutes to ensure sanitization.

After the sanitization step, the column is equilibrated with a 75 mM HEPES, 2.55 M sodium chloride, pH 7.0 buffer. The equilibration is complete when a minimum of 3 CV of equilibration buffer have been passed through the column and the pH of the effluent is 7.0±0.3 and the conductivity is 71.5 to 75.5 mS/cm.

The eluate from the QXL step is applied to the equilibrated HIC column. The column is then washed with the chase equilibration buffer until the A280 of the effluent decreases to between 0.8 and 1.0 AU. The CTLA4-Ig protein-containing effluent from each cycle of the HIC step is filtered through a 0.2 μm cellulose acetate filter into a common stainless steel collection vessel. This HIC product pool is held in the collection vessel at 2° to 8° C. The maximum hold time in the collection vessel is 3 days.

A CTLA4-Ig dimer product with a molar ratio of moles sialic acid to moles CTLA4-Ig protein that is ≥8 is collected, and a pool of CTLA4-Ig high molecular weight material is present at ≤2.5%.

Recombinant Protein A Affinity Chromatography for CTLA4-Ig Purification:

The recombinant Protein A Sepharose Fast Flow affinity resin (rPA) used in the downstream CTLA4-Ig production process is obtained from GE Healthcare (Waukesha, Wis. (formerly Amersham Biosciences)). The rPA column chromatography step further purifies the CTLA4-Ig protein. This step removes DNA and host cell proteins including monocyte chemotactic protein 1 (MCP-1).

An 80 to 140 cm inner diameter column is packed with rPA resin to a height of 18 to 25 cm, representing a volume of about 339 to 372 L. The column is qualified for use by determining HETP and $A_s$ of the packed column. A HETP of 0.02 to 0.08 cm and an $A_s$ of 0.8 to 1.2 are employed for qualification of the column. The maximum number of uses for the rPA resin established in a resin lifetime study is 60.

The rPA column operation is carried out at ambient temperature. The viral inactivation product pool is loaded onto the equilibrated rPA column. The rPA step is operated at a maximum flow rate of 26.7 L/min and an operating pressure of ≤13 psig. The maximum CTLA4-Ig protein load applied to the rPA column is 25 g of CTLA4-Ig protein per liter of resin.

The rPA column is equilibrated with a 25 mM Tris, 250 mM NaCl, pH 8.0 buffer. Equilibration is complete when a minimum of 3 CV of equilibration buffer have been passed through the column and the pH and conductivity values of the effluent are between 7.8 to 8.2 and 23.0 to 27.0 mS/cm, respectively.

The viral inactivation step product pool is applied to the equilibrated rPA column. The rPA chromatography step includes two wash steps. The first wash step is performed using a minimum of 5 CV of a 25 mM Tris, 250 mM NaCl, 0.5% Triton X-100, pH 8.0 buffer to remove weakly bound material from the rPA column. The second wash step is performed using a 25 mM Tris, 250 mM NaCl, pH 8.0 buffer. The second wash step uses a minimum of 5 CV to remove the residual Triton X-100 from the rPA column.

The CTLA4-Ig protein is eluted from the rPA chromatography column with a 100 mM glycine, pH 3.5 buffer. The eluate is diverted into a collection vessel when the A280 increases to 0.2 AU above the baseline. The column effluent is filtered through a 0.2 μm cellulose acetate filter into a collection vessel equipped with an agitator. The eluate is collected until the $A_{280}$ of the trailing edge of the elution peak decreases to a value of ≤0.2 AU. The pH of the eluate pool is adjusted to pH 7.5±0.2 with a 2 M HEPES, pH 8.0 buffer. The rPA chromatography step product pool is held at 2° to 8° C. for a maximum of 3 days.

A CTLA4-Ig dimer product with a molar ratio of moles sialic acid to moles CTLA4-Ig protein that is ≥8 is collected; a pool of CTLA4-Ig high molecular weight material is present at ≤2.5%; and a pool of MCP-1≤38 ng/mL is present.

QFF Anion Exchange Chromatography for CTLA4-Ig Purification:

The anion exchange chromatography step in the downstream CTLA4-Ig production process uses Q Sepharose Fast Flow (QFF) anion exchange chromatography resin (GE Healthcare (Waukesha, Wis. (formerly Amersham Biosciences). The objective of the QFF chromatography step is to reduce the residual Protein A levels and provide additional reduction of host cell DNA from the viral filtration step product pool. The QFF column step is also used to control the sialic acid to CTLA4-Ig protein molar ratio of the QFF chromatography step product pool and to provide additional control of in-process CTLA4-Ig HMW material levels. The primary in-process control point for the reduction of CTLA4-Ig HMW material is the HIC step.

A 60 to 140 cm inner diameter column is packed with QFF resin to a height of 28 to 35 cm, representing a volume of about 536 to 667 L. The column is qualified for use by determining the HETP and $A_s$ of the packed column. A HETP of 0.02 to 0.08 cm and an $A_s$ of 0.8 to 1.2 are employed for qualification of the column.

The QFF column operation is carried out at ambient temperature. The viral filtration step product pool is loaded onto the equilibrated QFF column. The QFF step is operated at a maximum flow rate of 38.7 L/min and an operating pressure of ≤35 psig. The maximum CTLA4-Ig protein load applied to the QFF column is 25 g of CTLA4-Ig protein per liter of resin.

The QFF chromatography column is first sanitized with a 1 N sodium hydroxide solution. The sanitization is performed using 2 to 4 CV of the 1 N sodium hydroxide solution. The sanitization is complete when the conductivity of the column effluent equals 136 to 202 mS/cm and the column is held for 60 to 120 minutes.

After the sanitization step, the column is equilibrated with a 25 mM HEPES, 100 mM sodium chloride, pH 8.0 buffer. The equilibration is complete when a minimum of 4 CV of equilibration buffer have been passed through the column and the pH of the effluent is 7.7 to 8.3 and the conductivity is 10.5 to 12.9 mS/cm.

The viral filtration step product pool contained in bioprocess bags is transferred into a sterile stainless steel collection vessel.

The viral filtration step product pool is applied to the equilibrated QFF column. The QFF chromatography step includes two wash steps. The first wash step is performed using a minimum of 5.0 CV of a 25 mM HEPES, 120 mM NaCl, pH 8.0 buffer. The second wash step is performed using a minimum 5.0 CV of a 25 mM HEPES, 130 mM NaCl, pH 8.0 buffer.

The CTLA4-Ig dimer is eluted from the QFF chromatography column using a 25 mM HEPES, 200 mM NaCl, pH 8.0 buffer. The eluate collection is initiated when the $A_{280}$ of the effluent begins to increase. During elution, the column effluent is filtered through a 0.2 μm cellulose acetate filter into the stainless steel collection vessel. The eluate is collected until the absorbance of the trailing edge of the elution peak decreases to ≤0.2 AU above the baseline. The collection vessel is then cooled to 2° to 8° C. The maximum hold time for the QFF chromatography step product pool at 2° to 8° C. is 3 days.

A CTLA4-Ig dimer product with a molar ratio of moles sialic acid to moles CTLA4-Ig protein that is ≥8 is collected; a pool of CTLA4-Ig high molecular weight material is present at ≤2.5%; a pool of CTLA4-Ig low molecular weight material (for example CTLA4-Ig monomer) is present at ≤0.5%; and a pool of MCP-1≤9.5 ng/mL is present.

The Pall Filtron TFF system is used in the concentration and diafiltration step of the downstream CTLA4-Ig production process. The objective of this step is to concentrate the QFF chromatography step product pool to 45 to 55 g/L and to exchange the elution buffer used in the QFF chromatography step with the final buffer used for CTLA4-Ig compositions. The concentrated CTLA4-Ig protein product pool is transferred through a 0.2 polyvinylidene fluoride filter and into a 50-L bioprocess bag.

Example 16: CTLA4-Ig-Molar Ratio Determination of Amino Monosaccharides

This example provides methods to obtain molar ratios of amino monosaccharides (N-acetyl galactosamine, N-acetyl glucosamine) to protein in CTLA4-Ig samples.

Instrumentation: Capillary Electrophoresis System Beckman P/ACE MDQ CE System; Detector Beckman Laser-Induced-Fluorescence (LIF) detection system(coupled with P/ACE MDQ); Uncoated capillary (i.d. 25 µm; o.d. 360 µm), 27-31 cm total length to accommodate either P/ACE MDQ or 5510 PolyMicro Technologies, Cat. No. TSP025375; Maxi-Mix mixer Thermolyne, (VWR Catalog No. 58810-185)

Reagents:

Hydrolysis Solution (4 N HCl Aqueous Solution)

Add 160 mL of 6 N HCl and 80 mL of HPLC grade water to a 250 mL glass bottle. Stir to mix well.

Store at 2-8° C. for up to 6 months.

Derivatization Solution I (0.1 M APTS Aqueous Solution)

Add 192 µL of HPLC grade water to 10 mg powder of APTS in a glass vial.

Vortex the vial 5-10 seconds to completely dissolve the APTS.

Store at −20° C. for up to one year.

Derivatization Solution II (1 M Acetic Acid and 0.25 M NaBH$_3$CN)

Dilute 20 µL acetic acid with 320 µL HPLC grade water (17 fold dilution) in a 0.4 mL centrifuge tube to make a 1 M acetic acid solution.

Weigh 2.0±0.5 mg of NaBH$_3$CN into a cryogenic vial.

Using the following formula, add an appropriate volume of the 1 M acetic acid solution to make 0.25 M NaBH$_3$CN. Volume (µL)=103×(weight of NaBH$_3$CN in mg)/(62.84 g/mol×0.25 mol/L)

Sodium cyanoborohydride (NaBH$_3$CN) should be stored in dark in a desiccator. • Subdividing of the reagent into a series of 2.0 mL cryovials for storage is recommended to avoid repeated opening of the original reagent bottle as follows: • Weigh 1.0 g±0.2 mg of Sodium Cyanoborohydride into 2.0 mL cryovial. Aliquot out the entire contents of Sodium Cyanoborohydride from the original bottle in this manner. • Cap tightly and label cryovials sequentially (1,2,3, etc.) along with reagent name, lot number, and a 6 month expiration date. • The vials should be sealed with parafilm to avoid moisture. • Weigh out Sodium Cyanoborohydride for Derivatization Solution II no more than three times from the same cryovial. Make note of this and the cryovial sequence number on the lab worksheet. • Either a reagent peak observed in the CE profile or poor labeling may occur after repeated opening of the cryovial or with that particular lot of Sodium Cyanoborohydride. If this effects the results, discard the cryovial being used and either weigh out reagent from a cryovial with the next sequence number or from a new lot of Sodium Cyanoborohydride.

Re-Acetylation Buffer (25 mM Sodium Bicarbonate, pH 9.5)

Weigh 0.210±0.02 g of sodium bicarbonate into a clean 100 mL clean glass beaker.

Add 90 mL of HPLC grade water, and mix on a stir plate until salts are completely dissolved.

Adjust the pH to 9.5±0.1 with 10 N NaOH.

Add HPLC grade water to make the final volume 100 mL. Filter (step 1.26) the solution and store at room temperature for up to 3 months.

Running Buffer (60±5 mM Sodium Tetraborate, pH 9.25)

Weigh 1.21±0.02 g sodium tetraborate into a 100 mL clean glass beaker.

Add 90 mL of HPLC grade water, and mix on a stir plate until salts are completely dissolved.

Adjust the pH to 9.25±0.10 with 10 N NaOH.

Add HPLC grade water to make the final volume 100 mL for a final concentration of 60±5 mM.

For a 55 mM solution, weigh 1.11 g (±0.02) sodium tetraborate and follow above instructions for dissolving and titrating.

For a 65 mM solution, weigh 1.31 g (±0.02) sodium tetraborate and follow above instructions for dissolving and titrating.

Store at room temperature for up to 3 months. Prepare fresh buffer if peak resolution is effected (R value <1.0).

Optional: Dilute tetraborate buffer solution (MicroSolv) by adding 120 mL of ultra pure water to 80 mL of 150 mM sodium tetraborate buffer for a final concentration of 60 mM (±5 mM). Titrate with 10N NaOH to bring the solution pH to 9.25 (±0.1).

For a 55 mM tetraborate solution, dilute 66 mL of 150 mM sodium tetraborate buffer into 114 mL of ultra pure water. Titrate as above.

For a 65 mM tetraborate solution, dilute 78 mL of 150 mM sodium tetraborate buffer into 102 mL of ultra pure water. Titrate as above.

Store the solution at room temperature for a maximum of 3 months. Prepare fresh buffer if peak resolution is effected (R value <1.0).

Capillary Rinsing Solutions

N NaOH Solution

Add 1 mL of 10 N NaOH solution to a 15 mL graduated plastic tube containing 9 mL of HPLC grade water. Mix well by vortexing 5-10 sec.

Store the solution at room temperature for up to 6 months.

N HCl Solution:

Add 1 mL of 6 N HCl solution to a 15 mL graduated plastic tube containing 5 mL of HPLC grade water. Mix well by vortexing 5-10 sec.

Store the solution at room temperature for up to 6 months.

3.6.3 80% methanol solution:

Add 8 mL HPLC grade methanol to a 15 mL graduated plastic tube containing 2 mL HPLC grade water. Mix well by vortexing 5-10 sec.

Store the solution at room temperature for up to 6 months.

Monosaccharide Standard Stock Solutions

N-Acetyl Glucosamine (GalNAc)

Accurately weigh 5±1 mg of GalNAc into a 2.0 mL cryogenic vial.

Add 1 mL of HPLC grade water and mix well by vortexing until dissolved.

Record the accurate concentration of the solution (mg/mL).

N-Acetyl Galactosamine (GlcNAc)

Accurately weigh 5±1 mg of GlcNAc into a 2.0 mL cryogenic vial.

Add 1 mL of HPLC grade water and mix well by vortexing until dissolved.

Record the accurate concentration of the solution (mg/mL).

N-Acetyl Mannosamine (ManNAc)

Accurately weigh 5±1 mg of ManNAc into a 2.0 mL cryogenic vial.

Add 1 mL of HPLC grade water and mix well by vortexing until dissolved.

Record the accurate concentration of the solution (mg/mL).

Store Monosaccharide Standard Stock Solutions at −20° C. for up to 1 year.

Monosaccharide Working Solution I: Internal Standard Working Solution

Dilute stock solution of ManNAc 100 fold with HPLC grade water by adding 20 μL of ManNAc stock solution into a 2 mL cryogenic vial which already contains 1980 of HPLC grade water. Vortex approximately 5 to 10 seconds.

Store the internal standard working solution at 2-8° C. for up to 6 months.

Monosaccharide Working Solution II: Amino Mix Standard Working Solution

In a 2.0 mL cryogenic vial containing 1960 μL of HPLC grade water, add 20 μL of stock solutions of GalNAc and GlcNAc, respectively. Vortex approximately 5 to 10 seconds.

Store the amino mix standard working solution at 2-8° C. for up to 6 months.

Sample and Reference Material Solutions.

Thaw frozen protein samples at 2-8° C., and gently mix by inversion.

Dilute both samples and reference material with HPLC grade water to about 1.0 mg/mL. Make note of concentration out to three significant figures.

CE Running Conditions

Running Buffer (step 2.5) 60 mM sodium tetraborate, pH 9.25

Capillary Cartridge temperature 25° C.

Voltage 25-30 kV, positive mode

Detector condition LIF detector, Excitation: 488 nm, Emission: 520 nm.

Sample injection Pressure injection mode, 20 s at 0.5 PSI

Run Time 10 minutes

Sample storage 10° C.

Procedure

Note: Use a 10 μL Pipettor and micro tips to transfer 10 μL sample volumes and appropriately sized Pipettors to transfer other reagents (see ranges in steps 2.10 through 2.14).

Hydrolysis

In a 0.65 mL centrifuge tube, add 10 μL of ManNAc working solution and 200 μL 4 N Hydrolysis Solution (step 3.1). This serves as a system blank.

In a 0.65 mL centrifuge tube, add 10 μL of ManNAc working solution and 10 μL of Amino Mix Standard Solution (step 3.9). Further add 200 μL of 4N Hydrolysis Solution. This serves as monosaccharide standard for quantitation and System Suitability. Prepare in duplicate.

In a 0.65 mL centrifuge tube, add 10 μL of ManNAc working solution and 10 μL of CTLA4-Ig reference material solution (approximately 1 mg/mL).

Further add 200 μL of 4N HCl solution. Prepare in duplicate.

In a 0.65 mL centrifuge tube, add 10 μL of ManNAc working solution and 10 μL of sample solution (approximately 1 mg/mL). Further add 200 μL of 4N HCl solution. Prepare in duplicate.

Vortex samples for approximately 10 seconds and centrifuge for approximately 5-10 seconds. Place samples in a 96-position vial rack and incubate in an oven at 95° C. for 6 hr.

After hydrolysis, place hydrolyzed samples at −20° C. for 10 minutes to cool down.

Briefly centrifuge the hydrolyzed samples until any condensate is forced to the bottom of the tube (5-10 seconds at high speed). Evaporate samples to dryness in SpeedVac.

Note: Turn off SpeedVac heat, and set the evaporating rate to "Low".

Reconstitute each sample with 100 μL of HPLC grade water and vortex 10-15 sec. Evaporate samples to dryness in SpeedVac.

Note: Turn off SpeedVac heat, and set the evaporating rate to "Low".

Re-Acetylation

Reconstitute each sample with 10 μL of M6 re-acetylation buffer and vortex 5-10 sec. to mix well. Add 4 μL of M3 re-acetylation reagent into each tube. Vortex for approximately 5-10 seconds. Incubate on ice for 30 minutes.

Note: The re-acetylation buffer (M6) and reagent (M3) can be replaced respectively with 25 mM $NaHCO_3$(add 20 μL) prepared in house and acetic anhydride (add 4 μL).

Evaporate samples to dryness in SpeedVac.

Note: Turn off SpeedVac heat, and set the evaporating rate to "Low".

Reconstitute each sample with 100 μL of HPLC grade water and vortex 10-15 sec. Evaporate samples to dryness in SpeedVac.

Note: Turn off SpeedVac heat, and set the evaporating rate to "Low".

Derivatization

Place the micro centrifuge in the oven to equilibrate to the oven temperature of 55° C.

Reconstitute each sample with 10 μL of Derivitization Solution I (0.1 M APTS solution, step 3.2). Vortex approximately 5-10 seconds.

Add 5 μL of the Derivatization Solution II (1M HAc and 0.25 M $NaBH_3CN$, step 3.3). Vortex approximately 5-10 seconds and centrifuge.

Quickly load the sample vials into the pre-warmed centrifuge, and place the centrifuge back in the 55° C. oven. Incubate for 3 hr while centrifuging at 2000 rpm. This prevents the condensation of solvent on vial surface.

Instrumentation Preparation

Installing a new capillary, rinse in high pressure mode (80 PSI) using the following steps:

1 N NaOH for 20 minutes.

HPLC grade water for 10 minutes.

60 mM sodium tetraborate buffer for 10 minutes.

Operation

Before each operation, run the washing/rinse sequences to rinse the capillary.

Then run the System Suitability Standard (monosaccharide standard) to ensure the system is suitable.

Using 1N NaOH may etch the inside of capillaries from different vendors and cause a shift in migration times throughout the run. If this causes the migration time of the last peak (GlcNAc) to be more than 10.0 minutes, it may be necessary to replace 1N NaOH with 0.1N NaOH or HPLC grade water for the step 2 rinse.

When using an equivalent capillary and the above washing procedure is not adequate using 80% methanol and/or 1N HCl may be necessary for the last peak (GlcNAc) to be within the exemplary values of 10.0 minutes.

Preparation for Injection

After derivatization, let samples cool down to room temperature. Centrifuge approximately 10 seconds at room temperature, until condensate is forced to the bottom of the tube.

Add 85 µL of HPLC grade water to each tube to bring the final volume of each sample to 100 µL. Vortex for 5-10 seconds.

Transfer 10 µL of sample from each tube to a CE micro vial and add 190 µL of HPLC grade water to each tube. Vortex for 5-10 seconds.

Rinse steps and Injection sequence:
Note: For every four injections, change the CE running buffer with newly prepared CE running buffer (due to ionic depletion effect). Perform capillary rinse at 40 psi.

| Step | Description | Run Time (min) |
|---|---|---|
| 1 (Rinse) | HPLC grade water | 1 |
| 2 (Rinse) | refer to section 5.4.2.3   1N NaOH or 0.1N NaOH OR HPLC grade water | 3 |
|  | Note: When using HPLC water for the step 2 rinse, steps 1, 2, and 3 may be combined in a single 3 minute run. | 1 |
| 3 (Rinse) | HPLC grade water | 1 |
| 4 (Rinse) | 60 mM sodium Tetraborate Run Buffer | 5 |
| 5 (Rinse) | Blank (Internal Standard Marker) | 10 |
| 6 (Rinse) | Repeat 1-4 | 10 |
| 7 (Rinse) | System Suitability (Mono Std prep 1) | 10 |
| 8 (Rinse) | Repeat 1-4 | 10 |
| 9 | System Suitability (Mono Std prep 1) | 10 |
| 10 (Rinse) | Repeat 1-4 | 10 |
| 11 | System Suitability (Mono Std prep 2) | 10 |
| 12 (Rinse) | Repeat 1-4 | 10 |
| 13 | System Suitability (Mono Std prep 2) | 10 |
| 14 (Rinse) | Repeat 1-4 | 10 |
| 15 | CTLA4-Ig prep1 | 10 |
| 16 (Rinse) | Repeat 1-4 | 10 |
| 17 | CTLA4-Ig prep2 | 10 |
| 18 (Rinse) | Repeat 1-4 | 10 |
| 19 | Sample 1 prep 1 | 10 |
| 20 (Rinse) | Repeat 1-4 | 10 |
| 21 | Sample 1 prep 1 | 10 |
| 22 (Rinse) | Repeat 1-4 | 10 |
| 23 | Sample 1 prep 2 | 10 |
| 24 (Rinse) | Repeat 1-4 | 10 |
| 25 | Sample1 prep 2 | 10 |
| 26 (Rinse) | Repeat 1-4 | 18 |
| 27 | Sample 2 prep1 | 10 |
| 28 (Rinse) | Repeat 1-4 | 10 |
| 29 | Sample 2 prep 1 | 10 |
| 30 (Rinse) | Repeat 1-4 | 10 |
| 31 | Sample 2 prep 2 | 10 |
| 32 (Rinse) | Repeat 1-4 | 10 |
| 33 | Sample 2 prep 2 | 10 |
| 34 (Rinse) | Repeat 1-4 | 10 |
| 35 | Sample 3 prep 1 | 15 |
| 36 (Rinse) | Repeat 1-4 | 10 |
| 37 | Sample 3 prep 1 | 10 |
| 38 (Rinse) | Repeat 1-4 | 10 |
| 39 | Sample 3 prep 2 | 10 |
| 40 (Rinse) | Repeat 1-4 | 10 |
| 41 | Sample 3 prep 2 | 10 |
| 42 (Rinse) | Repeat 1-4 | 10 |
| 43 | CTLA4-Ig Material prep 1 | 10 |
| 44 (Rinse) | Repeat 1-4 | 10 |
| 45 | CTLA4-Ig Material prep 2 | 10 |
| 46 (Rinse) | Repeat 1-4 | 10 |
| 47 | System Suitability (Mono Std prep 1) | 10 |
| 48 (Rinse) | Repeat 1-4 | 10 |
| 49 | System Suitability (Mono Std prep 1) | 10 |
| 50 | Repeat 1-4 | 10 |
| 51 | System Suitability (Mono Std prep 2) | 10 |
| 52 | Repeat 1-4 | 10 |
| 53 | System Suitability (Mono Std prep 2) | 10 |

System Suitability
Note: System suitability values are determined using the first injection of system suitability standard unless otherwise specified.

The electropherogram of the first system suitability should be similar to that shown in FIG. 80, where peak 1 is GalNAc; peak 2 is ManNAc; peak 3 is GlcNAc.

Note: When CE instruments other than Beckman PACE MDQ are to be used, the length of the capillary might be different from that specified in this method due to various configurations of cartridges holding the separation capillary. This would cause variations in analyte migration time, as well as peak intensity.

Resolution between two neighbor peaks is calculated for the first System Suitability standard by the instrument according to the following equation:

$$(R) = \frac{2(t_2 - t_1)}{W_1 + W_2}$$

Where:
R=resolution
$t_1$, $t_2$=migration times of the two neighbor peaks respectively
$W_1$, $W_2$=peak widths at baseline of the two neighbor peaks respectively The R value must be ≥1.0. If R<1.0, rinse the capillary with the washing/rinse sequences; if the problem persists, replace old buffer with freshly prepared Running Buffer or replace the capillary. For the last System Suitability injection, the last peak (GlcNAc) must have a tailing factor <1.4 using the following formula:

$$(T) = W_{0.05}/2f$$

Where:
T=tailing factor
$W_{0.05}$=width of peak at 5% of height
f=width of the peak front at peak maximum If T≥1.4, rinse the capillary with the washing/rinse sequences; if the problem persists, replace old buffer with freshly prepared run buffer or replace the capillary.

The replicate injections show the following exemplary values:
Peak Area Ratio of GlcNAc vs. MaNAc:RSD≤10% (calculated in step 7.1)
Migration time of GlcNAc should be ≤10.0 minutes
Profile should be equivalent to FIG. 80 where the three peaks are observed and the Internal Standard (ManNAc) is the number 2 peak.

If any of the above exemplary values are not reached prior to testing samples, first increase the voltage if the migration time of GlcNAc is greater than 10.0 minutes. Next, if the peak area ratio is ≥10%, prepare fresh CE buffer making certain of its pH or replace the capillary. After adjustment to the instrument, repeat System Suitability injections. When analyzing the peak profile, if a significant decrease in the peak height of ManNac occurs, check to make certain the fiber optic cable into the LIF module is not misaligned.

Determine monosaccharide standard percent RSD by comparing peak area ratios of internal standard and monosaccharide standard components. Divide the peak area for each monosaccharide component by the peak area of the internal standard for each monosaccharide standard injection. Calculate the percent RSD for GalNAc and GlcNAc for the two bracketed standards. The RSD should be 10%. If this averaging exemplary value is not met, then the capillary should be rinsed or replaced as above.

Calculations
Calculating Peak Area Ratio of GalNAc and GlcNAc relative to the Internal Standard (ManNAc). Used on replicate injections of first four System Suitability Standards so as to meet above exemplary values and performing same calculations on all of the bracketed, System Suitability Standards injected before and after sample(s).

Peak Area Ratio=Divide the peak area for each monosaccharide component (GlcNAc, GalNAc) by the peak area of the internal standard (ManNAc) for each System Suitability Standard injection.

$$\text{Peak Area Ratio} = \frac{\text{monosaccharide peak area}}{\text{MaNAc peak area}}$$

Calculate a mean of the Peak Area Ratios for GlcNAc and GalNAc in the System Suitability Standards. Also calculate a Standard Deviation (S.D.) and percent relative standard deviation (% RSD)
Exemplary Values: RSD for the Peak Area
  Ratio of GlcNAc ≤10%.

Two, bracketed, System Suitability Standards injected before and after sample(s): Percent RSD for the Peak Area Ratio of GlcNAc and GalNAc≤10%. If this averaging exemplary value is not met (RSD>10%), then the capillary needs to be re-rinsed with the rinse procedures and those samples and bracketed monosaccharide standards need to be run again. If the averaging exemplary value is still not met, replace the capillary and rinse. Run the samples and bracketed monosaccharide standards again.

$$\text{Standard Deviation} = \sqrt{\frac{n\Sigma x^2 - (\Sigma x)^2}{n(n-1)}}$$

Where:
n=number of measurements in the sample
x=individual measurements $$\% \, RSD = \frac{\text{Standard Deviation}}{\text{Average Measured Peak Area}} \times 100$$

Calculate the Molar Ratio of GalNAc/Protein:

$$R_{GalNAc} = \frac{A_{GalNAc} \times A_{ManNAc0} \times V_{GalNAc0} \times C_{GalNAc0} \times MW_{Abatacept}}{A_{ManNAc} A_{GalNAc0} \times Vp \times Cp \times MW_{GlcNAc}}$$

Where:
$R_{GalNAc}$=molar ratio of GalNAc vs. protein
$A_{GalNAc}$=peak area (µV·sec) of GalNAc in sample
$A_{ManNAc}$=peak area (µV·sec) of ManNAc in sample
$A_{ManNAc0}$=peak area (µV·sec) average of ManNAc in monosaccharide standard
$A_{GalNAc0}$=peak area (µV·sec) average of GalNAc in monosaccharide standard
$V_{GalNAc0}$=volume of GalNAc contained in monosaccharide working solution used for hydrolysis (in µL)
$C_{GalNAc0}$=concentration of GalNAc contained in monosaccharide working solution used for hydrolysis (in mg/mL)
Vp=volume of protein sample used for hydrolysis (in µL)
Cp=concentration of protein sample used for hydrolysis (in mg/mL)
$MW_{Abatacept}$=Molecular weight of Abatacept Reference Material as per Certificat of Analysis (COA)
$MW_{GlcNAc}$=Molecular weight of GalNAc (221.2 daltons)
Standards Bracketing When calculating molar ratios of CTLA4-Ig material and samples, use all eight of the bracketed System Suitability Standards. Average the peak areas for inclusion in this equation. This is to be used for the first three samples. For all other samples, always use the average peak area of the next four bracketed monosaccharide standards and the previous four bracketed monosaccharide standards for molar ratio calculations.
Calculate the Molar Ratio of GlcNAc/Protein $$R_{GalNAc} = \frac{A_{GalNAc} \times A_{ManNAc0} \times V_{GalNAc0} \times C_{GalNAc0} \times MW_A}{A_{ManNAc} A_{GalNAc0} \times Vp \times Cp \times MW_{GlcNAc}} \, CTLA4-Ig$$

Where:
$R_{GalNAc}$=molar ratio of GlcNAc vs. protein
$A_{GlcNAc}$=peak area (µV·sec) of GlcNAc in sample
$A_{ManNAc}$=peak area (µV·sec) of ManNAc in sample
$A_{ManNAc0}$=peak area (µV·sec) average of ManNAc in monosaccharide standard
$A_{GlcNAc0}$=peak area (µV·sec) average of GlcNAc in monosaccharide standard
$V_{GlcNAc0}$=volume of GlcNAc contained in monosaccharide working solution used for hydrolysis (in µL)
$C_{GlcNAc0}$=concentration of GlcNAc contained in monosaccharide working solution used for hydrolysis (in mg/mL)
Vp=volume of protein sample used for hydrolysis (in µL)
Cp=concentration of protein sample used for hydrolysis (in mg/mL)
$MW_{Abatacept}$=Molecular weight of CGLA4-Ig Reference Material
$MW_{GlcNAc}$=Molecular weight of GlcNAc (221.2 daltons)
Exemplary values. The percent RSD for the two, bracketed, amino System Suitability Standard peak area ratios should not exceed 10%. The average molar ratios for amino monosaccharides in the reference material should be within the ranges specified in the Table directly below. For each component, the % RSD for the four results (duplicate injection of duplicate preparations) must be ≤1=25%.

TABLE

Molar Ratio range of CTLA4-Ig Reference Material

| Monosaccharide | Range |
|---|---|
| GAlNAc | 2.0-3.2 |
| GlcNAc | 18-32 |

Example 17: Determination of Molar Ratio of Aminomonosaccharides (GalNAc and GlcNAc) by Capillary Electrophoresis (CE)

In one embodiment, the CTLA4-Ig composition has the characteristic of having from about 15-35 moles GlcNAc/mole of protein and from about 1.7-3.6 moles GalNac/moles protein. The following example describes a method of determining these molar ratios.

Reagents: Hydrolysis solution (4N HCl); Derivatization solution I (0.1M 8-amino-1,3,6, trisulfonic acid, trisodium salt (APTS) aqueous solution); Derivatization solution II (0.25M NaBH$_3$CN in 1M acetic acid); Re-acetylation buffer (25 mM sodium bicarbonate, pH9.5); Running buffer (60±5 mM sodium tetraborate, pH9.25); Capillary rinsing solutions (1N NaOH; 1N HCl; 80% methanol); Monosaccharide standard stock solutions of GalNAc, GlcNAc, and ManNAc at concentration of 5 mg/ml; Monosaccharide working solution I: Internal standard working solution is 100fold dilution of ManNAc stock solution; Monosaccharide working solution II: Amino mix standard working solutions, 100fold dilution of GalNAc and GlcNAc stock solutions.

Instrumentation: CE system is Beckman P/ACE MDQ CE system; Detector: Beckman laser induced (LIF) detection system coupled with P/ACE MDQ); Uncoated capillary (i.d. 25 µm, o.d. 360 µm) 27-31 cm total length to accommodate P/ACE MDQ. Capillary Electrophoresis running conditions: Running buffer (60 mM sodium tetraborate, pH 9.25); Capillary cartridge temperature: 25° C.; Voltage: 25-30 kV, positive mode; Detector condition: LIF detector, excitation at 488 nm, emission at 520m; Sample injection: pressure injection mode, 20s at 0.5PSI; Run time: 10 min; Sample storage: 10° C.

Hydrolysis: 10 µL of ManNAc working solution and 200 µL of 4N HCl were mixed to make the system blank. 10 µL of ManNAc working solution and 10 µL of Amino mix standard solution were mixed with 200 µL of 4N HCl to make the monosaccharide standard. 10 µL of ManNAc working solution and 10 µL of CTLA4-Ig dimer (approximately 1 mg/ml) were mixed with 200 µL of 4N HCl to make the test sample. All tubes were vortexed for 10 sec, and centrifuge for 10 sec, followed by incubation at 95° C. for 6 hours. After the hydrolysis step the samples were places at −20° C. for 10 min to cool down. Samples were spun down for 10 sec and evaporated to dryness in SpeedVac.

Re-acetylation: Hydrolyzed and dried samples were reconstituted with 100 µL of HPLC grade water. Reconstituted samples were re-acetylated by addition of 10 µL of M6 re-N-acetylation buffer (Glyko) and 4 µL of M3 re-acetylation reagent (Glyko), followed by mixing and with incubation on ice (30 min). Samples were spun down for 10 sec and evaporated to dryness in SpeedVac.

Derivatization: Reconstituted samples (100 µL of HPLC grade water) were equilibrated 55° C., followed by addition of 10 µL of Derivatization solution I, a brief mix, and addition of 5 µL of Derivatization solution II. Samples were loaded in a pre-warmed centrifuge and incubated for 3 hours at 55° C. while centrifuging at 2000 rpm.

Figure 29:
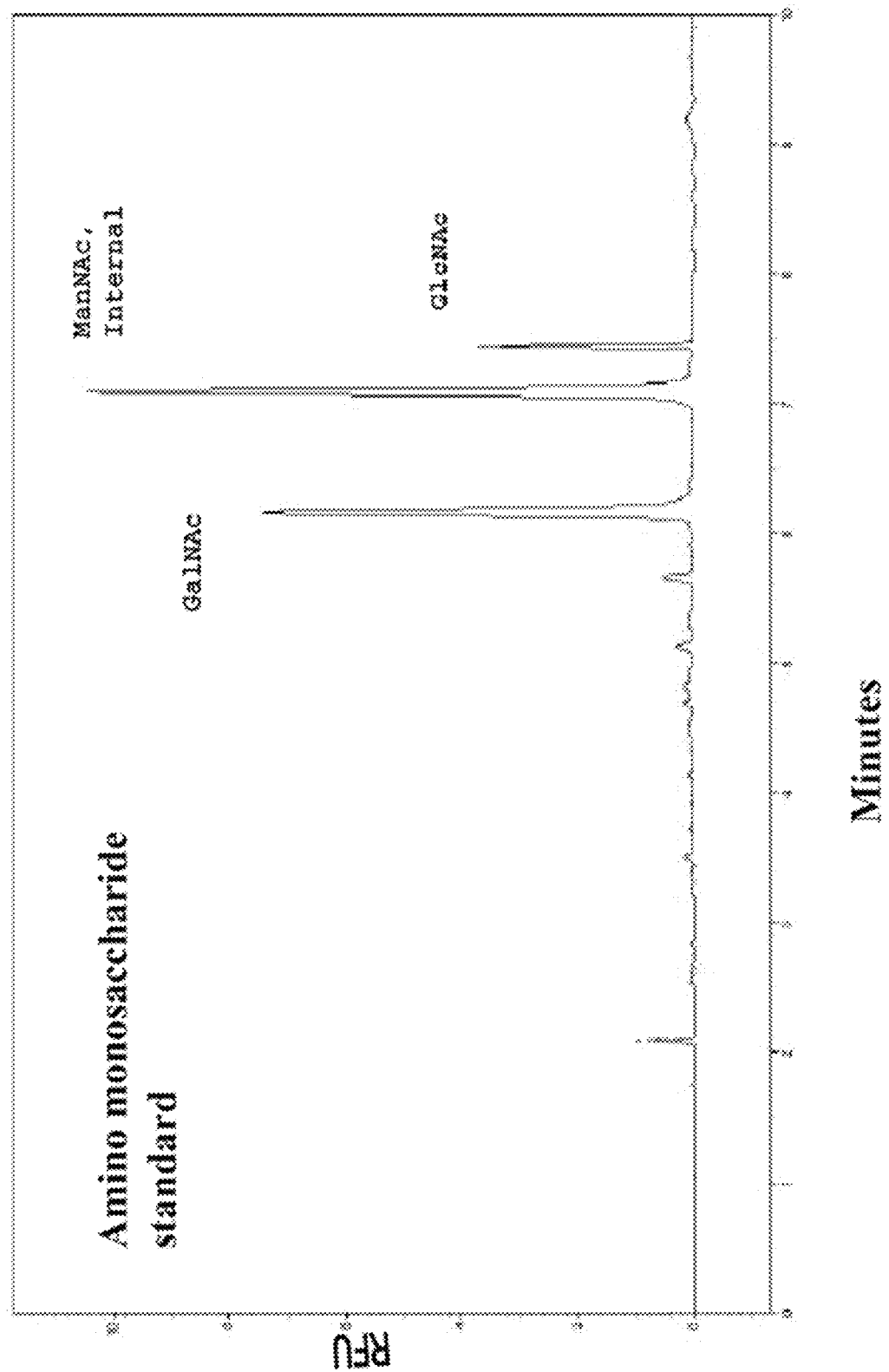
FIG. 29 shows an electropherogram of system suitability amino monosaccharides depicted as relative fluorescence units (RFU) versus time (min).

CE injection: The final volume of the samples after derivatization was brought to 100 µL by addition of HPLC grade water, and 10 µL of samples were transferred to a CE micro vial with 190 µL HPLC grade water. Before sample injections the CE cartridge was rinsed extensively with HPLC grade water (1-3 min run time), followed by an equilibrating rinse with running buffer (5 min run time). Following the initial rinse, monosaccharide standards and samples for analysis were injected in the CE cartridge (10 min run time). Following the injection run of each standard or test sample, the CE cartridge was rinsed and equilibrated with HPLC grade water and running buffer. The electopherograpm of the system suitability should be similar to FIG. 29.

Calculations: Calculating peak area ratio of GalNAc and GLCNAc relative to internal standard ManNAc.

Peak area ratio=monosaccharide peak area (GalNAc or GlcNAc)/ManNAc peak area, wherein the relative standard deviation (RSD) for the peak area ratio is equal or less that 10%.

Calculating ratio of monosaccharide (for example GalNAc) to CTLA4-Ig protein:

$$\text{Ratio}_{GalNAc} = (A_{GalNAc} \times A_{ManNAcO} \times V_{GalNAcO} \times C_{GalNAcO} \times MW_{CTLA4\text{-}Ig\ dimer}) / (A_{ManNAc} \times A_{GalNAcO} \times Vp \times Cp \times MW_{GalNAc})$$

Ratio$_{GalNAc}$=molar ratio of GalNAc versus protein
$A_{GalNAc}$=peak area (µV.sec) in GalNAc sample
$A_{ManNAc}$=peak area (µV.sec) in ManNAc sample
$A_{ManNAcO}$=peak area (µV.sec) average of ManNAc in monosaccharide standard
$A_{GalNAcO}$=peak area (µV.sec) average of GalNAc in monosaccharide standard
$V_{GalNAcO}$=volume of GalNAc contained in monosacchride working solution used for hydrolysis (in µL)
$C_{GalNAcO}$=concentration of GalNAc contained in monosacchride working solution used for hydrolysis (in mg/ml)
Vp=volume of protein sample used for hydrolysis (in µL)
Cp=concentration of protein sample used for hydrolysis (in mg/ml)
$MW_{CTLA4\text{-}Ig}$=Molecular weight of CTLA4-Ig dimer
$MW_{GalNAc}$=221.2 daltons.

TABLE 18

Average Molar Ratio of Monosaccharide to CTLA4-Ig molecules or dimer

| MONOSACCHARIDE | RANGE |
|---|---|
| GalNAc | 2.0-3.2 |
| GlcNAc | 18-32 |

Example 18: Determination of Molar Ratio of Neutral Monosaccharides (Mannose, Fucose and Galactose) by Capillary Electrophoresis (CE)

Reagents: Hydrolysis solution (2M trifluoroacetic acid (TFA)); Derivatization solution I (0.1M 8-amino-1,3,6, trisulfonic acid, trisodium salt (APTS) aqueous solution); Derivatization solution II (0.25M NaBH$_3$CN in 1M acetic acid); Running buffer (60±5 mM sodium tetraborate, pH9.25); Capillary rinsing solutions (1N NaOH; 1N HCl; 80% methanol); Monosaccharide standard stock solutions of mannose (Man), fucose (Fuc), galactose (Gal), and xylose (Xyl) at concentration of 5 mg/ml; Monosaccharide working solution I: Internal standard working solution is 100 fold dilution of Xyl stock solution; Monosaccharide working solution II: Neutral mix standard working solutions, 100 fold dilution of Man, Fuc and Gal stock solutions.

Instrumentation: CE system is Beckman P/ACE MDQ CE system; Detector: Beckman laser induced (LIF) detection system coupled with P/ACE MDQ); Uncoated capillary (i.d. 25 µm, o.d. 360 µm) 27-31 cm total length to accommodate P/ACE MDQ.

Capillary Electrophoresis running conditions: Running buffer (60 mM sodium tetraborate, pH 9.25); Capillary cartridge temperature: 25° C.; Voltage: 25-30 kV, positive mode; Detector condition: LIF detector, excitation at 488 nm, emission at 520m; Sample injection: pressure injection mode, 20s at 0.5PSI; Run time: 10 min; Sample storage: 10° C.

Hydrolysis: 10 µL of Xylose working solution and 200 µL of 2M TFA were mixed to make the system blank. 10 µL of Xylose working solution and 10 µL of Neutral mix standard solution were mixed with 200 µL of 2M TFA to make the monosaccharide standard. 10 µL of Xylose working solution and 10 µL of CTLA4-Ig dimer (approximately 1 mg/ml)

were mixed with 200 μL of 2M TFA to make the test sample. All tubes were vortexed for 10 sec, and centrifuge for 10 sec, followed by incubation at 95° C. for 6 hours. After the hydrolysis step the samples were places at −20° C. for 10 min to cool down. Samples were spun down for 10 sec and evaporated to dryness in SpeedVac.

Derivatization: Samples were reconstituted with 100 μL of HPLC grade water and were equilibrated 55° C., followed by addition of 10 μL of Derivatization solution I, a brief mix, and addition of 5 μL of Derivatization solution II. Samples were loaded in a pre-warmed centrifuge and incubated for 3 hours at 55° C. while centrifuging at 2000 rpm.

Figure 30:
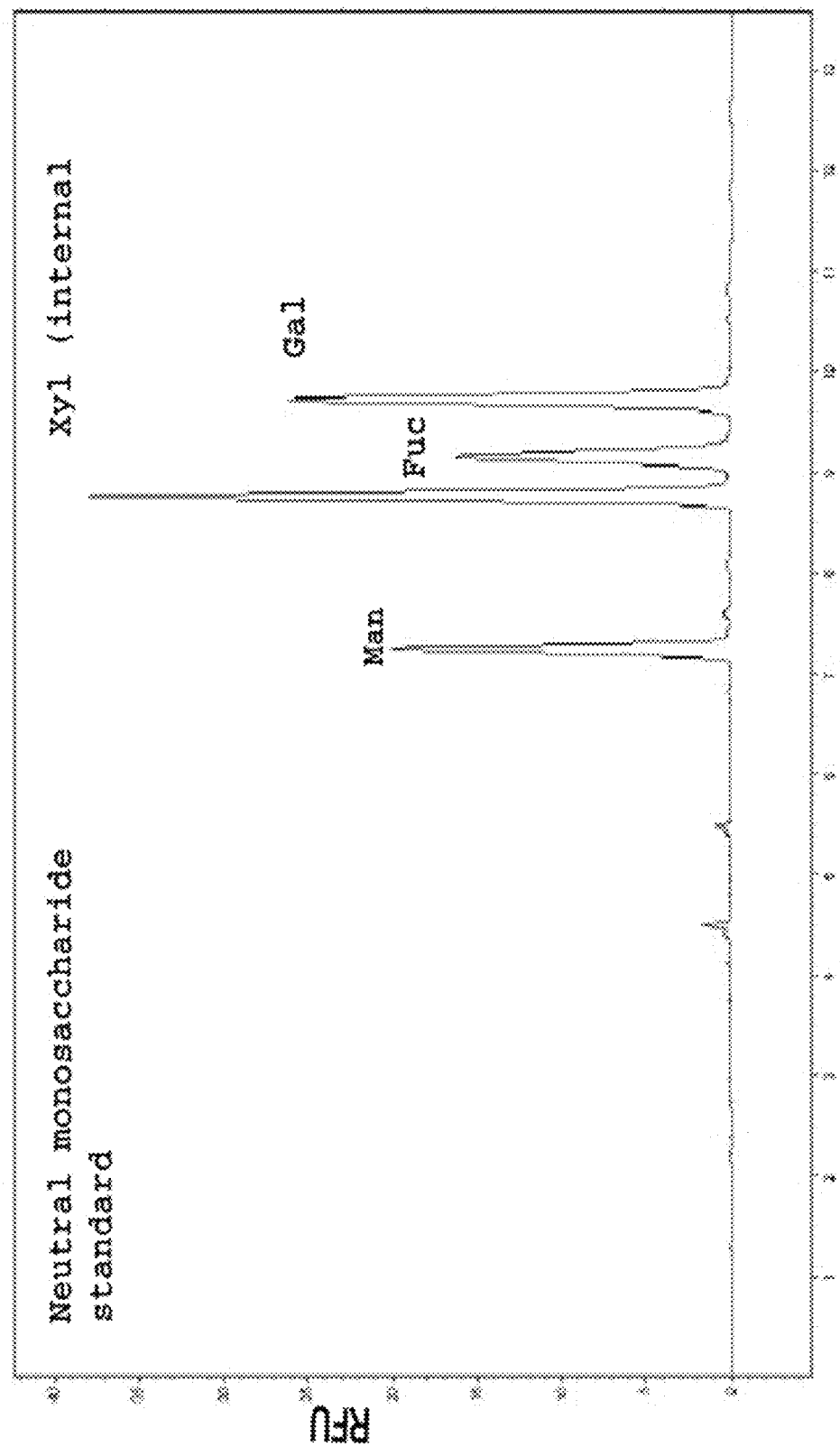
FIG. 30 shows an electropherogram of system suitability neutral monosaccharides depicted as relative fluorescence units (RFU) versus time (min).

CE injection: The final volume of the samples after derivatization was brought to 100 μL by addition of HPLC grade water, and 10 μL of samples were transferred to a CE micro vial with 190 μL HPLC grade water. Before sample injections the CE cartridge was rinsed extensively with HPLC grade water (1-3 min run time), followed by an equilibrating rinse with running buffer (5 min run time). Following the initial rinse, monosaccharide standards and samples for analysis were injected in the CE cartridge (15 min run time). Following the injection run of each standard or test sample, the CE cartridge was rinsed and equilibrated with HPLC grade water and running buffer. The electopherogarpm of the system suitability should be similar to FIG. 30.

Calculations: Calculating peak area ratio of Man, Gal and Fuc relative to internal standard Xylose.

Peak area ratio=monosaccharide peak area (Gal, Fuc or Man)/Xylose peak area, wherein the relative standard deviation (RSD) for the peak area ratio is equal or less that 10%.

Calculating ratio of monosaccharide (for example Man) to CTLA4-Ig protein:

$$\text{Ratio}_{Man} = (A_{Man} \times A_{XylO} \times V_{ManO} \times C_{ManO} \times MW_{CTLA4\text{-}Ig\ dimer})/(A_{Xyl} \times A_{ManO} \times Vp \times Cp \times MW_{Man})$$

$\text{Ratio}_{Man}$=molar ratio of Man versus protein
$A_{Man}$=peak area (μV.sec) in Man in sample
$A_{Xyl}$=peak area (μV.sec) in Xyl in sample
$A_{XylO}$=peak area (μV.sec) average of Xyl in monosaccharide standard
$A_{ManO}$=peak area (μV.sec) average of Man in monosaccharide standard
$V_{ManO}$=volume of Mannose contained in monosacchride working solution used for hydrolysis (in μL)
$C_{ManO}$=concentration of Mannose contained in monosacchride working solution used for hydrolysis (in mg/ml)
Vp=volume of protein sample used for hydrolysis (in μL)
Cp=concentration of protein sample used for hydrolysis (in mg/ml)
$MW_{CTLA4\text{-}Ig}$=Molecular weight of CTLA4-Ig dimer
$MW_{Man}$=180.2 daltons.

TABLE 19

Average Molar Ratio of Monosaccharide to CTLA4-Ig molecules or dimer

| MONOSACCHARIDE | RANGE |
|---|---|
| Mannose | 10-20 |
| Fucose | 4.2-7.0 |
| Galactose | 9.2-17 |

Example 19: Production of CTLA4$^{A29YL104E}$-Ig

CTLA4$^{A29YL104E}$-Ig is a genetically engineered fusion protein, which consists of the functional binding domain of modified human CTLA-4 and the Fc domain of human immunoglobulin of the IgG1 class. Two amino acid substitutions were made in the B7 binding region of the CTLA-4 domain (L104E and A29Y) to generate this molecule. It is is comprised of two glycosylated polypeptide chains of 357 amino acids each. It exists as covalent dimer linked through an inter-chain disulfide bond. $CTLA4^{A29YL104E}$-Ig has an average mass of approximately 91,800 Da as determined by matrix-assisted laser desorption-ionization time-of-flight (MALDI-TOF) mass spectrometry.

$CTLA4^{A29YL104E}$-Ig is a modified form of CTLA4-Ig. The modification consists of point mutations that result in two amino acid substitutions (L104E and A29Y). Relative to CTLA4-Ig, $CTLA4^{A29YL104E}$-Ig binds CD80 (B7-1) with ~2-fold increased avidity, and binds CD86 (B7-2) with ~4-fold increased avidity. $CTLA4^{A29YL104E}$-Ig is approximately 10-fold more effective than abatacept at inhibiting T cell proliferation, cytokine production, and CD28-dependent killing of target cells by natural killer cells. $CTLA4^{A29YL104E}$-Ig causes modest inhibition of B7-1 mediated T cell proliferation but is markedly more potent at blocking B7-2 mediated T cell proliferation. This Example describes the production of $CTLA4^{A29YL104E}$-Ig molecules comprising SEQ ID NO:4. The methods described in this Example can be adapted and extended for the production of other recombinant proteins, including but not limited to, secreted proteins such as cytokines and other hormones, secreted proteins that are members of the Ig superfamily or comprise a portion of an Ig superfamily protein, and generally any protein expressed in CHO cells.

A process flow diagram for the $CTLA4^{A29YL104E}$-Ig culturing steps is shown in FIG. 23. $CTLA4^{A29YL104E}$-Ig is produced in 5000-L production bioreactors with an approximate working volume of 4000 L. One batch of drug substance is produced from a single production bioreactor derived from a single vial from a cell bank. The production process involves three-stages consisting of inoculum expansion, production cell culture and downstream purification. The inoculum expansion stage is conducted using animal component-free medium. The production cell culture stage is also performed in animal component-free medium with the exception of the use of D-galactose.

Cell Culture Media.

All media are prepared in clean medium vessels of the appropriate size and sterilized by filtration. The composition of the medium utilized for inoculum expansion is presented in the Table below.

Inoculum Cell Growth Basal Medium

| Component | Concentration |
|---|---|
| CD-CHO, 25x Concentrate Acid Solubles I | 40 mL/L |
| CD-CHO, 25x Concentrate Acid Solubles II | 40 mL/L |
| CD-CHO, 25x Concentrate Salts I | 40 mL/L |
| CD-CHO, 25x Concentrate Salts II | 40 mL/L |
| L-glutamine | 0.88 g/L |
| Sodium Bicarbonate | 2.22 g/L |
| Recombinant Human Insulin (10 mg/mL) | 0.1 mL/L |
| Methotrexate (20 mM) | 0.05 mL/L |

| Seed and Production Bioreactor Cell Growth Basal Medium | |
| --- | --- |
| Component | Concentration |
| CD-CHO, 25x Concentrate Acid Solubles I | 40 mL/L |
| CD-CHO, 25x Concentrate Acid Solubles II | 40 mL/L |
| CD-CHO, 25x Concentrate Salts I | 40 mL/L |
| CD-CHO, 25x Concentrate Salts II | 40 mL/L |
| L-glutamine | 1.32 g/L |
| Sodium Bicarbonate | 2.22 g/L |
| Recombinant Human Insulin (10 mg/mL) | 0.1 mL/L |

| Production Bioreactor Feed Medium | |
| --- | --- |
| Component | Concentration |
| eRDF powder$^a$ | 25.2 g/L |
| Dextrose | 30.9 g/L |
| D-galactose | 12.5 g/L |
| L-glutamine | 4.1 g/L |
| Recombinant Human Insulin (10 mg/mL) | 1.0 mL/L |
| Dextran Sulfate (added as bolus feed) | 50 mg/L |

Inoculum Expansion

A frozen vial from the cell bank is thawed at a controlled temperature and centrifuged to remove the cryoprotectant media. The cells are resuspended in inoculum medium and recovered in a T-flask. A minimum cell viability after thaw of 80% is an exemplary value. Temperature and carbon dioxide are controlled during the T-flask incubation step. The T-flask is incubated until a viable cell number of $1.0 \times 10^7$ cells is obtained, and the contents are transferred into a shake flask. The culture is expanded through a series of shake flasks to achieve the required inoculum volume. The seeding density range for the shake flask passages is 1.0 to $3.0 \times 10^5$ viable cells/mL. Temperature, carbon dioxide, and shaker speed are controlled during the shake flask incubation steps. The shake flask cultures are pooled into a sterile inoculum transfer vessel upon reaching a viable cell density range of 1.5 to $3.0 \times 10^6$ cells/mL. Approximately 20 liters from the final shake flask inoculum expansion step is transferred to the 140-L seed bioreactor to achieve an initial cell density range of 0.2 to $1.0 \times 10^6$ viable cells/mL.

Seed Bioreactor Operation

A 140-L seed bioreactor with a working volume of approximately 90 liters is operated in batch mode. The temperature, pH, pressure, and dissolved oxygen concentration in the 140-L seed bioreactor are monitored and controlled using a distributed control system (DCS). Samples are obtained daily from the 140-L seed bioreactor to monitor cell growth. The seeding density range of the 140-L seed bioreactor is 0.2 to $1.0 \times 10^6$ viable cells/mL. The 140-L seed bioreactor culture is used to inoculate a 1100-L seed bioreactor when a viable cell density of $0.5 \times 10^6$ cells/mL is achieved. The duration of the 140-L seed bioreactor step is approximately 3 days. The initial target viable cell density in the 1100-L seed bioreactor is 0.4 to $1.5 \times 10^6$ viable cells/mL.

The 1100-L seed bioreactor contains an initial culture volume of 260 liters. The 1100-L seed bioreactor is operated in batch mode. The temperature, pH, pressure, and dissolved oxygen concentration in the 1100-L seed bioreactor are monitored and controlled using a DCS. The volume of the culture is increased to 900 liters with basal medium when the viable cell density has reached $\geq 1.5 \times 10^6$ cells/mL. Samples are obtained daily from the 1100-L seed bioreactor to monitor cell growth. The 1100-L seed bioreactor culture is used to inoculate a 5000-L production bioreactor when a viable cell density of $\geq 2.0 \times 10^6$ cells/mL is achieved. The duration of the 1100-L seed bioreactor step is approximately 4 days. The initial target viable cell density in the 5000-L production bioreactor is 0.4 to $1.5 \times 10^6$ viable cells/mL.

Production Bioreactor Operation

The 5000-L production bioreactor contains an initial culture volume of 3000 liters. The 5000-L production bioreactor is operated in fed-batch mode with temperature, pH, pressure, and dissolved oxygen concentration monitored and controlled using a DCS. A bolus of dextran sulfate is added to the culture at approximately 72 hours. During the operation of the production bioreactor, the culture temperature setpoint is shifted from 37° to 34° C. at 144±8 hours. The temperature shift and the dextran sulfate addition are performed to prolong the duration of high cell viability in the 5000-L production bioreactor step. Samples are obtained from the bioreactor to monitor cell growth and viability, glucose, lactate and ammonia concentration. The samples are also tested for CTLA4$^{A29YL104E}$-Ig concentration and sialic acid to CTLA4$^{A29YL104E}$-Ig protein molar ratio. The feed medium is added to the bioreactor to maintain a desired glucose concentration. The primary harvest criterion for the production bioreactor is the sialic acid to CTLA4$^{A29YL104E}$-Ig protein molar ratio. The production bioreactor is harvested at a target sialic acid to CTLA4$^{A29YL104E}$-Ig protein molar ratio of The duration of the 5000-L production bioreactor step is approximately 14 days. The harvest volume of the 5000-L production bioreactor is approximately 4000 liters.

Cell Removal and Product Concentration

Cells are removed from the culture broth by tangential flow microfiltration using 0.65 μm membranes. The microfiltration permeate is concentrated by tangential flow ultrafiltration using 30 kDa nominal molecular weight cutoff (NMWCO) membranes. Transmembrane pressure and flow rates are controlled during the microfiltration and ultrafiltration steps. The concentrate is then passed through a series of membrane filters, with a final filtration through a 0.2 μm single-use filter. The pH of the concentrate is adjusted to 8.0 by the addition of a 0.5 M Tris solution. The microfiltration and ultrafiltration filters are multi-use. The microfiltration filters are cleaned with sodium hypochlorite and Triton X-100 and stored in phosphoric acid. The ultrafiltration filters are cleaned with sodium hypochlorite and sodium hydroxide and then stored in sodium hydroxide.

Example 20: Purification of Recombinant CTLA4$^{A29YL104E}$-Ig

Example 20-A

An example of a purification process of CTLA4$^{A29YL104E}$-Ig is shown in the flow diagram in FIG. 89. A description of a purification process is provided by this example.

Viral Inactivation

The pH of the clarified concentrated harvest material is adjusted to 8.0 by the addition of a 0.5 M Tris solution. Potential adventitious viral agents are inactivated by the addition of 20% Triton X-100 to a final concentration of 0.5% (v/v). The Triton X-100-treated protein solution is mixed for 2 hours.

Affinity Chromatography

Affinity chromatography using a column of MabSelect Protein A resin (GE Healthcare, formerly known as Amersham Biosciences) is used to capture the CTLA4$^{A29YL104E}$-

Ig protein from the in-process material from the viral inactivation step and to separate the belatacept protein from the majority of impurities.

The MabSelect Protein A column is equilibrated with a 25 mM NaH$_2$PO$_4$, 150 mM NaCl, pH 7.5 buffer. The dynamic binding capacity of the affinity resin is 25 g of CTLA4$^{429YL104E}$-Ig protein per liter of resin at a linear velocity of 350 cm/hour. The 157-L column bed is capable of binding approximately 3.9 kg of CTLA4$^{429YL104E}$-Ig protein.

The Triton X-100-treated in-process material is applied to the Mab Select Protein A column, and the column is washed with a minimum of 3 column volumes (CV) of equilibration buffer to remove weakly retained impurities. These impurities include the cytokine monocyte chemotactic protein-1 (MCP-1) and Triton X-100. The CTLA4$^{A29YL104E}$-Ig protein is then eluted from the column with a 250 mM glycine, pH 3.0 buffer. The CTLA4$^{A29YL104E}$-Ig protein elutes as a narrow peak in approximately 2 to 3 CV of elution buffer and is collected into a tank containing 2 M HEPES, pH 7.5 buffer in order to increase the pH rapidly and thereby minimize the formation of belatacept high molecular weight (HMW) species.

Anion Exchange Chromatography

Anion exchange chromatography using Q-Sepharose Fast Flow (QFF) resin (GE Healthcare) is used primarily to enrich the amount of more highly sialylated species of the CTLA4$^{A29YL104E}$-Ig protein. The pH-adjusted belatacept product pool from the MabSelect Protein A column is diluted approximately two-fold with water for injection (WFI) prior to application to the QFF column.

The QFF column is equilibrated with a 50 mM HEPES, 50 mM NaCl, pH 7.0 buffer. The pH- and conductivity-adjusted MabSelect Protein A step product pool is applied to the QFF column, and the column is washed with a minimum of 3 CV of equilibration buffer to remove weakly bound impurities. The column is then washed with 50 mM HEPES, 140 mM NaCl, pH 7.0 buffer, to remove CTLA4$^{A29YL104E}$-Ig protein species with low sialic acid content. The more highly sialylated species of the CTLA4$^{A29YL104E}$-Ig protein are subsequently eluted from the column using 5 CV of 50 mM HEPES, 200 mM NaCl, pH 7.0 buffer.

Hydrophobic Interaction Chromatography

Hydrophobic interaction chromatography (HIC) using Toyopearl Phenyl 650M resin (Tosoh Biosciences) is used primarily to reduce the amount of CTLA4$^{A29YL104E}$-Ig HMW species in the product pool from the QFF chromatography step. Prior to application to the HIC column, the QFF chromatography step product pool is diluted using 50 mM HEPES, pH 7.0 buffer and 50 mM HEPES, 3.6 M ammonium sulfate, pH 7.0 buffer to achieve a conductivity of approximately 135 mS/cm and a CTLA4$^{A29YL104E}$-Ig concentration of ≤1 g/L in the QFF product pool.

The HIC column is equilibrated with a 50 mM HEPES, 1.2 M ammonium sulfate, pH 7.0 buffer. The concentration- and conductivity-adjusted CTLA4$^{A29YL104E}$-Ig QFF chromatography step product pool is applied to the column. The column is then washed with a 50 mM HEPES, 1.2 M ammonium sulfate, pH 7.0 buffer to remove weakly bound impurities. The CTLA4$^{A29YL104E}$-Ig protein is eluted from the HIC column using a 50 mM HEPES, 0.55 M ammonium sulfate, pH 7.0 buffer.

Viral Filtration

Concentration and diafiltration of the CTLA4$^{A29YL104E}$-Ig product pool from the HIC step is achieved by ultrafiltration (UF). The UF step utilizes a 30-kDa NMWCO membrane and a 25 mM $NaH_2PO_4$, 10 mM NaCl, pH 7.5 buffer. The UF step is followed by a viral filtration step using a 15-nm Planova membrane (Asahi Kasei). The CTLA4$^{A29YL104E}$-Ig protein product pool is then adjusted to a protein concentration of 25 g/L by UF using a 30-kDa NMWCO membrane.

Column Sanitization and Storage

The Mab Select Protein A chromatography column is sanitized using 0.1 N NaOH solution, washed with 25 mM $NaH_2PO_4$, 150 mM NaCl, pH 7.5 buffer to lower the pH, and then stored in 20% ethanol at 2° to 8° C. The QFF chromatography column is sanitized with 1 N NaOH solution and stored in 0.1 N NaOH solution at room temperature. The HIC column is sanitized with 0.1 N NaOH solution, washed with 20% ethanol, and stored in 20% ethanol at room temperature.

Example 20-B: A Further Example of Such Purification Method Follows

Viral Inactivation

The pH of the clarified concentrated harvest material is adjusted to 8.0 by the addition of a 0.5 M Tris solution. Potential adventitious viral agents are inactivated by the addition of 20% Triton X-100 to a final concentration of 0.5% (v/v). The Triton X-100-treated protein solution is mixed for 2 hours.

Protein A Affinity Chromatography for CTLA4$^{A29YL104E}$-Ig Purification:

Affinity chromatography using a column of Mab Select Protein A resin (GE Healthcare, formerly known as Amersham Biosciences) is used to capture CTLA4$^{A29YL104E}$-Ig from the in-process material from the viral inactivation step and to separate CTLA4$^{A29YL104E}$-Ig from the majority of impurities.

A 140 cm inner diameter column is packed with MabSelect PrA resin to a height of 18 to 25 cm, representing a volume of about 339 to 372 L. The column is qualified for use by determining HETP and $A_s$ of the packed column. A HETP of 0.02 to 0.08 cm and an $A_s$ of 0.8 to 1.2 are employed for qualification of the column.

The MabSelect PrA column operation is carried out at ambient temperature. The viral inactivation product pool is loaded onto the equilibrated MabSelect PrA column. The MabSelect PrA step is operated at a maximum flow rate of 26.7 L/min and an operating pressure of ≤13 psig. The maximum CTLA4$^{A29YL104E}$-Ig protein load applied to the MabSelect PrA column is 25 g of CTLA4$^{A29YL104E}$-Ig protein per liter of resin at a linear velocity of 350 cm/hour. The column bed is capable of binding approximately 3.9 kg of CTLA4$^{A29YL104E}$-Ig protein.

The MabSelect PrA column is equilibrated with a 25 mM $NaH_2PO_4$, 150 mM NaCl, pH 7.5 buffer. Equilibration is complete when a minimum of 3 CV of equilibration buffer have been passed through the column and the pH and conductivity values of the effluent are between 7.3 to 7.7 and 14.5 to 17.5 mS/cm, respectively.

The Triton X-100-treated in-process material is applied to the equilibrated MabSelect PrA column. The column is washed with a minimum of 3 CV of a 25 mM $NaH_2PO_4$, 150 mM NaCl, 0.5% Triton X-100, pH 7.5 buffer to remove weakly retained impurities from the Mab Select PrA column. These impurities include the cytokine monocyte chemotactic protein-1 (MCP-1) and Triton X-100. Subsequent wash steps are performed using a 25 mM $NaH_2PO_4$, 150 mM NaCl, pH 7.5 buffer to remove the residual Triton X-100 from the Mab Select PrA column.

The CTLA4$^{A29YL104E}$-Ig is eluted from the MabSelect PrA chromatography column with a 250 mM glycine, pH 3.0 buffer. The eluate is diverted into a collection vessel when the $A_{280}$ increases to 0.2 AU above the baseline. The column effluent is filtered through a 0.2 μm cellulose acetate filter into a collection vessel equipped with an agitator. The eluate is collected until the A280 of the trailing edge of the elution peak decreases to a value of ≤0.2 AU. The CTLA4$^{A29YL104E}$-Ig elutes as a narrow peak in approximately 2 to 3 CV of elution buffer. The pH of the eluate pool is adjusted to pH 7.5±0.2 with a 2 M HEPES, pH 7.5 buffer in order to increase the pH rapidly and thereby minimize the formation of CTLA4$^{A29YL104E}$-Ig high molecular weight (HMW) species. The MabSelect PrA chromatography step product pool is held at ambient temperature for a maximum of 5 days. The product pool may be cooled for storage; the stability profile of the CTLA4$^{A29YL104E}$-Ig was the same at 5° C. and 22° C. The product may be stored for up to 5 days.

A CTLA4$^{A29YL104E}$-Ig dimer product with a molar ratio of moles sialic acid to moles CTLA4$^{A29YL104E}$-Ig protein that is about 6, or from about 5.2 to about 7.6, is collected.

QFF Anion Exchange Chromatography for CTLA4$^{A29YL104E}$-Ig Purification:

Anion exchange chromatography using Q-Sepharose Fast Flow (QFF) resin (GE Healthcare) is used primarily to enrich the amount of more highly sialylated species of the CTLA4$^{A29YL104E}$-Ig as well as reduce the residual Protein A levels. The pH-adjusted CTLA4$^{A29YL104E}$-Ig product pool from the MabSelect Protein A column is diluted approximately two-fold with water for injection (WFI) prior to application to the QFF column.

A 80 cm inner diameter column is packed with QFF resin to a height of 27 to 35 cm, representing a volume of about 136 to 176 L. The column is qualified for use by determining the HETP and $A_s$ of the packed column. A HETP of 0.02 to 0.08 cm and an asymmetry ($A_s$) of 0.8 to 1.2 are employed for qualification of the column.

The QFF column operation is carried out at ambient temperature. The QFF column is equilibrated with a 50 mM HEPES, 50 mM NaCl, pH 7.0 buffer. The pH- and conductivity-adjusted MabSelect Protein A step product pool is applied to the QFF column. The QFF step is operated at a maximum flow rate of 16.4 L/min (196 cm/h) and a maximum operating pressure of 35 psi.

The column is sanitized both prior to and following use with a 1 N NaOH solution. A minimum of 2 column volumes of the sodium hydroxide solution is passed over the column. The column is then held static for 60 to 120 minutes. The acceptable conductivity range for the solution and the column effluent is 136 to 202 mS/cm.

The column is equilibrated with a minimum of 5 column volumes of a 50 mM HEPES, 50 mM sodium chloride, pH 7.0 buffer. The pH and conductivity ranges for this buffer are 6.8 to 7.2 and 5.0 to 7.0 mS/cm, respectively. These ranges are also used to determine whether the column is equilibrated.

The pH- and conductivity-adjusted MabSelect Protein A step product pool is applied to the QFF column, and the column is washed with a minimum of 3 CV of equilibration buffer to remove weakly bound impurities. The column is then washed with 50 mM HEPES, 135 mM NaCl, pH 7.0 buffer, to remove CTLA4$^{A29YL104E}$-Ig species with low sialic acid content.

The more highly sialylated species of the CTLA4$^{A29YL104E}$-Ig are eluted from the QFF chromatography column using a 50 mM HEPES, 200 mM NaCl, pH 7.0 buffer. The eluate collection is initiated when the elution buffer is first applied to the column. During elution, the column effluent is filtered through a 0.2 μm filter into the collection vessel. The eluate is collected until the absorbance of the trailing edge of the elution peak decreases to ≤0.2 AU above the baseline. The CTLA4$^{A29YL104E}$-Ig elutes from the column using ≤5 CV of 50 mM HEPES, 200 mM NaCl, pH 7.0 buffer. The collection vessel is then cooled to 2° to 8° C. The maximum hold time for the QFF chromatography step product pool at 2° to 8° C. is 3 days.

A CTLA4$^{A29YL104E}$-Ig dimer product with a molar ratio of moles sialic acid to moles CTLA4$^{A29YL104E}$-Ig protein that is about 6, or from about 5.2 to about 7.6 is collected.

Phenyl Sepharose FF HIC for CTLA4$^{A29YL104E}$-Ig Purification:

Hydrophobic interaction chromatography (HIC) using Toyopearl Phenyl 650M resin (Tosoh Biosciences) is used primarily to reduce the amount of CTLA4$^{A29YL104E}$-Ig HMW species in the product pool from the QFF chromatography step.

A 100 cm inner diameter column is packed with Phenyl Sepharose Phenyl 650M resin to a height of 18 to 22 cm, representing a volume of about 141 to 173 L. The column is qualified for use by determining the HETP and $A_s$ of the packed column. A HETP of 0.02 to 0.08 cm and an $A_s$ of 0.8 to 1.2 are employed for qualification of the HIC column.

The HIC column operation is carried out at ambient temperature. Prior to application to the HIC column, the QFF chromatography step product pool is diluted using 50 mM HEPES, pH 7.0 buffer and 50 mM HEPES, 3.6 M ammonium sulfate, pH 7.0 buffer to achieve a conductivity of approximately 135 mS/cm and a CTLA4$^{A29YL104E}$-Ig concentration of ≤1 g/L in the QFF product pool. The HIC step is operated at a maximum flow rate of 22.7 L/min (173 cm/h) and at a maximum operating pressure of 45 psi. Multiple cycles of the HIC step can be employed based on the amount of CTLA4$^{A29YL104E}$-Ig present in the QXL eluate pool.

The HIC column is first sanitized with a 1 N sodium hydroxide solution. The sanitization is complete when 2 to 4 CV of the 1 N sodium hydroxide solution have been passed through the column. The column is then held for 60 to 120 minutes to ensure sanitization.

After the sanitization step, the HIC column is equilibrated with a 50 mM HEPES, 1.2 M ammonium sulfate, pH 7.0 buffer. The equilibration is complete when a minimum of 3 CV of equilibration buffer have been passed through the column and the pH of the effluent is 7.0±0.3 and the conductivity of approximately 135 mS/cm.

The concentration- and conductivity-adjusted CTLA4$^{A29YL104E}$-Ig QFF chromatography step product pool is applied to the column. The column is then washed with a 50 mM HEPES, 1.2 M ammonium sulfate, pH 7.0 buffer to remove weakly bound impurities. The CTLA4$^{A29YL104E}$-Ig is eluted from the HIC column using a 50 mM HEPES, 0.55 M ammonium sulfate, pH 7.0 buffer. This HIC product pool is held in the collection vessel at 2° to 8° C. The maximum hold time in the collection vessel is 3 days.

A CTLA4$^{A29YL104E}$-Ig dimer product with a molar ratio of moles sialic acid to moles CTLA4$^{A29YL104E}$-Ig protein that is about 6, or from about 5.2 to about 7.6; a pool of CTLA4$^{A29YL104E}$-Ig high molecular weight material is present at ≤2.5%; a pool of CTLA4$^{A29YL104E}$-Ig low molecular weight material (for example CTLA4$^{A29YL104E}$-Ig monomer) is present at ≤0.5%; and a pool of MCP-1≤9.5 ng/mL is present.

Viral Filtration.

Concentration and diafiltration of the CTLA4$^{A29YL104E}$-Ig product pool from the HIC step is achieved by ultrafiltration (UF). The UF step utilizes a 30-kDa NMWCO membrane and a 25 mM NaH$_2$PO$_4$, 10 mM NaCl, pH 7.5 buffer. The UF step is followed by a viral filtration step using a 15-nm Planova membrane (Asahi Kasei). The CTLA4$^{A29YL104E}$-Ig product pool is then adjusted to a protein concentration of 25 g/L by UF using a 30-kDa NMWCO membrane.

The Pall Filtron TFF system is used in the concentration and diafiltration step of the downstream CTLA4$^{A29YL104E}$-Ig production process. The objective of this step is to concentrate the HIC chromatography step product pool to 45 to 55 g/L and to exchange the elution buffer used in the HIC chromatography step with the final buffer used for CTLA4$^{A29YL104E}$-Ig compositions. The concentrated CTLA4$^{A29YL104E}$-Ig product pool is transferred through a 0.2 μm polyvinylidene fluoride filter and into a 50-L bioprocess bag.

Example 21: Biological Activity—Determination of Bio-Specific Binding of CTLA4A29YL104E-IG to the B-7Ig Co-Receptor by Surface Plasmon Resonance Surface Plasmon Resonance (B7 Binding)

This method measures the binding of CTLA4$^{A29YL104E}$-Ig to a representative B7 co-receptor by surface plasmon resonance. B7Ig is immobilized at high density via primary amino groups to the surface of an activated CM5 sensorchip. CTLA4$^{A29YL104E}$-Ig material, Quality Controls, and samples are diluted to concentrations between 0.125 and 8 ng/mL and injected over the B7Ig surface to generate binding sensorgrams. The initial rate (slope) of CTLA4$^{A29YL104E}$-Ig binding to immobilized B7Ig is measured under mass transfer (diffusion) limited conditions on this B7Ig surface. The initial binding rate in resonance units per second (RU/s) correlates directly with the active concentration. The binding rates of samples are converted into an active concentration using the reference standard curve where the binding rate of a CTLA4$^{A29YL104E}$-Ig material is plotted against concentration. The final results are either expressed as percent binding of sample relative to CTLA4$^{A29YL104E}$-Ig material.

Figure 6:
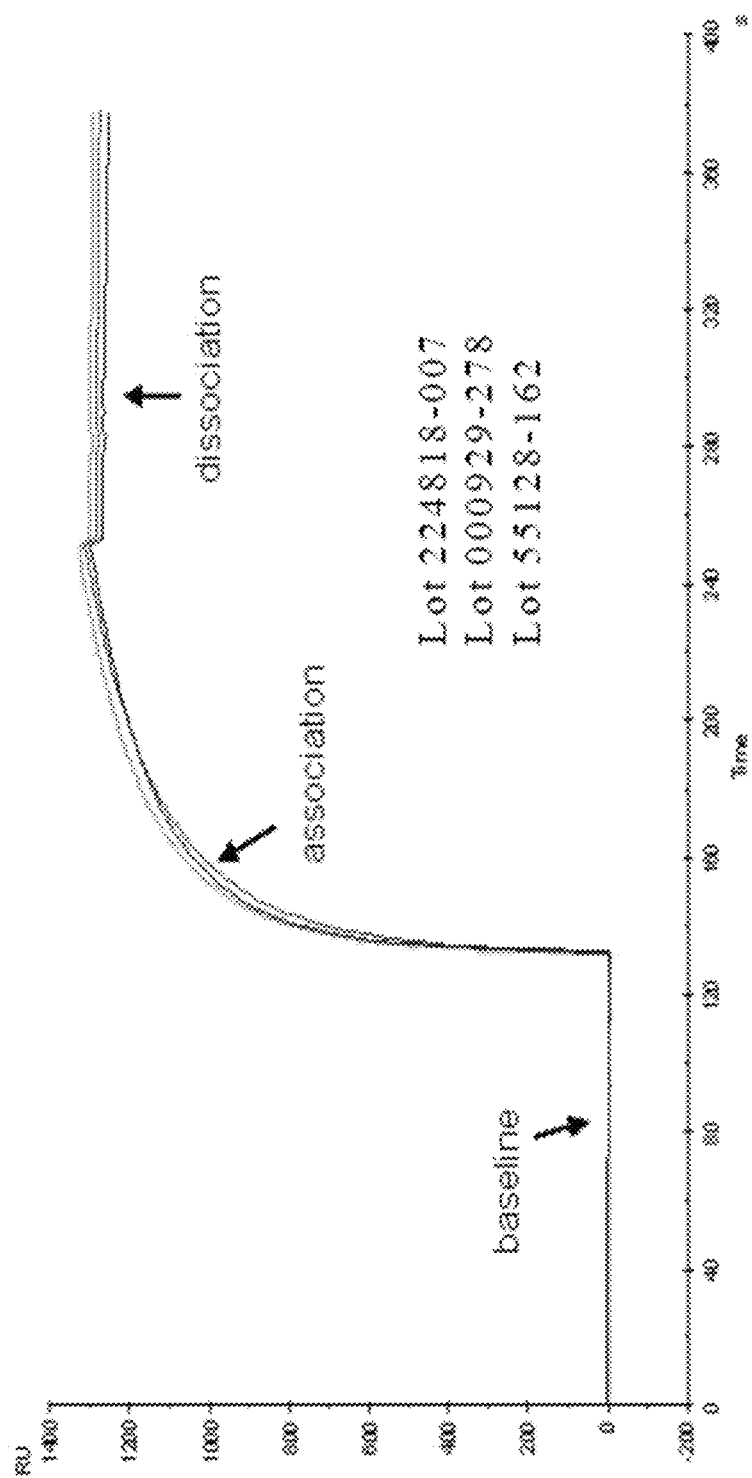
FIG. 6 is a graph depicting binding of CTLA4$^{A29YL104E}$-Ig samples to goat anti-human IgG Fc antibody. Binding of CTLA4$^{A29YL104E}$-Ig samples was detected by measuring the response obtained on this surface, compared to an unmodified sensorchip surface. The various lots represent three different CTLA4$^{A29YL104E}$-Ig samples.

The presence of the human IgG1 Fc region in CTLA4$^{A29YL104E}$-Ig was detected using surface plasmon resonance (SPR). SPR enables measurement of biospecific interactions in real time. An antibody fragment specific for the Fc region of human IgG (goat F$_{(ab')2}$ anti-human IgG Fc) was covalently immobilized on the surface of a sensorchip. Binding of CTLA4$^{A29YL104E}$-Ig samples was detected by measuring the response obtained on this surface, compared to an unmodified sensor chip surface. The results in resonance units bound for the Process B, Process C and the Co-mixture are comparable as shown in FIG. 6 and Table 23.

TABLE 23

Detection of Human IgG Fc in CTLA4$^{A29YL104E}$-Ig Drug Substance Lots Using SPR

| Lot No | RU bound to anti-Fc Antibody | RU bound to unmodified surface |
|---|---|---|
| Lot A | 1295 | 1 |
| Lot B | 1309 | 1 |
| Co-mixture | 1268 | 1 |

Human Cell IL 2 Inhibition Assay

The method is based on the inhibition of IL-2 production from T cells by CTLA4$^{A29YL104E}$-Ig when stimulated with anti-CD3 and B cells. Jurkat T cells, transfected with the luciferase gene under the control of the IL-2 promoter, are co-stimulated with Daudi B cells and anti-CD3 in the presence of various concentrations of CTLA4$^{A29YL104E}$-Ig. The co-stimulation activates the IL-2 promoter, which in turn produces luciferase protein. The resulting luminescent signal is measured using a luciferase assay system. In this system, CTLA4$^{A29YL104E}$-Ig produces a dose-dependent decrease in luciferase activity.

The results for the Process B Lot 000929-278, Process C Lot 224818-2004-007 and the co-mixture Lot 55128-162 are comparable as shown in Table 24. The EC$_{50}$ values, slope factors, and upper and lower asymptotes are similar for all three samples, within one standard deviation. This indicates that CTLA4$^{A29YL104E}$-Ig from the Process C and from the Process B behave comparably in the in vitro potency assay.

TABLE 24

Comparison of Human IL-2 Promoter Mediated Luciferase Activity in the In Vitro Potency Bioassay. Dose Response Curve Parameters for Processes of the Invention

| Lot No. | EC$_{50}$ (ng/mL) | Slope Factor | Upper Asymptote (CPS) | Lower Asymptote (CPS) |
|---|---|---|---|---|
| Process A | 19.1 ± 1.9 | −0.91 ± 0.06 | 85,000 ± 15,000 | 30,000 ± 6,000 |
| Co-mixture | 21.5 ± 2.7 | −0.93 ± 0.08 | 88,000 ± 16,000 | 29,000 ± 5,000 |
| Process B | 21.8 ± 1.4 | −0.91 ± 0.09 | 81,000 ± 17,000 | 27,000 ± 7,000 |

Materials:
Sensor Chip CMS, certified grade Biacore (Catalog No. BR-1000-13)
HBS-EP Buffer BIA Certified 10 mM HEPES pH 7.4, 150 mM NaCl, 3.4 mM EDTA, 0.005% v/v
Surfactant P20 Biacore (Catalog No. BR-1001-88)
Amine Coupling Kit BIA Certified 115 mg N-hydroxysuccinimide (NHS), 750 mg 1-ethyl-3-(3 dimethylaminopropyl) carbodiimde hydrochloride (EDC), 10.5 mL ethanolamine HCl Biacore (Catalog No. BR-1000-50)
Biacore C Instrument with a PC compatible computer Biacore, (Catalog No. BR-1100-51)
Biacore C Control Software Biacore, as provided with Biacore C instrument, version 1.0.1
Amine Coupling Kit BIA Certified: The kit contains one vial each: 115 mg NHS, 750 mg EDC, and 10.5 mL ethanolamine. Prepare each vial according to manufacturers directions. Aliquot 200 μL volumes of NHS and EDC solutions into individual plastic/glass vials of appropriate size and cap. These solutions are stable for 2 months when stored at −20° C. Aliquot 200 μL of Ethanolamine into individual plastic/glass vials of appropriate size and cap. This solution is stored at 2-8° C. and is stable according to manufacturer's directions.

To ensure good binding to the flow cell, a flow cell will be used for one week or 286 injections, which ever comes first. A new flow cell will be immobilized at the beginning of each week. Immobilization of B7.1 Ig in Preparation For Sample Testing. NOTE: Aliquot 200 μL of all solutions into 7 mm Biacore tubes for analysis. Thaw one vial containing B7.1 Ig at ambient temperature. Dilute B7.1 Ig using 10 mM Acetate pH 5.0 buffer (1.7) to achieve a surface mass of between 3000-9000 Resonance Units (RU). Thaw one vial (200 µL) each of EDC, and NHS to ambient temperature. Remove Ethanolamine HCl from the refrigerator and allow warming to room temperature. From the Biacore software: Open the published project "B7 Ig Immobilization" selected from the "Immobilization Wizard" Open the published file "B7 Immobilization." Step through the wizard and confirm or change selection by clicking "Next." Under "User Information" select flow cell and provide experimental information in the "Notebook" tab. Place reagent and ligand vials in sample rack as outlined. Review instructions. Save the template file as: B7 Immob BIOQC# Date Initials Chip # Flow cell #.blw. Start immobilization by clicking on "Start." Save result file as: B7 Immob BIOQC# Date Initial chip # flow cell #.blr. When the assay is finished, print the Wizard results and sensorgram.

Example 22: Carbohydrate Content Analysis of a CTLA4$^{A29YL104E}$-Ig Composition, Tryptic Peptide Mapping and IEF Tryptic Digest Peptide Mapping In this trypsin digest method, CTLA4$^{A29YL104E}$-Ig samples are denatured using guanidine-HCl, and reduced and alkylated using DTT and IAA. Samples are desalted using an NAP-5 column and digested with trypsin. The digestion mixture is separated by reversed phase (C18) chromatography and peaks are detected by UV absorbance at 215 nm.

Reagents:

Mobile Phase A solution (0.02% Trifluoroacetic Acid (TFA) in Water (v/v)); Mobile Phase B solution (0.02% TFA in 95 ACN (Acetonitrile) and 5% Water (v/v)); Alkylating Agent (200 mM Iodoacetamide (IAA)); Dilution Buffer (100 mM Tris, 25 mM NaCl, pH 8.0); Denaturing Buffer (8 M Guanidine, 50 mM TRIS, pH 8.0); Digestion Buffer (50 mM TRIS, 10 mM CaCl2, pH 8.0); Reducing Agent (100 mM DTT).

Instrumentation:

(equivalent instrumentation may be used) NAP-5 columns (Amersham, cat. #17-0853-02); HPLC Column Heater; Water's Alliance HPLC system with column heater and UV detector. An overview of this analysis is shown in FIG. 90.

Reduction and Alkylation:

Samples (for example, CTLA4$^{A29YL104E}$-Ig, etc.) were diluted to 10 mg/ml by adding water to a final volume of 100 µL (1 mg). 560 µl of denaturing buffer and 35 µL of Reducing Agent (100 mM DTT) were added to the 100 µl samples, were mixed, and spun down in a microcentrifuge for 3 seconds. Samples were then incubated at 50° C. for 20 minutes ±2 minutes. 35 µL of Alkylating Agent (200 mM IAA) was then added to each sample, and again were mixed, and spun down in a microcentrifuge for 3 seconds. Samples were then covered with aluminum foil and incubated at 50° C. for 20 min. ±2 minutes. After the NAP-5 columns were equilibrated by pouring 3 columns volumes (about 7-8 mL) of digestion buffer, 500 µl of the reduced and alkylated mixtures were poured over the NAP-5 columns, allowing the liquid to drain through column. Samples were then collected from the NAP-5 columns via eluting sample off of the column with 1 mL of digestion buffer.

Digestion:

Samples were digested with 20 µL of trypsin (0.5 µg/µL) in 38° C. water bath for 4 hours (±0.5 hr). Upon completion of digest, samples were acidified with 2.5 of TFA. Samples were then placed into autosampler vials for subsequent analysis.

Instrument Method:

The instrument method is shown below:

| Time (min) | Flow (mL/min) | Mobile Phase A | Mobile Phase B |
|---|---|---|---|
| 0 | 0.7 | 100 | 0 |
| 17 | 0.7 | 83 | 17 |
| 27 | 0.7 | 78 | 22 |
| 42 | 0.7 | 73 | 27 |
| 58 | 0.7 | 65 | 35 |
| 74 | 0.7 | 52 | 48 |
| 79 | 0.7 | 0 | 100 |
| 84 | 0.7 | 100 | 0 |
| 88 | 0.7 | 100 | 0 |

The column was equilibrated with 100% Mobile Phase A buffer for 25 minutes prior to the first injection. UV absorbance was monitored at 215 nm while column temperature was maintained at 37° C. and the autosampler temperature at 4° C. A mobile phase A buffer blank was run before the first system suitability standard, thereafter followed by a single 50 µL injection of each sample. A reference material injection should bracket every six sample injections.

Number of Theoretical Plates:

Column efficiency, evaluated as the number of theoretical plates, can be measured quantitatively using the retention time and the width of peak according to the Equation:

$$N = 16\left(\frac{t}{w}\right)^2$$

Where:

"w" is the peak width at the baseline measured by extrapolating the relatively straight sides to the baseline, "t" is the retention time of the peak measured from time of injection to time of elution of peak maximum.

If the N<50000, re-equilibrate the column.

Figure 31:
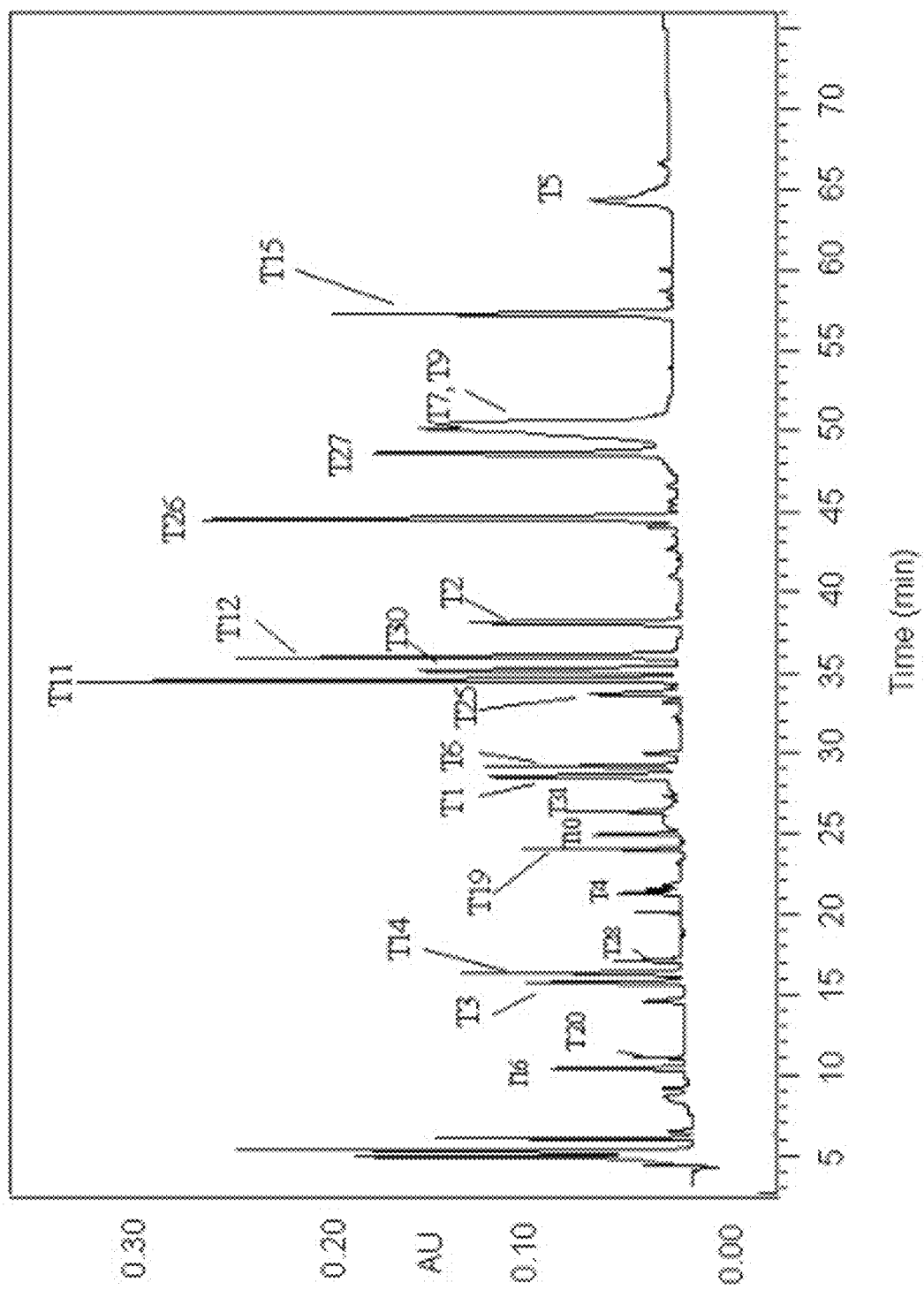
FIG. 31 represents a tryptic peptide map of CTLA4$^{A29YL104E}$-Ig with peptides labeled. Table 23 corresponds with the labeled peptides.
Figures 32A, 32B:
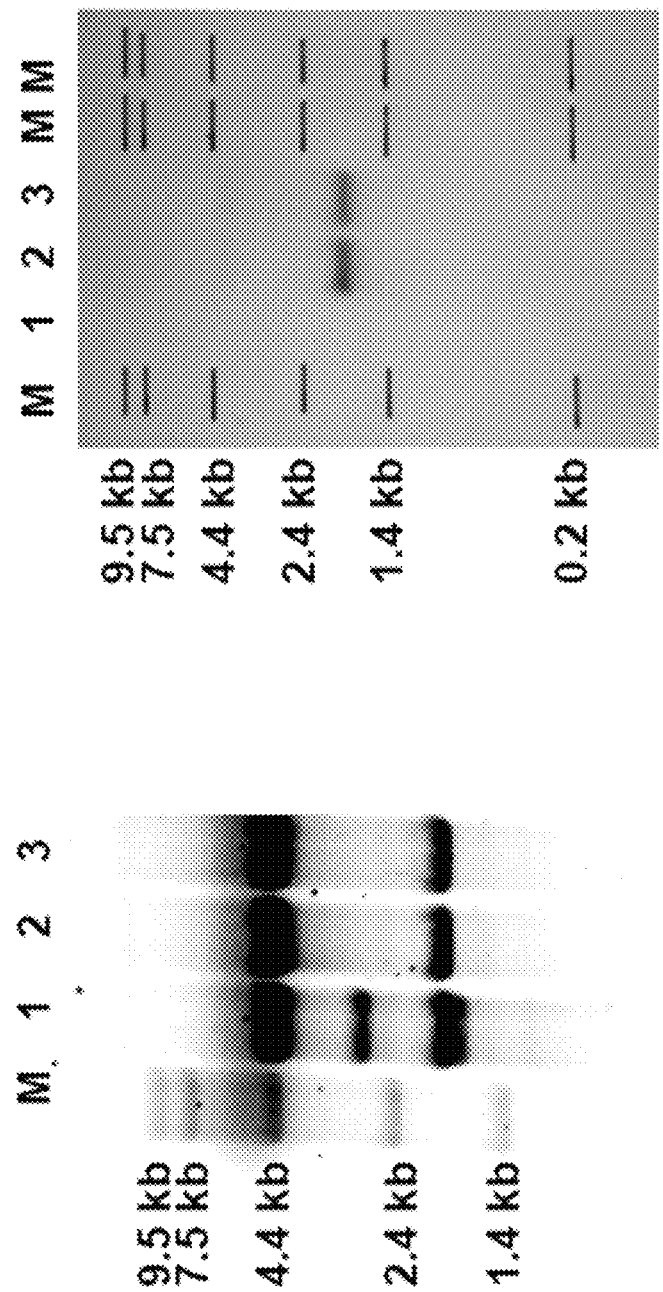
FIG. 32A-32B shows a Northern Hybridization Analysis of the CTLA4$^{A29YL104E}$-Ig. Panel A depicts an Ethidium bromide-stained agarose gel wherein Lane M is RNA marker; Lane 1 is total CHO RNA; Lane 2 is total MCB RNA; and Lane 3 is total EPCB RNA. Panel B is the corresponding autoradiogram wherein Lane M is RNA marker; Lane 1 is total CHO RNA; Lane 2 is total MCB RNA; and Lane 3 is total EPCB RNA.

Resolution:

Determine The resolution (R) between 2 peaks, for example peak T2 and peak T12 as indicated in FIG. 31, can be determined using the following equation:

$$R = \frac{2(t_2 - t_1)}{(w_1 + w_2)}$$

Where:

$t_1$, $t_2$=retention times of fragments peak T2 and peak T12, respectively $w_1$, $w_2$=tangent-defined peak width at baseline of the peaks with retention times ti and t2, respectively.

If R<1.5, the column should be re-equilibrate and if the problem persists, the column should be replaced.

FIG. 31 and Table 25 show the peptide fragments obtained from a trypsin digestion of CTLA4$^{A29YL104E}$-Ig. The region showing peptides T7 and T9 at ~50 minutes sometimes reflects incomplete sample digestion and peaks can show different qualities from day to day; however, within a run all samples show comparability.

TABLE 25

Tryptic Peptide Fragments of CTLA4$^{A29YL104E}$-Ig

| Fragment No. | Residue No. | Theoretical Mass | Observed Mass | Peptide Sequence |
|---|---|---|---|---|
| T1 | 1-14 | 1465.8 | 1464.8 | MHVAQPAVVLASSR |
| T2 | 15-28 | 1485.7 | 1484.8 | GIASFVCEYASPGK |
| T3 | 29-33 | 666.3 | 666.4 | YTEVR |
| T4 | 34-38 | 586.7 | 586.4 | VTVLR |
| T5[a] | 39-83[c] | 4900.4 | —[d] | QADSQVTEVCAATYMMGNELTFLDDSICTGTSSGNQVNLTIQGLR |
| T6 | 84-93 | 1171.4 | 1170.5 | AMDTGLYICK |
| T7[b] | 94-128[c] | 3983.5 | —[d] | VELMYPPPYYEGIGNGTQIYVIDPEPCPDSDQEPK |
| T8[b] | 129-132 | 435.4 | ND | SSDK |
| T9[b] | 133-158[c] | 3345.7 | —[d] | THTSPPSPAPELLGGSSVFLFPPKPK |
| T10 | 159-165 | 834.9 | 834.5 | DTLMISR |
| T11 | 166-184 | 2140.3 | 2138.5 | TPEVTCVVVDVSHEDPEVK |
| T12 | 185-198 | 1677.8 | 1677.8 | FNWYVDGVEVHNAK |
| T13 | 199-202 | 500.6 | 500.3 | TKPR |
| T14[a] | 203-211[c] | 1189.2 | —[d] | EEQYNSTYR |
| T15 | 212-227 | 1808.1 | 1808 | VVSVLTVLHQDWLNGK |
| T16 | 228-230 | 438.5 | 438.2 | EYK |
| T17 | 231-232 | 307.4 | ND | CK |
| T18 | 233-236 | 446.5 | ND | VSNK |
| T19 | 237-244 | 838.0 | 837.4 | ALPAPIEK |
| T20 | 245-248 | 447.5 | 447.2 | TISK |
| T21 | 249-250 | 217.2 | ND | AK |
| T22 | 251-254 | 456.5 | 456.3 | GQPR |
| T23 | 255-265 | 1286.4 | 1285.6 | EPQVYTLPPSR |
| T24 | 266-270 | 604.7 | 604.3 | DELTK |
| T25 | 271-280 | 1161.4 | 1160.7 | NQVSLTCLVK |
| T26 | 281-302 | 2544.7 | 2544 | GFYPSDIAVEWESNGQPENNYK |
| T27 | 303-319 | 1874.1 | 1873.9 | TTPPVLDSDGSFFLYSK |
| T28 | 320-324 | 574.7 | 574.3 | LTVDK |
| T29 | 325-326 | 261.28 | ND | SR |
| T30 | 327-349 | 2803.09 | 2802.1 | WQQGNVFSCSVMHEALHNHYTQK |
| T31 | 350-356 | 659.7 | 659.2 | SLSLSPG |
| T6 | 84-93 | 1171.4 | 1170.5 | AMDTGLYICK |
| T7[b] | 94-128[c] | 3983.5 | —[d] | VELMYPPPYYEGIGNGTQIYVIDPEPCPDSDQEPK |
| T8[b] | 129-132 | 435.4 | ND | SSDK |
| T9[b] | 133-158[c] | 3345.7 | —[d] | THTSPPSPAPELLGGSSVFLFPPKPK |
| T10 | 159-165 | 834.9 | 834.5 | DTLMISR |

TABLE 25-continued

Tryptic Peptide Fragments of CTLA4$^{A29YL104E}$-Ig

| Fragment No. | Residue No. | Theoretical Mass | Observed Mass | Peptide Sequence |
|---|---|---|---|---|
| T11 | 166-184 | 2140.3 | 2138.5 | TPEVTCVVVDVSHEDPEVK |
| T12 | 185-198 | 1677.8 | 1677.8 | FNWYVDGVEVHNAK |
| T13 | 199-202 | 500.6 | 500.3 | TKPR |
| T14[a] | 203-211[c] | 1189.2 | —[d] | EEQYNSTYR |
| T15 | 212-227 | 1808.1 | 1808 | VVSVLTVLHQDWLNGK |
| T16 | 228-230 | 438.5 | 438.2 | EYK |
| T17 | 231-232 | 307.4 | ND | CK |
| T18 | 233-236 | 446.5 | ND | VSNK |
| T19 | 237-244 | 838.0 | 837.4 | ALPAPIEK |
| T20 | 245-248 | 447.5 | 447.2 | TISK |
| T21 | 249-250 | 217.2 | ND | AK |
| T22 | 251-254 | 456.5 | 456.3 | GQPR |
| T23 | 255-265 | 1286.4 | 1285.6 | EPQVYTLPPSR |
| T24 | 266-270 | 604.7 | 604.3 | DELTK |
| T25 | 271-280 | 1161.4 | 1160.7 | NQVSLTCLVK |
| T26 | 281-302 | 2544.7 | 2544 | GFYPSDIAVEWESNGQPENNYK |
| T27 | 303-319 | 1874.1 | 1873.9 | TTPPVLDSDGSFFLYSK |
| T28 | 320-324 | 574.7 | 574.3 | LTVDK |
| T29 | 325-326 | 261.28 | ND | SR |
| T30 | 327-349 | 2803.09 | 2802.1 | WQQGNVFSCSVMHEALHNHYTQK |
| T31 | 350-356 | 659.7 | 659.2 | SLSLSPG |

[a]Peptides with N-linked carbohydrate
[b]Peptides with O-linked carbohydrate
[c]Masses for T5, T7, T9 and T14 are masses without the carbohydrate moieties
[d]A number of masses corresponding to glycosylated peptides were observed Isoelectric Focusing Isoelectric focusing (IEF) is used to evaluate the isoelectric points (pI) of the various isoforms of CTLA4$^{A29YL104E}$-Ig in both drug substance and drug product. This method uses Pharmacia Biotech Ampholine® PAGplates at pH gradient of 4.0-6.5 and a Multiphore II Flatbed Electrophoresis System. Samples (for example, CTLA4$^{A29YL104E}$-Ig, etc.) are diluted in Milli-Q water and loaded directly onto the gel using sample application strips. The gel is focused for 2.5 hours under increasing voltage using a 100 mM β-alanine soaked cathode strip and a 100 mM glutamic acid/500 mM phosphoric acid soaked anode strip. After focusing, the gel is fixed using sulfosalicylic acid/trichloroacetic acid and then stained using a Coomassie blue staining system. After staining, the wet gel is scanned into a digital image file using a laser-based densitometer at a 50 or 100 µm spatial resolution with up to 4096 levels of optical density resolution. CTLA4$^{A29YL104E}$-Ig focuses into 10 to 15 bands ranging from a pI of 4.5 to 5.5.

Isoelectric focusing of native CTLA4$^{A29YL104E}$-Ig on a gel (pH 4.0-6.5) generates a similar banding pattern in the pI range of 4.6-5.5 for the Process C Lot 224818-2004-007, Process B Lot 000929-287 and Co-mixture Lot 55128-162 as shown in FIG. 11. This procedure shows that Process B and C materials are comparable when analyzed on the same IEF gel.

Isoelectric focusing standards should be easily distinguished from background (See FIG. 11).

| Protein Standard | pI |
|---|---|
| Lentil Lectin | 8.65 |
|  | 8.45 |
| Horse Myoglobin | 7.35 |
|  | 6.85 |
| Conalbumin | 5.90 |
| Lactoglobulin | 5.20 |
| Soybean Trypsin Inhibitor | 4.55 |
| Amyloglucosidase | 3.50 |

CTLA4$^{A29YL104E}$-Ig is identified as multiple bands (>10) that have a pI range from about 4.5 to about 5.5 (FIG. 31).

CTLA4$^{A29YL104E}$-Ig is a second generation CTLA4-Ig fusion glycoprotein which consists of the modified ligand-binding domain of cytotoxic T lymphocyte antigen 4

(CTLA4) and the constant region of human IgG$_1$ heavy chain. This novel molecule has therapeutic application as an immunosuppressant. CTLA4$^{A29YL104E4}$g contains multiple charge isoforms which can be resolved by isoelectric focusing (IEF). An IEF method for the analysis of CTLA4$^{A29YL104E}$-Ig drug substance and drug product has been developed. This method is used to examine CTLA4A29YL104E-Ig in a AMPHOLINE® PAG plate pH 4.0–6.5 Multiphore II flatbed electrophoresis system. CTLA4$^{A29YL104E}$-Ig drug substance, drug product, and reference material are diluted in Milli-Q water and loaded directly onto the gel. The gel is focused for 2.5 hours under increasing voltage using a 100 mM β-alanine soaked cathode strip and a 100 mM glutamic acid/500 mM phosphoric acid soaked anode strip. After focusing, the gel is fixed and stained with Coomassie blue. The stained gel is scanned by laser densitometry and semi-quantitative analysis of gel bands is performed on the digital image file.

Materials:

| | |
|---|---|
| Ampholine PAG Plate Gel pH 4.0-6.5 | GE Healthcare (Cat No. 80-1124-81) |
| IEF Electrode Strips 6 × 280 mm | GE Healthcare (Cat No. 80-1004-40) |
| Sample Application pieces | GE Healthcare (Cat No. 80-1129-46) |

Equipment:

| | |
|---|---|
| Multiphor II Electrophoresis System | GE Healthcare (Cat No. 18-1018-06) |
| Cooling Plate 125 × 260 mm | GE Healthcare (Cat No. 80-1106-54) |
| Power Supply | NOVEX (Model Basic 3540) BioRad (Model PAC3000) |
| Thermostatic Circulator | VWR (Model 13271-074/ 1160S 1160A) |
| Orbital Shaker | IKA (Model KS250/260) |
| Personal Densitometer SI | GE Healthcare (Model 375) |
| ImageQuantTL Software | GE Healthcare |
| Reagent Preparation: | |

Anode Buffer Solution (100 mL): 0.1 M Glutamic Acid in 0.5 M Phosphoric Acid; 3.4 mL 85% Phosphoric Acid; 1.47±0.02 g Glutamic Acid; Milli-Q water. Add Glutamic Acid to 50 mL of Milli-Q water. Add 85% phosphoric acid and Q.S. to 100 mL, stir to mix. Assign an expiration date of 6 months and store at 4° C.

Cathode Buffer Solution (100 mL): 0.1 M β-Alanine, 0.9±0.02 g β-Alanine, Milli-Q water. Q.S. reagent to 100 mL with Milli-Q water, stir to mix. Assign an expiration date of 6 months and store at 4° C.

Fixing Solution (2000 mL): 3.5% 5-Sulfosalicylic Acid in 12% Trichloroacetic acid, 240±5.0 g Trichloroacetic Acid, 70±2.0 g 5-Sulfosalicylic Acid, Milli-Q water. Combine reagents and Q.S. to 2000 mL with Milli-Q water. Assign an expiration date of 3 months and store at room temperature.

Apparatus and Gel Preparation. Connect the Multiphore II electrophoresis unit's cooling platform to the Multi-Temp thermostatic circulator and set the temperature to 10° C. Allow the circulator to reach 10±2° C. Remove the gel from the refrigerator. Using a scissors, carefully cut along all four sides of the envelope making sure not to cut into the gel/gel support. Add approximately 1.0 mL of Milli-Q water to one edge of the cooling platform. Place one edge of the gel/gel support into the water so that the water moves across the entire edge of the gel. Carefully apply the gel across the cooling platform, avoiding the formation of air bubbles. Remove the transparent film from the surface of the gel. Soak each electrode strip with approximately 3.0 mL of the appropriate electrode solution (Table directly below). Apply the electrode strips approximately 10 mm from the top and bottom edges of the gel. Place the cathode strip closest to the (−) marks and the anode strip closest to the ☐☐ (+) marks on the cooling platform. After the electrode strips have been applied, cut the strips to fit the gel, avoiding contact with the gel support.

| Electrode Solutions and Electrophoresis Parameter Settings | | | | | | |
|---|---|---|---|---|---|---|
| pH Range | Anode Solution | Cathode Solution | Voltage (V) | Current (mA) | Power (W) | Time (h) |
| 4.0-6.5 | 0.1M Glutamic Acid in 0.5M H$_3$PO$_4$ | 0.1M β-Alanine | 2000 | 25 | 25 | 2.5 |

Apply the sample application pieces approximately 10 mm above the cathode strip. Using the electrophoresis parameters defined in the Table directly above, pre-focus the gel until the voltage reaches 300 V.

IEF pI Marker and Staining Control Preparation. Reconstitute the IEF p1 Marker with 100 μL of Milli-Q water. Reconstitute the Carbonic Anhydrase II staining control with 1000 μL Milli-Q water to make a 1.0 mg/mL stock solution. Add 10 μL of stock solution (1.0 mg/mL) to 90 μL Milli-Q water for a final loading concentration of 0.10 mg/mL.

Sample Preparation. Dilute the CTLA4$^{A29YL104E}$-Ig reference material and samples to a concentration of 2 mg/mL. Example: If the CTLA4$^{A29YL104E}$-Ig sample has a concentration of 25 mg/mL, use the following dilution to prepare the final loading concentration of 2 mg/mL:

10 μL (of 25 mg/mL)+115 μL Milli-Q water=2 mg/mL

NOTE: If the sample concentration is ≤2.0 mg/mL, then load the sample without dilution.

Gel Loading. Load gels to facilitate sample identification based on the running pattern. Do not load the gel symmetrically. Load the IEF pI marker, staining control, CTLA4$^{A29YL104E}$-Ig reference material, and CTLA4$^{A29YL104E}$-Ig samples as outlined in the Table directly below. Load all samples onto the sample application pieces.

| Gel Loading Pattern | | | | |
|---|---|---|---|---|
| Lane | Description | Loading Concentration (μg/μL) | Loading Volume (μL) | Protein Load (μg) |
| 1 | IEF pI Marker* | — | 10.0 | — |
| 2 | IEF pI Marker | — | 10.0 | — |
| 3 | CTLA4$^{A29YL104E}$-Ig Reference Material | 2.0 | 10.0 | 20 |
| 4 | Sample 1 | 2.0 | 10.0 | 20 |
| 5 | Staining Control | 0.10 | 10.0 | 1.0 |
| 6 | Sample 2 | 2.0 | 10.0 | 20 |
| 7 | CTLA4$^{A29YL104E}$-Ig Reference Material | 2.0 | 10.0 | 20 |
| 8 | IEF pI Marker | — | 10.0 | — |

*IEF pI marker load in Lane 1 is necessary to define gel orientation. Begin the loading pattern within lane 2 and repeat the loading pattern for additional samples. The IEF pI marker must be loaded at least every tenth lane (Example: MRS$_1$S$_2$S$_3$S$_4$S$_5$S$_6$RM; M—marker; R—reference material, S$_x$—sample).

Gel Processing. Place the electrode holder onto the Multiphor II unit and align the electrodes with the center of the electrode strips on the gel. Connect the two electrodes from the electrode holder to the base unit and place the safety lid in position. Using adhesive tape, cover the holes in the safety lid to prevent the gel from drying. Connect the electrodes to the power supply. Run the electrophoresis at the appropriate voltage, current, and power. When electrophoresis is complete, turn off the power supply and remove the safety cover and electrode holder. Carefully remove the electrode strips and the sample application pieces from the gel. Remove the entire gel and gel support from the cooling plate and place in a 280×180×40 mm PYREX™ dish containing 200 mL fixing solution. Cover the dish with plastic wrap and place on an orbital shaker at room temperature for a minimum of 20 minutes. NOTE: The gel should be fixed for a maximum of 1 hour. When fixation is complete, wash the gel 3 times for 5 minutes each with approximately 200 mL of Milli-Q water. Mix the GelCode Blue stain reagent solution by inverting the bottle several times. It is important to mix the stain reagent before dispensing to ensure that a homogeneous sample of the reagent is used. Add approximately 200 mL of the stain reagent to the dish. Cover the dish with plastic wrap and place on an orbital shaker at room temperature for 18 to 20 hours to achieve optimal band development. When staining is complete, wash the gel by replacing the stain reagent with approximately 200 mL Milli-Q water. Perform a minimum of 3 water changes over a 1-2 hour period for optimal results.

Gel Scanning and Analysis. Scan the gel using the scan parameters defined in the Table directly above. Analysis of the gel is performed on the scanned image file.

| Gel Scanning and Analysis Parameters | |
|---|---|
| | Setting |
| Scan Parameters | |
| Scan Pixel Size | 100 |
| Scan Digital Resolution | 12 bits |
| Band Detection Parameters | |
| Minimum Slope | Initial 100 |
| Noise Reduction | Initial 10 |
| % Maximum Peak | Initial 0 |
| Lane % width | Set at 90% |

NOTE:
Table 3 outlines general guidelines for the analysis of gel images. Refer to the ImageQuant TL (v2003.03) manual and on-screen instructions for detailed information on the appropriate adjustment of each band detection parameter.

Open a gel image file (scanned raw data) from ≤1D Gel Analysis> in ImageQuantTL. Go to <Contrast> on toolbar and lower the <Image Histogram> parameter until all bands are clearly visible. Select <Lane Creation> and choose <Manual> to set up <Number of Lanes> to be analyzed. Adjust <Lane % Width> up to 100% to cover the gel lanes. Properly align single lanes if necessary. Use <Rolling Ball> method to subtract background. This is not critical for IEF gel image analysis. Detect bands using the initial <Minimum Slope>, <Noise Reduction>, and <% Maximum Peak> settings listed in Table 3. Adjustment of these values is necessary to accurately identify bands. Manually correct any missed bands and misidentified bands. Compute band pI value by using the standard pI marker from the labeled markers listed in the System Suitability Section for the pH/pI 4.0-6.5 gel. Do not perform the calibration and normalization steps. Export the data contained within the Measurements Window into an Excel sheet for further calculation and reporting. Import the Excel data into the validated spreadsheet to perform quantitative analysis for reporting results.

SYSTEM SUITABILITY. Isoelectric focusing standards (pI markers) must be readily distinguished from background and display limited distortion by visual inspection of the scanned gel image (see Table directly below for the listed pI markers).

| Isoelectric focusing standards | |
|---|---|
| Protein | pI Value |
| Trypsinogen | 9.30 |
| Lentil lectin, basic | 8.65 |
| Lentil lectin, middle | 8.45 |
| Lentil lectin, acidic | 8.15 |
| Myoglobin, basic | 7.35 |
| Myoglobin, acidic | 6.85 |
| Carbonic anhydrase B (human) | 6.55 |
| Carbonic anhydrase B (bovine) | 5.85 |
| B-Lactoglobulin A | 5.20 |
| Soybean Trypsin Inhibitor | 4.55 |
| Methyl red (dye) | 3.75 |
| Amyloglucosidase | 3.50 |

NOTE:
Not all of the isoelectric focusing standards will appear on the gel because the pH/pI range of the gel is 4.0-6.5. The pI markers at 3.50, 4.55, 5.20, and 5.85 are to be identified and labeled on the gel.

The banding pattern of CTLA4$^{A29YL104E}$-Ig reference material and test articles should display limited distortion by visual inspection of the scanned gel image. A staining control of carbonic anhydrase II (pI 5.4) at a low level of protein load (1.0 μg) is used to demonstrate consistent gel staining. The band must be easily distinguished from the background by visual inspection of the scanned gel image. CTLA4$^{A29YL104E}$-Ig reference material must contain 8 to 15 bands with band intensity 0.0% within the pI range of 4.5 to 5.6. CTLA4$^{A29YL104E}$-Ig reference material bands within the pI range of 4.5 to 5.6 must have a cumulative percent intensity of ≥95%.

DATA CALCULATION. The following equation is utilized for the calculation of the cumulative percent intensity of CTLA4$^{A29YL104E}$-Ig samples relative to reference material:

$$\text{Cumulative Percent Intensity} = \frac{\text{Sample \% Band Intensity } (pI\ 4.5\text{-}5.6)}{\text{Reference \% Band Intensity } (pI\ 4.5\text{-}5.6)} \times 100$$

Example: If the sample has a % Band Intensity (pI 4.5-5.6) of 95% and the reference material has a % Band Intensity (pI 4.5-5.6) of 100%, the Cumulative % Intensity will be 95%.

The CTLA4$^{A29YL104E}$-Ig material in one embodiment will have bands with a relative band intensity ≥1.0% within the pI range of 4.5-5.6. The CTLA4$^{A29YL104E}$-Ig material has a cumulative percent intensity relative to that of CTLA4$^{A29YL104E}$-Ig reference material within the pI range of 4.5-5.6.

Example 23: Transfection and Generation of Cell Lines

Prior to electroporation, the expression vector pD16LEA29Y was linearized with BstBI enzyme to produce compatible 4 bp overhangs. The linearized vector and sheared herring sperm carrier DNA (as carrier) were co-precipitated with ethanol and aseptically resuspended in PF CHO medium (JRH Biosciences) for electroporation into DG44 cells.

Following electroporation, the cells were allowed to recover in non-selective medium. The cells were then seeded into 96 well plates in selective media of PF CHO containing 500 ng/mL of recombulin (Gibco), 4 mM L-glutamine (Gibco) and methotrexate (ICN).

CTLA4$^{A29YL104E}$-Ig producing cell lines from this plating were chosen for expression amplification using the following progression of methotrexate (MTX) concentrations added to the media:

20 nM⇒50 nM⇒100 nM⇒250 nM⇒500 nM⇒1 µM MTX.

Entire CTLA4$^{A29YL104E}$-Ig expression plasmid is integrated into the cell cell genome.

Production Cell Line Selection

The final production cell line GF1.1.9 was isolated after two rounds of limiting dilution cloning of the best performing, amplified master well cell lines. Selection of cell line GF1.1.9 was based on growth pattern, titer, and product containing a reduced amount of high molecular weight component and higher sialic acid content relative to material produced from the other clones.

Example 24: Genetic Characterization of a CTLA4$^{A29Y104E}$-Ig

Genomic Stability Studies

DNA and RNA isolated from cells derived a cell bank were used for Southern and Northern hybridization analysis, and sequencing of the cDNA for a CTLA4$^{A29YL104E}$-Ig coding sequence. The results were compared with the results obtained from CTLA4$^{A29YL104E}$-Ig.

The results for the Northern hybridization analysis, and cDNA sequencing estimation are presented below.

Northern Hybridization Analysis

A culture inoculated with cells from the cell bank was expanded and used to isolate RNA for the Northern hybridization analysis. The culture prepared represents cells approximately 27 generations beyond the in vitro cell age used in the CTLA4$^{A29YL104E}$-Ig production process. Total RNA was extracted from cells derived from the CTLA4$^{A29YL104E}$-Ig cell bank and from cells from the expanded CTLA4$^{A29YL104E}$-Ig cells. A control utilizing total RNA from the parental CHO cell line was also used in these experiments. Approximately 5 μg of total RNA was subjected to agarose gel electrophoresis under denaturing conditions. The RNA in the gel was blotted onto a nylon membrane and hybridized with a $^{32}$P-labeled 1.2 kb HindIII/XbaI DNA fragment containing the CTLA4$^{A29YL104E}$-Ig gene. The 1.2 kb HindIII/XbaI DNA fragment used for the probe was isolated from plasmid pD16LEA29Y.

A mRNA species of approximately 1.7 kilobases that hybridized to the CTLA4$^{A29YL104E}$-Ig gene probe was detected in the total RNA sample from the cell bank as shown in FIG. 32. Panel A and Panel B shown in FIG. 32 represent the ethidium bromide-stained agarose gel and the corresponding autoradiogram, respectively.

These results indicate that only one transcript encoding CTLA4$^{A29YL104E}$-Ig is expressed in cultures derived from the CTLA4$^{A29YL104E}$-Ig expanded cell bank. In addition, no detectable changes in the CTLA4$^{A29YL104E}$-Ig mRNA transcript were observed in these samples as compared to the results obtained using the cell bank.

Example 25: Size Exclusion Chromatography

A size exclusion method has been developed to analyze CTLA4$^{A29YL104E}$-Ig compositions using a 7.8 mm×300 mm TosoHaas TSK-3000 SWXL column equipped with a guard column with detection at 280 nm. CTLA4$^{A29YL104E}$-Ig is evaluated for product homogeneity including monomer (single chain), dimer, or high molecular weight species (e.g., tetramer). The method shows good precision (<2%) at a nominal concentration of ~10 mg/mL and is linear from ~0.5-15 mg/mL ($r^2$=0.999). The DL (Detection Limit) is ~2.26 Φg/mL and the QL (Quantitation Limit) is −7.53 Φg/mL. These soluble CTLA4-Ig molecules are fusion proteins consisting of the ligand binding domain of cytotoxic T lymphocyte antigen 4 (CTLA4) and the constant region of human IgG1 heavy chain with potential therapeutic application as immunosuppresants. These compounds exert their physiological effects through binding to B7 antigens (CD80 and CD86) on the surface of various antigen-presenting cells (APC), thus blocking the functional interaction of B7.1 and B7.2 with CD28 on the surface of T-cells. This blockade results in the suppression of T-cell activation, hence, the immune response. Although LEA29Y only differs from CTLA4Ig at two amino acid residues, $Leu_{104}$-glu and $Ala_{29}$-Try, the molecules have significantly different avidity towards B7.1 and B7.2 antigens. LEA29Y shows a 5 to 10 fold greater avidity for the human form of B7.2 (CD86), and similar avidity for human B7.1 (CD80), compared with the parental CTLA4Ig.

Size exclusion chromatography with a TSK-3000 SWXL column (7.8 mm×300 mm) equipped with a guard column and detection at 280 nm is used to analyze CTLA4$^{A29YL104E}$-Ig drug substance for homogeneity. CTLA4$^{A29YL104E}$-Ig dimer, high molecular weight (HMW) and low molecular weight (LMW) species are differentiated.

Size exclusion chromatography (SEC) is used to evaluate CTLA4$^{A29YL104E}$-Ig for product homogeneity. FIGS. 33A, 33B and 33C shows the SEC chromatogram of CTLA4$^{A29YL104E}$-Ig for Process B, Process C and the co-mixture lot. SEC of CTLA4$^{A29YL104E}$-Ig indicates that the Process C material is 99.8 area percent dimer, 0.2 area percent HMW species and no detectable LMW species. These results are comparable with the Process B material (dimer 97.4 area percent, HMW 2.6 area percent, and LMW<DL).

Reagents: 4N KOH (100 mL); System Suitability Standard (molecular weight markers dissolved in HPLC grade water); Mobile phase Running Buffer (0.2 M KH2$PO_4$, 0.9% NaCl, pH 6.8); 4N NaOH; Dilution Buffer (25 mM $NaH_2PO_4$-$H_2O$, 10 mM NaCl, pH 7.5)

INSTRUMENTATION AND CONDITIONS—Equivalent instrumentation may be substituted:

| | |
|---|---|
| Pump Type | Waters Model 600 |
| Column | Toso Haas 5: m TSK 3000 SWXL, 300 mm × 7.8 m I.D. Hewlett Packard, (Catalog No. 79912S3-597) equipped with 5: m TSK 3000 SWXL, 40 mm × 6.0 mm I.D. guard column, Hewlett Packard, (Catalog No. 79912S3-527) |
| Detector | Waters Model 486. Allow 15 minutes warm up |
| Wavelength | 280 nm |
| Flow Rate | 1 mL/min |
| Integration System | VG Multichrom |
| Injection System | Waters Model 717 Plus Autosampler equipped with refrigeration to 4° C. |
| Injection Volume | 20 mL |
| Assay Target Concentration | 10 mg/mL |
| Mobile Phase | 0.2M $KH_2PO_4$, 0.9% NaCl, pH 6.8 with KOH |
| Assay Run Time | 20 min |
| Column Temperature | Ambient |

| Retention Time | CTLA4$^{A29YL104E}$-Ig ~8.5 min ± 0.5 min, high molecular weight species at ~7.5 min ± 0.5 min |
|---|---|

Standards and samples (10 mg/ml) were prepared as 50 ml volumes in labeled autosampler vials. Samples were prepared in duplicate.

Calculations

Resolution (R) Determination and Retention Time Evaluation:

20 mL of system suitability standards are injected to calculate the resolution between 2 peaks from a chromatogram generated using such standards (for example, one peak, Peak 1, having a retention time ~8.5 minutes and a second peak, Peak 2, having a retention time ~10 minutes) using the following equation:

$$\text{Resolution } (R) = \frac{2(t_2 - t_1)}{W_2 + W_1}$$

Where:
$t_1$=Retention time of Peak 1
$t_2$=Retention time of Peak 2
$W_1$=Peak width of Peak 1
$W_2$=Peak width of Peak 2

$$\text{Resolution } (R) = \frac{2(t_2 - t_1)}{W_2 + W_1}$$
$$= \frac{2(10.07 - 8.52)}{.57 + .86}$$
$$= 2.12 \unrhd 1.3$$

Peak width equals width (in minutes) at the base of the peak after extrapolating the relatively straight sides of the peak to the baseline. Retention time and peak widths are measured in the same units.

R must be ⊒ 1.3 and the retention time for the peak should be ~8.5 ∀ 0.5 minutes.

Number of Theoretical Plates Determination:

From the system suitability standard chromatogram, the efficiency of the column can be determined by calculating the number of theoretical plates according to the following equation:

$$N = 16\left(\frac{t}{w}\right)^2$$

Where:
(t)=is the retention time of Peak 2 (in minutes)
(w)=is the width (in minutes) at baseline of Peak 2 obtained by extrapolating the sides of the peak to the baseline as seen in FIG. 1.

N should be ⊒ 2500.

Figure 33A:
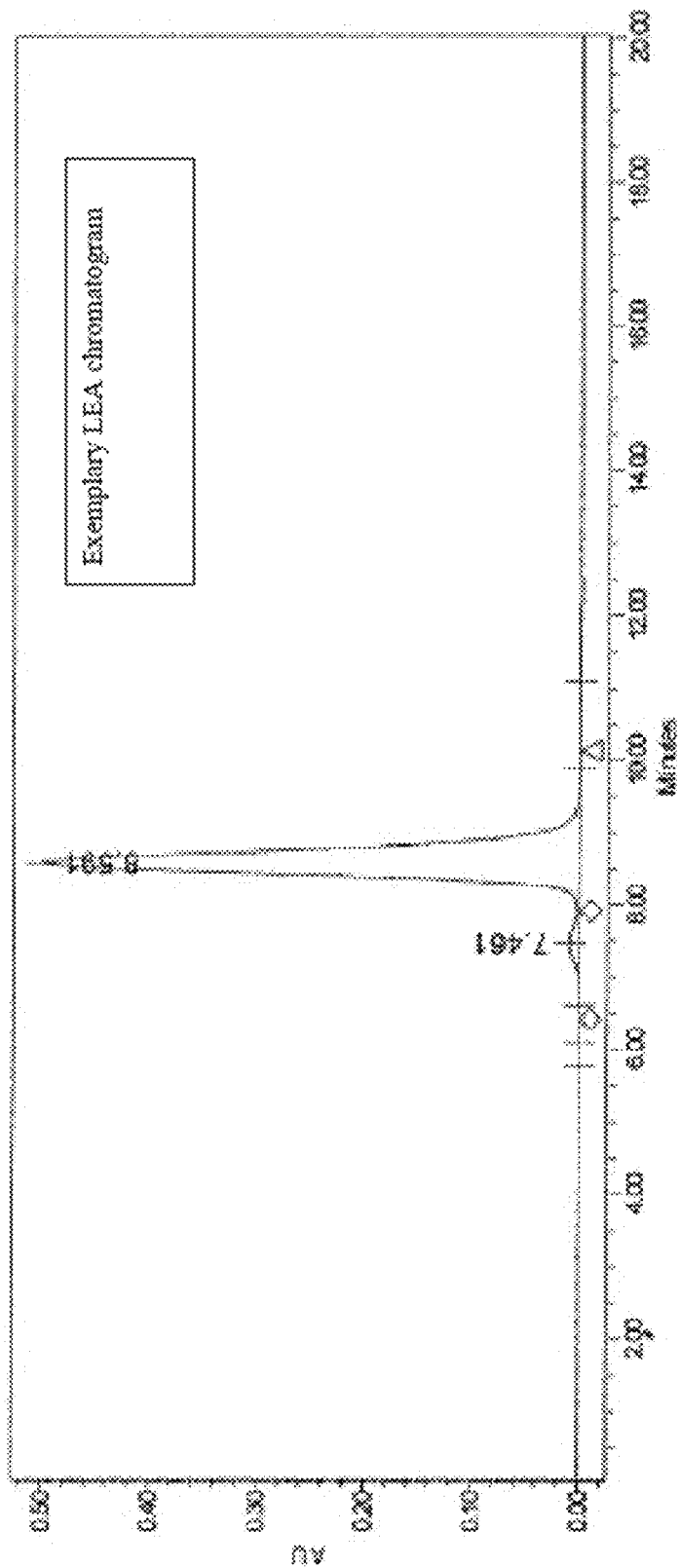
FIG. 33A-33C depict size exclusion chromatograms, which distinguish CTLA4$^{A29YL104E}$-Ig dimers from high and low molecular weight species.
Figure 33B:
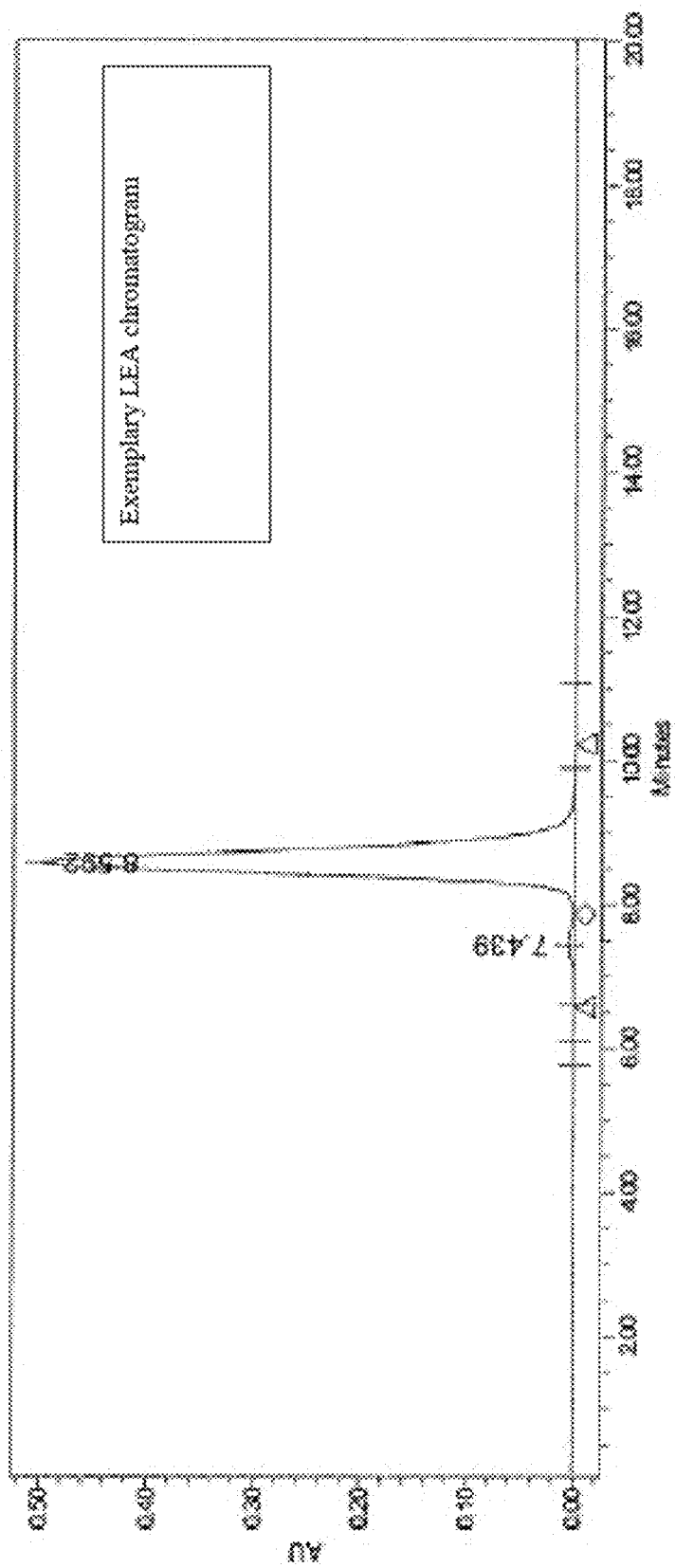
Figure 33C:
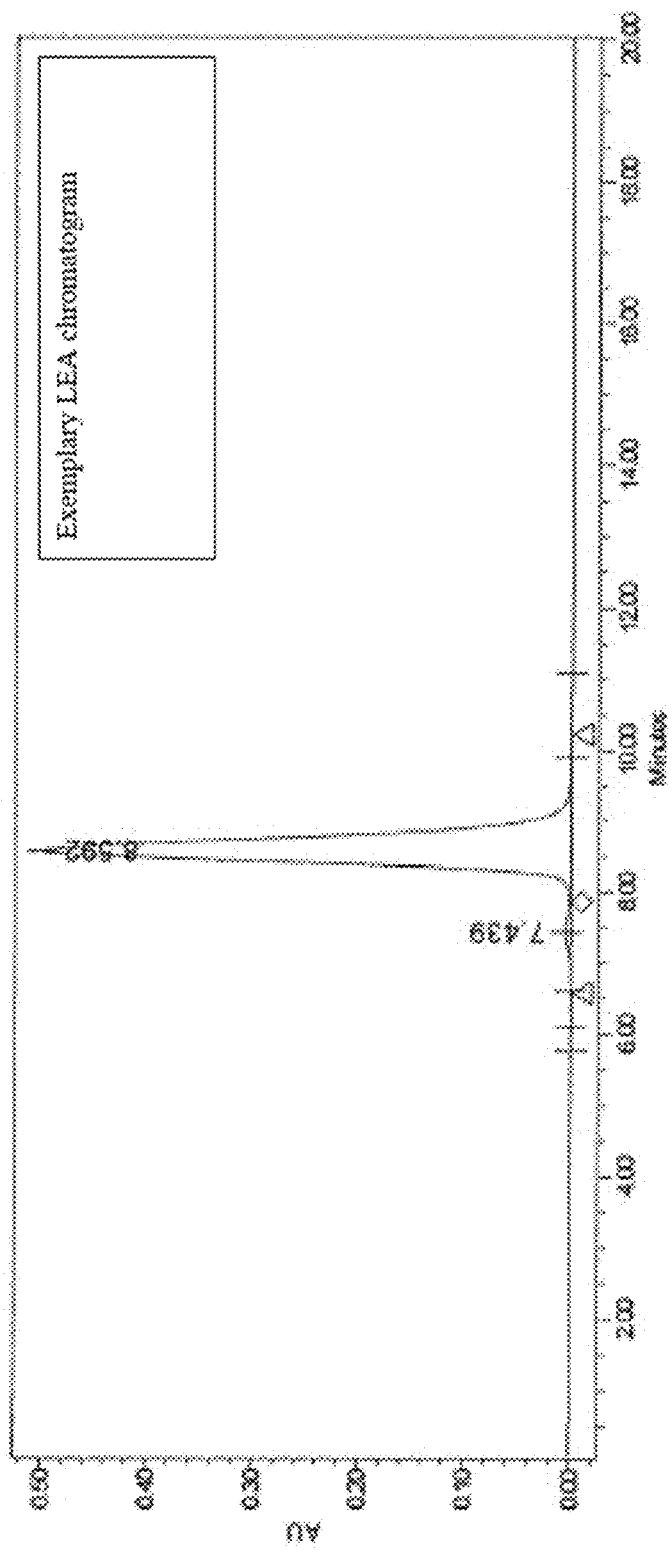

Integration of Peaks:

The peak areas in the chromatogram were integrated (for example, FIGS. 33A, 33B and 33C). The CTLA4$^{A29YL104E}$-Ig dimer peak is at ~8.5 minutes and the high molecular weight species peak is at ~7.4 minutes.

Area percentages can be calculated according to the formulas below:

$$\text{Area \% M dimer} = 100 - (\text{Area \% High Molecular Weight Species} + \text{Area \% Low Molecular Weight Species})$$

$$\text{Area \% High Molecular Weight Species} = \frac{(B)}{(A) + (B) + (C)} \times 100$$

$$\text{Area \% Low Molecular Weight Species} = \frac{(C)}{(A) + (B) + (C)} \times 100$$

Where:
A=CTLA4$^{A29YL104E}$-Ig dimer peak area
B=Total area of all peaks with retention times less than CTLA4$^{A29YL104E}$-Ig dimer
C=Total area of all peaks with retention times greater than CTLA4$^{A29YL104E}$-Ig dimer peak (excluding inclusion volume).

The % RSD of the total area counts (excluding the inclusion volume) is determined. The % RSD of the total area counts must be 2% or less. If area is <2707 area counts, report results as # DL, (Detection Limit) (~2.26 µg/mL). If area counts are between 2707-9014, report results as # QL (Quantitation Limit) (~7.53 µg/mL). If area counts are ⊒ 9014, report results to nearest tenth of a percent.

Example 26: SDS-Page and Disulfide Bonds

Sodium Dodecyl Sulfate Polyacrylamide Gel Electrophoresis

A sodium dodecyl sulfate polyacrylamide gel electrophoresis (SDS-PAGE) procedure for the analysis of CTLA4$^{A29YL104E}$-Ig is used as a purity test. Samples are prepared in a Tris-HCl (pH 6.8), SDS, sucrose, and bromophenol blue sample buffer in the presence (reduced) or absence (non-reduced) of dithiothreitol (DTT). Samples are placed in an 80° C. water bath for two minutes and electrophoresed in pre-cast, gradient (4-20%) polyacrylamide SDS gels using a Tris-glycine SDS running buffer. After electrophoresis, the gels are fixed and stained using a Coomassie blue or silver staining system. Non-reduced CTLA4$^{A29YL104E}$-Ig is observed as one large band with an apparent approximate molecular weight of ~10 µL kD. CTLA4$^{A29YL104E}$-Ig is observed as one major band with an apparent approximate molecular weight of ~53 kD.

Figure 34:
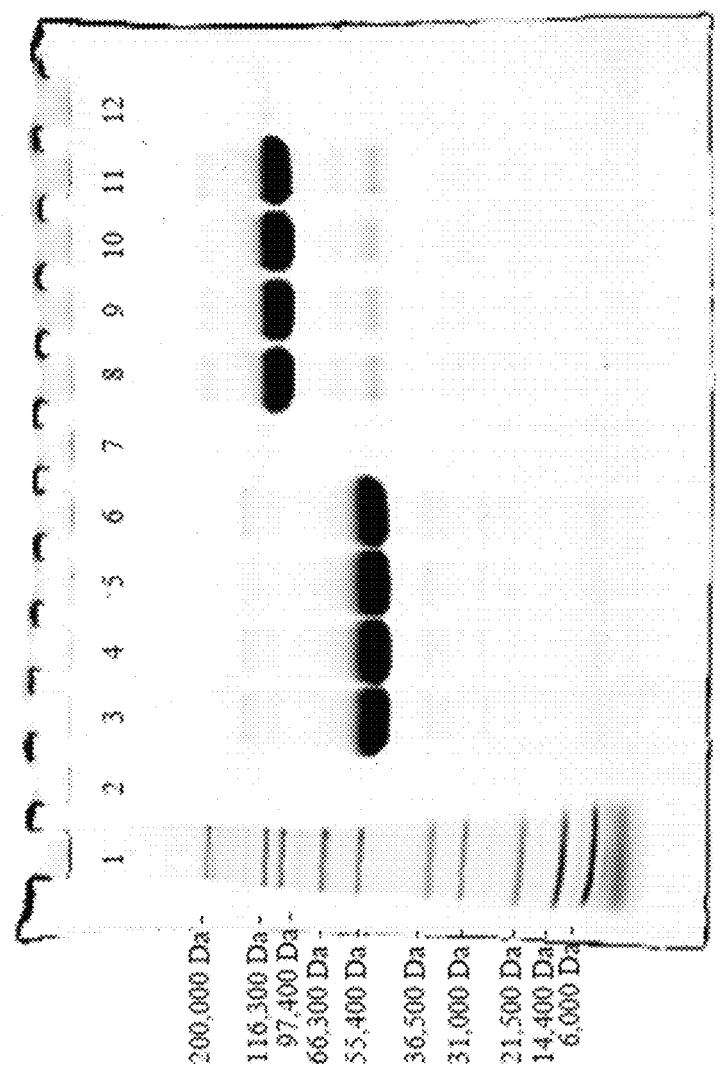
FIG. 34 shows an SDS-PAGE (Reduced and Non-Reduced) analysis of CTLA4$^{A29YL104E}$-Ig stained with Coomassie Blue. Lane 1 is loaded with molecular weight markers; Lanes 2, 7, and 12 are blank; Lanes 3-6 are CTLA4$^{A29YL104E}$-Ig samples (reduced); Lanes 8-11 are CTLA4$^{A29YL104E}$-Ig samples (non-reduced).
Figure 35:
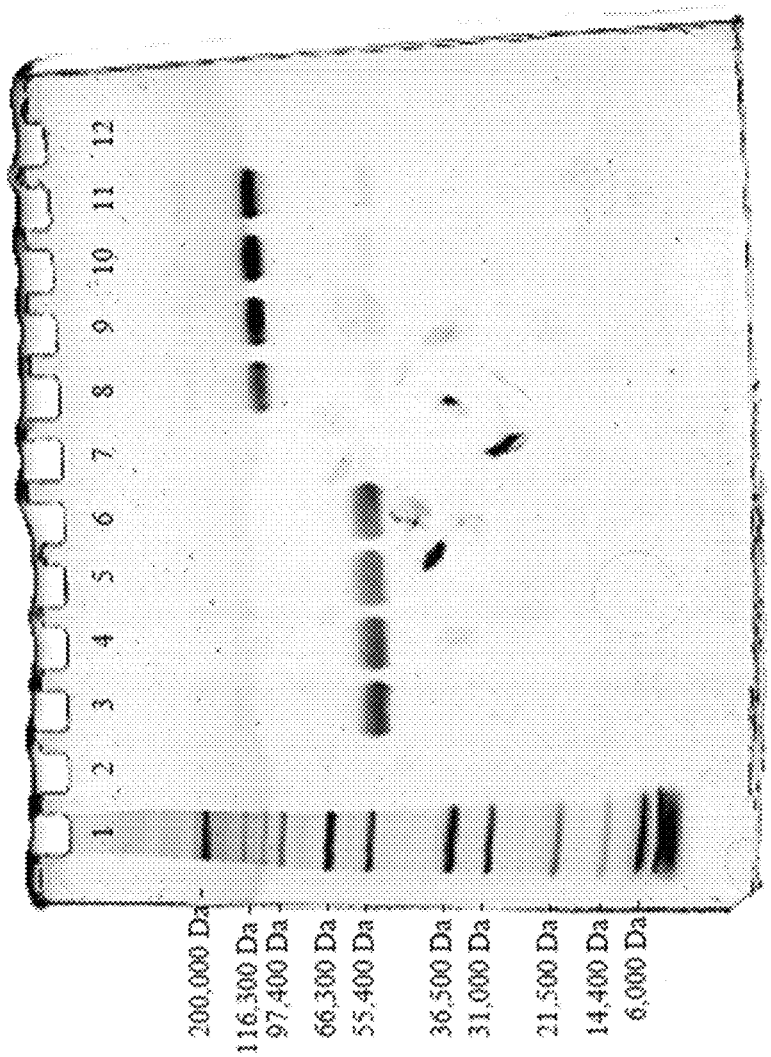
FIG. 35 shows an SDS-PAGE (Reduced and Non-Reduced) analysis of CTLA4$^{A29YL104E}$-Ig subjected to silver-staining. Lane 1 is loaded with molecular weight markers; Lanes 2, 7, and 12 are blank; Lanes 3-6 are CTLA4$^{A29YL104E}$-Ig samples (reduced); Lanes 8-11 are CTLA4$^{A29YL104E}$-Ig samples (non-reduced).

Samples of Process B Lot 000929-278, Process C Lot 224818-2004-007 and the co-mixture Lot 551218-162 were electrophoretically resolved using 4-20% gradient SDS-PAGE gels under both reducing and non-reducing conditions. Gels were separately stained with either Coomassie or silver stain as shown in FIG. 34 and FIG. 35. SDS-PAGE of non-reduced CTLA4$^{A29YL104E}$-Ig showed a major band at approximately 104 kDa representing the intact monomer. Three minor bands, not easily seen on electronic reproductions, were also observed at ~200, 65, and 53 kDa. Reduced samples of CTLA4$^{A29YL104E}$-Ig show a major band at approximately 53 kDa representing the single chain form and a minor band at ~150 kDa. This comparison shows that the three tested materials are comparable when analyzed on the same gel.

Disulfide Bonds

Disulfide bonds were characterized for Process C drug substance using Lot 224818-2004-007. Each chain of CTLA4$^{A29YL104E}$-Ig contains nine cysteines. These are Cys21, Cys48, Cys66, Cys92, Cys120, Cys171, Cys231, Cys277 and Cys335. Peptide mapping with on-line LC/MS/MS of both reduced and non-reduced CTLA4$^{A29YL104E}$-Ig was used to identify the sites of intra- and intermolecular disulfide linkages in CTLA4$^{A29YL104E}$-Ig. A list of the peptides obtained from peptide mapping of non-reduced CTLA4$^{A29YL104E}$-Ig along with the expected and observed MW is shown in Table 27.

Figure 36:
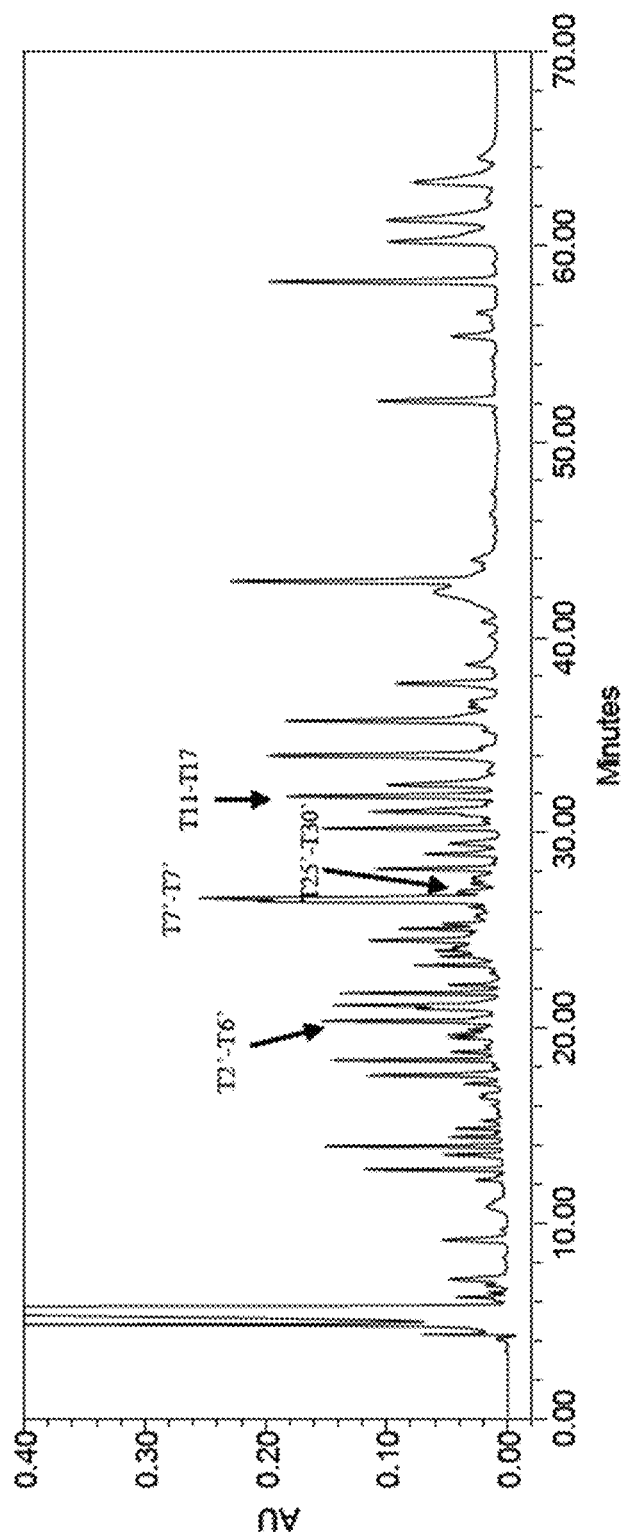
FIG. 36 depicts a peptide map of non-reduced CTLA4$^{A29YL104E}$-Ig using a combination of trypsin and chymotrypsin digestion.

The disappearance of certain peaks in the non-reduced peptide map and the appearance of new peaks in the reduced peptide map provided evidence of three disulfide-linked peptides: T2-T6, T11-T17, and T25-T30 which corresponded to the disulfide bonds of Cys21-Cys92, Cys171-Cys231 and Cys277-Cys335. Peptides T5 and T7 have relatively high molecular weight and contain N-linked carbohydrates, which makes it difficult to locate disulfide linkages. To generate shorter and carbohydrate-free peptides, CTLA4$^{A29YL104E}$-Ig was digested with a mixture of trypsin and chymotrypsin. As a result of the additional chymotrypsin cleavage, T7 was shortened from a 35-amino-acid peptide to a 15-amino-acid peptide, designated T7'-T7', in which the N-linked carbohydrate is removed. Disulfide-linked peptide T7'-T7' appears in the unreduced map (see FIG. 36). MS/MS on T7'-T7' confirmed its sequence and inter-chain disulfide linkage at Cys120-Cys120.

TABLE 27

Peptide Sequence and MW of Disulfide-Linked Peptides from Trypsin Digestion of CTLA4$^{A29YL104E}$-Ig under Non-Reducing Conditions

| Disulfide Link | Sequence | Theoretical MW | Observed MW |
|---|---|---|---|
| T2-T6 (C21-C92) | GIASFVCEYASPGK<br>\|<br>AMDTGLYICK | 2539.2 | 2539.6 |
| T11-T17 (C171-C231) | TPEVTCVVVDVSHEDPEVK<br>\|<br>CK | 2328.1 | 2328.4 |
| T25-T30 (C277-C335) | NQVSLTCLVK<br>\|<br>WQQGNVFSCSVMHEALHNHYTQK | 3844.8 | 3846.3 |
| T5 (C48-C66) | QADSQVTEVCAATYMMG<br>\|<br>NRLGQITLNVQNGSSTGTCISDDLFTLE | Glycopeptide[a] | |
| T7-T7 (C120-C120) | VELMYPPPYYEGIGNGTQIYVIDPEPCPDSDQEPK<br>\|<br>VELMYPPPYYEGIGNGTQIYVIDPEPCPDSDQEPK | Glycopeptide | |

[a] Peptides T5 and T7-T7 give rise to several masses due to heterogeneity of N-linked glycosylation making it difficult to locate disulfide linkages.

Treatment with a mixture of trypsin and chymotrypsin also resulted in the formation fragments, which corresponded to shorter versions of other disulfide linked peptides that were observed on hydrolysis of CTLA4$^{A29YL104E}$-Ig by trypsin alone. These are shown in Table 28.

TABLE 28

Peptide Sequence and MW of Disulfide-Linked Peptides of CTLA4$^{A29YL104E}$-Ig with (Trypsin and Chymotrypsin) Digestion

| Disulfide Link | Sequence | Theoretical MW | Observed MW |
|---|---|---|---|
| T2'-T6' (C21-C92) | VCEY<br>\|<br>ICK | 872.4 | 872.4 |
| T11-T17 (C171-C231) | TPEVTCVVVDVSHEDPEVK<br>\|<br>CK | 2328.1 | 2328.6 |
| T25'-T30' (C277-C335) | CLVK<br>\|<br>SCSVM | 984.5 | 984.5 |
| T7'-T7' (C120-C120) | VIDPEPCPDSDQEPK<br>\|<br>VIDPEPCPDSDQEPK | 3333.5 | 3333.2 |
| T5 (C48-C66) | QADSQVTEVCAATYMMGNRLGQITLV<br>\|<br>QNGSSTGTCISDDLFTLE | glycopeptide | |

Figure 37:
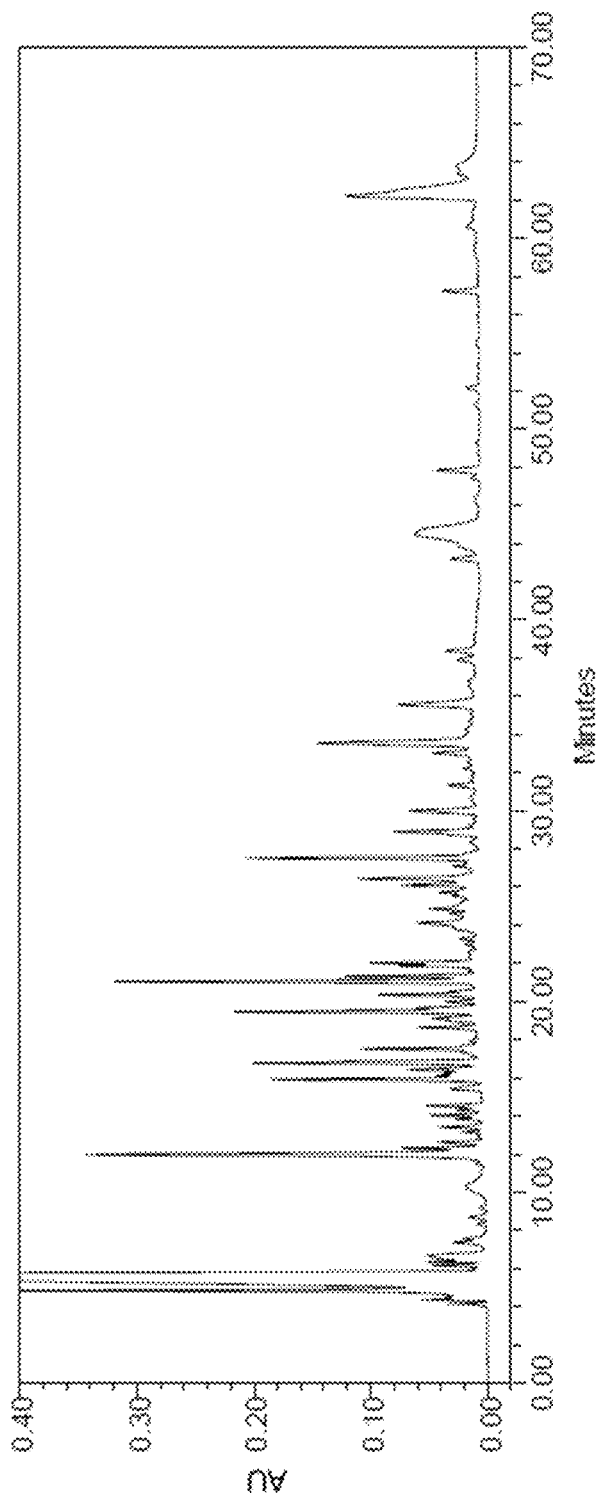
FIG. 37 depicts a peptide map of non-reduced CTLA4$^{A29YL104E}$-Ig using a combination of trypsin and elastase digestion.

The digestion of CTLA4$^{A29YL104E}$-Ig with a mixture of trypsin and chymotrypsin established the disulfide pairing in T7-T7 and confirmed the disulfide bonds seen with digestion by trypsin alone. However, this enzyme mixture did not have any effect on peptide T5, which is also a glycopeptide. In order to remove the N-linked carbohydrates from T5, CTLA4$^{A29YL104E}$-Ig was digested with a mixture of trypsin and elastase as shown in FIG. 37. This mixture of enzymes hydrolyzed T5 at four different sites generating a shorter peptide designated (T5'-T5") as shown in Table 29. This generated peptide had the expected mass of 1259 Da and contained the disulfide linkage corresponding to Cys46-Cys66. The peptide map profile obtained from the hydrolysis of non-reduced CTLA4$^{A29YL104E}$-Ig by a mixture of trypsin and elastase, is shown in FIG. 37 and the sequence of peptide T5'-T5" is in Table 29.

TABLE 29

Peptide Sequence and MW of Peptide T5'-T5" Obtained by Digestion of CTLA4$^{A29YL104E}$-Ig with a Mixture of Trypsin and Elastase

| Disulfide Link | Sequence | Theoretical MW | Observed MW |
|---|---|---|---|
| T5 (C48-C66) | EVC<br>\|<br>TCISDDLF | Glycopeptide | |

The results indicate that CTLA4$^{A29YL104E}$-Ig has four intra-molecular disulfide linkages at positions Cys21-Cys92 (T2-T6), Cys48-Cys66 (corresponding to one single peptide T5), Cys171-Cys231 (T11-T17) and Cys277-Cys335 (T25-T30) and one inter-chain disulfide linkage at positions Cys120-Cys120 (T7-T7). The data accounted for all eighteen cysteine residues. No mispairing was observed.

Example 27: CTLA4$^{A29YL104E}$-Ig Formulation

CTLA4$^{A29YL104E}$-Ig for Injection, 100 mg/vial is a sterile non-pyrogenic lyophile. The composition of drug product is given in Table 30. It is a white to off white, whole or fragmented cake provided in Type I glass vials stoppered with gray butyl stoppers and sealed with aluminum seals. This product includes 10% overfill to account for vial, needle, and syringe holdup.

Prior to administration, CTLA4$^{A29YL104E}$-Ig for Injection, 100 mg/vial is constituted with 4.2 mL of Sterile Water for Injection, USP to yield a concentration of 25 mg/mL. It can be further diluted to a concentration as low as 1 mg/mL with 5% Dextrose Injection, USP or 0.9% Sodium Chloride Injection, USP. Constituted and diluted solutions are clear, colorless and essentially free of particulate matter on visual inspection.

TABLE 30

Composition of CTLA4$^{A29YL104E}$-Ig for Injection, 100 mg/vial

| Component | Function | Quantity per Vial (mg) |
|---|---|---|
| CTLA4$^{A29YL104E}$-Ig | Active Ingredient | 110$^a$ |
| Sucrose | Lyoprotectant | 220 |
| Sodium Phosphate Monobasic Monohydrate | Buffering Agent | 15.18 |
| Sodium Chloride | Ionic Strength Adjustment | 2.55 |
| 1N Sodium Hydroxide | pH Adjustment | To 7.5 ± 2 |
| 1N Hydrochloric Acid | pH Adjustment | To 7.5 ± 2 |
| Water for Injection$^b$ | Solvent | q.s. to 5.5 mL |

$^a$Each vial contains 10% overfill for vial, needle and syringe holdup of the reconstituted solution.
$^b$Removed during lyophilization The glass transition temperature of the frozen solution to be freeze dried was determined to be −28.9° C. Freeze drying studies were conducted at various shelf temperatures in order to determine the highest possible shelf temperature allowable during primary drying, without compromising product quality. Based on these studies, a shelf temperature of −20° C. was selected for the primary drying step during the freeze-drying of CTLA4$^{A29YL104E}$-Ig. At the end of the freeze-drying cycle, the vials are stoppered under reduced pressure.

The production process involves freezing vials containing bulk solution for lyophilization (with appropriate excipients) in a freeze dryer chamber, followed by sublimation of frozen water under controlled temperature and pressure. Temperature and pressure conditions in the chamber are optimized in order to have efficient sublimation without compromising product quality.

Compatibility of the solution with various product contact surfaces and packaging components was studied. The solution was found to be compatible with stainless steel 316L, silicone tubing, Acrodisc™, HT Tuffryn (polysulfone), Millipore PVDF (polyvinylene fluoride) filter membranes and the selected container closure system.

CTLA4$^{A29YL104E}$-Ig for Injection, 100 mg/vial is packaged in 15 cc Type I flint tubing glass vials and stoppered with a 20 mm Daikyo gray butyl D-21-7-S/B2-TR fluro-resin coated stopper and sealed with a 20 mm aluminum flip-off seal.

Vial selection for CTLA4$^{A29YL104E}$-Ig for Injection was based on the fill volume of 5.5 mL to ensure efficient freeze-drying and 20 mm Daikyo gray butyl D-21-7-S/B2-TR fluro-resin coated stopper selection was based on the compatibility data.

Extensive use time compatibility studies have been conducted. CTLA4$^{A29YL104E}$-Ig for Injection 100 mg/mL when constituted to 25 mg/mL with sterile water for injection may be stored at ambient room temperatures from 15°-25° C. (59°-77° F.) and room light for 24 hours. Constituted solution when further diluted to either 1 mg/ml or 10 mg/mL with 0.9% Sodium Chloride Injection (Normal Saline/NS) or with 5% Dextrose Injection (D5W) and stored in either a PVC or Intra Via non-PVC bag at ambient room temperatures from 15°-25° C. (59°-77° F.) and room light, showed no loss in potency or increase in high molecular weight species over a period of 24 hours. The diluted solution must be filtered through a 0.2 μm or a 1.2 μm mixed cellulose/acetate filter prior to administration. The diluted solution is compatible with 0.2 μm and 1.2 μm mixed cellulose/acetate filters.

The product is incompatible with silicone. It interacts with silicone to form visible particles. Therefore, contact with silicone treated surfaces such as siliconized syringes should be avoided.

Example 28: CTLA4-Ig Production Process

CTLA4-Ig is produced as a secreted protein in large-scale cell culture using a Chinese hamster ovary (CHO) cell line. The CTLA4-Ig production process is initiated using a series of flask and seed bioreactor inoculum expansion steps. The contents of a final seed bioreactor are used to inoculate a 5000-L production bioreactor. The cell culture harvest from the 5000-L production bioreactor is clarified and concentrated by microfiltration and ultrafiltration. The cell-free harvest material is adjusted for pH and conductivity in preparation for downstream processing. CTLA4-Ig is purified using a series of chromatographic and filtration steps.

The downstream CTLA4-Ig production process includes two anion exchange chromatography steps, one hydrophobic interaction chromatography step and one affinity chromatography step. The purpose of these steps is to purify the CTLA4-Ig protein, to remove high molecular weight CTLA4-Ig material and to control the sialic acid content of the CTLA4-Ig drug substance. The downstream processing steps also include a viral inactivation step and a viral filtration step to clear potential adventitious viral agents. Purified CTLA4-Ig drug substance is filled into 2-L polycarbonate bottles and frozen at a target temperature of −70° C. prior to storage at a target temperature of −40° C. The frozen drug substance is thawed.

N-acetylneuraminic acid (NANA) is the primary sialic acid species present in CTLA4-Ig drug substance. References to sialic acid throughout this section refer specifically to this species. Minor levels of N-glycolylneuraminic acid (NGNA) are also present in CTLA4-Ig drug substance. The levels of both NANA and NGNA are determined for the final CTLA4-Ig drug substance. A process flow diagram for the CTLA4-Ig production process is shown in FIG. 91.

CTLA4-Ig is produced in 5000-L production bioreactors with an approximate working volume of 4300 L. One batch of CTLA4-Ig drug substance is made from a single production bioreactor derived from a single vial from the cell bank. The upstream cell culture production process is initiated using a single vial of cells from a cell bank. The vial is thawed and the entire contents used to seed a T-flask containing cell culture growth medium. The cells are then expanded in a series of spinner flasks. Flasks from the final spinner flask inoculum expansion step are used to inoculate the 140-L seed bioreactor. The 140-L seed bioreactor has a working volume of approximately 100 L. The contents of the 140-L seed bioreactor are used to inoculate the 1100-L seed bioreactor. The 1100-L seed bioreactor has a working volume of approximately 600 L. The contents of the 1100-L seed bioreactor are used to seed the 5000-L production bioreactor. The cells are cultivated in the 5000-L production bioreactor for approximately 14 days. Following the production bioreactor step, the cell culture broth from a single bioreactor is transferred to a harvest vessel for further processing. A tangential flow microfiltration (MF) unit is used to separate the secreted CTLA4-Ig protein from host cells and cell debris. The CTLA4-Ig protein-containing MF permeate is then concentrated by ultrafiltration (UF) and adjusted for pH and conductivity in preparation for the first chromatography step.

The purification and downstream processing steps for CTLA4-Ig drug substance consist of anion exchange chromatography, hydrophobic interaction chromatography (HIC), viral inactivation, affinity chromatography, tangential flow UF concentration and diafiltration, viral filtration, a second anion exchange chromatography and UF concentration and diafiltration. The HIC step utilizes multiple cycles per CTLA4-Ig batch depending on the quantity of CTLA4-Ig to be processed. In-process material from multiple HIC step cycles are pooled for the subsequent viral inactivation step. In-process material from different lots are not pooled. Multiple viral filters may be used in parallel to process a single lot of CTLA4-Ig. Following viral filtration, the filtrates are pooled for further processing.

Each lot of CTLA4-Ig is filtered through a 0.2 μm filter into 2-L polycarbonate (PC) bottles and temporarily stored at 2° to 8° C. The 2-L PC bottles of CTLA4-Ig are frozen at a target temperature of −70° C. and then stored at a target temperature of −40° C. Bottles of drug substance are thawed in an incubator at 22° to 24° C. and cooled to 2° to 8° C. prior to shipment.

Production

CTLA4-Ig is produced in large-scale cell culture using a Chinese hamster ovary (CHO) cell line. The CTLA4-Ig upstream production process is initiated with the thaw of a frozen vial from a cell bank. The culture is propagated in a T-flask, followed by a series of spinner flask cultures. These cultures are transferred to a 140-L seed bioreactor. The culture from the 140-L seed bioreactor is transferred to a 1100-L seed bioreactor. The culture from the 1100-L seed bioreactor is used to inoculate a 5000-L production bioreactor. The production bioreactor is harvested primarily based on a target sialic acid to CTLA4-Ig protein molar ratio. The cell culture harvest is clarified and concentrated using a combination of microfiltration (MF) and ultrafiltration (UF). Finally, the concentrated cell-free harvest material is adjusted to achieve a specified conductivity and pH in preparation for downstream processing.

Cell Culture and Feed Media Preparation

Solid and liquid media components are weighed and measured. Two cell culture media are used in the process. Medium 127-G is used in the T-flask, spinner flask, seed bioreactor and production bioreactor steps. Medium 117-E is used as a feed medium in the production bioreactor step. The composition of Medium 127-G is shown in the table directly below.

| Component | Concentration |
| --- | --- |
| CD-CHO 25x Acid Solubles I | 40.0 mL/L |
| CD-CHO 25x Acid Solubles II | 40.0 mL/L |
| CD-CHO 25x Salts I | 40.0 mL/L |
| CD-CHO 25x Salts II | 40.0 mL/L |
| L-Glutamine | 0.585 g/L |
| r-human Insulin (10 mg/mL solution) | 0.1 mL/L |
| Methotrexate (20 mM solution) | 5 μL/L |
| Sodium Bicarbonate | 2.22 g/L |
| Water For Injection | As required |
| 1N HCl Solution | 0-5 mL/L to adjust pH |
| 10N NaOH Solution | 0-10 mL/L to adjust pH |

The composition of Medium 117-E is shown below.

| Component | Concentration |
| --- | --- |
| eRDF-1 Medium | 16.47 g/kg |
| Dextrose | 30.29 g/kg |
| D-Galactose | 12.38 g/kg |
| L-Glutamine | 4.02 g/kg |
| r-human Insulin (10 mg/mL solution) | 0.98 mL/kg |
| TC Yeastolate | 4.90 g/kg |
| Water For Injection | As required |
| 1N HCl Solution | 0-5 mL/kg to adjust pH |
| 10N NaOH Solution | 0-2 mL/kg to adjust pH |

The composition of e-RDF-1 Medium is below:

| Component | Concentration (mg/L) |
| --- | --- |
| Cupric Sulfate 5 $H_2O$ | 0.0008 |
| Ferrous Sulfate 7 $H_2O$ | 0.220 |
| Magnesium Sulfate ($MgSO_4$) | 66.20 |
| Zinc Sulfate 7 $H_2O$ | 0.230 |
| Sodium Pyruvate | 110.0 |
| DL-Lipoic Acid Thioctic | 0.050 |
| Linoleic Acid | 0.021 |
| L-Alanine | 6.68 |

-continued

| Component | Concentration (mg/L) |
| --- | --- |
| L-Arginine | 581.44 |
| L-Asparagine | 94.59 |
| L-Aspartic Acid | 39.93 |
| L-Cystine 2 HCl | 105.38 |
| L-Glutamic Acid | 39.7 |
| Glycine | 42.8 |
| L-Histidine HCl—H$_2$O | 75.47 |
| L-Isoleucine | 157.40 |
| L-Leucine | 165.30 |
| L-Lysine HCl | 197.26 |
| L-Methionine | 49.24 |
| L-Phenylalanine | 74.30 |
| L-Proline | 55.3 |
| L-Hydroxyproline | 31.5 |
| L-Serine | 85.10 |
| L-Threonine | 110.8 |
| L-Tryptophan | 18.40 |
| L-Tryosine 2 Na 2H$_2$O | 108.10 |
| L-Valine | 108.9 |
| Para Amino Benzoic Acid | 0.51 |
| Vitamin B12 | 0.339 |
| Biotin | 1.00 |
| D-Ca Pantothenate | 1.29 |

The table is continued below:

| Component | Concentration (mg/L) |
| --- | --- |
| Choline Chloride | 12.29 |
| Folic Acid | 1.96 |
| i-Inositol | 46.84 |
| Niacinamide | 1.47 |
| Pyridoxal HCl | 1.00 |
| Pyridoxine HCl | 0.420 |
| Riboflavin | 0.21 |
| Thiamine HCl | 1.59 |
| Putrescine 2HCl | 0.020 |

The 127-G cell culture medium used in the T-flask and spinner flasks in the process is prepared in medium vessels equipped with an agitator for mixing and a graduated sight glass for volume determination. The batch size of Medium 127-G used in the T-flask and spinner flask inoculum expansion steps is 75 L. Medium 127-G is prepared using Water For Injection (WFI). Solid and liquid medium components are added to the WFI. The medium is mixed for the required period of time after the addition of each component. WFI is added to bring the medium to the final batch volume of 75 L. A sample is removed from the final medium preparation and the glucose concentration, pH, and osmolality of the sample are measured to ensure that the medium meets the defined acceptance criteria. The medium is filtered through a 0.2 µm filter and dispensed into sterile polyethylene terephthalate glycol (PETG) bottles. The Medium 127-G prepared for the T-flask and spinner flask inoculum expansion steps is stored at 2° to 8° C. for a maximum of 42 days. Medium 127-G for the 140-L and 1100-L seed bioreactor steps is prepared in vessels equipped with an agitator for mixing. The batch size of Medium 127-G used in the 140-L seed bioreactor step is 120 L. The vessel used to prepare the medium for the 140-L seed bioreactor is equipped with a graduated sight glass for volume determination. The batch size of Medium 127-G used in the 1100-L seed bioreactor step is 600 kg. The vessel used to prepare the medium for the 1100-L seed bioreactor is equipped with a differential pressure transmitter for weight determination.

The required volumes of Medium 127-G are transferred to the 140-L and 1100-L seed bioreactors through consecutive 0.2 ∝m and 0.1 µm filters. The Medium 127-G prepared for the 140-L and 1100-L seed bioreactor steps may be held at 37° C. for a maximum of 48 hours. The medium may be held at 4° C. for an additional 84 hours.

Preparation of 127-G and 117-E Cell Culture Media Used in a 5000-L Production Bioreactor Step.

Medium 127-G for the 5000-L production bioreactor step is prepared in a medium preparation vessel equipped with an agitator and differential pressure transmitter for weight determination. The batch size of Medium 127-G used in the 5000-L production bioreactor step is 2900 kg. The required volume of Medium 127-G is transferred to the 5000-L production bioreactor through consecutive 0.2 µm and 0.1 µm filters. The Medium 127-G prepared for the 5000-L production bioreactor step may be held at 37° C. for a maximum of 48 hours. The medium may be held at 4° C. for an additional 84 hours.

Feed medium 117-E is prepared in a medium preparation vessel equipped with an agitator for mixing and a differential pressure transmitter for weight determination. The batch size of Medium 117-E used in the 5000-L production bioreactor step is 1800 kg. The Medium 117-E components are added to a specified weight of WFI in the medium preparation vessel. The medium is mixed for the required period of time after the addition of each component. WFI is added to bring the medium to the specified final weight. A sample is removed from the final medium preparation and the glucose concentration, pH, and osmolality of the sample measured in order to ensure that the medium meets the defined acceptance criteria. The required volume of Medium 117-E is transferred to a feed medium holding tank through consecutive 0.2 µm and 0.1 ∝m filters. The Medium 117-E prepared for the 5000-L production bioreactor step may be held at 37° C. for a maximum of 2 days. The medium may be held at 4° C. for an additional 4 days.

Inoculum Expansion Steps in the T-Flask and Spinner Flask Inoculum Expansion Steps The objective of the T-flask and spinner flask inoculum expansion steps of the CTLA4-Ig production process is to serially propagate cells from the cell bank vial to provide a sufficient number of viable cells to inoculate the 140-L seed bioreactor. A single vial from the cell bank is removed from the vapor phase of a liquid nitrogen storage freezer and thawed in a water bath at 37° C. The entire contents of the vial are aseptically transferred into a sterile 15-mL conical centrifuge tube. Medium 127-G is added to bring the final volume to 10 mL. The cell suspension is centrifuged, the supernatant discarded and the cell pellet resuspended in 10 mL of 127-G cell culture medium. The resuspended cells are transferred to a T-175 flask containing 10 mL of Medium 127-G. The viable cell density and the percent viability of the culture in the T-175 flask are determined. The percent viability at this step of 84% was established. Medium 127-G is added to the T-175 flask to achieve a target viable cell density of $2.1 \times 10^5$ cells/mL.

The T-175 flask is incubated at 37° C. in an atmosphere of 6% carbon dioxide for a maximum of four days to achieve a target final cell number of $1.80 \times 10^7$ viable cells. Following the T-175 flask step, the culture is expanded using a series of 0.25-L, 1-L, and 3-L spinner flask steps. At each passage, the cells are seeded at a target density of $2.0 \times 10^5$ viable cells/mL. The spinner flask cultures are incubated at 37° C. in an atmosphere of 6% carbon dioxide.

Cell culture material from the final 3-L spinner flask inoculum expansion step is pooled in a sterilized 20-L inoculum transfer vessel. The final viable cell density at the 3-L spinner flask inoculum expansion step of 1.0 to $2.0 \times 10^6$ cells/mL and a minimum percent cell viability of ≥80% were established. These exemplary values ensure that a sufficient number of viable cells is used to inoculate the 140-L seed bioreactor. A total volume of 12 L to 18 L of the pooled cell culture from the final 3-L spinner flask inoculum expansion step is used to inoculate the 140-L seed bioreactor.

140-L and 1100-L Seed Bioreactor Inoculum Expansion Steps

The objective of the 140-L and 1100-L seed bioreactor inoculum expansion steps of the CTLA4-Ig production process is to provide a sufficient number of viable cells to inoculate the 5000-L production bioreactor. The seed bioreactors are operated in batch mode using cell culture medium 127-G. Temperature, pH, dissolved oxygen, pressure, agitation and gas flow rates for air, oxygen, and carbon dioxide are controlled by a distributed control system (DCS) and provide conditions for optimal growth of the culture in the seed bioreactors. The seed bioreactors are operated at 37° C. Culture samples are removed from the seed bioreactors for the determination of viable cell density, percent viability and metabolite concentrations.

The 140-L seed bioreactor is inoculated with pooled inoculum from the 3-L spinner flask inoculum expansion step to a target initial viable cell density of $2.0 \times 10^5$ cells/mL. The final viable cell density at the 1100-L seed bioreactor inoculum expansion step of 1.0 to $2.5 \times 10^6$ cells/mL and a minimum percent cell viability of 80% were established. These acceptance criteria ensure that a sufficient number of viable cells is used to inoculate the 5000-L production bioreactor. The cell culture from the 1100-L seed bioreactor is transferred to the 5000-L production bioreactor to achieve a target initial viable cell density of $1.5 \times 10^5$ cells/mL.

Production Bioreactor Step

The objective of the 5000-L production bioreactor step is to expand the number of viable cells and to produce the CTLA4-Ig protein. The duration of the production bioreactor step is approximately 14 days. Inoculum from the 1100-L seed bioreactor is seeded into a 5000-L production bioreactor containing cell culture medium 127-G. The production bioreactor is operated in fed-batch mode. Temperature, pH, dissolved oxygen, pressure, agitation and gas flow rates for air, oxygen, and carbon dioxide are controlled by the DCS and provide conditions for optimal growth of the culture and production of the CTLA4-Ig protein in the production bioreactor.

A three-stage temperature control strategy is used during the 5000-L production bioreactor step to optimize cell growth and CTLA4-Ig production. The initial incubation temperature of the production bioreactor is controlled at 37° C. to achieve optimal cell growth. The temperature is lowered to 34° C. when a viable cell density of $4.0 \times 10^6$ cells/mL is achieved in the production bioreactor or at 144 hours from the time of inoculation, whichever occurs first. The temperature is lowered to 32° C. at 240 hours and maintained at 32° C. until harvest. Daily samples are obtained from the 5000-L production bioreactor to monitor cell growth, cell viability, metabolite concentrations, CTLA4-Ig titer and the sialic acid to CTLA4-Ig protein molar ratio.

Feeding of Medium 117-E to the production bioreactor is initiated between 12 to 24 hours from the time of inoculation. Medium 117-E is added daily to achieve a target of 1% (v/v) of feed medium to culture volume or a sufficient volume of the feed medium 117-E to bring the glucose concentration to 3 g/L. This feeding strategy provides sufficient levels of glucose and other nutrients to the culture to support the production of CTLA4-Ig protein during the production bioreactor step.

Medium 117-E is supplemented with D-galactose to promote increased glycosylation of CTLA4-Ig protein. Galactose supplementation results in an increase in the terminal sialic acid content of the CTLA4-Ig protein. The sialic acid to CTLA4-Ig protein molar ratio is an important harvest criterion in the CTLA4-Ig production process.

A three-stage strategy is also used to control the dissolved oxygen and agitation rate in the production bioreactor. The initial agitation rate of 30 rpm ensures uniformity of physical conditions and prevents settling of the cells within the 5000-L production bioreactor. The initial dissolved oxygen setpoint of 40% ensures availability of sufficient levels of dissolved oxygen to support the growth of the culture in the production bioreactor. The setpoints for dissolved oxygen and agitation rate are increased at 96 hours from the time of inoculation to 50% and 40 rpm, respectively. At 120 hours from the time of inoculation, the setpoints for dissolved oxygen and agitation rate are further increased to 60% and 50 rpm, respectively. This strategy ensures sufficient levels of dissolved oxygen to maintain the cell culture during the production bioreactor step. The titer of CTLA4-Ig protein increases during the course of the production bioreactor step. The culture viability is monitored throughout the course of this step. The sialic acid to CTLA4-Ig protein molar ratio is monitored twice daily from 6 days from the time of inoculation until the time of harvest. The sialic acid to CTLA4-Ig protein molar ratio peaks at approximately 10 at around day 8 from the time of inoculation and then decreases gradually over the remainder of the production bioreactor step. The primary harvest criterion for the production bioreactor is the sialic acid to CTLA4-Ig protein molar ratio. The production bioreactor is harvested at a target sialic acid to CTLA4-Ig protein molar ratio of 8.0.

A minimum cell viability value of 38% was also established for harvest of the culture. These harvest criteria ensure the consistency of the in-process harvest material for downstream processing to CTLA4-Ig drug substance. The total number of cell generations from the initiation of the inoculum expansion through the harvest of the production bioreactor in the CTLA4-Ig upstream production process is approximately 38 generations. The cell line used in the process was demonstrated to be stable for 105 generations in a cell line stability study.

Harvest Operation Steps

The objective of the harvest operation steps is to remove cells and cell debris from the harvest material and to concentrate the in-process stream containing CTLA4-Ig protein for further downstream processing. The MF and OF systems are sanitized prior to processing the harvest material. The MF and UF systems are flushed with a peracetic acid solution. The MF and UF systems are then treated with a bleach solution and a sodium hydroxide solution, respectively. Finally, the MF and UF systems are flushed with WFI until a conductivity of ≤3 μS/cm in the retentate and permeate is achieved. The cell culture broth from the 5000-L production bioreactor is transferred to a harvest vessel. Tangential flow MF with 0.65 μm polyvinylidene fluoride membranes is used for the removal of cells and cell debris from the in-process harvest material containing CTLA4-Ig protein. The cell-free MF permeate is collected in a permeate vessel. The cell-free MF permeate is simultaneously concentrated by tangential flow UF using polyethersulfone membranes of 30 kilodalton (kDa) nominal molecular weight cutoff. The UF permeate is used as the diafiltration medium for the MF process step. A 0.1 N phosphoric acid solution is used for storage of the MF system. A 0.1 N sodium hydroxide solution is used for storage of the OF system. Temperature, permeate and retentate flowrates and transmembrane pressures are monitored and controlled during the MF and UF operation. Flow rates are measured by in-line flowmeters present on the filtration skids. Sensors are used to measure pressure and temperature. The MF retentate flow rate of 163 to 235 L/min and the MF transmembrane pressure of ≤3.8 psig were established. These values ensure consistency in the performance of the harvest operation steps.

The final step in the harvest operation is a pH and conductivity adjustment of the clarified and concentrated in-process harvest material. The pH and conductivity of the concentrated in-process harvest material are adjusted for capture of the CTLA4-Ig protein during the first downstream chromatography processing step. The pH is adjusted to 8.0 by the addition of a 2 M Tris solution and the conductivity of the concentrated permeate is reduced to 10 mS/cm by the addition of WFI. The concentrated and adjusted in-process harvest material is then filtered through three parallel and one consecutive filter housing containing 0.2 μm disposable filters and transferred to a surge tank in the downstream purification area.

TABLE 31

Composition of CD-CHO Medium

| Component | Concentration |
|---|---|
| CD-CHO 25x Acid Solubles I | 40.0 mL/L |
| CD-CHO 25x Acid Solubles II | 40.0 mL/L |
| CD-CHO 25x Concentrate Salt I | 40.0 mL/L |
| CD-CHO 25x Concentrate Salt II | 40.0 mL/L |
| L-Glutamine | 0.585 g/L |
| r-human Insulin (10 mg/mL Solution) | 0.1 mL/L |
| Methotrexate (25 mg/mL Solution) | 0.0018 mL/L |
| Sodium Bicarbonate | 2.22 g/L |
| Water For Injection | As required |
| 1M HCl Solution | As required to adjust pH |
| 10N NaOH Solution | As required to adjust pH |

TABLE 32

Composition of eRDF Feed Medium

| Component | Concentration |
|---|---|
| eRDF-1 Medium | 16.80 g/L |
| Dextrose | 30.9 g/L |
| D-Galactose | 12.6 g/L |
| L-Glutamine | 4.10 g/L |
| r-human Insulin (10 mg/mL Solution) | 1.00 mL/L |
| TC Yeastolate | 5 g/L |
| Water For Injection | As required |
| 1M HCl Solution | As required to adjust pH |
| 10N NaOH Solution | As required to adjust pH |

TABLE 33

Composition of Modified 50% CD-CHO Medium

| Component | Concentration |
|---|---|
| CD-CHO 25x Acid Solubles I | 20.0 mL/L |
| CD-CHO 25x Acid Solubles II | 20.0 mL/L |
| CD-CHO 25x Concentrate Salt I | 20.0 mL/L |
| CD-CHO 25x Concentrate Salt II | 20.0 mL/L |
| D-Galactose | 0.4 g/L |

TABLE 33-continued

Composition of Modified 50% CD-CHO Medium

| Component | Concentration |
|---|---|
| r-human Insulin (10 mg/mL Solution) | 0.05 mL/L |
| Sodium Bicarbonate | 1.11 g/L |
| Water For Injection | As required |
| 1M HCl Solution | As required to adjust pH |
| 10N NaOH Solution | As required to adjust pH |

Example 29—CTLA4-Ig Purification Process

The final pH- and conductivity-adjusted material from the harvest operation step described in Example 28 is first processed using an anion exchange chromatography step. The product pool from this first anion exchange chromatography step is then processed using a hydrophobic interaction chromatography step. The CTLA4-Ig-containing material is then treated with Triton X-100 to inactivate potential adventitious viral agents. The Triton X-100-treated material is processed using a recombinant Protein A affinity chromatography step. The product pool from the recombinant Protein A chromatography step is concentrated and diafiltered. A viral filtration step for the removal of potential adventitious viral agents is then performed. The filtrate is further purified using a second anion exchange chromatography step. Finally, the purified CTLA4-Ig protein is concentrated and diafiltered into the final drug substance buffer.

CTLA4-Ig is a genetically-engineered fusion protein which consists of the functional binding domain of human Cytotoxic T-Lymphocyte Antigen-4 and the Fc domain of human monoclonal immunoglobulin of the IgG1 class. CTLA4-Ig dimer is comprised of two homologous glycosylated polypeptide chains of approximately 46 kDa each which are covalently linked through a single disulfide bond. A process flow diagram for the downstream steps of CTLA4-Ig production process is shown in FIG. 92. CTLA4-Ig is produced in 5000-L production bioreactors using a Chinese hamster ovary (CHO) cell line. Chromatographic and filtration steps in the downstream CTLA4-Ig production process are performed at ambient temperature. In-process material is stored at 2 to 8° C. between processing steps. The downstream process is initiated with the receipt of in-process harvest material from the harvest operation steps. This material is first processed through an anion exchange chromatography column using Q Sepharose™ Extreme Load (QXL) resin. The QXL column functions to capture the CTLA4-Ig protein from the harvest material. The QXL column capture step also accomplishes a volume reduction for further downstream processing.

The QXL product pool is passed through a hydrophobic interaction chromatography (HIC) column utilizing a Phenyl Sepharose Fast Flow resin. During this step, CLTA-Ig high molecular weight (HMW) material and Chinese hamster ovary host cell proteins (CHOP) are bound to the column. The CLTA4-Ig dimer protein does not bind to the HIC resin and passes through the column. Following the HIC step, a viral inactivation (VI) using Triton® X-100 detergent is performed to inactivate potential adventitious viral agents. The next step utilizes a recombinant Protein A Sepharose Fast Flow (rPA) resin affinity column. In this chromatography step, the levels of CHOP and monocyte chemotactic protein 1 (MCP-1) are reduced. The rPA step is defined as a viral clearance step. Following affinity chromatography step, the CLTA4-Ig protein is concentrated and dialyzed using 30 kDa ultrafiltration (UF) membranes and processed through Planova™ 15 nm filters to remove potential adventitious agents. Upon completion of the viral filtration (VF) step, the CLTA4-Ig protein is processed on a second anion exchange column using Q Sepharose Fast Flow (QFF) resin. The QFF chromatography step reduces residual recombinant protein A and DNA levels. The QFF step is defined as a viral clearance step. Finally, the CLTA4-Ig protein is concentrated and diafiltered using a 30 kDa UF membrane against a solution of 25 mM sodium phosphate, 50 mM NaCl, pH 7.5. The CLTA4-Ig drug substance is then filtered through a 0.2 µm filter prior to the final fill step.

The process-related impurities CHOP, MCP-1, residual recombinant protein A, DNA and Triton X-100 are reduced at specific downstream processing steps of the CTLA4-Ig production process. PPs with action limits are established at the primary in-process control point for each impurity.$_3$ Product pool CHOP and MCP-1 are identified as PPs for the rPA chromatography step. Product pool residual recombinant protein A ligand, DNA and Triton X-100 are identified as PPs for the QFF chromatography step. Based on the known structure and chromatographic retention of insulin, the HIC, rPA and QFF steps should provide significant clearance of insulin based on orthogonal modes of interaction. In addition, insulin, with a molecular weight of 5.8 kDa, should be cleared by the three 30 kDa concentration/diafiltration steps in the harvest and downstream process. The rPA step provides ≥3.0 $\log_{10}$ clearance of methotrexate (MTX). In addition, MTX, with a molecular weight of 0.455 kDa, should be cleared by the three 30 kDa concentration/diafiltration steps in the harvest and downstream process. Insulin and MTX are added to the fermentation media in fixed amounts and are consumed as a function of cellular metabolism during the 5000-L fermentation process prior to downstream processing. Insulin and MTX are measured at multiple points in the downstream process. The insulin and MTX levels at each of these points have been below the level of quantitation for past runs completed.

Buffers:

The objective of buffer preparation is to produce downstream processing buffers that meet exemplary values, action limits and alert limits. Consistent buffer quality is essential to ensure reproducible chromatographic performance. The downstream steps of CTLA4-Ig Process CD-CHO1 require 17 buffers and solutions. Buffers and solutions are prepared and used for specific processing steps within a lot. Buffers that have contact with the CTLA4-Ig in-process material are considered to be significant process buffers. The product-contact buffers include equilibration, wash, elution and product pool adjustment buffers. The buffers and solutions used in cleaning and sanitization steps and functional testing of the ultraviolet (UV) detectors in the chromatography skids have broad specification ranges. Due to the broad specification ranges for these buffers and solutions and the absence of product contact, no PPs are designated for these buffers and solutions. The PPs defined for the ten product-contact buffers and corresponding exemplary values are summarized. The maximum hold time limit for these buffers is three days, and is derived from the buffer vessel hold studies$_9$, and supported by the buffer stability studies. The product-contact buffers also have designated PPs with corresponding alert limits. The PPs and corresponding alert limits for these buffers are presented. Buffers and solutions that do not come into contact with CTLA4-Ig in-process material have designated PPs with alert or action limits and are presented. Non product-contact buffers and solutions are not tested for endotoxin because they are either sanitization solutions or chromatography resin cleaning buffers or solutions that are followed by column sanitization steps.

Q Sepharose Extreme Load Anion Exchange Chromatography Step.

Anion exchange chromatography is performed using QXL resin from GE Healthcare (formerly Amersham Biosciences). A 1.0 m inner diameter column is packed with QXL resin to a height of 17 to 24 cm, representing a volume of 133 to 188 L. The column is qualified for use by determining the height equivalent to a theoretical plate (HETP) and asymmetry (As) of the packed column. A HETP of 0.02 to 0.08 cm and an As of 0.8 to 1.2 are required for qualification of the QXL column. The QXL column functions to capture the CTLA4-Ig protein from the in-process harvest material. The QXL capture step also accomplishes a volume reduction for further downstream processing. The QXL column operation is carried out at ambient temperature. The clarified cell culture broth is loaded onto an equilibrated QXL column. The QXL chromatography step is performed using a maximum flow rate of 28 L/min. The column inlet pressure is maintained below 35 psig. The maximum abatacept protein load for the QXL column is 28 grams of abatacept per liter of resin. The column is prepared by equilibration with 25 mM HEPES, 100 mM NaCl, pH 8.0 buffer. Following column equilibration, the harvest material is loaded onto the column with continuous monitoring of the UV absorption of the effluent at 280 nm. Following load application, the column is washed with 25 mM HEPES, 120 mM NaCl, pH 8.0 buffer. The CTLA4-Ig protein is eluted from the column with 25 mM HEPES, 850 mM NaCl, pH 7.0 buffer. The table directly below shows process parameters for the Q Sepharose Extreme Load Chromatography Step.

| Parameter | Setpoint/Target Value | Action Limits | Acceptance Criteria |
|---|---|---|---|
| Protein Load$^{a,b}$ | N/A$^c$ | N/A | ≤28 g/L$_{resin}$ |
| Product Pool Bioburden$^a$ | N/A | N/A | <1 cfu/mL |
| Product Pool Endotoxin$^{b,d}$ | N/A | N/A | ≤50 EU/mL |

Harvest hold time ensures process consistency with alert limits established. The pre-filtration product pool bioburden parameter is assigned interim alert and action limits of <10 cfu/mL and <100 cfu/mL, respectively. The six QXL PPs defined by action limits are column height, flow rate, wash buffer conductivity, elution peak end optical density (OD), step yield and load bioburden. The column height range was established to provide sufficient volume of resin to capture the product from the harvest material. The action limits for this parameter were established from data. Flow rate is an important factor to ensure the consistency and performance of a chromatographic step. It is defined for the QXL step as a PP with a maximum action limit. The wash buffer conductivity is established to remove weakly bound impurities from the QXL resin. Scale-down ranging studies determined that this parameter is an important factor in maintaining the consistency of the QXL step. The elution peak end OD is defined to minimize the level of CTLA4-Ig HMW material in the product pool. CTLA4-Ig HMW material elutes at the end of the elution peak. The step yield action limits ensure process consistency for the QXL step. The action limits for flow rate, elution peak end OD and step yield PPs were established. Load bioburden is assigned an action limit of <1 cfu/mL. Twelve of the QXL PP are defined by alert limits as presented.

Buffer pH and conductivity values in the process are monitored. Buffers not meeting pH and conductivity exemplary values at the time of preparation are rejected and the buffer lot discarded. For the QXL step, equilibration buffer conductivity and pH, wash buffer pH, and elution buffer conductivity and pH are defined. Column inlet pressure ensures consistency during the bind-and-elute chromatography step. The QXL step is performed at a maximum pressure limit of 35 psig. The pressure limit of 35 psig is employed to prevent compression of the QXL resin in accordance with the manufacturer's specification. Product pool conductivity is a PP with an alert limit. Product pool conductivity is assigned an alert limit to ensure that the CTLA4-Ig HMW material and CHOP in the QXL product pool bind effectively to the subsequent HIC column. The alert limits of 58.5 to 69.1 mS/cm were established. Product pool titer, sialic acid (SA)N-acetylneuraminic acid (NANA) molar ratio, CTLA4-Ig HMW material and CHOP are assigned alert limits in order to ensure process consistency. Product pool titer and SA alert limits were established.

The in-process material from the harvest operation step is loaded onto the QXL column. The column is washed with a minimum of 10 CV of wash buffer (25 mM HEPES, 120 mM NaCl, pH 8.0), and the absorbance at 280 nm ($A_{280}$) of the column effluent is measured at the end of the wash step. The abatacept is then eluted from the column with a 25 mM HEPES, 850 mM NaCl, pH 7.0 buffer. The eluate is diverted into a collection vessel when the $A_{280}$ increases to ≥0.02 absorbance units (AU) above the AU value at the end of the wash step. The eluate is collected until the $A_{280}$ of the trailing edge of the elution peak decreases to a value of ≤1.0 AU. Elution buffer is added directly to the eluate collection vessel to achieve a target weight of 600±10 kg of the eluate. An agitation rate of 30±5 rpm in the eluate collection vessel is used to ensure that the contents are well-mixed. After a mixing period of ≥5 minutes, the contents of the collection vessel are filtered through a 0.2 cellulose acetate filter directly into a holding vessel. An additional ≤50 kg of elution buffer is added to the collection vessel and then filtered through the 0.2 μm cellulose acetate filter into the same holding vessel. The contents of the holding vessel are stored at 2° to 8° C. for up to 72 hours.

TABLE 5

Process Parameters for the
Q Sepharose Extreme Load Chromatography Step

| Parameter[a] | Setpoint/Target Value | Alert Limit | Action Limit |
|---|---|---|---|
| Harvest Hold Time[b] | N/A[c] | ≤10 hours | ≤24 hours |
| Prefiltration Product Pool Bioburden[d] | N/A | <10 cfu/mL | <100 cfu/mL |
| Column Height[e] | N/A | N/A | 17-24 cm |
| Flow Rate | 15-28 L/min | N/A | ≤28 L/min |
| Wash Buffer Conductivity[f] | N/A | N/A | 11.0-15.0 mS/cm |
| Elution Peak End OD | 1.00 AU[g] | N/A | 0.97-1.03 AU[h] |
| Step Yield | N/A | N/A | 69-107% |
| Load Bioburden[i] | N/A | N/A | <1 cfu/mL |
| Equilibration Buffer Conductivity | N/A | 10.7-12.7 mS/cm | N/A |
| Equilibration Buffer pH | N/A | 7.8-8.2 | N/A |

TABLE 5-continued

Process Parameters for the
Q Sepharose Extreme Load Chromatography Step

| Parameter[a] | Setpoint/Target Value | Alert Limit | Action Limit |
|---|---|---|---|
| Wash Buffer pH | N/A | 7.7-8.3 | N/A |
| Elution Buffer Conductivity | N/A | 69.8-77.1 mS/cm | N/A |
| Elution Buffer pH | N/A | 6.7-7.3 | N/A |
| Load Time[j] | N/A | ≤6 hour | N/A |
| Column Inlet Pressure | N/A | ≤35 psig | N/A |
| Product Pool Conductivity[k] | N/A | 58.5-69.1 mS/cm | N/A |
| Product Pool Titer | NA | ≥2.0 g/L | N/A |

Phenyl Sepharose Fast Flow Hydrophobic Interaction Chromatography Step

The primary objective of the HIC step is to reduce the level of CTLA4-Ig high molecular weight species (e.g., tetramer) present in the QXL product pool. The CTLA4-Ig tetramer does not bind to the HIC resin under the loading conditions used for the HIC step.

The HIC step is performed using a Phenyl Sepharose Fast Flow resin from GE Healthcare. The HIC column binds CTLA4-Ig HMW material and CHOP, thereby reducing their concentrations in the CTLA4-Ig protein stream. The HIC column is prepared by equilibration with 25 mM HEPES, 850 mM NaCl, pH 7.0 buffer. The CTLA4-Ig product pool from the QXL step is applied to the equilibrated column. Following load application, 25 mM HEPES, 850 mM NaCl, pH 7.0 buffer is applied to the column. CTLA4-Ig is collected from the column in the flowthrough and column chase fractions. The HIC column is operated in multiple cycles to process a single lot of CTLA4-Ig depending on the total mass of CTLA4-Ig in the QXL product pool. The column is cleaned and sanitized between cycles and lots.

The HIC load bioburden PP is defined by alert and action limits. The HIC load bioburden PP is assigned interim alert and action limits of <10 cfu/mL and <100 cfu/mL, respectively. The five HIC values defined for the column are column height, flow rate, chase end OD, step yield and load hold time. The column height was determined to provide sufficient resin volume to process the elution pool from the QXL column in one, two or three cycles per lot. The action limits for this parameter were established from data. Flow rate is an important factor to ensure the consistency and performance of a chromatographic step. It is defined for the HIC step as a process parameter with a maximum action limit. The chase end OD is defined to minimize the level of CTLA4-Ig HMW material in the product pool. CTLA4-Ig HMW material elutes at the end of the product peak. Process step yield ensures process consistency for the HIC step. The action limits for flow rate, chase end OD and step yield PPs were established. Action limits for load hold time ensure process consistency. The action limit for the load hold time PP of 5 days is supported by the product vessel hold time studies and the biochemical stability study. Nine HIC PPs are defined by alert limits as presented. Buffer pH and conductivity parameters in the downstream process are identified as PPs with alert limits. Buffers not meeting pH and conductivity exemplary values at the time of preparation are rejected and the buffer lot discarded. For the HIC step, the conductivity and pH of the equilibration/chase buffer are defined as PPs with alert limits.

Column inlet pressure ensures consistency during the chromatography step. The HIC step is performed at a maximum pressure limit of 13 psig. The pressure limit of 13 psig is employed to prevent compression of the HIC resin in accordance with the manufacturer's specification. The product pool titer and SA alert limits ensure process consistency and were established in the PAR report[12]. Product pool DNA, CHOP and MCP-1 are assigned alert limits at this step in order to facilitate the quantification of their removal in the subsequent rPA step.

TABLE 7

Process Parameters for the Phenyl Sepharose Fast Flow Hydrophobic Interaction Chromatography Step

| Parameter[a] | Setpoint/Target Value | Alert Limit | Action Limit |
|---|---|---|---|
| Load Bioburden[b] | N/A[c] | <10 cfu/mL | <100 cfu/mL |
| Column Height[d] | N/A | N/A | 18-22 cm |
| Flow Rate | 7.6-18 L/min | N/A | ≤18 L/min |
| Chase End OD | 1.0 AU[e] | N/A | 0.8-1.0 AU[e] |
| Step Yield | N/A | N/A | 55-79% |
| Load Hold Time | N/A | N/A | ≤5 days |
| Equilibration Chase Buffer Conductivity | N/A | 71.5-75.5 mS/cm | N/A |
| Equilibration/Chase Buffer pH | N/A | 6.7-7.3 | N/A |
| Load Tank Temperature | 22° C. | 19-25° C. | N/A |
| Column Inlet Pressure | N/A | ≤13 psig | N/A |
| Product Pool Titer | N/A | ≥1.0 g/L | N/A |
| Product Pool SA NANA Molar Ratio | N/A | 6.8-11.4 | N/A |
| Product Pool CHOP[f] | N/A | ≤6600 ng/mL | N/A |
| Product Pool DNA[f] | N/A | ≤45,000,000 pg/mL | N/A |
| Product Pool MCP-1[g] | N/A | ≤5600 ng/mL | N/A |

[a]Information was obtained from Table 2 in PAR Final Report: Purification[12].

Viral Inactivation Step:

Inactivation of potential adventitious viral agents in the product pool from the HIC step is achieved by the addition of 20% Triton X-100 to a final concentration of 0.5% (v/v). The detergent-treated solution is mixed and held at 22±3° C. for one to four hours before proceeding to the next step. The five PPs defined for the VI step are presented. The upper limit of the 20% Triton X-100 addition parameter is 3.8%. See the Table directly below showing process parameters for the viral inactivation step.

| Parameter | Setpoint/Target Value | Action Limit | Acceptance Criteria |
|---|---|---|---|
| 20% Triton X-100 Addition[a,b] | 2.5% (volume % of HIC pool) | N/A[c] | 1.3-3.8% (volume % of HIC pool) |
| Duration of Mixing[d] | N/A | N/A[c] | ≥20 minutes |
| Agitation Rate[d] | 30 rpm | 25-35 | ≥20 rpm |
| Product Pool Bioburden[b] | N/A | N/A | <1 cfu/mL |
| Product Pool Endotoxin[b,e] | N/A | N/A | ≤5.0 EU/mL |

TABLE 9

Process Parameters for the Viral Inactivation Step

| Parameter[a] | Setpoint/Target Value | Alert Limit | Action Limit |
|---|---|---|---|
| Tank Temperature at Triton X-100 Addition[a,b] | 22° C. | 19-25° C. | 2-25° C. |
| Load Hold Time[c] | N/A[d] | N/A | ≤5 days |

TABLE 9-continued

Process Parameters for the Viral Inactivation Step

| Parameter[a] | Setpoint/Target Value | Alert Limit | Action Limit |
|---|---|---|---|
| Triton X-100 Incubation Time[a,b] | N/A | N/A | 1-4 hours |
| Step Yield[a] | N/A | N/A | 94-108% |

[a]Information was obtained from Table 3 in PAR Final Report: Purification[12].

Recombinant Protein A Sepharose Fast Flow Affinity Step.

Affinity chromatography is performed using an immobilized rPA resin from GE Healthcare. The rPA chromatography step further purifies the CTLA4-Ig protein by reducing the levels of CHOP, MCP-1 and potential adventitious viral agents. The affinity chromatography column is equilibrated with 25 mM Tris, 250 mM NaCl, pH 8.0 buffer. After equilibration of the column, the Triton X-100 treated material from the VI step is applied to the affinity chromatography column. The column is first washed with 25 mM Tris, 250 mM NaCl, 0.5% Triton X-100, pH 8.0 buffer, followed by a second wash with 25 mM Tris, 250 mM NaCl, pH 8.0 buffer. The CTLA4-Ig protein is eluted from the column with 100 mM Glycine, pH 3.5 buffer. The pH of the product pool from the affinity column is adjusted to 7.5±0.2 with 2 M HEPES, pH 8.0 buffer. The four PPs defined for the rPA step are presented in Table 10. The rPA chromatography step was identified as a viral clearance step, thus, column bed height was established as a new PP with exemplary values of 21 to 25 cm. Product pool CHOP and product pool MCP-1 were previously identified as PPs for the rPA step. These impurities were redefined as PPs with action limits. See the Table directly below showing process parameters for the recombinant Protein A Sepharose Fast Flow Chromatography Step.

| Parameter[a] | Setpoint/Target Value | Action Limit | Acceptance Criteria |
|---|---|---|---|
| Column Height[b] | N/A[c] | N/A | 21-25 cm |
| Protein Load | N/A | N/A[c] | ≤25 g/L$_{resin}$ |
| Product Pool Bioburden | N/A | N/A | <1 cfu/mL |
| Product Pool Endotoxin[d] | N/A | N/A | ≤0.50 EU/mL |

[a]Information was obtained from Table 4 in PAR Final Report: Purification[12].

Three PPs for the rPA step are defined by both alert and action limits, as presented. Load hold time ensures process consistency with alert limits established in the PAR report. Action limits for load hold time ensure process consistency. The action limit for the load hold time PP of ≤48 hours is supported by the product vessel hold time studies and the biochemical stability study. Ranging studies identified elution buffer pH as a significant factor affecting the level of CTLA4-Ig HMW material in the rPA product pool. The alert limits for the elution buffer pH were established. The action limit for the elution buffer pH was established from the scale-down ranging study. The rPA load bioburden PP was assigned interim alert and action limits of <10 cfu/mL and <100 cfu/mL, respectively.

The seven rPA PPs defined by action limits are column inlet pressure, flow rate, step yield, product pool initial pH, product pool HMW, product pool CHOP and product pool MCP-1. The pressure limit of ≤13 psig is employed to prevent compression of the rPA resin in accordance with the manufacturer's specification. Flow rate is an important factor to ensure the consistency and performance of a chromatographic step. It is defined for the rPA step as a PP with a maximum action limit. The action limits for step yield and product pool initial pH ensure process consistency for the rPA step. Action limits for flow rate and product pool initial pH were established. The potential formation of CTLA4-Ig HMW material during peak elution necessitates the definition of an action limit of ≤2.5% for this parameter. The action limit range of 66 to 108% was established using the mean±3 standard deviations data from a single lot of rPA resin. This range is consistent with the step yields observed in the resin lifetime study. The process-related impurities CHOP and MCP-1 were previously identified as PPs for the rPA step. In this report, these impurities were redefined as PPs with action limits. Product pool CHOP and MCP-1 are defined as CQAs with exemplary values to ensure control of these process-related impurities. Twelve of the rPA PPs are defined by alert limits as presented. Buffer pH and conductivity parameters in the downstream process are identified as PPs with alert limits. Buffers not meeting pH and conductivity exemplary values at the time of preparation are rejected and the buffer lot discarded. For the rPA step, equilibration/wash 2 buffer conductivity and pH, wash 1 buffer conductivity and pH, and elution buffer conductivity are defined as PPs with alert limits.

TABLE 11

Process Parameters for the Recombinant Protein A Fast Flow Chromatography Step

| Parameter[a] | Setpoint/Target Value | Alert Limit | Action Limit |
|---|---|---|---|
| Load Hold Time[b] | N/A[c] | ≤43 hours | ≤48 hours |
| Elution Buffer pH | N/A | 3.4-3.7 | 3.2-3.8 |
| Load Bioburden[d] | N/A | <10 cfu/mL | <100 cfu/mL |
| Column Inlet Pressure | N/A | N/A | ≤13 psig |
| Flow Rate | 6.7-9.6 L/min | N/A | ≤9.6 L/min |
| Step Yield | N/A | N/A | 66-108% |
| Product Pool Initial pH | N/A | N/A | ≥5.8 |
| Product Pool HMW | N/A | N/A | ≤2.5% |
| Product Pool CHOP | N/A | N/A | ≤380 ng/nL |
| Product Pool MCP-1 | N/A | N/A | ≤38 ng/mL |
| Equilibration/Wash 2 Buffer Conductivity | N/A | 23.0-27.0 mS/cm | N/A |
| Equilibration/Wash 2 Buffer pH | N/A | 7.8-8.2 | N/A |
| Wash 1 Buffer Conductivity | N/A | 22.2-27.4 mS/cm | N/A |
| Wash 1 Buffer pH | N/A | 7.7-8.2 | N/A |
| Elution Buffer Conductivity | N/A | 0.5-1.5 mS/cm | N/A |
| Product Pool Final pH | 7.5 | 7.3-7.7 | N/A |
| Product Pool Titer | N/A | ≥6.0 g/L | N/A |
| Product Pool SA NANA Molar Ratio | N/A | 8.0-11.0 | N/A |
| Product Pool Volume after pH Adjustment[e] | N/A | 127-294 kg | N/A |
| Product Pool DNA | N/A | ≤47000 pg/mL | N/A |
| Product Pool Residual Recombinant Protein A[f] | N/A | ≤160 ng/mL | N/A |
| Product Pool Triton X-100[g] | N/A | ≤4.0 μg/mL | N/A |

[a]Information was obtained from Table 4 in PAR Final Report: Purification[12].

Concentration/Diafiltration and Viral Filtration Step.

Upon elution from the rPA column, the product pool is concentrated to achieve a target volume within a limit of CTLA4-Ig concentration. The concentrate is then subjected to diafiltration with 25 mM HEPES, 100 mM NaCl, pH 8.0 buffer using a UF system with 30 kDa nominal molecular weight cutoff (NMWC) membranes. Following diafiltration, a filter train is used to remove potential adventitious viral particles. The filter train consists of a 0.2 μm filter, a 0.1 μm filter and 15 nm membrane filters (Planova 15N filter). Filters used in the VF step (0.2 μm, 0.1 μm, and 15 nm) are single-use filters. The upper limit of the range for post-UF CTLA4-Ig concentration and Planova differential pressure were increased based on the demonstrated viral clearance using these conditions. See table below for showing Process Parameters for the Viral Filtration Step.

| Parameter | Setpoint/Target Value | Action Limit | Acceptance Criteria |
|---|---|---|---|
| Post-UF Abatacept Concentration[a,b] | N/A[c] | N/A | 6.0-22 g/L |
| Load Volume to Surface Area Ratio[a] | ≤36 kg/m² | N/A | ≤100 kg/m² |
| Planova Differential Pressure[a,d] | N/A | N/A | ≤14 psid |
| Product Pool Bioburden[e] | N/A | N/A | <1 cfu/mL |
| Product Pool Endotoxin[e,f] | N/A | N/A | ≤0.50 EU/mL |

TABLE 13

Process Parameters for the Viral Filtration Step

| Parameter[a] | Setpoint/Target Value | Alert Limit | Action Limit |
|---|---|---|---|
| UF I Product Pool Bioburden[b] | N/A[c] | <10 cfu/mL | <100 cfu/mL |
| Difiltration Volumes | N/A | N/A | ≥5.0 |
| Step Yield | N/A | N/A | 86-114% |
| Load Hold Time[d] | N/A | N/A | ≤5 days |
| UF[e] Feed Pressure | N/A | ≤35 psig | N/A |
| UF[e] Retentate Flow | N/A | 2.5-7.5 L/min | N/A |
| Filtrate Conductivity | N/A | 10.7-12.7 mS/cm | N/A |

[a]Information was obtained from Table 5 in PAR Final Report: Purification[12].
[b]Information was obtained from BD-2005-706.0[15].

Q Sepharose Fast Flow Anion Exchange Chromatography Step.

The objective of the QFF chromatography step is to reduce the residual Protein A levels and provide additional reduction of host cell DNA from the viral filtration step product pool. The QFF column step is also used to control the sialic acid to CTLA4-Ig molecules or protein molar ratio of the QFF chromatography step product pool and to provide additional control of the HMW material levels. The QFF anion exchange chromatography step also can remove residual recombinant protein A, host cell DNA, Triton X-100 and potential adventitious viral agents.

Anion exchange chromatography is performed using QFF resin from GE Healthcare. The QFF column is equilibrated with 25 mM HEPES, 100 mM NaCl, pH 8.0 buffer. After column equilibration, the Planova filtrate is applied to the QFF column. The column is first washed with 25 mM HEPES, 120 mM NaCl, pH 8.0 buffer followed by a second wash with 25 mM HEPES, 130 mM NaCl, pH 8.0 buffer. The CTLA4-Ig protein is eluted from the column with 25 mM HEPES, 200 mM NaCl, pH 8.0 buffer.

| Parameter[a] | Setpoint/Target Value | Action Limit | Acceptance Criteria |
|---|---|---|---|
| Column Height[a,b] | N/A[c] | N/A | 28-35 cm |
| Protein Load[a] | N/A | N/A | ≤25 g/L$_{resin}$ |

-continued

| Parameter[a] | Setpoint/Target Value | Action Limit | Acceptance Criteria |
|---|---|---|---|
| Product Pool Bioburden[d] | N/A | N/A | <1 cfu/mL |
| Product Pool Endotoxin[a,d] | N/A | N/A | ≤0.50 EU/mL |

The QFF load bioburden value is <10 cfu/mL or <100 cfu/mL, respectively. The twelve QFF PPs defined by action limits are flow rate, wash 2 buffer conductivity, elution buffer conductivity, load hold time, step yield, and the levels of residual Protein A, DNA, Triton X-100, SA, HMW, CHOP and MCP-1 in the QFF product pool. Flow rate is a factor to consider in ensuring the consistency and performance of a chromatographic step. It is defined for the QFF step as a process parameter with a maximum action limit established in the PAR report. The conductivity values of the wash 2 and elution buffers are PPs with action limits, because they are significant in determining step yield and product quality. The action limits for these parameters were determined during scale-down QFF ranging studies. Action limits for load hold time ensure process consistency. The action limit for the load hold time PP of ≤5 days is supported by product vessel hold time studies and a biochemical stability study. Step yield ensures process consistency for the QFF step. The quality parameters, product pool SA, HMW, CHOP and MCP-1 must be tightly controlled on the final chromatographic step. The action limits for the step yield, and the level of SA, CHOP and MCP-1 in the QFF product pool were established. The process-related impurities residual protein A, DNA and Triton X-100 were previously identified as PPs for the QFF step. These impurities were redefined as PPs with action limits. Residual protein A, DNA and Triton X-100 are defined as CQAs with exemplary values to ensure control of these process-related impurities. In this example, the action limit for product pool HMW was revised from ≤2.5 to ≤2.0%.

Buffer pH and conductivity parameters in the downstream process are identified as PPs with alert limits. Buffers not meeting pH and conductivity exemplary values at the time of preparation are rejected and the buffer lot discarded. For the QFF step, equilibration buffer conductivity and pH, wash 1 buffer conductivity and pH, wash 2 buffer pH and elution buffer pH are defined as PPs with alert limits. These limits were established. Column inlet pressure ensures consistency during the bind-and-elute chromatography step. The QFF step is performed at a maximum pressure limit of 35 psig according to the manufacturer's specification. The parameters wash 1 buffer volume, wash 2 buffer volume, product pool titer and product pool volume are assigned alert limits[12] to ensure process consistency.

TABLE 15

Process Parameters for the Q Sepharose Fast Flow Chromatography Step

| Parameter[a] | Setpoint/Target Value | Alert Limit | Action Limit |
|---|---|---|---|
| Load Bioburden[b] | N/A[c] | <10 cfu/mL | <100 cfu/mL |
| Flow Rate[d] | 4.8-8.7 L/min | N/A | ≤8.7 L/min |
| Wash 2 Buffer Conductivity[e] | N/A | N/A | 12.8-15.2 mS/cm |
| Elution Buffer Conductivity[e] | N/A | N/A | 18.5-20.9 mS/cm |
| Load Hold Time[f] | N/A | N/A | ≤5 days |
| Step Yield | N/A | N/A | 65-104% |
| Product Pool Residual Recombinant Protein A | N/A | N/A | ≤9.5 ng/mL |
| Product Pool DNA[g] | N/A | N/A | ≤20 pg/mL |
| Product Pool Triton X-100[h] | N/A | N/A | ≤4.0 µg/mL |
| Product Pool SA NANA Molar Ratio | N/A | N/A | 8.0-11.9 |
| Product Pol HMW | N/A | N/A | ≤2.0% |
| Product Pool CHOP | N/A | N/A | ≤95 ng/mL |
| Product Pool MCP-1 | N/A | N/A | ≤9.5 ng/mL |
| Equilibration Buffer Conductivity | N/A | 10.5-12.9 mS/cm | N/A |
| Equilibration Buffer pH | NA | 7.7-8.3 | N/A |
| Wash 1 Buffer Conductivity | N/A | 12.4-14.4 mS/cm | N/A |
| Wash1 Buffer pH | N/A | 7.7-8.3 | N/A |
| Wash 2 Buffer pH | N/A | 7.7-8.3 | N/A |
| Elution Buffer pH | N/A | 7.7-8.3 | N/A |
| Column Inlet Pressure | N/A | ≤35 psig | N/A |
| Wash 1 Buffer Volume | N/A | 5.0-5.3 CV | N/A |
| Wash 2 Buffer Volume | N/A | 5.0-5.4 CV | N/A |
| Product Tool Titer | N/A | ≥0.65 g/L | N/A |
| Product Pool Volume | N/A | ≤800 kg | N/A |

[a]Information was obtained from Table 6 in PAR Final Report: Purification[12].

Concentration/Diafiltration and Fill Steps.

The product pool from the QFF anion exchange chromatography step is concentrated and subjected to diafiltration with 25 mM sodium phosphate, 50 mM NaCl, pH 7.5 buffer using a UF system with 30 kDa NMWC membranes. The diafiltered concentrate is filtered through a 0.2 µm filter into sterile containers and stored at 2 to 8° C. The drug substance may be frozen at −70° C. and stored at −40° C., if required. The single PP defined for the concentration/diafiltration and fill step is presented. See the Table directly below showing Process Parameters for the Drug Substance Concentration/Diafiltration and Fill Steps.

| Parameters | Setpoint/Target | Action Limits | Acceptance Criteria |
|---|---|---|---|
| Final Concentration[a,b] | 50 g/L | 48-52 g/L | 45-55 g/L |

The UF II product pool bioburden PP is assigned interim alert and action limits of <10 cfu/mL and <50 cfu/mL, respectively. The six PPs defined by action limits for the concentration/diafiltration and fill step are diafiltration volumes, filtrate conductivity and pH, step yield, load hold time, and process yield as presented. The lower limit of diafiltration volumes was established to ensure complete buffer exchange of the CTLA4-Ig protein into the final drug substance buffer prior to the fill step. Filtrate conductivity and filtrate pH further ensure consistent drug substance formulation. Step yield ensures process consistency for the concentration/diafiltration and fill step. The action limits for diafiltration volumes, filtrate conductivity and pH, and step yield were established. Action limits for load hold time ensure process consistency. The UF II load hold time of ≤5 days is supported by the product vessel hold time studies and the biochemical stability study. The process yield action limit of 20 to 62% was recommended. Two PPs are defined by alert limits to ensure process consistency for the step, as presented.

TABLE 17

Process Parameters for the Drug Substance Concentration/Diafiltration and Fill Steps

| Parameters[a] | Setpoint | Alert Limit | Action Limit |
|---|---|---|---|
| UF II Product Pool Bioburden[b] | N/A[c] | <10 cfu/mL | <50 cfu/mL |
| Diafiltration Volumes | N/A | N/A | ≥5.0 |
| Filtrate Conductivity | N/A | N/A | 8.3-10.3 mS/cm |
| Filtrate pH | N/A | N/A | 7.3-7.7 |
| Step Yield | N/A | N/A | 73-110% |
| Load Hold Time[d] | N/A | N/A | ≤5 days |
| Process Yield[e] | N/A | N/A | 20-62% |
| UF Feed Pressure | N/A | ≤35 psig | N/A |
| UF Retentate Flow | N/A | 2.5-7.5 L/min | N/A |

[a]Information was obtained from Table 7 in PAR Final Report: Purification[12].

Example 30: Drug Substance Final Fill Step

After completion of the concentration and diafiltration II step of CTLA4-Ig, the CTLA4-Ig drug substance is filled from the 300-L bioprocess bag into pre-sterilized 2-L and 10-L Biotainer PC bottles within a Class 100 environment.

The exterior of each bottle is disinfected with a 70% isopropanol solution. The seal from around the cap of each bottle is removed and the bottle is tared prior to filling. A calculation is recorded in the batch record to ensure that the fill weight is between 500 grams to 1950 grams for 2-L bottles and between 7500 grams to 10200 grams for 10-L bottles. The drug substance is dispensed using a peristaltic pump into the Biotainer bottles through a single-use 0.45/0.2 μm filter and filling bell. The bottles are capped and the caps tightened to a specified torque setting. The cap of each filled bottle is sealed with tape and the tape is initialed and dated. Each bottle is labeled with identifying information as well as the date of fill, the sequential number of the filled bottle within the lot and the initials of the operator.

During the filling process, air and surface microbial monitoring and particle counts are performed. Drug substance samples are obtained during the filling operation. One sample is obtained prior to the fill of the first bottle for endotoxin testing. Additional samples for endotoxin testing are obtained in the middle and at the end of the filling process. During the filling process, a sample is obtained for drug substance release testing.

Example 31: Immunogenicity Studies

CTLA4-Ig is a soluble fusion protein that consists of the extracellular domain of human cytotoxic T-lymphocyte-associated antigen 4 (CTLA-4) linked to the modified Fc (hinge, CH2 and CH3 domains) portion of human immunoglobulin (Ig) G1. It is the first in a new class of agents approved for the treatment of rheumatoid arthritis (RA) that selectively modulates the CD80/CD86:CD28 co-stimulatory signal employed for full T-cell activation. In RA, it is postulated that an unknown antigen is presented via the major histocompatibility complex and activates autoreactive T cells in the presence of a co-stimulatory signal. Subsequently, activated T cells recruit and activate downstream immune cells, orchestrating and perpetuating the cellular processes that lead to inflammation and joint destruction (Choy and Panayi (2001) *N Engl J Med*, 344(12):907-916).

Therapeutic recombinant biologic agents, such as CTLA4-Ig, can be immunogenic and therefore have the potential to elicit an antibody response. Immunogenicity against biological agents can theoretically impact safety, efficacy and pharmacokinetics. Antibody-mediated clearance of a biologic therapy may result in a reduction in drug levels, resulting in decreased efficacy. The antibody response may also prevent the drug from binding to its pharmacologic target, which will also decrease efficacy. This can lead to a need for dose escalation over time—so-called 'dose creep.' Dose creep has been reported with the prolonged use of the anti-TNF antibody, infliximab, in the treatment of RA (Anderson (2005) *Semin Arthritis Rheum*, 34(5 Suppl1):19-22) and this has recently been noted as being a result of anti-infliximab antibodies leading to a reduction in clinical efficacy in some patients (Haraoui et al., (2006) *J Rheumatol*, 33(1):31-36).

Here, the formation of anti-CTLA4-Ig and anti-CTLA-4 antibodies, and their potential effect on the efficacy and safety of CTLA4-Ig treatment were examined. Since CTLA4-Ig is likely to inhibit an immune response to itself, based on its activity as a selective co-stimulation modulator and responses observed in non-clinical models, the effect of missing 1-2 doses or discontinuing therapy on the level of immunogenicity was also examined. Finally, seropositive samples were tested for neutralizing antibody activity.

Materials and Methods

Studies Evaluated

To determine whether CTLA4-Ig induces an immunogenic response in patients with RA, an antibody response was assessed across multiple Phase II and III clinical trials, comprising six DB and four OL study periods in 2,237 RA patients, which included patients who had inadequate responses to methotrexate (MTX) or anti-TNF therapy. One study (Phase IIa) also assessed CTLA4-Ig for the treatment of RA as monotherapy (Table 40). Samples were generally evaluated pre-study, throughout treatment, and 56 and/or 85 days following the last dose to allow time for clearance of CTLA4-Ig.

TABLE 40

Overview of the studies included in this evaluation

| Phase Study No. | Study design | Background anti-rheumatic therapy | Patients in comparator group | No. of patients randomized and treated with CTLA4-Ig | | Total |
|---|---|---|---|---|---|---|
| | | | | 10 mg/kg or fixed dose | Other doses (mg/kg) | |
| Trials in RA patients with an inadequate response to MTX | | | | | | |
| Phase II IM101 100 | Randomized, dose-ranging, placebo-controlled, DB trial in patients with active RA while on MTX | Days 1-180: MTX (10-30 mg/wk) Day 181-360: Adjustment allowed (+1 other non-biologic RA therapy) | 119 | 115 | 105 (2.0) | 339 |
| Phase III IM101 102 | Randomized, placebo-controlled, DB inpatients with active RA while on MTX | Days 1-169: MTX (10-30 mg/wk) Days 170-365: Adjustment allowed (+1 other non-biologic RA therapy) | 219 | 433 | 0 | 652 |
| Trials in RA patients with an inadequate response to TNF blocking agents | | | | | | |
| Phase III IM101 029 | Randomized, placebo-controlled, DB trial inpatients with active RA on background DMARDs who have failed therapy with TNF-blocking agents due to lack of efficacy | Days 1-169: Any non-biologic RA therapy or anakinra | 133 | 258 | 0 | 391 |
| Safety study in RA | | | | | | |
| Phase III IM101 031 | Randomized, placebo-controlled, DB safety study in patients with RA (with or without pre-existing comorbidities) on background DMARDs and/or biologics | Days 1-85: Stable doses: ±Non-biologic RA therapy ±Biologic RA therapy Days 86-365: Adjustment allowed: ±Non-biologic RA therapy ±Biologic RA therapy | 482 | 959 | 0 | 1441 |
| Other supportive studies | | | | | | |
| Phase II IM101 101 | Randomized, placebo-controlled, DB trial in patients with active RA while on ETAN | Days 1-180: ETAN (25 mg 2x/wk) Days 181-360: Adjustment allowed (±ETAN, +1 non-biologic DMARD) | 36 | 0 | 85 (2.0) | 121 |
| Phase IIa IM103 002 | Randomized, dose-ranging, placebo-controlled, DB trial in RA patients who failed at least 1 | None | 32 | 33 | 26 (0.5) 32 (2.0) | 122 |

TABLE 40-continued

Overview of the studies included in this evaluation

| Phase Study No. | Study design | Background anti-rheumatic therapy | Patients in comparator group | No. of patients randomized and treated with CTLA4-Ig ||| Total |
|---|---|---|---|---|---|---|---|
| | | | | 10 mg/kg or fixed dose | Other doses (mg/kg) | | |
| | DMARD or ETAN; 85 days; follow-up through Day 169 | | | | | | |
| | PK trials in healthy patients in RA program | | | | | | |
| Phase II IM101 017 | OL, uncontrolled, single-dose, PK study in healthy patients | None | 0 | 30 | 0 | | 30 |
| | OL extensions in RA | | | | | | |
| Phase II IM101 100 | OL, uncontrolled trial; 84, 68, and 67 patients from previous DB 10 mg/kg, 2 mg/kg, and placebo arms, respectively | Day 361+: MTX ±1 Non-biologic RA therapy | 0 | 219* | 0 | | 219 |
| Phase II IM101 101 | OL, uncontrolled trial; 58 and 22 patients from previous DB 2 mg/kg and placebo arms, respectively | Day 361+: ±ETAN ±1 Non-biologic RA therapy | 0 | 80* | 0 | | 80 |
| Phase III IM101 029 | OL, uncontrolled trial; 218 and 99 patients from previous DB 10 mg/kg, and placebo arms, respectively | Days 170+ Any non-biologic RA therapy or anakinra | 0 | 317* | 0 | | 317 |
| Phase III IM1011 02 OL | OL, uncontrolled trial; 378 and 161 patients from previous DB 10 mg/kg and placebo arms, respectively | Day 360+ MTX (10-30 mg/wk) +1 non-biologic RA therapy | 0 | 539* | 0 | | 539 |

RA = rheumatoid arthritis;
MTX = methotrexate;
DB = double-blind;
TNF = tumor necrosis factor;
DMARD = disease-modifying antirheumatic drug;
ETAN = etanercept;
OL = open-label;
PK = pharmacokinetic
*Subjects in the OL, uncontrolled periods are a subset of those who completed the DB, placebo-controlled study periods The incidence and type of prespecified peri-infusional adverse events (AEs), overall AEs and serious AEs (SAES), and discontinuations were examined in patients who developed a positive antibody response against CTLA4-Ig or CTLA-4. The effect of immunogenicity on efficacy was also examined by evaluating American College of Rheumatology (ACR) 20 and Health Assessment Questionnaire responses in patients with a positive antibody response.

Immunogenicity Assays
Basic Assay Formats:
Because of high, pre-existing cross-reactivity directed against the Fc portion of CTLA4-Ig in human serum, particularly in RA populations, two direct-format enzyme-linked immunosorbent assays (ELISAs) were used to evaluate the antibody response. The anti-CTLA4-Ig assay measured the antibody response to all portions of the molecule, but had lower sensitivity. The anti-CTLA-4 assay measured the antibody response to the CTLA-4 portion only, removing the Ig region and thus conferring greater sensitivity. Both assays were used in either an endpoint titer (EPT) format (Assay A) or a screening format (Assay B).

Assay A Format: Phase II Double-Blind Clinical Immunogenicity Assay Methods

The anti-CTLA4-Ig assay and the anti-CTLA-4 assay used during Phase II RA trials were collectively referred to as Assay A. In Assay A, CTLA4-Ig or CTLA-4 was adsorbed onto 96-well microtiter plates that were then incubated with test serum (3-fold serial dilutions starting at 1:10). Bound antibodies were detected using an alkaline-phosphatase conjugated anti-human antibody cocktail (Southern Biotech, Birmingham, US) and visualised using a p-NitroPhenyl Phosphate (PNPP) substrate. Since no human anti-CTLA4-Ig antibodies or positive control serum were available, these assays were validated using CTLA4-Ig-specific anti-sera generated in a cynomolgus monkey. Results from each assay were expressed as EPT values. A patient was considered to have seroconverted when his/her EPT increased by two or more serial dilutions (≥9-fold) relative to that individual's pre-dose (Day 1) EPT.

Assay B Format: Phase III and Phase II Open-Label Clinical Immunogenicity Assay Methods For the Phase III trials, and 2-year Phase II OL periods, both the anti-CTLA4-Ig and anti-CTLA-4 assays were modified to reduce non-specific background, improve sensitivity, and the method to determine positivity was changed and were collectively referred to as Assay B. These assays were also validated using CTLA4-Ig-specific antibodies purified from cynomolgus monkey anti-serum. For each ELISA, 96-well microtiter plates coated with CTLA4-Ig (0.25 µg/mL) or CTLA-4 (0.5 µg/mL), were incubated with test serum diluted 1:400 for 2 hours at 22±5° C. (anti-CTLA4-Ig) or diluted 1:25 for 2 hours at 32-40° C. (anti-CTLA-4). After the primary incubation, bound antibodies were detected with a horseradish-peroxidase (HRP) conjugated anti-human antibody cocktail, followed by tetramethylbenzidine substrate.

Results for the anti-CTLA4-Ig assay were expressed as a post-/pre-ratio calculated by dividing post-dose sample OD values by the corresponding pre-dose sample OD value analyzed on the same plate. Positivity was based on cut-off values established using placebo-treated RA patient samples. If the ratio value was less than the cut-off, the sample was considered negative and reported as a titer value <400. Any value that exceeded this cut-off was considered conditionally positive.

Results for the anti-CTLA-4 assay were expressed as a 'Ratio 1' value calculated by dividing the mean patient serum sample OD by the mean OD of the negative control on the same plate. Positivity was based on values established using pooled serum from placebo-treated RA patients as the negative control. If the value was less than the specified cut-off, the sample was considered negative and reported as a titer value of <25. Any value that exceeded this cut-off was considered conditionally positive.

Confirmatory Analyses

Conditionally positive samples identified in each assay (anti-CTLA4-Ig and anti-CTLA-4) and in each assay format (Assays A and B), were evaluated in an immunodepletion assay to determine specificity of the response. Anti-CTLA4-Ig positive samples were pre-incubated with approximately 40 µg/mL of either CTLA4-Ig (the CTLA-4 portion of the molecule), another unrelated Ig fusion protein (CD40Ig) or an unrelated protein (ovalbumin) to identify the region of the molecule against which the anti-CTLA4-Ig reactivity might be directed (CTLA-4, Ig or junction region). Anti-CTLA-4 positive samples were similarly pre-incubated with either CTLA4-Ig, the CTLA-4 portion or ovalbumin to confirm the specificity of the anti-CTLA-4 reactivity. Following pre-incubation, all samples were re-analyzed in the same original assay format described above. Samples where the pre-incubation resulted in 30% reduction in OD of the pre-incubated sample compared with the untreated sample, were considered confirmed positives. If confirmed, samples were titrated to identify the serum dilution that results in a ratio value equal to the cut-off of the particular assay and this value was reported as the EPT.

Neutralizing-Antibody Activity Assessments

A bioassay was conducted to assess the ability of patient samples with drug-specific antibodies against CTLA-4 to inhibit or neutralize the activity of CTLA4-Ig (inhibit binding to CD80/86), by preventing it from binding CD80/86 on the T cell surface. Stable Jurkat T-cell transfectants expressing a luciferase gene under the control of the interleukin (IL)-2 promotor were co-stimulated with Daudi B-cells in the presence of anti-CD3 antibody. This co-stimulation, mediated through the interaction between CD28 on the Jurkat T cell and CD80/86 on the Daudi B cell in combination with anti-CD3 antibody, activates the IL-2 promoter, leading to increased transcription of the luciferase gene and, hence, increased luciferase protein expression. The luminescent signal is measured using a Luciferase Assay System. Since CTLA4-Ig blocks the CD80/86:CD28 interaction, adding CTLA4-Ig to the cell mixture blocks this IL-2 promoter activation and decreases luminescence, whereas pre-incubation with a neutralizing antibody would restore the co-stimulation interactions and result in an increase in luminescence.

CTLA4-Ig neutralizing antibody activity was evaluated by determining the CTLA4-Ig response at concentrations of 0.1, 0.25 or 0.5 µg/mL in the bioassay in the presence of 1:25 post-dose seropositive serum and statistically comparing it to the response in the presence of its corresponding Day 1 sample. An anti-human CTLA-4 murine monoclonal antibody (11D4) with CTLA4-Ig-neutralizing activity in the bioassay was used as a positive control in each analytical run. Owing to limitations inherent in the bioassay test method, only post-dose samples with existing levels of CTLA4-Ig µg/mL could be evaluated, since higher drug levels interfered with the neutralizing response, and further sample dilution would decrease assay sensitivity.

Pharmacokinetic Evaluation

Population pharmacokinetic (POPPK) analysis was performed on serum sample data from patients from the DB periods of the Phase II/III trials where a positive immune response was confirmed. The validated POPPK model was applied to individual patient serum concentration data and maximum a posteriori Bayesian estimates of individual PK parameter values were obtained. The distribution of clearance, volume estimates, steady-state area under curve (AUC) values, and minimum concentration of the drug in the body after dosing ($C_{min}$) values for these patients were compared with the distribution of these values in a larger data set of patients from the same trials who did not develop an immune response.

Results

Incidence of Anti-CTLA4-Ig and Anti-CTLA-4 Responses

Figure 38:
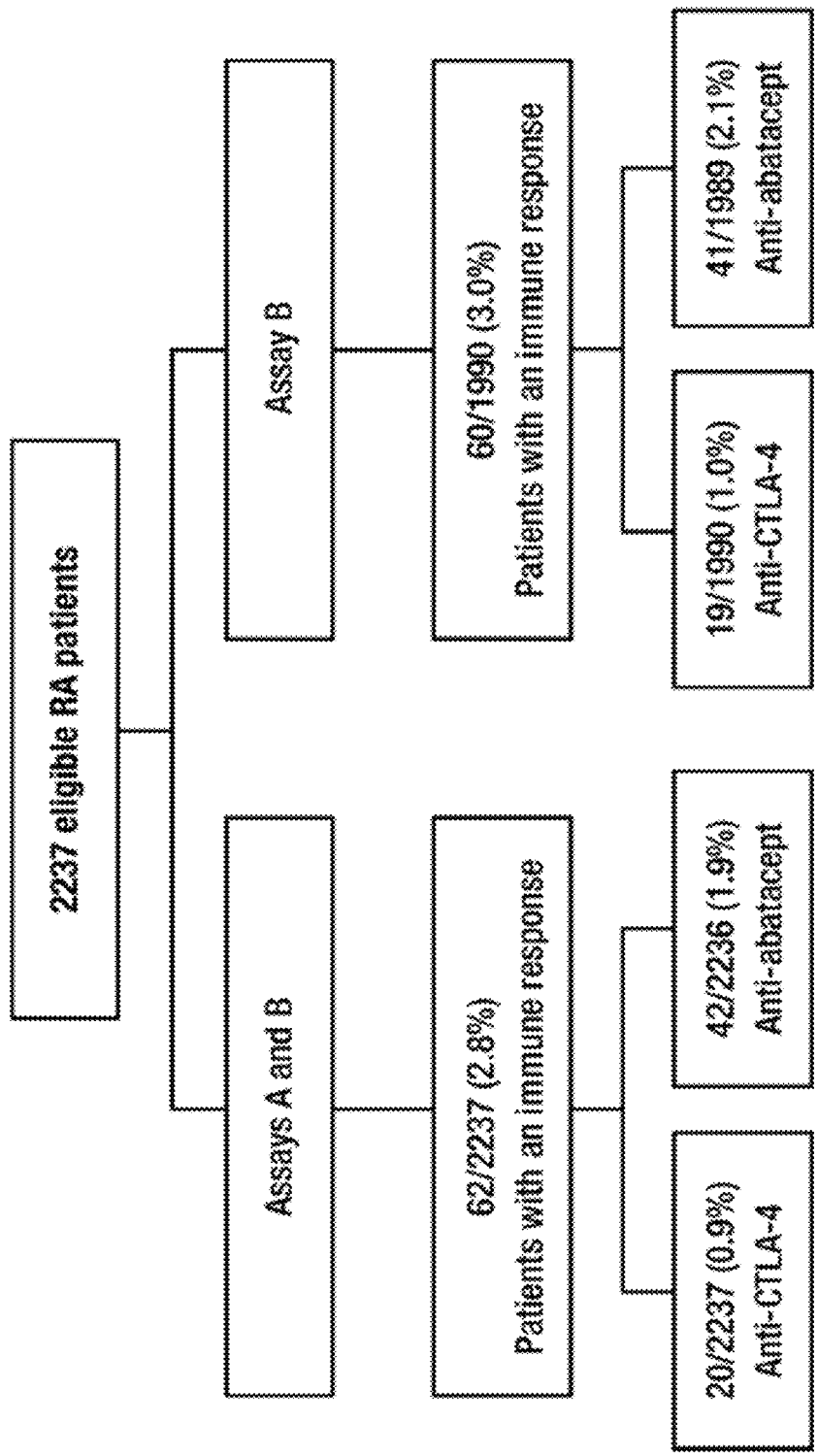
FIG. 38 is a diagram that depicts patients with anti-CTLA4-Ig or anti-CTLA-4 responses. Antibody response to the whole CTLA4-Ig molecule (CTLA-4 and Ig portion) and the CTLA-4 portion only were determined using Assays A and B, as outlined in the Example 32.

A total of 2,237 patients had both pre- and post-baseline serum samples and were eligible for assessment. Of these, 62 (2.8%) patients had evidence of an anti-CTLA4-Ig or anti-CTLA-4 response, as determined using Assay A or B (FIG. 38). No patients demonstrated an immune response to both the Fc and CTLA-4 domains of CTLA4-Ig. Three patients had a response to the junction region. When the more sensitive Assay B was used, an antibody response to CTLA4-Ig was detected in 60 of 1,990 patients (3.0%) (FIG. 38).

Of the patients evaluated in the Phase III studies (n=1, 764), 203 discontinued CTLA4-Ig therapy during the DB or OL periods, or did not enter into the subsequent OL study period and had sera collected 56 and/or 85 days after discontinuation of therapy. Of the 203 patients, 15 (7.4%) had an immunopositive response to either CTLA4-Ig (whole molecule; n=5, 2.5%) or CTLA-4 (n=10, 4.9%; Table 42). Of the remaining 1,561 RA patients who completed the Phase III DB period and continued into OL treatment, 40 (2.6%) had a positive antibody response during the DB or OL periods: 33 (2.1%) to CTLA4-Ig and 7 (0.4%) to CTLA-4. Interestingly, in the Phase IIa study of CTLA4-Ig as monotherapy, no patients seroconverted for CTLA4-Ig or the CTLA-4 portion of the molecule; however, the less sensitive Assay A format was employed.

A total of 191 patients had a more than 30-day period without CTLA4-Ig between their participation in the DB and OL periods. Of these, 3 (1.6%) patients had a positive antibody response to CTLA4-Ig and 1 (0.5%) patient had a positive antibody response to CTLA-4 during the OL period (Table 41). Sera were also analyzed from 587 RA patients who missed 1-2 doses of study medication and restarted at any point during the study. Of these patients, 15 (2.6%) demonstrated a positive antibody response to CTLA4-Ig and seven (1.2%) had a positive antibody response to CTLA-4 (Table 41).

TABLE 41

Number (%) of seropositive patients with interrupted use of CTLA4-Ig

| Description of interruption in scheduled CTLA4-Ig use | Number positive responses/number evaluated (%) | | |
|---|---|---|---|
| | Anti-CTLA4-Ig | Anti-CTLA-4 | Total |
| Missed 1-2 doses and restarted use of CTLA4-Ig | 15/587 (2.6) | 7/587 (1.2) | 22/587 (3.7) |
| >30 days without CTLA4-Ig between DB and OL periods | 3/191 (1.6%) | 1/191 (0.5%) | 4/191 (2.1%) |
| Discontinued during Phase III of the DB (sera collected 56 and 85 days after dosing) | 5/203 (2.5) | 10/203 (4.9) | 15/203 (7.4) |

CTLA-4 = cytotoxic T-lymphocyte-associated antigen-4;
DB = double-blind;
OL = open-label Effect of Concomitant Methotrexate on Immunogenicity A total of 2451 patients received concomitant MTX and 493 patients did not. Overall, the percentage of patients with a positive antibody response to CTLA4-Ig was generally similar whether they were receiving concomitant MTX or not (2.3% vs 1.4%) (Table 42).

TABLE 42

Number of patients (%) with anti-CTLA4-Ig or anti-CTLA-4 responses with or without receiving concomitant methotrexate.

| Concomitant Treatment | Number of positive patients/number evaluated (%) | | |
|---|---|---|---|
| | Anti-CTLA4-Ig | Anti-CTLA-4 | Total |
| Methotrexate | 40/2451 (1.6) | 16/2451 (0.6) | 56/2451 (2.3) |
| No Methotrexate | 2/493 (0.4) | 5/493 (1.0) | 7/493 (1.4) |

CTLA-4 = cytotoxic T-lymphocyte-associated antigen-4

Impact of Immunogenicity on the Safety and Efficacy of CTLA4-Ig

The rates of AEs, SAES, peri-infusional AEs for all positive patients were assessed and no relationship between immunogenicity and safety was observed. Similarly, no relationship between immunogenicity and efficacy was noted; however, interpretation of these data is restricted due to the limited number of patients who seroconverted.

Neutralizing Activity of Anti-CTLA-4 Antibodies

Twenty-four serum samples from 20 patients were confirmed positive for anti-CTLA-4 reactivity in the anti-CTLA-4 antibody screening assay. Of these, 14 samples (collected from 13 patients) met the exemplary values (≤1 μg/mL CTLA4-Ig) for evaluation in the neutralization bioassay. Of these 13 samples, 1 was positive at Day 56 and 10 were positive at Day 85 post-dose. Nine of the 14 samples (taken from 8 patients) exhibited neutralizing antibody activity. With the exception of septicemia in one patient, there were no medically significant AEs reported in these patients at, or near, the time of seroconversion that were considered related or possibly related to therapy in these eight patients. Efficacy data were not collected during the period following study discontinuation (56 and 85 days after discontinuation), a period when the predominant number of samples were suitable for evaluation of neutralizing antibodies. As such, it was not possible to evaluate the effects of neutralizing antibodies on efficacy.

Pharmacokinetic Evaluation

Figure 39:
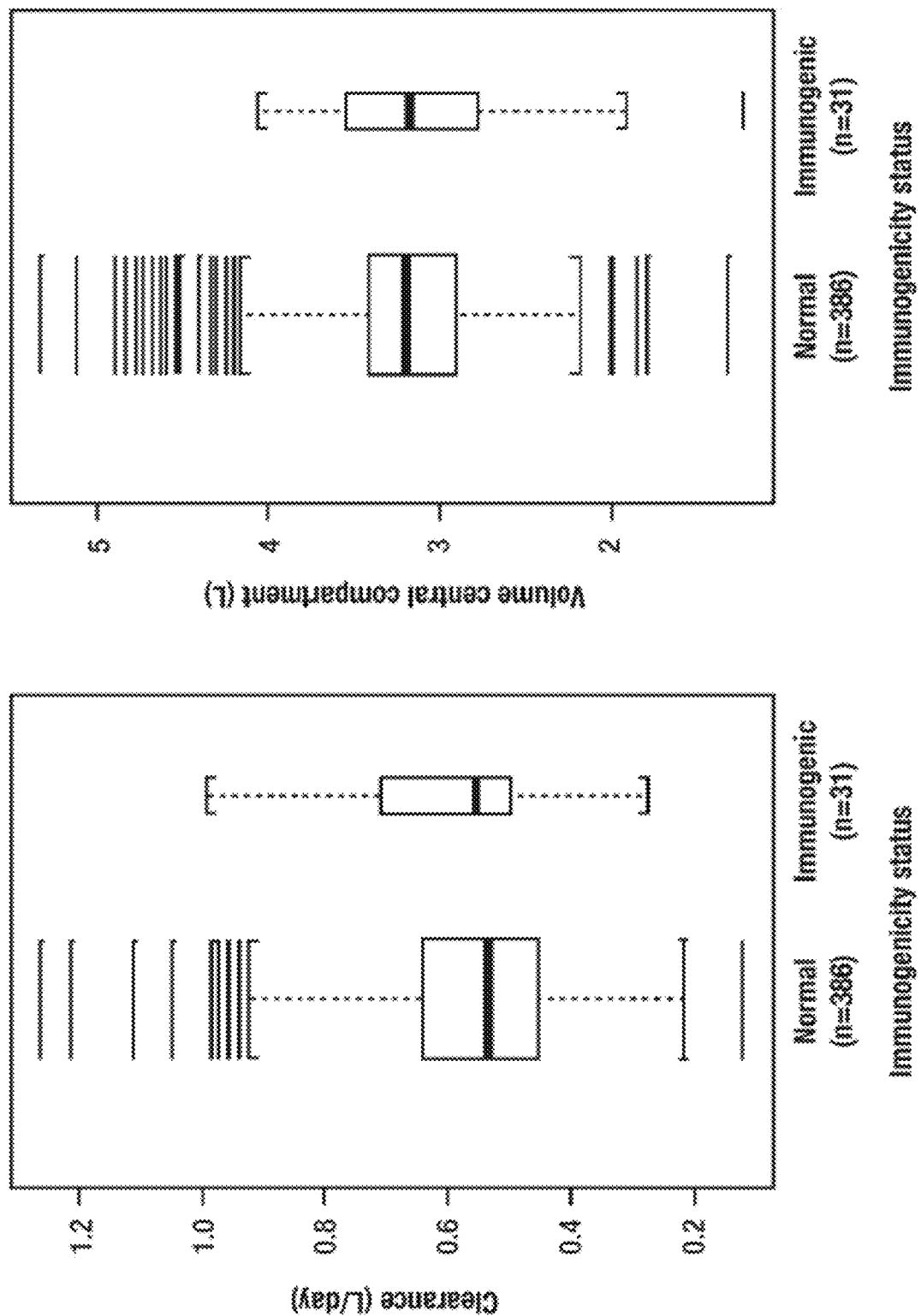
FIG. 39 is a schematic demonstrating the distribution of clearance and the volume of central compartment by immunogenicity status.

Pharmacokinetic parameters were estimated for 31 of the 32 patients who had a positive antibody response during the DB period of the Phase II/III trials. Sera samples for PK analysis were not necessarily collected on the day that a positive immune response was documented. Population PK modelling of patient data from the DB study periods suggested that the predicted PK parameters in the 31 immunopositive patients were comparable to those in a larger population of patients (n=386) without a positive immune response. Trough serum concentrations on the study day during the DB period when seroconversion was documented ranged from 1.16-24.21 μg/mL, with the majority of serum concentrations between 5-20 μg/mL. Seroconversion did not appear to affect serum trough levels. Distribution of clearance and volume of central compartment by immunogenicity status is shown in FIG. 39.

MSD Electrochemiluminescence Assay.

In an effort to improve the sensitivity of the binding immunogenicity assay and the ability to detect antibodies in the presence of drug (drug tolerance), a new generation of immunogenicity assays is being developed to monitor anti-drug antibodies to CTLA4-Ig by employing the Meso-Scale Discovery (MSD) technology. This new technology uses a label that emits light upon electrochemical stimulation initiated at the electrode surface of a microplate. The MSD format has been shown to have improved sensitivity and a better ability to detect antibodies in the presence of drug compared to the ELISA format. This solution-phase technology allows the labeled drug to more efficiently compete with the drug in the serum, and has a greater dynamic range, signal to noise ratio, and increased surface capacity over the ELISA format. Unlike the current ELISAs, which use either the CTLA4 portion of the molecule or the whole molecule as the capture reagent, the new assay is a bridging assay that employ a biotinylated and ruthenium-labeled CTLA4-Ig molecule that is incubated with patient samples prior to being added to an avadin-coated MSD plate. The electrochemiluminescence signal emitted by the ruthenium tag is measured using an MSD instrument. Positive samples, based on the validated assay cut-point, will be further evaluated by immunodepletion with either CTLA4-Ig, CTLA4-T, or CD40Ig in the MSD assay to confirm positivity and demonstrate to what portion of the CTLA4-Ig molecule the immunogenicic response is directed, and endpoint titer is defined.

Example 32: Pharmacokinetic Parameters in Monkeys

Six female cynomolgus monkeys per group were administered a single intravenous 10-mg/kg dose of CTLA4-Ig produced from the CD-CHO1 process. A control group of six female monkeys received saline (1 ml/kg). To assess bioactivity of CTLA4-Ig, all monkeys were immunized intramuscularly with 10 mg/animal of the T-cell-dependent antigen keyhole limpet hemocyanin (KLH) within 30 min prior to dosing.

Animals were observed for 6 weeks following treatment. Blood samples were obtained predose; at 3 and 30 min; at 1, 2, 4, 8, 24, and 48 hr; and on days 4, 8, 11, 15, 22, 29, 36, and 43 postdose to determine and compare the pharmacokinetic profiles. In the pharmacokinetic report, these study days correspond to days 0, 1, 2, 3, 7, 10, 14, 21, 28, 35, and 42, respectively. Serum samples were analyzed for CTLA4-Ig by a ELISA method. A comparable blood sample was collected from control animals on the same days and, when appropriate, used to assess the anti-KLH antibody response. Assessment of the formation of CTLA4-Ig-specific antibodies was performed on serum obtained from CTLA4-Ig-treated animals prestudy and weekly thereafter. KLH-specific antibody formation was determined on serum samples obtained from all animals prior to immunization and approximately weekly thereafter for 4 weeks postimmunization. Additional exemplary values for evaluation included survival, clinical signs, physical examinations (including neurologic, respiratory rate and auscultation assessments), body weights, body temperatures, and food consumption.

Clinical-pathology evaluations were conducted prestudy and on day 45. All animals were returned to stock following completion of the study.

TABLE 43

Pharmacokinetic parameters of CTLA4-Ig produced from a process of the invention.

| BMS-188667 Process (Lot Number) | Cmax (µg/mL) | AUC(0-T)[b] (µg · h/mL) | T-HALF (H) | CLT (mL/h/kg) | Vss (mL/kg) |
|---|---|---|---|---|---|
| CD-CHO1 (Lot #MQJ611) | 330.22 (53.52) | 19916.75 (3123.04) | 121.47 (19.57) | 0.50 (0.08) | 73.40 (12.59) |

Figure 40:
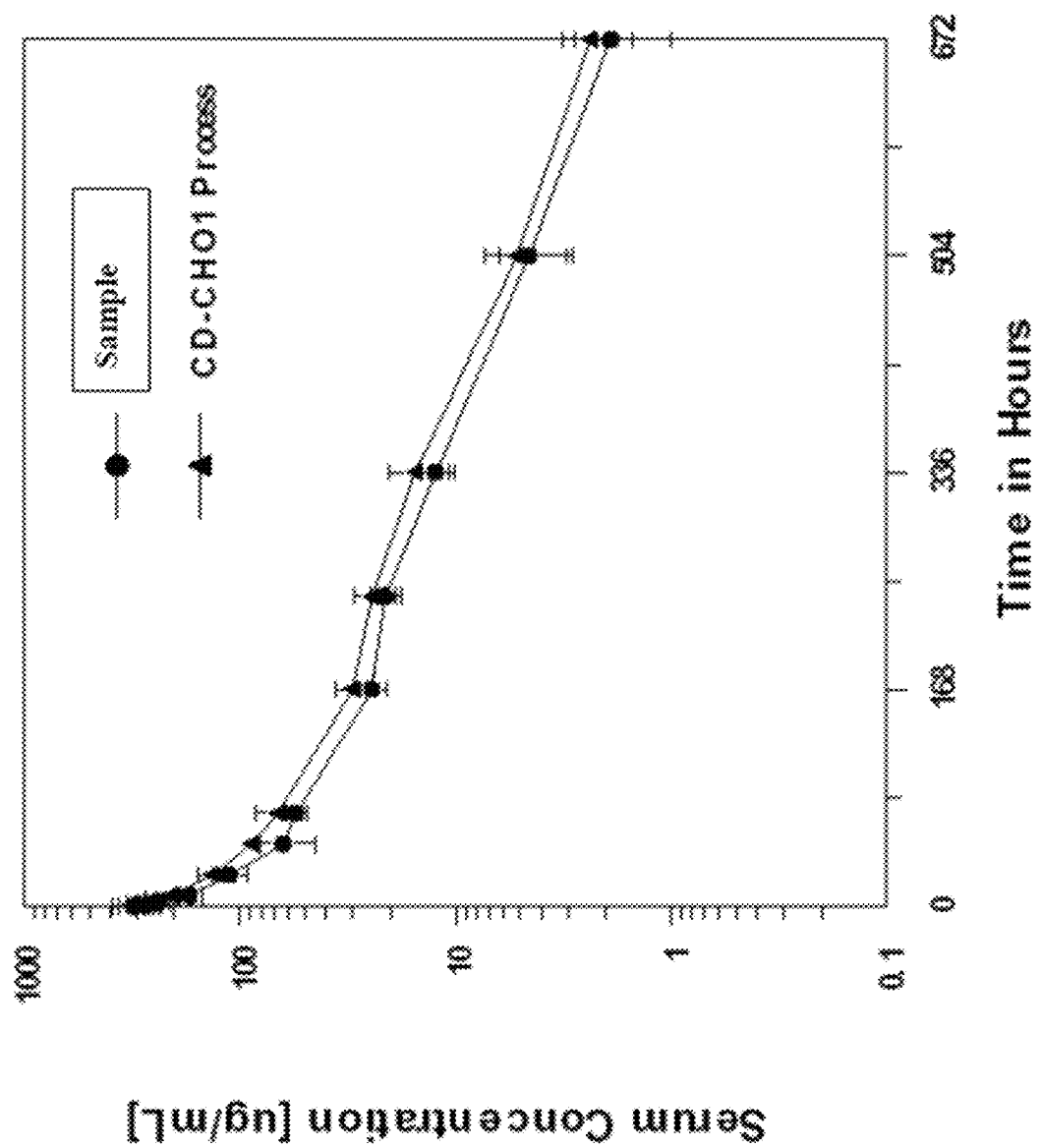
FIG. 40 is a graph demonstrating profiles of mean (SD) CTLA4-Ig serum concentrations over time in monkeys adminstered 10 mg/kg of drug substance produced by a process of the invention.

Drug-specific antibody responses occurred on or after day 29 in three of six monkeys treated with the CD-CHO1-process material (Table 43; FIG. 40). Minimal increases (20%) in blood urea nitrogen (BUN) and decreases (14%) in serum potassium in monkeys treated with the CD-CHO1 process material were not physiologically or toxicologically meaningful because values were only marginally outside historical control ranges and, for BUN, a concomitant increase in serum creatinine was not present. No other changes in clinical pathology parameters were noted. Marked suppression of the KLH antibody response (≥94% of the peak control response) was observed in monkeys administered the CD-CHO1 process material. Immunogenicity was markedly delayed until CTLA4-Ig serum levels fell below immunosuppressive levels of approximately 1 µg/mL on or after day 29.

Clinical Pathology. Blood samples were collected from the femoral vein of fasted animals prior to dosing (day −13) and following the last pharmacokinetic bleeding (day 45). Urinalyses were performed on urine collected over an 18-hr period prestudy (day −13) and following the last pharmacokinetic sampling (day 45). The following analytical parameters were determined: Hematology: Hemoglobin, hematocrit, erythrocyte count, mean corpuscular volume, mean corpuscular hemoglobin, mean corpuscular hemoglobin concentration, reticulocyte count, total and differential leukocyte counts, platelet count, and evaluation of cell morphology in peripheral blood smears were determined. Coagulation: Prothrombin time, activated partial thromboplastin time, and plasma fibrinogen were determined. Serum Chemistry: Urea nitrogen, creatinine, glucose, total cholesterol, total protein, albumin, globulins, albumin/globulin ratio, alanine aminotransferase, aspartate aminotransferase, alkaline phosphatase, total bilirubin, triglycerides, gamma glutamyltransferase, sodium, potassium, calcium, chloride, and phosphorus were determined. Urinalysis: Output, specific gravity, pH, color and appearance, and qualitative determinations of glucose, protein, ketones, bilirubin, occult blood, and urobilinogen were determined. Urinary sediments were examined microscopically.

Specific Antibody Response. Drug-specific antibody responses of comparable magnitude occurred in three of six monkeys treated with the CD-CHO1 process material, on or after day 29. As expected, immunogenicity with the process was markedly delayed until CTLA4-Ig serum levels fell below immunosuppressive levels of approximately 1 µg/mL on or after day 29. The mean CTLA4-Ig-specific antibody responses for monkeys given CD-CHO1 process material became positive on day 36 and peaked on day 43 (the last time point assessed). Peak antibody titers in individual monkeys given the CD-CHO1 process materials ranged from 23 to 10,448.

Example 33: On-Column Disaggregation

The disaggregation process across an affinity chromatography resin is useful and has applicability to all IgG-Fc based recombinant molecules produced in mammalians cells. Chaotropes can be used to disrupt high molecular weight protein or material. This disaggregation can be done on-column for any such protein. This example provides a method for performing the disaggregation process on an exemplary material: i.e., CTLA4-Ig.

CTLA4-Ig high molecular weight (HMW) material produced in the production bioreactor can be partially converted into the functional CTLA4-Ig dimer by the use of chaotropic agents either in solution (batch mode) or in conjunction with the affinity chromatographic step (on-column mode). This process is referred to as "disaggregation." Based on analytical characterization studies of disaggregated CTLA4-Ig material, the disaggregated material appears to be biochemically comparable to control material not subjected to disaggregation process.

In a fermentation process producing CTLA4-Ig molecules of the present invention, approximately 20 to 25% of the resulting CTLA4-Ig protein can be in the form of HMW material (i.e., aggregate). Recovering a portion of this material as a functional dimer, therefore, has the potential of an overall process yield enhancement of ≥10%.

Batch Mode Disaggregation Process

Disaggregation has been demonstrated in batch mode (in solution) by treatment with moderate concentrations of chaotropic agents such as guanidine hydrochloride or urea followed by rapid dilution into a low salt refolding buffer to help the molecule gain its native conformation.

Figure 41:
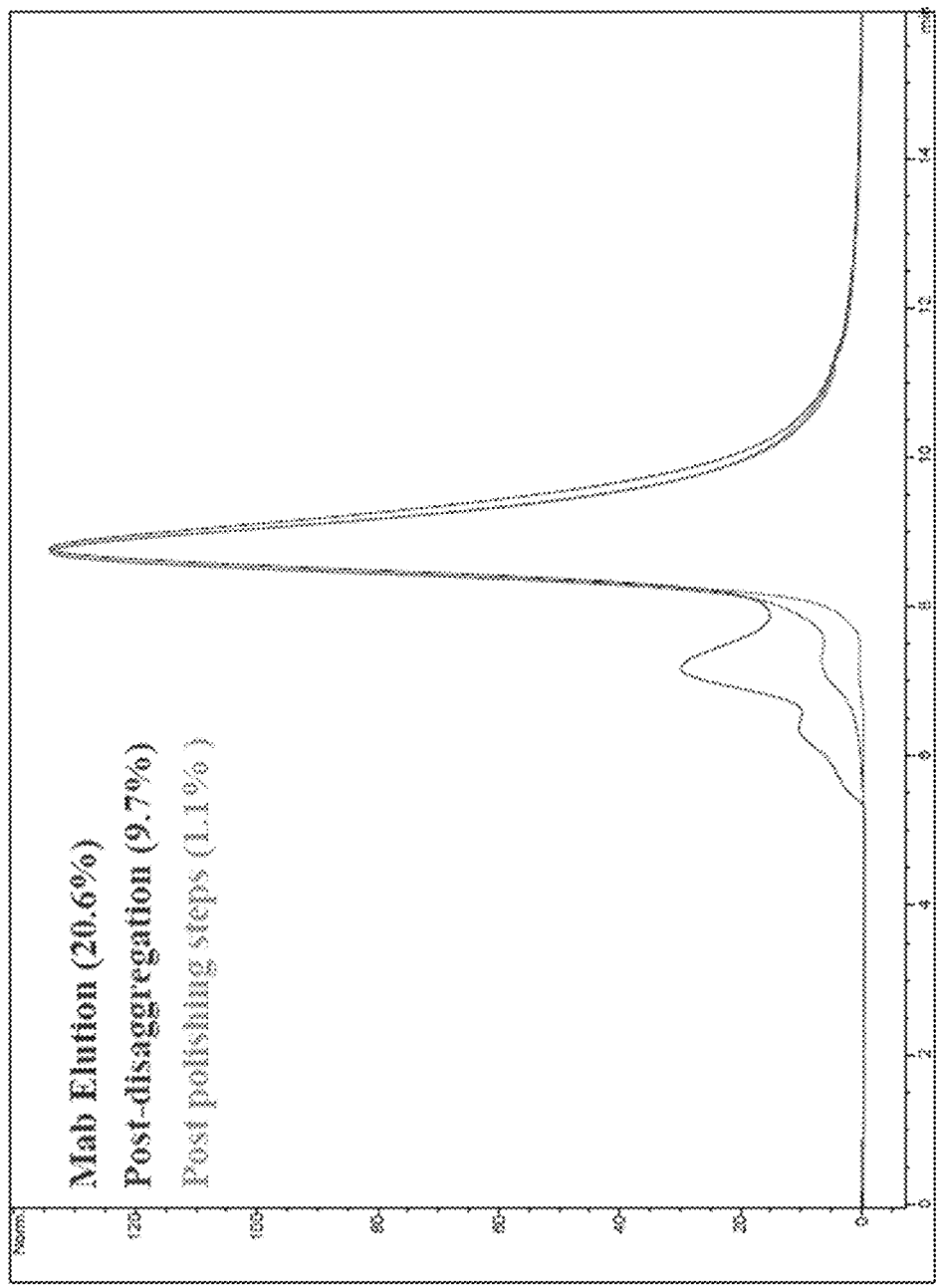
FIG. 41 is a graph of a Size Exclusion Chromatography (SEC) chromatogram of Protein A (MAbSelect) purified from control and disaggregated CTLA4-Ig material.

CTLA4-Ig purified using Protein A (resin used MAbSelect) was adjusted to a final concentration of ~4-5 mg/ml to be used as a starting material for these batch experiments. This was then contacted in a 1:1 volume ratio with 2× concentrated chaotropic buffers to achieve a final chaotrope concentration of 1-3 M (for Guanidine Hydrochloride) and 2-7 M (for Urea). Guanidine Hydrochloride concentrations ≥2 M and Urea concentrations >=4 M were effective in causing disaggregation of CTLA4-Ig HMW material. The mobile phase used for these experiments was a phosphate buffered system at a pH range of 6.5-7.0. The disaggregation reaction was quenched by rapid dilution (in a volume ratio of 1:5) into a refolding buffer consisting of 50 mM Tris, 25 mM NaCl, pH 8.5. In batch disaggregation experiments, 50 to 60% of the HMW material is converted to CTLA4-Ig dimer with a ≥95% step yield. The decrease in the level of HMW material observed following the disaggregation step is shown in FIG. 41.

On-Column Disaggregation Process

To overcome potential tank and mixing limitations during scale-up of the batch disaggregation process, a process combining the Protein A capture step and the disaggregation step was evaluated. This process involved using the chaotropic solution as the elution buffer for the Protein A step followed by collection of the elution pool into the refolding/dilution buffer.

Similar performance in disaggregation efficiency was observed using the batch and on-column processes. The on-column disaggregation process would have the distinct advantage of decreasing the number of processing steps. Experimental details for the Protein A step using the on-column disaggregation step are summarized in the following table. Resin used: MAbSelect (from GE Healthcare); Column bed height: 20-25 cm

| Step | Buffer | Buffer volume | Residence time (min) |
|---|---|---|---|
| Equilibration | 25 mM phosphate, 150 mM NaCl, pH 7.5 | >3 CV To be continued until the effluent pH & conductivity are close those of the equilibration buffer or until there is no further change in pH and conductivity with each progressive column volume of buffer used | 5 |
| Column load | Harvested cell culture fluid | >30 g/l of resin | 5 |
| Wash | 25 mM phosphate, 150 mM NaCl, pH 7.5 | >3 CV To be continued until absorbance has returned to <0.2 AU | 5 |
| Elution | 25 mM phosphate, 2.65M GdHCl, pH 6.5 (±0.2) | Peak collection initiated when absorbance reaches 0.2 AU above baseline Peak collection ended when absorbance returns to 0.2 AU above baseline | 10 |
| Peak dilution | 50 mM Tris, 25 mM NaCl, pH 8.5 | The elution peak is to be immediately collected into the dilution buffer in a volume ratio of 1:5. | N/A |
| Column cleaning | 0.1N NaOH | ~3 CV | 5 |
| Column storage | 20% Ethanol | ~3 CV | 5 |

Feasibility of Incorporation into the Downstream Process

A sample 3-column purification train was performed to generate final process material with and without use of an on-column Protein A disaggregation step. The chromatographic step yields obtained from the two purification trains are provided in Table 44.

TABLE 44

Chromatographic Yields for the 3 column process with and without Disaggregation

| Process step | Step Yield (%) | |
|---|---|---|
| | 3-column process (control) | 3-column process with On-column Disaggregation step |
| Protein A | 95 | 95 |
| HIC | 60 | 69 |
| AEX | 84 | 87 |
| Overall Chromatographic Yield | 48 | 58 |

The incorporation of the disaggregation step in a sample 3-column process resulted in an approximately 10% improvement in process yield. The product pools from the two process sequences were analyzed to evaluate the biochemical comparability of the resulting CTLA4-Ig material.

Figure 42:
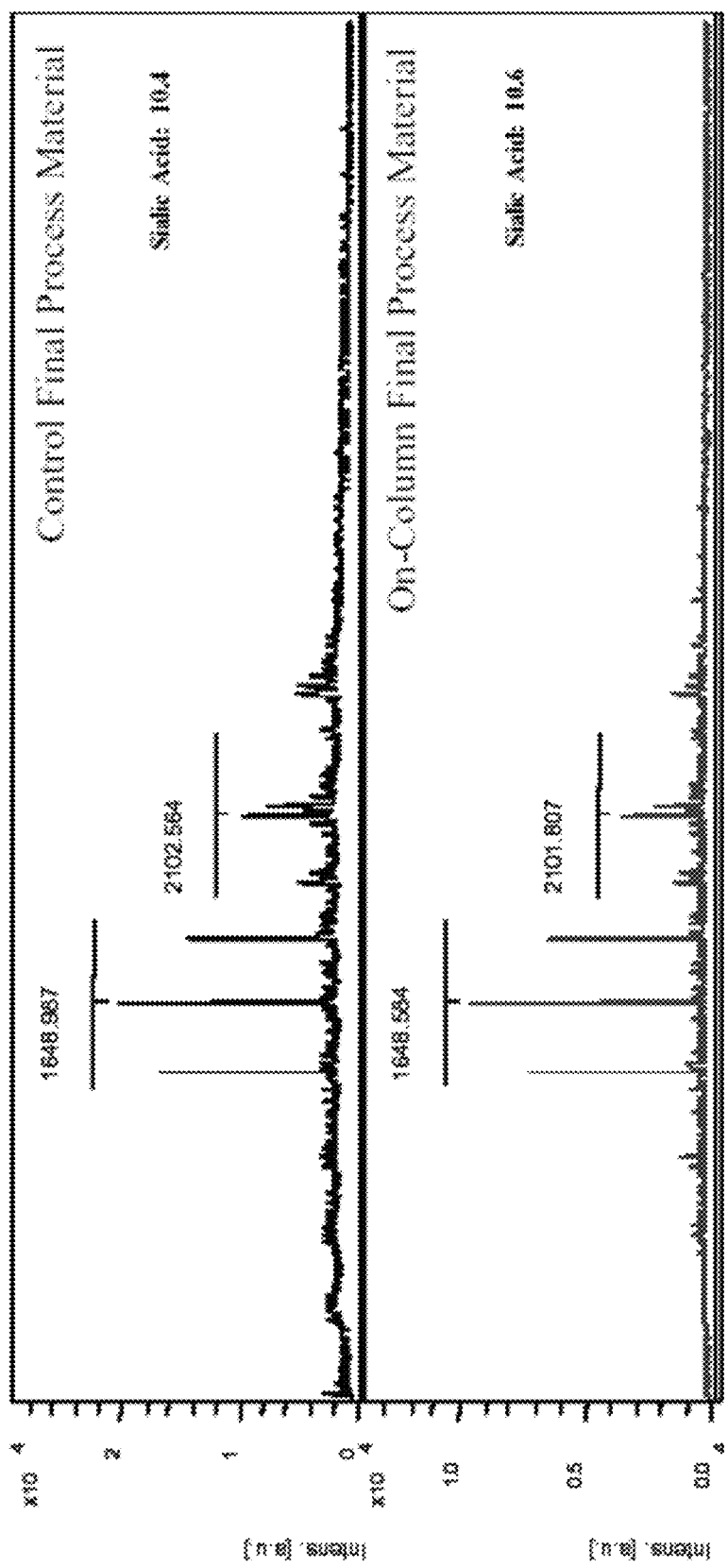
FIG. 42 is a graph of an N-glycan analysis comparing the Disaggregation Processed Material (ii) to Control (i).

The N-glycan analyses by MALDI-TOF of the two product pools are shown in FIG. 42. Based on this analyses, the material appears comparable. This MALDI-TOF result was confirmed using an HPLC-based N-glycan assay method. The HPLC analyses demonstrated a <1.7% difference in the biantenarry sialic acid peak between the control and disaggregated final process material.

Tryptic peptide mapping was also performed on the two product pools to quantify the percent of deamidated and oxidized peptides present in the purified material. The results (summarized in Table 45) demonstrated comparable deamidation and oxidation levels for the two samples.

TABLE 45

Peptide Map Results

| Sample | T26 deamidation site (% area) | T6 oxidation site (% area) |
|---|---|---|
| Control 3-column process | 0.76 | 0.35 |
| 3-column process with Disaggregation step | 0.69 | 0.33 |
| Standard material (5 g/L) | 0.94 | 0.37 |

Additionally, the B7-binding assay results were 101% and 98% for the control and on-column disaggregated material, respectively.

A method for disaggregating IgG-Fc based recombinant molecules, such as those produced by mammalians cells, comprising the step of contacting a composition comprising such molecules in aggregated form with a chaotropic agent (such as guanidine hydrochloride or urea) in an amount and for a time sufficient to disaggregate at least a portion of such aggregated molecules, optionally followed by contacting said disaggregated portion of molecules with a refolding and/or quenching agent (such as by rapid dilution into a low salt refolding buffer to help such molecules gain native conformation). Contact with the chaotropic agent can, for example, be carried out in batch, semi-batch or continuous mode, as well as, for example, in solution (such as in batch mode), or in conjunction with a chromatographic step, such as during an affinity chromatographic step (on-column mode).

A process combining an on-column purification, such as a Protein A capture step, with the aforementioned disaggregation method can enhance overall process efficiency and is another embodiment of the invention. Therefore, the present invention contemplates a method for disaggregating IgG-Fc based recombinant molecules, such as those produced by mammalians cells, comprising the step of contacting a composition comprising such molecules in aggregated form with a chaotropic agent (such as guanidine hydrochloride or urea) in an amount and for a time sufficient to disaggregate at least a portion of said aggregated molecules, wherein said contacting occurs on a chromatography column, such as where said chaotropic agent is employed in solution for elution of said column (such as the elution buffer for a Protein A column), optionally followed by contacting said disaggregated portion of molecules with a refolding and/or quenching agent (such as by rapid dilution into a low salt refolding buffer to help the molecule gain native conformation).

The composition to be contacted with such chaotropic agent can comprise IgG-Fc based recombinant molecules in forms other than an aggregated form (such as single chain forms or dimers), in addition to comprising said molecules in aggregated form.

Exemplary IgG-Fc based molecules can include glycoproteins such as the CTLA4-Ig molecules of the present invention.

Example 34: Pharmacokinetics

A Phase 2B, Multi-Center, Randomized, Double-Blind, Placebo-Controlled Study To Evaluate The Safety And Clinical Efficacy Of Two Different Doses of CTLA4-Ig Administered Intravenously To Subjects With Active Rheumatoid Arthritis While Receiving Methotrexate): In this study, subjects received CTLA4-Ig at 2 different doses (2 and 10 mg/kg) or placebo in combination with MTX. CTLA4-Ig was produced according to a process of the invention, and supplied in individual vials containing 200 mg of CTLA4-Ig. CTLA4-Ig was administered IV to subjects on Days 1, 15, and 30, and every 30 days thereafter for a year. Multiple dose PK was derived from the serum concentration vs time data obtained during the dosing interval between Days 60 and 90 from subjects who were enrolled into a site-specific PK substudy. For the subjects in the PK substudy, blood samples were collected before dosing on Day 60, and for a PK profile beginning on Day 60 at 30 minutes (corresponding to the end of CTLA4-Ig infusion), at 4 hours after the start of infusion, and weekly thereafter until Day 90. A total of 90 subjects were enrolled to participate in the PK substudy. However, complete PK profiles between the dosing interval from Day 60 to 90 were obtained from 29 subjects (15 subjects dosed at 2 mg/kg; 14 subjects dosed at 10 mg/kg).

A summary of the PK parameters is presented in Table 46. The results from the study showed that both Cmax and AUC(TAU), where TAU=30 days, increased in a dose proportional manner. For nominal doses increasing in the ratio of 1:5, the geometric means of Cmax increased in the ratio of 1:5.2, while the geometric mean for AUC(TAU) increased in the ratio of 1:5.0. In addition, T-HALF, CLT, and Vss values appeared to be independent of dose. In these RA subjects, the mean T-HALF, CLT, and Vss values were around 13 days, ~0.2 mL/h/kg, and ~0.07 L/kg, respectively. The small Vss indicates that CTLA4-Ig is confined primarily to the extracellular fluid volume. Based on the dosing schema of dosing at 2 and 4 weeks after the first infusion, then once a month thereafter, steady-state conditions for CTLA4-Ig were reached by the third monthly dose. Also, as a result of the dosing schema, serum concentrations were above steady-state trough concentrations during the first 2 months of treatment. Comparison of the trough (Cmin) values at Days 60, 90, and 180 indicated that CTLA4-Ig does not appear to accumulate following monthly dosing. The mean Cmin steady-state values for all subjects receiving monthly IV doses of 2 and 10 mg/kg CTLA4-Ig ranged between 4.4 to 6.7 µg/mL and 22.0 to 28.7 µg/mL, respectively.

TABLE 46

Summary of Multiple PK studies in Rheumatoid Arthritis Subjects

| | | | | | Pharmacokinetic Parameters of Abatacept | | | | |
|---|---|---|---|---|---|---|---|---|---|
| | | | | Treat- | Geometric Mean (% CV) | | Mean (SD) | | |
| Study Objective | Study Design | # Subjects (M/Fem) | Age: (Mean range) | ment Dose (mg/kg) | Cmax (µg/mL) | AUC (TAU) (µg · h/mL) | T-HALF (Days) | CLT (mL/h/kg) | Vss (L/kg) |
| Assess the efficacy, safety, multiple dose PK and immunogenic potential of intravenously administered doses of abatacept | Randomized double-blind, placebo-controlled, multiple dose study. 30-minute IV infusion | 29 (18/11) | 54 (34-83) | 2.0 (N =15) 10.0 (N = 14) | 54.9 (29) 284.2 (23) | 9573.5 (30) 47624.2 (31) | 13.5 (5.9) 13.1 (5.3) | 0.23 (0.13) 0.22 (0.09) | 0.07 (0.04) 0.07 (0.03) |

In RA patients, after multiple intravenous infusions, the pharmacokinetics of CTLA4-Ig showed proportional increases of $C_{max}$ and AUC over the dose range of 2 mg/kg to 10 mg/kg. At 10 mg/kg, serum concentration appeared to reach a steady-state by day 60 with a mean (range) trough concentration of 24 (1-66) mcg/mL. No systemic accumulation of CTLA4-Ig occurred upon continued repeated treatment with 10 mg/kg at monthly intervals in RA patients.

Population pharmacokinetic analyses in RA patients revealed that there was a trend toward higher clearance of CTLA4-Ig with increasing body weight. Age and gender (when corrected for body weight) did not affect clearance. Concomitant methotrexate (MTX), nonsteroidal anti-inflammatory drugs (NSAIDs), corticosteroids, and TNF blocking agents did not influence CTLA4-Ig clearance.

Example 35: Determination of Molar Ratio of Mannose, Fucose, and Galactose by CE A capillary electrophoresis method as been developed for the quantitative analysis of neutral monosaccharide content in LEA2 CTLA4$^{A29YL104E}$-Ig. Neutral monosaccharides, including mannose, fucose, and galactose are released from CTLA4$^{A29YL104E}$-Ig samples by acidic hydrolysis at a high temperature condition (2M trifluoroacetic acid, 6 hours at 95° C.). The released neutral monosaccharides are then fluorescently labeled with aminopyrene trisulfonic acid (APTS), in the presence of acetic acid as a catalyst, and NaBH$_3$CN as a reducing reagent (67 mM APTS, 330 mM HAc, 83 mM NaBH$_3$CN, 3 hours at 55° C.). Xylose is added to each sample and serves as an internal standard. Ratio of the peak area of each neutral monosaccharide against that of the internal standard is utilized for quantitation.

Reagents: Hydrolysis solution (2M trifluoroacetic acid (TFA)); Derivatization solution I (0.1M 8-amino-1,3,6, trisulfonic acid, trisodium salt (APTS) aqueous solution); Derivatization solution II (0.25M NaBH$_3$CN in 1M acetic acid); Running buffer (60±5 mM sodium tetraborate, pH9.25); Capillary rinsing solutions (1N NaOH; IN HCl; 80% methanol); Monosaccharide standard stock solutions of mannose (Man), fucose (Fuc), galactose (Gal), and xylose (Xyl) at concentration of 10 mg/ml; Monosaccharide working solution I: Internal standard working solution is 100 fold dilution of Xyl stock solution; Monosaccharide working solution II: Neutral mix standard working solutions, 100 fold dilution of Man, Fuc and Gal stock solutions.

Instrumentation: CE system is Beckman P/ACE MDQ CE system; Detector: Beckman laser induced (LIF) detection system coupled with P/ACE MDQ); Uncoated capillary (i.d. 25 µm, o.d. 360 µm) 27-31 cm total length to accommodate P/ACE MDQ.

Capillary Electrophoresis running conditions: Running buffer (60 mM sodium tetraborate, pH 9.25); Capillary cartridge temperature: 25° C.; Voltage: 25-30 kV, positive mode; Detector condition: LIF detector, excitation at 488 nm, emission at 520m; Sample injection: pressure injection mode, 20s at 0.5PSI; Run time: 10 min; Sample storage: 10° C.

Hydrolysis: 10 µL of Xylose working solution and 200 µL of 2M TFA were mixed to make the system blank. 10 µL of Xylose working solution and 10 µL of Neutral mix standard solution were mixed with 200 µL of 2M TFA to make the monosaccharide standard. 10 µL of Xylose working solution and 10 µL of sample (for example, CTLA4$^{A29YL104E}$-Ig, approximately 1 mg/ml) were mixed with 200 µL of 2M TFA to make the test sample. All tubes were vortexed for 10 sec, and centrifuge for 10 sec, followed by incubation at 95° C. for 6 hours. After the hydrolysis step the samples were places at −20° C. for 10 min to cool down. Samples were spun down for 10 sec and evaporated to dryness in Speed-Vac.

Derivatization: Samples were reconstituted with 10 µL of Derivatization solution I. Sample was briefly mixed, and 5µL of Derivatization solution II was added. Samples were loaded in a pre-warmed centrifuge and incubated for 3 hours at 55° C. while centrifuging at 2000 rpm.

CE injection: The final volume of the samples after derivatization was brought to 100 µL by addition of HPLC grade water, and 10 µL of samples were transferred to a CE micro vial with 190 µL HPLC grade water. Before sample injections the CE cartridge was rinsed extensively with HPLC grade water (1-3 min run time), followed by an equilibrating rinse with running buffer (5 min run time). Following the initial rinse, monosaccharide standards and samples for analysis were injected in the CE cartridge (15 min run time). Following the injection run of each standard or test sample, the CE cartridge was rinsed and equilibrated with HPLC grade water and running buffer (Table 51). The electropherogrpm of the system suitability should be similar to FIG. 44 wherein peak 1 is mannose; peak 2 is xylose; peak 3 is fucose; and peak 4 is galactose.

TABLE 51

Instrument Method

| Time | Event | Value | Duration | Summary | Description |
|---|---|---|---|---|---|
| | Rinse - Pressure | 40.0 psi | 3.00 min | forward | Water rinse |
| | Rinse - Pressure | 40.0 psi | 5.00 min | forward | Running buffer rinse |
| | Inject - Pressure | 0.5 psi | 20.00 sec | override, forward | Injection |
| 0.00 min | Separate - Voltage | 30 kV | 15.00 min | 0.17 min ramp, normal polarity | Separation |
| 0.05 min | Auto Zero | | | | |
| 15.00 min | Stop Data | | | | |
| 15.00 min | End | | | | |

Figure 44:
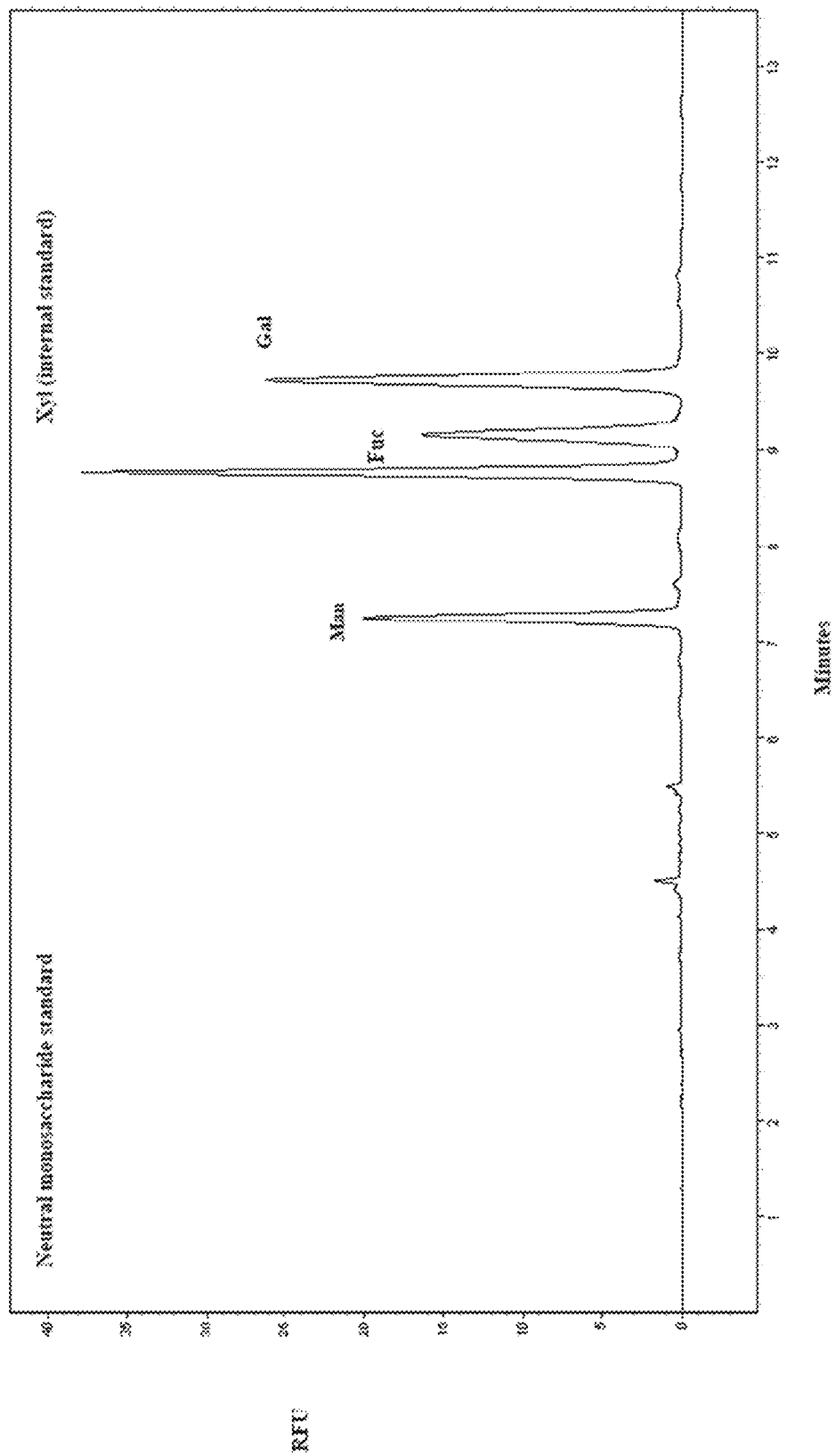
FIG. 44 shows an electropherogram of neutral monosacchraides depicted as relative fluorescence units (RFU) versus time (min).

System Suitability:

The electropherogram of the system suitability should be similar to that shown in FIG. 44, where peak 1 is mannose; peak 2 is xylose; peak 3 is fucose; and peak 4 is galactose.

When CE instruments other than the Beckman MDQ system are used, the length of the capillary may be different from that specified in this method. This will cause variations in analyte migration time, as well as peak intensity. But the peak pattern of monosaccharide analytes should remain the same.

Resolution between two neighbor peaks for the first System Suitability standard can be calculated according to the following equation:

$$R = 2(t_2 - t_1)/(W_1 + W_2)$$

Where,

R: resolution $t_2$, $t_1$: migration times of the two neighbor peaks respectively $W_1$, $W_2$: peak widths at baseline of the two neighbor peaks respectively R value must be ≥1.0. If R<1.0, rinse the capillary using the washing/rinse sequences. If the problem persists, replace old buffer with freshly prepared run buffer or replace the capillary.

For the last System Suitability injection, the last peak (galactose) must have a tailing factor ≤1.4 using the following formula:

$$T = W_{0.05}/2f$$

Where: T: tailing factor $W_{0.05}$: width of peak at 5% of height f: width of the peak front at peak maximum If T≥1.4, rinse the capillary with the washing/rinse sequences; if the problem persists, replace old buffer with freshly prepared running buffer or replace the capillary. Peak Area Ratio of galactose and xylose must have an RSD of ≤10%. The migration time of galactose needs to be ≤15.0 minutes. The electropherogram profile should be equivalent to FIG. 44.

The monosaccharide standard percent RSD can be determined by comparing peak area ratios of internal standard and monosaccharide standard components via dividing the peak area for each monosaccharide component by the peak area of the internal standard for each monosaccharide standard injection. The percent RSD can be calculated for mannose, fucose, and galactose. The RSD should be ≤10%.

Determination of the Molar Ratios of Neutral Monosaccharides to Protein

Peak area ratios of neutral monosccahrides (for example, Man, Gal and Fuc) relative to internal standard Xylose can be calculated according to the formulas provided below in order to determine the molar ratios of each neutral monosaccharide to protein. For example, the peak area ratio is equal to a monosaccharide peak area (Gal, Fuc or Man) divided by the Xylose peak area, wherein the relative standard deviation (RSD) for the peak area ratio is equal or less that 10%. The following equations can be used to calculate the following:

For Molar Ratio of Mannose/Protein:

$$R_{man} = \frac{A_{man} \times A_{xyl0} \times V_{man0} \times C_{man0} \times MW_{LEA29Y}}{A_{xyl} \times A_{man0} \times V_p \times C_p \times 180.2}$$

Where, $R_{man}$: molar ratio of mannose vs. protein $A_{man}$: peak area (µV.sec) of mannose in sample $A_{xyl}$ is peak area (µV.sec) of xylose in sample $A_{xyl0}$: peak area (µV.sec) average of xylose in monosaccharide standard $A_{man0}$: peak area (µV.sec) average of mannose in monosaccharide standard $V_{man0}$: volume of mannose contained in monosaccharide working solution used for hydrolysis (in µL)

$C_{man0}$: concentration of mannose contained in monosaccharide working solution used for hydrolysis (in mg/mL)

$V_p$: volume of protein sample used for hydrolysis (in µL)

$C_p$: concentration of protein sample used for hydrolysis (in mg/mL)

$MW_{LEA29Y}$: Molecular weight of LEA29Y (or CTLA4$^{A29YL104E}$-Ig) (91,232 Da)

MW of mannose: 180.2 daltons.

For Molar Ratio of Fucose/Protein:

$$R_{fuc} = \frac{A_{fuc} \times A_{xyl0} \times V_{fuc0} \times C_{fuc0} \times MW_{LEA29Y}}{A_{xyl} \times A_{fuc0} \times V_p \times C_p \times 164.2}$$

Where,
$R_{fc}$: molar ratio of fucose vs. protein
$A_{fuc}$: peak area (μV.sec) of fucose in sample
$A_{xyl}$: is peak area (μV.sec) of xylose in sample
$A_{xyl0}$: peak area (μV.sec) average of xylose in monosaccharide standard
$A_{fuc0}$: peak area average (μV.sec) of fucose in monosaccharide standard
$V_{fuc0}$: volume of fucose contained in monosaccharide working solution used for hydrolysis (in μL)
$C_{fuc0}$: concentration of fucose contained in monosaccharide working solution used for hydrolysis (in mg/mL)
$V_p$: volume of protein sample used for hydrolysis (in μL)
$C_p$: concentration of protein sample used for hydrolysis (in mg/mL)
$MW_{LEA29Y}$: Molecular weight of LEA29Y (or CTLA4$^{A29YL104E}$-Ig) (91,232 Da)
MW of fucose: 164.2 daltons.

For Molar Ratio of Galactose/Protein:

$$R_{gal} = \frac{A_{gal} \times A_{xyl0} \times V_{gal0} \times C_{gal0} \times MW_{LEA29Y}}{A_{xyl} \times A_{gal0} \times V_p \times C_p \times 180.2}$$

Where,
$R_{gal}$: molar ratio of galactose vs. protein
$A_{gal}$: peak area (μV.sec) of galactose in sample
$A_{xyl}$: is peak area (μV.sec) of xylose in sample
$A_{xyl0}$: peak area (μV.sec) average of xylose in monosaccharide standard
$A_{gal0}$: peak area (μV.sec) average of galactose in monosaccharide standard
$V_{gal0}$: volume of galactose contained in monosaccharide working solution used for hydrolysis (in μL)
$C_{gal0}$: concentration of galactose contained in monosaccharide working solution used for hydrolysis (in mg/mL)
$V_p$: volume of protein sample used for hydrolysis (in μL)
$C_p$: concentration of protein sample used for hydrolysis (in mg/mL)
$MW_{LEA29Y}$: Molecular weight of LEA29Y (or CTLA4$^{A29YL104E}$-Ig) (91,232 Da)
MW galactose: 180.2 daltons.

TABLE 52

Average Molar Ratio of Monosaccharide to CTLA4$^{A29YL104E}$-Ig protein.

| MONOSACCHARIDE | RANGE |
|---|---|
| Mannose | 11-23 |
| Fucose | 4.2-7.5 |
| Galactose | 9.2-18 |

Example 36: Determination of Molar Ratio of GalNAc and GlcNAc by CE

A capillary electrophoresis method has been developed for the quantitative analysis of amino monosaccharide content in CTLA4$^{A29YL104E}$-Ig, a glycoprotein with 6 N-linked glycosylation sites and at least 1 O-linked glycosylation site. Amino monosaccharides, including N-acetyl galactosamine (GalNAc) and N-acetyl glucosamine (GlcNAc) are released from CTLA4$^{A29YL104E}$-Ig sample by acidic hydrolysis at a high temperature condition (4N HCl, 6 hours at 95° C.). The released amino monosaccharides go through a re-acetylation step by incubating with acetic anhydride on ice for half an hour. They are then fluorescently labeled with aminopyrene trisulfonic acid (APTS), in the presence of acetic acid as a catalyst, and NaBH$_3$CN as a reducing reagent (67 mM APTS, 330 mM HAc, 83 mM NaBH$_3$CN, 3 hours at 55° C.). N-acetyl mannosamine is added to each sample and serves as an internal standard. Ratio of the peak area of each amino monosaccharide against that of the internal standard is utilized for quantitation.

Reagents: Hydrolysis solution (4N HCl); Derivatization solution I (0.1M 8-amino-1,3,6, trisulfonic acid, trisodium salt (APTS) aqueous solution); Derivatization solution II (0.25M NaBH$_3$CN in 1M acetic acid); Re-acetylation buffer (25 mM sodium bicarbonate, pH9.5); Running buffer (60±5 mM sodium tetraborate, pH9.25); Capillary rinsing solutions (1N NaOH; 1N HCl; 80% methanol); Monosaccharide standard stock solutions of GalNAc, GlcNAc, and ManNAc at concentration of 10 mg/ml; Monosaccharide working solution I: Internal standard working solution is 100 fold dilution of ManNAc stock solution; Monosaccharide working solution II: Amino mix standard working solutions, 100 fold dilution of GalNAc and GlcNAc stock solutions.

Instrumentation: CE system is Beckman P/ACE MDQ CE system; Detector: Beckman laser induced (LIF) detection system coupled with P/ACE MDQ).

Capillary Electrophoresis running conditions: Running buffer (60 mM sodium tetraborate, pH 9.25); Capillary cartridge temperature: 25° C.; Voltage: 25-30 kV, positive mode; Detector condition: LIF detector, excitation at 488 nm, emission at 520m; Sample injection: pressure injection mode, 20s at 0.5PSI; Run time: 10 min; Sample storage: 10° C.

Hydrolysis: 10 μL of ManNAc working solution and 200 μL of 4N HCl were mixed to make the system blank. 10 μL of ManNAc working solution and 10 μL of Amino mix standard solution were mixed with 200 μL of 4N HCl to make the monosaccharide standard. 10 μL of ManNAc working solution and 10 μL of sample (for example, CTLA4$^{A29YL104E}$-Ig sample, etc.; approximately 1 mg/ml) were mixed with 200 μL of 4N HCl to make the test sample. All tubes were vortexed for 10 sec, and centrifuge for 10 sec, followed by incubation at 95° C. for 6 hours. After the hydrolysis step, the samples were placed at −20° C. for 10 min to cool down. Samples were spun down for 10 sec and evaporated to dryness in SpeedVac.

Re-acetylation: Hydrolyzed and dried samples were reconstituted with 20μL of re-acetylation buffer and 4 μL of acetic anhydride, followed by mixing and with incubation on ice (30 min). Samples were spun down for 10 sec and evaporated to dryness in SpeedVac. Sample were each reconstituted with 100 μl of HPLC grade water and were evaporated to dryness with a SpeedVac.

Derivatization: Reconstituted samples (10 μL of Derivatization solution I HPLC) were provided 5 μL of Derivatization solution II. After mixing, samples were loaded in a pre-warmed centrifuge and incubated for 3 hours at 55° C. while centrifuging at 2000 rpm.

CE injection: The final volume of the samples after derivatization was brought to 100 μL by addition of HPLC grade water, and 10 μL of samples were transferred to a CE micro vial with 190 µL HPLC grade water. Before sample injections the CE cartridge was rinsed extensively with HPLC grade water (1-3 min run time), followed by an equilibrating rinse with running buffer (5 min run time). Following the initial rinse, monosaccharide standards and samples for analysis were injected in the CE cartridge (10 min run time). Following the injection run of each standard or test sample, the CE cartridge was rinsed and equilibrated with HPLC grade water and running buffer. The electopherograpm of the system suitability should be similar to FIG. 45, wherein peak 1 is GalNAc; peak 2 is ManNAc; and peak 3 is GlcNAc.

TABLE 53

Instrument Method

| Time | Event | Value | Duration | Summary | Description |
|---|---|---|---|---|---|
| | Rinse - Pressure | 40.0 psi | 3.00 min | forward | Water rinse |
| | Rinse - Pressure | 40.0 psi | 5.00 min | forward | Running buffer rinse |
| | Inject - Pressure | 0.5 psi | 20.00 sec | override, forward | Injection |
| 0.00 min | Separate - Voltage | 30 kV | 10.00 min | 0.17 min ramp, normal polarity | Separation |
| 0.05 min | Auto Zero | | | | |
| 10.00 min | Stop Data | | | | |
| 10.00 min | End | | | | |

Figure 45:
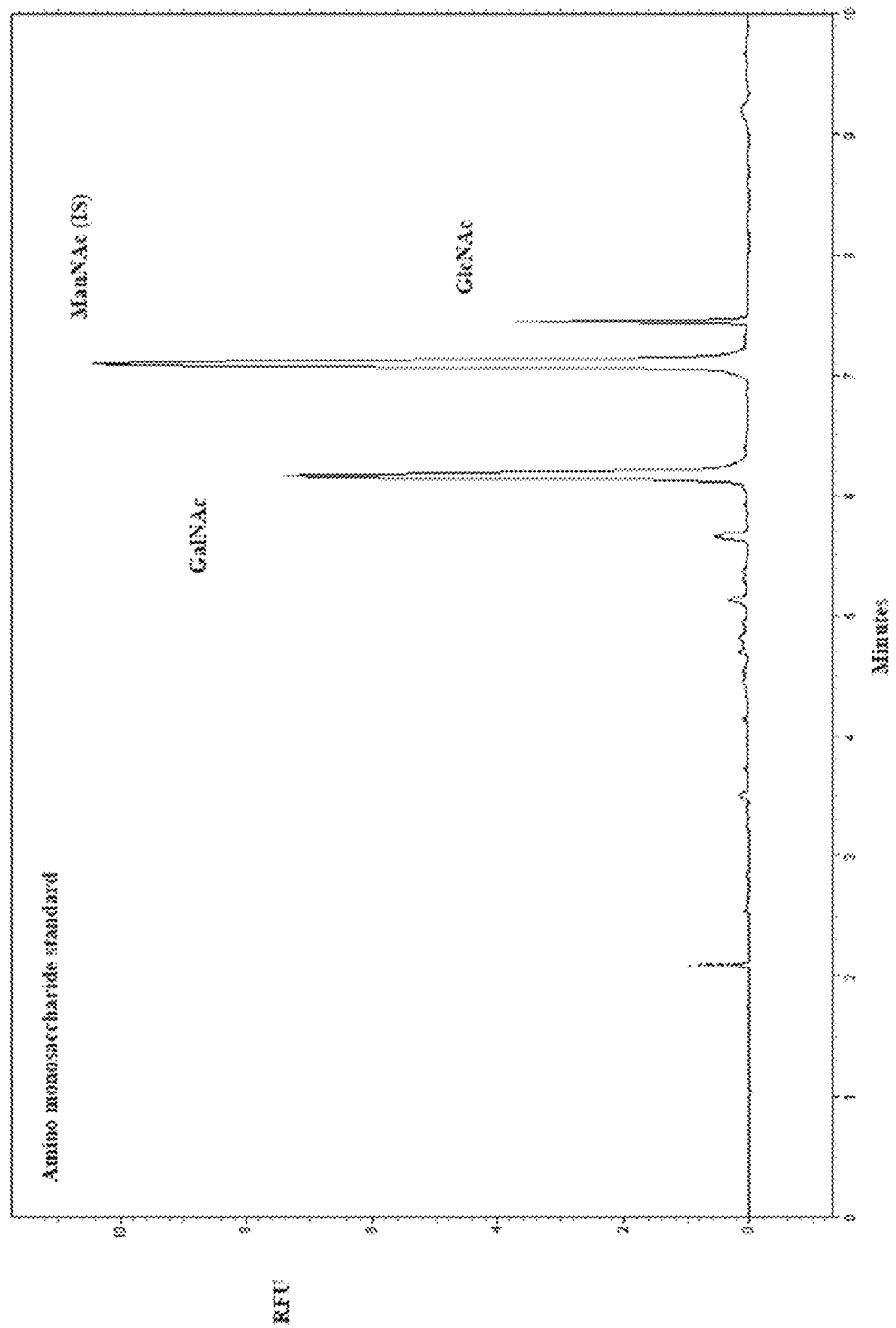
FIG. 45 shows an electropherogram of amino monosacchraides depicted as relative fluorescence units (RFU) versus time (min).

System Suitability:

The electropherogram of the system suitability should be similar to that shown in FIG. 45, where peak 1 is GalNAc; peak 2 is ManNAc; and peak 3 is GlcNAc When CE instruments other than the Beckman MDQ system are used, the length of the capillary may be different from that specified in this method. This will cause variations in analyte migration time, as well as peak intensity. But the peak pattern of monosaccharide analytes should remain the same.

Resolution between two neighbor peaks for the first System Suitability standard can be calculated according to the following equation:

$$R = 2(t_2 - t_1)/(W_1 + W_2)$$

Where,

R: resolution $t_2$, $t_1$: migration times of the two neighbor peaks respectively $W_1$, $W_2$: peak widths at baseline of the two neighbor peaks respectively R value must be ≥1.0. If R<1.0, rinse the capillary using the washing/rinse sequences. If the problem persists, replace old buffer with freshly prepared run buffer or replace the capillary.

For the last System Suitability injection, the last peak (GlcNAc) must have a tailing factor <1.4 using the following formula:

$$T = W_{0.05}/2f$$

Where: T: tailing factor $W_{0.05}$: width of peak at 5% of height f: width of the peak front at peak maximum If T≥1.4, rinse the capillary with the washing/rinse sequences; if the problem persists, replace old buffer with freshly prepared running buffer or replace the capillary. Peak Area Ratios of GlcNAc and ManNAc must have an RSD of ≤10%. The migration time of GlcNAc must be ≤10.0 minutes. The electropherogram profile should be equivalent to FIG. 45.

The monosaccharide standard percent RSD can be determined by comparing peak area ratios of internal standard and monosaccharide standard components via dividing the peak area for each monosaccharide component by the peak area of the internal standard for each monosaccharide standard injection. The percent RSD can be calculated for GalNAc and GlcNAc. The RSD should be ≤10%.

Determination of the Molar Ratios of Amino Monosaccharides to Protein

Peak area ratios of Amino monosccahrides (for example, GalNAc and GlcNAc) relative to internal standard ManNAc can be calculated according to the formulas provided below in order to determine the molar ratios of each amino monosaccharide to protein. For example, the peak area ratio is equal to a monosaccharide peak area (GalNAc or GlcNAc) divided by the ManNAc peak area, wherein the relative standard deviation (RSD) for the peak area ratio is equal or less that 10%. The following equations can be used to calculate the following For Molar Ratio of GalNAc/Protein:

$$R_{GalNAc} = \frac{A_{GalNAc} \times A_{ManNAc0} \times V_{GalNAc0} \times C_{GalNAc0} \times MW_{LEA29Y}}{A_{ManNAc} \times A_{GalNAc0} \times V_p \times C_p \times 221.2}$$

Where, $R_{GalNAc}$: molar ratio of GalNAc vs. protein $A_{GalNAc}$: peak area (µV.sec) of GalNAc in sample $A_{ManNAc}$: peak area (µV.sec) of ManNAc in sample $A_{ManNAc0}$: peak area (µV.sec) average of ManNAc in monosaccharide standard $A_{GalNAc0}$: peak area (µV.sec) average of GalNAc in monosaccharide standard $V_{GalNAc0}$: volume of GalNAc contained in monosaccharide working solution used for hydrolysis (in µL)

$C_{GalNAc0}$: concentration of GalNAc contained in monosaccharide working solution used for hydrolysis (in mg/mL)

$V_p$: volume of protein sample used for hydrolysis (in µL)

$C_p$: concentration of protein sample used for hydrolysis (in mg/mL)

$MW_{LEA}29Y$: Molecular weight of LEA29Y (or CTLA4$^{A29YL104E}$-Ig) (91,232 Da)

MW GalNAc: 221.2 Daltons.

For Molar Ratio of GlcNAc/Protein:

$$R_{GlcNAc} = \frac{A_{GlcNAc} \times A_{ManNAc0} \times V_{GlcNAc0} \times C_{GlcNAc0} \times MW_{LEA29Y}}{A_{ManNAc} \times A_{GlcNAc0} \times V_p \times C_p \times 221.2}$$

Where, $R_{GlcNAc}$: molar ratio of GlcNAc vs. protein
$A_{GlcNAc}$: peak area (μV.sec) of GlcNAc in sample
$A_{ManNAc}$: peak area (μV.sec) of ManNAc in sample
$A_{ManNAc0}$: peak area (μV.sec) average of ManNAc in monosaccharide standard
$A_{GlcNAc0}$: peak area (μV.sec) average of GlcNAc in monosaccharide standard
$V_{GlcNAc0}$: volume of GlcNAc contained in monosaccharide working solution used for hydrolysis (in μL)
$C_{GlcNAc0}$: concentration of GlcNAc contained in monosaccharide working solution used for hydrolysis (in mg/mL)
$V_p$: volume of protein sample used for hydrolysis (in μL)
$C_p$: concentration of protein sample used for hydrolysis (in mg/mL)
$MW_{LEA29Y}$: Molecular weight of LEA29Y (or CTLA4$^{A29YL104E}$-Ig) (91,232 Da)
MW GlcNAc: 221.2 Daltons

TABLE 54

Average Molar Ratio of moles Monosaccharide to moles CTLA4$^{A29YL104E}$-Ig protein.

| MONOSACCHARIDE | RANGE |
|---|---|
| GalNAc | 2.0-3.2 |
| GlcNAc | 18-32 |

Example 37: N-Linked Oligosaccharide Carbohydrate Profiling of CTLA4$^{A29YL104E}$-Ig by High Performance Anion Exchange Chromatography The carbohydrate structures present on glycoproteins can affect their function and in vivo clearance. It is therefore important to monitor the structural consistency of the carbohydrates of recombinantly produced batches of glycoproteins. Here, N-linked (asparagine-linked) carbohydrates present on CTLA4$^{A29YL104E}$-Ig are monitored. In this method, oligosaccharides are cleaved by enzymatic digestion with PNGase F (Peptide: N-Glycosidase F), separated by high performance anion exchange chromatography (HPAEC), and monitored by electrochemical detection (integrated amperometry). The chromatogram generated is the N-linked carbohydrate profile, wherein profiles of CTLA4$^{A29YL104E}$-Ig samples should be similar to such.

Reagents for Mobile Phases for Isolation of Oligosaccharides by Reversed Phase and Graphite Carbon HPLC:

Eluent 1 (0.05% Trifluoroacetic Acid (TFA) in HPLC grade water); Eluent 2: (0.05% TFA in 60% Acetonitrile (ACN), 40% HPLC Water (60:40, ACN: H$_2$O); Eluent 3: 0.05% TFA in 40% Acetonitrile, 40% Isopropanol (IPA), 20% HPLC Water (40:40:20, ACN: IPA:H$_2$O)).

Reagents for Preparation of Mobile Phases for HPAEC Oligosaccharide Carbohydrate Profiling:

Eluent 1: 500 mM Sodium Acetate (NaOAc); Eluent 2: 400 mM Sodium Hydroxide (NaOH); Milli-Q Water; 4M Sodium Hydroxide (approximately 4M NaOH); 50 mM Sodium Phosphate Buffer, 0.02% Sodium Azide, pH=7.5; PNGase F Enzyme Working Stock in 50 mM Sodium Phosphate Buffer, 0.02% Sodium Azide, pH=7.5; Stachyose Stock Solution (1.25 mg/mL); Stachyose System Suitability Standard (12.5 μg/mL).

INSTRUMENTATION AND CONDITIONS—(Equivalent instrumentation may be substituted.)

Instrumentation:

| | |
|---|---|
| Alliance HPLC system equipped with a calibrated temperature-controlled autosampler (37° C.), a Rheodyne switching valve apparatus and UV detector | Waters Corporation |
| Synergi 6-column selector | Phenomenex, (Catalog No. AV0-6080) |
| Column 1: Luna 5μ, C18(2) 4.6 × 150 mm | Phenomenex, (Catalog No. 00F-4252-E0) |
| Column 2: HyperCarb 5μ 4.6 mm × 100 mm | Phenomenex, (Catalog No. CH0-3301) |
| Dionex DX-500 HPLC System includes: GP50 Gradient Pump AS50 autosampler (refrigerated) Eluent Degas Module Liquid Chromatography Module ED40 detector DX-LAN PeakNet Software (version 5.1 or upgrade) on suitable computer system | Dionex Corporation |
| Column: CarboPac PA-1 4 × 250 mm | Dionex Corporation, (Catalog No. 35391) |
| Guard Column: CarboPac PA-1 4 × 50 mm | Dionex Corporation, (Catalog No. 43096) |
| Millennium Data Collection system | Version 3.2 |

Sample Preparation:

To a 1.7 mL Eppendorf tube, 80 μL of 50 mM NaPhosphate buffer containing 0.02% NaAzide, pH 7 and 80 μL of sample (~25 μg/μL for a total of 2 mg of CTLA4$^{A29YL104E}$-Ig etc.) were added followed by 16 μL of 10× Denaturing Buffer (5% SDS, 10% β-Mercaptoethanol). Samples were mixed thoroughly and subsequently boiled for 2 minutes to denature proteins. Vials were cooled to room temperature, then 16 μL of NP40 (10%) and 40 μL of the PNGase F working stock were added and subsequently mixed. After samples were incubated at 37° C. for 24±2 hours, they were transferred into an HPLC autosampler vial, ready for injection on the HPLC instrument.

Chromatography Conditions for Oligosaccharide Isolation:

| | |
|---|---|
| Column Temperature | Ambient (22-25° C.) |
| Flow Rate Program | Initial to 30.0 min 1.0 mL/min |
| | 30.0 to 35.0 min, 1.0-2.0 mL/min |
| | 35.0 to 40.0 min, 2.0-1.0 mL/min |
| | 40.0 to 50.0 min, 1.0 mL/min |
| | 50.0 to 60.0 min, 1.0-0.1 mL/min |

Mobile Phases and Gradient Program

| Gradient Conditions | | | | |
|---|---|---|---|---|
| 1: 0.05% TFA | Time | | | |
| 2: 0.05% TFA in ACN/H$_2$O (60:40) | (min) | % 1 | % 2 | % 3 |
| 3: 0.05% TFA in | | | | |

| Mobile Phases and Gradient Program | | | | |
|---|---|---|---|---|
| ACN/IPA/H$_2$O (40/40/20) | Initial | 100 | 0 | 0 |
| | 15.00 | 80 | 20 | 0 |
| | 15.01 | 0 | 100 | 0 |
| | 25.00 | 0 | 100 | 0 |
| | 30.00 | 0 | 0 | 100 |
| | 35.00 | 0 | 0 | 100 |
| | 40.00 | 100 | 0 | 0 |
| | 50.00 | 100 | 0 | 0 |
| | 60.01 | 100 | 0 | 0 |
| Autosampler Temperature | 37° C. | | | |
| Injection Volume | 100 µL | | | |
| Run Time | 50 minutes | | | |
| Data Collection Time | 50 minutes | | | |

| Column Switching Events for 6 column switching valve and Waters Alliance Rheodyne apparatus | | |
|---|---|---|
| Time (min) | Event | Function |
| Initial | Switch 1 | Off |
| Initial | Switch 2 | On |
| Initial | Switch 3 | On |
| Initial | Switch 4 | Off |
| 11.0 | Switch 4 | On |
| 30.0 | Switch 4 | Off |
| 30.0 | Switch 1 | On |
| 30.0 | Switch 2 | Off |
| 40.0 | Switch 2 | On |
| 40.0 | Switch 1 | Off |

Chromatography Conditions for Oligo Profile by Anion-Exchange Chromatography:

| Column Temperature | Ambient (22-25° C.) |
|---|---|
| Flow Rate | 1 mL/min |
| Mobile Phases and Gradient Conditions | Gradient Program |

*the second value for some gradient steps below indicate the extent to which the gradient may be modified in order to adjust the retention time of the system suitability standard

| 1: 500 mM NaOAc | Time | | | |
|---|---|---|---|---|
| 2: 400 mM NaOH | (min) | % 1 | % 2 | % 3 |
| 3: Milli-Q Water | | | | |
| | Initial | 0 | 50-35 | 50-65 |
| | 0.0 | 0 | 50-35 | 50-65 |
| | 1.0 | 0 | 50-35 | 50-65 |
| | 2.0 | 4 | 50-40 | 46-56 |
| | 60.0 | 45 | 50 | 5 |
| | 61.0 | 0 | 50 | 50 |
| | 80.0 | 0 | 50 | 50 |

| ED40 Detector Settings | | | |
|---|---|---|---|
| Mode | Integrated Amperometry | | |
| Applied Potentials | Time | Pot. | Integ. |
| | 0.00 | +0.05 | |
| | 0.20 | +0.05 | Begin |
| | 0.40 | +0.05 | End |
| | 0.41 | +0.75 | |
| | 0.60 | +0.75 | |
| | 0.61 | −0.15 | |
| | 1.00 | −0.15 | |
| Range | 200 nC | | |
| Analog Output Setup | Output = offset | | |
| | Zero position = 5% full scale | | |

| ED40 Detector Settings | |
|---|---|
| Mode | Integrated Amperometry |
| | Volts full scale = 1.0 v |
| | Rise time = 1 sec |
| | Polarity = + |
| Autosampler Temperature | 4° C. |
| Injection Volume | 30 µL |
| Run Time | 80 minutes |

Approximate Retention Time (RT; minutes) according to RT of System Suitability (SS) Approximate Retention Time (min) Standard

| SS: | 9.6 |
|---|---|
| Peak 1A: | 10.5 |
| Peak 1B: | 11.5 |
| Peak 1C: | 12.5 |
| Peak 1D: | 13.5 |
| Peak 1E: | 15.0 |
| Peak 2: | 24.5 |
| Peak 3: | 37.5 |

Figure 46:
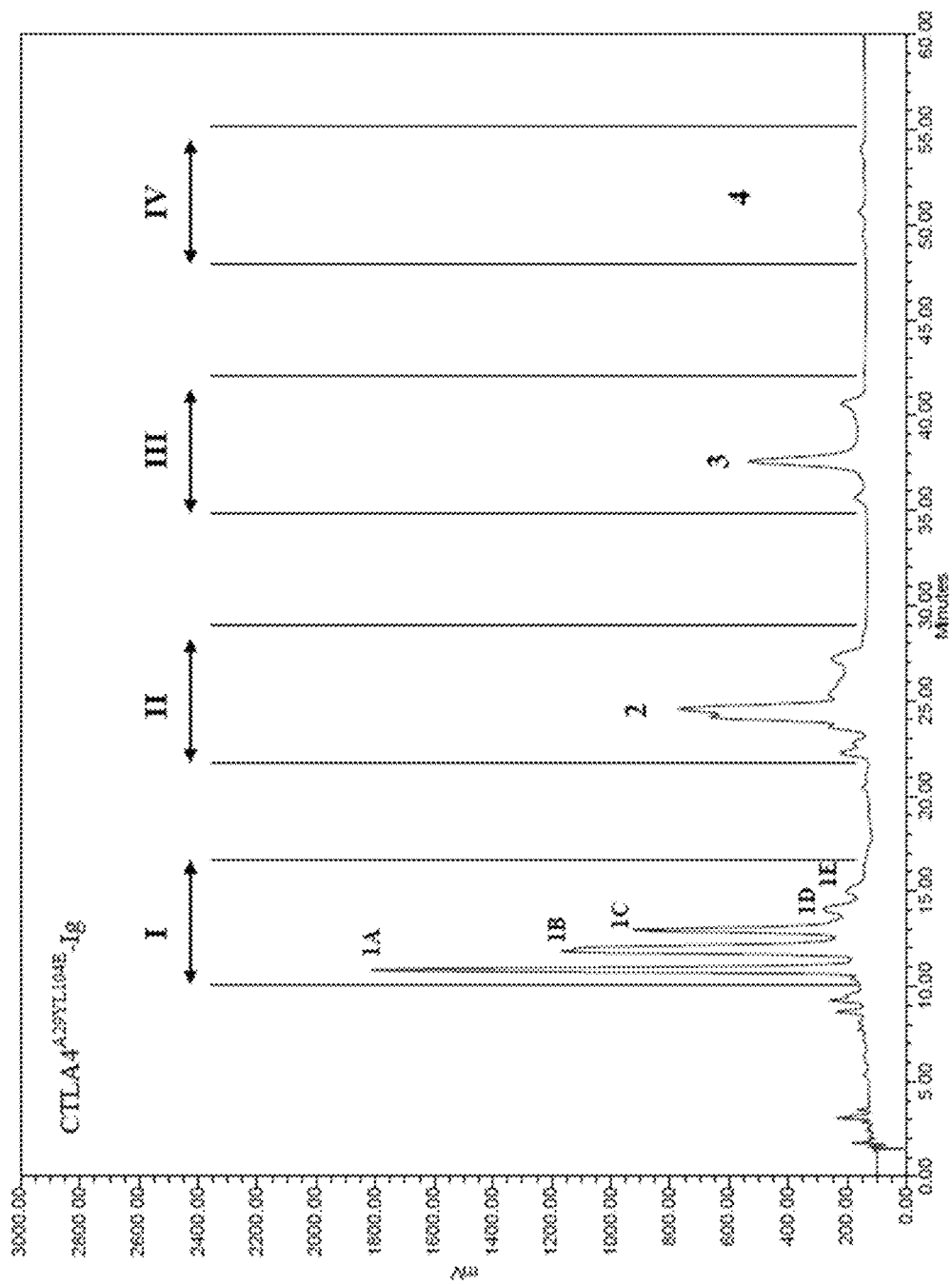
FIG. 46 represents the comparative N-linked oligosaccharide carbohydrate profiles for CTLA4$^{A29YL104E}$-Ig molecules comprising SEQ ID NO:4. Four oligosaccharide domains are observed, wherein Domain I contains non-sialylated species, while Domains II, III, and IV contain mono-sialylated, di-sialylated and tri-sialylated species, respectively.

The CTLA4$^{A29YL104E}$-Ig samples can have a carbohydrate profile depicted in the chromatogram of FIG. 46. The retention times of each domain, as identified in FIG. 46, should be approximately:

Domain I (Peak 1A, 1B, 1C, 1D and 1E) 10-17 min
Domain II: 21-29 min
Domain III: 33-43 min
Domain IV: 48-56 min Retention times are system dependent and should shift similarly as stachyose.

Calculations

Theoretical Plates (N):

The number of Theoretical Plates (N) can be determined based on the Stachyose peak using the formula below. This is done through the Millennium data analysis system or may also be done manually.

$$N = 16(t/W)^2$$

Where:
t: retention time measured from time of injection to peak elution time at maximum height.
W: width of peak by extrapolation of sides to baseline.

N must be ≥6000. If the plate count is less than 6000, the column should be replaced.

Tailing Factor (T): The column Tailing Factor (T) can be calculated based on the Stachyose peak using the formula below. This is done through the Millennium data analysis system or may also be done manually.

$$T = (W_{0.05}/2f)$$

Where:
$W_{0.05}$: width of peak at 5% of height (0.05 h).
f: the measurement (width) from front edge of peak at $W_{0.05}$ to middle of peak at maximum height.

T must be ≤0.2. If the tailing factor is greater than 1.2, the buffer composition should be evaluated, the column should be replaced or cleaned.

% Domain Area:
Domain I: Sum of the peak areas at approximate retention times 10-15 minutes (Peaks 1A-1E; for example, FIG. 46)
Domain II: Sum of the peaks from 21-27 minutes Domain III: Sum of the peaks from 34-40 minutes
Domain IV: Peak area for peaks at 45-56 minutes $$\text{Domain Area \%} = \frac{\text{Individual Domain Area}}{\text{Sum of the all Domain Areas}} \times 100\%$$

Percent Main Peak Area: The % Peak Area for each of the five major peaks can be calculated for the following using the equation below: Peaks 1A, 1B, 1C, 2 (two non-resolved species), 3 (two non-resolved species), and 4.

$$\text{Peak Area Percent} = \frac{\text{Peak Area for Individual Peak}}{\text{Sum of the } allDomainAreas} \times 100\%$$

Example 38: Capillary Electrophoretic Identification of CTLA4$^{A29YL104E}$-Ig in Drug Substance and Drug Product CTLA4$^{A29YL104E}$-Ig is a water-soluble glycoprotein with immunosuppressant activity. A capillary electrophoresis method using an uncoated fused silica capillary was used for the identification of CTLA4$^{A29YL104E}$-Ig. Samples (for example, CTLA4$^{A29YL104E}$-Ig, etc.) are heated for 5 minutes at 70° C. and then analyzed immediately by UV detection set at 214 nm to confirm identification.

Additionally, a 1:1 mixture of CTLA4$^{A29YL104E}$-Ig and CTLA4-Ig material was mixed and injected to confirm that the two proteins could be separated and differentiated. This method can distinguish between CTLA4$^{A29YL104E}$-Ig from CTLA4-Ig by comparing the migration time of CTLA4$^{A29YL104E}$-Ig material to sample.

EQUIPMENT (Equivalent equipment may be substituted):

| | |
|---|---|
| Capillary Electrophoresis Instrument | Beckman P/ACE MDQ |
| Detector Module | UV at 214 nm |
| Capillary | Polymicro Technologies Inc., 360 µm o.d./75 µm i.d., Uncoated, (Part No. 2000019, TSP075375) |
| Capillary window maker | MicroSolve Technology, (Catalog No. 07200-S) |

REAGENTS and SOLUTIONS: Running Buffer (14.4 mM sodium borate; 17.3 mM sodium dodecyl sulfate; 2.0% Acetonitrile); Phosphate Dilution Buffer (22.3 mM sodium phosphate, dibasic; 4.2 mM sodium phosphate, monobasic; 53.4 mM sodium chloride); Borate Dilution Buffer (83.5 mM NaBO$_2$, pH 9.6); Reference or Sample Working Solutions (10±1 mg/mL sample in phosphate dilution buffer); Reference or Sample Injection Solutions (10.0 µL sample+ 50 µL of borate dilution buffer); Sample 1:1 CTLA4-Ig-CTLA4$^{A29YL104E}$-Ig Mixture Solution (10.0 µL CTLA4-Ig sample+10.0 µL CTLA4$^{A29YL104E}$-Ig sample+50 µL of borate dilution buffer); Injection Solution.

RUN CONDITIONS:

| | |
|---|---|
| UV Detector Wavelength | 214 nm |
| Data Rate | 4 Hz |
| Peak Width (points) | 16-25 |
| Injection | 10 seconds (0.5 psi) |
| Total Length * | ~60 cm |
| Capillary Effective Length** | ~50 cm |
| Capillary Cartridge Temperature | 15° C. |
| Voltage | 19 kV-23 kV |
| Run Time | 15 minutes |

Figure 47:
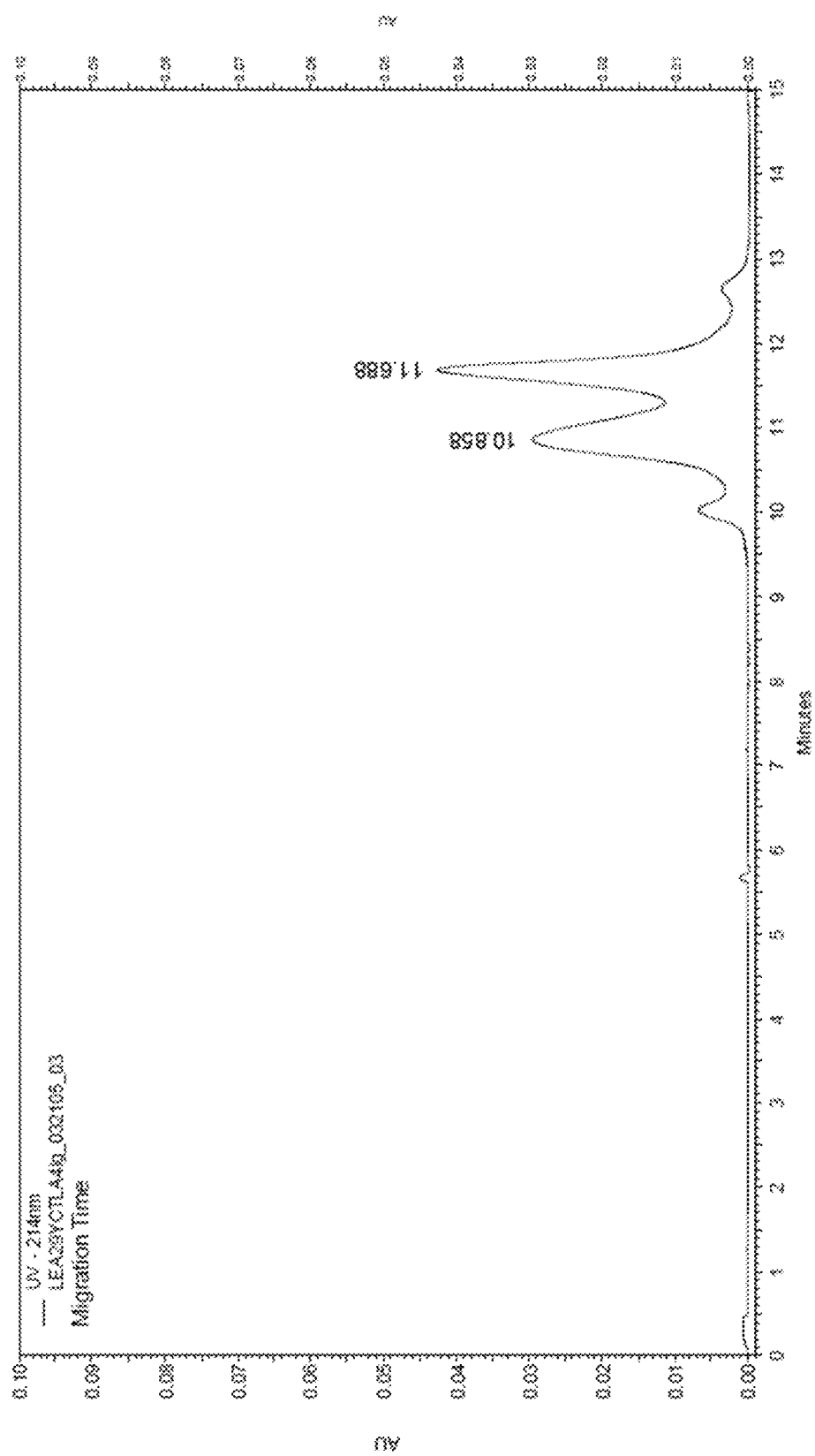
FIG. 47 is a graph of a capillary electrophoretic separation of CTLA4-Ig that was mixed 1:1 with CTLA4$^{A29YL104E}$-Ig. The main peak migration times are approximately 0.8 minutes apart.

* Total Length: from capillary inlet to outlet
**Effective Length: from capillary inlet to the detection window The CTLA4-Ig sample migration time of the main peak is about 11.0±0.4 minutes. The CTLA4$^{A29YL104E}$-Ig sample migration time of the main peak is about 12.0±0.4 minutes. The main peak migration times between each sample should be at least 0.6 minutes apart (FIG. 47).

Example 39: Hydrolysis and HPLC Analysis for the N-Acetylneuraminic Acid and N-Glycolyl Neuraminic Acid Content Determination on CTLA4$^{A29YL104E}$-Ig The degree of sialylation in recombinant proteins can affect the pharmacokinetics and rate of clearance. CTLA4$^{A29YL104E}$-Ig is a recombinant protein possessing both N- and O-linked carbohydrate sites. The glycans occupying these sites possess variable degrees of sialylation. Besides structural heterogeneity of its sialylation, the content of individual sialic acid could vary from lot to lot. An overall measure of the ratio of sialic acid to protein is therefore obtained.

N-Acetyl Neuraminic acid (NANA) and N-Glycolyl Neuraminic Acid (NGNA) content present CTLA4$^{A29YL104E}$-Ig was examined. The sialic acids are liberated from the protein by acid hydrolysis and then fluorescently labeled with DMB. The labeled sialic acids are separated on an RP-HPLC C-18 column and quantitated from a response factor of a concurrently run sialic acid standard. Data analysis and report values (as molar ratio of NANA or NGNA to protein) are specified within this example method. This example describes the method used to determine the amount of N-Acetyl Neuraminic acid (NANA) and N-Glycolyl Neuraminic Acid (NGNA) present in CTLA4$^{A29YL104E}$-Ig. The sialic acids are liberated from the protein by acid hydrolysis. The released NANA and NGNA are then fluorescently labeled with 1, 2,-diamino-4, 5-methylnoxybenzene (DMB). The labeled sialic acids are separated on a RP-HPLC C-18 column and detected by fluorescent detection (Ex=373 nm, Em=448 nm). NANA and NGNA are quantitated based on the response factors of a concurrently run NANA and NGNA standards. The test results are reported as molar ratio (MR) of NANA and NGNA to protein respectively.

Reagents and Solutions: 1.0 M H$_2$SO$_4$; 50 mM H$_2$SO$_4$; Fluorescence Labeling Reagent (18 mM sodium hydrosulfite (Na$_2$S$_2$O$_4$), 7% 2-mercaptoethanol, 7 mM 1,2-diamino-4,5-methylene-dioxybenzene dihydrochloride (DMB)); Mobile Phase Running Buffer A (20% Methanol); Mobile Phase Running Buffer B (70% Methanol); N-Acetyl Neuraminic Acid Standard Solution (1 mg/mL); N-Glycolyl Neuraminic Acid Standard Solution (1 mg/mL); System Suitability Standards (50 µL of the NANA or NGNA solutions in 900 µL of water); Sample Solutions (for example, 2 mg/ml of CTLA4$^{A29YL104E}$-Ig, etc.); NANA working Stock Standard Solution (dilute stock to 50 µg/mL); NGNA working Stock Standard Solution (dilute stock to 50 µg/mL).

Hydrolysis: 20 µL of each NANA standard, NGNA standard, CTLA4$^{A29YL104E}$-Ig, and system suitability standard solution was aliquotted into separate 1.5 mL centrifuge tubes and 200 μL of 50 mM sulfuric acid solution was added to each vial. The contents were gently mixed and incubated at 80EC for 1 hour ∀ 5 minutes. When hydrolysis is complete, the sampled were quickly centrifuged.

Fluorescence labeling: Fluorescence labeling reagent (200 μL) was added to each sample and mixed thoroughly. Samples were then incubated in the dark at 80EC for 45 ∀ 5 and subsequently cooled.

INSTRUMENTATION AND CHROMATOGRAPHIC CONDITIONS (Equivalent instrumentation may be substituted):

| | |
|---|---|
| Ternary Pump System | Hewlett Packard Model 1090 |
| RP C-18 HPLC Column, 4.6 × 50 mm, 3μ | Jones Chromatography, (Catalog No. 4M5313) |
| Fluorescence Detector | Hewlett Packard Model 1046A |
| Autosampler | Hewlett Packard Model 1090 equipped with refrigeration to 4° C. |
| Integration System | VG/Multichrom |
| HPLC Chemstation (DOS Series) | Hewlett Packard |

Chromatographic Parameters
Flow: 1.0 mL/min
Mobile Phase A: 20% MeOH/water
Mobile Phase B: 70% MeOH/water

| | Time | % A | % B |
|---|---|---|---|
| Linear Gradient: | 0.01 | 98 | 2.0 |
| | 1.0 | 98 | 2.0 |
| | 4.0 | 90 | 1.0 |
| | 4.01 | 98 | 2.0 |
| | 6.00 | 98 | 2.0 |
| Injection Volume: | 10 μL | | |
| Run Time: | 6 min | | |
| Column Temperature: | Room Temperature | | |
| Retention Time (NANA): | 3.1 ∀ 0.5 min | | |
| Retention Time (NGNA): | 2.3 ∀ 0.5 min | | |
| Max. Pressure: | 300 bar | | |
| Excitation Wavelength: | 373 nm | | |
| Emission Wavelength: | 448 nm | | |
| PMT Gain: | 8 | | |

HPLC System: Waters 2690/2695 separations module or equivalent.
Fluorescence Detector: Waters 2475 Multi wavelength Fluorescence
Detector or equivalent.
Data Acquisition: Waters Millennium 32 or Empower.
Column: Luna 5μ, C18, 100 A, 150×4.6 mm, Phenomenex, (Catalog No. 00F-4252-E0)
Digital Heat block WVR, (Catalog No. 13259-056) or equivalent.
Mini Centrifuge WVR, (Model No. C-1200) or equivalent.
Mobile Phase A: 10% (v/v) MeOH/90% water
Mobile Phase B: 70% (v/v) MeOH/30% water
Flow Rate: 1 mL/min
Injection Volume: 10 μL
Run Time: 30 min
Column Temperature: Room Temperature
Excitation Wavelength: 373 nm
Emission Wavelength: 448 nm
Gain: 1

Elution Gradient:

| Time | Flow | % A | % B | Curve |
|---|---|---|---|---|
| Initial | 1.0 | 85.0 | 15.0 | * |
| 20.00 | 1.0 | 85.0 | 15.0 | 6 |
| 20.50 | 1.0 | 0.0 | 100.0 | 6 |
| 25.00 | 1.0 | 0.0 | 100.0 | 6 |
| 25.50 | 1.0 | 85.0 | 15.0 | 6 |
| 30.00 | 1.0 | 85.0 | 15.0 | 6 |
| 35.00 | 0.05 | 0.0 | 100.0 | 11 |

Sialic acid standards preparation (~5 mM). N-Acetyl Neuraminic Acid(NANA, MW=309.3) Standard (~5 mM). Accurately weigh 154.5±1.0 mg of N-Acetyl Neuraminic Acid into a 100 mL volumetric flask. Dissolve and Q.S. to the volume with DI water, mix well. Aliquot the solution into 2 mL cryogenic vials.

$$\text{Conc. }(mM) = \frac{\text{Wt (mg)} \times P}{309.3 \times 100 \text{ (mL)}}$$

P=Purity of NANA—from Vendor COA (i.e., 99%=0.99).
N-Glycolyl Neuraminic Acid (NGNA, MW=325.7) Standard (~0.25 mM). Accurately weigh 8.0±1.0 mg of N-Glycolyl Neuraminic Acid into a 100 mL volumetric flask. Dissolve and Q.S. to the volume with DI water, mix well. Aliquot the solution into a 2 mL cryogenic vial.

$$\text{Conc. }(mM) = \frac{\text{Wt (mg)} \times P}{325.7 \times 100 \text{ (mL)}}$$

P=Purity of NGNA—from Vendor COA (i.e., 99%=0.99). The aliquoted sialic acid standards can be stored at −20° C. for up to six months.

Sialic acid standard mixture preparation. Sialic acid standard mixture for system suitability and quantitation (50 μM NANA, 1 μM NGNA). Add 1 mL of 5 mM NANA, 400 μl of 0.25 mM NGNA into a 100 mL volumetric flask. Q.S. to the volume with DI water and mix well. Aliquot the sialic acid standard mixture into 2 mL cryogenic vials. The aliquoted sialic acid standard mixture can be stored at −20° C. for up to six months.

Sample and reference material preparation. Thaw frozen protein samples at 2–8° C., mix well. Dilute both samples and reference material to approximate 0.5 mg/mL CTLA4$^{A29YL104E}$-Ig (e.g. Protein Conc.=25.0 mg/ml, add 50.0 μl of protein into 2450 μl of water). Centrifuge the diluted test samples and reference material for 5 minutes at 10,000 rpm in order to remove particulates.

Hydrolysis. Blank: To a 2.0 mL centrifuge tube, add 50 μL of DI water and 200 μL of 50 mM sulfuric acid. This serves as blank. Sialic acid standard for system suitability and quantitation. To a 2.0 mL centrifuge tube, add 50 μL of sialic acid standard mixture and 200 μL of 50 mM sulfuric acid. Prepare in duplicate. Denote as Std1 and Std2. Reference Material: To a 2.0 mL centrifuge tube, add 50 μL of diluted CTLA4$^{A29YL104E}$-Ig reference material (~0.5 mg/mL), and 200 μL of 50 mM sulfuric acid. Prepare in duplicate, denote as RM1 and RM2. Test Samples: To a 2.0 mL centrifuge tube, add 50 μL of diluted CTLA4$^{A29YL104E}$-Ig drug substance (~0.5 mg/mL), and 200 μL of 50 mM sulfuric acid. Prepare in duplicate. Denoted as S1-1, S1-2; S2-1, S2-2; S3-1, S3-2; etc. Vortex samples for approximately 5 seconds and centrifuge for approximately 5-10 seconds. Place samples in a heating block and incubate at 80° C.±5° C. for 1 hour ☐±5 minutes. Allow the hydrolyzed samples to cool to room temperature. Centrifuge hydrolyzed samples briefly to force condensate into the tube (~10 seconds at high speed).

Derivatization. Pre-heat the heating block to 80° C.±5° C. Add 200 μL of fluorescence labeling reagent to each hydrolyzed sample. Vortex approximately 5 seconds and centrifuge for ~10 seconds. Place samples in an 80° C.±5° C. heating block for 40±5 minutes. Cover the heating block with aluminum foil, as the labeling solution is light sensitive. Let derivatized samples cool to room temperature. Vortex and centrifuge samples for approximately 10 seconds to force condensate into the tube.

Preparation for injection. Ensure that the column is equilibrated with mobile phase prior to analysis. Transfer sufficient sample (100-200 μL) from each centrifuge tube into an autosampler vial with limited insert. A typical autosampler loading for 10 sample injections is as follows:

| Sample# | Description | # of injections |
|---|---|---|
| 1 | Blank | 1 |
| 2 | Std1 | 2 |
| 3 | Std1 | 2 |
| 4 | Std2 | 2 |
| 5 | RM1 | 1 |
| 6 | RM2 | 1 |
| 7 | S1-1 | 1 |
| 8 | S1-2 | 1 |
| 9 | S2-1 | 1 |
| 10 | S2-2 | 1 |
| 11 | S3-1 | 1 |
| 12 | S3-2 | 1 |
| 13 | S4-1 | 1 |
| 14 | S4-2 | 1 |
| 15 | Std1 | 1 |
| 16 | Std2 | 1 |

Where Std1 and Std2 are the preparations of Sialic Acid Standard Mixture Solution; RM1 and RM2 are the preparations for control samples; and S is a sample injection. The first four (Sample#2 & 3) of Sialic Acid Standard (Std1) injections will be used for System Suitability purposes. The four injections of Sample#3 (Std1) and Sample#4 (Std2) will be used for calculation. For additional sample injections, repeat autosampler loading 5 to 16.

Figure 48:
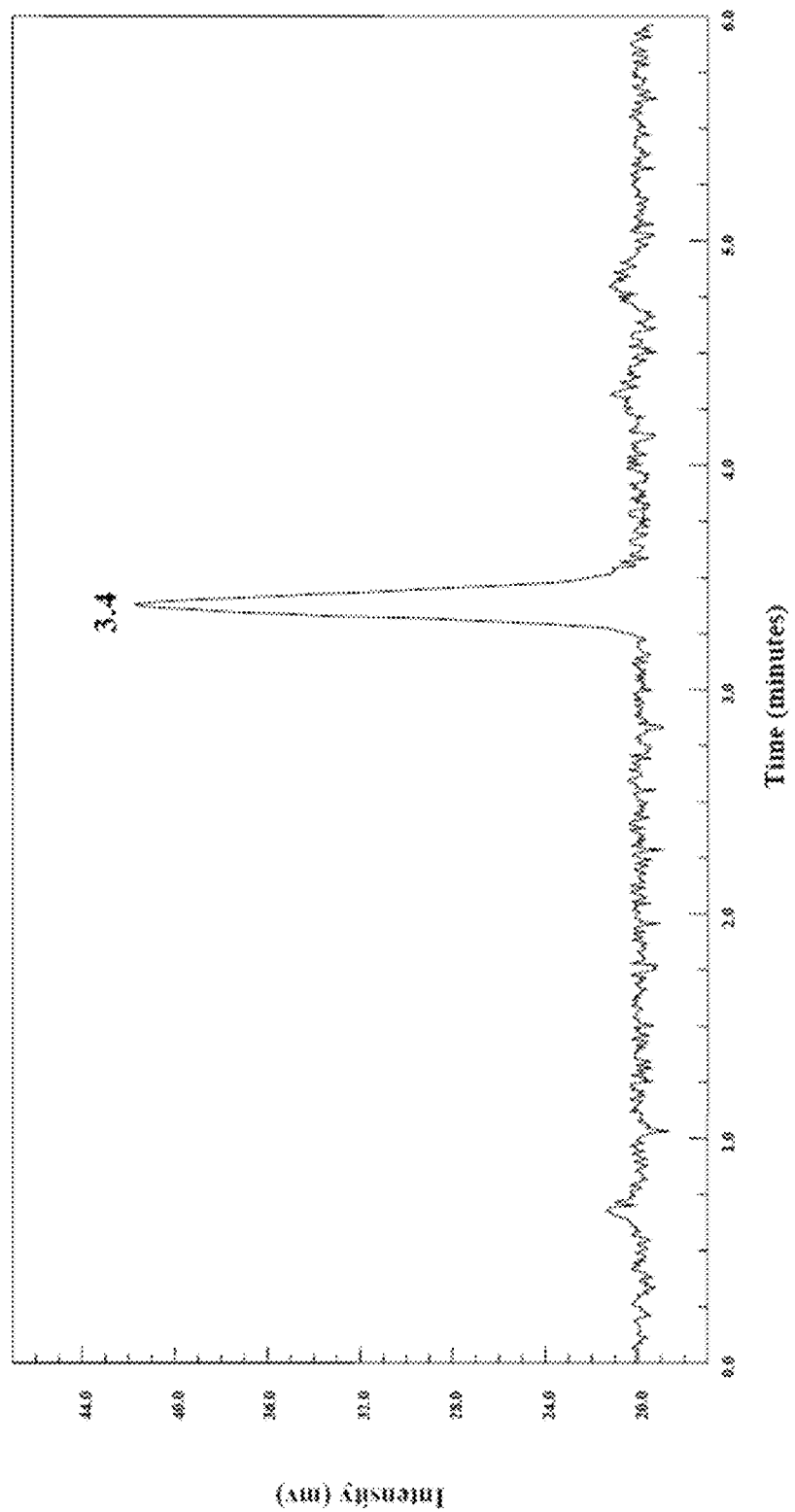
FIG. 48 is a chromatogram of hydrolyzed CTLA4$^{A29YL104E}$-Ig material, wherein a NANA Peak is observed at 3.4 minutes.

SYSTEM SUITABILITY. The chromatogram profile of the system suitability samples should be similar to chromatogram shown in FIG. 48. For the first injection of System Suitability Standard (Std1), The USP resolutions (R) for NGNA and NANA must be ≥1.5. Four injections of the System Suitability Standard (Std1) must meet the following exemplary values: The RSD of the peak area for NANA must be 5%. The RSD of the peak area for NGNA must be ≤10%. The migration time of NGNA peak must be eluted at 11.3±2.0 minutes. The migration time of NANA peak must be eluted at 16.0±2.5 minutes. The RSD of peak area of four standard injections, (Std1, Sample#3) and (Std2, Sample#4) must be ≤10%. The RSD of peak area of all bracket standard injections from the sequence must be ≤15%.

Preparation of HPLC System: Columns were equilibrated with 98% Buffer A and 2% Buffer B at 1 mL/min for 15 minutes. 10 μL of fluorescently labeled system suitability solution was injected into the system. Peak resolution and the number of theoretical plates can then be calculated using the following equations:

$$R = \frac{2(T2 - T1)}{W2 + W1}$$

Where: R=Resolution
T1=Retention time (min) of N-glycolyneuaminic acid
T2=Retention time (min) of N-acetylneuraminic acid
W1=Peak width at baseline of N-glycolylneuraminic acid (min)
W2=Peak width at baseline of NANA (min)
Resolution value must be ∃ 1.5.

The number of theoretical plates can be calculated using the following equation:

$$N = 16(T2/W2)^2$$

Where:
N=Number of Theoretical Plates
T2=Retention time (min) of N-acetylneuraminic acid
W2=Peak width at baseline of N-acetylneuraminic acid (min)

Number of theoretical plates must be 2000. The CTLA4$^{A29YL104E}$-Ig hydrolysis profile chromatogram should be similar to FIG. 48.

Samples were analyzed by Reverse Phase HPLC (RP-HPLC) in the following order: NANA and NGNA standards were first injected followed by injection of samples, in duplicate if needed (for example, CTLA4$^{A29YL104E}$-Ig etc.). After sample analysis, the column was washed with Mobile Phase B for 20 minutes at 0.5 mL/minute. If needed, the column can be reversed.

Determination of the Molar Ratio (MR) of Sialic Acid (NANA or NGNA) to Protein.

The molar ratio of sialic acids to protein can be calculated by Millennium or Empower software.

Dilution factor:

$$D = \frac{V_{protein} + V_{water}}{V_{protein}}$$

where,
$V_{protein}$=volume of protein stock solution added (μl),
$V_{water}$=volume of water added (μl)
Protein working solution (protein used for hydrolysis) concentration (μM):

$$C_{protein} = \frac{C_{A280}}{MW_{beletacept}} \times \frac{1}{D} \times 10^6$$

where,
$C_{protein}$=Concentration of the protein working solution (04),
$C_{A280}$=$A_{280}$ concentration of the protein stock solution (mg/ml),
$MW_{CTLA4A29YL104E-Ig}$=molecular weight of CTLA4A29YL104E-Ig, 91232 Da.
Concentration of Sialic Acids in the protein working solution (μM):

$$C_{unknown} = C_{std} \times \frac{A_u}{A_{std}}$$

where, $C_{unknown}$=Concentration of sialic acid (NANA or NGNA) in the unknown sample $C_{std}$=Concentration of sialic acid (NANA or NGNA) in the standard (μM)

$A_u$=peak area of sialic acid (NANA or NGNA) in the unknown sample $A_{std}$=peak area of sialic acid (NANA or NGNA) in the standard Molar ratio (M.R.) of sialic acid (NANA or NGNA) to protein:

$$M.R. = \frac{C_{unknown}}{C_{protein}}$$

Calculation of total Molar ratio of sialic acid to protein (TSA):

TSA=NANA Molar Ratio+NGNA Molar Ratio

The relative standard deviation for the area counts of two bracketed NANA standards should be <10%. The relative standard deviation for the area counts of two bracketed NGNA standards should be <10%. The relative standard deviation for the area counts of two independent hydrolysates should be <10%.

In one embodiment, the average molar ratios for sialic acids in the CTLA4$^{A29YL104E}$-Ig the must be within the ranges specified in the Table directly below.

| Molar Ratio Range of CTLA4$^{A29YL104E}$-Ig Material | |
| --- | --- |
| Monosaccharide | Range |
| NANA | 5.0-10.0 |
| NGNA | <1.5 |

The % deviation of molar ratio for sialic acids in the reference material and samples for the two sample preparations must be ≤15%, ≤20%, ≤25%, ≤30%, or ≤35%.

Example 40: An In-Vitro Cell Based Bioassay for CTLA4$^{A29YL104E}$-Ig

T cells require two signals for activation and subsequent proliferation. The first signal is provided by the interaction of an antigenic peptide with the TCR-CD3 complex. The second co-stimulatory signal occurs with the interaction between CD28 on the T cell and the B7 protein on an antigen-presenting cell. Upon receipt of these two signals, T cells secrete the cytokine Interleukin 2 (IL-2). Release of IL-2 leads to cellular activation and proliferation. CTLA4$^{A29YL104E}$-Ig, a soluble, immunosuppressive compound, also binds to the B7 protein on the antigen presenting cell, thus blocking functional interaction with CD28 and preventing the co-stimulatory signal that is necessary for IL-2 production.

In this method, Jurkat T cells transfected with the luciferase gene, under the control of the IL-2 promoter, are co-stimulated with Daudi B cells in the presence of anti-CD3. The co-stimulation activates the IL-2 promoter, which in turn produces luciferase protein. The resulting luminescent signal is measured using a Luciferase Assay System. In this system, CTLA4$^{A29YL104E}$-Ig produces a dose-dependent decrease in luciferase activity.

This method examines the effect of CTLA4$^{A29YL104E}$-Ig on the co-stimulatory signal needed for IL-2 production. The presence of soluble CTLA4$^{A29YL104E}$-Ig prevents signaling between the T cell and antigen-presenting cell. Without this signal, IL-2 is not produced, thus preventing the clonal expansion of T cells. A vector with the luciferase gene was created using the IL-2 promoter. Jurkat T cells were then transfected with this reporter vector. A positive clone, Jurkat.CA, was selected and used in the method.

This bioassay involves stimulating transfected T cells (Jurkat.CA) with anti-CD3 and B cells (Daudi). Co-stimulation provided by the B cells is inhibited by the addition of CTLA4$^{A29YL104E}$-Ig. Jurkat.CA and Daudi cells are seeded into the wells of a 96 well, white, opaque, flat-bottom plate and stimulated with anti-CD3 in the presence of different concentrations of CTLA4$^{A29YL104E}$-Ig. After a 16 to 20 hour incubation at 37° C., the wells are assayed for luciferase activity. Inhibition of co-stimulation by CTLA4$^{A29YL104E}$-Ig is seen as a dose-dependent decrease in luciferase activity. FIG. 93 is a procedure flow chart.

REAGENTS: Daudi Cell Culture Media (10% fetal bovine serum, 1% MEM sodium pyruvate in RPMI 1640); Jurkat.CA Cell Culture Media (10% calf serum, 1% MEM sodium pyruvate, 400 μg/mL of geneticin in RPMI 1640); Bioassay Media (0.2 μg/mL of anti-CD3 antibody and 1% penicillin-streptomycin solution in Daudi Cell Culture Media); Bright-Glo Luciferase Solution from assay system (Promega, Catalog # E2620).

INSTRUMENTATION: Nikon, Diaphot 200 Inverted microscope; Packard TopCount NXT Luminometer; Tecan Genesis Liquid Handler; Coulter Vi-Cell Cell Counter; Zymark RapidPlate-96.

Preparation of Working Solutions: 3 mL of CTLA4$^{A29YL104E}$-Ig solutions (5000 ng/mL) in bioassay media.

Daudi Cell Culture Media. Add 300 mL of RPMI 1640 to a 1 L Corning filter unit. Then add 100 mL of fetal bovine serum and 10 mL of MEM sodium pyruvate. Add enough RPMI 1640 to make 1 liter. Filter and store at 4° C. for up to one month.

Jurkat.CA Cell Culture Media. Add 300 mL of RPMI 1640 to a 1 L Corning filter unit. Then add 100 mL of calf serum, 10 mL of MEM sodium pyruvate, and 8 mL of geneticin at 50 mg/mL (final concentration is 400 μg/mL). Add enough RPMI 1640 to make 1 liter. Filter and store at 4° C. for up to one month.

Bioassay Media. Add 100 mL of Daudi Cell Culture Media (2.1) to a 100 mL media bottle. Then add anti-CD3 antibody to a concentration of 0.2 μg/mL and 1 mL of penicillin-streptomycin solution (1.11). Mix gently by inversions and store at room temperature for no longer than 8 hours.

Bright-Glo Luciferase Solution. Prepare the solution, as described in the system (1.21), by adding assay buffer to the luciferase substrate and mixing by inversion. The reagent should be used within 2 hours or stored at −20° C. and protected from light for up to 4 weeks.

Cell Line Maintenance. Determine the number of cells per mL for both the Jurkat.CA and Daudi cells lines by counting with a cell counter. Cells should be between $1 \times 10^5$ and $1.5 \times 10^6$ cells/mL. Combine $12 \times 10^6$ Jurkat.CA cells and $12 \times 10^6$ Daudi cells in a sterile centrifuge tube. Centrifuge the cells at ~125×g for 10 minutes at room temperature. Thoroughly re-suspend the cells in 9 mL of Daudi cell culture media (2.1) by gently pipetting repeatedly with a serological pipet until no cell clumps are visible to give a concentration of $2.7 \times 10^6$ cells/mL. Verify the cell concentration by counting cells on a cell counter. Seed the resuspended cells into the wells of a 96 well plate (1.3) at 75 mL per well (200,000 cells per well). Incubate the plate at incubator set points of 37° C., 5% $CO_2$, and 85% humidity while the standards, quality controls, and samples are prepared. Preparation of the nominal concentrations of $CTLA4^{A29YL104E}$-Ig for the standards, quality controls, and samples 1 and 2. Prepare 3 mL of $CTLA4^{A29YL104E}$-Ig material working solution at 5000 ng/mL in bioassay media (2.3) for use in the standard curve. Prepare 3 mL of $CTLA4^{A29YL104E}$-Ig material working solution at 5000 ng/mL in bioassay media (2.3) for use in the quality control curve. Prepare 3 mL of each of the two $CTLA4^{A29YL104E}$-Ig Sample working solutions at 5000 ng/mL in bioassay media (2.3) for use in the sample curves. (Approximate concentrations for CTLA4A29YL104E-Ig samples may be used to prepare the 8 point curves and relative potency values may be corrected as described in 5.5 when the determined concentration is available).

Eight point curves were prepared for the standard, quality control and samples at the concentrations of 5000, 200, 100, 50, 25, 10, 5, and 0.1 ng/mL $CTLA4^{A29YL104E}$-Ig as shown in Table 55 below for final concentrations in the assay, after twofold dilution into the plate, of 2500, 100, 50, 25, 12.5, 5, 2.5, and 0.05 ng/mL.

TABLE 55

Dilutions used to generate standard curves.

| Curve Point | Standard Curve | Quality Control | Sample 1 | Sample 2 |
|---|---|---|---|---|
| 1 | 5000 ng/mL | 5000 ng/mL | 5000 ng/mL | 5000 ng/mL |
| 2 | 200 | 200 | 200 | 200 |
| 3 | 100 | 100 | 100 | 100 |
| 4 | 50 | 50 | 50 | 50 |
| 5 | 25 | 25 | 25 | 25 |
| 6 | 10 | 10 | 10 | 10 |
| 7 | 5 | 5 | 5 | 5 |
| 8 | 0.1 | 0.1 | 0.1 | 0.1 |

Two plate maps may be used. The random plate map requires the use of a liquid handler for setup. The ordered plate map has adjacent triplicates and each curve point for the test articles added in a sequential ordered layout. For the random plate map, add 75 µL of each solution (4.8) to the appropriate wells of the plate containing cells (4.5) as shown in the plate map below. For the ordered plate map, add 75 µL of each solution (4.8) to the appropriate wells of two plates containing cells (4.5) as shown in the plate map below.

Seal the plate(s) with TopSeal-A (1.22). Ensure that the seal is tightly in place. There should be no air gaps. Incubate the plate(s) at incubator set points of 37° C., 5% $CO_2$, and 85% humidity for 16 to 20 hours. Equilibrate the plate(s) and Bright-Glo luciferase solution (2.4) to instrument temperature. Add 150 µL of Bright-Glo luciferase solution to each well simultaneously and mix. Place the plate in the TopCount NXT immediately after mixing to equilibrate in the dark for 10 minutes. Measure the luminescent signal in a TopCount NXT using a 1 second integration per well or as appropriate to the particular type of luminometer used. The output from the TopCount NXT is recorded. When using the ordered plate map, two plates will be read. The first plate (upright) will be read with well A1 in the upper left hand corner. The second plate (inverted) will be read with well A1 in the lower right hand corner.

Bioassay Random Plate Map Setup:

| | 1 | 2 | 3 | 4 | 5 | 6 | 7 | 8 | 9 | 10 | 11 | 12 |
|---|---|---|---|---|---|---|---|---|---|---|---|---|
| A | QC 0.05 | Smp1 12.5 | Stnd 0.05 | Stnd 2500 | QC 12.5 | Stnd 100 | Stnd 5 | Smp2 5 | Smp2 12.5 | Stnd 2.5 | Smp1 12.5 | Stnd 25 |
| B | Stnd 5 | Smp2 25 | Smp1 5 | Smp1 0.05 | Smp1 12.5 | QC 2.5 | Stnd 0.05 | QC 2500 | Smp1 25 | QC 25 | QC 5 | Smp2 100 |
| C | Smp2 5 | Stnd 100 | QC 5 | Stnd 2.5 | QC 0.05 | QC 5 | Smp2 100 | Smp1 0.05 | QC 100 | Smp1 100 | QC 50 | Stnd 5 |
| D | Smp1 100 | Smp2 12.5 | Smp1 50 | QC 50 | Smp1 2500 | Smp2 2500 | Smp1 2.5 | Stnd 25 | Smp2 5 | Stnd 2500 | Stnd 100 | Smp1 50 |
| E | QC 100 | Smp2 100 | QC 25 | Smp2 2500 | Smp2 12.5 | Smp2 50 | Stnd 2500 | Smp1 25 | Smp1 5 | Smp1 2.5 | Smp1 0.05 | Smp2 2.5 |
| F | QC 2500 | Stnd 12.5 | Smp1 2.5 | Stnd 25 | Stnd 12.5 | Smp1 5 | Stnd 2.5 | Smp2 2.5 | Smp2 0.05 | Stnd 2500 | QC 2.5 | Smp2 50 |
| G | QC 2.5 | Smp2 50 | Smp2 0.05 | Smp1 25 | Smp2 0.05 | QC 50 | Smp1 100 | QC 100 | Stnd 0.05 | QC 0.05 | Smp1 2500 | Smp2 2500 |
| H | Stnd 50 | Smp1 2500 | Smp2 2.5 | QC 12.5 | QC 25 | Smp2 25 | Smp1 50 | Stnd 50 | Stnd 50 | QC 12.5 | Smp2 25 | Stnd 12.5 |

Stnd: Standard from 2500 to 0.05 ng/mL final concentration in the well.
QC: Quality Control from 2500 to 0.05 ng/mL mL final concentration in the well.
Smp1, Smp2: Samples 1 to 2 from 2500 to 0.05 ng/mL mL final concentration in the well.

Bioassay Ordered Plate Map Setup:

| | 1 | 2 | 3 | 4 | 5 | 6 | 7 | 8 | 9 | 10 | 11 | 12 |
|---|---|---|---|---|---|---|---|---|---|---|---|---|
| A | Stnd 2500 | Stnd 2500 | Stnd 2500 | Stnd 100 | Stnd 100 | Stnd 100 | Stnd 50 | Stnd 50 | Stnd 50 | Stnd 25 | Stnd 25 | Stnd 25 |
| B | Stnd 12.5 | Stnd 12.5 | Stnd 12.5 | Stnd 5 | Stnd 5 | Stnd 5 | Stnd 2.5 | Stnd 2.5 | Stnd 2.5 | Stnd 0.05 | Stnd 0.05 | Stnd 0.05 |
| C | QC 2500 | QC 2500 | QC 2500 | QC 100 | QC 100 | QC 100 | QC 50 | QC 50 | QC 50 | QC 25 | QC 25 | QC 25 |

-continued

| 1 | 2 | 3 | 4 | 5 | 6 | 7 | 8 | 9 | 10 | 11 | 12 |
|---|---|---|---|---|---|---|---|---|----|----|----|
| D QC 12.5 | QC 12.5 | QC 12.5 | QC 5 | QC 5 | QC 5 | QC 2.5 | QC 2.5 | QC 2.5 | QC 0.05 | QC 0.05 | QC 0.05 |
| E Smp1 2500 | Smp1 2500 | Smp1 2500 | Smp1 100 | Smp1 100 | Smp1 100 | Smp1 50 | Smp1 50 | Smp1 50 | Smp1 25 | Smp1 25 | Smp1 25 |
| F Smp1 12.5 | Smp1 12.5 | Smp1 12.5 | Smp1 5 | Smp1 5 | Smp1 5 | Smp1 2.5 | Smp1 2.5 | Smp1 2.5 | Smp1 0.05 | Smp1 0.05 | Smp1 0.05 |
| G Smp2 2500 | Smp2 2500 | Smp2 2500 | Smp2 100 | Smp2 100 | Smp2 100 | Smp2 50 | Smp2 50 | Smp2 50 | Smp2 25 | Smp2 25 | Smp2 25 |
| H Smp2 12.5 | Smp2 12.5 | Smp2 12.5 | Smp2 5 | Smp2 5 | Smp2 5 | Smp2 2.5 | Smp2 2.5 | Smp2 2.5 | Smp2 0.05 | Smp2 0.05 | Smp2 0.05 |

Stnd: Standard from 2500 to 0.05 ng/mL mL final concentration in the well.
QC: Quality Control from 2500 to 0.05 ng/mL mL final concentration in the well.
Smp1, Smp2: Samples 1 to 2 from 2500 to 0.05 ng/mL mL final concentration in the well.

200,000 cells were added per well of a 96 well plate and were incubated at 37° C., 5% $CO_2$, and 85% humidity. $12\times10^6$ Jurkat.CA cells and $12\times10^6$ Daudi cells were combined in a sterile centrifuge tube. The cells were centrifuged at ~125×g for 10 minutes at room temperature and were thoroughly re-suspend in 9 mL of Daudi cell culture media by gently pipetting repeatedly with a serological pipet until no cell clumps were visible to give a concentration of $2.7\times10^6$ cells/mL. 75 µL of each solution from Table 55 was added to the appropriate wells of the plate containing cells The plate(s) were then sealed with TopSeal-A and incubated at 37° C., 5% $CO_2$, and 85% humidity for 16 to 20 hours. After the plates and Bright-Glo luciferase solution were equilibrated to the instrument temperature, 150 µL of Bright-Glo luciferase solution was added to each well simultaneously and were mixed. A plate is then placed in the Top-Count NXT immediately after mixing for equilibration in the dark for 10 minutes. The luminescent signal was then measured in a TopCount NXT using a 1 second integration per well or as appropriate to the particular type of luminometer used.

The output from the TopCount NXT was recorded, read into a standard analysis program, and data were transformed by taking their logarithm (base 10). The transformed data from each article were fit to a four-parameter logistic model as shown in the equation below:

$$\text{Log}_{10}(y_{jk}) = D + \frac{(A-D)}{1+\left(\frac{x_j}{C}\right)^B} \quad \text{Equation 1}$$

Where:

A is the top plateau of the curve, D is the bottom plateau of the curve, B is the slope factor, and C is the concentration that produces an effect equal to the average of A and D.

An $R^2$ statistic, and a lack-of-fit F-test can be calculated for each article. A ratio of the minimum, maximum and slope of the test articles relative to the standard material can also be calculated. In addition, confidence intervals for the ratios can also be computed.

The relative potency of each article was determined by fitting a single equation to the data from the article of interest combined with the data from the reference article.

$$\text{Log}_{10}(y_{ijk}) = D + \frac{(A-D)}{1+\left(\frac{x_{ij}}{C_A * \left(\frac{C_R}{C_A}\right)^I}\right)^B}$$

Where:

A, B and D parameters are common to both the reference and test article and $C_R$ is the reference parameter, $C_A$ is the test article parameter, and the ratio $C_R/C_A$ is the relative potency. The superscript I is an indicator variable. It is set equal to 1 if the data come from the article of interest, and 0 if the data come from the standard material.

The relative potency of each test article was translated to a percentage scale and the relative potency was given as output from the program.

Adjustment of Relative Potency Values Obtained with Approximate Concentrations:

Due to the time lag between sample receipt and obtaining a precise protein concentration, a sample may be tested in the assay at an approximate concentration and results adjusted when the precise concentration is determined. This adjustment is performed using Equation 2 below where the relative potency determined in the assay is multiplied by the ratio of the $\text{CTLA4}^{A29YL104E}$-Ig concentration used to set up the assay to the determined $\text{CTLA4}^{A29YL104E}$-Ig sample concentration.

$$\text{Reportable Relative Potency} = \frac{\text{Observed Relative Potency} * \text{Concentration Used}}{\text{Determined Concentration}} \quad \text{Equation 2}$$

Example:
Sample was tested at a protein concentration of 25 mg/mL in the assay.
Relative Potency determined was 105%.
Determined $\text{CTLA4}^{A29YL104E}$-Ig concentration was determined to be 25.5 mg/mL
Reportable Relative Potency=(105*25)/25.5=103%.
Standard Material: The $EC_{50}$ value for the Standard of the output should be between 5 and 35 ng/mL. The difference between the 2500 ng/mL and the 0.05 ng/mL concentration standards (range) should be ≥40,000 counts per second (CPS). The R-squared value for the reference should be greater than 0.95.

The test article relative potency values in Table 9 must be between 25 and 175% of the reference standard, which is the range of the assay. If the relative potency values are outside this range, then the sample must be diluted or concentrated in order to fall within this range and the sample reanalyzed.

Daudi B Cell Line:

Source: Daudi cells were obtained from ATCC. A master bank was generated comprised of 64 vials. A working bank was created from a master bank vial after 4 passages. (NOTE: Passage 0 is considered the thaw and then 3 additional passages were made prior to working bank generation).

Media: Daudi cells are grown in RPMI 1640 medium (containing HEPES and L-glutamine) supplemented with 10% fetal bovine serum and 1% sodium pyruvate.

Incubator Conditions: Cells are maintained in a vented T-flask at 37° C., 5% $CO_2$, and 70-90% humidity.

Thawing Protocol: A vial of cells is removed from a liquid nitrogen freezer and thawed in a 37° C. water bath. The contents are mixed with 10 mL of culture medium. Cells are counted and then collected by centrifugation at 125×g for 10 minutes. Following centrifugation, the supernatant is removed and the cells are suspended in fresh media at $3 \times 10^5$ viable cells/mL. The cells are defined to be at passage 0 at this point.

Growth Properties: The cell line grows in suspension.

Subculturing: Cultures are maintained by passage twice a week with no longer than 5 days between passages. Cells are passaged in a vented T-flask with fresh medium between $0.5 \times 10^5$ and $2 \times 10^5$ viable cells/mL. Cells should not reach a density greater than $1.5 \times 10^6$ cells/mL. Cells should be greater than 80% viable as assessed by trypan blue staining. The date and passage number should be labeled on the T-flask after passage.

Doubling Times: The doubling time ranges from 18 to 26 hours.

Passage Limitations: The cells from a working bank should be passed 3 times before using in the bioassay i.e. they should be at passage 3 or higher. The cells should only remain in culture for 20 passages. A new working vial should be thawed at that time.

Freezing Protocol: Cells are frozen from 5 to $10 \times 10^6$ cells/mL in a cryovial. Cryoprotectant medium is prepared by supplementing complete culture medium with 5% (v/v) DMSO. The cells are frozen at a rate of 1° C./minute until they reach liquid nitrogen temperature (~190° C.).

Jurkat.CA T Cell Line:

Source: Jurkat T cells were transfected with a plasmid encoding a CTLA4-Ig molecule. A working bank was created from a master bank vial after 3 passages (NOTE: Passage 0 is considered the thaw and then 2 additional passages were made prior to working bank generation).

Media: Jurkat.CA cells are grown in RPMI 1640 medium (containing HEPES and L-glutamine supplemented with 10% calf serum and 1% sodium pyruvate supplemented with geneticin (G418 sulfate) at a final concentration of 400 µg/mL.

Incubator Conditions: Cells are maintained in a vented T flask at 37° C., 5% $CO_2$, and 70-90% humidity.

Thawing Protocol: A vial of cells is removed from a liquid nitrogen freezer and thawed in a 37° C. water bath. The contents are mixed with 10 mL of culture medium. Cells are counted and then collected by centrifugation at 125×g for 10 minutes. Following centrifugation, the supernatant is removed and the cells are suspended in fresh media at $3 \times 10^5$ viable cells/mL. The cells are defined to be at passage 0 at this point.

Growth Properties: The cell line grows in suspension.

Subculturing: Cultures are maintained by passage twice a week with no longer than 5 days between passages. Cells are passaged in a vented T-flask with fresh medium between 0.5 and $2 \times 10^5$ viable cells/mL. Cells should not reach a density greater than $1.5 \times 10^6$ cells/mL. Cells should be greater than 80% viable as assessed by trypan blue staining. The date and passage number should be labeled on the T-flask after passage.

Doubling Times: The doubling time ranges from 18 to 26 hours.

Passage Limitations: The cells from a working bank should be passed 3 times before using in the bioassay i.e. they should be at passage 3 or higher. The cells should only remain in culture for 20 passages. A new working vial should be thawed at that time.

Freezing Protocol: Cells are frozen from 5 to $10 \times 10^6$ cells/mL in a cryovial. Cryoprotectant medium is prepared by supplementing complete culture medium with 5% (v/v) DMSO. The cells are frozen at a rate of 1° C./minute until they reach liquid nitrogen temperature (~190° C.).

Example 41: Determination of Bio-Specific Binding of $CTLA4^{A29YL104E}$-Ig to the B7.1-Ig Receptor by Surface Plasmon Resonance (BIAcore)

The relative binding of $CTLA4^{A29YL104E}$-Ig samples to the B7.1Ig receptor was measured by surface plasmon resonance using the BIAcore instrument. In this assay $CTLA4^{A29YL104E}$-Ig binds to a B7.1Ig immunoglobulin fusion protein derived from the APC cell membrane protein B7.1. After immobilizing the B7.1Ig receptor to a high density on the surface of an activated sensor chip, $CTLA4^{A29YL104E}$-Ig material, quality controls, and samples are diluted to generate binding sensorgrams. The initial binding rate (slope)/Resonance Units (RU) bound of $CTLA4^{A29YL104E}$-Ig to immobilized B7.1Ig surface is measured under the mass transfer (diffusion) limited conditions on this high density B7.1Ig surface. The initial binding rate in resonance units per second (RU's) correlates directly with the bioactive concentration. The binding rates of samples are calculated into an active concentration using the reference standard curve where the binding rate of a $CTLA4^{A29YL104E}$-Ig material is plotted against the concentration. The final results are either expressed by percent binding of sample relative to $CTLA4^{A29YL104E}$-Ig material or as a concentration. A method outline is shown in FIG. 94.

REAGENTS: Amine Coupling Kit BIA Certified (kit contains one vial each: 115 mg N-hydroxysuccinimide (NHS), 750 mg N-ethyl-N'-(3-dimethyl) (EDC), and ethanolamine); Regeneration Buffer (10 mM Sodium Citrate, 100 mM NaCl, pH 4.0);

INSTRUMENTATION: BIAcore C Instrument with a PC compatible computer (BIAcore (Catalot No.BR-1100-51)); BIAcore C Control Software version 1.0.2; BIAcore Evaluation Software 1.0; BIAcore 96-well microtiter plate U-shape BIAcore (Catalog No. BR-1005-03); BIAcore 96-well micorplate Foils plate sealer (Catalog No. BR-1005-78).

| MATERIALS | |
|---|---|
| Sensor Chip CM5, certified grade | BIAcore AB (Catalog No. BR-1000-12) |
| BIACORE ® C Instrument Handbook | BIAcore (Catalog No. BR-1005-11) |
| HBS Buffer BIA certified 10 mM HEPES pH 7.4, 150 mM NaCl, 3.4 mM EDTA 0.005% v/v Surfactant P20 | BIAcore (Catalog No. BR1001-88) |
| BIAnormalizing Solution (40% glycerol solution) | BIAcore AB (Catalog No. BR-1002-22) |
| Amine Coupling Kit BIA certified 115 mg N-hydroxysuccinimide 750 mg N-ethyl-N'-(3-dimethyl) | BIAcore (Catalog No. BR-1000-50) |
| Sodium Chloride (NaCl) | Sigma (Catalog No. S-9888) |
| Acetate Buffer pH 5.0 | BIAcore (Catalog No. BR-1003-51) |
| Sodium Citrate ($C_6H_5Na_3O$) | Sigma (Catalog No. S-4641) |
| Hydrochloric Acid (HCl) | Fisher Scientific (Catalog No. A144-212) |
| BIAcore Maintenance Kit | BIAcore (Catalog No. BR-1006-67) |

REAGENTS

Amine Coupling Kit BIA Certified. The kit contains one vial each: 115 mg N-hydroxysuccinimide, 750 mg N-ethyl-N'-(3-dimethyl) and ethanolamine. Aliquot each solution according to manufacturer's directions and store as indicated below:

Store aliquots of 11.5 mg/ml N-hydroxysuccinimide (NETS) at −20° C. This frozen aliquot expires 2 months from the date of preparation. Store aliquots of 75 mg/ml 1-ethyl-3-(3-dimethylaminopropyl)carbodiimide hydrochloride (EDC) at −20° C. This frozen aliquot expires 2 months from the date of preparation. Store aliquots of 1.0 M ethanolamine-HCl pH 8.5 at −20° C. This frozen aliquot expires 2 months from the date of preparation. Regeneration Buffer (10 mM Sodium Citrate, 100 mM NaCl, pH 4.0). Analytically weigh out 1.5±0.1 g Sodium Citrate and 2.9±0.1 g NaCl. Add to 500 mL Milli-Q Water and adjust pH to 4.0 with 1 N HCl. Filter the solution with a 0.22 μm filter then aliquot the 500 mL into 45 mL/50 mL conical tubes. Solution expires 6 months from the date of preparation when stored at 2-8° C.

| INSTRUMENTATION | |
|---|---|
| BIAcore C Instrument with a PC compatible computer | BIAcore (Catalot No. BR-1100-51) |
| BIAcore C Control Software: | BIAcore, as provided with BIAcore C instrument, version 1.0.2 |
| Evaluation Software | BIAcore, as provided with BIAcoreC instrument, version 1.0 |
| pH Meter | ORION, Model 720A+ |

PREPARATION OF SENSOR CHIP. Insert a new Sensor Chip CM5 into the cassette port on the detector unit of the instrument. Prime the system as described in the BIAcore C Handbook using HBS-EP buffer.

OPERATION OF BIAcore C INSTRUMENT FOR METHOD FUNCTION. The BIAcore C instrument is controlled from a compatible PC computer under Microsoft Windows environment with the BIAcore C Control Software. Refer to the Work Instructions, "Operation of BIAcore C Instrument" and "Calibration and Maintenance of BIAcore C Instrument" for use and maintenance of BIAcore C instrument.

Immobilization Method of B7.1Ig
Preparation of B7.1Ig:
A vial containing B7.1Ig was thawed at 22.5±5° C. and diluted to a concentration that immobilizes 3000-9000 RU, using 10 mM Acetate pH 5.0 buffer as diluent. A vial of EDC, NHS, and Ethanolamine were each thawed from the Amine Coupling Kit as described. Reagent and ligand vials were then placed in sample rack as instructed by the BIAcore program, and immobilization was initiated according to BIAcore instrument instructions.

Preparation of CTLA4$^{A29YL104E}$-Ig Standard Curve

Standards and samples (such as CTLA4$^{A29YL104E}$-Ig, etc.) were thawed at room temperature. Standards used to generate a standard curve were diluted to the target concentrations of the standard curve (250, 500, 1000, 2000, 4000, and 8000 ng/mL).

For the dilution of a standards sample (such as a CTLA4$^{A29YL104E}$-Ig material stock) and the concentration was 25 mg/mL, one could perform the following dilutions:
 i. Dilute 1/50 (500 μg/mL) by adding 20 μL to 980 μL HBS-EP
 ii. Dilute to 16 μg/mL by adding 30 μL of 500 μg/mL to 908 μL HBS-EP
 iii. Serially dilute in ½ steps (500 μL of previous dilution+ 500 μL HBS-EP) down to 250 ng/mL Each standard can be analyzed in duplicate injections that will result in 2 slope values.

QUALITY CONTROL SAMPLES. Quality Control (QC) samples of CTLA4$^{A29YL104E}$-Ig are prepared in HBS-EP buffer at the three target concentration levels of 750, 2500, and 5000 ng/mL and are frozen in 7 mm plastic vials as 200 μL aliquots at −80° C. The CTLA4$^{A29YL104E}$-Ig concentrations in the QC samples are determined in three independent concentration analysis experiments using this method. In each experiment all QC sample injections must be acceptable, detecting within ±20% of nominal concentrations. The qualified and frozen QC samples expire 6 months after preparation. On the day of an experiment, thaw one vial each of the three QC samples at room temperature. Place QC samples in the sample rack positions as described in the method wizard and analyze each QC with triplicate injections. Alternatively, QCs can be prepared fresh on the day of analysis.

CTLA4$^{A29YL104E}$-Ig TEST SAMPLES. CTLA4$^{A29YL104E}$-Ig samples have to be diluted to a concentration within the range of the assay (between 750 and 5000 ng/mL). Sample with a known approximate CTLA4$^{A29YL104E}$-Ig concentration should be diluted to a target concentration of 2000 ng/mL. After thawing samples at room temperature they are diluted to a target concentration of 2000 ng/mL using HBS-EP buffer. Sample dilutions can be prepared for analyses in either BIAcore certified polypropylene test tubes or a 96-well microtiter plate. The following is an example for the dilution of a CTLA4$^{A29YL104E}$-Ig test sample:

After thawing samples at room temperature, CTLA4$^{A29YL104E}$-Ig samples were diluted to a concentration within the range of the assay (such as, between 750 ng/ml and 5000 ng/mL). Samples with known approximate CTLA4$^{A29YL104E}$-Ig concentration should be diluted to a target concentration of 2000 ng/mL using HBS-EP buffer in either BIAcore certified polypropylene test tubes or a 96-well microtiter plate.

The following was an example for the dilution of a CTLA4$^{A29YL104E}$-Ig sample (concentration=25.0 mg/mL):
  i. Dilute 1/50 (500 µg/mL) by adding 20 µL to 980 µL HBS-EP
  ii. Dilute 1/25 (20 µg/mL) by adding 30 µL of 500 µg/mL to 720 µL HBS-EP
  iii. Dilute 1/10 (2 µg/mL) by adding 100 µL of 20 µg/mL to 900 µL HBS-EP Vortex each dilution at moderate speed for 2-4 seconds. Samples are prepared in triplicate (three independent dilutions from the stock sample solution), and each dilution is analyzed with one injection. Samples were prepared in triplicate (three independent dilutions from the stock sample solution), and each dilution was analyzed with one injection.

STARTING ANALYSIS USING THE BIACORE C SOFTWARE: Open BIAcore C Control Software and select File→Project→Published→8164-2→Concentration Analysis Wizard, Click on "Next" and select a published template appropriate for the analysis to be performed, for example "CTLA4$^{A29YL104E}$-Ig Sample Concentration Analysis. blw". Enter the maximum number of samples for the planned analysis. This number of samples includes replicates, so, for example, to analyze 8 samples in triplicate the number 24 should be entered. Select Flow Cell (1-4) on which the B7.1Ig ligand was immobilized. Click on "Next" and enter sample ID's, dilution factors, and number of replicates. Click on "Next" and check vial positions. At this point the positions of vials can be moved to the desired locations. Click on "Next" and confirm the set-up and choices for the assay on the "Preparation for Analysis" screen. Click on "Next" on to scroll down. Place the standards, QC's, regeneration solutions, and test samples in the appropriate positions. Click on "Start" to start the analysis.

DATA EVALUATION. Start BIAcore C Software and open the BIAcore file***.blr that was generated. Then select "Wizard Results" from the "View" menu to evaluate the data.

Exemplary Values for B7.1Ig Surface

The mass of B7.1Ig immobilized on an activated flow cell was expressed as RU's (resonance units). The surface mass should be between 3000 to 9000 RU's for optimal assay performance. If the surface mass does not meet this exemplary value, an adjustment of the activation time (EDC/NHS injection) or the B7.1Ig concentration can be made and another flow cell can be immobilized.

Exemplary Values for Baseline Drift

The baseline drift of each run was calculated as the percent change of the baseline ("absolute response values") between each cycle relative to the immobilized surface mass of the ligand. The largest percent change between any two cycles of the run must be ≤5.0%. For example: if Baseline at cycle 20=13500 RU, Baseline at cycle 23=13650 RU, and B7.1Ig surface density=6000 RU, then Baseline drift=(13650-13500)/6000×100=2.5%.

Exemplary Values for the Standards

Exemplary values apply to the standard curve concentrations at or above 500 ng/mL. The coefficient of variation (% CV) of the values at each slope values at each standard concentration used to determine the standard curve must be within ±10%. The mean calculated concentration values (ng/mL) at each standard concentration must be within 15% of the target (nominal) value. The difference between the calculated concentration and the target (nominal concentration) can be divided by the target (nominal) concentration and multiplied by 100. For example, at standard 500 ng/mL, the BIAcore C calculated concentration is 510 ng/mL. The % deviation will be calculated as follows: (510 ng/mL-500 ng/mL)/500 ng/mL×100%=2.0%.

Exemplary values for QC Samples: The % CV of the triplicate calculated concentration values for each QC sample target concentration must be within ±10%. QC sample results must be within ±15% of their respective target values for at least seven of the nine QC determinations. The difference in slope values between the first and last QC injection at the 2500 ng/mL level must be within ±5.0%. For example, the first slope value is 10.366 RU/s and the last slope vales is 10.230 RU/s, the percent difference will be as following:

(10.366-10.230)/10.366×100%=1.3%

Exemplary Values for Test Samples

The % CV of the triplicate observations obtained for each test sample target concentration must be within 20%. The slope values for a sample must be in the range of the method: average slope at quality control sample 1 ≤ average slope of sample ≤ average slope of quality control sample 3.

Sample Results Calculations

To determine the percent binding of a test sample relative to the CTLA4$^{A29YL104E}$-Ig material, the concentration value for each test sample is calculated from the standard curve in ng/mL. The Results Wizard of the BIAcore instrumentation calculates the CTLA4$^{A29YL104E}$-Ig concentration in the undiluted sample in mg/mL based on the dilution factor entered for each sample.

Determining the Percent Binding:

The calculated mean concentration value for each sample tested can be multiplied by 100 and divided by the reported protein concentration of the sample as determined by absorbance measured at 280 nm ($A_{280}$). The value can then be reported to the nearest whole number as percent binding relative to standard samples. For example, the sample was diluted by a dilution factor of 12,500 (sample protein concentration of approximately 25 mg/mL). The calculated average CTLA4$^{A29YL104E}$-Ig concentration from the triplicate injections of the sample is 25.3 mg/mL. The $A_{280}$ for the sample is 24.2 mg/mL. The calculated percent binding relative to standard samples can be as follows: 25.3 mg/mL/24.2 mg/mL×100%=104.545%.

CTLA4$^{A29YL104E}$-Ig Immobilization Wizard Template

| Immobilization Injection Parameters | | | | |
| --- | --- | --- | --- | --- |
|  | EDC/NHS | B7.1-Ig | Ethanolamine | Citrate |
| Contact Time (min) | 7 | 7 | 6 | 2 |
| Flow Rate (µL/min) | 5 | 5 | 5 | 10 |
| Injection Volume (µL) | 35 | 35 | 30 | 20 |

| | | | Immobilization Report Points | | | | | |
|---|---|---|---|---|---|---|---|---|
| ID | Time (s) | Before/ After | Start of/ End of | Injection | Type | Relative to | Window (s) | Report |
| Baseline | 10 | Before | Start of | $1^{st}$ Inj | AbsResp | — | 5 | No |
| Activation | 10 | Before | Start of | $2^{nd}$ Inj | RelResp | Baseline | 5 | No |
| Immobilization Level | 85 | After | End of | $3^{rd}$ Inj | RelResp | Baseline | 5 | Yes |

Example 42: Correlations Between Carbohydrate Analytical Data of CTLA4-Ig and Pharmacokinetic Data The carbohydrate structures on CTLA4-Ig play an important role in the pharmacokinetics (PK) of the CTLA4-Ig therapeutic composition. Several analytical methods have been developed to characterize these carbohydrate structures. Two analytical parameters correlate well with clearance rates: the sialic acid (NANA) to CTLA4-Ig protein ratio and the percent Domain III and IV from the carbohydrate profile. A third parameter (the galactose to mannose ratio from the monosaccharide analysis) also appears to correlate well. For example, the specifications for these parameters can be:

NANA:CTLA4-Ig Protein Ratio ≥8.0

Carbohydrate Profile Domains III and IV ≥25% (Method 1)

Galactose:Mannose Ratio ≥0.65

An important step in the CTLA4-Ig fermentation process can be the selection of harvest parameters that will maximize yield (titer) of the final product comprising characteristics specified herein (see Table 6). One of the parameters (NANA:protein ratio) is sufficiently rapid and accurate to be used as one of the harvest parameters. A target molar ratio of NANA to CTLA4-Ig protein of about 8.0 can ensure that most harvests will have a NANA ratio >7.0. Enhancements during purification can subsequently produce CTLA4-Ig molecules with a NANA ratio >9.0.

CTLA4-Ig is a glycoprotein with several N-linked and O-linked glycosylation sites. The N-linked carbohydrate structures are typically bi- or tri-antennary and, if fully sialylated, terminate with the carbohydrates NANA-Gal-GlcNAc. Most molecules are only partially sialylated and contain some carbohydrate chains terminating with Gal or GlcNAc. The absence of terminal sialic acid (NANA) residues is a factor leading to increased exposure rates from the blood stream. In this example, data is presented indicating that terminal galactose also provides some protection from rapid clearance.

A primary parameter used to evaluate glycosylation is the NANA:CTLA4-Ig protein molar ratio. Monkey PK studies had shown that acceptable clearance could be achieved using CTLA4-Ig molecules with a NANA ratio of 6.9. The first lot of Process Y CTLA4-Ig material (CTLA4-Ig composition obtained from the Y Process) tested in monkeys had a NANA ratio of 7.1. Surprisingly, it was found to clear twice as rapidly as CTLA4-Ig material with a NANA ratio of 6.9. A review of the monosaccharide analysis of the two samples indicated that the X Process material had significantly more galactose than the CD-CHO process material. A process was developed which included galactose in the feed (CD-CHO1). The CTLA4-Ig produced by this process had higher levels of both galactose and sialic acid than the Y Process material. The analytical and PK data for material from the CD-CHO1 process is discussed below and compared with the Process Y and Process X material.

Analytical Methods

The carbohydrate profile assay consists of the enzymatic removal of the entire carbohydrate structures and their separation by anion exchange chromatography. The carbohydrate peaks resolve into four or five clusters ("domains") based largely upon the number of sialic acid residues in each structure. Domain I is largely asialylated, Domain II is monosialylated, Domain III is di-sialylated, Domain IV is tri-sialylated and Domain V is tetra-sialyated. The area under each peak or domain can be determined and reported as a percentage of the total area under all the peaks.

The clearance rate was determined by injecting monkeys in triplicate with 10 mg/kg of CTLA4-Ig, then following the decrease in serum concentration over a 28-day period. The clearance rate is related to the measured "area under the curve" or AUC. The AUC is related to clearance, a higher clearance rate is related to a smaller AUC and a lower clearance rate to a larger AUC value. Higher values represent slower clearance of CTLA4-Ig.

Figure 49:
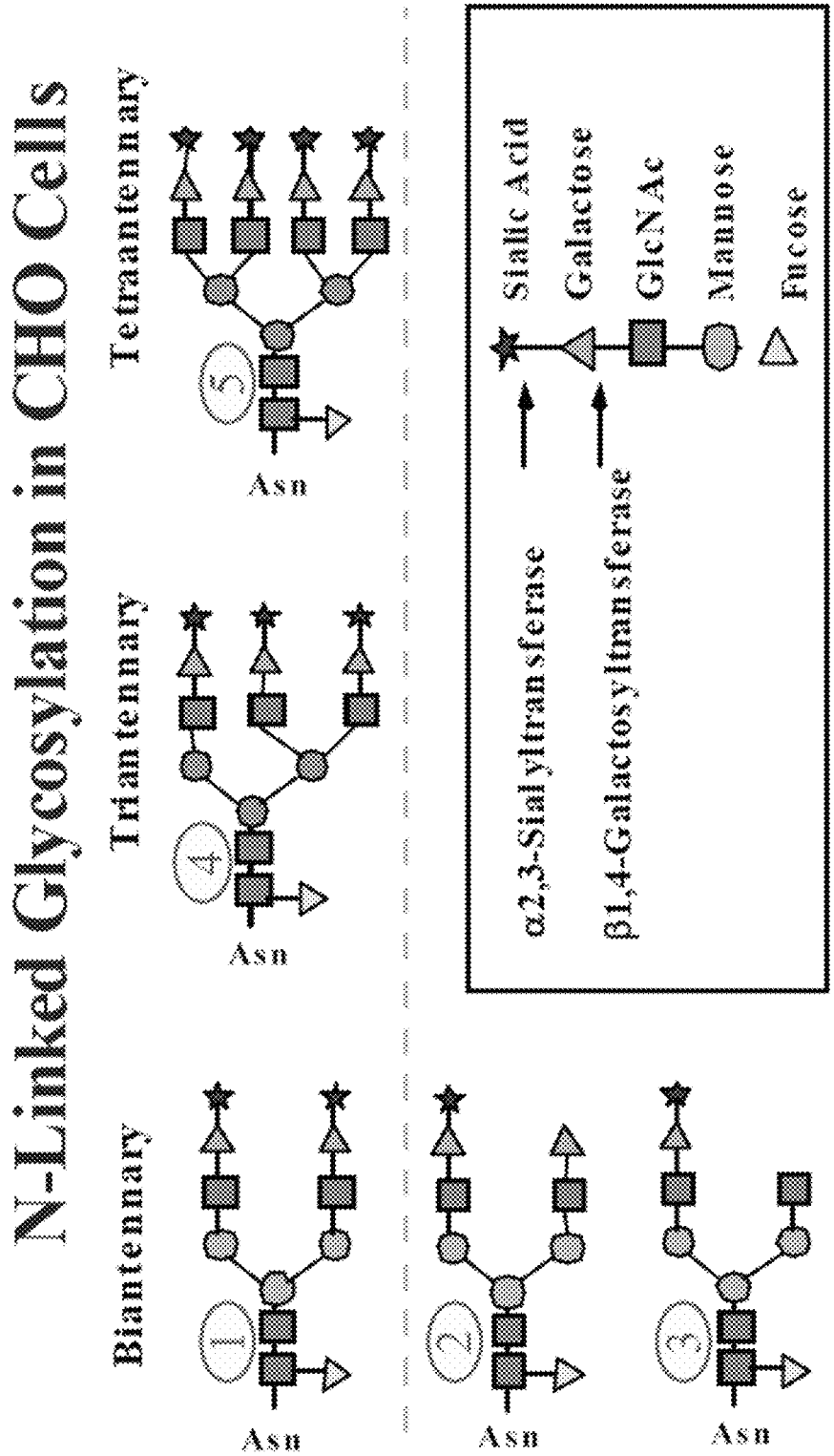
FIG. 49 depicts several of the various N-linked carbohydrate structures found in mammalian proteins. All chains share a common core structure containing two GlcNAc and three mannose residues.

FIG. 49 depicts several of the many N-linked carbohydrate structures found in mammalian proteins. All chains share a common core structure containing two GlcNAc and three mannose residues. From this core, two to four chains extend out consisting of one of three structures: -GlcNAc-Gal-NANA, -GlcNAc-Gal, or -GlcNAc (FIG. 49, structures (1), (2), and (3)). Assuming that the terminal sialic acid (NANA) is responsible for reducing clearance of the protein from the bloodstream. It came as a surprise that the clearance rate of CTLA4-Ig doubled in a monkey PK study (Table 56) even though the NANA ratio remained the same (Table 56—samples CTLA4-Ig S 1 and CTLA4-Ig (–) Gal, respectively, in FIGS. 50-51). One difference observed between the samples, prepared in different media, was the galactose-to-protein molar ratio, which was significantly higher in the sample prepared by the Process X than by Process Y (CTLA4-Ig). This suggested that the clearance rate was primarily determined by terminal GlcNAc residues, and that terminal galactose might provide some protection. To increase the galactosylation of CTLA4-Ig, galactose was added to the feed for the Y Process. The new process (CD-CHO1; CTLA4-Ig S2 in FIGS. 50-51) significantly increased both the galactose and NANA molar ratios of the CTLA4-Ig in the bioreactors.

Figure 61:
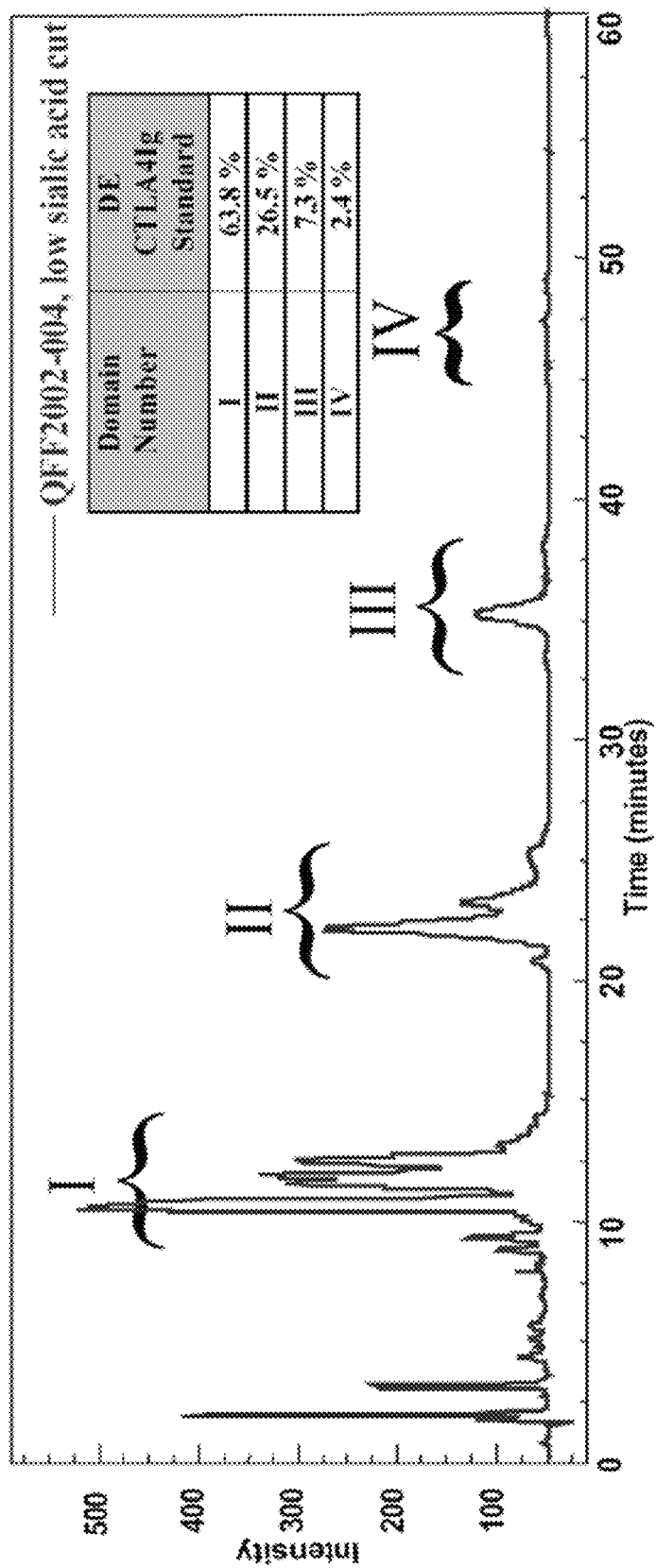
FIG. 61 depicts a trace of a N-linked carbohydrate chromatogram of the N-linked carbohydrates released from CTA4-Ig (as obtained from methods such as those described in Examples 3, 44, 22 and 37). This trace was obtained from CTLA4-Ig material that was recovered from the wash step of the QFF column, producing a cut of CTLA4-Ig material with low sialic acid. The relative amount of Domain I and II is increased and Domains III and Iv are decreased, compared to the traces shown in FIGS. 60, 59 and 58. The percentages of N-linked carbohydrates in each Domain is shown in the inset table.

Further monkey PK studies have been carried out. These have included CTLA4-Ig product produced by the three different processes (Process X, Process Y, and the CD-CHO1 Process; CTLA4-Ig S1, CTLA4-Ig (–) Gal, and CTLA4-Ig S2 respectively in FIGS. 50-51). In addition, CTLA4-Ig with a very low NANA ratio (recovered from a wash step in the purification procedure; see FIG. 61) has been tested. The analytical and PK data from all of the samples tested to date are compiled in Table 56. In the most recent PK study (Table 56), CTLA4-Ig produced from an extended Process Y fermentation run (CTLA4-Ig S3) was evaluated.

Figure 50:
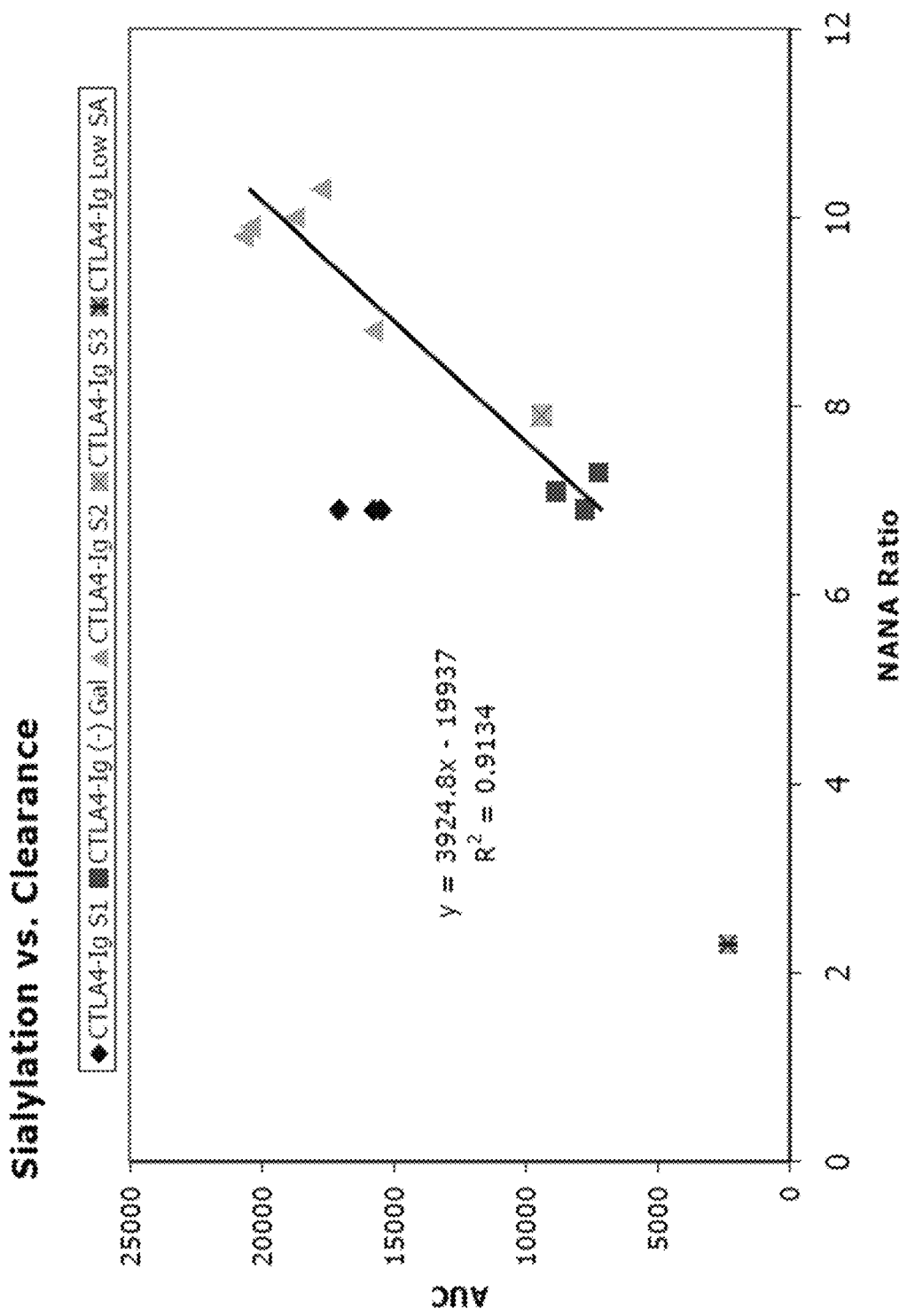
FIG. 50 is graph depicting CTLA4-Ig exposure (AUC) as a function of sialylation of the glycoprotein (NANA ratio).

FIG. 50 shows the correlation between the NANA ratio and the monkey PK AUC values for all of the samples in the four studies. Samples prepared by the Y Process (see CTLA4-Ig (−) Gal in FIG. 50) and the CD-CHO1 Process (CTLA4-Ig S2 in FIG. 50) showed a strong correlation between these parameters indicating that the NANA ratio has a significant impact on the clearance rate of CTLA4Ig. Analysis of the trendline for these points indicates that at NANA=9, CTLA4-Ig prepared by the Y (CTLA4-Ig (−) Gal) or CD-CHO1 (CTLA4-Ig S2) process will clear at about the same rate as the Process X material CTLA4-Ig S1). Reducing the NANA ratio to 8 reduces the AUC in the monkey PK by about 25%, while increasing the ratio to 10 increases the AUC by about 25%. Although there is a strong correlation between NANA and AUC within the context of the Y (CTLA4-Ig (−) Gal) and CD-CHO1 (CTLA4-Ig S2) processes, it is important to remember that NANA=7 for X material (CTLA4-Ig S1) with the same clearance rate as CD-CHO1 material (CTLA4-Ig S2) with a NANA ratio of 9. Therefore, the NANA ratio is not solely responsible for determining the clearance rate of CTLA4-Ig.

TABLE 56

Carbohydrate Evaluation of CTLA4-Ig.

| ASSAY | Ferm. Process PARAMETER | X Process MEAN | SD | Y Process MEAN | SD | Y Process MEAN | SD |
|---|---|---|---|---|---|---|---|
| Sialic Acid Carbohydrate Profile | NaNA:PROT. | 6.9 | | 7.1 | | 6.9 | |
| | % Domain 1 (PA) | | | | | | |
| | % Domain 2 (PA) | | | | | | |
| | % Domain 3 (PA) | | | | | | |
| | % Domain 4 (PA) | | | | | | |
| | % Domain 1 (M-1) | 42.4% | | 49.1% | | 43.1% | |
| | % Domain 2 (M-1) | 28.2% | | 31.1% | | 32.8% | |
| | % Domain 3 (M-1) | 21.1% | | 15.9% | | 19.7% | |
| | % Domain 4 (M-1) | 7.4% | | 3.8% | | 3.7% | |
| Monosaccharide Analysis | Mannose | 17.3 | | 17.2 | | 15.0 | |
| | Fucose | 5.7 | | 5.7 | | 6.7 | |
| | Galactose | 13.1 | | 8.1 | | 9.1 | |
| | GalNAc | 2.7 | | 3.4 | | 3.2 | |
| | GlcNAc | 19.9 | | 21.3 | | 26.3 | |
| | Gal:Man | 75.7% | | 47.1% | | 60.7% | |
| | Gal:GlcNAc | 65.8% | | 38.0% | | 34.6% | |
| Monkey PK DS02051-1 | AUC (hrs * µg/ml) | 17060 | 1171 | 8832 | 2203 | | |
| Monkey PK DS02051-2 | AUC (hrs * µg/ml) | 15753 | 4395 | | | 7765 | 1247 |
| Monkey PK DS02051-3 | AUC (Hrs * µg/ml) | 15459 | | | | | |
| Monkey PK DS03228 | AUC (Hrs * µg/ml) | | | | | | |

| ASSAY | Ferm. Process PARAMETER | Y Process MEAN | SD | CD-CH01 MEAN | SD |
|---|---|---|---|---|---|
| Sialic Acid Carbohydrate Profile | NaNA:PROT. (M-2) | 7.3 | | 9.9 | |
| | % Domain 1 (PA) | | | | |
| | % Domain 2 (PA) | | | 36.0% | |
| | % Domain 3 (PA) | | | 35.6% | |
| | % Domain 4 (PA) | | | 23.1% | |
| | % Domain 1 (M-1) | 42.9% | | 5.2% | |
| | % Domain 2 (M-1) | 33.5% | | 33.6% | |
| | % Domain 3 (M-1) | 18.4% | | 31.6% | |
| | % Domain 4 (M-1) | 3.6% | | 27.5% | |
| | | | | 5.9% | |
| Monosaccharide Analysis | Mannose | 19.6 | | 18.0 | |
| | Fucose | 4.6 | | 4.8 | |
| | Galactose | 11.1 | | 15.8 | |
| | GalNAc | 3.3 | | 3.3 | |
| | GlcNAc | 21.9 | | 22.3 | |
| | Gal:Man | 56.6% | | 87.8% | |
| | Gal:GlcNAc | 50.7% | | 70.9% | |
| Monkey PK DS02051-1 | AUC (hrs * µg/ml | | | | |
| Monkey PK DS02051-2 | AUC (hrs * µg/ml) | 7266 | 787 | 20445 | 2425 |
| Monkey PK DS02051-3 | AUC (Hrs * µg/ml) | | | | |
| Monkey PK DS03228 | AUC (Hrs * µg/ml) | | | | |

TABLE 56-continued

Carbohydrate Evaluation of CTLA4-Ig.

| ASSAY | Ferm. Process PARAMETER | Process X MEAN | SD | (d12) CD-CH01 MEAN | SD | (d16) CD-CHO1 MEAN | SD |
|---|---|---|---|---|---|---|---|
| Sialic Acid | NaNA:PROT. | 2.3 | | 9.8 | | 8.8 | |
| Carbo- | % Domain 1 (PA) | 63.8% | | 34.1% | | 42.0% | |
| hydrate | % Domain 2 (PA) | 26.5% | | 28.3% | | 30.1% | |
| Profile | % Domain 3 (PA) | 7.3% | | 25.7% | | 22.4% | |
| | % Domain 4 (PA) | 2.4% | | 10.7% | | 5.3% | |
| | % Domain 1 (M-1) | | | 34.8% | | 38.2% | |
| | % Domain 2 (M-1) | | | 28.7% | | 34.8% | |
| | % Domain 3 (M-1) | | | 30.1% | | 22.5% | |
| | % Domain 4 (M-1) | | | 6.1% | | 4.3% | |
| | % Domain 1 (M-2) | | | 37.8% | | 44.4% | |
| | % Domain 2 (M-2) | | | 34.5% | | 32.8% | |
| | % Domain 3 (M-2) | | | 22.8% | | 19.6% | |
| | % Domain 4 (M-2) | | | 5.0% | | 3.2% | |
| Mono- | Mannose | 17.9 | | 13.6 | | 14.5 | |
| saccharide | Fucose | 5.5 | | 5.4 | | 5.3 | |
| Analysis | Galactose | 4.1 | | 12.8 | | 11.4 | |
| | GalNAc | 2.9 | | 2.1 | | 2.2 | |
| | GlcNAc | 22.0 | | 26.3 | | 19.9 | |
| | Gal:Man | 22.9% | | 94.1% | | 78.6% | |
| | Gal:GlcNAc | 18.6% | | 48.7% | | 57.3% | |
| Monkey PK DS02051-1 | AUC (hrs * µg/ml) | | | | | | |
| Monkey PK DS02051-2 | AUC (hrs * µg/ml) | 2337 | 414 | | | | |
| Monkey PK DS02051-3 | AUC (Hrs * µg/ml) | | | 20707 | | 15779 | |
| Monkey PK DS03228 | AUC (Hrs * µg/ml) | | | | | | |

| ASSAY | Ferm. Process PARAMETER | (d14) Process X MEAN | SD SD | (d16) CD-CHO1 MEAN | SD SD | (d16) CTLA4-Ig S3 CD-CHO1 MEAN | SD SD |
|---|---|---|---|---|---|---|---|
| Sialic Acid | NaNA:PROT. (BAS) | 10.0 | | 10.3 | | 7.9 | |
| Carbo- | % Domain 1 (PA) | 38.6% | | 41.3% | | 56.2% | |
| hydrate | % Domain 2 (PA) | 30.1% | | 32.2% | | 26.9% | |
| Profile | % Domain 3 (PA) | 23.1% | | 21.9% | | 13.1% | |
| | % Domain 4 (PA) | 7.6% | | 4.6% | | 3.7% | |
| | % Domain 1 (M-1) | | | 39.5% | | 49.0% | |
| | % Domain 2 (M-1) | | | 31.8% | | 29.1% | |
| | % Domain 3 (M-1) | | | 21.9% | | 15.7% | |
| | % Domain 4 (M-1) | | | 7.8% | | 6.3% | |
| | % Domain 1 (M-2) | 38.2% | | 36.2% | | 47.1% | |
| | % Domain 2 (M-2) | 33.7% | | 34.3% | | 33.6% | |
| | % Domain 3 (M-2) | 24.6% | | 21.1% | | 14.5% | |
| | % Domain 4 (M-2) | 3.6% | | 8.4% | | 4.8% | |
| Mono- | Mannose | 14.8 | | 14.7 | | 11.8 | |
| saccharide | Fucose | 5.3 | | 4.9 | | 5.7 | |
| Analysis | Galactose | 13.0 | | 12.6 | | 11.5 | |
| | GalNAc | 2.2 | | 2.2 | | 2.3 | |
| | GlcNAc | 20.2 | | 16.3 | | 28.4 | |
| | Gal:Man | 87.8% | | 85.7% | | 97.5% | |
| | Gal:GlcNAc | 64.4% | | 77.3% | | 40.5% | |
| Monkey PK DS02051-1 | AUC (hrs * µg/ml) | | | | | | |
| Monkey PK DS02051-2 | AUC (hrs * µg/ml) | | | | | | |
| Monkey PK DS02051-3 | AUC (Hrs * µg/ml) | 18750 | | | | | |
| Monkey PK DS03228 | AUC (Hrs * µg/ml) | | | 17739 | 2546 | 9425 | 1504 |

M-1 indicates that the CTLA4-Ig material was analyzed using Method 1,
M-2 indicates that the CTLA4-Ig material was analyzed using a slightly different, Method 2.
"PA" indicates material that is a Protein A purified sample from fermentation broth.

Another monkey PK study (Table 56) was performed to compare clearance rates of CTLA4Ig produced by the three different processes (Process X, Process Y, and CD-CHO1 Process). In addition, CTLA4Ig with a very low NANA ratio (recovered from a wash step in the purification procedure (PA)) was included in the study. CTLA4Ig prepared by the CD-CHO process in either 50 L or 5000 L bioreactors had NANA molar ratios close to the X Process material, and in the PK study, both had AUC values of about half the Process X value. CTLA4Ig produced by the CD-CHO1 process had a higher NANA ratio than the Process X material (9.9 vs. 6.9) and an AUC value about 30% higher, indicating a slower clearance rate. The poorly sialylated and galactosylated wash material (NANA=2.3) cleared extremely quickly (AUC=2337 hr-µg/ml vs. 15753 for the Process X material).

Another monkey PK study (Table 56) compared CTLA4Ig prepared by the CD-CHO1 process in 5,000 L bioreactors and harvested on different days. During the course of a fermentation run, the NANA ratio typically peaks at about Day 8, then gradually declines. From two runs, aliquots were removed on Days 12, 14, and 16, then purified. After purification, NANA ratios ranged from 8.8 to 10.0. Day 12 and 14 samples (NANA=9.8 and 10.0 respectively) had AUC values 20-30% higher than the Process X material. The Day 16 sample (NANA=8.8) had an AUC value almost identical to the Process X material.

Another analytical tool to evaluate the glycosylation of CTLA4-Ig is the carbohydrate profile. Entire N-linked carbohydrate structures are enzymatically removed and separated by anion exchange HPLC. A large number of peaks are generated which resolve into four or five domains (see FIGS. 57-61). Domains I and II are largely asialylated and mono-sialylated structures, while Domains III and IV and V are largely di- and tri- and tetra-sialylated structures.

Figure 51:
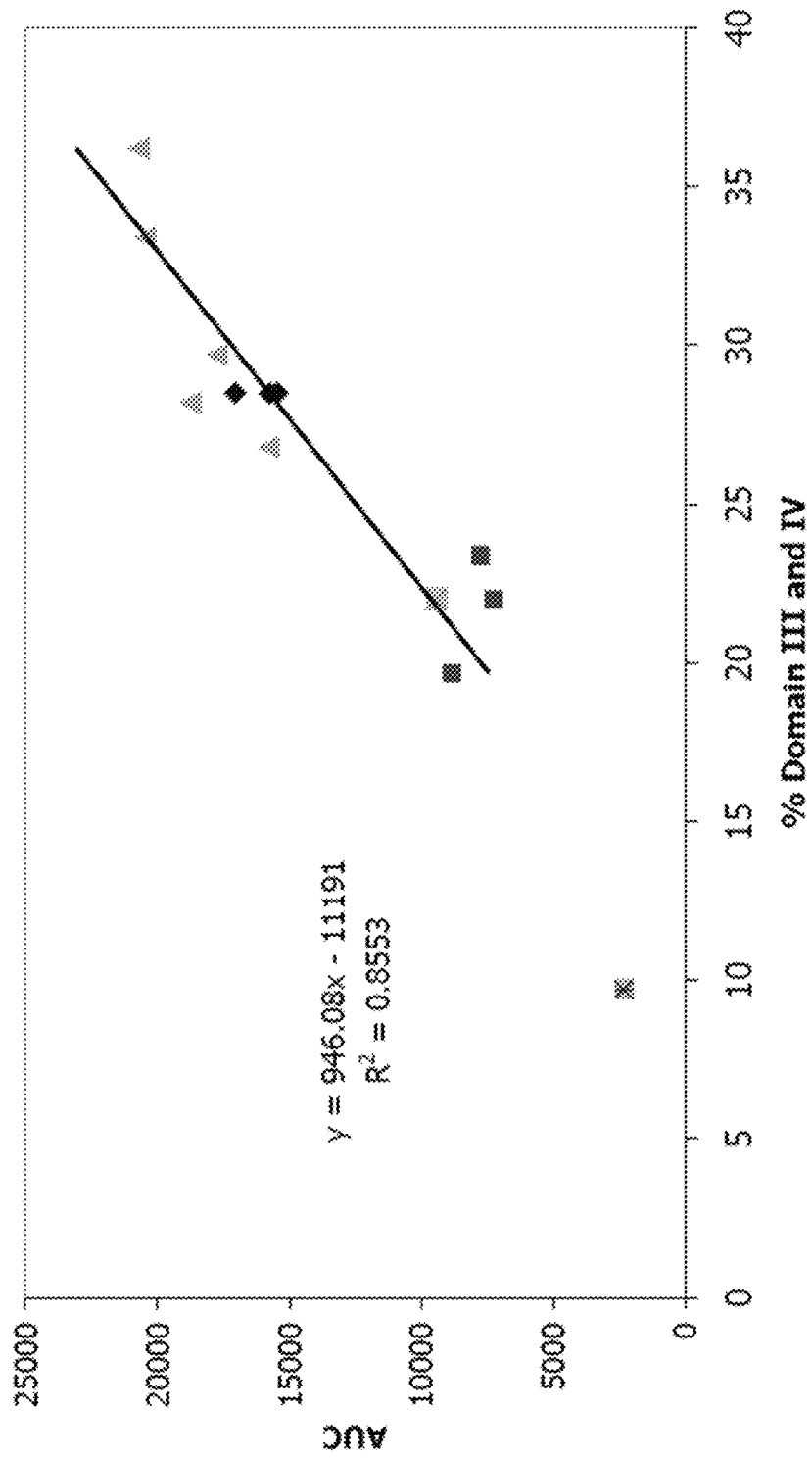
FIG. 51 is graph depicting CTLA4-Ig exposure (AUC) as a function CTLA4-Ig's carbohydrate profile. A large number of peaks were generated by anion exchange HPLC which were resolved into four or five domains. Domains 1 and 2 are largely asialylated and mono-sialylated structures, while domains 3 and 4 are largely di- and tri-sialylated structures.

It was empirically observed that the percentage of the total profile in Domains III and IV correlated well with the AUC for all of the samples, including the Process X material (FIG. 51). Most of the structures in these domains are expected to be fully sialylated and galactosylated. Using data from the M-1 group, a Domain III and IV percentage of about 29% should have the same clearance rate as the Process X material. Domain III and IV data from Method 2 is typically about 4% lower (21% vs. 25%) than data generated by Method 1.

Figure 56:
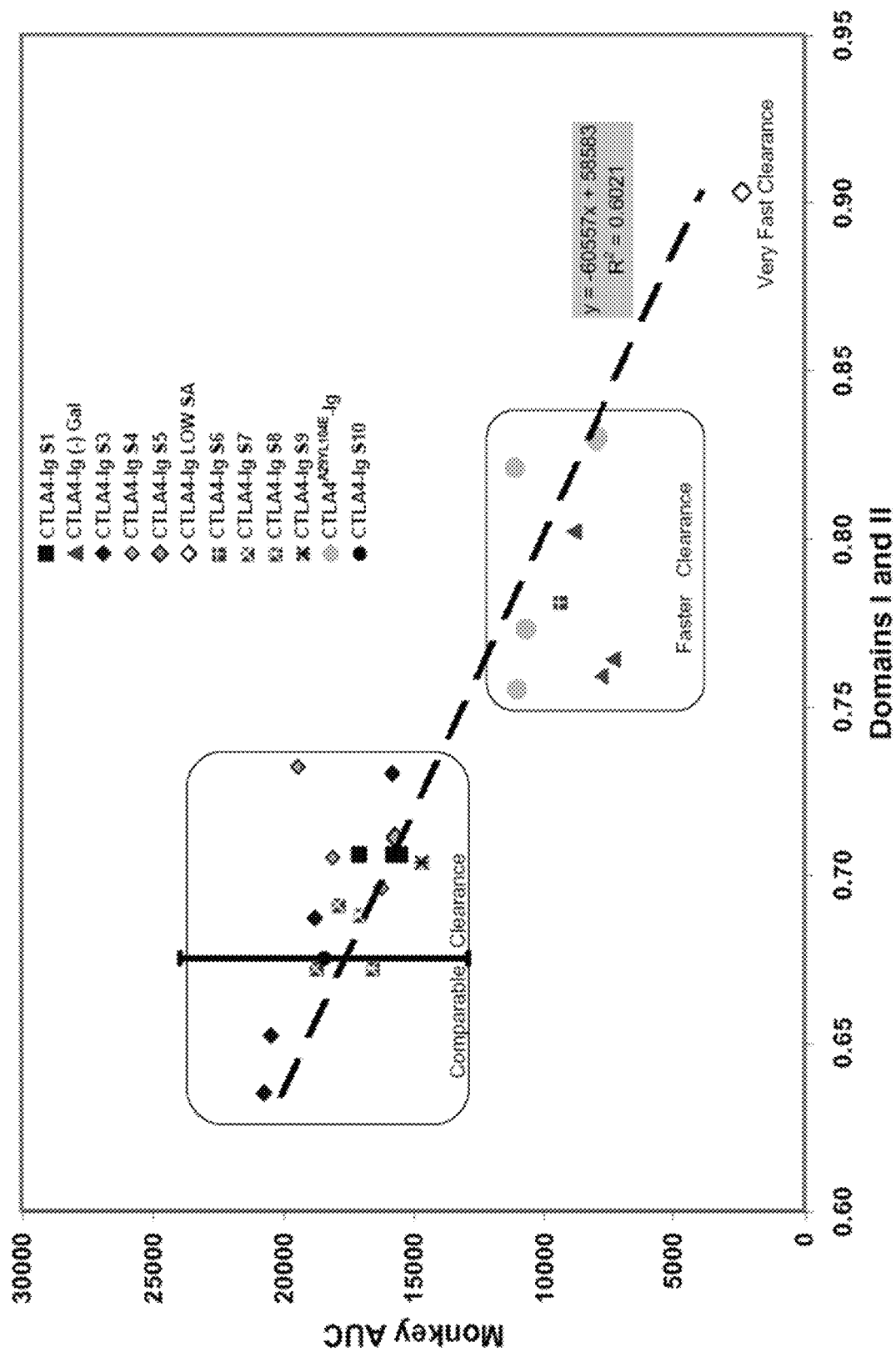
FIG. 56 depicts a graph of pharmacokinetic data showing monkey AUC on the Y axis and percent of N-linked glycosylation as shown in Domains I and II from a carbohydrate profile on the X axis. See methods of determining the N-linked carbohydrate profile in, for example, Examples 3, 44, 22 and 37. As the percentage of Domains I and II increases (and the percentage of Domains III, IV and V decreases), clearance increases. Note that the negative control, the CTLA4-Ig with low sialic acid is cleared very rapidly. Note that the CTLA4-Ig variant, LEA (CTLA4-Ig$^{A29YL104E}$-Ig) is included in this graph.
Figure 57A:
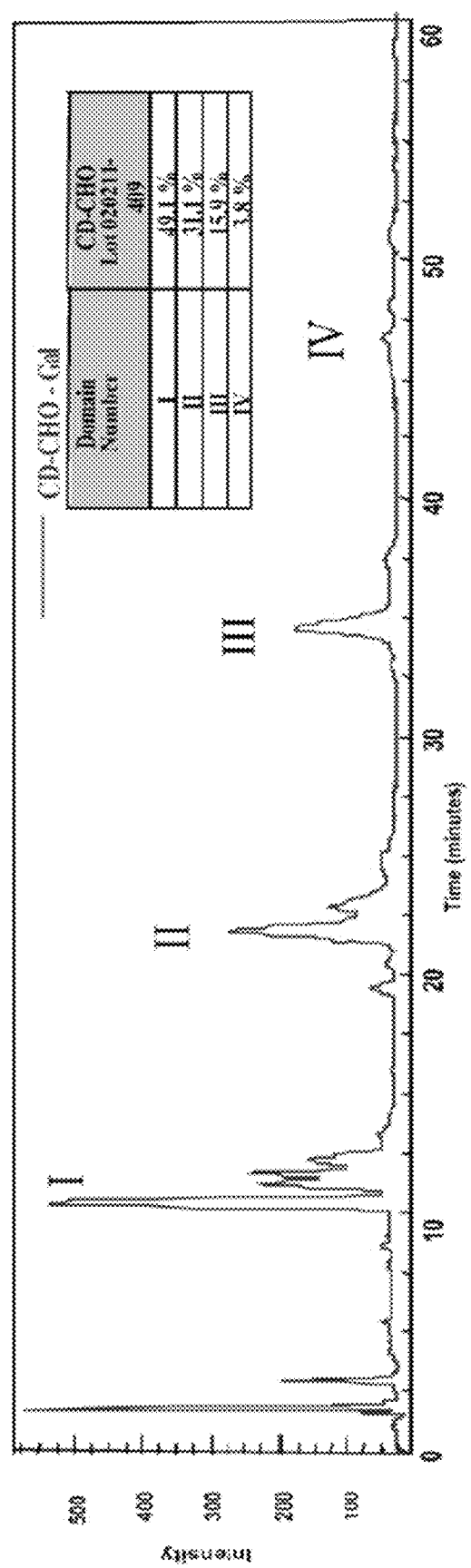
FIGS. 57A and 57B depict a trace of a N-linked carbohydrate chromatogram of the N-linked carbohydrates released from CTA4-Ig (as obtained from methods such as those described in Examples 3, 44, 22 and 37). The trace in FIG. 57A is of from an analysis of CTLA4-Ig produced in a culture method without additional galactose added to the culture. The trace in FIG. 57B did have galactose added to the culture. The percentages of N-linked carbohydrates in each Domain is shown in the inset table.
Figure 57B:
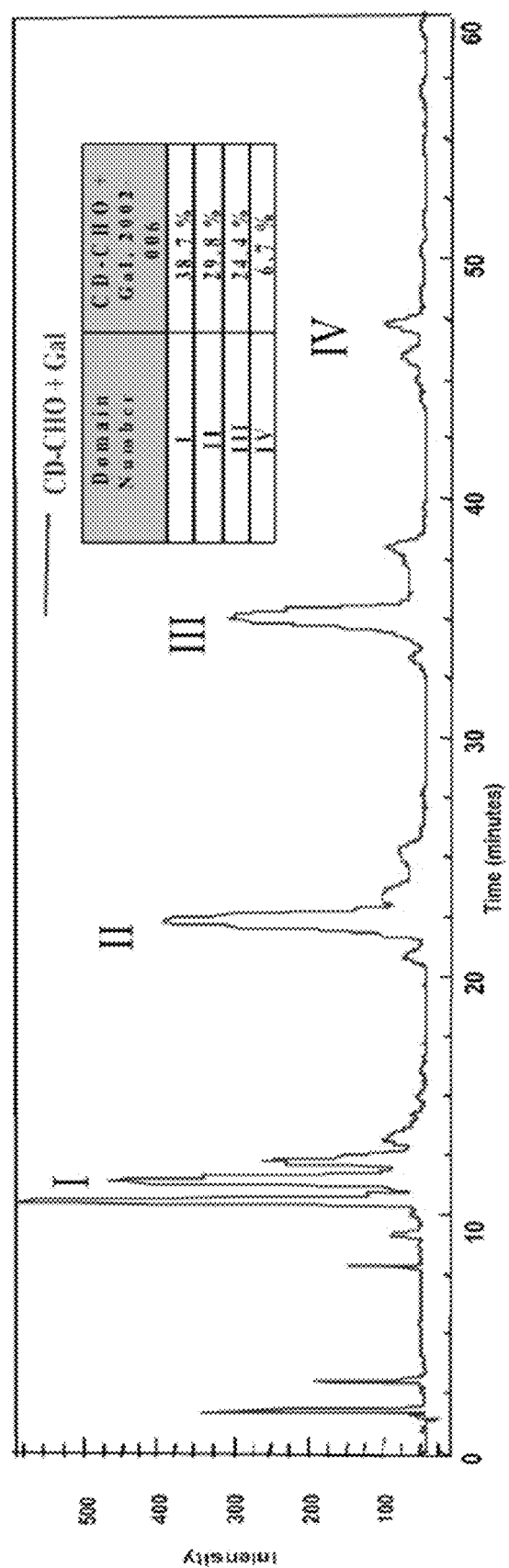
Figure 58:
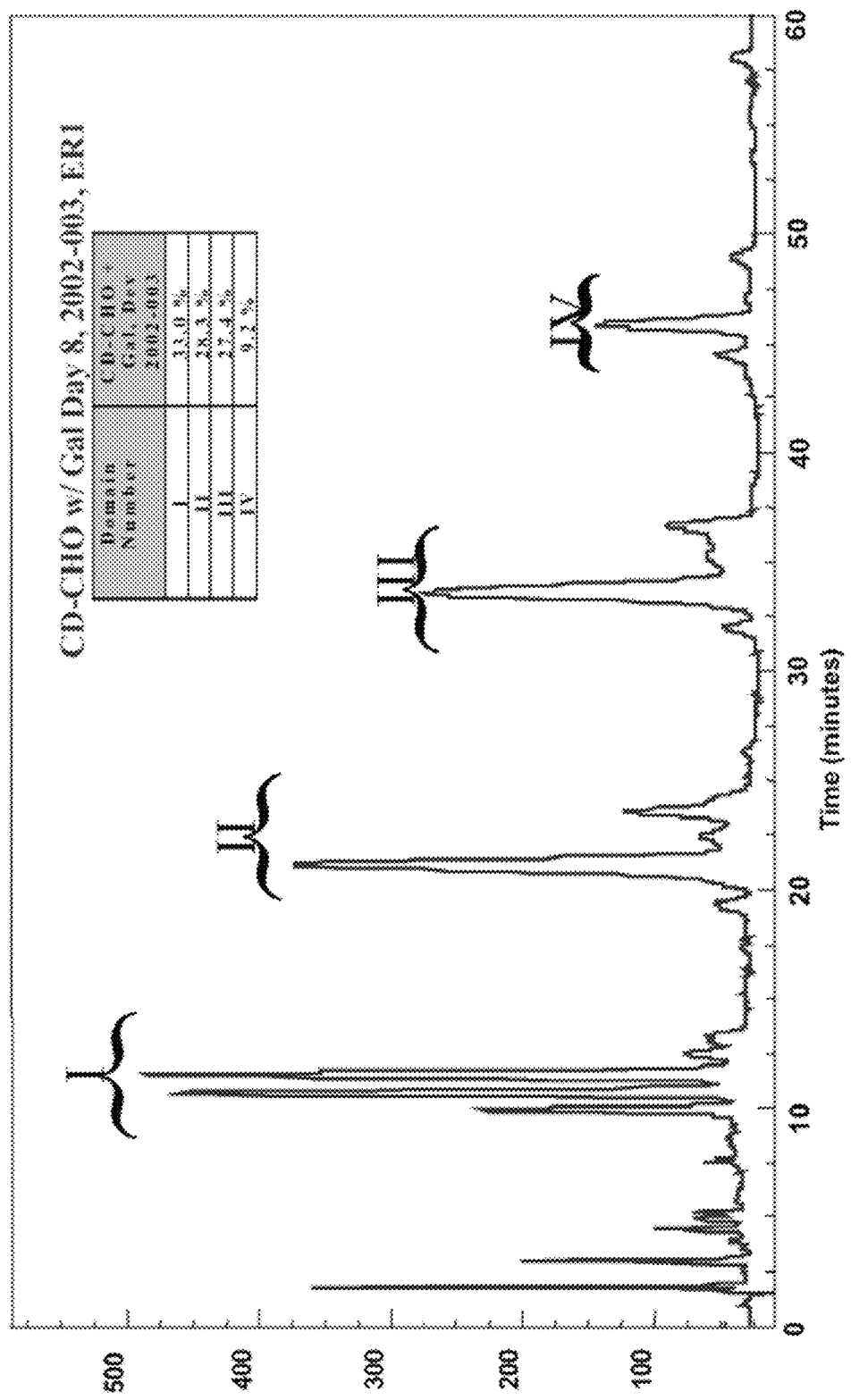
FIG. 58 depicts a trace of a N-linked carbohydrate chromatogram of the N-linked carbohydrates released from CTA4-Ig (as obtained from methods such as those described in Examples 3, 44, 22 and 37). This is from an analysis of CTLA4-Ig produced in a culture method with galactose added to the culture at day 8. This trace of from an analysis of CTLA4-Ig produced in a culture method without additional galactose added to the culture. The percentages of N-linked carbohydrates in each Domain is shown in the inset table.
Figure 59:
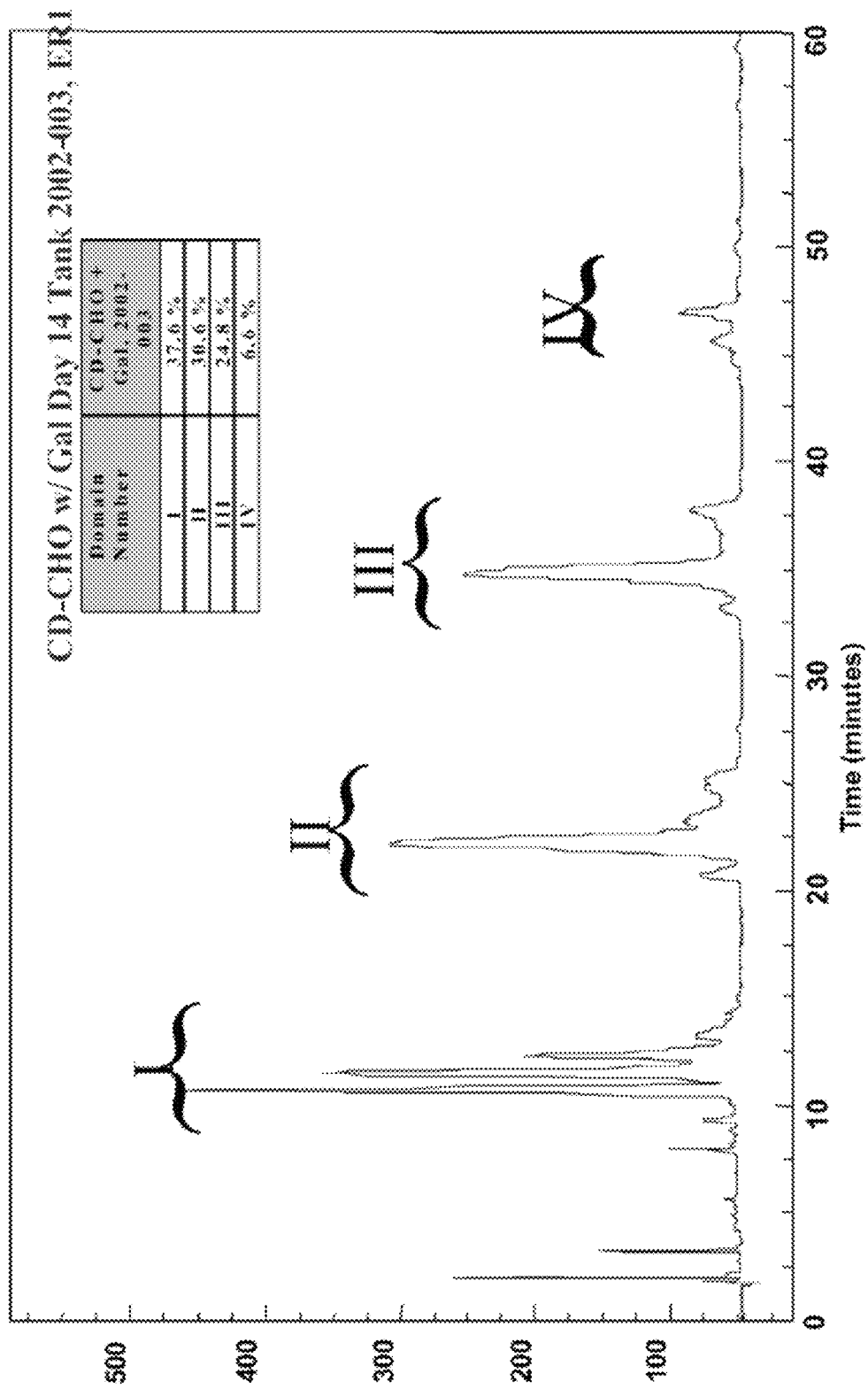
FIG. 59 depicts a trace of a N-linked carbohydrate chromatogram of the N-linked carbohydrates released from CTA4-Ig (as obtained from methods such as those described in Examples 3, 44, 22 and 37). This is from an analysis of CTLA4-Ig produced in a culture method with galactose added to the culture at day 14. This trace of from an analysis of CTLA4-Ig produced in a culture method without additional galactose added to the culture. The percentages of N-linked carbohydrates in each Domain is shown in the inset table.
Figure 60A:
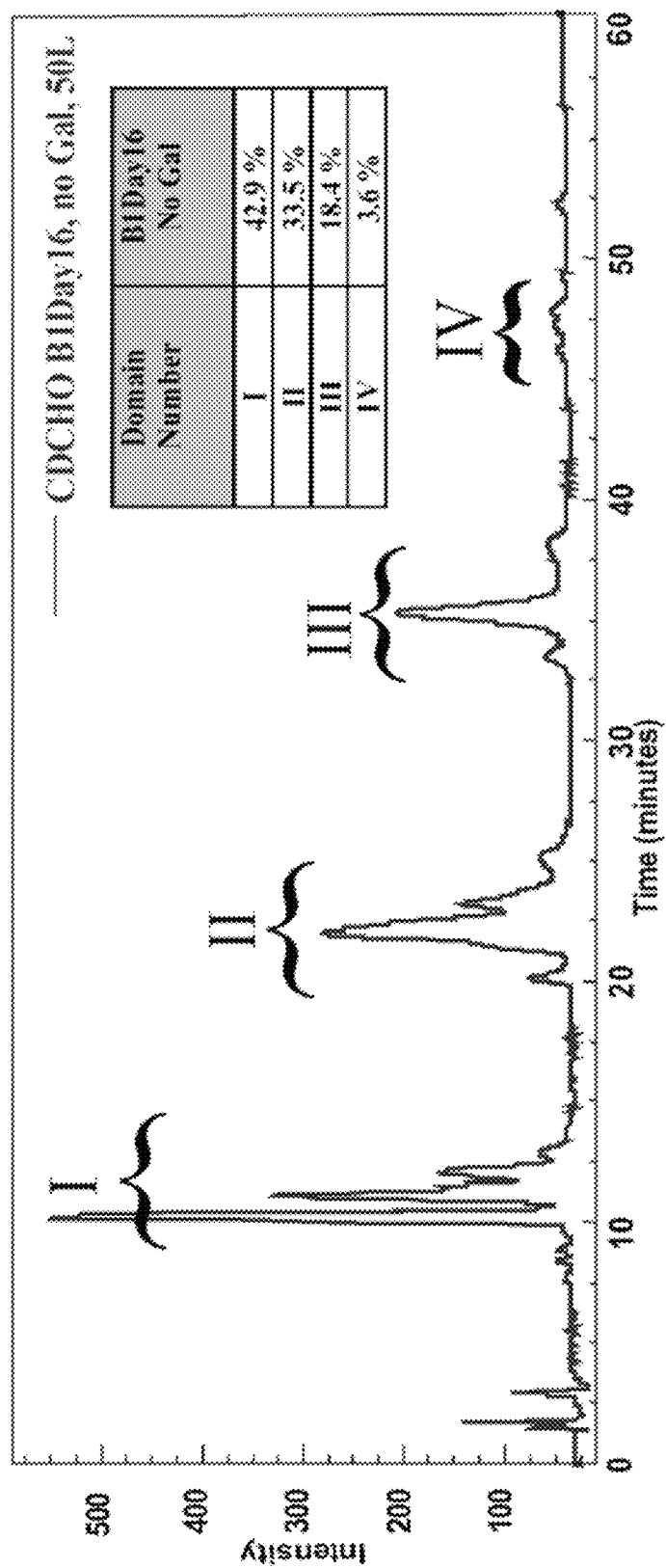
FIGS. 60A and 60B depicts a trace of a N-linked carbohydrate chromatogram of the N-linked carbohydrates released from CTA4-Ig (as obtained from methods such as those described in Examples 3, 44, 22 and 37).
Figure 60B:
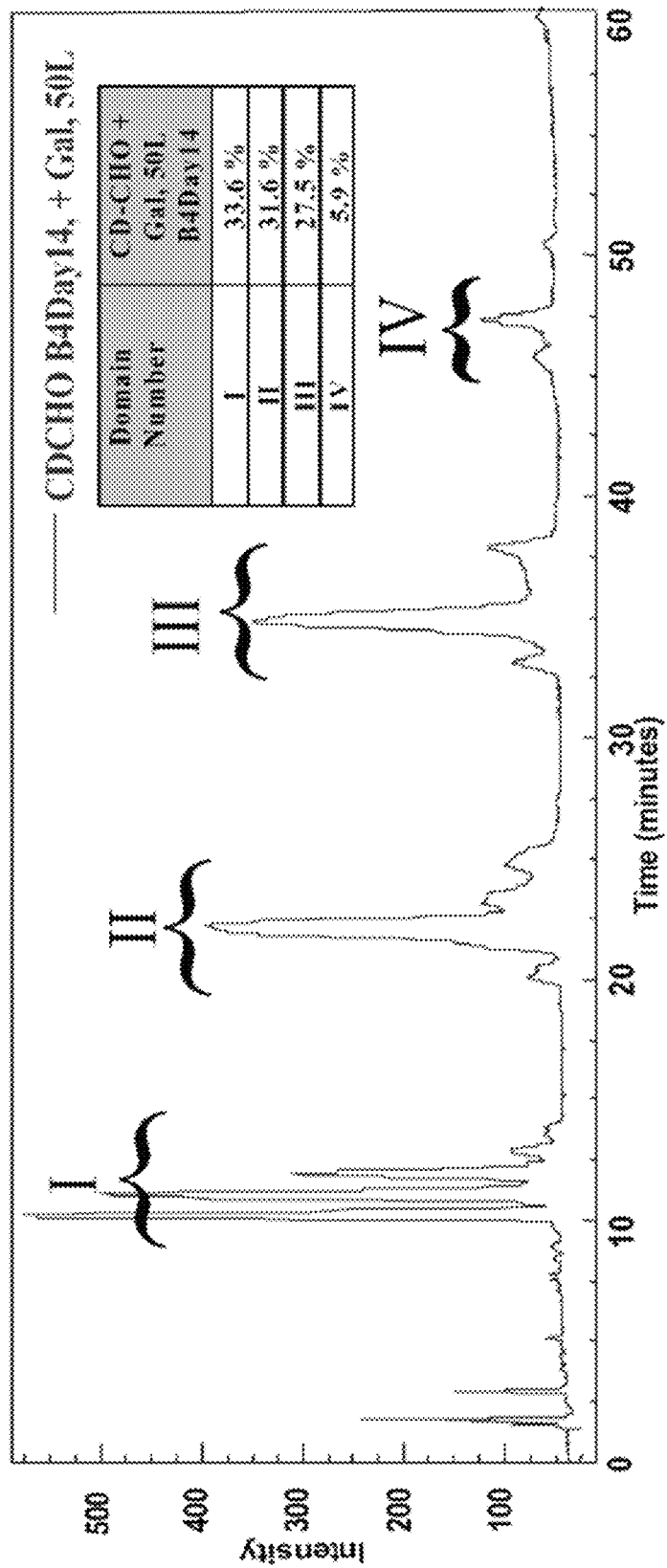

In addition, the percentage of the total profile in Domains I and II also were observed to correlate well with the AUC for all of the samples (FIG. 56). Most of the structures in these domains are expected to be largely asialylated and mono-sialylated structures. FIG. 56 shows that the clearance rate was higher in samples with a lower percentage of Domains I and II versus those samples with a higher percentage of Domains I and II. The decreased glycosylation of Domains I and II correlate with the presumably increased presence of peptides glycosylated in Domains III and IV.

Although the sialic acid to protein molar ratio has been traditionally used to predict the clearance rate for CTLA4Ig, different fermentation media have produced molecules with the same NANA ratio but different clearance rates in monkey PK studies. To develop a better way to predict clearance rates, two other sets of analytical data (monosaccharide analysis and carbohydrate profile) were evaluated and compared to monkey PK data. The most predictive analytical parameter was the extent of galactosylation of CTLA4Ig. To reduce analytical variability of this assay, the galactose molar ratio was normalized to the mannose molar ratio. The resulting Gal:Man ratio correlated well with the AUC results from the monkey PK study for all of the samples, including the Process X material. This result is consistent with a model that the clearance rate of CTLA4Ig is primarily determined by the number of exposed terminal GlcNAc residues on the molecule. If this model is correct, the extent of galactosylation should predict clearance rates better than sialylation. To ensure pharmacokinetic comparability (AUC ≥75% of material from the X Process), a specification for the galactose to mannose ratio of Gal:Man ≥0.65 is recommended for purified bulk CTLA4-Ig drug substance (BDS).

When only material prepared by the Y Process or CD-CHO1 process is analyzed, the NANA to protein molar ratio can predict clearance rates accurately. This relationship does not apply, however, to material prepared by the X Process. To be comparable to X Process material, CTLA4-Ig prepared by the Y Process or the CD-CHO1 process must have a NANA ratio 2 units higher (NANA=9 for CD-CHO1 is comparable to NANA=7 for the X Process material). Because the sialic acid assay is accurate and has a rapid turn-around time, it is useful as an in-process analytical tool to monitor the quality of the CTLA4Ig during a fermentation run.

To maintain comparable pharmacokinetics (AUC ≥75% of reference), a specification of NANA ≥8 is recommended for purified BDS. This value also represents a reasonable target for harvesting the fermentation runs. Because the purification process can increase the sialic acid ratio by at least 2 units, setting the harvest target at NANA=8 will ensure an actual harvest value of at least NANA=7. The purification process can increase this value to at least NANA=9, which is comparable to the Process X material and well above the aforementioned recommended minimum specification of the BDS.

The carbohydrate profile also predicted the monkey PK results well for both Process X material and Process Y material when the percent area under Domains III and IV was compared to the AUC. Domains III and IV consist largely of fully sialylated and galactosylated carbohydrate structures.

The data in Table 56 can be further presented so as to show a correlation between the AUC value, the NANA value, the Gal value, and the total percentage of sum of the AUC of Domains II and IV. See below:

| AUC | NANA | Gal | Sum of Domains III and IV |
|---|---|---|---|
| 2,337 | 2.3 | 4.1 | 9.7 |
| 8,832 | 7.1 | 8.1 | 19.7 |
| 7,266 | 7.3 | 11.1 | 22.0 |
| 9,425 | 7.9 | 11.5 | 22.0 |
| 7,765 | 6.9 | 9.1 | 23.4 |
| 15,779 | 8.8 | 11.4 | 26.8 |
| 18,750 | 10 | 13.0 | 28.2 |
| 17,060 | 6.9 | 13.1 | 28.5 |
| 15,753 | | | |
| 15,459 | | | |
| 17,739 | 10.3 | 12.6 | 29.7 |
| 20,445 | 9.9 | 15.8 | 33.4 |
| 20,707 | 9.8 | 12.8 | 36.2 |

This table above shows that there is a correlation between the sum of Domains III (and IV) and the PK outcome of the composition. The AUC of Domains III and IV and V are directly related to the molar ratio of NANA and Gal to moles of CTLA4-Ig protein. Therefore, the invention provides for compositions characterized in that their carbohydrate profile contains a sum of Domains III and IV, or a sum of Domains III, IV and V of from 18 to about 37 AUC %. In one embodiment, the sum of Domains II, IV and V is about 19 to about 36, is about 20 to about 35, is about 21 to about 34, is about 22 to about 33, is about 23 to about 32, is about 24 to about 31, is about 25 to about 30, is about 26 to about 29, is about 27 to about 28 AUC %. In one embodiment, the invention provides for CTLA4-Ig compositions characterized in that the Domain III has an AUC % of the total of 19±4; and Domain IV has an AUC % of the total of 7±4.

Example 43: Tryptic Peptide Mapping of CTLA4-IG

CTLA4-Ig derived from transfected Chinese Hamster Ovary (CHO) cells is a glycoprotein with a molecular mass of approximately 92500 Daltons. Peptide mapping is a highly sensitive method for determining the identity of the primary structure of a protein and is useful in detecting post-translational modifications. The protein is denatured using guanidine-HCl, reduced, and alkylated using DTT and IAA. The protein is desalted using NAP-5 columns and the digest mixture is analyzed by reversed phase (C18) chromatography. Peak detection is done by UV absorbance at 215 nm.

Reagents:

Mobile Phase A solution (0.02% Trifluoroacetic Acid (TFA) in Water (v/v)); Mobile Phase B solution (0.02% TFA in 95 ACN (Acetonitrile) and 5% Water (v/v)); Alkylating Agent (200 mM Iodoacetamide (IAA)); Dilution Buffer (100 mM Tris, 25 mM NaCl, pH 8.0); Denaturing Buffer (8 M Guanidine, 50 mM TRIS, pH 8.0); Digestion Buffer (50 mM TRIS, 10 mM $CaCl_2$), pH 8.0); Reducing Agent (100 mM DTT).

Instrumentation:

(equivalent instrumentation may be used) NAP-5 columns (Amersham, cat. #17-0853-02); HPLC Column Heater; Water's Alliance HPLC system with column heater and UV detector.

Reduction and Alkylation:

Samples (for example, $CTLA4^{A29YL104E}$-Ig, standards, etc.) were diluted to 10 mg/ml by adding water to a final volume of 100 μL (1 mg). 560 μl of denaturing buffer and 35 μL of Reducing Agent (100 mM DTT) were added to the 100 μl samples, were mixed, and spun down in a microcentrifuge for 3 seconds. Samples were then incubated at 50° C. for 20 minutes±2 minutes. 35 μL of Alkylating Agent (200 mM IAA) was then added to each sample, and again samples were mixed, and spun down in a microcentrifuge for 3 seconds. Samples were subsequently incubated at 50° C. for 20 min.±2 minutes, in the dark. After the NAP-5 columns were equilibrated by pouring 3 columns volumes (about 7-8 mL) of digestion buffer, 500 μl of the reduced and alkylated mixtures were poured over the NAP-5 columns, allowing the liquid to drain through column. Samples were then collected from the NAP-5 columns via eluting sample off of the column with 1 mL of digestion buffer.

Digestion:

Samples were digested with 20 μL of trypsin (0.5 μg/μL) in 38° C. water bath for 4 hours (±0.5 hr). Upon completion of digest, samples were acidified with 2.5 μL of TFA. Samples were then placed into autosampler vials for subsequent analysis.

Instrument Method:

The instrument method is shown below:

| Time (min) | Flow (mL/min) | Mobile Phase A | Mobile Phase B |
|---|---|---|---|
| 0 | 0.7 | 100 | 0 |
| 17 | 0.7 | 83 | 17 |
| 27 | 0.7 | 78 | 22 |
| 42 | 0.7 | 73 | 27 |
| 58 | 0.7 | 65 | 35 |
| 74 | 0.7 | 52 | 48 |
| 79 | 0.7 | 0 | 100 |
| 84 | 0.7 | 100 | 0 |
| 88 | 0.7 | 100 | 0 |

Figure 52:
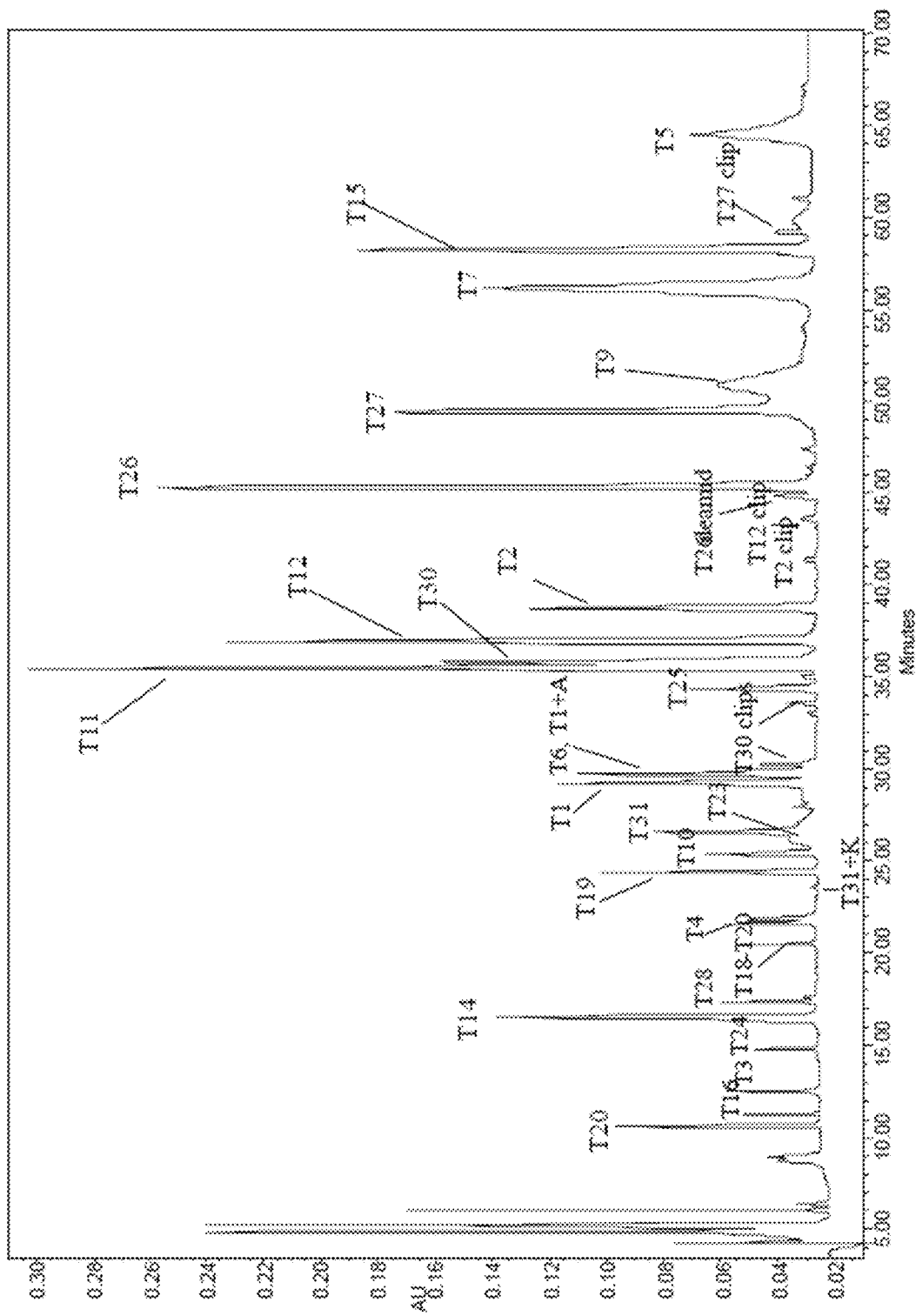
FIG. 52 represents a tryptic peptide map of CTLA4$^{A29YL104E}$-Ig with peptides labeled. Table 56 corresponds with the labeled peptides.
Figure 53:
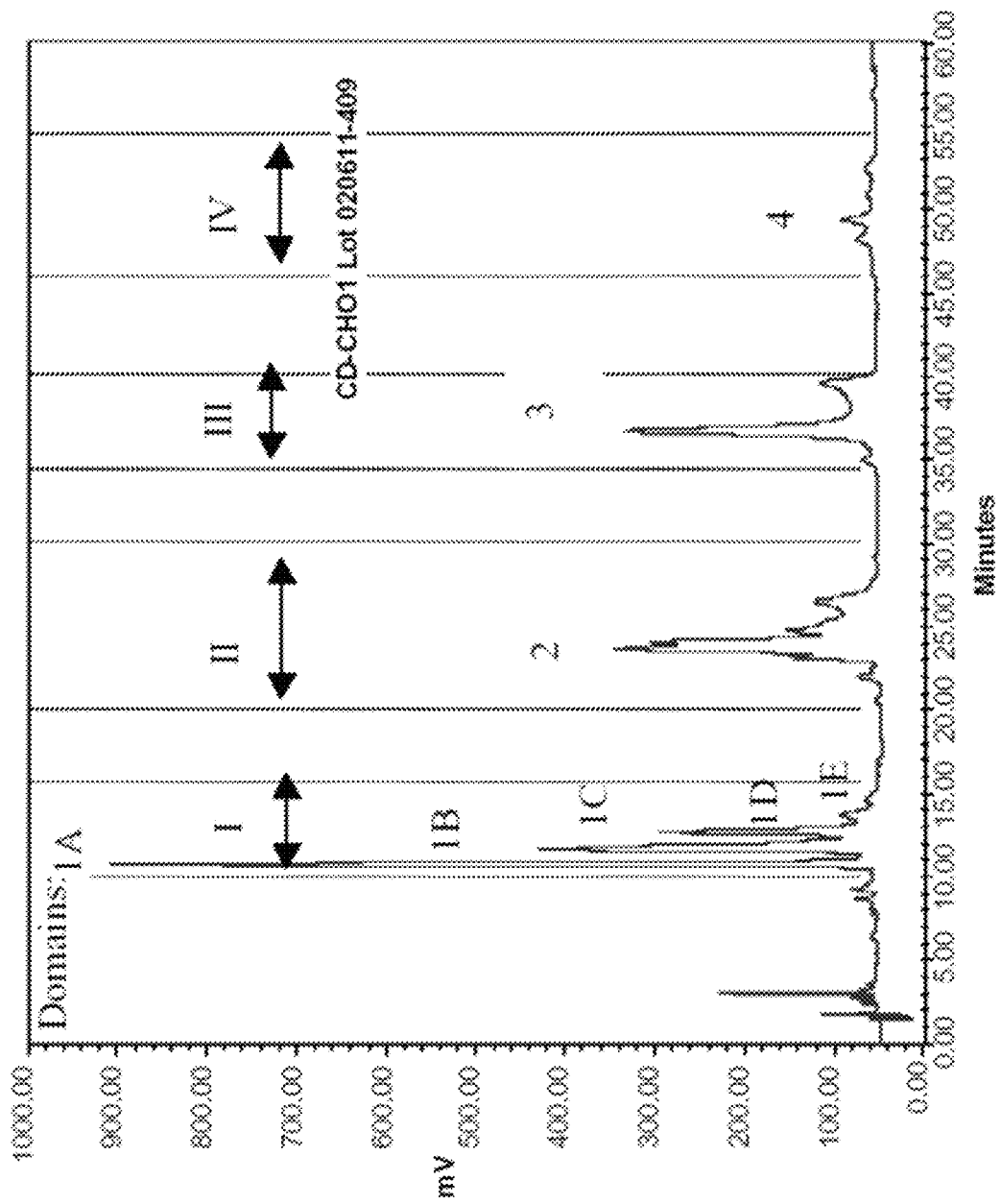
FIG. 53 represents the comparative N-linked oligosaccharide carbohydrate profiles for CTLA4-Ig molecules comprising SEQ ID NO:2. Four oligosaccharide domains are observed, wherein Domain I contains non-sialylated species, while Domains II, III, and IV contain mono-sialylated, di-sialylated and tri-sialylated species, respectively.
Figure 54A:
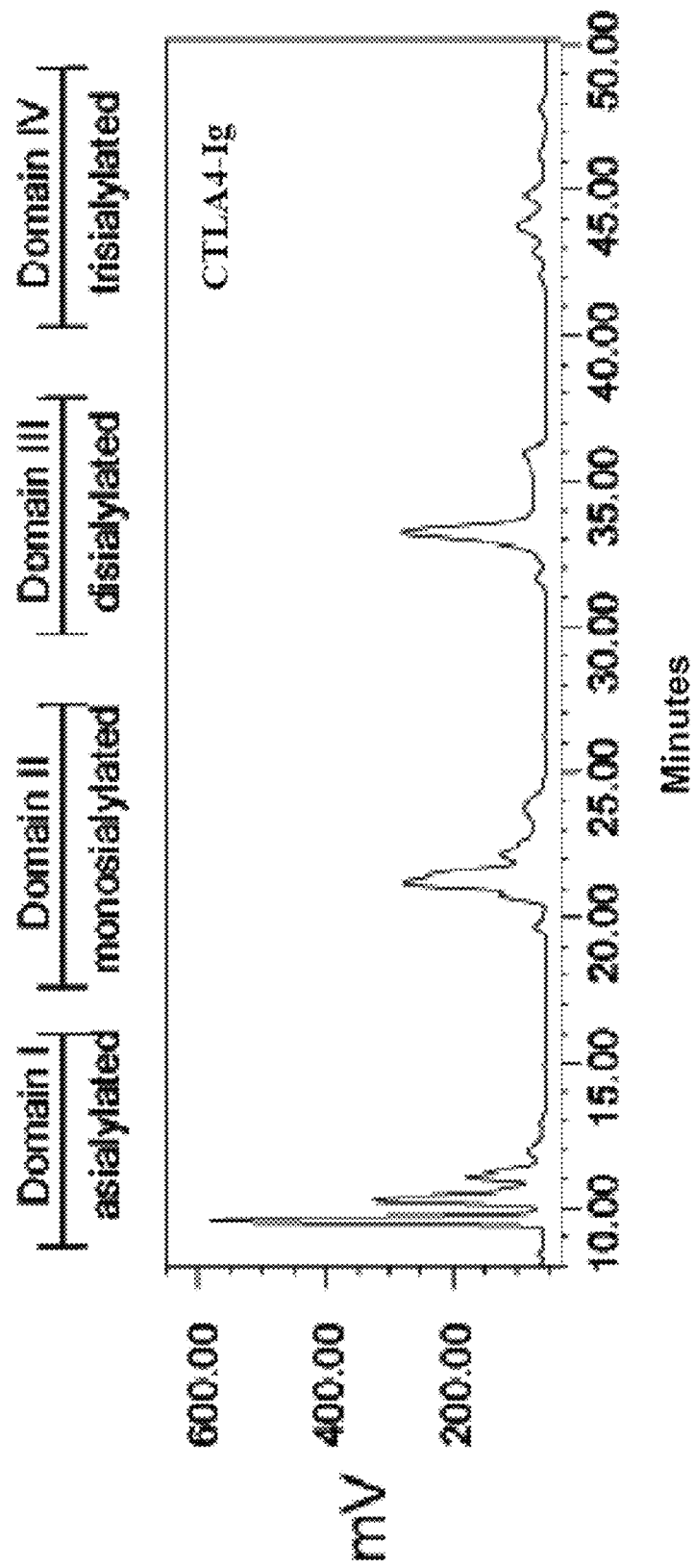
FIG. 54 A-54D is a graph that represents the oligosaccharide profiles of CTLA4-Ig and Peptides T5, T7, and T14 by HPAEC-PAD.
Figure 54B:
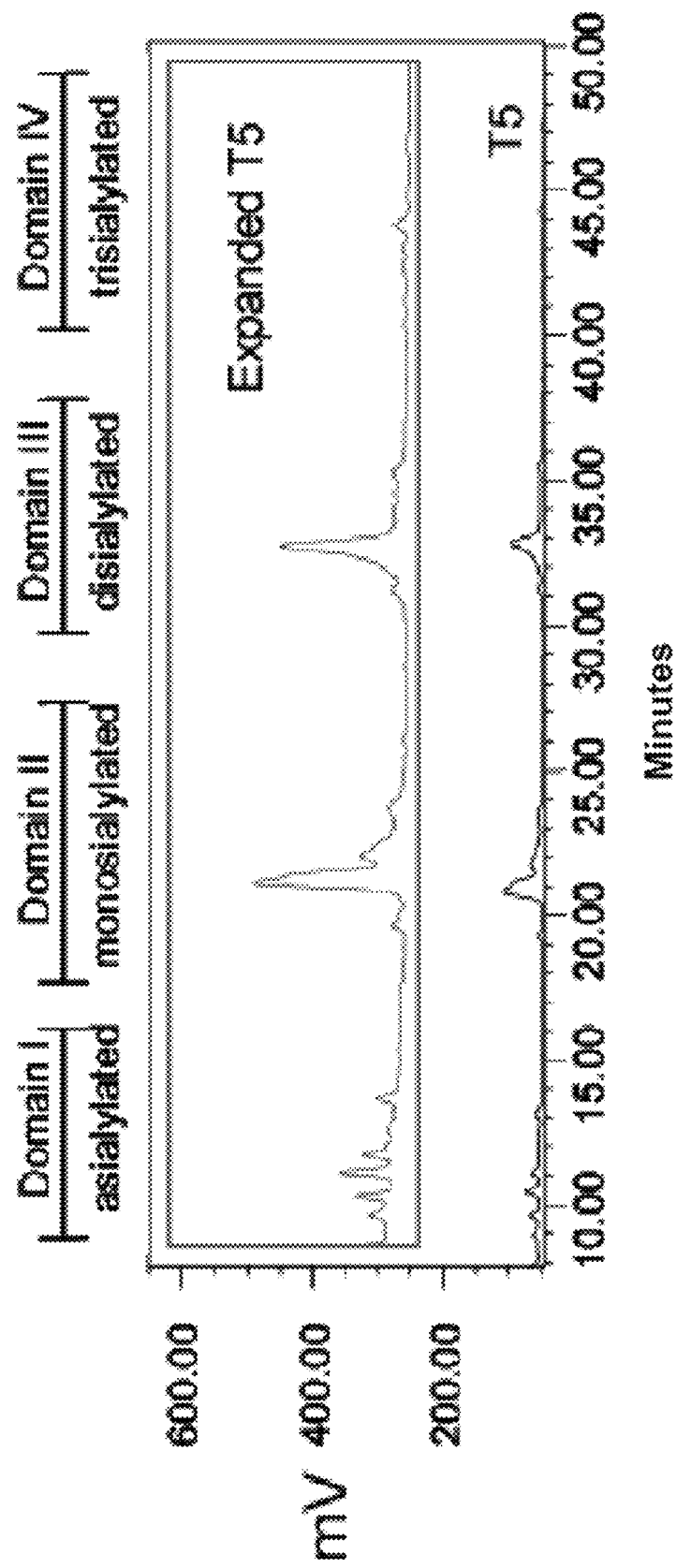
Figure 54C:
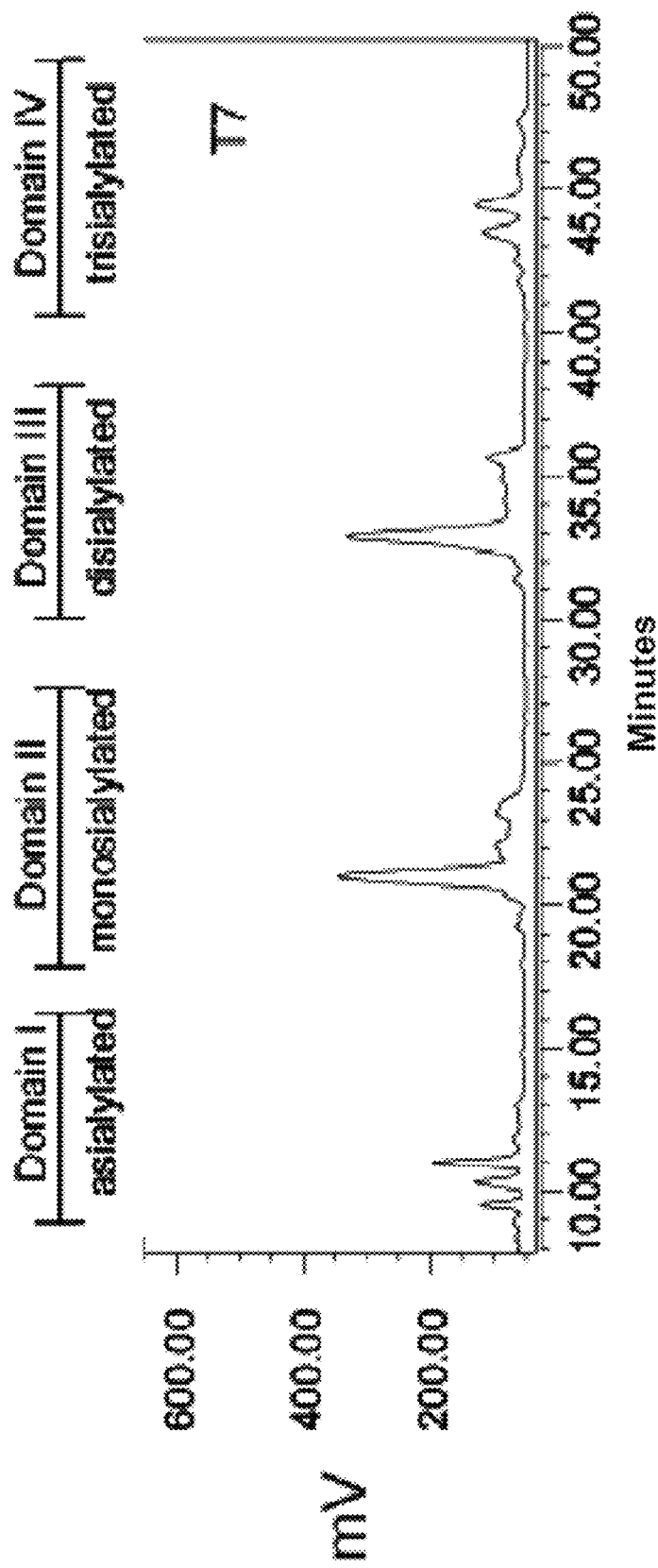
Figure 54D:
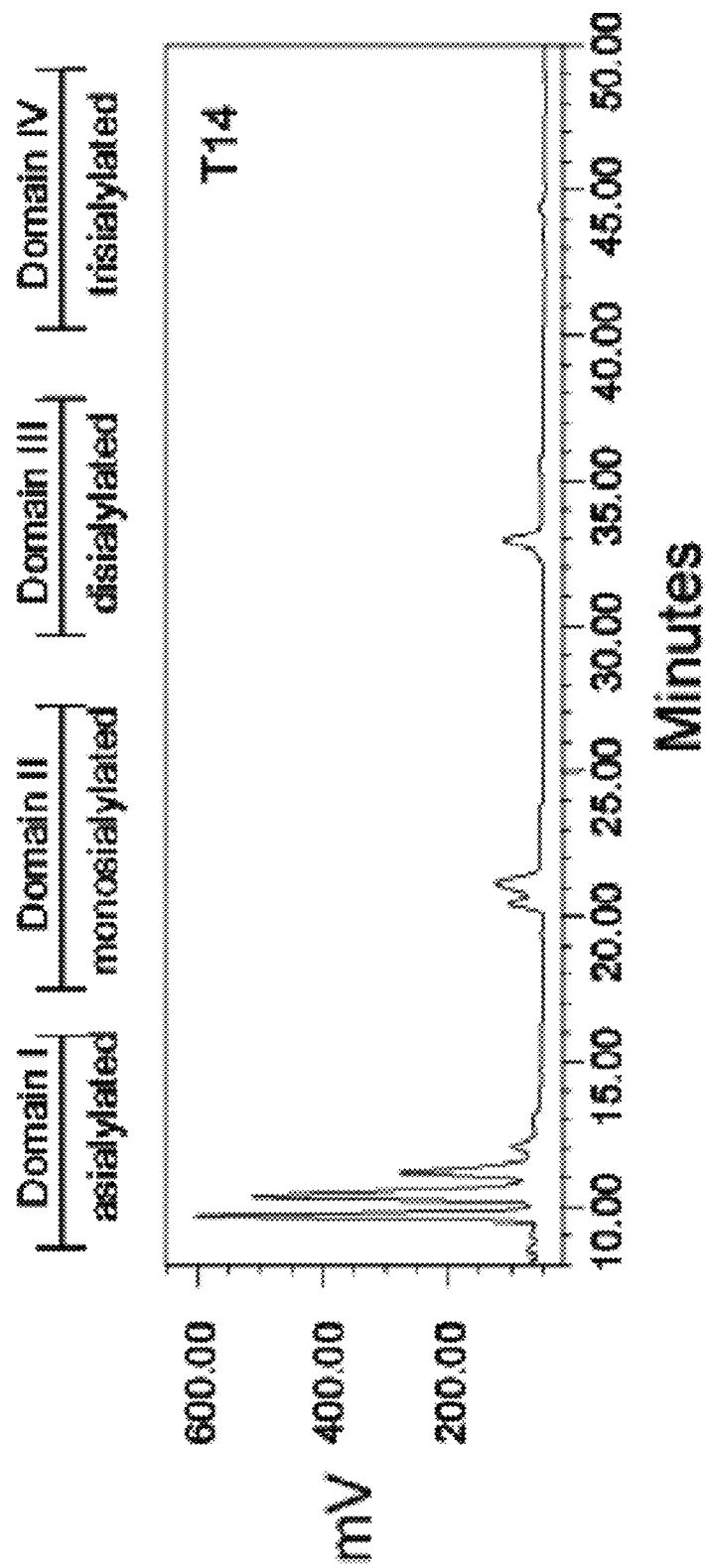

The column was equilibrated with 100% Mobile Phase A buffer for 25 minutes prior to the first injection. UV absorbance was monitored at 215 nm while column temperature was maintained at 37° C. and the autosampler temperature at 4° C. A mobile phase A buffer blank was run before the first system suitability standard, thereafter followed by a single 50 μL injection of each sample. A reference material injection should bracket every six-sample injections. The peptide map chromatogram generated for a CTLA4-Ig sample is depicted by FIG. 52. The retention time differences for peaks T2, T3, T15, and T19 (FIG. 52 and Table 57) between the initial and bracketing reference material chromatograms must be ±0.5 min.

TABLE 57

Theoretically Expected Fragments of CTLA4-Ig Digested with Trypsin

| Fragment No. | Residue No. | Monoisotopic Mass | Average Mass | Sequence |
|---|---|---|---|---|
| T1 | 1-14 | 1464.8 | 1465.7 | MHVAQPAVVLASSR |
| T2 | 15-28 | 1484.7 | 1485.6 | GIASFVCEYASPGK |
| T3 | 29-33 | 574.3 | 574.6 | ATEVR |
| T4 | 34-38 | 586.4 | 586.7 | VTVLR |
| T5* | 39-83 | 4895.2 | 4898.3 | QADSQVTEVCAATYMMGNELTFLDDSICTGT SSGNQVNLTIQGLR |
| T6 | 84-93 | 1170.5 | 1171.4 | AMDTGLYICK |
| T7* | 94-128 | 3993.9 | 3996.4 | VELMYPPPYYLGIGNGTQIYVIDPEPCPDSDQ EPK |
| T8** | 129-132 | 435.2 | 435.4 | SSDK |

TABLE 57-continued

Theoretically Expected Fragments of CTLA4-Ig Digested with Trypsin

| Fragment No. | Residue No. | Monoisotopic Mass | Average Mass | Sequence |
|---|---|---|---|---|
| T9** | 133-158 | 2687.4 | 2689.1 | THTSPPSPAPELLGGSSVFLFPPKPK |
| T10 | 159-165 | 834.4 | 835.0 | DTLMISR |
| T11 | 166-184 | 2138.0 | 2139.3 | TPEVTCVVVDVSHEDPEVK |
| T12 | 185-198 | 1676.8 | 1677.8 | FNWYVDGVEVHNAK |
| T13 | 199-202 | 500.3 | 500.6 | TKPR |
| T14* | 203-211 | 1188.5 | 1189.2 | EEQYNSTYR |
| T15 | 212-227 | 1807.0 | 1808.1 | VVSVLTVLHQDWLNGK |
| T16 | 228-230 | 438.2 | 438.5 | EYK |
| T17 | 231-232 | 306.1 | 306.3 | CK |
| T18 | 233-236 | 446.2 | 446.5 | VSNK |
| T19 | 237-244 | 837.5 | 838.0 | ALPAPIEK |
| T20 | 245-248 | 447.3 | 447.5 | TISK |
| T21 | 249-250 | 217.1 | 217.3 | AK |
| T22 | 251-254 | 456.2 | 456.5 | GQPR |
| T23 | 255-265 | 1285.7 | 1286.5 | EPQVYTLPPSR |
| T24 | 266-270 | 604.3 | 604.7 | DELTK |
| T25 | 271-280 | 1160.6 | 1161.4 | NQVSLTCLVK |
| T26 | 281-302 | 2543.1 | 2544.7 | GFYPSDIAVEWESNGQPENNYK |
| T27 | 303-319 | 1872.9 | 1874.1 | TTPPVLDSDGSFFLYSK |
| T28 | 320-324 | 574.3 | 574.7 | LTVDK |
| T29 | 325-326 | 261.1 | 261.3 | SR |
| T30 | 327-349 | 2800.3 | 2802.1 | WQQGNVFSCSVMHEALHNHYTQK |
| T31 | 350-356 | 1659.3 | 659.7 | SLSLSPG |

*Contains N-linked carbohydrate
**Contains O-linked carbohydrate

Number of Theoretical Plates: Column efficiency, evaluated as the number of theoretical plates, can be measured quantitatively using the retention time and the width of peak according to the Equation:

$$N = 16\left(\frac{t}{w}\right)^2$$

Where:
"w" is the peak width at the baseline measured by extrapolating the relatively straight sides to the baseline, "t" is the retention time of the peak measured from time of injection to time of elution of peak maximum.
If the N<50000, re-equilibrate the column.
Resolution:
The resolution (R) between 2 peaks, for example peak T30 and peak T12 as indicated in FIG. 52, can be determined using the following equation:

$$R = \frac{2(t_2 - t_1)}{(w_1 + w_2)}$$

Where:
$t_1$, $t_2$=retention times of fragments peak T30 and peak T12, respectively
$w_1$, $w_2$=tangent-defined peak width at baseline of the peaks with retention times ti and t2, respectively.
If R<1.5, the column should be re-equilibrate and if the problem persists, the column should be replaced.
Exemplary Values:
The difference between the relative peak areas for peaks T3, T15, and T19 in the test article and reference material must be 10.0%. The relative peak area of a peak is defined as the peak area expressed as a percentage of the peak area of peak T2. The difference between the relative peak areas of the test article and the initial system suitability reference is obtained as shown below. The relative peak area ($R_{SX}$) can be calculated for each of the peaks T3, T15, and T19 in the chromatogram of the test article by using the formula:

$$R_{SX} = (A_{SX}/A_{S2})*100$$

Where:
$R_{SX}$=relative peak area of peak X in the chromatogram
$A_{SX}$=area of peak X in the sample and
$A_{S2}$=area of peak T2 in the sample.

Similarly, the relative peak areas ($R_{RX}$) can be calculated for each of the peaks T3, T15, and T19 in the chromatogram of the standard. The difference between the relative peak areas in the sample and the standard (DX) can subsequently be calculated by using the formula:

$$D_X = [(R_{SX}-R_{RX})/(R_{RX})]*100.$$

If a single additional peak is present in the sample, the relative peak height for that peak as compared to peak T11 can be determined by using the following formula:

Relative peak height $R_T = (H_T/H_{11})*100$ where $H_T$=height of the peak with retention time t min
$H_{11}$=height of peak $T_{11}$, the tallest peak in the chromatogram.

In one embodiment, if the relative peak height of the new peak is ≤5.0%, then the profile is considered to be consistent with the profile of CTLA4-Ig standard. If the relative peak height of the new peak is >5.0%, then the profile is considered to be not consistent with the profile of the CTAL4-Ig standard material.

The percent oxidation data was acquired by use of a RP-HPLC tryptic mapping assay that quantifies the area percent oxidation of Met85 in the protein to methionine sulfoxide. Percent oxidation in the method is obtained by measuring UV peak areas in the RP-HPLC tryptic map for the T6 tryptic peptide, comprised of residues 84-93 containing Met85, and the corresponding oxidized tryptic peptide, T6ox, containing Met(O)85. The area percent oxidation of Met85 to Met(O)85 is proportional to the area percent of the T6ox peak:

Percent Oxidation=$100*A_{T6ox}/(A_{T6ox}+A_{T6})$ where,
$A_{T6}$=peak area for T6 tryptic peptide, (84-93).
$A_{T6ox}$=peak area for T6ox tryptic peptide, Met(O)$^{85}$(84-93).

The percent deamidation data was acquired by use of a RP-HPLC tryptic mapping assay that quantifies the area percent oxidation of deamidation in the assay is obtained by measuring UV peak areas in the RP-HPLC tryptic map for the T26 tryptic peptide, comprised of residues 281-302 containing Asn294, and the corresponding deamidated tryptic peptide, T26deam1, containing isoAsp294. The area percent deamidation of Asn294 to isoAsp294, then, is proportional to the area percent of the T26deam1 peak:

Percent Deamidation =

$$100 * \frac{A_{T26deam1}}{A_{T26} + A_{T26deam1} + A_{T26deam2} + A_{T26deam3} + A_{T26deam4}}$$

where,
AT26=peak area for T26, (281-302)
AT26deam1=peak area for T26deam1, isoAsp$^{294}$ (281-302).
AT26deam2=peak area for T26deam2, Asp$^{299}$ (281-302).
AT26deam3=peak area for T26deam3, Asp$^{294}$ (281-302).
AT26deam4=peak area for T26deam4, Asu$^{294}$ (281-302).

Example 44: CTLA4-Ig N-Linked Oligosaccharide Carbohydrate Profiling by High Performance Anion Exchange Chromatography with Electrochemical Detection The carbohydrate structures present on glycoproteins can affect their function and in vivo clearance. It is therefore important to monitor the structural consistency of the carbohydrates of recombinantly produced batches of glycoproteins. CTLA4-Ig is a recombinant protein containing both N-linked and O-linked (serine-linked) glycosylation sites. Here, N-linked (asparagine-linked) carbohydrates present on CTLA4-Ig are monitored. In this method, oligosaccharides are cleaved by enzymatic digestion with PNGase F (Peptide: N-Glycosidase F), then isolated by reversed-phase HPLC in a two-column system, separated by high performance anion exchange chromatography (HPAEC), and monitored by electrochemical detection (integrated amperometry). The chromatogram generated is the N-linked carbohydrate profile, wherein profiles of CTLA4-Ig samples should be similar to such.

This method describes the procedure to determine the HPAEC oligosaccharide profile of N-linked oligosaccharides released from CTLA4-Ig samples. A purpose of the method is to provide chromatographic profiles of CTLA4-Ig drug substance N-linked oligosaccharides which can be used for comparative analysis between. The glycosylation on the CTLA4-Ig contains N-linked oligosaccharides. These oligosaccharides are liberated by enzymatic hydrolysis with PNGase F over the course of 22 hours. The free oligosaccharides are profiled using high pH anion exchange chromatography employing electrochemical detection. Oligosaccharide profiles of drug substance are evaluated against concurrently run samples of reference material. Results are reported as percent deviation of selected domains and peaks from the same peaks in the reference standards.

| % Diff | Percent Difference |
|---|---|
| % RSD | Percent Relative Deviation |
| HPAEC | High pH Anion Exchange Chromatography |
| HPLC | High Performance Liquid Chromatography |
| NaOAc | Sodioum Acetate |
| NaOH | Sodium Hydroxide |
| PNGase F | Peptide: N-Glycosidase F |

MATERIALS. Equivalent materials may be substituted unless otherwise specified.

| Waters Total Recovery Vials with bonded PTFE/silicone septa | Waters Corporation, Catalog No. 186000234 |
|---|---|
| Microcon YM 10 Centrifugal Filter Devices | Millipore, Catalog No. 42407 |
| RapiGest SF | Waters Corporation, Catalog No. 186001861 |

INSTRUMENTATION AND CONDITIONS. Equivalent instrumentation may be used unless otherwise specified.
Instrumentation:

| Alliance HPLC system equipped with: Autosampler (refrigerated), Eluent Degas Module | Waters Corporation |
|---|---|

| Model 2465 Electrochemical Detector | |
|---|---|
| Column: CarboPac PA-1 4 × 250 mm | Dionex Corporation, Catalog No. 35391 |
| Guard Column: CarboPac PA-1 4 × 50 mm | Dionex Corporation, Catalog No. 43096 |
| Empower Data Collection system | Version 3.2 or current validated BMS version |

Chromatography Conditions for Oligosaccharide Profile by Anion-Exchange Chromatography

| Column Temperature | 29° C. |
|---|---|
| Flow Rate | 1 mL/min |
| Mobile Phases and Gradient Conditions | Gradient Program |
| 1: 500 mM NaOAc  2: 400 mM NaOH  3: HPLC Grade Water | Time (min) / % 1 / % 2 / % 3  Initial / 0 / 30 / 70  0.0 / 0 / 30 / 70  11.0 / 0 / 30 / 70  12.0 / 4 / 30 / 66  20.0 / 10 / 30 / 60  80.0 / 45 / 30 / 25  81.0 / 0 / 30 / 70  100 / 0 / 30 / 70 |
| Waters 2465 settings | |
| Mode | Pulse |
| Empower settings | Range = 5 µA  E1 = +0.05 V E2 = +0.75 V E3 = −0.15 V  t1 = 400 msec t2 = 200 msec t3 = 400 msec  Sampling time(ts) = 100 msec  Time constant(filter)t = 0.1 sec  Range offset = 5%  Polarity +  Temperature = 29° C. |

NOTE:
Equilibrate the column and detector with the initial mobile phase at the analysis flow rate for approximately 2 hours, or until baseline is stable before making injections.

| Autosampler Temperature set to: | 4° C. |
|---|---|
| Injection Volume | 60 µL |
| Run Time | 100 minutes |
| Approximate Retention Times (RT; minutes) of dominant peaks in each Domain (see FIG. 1); values may vary depending on RT of System Suitability (SS) Standard | |
| | Approximate RTs (min) |
| SS: | 18.5 |
| Peak 1A: | 20.0 |
| Peak 1B: | 20.8 |
| Peak 1C: | 21.4 |
| Peak 1D: | 22.4 |
| Peak 1E: | 23.1 |
| Peak 2: | 31.5 |
| Peak 3: | 44.8 |
| Peak 4: | 58.5 |

Electrode Cleaning (Waters 2465). Follow cleaning instructions in the detector manual. Use the diamond slurry provided in the flow cell kit to polish the surface of the electrode(s). If polishing does not yield acceptable results, replace the electrodes with a new flow cell kit. Re-build the flow cell using a new spacer (50 µm).

REAGENTS. NOTE: Label and document all reagent preparations according to departmental procedures.

Preparation of Mobile Phases for HPAEC Oligosaccharide Carbohydrate Profiling.

HPAEC Eluent 1: 500 mM Sodium Acetate (NaOAc). Weigh 20.51±0.05 g of Sodium Acetate (anhydrous) into a 500 mL graduated cylinder containing 400 mL of HPLC grade water. Bring volume to 500 mL with HPLC grade water and stir for 5 minutes using a plastic serological pipette until completely mixed. Filter the solution through a 0.2 nylon filter. Transfer to a 1 L eluent bottle. Cap the bottle loosely and sparge with helium for 20 minutes. Tighten cap and pressurize the bottle with helium. Store solution at room temperature under helium for up to three weeks.

HPAEC Eluent 2: 400 mM Sodium Hydroxide (NaOH). Using a 1 L graduated cylinder, measure 960 mL of HPLC grade water and transfer to a clean 1 L eluent bottle. Using a serological plastic pipet, add 40.0 mL of 10 N NaOH directly into the eluent bottle and mix the eluent by swirling. Cap the bottle loosely and sparge with helium for 20 minutes. Tighten cap and pressurize the bottle with helium. Store solution at room temperature under helium for up to three weeks.

HPAEC Eluent 3: HPLC grade Water. Fill a 1 L eluent bottle with approximately 1 L of HPLC grade water. Place eluent bottle on system, cap loosely, and sparge for approximately 20 minutes. Tighten cap and pressurize the bottle with helium. Store solution at room temperature under helium for up to three weeks.

50 mM Sodium Phosphate Buffer, 0.02% Sodium Azide, pH=7.5. Sodium Azide ($NaN_3$) should be handled with care to avoid inhalation (toxic) and contact with skin (irritant). Consult the MSDS sheet for additional requirements. After weighing of $NaN_3$, the balance area should be thoroughly cleaned.

| $NaH_2PO_4 \cdot H_2O$ | 6.9 g |
|---|---|
| $Na\ N_3$ | 0.2 g |
| $H_2O$ | 1.0 liter final volume |

Weigh out 6.9 g±0.1 g of $NaH_2PO_4 \cdot H_2O$ and 0.2 g NaN3 and dissolve in 800 mL of HPLC grade $H_2O$ in a 1 L reagent bottle using continuous mixing with a magnetic stirring bar. Using a pH meter, adjust the pH of the solution to 7.5 using 10M NaOH. Bring the final volume to 1.0 liter using a 1 L graduated cylinder. Store solution at room temperature for up to six months. PNGase F Enzyme Working Stock in 50 mM Sodium Phosphate Buffer, 0.02% Sodium Azide, pH=7.5.

| 50 mM Sodium Phosphate Buffer 0.02% Sodium Azide, pH = 7.5. | 1.8 mL |
|---|---|
| PNGase F from Kit, Catalog No. P0704L | 0.2 mL |

Pipette 1.8 mL of 50 mM Sodium Phosphate Buffer, 0.02% Sodium Azide, pH 7.5 into a 1.8 mL cryogenic vial. Add 0.2 mL of PNGase F from kit and mix thoroughly. Store solution at −20° C. or less for up to six months. The solution may be aliquoted prior to freezing.

External System Suitability Standard. Stachyose Stock Solution (1.25 mg/mL): Weigh 0.125 g of Stachyose onto a weighing paper. Using an analytical balance and transfer to a 100 mL volumetric flask. Fill to mark with HPLC grade water and mix thoroughly. Aliquot in 2 mL portions into Nalgene cryovials. Store solution at −20° C. or less for up to six months.

Stachyose System Suitability Standard (12.5 µg/mL): Pipet 1 mL of the 1.25 mg/mL stock into a 100 mL volumetric flask. Fill to mark with HPLC grade water and mix thoroughly. Aliquot in 200 µL portions into 0.65 mL microfuge tubes. Place tubes in appropriately labeled storage box. Store system suitability solution at −20° C. or less for up to six months.

Standard and Sample Preparation.

Reference Material Preparation. To a vial containing 1 mg of lyophilized RapiGest SF, add 625 µL of 50 mM NaPhosphate buffer containing 0.02% NaAzide, pH 7.5. NOTE: A single pool of RapiGest SF containing buffer should be used for all samples within a sample set. Several vials of RapiGest SF may be reconstituted and combined to provide adequate volume. To a 0.65 mL Eppendorf tube add 120 µL of the RapiGest SF containing buffer. Add 40 µL of Reference Material (~50 mg/mL). The final RapiGest SF concentration should be 0.12% w/v. Add 40 µL of the PNGase F working stock, mix thoroughly, spin down the sample, and place at 38±2° C. for 22±2 hours (water bath or the Alliance autosampler compartment). Pipet sample into a microcon YM-10 centrifugal filter and centrifuge at 13,000 g for 30 minutes. Place 200 µL of HPLC water in the filter and rinse into the filtrate by centrifuging for an additional 30 minutes at 13,000 g. Vortex the combined filtrate for 15 seconds and centrifuge the sample for 10 seconds. Using a pipette transfer the resulting solution (~380 µL) to an HPLC total recovery autosampler vial.

Sample Preparation: To a 0.65 mL Eppendorf tube add 120 µL of the RapiGest SF containing buffer. Add 40 µL of protein sample (this volume should equate to between 1 and 2 mg of CTLA4-Ig). The final RapiGest SF concentration should be 0.12% w/v. Add 40 µL of the PNGase F working stock mix thoroughly by vortexing for 10 seconds. Spin down the sample, and place at 38±2° C. for 22±2 hours (water bath or the Alliance autosampler compartment). Pipet sample into a microcon YM-10 centrifugal filter and centrifuge at 13,000 g for 30 minutes. Place 200 µL of HPLC water in the filter and rinse into the filtrate by centrifuging for an additional 30 minutes at 13,000 g. Vortex the combined filtrates for 15 seconds and centrifuge the sample for 10 seconds. Transfer the resulting solution (~380 uL) to a total recovery HPLC autosampler vial.

Electrochemical Detector Cell Stabilization: Inject 30 µL of the external stachyose system suitability standard (12.5 µg/mL). Ensure the peak height for stachyose is 800 nA. Ensure there is no excessive electrical noise from the cell and the baseline is flat. If the stachyose sensitivity or the baseline is unacceptable, check the buffer composition, clean the electrode or replace the electrode. If excessive noise is present, check cell to ensure removal of all air bubbles. Restabilize the cell and re-inject stachyose standard. If problems persist, take other appropriate actions or contact your supervisor.

Theoretical Plates (N): Determine the number of Theoretical Plates (N) based on the Stachyose peak using the formula below. This is done through the Empower data analysis system or may also be done manually.

$$N=16(t/W)^2$$

WHERE:
t: retention time measured from time of injection to peak elution time at maximum height
W: width of peak by extrapolation of sides to baseline.
N must be ≥6000. If the plate count is less than 6000, adjust the run gradient or replace column.

Tailing Factor (T): Determine column Tailing Factor (T) based on the Stachyose peak using the formula below. This is done through the EMPOWER data analysis system or may also be done manually.

$$T=(W_{0.05}/2f)$$

WHERE:
$W_{0.05}$: width of peak at 5% of height (0.05h).
f: the measurement (width) from front edge of peak at $W_{0.05}$ to the apex of the peak.

T must be ≤1.2. If the tailing factor is greater than 1.2, check buffer composition, replace the column or clean the column and re-inject system suitability standard.

Stachyose System Suitability Standard Retention Time Verification: The retention time is system dependent. The stachyose system suitability standard should exhibit a retention time of 18.5±2.0 minutes.

CTLA4-Ig Reference Material—Observe the carbohydrate profile from the first bracketing reference material injected prior to injection of samples. The carbohydrate profile should be similar to that shown in FIG. 67. Absolute retention times are system dependent. Ensure that the difference in retention times between the first peak in Domain I (Peak 1A) and the main peak in Domain III (Peak 3) is between 22 minutes and 28 minutes. If delineation of peaks does not resemble that obtained in FIG. 67 take appropriate actions (e.g. check instrument function, clean column, check/replace buffers, replace column) and re-evaluate. The following procedure may be used to clean the column: turn off the cell and clean the column with 80% Eluent 1, 20% Eluent 2 for 5 minutes followed by 50% Eluent 1, 50% Eluent 2 for 10 minutes. Re-equilibrate the column and cell (with cell turned on) at initial conditions and re-evaluate.

Injection Sequence:
Set up the injection sequence of isolated oligosaccharides as follows:
Stachyose Standard (30 µL)
Reference Material (60 µL)
Sample(s) (60 µL)
Reference Material (60 µL)
It is recommended that ≤five samples be run between bracketing reference material injections.

DATA ANALYSIS: Process the Chromatograms. Process the chromatograms for the Reference Material and samples in EMPOWER. Set integration parameters so that peak delineation and the baseline is similar to that shown in FIG. 67, integration lines may need to be placed manually. Perform calculations for relative Domain areas and relative peak areas (see tables included in Brief Description of FIG. 67 and at the end of this example). Determine the average values for these parameters for the Reference Material and for each sample if replicate injections were made.

For the Reference Material, determine relative deviation for Domains I, II, III, Peaks 1A and 1B for each replicate with respect to the average of all replicates.

Comparison of Profiles of Sample to Reference Material Profiles.

Visual ComparisonDetermine if both samples and Reference Material have the same number of Domains and primary peaks. Primary peaks are those peaks labeled in the description of FIG. 67 (Peaks 1A, 1B, 1C, 1D, 2, 3 and 4). Relative Quantitation Comparison. Compare the relative areas of samples (Domains I, II, and III and Peaks 1A, and 1B; if replicate injections were made of samples use their average values) with the average relative areas from the bracketing Reference Material injections. Determine the relative difference of these areas from the average Reference Material values.

Calculations. % Domain Area (Relative Domain Area): Calculate the % Domain area for the Domains of the profiles for the Reference Material and samples. Refer to FIG. 67 for pattern of Domain areas. Following the example in FIG. 67, calculate the Domain percent ratios by using the following information and formula (retention times are system dependent and reflect result in FIG. 67:

Domain I: Sum of the peak areas at approximate retention times 18-24 minutes (Peaks 1A-1E)
Domain II: Sum of the peaks from 26-38 minutes
Domain III: Sum of the peaks from 39-50 minutes
Domain IV: Sum of the peaks from 51-64 minutes
Domain V Sum of the peaks from 65-75 minutes NOTE: Retention time windows for Domains will shift according to variations in daily chromatographic performance. Adjust times accordingly.

$$\text{Domain Area \%} = \frac{\text{Individual Domain Area}}{\text{Sum of all Domain Areas}} \times 100\%$$

For Domains I-III also calculate the average values in the bracketing reference material injections, as well as in samples if replicate injections are made.

% Peak Area (Relative Peak Area). Calculate the % peak area for Peaks 1A, 1B, 1C, and 3 of the profiles for the Reference Material and samples. Refer to FIG. 67 for pattern of peak areas; retention times are system dependent. Calculate the peak percent ratios by using the following information and formula:

$$\text{Individual Peak Area \%} = \frac{\text{Individual Peak Area}}{\text{Sum of the all Domain Areas}} \times 100\%$$

For each of Peaks 1A and 1B, also calculate the average values in the bracketing reference material injections, as well as in samples if replicate injections are made.

Calculation of the Percent Difference from Average Reference Material Values. Use the following formula to calculate percent differences in average relative areas of Domains I-III, Peaks 1A and 1B of samples compared to Reference Material:

% Diff=|RM−S|RM×100

WHERE:
RM=average relative area value of interest for Reference Material
S=average relative area value of interest for a sample
| |=absolute value Results: Results are to be reported are the calculated percent difference from reference material for Domain I, Domain II, Domain II, peak 1A and peak 1B. Include an integrated representative chromatogram for both the Reference Material and the sample. Include the relative area percentages of Domains I-III and Peaks 1A and 1B to a tenth of a percent for both sample and Reference Material (average of bracketing injections). Additionally, for each of the bracketing Reference Material injections, the % Domain Areas for Domain I, II and III and % Peak Areas for Peak 1A and 1B should be within 15% of their average values.

FIGS. 56-61, 67, 75 and 81-83 show resultant data from N-linked oligosaccharide profiles as are described herein.

FIG. 67 depicts a typical N-Linked Oligosaccharide Profile (Domains I, II, III, IV and V, and Peaks 1A and 1B within 5% of Lot averages). Peaks 1A, 1B and 1C represent the asialo N-linked oligosaccharide structures of G0, G1 and G2.

| Domain/Peak | Retention Time (minutes) | Area Percentage | Peak Height Relative to Tallest Peak | Area Percentage of Parent Domain | Domain Composition |
|---|---|---|---|---|---|
| Domain I | 19.413 | 31.3 | . | . | 5 Peaks |
| Domain II | 29.076 | 33.2 | . | | 5 Peaks |
| Domain III | 42.819 | 24 | | | 5 Peaks |
| Domain IV | 55.899 | 9.4 | | | 6 Peaks |
| Domain V | 67.546 | 2.2 | | | 6 Peaks |
| Peak 1A | 19.413 | 7.3 | 89.8 | 23.3 | |
| Peak 1B | 20.29 | 10.7 | 100 | 34.2 | |
| Peak 1C | 21.032 | 8.8 | 94.3 | 28.1 | |
| Peak 1D | 21.925 | 2.8 | 27.5 | 8.95 | |
| Peak 1E | 22.685 | 1.7 | 11.8 | 5.43 | |
| Peak 2 | 30.763 | 18.3 | 88.9 | 55.1 | |
| Peak 3 | 43.823 | 14.5 | 57.8 | 60.4 | |
| Peak 4 | 57.368 | 4.4 | 20.1 | 46.8 | |

FIG. 67 shows a typical N-linked carbohydrate profile for a CTLA4-Ig composition. The table directly above shows tabulated data for the N-linked oligosaccharide profile of CTLA4-Ig.

The table directly below shows observed ranges of CTLA4-Ig.

| Domain/Peak | Minimum Area % | Maximum Area % |
|---|---|---|
| Domain I | 24.5 | 35.2 |
| Domain II | 26.3 | 34.1 |
| Domain III | 21.9 | 31.5 |
| Domain IV + V | 7.9 | 18.6 |
| Peak 1A | 4.5 | 11.2 |
| Peak 1B | 8.7 | 11.8 |

Example 45: An In-Vitro Cell Based Bioassay for CTLA4-Ig

T cells require two signals for activation and subsequent proliferation. The first signal is provided by the interaction of an antigenic peptide with the TCR-CD3 complex. The second co-stimulatory signal occurs with the interaction between CD28 on the T cell and the B7 protein on an antigen-presenting cell. Upon receipt of these two signals, T cells secrete the cytokine Interleukin 2 (IL-2). Release of IL-2 leads to cellular activation and proliferation. CTLA4-Ig, a soluble, immunosuppressive compound, also binds to the B7 protein on the antigen presenting cell, thus blocking functional interaction with CD28 and preventing the co-stimulatory signal that is necessary for IL-2 production.

In this method, Jurkat T cells transfected with the luciferase gene, under the control of the IL-2 promoter, are co-stimulated with Daudi B cells in the presence of anti-CD3. The co-stimulation activates the IL-2 promoter, which in turn produces luciferase protein. The resulting luminescent signal is measured using a Luciferase Assay System. In this system, CTLA4-Ig produces a dose-dependent decrease in luciferase activity.

This method examines the effect of CTLA4-Ig on the co-stimulatory signal needed for IL-2 production. The presence of soluble CTLA4-Ig prevents signaling between the T cell and antigen-presenting cell. Without this signal, IL-2 is not produced, thus preventing the clonal expansion of T cells. A vector with the luciferase gene was created using the IL-2 promoter. Jurkat T cells were then transfected with this reporter vector. A positive clone, Jurkat.CA, was selected and used in the method.

This bioassay involves stimulating transfected T cells (Jurkat.CA) with anti-CD3 and B cells (Daudi). Co-stimulation provided by the B cells is inhibited by the addition of CTLA4-Ig. Jurkat.CA and Daudi cells are seeded into the wells of a 96 well, white, opaque, flat-bottom plate and stimulated with anti-CD3 in the presence of different concentrations of CTLA4-Ig. After a 16 to 20 hour incubation at 37° C., the wells are assayed for luciferase activity. Inhibition of co-stimulation by CTLA4-Ig is seen as a dose-dependent decrease in luciferase activity. FIG. 95 shows a procedure flow chart.

Reagents:

Daudi Cell Culture Media (10% fetal bovine serum, 1% MEM sodium pyruvate in RPMI 1640); Jurkat.CA Cell Culture Media (10% calf serum, 1% MEM sodium pyruvate, 400 μg/mL of geneticin in RPMI 1640); Bioassay Media (0.2 μg/mL of anti-CD3 antibody and 1% penicillin-streptomycin solution in Daudi Cell Culture Media); Bright-Glo Luciferase Solution from assay system (Promega, Catalog # E2620).

Instrumentation:

Nikon, Diaphot 200 Inverted microscope; Packard TopCount NXT Luminometer; Tecan Genesis Liquid Handler; Coulter Vi-Cell Cell Counter; Zymark RapidPlate-96.

Preparation of Working Solutions:

3 mL of CTLA4-Ig solutions (5000 ng/mL) in bioassay media.

Eight point curves were prepared for the standard, quality control, and samples at the concentrations of 100, 4, 2, 1, 0.5, 0.2, 0.1, and 0.002 μg/mL CTLA4-Ig as shown in Table 58 below for final concentrations in the assay, after two-fold dilution into the plate, of 50, 2, 1, 0.5, 0.25, 0.1, 0.05, and 0.001 μg/mL.

TABLE 58

Dilutions used to generate standard curves.

| Curve Point | Standard Curve | Quality Control | Sample 1 | Sample 2 |
|---|---|---|---|---|
| 1 | 100 μg/mL | 100 μg/mL | 100 μg/mL | 100 μg/mL |
| 2 | 4 | 4 | 4 | 4 |
| 3 | 2 | 2 | 2 | 2 |
| 4 | 1 | 1 | 1 | 1 |
| 5 | 0.5 | 0.5 | 0.5 | 0.5 |
| 6 | 0.2 | 0.2 | 0.2 | 0.2 |
| 7 | 0.1 | 0.1 | 0.1 | 0.1 |
| 8 | 0.002 | 0.002 | 0.002 | 0.002 |

200,000 cells were added per well of a 96 well plate and were incubated at 37° C., 5% $CO_2$, and 85% humidity. $12 \times 10^6$ Jurkat.CA cells and $12 \times 10^6$ Daudi cells were combined in a sterile centrifuge tube. The cells were centrifuged at ~125×g for 10 minutes at room temperature and were thoroughly re-suspend in 9 mL of Daudi cell culture media by gently pipetting repeatedly with a serological pipet until no cell clumps were visible to give a concentration of $2.7 \times 10^6$ cells/mL. 75 μL of each solution from Table 58 was added to the appropriate wells of the plate containing cells. The plate(s) were then sealed with TopSeal-A and incubated at 37° C., 5% $CO_2$, and 85% humidity for 16 to 20 hours. After the plates and Bright-Glo luciferase solution were equilibrated to the instrument temperature, 150 μL of Bright-Glo luciferase solution was added to each well simultaneously and were mixed. A plate is then placed in the TopCount NXT immediately after mixing for equilibration in the dark for 10 minutes. The luminescent signal was then measured in a TopCount NXT using a 1 second integration per well or as appropriate to the particular type of luminometer used.

The output from the TopCount NXT was recorded, read into a standard anlysis program, and data were transformed by taking their logarithm (base 10). The transformed data from each article were fit to a four-parameter logistic model as shown in the equation below:

$$\mathrm{Log}_{10}(y_{jk}) = D + \frac{(A-D)}{1+\left(\frac{x_j}{C}\right)^B} \qquad \text{Equation 1}$$

Where:

A is the top plateau of the curve, D is the bottom plateau of the curve, B is the slope factor, and C is the concentration that produces an effect equal to the average of A and D.

An $R^2$ statistic, and a lack-of-fit F-test can be calculated for each article. A ratio of the minimum, maximum and slope of the test articles relative to the standard material can also be calculated. In addition, confidence intervals for the ratios can also be computed.

The relative potency of each article was determined by fitting a single equation to the data from the article of interest combined with the data from the reference article.

$$\mathrm{Log}_{10}(y_{ijk}) = D + \frac{(A-D)}{1+\left(\frac{x_{ij}}{C_A * \left(\frac{C_R}{C_A}\right)^I}\right)^B} \qquad \text{Equation 2}$$

Where:

A, B and D parameters are common to both the reference and test article and $C_R$ is the reference parameter, $C_A$ is the test article parameter, and the ratio $C_R/C_A$ is the relative potency. The superscript I is an indicator variable. It is set equal to 1 if the data come from the article of interest, and 0 if the data come from the CTLA4-Ig material.

The relative potency of each test article was translated to a percentage scale and the relative potency was given as output from the program.

The eight relative potency results of the output from each of the eight data sets analyzed can be averaged and the standard deviation can be calculated using Equations 3 and 4, respectively. The average result is reported as "percent relative potency" rounded to the nearest whole number.

$$\mathrm{Average} = \frac{Value1 + Value2 + Value3 + Value4 + Value5 + Value6 + Value7 + Value8}{8} \qquad \text{Equation 3}$$

$$\mathrm{Standard\ Deviation} = \sqrt{\frac{8\Sigma x^2 - (\Sigma x)^2}{8(8-1)}} \qquad \text{Equation 4}$$

Where:
8 is the number of potency measurements
x=individual measurements

Adjustment of Relative Potency Values Obtained with Approximate Concentrations:

Due to the time lag between sample receipt and obtaining a precise protein concentration, a sample may be tested in the assay at an approximate concentration and results adjusted when the precise concentration is determined. This adjustment is performed using Equation 5 below where the relative potency determined in the assay is multiplied by the ratio of the CTLA4-Ig concentration used to set up the assay to the determined CTLA4-Ig sample concentration.

Reportable Relative Potency = $\dfrac{\text{Observed Relative Potency} * \text{Concentration Used}}{\text{Determined Concentration}}$  Equation 5

Example:
Sample was tested at a protein concentration of 25 mg/mL in the assay.
Relative Potency determined was 105%.
Determined CTLA4-Ig concentration was determined to be 25.5 mg/mL Reportable Relative Potency=(105*25)/25.5=103%.

The test article relative potency values must be between 25 and 175% of the reference standard, which is the range of the assay. If the relative potency values are outside this range, then the sample must be diluted or concentrated in order to fall within this range and the sample reanalyzed.

Example 46: Structural Characterization of O-Linked Oligosaccharides

The O-linked glycosylation of CTLA4-Ig was characterized by peptide mapping followed by ESI-MS/MS, and by MALDI-TOF.

Analysis of T8 and T9 by Peptide Mapping with ESI-MS/MS

A modified manual version of the tryptic digestion method with in-line ESI-MS/MS using a Finnigan Ion Trap mass spectrometer was performed in order to characterize O-linked glycopeptides T8 and T9 (refer to Table 59 for peptide identity).

Figure 62:
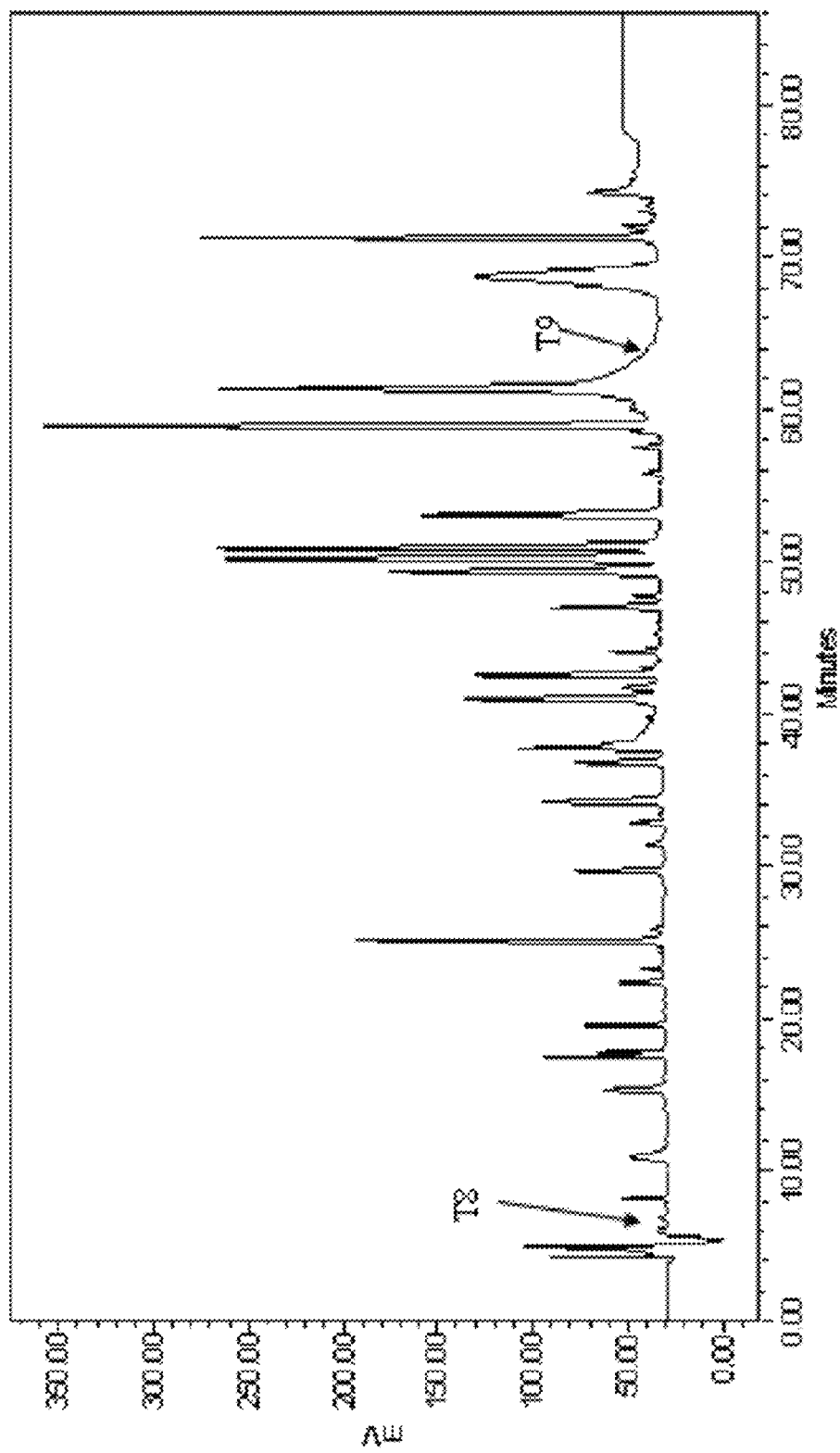
FIG. 62 shows the tryptic peptide map of CTLA4-Ig indicating that T8 elutes at the end of the solvent front, and T9 elutes at the shoulder of T27.

FIG. 62 shows the tryptic peptide map of CTLA4-Ig indicating that T8 elutes at the end of the solvent front, and T9 elutes at the shoulder of T27.

Figure 63:
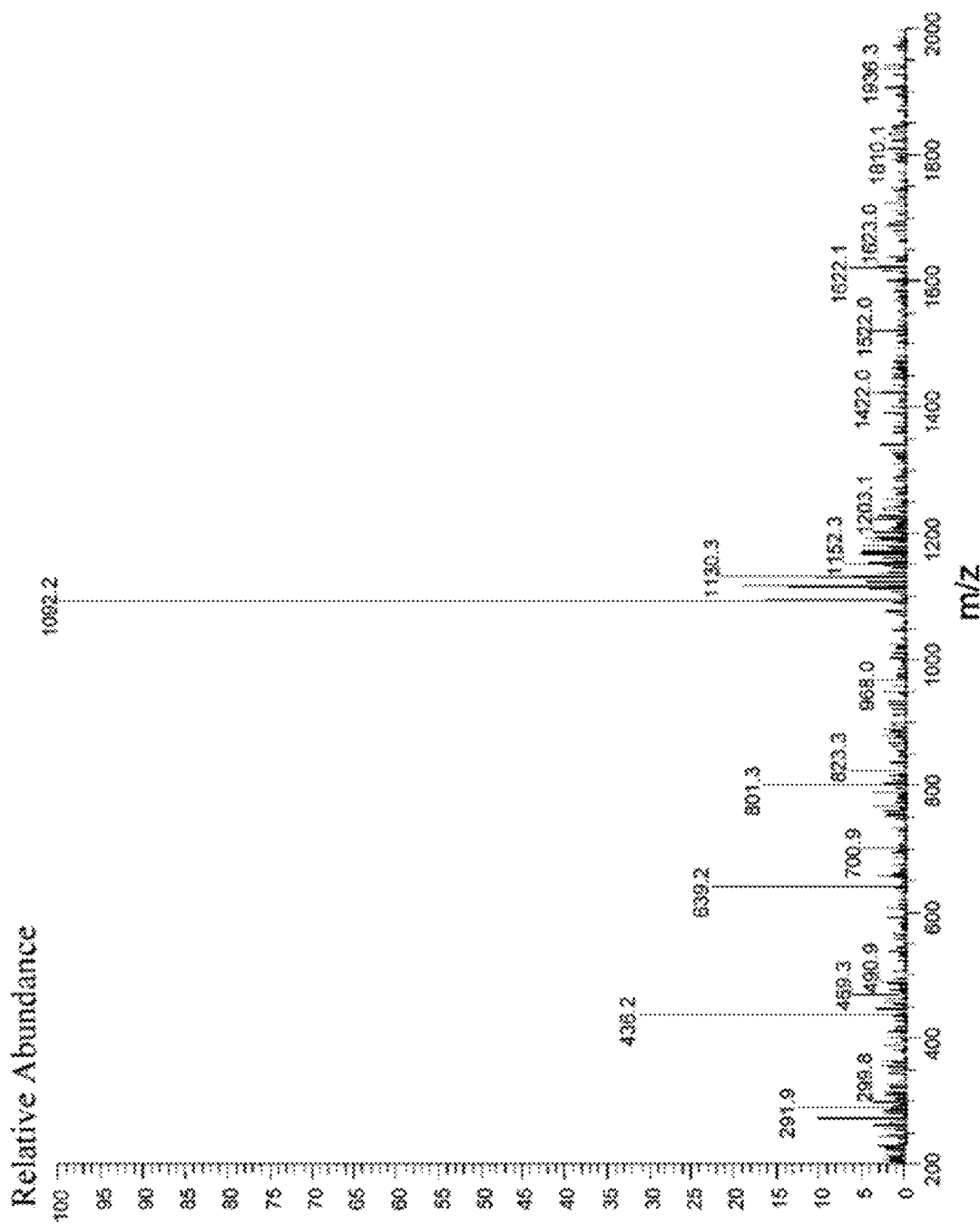
FIG. 63 is a graph that represents the full mass spectrum corresponding to glycopeptide T8 from CTLA4-Ig.

The full mass spectrum of peptide T8 is shown in FIG. 63, where peak 436.2 corresponds to the expected MW of the singly-charged unmodified peptide T8, and peak 1092.2 correspond to the MW of the singly-charged glycosylated T8. The mass corresponding to the major peak and its structure (T8-HexNAc-Hex-NeuAc) are shown in FIG. 96.

Figure 64:
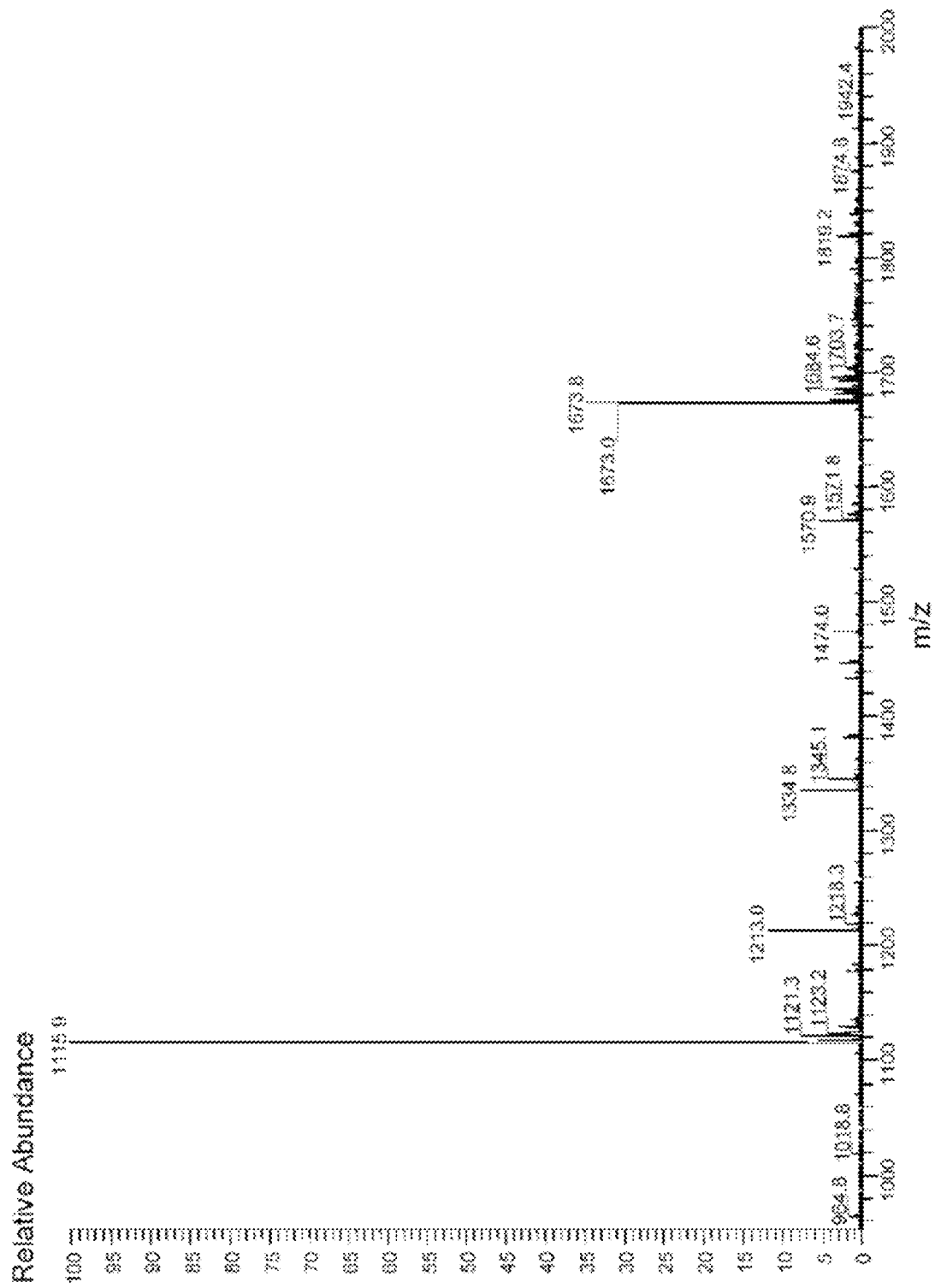
FIG. 64 is a graph that represents the full mass spectrum corresponding to glycopeptide T9 from CTLA4-Ig.

The full mass spectrum of peptide T9 is shown in FIG. 64, where doubly- and triply-charged ions of the glycopeptides appear, corresponding to a range of heterogeneous glycoforms. Major peak 1115.9 corresponds to the MW of the triply charged T9 glycosylated with HexNAc-Hex-NeuAc. Peaks 1213.0 and 1334.8 correspond to molecular weights of the triply-charged T9, glycosylated with HexNAc (NeuAc)-Hex-NeuAc, and (HexNAc-Hex-NeuAc)$_2$, respectively (FIG. 97). The dominant glycoform is monosialylated T9-HexNAc-Hex-NeuAc while the other glycoforms are present at a much lower abundance.

In order to determine the O-linked sites, peptide mapping of CTLA4-Ig was performed as previously described in Example 4 and the fraction T8-9 (due to incomplete digestion by trypsin) was collected and subjected to Edman sequencing. The sequencing data showed that in the 1st cycle, an extra peak appears in addition to Ser. The retention time of the extra peak does not agree with that of any of the standard amino acids, suggesting that Ser at position 1 in T8 (Ser 129) is modified and contains O-linked glycans. The appearance of both Ser and the extra peak indicate that Ser is partially modified. This is in agreement with the MS data for T8. The sequencing experiments also reveal the O-linked site in T9 as Ser 139. In conclusion, two O-linked glycosylation sites were identified at amino acid residues serine 129 and serine 139. The predominant glycan attached to the two sites is HexNAc-Hex-NeuAc.

MALDI-TOF Analysis of T9 Peptide

Figure 65:
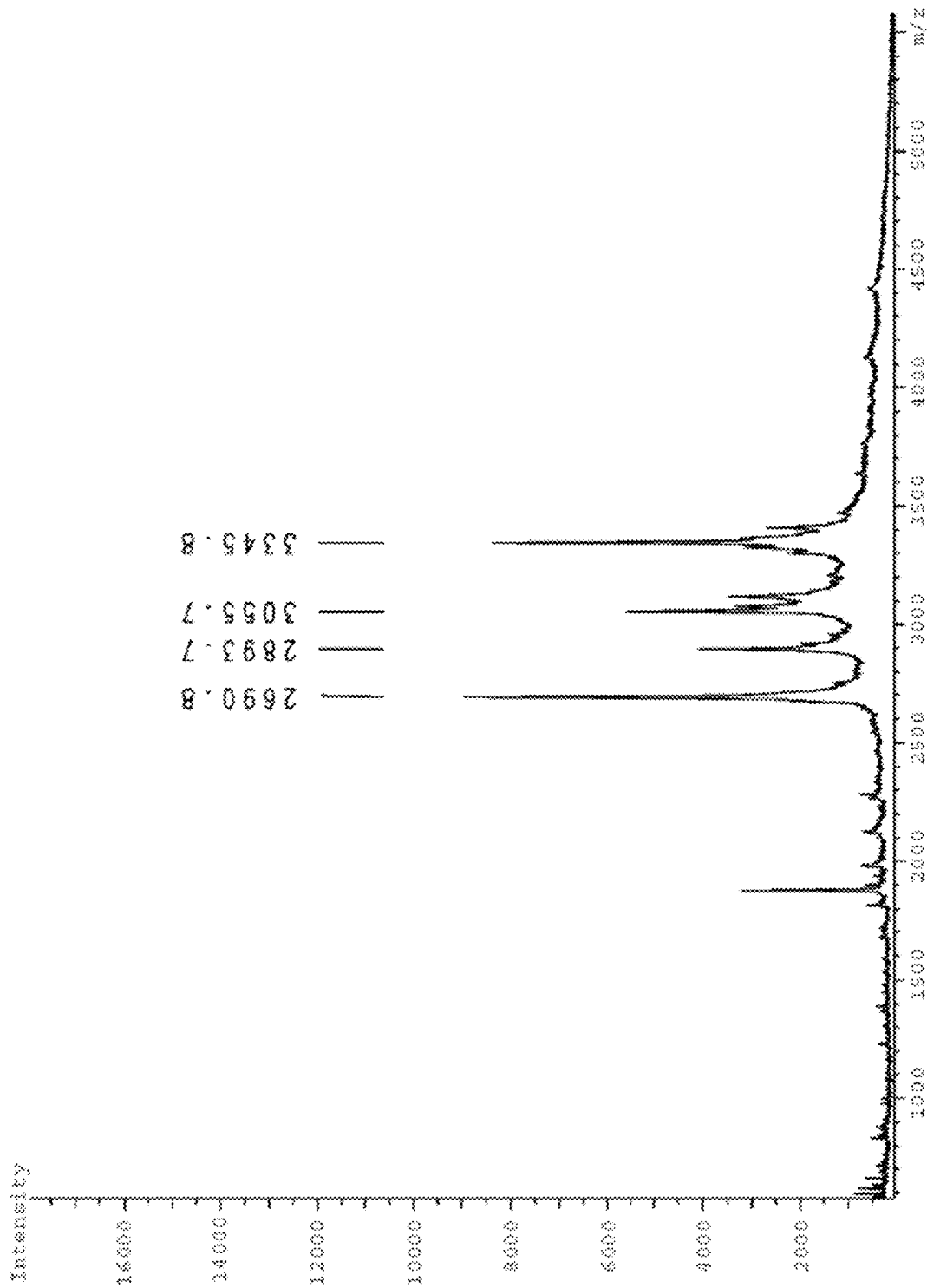
FIG. 65 is a graph that represents the MALDI-TOF data for the T9 peptide fragment from CTLA4-Ig.

MALDI-TOF analysis of peptide T9 demonstrates the presence of several glycoforms (FIG. 65). The peak with a MW of 2690.8 is consistent with the T9 fragment. The peak with a MW of 2893.7 correlates to T9 plus HexNAc. The peak with a MW of 3055.7 correlates to T9 plus HexNAc-Hex. The peak with a MW of 3345.8 indicates T9 plus HexNAc-Hex-NANA. Galactose and N-Acetyl Galactosamine were detected in T9 based on monosaccharide analysis, therefore the major O-linked species in T9 is postulated to be GalNAc-Gal-NANA. MALDI-TOF analysis of peptide T8 was not performed due to low recovery yields.

Example 47: Oxidation and Deamidation Variants in CTLA4-Ig

Oxidation and deamidation are common product variants of peptides and proteins. They can occur during fermentation, harvest/cell clarification, purification, drug substance/drug product storage, and during sample analysis.

Protein oxidation is typically characterized by the chemical addition of one or more oxygen atoms to the protein. Several amino acids, Met, Cys, Tyr, His and Trp, are more susceptible to oxidation compared to other natural amino acids. The amino acid with the highest degree of susceptibility to oxidation is methionine. The majority of protein oxidations identified to date have been the oxidation of methionine to the sulfoxide variant. Oxidation in proteins can be caused by several different mechanisms. The common mechanism of oxidation occurs from light exposure or transition metal catalysis.

Deamidation is the loss of NH$_3$ from a protein forming a succinimide intermediate that can undergo hydrolysis. The succinimide intermediate results in a 17 u mass decrease of the parent peptide. The subsequent hydrolysis results in an 18 u mass increase. Isolation of the succinimide intermediate is difficult due to instability under aqueous conditions. As such, deamidation is typically detectable as 1 u mass increase. Deamidation of an asparagine results in either aspartic or isoaspartic acid. The parameters affecting the rate of deamidation include pH, temperature, solvent dielectric constant, ionic strength, primary sequence, local polypeptide conformation, and tertiary structure. The amino acid residues adjacent to Asn in the peptide chain affect deamidation rates. Gly and Ser following an Asn in protein sequences results in a higher susceptibility to deamidation.

Materials and Methods
Sample:
CTLA4-Ig Standard
Trypsin/Asp-N/Trypsin and Chymotrypsin Peptide Mapping of CTLA4-Ig:

Proteins were denatured and reduced in 50 mM Tris buffer (pH 8.0) containing 6 M Guanidine and 5 mM dithiothreitol (DTT). After 20-minutes incubation at 50° C., iodoacetamide (IAM) was added to a final concentration of 10 mM and the sample was incubated in darkness at 50° C. for an additional 20 minutes. The reduced and alkylated mixture was loaded onto a NAP-5 column, and then eluted out with 50 mM Tris, 10 mM CaCl$_2$), pH 8.0. Sequence grade trypsin (2% w/w, enzyme:protein) was added and incubated for 4 hours at 37° C. In the case of Asp-N digestion, sequence grade Asp-N(4% w/w, enzyme:protein) was added and the sample was incubated for 16 hours at 37° C.

In the case of trypsin and chymotrypsin digestion, the protein was in 50 mM sodium phosphate buffer, pH 7.5. Sequence grade trypsin (4%, w/w, enzyme:protein) was added and the sample was incubated for 4 hours at 37° C. Chymotrypsin was added (4%, w/w, enzyme:protein) and the sample incubated for 16 hours at 37° C. Samples were stored at −20° C. after the digestion.

Peptide mixtures were separated by gradient elution from an Atlantis C18 column (2.1×250 mm) on a Waters Alliance HPLC Workstation (Waters, Milford, Mass.) at 0.120 mL/min. The column was directly connected to the Q-Tof micro (Waters, Milford, Mass.) equipped with an electrospray ionization spray source and mass spectra were collected. In the case of Asp-N peptide mapping, peptide mixtures were separated on a Varian C18 column (4.6×250 mm) at 0.7 mL/min using the same HPLC workstation. The columns were equilibrated with solvent A (0.02% TFA in water) and peptides were eluted by increasing concentration of solvent B (95% Acetonitrile/0.02% TFA in water). A post-column splitter valve was used to direct 15% of the flow to the Q-Tof micro. The instrument was run in the positive mode (m/z 100-2000). The capillary voltage was set to 3000 V.

MS/MS Analysis of Peptides:

Fractions from reversed phase chromatography were collected and infused into the Q-Tof micro at a flow rate of 20 µL/minute. The MS/MS spectra were acquired using a collision energy optimized for the individual peptide (ranging from 25 to 42 eV).

Results

Figure 66A:
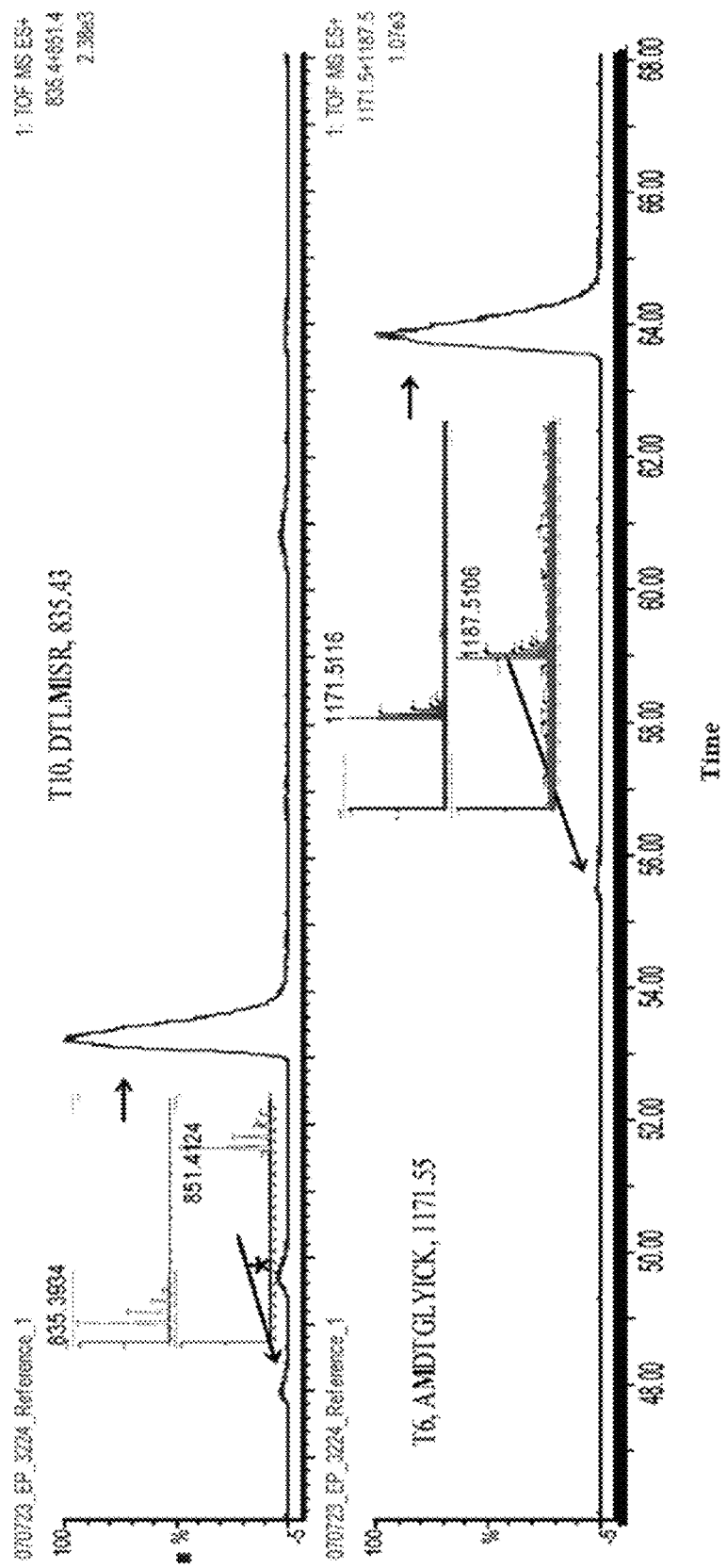
FIG. 66A-66B depicts ion chromatograms and mass spectra of oxidized and native tryptic peptides from CTLA4-Ig.
Figure 66B:
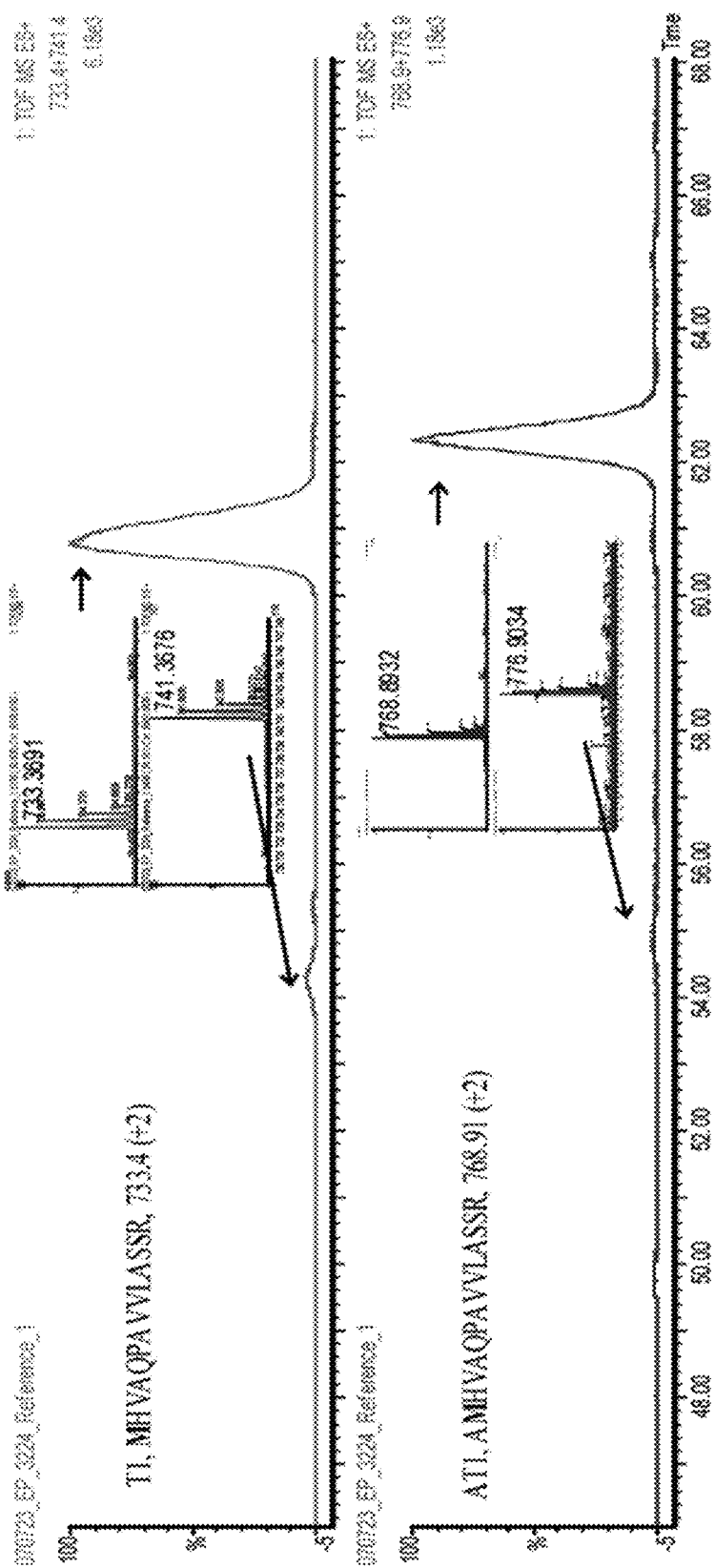

Oxidation of CTLA4-Ig:

CTLA4-Ig has seven methionines per single chain: Met$^1$, Met$^{53}$, Met$^{54}$, Met$^{85}$, Met$^{97}$, Met$^{162}$ and Met$^{338}$. Peptide mapping was used to identify the oxidative product variants at each of these sites. Oxidations of Met$^1$, Met$^{85}$ and Met$^{162}$ are identified using the tryptic peptide mapping technique (FIGS. 66A and 66B). No oxidation of Met$^{338}$ is detected. The tryptic fragments containing Met$^{53}$, Met$^{54}$ or Met$^{97}$ are large peptides containing heterogeneous N-linked carbohydrates. These peptides are not amenable to identification and relative quantitation of oxidation. Therefore, proteolysis using multiple enzymes, which produce shorter, non-glycosylated peptides was performed. The Asp-N peptide EVCAATYMMGN (46-56) and tryptic/chymotryptic peptide MYPPPY (97-102) are used to determine oxidation of Met$^{53}$, Met$^{54}$ and Met$^{97}$. The relative quantitation of methionine oxidation is calculated according to the peak area percent of the extracted ion chromatograms. The relative amounts of oxidized peptides are listed in Table 63. Oxidation on six out of the seven CTLA4-Ig methionines per single chain is detected. Peaks A and B are the singly oxidized forms of peptide EVCAATYMMGN (46-56) (peak 3). Peptides from peaks 2A and 2B are isobaric and have a mass increase of 16 u as compared with the unmodified peptide mass. Each peak represents oxidation at different Met. The degree of the oxidation is different at the two sites.

TABLE 63

The Oxidation of Met in CTLA4-Ig

| Met | Peptide | Expected Mass Non-oxidized | Observed Mass Non-oxidized | Expected Mass Oxidized | Observed Mass Oxidized | Oxidation Percent |
|---|---|---|---|---|---|---|
| 1 | AT1: AMHVAQPAVVLASSR | 768.9 (+2) | 768.9 | 776.91 (+2) | 776.9 | 0.9 |
| 1 | T1: MHVAQPAVVLASSR | 733.4 (+2) | 733.4 | 741.4 (+2) | 741.4 | 2.4 |
| 53 | D5: EVCAATYMMGN | 1246.5 | 1246.6 | 1262.5 | 1262.5 | 3.4 |
| 54 | D5: EVCAATYMMGN | 1246.5 | 1246.6 | 1262.5 | 1262.6 | 4.3 |
| 85 | T6: AMDTGLYICK | 1171.6 | 1171.5 | 1187.6 | 1187.5 | 1.0 |
| 97 | MYPPPY | 767.3 | 767.9 | 783.3 | 783.9 | 1.5 |
| 162 | T10: DTLMISR | 835.4 | 835.4 | 851.4 | 851.4 | 1.7 |
| 338 | T30: WQQGDVFSCSVMHEALHNHYTQK | 1401.1 (+2) | 1401.1 | 1409.1 (+2) | | |

*Due to the minor contribution of AT1 oxidation, the percent of AT1 oxidation is not included in the calculation of the estimated amount of the CTLA4-Ig oxidation.

The total estimated amount of CTLA4-Ig methionine oxidation is calculated to be 2.0% for CTLA4-Ig. This is calculated by adding the total percentage of oxidation at each site and dividing by the total number of methionines, which is seven. MS/MS analysis was performed on oxidized and native peptides listed in Table 63.

All peptides, with the exception of D5, are sequenced using MS/MS. The oxidized amino acid is determined by the mass difference within the b and y ion series. The MS/MS spectra of the oxidized and native T1 peptide entails the doubly charged precursor ions at m/z 741.4 and 733.4. The mass difference is 8 u (for the double charge state) that is 16 u when corrected for the charge state. The tryptic peptide T1 (1-14) contains the Met[1] residue. The native peptide and its oxidized derivative are baseline separated by reversed phase chromatography. The ion chromatogram for doubly charged ions of T1 and its derivatives is shown in FIGS. 66A and 66B. The b and y ion series are the predominant ions produced in collision induced dissociation. y6-y13 ions have the same modified and unmodified ion masses. The b2 ion of the oxidized peptide is 16 u higher than the corresponding b2 ion of the native peptide. The b and y ion series taken together with the peptide masses identify methionine 1 as the amino acid modified in the T1 peptide. In the same way, Met oxidations in AT1, T6, T10, and MYPPPY (97-102) peptides are identified.

Deamidation of CTLA4-Ig:

CTLA4-Ig has 15 asparagines per single chain. Three asparagines are known to be attached to N-linked carbohydrate structures. Peptide mapping was used to identify and relatively quantify deamidation occurring at the other 12 Asn residues. Deamidations of $Asn^{186}$, $Asn^{225}$, $Asn^{271}$, $Asn^{294}$ and $Asn^{344}$ are identified by the LC/MS tryptic peptide map (Table 64). The relative quantitation of asparagine deamidation is calculated according to the peak area percent of the extracted ion chromatograms. The relative amounts of deamidated peptides are listed in Table 64. The total estimated amount of CTLA4-Ig asparagine deamidation is calculated to be 0.3% for CTLA4-Ig. This is calculated by adding the total percentage of deamidation at each site and dividing by 15. MS/MS analysis was performed on deamidated and native peptides listed in Table 64.

Asn residue mass; this corresponds to either aspartic or isoaspartic acid. In the same way, deamidations in T12, T25, T26 and T30 were identified and the fragment ions identify the modification sites.

Asparagine deamidations and methionine oxidations are determined from LC/MS and LC/MS/MS analyses of the endopeptidase cleavage of CTLA4-Ig. The modifications are identified by shifts in masses between the modified and unmodified peptides. The modified amino acids are identified by MS/MS sequencing. Six methionine oxidations and five asparagine deamidations per single chain are present in CTLA4-Ig material in a small percentage. CTLA4-Ig $Met^1$, $Met^{53}$, $Met^{54}$, $Met^{85}$, $Met^{97}$, and $Met^{162}$ are all found to be oxidized. These oxidations determined from CTLA4-Ig are found to be less than 2.5% of all CTLA4-Ig methionines. CTLA4-Ig $Asn^{186}$, $Asn^{225}$, $Asn^{271}$, $Asn^{294}$, and $Asn^{344}$ are all found to be deamidated in low amounts. These deamidations determined from CTLA4-Ig are found to be less than 0.5% of all CTLA4-Ig asparagines.

Example 48—Bacterial Endotoxin Assays for CTLA4-Ig and $CTLA^{A29YL104E}$-Ig

In one embodiment, the CTLA4-Ig composition drug substance has less than or equal to 0.15 EU/mg bacterial endotoxin. CTLA4-Ig is assayed for the presence of bacterial endotoxins using the Limulus Amebocyte Lysate (LAL) gel clot technique based on USP<85>. In preparing for and applying the assay, observe precautions in handling the specimens in order to avoid gross microbial contamination;

TABLE 64

The Deamidation of Asn in CTLA4-Ig

| AsnPeptide | Expected Mass Non-deamidated | Observed Mass Non-deamidated | Expected Mass Deamidated | Observed Mass Deamidated | Deamidation Percent |
|---|---|---|---|---|---|
| 186T12: FNWYVDGVEVHNAK | 839.4 (+2) | 839.4 | 839.9 (+2) | 839.9 | 0.9 |
| 225T15: VVSVLTVLHQDWLNGK | 904.5 (+2) | 904.5 | 905.0 (+2) | 905.0/905.0 | 1.5/0.8 |
| 271T25: NQVSLTCLVK | 1161.6 | 1161.7 | 1162.6 | 1162.7 | 0.3 |
| 294T26: GFYPSDIAVEWESNGQPENNYK | 1272.6 (+2) | 1272.6 | 1273.1 (+2) | 1273.1 | 1.2 |
| 344T30: WQQGNVFSCSVMHEALHNHYTQK | 1401.1 (+2) | 1401.2 | 1401.6 (+2) | 1401.7 | 0.2 |

The deamidated amino acid is determined by the mass difference within the b and y ion series. For example, if there are two deamidated peaks for peptide T15—masses 905.0 u. Peak 1 elutes prior to the native peak; peak 3 elutes after the native peak. Tryptic peptides and their deamidated forms are baseline separated on the reversed phase column. MS/MS analysis was performed on tryptic peptides and deamidated peptides are listed in Table 64. Peaks 1-3 contain the same y1 and y2 ions, indicating that the C-terminal amino acids are the same for all three peaks; however, the y3-y14 ions from peaks 1 and 3 are 1 u higher than the corresponding ions from peak 2. The mass difference between y2 and y3 is 114 u for peak 2; this corresponds to an Asn residue. The 115 u for peaks 1 and 3 is a 1 u mass increase compared to the treat any containers or utensils employed to destroy extraneous endotoxins that may be present on their surfaces such as heating in a dry-heat oven using a validated cycle.

LAL Reagent: (Associates of Cape Cod, Inc.— or equivalent) Lyophilized Limulus

Amebocyte Lysate (LAL) reagent such as Pyrotell should be stored according to manufacturer's instructions. Reconstituted LAL reagent may be held frozen for no longer than one month, and should not be thawed or frozen more than once.

Endotoxin Standards: (Associates of Cape Cod, Inc.— or equivalent) The control standard endotoxin (CSE) used in the tests must be traceable and standardized against Reference Standard Endotoxin (RSE). Store unreconstituted containers of endotoxin in a refrigerator; once reconstituted, they may be held at 2°-8° C. for no longer than 14 days, unless validation for longer periods shows suitable reactivity.

Testing of Production Lots

The lack of product inhibition or enhancement of the LAL procedure should be validated for each drug formulation. Testing of production lots is performed using three individual units representing beginning, middle, and end of production. These units can be run individually or pooled. A representative positive product control of the sample at the test concentration, inoculated with twice the amount of CSE (or RSE) as the labeled sensitivity of the lysate, must be included for a valid test. Adjust the pH so that the final product/lysate solution is in the range of 6.0 to 8.0, using sterile endotoxin-free HCl, NaOH or suitable buffer. In some situations, it may be helpful to use a buffering agent such as Pyrosol as an alternative to pH adjustment. Refer to the manufacturer's directions for specific use.

Use of Buffering Agent for Lysate Reconstitution

A buffering agent such as Pyrosol (Associates of Cape Cod, Inc.) issued to reconstitute the lysate used for testing and is designed to amplify the buffering capacity of the lysate. Pyrosol-reconstituted lysate may be used to test samples or sample dilutions that may otherwise require adjustment of pH with acid or base or which precipitate on adjustment of pH. When combined with the test sample, Pyrosol-reconstituted lysate gives a pink color to indicate that the pH is in range for a valid test. If outside that range, the color will be yellow or purple; in this case, the test sample would require additional pH adjustment. Specific methods will dictate the use of Pyrosol for lysate reconstitution.

Use of Glucan-Inhibiting Buffer for Lysate Reconstitution

A glucan-inhibiting buffer such as Glucashield (Associates of Cape Cod, Inc.) is used to reconstitute the lysate used for testing and is designed to block potential glucan interference. Glucashield-reconstituted lysate may be used to test samples or sample dilutions that may contain glucan contamination. Interference from glucan contamination can give false positives in certain test materials, so using a Glucashield-reconstituted lysate may block or reduce interference allowing for a reduced number of false positives. Specific methods will dictate the use of Glucashield for lysate reconstitution.

Sample Dilutions

If necessary to approximate the level of endotoxin concentration in the sample, prepare an appropriate series of dilutions of the sample in sterile endotoxin-free water. Vortex and add 0.1 mL of each preparation to be tested to each of two sterile endotoxin-free 10×75 mm glass test tubes.

Preparation of Endotoxin Standard Solutions for Standard Curve

Reconstitute the vial of endotoxin with endotoxin-free water as per the manufacturer's instructions. Mix the vial vigorously on a vortex mixer intermittently for 30 minutes. Preserve the concentrate in a refrigerator at 2°–8° C. for no more than 4 weeks. Mix vigorously using a vortex mixer for not less than 3 minutes prior to use. Consult the manufacturer's Certificate of Analysis to verify the concentration of the endotoxin stock, and prepare a standard endotoxin dilution series, designed to bracket the endpoint, such as in the following example:

0.5 mL (1000 EU/mL)+9.5 mL endotoxin-free water=50 EU/mL
5.0 mL (50 EU/mL)+5.0 mL endotoxin-free water=25 EU/mL
1.0 mL (25 EU/mL)+9.0 mL endotoxin-free water=2.5 EU/mL
1.0 mL (2.5 EU/mL)+9.0 mL endotoxin-free water=0.25 EU/mL
5.0 mL (0.25 EU/mL)+5.0 mL endotoxin-free water=0.125 EU/mL
5.0 mL (0.125 EU/mL)+5.0 mL endotoxin-free water=0.06 EU/mL
5.0 mL (0.06 EU/mL)+5.0 mL endotoxin-free water=0.03 EU/mL
5.0 mL (0.03 EU/mL)+5.0 mL endotoxin-free water=0.015 EU/mL Be sure to vigorously vortex each dilution for at least 30 seconds before proceeding to the next dilution. Include a negative water control of the diluent used. Vortex and add 0.1 mL of each of the 0.125 EU/mL, 0.06 EU/mL, 0.03 EU/mL, 0.015 EU/mL concentrations (or alternate curve) and the negative water control, to each of two sterile endotoxin-free 10×75 mm glass test tubes to provide two replicate curves.

Preparation of LAL Reagent Solution

Remove the lyophilized LAL reagent from the freezer. Aseptically add 5.0 mL of endotoxin-free water (unless otherwise directed by a specific method to use a reconstitution buffer) to the vial. Swirl or roll the vial to dissolve the reagent.

Preparation of Positive Product Control

All products must be tested with a positive product control. Refer to the applicable Specific Method for instructions on preparation of the positive control. If no instruction is provided, prepare the positive product control to contain an endotoxin spike at 2× the level of the lysate sensitivity, in combination with the product at its test level. When testing Water for Injection or High Quality Process Water, use a dilution of the reconstituted endotoxin standard so that when added to the sample, the endotoxin concentration will be 2× the LAL solution sensitivity. For example, if the lysate sensitivity=0.06 EU/mL, add 0.1 mL of a 2.5 EU/mL endotoxin solution to 1.9 mL of test sample (in the form as added to the LAL solution)=0.125 EU/mL. The volume of the endotoxin solution is not greater than 0.1 mL and the overall dilution is not less than 1:20.

Test Procedure

1. Aseptically dispense 0.1 mL of the LAL reagent solution into each of the test sample tubes and endotoxin standard tubes, being cautious not to crosscontaminate between tubes. NOTE: Place any remaining reagent in a freezer at about minus 10° C. to minus 25° C.

2. Refer to the specific lysate insert for mixing instructions of the product-lysate mixture.

3. Place each tube in an incubating device such as a water bath or heating block maintained at 37°±1° C. Record the incubation start time and the temperature of the water bath or heating block.

4. Incubate each tube, undisturbed, for 60±2 minutes.

5. Following the incubation, record the incubation end time and observe each tube by gently inverting the tube 180°. A positive result is denoted by a firm gel which remains firm when inverted carefully, a negative result is characterized by the absence of such a gel, or by the formation of a viscous gel that does not maintain its integrity. Handle the tubes carefully and avoid subjecting them to vibrations which could cause false negative observations.

Evaluation

The lowest concentration in each replicate series to give a positive result is called the endpoint. Calculate the geometric mean endpoint for the test by the following procedure: Geometric Mean=The antilogarithm of the logarithmic sum of the gelation endpoints divided by the number of replicate endpoint assays. The test is valid provided the geometric mean endpoint is within a two-fold dilution of the labeled lysate sensitivity, the positive product control is positive, and the negative water control is negative. Determine the approximate bacterial endotoxin level in or on the test item by comparing the labeled lysate sensitivity with the positive or negative results coupled with the dilution factors of the item tested. The article meets the requirements of the test if there is no formation of a firm gel at the level of endotoxin specified in the individual monographs or specification.

Method for CTLA4$^{429YL104E}$-Ig

This method is used to quantify bacterial endotoxins in samples of CTLA4$^{429YL104E}$-Ig drug substance and drug product using the kinetic turbidimetric LAL method. The results are reported as EU/mL and EU/mg drug product equivalent.

Terms:
- LAL—Limulus Amebocyte Lysate
- CSE—Control Standard Endotoxin
- EU—United States Pharmacopoeia Endotoxin Units
- EU/mg—United States Pharmacopoeia Endotoxin Units per milligram
- EU/mL—United States Pharmacopoeia Endotoxin Units per milliliter
- LRW—LAL Reagent Water Limulus Amebocyte Lysate Turbidimetric (PYROTELL-T®) Solution. Allow vials of PYROTELL-T® and PYROSOL® to warm to room temperature for 30 minutes before opening. Remove metal seal from PYROTELL-T® and aseptically remove stopper. Reconstitute PYROTELL-T® with 5.0 mL PYROSOL® Reconstitution Buffer. Swirl bottle gently to mix until completely dissolved. Reconstitute buffer immediately before use. Reconstituted PYROTELL-T® can be kept at 2-8° C. for no more than 24 hours. Cover the top of container with a layer of PARAFILM®.

Control Standard Endotoxin Solution. Allow vial of CSE (1.2) to warm to room temperature for 30 minutes before opening. Remove metal seal from the vial and aseptically remove stopper. Carefully lift the stopper just enough to allow air to enter, thereby breaking the vacuum. Reconstitute Control Standard Endotoxin (CSE) with 5.0 mL of LRW (1.4). Seal with PARAFILM®. Vortex vigorously for one minute, at 5-10 minute intervals over a 30-60 minute interval at room temperature. CSE is then ready for use. Refer to the manufacture's Certificate of Analysis to obtain the Control Standard Endotoxin (CSE) potency in USP-EU per vial vs. the specific lot of PYROTELL-T®. Calculate the USP-EU/mL of the CSE in the vial. Reconstituted CSE can be kept at 2-8° C. for 30 days. After each use, seal container with new PARAFILM®.

Example:
For a vial having a potency of 6,000 USP-EU/vial reconstituted with 5.0 mL of LRW, the potency would be 1,200 USP-EU/mL.

$$\text{Potency} = \frac{6{,}000 \text{ EU/vial}}{5.0 \text{ mL}} = 1{,}200 \text{ EU/mL}$$

Set Up Assay Parameters in PYROSOFT-11® Software. General Parameters. Set up parameters in the General Test Information Tab as shown in the below Table.

| General Test Information | |
|---|---|
| Parameter | Value |
| Valid Temp Range Min. | 36.5 |
| Valid Temp Range Max. | 37.5 |
| Range for Spike Recovery Min. | 50 |
| Range for Spike Recovery Max. | 200 |
| Threshold OD (mAbs) | 20 |
| Max OD Stored (mAbs) | 100 |
| Maximum Test Time (mins) | 120 |
| Baseline Adj. Active | Check |
| Auto-end | Uncheck |
| Check negative control | Uncheck |

| Options | |
|---|---|
| Parameter | Value |
| Flag Correlation Coefficient | Checked |
| Display Correlation Coefficient | Not checked |
| Flag Coefficient of Variation | Not checked |
| Extrapolate beyond | Not checked |
| Auto Test ID | Not checked |
| Show Pass Fail Results | Checked |
| Auto-Print | Not checked |

| Tube Assignments - Example | | | | |
|---|---|---|---|---|
| Tube No. | Sample Description | Standard/Spike Concentration | Units | Sample Dilution* |
| 1 | Negative Control | | EU/mL | |
| 2 | Negative Control | | EU/mL | |
| 3 | Standard | 0.064 | EU/mL | |
| 4 | Standard | 0.064 | EU/mL | |
| 5 | Standard | 0.032 | EU/mL | |
| 6 | Standard | 0.032 | EU/mL | |
| 7 | Standard | 0.016 | EU/mL | |
| 8 | Standard | 0.016 | EU/mL | |
| 9 | Standard | 0.008 | EU/mL | |
| 10 | Standard | 0.008 | EU/mL | |
| 11 | Standard | 0.004 | EU/mL | |
| 12 | Standard | 0.004 | EU/mL | |
| 13 | Standard | 0.002 | EU/mL | |
| 14 | Standard | 0.002 | EU/mL | |
| 15 | Sample 1 | | EU/mL | 1:1 |
| 16 | Sample 1 | | EU/mL | 1:1 |
| 17 | Sample 1 Spike | 0.016 | EU/mL | 1:1 |
| 18 | Sample 1 Spike | 0.016 | EU/mL | 1:1 |
| 19 | Sample 2 | | EU/mL | 1:1 |
| 20 | Sample 2 | | EU/mL | 1:1 |
| 21 | Sample 2 Spike | 0.016 | EU/mL | 1:1 |
| 22 | Sample 2 Spike | 0.016 | EU/mL | 1:1 |
| 23 | Sample 3 | | EU/mL | 1:1 |
| 24 | Sample 3 | | EU/mL | 1:1 |
| 25 | Sample 3 Spike | 0.016 | EU/mL | 1:1 |
| 26 | Sample 3 Spike | 0.016 | EU/mL | 1:1 |
| 27 | Sample 4 | | EU/mL | 1:1 |
| 28 | Sample 4 | | EU/mL | 1:1 |
| 29 | Sample 4 Spike | 0.016 | EU/mL | 1:1 |
| 30 | Sample 4 Spike | 0.016 | EU/mL | 1:1 |
| 31 | Positive Water Control | 0.016 | EU/mL | |
| 32 | Positive Water Control | 0.016 | EU/mL | |

Prepare Standard Curve Concentrations. Prepare Control Standard Endotoxin (CSE, 2.2) working stock solution at 4

USP-EU/mL. Prepare a working solution of CSE at a potency of 4 EU/mL. Calculate the volume of LRW needed for the dilution using Equation 1. Add 20 μL of CSE solution (2.2) to the appropriate amount (Equation 1) of LRW (1.4) in a polystyrene tube (1.9). Vortex dilution for 30 seconds.
Example:
For CSE solution at a potency of 1,200 EU/mL add 20 μL of CSE solution to 5,980 μL of LRW.

$$LRW Volume = \left(\frac{20\ \mu L * 1{,}200\ EU/mL}{4\ EU/mL}\right) - 20\ \mu L$$

Prepare CSE working stock solution at 0.64 EU/mL. Prepare a working solution of CSE at a potency of 0.64 USP-EU/mL by adding 1.6 mL of CSE stock solution at 4 USP-EU/mL to 8.4 mL of LRW in a polystyrene tube. Vortex for 30 seconds.

Prepare Standard Stock Solutions. Standard Stock Solutions are prepared at 0.128, 0.064, 0.032, 0.016, 0.008, and 0.004 EU/mL from the working solution of CSE in polystyrene tubes. Vortex each tube for 30 seconds after dilution. A dilution scheme is shown in the Table below.

Dilution Scheme for Standard Stock Solutions

| Volume (μL) of Concentration (EU/mL) | LRW (mL) | Final Stock Concentration (EU/mL)* |
|---|---|---|
| 2 mL of 0.64 EU/mL solution | 8 | 0.128 |
| 4 mL of 0.128 EU/mL solution | 4 | 0.064 |
| 4 mL of 0.064 EU/mL solution | 4 | 0.032 |
| 4 mL of 0.032 EU/mL solution | 4 | 0.016 |
| 4 mL of 0.016 EU/mL solution | 4 | 0.008 |
| 4 mL of 0.008 EU/mL solution | 4 | 0.004 |

*The final two-fold dilution occurs in the reaction tubes.

Sample Preparation. Drug Substance Sample Preparation. Prepare a sample dilution to 0.25 mg/mL. Calculate the volume of LRW needed for the dilution using the Equation below. Carefully remove top of sample container and add 50 μL of sample to the appropriate amount (Equation below) of LRW in a polystyrene tube to make a 0.25 mg/mL solution. Vortex sample for 30 seconds. Cover the top of sample container with layer of PARAFILM®.
Example:
For a sample having a concentration of 24.7 mg/mL add 50 μL (0.05 mL) of sample to 4.89 mL of water $$LRW\ Volume\ (mL) = \left(\frac{0.05 * Protein\ Concentration\ (mg/mL)}{0.25\ mg/mL}\right) - 0.05\ mL \quad \text{Equation 2}$$

Drug Product Lyophile Sample Preparation. NOTE: A single Drug Product lot consists of three separate samples, "beginning", "middle", and "end". Reconstitute a vial of drug product with LAL Reagent water according to the Product Identification (PI) specifications. Dilute the reconstituted sample to 0.25 mg/mL. Calculate the volume of LRW needed for the dilution using Equation 2. Carefully remove top of sample container and add 50 μL of sample to the appropriate amount (Equation 2) of LRW in a polystyrene tube to make a 0.25 mg/mL solution. Vortex sample for 30 seconds. Cover the top of sample container with PARAFILM®.

Drug Product Ready-to-Use Sample Preparation. Dilute the sample to 0.25 mg/mL. Calculate the volume of LRW needed for the dilution using Equation 3. Carefully remove top of sample container and add 10 μL of sample to the appropriate amount (Equation 3) of LRW in a polystyrene tube to make a 0.25 mg/mL solution. Vortex sample for 30 seconds. Cover the top of sample container with PARAFILM®.
Example:
For a sample having a concentration of 125.0 mg/mL add 10 μL (0.01 mL) of sample to 4.99 mL of water $$LRW\ Volume\ (mL) = \left(\frac{0.01 * Protein\ Concentration\ (mg/mL)}{0.25\ mg/mL}\right) - 0.01\ mL \quad \text{Equation 3}$$

Drug Product Ready-to-Use Placebo. Dilute the placebo (as if it were at a nominal drug product protein concentration of 125 mg/mL) to 0.25 mg/mL. This is equivalent to a 1:500 dilution. Calculate the volume of LRW needed for the dilution using Equation 3. Carefully remove top of sample container and add 10 μL of sample to the appropriate amount (Equation 3) of LRW in a polystyrene tube to make an 0.25 mg/mL equivalent solution.

Positive Water Control. The positive control is prepared from the standard curve by adding 100 μL of 0.032 EU/mL standard to 100 μL of LRW in the reaction tubes.

Reaction Tube Setup-Example

| Tube No. | Description | Standard Stock Conc. (EU/mL) | Standard/ Samples (μL) | LRW (μL) | Spike Soln. (μL) | Final Conc. (EU/mL) |
|---|---|---|---|---|---|---|
| 1 | Negative Control | — | 0 | 200 | 0 | 0.000 |
| 2 | Negative Control | — | 0 | 200 | 0 | 0.000 |
| 3 | Std. 1 | 0.004 | 100 | 100 | 0 | 0.002 |
| 4 | Std. 1 | 0.004 | 100 | 100 | 0 | 0.002 |
| 5 | Std. 2 | 0.008 | 100 | 100 | 0 | 0.004 |
| 6 | Std. 2 | 0.008 | 100 | 100 | 0 | 0.004 |
| 7 | Std. 3 | 0.016 | 100 | 100 | 0 | 0.008 |
| 8 | Std. 3 | 0.016 | 100 | 100 | 0 | 0.008 |
| 9 | Std. 4 | 0.032 | 100 | 100 | 0 | 0.016 |
| 10 | Std. 4 | 0.032 | 100 | 100 | 0 | 0.016 |
| 11 | Std. 5 | 0.064 | 100 | 100 | 0 | 0.032 |
| 12 | Std. 5 | 0.064 | 100 | 100 | 0 | 0.032 |
| 13 | Std. 6 | 0.128 | 100 | 100 | 0 | 0.064 |
| 14 | Std. 6 | 0.128 | 100 | 100 | 0 | 0.064 |
| 15 | Sample 1 | — | 100 | 100 | 0 | unknown |
| 16 | Sample 1 | — | 100 | 100 | 0 | unknown |
| 17 | Sample 1 Spike | — | 100 | 0 | 100 | Constitutive +0.016 |
| 18 | Sample 1 Spike | — | 100 | 0 | 100 | Constitutive +0.016 |
| 19 | Sample 2 | — | 100 | 100 | 0 | unknown |
| 20 | Sample 2 | — | 100 | 100 | 0 | unknown |
| 21 | Sample 2 Spike | — | 100 | 0 | 100 | Constitutive +0.016 |
| 22 | Sample 2 Spike | — | 100 | 0 | 100 | Constitutive +0.016 |
| 23 | Sample 3 | — | 100 | 100 | 0 | unknown |
| 24 | Sample 3 | — | 100 | 100 | 0 | unknown |
| 25 | Sample 3 Spike | — | 100 | 0 | 100 | Constitutive +0.016 |
| 26 | Sample 3 Spike | — | 100 | 0 | 100 | Constitutive +0.016 |
| 27 | Sample 4 | — | 100 | 100 | 0 | unknown |

| Reaction Tube Setup-Example | | | | | | |
|---|---|---|---|---|---|---|
| Tube No. | Description | Standard Stock Conc. (EU/mL) | Standard/ Samples (µL) | LRW (µL) | Spike Soln. (µL) | Final Conc. (EU/mL) |
| 28 | Sample 4 | — | 100 | 100 | 0 | unknown |
| 29 | Sample 4 Spike | — | 100 | 0 | 100 | Constitutive +0.016 |
| 30 | Sample 4 Spike | — | 100 | 0 | 100 | Constitutive +0.016 |
| 31 | Positive Water Control | 0.032 | 0 | 100 | 100 | 0.016 |
| 32 | Positive Water Control | 0.032 | 0 | 100 | 100 | 0.016 |

Add PYROTELL-T® Reagent. Add 50 µL of PYROTELL-T® solution to each reaction tube (negative control, standards, samples, spiked samples, and positive water control) with a repeat pipetor. Vortex each tube for 1-2 seconds, and insert it in the assigned well (Table 1) in the Pyros Kinetix instrument.

Data Analysis.

Analysis. The PYROSOFT®-11 software will perform an autoanalysis of all standards, controls, and samples and report sample results in EU/mL at the completion of the run. Each duplicate sample is reported as a mean value of the two. If one of the tubes of a duplicate pair value is undetected by PYROSOFT®-11 software, that tube may be excluded from further data analysis, and the results recalculated. Spike recovery (positive sample control) will be calculated based on the amount of endotoxin in the sample plus the amount of endotoxin spiked into the sample (0.016 EU/mL).

Convert EU/mL value to EU/mg value of Diluted Drug Substance or Drug Product Sample Raw data is generated as EU/mL and reported as EU/mg of protein. To convert EU/mL to EU/mg, divide the endotoxin value (EU/mL) by the protein concentration (0.125 mg/mL). Results are reported to one significant figure.

Example:

For a sample having 0.23 EU/mL in the assay, the reportable EU/mg value will be 2 EU/mg (1.8 rounded to one significant figure).

$$\left(\frac{0.23 \text{ EU/mL}}{0.125 \text{ mg/mL}}\right) = 1.84 \text{ EU/mg} = 2 \text{ EU/mg}$$

Result for Drug Substance Sample. The result is determined to one significant figure. The QL of the assay is 0.02 EU/mg. If the sample is 0.02 EU/mg the reportable result is [<QL, (QL=0.02 EU/mg)]. Result for Drug Product Sample. The mean of the three samples for each lot of drug product ("beginning", "middle", and "end") in EU/mg is the reportable result for drug product samples at one significant figure. For the case where one or more of the samples for a lot are <QL (0.02 EU/mg), the value of 0.02 EU/mg will be used for calculating the mean. If the mean reportable result is 0.02 EU/mg the reportable result is [<QL, (QL=0.02 EU/mg)].

Example:

| Sample From a Lot of Drug Product | Value EU/mg |
|---|---|
| Beginning | <QL = 0.02 EU/mg |
| Middle | 0.023 |
| End | 0.031 |
| Reportable Value (Mean) | 0.02 EU/mg |

For this example, the drug product placebo would be reported as: 3 EU/mL, equivalent to 0.02 EU/mg at a nominal drug product concentration of 125 mg/mL.

System Suitability. Drug Substance samples should be received in polystyrene containers at 2-8° C. If samples are received in different containers at a different temperature, they may not be used in the assay. The coefficient of determination for the standard curve ($r^2$) must be ≥0.99. If the $r^2$ value is <0.99, the assay is not valid and must be repeated. The mean measured endotoxin concentration for the negative control must be <0.002 EU/mL. If the negative control is ≥0.002 EU/mL, the assay is not valid and must be repeated. The spiked sample value must fall within the range of 50-200% of the expected value. If the spiked sample value is ≤49% or ≥201% of the expected value, the assay is not valid and must be repeated. The mean measured endotoxin concentration for the positive water control must fall within the range of 50-200% of the same concentration in the standard curve. If the positive water control value is ≤49% or ≥201% of the expected value, the assay is not valid and must be repeated. Endotoxin values for the samples must fall within the range of the endotoxin standard curve (between 0.002 and 0.064 USP-EU/mL). If samples are <0.002 EU/mL, they are below the QL of the assay and reported per section 5.4. If samples are ≥0.064 USP-EU/mL, the samples must be further diluted into the range of the assay.

Example 49—Microbial Limits Test (Bioburden) for CTLA4-Ig

This method provides test procedures for the estimation of the number of viable aerobic microorganisms present and for freedom from designated microbial species. In one embodiment, the CTLA4-Ig composition should have bioburden at a level of ≤1 CFU/10 mL. In preparing for and in applying the tests, observe aseptic precautions in handling the specimens. The term "Growth" is defined as the presence and presumed proliferation of viable microorganisms. The validity of the test results rest largely upon demonstration that the test specimens to which they are applied do not, of themselves, inhibit the growth, under the test conditions, of microorganisms that may be present. This demonstration should include challenging appropriately prepared specimens of the material to be tested with separate viable cultures of appropriate challenge organisms to assure that the test will not inhibit growth of these classes of organism, should they be present in the material tested. That portion of any beta-lactam product which is used for testing must be treated with suitable amount of penicillinase in accordance with the validated procedures.

Diluting Fluids and Media

1. Preparation of Culture Media and Diluting Fluids. Culture media and diluting fluids may be prepared, or dehydrated culture media may be used provided that, when reconstituted as directed by the manufacturer or distributor, they have similar ingredients and/or yield media comparable to those obtained from the formulae given herein. In preparing media by the formulae, dissolve the soluble solids in the water, using heat if necessary, to effect complete solution, and add solutions of hydrochloric acid or sodium hydroxide in quantities sufficient to yield the desired pH in the medium when it is ready for use. Media are to be sterilized in an autoclave using a validated sterilization procedure. Determine the pH after sterilization at 25°±2° C.
Growth Promotion a) Each batch of autoclaved medium is tested for its growth promoting ability by inoculating duplicated test containers of each medium with less than 100 microorganisms and incubating according to the conditions specified below. Organisms may not be more than 5 passages from the culture originally received from ATCC.

b) The test medium is satisfactory if evidence of growth appears within 48-72 hours for bacteria and 5 days for fungi. The growth promotion test may be conducted simultaneously with the use of the test medium for materials testing. However, the materials testing is considered invalid if this growth promotion test is not successful.

sterile Phosphate Buffer pH 7.2. Shake well until the tablets completely disintegrate or dissolve, and transfer 1.0 mL to each of two sterile petri dishes.

vi) Capsule Shells—Transfer 25 capsule shells to 100 mL Sterile Phosphate Buffer pH 7.2 and warm in a water bath (approximately 45° C.) for about 15 minutes, shaking intermittently to dissolve. Shake well and transfer 1.0 mL to each of two sterile petri dishes.

vii) Ointments—Into a sterile container, pool approximately 5 mL from each of 3 samples taken from across the lot and mix. Transfer 0.1 mL of this pooled sample to each of ten petri dishes. Spread the sample over the media surface with the aid of a sterile bent glass rod (hockey stick). Using a separate sterile rod for each plate incubate as described in "Total Aerobic Count."

b) Membrane Filtration. As an alternative to pour plating procedures, a suitable, validated membrane filtration test procedure may be used. This may be especially useful for products containing inhibitory substances.

Test Microorganisms for Use in Growth Promotion Testing of Media

| TEST | MEDIUM | TEST MICROORGANISMS | | ATCC# | INCUBATION TEMPERATURE |
|---|---|---|---|---|---|
| Total Aerobic | TSA | (1) | *Staphylococcus aureus* | 6538 | 30°-35° C. |
| Microbial Count | | or: | *Micrococcus luteus* | 9341 | 30°-35° C. |
| | | (2) | *Bacillus subtilis* | 6633 | 30°-35° C. |
| | | (3) | *Escherichia coli* | 8739 | 30°-35° C. |
| Total Combined | SDA | (1) | *Candida albicans* | 10231 | 20°-25° C. |
| Molds and Yeasts Count | | (2) | *Aspergillus niger* | 16404 | 20°-25° C. |
| Absence of *Pseudomonas aeruginosa* | TSB | (1) | *Pseudomonas aeruginosa* | 9027 | 30°-35° C. |
| Absence of *Staphylococcus aureus* | TSB | (1) | *Staphyloccocus aureus* | 6538 | 30°-35° C. |
| Absence of *Salmonella* | FLM | (1) | *Salmonella choleraesuis* | 13311 | 30°-35° C. |
| | | or: | *Salmonella typhimurium** | | 30°-35° C. |
| Absence of *Escherichia coli* | FLM | (1) | *Escherichia coli* | 8739 | 30°-35° C. |

*Other non-pathogenic *Salmonella* species may also be suitable.

Procedure for Total Aerobic Microbial Count or Total Combined Molds and Yeast Count a) Sample Preparation. Unless otherwise directed by the Specific Method, prepare the specimen for testing as follows. Refer to the appropriate section below for additional information regarding media and incubation procedures depending on which test is being performed.

i) Bulk Powders and Raw Materials—Dissolve or suspend 10 grams or 10 mL of sample in 90 mL of sterile Phosphate Buffer pH 7.2. Mix well and transfer 1.0 mL to each of two sterile petri dishes.

ii) Capsules—Aseptically transfer 2 capsule shells and their contents to 20 mL of sterile Phosphate Buffer pH 7.2. Warm in a water bath (approximately 45° C.) for about 10 minutes. Shake vigorously until the suspension becomes uniform, and transfer 1.0 mL to each of two sterile petri dishes.

iii) Powders for suspension—Reconstitute the sample according to the label directions using sterile Phosphate Buffer pH 7.2 as the diluent. Shake well and transfer 1.0 mL to each of two sterile petri dishes.

iv) Solutions/Suspensions—Transfer 1.0 mL to each of two sterile petri dishes.

v) Tablets—Transfer 4 tablets (hard tablets should first be pulverized with a sterile mortar and pestle) to 20 mL of c) Retesting. For the purpose of confirming a doubtful result by any of the following procedures, a retest may be performed using two and one-half times(minimum) the initial sample size, with appropriate diluent adjustments.

Test for Total Aerobic Microbial Count

1. Prepare the samples to be tested as described. To each plate, add 15-20 mL of sterile TSA which has been melted and cooled to approximately 45° C. Cover each dish, and gently tilt or swirl the dish to mix the sample with the agar and allow the contents to solidify at room temperature. Invert the plates and incubate for 48 to 72 hours at 30°-35° C.

2. Following incubation, examine the plates for growth using a magnification device such as a Quebec Colony Counter, count the number of colonies and calculate the results on a unit basis (per tablet, capsule, mL, gram, etc.) as designated in the materials specification and evaluate for acceptability against the materials specification.

3. Further characterize bacterial contamination by gram stain and microscopic morphology. Subject gram-negative bacteria and gram-positive cocci to biochemical testing (or alternate suitable means of identification).

Note: When counting colonies, in order to facilitate differentiation of colonial growth from the material being tested, it is at times advisable to use a 2% solution of 2,3,5-triphenyltetrazolium chloride (TTC) as an enhancing agent for observing microbial growth. TTC is a colorless oxidation-reduction indicator that turns red when it is hydrogenated by reducing sugars found in living cells, thereby turning the colony a deep-red color. To use TTC, flood the Petri plate with approximately 1 mL of the 2% solution, and incubate the plate at 30°-35° C. for approximately 2 hours. Microbial colonies will stand out sharply from other material present on the plate and can be more easily counted.

C. Test for Total Combined Molds and Yeasts Count. 1. Prepare the samples to be tested as described. To each plate, add 15-20 mL of sterile SDA which has been melted and cooled to approximately 45° C. Cover each dish, and gently tilt or swirl the dish to mix the sample with the agar and allow the contents to solidify at room temperature. Invert the plates and incubate for 5 to 7 days at 20°-25° C. [NOTE: Do not disturb the plates during incubation, because the dispersal of mold within the plate could yield a higher count than actually present.]

2. Following incubation, examine the plates for growth using a magnification device such as a Quebec Colony Counter, count the number of colonies and calculate the results on a unit basis (per tablet, capsule, mL, gram, etc.) as designated in the materials specification and evaluate for acceptability against the materials specification.

3. Further characterize fungal contamination by macroscopic and microscopic morphology. Where appropriate, subject yeasts to biochemical testing (or alternate suitable means of identification).

Procedure for Testing Absence of Objectionable Organisms a) Sample Preparation—Unless otherwise directed by the Specific Method, prepare the sample for testing as described above in Sample Preparation section for the Total Aerobic and Total Combined Molds and Yeasts. Refer to the appropriate section below for additional information depending on which test is being performed.

b) Membrane Filtration—As an alternative to preenrichment procedures, a suitable, validated membrane filtration test procedure may be used. This may be especially useful for products containing inhibitory substances.

c) Retesting—For the purpose of confirming a doubtful result by any of the following procedures, a retest may be performed using two and one-half times (minimum) the initial sample size, with appropriate diluent adjustments.

B. Test for Absence of *Staphylococcus aureus* and *Pseudomonas aeruginosa*. To the sample add TSB to make 100 mL, mix and incubate for 24-48 hours at 30°-35° C. Examine the medium for growth, and if present, using an inoculating loop, streak a portion to a selective medium, incubate and examine for the characteristics listed below (commercially available identification kits may be substituted for the individual reaction tests):

Characteristics of *Staphylococcus aureus*:

| Medium: | Vogel-Johnson | Mannitol-Salt | Baird-Parker |
|---|---|---|---|
| Morphology: | black colonies surrounded by yellow zones | yellow colonies with yellow zones | black, shiny colonies surrounded by clear zones 2-5 mm |
| Coagulase Test*: | Positive | positive | positive |
| Gram Stain: | positive cocci (clusters) | positive cocci (clusters) | positive cocci (clusters |

*Transfer representative suspect colonies from the selective agar to individual tubes containing 0.5 mL mammalian (preferably rabbit or horse) plasma, incubate at 37° C., examine at 3-4 hours and subsequently at suitable intervals up to 24 hours for coagulation.

Characteristics of *Pseudomonas aeruginosa*

| Medium: | Centrimide: | PSF* | PSP* |
|---|---|---|---|
| Morphology: | Greenish | colorless to yellowish | greenish |
| Fluorescence in UV light: | Greenish | yellowish | blue |
| Oxidase**: | Positive | positive | positive |
| Gram Stain: | negative rods | negative rods | negative rods |

*For the Pigment test, streak representative suspect colonies from the Centrimide Agar to PSF dishes and PSP dishes. Cover and incubate at 35° ± 2° C. for a minimum three days. Examine the plates under UV light.
**For the Oxidase test, confirm any suspect colonies by transferring to strips or dishes impregnated with N,N-dimethyl-p-phenylenediamine dihydrochloride; if there is no development of a pink color changing to purple, the sample meets the requirements for the absence of *Pseudomonas aeruginosa*. Note that commercially available test kits which have been demonstrated to perform in an acceptable fashion may also be used.

If no growth is observed, or if none of the colonies found conform to the set of characteristics listed in the tables above, the sample meets the requirements of the test for absence of that organism.

Test for Absence of *Salmonella* Species and *Escherichia coli*

Transfer the sample to a sterile container to contain a total 100 mL of Fluid Lactose Medium and incubate at 30°-35° C. for 24-48 hours. Gently shake and examine for growth. (Commercially available identification kits may be substituted for the individual reaction tests.) a) *Salmonella*—If growth is present in the Fluid Lactose Medium:

1. Transfer 1.0 mL portions to 10 mL tubes of Fluid Selenite-Cystine Medium and Fluid Tetrathionate Medium, mix and incubate at 30°-35° C. for 24-48 hours.

2. By means of an inoculating loop, streak portions from both media onto Brilliant Green Agar Medium, Xylose-Lysine-Desoxycholate Agar Medium, and Bismuth Sulfite Agar Medium. Cover, invert, and incubate at 30°-35° C. for 24-48 hours and examine for the morphological characteristics listed below:

| Characteristics of *Salmonella* | | | |
|---|---|---|---|
| Medium: | Brilliant Green | Xylose-Lysine-Desoxycholate | Bismuth Sulfite |
| Morphology: | small, transparent, colorless or pink to white opaque (frequently surrounded by pink to red zone) | red, with or without black centers | black or green |

3. Further identification may be conducted by transferring suspect colonies to a buttslant tube of Triple-sugar-Iron-Agar Medium by first streaking the surface of the slant and then stabbing the wire well beneath the surface. Incubate at 30°-35° C. for 24-48 hours and examine. If no tubes show evidence of alkaline (red) slants and acid(yellow) butts (with or without concomitant blackening of the butt), the sample meets the requirements of the test for the absence of the genus *Salmonella*.

b) *Escherichia coli*—If growth is present in the Fluid Lactose Medium: 1. By means of an inoculating loop, streak a portion to MacConkey Agar Medium. Cover, invert, and incubate at 30°-35° C. for 24-48 hours.

2. If none of the resultant colonies displays a brick-red appearance (with a possible surrounding zone of precipitated bile) and are gram negative rods (Cocco-Bacilli), the sample meets the requirements of the test for the absence of *Escherichia coli*.

3. If colonies match this description, transfer them to Levine-Eosin-Methylene Blue Agar Medium. Cover the dishes, invert and incubate at 30°-35° C. for 24-48 hours. If none of the colonies exhibits both a characteristic metallic sheen under reflected light and a blue-black appearance under transmitted light, the sample meets the requirements of the test for the absence of *Escherichia coli*.

Media Formulae

1. Phosphate Buffer pH 7.2
   a) Stock Solution: Monobasic Potassium Phosphate 34.0 g; Water (distilled or deionized) 1000 mL; Sodium Hydroxide TS 175 mL. Dissolve 34 grams of Monobasic Potassium; Phosphate in about 500 mL of water contained in a 1000-mL volumetric flask. Adjust to pH 7.1-7.3 by the addition of Sodium Hydroxide TS (about 175 mL), add water to volume and mix. Sterilize and store under refrigeration (2°-8° C.) until use.
   b) Working Solution. For use, dilute the stock solution with water at a ratio of 1 to 800 and sterilize.
2. TSA (Trypticase Soy Agar/Soybean-Casein Digest Agar). Pancreatic Digest of Casein 15.0 g; Papaic Digest of Soybean Meal 5.0 g; Sodium Chloride 5.0 g; Agar 15.0 g; Water 1000 mL; pH after sterilization: 7.3±0.2.
3. TSB (Trypticase Soy Broth/Soybean-Casein Digest Broth). Pancreatic Digest of Casein 17.0 g; Papaic Digest of Soybean Meal 5.0 g; Sodium Chloride 5.0 g; Dibasic Potassium Phosphate 2.5 g; Dextrose 2.5 g; Water 1000 mL; pH after sterilization: 7.3±0.2; 4. SDA (Sabouraud Dextrose Agar); Dextrose 40 g; Mixture of equal parts of Peptic Digest of animal tissue and pancreatic digest of Casein 10.0 g; Agar 15.0 g; Water 1000 mL; Mix and boil to effect solution; pH after sterilization: 5.6±0.2.
5. FLM (Fluid Lactose Medium). Beef Extract 3.0 g; Pancreatic Digest of Gelatin 5.0 g; Lactose 5.0 g; Water 1000 mL; Cool as quickly as possible after sterilization. pH after sterilization: 7.1±0.2.

Example 50—Isoelectric Focusing Gel Analysis of CTLA4-Ig

The purpose of this example is to determine the isoelectric point, number of isoforms, and micro heterogeneity of CTLA4-Ig.

Materials

IEF Calibration Kit (pH 3 to 10), (Amersham Pharmacia, Catalog No. 17-0471-01) or (pH 2.5 to 6.5), (Amersham Pharmacia, Catalog No. 17-0472-01).
Ampholine PAGplate gel: pH 4.0 to 6.5, (Amersham Pharmacia, Catalog No. 80-1124-81).
IEF Sample Applicators, (Amersham Pharmacia, Catalog No. 80-1129-46).
IEF Electrode Strips, (Amersham Pharmacia, Catalog No. 80-1104-40).
Phosphoric Acid (85%), (EMD, Catalog No. PX0995-6).

Equipment

Multiphor II Electrophoresis System, (GE Healthcare, Catalog No. 18-1018-06).

Preparation of Reagents

Anode Buffer Solution (0.1 M Glutamic Acid in 0.5 M Phosphoric Acid) (wicks soaked with this are placed on the (+) side of the slab).

Example:
3.4 mL 85% Phosphoric Acid.
1.47 g±0.02 g Glutamic Acid.
HPLC Grade water.
Combine above reagents in a 100 mL graduated cylinder, bring to 100 mL with HPLC Grade water, cap and invert several times to mix.
Store solution at 2-8° C. for up to six months.
Cathode Buffer Solution (0.1 M β-Alanine) (wicks soaked with this are placed on the (−) side of the slab).

Example:
0.9 g±0.02 g β-Alanine.
HPLC Grade water.
Combine above reagents in a 100 mL graduated cylinder, bring to 100 mL with HPLC Grade water, cap and invert several times to mix.
Store solution at 2-8° C. for six months.
Fixing Solution (3.5% 5-Sulfosalicylic Acid in 12% Trichloroacetic acid).

Example:
240 g±5.0 g Trichloroacetic Acid.
70 g±2.0 g 5-Sulfosalicylic Acid.
2000 mL HPLC water.
Combine above reagents to make up to 2000 mL volume.
Store solution at room temperature for up to three months.

Staining Solution:
Mix the GelCode Blue Reagent solution immediately before use by gently inverting and swirling the bottle several times.
Note: It is important to mix stain reagent before pouring or dispensing to ensure that a homogeneous sample of reagent is used.

Staining Control Preparation:
Reconstitute the Carbonic Anhydrase II with HPLC Grade water to make 1.0 mg/mL stock solution.
10 µL of stock solution is combined with 90 µL of HPLC Grade water to get a 0.10 µg/µL working solution.
Load 10 µL of the 0.10 µg/µL solution on the gel (1.0 µg load).

Procedure

Sample Dilution

Prepare a 20 µg/10 µL solution of sample and reference material in HPLC water.

$$\frac{\text{Desired concentration (2 µg/µL)}}{\text{Sample concentration (50 µg/µL)}} \times 200 \text{ µL} =$$

µl of sample added to a 200 µl final volume

Example: $\frac{2 \text{ µg/µL}}{50 \text{ µg/µL}} \times 200 \text{ µL} =$ $0.04 \times 200$ µl = 8 µl sample (add 192 µl *HPLC* water)

Apparatus and Gel Preparation

Connect the Multiphore II electrophoresis unit's cooling plate to the Thermostatic Circulator and set the temperature at 10±2° C.

Note: Allow circulator at least 20 minutes to reach the above temperature.

Remove the gel from the refrigerator. Carefully cut along the sides of the envelope making sure not to cut the gel/gel support.

Add approximately 1.0 mL: HPLC Grade water to one edge of the cooling platform.

Place one edge of the gel/gel support into the water so the capillary action carries the water across the entire edge of the gel. Slowly, making sure air bubbles are not trapped, apply the gel across the cooling platform. Additional HPLC Grade water may be applied if needed.

Remove transparent film from the gel surface.

Soak one electrode with Anode Buffer Solution and place on the edge of the gel nearest the (+) markings of the cooling platform.

Soak one electrode in the Cathode Buffer Solution and place on the other side of the gel, which is nearest the (−) markings on the cooling plate.

After the electrode strips have been applied, carefully cut the excess using a new razor blade, so that the strips end at the edge of the gel, and not the gel support.

Apply sample application pieces on the side nearest the (−) markings on the cooling platform, making sure there is good contact between the sample application pieces and the gel. Note: Make sure the IEF sample applicators do not touch the cathode buffer soaked strip, do not wick up cathode buffer, and are sufficiently separated to assure each sample runs separately. The sample applicators should be firmly placed on the slab gel.

Place the electrode holder of the Multiphor II unit and align the electrodes along the center of the electrode strips on the gel. Connect the two electrodes from the electrode holder to the base unit and place the safety lid in position. Using adhesive tape, cover the holes in the safety lid to prevent the gel from drying. Connect the electrodes to the power supply.

Prefocus the gel with the power supply set at the settings below, until the voltage reaches ≥300 V.

TABLE 1

Power supply settings to prefocus IEF gels.

| Run Parameters | Setting |
| --- | --- |
| Voltage (variable parameter) | 2000 volts maximum |
| Current (constant parameter) | 25 mAmps |
| Power (constant parameter) | 25 watts |

Gel Loading

After the gel has been prefocused, turn off the power supply, remove the safety lid, disconnect the electrodes and remove the electrode holder from the Multiphor II unit.

Load samples onto the sample applicators in a specific sequence. For this procedure, make sure the (−) cathode buffer strip side is closest to the analyst. Samples are loaded from right to left. First make two or more applications of the IEF calibration standards (lanes 1 & 2), one of the reference material (lane 3), one of the test sample #1 (lane 4), one of the staining control preparation (lane 5), one of test sample #2 (lane 6), one of the reference material (lane 7) and one of the IEF calibration standard (lane 8).

Add the third and fourth sample by applying one application of reference material (lane 9), one application of test sample #3 (lane 10), one application of the staining control reparation (lane 11), one application of test sample #4 (lane 12), one application of reference material (lane 13) and one application of IEF calibration standard (lane 14). The fifth and sixth samples are applied by repeating the same pattern as samples 3 and 4, using lanes 15 to 20. Sample loading pattern is shown in Table 2.

TABLE 2

Sample Dilution and Gel Loading Pattern

| Lane | Description | Working Concentration (µg/µL) | Loading Volume (µL) | Protein Load (µg) |
| --- | --- | --- | --- | --- |
| 1 | IEF pI Marker* | — | 10 | — |
| 2 | IEF pI Marker | — | 10 | — |
| 3 | Reference Material | 2.0 | 10 | 20 |
| 4 | Sample 1 | 2.0 | 10 | 20 |
| 5 | Staining Control | 0.10 | 10 | 1.0 |
| 6 | Sample 2 | 2.0 | 10 | 20 |
| 7 | Reference Material | 2.0 | 10 | 20 |
| 8 | IEF pI Marker | — | 10 | — |
| 9 | Reference material | 2.0 | 10 | 20 |
| 10 | Sample 3 | 2.0 | 10 | 20 |
| 11 | Staining Control | 0.10 | 10 | 1.0 |
| 12 | Sample 4 | 2.0 | 10 | 20 |
| 13 | Reference Material | 2.0 | 10 | 20 |
| 14 | IEF pI Marker | — | 10 | — |
| 15 | Reference Material | 2.0 | 10 | 20 |
| 16 | Sample 5 | 2.0 | 10 | 20 |
| 17 | Staining Control | 0.10 | 10 | 1.0 |
| 18 | Sample 6 | 2.0 | 10 | 20 |
| 19 | Reference Material | 2.0 | 10 | 20 |
| 20 | IEF pI Marker | — | 10 | — |

Electrophoresis. When the gel is loaded, place the electrode holder of the Multiphor II unit and align the electrodes along the center of the electrode strips on the gel. Connect the two electrodes from the electrode holder to the base unit and place the safety lid in position. Using adhesive tape, cover the holes in the safety lid to prevent the gel from drying. Connect the electrodes to the power supply. Set appropriate voltage, current and power settings and begin the run.

TABLE 3

Power supply settings to run the IEF gels.

| Run Parameters | Setting |
| --- | --- |
| Voltage (variable parameter) | 2000 volts maximum |
| Current (constant parameter) | 25 mAmps |
| Power (constant parameter) | 25 watts |
| Time (constant parameter) | 2.5 hours |

After the gel has been run, turn off the power supply, remove the safety lid, disconnect the electrodes, and remove the electrode holder from the Multiphor II unit. Carefully remove the electrode strips and the sample applicators from the gel.

Note: You can place the slab gel directly in the fixing solution and let the electrode strips and application pieces float off the gel.

Remove the gel/gel support from the cooling plate and place in a flat dish containing a sufficient volume of fixing solution (step 3.3) to keep the gel wet. Cover with plastic wrap and put on an orbital platform and incubate 20-60 minutes. Record start and stop time on the IEF worksheet.

NOTE: IEF gels left in fixative too long sometimes delaminate. This is avoided by limiting the fix time to approximately one hour. 4.5 Staining the gel.

After fixing, rinse the gel 3×5 minutes with a sufficient volume of HPLC Grade water to keep the gel wet. Record start and stop times on the IEF worksheet.

After mixing the GelCode Blue Stain Reagent solution before using (step 3.4), place the gel in a sufficient volume of the stain to keep the gel wet. Incubate 15-24 hours in a tightly sealed container, to prevent reagent evaporation. Record start and stop times on the IEF worksheet.

Stained gels are destained by replacing Stain Solution with HPLC Grade water. Rinse the gel at least three water changes over a 1-2 hour period. Record start and stop times on the IEF worksheet. After destaining, the gel is ready for scanning.

Note: Additional washes may be required to reduce background staining on the IEF gel.

System Suitability

Isoelectric focusing standards should be easily distinguished from background. Protein standards that migrate to pI values between 4.0 and 6.5 are visible on the gel. Protein standards with pIs that are outside this range are not visible on the gel. The pI markers at 3.50, 4.55, 5.20, and 5.85 are identified and labeled on the gel image.

TABLE 4

Components of the IEF calibration standards.

| Protein Standard | pI |
|---|---|
| Trypsinogen | 9.30 |
| Lentil Lectin basic band | 8.65 |
| Lentil Lectin middle band | 8.45 |
| Lentil Lectin acidic band | 8.15 |
| Myoglobin basic band | 7.35 |
| Myoglobin acidic band | 6.85 |
| Human carbonic anhydrase B | 6.55 |
| Bovine carbonic anhydrase B | 5.85 |
| β-Lactoglobulin A | 5.20 |
| Soybean Trypsin Inhibitor | 4.55 |
| Amylogucoside | 3.50 |

A staining control of carbonic anhydrase II standard (pI 5.4) at a low level of protein loading (1.0 µg) is used for visualization of gel staining consistency. This band must be easily distinguished from the background by visual inspection of the scanned gel image.

The CTLA4-Ig reference material should be enumerated at 10-22 bands within the pI range of 4.3 to 5.6.

The cumulative percent intensity of the most prominent bands of CTLA4-Ig reference material should be ≥90% within the pI range of 4.3 to 5.3.

For reference material, confirm by visual inspection that there are three major bands focused between the pI markers 4.5-5.2 (see Figure for the major bands pattern).

Gel Scanning and Analysis

After electrophoresis and staining, all the gels are scanned using a densitometer. The image files are stored on the computer local hard drive/network and archived via the local area network. The analysis of scanned gel images is performed using ImageQuant TL software (v2003.03). The scanning and analysis parameters are listed in Table 5. Scans are generated and quantitated using departmental procedures.

TABLE 5

Gel Scanning and Analysis Parameters

| | Setting |
|---|---|
| Scan Parameters | |
| Scan Pixel Size | 100 |
| Scan Digital Resolution | 12 bits |
| Band Detection Parameters | |
| Minimum Slope | Initial 100 |
| Noise Reduction | Initial 10 |
| % Maximum Peak | Initial 0 |
| Lane % width | Set at 90% |

Note: The above procedures provide basic steps for the analysis of gel images. The scanparameters in table are defined. The band detection parameters in table are suggested initial settings. Adjustment of the band detection parameters may be necessary to accurately identify bands due to physical property changes of gel (such as gel shrinkage after staining/destaining) and alteration of gel band shape and shifting. Manually correct any missed or misidentified bands.

Scan the gels using the scan parameters defined in Table. All analysis and assessments of the gel are made from the scanned image. Open a gel image file (scanned raw data) from ≤1D Gel Analysis> in ImageQuantTL. Go to <Contrast> on toolbar and lower the <Image Histogram> parameter until all bands are clearly visible. Select <Lane Creation> and choose <Manual> to set up <Number of Lanes> to be analyzed. Adjust <Lane % Width> up to 100% to cover the gel lanes. Properly align single lanes if necessary. Use <Rolling Ball> method to subtract background. Detect bands using the initial <Minimum Slope>, <Noise Reduction>, <% Maximum Peak> settings listed in Table 3. Adjustment of these values is necessary to accurately identify bands. Compute band pI value by using the standard pI marker from the labeled markers listed in the System Suitability Section for the pH/pI 4.0-6.5 gel. Skip the calibration and normalization steps. Enumerate the number of bands within the 4.3 to 5.6 pI range. Export the results into Excel sheet for further documentation and reporting. Calculation of Cumulative Percent Intensity of Samples Relative to Reference Material. Note: The cumulative percent intensity for a sample is the percentage of bands that migrate within the pI range of 4.3-5.3, as compared to 100% of all bands present in the lane. The following equation should be used for the calculation of cumulative percent intensity of samples relative to reference material:

$$\text{Sample Relative Percent (\%)} = \frac{\text{Sample \% Band Intensity } (pI\ 4.3 - 5.3)}{\text{Reference \% Band Intensity } (pI\ 4.3 - 5.3)} \times 100$$

Note: Refer to the gel loading pattern, the reference material next to the sample should be used for the calculation. If the reference material has a cumulative value of 100%, and the sample has a 95% value, the sample relative percent is 95/100*100=95%. If the reference has a cumulative value of 95%, and the sample has a 100% value, the sample relative percent is 100/95*100=105%.

Reporting Results

Report the number of bands enumerated within pI of range 4.3-5.6. Report the cumulative percent intensity relative to that of CTLA4-Ig reference material within the pI range of 4.3-5.3 (see Figure for an example of the report for the quantitative IEF gel analysis defined in this method). Confirm by visual inspection that there are three major bands focused between the pI markers 4.5-5.2 relative to reference material (see FIG. 1 for the major bands pattern) and report number of major bands observed within pI markers 4.5-5.2. Confirm by visual inspection that there are no new significant bands between pI makers 4.5-5.2 relative to reference material.

In certain embodiments, the results of this method will show bands in a pI range of from 4.3-5.6, or 4.3-5.3, with there being identified from 10 to 22 bands, with the cumulative band intensity from 90-110%. In another embodiment, the pI range is from 4.5-5.2 with 3 major bands. In another embodiment, the pI range is 4.3-5.6 with 10 to 22 bands. In another embodiment, the pI range is 4.3-5.3 with a cumulative band intensity of from 95-105%. In another embodiment, the pI range is from 4.5-5.2 with 2 prominent bands.

Example 51: SDS-PAGE of CTLA4-Ig

The example shows the examination of CTLA4-Ig under both reduced and non-reduced conditions by SDS-PAGE.
Materials
Tris-Glysine (Tris-Gly) SDS sample buffer 2× (Invitrogen, Catalog No. LC2676).
NuPAGE "Sample Reducing Agent 10× (Invitrogen, Catalog No. NP0004).
4-20% Tris-Glycine Gel—1.0 mm×12 wells (Invitrogen, Catalog No. EC60252BOX).
Tris-Glycine SDS Running Buffer 10× (Invitrogen, Catalog No. LC2675).
Mark12™ Wide-Range Unstained Standard (Invitrogen, Catalog No. LC5677).
GelCode Blue Stain Reagent (Coomassie Blue), (Pierce, Catalog No. 24590: 500 mL Catalog No. 24592: 3.5 L).
SilverSnap® Stain Kit II (silver stain) (Pierce, Catalog No. 24612).
Instrumentation:
Xcell SureLock Mini Cell (Invitrogen, Catalog No. EI0001).
Power supply for electrophoresis (OWL Separation Systems, Catalog No. OSP-300).
Reagents:
Fixing solution for Coomassie Blue Stain (50% Methanol and 7% Acetic Acid in HPLC Grade water).
Example:
To an appropriately sized, graduated container containing a stir bar:
Add 500 mL of Methanol.
Add 70 mL Acetic Acid.
Adjust volume to 1000 mL with HPLC Grade water.
Store at room temperature for up to six months.
Coomassie Blue Stain (GelCode Blue).
Use straight from container. Add sufficient amount to cover the gel, approximately 50 mL for one mini gel (10×10 cm) in a small tray.
Store at 2-8o C for up to one year.
Silver Stain Fixing Solution (30% Ethanol and 10% Acetic Acid in HPLC Grade water).
To an appropriately sized, graduated container containing a stir bar: Add 300 mL Ethanol. Add 100 mL Acetic Acid. Adjust volume to 1000 mL with HPLC Grade water. Mix solution and store solution at room temperature for up to six months. Gel Wash Solution (10% Ethanol).
To a 50 mL centrifuge tube: Add 1.0 mL Enhancer (Silver Stain Kit). Add 50 mL Silver Stain (Silver Stain Kit). Cap the tube and mix by gently vortexing for 3 to 5 seconds. Developer Working Solution. Prepare immediately before use.
To a 50 mL centrifuge tube: Add 1 mL Enhancer (Silver Stain Kit). Add 50 mL Developer (Silver Stain Kit). Cap the tube and mix by gently vortexing for 3 to 5 seconds. 1× Tris-Glycine SDS Running Buffer. Prepare on the day of use. To a graduated cylinder: Add 900 mL HPLC Grade water. Add 100 mL Tris-Glycine-SDS 10× Running Buffer. Combine the above reagents cover with parafilm and invert several times to mix.
Staining Control.
Add 1 mL of HPLC Grade water to a vial containing 2 mg Trypsin inhibitor (staining control). This will yield a 2 µg/4 stock solution stable for six months at −200 C. To prevent degradation due to numerous freeze thaw cycles, transfer 50 aliquots into small tubes and store at −200 C. Add 25 µL of stock solution to 75 µL of HPLC Grade water to give a 0.5 µg/µL solution. Add 40 µL of the 0.5 µg/µL solution to 160 µL of HPLC Grade water to give a concentration of 0.1 µg/4. Add 10 µL of the 0.1 µg/µL solution, 50 µL of 2× TrisGly Sample Buffer, and 40 µL of HPLC Grade water to a microcentrifuge tube. The final concentration of the Trypsin inhibitor staining control is 0.01 µg/4. Samples analyzed for release and stained with Coomassie Blue are loaded at a concentration of 10 mg per 10 µL.

For Coomassie Blue gels, dilute the Reference Material and sample in HPLC Grade water to a concentration of 10 µg/µL. Example: Add 80 µL of 50 µg/µL Reference Material sample solution+320 µL of HPLC Grade water. For Non-reduced Samples, add 10 µL of the 10 µg/µL solution concentration to 50 µL of 2× Tris-Gly sample buffer, and 40 µL of HPLC Grade water into a microcentrifuge tube. For the Reduced Samples, add 10 µL of the 10 µg/µL solution, to 50 µL of 2× TrisGly Sample Buffer, 30 µL of HPLC Grade water and 10 µL of 10× Reducing Agent. For Silver Stained Gels, further dilute the 10 µg/µL solution to 1 µg/µL in HPLC Grade water. Example: Add 40 µL of 10 µg/µL solution+360 µL HPLC Grade water. For Non-reduced Samples add 10 µL of the 1 µg/µL solution to 50 µL of 2× TrisGly Sample Buffer, and 40 µL of HPLC Grade water in a microcentrifuge tube. For the Reduced Samples, add 10 µL of the 1 µg/µL solution, 50 µL of 2× TrisGly Sample, 30 µL of HPLC Grade water and 10 µL of 10× Reducing Agent to a microcentrifuge tube. For the Blank, combine 50 µL of 2× TrisGly Sample Buffer and 50 µL of HPLC Grade water in a microcentrifuge tube.

TABLE 6

The Molecular Weight (kDa) range for expected minor protein bands that may be present in reduced and non-reduced abatacept samples

| Band(s) description | Non-Reduced (kDa) | Reduced (kDa) |
| --- | --- | --- |
| Minor Band(s) | NA | 15-45 |
| Minor Band(s) | 30-70 | NA |
| Minor Band(s) | NA | 80-155 |
| Minor Band(s) | 175-230 | 175-200 |

Remove gel(s) from their wrapping and rinse the outside with HPLC Grade water to remove polyacrylamide pieces. Carefully remove the well comb making sure that the wells are straightened with a gel loading tip if necessary. Fill wells with HPLC Grade water and flick so that the water is removed from the wells. Repeat well rinsing two more times. 5.2 Insert gels into the XCell apparatus so that the short plate face faces the inner chamber. If only one gel is being used, insert a plexiglass plate on the opposite side. Wedge the gel(s) tightly forming an inner and outer chamber. Fill the inner chamber with 1× Tris-Glycine SDS Running Buffer. Check for leaks, then fill the outer chamber with 1× Tris-Glycine SDS Running Buffer. All gels must contain at least one Blank lane and one Molecular Weight Marker lane. Add a Staining Control for Coomassie Blue stained gels only. Use gel loading tips. Load at least one "Blank" between reduced and non-reduced samples. Treat the Molecular Weight Markers as reduced sample. This will help prevent reduction of the non-reduced samples due to leaching of reducing agent. Attach the top of the Xcell apparatus and connect the electrodes to the power supply. Adjust the current to 25 mAmps per gel, and set the voltage (v) and power (w) to maximum. If running two gels, set the current to 50 mAmps. Adjust the current when running two gels in one apparatus, or multiple Xcell apparition the same power supply. Electrophorese for 60±5 minutes or until the buffer front moves at least 80% of the available migration distance. Record start time and stop time on the worksheet. Carefully separate the two plastic plates holding the gel by prying with a gel knife. After separation of the gel, follow procedure for staining.

Coomassie Blue Staining

Place the gel in 50 mL of Coomassie Blue Fixing Solution (50% Methanol and 7% Acetic Acid) for 15 minutes. Rinse the gel 3 times with ~100 mL of HPLC Grade water for 5 minutes, for a total of 15 minutes. Add the Coomassie Blue stain directly to the gel(s) and incubate for 15 to 24 hours. Stained gels are destained by replacing the Coomassie Blue Stain reagent with 100 mL of HPLC Grade water. After 1 hour of destaining, the gel is ready for scanning.

Gel Scanning and Analysis.

After electrophoresis and staining, the gels are scanned using a densitometer. The image files are stored on the computer local hard drive and/or network and archived via the local area network. The analysis of scanned gel images is performed using ImageQuant TL software (v2003.03). Scans are generated and quantitated using departmental procedures.

TABLE 4

Gel Scanning and Analysis Parameters

| | Setting |
|---|---|
| Scan Parameters | |
| Scan Pixel Size | 100 |
| Scan Digital Resolution | 12 bits |
| Band Detection Parameters | |
| Minimum Slope | Initial 100 |
| Noise Reduction | Initial 10 |
| % Maximum Peak | Initial 0 |
| Lane % width | Set at 90% |

By visual inspection, the major band of reduced CTLA4-Ig must appear as a broad band that migrates to a position proximal to the 55,400 Da molecular weight marker (Glutamic dehydrogenase).

Example 52—Determination of Chinese Hamster Ovary (Cho) Host Cell Protein Impurities in CTLA4$^{A29YL104E}$-Ig Drug Substance by Elisa This example describes an enzyme-linked immunosorbent assay (ELISA) to quantitate contamination levels of CD-CHO1 residual host cell proteins (HCP) in test samples. A rabbit polyclonal anti-CD CHO1 HCP IgG is first coated on a microtiter plate. HCP reference standards, quality controls and CTLA4$^{A29YL104E}$-Ig drug substance samples are incubated with the bound rabbit anti-CD CHO1 HCP IgG. After washing the microtiter plates, polyclonal rabbit anti-CD CHO1 HCP Biotin IgG antibody is added which binds to the HCP captured during the initial step. The microtiter plates are washed to remove any unbound polyclonal antibodies. Streptavidin-horseradish peroxidase is added and the microtiter plate is again washed to remove any unbound conjugated antibodies. TMB chromogen is then added to yield a colorimetric reaction. The reaction is terminated with sulfuric acid and absorbance is measured at 450 nm in a 96-well microplate reader. Color develops in proportion to the amount of HCP captured. Sample concentrations are determined based on a standard curve generated by plotting the absorbance versus HCP concentration in the range from 4.11 ng/mL to 3000 ng/mL.

The Chinese Hamster Ovary (CHO) cell line (DG44) is used in the production of CTLA4$^{A29YL104E}$-Ig. For the production of CD-CHO1 protein (HCP), DG44 cells were stably transfected with the recombinant vector pD16 and grown in CD-CHO1 medium supplemented with galactose and Recombulin. The polyclonal antibodies for this version of the ELISA were generated in New Zealand white rabbits immunized with a concentrate of the CD-CHO1 HCP material. Rabbit antibodies were affinity purified (Protein A), then dialyzed into phosphate buffered saline and concentrated. Approximately 50 mg of the IgG fraction of rabbit anti-CD-CHO1 antibody was biotinylated using N-hydroxysulfosuccinimide ester chemistry. The unmodified rabbit ant-CHO1 antibody is used to coat 96-well microtiter plates. It captures CD-CHO1 HCP which are detected by the biotinylated rabbit anti-CD-CHO1 antibodies. Streptavidin Horseradish Peroxidase conjugate binds to biotin and a colorimetric reaction with TMB chromogen is used to quantify CD-CHO1 HCP.

This method, shown in FIG. 98, is designed to quantitatively determine residual levels of CD-CHO1 host cell proteins by ELISA for release testing of CTLA4$^{A29YL104E}$-Ig drug substance material.

Rabbit anti-CD-CHO1 antibody is biotinylated using a biotinylation kit with Sulfosuccinimidyl-6 (biotinamido) hexanote as biotinylatiom reagent. The biotinylation reagent from PIERCE (product #21335) with Sulfo-NHS-LC-Biotin can be used. The antibody is labeled according to the manufacturer's recommendations in the manual supplied with the biotinylation reagent. After labeling and separation on the supplied size exclusion column, the biotin incorporation is determined and the sample is frozen in aliquots of 50 μL or smaller at or below −70° C. The biotin/IgG ratio of the final product should be between 2 and 4. Store at or below −70° C.

Plate Coating. Prepare an 8 μg/mL solution of purified rabbit anti-CD-CHO1 HCP IgG in Carbonate Buffer to be used for coating microtiter plates (12 mL of solution is required per microtiter plate). Add 100 μL of this solution to each well of an Immulon 4 microtiter plate using a calibrated multichannel pipettor. Cover the microtiter plate with parafilm and incubate at 4° C. for 18±2 hours.

Plate Washing and Blocking. Wash plate three times with Wash Buffer using plate washer instrument. Add 300 μL SeaBlock to each well using a calibrated multichannel pipettor. Incubate the plate for 1 hour at 22.5±5° C. Prepare concentrations of CD-CHO1 Protein Reference Standards and Quality Control samples in 15 mL graduated sterile polypropylene tubes. Dilute Reference material and Quality Control samples using Teknova Diluent (1.21). Standard concentration are prepared on the day of the experiment at the concentrations listed in the example below:

Dilutions for Standard Curve Samples (Example for Daily Preparation)

Stock concentration of CD-CHO1 protein is 5.7 mg/mL

| Dilution A: | 26.3 μL (5.7 mg/mL) + 4.973 mL PTB Diluent = 30 μg/ml | |
|---|---|---|
| Dilution B: | 0.6 mL (30 μg/mL) + 5.4 mL Diluent | 3000 ng/mL |
| | 2 mL (3000 ng/mL) + 4 mL Diluent | 1000 ng/mL |
| | 2 mL (1000 ng/mL) + 4 mL Diluent | 333.3 ng/mL |
| | 2 mL (333.3 ng/mL) + 4 mL Diluent | 111.1 ng/mL |

| | |
|---|---|
| 2 mL (111.1 ng/mL) + 4 mL Diluent | 37.0 ng/mL |
| 2 mL (37.0 ng/mL) + 4 mL Diluent | 12.3 ng/mL |
| 2 mL (12.3 ng/mL) + 4 mL Diluent | 4.11 ng/mL |
| 0 + 4 mL Diluent | 0 ng/mL |

QC Concentration Analysis, Storage, and Expiration

Quality Control (QC) samples at three different target concentrations (25, 100, and 700 ng/mL) are prepared and used fresh on the day of analysis or prepared in larger amounts and stored frozen in aliquots at or below −70° C. Frozen aliquots are analyzed in three independent experiments. The average result from the three experiments is reported in a Certificate of Analysis (COA) for each of the three QC samples. On the day of the experiment, frozen QC samples are thawed and analyzed as described below. After thawing each QC sample is vortexed at medium speed 2-4 seconds. Frozen QC samples expire 6 months after preparation date. They are used at their nominal concentration reported on the COA. Freshly prepared QC expires 24 hours after preparation.

Dilutions for Quality Control (QC) Samples (Example)

Dilution A: 26.3 µL (5.7 mg/mL)+4.973 mL Diluent=30 µg/mL
233 µL (30 µg/mL)+9.767 mL Diluent=700 ng/mL (QC 1)
1.43 mL (700 ng/mL)+8.57 mL Diluent=100 ng/mL (QC 2)
2.5 mL (100 ng/mL)+7.5 mL Diluent=25 ng/mL (QC 3)
Sample Preparation. Dilute drug substance samples to approximately 12.5, 6.25, and 3.125 mg/mL.
Dilution A: 400 µL sample (−25 mg/mL)+400 µL Diluent=12.5 mg/mL
Dilution B: 400 µL (−12.5 mg/mL)+400 µL Diluent=6.25 mg/mL
Dilution C: 400 µL (−6.25 mg/mL)+400 µL Diluent=3.125 mg/mL
Plate Washing. Wash plates three times with Wash Buffer using plate washer. Add 100 µL per well of each standard concentration, samples and QC samples in triplicate to the blocked and washed plate. Each QC concentration is added twice to a total of six wells per plate. See plate map in the Method Attachment for suggested placement. Incubate for 1 hour at 22.5±5° C. Repeat step washing 5 times. Dilute rabbit anti-CD-CHO1 HCP Biotin to 2 µg/mL in Teknova Buffer. Vortex the solution approximately 2-4 seconds at medium speed. Add 100 µL per well. Incubate for 1 hour at 22.5±5° C. Repeat step washing 5 times. Dilute Streptavidin-HRP (SA-HRP) appropriately in Teknova buffer (example: a 1/20,000 dilution usually results in acceptable absorbance readings). Add 100 µL of SA-HRP dilution to each well and incubate at 22.5±5° C. for 1 hour. Remove the TMB chromogen from refrigerator and decant a minimum of 10 mL per plate into a suitable container. Place in a dark location and allow to come to room temperature. Repeat step washing 5 times. Add 100 µL of TMB chromogen to each well and incubate at 22.5±5° C. for approximately 2 minutes. Stop chromogen reaction by adding 100 µL of 1 N $H_2SO_4$ to each well. Add Stop Solution in the same order to plates and wells as the chromogen was added to ensure the same reaction times of chromogen with the enzyme in each well. Measure absorbance at 450 nm with a reference wavelength of 630 nm on an appropriate 96 well plate reader.

DATA ANALYSIS. The Softmax program template "CHO1 Elisa template.ppr" is set up to generate mean values, standard deviations, % CVs, calculated concentrations, curve fit parameters, etc. Standard Curve. Reference standard data are fitted to a standard curve using a four-parameter curve fit function:

$$Y=((A-D)/(1+(X/C^{\wedge}B))+D$$

Where:

Y=absorbance value ($A_{450}-A_{630}$)

A=absorbance value corresponding to the minimum asymptote

D=absorbance value corresponding to the maximum asymptote

C=absorbance corresponding to one half the absolute difference between the maximum and minimum asymptote values (inflection point).

B=the slope at the inflection point of the curve

X=concentration of CD-CHO1 HCP

The Softmax program template "CHO1 Elisa template.ppr" determines the correlation coefficient ($R^2$) of the regression line for the standards using the calculated mean.

EXEMPLARY VALUES. Determine if the results for Standards, QC, and samples meet the exemplary values listed below. Exemplary values for the Standards. The correlation coefficient ($R^2$) for the Standard Curve must be ≥0.99. The mean background for the zero ng/mL standard concentration must be ≤0.2 absorbance units. If two or more of the seven nominal concentrations of the Standard Curve, excluding zero and concentrations below the QL (12.3 ng/mL), do not meet conditions 6.1.4 and 6.1.5, the assay is considered invalid and must be repeated. The mean of the calculated values (ng/mL) at each standard concentration used to determine the Standard Curve, excluding zero and concentrations below the QL (12.3 ng/mL), must be within 20% of the target (nominal) value. The coefficient of variation (% CV) of the triplicate absorbance values at each Standard concentration, excluding zero and concentrations below the QL (12.3 ng/mL), must be less than 20%. To ensure that at least two congruent data points are available for calculation; the standards, quality controls and samples are loaded in triplicate wells. Analyze each triplicate value separately. Drop the value that lies furthest from the target. Recalculate the curve and reanalyze the exemplary values.

Example:

| Target Value (ng/mL) | Actual Value (ng/mL) |
|---|---|
| 25 | 12 |
|  | 24 |
|  | 26 |

The single value that is furthest from the target value of 25 ng/mL is 12 ng/mL. By eliminating the 12 ng/mL value from the triplicate, the mean of the remaining values meet all of the exemplary values. If it is shown that the mean of the remaining two values still do not meet the exemplary values, then the single point is eliminated and the curve is recalculated.

Example:

| Target Value (ng/mL) | Actual Value (ng/mL) |
|---|---|
| 25 | 5.0 |
|  | 5.5 |
|  | 10 |

The mean value is ≥20% from the target regardless of which value is eliminated, therefore, the single point is dropped from the curve and the curve will be recalculated.

Exemplary values for QC Samples. A QC sample is a set of six wells at the stated concentration. At least four of the six wells for a QC sample must be within 20% of the nominal for the QC sample to be acceptable. All three QC samples must be acceptable. If these exemplary values are not met, the assay must be repeated.

Exemplary values for Test Samples. The absorbance value for the test sample assayed must be less than the highest QC. If the value exceeds that of the highest QC, the test sample must be diluted sufficiently so as to obtain a mean value between 700 and 12.3 ng/mL. At least one of the three sample dilutions (12.5, 6.25, and 3.125 mg/mL) must fall within the range of the standard curve for a reportable result, unless the absorbance for all dilutions are below the QL of the assay. In that case the test samples are reported as <QL. The mean of the triplicate absorbance values of the sample dilutions that are greater than the QL and fall within the range of the assay should exhibit a CV of less than 20%.

CALCULATION AND REPORTING RESULTS OF CD-CHO1 HCP CONCENTRATION IN SAMPLES. Calculation of CD-CHO1 HCP concentration in samples. Multiply the mean sample results by the appropriate dilution factor (i.e. 2, 4, and 8) to obtain the concentration of CD CHO1 HCP in the undiluted sample in ng/mL for each of the dilutions. Determine the mean for results of those dilutions that fall within the range of the assay. Divide the result from by the reported CTLA4$^{A29YL104E}$-Ig protein concentration (mg/mL) to obtain the concentration of CD $C_H$01 HCP in ng/mg of CTLA4$^{A29YL104E}$-Ig.

Example Calculation:
Mean sample result: 235 ng CD-CHO1 HCP/mL=9.4 ng/mg
Protein Conc.: 25.0 mg/mL
NOTE: ng CD-CHO1 HCP/mg product (ng/mg) is equivalent to parts per million (ppm).

Example 53: Determination of Protein A Levels in CTLA4$^{A29YL104E}$-Ig by ELISA This enzyme-linked immunosorbant assay (ELISA) quantitates contamination levels of Protein A in CTLA4$^{A29YL104E}$-Ig test samples. Rabbit anti-Protein A is first coated on a microtiter plate. Protein A reference standards, quality controls, recovery controls, and CTLA4$^{A29YL104E}$-Ig samples are incubated with the bound rabbit anti-Protein A IgG. After washing the microtiter plates, biotinylated monoclonal anti-rabbit Protein A IgG antibody is added which binds to the Protein A captured during the initial step. The microtiter plates are washed to remove any unbound monoclonal antibodies. Streptavidin-horseradish peroxidase is then added after one hour of incubation; the microtiter plate is again washed to remove any unbound conjugated antibodies. TMB chromogen is then added to yield a colorimetric reaction. The reaction is terminated with sulfuric acid and optical densities are measured at 450 nm in a 96-well microplate reader. Color develops in proportion to the amount of Protein A captured. Sample concentrations are determined based on a standard curve generated by plotting the optical density versus Protein A concentration in the range from 0.188 ng/mL to 12 ng/mL. A method outline is shown in FIG. 99.

Plate Coating with Capture Antibody. Prepare a 1 µg/mL solution of rabbit anti-Protein A antibody in Coating Buffer and add 100 µL of the solution to each well of an Costar microtiter plate. Incubate at 4° C. for 18±2 hours.

Plate Washing and Blocking. Wash plates three times with Wash solution using the plate washer. Add 200 µL of SUPERBLOCK™ to each well. Incubate the microtiter plate for 60 minutes at ambient temperature. Preparation of Reference Standard Prepare Reference Standard by mixing the appropriate amount of Protein A Reference Material into the appropriate volume of acetate buffer. Vortex solution at medium speed for 2-4 seconds. Incubate Reference Standard, Quality Control, and Recovery Control samples for 10 minutes at ambient temperature before addition to microtiter plate.

Example: Reference Material Protein A, stock concentration 2.3 mg/mL
1:200 10 µL (2.3 mg/mL)+1990 µL (Acetate Buffer)=11500 ng/mL
1:479 10 µL (11500 ng/mL)+4780 µL (Acetate Buffer)=24 ng/mL
2 mL (24 ng/mL)+2 mL (Acetate Buffer)=12 ng/mL
2 mL (12 ng/mL)+2 mL (Acetate Buffer)=6 ng/mL
2 mL (6 ng/mL)+2 mL (Acetate Buffer)=3 ng/mL
2 mL (3 ng/mL)+2 mL (Acetate Buffer)=1.5 ng/mL
2 mL (1.5 ng/mL)+2 mL (Acetate Buffer)=0.75 ng/mL
2 mL (0.75 ng/mL)+2 mL (Acetate Buffer)=0.375 ng/mL
2 mL (0.375 ng/mL)+2 mL (Acetate Buffer)=0.188 ng/mL
0 mL+2 mL (Acetate Buffer)=0 ng/mL Each standard concentration is analyzed in triplicate. Place samples on microtiter plate as described in the method attachment. Preparation of the Quality Control Samples. Quality Control (QC) samples of Protein A are prepared in acetate buffer at three target concentration levels of 0.5, 2, and 5 ng/mL. They are either prepared fresh on the day of the experiment or in larger quantities and frozen in 750 µL aliquots at ≤-70° C. The Protein A concentrations in the frozen QC samples are pre-determined in three independent Protein A ELISA experiments using this method and the average concentration results are reported as the "nominal" QC concentrations in a Certificate of Analysis for each QC sample.

On the day of an experiment, thaw one vial each of the three QC samples at room temperature. Analyze each QC concentration twice (in two triplicate analyses per concentration). Place QC samples on microtiter plate as described in the method attachment.

Reference Material Protein A, 2.3 mg/mL
1:200 10 µL (2.3 mg/mL)+1990 µL (Acetate Buffer)=11500 ng/mL
1:479 10 µL (11500 ng/mL)+4780 µL (Acetate Buffer)=24 ng/mL
833.3 µL (24 ng/mL)+3.166 mL (Acetate Buffer)=5 ng/mL (QC1)
1.600 mL (5 ng/mL)+2.4 mL (Acetate Buffer)=2 ng/mL (QC2)
1 mL (2 ng/mL)+3 mL (Acetate Buffer)=0.5 ng/mL (QC3)

Preparation of the Test Samples. Prepare concentrations of 2.5 mg/mL, 1.25 mg/mL, and 0.625 mg/mL of the CTLA4$^{A29YL104E}$-Ig test samples in polypropylene tubes using acetate buffer (pH 3.5). Test samples are incubated for approximately 10 minutes at ambient temperature before adding to microtiter plate.

Plate Washing. Wash plates three times with wash solution using the plate washer. Plate washer should be set to fill wells with 300 µL wash buffer, zero soak time. Add 100 µL of each Reference Standard, Quality Control, Recovery Control, and test samples to each well and incubate for one hour at ambient temperature. Repeat Step. Dilute biotinylated anti-protein A antibody with Teknova diluent to a desired concentration as indicated by optimization for each new lot. For example, make 1:64,000 dilution for the monoclonal anti-protein A biotin conjugate, vortex at medium speed and add 100 µL to each well using a multichannel pipettor. Incubate at ambient temperature for one hour.

Dilute Streptavidin-Horseradish Peroxidase with Teknova diluent to a desired concentration as indicated by optimization for each new lot. For example, make 1:80,000 dilution for the Streptavidin-Horseradish Peroxidase. Vortex at medium speed and add 100 µL to each well and incubate for 30 minutes at ambient temperature. Repeat Step but, wash five times. Add 100 µL TMB chromogen to each well. Incubate at room temperature for approximately 2 minutes. The optical density for the highest concentration for the standard curve should be between 0.980 and 1.400. Stop chromogen reaction by adding 100 µL/well of 1 N $H_2SO_4$. Add stop solution in the same order to plates and wells as the chromogen was added to ensure the same reaction times of chromogen with the enzyme in each well. Measure absorbance at 450 nm with a reference wavelength of 630 nm on an appropriate 96 well plate reader.

DATA ANALYSIS. Refer to the Softmax program template for the Protein A ELISA as it generates mean, standard deviations, and % CVs, etc. All of the calculations performed in Data Analysis sections will be performed using the Protein A ELISA template.ppr in SoftMax Pro.

Average the triplicate absorbance values (Abs) obtained for each reference and sample concentration assayed. Model the data for the Protein A standards using an unweighted four parameter regression of the form:

$$Abs = \frac{Min - max}{1 + (C/ED_{50})B} + max$$

Where:
Abs=absorbance
min=absorbance value corresponding to the minimal asymptote
max=absorbance value corresponding to the maximal asymptote
$ED_{50}$=absorbance corresponding to one half the absolute difference between the maximal and minimal asymptotic values
B=the slope the inflection point of the curve fit
C=Concentration of Protein A
Exemplary Values.
Exemplary values for the Standards. The exemplary values for the standards applies to those values at or above the quantitative limit (QL), as values below the QL are used only to help establish the extremes of the curve. The coefficient of determination ($R^2$) for the standard curve should be ≥0.99. The mean background for the zero ng/mL standard should be ≤0.08 absorption units. The mean of the calculated values (ng/mL) at each standard concentration used to determine the standard curve except zero and the QL must be within 15% of the target (nominal) value. The mean of the triplicate absorbance values of the QL of the standard curve must exhibit a % CV of less than 20% and be within 20% of target.

Example 54—ELISA for the Determination of MCP-1 Like Protein in CTLA4$^{A29YL104E}$-Ig This ELISA is performed to determine the concentration of MCP-1 like protein in CTLA4$^{A29YL104E}$-Ig. The concentrations of a standard curve (0.4 to 25.6 ng/mL), Quality Control, and test samples are applied to goat anti-mouse MCP-1 absorbed microtiter plates, and incubated for 60 minutes at ambient temperature (22.5±5° C.). Plates are washed, secondary antibody (rabbit anti-rat MCP-1 IgG) is added, and incubated for 60 minutes at 22.5±5° C. Plates are washed, goat anti-rabbit IgG Horseradish Peroxidase is added to each well, and incubated for 30 minutes at 22.5±5° C. Plates are washed and TMB Chromogen is added to yield a colorimetric reaction. After stopping the reaction with 1N $H_2SO_4$, optical densities are measured at 450 nm in a 96-well microplate reader, and the data is modeled using a 4-parameter regression curve. The concentration of MCP-1 like protein is then calculated for each test sample relative to the MCP-1 reference material. The concentration is reported in ng MCP-1 like protein per mg (parts per million, ppm) of sample by dividing the result obtained relative to the standard curve and the undiluted sample concentration. This method allows for the determination of MCP-1 like impurities in cell culture derived biological samples including in-process, purified drug substance, and drug product. MCP-1 like protein may be present in biological samples produced in Chinese Hamster Ovary (CHO) cell culture. Two polyclonal antibodies were identified that bind to an MCP-1 like impurity purified from CHO cells. The antibodies are directed against murine and rat MCP-1 (intact) and both do cross react with MCP-1 like protein from CHO cells which is demonstrated in this report.

Plate Coating. For coating, dilute goat anti-mouse MCP-1 antibody to 5 µg/mL with Coating Buffer. Coat plates with 100 µL/well. Cover plates with plate sealers and incubate at 22.5±5° C. for 12 to 18 hours. Plate Washing. Wash plates three times with Wash Solution using a plate washer. Washer should be set at three washes, 300 µL/well with a zero soak time. Alternatively, plates may be washed manually. Add 300 µL of solution to each well of each plate using a calibrated multichannel pipettor. Empty wells by flicking out into a sink and blot gently on paper towels. Repeat three times.

Plate Blocking. Add 300 µL Coating Stabilizer & Block Buffer to each well using a calibrated multichannel pipettor. Incubate the plates for one to two hours at 22.5±5° C. Plate Washing and Storage. Wash plates three times with Wash Solution as described under 4.2. Fill plates with 300 µL Coating Buffer per well, cover with plate sealers and store in the dark at 2-8° C. for up to one week.

Preparation of the Standards. From the MCP-1 like protein stock, prepare a 25.6 ng/mL solution in PTB and dilute from there in serial dilution steps (1:2) to 12.8, 6.4, 3.2, 1.6, 0.8, 0.4, and 0 ng/mL using PTB as diluent. Alternatively, frozen standards can be used by preparing a large quantity of standards. Aliquot and store at −70° C. to −80° C. Avoid repeated freeze/thaw. Frozen Standards need to be qualified against Quality Controls in three independent ELISA runs. The Frozen Standards and QC must be acceptable in each run. After completion of three acceptable runs, a Certificate of Analysis is issued. Frozen Standards will be used at their nominal concentrations. They expire 3 months from the date of preparation.

Example for a MCP-1 Reference with a stock concentration of 0.97 mg/mL:
  Prepare 2.5 mL of 5200 ng/mL in PTB:
  13.4 mL stock+2.487 mL Diluent
  b) Prepare 160 mL of 25.6 ng/mL in PTB:
  788 mL stock a +160 mL Diluent
    Mix each solution by vortexing the tube for approximately 2-3 seconds and then gently inverting 2-3 times.

Quality Control. Quality Controls (QCs) are MCP-1 like protein prepared at nominal concentrations of 17.7 ng/mL, 5.3 ng/mL, and 1.2 ng/mL in PTB. Prepare a large quantity of QCs, aliquot, and store at −70° C. to −80° C. for up to 3 months. Avoid repeated freeze/thaw. The Quality Controls are qualified against standard curve in three independent ELISA runs. The QC must be acceptable in each run. After completion of three acceptable runs the average result for each acceptable QC is reported and a Certificate of Analysis is issued. QC will be used at their calculated concentrations. They expire three months from the date of preparation. Example for preparing frozen QC dilutions from an MCP-1 Reference with a stock concentration of 0.97 mg/mL:
  a) Prepare 2.5 mL of 5200 ng/mL in PTB:
  13.4 mL stock+2.487 mL Diluent
  b) Prepare final dilution of MCP-1 like protein Quality Control samples as follows:

| Concentration of MCP-1 (ng/mL) | 5200 ng/mL MCP-1 Like Protein to Add (µL) | Amount of PTB Buffer to Add (mL) | Total Volume (mL) |
| --- | --- | --- | --- |
| 17.7 | 409 | 119.6 | 120 |
| 5.3 | 122 | 119.9 | 120 |
| 1.2 | 28 | 120 | 120 |

Mix each solution by vortexing 2-3 seconds and then gently inverting 2-3 times. Alternatively, QC can be prepared fresh on the day of analysis.

Test samples. Test samples are prepared by adding 200 µL of the test sample to 200 µL of PTB and vortex for 2-4 seconds. Add reference standards, quality controls (×2), and test samples to the plate, in triplicate, 100 µL per well and incubate for 1 hour at 22.5±5° C. (do not use outer wells). Prepare secondary rabbit anti-rat MCP-1 antibody in PTB buffer at a concentration of 2 µg/mL in sufficient volume for plates used in the assay. Vortex the solution approximately 2-4 seconds. Repeat wash, but wash five times. Add 100 µL of the secondary antibody solution to each well and incubate for 60 minutes at 22.5±5° C. Prepare tertiary goat anti-rabbit HRP conjugate solution (e.g. 1:20,000 dilution or appropriate dilution) using PTB as diluent. Vortex the solution approximately 2-4 seconds. Repeat wash. Add 100 µL HRP conjugate to each well and incubate at 22.5±5° C. in the dark for 30 minutes. Repeat wash. Add 100 µL of TMB to each well and incubate at 22.5±5° C. in the dark for 3-6 minutes or until appropriate color has developed. Stop chromogen reaction by adding 100 µL of 1N $H_2SO_4$ in the same order as the addition of chromogen was made. Read optical densities at 450 nm with a reference wavelength of 630 nm on an appropriate 96-well plate reader.

Data Reduction

Use the Softmax™ Software with the protocol file MCP-1.ppr to construct a standard curve using an unweighted four parameter regression of the form.

$$Absorbency_{450} = \frac{A - D}{1 + \left(\frac{x}{c}\right)^b} + D$$

Where:
  A=Absorbency$_{450}$ value corresponding to the minimal asymptote.
  D=Absorbency$_{450}$ value corresponding to the maximal asymptote.
  c=concentration corresponding to one half the absolute difference between the maximal and minimal asymptotic values.
  B=the approximated slope of the linear portion of the curve.
  X=concentration of reference standard.

Report results only for samples with acceptable data for standard curves, quality controls, and test samples.

Exemplary values for the Standards. The exemplary values for the standards apply to those values at or above the QL (0.8 ng/mL), as values below the QL are used only to help establish the extremes of the curve. The mean background (the zero ng/mL standard) must be ≤0.1 absorption units. The mean back-calculated MCP-1 concentration (ng/mL) at each standard concentration used to determine the standard curve, must be within 15% of the target (nominal) value. The coefficient of variance (% CV) of the triplicate $A_{450}$ values at each standard concentration used to determine the standard curve, must be ≤15%. The mean of the triplicate $A_{450}$ values at the QL of the standard curve must exhibit a % CV of ≤20% and back-calculate to within 20% of the target (nominal concentration, 0.8 ng/mL). Each value of the triplicate used to calculate the mean will be analyzed separately. The value that lies furthest from the mean will be dropped, the curve re-calculated, and the exemplary values re-analyzed. If it is shown that the mean of the remaining two values still do not meet the exemplary values, then the single point is eliminated and the curve is re-calculated.

Exemplary values for QC Samples. A QC sample is defined as a set of three wells at the stated concentration, therefore, for the three nominal concentrations stated in this method there are a total of six QC samples. The back-calculated concentrations of at least two of the three wells for a QC sample must be within 20% of the previously determined target concentration (see COA) for the QC sample to be acceptable. At least four of the six QC samples must be acceptable; two of the six QC samples (not two at the same concentration) may be unacceptable and not more than 6 of the 18 QC sample wells may deviate more than 20% from the respective target concentrations. If these exemplary values are not met, the assay must be repeated.

Exemplary values for Test Samples. The mean calculated MCP-1 concentration must be less than the concentration of the Highest QC. If the mean calculated MCP-1 concentration is ≥0.8 ng/mL (the QL) the % CV of the triplicate determinations must be ≤20%. If this condition is not met the sample result is not valid and must be repeated. If this criterion is met, the average MCP-1 concentration is used to calculate the final result. If the calculated MCP-1 concentration is <0.8 ng/mL (QL) the sample is reported as <QL and the value "<0.8 ng/mL" is used in calculation of the final result.

Example 55—Detection of Cho DNA in CTLA4$^{A29YL104E}$-Ig and CTLA4-Ig by Quantitative Polymerase Chain Reaction This procedure was developed to detect residual CHO DNA in samples of drug substance using a real-time quantitative polymerase chain reaction (qPCR) assay. PCR is the replication of a mixture of DNA. This assay uses a fluorogenic probe to detect a specific CHO PCR product as it accumulates during the assay. The rate of amplification of the PCR product is directly proportional to the amount of starting DNA present in the sample.

Conversion of DNA Value to picogram/milligram. The pg/mL value is divided by the concentration of the sample, determined by the absorbance at 280 nm. Example calculation for a sample having a protein concentration of 50 mg/mL and a reported value from Bioreliance=0.67 fg/µL. Step 1: Conversion to pg/mL=0.67 pg/mL. Step 2: Conversion to pg/mg=(0.67 pg/mL/50.0 mg/mL)=0.013 pg/mg.

Example 56: Analysis of CTLA4$^{A29YL104E}$-Ig by SDS-Page

This example describes the analysis of CTLA4$^{A29YL104E}$-Ig for the assessment of purity for CTLA4$^{A29YL104E}$-Ig drug substance and drug product. CTLA4$^{A29YL104E}$-Ig is an engineered fusion protein consisting of a modified ligand binding domain of cytotoxic T lymphocyte antigen 4 (CTLA4) and the Fcγ1 region of human IgG. CTLA4$^{A29YL104E}$-Ig has a molecular weight of ~92 k Daltons and an apparent molecular weight of 97 k Dalton (non-reduced) or 55 k Dalton (reduced). Electrophoresis of CTLA4$^{A29YL104E}$-Ig on 4-20% gradient SDS-polyacrylamide gels separate the main monomeric species from higher molecular weight species (aggregates, dimers, and higher order multimers) as well as any low molecular weight species (degradation fragments). Densitometric scanning and ImageQuantTL™ quantitation of Coomassie Blue stained gels yield a measure of protein purity. Results are reported as percent purity of CTLA4$^{A29YL104E}$-Ig under reduced and non-reduced conditions.

Reagents

NOTE: All reagents may be substituted with equivalent alternatives. 1× Tris-Glycine-SDS Running Buffer. Add 100 mL Tris-Glycine-SDS 10× Running buffer to a 1 liter graduated cylinder. Q.S. to 1 liter with Milli-Q or HPLC grade water. Cover, invert several times to mix. This reagent should be prepared on the day of assay. NOTE: Prepare additional volume if needed.

Coomassie Blue Staining Reagent. Mix the GelCode Blue Stain Reagent solution immediately before use by gently inverting or tipping and swirling the bottle several times. Such mixing is especially important when using the 3.5 L GelCode container with a manual pump (Catalog No. 24592). Do not shake bottle to mix the solution. NOTE: It is important to mix the stain reagent before dispensing to ensure that the solution is homogeneous.

Fixing Solution: 50% Methanol/7% Acetic Acid in Water. Combine 500 mL methanol and 70 mL acetic acid in a 1 liter graduated cylinder. Q.S. with Milli-Q water to 1 liter and mix. The fixing solution is stable at room temperature for up to six months. NOTE: The fixing solution should be prepared in a chemical fume hood.

Staining Control Preparation. Reconstitute the trypsin inhibitor to make a 2 mg/mL stock solution using Milli-Q water. Prepare 50 µL aliquots and freeze at −30±10° C. for up to 6 months. Use the following dilution plan to dilute the stock protein solution to a working concentration:

25 µL of stock solution+75 µL Milli-Q water=0.5 µg/µL
40 µL of 0.5 µg/µL+160 µL Milli-Q water=100 ng/µL Use Table directly below to prepare the Staining Control loading solution.

| Sample Preparation for Staining Control | |
|---|---|
| Stain Control Preparation | Non-Reduced (µL) |
| Trypsin Inhibitor (100 ng/µL) | 10 |
| Tris-Glycine SDS Sample Buffer (2×) | 50 |
| Milli-Q Water | 40 |
| Total Volume | 100 |

Loading 10 µL of the Staining Control Preparation will yield a protein load of 100 ng.

Standard and Sample Preparation

Loading Pattern for Fixed Process, GLP/GMP Drug Substance, Drug Product, or Stability Samples. Dilution for Coomassie Blue Stained Gels. Dilute test articles and reference material to the working concentration of 1.0 µg/µL and load both reduced and non-reduced with molecular weight markers as described in Table directly below.

| Sample Dilution and Gel Loading for Coomassie Blue Stained Gel | | | | |
|---|---|---|---|---|
| Lane | Description | (NR/R) Condition | Working Concentration (µg/µL) | Loading Volume (µL) | Protein Load (µg) |
| 1 | Sample 1 | NR | 1.0 | 10 | 10 |
| 2 | Reference Material | NR | 1.0 | 10 | 10 |
| 3 | Blank[1] | NR | 0.0 | 10 | 0 |
| 4 | Sample 1 | R | 1.0 | 10 | 10 |
| 5 | Reference Material | R | 1.0 | 10 | 10 |
| 6 | Molecular Wt. Stds. | R | — | 10 | — |
| 7 | Reference Material | R | 1.0 | 10 | 10 |
| 8 | Sample 2 | R | 1.0 | 10 | 10 |
| 9 | Blank[1] | NR | 0.0 | 10 | 0 |
| 10 | Reference Material | NR | 1.0 | 10 | 10 |
| 11 | Sample 2 | NR | 1.0 | 10 | 10 |
| 12 | Staining Control | NR | 0.01 | 10 | 0.1 |

[1]Blank = Load 10 µL of 1 × NR sample buffer
NOTE:
The staining control band is included on the scanned gel image for visual inspection to assess system suitability. The staining control band is absent in the cropped gel image to maintain consistency of gel reporting.

Sample Preparation and Electrophoresis. Sample Dilution for a 10 µg/Lane Protein Load. Follow the method below to prepare samples for a 10 µg/10 µL load. Using Milli-Q water as the diluent, dilute test samples and reference material to 10 mg/mL CTLA4A29YL104E-Ig. Approximate concentrations may be used for calculations. For example: If a sample of CTLA4A29YL104E-Ig drug substance has a concentration of 25 mg/mL, prepare a 1:2.5 dilution (add 40 µL of sample to 60 µL of Milli-Q water). Follow Table directly below to prepare the final sample for electrophoresis. Use microfuge tubes for these dilutions.

| Dilution of Test Samples | | |
|---|---|---|
| Reagent | Reduced (µL) | Non-Reduced (µL) |
| Test Article at 10 mg/mL | 10 | 10 |
| Tris-Glycine SDS Sample Buffer (2X) | 50 | 50 |
| NuPAGE Reducing Agent (10X) | 10 | NA |
| Milli-Q Water | 30 | 40 |
| Total Volume | 100 | 100 |

NOTE: Adjust the volume of protein solution and Milli-Q water as needed to achieve a final volume of 100 µL. NOTE: If the sample concentration is <10 mg/mL, prepare the final sample according to the Table above. Adjust the volume of protein solution and water to maximize the protein load on the gel.

Sample Heating. After preparing sample dilutions, close the microfuge tubes and vortex the tubes to mix the solution. Heat sample(s) in a water bath at 80±5° C. for 2.0±0.5 minutes (use calibrated timer). Remove sample (s) from the heat and allow them to cool to room temperature. Invert tubes several times to remove condensation from the top and sides of the tubes.

Apparatus and Gel Preparation. Remove gel from its packaging and carefully remove the comb making sure that the walls of the wells are straight. The wells can be straightened with a gel loading tip if necessary. Insert the gel into the electrophoresis unit so that the short glass plate faces the inner chamber. If only a single gel is to be run, insert a plexiglass spacer on the opposite side. Wedge the gel(s) tightly to seal the inner chamber from the outer chamber. Completely fill the inner chamber with 1× Tris-Glycine-SDS running buffer. Check for leaks, then fill outer chamber to the bottom of the wells with 1× Tris-Glycine SDS running buffer. Gently rinse wells using a pipette with 1× Tris-Glycine-SDS running buffer to remove any residual acrylamide. Repeat well rinsing until wells are completely clear and defined.

Sample Loading. Using gel loading tips, load each well with 10 µL of sample. Fill all blank lanes with 10 µL of 1× Non-Reducing Sample Buffer. This will help prevent reduction of the non-reduced sample due to leaching of the reducing agent and will maintain a similar salt concentration across the entire gel.

Electrophoresis. Attach the gel box cover, and connect the electrodes to the power supply. Adjust the current to 25 mAmps/gel (mA) and set the voltage (v) and power (w) to maximum. NOTE: Power supply setting may vary from vendor to vendor. Adjust setting to achieve 25 mA/gel. Electrophorese the gel for 60 minutes or until the sample buffer dye front just reaches the bottom of the gel. Turn off the power supply, disconnect leads, and remove gel(s) from device. Carefully pry the plastic plates apart. Hold the plastic plate with the gel attached over the appropriate fixing solution for the staining technique. Submerge gel into the solution until the gel dislodges from the plastic plate.

Gel Fixing. NOTE: All steps are performed at room temperature with gentle rocking on the orbital shaker. NOTE: Perform staining in a tightly sealed container to prevent reagent evaporation. NOTE: Although the volume cited can be used, it is imperative that the gel be completely covered in all steps. The size of the gel and staining tray must be taken into account in determining volumes needed. After electrophoresis, add 50 mL of the fixing solution (50% methanol/7% acetic acid solution) for 15 minutes. Rinse the gel 3 times for 5 minutes each with ~100 mL Milli-Q water. Mix the Coomassie Stain Reagent solution before use, and add 50 mL for an 8×10 cm mini gel. Additional reagent may be required if a larger tray is used. Gently shake the tray using an Orbital Shaker for 20±1 hours. For consistency, stain all gels in the same run for the same duration. Destain by replacing the Coomassie Stain Reagent with 100 mL of Milli-Q water. After 1 hour of destaining, the gel is ready for scanning.

Gel Scanning and Analysis

After electrophoresis and staining, all gels are scanned using a densitometer and analyzed using ImageQuantTL™ software. The image files are stored on the computer local hard drive and archived via the local area network. The scanning and analysis parameters are listed in the Table directly below.

| Gel Scanning and Analysis Parameters | |
|---|---|
| | Setting |
| Scan Parameters | |
| Scan Pixel Size | 100 |
| Scan Digital Resolution | 12 bits |
| Band Detection Parameters | |
| Background Correction | Radius set at 200 |
| Minimum Slope | Initial 500 |
| Noise Reduction | Initial 5 |
| % Maximum Peak | Initial 0 |
| Lane % width | Set at 75% |

NOTE:
The Scan Parameters in this Table must not be changed during scanning. The Band Detection Parameters, Lane % width (set at 75%) and Background Correction (set at 200 Radius), are recommended for all scanned gel image analysis (any changes will need to be documented). Adjustment of Minimum Slope, Noise Reduction, and % Maximum Peak parameters may be necessary to accurately identify bands due to differences in the physical properties of the gel, such as gel shrinkage after staining/destaining or differences in the shape of the gel band shape. Manually correct any missed or misidentified bands. Refer to the ImageQuantTL (v2003.03) manual and on-screen instructions for additional information for band detection parameters.

Scan the gel using the scan parameters listed in above Table. All analysis and assessments of the gel should be made from the scanned image. Open a gel image file (scanned image) from <1D Gel Analysis> in the ImageQuantTL software. Go to <Contrast> on toolbar and set the <Image Histogram—High> parameter to 0.3 to enhance the gel image for clear visualization of all bands. NOTE: This step is for easy visualization of the gel image for the following analysis and has no impact on the quantitative result. Do not use the enhanced gel image for the purpose of visual assessment of gel bands or gel reporting. Select <Lane Creation> and choose <Manual> to set up <Number of Lanes> to be analyzed. Set <Lane % Width> to 75%. Properly align single lanes if necessary. Use the <Rolling Ball> method to subtract the background. To accurately account for background, set <Radius> to 200. Detect bands using the initial <Minimum Slope>, <Noise Reduction>, and <% Maximum Peak> settings listed in Table 4. Adjustment of these values may be necessary to accurately identify bands. Manually assess any missed or misidentified bands. Determine the band molecular weight by using the molecular weight marker listed below. Skip the calibration and normalization steps. Export the results including the molecular weights, band volume, and band % into an Excel worksheet for further documentation and reporting. Eleven of the twelve molecular weight standards listed in Table 5 should be easily distinguished from background (FIG. 78). Note: The Insulin B chain (3,500 Da) and Insulin A chain (2,500 Da) may appear as a single broad band or the Insulin A chain may not be visually identified on the gel.

| Mark 12 Molecular Weight Standards | |
|---|---|
| Protein Marker | Molecular Weight (Daltons) |
| Myosin (rabbit muscle) | 200,000 |
| β-galactosidase (*E. coli*) | 116,300 |
| Phosporylase B (rabbit muscle) | 97,400 |
| Bovine serum albumin | 66,300 |

| Mark 12 Molecular Weight Standards | |
| --- | --- |
| Protein Marker | Molecular Weight (Daltons) |
| Glutamic dehydrogenase (bovine liver) | 55,400 |
| Lactate dehydrogenase (porcine muscle) | 36,500 |
| Carbonic anhydrase (bovine erythrocyte) | 31,000 |
| Trypsin inhibitor (soybean) | 21,500 |
| Lysozyme (chicken egg white) | 14,400 |
| Aprotinin (bovine lung) | 6,000 |
| Insulin B chain (bovine pancreas) | 3,500 |
| Insulin A chain (bovine pancreas) | 2,500 |

In this example, the major bands of the test article, for both non-reduced (monomer) and reduced (single chain), are to be in the same relative position on the gel as the CTLA4A29YL104E-Ig reference material. See FIG. 78. The staining control of soybean trypsin inhibitor (21,500 Da) standard at 100 ng/load must be visible on the scanned gel image (FIG. 78, lane 12). With the exception of a minor band under non-reducing condition that is commonly observed (single chain) proximal to the 55,400 Da molecular weight marker, the relative percent intensity of any additional band in the Coomassie blue stained gel should be ≤2% for reference material. NOTE: A molecular weight estimation of the main band cannot be accurately determined due to its non-gaussian distribution. Visual inspection of the reduced reference material is to yield a single broad band migrating to a position proximal to the 55,400 Da molecular weight marker (See FIG. 78). The percent purity for reduced major band must be 97%. Visual inspection of the non-reduced reference material major band must yield a single broad band migrating to a position proximal to the 97,400 Da and 116,300 Da molecular weight markers (FIG. 78, lane 2). The percent purity of the reference material major band must be ≥97%. Visual inspection of the non-reduced reference material major band must yield a single broad band migrating to a position proximal to the 97,400 Da and 116,300 Da molecular weight markers (FIG. 78, lane 2). The percent purity of the reference material major band must be 97%.

Example 57—an HPLC Method for the Quantitative Determination of Triton X-100 in CTLA4$^{A29YL104E}$-Ig Triton X-100 is determined at low parts per million (ppm) level (<10 ppm) in protein samples of CTLA4$^{A29YL104E}$-Ig by HPLC. The method involves extraction of Triton X-100 onto solid phase extraction media followed by washing with water to remove residual protein and elution of the Triton X-100 with acetonitrile. The acetonitrile eluate is chromatographed using a Phenomenex Hypersil C1 column and a mobile phase consisting of acetonitrile:water (80:20). Detection is by UV at 225 nm. The method is linear between 1-22 ppm with the limit of detection being 0.25 ppm. CTLA4$^{A29YL104E}$-Ig, a potential immunosuppressant agent, is a second generation fusion protein, consisting of the ligand binding domain of cytotoxic T lymphocyte antigen 4 (CTLA4) and the constant region of human IgG1 heavy chain. Triton X-100 an nonionic surfactant, is used for viral inactivation in the purification of CTLA4$^{A29YL104E}$-Ig. Even though Triton X-100 is removed, residual levels or absence of the surfactant from the protein needs to be established for product quality and regulatory purposes. To this end, a method capable of detecting and quantitating trace levels of Triton X-100 was developed. Triton X-100 is extracted from the protein onto a SPE media and eluted with acetonitrile for analysis by HPLC.

Standard Preparation

Blank. Any sample or reference standard previously analyzed by this method and found not to contain detectable levels of Triton X-100 may be used as the blank. The protein concentration in the blank and sample should be similar. The blank should be run along with the sample(s).

Stock Standard Solution. Accurately weigh 10.0 ∀ 1.0 mg Triton X-100 into a 100 mL volumetric and dilute to volume with water and mix. NOTE: Triton X-100 dissolves slowly in water. Examine the solution for complete dissolution (typically after 15 minutes) before use. Triton X-100 is more viscous than water, so undissolved amounts are visible in the presence of water.

Working Standard Solution. Spike 25 μL of the Triton X-100 stock standard solution into 0.5 mL of the CTLA4$^{A29YL104E}$-Ig blank. Mix thoroughly by vortex or other appropriate means. This working standard solution contains approximately 5 ppm (or 5 μg/mL wt. vol.) of Triton X-100. NOTE: The standard solutions should be prepared fresh daily.

Sample Preparation. The sample is used as is. The blank should be run along with the sample(s). Extraction of Triton X-100 from Standard and Sample Solutions. The extraction steps described below are performed under a vacuum of 3-5 inches of Hg.

Activation of the Solid Phase Extraction (SPE) Media. Lift the lid of the vacuum manifold and place test tubes in the rack inside the manifold. These are "waste" test tubes. Replace the lid and place SPE tubes on the vacuum manifold, making sure that there is a "waste" test tube underneath each SPE tube. Add one mL of acetonitrile to each tube, and apply vacuum to the tubes until all the acetonitrile has passed through the media bed. Repeat step. Concentration of Triton X-100 on the SPE Media from Standard/Sample Matrix. Into separate activated SPE tubes, pipette 0.50 mL each of the working standard solution, samples, and blank. Apply vacuum to the SPE tubes until the solution has completely passed through the media bed. Removal of Residual Protein from the SPE Bed. Add one mL of water to each SPE tube, and apply vacuum to the tubes until the water has passed through the media bed. Repeat step. Elution of Triton X-100 from the SPE Bed. Turn off the vacuum to the manifold to bring the unit to normal pressure. Gently lift the lid of the manifold, with the standard and sample SPE tubes still attached. Replace the "waste" test tubes with a set of pre-labeled test tubes (for standard, blank, and samples) to collect any Triton X-100 that may be eluted from the SPE beds in the following steps. These are the eluate test tubes. Replace the lid of the manifold, making sure that each sample, blank, and standard SPE bed has the respective eluate test tube underneath. Add 0.50 mL acetonitrile to each SPE tube, and apply vacuum to the tubes until all the acetonitrile has passed through the media bed. Turn off the vacuum to the manifold, and lift the lid to retrieve the eluate test tubes. Place the acetonitrile eluates of the standard, samples, and blank into autosampler vials for injection into the chromatographic system.

System Suitability

Equilibrate the column/system with the mobile phase for about an hour before beginning injections. Obtain the chromatogram of the standard solution. The retention time for Triton X-100 should be 5 ∀ 1 minutes. The efficiency of the column for Triton X-100, evaluated as the number of theoretical plates, N, must be >2000 plates/column when calculated according to the following equation:

$$N = 16\left(\frac{t}{w}\right)^2$$

Where:
t is the retention time of Triton X-100 peak, and w is the width at baseline of the Triton X-100 peak obtained by extrapolating the sides of the peak to the baseline. Make at least three injections of the standard solution. The percent RSD of the area counts of the last three injections should not be more than 3.0%.

Subtract the blank chromatogram from the standard and sample chromatograms and proceed with the following calculations:

Concentration of Triton $X$-100 (ppm) =

$$\frac{\text{area of sample}}{\text{area of standard}} \times \text{wt. of Triton} \times 100 \text{ (mg)} \times 0.5 \text{ ppm}$$

Where:

$$0.5 = \frac{1000 \text{ μg}}{1 \text{ mg}} \times \frac{1}{100 \text{ mL}} \times \frac{25 \text{ microliters}}{0.5 \text{ mL}} \times \frac{1 \text{ mL}}{1000 \text{ microliters}}$$

Example 58—Assay for Determining CTLA4-Ig Composition CHO Cellular DNA Content This procedure was developed to detect residual CHO DNA in samples of CTLA4-Ig drug substance using a real-time quantitative polymerase chain reaction (qPCR) assay. PCR is the replication of a mixture of DNA. This assay used a fluorogenic probe to detect a specific CHO PCR product as it accumulates during the assay. The rate of amplification of the PCR product is directly proportional to the amount of starting DNA present in the sample. The objective is to detect the amount of CHO genomic DNA in samples of CTLA4-Ig compositions.

Sample is analyzed by detecting CHO DNA in Biological Samples by Quantitive Polymerase Chain Reaction Analysis. Calculations are carried out and results are reported to two significant figures in the units of pg/mg. If the results are less than the quantitation limit of the assay, the results are reported as <Q.L. and the Q.L. of the assay is recorded. There is a conversion of DNA Value to picogram/milligram. The pg/mL value is divided by the concentration of the sample, determined by the absorbance at 280 nm. Example calculation for a sample having a protein concentration of 50 mg/mL and a reported value from Bioreliance=0.67 fg/4. Step 1: Conversion to pg/mL=0.67 pg/mL Step 2: Conversion to pg/mg=(0.67 pg/mL/50.0 mg/mL)=0.013 pg/mg.

Example 59—Determination of MCP-1 Protein in Biological Samples and in CTLA4-Ig Compositions The example sets out methods used to quantitate residual MCP-1-like protein in biological samples and samples of CTLA4-Ig.

Materials:

| | |
|---|---|
| Goat Anti-mouse MCP-1 (anti-murine JE [MCP-1]) Neutralizing Antibody | R&D Systems, (Catalog No. AB-479-NA), Store at −20° C. |
| Rabbit Anti-rat MCP-1 | Pepro Tech, (Catalog No. 500-P76), Store at −20° C. |
| Goat Anti-rabbit IgG (H + L) HRP Conjugated | Southern Biotech (Catalog No. 4050-05, Store at 2-8° C. |

Reagents

Phosphate Buffered Saline (PBS, 10 mM Phosphate Buffer, 137 mM NaCl, 2.7 mM KCl, pH 7.3 to 7.5). Prepare according to manufacturer's directions on the bottle. To a vessel of sufficient size, add HPLC Grade water, PBS pellets and a stir bar. On a stirring plate mix until the pellets and salt are dissolved. Adjust pH 7.3 to 7.5 as necessary with Sodium Hydroxide or Hydrochloric Acid. Stir until well mixed. Filter through a disposable 0.22 μm filter unit. Store the solution at 2-8° C. for up to 30 days from the date of preparation.

MCP-1 (Monocyte chemotactic protein-1) is a human protein which plays a role in the recruitment of monocytes to sites of injury and infection. A protein can be considered MCP-1-like based on homology and cross-reactivity with antibodies against MCP-1. Since the antibodies used in the ELISA only recognize a portion of the target protein, truncated forms of MCP-1 may react in the assay even though they may not be technically active. Thus any variant of hamster MCP-1 which reacts in the assay will be quantified so that the assay detects full-length MCP-1 and any variants of MCP-1 which contain the correct epitopes. Note that by using a polyclonal antibody mixture, it is more likely that a number of epitopes will be represented.

Wash Solution (1.0 mM Phosphate Buffer, 137 mM NaCl, 0.27 mM KCl, pH 7.3 to 7.5 containing 0.01% v/v Tween 20). To 4.0 L of Distilled or HPLC Grade water, add a stir bar, 2 PBS tablets, 28.8 g of NaCl, and 0.4 mL of Tween 20. Mix gently until all contents are dissolved. Adjust pH 7.3 to 7.5 as necessary with Sodium Hydroxide or Hydrochloric Acid. Store at 2-8° C. for up to 30 days from the date of preparation.

Diluent (PBS, pH 7.3 to 7.5 containing 1% w/v BSA, and 0.05% v/v Tween 20). (Please note this is an alternative to the use of commercially available diluent). To 4 L Phosphate buffered saline, add a stir bar, 40 g of BSA and 2 mL of Tween 20. Mix gently until all contents are dissolved. Filter through 0.22 μm filter. Store at 2-8° C. for up to 30 days from the date of preparation when stored unopened or 7 days after opening.

Plate Coating Reagent. Reconstitute several vials of goat anti-mouse MCP-1 antibody as per manufacturer's instructions, mix by gently inverting several times, and combine. Prepare aliquots and store at −20° C. for up to one year (not to exceed the manufacturer's expiration date). Avoid repeated freeze thaw. Alternatively, the lyophilized sample vials can be stored at −20° C. for greater than six months. Upon reconstitution, the antibody can be stored at 2-4° C. for one month.

Secondary Reagent. Reconstitute one vial of rabbit anti-rat MCP-1 antibody as per manufacturer's instructions, mix by gently inverting several times. The solution is stored at 2-8° C. for up to four weeks. Alternatively the lyophilized sample vials are stable at −20° C. for greater than one year.

Tertiary Reagent. Pool several vials of goat anti-rabbit IgG (H+L) HRP and mix by gently inverting several times. Prepare aliquots and store at −20° C. for up to 2 years (not to exceed the manufacturer's expiration date). Avoid repeated freeze thaw. Once thawed, the vial can be stored at 2 to 8° C. for up to 30 days.

Preparation of Standards. From the MCP-1-like Protein stock, prepare a 25.6 ng/mL solution in diluent and dilute from there in serial dilution (2 fold) steps to 12.8, 6.4, 3.2, 1.6, 0.8, and 0.4. The 0 ng/mL standard is undiluted diluent.

Example for preparing Standards using MCP-1 Reference material with a stock concentration of 0.97 mg/mL:
b) (Solution A) Prepare 2.5 mL of 5200 ng/mL in diluent: 13.4 uL stock+2.487 mL diluent
c) (Solution B) Prepare 3.9 mL of 25.6 ng/mL in diluent: 19.2 uL stock a +3.881 mL diluent Prepare remaining standards using the volumes defined below:

| Working Solution | Volume (mL) | Diluent (mL) | Final Concentration (ng/mL) |
|---|---|---|---|
| 25.6 ng/mL | 1 mL | 0 | 25.6 ng/mL |
| 25.6 ng/mL | 1 mL | 1 mL | 12.8 ng/mL |
| 12.8 ng/mL | 1 mL | 1 mL | 6.4 ng/mL |
| 6.4 ng/mL | 1 mL | 1 mL | 3.2 ng/mL |
| 3.2 ng/mL | 1 mL | 1 mL | 1.6 ng/mL |
| 1.6 ng/mL | 1 mL | 1 mL | 0.8 ng/mL |
| 0.8 ng/mL | 1 mL | 1 mL | 0.4 ng/mL |

Mix each solution by vortexing at medium setting for approximately 2-3 seconds and then gently inverting 2-3 times.

Preparation of Quality Control Samples. Prepare Quality Control (QC) samples from a vial of MCP-1 like protein in diluent. Prepare a 520 ng/mL solution stock concentration from which the following quality control samples for freezing are made: 11.0 ng/mL, 5.3 ng/mL, and 1.2 ng/mL. Dilute as described in the table below.

Example for Preparing QCs Using MCP-1 Reference Material with a Stock Concentration of 0.97 mg/mL a) (Solution A) Prepare 2.5 mL of 5200 ng/mL in diluent: 13.4 uL stock+2.487 mL diluent
b) (Solution B) Prepare 5.0 mL of 520 ng/mL in diluent: 500 uL stock a +4.500 mL diluent
c) Prepare final dilution of MCP-1 like protein QC samples as follows:

| QC Identification | Concentration of MCP-1 (ng/mL) | QC Solution B to Add (µL) | Amount of Diluent to Add (mL) | Total Volume (mL) |
|---|---|---|---|---|
| QC 1 | 11.0 | 106 | 4.894 | 5.0 |
| QC 2 | 5.3 | 53 | 5.147 | 5.2 |
| QC 3 | 1.2 | 12 | 5.188 | 5.2 |

Mix each solution by vortexing at medium setting for approximately 2-3 seconds and then gently inverting 2-3 times.

Preparation of Test Samples. Each test sample consists of diluted test article. Test samples are prepared by adding 200 µL of the test sample to 200 µL of diluent. Mix each solution by vortexing at medium speed for approximately 2-3 seconds and then gently inverting 2-3 times.

Procedure. Plate Coating. Dilute goat anti-mouse MCP-1 antibody to 5 µg/mL with PBS. Mix the antibody and PBS solution by vortexing at medium setting for approximately 2-3 seconds and then gently inverting 2-3 times. Using a multichannel pipette, add 100 µL of this solution to each well. Cover plates with plate sealers and incubate at room temperature for 12 to 18 hours. Plate Washing. Wash plates three times with Wash Solution using a plate washer. Set washer at three washes, 300 µL/well with a zero soak time. Alternatively, plates may be washed manually. Add 300 µL of Wash Solution to each well of each plate using a multi-channel pipettor. Empty wells by flicking out into a sink and blot gently on paper towels. Repeat three times. Plate Blocking. Add 300 µL CSBB to each well using a multi-channel pipettor. Incubate the plates for approximately 60±10 minutes at room temperature. Addition of Samples. Add reference standards, quality controls (two sets of each concentration), and test samples to the plate, in triplicate, 100 µL/well, and incubate for approximately 60±10 minutes at room temperature. Do not use outer wells. Prepare secondary rabbit anti-rat MCP-1 antibody. Dilute rabbit anti-rat MCP-1 antibody stock to 2 µg/mL or appropriate dilution (as per lot equivalency testing or COA) in diluent in sufficient volume for plates used in the assay. Vortex the solution approximately 2-4 seconds at medium speed. Repeat plate washing, but wash five times. Using a multichannel pipette, add 100 µL of the secondary antibody solution to each well and incubate for 60±10 minutes at room temperature. Prepare tertiary goat anti-rabbit HRP conjugate solution (0.5 µg/mL or appropriate dilution) using diluent. Mix HRP conjugate by vortexing at medium setting for approximately 2-3 seconds and then gently inverting 2-3 times. Dilute to the concentration established as per departmental SOP for reagent qualification. Repeat plate washing five times. Using a multichannel pipette, add 100 µL HRP conjugate to each well and incubate at room temperature in the dark for approximately 30±5 minutes. Repeat plate washing five times. Using a multichannel pipette, add 100 µL of TMB to each well and incubate at ambient temperature in the dark for approximately 2.5-4 minutes. Using a multichannel pipette, stop the TMB reaction by adding 100 µL of 1.0N $H_2SO_4$ in the same order as the addition of TMB was made. Read the optical densities at 450 nm with a reference wavelength of 630 nm on a 96-well plate reader.

Exemplary values. The exemplary values for the standards applies to those values at or above the Quantitative Limit (QL) (0.8 ng/mL), as values below the QL are used only to help establish the extremes of the curve. The mean, using the calculation below, background (the zero ng/mL standard) must be absorption units.

$$\frac{X_1 + X_2 + X_3 \ldots X_n}{N}$$

Where: $X_{1,2,3}$=a specific value in a set of data
N=number of values in a set of data Each standard concentration used to determine the standard curve, excluding the zero, 0.4 and the QL (0.8 ng/mL), must be within 15% of the target (nominal) value. The coefficient of variance (% CV) of the triplicate $AB_{450}$ values at each standard concentration used to determine the standard curve, with the exception of the zero, 0.4 and the QL (0.8 ng/mL), must be ≤15%. The mean calculated MCP-1 concentration for a test sample of CTLA4-Ig composition should be ≤11.0 ng/mL. If the mean calculated MCP-1 concentration is ≥0.8 ng/mL (the assay QL) calculate the % CV of the triplicate determinations and the exemplary values must be ≤20%. If the exemplary values are met, the mean MCP-1 concentration is used to compute ppm. If the calculated MCP-1 concentration is ≤0.8 ng/mL (assay QL) the sample is reported as <QL and the value "<0.8 ng/mL" is used in computation of ppm. The % CV of the triplicate determination is not considered.

A QC sample is defined as a set of three wells at the stated concentration, therefore, for the three nominal concentrations stated in this method there are a total of six QC samples. The concentrations of at least two of the three wells for a QC sample must be with 20% of the stated nominal concentration for the QC sample to be acceptable. At least twelve of the eighteen QC sample determinations must be within 20% of their respective target values. Six of the eighteen QC samples (not three at the same concentration) may deviate more than 20% from the respective nominal value. At least four of the six QC samples must be acceptable. Two are permitted to be unacceptable, provided that they are not both at the same concentration.

Data Evaluation. Use the Softmax™ Software with the protocol file MCP-1.ppr to construct a standard curve using an unweighted four parameter regression of the form.

$$Absorbency_{450} = \frac{A - D}{1 + \left(\frac{x}{c}\right)^b} + D$$

Where:
A=Absorbency$_{450}$ value corresponding to the minimal asymptote
D=Absorbency$_{450}$ value corresponding to the maximal asymptote
c=Concentration corresponding to one half the absolute difference between the maximal and minimal asymptotic values
b=the approximated slope of the linear portion of the curve
x=concentration of reference standard Calculations for the Concentration of MCP-1-Like Protein. The amount of MCP-1 like protein in the test sample may be calculated using the Softmax Plate Reader Software. The example below illustrates how final results may be reported. A two fold dilution of each sample is assayed. The calculated concentration is multiplied by the appropriate dilution factor (2) to give the concentration in the undiluted test article.

Examples:
1) Diluted test sample is 10.0 ng/mL.
MCP-1 like protein concentration in undiluted test article is: 10 ng/mL×2=20 ng/mL MCP-1
2) Diluted sample result is "≤0.8 ng/mL".
MCP-1 like protein concentration in undiluted test article is:
"<0.8 ng/mL"×2="<1.6 ng/mL" MCP-1

To report the final result in ng MCP-1-like protein per mg of sample (ppm), divide the result obtained above by the undiluted sample concentration.

Examples:
1) Test sample protein concentration=50 mg/mL
MCP-1 like protein concentration=200 ng/mL:
200 ng/mL MCP-1/50 mg/mL=4 ng/mg
Sample is reported as 4 ppm (parts per million)
2) Test sample protein concentration=50 mg/mL
MCP-1 like protein concentration="≤1.6 ng/mL":
"<1.6 ng/mL" MCP-1/50 mg/mL="<0.032 ng/mg"
Sample is reported as "<QL, (<0.032 ppm)"

Example 60: Assay for Determination Residual Levels of CD-CHO1 Protein by ELISA for Release Testing of CTLA4-Ig Drug Substance Material Carbonate Buffer. To a suitable vessel containing a stir bar add; 200 mL with HPLC grade water, contents of 2 carbonate buffer capsules. Using a stir plate, mix until material is in solution. Using a pH meter adjust pH to 9.6 as necessary with either 1N NaOH or H$_2$SO$_4$. Using a stir plate, mix solution for a minimum of 5 minutes. Filter solution through a 0.22 µm filter. Store solution at 2-8° C. for up to 30 days and label as per department procedures.

Wash Buffer (PBS containing 0.05% v/v Tween 20, pH 7.4). To a 4 L Bottle of HPLC grade water add, a stir bar, 20 PBS tablets, Add 2 mL of Tween 20. Using a stir plate, mix until material is in solution. Using a pH meter adjust pH to 7.4 as necessary with either 1N NaOH or 1N HCl. Using a stir plate, mix solution for a minimum of 5 minutes. Store solution at 2-8° C. for up to 30 days and label as per department procedures.

Streptavidin-HRP. Add 0.5 mL of HPLC grade water to a vial of Streptavidin-HRP. To mix, cap vial and vortex gently for approximately 10 seconds. Add 0.5 mL of glycerol to the vial of Streptavidin-HRP. Mix. Check solution clarity by drawing solution into a clean pasteur pipette. If solution is not clear, mix as per 3.3.2 and repeat 3.3.5 until solution is clear. Determine the appropriate dilution scheme to be used for the lot of Streptavidin HRP according to department procedures. Aliquot 20 µL volumes to 0.5 mL screw cap tubes. Cap and place in a Cell Storage Box. Store solution at −20° C. for up to 365 days and label as per department procedures.

Stop Solution (1 N H$_2$SO$_4$). In a fume hood, place a suitable container onto a stir plate. Add a stir bar. Add 485.6 mL HPLC grade water. Turn on stir place to start stirring of water. Slowly add 14.4 mL of concentrated H$_2$SO$_4$. The solution is stable for 90 days when stored at room temperature. Label the solution as per department procedures.

Procedure. Plate Coating. Prepare an 8 µg/mL solution of purified rabbit anti-CD CD CHO1 antibody in Carbonate Buffer to be used for coating microtiter plates (10 mL of solution is required per microtiter plate). Add 100 µL of this solution to each well of an Immulon 4 microtiter plate using a multichannel pipettor. Cover the microtiter plate with parafilm and incubate at 2-8° C. for 18±2 hours.

Plate Washing. Wash plate three times with 300 µL Wash Buffer using plate washer instrument. (Alternatively, plate may be washed manually using a multichannel pipettor.) Following the last wash, the plate should be turned upside down and tapped against a paper towel laid on a hard surface.

Plate Blocking. Using a multichannel pipette, add 300 µL SeaBlock to each well. Incubate the plate in the dark for 1 hour (±6 minutes) at room temperature. Plates may either be wrapped with aluminum foil or placed in a cabinet or drawer. Preparation of Standard Curve samples using Teknova Diluent in 15 mL graduated sterile polypropylene tubes according to the dilution scheme below. Note: The dilution scheme below is for 5 plates. Adjust volumes as necessary for the number of plates in the assay. Obtain protein concentration of the CD-CHO1 Protein Reference Standard (Ref Std) from the Certificate of Analysis (COA). Prepare a 30 µg/mL solution of CD-CHO1 Protein Ref Std. Calculate required volume of CD-CHO1 Protein Ref Std to obtain a 30 µg/mL solution. Minimum transfer volume for the CD-CHO1 Protein Ref Std should be 10 µL.

$$\text{Formula: Volume} = \frac{\text{Desired Concentration} \times \text{Desired Volume}}{\text{Reference Material Concentration}}$$

Note: Ensure Units are Compatible.
Example:

$$\frac{30 \text{ µg/mL} \times 10 \text{ mL}}{25 \text{ mg/mL}} = 12 \text{ µL}$$

Calculate volume of diluent by subtracting the required volume of CD-CHO1 Protein Ref Std from the desired volume.

(Desired Volume)−(Ref Std volume)=(Diluent volume)     Formula:

Example: 10.0 mL-0.012 mL=9.988 mL Diluent

Add calculated volume of CD-CHO1 Protein Ref Std to a 15 mL sterile tube which contains calculated diluent volume. Cap tube and vortex at a setting between for 2-4 seconds. Prepare remaining standards. The table below is shown as an example:

| Working Concentration (ng/mL) | Volume (mL) | Diluent (mL) | Total Volume (mL) | Concentration (ng/mL) |
|---|---|---|---|---|
| 30,000 | 0.6 | 5.4 | 6.0 | 3,000 |
| 3,000 | 2.0 | 4.0 | 6.0 | 1,000 |
| 1,000 | 2.0 | 4.0 | 6.0 | 333.3 |
| 333.3 | 2.0 | 4.0 | 6.0 | 111.1 |
| 111.1 | 2.0 | 4.0 | 6.0 | 37.0 |
| 37.0 | 2.0 | 4.0 | 6.0 | 12.3 |
| 12.3 | 4.0 | 2.0 | 6.0 | 8.2 |
| NA | NA | 4.0 | 4.0 | 0 |

Cap tube following each dilution step and vortex gently for 2-4 seconds prior to proceeding to next dilution step.

Prepare Quality Control (QC) solutions using Teknova Diluent in 15 mL graduated sterile polypropylene tubes according to the dilution scheme below. Obtain protein concentration of the CD-CHO1 Protein Reference Material (Ref Mat) from the Certificate of Analysis (COA). Prepare a 30 µg/mL solution of CD-CHO1 Protein Reference Standard (Ref Mat). Cap tube and vortex at a setting between for 2-4 seconds. Prepare QC solutions at the concentrations of 700, 100, and 25 ng/mL. An example dilution scheme is shown below:

| | Working Concentration (ng/mL) | Volume (mL) | Diluent (mL) | Total Volume (mL) | Concentration (ng/mL) |
|---|---|---|---|---|---|
| QC 1 | 30,000 | 0.233 | 9.767 | 10.0 | 700 |
| QC 2 | 700 | 1.430 | 8.570 | 10.0 | 100 |
| QC 3 | 100 | 2.500 | 7.500 | 10.0 | 25 |

Cap tube for each QC solution and vortex gently for 2-4 seconds. Quality Control solutions can be prepared fresh on the day of the assay or they can be aliquotted and frozen. Determine the actual concentration of the three QC solutions in three independent experiments. Average the results from the three experiments for each QC solution and issue a COA for each of the three QC solutions. These experimentally determined QC concentrations are to be used as target values when performing analysis on CTLA4-Ig samples. Store QC solutions in ready to use aliquots at −70° C. QC solutions expire 6 months after preparation. Remove QC solutions from storage on the day of assay and thaw at room temperature. Vortex thawed QC solutions at medium speed for 2-4 seconds before use.

Sample Preparation. Prepare approximately a 12.5 mg/mL solution for each CTLA4-Ig sample to be analyzed in diluent by adding 250 µL drug substance sample to 750 µL diluent. Cap tube and vortex gently for 2-4 seconds. Prepare a 6.25 mg/mL solution for each CTLA4-Ig sample to be analyzed by adding 400 of the 12.5 mg/mL solution to a tube containing 400 µL of diluent. Cap tube and vortex gently for 2-4 seconds. Prepare a 3.125 mg/mL solution for each CTLA4-Ig sample to be analyzed by adding 400 of the 6.25 mg/mL solution to a tube containing 400 µL of diluent. Cap tube and vortex gently for 2-4 seconds. Wash Plate by repeating wash step. Add 100 µL per well of each standard concentration, samples, and QC solutions in triplicate to the blocked and washed plate. Each QC solution is added twice to a total of six wells per plate. Incubate for 1 hour in the dark (±6 minutes) at room temperature. Repeat wash 5 times. Remove Streptavidin-HRP from freezer and allow to come to room temperature. Dilute rabbit anti-CD CHO1-Biotin antibody to 2 µg/mL in Teknova Buffer. Vortex the solution approximately 2-4 seconds at medium speed. Using a multichannel pipette, add 100 µL per well. Incubate for 1 hour (±6 minutes) in the dark at room temperature. Dilute Streptavidin-HRP to the concentration established for use in the assay based on the qualification of the reagent lot as per department procedure. Cap and vortex the solution approximately 2-4 seconds at medium speed. Using a multichannel pipette, add 100 µL of Streptavidin-HRP dilution to each well. Incubate at room temperature in the dark for 1 hour (±6 minutes). Repeat. Using a multichannel pipette add 100 µL of TMB chromogen to each well. Incubate at ambient temperature for 2 minutes (±12 seconds). Using a multichannel pipette, add 100 µL/well of Stop Solution (1 N $H_2SO_4$). Add Stop Solution in the same order to plates and wells as the chromogen was added to ensure the same reaction times of chromogen with the enzyme in each well. Using a SpectraMax Plus plate reader, measure absorbance at 450 nm with a reference wavelength of 630 nm on an appropriate 96 well plate reader.

Data Evaluation. Refer to the Softmax program template as it generates mean, standard deviations and % CVs, etc. Determine each exemplary values using the triplicate absorbance values obtained for each reference, QC and sample dilutions assayed. Generate Standard Curve. Model reference standard data using a four-parameter regression of the form.

$$AB = \frac{\min - \max}{1 + \left(\frac{C}{ED_{50}}\right)^B}$$

Where:
AB=Absorbency at 450 nanometers
A=Absorbency value corresponding to the minimal asymptote
D=Absorbency value corresponding to the maximal asymptote
c=Concentration corresponding to one half the absolute difference between the maximal and minimal asymptotic values B=the approximated slope of the linear portion of the curve x=Concentration of CD-CHO1 reference material Determine the coefficient of determination ($R^2$) of the regression line for the standards using the calculated mean using the formula above. Calculation of CD-CHO1 concentration in samples. Multiply the mean sample results by the appropriate dilution factor (i.e. 4, 8, and 16) to obtain the concentration of CD-CHO1 in the original sample in ng/ml. Divide the results by the reported CTLA4-Ig protein concentration (mg/ml) to obtain the concentration of CD-CHO1 in ng/mg of CTLA4-Ig. Determine the mean of the all of the results, which fall within the range of the standard curve. Calculate the CD-CHO1 protein concentration in the undiluted sample by applying the dilution factor. To determine the CD-CHO1 protein concentration relative to the CTLA4-Ig sample concentration divide by the undiluted concentration.

Example Calculation:

$$\frac{\text{Mean Sample Result}}{BMS-188667\ \text{Concentration}} = \frac{235\ ng\ CD\ CHOP/\text{mL}}{50\ \text{mg/mL}} = 4.7\ ng/\text{mg}$$

Note: ng CD CHO1 mg product (ng/mg) is equivalent to parts per million (ppm).

Exemplary values. Exemplary values for the Standards. The coefficient of determination ($R^2$) for the Standard Curve should be ≥0.99. The mean background for the zero ng/mL Standard should be ≤0.10 absorption units. The mean of the calculated values (ng/mL) at each standard concentration used to determine the Standard Curve, excluding zero and concentrations below QL (12.3 ng/mL), must be within 20% of the target (nominal) value, as determined by the software. The coefficient of variation (% CV) of the triplicate absorbance values at each Standard concentration used to determine the Standard Curve, excluding zero and concentrations below QL (12.3 ng/mL), must be less than 20%, as determined by the software. To ensure that at lease two congruent data points are available for calculation, the standards, quality controls, and samples are loaded in triplicate wells. Analyze each triplicate value separately. Drop the value that lies furthest from the target.

Example:

| Target Value (ng/mL) | Actual Value (ng/mL) |
| --- | --- |
| 50 | 25 |
|  | 48 |
|  | 49 |

The single value that is furthest from the target value of 50 ng/mL is 25 ng/mL. By eliminating the 25 ng/mL value from the triplicate, the mean of the remaining values meet all of the exemplary values.

If it is shown that the mean of the remaining two values still do not meet the exemplary values, then the single point is eliminated and the curve is recalculated.

Example:

| Target Value (ng/mL) | Actual Value (ng/mL) |
| --- | --- |
| 50 | 10 |
|  | 10.5 |
|  | 25 |

The mean value is ≥20% from the target regardless of which value is eliminated, therefore, the single point is dropped from the curve and the curve will be recalculated. Only 2 points on the standard curve may be eliminated.

Exemplary values for QC Samples. A QC sample is defined as a set of three wells at the stated concentration, therefore, for the three nominal concentrations stated in this method there are a total of six QC samples. At least two of the three wells for a QC sample must be within 20% of the nominal for the QC sample to be acceptable. At least four of the six QC samples must be within 20% of their respective target concentrations; two of the six QC samples (not two at the same concentration) may exceed the 20% deviation from nominal, as calculated by the software. Not more than 6 of the 18 QC sample wells may deviate more than 20% of the respective target concentrations.

Exemplary values for Test Samples. The average absorbance for the test sample assayed must be less than the highest point on the standard curve. If the average absorbance of the sample exceeds the average absorbance 3000 ng/mL standard, the test sample must be diluted sufficiently so as to obtain a mean absorbance between 3000 and 12.3 ng/mL. The average absorbance of at least one of the three sample dilutions (12.5, 6.25 and 3.125 mg/ml) must fall within the range of the standard curve for a reportable result, unless the average absorbance for all dilutions are below the average absorbance of the QL (12.3 ng/mL standard). In that case the test samples are reported as <QL. The mean of the triplicate absorbance values of the Sample dilutions that are greater than the QL and fall within the range of the standard curve must exhibit a CV of less than 20%, as determined by the software. If upon elimination of one of the triplicate absorbance and recalculation the CV is still ≥20% or if two Sample dilutions have CV's for the absorbance greater then 20% and fall within the range of the standard curve the analysis this Sample must be repeated.

Example 61—Assay for Residual Amount of Triton X-100 in CTLA4-Ig Composition

Materials

| | |
| --- | --- |
| HPLC Vials | Waters, Total Recovery Vial Kit, Screw Cap with bonded preslit PTFE/Silicone Septa (Catalog 186000385) Note: Glass vials are required |
| Solid Phase Extraction Tubes | Waters OASIS HLB, 30 mg/lcc, (Catalog No. WAT094225) |
| Column | Thermo Electron Corp. SAS Hypersil, 5µ, 4.6 × 250 mm (Part Number 30505-254630) |

| Instrumentation | |
| --- | --- |
| Liquid Chromatograph | Waters 2695 Separations Module |
| Detector | Waters 2487 Dual Wavelength UV Detector |
| SPE Column Processor | JT Baker Vacuum Manifold, Model Spe-21 |
| Analytical Balance | Any balance capable of accurately weighing 0.01 mg |
| Integration | Waters Empower Data System |

Preparation of Reagents

Mobile Phase Preparation: Acetonitrile: Water(80:20). For 1 L, thoroughly mix with a stir bar, 800 mL of acetonitrile and 200 mL of purified or HPLC grade water. Filter through a 0.2 µm nylon filter. Degas mobile phase using an inline degasser such as an Alliance system, or using helium sparge. Prepare fresh daily.

2N NaOH. Weigh, and quantitatively transfer 80±1 g of solid NaOH to a 1 L flask. Bring to volume with purified or HPLC grade water. Mix well with stir bar and filter through a 0.22 µm filter apparatus. Alternatively, serial dilute 10N NaOH solution. Store up to 6 months at room temperature.

Drug Substance Buffer. Weigh and quantitatively transfer 3.45 g $NaH_2PO_4 \cdot H_2O$ and 2.92 g NaCl to a 1 L flask. Add approximately 800 mL of purified or HPLC grade water. Mix well with a stir bar, and bring to volume with purified or HPLC grade water. Adjust pH to 7.5 with 2N NaOH. Filter solution through a 0.22 µm filter unit. Store up to 4 months at 4° C.

Preparation of Standard Sample Blank. Any CTLA4-Ig sample or reference material previously analyzed and found not to contain detectable levels of Triton X-100 may be used as the Sample Blank. The Sample Blank protein should be run along with the samples(s). Triton X-100 dissolves slowly in water. Examine the solution for complete dissolution (typically after 15 minutes) before use. Triton X-100 is more viscous than water, so undissolved amounts are visible in the presence of water.

Preparation of 10.0 µg/mL Triton X-100 Stock Standard #1. Accurately weigh 10.0±1.0 mg Triton X-100 into a 100 mL volumetric flask and dilute to volume with water; and mix gently with a stir bar. Label as TX100 Stock Standard A. Take 10 mL of TX100 Stock Standard A into a 100 mL volumetric flask. Dilute to volume with water. Label as TX100 Stock Standard #1. Prepare fresh daily.

Preparation of 10.0 µg/mL Triton X-100 Stock Standard #2. Accurately weigh 10.0±1.0 mg Triton X-100 into a 100 mL volumetric flask and dilute to volume with water; and mix gently with a stir bar. Label as TX100 Stock Standard B. Take 10 mL of TX100 Stock Standard B into a 100 mL volumetric flask. Dilute to volume with water. Label as TX100 Stock Standard #2. Prepare fresh daily.

Preparation of TX100 System Suitability Evaluation Solution #1 (SS#1). From TX100 Stock Standard #1 prepare a 5.0 µg/mL TX100 System Suitability Evaluation Solution by diluting 300 µL of TX100 Stock Standard #1 with 300 µL of acetonitrile. Mix well by pipetting up and down.

Preparation of TX100 System Suitability Evaluation Solution #2 (SS#2). From TX100 Stock Standard #2 prepare a 5.0 µg/mL TX100 System Suitability Evaluation Solution by diluting 300 µL of TX100 Stock Standard #1 with 300 µL of acetonitrile. Mix well by pipetting up and down.

Preparation of TX100 Pass Control, Limit Standard, Fail Control. From the TX Stock Standard #1, prepare the solution identified in Table below.

| Solution Identification | Dilution Procedures |
| --- | --- |
| Pass Control (0.4 µg/mL) | Dilute 20 µL with 480 µL of CTLA4-Ig DS |
| Limit Standard (0.5 µg/mL) | Dilute 25 µL with 475 µL of CTLA4-Ig DS |
| Fail Control (0.6 µg/mL) | Dilute 30 µL with 470 µL of CTLA4-Ig DS |

Preparation of Sample. The sample is used without concentration or dilution. Procedure: Extraction of Triton X-100 from Standard and Sample Solution. CAUTION: The extraction steps described below are performed under a vacuum of 3-3.5 inches Hg.

Activation of the Solid Phase Extraction (SPE) Media. Lift the lid of the vacuum manifold and place empty 12×75 mm test tubes in the rack inside the manifold. These are "waste" test tubes. Replace the lid and place SPE cartridges on the vacuum manifold, making sure that there is a "waste" test tube underneath each SPE tube. Add 1000 µL of acetonitrile to each SPE cartridge, and apply vacuum until all the acetonitrile has passed through the media bed. Repeat with an additional 1000 µL of acetonitrile. Add 500 µL of purified or HPLC grade water to each SPE cartridge and apply vacuum until all water has passed through the media bed. Repeat with an additional 500 µL of purified or HPLC grade water.

Concentration of Triton X-100 on the SPE Media for the Limit Standard and Controls. Pipette 500 µL each of the Limit Standard, Pass Control, Fail Control Blank, and samples into separate, activated SPE cartridges. Apply vacuum to the SPE tubes until each solution has completely passed through the media bed.

Removal of Residual Protein from the SPE Bed. Add 1000 µL of water to each SPE cartridge, and apply vacuum to the tubes until the water has passed through the media bed. Repeat step with an additional 1000 µL of water.

Elution of Triton X-100 from the SPE bed Turn off the vacuum to the manifold to release the unit pressure to zero. Gently lift the lid of the manifold, with the SPE cartridges still attached. Replace the "waste" test tubes with a set of pre-labeled "eluate" test tubes or autosampler vials (prelabeled limit standard, pass control, fail control, blank, and samples) to collect any Triton X-100 that elutes from the SPE beds. Replace the lid of the manifold, making sure that each limit standard, pass control, fail control, blank, and samples SPE cartridge has a respective eluate test tube, or autosampler vial underneath. Add 500 µL acetonitrile to each SPE cartridge, and apply vacuum to the tubes until all the acetonitrile has passed through the media bed. Turn off the vacuum to the manifold, and lift the lid to retrieve the eluate test tubes, or autosampler vials. If using eluate test tubes, place the acetonitrile eluates of the limit standard, pass control, fail control, blank, and samples into autosampler vials for injection into the chromatographic system. If using autosampler vials to collect the eluate, place the vials directly into the chromatographic system.

| Run Conditions | |
| --- | --- |
| Wavelength | 225 nm |
| Sensitivity | 0.1 AUFS |
| Mobile Phase | Acetonitrile:water (80:20) |
| Flow Rate | 0.8 mL/min |
| Injection Volume | 25 µL |
| Column Temperature | Ambient (20-25° C.) |
| Approximate Retention Time | Triton X-100: 5.0 ± 1 minute |
| Total Run Time | 10 minutes |
| Autosampler Temperature | 10 ± 4° C. |

System Suitability. Set up the chromatographic system; allow lamp to warm up and system to equilibrate with mobile phase for at least one hour prior to analysis. Inject SS #1 a minimum of four times. Use the second SS #1 injection for all system suitability analyses, unless otherwise specified. The retention time for Triton X-100 should be 5.0±1 minutes. The efficiency of the column for Triton X-100, evaluated as the number of theoretical plates (N), must be ≥2000 plates/column when calculated according to the following equation:

$$N = 16\left(\frac{t}{w}\right)^2$$

Where:
t=retention time of Triton X-100 peak measured from time of injection to time of elution of peak maximum.
w=width of the Triton X-100 peak measured extrapolating the sides of the peak to the baseline.

The resolution between the Triton X-100 peak and the nearest adjacent peak (if present) must be ≥1.

$$R = \frac{2(t_2 - t_1)}{W_1 + W_2}$$

Where:
t=retention times of the Triton X-100 peak and the adjacent peak in the standard.
W=corresponding widths of the bases of the peaks obtained by extrapolating the sides of the peaks to the baseline.

Calculate the response factors of the last three SS#1 injections using the following equation:

$$RF = \frac{A}{W}$$

Where:
A=Area of Triton X-100 peak
W=Weight of Triton X-100 (in mg) used in the preparation of the corresponding TX100 stock standard solution The response factors of the last three injections of SS#1 must have a relative standard deviation (RSD) of ≤10%. Calculate the % RSD using the following equation:

$$\% \; RSD = \frac{\text{Standard Deviation}}{\text{Mean}} \times 100$$

$$\text{Standard Deviation} = \sqrt{\frac{n\Sigma x^2 - (\Sigma x)^2}{n(n-1)}}$$

Where:
n=number of measurements in the sample
x=individual measurements

Compare the response factor of the single injection of SS#2 to the average response factor of the last three injections of SS#1. The percent difference between the SS#2 response factor and the average response factor of the three SS#1 injections must be 10%. Calculate the percent difference using the following equation.

$$\% \; \text{Difference} = \left| \left[ \frac{RF_1 - RF_2}{RF_1} \right] \times 100 \right|$$

Where:
RF1=Average response factor of the three SS#1 injections
RF2=Response factor of SS#2

Make a single injection of Sample Blank post-SPE. If Triton X-100 levels are found, make two more injections of the Sample Blank. If Triton X-100 is present discard the CTLA4-Ig Drug Substance and make new Limit Standard, and Controls with a new lot of CTLA4-Ig Drug Substance previously analyzed and found to contain no detectable levels of Triton X-100. If the above exemplary values are not met, extend the equilibration of the column for another hour and reinject the standard solution. If the exemplary values are still not met, execute the following steps. Check for leaks making sure all tubing connections are secure. If extended equilibration does not work, adjust the organic content of the mobile phase and/or make a new batch of the mobile phase, and re-prepare the SS#1 and SS#2. Change the column if extended equilibration and/or mobile phase adjustment do not result in the exemplary values being met. Before repeating equilibrate for at least one hour.

Injection Sequence. Preliminary equilibration of HPLC system and successful running of above. Make a single injection of drug substance buffer post-SPE, refer to section above as a calibration blank. Observe that there is no Triton X-100 response. If a peak is present at the retention time of the Triton X-100 peak, continue to inject the blank until no response is noted. Make a single injection of CTLA4-Ig drug substance post-SPE, refer to section above as a sample blank. Observe that there is no Triton X-100 response. This chromatogram will be subtracted from the standard, control and sample chromatograms before data processing is performed. Make duplicate injections of the Pass Control, Limit Standard, an Fail Control. Make a single injection of the drug substance buffer, and no triton X-100 response must be noted. Make duplicate injections of the samples. The sample injections are bracketed by duplicate injections of Limit Standard and one injection of the drug substance buffer so that, there are no more than 10 sample injections between bracketing Limit Standard and Drug Substance injections. The end of the run must be completed with duplicate injections of the Limit Standard, and one injection of the drug substance buffer blank.

Data Processing. Subtract the chromatogram of the Sample Blank injection from all standard, control, and sample chromatograms before proceeding with data processing. Assure the Triton X-100 peak in the Limit Standard, Control, and sample chromatograms are properly integrated. The Triton X-100 peak in the sample, if present, must be within the same retention time window as the Limit Standard. Average the peak area of each set of duplicate injections. Duplicate injections must have a % difference in peak area of ≤10%. If a duplicate injection of the Limit Standard, Pass Control, or Fail Control do not meet this criterion, the entire run is considered invalid and will need to be repeated. If the duplicate injections of the sample fail do not meet this criterion, the sample is considered invalid and will need to be repeated. All other samples, control, and standards are considered valid as long as they meet the ≤10% criterion. The averaged peak area for the Triton X-100 peak in all bracketing Limit Standards, including the final injections, must be within 10% of the initial averaged peak area of the Limit Standard. If any intermediate Limit Standard fails to meet the 10% comparison requirement, all samples analyzed after the last passing Limit Standard are considered invalid and must be reanalyzed.

Evaluation of Limit Standard, Pass Control, Fail Control Samples. Compare the averaged Triton X-100 peak areas for the Limit Standard, Pass Control, and Fail Control. The peak area of the Fail Control sample must be greater than that of the Limit Standard. The peak area of the Pass Control sample must be less than that of the Limit Standard. If both conditions are met, continue on to the evaluation of the samples.

Evaluation of Samples. The averaged Triton X-100 peak area of the Limit Standard must be corrected to account for the amount of material weighed in the preparation of Triton X-100 Stock Standard #1, as follows:

$$A_L = A_{LS} X(10.00 \; mg/Wt.)$$

Where:

$A_L$=Peak area corrected to 0.5 µg/mL limit $A_{LS}$=Averaged Triton X-100 peak area of bracketing Limit Standards Note: $A_L$ is the corrected area at the 0.5 µg/mL limit and will be used for comparison to samples.

Compare the average Triton X-100 peak area from the sample to $A_L$. If peak area ≤$A_L$, sample passes specification. If peak area >$A_L$, sample fails specification. Report the results passing specification as "<0.50 ppm" or failing specification as ">0.50 ppm" or as otherwise required by reporting convention.

Example 62—Assay to Quantitate the Amount of Residual Protein A in CTLA4-Ig Drug Substance Material

| Materials | |
|---|---|
| Rabbit anti-Protein A Antibody | Sigma, (Catalog No. P3775) |
| Biotinylated anti-Protein A monoclonal antibody | Sigma, (Catalog No. B3150) |

Reagents

Carbonate Coating Buffer. To a suitable vessel add; Add a stir bar. Add 500 mL of HPLC grade, or Millipore, water. Add contents of 5 carbonate capsules. Stir until well mixed. Check and adjust pH to 9.6±0.1 using NaOH (1.16) or HCl (1.23). Pour solution into a 500 mL filter sterilization system. Apply a vacuum to filter sterilize the solution. Under aseptic conditions remove filter unit and cap bottle. The solution is stable for 30 days when stored at 2-8° C. Label the solution as "Carbonate Coating Buffer". Wash buffer: (PBS+0.05% Tween 20): To a 4 L bottle of HPLC grade, or Millipore, water add; Add a stir bar. Add 20 PBS tablets. Add 2.0 mL of Tween 20. Check and adjust pH to 7.4±0.1 using NaOH or HCl. Using a stir plate, stir until well mixed. The solution is stable for 30 days when stored at 2-8° C. Label the solution as "Wash Buffer". Stop Solution (1 N $H_2SO_4$) or use 1.000 Normal Sulfuric Acid from VWR without diluting. In a fume hood place a suitable container onto a stir plate: Add a stir bar Add 485.6 mL of HPLC grade, or Millipore, water. Turn on stir plate to start stirring of water. Slowly add 14.4 mL of concentrated $H_2SO_4$. The solution is stable for 30 days when stored at room temperature. Label the container as "Stop Solution".

Acetate Buffer (0.5M Acetic Acid, 0.1M Sodium Chloride, 0.1% Tween 20, pH 3.5). In a fume hood place a suitable container onto a stir plate: Add a stir bar. Add 400 mL of HPLC grade, or Millipore, water. Turn on stir plate to start stirring of water. Slowly add 14.8 mL of concentrated Glacial Acetic Acid. Stir until well mixed. Add 2.9 g Sodium chloride. Stir until well mixed. Check and adjust pH to 3.5±0.1 using NaOH or HCl. Add 0.5 mL Tween 20. Stir until well mixed. Adjust to a final volume of 500 mL with HPLC grade, or Millipore water. Stir until well mixed. The solution is stable for 30 days when stored at 2-8° C. Label the container as "Acetate Buffer."

Rabbit anti-Protein A Antibody. Remove vial from the refrigerator and allow to come to room temperature. Add 2.0 mL of HPLC grade, or Millipore, water. Aliquot 20 µL volumes to 0.5 mL screw cap tubes. Cap and place in a Cell Storage Box. The solution is stable for 365 days when stored at –20° C. Biotinylated anti-Protein A Antibody Remove vial from the refrigerator and allow to come to room temperature. Add 1.0 mL of HPLC grade, or Millipore water. Aliquot 60 µL volumes to 2.0 mL screw cap tubes. Cap and place in a Cell Storage Box. The solution is stable for 365 days when stored at –20° C.

Streptavidin-HRP. Add 0.5 mL of HPLC grade, or Millipore, water to a vial of Streptavidin-HRP. To mix, cap vial and vortex gently for approximately 10 seconds. Add 0.5 mL of glycerol to the vial of Streptavidin-HRP. Cap vial and gently invert vial several times. Check solution clarity by drawing solution into a clean pasteur pipette. Aliquot 20 µL volumes to 0.5 mL screw cap tubes. Cap and place in a Cell Storage Box. The solution is stable for 365 days when stored at –20° C.

Preparation of Standard. Obtain protein concentration of the Protein A Reference Material (ref mat) from the Certificate of Analysis (COA). Prepare a 11,500 ng/mL solution of Protein A ref mat, by thawing out the stock Protein A solution at room temperature. Calculate required volume of Protein A ref mat to obtain a 11,500 ng/mL solution. Minimum transfer volume should be 10 µL.

$$\text{Formula: Volume} = \frac{\text{Desired Concentration} \times \text{Desired Volume}}{\text{Reference Material Concentration}}$$

Note: Ensure units are compatible.

$$\frac{2.3 \text{ µg/mL} \times 10 \text{ mL}}{0.25 \text{ mg/mL}} = 92 \text{ µL}$$

Example:

Calculate volume of Acetate buffer (3.4) by subtracting the required volume of Protein A ref mat from the desired volume.

Formula: (Desired Volume)−(Ref Std volume)=(Diluent volume)

Example: 10.0 mL−0.920 mL=9.180 mL Diluent

Add calculated volume of Protein A ref mat to a 15 mL sterile tube which contains calculated Acetate Buffer volume. Cap tube. Gently vortex (setting 4 on Vortex Genie 2) for 2-4 seconds. Prepare remaining standards using volumes defined below:

| Working Concentration (ng/mL) | Working Conc. Volume (mL) | Acetate Buffer (mL) | Total Volume (mL) | Final Concentration (ng/mL) |
|---|---|---|---|---|
| 2,300,000 (2.3 mg/mL) | 0.010 | 1.990 | 2.0 | 11,500 |
| 11,500 | 0.010 | 4.780 | 4.790 | 24.0 |
| 24.0 | 2.0 | 2.0 | 4.0 | 12.0 |
| 12.0 | 2.0 | 2.0 | 4.0 | 6.00 |
| 6.00 | 2.0 | 2.0 | 4.0 | 3.00 |
| 3.00 | 2.0 | 2.0 | 4.0 | 1.50 |
| 1.50 | 2.0 | 2.0 | 4.0 | 0.75 |
| 0.75 | 2.0 | 2.0 | 4.0 | 0.375 |
| 0.375 | 2.0 | 2.0 | 4.0 | 0.188 |
| N/A | N/A | 2.0 | 2.0 | 0 |

Cap tube following each dilution step and vortex gently for 2-4 seconds prior to proceeding to next dilution step. Incubate Reference Standard and Quality Control samples for 10 minutes at room temperature before addition to microtiter plate. Each Standard concentration is analyzed in triplicate wells.

Preparation of Test Samples. Prepare concentrations of 5 mg/mL, 2.5 mg/mL and 1.25 mg/mL of the CTLA4-Ig test samples in polypropylene tubes using Acetate buffer. Thaw CTLA4-Ig sample at room temperature before using to prepare dilutions. Calculate required volume of test sample to obtain a 5.0 mg/mL solution. Minimum transfer volume should be 10 µL.

$$\text{Formula Volume} = \frac{\text{Desired Concentration} \times \text{Desired Volume}}{\text{Test Sample Concentration}}$$

Example:

$$\frac{5.0 \text{ mg/mL} \times 1.0 \text{ mL}}{25 \text{ mg/mL}} = 200 \text{ µL}$$

5.1.3 Calculate volume of Acetate buffer by subtracting the required volume of test sample from the desired volume.

(Desired Volume)−(test sample volume)=(Diluent volume)   Formula:

1.0 mL−0.200 mL=0.800 mL Diluent   Example:

Add calculated volume of test sample to a 15 mL sterile tube which contains calculated Acetate Buffer volume. Cap tube and gently vortex (setting 4 on Vortex Genie 2) for 2-4 seconds. est samples are incubated for 10 minutes at room temperature before adding to microtiter plate.

Preparation of Quality Control Samples. Obtain protein concentration of the Protein A Reference Material from the COA. Prepare a 11,500 ng/mL solution of Protein A ref mat. Prepare Quality Control (QC) samples as described in the table below.

| Working Concentration (ng/mL) | Working Conc. Volume (mL) | Acetate Buffer (mL) | Total Volume (mL) | Final Concentration (ng/mL) |
|---|---|---|---|---|
| 2,300,000 (2.3 mg/mL) | 0.010 | 1.990 | 2.0 | 11,500 |
| 11,500 | 0.010 | 4.780 | 4.790 | 24.0 |
| 24.0 | 0.8333 | 3.166 | 4.0 | 5.0 (QC1) |
| 5.0 | 1.6 | 2.4 | 4.0 | 2.0 (QC1) |
| 2.0 | 1.0 | 3.0 | 4.0 | 0.5 (QC1) |

Aliquot 700 µL volumes to 2.0 mL screw cap tubes. Cap and place in a Cell Storage Box. The solution is stable for 180 days when stored at −70° C. or below. The Protein A concentrations in the QC samples are to be pre-determined by: Performing 3 independent Protein A ELISA assays using this method. The 18 results (3 independent assays times 6 wells per assay) will be averaged. The Protein A concentration for each QC sample will be assigned to each preparation. On the day of an experiment, thaw one vial of each QC samples at room temperature, or make QC samples fresh from stock vial of Protein A. Vortex gently (setting 4 on Vortex Genie 2) for 2-4 seconds.

Procedure. Plate Coating with Capture Antibody. Obtain protein concentration of the Rabbit anti-Protein A Antibody from the manufacturers COA. Calculate required volume of Rabbit anti-Protein A Antibody to obtain 10 mL of a 100 µg/mL solution. Minimum transfer volume should be 10 µL.

$$\text{Formula Volume} = \frac{\text{Desired Concentration} \times \text{Desired Volume}}{\text{Antibody Concentration}}$$

Note: Ensure units are compatible.
Example:

$$\frac{100 \text{ µg/mL} \times 3 \text{ mL}}{25 \text{ mg/mL}} = 12 \text{ µL}$$

Calculate volume of Diluent by subtracting the required volume of Rabbit anti-Protein A Antibody from the desired volume.

(Desired Volume)−(Antibody Volume)=(Diluent Volume)   Formula:

3.0 mL−0.012 mL=2.988 mL Diluent   Example:

Add calculated volume of Rabbit anti-Protein A Antibody to a 15 mL sterile tube, which contains calculated diluent volume. Cap tube and vortex gently for 2-4 seconds. Prepare a 1 µg/mL solution of rabbit anti-Protein A antibody in Coating Buffer, using the formulas. Add 100 µl of the solution to each well of an Immulon IV microtiter plate. Incubate at 2-8° C. for 18±2 hours. Wash plates three times with Wash Solution using the plate washer with 300 µL wash buffer and zero soak time. The plates may alternatively be washed using a multi channel pipette. Using a multichannel pipette add 200 µL of SuperBlock™ to each well. Incubate the microtiter plate in the dark for 60 minutes at room temperature. Repeat wash. Add 100 µL of each Reference Standard, Quality Control and test samples to assay plate. Incubate the microtiter plate in the dark for 60 minutes, ±10 minutes, at room temperature. Repeat wash. Obtain protein concentration of the Biotin anti-Protein A Antibody from the manufacturers COA. Prepare 1.0 mL of a 1.0 mg/mL solution of Biotin anti-Protein A Antibody in diluent. Vortex at medium speed. Add 50 µL of 1 mg/mL solution (7.9.1) to 0.950 mL of diluent. Vortex at medium speed. Add 150 µL of 50 µg/mL solution (7.9.3) to 14.850 mL of diluent. Add 100 µL to each well using a multichannel pipettor. Incubate at room temperature for 60 minutes ±10 minutes. Repeat wash. Dilute Streptavidin-HRP as follows: Add 10 µL of Streptavidin-HRP to 0.990 µL of Diluent to yield 0.01 mg/mL Streptavidin-HRP. Vortex at medium speed. Add 80 µL of 0.01 mg/ml Streptavidin-HRP to 39.920 mL of Diluent. Vortex at medium speed. Add 100 µL to each well using a multichannel pipettor. Incubate for 30 minutes, ±5 minutes, at room temperature. Remove TMB from refrigerator and decant a minimum of 10 mL per plate of TMB into a suitable container. Place in a dark location and allow to come to room temperature. Repeat wash, but wash five times. Add 100 µL TMB chromogen to each well. Incubate at room temperature for approximately 2 minutes, ±1 minute. Stop chromogen reaction by adding 100 µL/well of Stop Solution. Add Stop Solution in the same order to plates and wells as the chromogen was added to ensure the same reaction times of chromogen with the enzyme in each well. Measure absorbance (AB) at 450 nm with a reference wavelength of 630 nm.

Exemplary values. Exemplary values for the Standard Curve. The exemplary values for the standards applies to those values at or above the quantitative limit (QL), as values below the QL are used only to help establish the extremes of the curve. The coefficient of determination ($R^2$)

for the standard curve should be ≥0.99, as determined by the SoftMax PRO software. The mean background for the zero ng/mL standard should be ≤0.08 absorption units. The mean of the calculated values (ng/mL) at each standard concentration used to determine the standard curve except zero and the QL must be within 15% of the target (nominal) value, as determined by the software. The coefficient of variation (% CV) of the triplicate $AB_{450}$ values at each standard concentration used to determine the standard curve, excluding zero and QL must be ≤15%, as determined by the software. The mean of the triplicate absorbance values of the QL of the standard curve must exhibit a % CV of less than 20% and be within 20% of target, as determined by the software. To ensure that at lease two congruent data points are available for calculation, the standards, controls and samples are loaded in triplicate wells. Each value of the triplicate used to calculate the mean will be analyzed separately.

For example:

| Target Value (ng/mL) | Actual Value (ng/mL) |
|---|---|
| 2.5 | 1.2 |
|  | 2.3 |
|  | 2.5 |

The single value that is furthest from the target value of 2.5 ng/mL is 1.2 ng/mL. By eliminating the 1.2 ng/mL value from the triplicate, the mean of the remaining values meet all of the exemplary values. If, upon re-calculation, another point does not meet the exemplary values, then the assay is not valid and must be redone. If it is shown that the mean of the remaining two values still do not meet the exemplary values, then the single point (all 3 wells) is eliminated and the curve is re-calculated.

Exemplary values for QC Samples. A QC sample is defined as a set of three wells at the stated concentration, therefore, for the three nominal concentrations stated in this method there are a total of six QC samples (for a total of 18 wells). At least two of the three wells for a QC sample must be within 20% of the nominal for the QC sample to be acceptable. At least four of the six QC samples must be acceptable; two of the six QC samples (not two at the same concentration) and not more than 6 of the 18 QC sample wells may deviate more than 20% of the respective target concentrations.

Exemplary values for Test Samples. Each of the values of the triplicate of the test sample assayed must be within 20% of the mean value at that concentration, as determined by the software. If two or more mean $AB_{450}$ values cannot be calculated because they lie above the highest point on the standard curve, then the sample must be re-assayed at higher dilutions until at least two of the three values fall on the standard curve. The % CV of the triplicate observations obtained for each test sample target concentration must be ≤20%, as determined by the software.

Calculations. Refer to the SoftMax program template for the Protein A ELISA as it generates mean, standard deviations and % CV. Average the triplicate Absorbance (AB) values obtained for each reference and sample concentration assayed. Model the data for the Protein A standards using an unweighted four parameter regression of the form:

$$AB = \frac{min - max}{1 + \left(\frac{C}{ED_{50}}\right)^B}$$

Where:
min=AB value corresponding to the minimal asymptote
max=AB value corresponding to the maximal asymptote
$ED_{50}$=AB corresponding to one half the absolute difference between the maximal and minimal asymptotic values
B=the approximated slope of the linear portion of the curve
C=Concentration of Protein A Calculation of Protein A concentration in samples. Multiply the mean sample results by the appropriate dilution factor (i.e. 2, 4, and 8), to obtain the concentration of Protein A in the original sample in ng/mL. Divide the results by the reported CTLA4-Ig protein concentration (mg/mL) to obtain the concentration of Protein A, in ng/mg, in CTLA4-Ig.

Example Calculation:

$$\frac{\text{Mean Sample Result}}{\text{Abatacept Concentration}} = \frac{235 \text{ ng Protein } A/mL}{50 \text{ mg/mL}} = 4.7 \text{ ng/mg}$$

Note: ng Protein A/mg CTLA4-Ig (ng/mg) is equivalent to parts per million (ppm).

Calculations for the Concentration of Protein A in Ng/mL of Samples. The amount of Protein A in the test samples is calculated using current SoftMax software using the regression equation. Three dilutions of each sample are assayed. The calculated concentration is multiplied by the appropriate dilution factor to give the concentration in the initial test sample.

Example:
The concentration of the test sample is 50 mg/mL.

| Sample Dilution | Dilution Factor |
|---|---|
| 5 mg/mL | 10 |
| 2.5 mg/mL | 20 |
| 1.25 mg/mL | 40 |

5 mg/mL sample—ELISA data determines concentration of Protein A is 10 ng/mL
10 ng/mL×10 (dilution factor)=100 ng/mL Protein A in the test sample
2.5 mg/mL sample—ELISA data determines concentration of Protein A is 5.0 ng/mL
5 ng/mL×20 (dilution factor)=100 ng/mL Protein A in the test sample
1.25 mg/mL sample—ELISA data determines concentration of Protein A is 2.5 ng/mL
2.5 ng/mL×40 (dilution factor)=100 ng/mL Protein A in the test sample
Calculate the mean concentration from the three values.
Reporting of Results. Results may be reported in terms of "% w/w Total Protein, ng Protein A/mg Total Protein", otherwise referred to as "ppm" (w/w).

0.0001% w/w=1 ng/mg=1 ppm (w/w)   Example:

Example Calculation:

$$\frac{0.0001 \text{ mg/mL Protein } A}{50 \text{ mg/mL Test Sample}} \times 100\% = 2 \text{ ng/mg} = 2 \text{ ppm}$$

Samples which result in an $AB_{450}$ value smaller than the $AB_{450}$ of QL (0.188 ng/mL) should be reported as "less than QL." Samples which result in an $AB_{450}$ value larger than the $AB_{450}$ of QL (0.188 ng/mL) should be reported to the nearest whole number as parts per million (ppm).

Example:
Sample concentration is 50 mg/mL. The highest sample concentration analyzed is 5 mg/mL (1/10 dilution). The $AB_{450}$ of the sample is smaller than QL.

$QL = 0.188$ ng/mL $\leq 0.188$ ng/5 mg $\leq 0.04$ ng/mg

Report as "$\leq$, QL=0.04 ppm"

Example 63: Methods to Obtain Molar Ratios of Amino Monosaccharides (N-Acetyl Galactosamine, N-Acetyl Glucosamine) to Protein in CTLA4-Ig Drug Substance Samples Reagents Hydrolysis Solution (4 N HCl aqueous solution). Add 160 mL of 6 N HCl and 80 mL of HPLC grade water to a 250 mL glass bottle. Stir to mix well. Store at 2-8° C. for up to 6 months. Derivatization Solution I (0.1 M APTS aqueous solution). Add 192 µL of HPLC grade water to 10 mg powder of APTS in a glass vial. Vortex the vial 5-10 seconds to completely dissolve the APTS. Store at −20° C. for up to one year.

Derivatization Solution II (1 M acetic acid and 0.25 M NaBH$_3$CN). Dilute 20 µL acetic acid with 320 µL HPLC grade water (17 fold dilution) in a 0.4 mL centrifuge tube to make a 1 M acetic acid solution. Weigh 2.0±0.5 mg of NaBH$_3$CN into a cryogenic vial. Using the following formula, add an appropriate volume of the 1 M acetic acid solution to make 0.25 M NaBH$_3$CN. Volume (µL)=$10^3 \times$ (weight of NaBH$_3$CN in mg)/(62.84 g/mol×0.25 mol/L). Note: Prepare immediately before use. Sodium cyanoborohydride (NaBH$_3$CN) should be stored in dark in a desiccator. Subdividing of the reagent into a series of 2.0 mL cryovials for storage is recommended to avoid repeated opening of the original reagent bottle as follows: Weigh 1.0 g±0.2 mg of Sodium Cyanoborohydride into 2.0 mL cryovial. Aliquot out the entire contents of Sodium Cyanoborohydride from the original bottle in this manner. Cap tightly and label cryovials sequentially (1, 2, 3, etc.) along with reagent name, lot number, and a 6 month expiration date. The vials should be sealed with parafilm to avoid moisture. Weigh out Sodium Cyanoborohydride for Derivatization Solution II no more than three times from the same cryovial. Make note of this and the cryovial sequence number on the lab worksheet. Either a reagent peak observed in the CE profile or poor labeling may occur after repeated opening of the cryovial or with that particular lot of Sodium Cyanoborohydride. If this effects the results, discard the cryovial being used and either weigh out reagent from a cryovial with the next sequence number or from a new lot of Sodium Cyanoborohydride.

Re-acetylation Buffer (25 mM sodium bicarbonate, pH 9.5). Weigh 0.210±0.02 g of sodium bicarbonate into a clean 100 mL clean glass beaker. Add 90 mL of HPLC grade water, and mix on a stir plate until salts are completely dissolved. Adjust the pH to 9.5±0.1 with 10 N NaOH. Add HPLC grade water to make the final volume 100 mL. Filter the solution and store at room temperature for up to 3 months. Running Buffer (60±5 mM Sodium tetraborate, pH 9.25). Weigh 1.21±0.02 g sodium tetraborate into a 100 mL clean glass beaker. Add 90 mL of HPLC grade water, and mix on a stir plate until salts are completely dissolved. Adjust the pH to 9.25±0.10 with 10 N NaOH. Add HPLC grade water to make the final volume 100 mL for a final concentration of 60±5 mM. For a 55 mM solution, weigh 1.11 g (±0.02) sodium tetraborate and follow above instructions for dissolving and titrating. For a 65 mM solution, weigh 1.31 g (±0.02) sodium tetraborate and follow above instructions for dissolving and titrating. Store at room temperature for up to 3 months. Prepare fresh buffer if peak resolution (as defined in system suitability section) is effected (R value <1.0). Optional: Dilute tetraborate buffer solution (MicroSolv) by adding 120 mL of ultra pure water to 80 mL of 150 mM sodium tetraborate buffer for a final concentration of 60 mM (±5 mM). Titrate with 10 N NaOH to bring the solution pH to 9.25 (±0.1). For a 55 mM tetraborate solution, dilute 66 mL of 150 mM sodium tetraborate buffer into 114 mL of ultra pure water. Titrate as above. For a 65 mM tetraborate solution, dilute 78 mL of 150 mM sodium tetraborate buffer into 102 mL of ultra pure water. Titrate as above. Store the solution at room temperature for a maximum of 3 months. Prepare fresh buffer if peak resolution (as defined in system suitability section) is effected (R value <1.0).

Capillary Rinsing Solutions.

1 N NaOH solution: Add 1 mL of 10 N NaOH solution to a 15 mL graduated plastic tube containing 9 mL of HPLC grade water. Mix well by vortexing 5-10 sec. Store the solution at room temperature for up to 6 months.

1 N HCl solution: Add 1 mL of 6 N HCl solution to a 15 mL graduated plastic tube containing 5 mL of HPLC grade water. Mix well by vortexing 5-10 sec. Store the solution at room temperature for up to 6 months. 80% methanol solution: Add 8 mL HPLC grade methanol to a 15 mL graduated plastic tube containing 2 mL HPLC grade water. Mix well by vortexing 5-10 sec. Store the solution at room temperature for up to 6 months.

Monosaccharide Standard Stock Solutions:

N-Acetyl Glucosamine (GalNAc). Accurately weigh 5±1 mg of GalNAc into a 2.0 mL cryogenic vial. Add 1 mL of HPLC grade water and mix well by vortexing until dissolved. Record the accurate concentration of the solution (mg/mL).

N-Acetyl Galactosamine (GlcNAc): Accurately weigh 5±1 mg of GlcNAc into a 2.0 mL cryogenic vial. Add 1 mL of HPLC grade water and mix well by vortexing until dissolved. Record the accurate concentration of the solution (mg/mL).

N-Acetyl Mannosamine (ManNAc): Accurately weigh 5±1 mg of ManNAc into a 2.0 mL cryogenic vial. Add 1 mL of HPLC grade water and mix well by vortexing until dissolved. Record the accurate concentration of the solution (mg/mL).

Store Monosaccharide Standard Stock Solutions at −20° C. for up to 1 year:

Monosaccharide Working Solution I: Internal Standard Working Solution. Dilute stock solution of ManNAc 100 fold with HPLC grade water by adding 20 µL of ManNAc stock solution into a 2 mL cryogenic vial which already contains 1980 µL of HPLC grade water. Vortex approximately 5 to 10 seconds. Store the internal standard working solution at 2-8° C. for up to 6 months.

Monosaccharide Working Solution II: Amino Mix Standard Working Solution. In a 2.0 mL cryogenic vial containing 1960 µL of HPLC grade water, add 20 µL of stock solutions of GalNAc and GlcNAc, respectively. Vortex approximately 5 to 10 seconds. Store the amino mix standard working solution at 2-8° C. for up to 6 months.

Sample and reference material solutions. Thaw frozen protein samples at 2-8° C., and gently mix by inversion. Dilute both samples and reference material with HPLC grade water to about 1.0 mg/mL. Make note of concentration out to three significant figures.

| CE Running Conditions. | |
| --- | --- |
| Running Buffer (step 2.5) | 60 mM sodium tetraborate, pH 9.25 |
| Capillary Cartridge temperature | 25° C. |
| Voltage | 25-30 kV, positive mode |
| Detector condition | LIF detector, Excitation: 488 nm, Emission: 520 nm. |
| Sample injection | Pressure injection mode, 20 s at 0.5 PSI |
| Run Time | 10 minutes |
| Sample storage | 10° C. |

Procedure

Hydrolysis. In a 0.65 mL centrifuge tube, add 10 µL of ManNAc working solution and 200 µL 4 N Hydrolysis Solution. This serves as a system blank. In a 0.65 mL centrifuge tube, add 10 µL of ManNAc working solution and 10 µL of Amino Mix Standard Solution. Further add 200 µL of 4N Hydrolysis Solution. This serves as monosaccharide standard for quantitation and System Suitability. Prepare in duplicate. In a 0.65 mL centrifuge tube, add 10 µL of ManNAc working solution and 10 µL of CTLA4-Ig reference material solution (approximately 1 mg/mL). Further add 200 µL of 4N HCl solution. Prepare in duplicate. In a 0.65 mL centrifuge tube, add 10 µL of ManNAc working solution and 10 µL of sample solution (approximately 1 mg/mL). Further add 200 µL of 4N HCl solution. Prepare in duplicate. Vortex samples for approximately 10 seconds and centrifuge for approximately 5-10 seconds. Place samples in a 96-position vial rack and incubate in an oven at 95° C. for 6 hr. After hydrolysis, place hydrolyzed samples at −20° C. for 10 minutes to cool down. Briefly centrifuge the hydrolyzed samples until any condensate is forced to the bottom of the tube (5-10 seconds at high speed). Evaporate samples to dryness in SpeedVac. Reconstitute each sample with 100 µL of HPLC grade water and vortex 10-15 sec. Evaporate samples to dryness in SpeedVac.

Re-acetylation. Reconstitute each sample with 10 µL of M6 re-acetylation buffer and vortex 5-10 sec. to mix well. Add 4 µL of M3 re-acetylation reagent into each tube. Vortex for approximately 5-10 seconds. Incubate on ice for 30 minutes. Evaporate samples to dryness in SpeedVac. Reconstitute each sample with 100 µL of HPLC grade water and vortex 10-15 sec. Evaporate samples to dryness in SpeedVac.

Derivatization. Place the micro centrifuge in the oven to equilibrate to the oven temperature of 55° C. Reconstitute each sample with 10 µL of Derivitization Solution I (0.1 M APTS solution). Vortex approximately 5-10 seconds. Add 5 µL of the Derivatization Solution II (1M HAc and 0.25 M NaBH₃CN). Vortex approximately 5-10 seconds and centrifuge. Quickly load the sample vials into the pre-warmed centrifuge, and place the centrifuge back in the 55° C. oven. Incubate for 3 hr while centrifuging at 2000 rpm. This prevents the condensation of solvent on vial surface.

Instrumentation Preparation.

5.4.1 Installing a new capillary, rinse in high pressure mode (80 PSI) using the following steps: 1 N NaOH for 20 minutes; HPLC grade water for 10 minutes. 60 mM sodium tetraborate buffer for 10 minutes.

Daily Operation

Before each day's operation, run the washing/rinse sequences to rinse the capillary.

Then run the System Suitability Standard (monosaccharide standard) to ensure the system is suitable.

Using 1N NaOH may etch the inside of capillaries from different vendors and cause a shift in migration times throughout the run. If this causes the migration time of the last peak (GlcNAc) to be more than 10.0 minutes, it may be necessary to replace 1N NaOH with 0.1N NaOH or HPLC grade water for the step 2 rinse.

When using an equivalent capillary and the above washing procedure is not adequate using 80% methanol and/or 1N HCl may be necessary for the last peak (GlcNAc) to be within the exemplary values of 10.0 minutes.

Preparation for Injection

After derivatization, let samples cool down to room temperature. Centrifuge approximately 10 seconds at room temperature, until condensate is forced to the bottom of the tube.

Add 85 µL of HPLC grade water to each tube to bring the final volume of each sample to 100 µL. Vortex for 5-10 seconds.

Transfer 10 µL of sample from each tube to a CE micro vial and add 190 µL of HPLC grade water to each tube. Vortex for 5-10 seconds.

Rinse steps and Injection sequence:

Note: For every four injections, change the CE running buffer with newly prepared CE running buffer (due to ionic depletion effect). Perform capillary rinse at 40 psi.

| Step | Description | Run Time (min) |
| --- | --- | --- |
| 1 (Rinse) | HPLC grade water | 1 |
| 2 (Rinse) | 1N NaOH or 0.1N NaOH | 3 |
| | OR | |
| | HPLC grade water Note: When using HPLC water for the step 2 rinse, steps 1, 2, and 3 may be combined in a single 3 minute run. | 1 |
| 3 (Rinse) | HPLC grade water | 1 |
| 4 (Rinse) | 60 mM sodium Tetraborate Run Buffer | 5 |
| 5 (Rinse) | Blank (Internal Standard Marker) | 10 |
| 6 (Rinse) | Repeat 1-4 | 10 |
| 7 (Rinse) | System Suitability (Mono Std prep1) | 10 |
| 8 (Rinse) | Repeat 1-4 | 10 |
| 9 | System Suitability (Mono Std prep 1) | 10 |
| 10 (Rinse) | Repeat 1-4 | 10 |
| 11 | System Suitability (Mono Std prep 2) | 10 |
| 12 (Rinse) | Repeat 1-4 | 10 |
| 13 | System Suitability (Mono Std prep 2) | 10 |
| 14 (Rinse) | Repeat 1-4 | 10 |
| 15 | CTLA4-Ig Ref. Mat. prep 1 | 10 |
| 16 (Rinse) | Repeat 1-4 | 10 |
| 17 | CTLA4-Ig Ref. Mat. prep 2 | 10 |
| 18 (Rinse) | Repeat 1-4 | 10 |
| 19 | Sample 1 prep 1 | 10 |
| 20 (Rinse) | Repeat 1-4 | 10 |
| 21 | Sample 1 prep 1 | 10 |
| 22 (Rinse) | Repeat 1-4 | 10 |
| 23 | Sample 1 prep 2 | 10 |
| 24 (Rinse) | Repeat 1-4 | 10 |
| 25 | Sample1 prep 2 | 10 |
| 26 (Rinse) | Repeat 1-4 | 18 |
| 27 | Sample 2 prep1 | 10 |
| 28 (Rinse) | Repeat 1-4 | 10 |
| 29 | Sample 2 prep 1 | 10 |
| 30 (Rinse) | Repeat 1-4 | 10 |
| 31 | Sample 2 prep 2 | 10 |
| 32 (Rinse) | Repeat 1-4 | 10 |

| Step | Description | Run Time (min) |
|---|---|---|
| 33 | Sample 2 prep 2 | 10 |
| 34 (Rinse) | Repeat 1-4 | 10 |
| 35 | Sample 3 prep 1 | 15 |
| 36 (Rinse) | Repeat 1-4 | 10 |
| 37 | Sample 3 prep 1 | 10 |
| 38 (Rinse) | Repeat 1-4 | 10 |
| 39 | Sample 3 prep 2 | 10 |
| 40 (Rinse) | Repeat 1-4 | 10 |
| 41 | Sample 3 prep 2 | 10 |
| 42 (Rinse) | Repeat 1-4 | 10 |
| 43 | CTLA4-Ig Reference Material prep 1 | 10 |
| 44 (Rinse) | Repeat 1-4 | 10 |
| 45 | CTLA4-Ig Reference Material prep 2 | 10 |
| 46 (Rinse) | Repeat 1-4 | 10 |
| 47 | System Suitability (Mono Std prep 1) | 10 |
| 48 (Rinse) | Repeat 1-4 | 10 |
| 49 | System Suitability (Mono Std prep 1) | 10 |
| 50 | Repeat 1-4 | 10 |
| 51 | System Suitability (Mono Std prep 2) | 10 |
| 52 | Repeat 1-4 | 10 |
| 53 | System Suitability (Mono Std prep 2) | 10 |

*Note: Repeat sequence for up to three samples in duplicate and bracket with 2 injections of each preparation of Monosaccharide standard. Use all eight System Suitability Standard injections for samples placed in groups of three. If running more than three samples, run the additional samples as shown in the above sequence beginning with line 19. Complete the sequence by running the System Suitability (Mono Std) as shown in lines 47 thru 53 in Table.
**Bracket samples with two injections of each preparation of CTLA4-Ig reference material.

System Suitability Note: System suitability values are determined using the first injection of system suitability standard unless otherwise specified. The electropherogram of the first system suitability should be similar to that shown in FIG. 1, where peak 1 is GalNAc; peak 2 is ManNAc; peak 3 is GlcNAc. Note: When CE instruments other than Beckman PACE MDO are to be used, the length of the capillary might be different from that specified in this method due to various configurations of cartridges holding the separation capillary. This would cause variations in analyte migration time, as well as peak intensity.

Resolution between two neighbor peaks is calculated for the first System Suitability standard by the instrument according to the following equation:

$$R = \frac{2(t_2 - t_1)}{(W_1 + W_2)}$$

Where:
R=resolution
$t_2$, $t_1$=migration times of the two neighbor peaks respectively
$W_1$, $W_2$=peak widths at baseline of the two neighbor peaks respectively The R value must be ≥1.0. If R<1.0, rinse the capillary with the washing/rinse sequences; if the problem persists, replace old buffer with freshly prepared Running Buffer or replace the capillary.

For the last System Suitability injection, the last peak (GlcNAc) must have a tailing factor ≤1.4 using the following formula:

$$T = W_{0.05}/2f$$

Where:
T=tailing factor
$W_{0.05}$=width of peak at 5% of height
f=width of the peak front at peak maximum If T≥1.4, rinse the capillary with the washing/rinse sequences; if the problem persists, replace old buffer with freshly prepared run buffer or replace the capillary.

6.1 The replicate injections of System Suitability Standards must meet the following exemplary values:
Peak Area Ratio of GlcNAc vs. MaNAc:RSD 10% (calculated in step 7.1)
Migration time of GlcNAc should be 10.0 minutes
Profile should be equivalent to FIG. 1 where the three peaks are observed and the Internal Standard (ManNAc) is the number 2 peak.

If any of the above exemplary values are not met prior to testing samples, first increase the voltage if the migration time of GlcNAc is greater than 10.0 minutes. Next, if the peak area ratio is >10%, prepare fresh CE buffer making certain of its pH or replace the capillary. After adjustment to the instrument, repeat System Suitability injections. When analyzing the peak profile, if a significant decrease in the peak height of ManNac occurs, check to make certain the fiber optic cable into the LIF module is not misaligned.

Determine monosaccharide standard percent RSD by comparing peak area ratios of internal standard and monosaccharide standard components. Divide the peak area for each monosaccharide component by the peak area of the internal standard for each monosaccharide standard injection. Calculate the percent RSD for GalNAc and GlcNAc for the two, bracketed standards. The RSD should be ≤10%. If this averaging exemplary value is not met, then the capillary should be rinsed or replaced as above.

Calculations
Calculating Peak Area Ratio of GalNAc and GlcNAc relative to the Internal Standard (ManNAc). Used on replicate injections of first four System Suitability Standards so as to meet exemplary values and performing same calculations on all of the bracketed, System Suitability Standards injected before and after sample(s).

Peak Area Ratio=Divide the peak area for each monosaccharide component (GlcNAc, GalNAc) by the peak area of the internal standard (ManNAc) for each System Suitability Standard injection.

$$\text{Peak Area Ratio} = \frac{\text{monosaccharide peak area}}{\text{MaNAc peak area}}$$

Calculate a mean of the Peak Area Ratios for GlcNAc and GalNAc in the System Suitability Standards. Also calculate a Standard Deviation (S.D.) and percent relative standard deviation (% RSD)

Exemplary values: RSD for the Peak Area Ratio of GlcNAc≤10%. Two, bracketed, System Suitability Standards injected before and after sample(s): Percent RSD for the Peak Area Ratio of GlcNAc and GalNAc≤10%.

If this averaging exemplary value is not met (RSD>10%), then the capillary needs to be re-rinsed with the rinse procedures and those samples and bracketed monosaccharide standards need to be run again. If the averaging exemplary value is still not met, replace the capillary and rinse as stated. Run the samples and bracketed monosaccharide standards again.

$$\text{Standard Deviation} = \sqrt{\frac{n\Sigma x^2 - (\Sigma x)^2}{n(n-1)}}$$

Where:
n=number of measurements in the sample
x=individual measurements $$\% \ RSD = \frac{\text{Standard Deviation}}{\text{Average Measured Peak Area}} \times 100$$

Calculate the molar ratio of GalNAc/Protein:

$$R_{GalNAc} = \frac{A_{GalNAc} \times A_{ManNAc0} \times V_{GalNAc0} \times C_{GalNAc0} \times MW_{CTLA4\text{-}Ig}}{A_{ManNAc} \times A_{GalNAc0} \times Vp \times Cp \times MW_{GlcNAC}}$$

Where:
$R_{GalNAc}$=molar ratio of GalNAc vs. protein
$A_{GalNAc}$=peak area (μV·sec) of GalNAc in sample
$A_{ManNAc}$=peak area (μV·sec) of ManNAc in sample
$A_{ManNAc0}$=peak area (μV·sec) average of ManNAc in monosaccharide standard
$A_{GalNAc0}$=peak area (μV·sec) average of GalNAc in monosaccharide standard
$V_{GalNAc0}$=volume of GalNAc contained in monosaccharide working solution used for hydrolysis (in μL)
$C_{GalNAc0}$=concentration of GalNAc contained in monosaccharide working solution used for hydrolysis (in mg/mL)
Vp=volume of protein sample used for hydrolysis (in μL)
Cp=concentration of protein sample used for hydrolysis (in mg/mL)
$MW_{CTLA4\text{-}Ig}$=Molecular weight of CTLA4-Ig Reference Material
$MW_{GlcNAc}$=Molecular weight of GalNAc (221.2 daltons)

Standards Bracketing. When calculating molar ratios of CTLA4-Ig reference material and samples, use all eight of the bracketed System Suitability Standards. Average the peak areas for inclusion in this equation. This is to be used for the first three samples. For all other samples, always use the average peak area of the next four bracketed monosaccharide standards and the previous four bracketed monosaccharide standards for molar ratio calculations.

Calculate the molar ratio of GlcNAc/Protein $$R_{GalNAc} = \frac{A_{GalNAc} \times A_{ManNAc0} \times V_{GalNAc0} \times C_{GalNAc0} \times MW_{CTLA4\text{-}Igt}}{A_{ManNAc} \times A_{GalNAc0} \times Vp \times Cp \times MW_{GlcNAc}}$$

Where:
$R_{GlcNAc}$=molar ratio of GlcNAc vs. protein
$A_{GlcNAc}$=peak area (μV·sec) of GlcNAc in sample
$A_{ManNAc}$=peak area (μV·sec) of ManNAc in sample
$A_{ManNAc0}$=peak area (μV·sec) average of ManNAc in monosaccharide standard
$A_{GlcNAc0}$=peak area (μV·sec) average of GlcNAc in monosaccharide standard
$V_{GlcNAc0}$=volume of GlcNAc contained in monosaccharide working solution used for hydrolysis (in μL)
$C_{GlcNAc0}$=concentration of GlcNAc contained in monosaccharide working solution used for hydrolysis (in mg/mL)
Vp=volume of protein sample used for hydrolysis (in μL)
Cp=concentration of protein sample used for hydrolysis (in mg/mL)
$MW_{CTLA4\text{-}Ig}$=Molecular weight of CTLA4-Ig Reference Material as per COA
$MW_{GlcNAc}$=Molecular weight of GlcNAc (221.2 daltons)

Exemplary values. The percent RSD for the two, bracketed, amino System Suitability Standard peak area ratios should not exceed 10%. The average molar ratios for amino monosaccharides in the reference material must be within the ranges specified. For each component, the % RSD for the four results (duplicate injection of duplicate preparations) must be </=25%.

| Molar Ratio range of CTLA4-Ig Reference Material | |
|---|---|
| Monosaccharide | Range |
| GalNAc | 2.0-3.2 |
| GlcNAc | 18-32 |

Reporting Results. Report the average result as the number of GalNAc molecules per CTLA4-Ig molecule and number of GlcNAc molecules per CTLA4-Ig molecule. Report molar ratio results to two significant figures. For each component, the % RSD for the four results (duplicate injection of duplicate preparations) must be </=25%.

Example 64: Methods to Obtain Molar Ratios of Neutral Monosaccharides (Mannose, Fucose, Galactose) to Protein in CTLA4-Ig Drug Substance Samples Reagents Hydrolysis Solution (2 M TFA aqueous solution) Add 148 μL of TFA and 852 μL of HPLC grade water to a 1.7 microcentrifuge tube. Vortex for 5-10 seconds. Scale up as needed. Prepare solution immediately before use.

Derivatization Solution I (0.1 M APTS aqueous solution). Add 192 μL of HPLC grade water to 10 mg powder of APTS in a glass vial. Vortex the bottle 5-10 seconds to completely dissolve the APTS. Store at −20° C. for up to one year.

Derivatization Solution II (1 M acetic acid and 0.25 M NaBH$_3$CN). Dilute 20 μL acetic acid with 320 μL HPLC grade water (17 fold dilution) in a 0.4 mL centrifuge tube to make a 1 M acetic acid solution. Weigh 2.0±0.5 mg of NaBH$_3$CN into a cryogenic vial. Using the following formula, add an appropriate volume of the 1 M acetic acid solution to make 0.25 M NaBH$_3$CN.

Volume (μL)=$10^3$×(weight of NaBH$_3$CN in mg)/62.84 g/mol×0.25 mol/L)

Sodium cyanoborohydride (NaBH$_3$CN) should be stored in dark in a desiccator.

Subdividing of the reagent into a series of 2.0 mL cryovials for storage is recommended to avoid repeated opening of the original reagent bottle as follows:

Weigh 1 g±0.2 mg of Sodium Cyanoborohydride into 2.0 mL cryovial. Aliquot out the entire contents of Sodium Cyanoborohydride from the original bottle in this manner.

Cap tightly and label cryovials sequentially (1, 2, 3, etc.) along with reagent name, lot number, and a 6 month expiration date.

The vials should be sealed with parafilm to avoid moisture.

Weigh out Sodium Cyanoborohydride for Derivatization Solution II no more than three times from the same cryovial. Make note of this and the cryovial sequence number on the lab worksheet.

Either a reagent peak observed in the CE profile or poor labeling may occur after repeated opening of the cryovial or with that particular lot of Sodium Cyanoborohydride. If this effects the results, discard the cryovial being used and either weigh out reagent from a cryovial with the next sequence number or from a new lot of Sodium Cyanoborohydride.

Running Buffer (60±5 mM Sodium tetraborate, pH 9.25)
Weigh 1.21±0.02 g sodium tetraborate into a 100 mL clean, glass bottle.
Add 90 mL of HPLC grade water, and mix on a stir plate until salts are completely dissolved.
Adjust the pH to 9.25±0.10 with 10 N NaOH.
Add HPLC grade water to make the final volume 100 mL for a final concentration of 60 mM (±5 mM).
For a 55 mM solution, weigh 1.11 g (±0.02) sodium tetraborate and follow above instructions for dissolving and titrating.
For a 65 mM solution, weigh 1.31 g (±0.02 g) sodium tetraborate and follow above instructions for dissolving and titrating.
Store at room temperature for up to 3 months. Prepare fresh buffer if peak resolution (as defined in system suitability section) is effected (R value ≤1.0.
Optional: Dilute tetraborate buffer solution (MicroSolv) by adding 120 mL of ultra pure water to 80 mL of 150 mM sodium tetraborate buffer for a final concentration of 60 mM (±5 mM). Titrate with 10N NaOH to bring the solution pH to 9.25 (±0.1).
For a 55 mM tetraborate solution, dilute 66 mL of 150 mM sodium tetraborate buffer into 114 mL of ultra pure water. Titrate as above.
For a 65 mM tetraborate solution, dilute 78 mL of 150 mM sodium tetraborate buffer into 102 mL of ultra pure water. Titrate as above.
Store the solution at room temperature for a maximum of 3 months. Prepare fresh buffer if peak resolution (as defined in system suitability section) is effected (R value ≤1.0.

Capillary Rinsing Solutions
1 N NaOH solution
Add 1 mL of 10 N NaOH solution to a 14 mL graduated plastic tube containing 9 mL of HPLC grade water. Mix well by vortexing 5-10 sec.
Store the solution at room temperature for up to 6 months.
1 N HCl solution:
Add 1 mL of 6 N HCl solution to a 15 mL graduated plastic tube containing 5 mL of HPLC grade water. Mix well by vortexing 5-10 sec.
Store the solution at room temperature for up to 6 months.
80% methanol solution:
Add 8 mL HPLC grade methanol to a 15 mL graduated plastic tube containing 2 mL HPLC grade water. Mix well by vortexing 5-10 sec.
Store the solution at room temperature for up to 6 months.

Monosaccharide standard stock solutions
Mannose (Man)
Accurately weigh 5±1 mg of mannose into a 2.0 mL cryogenic vial.
Add 1 mL of HPLC grade water and mix well by vortexing 5-10 sec.
Record the accurate concentration of the solution (mg/mL).
Fucose (Fuc)
Accurately weigh 5±1 mg of fucose into a 2.0 mL cryogenic vial.
Add 1 mL of HPLC grade water and mix well by vortexing 5-10 sec.
Record the accurate concentration of the solution (mg/mL).
Galactose (Gal)
Accurately weigh 5±1 mg of galactose into a 2.0 mL cryogenic vial.
Add 1 mL of HPLC grade water and mix well by vortexing 5-10 sec.
Record the accurate concentration of the solution (mg/mL).
Xylose (Xyl)
Accurately weigh 5±1 mg of xylose into a 2.0 mL.
Add 1 mL of HPLC grade water and mix well by vortexing 5-10 sec.
Record the accurate concentration of the solution (mg/mL).
Store the monosaccharide standard stock solutions at −20° C. for up to 1 year.

Monosaccharide working solution I: Internal standard working solution. To make internal standard working solution, dilute stock solution of xylose 100 times with HPLC grade water by adding 20 μL of xylose stock solution (3.6.4) into a 2 mL cryogenic vial, which already contains 1980 μL of HPLC grade water. Vortex for approximately 5 to 10 seconds. Store this internal standard working solution at 2-8° C. for up to 6 months.

Monosaccharide working solution II: Neutral mix standard working solution. In a 2.0 mL cryogenic vial containing 1940 μL of HPLC grade water, add 20 μL of stock solutions of mannose, fucose, and galactose respectively. Vortex for approximately 5 to 10 seconds. Store this internal standard working solution at 2-8° C. for up to 6 months.

Sample and reference material solutions. Thaw frozen protein samples at 2-8° C. and gently mix by inversion. Dilute both samples and reference material with HPLC grade to about 1.0 mg/mL.

| CE Running Conditions | |
| --- | --- |
| Running Buffer | 60 mM sodium tetraborate, pH 9.25 |
| Capillary Cartridge temperature | 25° C. |
| Voltage | 25-30 kV, positive mode |
| Detector condition | LIF detector Excitation: 488 nm, Emission: 520 m |
| Sample injection | Pressure injection mode, 20 s at 0.5 PSI |
| Run Time | 15 minutes |
| Sample storage | 10° C. |

Procedure
Hydrolysis: In a 0.65 mL centrifuge tube, add 10 μL of xylose working solution and 200 μL 2M TFA solution. This serves as a system blank. In a 0.65 mL centrifuge tube, add 10 μL of xylose working solution and 10 μL of neutral mix standard working solution. Further add 200 μL of 2M TFA solution and vortex for 3-4 sec. This serves as monosaccharide standard for quantitation and System Suitability. Prepare in duplicate. In a 0.65 mL centrifuge tube, add 10 μL of xylose working solution and 10 μL of CTLA4-Ig reference material solution (approximately 1 mg/mL). Further add 200 μL of 2M TFA solution and vortex for 3-4 sec. Prepare in duplicate. In a 0.65 mL centrifuge tube, add 10 μL of xylose working solution and 10 μL of sample solution (approximately 1 mg/mL). Further add 200 μL of 2M TFA solution and vortex for 3-4 sec. Prepare in duplicate. Vortex samples for approximately 20 seconds and centrifuge for approximately 5 to 10 seconds. Place samples in a 96-position vial rack and incubate in an oven at 95° C. for 6 hr. After hydrolysis, place samples at −20° C. for 10 minutes to cool down. Briefly centrifuge hydrolyzed samples until any condensate is forced to the bottom of the tube (5 to 10 seconds at high speed). Evaporate samples to dryness in SpeedVac. Reconstitute each sample with 100 μL of HPLC grade water and vortex 10-15 sec. Evaporate samples to dryness in SpeedVac.

Derivatization: Place the micro centrifuge in the oven to equilibrate to the oven temperature of 55° C. Reconstitute each sample with 10 μL of Derivatization Solution I (0.1 M APTS solution). Vortex approximately 5-10 seconds. Add 5 μL of the Derivatization Solution II (1M HAc and 0.25 M NaBH$_3$CN). Vortex approximately 5-10 seconds and centrifuge. Quickly load the sample vials into the pre-warmed centrifuge, and place the centrifuge back in the 55° C. oven. Incubate for 3 hr while centrifuging at 2000 rpm. This prevents the condensation of solvent on vial surface.

Instrumentation Preparation: Installing a new capillary, rinse in high pressure mode (80 PSI) using the following steps:

1 N NaOH for 20 minutes.
HPLC grade water for 10 minutes.
60 mM sodium tetraborate buffer for 10 minutes.

Run the washing/rinse sequences to rinse the capillary. Then run the System Suitability Standard (monosaccharide standard) to ensure the system is suitable. Using 1N NaOH may etch the inside of capillaries from different vendors and cause a shift in migration times throughout the run. If this causes the migration time of the last peak (galactose) to be more than 15.0 minutes, it may be necessary to replace 1N NaOH with 0.1N NaOH or HPLC grade water for the step 2 rinse. When using an equivalent capillary and the above washing procedure is not adequate using 80% methanol and/or 1N HCl may be necessary for the last peak (galactose) to be within the exemplary values of 15.0 minutes.

Preparation for injection: After derivatization, let samples cool down to room temperature. Centrifuge approximately 10 seconds at room temperature, until condensate is forced to the bottom of the tube. Add 85 μL of HPLC grade water to each tube to bring the final volume of each sample to 100 μL. Vortex for 5-10 seconds. Transfer 10 μL of sample from each tube to a CE micro vial and add 190 μL of HPLC grade water to each tube. Vortex for 5-10 seconds.

Rinse steps and Injection sequence:

| Step | Description | Run Time (min) |
|---|---|---|
| 1 (Rinse) | HPLC grade water | 1 |
| 2 (Rinse) | 1N NaOH or 0.1N NaOH<br>OR<br>HPLC grade water<br>Note: When using HPLC water for the step 2 rinse, steps 1, 2, and 3 may be combined in a single 3 minute run. | 3<br><br>1 |
| 3 (Rinse) | HPLC grade water | 1 |
| 4 (Rinse) | 60 mM sodium Tetraborate Run Buffer | 5 |
| 5 | Blank (Internal Standard Marker) | 15 |
| 6 (Rinse) | Repeat 1-4 | 10 |
| 7 | System Suitability (Mono Std prep 1) | 15 |
| 8 (Rinse) | Repeat 1-4 | 10 |
| 9 | System Suitability (Mono Std prep 1) | 15 |
| 10 (Rinse) | Repeat 1-4 | 10 |
| 11 | System Suitability (Mono Std prep 2) | 15 |
| 12 (Rinse) | Repeat 1-4 | 10 |
| 13 | System Suitability (Mono Std prep 2) | 15 |
| 14 (Rinse) | Repeat 1-4 | 10 |
| 15 | CTLA4-Ig ref. mat. prep 1 | 15 |
| 16 (Rinse) | Repeat 1-4 | 10 |
| 17 | CTLA4-Ig Reference Material prep 2 | 15 |
| 18 (Rinse) | Repeat 1-4 | 10 |
| 19 | Sample 1 prep 1 | 15 |
| 20 (Rinse) | Repeat 1-4 | 10 |
| 21 | Sample 1 prep 1 | 15 |
| 22 (Rinse) | Repeat 1-4 | 10 |
| 23 | Sample 1 prep 2 | 15 |
| 24 (Rinse) | Repeat 1-4 | 10 |
| 25 | Sample 1 prep2 | 15 |
| 26 (Rinse) | Repeat 1-4 | 10 |
| 27 | Sample 2 prep1 | 15 |
| 28 (Rinse) | Repeat 1-4 | 10 |
| 29 | Sample 2 prep 1 | 15 |
| 30 | Repeat 1-4 | 10 |
| 31 | Sample 2 prep 2 | 15 |
| 32 (Rinse) | Repeat 1-4 | 10 |
| 33 | Sample 2 prep 2 | 15 |
| 34 (Rinse) | Repeat 1-4 | 10 |
| 35 | Sample 3 prep 1 | 15 |
| 36 (Rinse) | Repeat 1-4 | 10 |
| 37 | Sample 3 prep 1 | 15 |
| 38 (Rinse) | Repeat 1-4 | 10 |
| 39 | Sample 3 prep 2 | 15 |
| 40 (Rinse) | Repeat 1-4 | 10 |
| 41 | Sample 3 prep 2 | 15 |
| 42 (Rinse) | Repeat 1-4 | 10 |
| 43 | CTLA4-Ig Reference Material prep 1 | 15 |
| 44 (Rinse) | Repeat 1-4 | 10 |
| 45 | CTLA4-Ig Reference Material prep 2 | 15 |
| 46 (Rinse) | Repeat 1-4 | 10 |
| 47 | System Suitability (Mono Std prep 1) | 15 |
| 48 (Rinse) | Repeat 1-4 | 10 |
| 49 | System Suitability (Mono Std prep 1) | 15 |
| 50 | Repeat 1-4 | 10 |
| 51 | System Suitability (Mono Std prep 2) | 15 |
| 52 | Repeat 1-4 | 10 |
| 53 | System Suitability (Mono Std prep 2) | 15 |

*Repeat sequence for up to three samples in duplicate and bracket with 2 injections of each preparation of Monosaccharide standard. Use all eight System Suitability Standard injections for samples placed in groups of three. If running more than three samples, run the additional samples as shown in the above sequence beginning with line 19.
**Bracket samples with two injections of each preparation of CTLA4-Ig reference material.

System Suitability. The electropherogram of the first system suitability should be similar to where peak 1 is mannose; peak 2 is xylose; peak 3 is fucose; and peak 4 is galactose. Note: When CE instruments other than Beckman PACE MDQ are to be used, due to the various configuration of cartridges holding the separation capillary, the length of the capillary might be different from that specified in this method. This would cause variations in analyte migration time, as well as peak intensity.

Resolution between two neighbor peaks is calculated for the first System Suitability standard by the instrument according to the following equation:

$$R = \frac{2(t_2 - t_1)}{(W_1 + W_2)}$$

Where:
R=resolution
$t_2$, $t_1$=migration times of the two neighbor peaks respectively
$W_1$, $W_2$=peak widths at baseline of the two neighbor peaks respectively R value must be ≥1.0. If R<1.0, rinse the capillary with the washing/rinse sequences; if the problem persists, replace old buffer with freshly prepared run buffer or replace the capillary.

For the last System Suitability injection, the last peak (galactose) must have a tailing factor ≤1.4 using the following formula:

$$T = W_{0.05}/2f$$

Where:
T=tailing factor
$W_{0.05}$=width of peak at 5% of height
f=width of the peak front at peak maximum
If T≥1.4, rinse the capillary with the washing/rinse sequences; if the problem persists, replace old buffer with freshly prepared run buffer or replace the capillary.

Replicate injection of first four System Suitability Standards must meet the following exemplary values:
Peak Area Ratio of galactose vs. xylose:RSD 10%.
Migration time of galactose needs to be 15.0 minutes
Profile should be equivalent to FIG. 1 where the four peaks are observed and the Internal Standard (Xylose) is the number 2 peak.

If any of the above exemplary values are not met, first increase the voltage if the migration time of galactose is greater than 15.0 minutes. Next, if the peak area ratio is >10%, then prepare fresh CE buffer making certain of its pH or replace the capillary.

After adjustments to the instrument, repeat system suitability injections. When analyzing the peak profile, if a significant decrease in the peak height of Xylose occurs, check to make certain the fiber optic cable into the LIF module is not mis-aligned. Determine monosaccharide standard percent RSD by comparing peak area ratios of internal standard and monosaccharide standard components. Divide the peak area for each monosaccharide component by the peak area of the internal standard for each monosacharide standard injection. Calculate the percent RSD for mannose, fucose, and galactose for the two bracketed standards. The RSD should be ≤10%. If this averaging exemplary value is not met, then the capillary should be rinsed or replaced as above. Samples and bracketed monosaccharide standards need to be repeated.

Calculations. Calculating Peak Area Ratio of Man, Fuc, and Gal relative to the Internal Standard (Xylose). Used on replicate injections of first four System Suitability Standards so as to meet exemplary values and performing same calculations on all of the bracketed System Suitability Standards injected before and after sample(s). Peak Area Ratio=Divide the peak area for each monosaccharide component (Man, Fuc, and Gal) by the peak area of the internal standard (Xylose) for each System Suitability Standard injection.

$$\text{Peak Area Ratio} = \frac{\text{monosaccharide peak area}}{\text{Xylose peak area}}$$

Calculate a mean of the Peak Area Ratios for Man, Fuc, and Gal in the System Suitability Standards. Also calculate a Standard Deviation (S.D.) and percent relative standard deviation (% RSD). Exemplary values: RSD for the Peak Area Ratio of Galactose 10%. Two, bracketed, System Suitability Standards injected before and after sample(s):

Percent RSD for the Peak Area Ratio of Man, Fuc, and Gal 10%.

If this averaging exemplary value is not met (RSD ≥10%), then the capillary needs to be re-rinsed with the rinse procedures and those samples and bracketed monosaccharide standards need to be run again. If the averaging exemplary value is still not met, replace the capillary and rinse. Run the samples and bracketed monosaccharide standards again.

$$\text{Standard Deviation} = \sqrt{\frac{n\Sigma x^2 - (\Sigma x)^2}{n(n-1)}}$$

Where:
n=number of measurements in the sample
x=individual measurements $$\% \; RSD = \frac{\text{Standard Deviation}}{\text{Average Measured Peak Area}} \times 100\%$$

Calculate the molar ratio of Mannose/Protein $$R_{Man} = \frac{A_{Man} \times A_{Xy10} \times V_{Man0} \times C_{Man0} \times MW_{CTLA4\text{-}Ig}}{A_{Xyl} \times A_{Man0} \times V_p \times C_p \times MW_{Man}}$$

Where:
$R_{Man}$=molar ratio of Mannose (Man) vs. protein
$A_{Man}$=peak area (μV·sec) of Man in sample
$A_{Xyl}$=peak area (μV·sec) of Xylose (Xyl) in sample
$A_{Xyl0}$=peak area (μV·sec) average of Xyl in monosaccharide standard
$A_{Man0}$=peak area (μV·sec) average of Man in monosaccharide standard
$V_{Man0}$=volume of Man contained in monosaccharide working solution used for hydrolysis (in μL)
$C_{Man0}$=concentration of Man contained in monosaccharide working solution used for hydrolysis (in mg/mL)
Vp=volume of protein sample used for hydrolysis (in μL)
Cp=concentration of protein sample used for hydrolysis (in mg/mL)
$MW_{CTLA4\text{-}Ig}$=Molecular weight of CTLA4-Ig Reference Material as per Certificate of Analysis (COA)
$MW_{Man}$=Molecular weight of Mannose (180.2 daltons)

Standard Bracketing. When calculating molar ratios of CTLA4-Ig reference material and samples, use all eight of the bracketed System Suitability Standards. Average the peak areas for inclusion in this equation. This is to be used for the first three samples. For all other samples, always use the average peak area of the next four bracketed monosaccharide standards and the previous four bracketed monosaccharide standards for molar ratio calculations.

Calculate the molar ratio of Fucose/Protein:

$$R_{Fuc} = \frac{A_{Fuc} \times A_{Xy10} \times V_{Fuc0} \times C_{Fuc0} \times MW_{CTLA4\text{-}Ig}}{A_{Xyl} \times A_{Fuc0} \times V_p \times C_p \times MW_{Fuc}}$$

Where:
$R_{Fuc}$=molar ratio of Fucose (Fuc) vs. protein
$A_{Fuc}$=peak area (μV·sec) of Fuc in sample
$A_{Xyl}$=peak area (μV·sec) of Xylose (Xyl) in sample
$A_{Xyl0}$=peak area (μV·sec) average of Xyl in monosaccharide standard
$A_{Fuc0}$=peak area (μV·sec) average of Fuc in monosaccharide standard
$V_{Fuc0}$=volume of Fuc contained in monosaccharide working solution used for hydrolysis (in μL)

$C_{Fuc0}$=concentration of Fuc contained in monosaccharide working solution used for hydrolysis (in mg/mL)
Vp=volume of protein sample used for hydrolysis (in µL)
Cp=concentration of protein sample used for hydrolysis (in mg/mL)
$MW_{cTLA4-Ig}$=Molecular weight of CTLA4-Ig Reference Material as per Certificate of Analysis (COA)
$MW_{Fuc}$=Molecular weight of Fucose (164.2 daltons)
Calculate the molar ratio of Galactose/Protein:

$$R_{Gal} = \frac{A_{Gal} \times A_{Xy10} \times V_{Gal0} \times C_{Gal0} \times MW_{CTLA4-Ig}}{A_{Xy1} \times A_{Gal0} \times V_P \times C_P \times MW_{Gal}}$$

Where:
$R_{Gal}$=molar ratio of Galactose (Gal) vs. protein
$A_{Gal}$=peak area (µV·sec) of Gal in sample
$A_{Xyl}$=peak area (µV·sec) of Xylose (Xyl) in sample
$A_{Xyl0}$=peak area (µV·sec) average of Xyl in monosaccharide standard $A_{Gal0}$
$V_{Gal0}$=volume of Gal contained in monosaccharide working solution used for hydrolysis (in µL)
$C_{Gal0}$: =concentration of Gal contained in monosaccharide working solution used for hydrolysis (in mg/mL)
Vp=volume of protein sample used for hydrolysis (in µL)
Cp=concentration of protein sample used for hydrolysis (in mg/mL)
$MW_{CTLA4-Ig}$=Molecular weight of CTLA4-Ig Reference Material as per Certificate of Analysis (COA)
$MW_{Gal}$=Molecular weight of Gal (180.2 daltons)

Note: When calculating molar ratios of CTLA4-Ig reference material and samples, use the last System Suitability Standard and the next bracketed System Suitability Standard preparation. Average the peak areas for inclusion in this equation. This is to be used for the first six samples. For all other samples, always use the average peak area of the two bracketed monosaccharide standards for molar ratio calculations.

Exemplary values. The percent RSD for the two, bracketed, neutral System Suitability Standard peak area ratios should not exceed 10%. The average molar ratios for neutral monosaccharides in the reference material can be within the ranges specified in Table below. For each component, the % RSD for the four results (duplicate injections of duplicate preparations) must be ≤/=25%.

| Molar Ratio range of CTLA4-Ig Reference Material | |
|---|---|
| Monosaccharide | Range |
| Mannose | 11-18 |
| Fucose | 4.2-7.5 |
| Galactose | 9.2-18 |

Reporting Results. Report the average result as number of Mannose molecules per CTLA4-Ig molecule, number of Fucose molecules per CTLA4-Ig molecule, and number of Galactose molecules per CTLA4-Ig molecule. Report molar ratio results to two significant figures. For each component, the % RSD for the four results (duplicate injections of duplicate preparations) must be </=25%.

Example 65—Tryptic Mapping Quantitation of CTLA4-Ig Oxidation and Deamidation

The purpose of the method is to monitor the lot-to-lot consistency of CTLA4-Ig using a manual tryptic peptide mapping procedure with specific detection and quantitation of methionine oxidation and asparagine deamidation. Peptide mapping involves the proteolysis or other fragmentation of a protein to create a well-defined set of peptide fragments which are then analyzed, usually by HPLC. The chromatogram or peptide map is very sensitive to even the smallest change in the chemical structure of the protein and is thus useful for detecting and characterizing posttranslational modifications. The CTLA4-Ig protein sample is denatured in 8 M guanidine-HCl buffer and the cystine disulfide bridges reduced with dithiothreitol and S-alkylated with iodoacetamide prior to digestion with the proteolytic enzyme, trypsin. The resulting mixture of tryptic peptides is then analyzed by reversed phase high performance liquid chromatography (RP-HPLC) with UV detection at 215 and 280 nm. Some abbreviations are listed below:

| | |
|---|---|
| Asn | Asparagine |
| Asp | Aspartic Acid |
| Asu | Aminosuccinimide |
| isoAsp | Isoaspartic Acid |
| Met(O) | Methionine Sulfoxide |
| T26 | (281-302) tryptic peptide |
| T26deam1 | isoAsp294 (281-302) tryptic peptide |
| T26deam2 | Asp299 (281-302) tryptic peptide |
| T26deam3 | Asp294 (281-302) tryptic peptide |
| T26deam4 | Asu294 (281-302) tryptic peptide |
| T6 | (84-93) tryptic peptide |
| T6ox | Met(O)85(84-93) tryptic peptide |

Chemicals and Reagents
Mobile Phase A—0.1% TFA in HPLC grade water
Transfer entire contents of a 1 mL ampule of TFA to 1000 mL of HPLC grade water and mix thoroughly to prepare 0.1% TFA (Mobile Phase A). The 0.1% TFA may be stored at room temperature for up to two months.
Mobile Phase B—0.1% TFA in 80% ACN and 20% HPLC grade water
Transfer entire contents of a 1 mL ampule of TFA to 800 mL of acetonitrile and 200 mL HPLC grade water and mix thoroughly to prepare 0.1% TFA in 80% ACN (Mobile Phase B) which may be stored at room temperature for up to two months.
Dilution Buffer—100 mM TRIS, 25 mM NaCl, pH 7.6
Dissolve 14.0 g Trizma Pre-Set Crystal pH 7.6 and 1.46 g NaCl in 1000 mL of HPLC grade water by stirring the solution on a magnetic stir plate. Filter the solution through 0.2 µm filter unit. Store solution at 2 to 8° C. for up to two months.
Denaturing Buffer—8 M Guanidine, 50 mM TRIS, pH 8.0
Dissolve 152.8 g guanidine hydrochloride and 1.4 g Trizma Pre-Set Crystal pH 8 in 90 mL of HPLC grade water by stirring the solution on a magnetic stir plate. Adjust the pH to 8.0 with either HCl or NaOH and bring to the final volume of 200 mL with HPLC grade water. Filter the solution through 0.2 µm filter. Store solution at room temperature for up to six months.
Digestion Buffer—50 mM TRIS, 10 mM $CaCl_2$), pH 7.6
Dissolve 7.0 g Trizma Pre-Set Crystal pH 7.6 and 1.47 g $CaCl_2$) in 1000 mL of HPLC grade water by stirring the solution on a magnetic stir plate. Filter the solution through 0.2 µm filter. Store solution at 2 to 8° C. for up to two months.
Reducing Agent—200 mM dithiothreitol (DTT)
To 30.8±0.2 mg of DTT, add 1000 µL of water immediately before use and vortex until dissolved. Solution expires 24 hours from the time of preparation.

Alkylating Reagent—400 mM iodoacetamide (IAM)
To 74.0±0.5 mg iodoacetamide, add 1000 µL of water immediately before use and vortex until dissolved. Solution expires 24 hours from the time of preparation.
1.0 M HCl
Dilute 8.7 mL of concentrated hydrochloric acid to 100 mL with HPLC grade water. Store solution at room temperature for up to two months.

Standards and Controls

T6ox peptide standard, 30 µM

The T6ox tryptic peptide synthetic standard is Ala-Met(O)-Asp-Thr-Gly-Leu-Tyr-Ile-Cys-Lys•2TFA, FW 1358.4, ~95% purity by weight. Store the solid tightly-sealed at −20° C. and always warm to room temperature in a dessicator to prevent the absorption of moisture. Weigh out 1.0±0.1 mg of T6ox, record the exact weight, and dissolve in 1.50 mL of Digestion Buffer. Add 40 uL of 200 mM DTT and place at 37° C. for 20 min. Cool to room temperature, add 48 µL of 400 mM iodoacetamide and alkylate at room temperature in the dark, for 30 min. Dilute to a final volume of 24.5 mL with Digestion Buffer to give a 30±3 µM standard solution. Store 1 mL aliquots of the 30 µM T6ox standard at −70° C. for up to 24 months.

T26deam1 peptide standard, 30 µM

The T26deam1 tryptic peptide synthetic standard is Gly-Phe-Tyr-Pro-Ser-Asp-Ile-Ala-Val-Glu-Trp-Glu-Ser-isoAsp-Gly-Gln-Pro-Glu-Asn-Asn-Tyr-Lys•2TFA, FW 2773.7, ~85% purity by weight. Store the solid tightly-sealed at −20° C. and always warm to room temperature in a dessicator to prevent the absorption of moisture. Weigh out 1.0±0.1 mg of T26deam1, record the exact weight, and dissolve in 1 mL of 30% v:v acetonitrile in Digestion Buffer. Dilute to a final volume of 10.7 mL to give a 30±3 µM standard solution. Store 1 mL aliquots of the 30 µM T26deam1 standard at −70° C. for up to 24 months.

Preparation of Standards and Samples

Reduction and Alkylation

The protein concentration range for peptide mapping is approximately 20 mg/mL. If the protein concentration is ≥20 mg/mL, dilute the sample with dilution buffer to a final concentration of approximately 20 mg/mL. Prepare at least 100 µL of diluted solution. In a 1.7 mL centrifuge tube add 100 µL of 20 mg/mL (2 mg) CTLA4-Ig solution (sample or reference material) to 550 µL of Denaturing Buffer. Add 35 µL of 200 mM Reducing Reagent, vortex the tube for 3-5 seconds, then centrifuge for approximately 3 seconds. Incubate the tubes at 37° C. for 20±2 minutes. Add 38.5 µL of 400 mM Alkylating Reagent to each tube, vortex for 3-5 seconds, then centrifuge for approximately 3 seconds. Incubate the samples at room temperature in the dark for 20±2 minutes. Place the NAP-5 columns in a stand. Use one column per sample. While the samples are incubating in IAM, equilibrate the NAP-5 columns with 7.5 mL of Digestion Buffer. Discard the effluent per site procedures. Add 500 µL of the reduced and alkylated mixtures over the NAP-5 columns, allowing the liquid to drain through column. Discard the effluent per site procedures. Add 1.0 mL of Digestion Buffer into the NAP-5 columns and collect the effluent into 1.7 mL centrifuge tubes and gently mix the collected effluent.

Digestion. Reconstitute one trypsin vial (20 µg) for each mL of sample or reference material to be digested, plus one additional trypsin vial, with 86 µL each of trypsin buffer (supplied with the enzyme) to a give 0.25 µg/µL. Pool the contents of the trypsin vials together into one vial. Digest each sample with 80 µL of the above pooled trypsin solution per mL of sample at 37° C. for 120±12 minutes. Upon completion of the digestion, acidify the samples with 40 µL of 1.0 M HCl per mL of sample, and vortex for 3-5 seconds. Pipette 100 µL each of the digests of samples and the reference material into autosampler vials. Prepare an additional system suitability control containing 95 µL of reference material digest mixed with 5 µL of 30 µM T6ox peptide standard and 54 of 30 µM T26deam1 peptide standard to give a digest spiked with 5% T6ox and 5% T26deam1. Place all vials in the autosampler at 5±5° C. for HPLC analysis. Store all the remaining digest samples at −70° C.

Chromatographic Conditions

The table below shows the flow rate and the chromatography gradient.

| Time (min) | Flow (mL/min) | Mobile Phase A | Mobile Phase B |
|---|---|---|---|
| 0 | 0.25 | 100 | 0 |
| 4 | 0.25 | 100 | 0 |
| 10 | 0.25 | 92 | 8 |
| 72 | 0.25 | 72 | 28 |
| 84 | 0.25 | 60 | 40 |
| 92 | 0.25 | 0 | 100 |
| 94 | 0.40 | 0 | 100 |
| 95 | 0.40 | 100 | 0 |
| 109 | 0.40 | 100 | 0 |
| 110 | 0.25 | 100 | 0 |

Equilibrate column at 55° C. with 100% Mobile Phase A for at least 25 minutes prior to first injection. Monitor UV absorbance at 215 nm and 280 nm. Tubing from column to detector should have an inner diameter of ≤0.01" in order to minimize diffusion band-broadening. Maintain column temperature at 55±2° C. Maintain autosampler temperature at 5±5° C. Mobile Phase A is used as the blank injection. Bracket samples (not more than ten at a time) with reference material injections. The table below shows the injection sequence for the chromatographic analysis. Note that all injection volumes are 25 except for the control sample consisting of Reference Material spiked 5% T6ox and 5% T26deam1 peptide standards for which 28 µL is injected:

| Vial # | Injection | Sample Name | Inj. Volume (µL) |
|---|---|---|---|
| 1 | 1 | Blank (mobile phase A) | 25 |
| 2 | 1 | Reference Material | 25 |
| 3 | 1 | Sample 1 | 25 |
| 4 | 1 | Sample 2 | 25 |
| 5 | 1 | Sample 3 | 25 |
| 6 | 1 | Reference Material spiked with 5% T6ox and 5% T26deam1 | 28 |
| 2 | 1 | Reference Material | 25 |

Exemplary Values

Exemplary values. The peptide map profile for the reference material must be visually comparable to the chromatogram presented in FIG. 1 with regard to number, relative size and elution order of significant peaks for the 215 nm and 280 nm traces. The retention time differences for peaks T4, T25, and T27 in the initial and bracketing reference material should not exceed ±0.5 minutes. Number of Theoretical Plates (N) must be ≥100,000. If N <100,000, re-equilibrate the column. If the problem persists, replace the column. Resolution (R) must be ≥1.5 for the T2 and T12 peaks. If R<1.5, re-equilibrate the column. If the problem persists, replace the column. The 280 nm chromatogram of the reference standard spiked with 5% T6ox and T6deam1 must show an increase for the T6ox peak eluting at ~33.0 min, as shown in FIG. 84. The 215 nm chromatogram of the reference standard spiked with 5% T6ox and T6deam1 must show an increase for the T26deam1 peak eluting at ~66.5 min, as shown in FIG. 86.

Sample Exemplary values. The chromatograms of the first reference material injection and the sample must be visually equivalent with regard to number, relative size and elution order of significant peaks for the 215 nm and 280 nm traces as indicated for the labeled peaks in FIG. 84 with the exception oxidized and/or deamidated peaks for T6ox and T26deam which are reported separately. The retention times for peaks T4, T25, and T27 in the sample must be within ±0.5 minutes of the retention time for the corresponding peaks of the first reference material injection.

CALCULATIONS. NOTE: Use the 215 nm data for these calculations unless otherwise specified. The retention times of peaks T4, T25, and T27 (FIG. 84) in the bracketing reference material runs should not differ more than 0.5 min (FIG. 84).

Number of Theoretical Plates. Column efficiency, evaluated as the number of theoretical plates (N), is calculated using the retention time and the width of peak T27 from the reference material run, (FIG. 84), according to the following equation:

$$N = 16\left(\frac{t}{w}\right)^2$$

WHERE:

w=the peak width at the baseline measured by extrapolating the relatively straight sides to the baseline.

t=the retention time of the peak T27 measured from time of injection to time of elution of peak maximum.

Resolution. The resolution (R) between peak T12 and peak T2 (FIG. 84) is calculated using the following equation:

$$R = \frac{2(t_2 - t_1)}{(w_1 + w_2)}$$

WHERE:

$t_1$, $t_2$=retention times of peak T12 and peak T2, respectively $w_1$, $w_2$=tangent-defined peak width at baseline of the peaks with retention times $t_1$ and $t_2$, respectively.

For all samples and standards, calculate Percent Oxidation of Met85 from the 280 nm peak area data as follows:

Percent Oxidation=$100*A_{T6ox}/(A_{T6ox}+A_{T6})$

WHERE:

$A_{T6}$=peak area for T6, (84-93) in 280 nm trace $A_{T6ox}$=peak area for T6ox, Met(O)$^{85}$ (84-93), in 280 nm trace For all samples and standards, calculate the Percent Deamidation of Asn294 for the 215 nm peak area as data shown in FIG. 86:

PercentDeamidation=

$$100 * \frac{A_{T26deam1}}{A_{T26} + A_{T26deam1} + A_{T26deam2} + A_{T26deam3} + A_{T26deam4}}$$

WHERE:

$A_{T26}$=peak area for T26, (281-302), in 215 nm trace $A_{T26deam1}$=peak area for T26deam1, isoAsp$^{294}$(281-302), in 215 nm trace $A_{T26deam2}$=peak area for T26deam2, Asp$^{299}$(281-302), in 215 nm trace $A_{T26deam3}$=peak area for T26deam3, Asp$^{294}$(281-302), in 215 nm trace $A_{T26deam4}$=peak area for T26deam4, Asu$^{294}$(281-302), in 215 nm trace Theoretically Expected Fragments of CTLA4-Ig Tryptic Digest (Refer to FIG. 84)

| Fragment | Residue | Sequence |
|---|---|---|
| T1 | 1-14 | MHVAQPAVVLASSR |
| T2 | 15-28 | GIASFVCEYASPGK |
| T3 | 29-33 | ATEVR |
| T4 | 34-38 | VTVLR |
| T5* | 39-83 | QADSQVTEVCAATYMMGNELTFLDDSICTGTSSGNQVNLTIQGLR |
| T6 | 84-93 | AMDTGLYICK |
| T7* | 94-128 | VELMYPPPYYLGIGNGTQIYVIDPEPCPDSDQEPK |
| T8** | 129-132 | SSDK |
| T9** | 133-158 | THTSPPSPAPELLGGSSVFLFPPKPK |
| T10 | 159-165 | DTLMISR |
| T11 | 166-184 | TPEVTCVVVDVSHEDPEVK |
| T12 | 185-198 | FNWYVDGVEVHNAK |
| T13 | 199-202 | TKPR |
| T14* | 203-211 | EEQYNSTYR |
| T15 | 212-227 | VVSVLTVLHQDWLNGK |
| T16 | 228-230 | EYK |
| T17 | 231-232 | CK |
| T18 | 233-236 | VSNK |
| T19 | 237-244 | ALPAPIEK |
| T20 | 245-248 | TISK |
| T21 | 249-250 | AK |
| T22 | 251-254 | GQPR |
| T23 | 255-265 | EPQVYTLPPSR |
| T24 | 266-270 | DELTK |
| T25 | 271-280 | NQVSLTCLVK |
| T26 | 281-302 | GFYPSDIAVEWESNGQPENNYK |
| T27 | 303-319 | TTPPVLDSDGSFFLYSK |
| T28 | 320-324 | LTVDK |

| Fragment | Residue | Sequence |
|---|---|---|
| T29 | 325-326 | SR |
| T30 | 327-349 | WQQGNVFSCSVMHEALHNHYTQK |
| T31 | 350-356 | SLSLSPG |

*Contains N-linked carbohydrate.
** Contains O-linked carbohydrate.

Example 66—Healthy Single Dose Human Study

A single site, randomized, single-dose, study was used to evaluate the pharmacokinetics of CTLA4-Ig (produced by the CD-CHO1) process in healthy subjects. Thirteen (13) subjects who fulfilled the Inclusion and Exclusion Exemplary values were admitted to the clinical study unit and received CTLA4-Ig produced by Process CD-CHO1 as a single intravenous infusion of 10 mg/kg over 30 minutes. Each subject was observed in the clinical study unit for 24 hours following the infusion. Blood samples were collected at specified time points after dosing for up to 71 days for quantitation of CTLA4-Ig. The subjects were evaluated as to pharmacokinetics: Cmax, Tmax, AUC (INF), T-HALF, CLT, and Vss for each subject were derived from serum concentration versus time data. CTLA4-Ig was supplied as a 200 mg/vial formulation. Healthy subjects were administered a 30-minute IV infusion of 10 mg/kg CTLA4-Ig. Determinations of PK, safety, and immunogenic determinations were assessed at specified time points through Day 71 after dosing.

Statistical Methods:

Sample Size: The sample size of 13 subjects provided 90% confidence that the estimate of the ratio of geometric mean would be within 15% of the true value for Cmax, and within 10% of the true value for AUC(INF) for CTLA4-Ig. Statistical Analysis: Subject demographics, physical examinations, laboratory data, and vital signs were summarized. Incidence of adverse events was tabulated by body system and severity. For Cmax and AUC(INF) of CTLA4-Ig, 90% confidence intervals for the ratios of population geometric means for the Process CD-CHO1 were calculated from the results of an analysis of variance on log(Cmax) and log (AUC).

PHARMACOKINETIC RESULTS: The pharmacokinetic results were determined using a validated noncompartmental analysis program. Pharmacokinetic parameters were obtained from 13 subjects dosed with Process CD-CHO1 CTLA4-Ig. The following table lists the pharmacokinetic parameters for CTLA4-Ig in healthy subjects. The Table below shows the summary statistics for the CTLA4-Ig pharmacokinetic parameters.

| Pharmacokinetic Paramter | (N = 13) |
|---|---|
| Cmax (µg/mL) | |
| Geometric Mean | 284.7 |
| (CV %) | (23%) |
| AUC (INF) (µg · h/mL) | |
| Geometric Mean | 44403.0 |
| (CV %) | (18%) |
| Tmax (h) | |
| Median | 0.50 |
| (min, max) | (0.50, 2.00) |
| T-HALF (Days) | |
| Mean | 16.68 |
| (SD) | (3.24) |
| CLT (mL/h/kg) | |
| Mean | 0.23 |
| (SD) | (0.04) |
| Vss (L/kg) | |
| Mean | 0.09 |
| (SD) | (0.02) |

CTLA4-Ig had mean T-HALF values of approximately 17 days in healthy subjects, consistent with half lives obtained in psoriasis subjects (10-18 days) and rheumatoid arthritis patients (approximately 13 days). The observed mean Vss values of 0.09 to 0.10 L/kg indicated that CTLA4-Ig was confined primarily to the vascular system and did not distribute significantly into extravascular spaces.

The following table shows the serum concentrations (ng/ml) per subject.

| SUBJECT | TREATMENT | DAYS | TIME (HR) | CONCENTRATION (NG/ML) |
|---|---|---|---|---|
| | CDCHO1 | 1 | 0.00 | <LLQ |
| | | 1 | 0.25 | 138335.6 |
| | | 1 | 0.50 | 251679.1 |
| | | 1 | 1.00 | 266363.1 |
| | | 1 | 2.00 | 286465.6 |
| | | 1 | 6.00 | 243171.3 |
| | | 1 | 12.00 | 252164.9 |
| | | 2 | 0.00 | 170448.6 |
| | | 4 | 0.00 | 120068.1 |
| | | 8 | 0.00 | 67988.11 |
| | | 15 | 0.00 | 41464.24 |
| | | 22 | 0.00 | 22306.20 |
| | | 29 | 0.00 | 17333.61 |
| | | 43 | 0.00 | 10214.14 |
| | | 57 | 0.00 | 4759.26 |
| | | 71 | 0.00 | 2794.16 |

-continued

| Treatment | Subject | Cmax (mcg/mL) | AUC(INF) (mcg · h/mL) | Tmax (h) | T-Half (day) | Clearance (mL/h/Kg) | VSS (L/Kg) |
|---|---|---|---|---|---|---|---|
| CDCHO1 | | 286.47 | 49123.2 | 2.00 | 15.97 | 0.20 | 0.08 |
| | | 230.41 | 33477.3 | 1.00 | 16.15 | 0.30 | 0.11 |
| | | 247.04 | 40005.5 | 2.00 | 19.80 | 0.25 | 0.13 |
| | | 365.55 | 43112.7 | 0.50 | 17.58 | 0.23 | 0.09 |
| | | 255.18 | 46276.2 | 2.00 | 15.29 | 0.22 | 0.09 |
| | | 309.40 | 48848.2 | 1.00 | 18.95 | 0.20 | 0.09 |
| | | 278.31 | 35339.3 | 0.50 | 14.23 | 0.28 | 0.09 |
| | | 246.33 | 52238.7 | 0.50 | 20.52 | 0.19 | 0.10 |
| | | 174.57 | 38534.8 | 0.50 | 15.61 | 0.26 | 0.13 |
| | | 375.92 | 50418.0 | 0.50 | 13.70 | 0.20 | 0.07 |
| | | 426.97 | 50761.0 | 0.50 | 13.13 | 0.20 | 0.06 |
| | | 297.59 | 61322.4 | 0.50 | 23.45 | 0.16 | 0.10 |
| | | 300.22 | 36438.5 | 0.50 | 12.42 | 0.27 | 0.08 |
| CDCHO1 | N | 13 | 13 | 13 | 13 | 13 | 13 |
| | MEAN | 291.84 | 45068.89 | 0.92 | 16.68 | 0.23 | 0.09 |
| | S.D. | 67.29 | 8085.22 | 0.64 | 3.24 | 0.04 | 0.02 |
| | GEO.MEAN | 284.71 | 44403.04 | 0.77 | 16.40 | 0.23 | 0.09 |
| | C.V. | 23 | 18 | 69 | 19 | 18 | 23 |
| | MEDIAN | 286.47 | 46276.20 | 0.50 | 15.97 | 0.22 | 0.09 |
| | MIN | 174.57 | 33477.26 | 0.50 | 12.42 | 0.16 | 0.06 |
| | MAX | 426.97 | 61322.42 | 2.00 | 23.45 | 0.30 | 0.13 |

Serum Assay for CTLA4-Ig

Serum samples were analyzed for CTLA4-Ig by an enzyme-linked immunosorbent assay (ELISA) in a total of 25 analytical runs. All analytical results met the exemplary values established prior to sample analysis indicating that the ELISA method was precise and accurate for the quantitation of CTLA4-Ig in study samples. A summary of the standard curve parameters and mean QC data for CTLA4-Ig in serum are presented in Table 48. The between- and within-run variability of the analytical QCs for CTLA4-Ig was 4.5% and 3.5% CV, respectively. Mean observed concentrations of the analytical QC samples deviated less than ±8.9% from the nominal values (Table 48).

TABLE 48

Summary of Quality Control Data for the Assay of CTLA4-Ig in Human Serum

| Nominal Conc. | Low (3,000 ng/mL) | Mid (12,500 ng/mL) | High (24,000 ng/mL) |
|---|---|---|---|
| Mean Observed Conc. | 2.866 | 13.608 | 24.526 |
| % Dev. | −4.5 | 8.9 | 2.2 |
| Between Run Precision (% CV) | 4.5 | 2.8 | 3.0 |
| Within Run Precision (% CV) | 2.4 | 3.5 | 2.9 |
| Total Variation (% CV) | 5.1 | 4.5 | 4.2 |
| N | 75 | 75 | 75 |
| Number of Runs | 25 | 25 | 25 |

Pharmacokinetics of CTLA4-Ig

Figure 43:
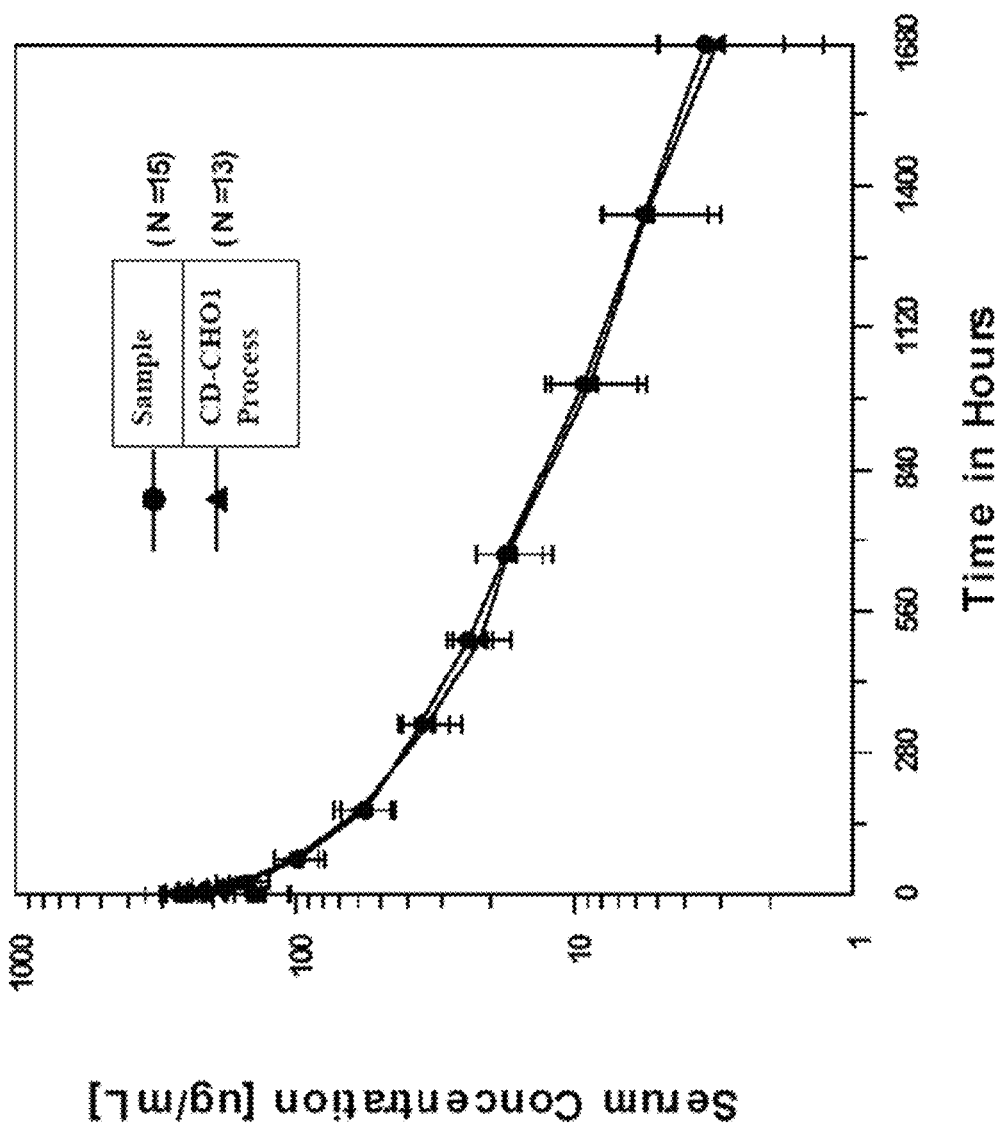
FIG. 43 is a graph depicting the mean CTLA4-Ig serum concentrations [μg/ml] versus time (over 71 days).

The mean and standard deviations for CTLA4-Ig serum concentrations for all subjects by process are presented in the Table directly below. The mean CTLA4-Ig serum concentrations versus time profiles over 71 days are presented in FIG. 43.

Mean Serum Concentration vs. Time Data for CTLA4-Ig (ng/ml)

| Day | Hr | MM | N | Mean | SD | % CV |
|---|---|---|---|---|---|---|
| • | • | 0 | 15 | 0.42 | 0.87 | 207.21 |
| • | • | 15 | 15 | 135475.0 | 28811.82 | 21.27 |
| • | • | 30 | 15 | 273867.9 | 71406.26 | 26.07 |
| • | 1 | 0 | 15 | 253311.5 | 43221.58 | 17.06 |
| • | 2 | 0 | 15 | 254479.4 | 39611.12 | 15.57 |
| • | 6 | 0 | 15 | 219082.5 | 44894.29 | 20.49 |
| • | 12 | 0 | 15 | 191885.0 | 45180.00 | 23.55 |
| 1 | 0 | 0 | 15 | 161732.2 | 28740.25 | 17.77 |
| 3 | 0 | 0 | 15 | 101411.4 | 18615.59 | 18.36 |
| 7 | 0 | 0 | 15 | 59375.96 | 13598.10 | 22.90 |
| 14 | 0 | 0 | 15 | 33676.97 | 8148.64 | 24.20 |
| 21 | 0 | 0 | 15 | 21909.72 | 5226.77 | 23.86 |
| 28 | 0 | 0 | 15 | 17193.52 | 5145.61 | 29.93 |
| 42 | 0 | 0 | 15 | 8828.95 | 3246.22 | 36.77 |
| 56 | 0 | 0 | 15 | 5244.51 | 2621.36 | 49.98 |
| 70 | 0 | 0 | 15 | 2970.32 | 1811.64 | 60.99 |

Summary statistics for the pharmacokinetic parameters (Cmax, AUC (INF), CLT, Vss, Tmax, and T-HALF) are presented in Table 50. The results indicated that CTLA4-Ig produced from a process of the invention had a mean T-HALF value of approximately 17 days (range from 7-25 days). The observed Vss values of 0.09 to 0.10 L/kg indicated that CTLA4-Ig was confined primarily to the extracellular fluid volume.

TABLE 50

Summary Statistics for Pharmacokinetic Parameters of CTLA4-Ig produced by the process of the invention

| Formulation | Cmax (µg/mL) Geom. Mean (CV %) | AUC(INF) (µg · h/mL) Geom. Mean (CV %) | Clearance (mL/h/kg) Mean (SD) | Vss (L/kg) Mean (SD) | Tmax (h) Median (min, max) | T-HALF (Days) Mean (SD) |
|---|---|---|---|---|---|---|
| Process (n = 13) | 284.71 (23%) | 44403.04 (185) | 0.23 (0.04) | 0.09 (0.02) | 0.50 (0.50, 2.00) | 16.68 (3.24) |

The results indicated that the mean T-HALF for CTLA4-Ig produced by process of the invention was approximately 17 days. Both clearance and volume of distribution values are also presented in Table 50.

Pharmacokinetics of CTLA4-Ig in healthy adult subjects after a single 10 mg/kg intravenous infusion and in RA patients after multiple 10 mg/kg intravenous infusions are set) out in Table 47.

TABLE 47

Pharmacokinetic Parameters (Mean, Range) in Healthy Subjects and RA Patients After 10 mg/kg Intravenous Infusion(s)

| PK Parameter | Healthy Subjects (After 10 mg/kg Single Dose n = 13) | RA Patients (After 10 mg/kg Multiple Doses[a])n = 14) |
|---|---|---|
| Peak Concentration ($C_{max}$) [mcg/mL] | 292 (175-427) | 295 (171-398) |
| Terminal half-life ($t_{1/2}$) [days] | 16.7 (12-23) | 13.1 (8-25) |
| Systemic clearance (CL) [mL/h/kg] | 0.23 (0.16-0.30) | 0.22 (0.13-0.47) |
| Volume of distribution (Vss) [L/kg] | 0.09 (0.06-0.13) | 0.07 (0.02-0.13) |

[a]Multiple intravenous infusions were administered at days 1, 15, 30, and monthly thereafter.

Example 67—DNA Sequence of Plasmid pcSDhuCTLA4Ig

```
        BglII
        ~~~~~
  1 GATCTCCCGA TCCCCTATGG TCGACTCTCA GTACAATCTG CTCTGATGCC GCATAGTTAA
    CTAGAGGGCT AGGGGATACC AGCTGAGAGT CATGTTAGAC GAGACTACGG CGTATCAATT

61 GCCAGTATCT GCTCCCTGCT TGTGTGTTGG AGGTCGCTGA GTAGTGCGCG AGCAAAATTT
    CGGTCATAGA CGAGGGACGA ACACACAACC TCCAGCGACT CATCACGCGC TCGTTTTAAA

121 AAGCTACAAC AAGGCAAGGC TTGACCGACA ATTGCATGAA GAATCTGCTT AGGGTTAGGC
    TTCGATGTTG TTCCGTTCCG AACTGGCTGT TAACGTACTT CTTAGACGAA TCCCAATCCG

?-----------------CMV Promoter-------------------
181 GTTTTGCGCT GCTTCGCGAT GTACGGGCCA GATATACGCG TTGACATTGA TTATTGACTA
    CAAAACGCGA CGAAGCGCTA CATGCCCGGT CTATATGCGC AACTGTAACT AATAACTGAT --------------------------------------------------------------
241 GTTATTAATA GTAATCAATT ACGGGGTCAT TAGTTCATAG CCCATATATG GAGTTCCGCG
    CAATAATTAT CATTAGTTAA TGCCCCAGTA ATCAAGTATC GGGTATATAC CTCAAGGCGC --------------------------------------------------------------
301 TTACATAACT TACGGTAAAT GGCCCGCCTG GCTGACCGCC CAACGACCCC CGCCCATTGA
    AATGTATTGA ATGCCATTTA CCGGGCGGAC CGACTGGCGG GTTGCTGGGG GCGGGTAACT --------------------------------------------------------------
361 CGTCAATAAT GACGTATGTT CCCATAGTAA CGCCAATAGG GACTTTCCAT TGACGTCAAT
    GCAGTTATTA CTGCATACAA GGGTATCATT GCGGTTATCC CTGAAAGGTA ACTGCAGTTA --------------------------------------------------------------
421 GGGTGGACTA TTTACGGTAA ACTGCCCACT TGGCAGTACA TCAAGTGTAT CATATGCCAA
    CCCACCTGAT AAATGCCATT TGACGGGTGA ACCGTCATGT AGTTCACATA GTATACGGTT --------------------------------------------------------------
481 GTACGCCCCC TATTGACGTC AATGACGGTA AATGGCCCGC CTGGCATTAT GCCCAGTACA
    CATGCGGGGG ATAACTGCAG TTACTGCCAT TTACCGGGCG GACCGTAATA CGGGTCATGT NcoI
                                                             ~~~
541 TGACCTTATG GGACTTTCCT ACTTGGCAGT ACATCTACGT ATTAGTCATC GCTATTACCA
    ACTGGAATAC CCTGAAAGGA TGAACCGTCA TGTAGATGCA TAATCAGTAG CGATAATGGT NcoI
    ~~~
    --------------------------CMV Promoter--------------------------
601 TGGTGATGCG GTTTTGGCAG TACATCAATG GGCGTGGATA GCGGTTTGAC TCACGGGGAT
    ACCACTACGC CAAAACCGTC ATGTAGTTAC CCGCACCTAT CGCCAAACTG AGTGCCCCTA --------------------------------------------------------------
661 TTCCAAGTCT CCACCCCATT GACGTCAATG GGAGTTTGTT TTGGCACCAA AATCAACGGG
    AAGGTTCAGA GGTGGGGTAA CTGCAGTTAC CCTCAAACAA AACCGTGGTT TTAGTTGCCC --------------------------------------------------------------
721 ACTTTCCAAA ATGTCGTAAC AACTCCGCCC CATTGACGCA AATGGGCGGT AGGCGTGTAC
    TGAAAGGTTT TACAGCATTG TTGAGGCGGG GTAACTGCGT TTACCCGCCA TCCGCACATG --------------------------------------------------------------
781 GGTGGGAGGT CTATATAAGC AGAGCTCTCT GGCTAACTAG AGAACCCACT GCTTACTGGC
    CCACCCTCCA GATATATTCG TCTCGAGAGA CCGATTGATC TCTTGGGTGA CGAATGACCG
```

```
                                                    HindIII             BamHI
     ----------->                                   ~~~~~~~             ~~~~~~
 841 TTATCGAAAT TAATACGACT CACTATAGGG AGACCCAAGC TTGGTACCGA GCTCGGATCC
     AATAGCTTTA ATTATGCTGA GTGATATCCC TCTGGGTTCG AACCATGGCT CGAGCCTAGG PstI
                  EcoRI   ~~~~~~                    ?-huCTLA-4 Ig-
                  ~~~~~~                            M   G   V   L
 901 ACTAGTAACG GCCGCCAGTG TGCTGGAATT CTGCAGATAG CTTCACCAAT GGGTGTACTG
     TGATCATTGC CGGCGGTCAC ACGACCTTAA GACGTCTATC GAAGTGGTTA CCCACATGAC ---------------------------------------------------------------
       L   T   Q   R   T   L   L   S   L   V   L   A   L   L   F   P   S   M   A   S
 961 CTCACACAGA GGACGCTGCT CAGTCTGGTC CTTGCACTCC TGTTTCCAAG CATGGCGAGC
     GAGTGTGTCT CCTGCGACGA GTCAGACCAG GAACGTGAGG ACAAAGGTTC GTACCGCTCG ---------------------------------------------------------------
       M   A   M   H   V   A   Q   P   A   V   V   L   A   S   S   R   G   I   A   S
1021 ATGGCAATGC ACGTGGCCCA GCCTGCTGTG GTACTGGCCA GCAGCCGAGG CATCGCCAGC
     TACCGTTACG TGCACCGGGT CGGACGACAC CATGACCGGT CGTCGGCTCC GTAGCGGTCG ---------------------------------------------------------------
       F   V   C   E   Y   A   S   P   G   K   A   T   E   V   R   V   T   V   L   R
1081 TTTGTGTGTG AGTATGCATC TCCAGGCAAA GCCACTGAGG TCCGGGTGAC AGTGCTTCGG
     AAACACACAC TCATACGTAG AGGTCCGTTT CGGTGACTCC AGGCCCACTG TCACGAAGCC ---------------------------huCTLA-4-Ig-------------------------
       Q   A   D   S   Q   V   T   E   V   C   A   A   T   Y   M   M   G   N   E   L
1141 CAGGCTGACA GCCAGGTGAC TGAAGTCTGT GCGGCAACCT ACATGATGGG AATGAGTTG
     GTCCGACTGT CGGTCCACTG ACTTCAGACA CGCCGTTGGA TGTACTACCC CTTACTCAAC ---------------------------------------------------------------
       T   F   L   D   D   S   I   C   T   G   T   S   S   G   N   Q   V   N   L   T
1201 ACCTTCCTAG ATGATTCCAT CTGCACGGGC ACCTCCAGTG GAAATCAAGT GAACCTCACT
     TGGAAGGATC TACTAAGGTA GACGTGCCCG TGGAGGTCAC CTTTAGTTCA CTTGGAGTGA NcoI
                   ~~~~~~
     ---------------------------------------------------------------
       I   Q   G   L   R   A   M   D   T   G   L   Y   I   C   K   V   E   L   M   Y
1261 ATCCAAGGAC TGAGGGCCAT GGACACGGGA CTCTACATCT GCAAGGTGAA GCTCATGTAC
     TAGGTTCCTG ACTCCCGGTA CCTGTGCCCT GAGATGTAGA CGTTCCACTT CGAGTACATG ---------------------------------------------------------------
       P   P   P   Y   L   G   I   G   N   G   T   Q   I   Y   V   I   D   P   E
1321 CCACCGCCAT ACTACCTGGG CATAGGCAAC GGAACCCAGA TTTATGTAAT TGATCCAGAA
     GGTGGCGGTA TGATGGACCC GTATCCGTTG CCTTGGGTCT AAATACATTA ACTAGGTCTT ---------------------------------------------------------------
       P   C   P   D   S   D   Q   E   P   K   S   S   D   K   T   H   T   S   P   P
1381 CCGTGCCCAG ATTCTGATCA GGAGCCCAAA TCTTCTGACA AAACTCACAC ATCCCCACCG
     GGCACGGGTC TAAGACTAGT CCTCGGGTTT AGAAGACTGT TTTGAGTGTG TAGGGGTGGC ---------------------------------------------------------------
       S   P   A   P   E   L   L   G   G   S   S   V   F   L   F   P   P   K   P   K
1441 TCCCCAGCAC CTGAACTCCT GGGGGGATCG TCAGTCTTCC TCTTCCCCCC AAAACCCAAG
     AGGGGTCGTG GACTTGAGGA CCCCCCTAGC AGTCAGAAGG AGAAGGGGGG TTTTGGGTTC ---------------------------------------------------------------
       D   T   L   M   I   S   R   T   P   E   V   T   C   V   V   V   D   V   S   H
1501 GACACCCTCA TGATCTCCCG GACCCCTGAG GTCACATGCG TGGTGGTGGA CGTGAGCCAC
     CTGTGGGAGT ACTAGAGGGC CTGGGGACTC CAGTGTACGC ACCACCACCT GCACTCGGTG ---------------------------------------------------------------
       E   D   P   E   V   K   F   N   W   Y   V   D   G   V   E   V   H   N   A   K
1561 GAAGACCCTG AGGTCAAGTT CAACTGGTAC GTGGACGGCG TGGAGGTGCA TAATGCCAAG
     CTTCTGGGAC TCCAGTTCAA GTTGACCATG CACCTGCCGC ACCTCCACGT ATTACGGTTC ---------------------------huCTLA-4 Ig-------------------------
       T   K   P   R   E   E   Q   Y   N   S   T   Y   R   V   V   S   V   L   T   V
1621 ACAAAGCCGC GGGAGGAGCA GTACAACAGC ACGTACCGTG TGGTCAGCGT CCTCACCGTC
     TGTTTCGGCG CCCTCCTCGT CATGTTGTCG TGCATGGCAC ACCAGTCGCA GGAGTGGCAG ---------------------------------------------------------------
       L   H   Q   D   W   L   N   G   K   E   Y   K   C   K   V   S   N   K   A   L
1681 CTGCACCAGG ACTGGCTGAA TGGCAAGGAG TACAAGTGCA AGGTCTCCAA CAAAGCCCTC
     GACGTGGTCC TGACCGACTT ACCGTTCCTC ATGTTCACGT TCCAGAGGTT GTTTCGGGAG

---------------------------------------------------------------
```

```
                P  A  P  I     E  K  T     I  S  K     A  K  G     Q     P  R  E     P  Q  V
1741 CCAGCCCCCA TCGAGAAAAC CATCTCCAAA GCCAAAGGGC AGCCCCGAGA ACCACAGGTG
     GGTCGGGGGT AGCTCTTTTG GTAGAGGTTT CGGTTTCCCG TCGGGGCTCT TGGTGTCCAC

SmaI
                            ~~~~~~~

------------------------------------------------------------------
        Y  T  L  P     P  S  R     D  E  L     T  K  N     Q  V  S     T  C  L
1801 TACACCCTGC CCCCATCCCG GGATGAGCTG ACCAAGAACC AGGTCAGCCT GACCTGCCTG
     ATGTGGGACG GGGGTAGGGC CCTACTCGAC TGGTTCTTGG TCCAGTCGGA CTGGACGGAC

------------------------------------------------------------------
           V  K  G  F     Y  P  S     D  I  A     V  E  W  E     S  N  G     Q  P  E
1861 GTCAAAGGCT TCTATCCCAG CGACATCGCC GTGGAGTGGG AGAGCAATGG GCAGCCGGAC
     CAGTTTCCGA AGATAGGGTC GCTGTAGCGG CACCTCACCC TCTCGTTACC CGTCGGCCTC

------------------------------------------------------------------
        N  N  Y  K     T  T  P     P  V  L     D  S  D  G     S  F  F     L  Y  S
1921 AACAACTACA AGACCACGCC TCCCGTGCTG GACTCCGACG GCTCCTTCTT CCTCTACAGC
     TTGTTGATGT TCTGGTGCGG AGGGCACGAC CTGAGGCTGC CGAGGAAGAA GGAGATGTCG

------------------------------------------------------------------
        K  L  T  V     D  K  S     R  W  Q     Q  G  N  V     F  S  C     S  V  M
1981 AAGCTCACCG TGGACAAGAG CAGGTGGCAG CAGGGGAACG TCTTCTCATG CTCCGTGATG
     TTCGAGTGGC ACCTGTTCTC GTCCACCGTC GTCCCCTTGC AGAAGAGTAC GAGGCACTAC

------------------------------------------------------------------
        H  E  A  L     H  N  H     Y  T  Q     K  S  L  S     L  S  P     G  K *
2041 CATGAGGCTC TGCACAACCA CTACACGCAG AAGAGCCTCT CCCTGTCTCC GGGTAAATGA
     GTACTCCGAG ACGTGTTGGT GATGTGCGTC TTCTCGGAGA GGGACAGAGG CCCATTTACT

SmaI                      XbaI
                              ~~~~~~~                     ~~~~
2101 GTGCGACGGC CGGCAAGCCC CCGCTCCCCG GGCTCTCGCG GTCGCACGAG GATGCTTCTA
     CACGCTGCCG GCCGTTCGGG GGCGAGGGGC CCGAGAGCGC CAGCGTGCTC CTACGAAGAT

XbaI                                    ?----BGH polyadenylation signal------
     ~~
2161 GAGGGCCCTA TTCTATAGTG TCACCTAAAT GCTAGAGCTC GCTGATCAGC CTCGACTGTG
     CTCCCGGGAT AAGATATCAC AGTGGATTTA CGATCTCGAG CGACTAGTCG GAGCTGACAC ------------------------------------------------------------------
2221 CCTTCTAGTT GCCAGCCATC TGTTGTTTGC CCCTCCCCCG TGCCTTCCTT GACCCTGGAA
     GGAAGATCAA CGGTCGGTAG ACAACAAACG GGGAGGGGGC ACGGAAGGAA CTGGGACCTT ------------------------------------------------------------------
2281 GGTGCCACTC CCACTGTCCT TTCCTAATAA AATGAGGAAA TTGCATCGCA TTGTCTGAGT
     CCACGGTGAG GGTGACAGGA AAGGATTATT TTACTCCTTT AACGTAGCGT AACAGACTCA ------------------------------------------------------------------
2341 AGGTGTCATT CTATTCTGGG GGGTGGGGTG GGGCAGGACA GCAAGGGGGA GGATTGGGAA
     TCCACAGTAA GATAAGACCC CCCACCCCAC CCCGTCCTGT CGTTCCCCCT CCTAACCCTT ------------------------>
2401 GACAATAGCA GGCATGCTGG GGATGCGGTG GGCTCTATGG CTTCTGAGGC GGAAAGAACC
     CTGTTATCGT CCGTACGACC CCTACGCCAC CCGAGATACC GAAGACTCGG CCTTTCTTGG 2461 AGCTGGGGCT CTAGGGGGTA TCCCCACGCG CCCTGTAGCG GCGCATTAAG CGCGGCGGGT
     TCGACCCCGA GATCCCCCAT AGGGGTGCGC GGGACATCGC CGCGTAATTC GCGCCGCCCA 2521 GTGGTGGTTA CGCGCAGCGT GACCGCTACA CTTGCCAGCG CCCTAGCGCC CGCTCCTTTC
     CACCACCAAT GCGCGTCGCA CTGGCGATGT GAACGGTCGC GGGATCGCGG GCGAGGAAAG 2581 GCTTTCTTCC CTTCCTTTCT CGCCACGTTC GCCCTGTGGA ATGTGTGTCA GTTAGGGTGT
     CGAAAGAAGG GAAGGAAAGA GCGGTGCAAG CGGGACACCT TACACACAGT CAATCCCACA 2641 GGAAAGTCCC CAGGCTCCCC AGCAGGCAGA AGTATGCAAA GCATGCATCT CAATTAGTCA
     CCTTTCAGGG GTCCGAGGGG TCGTCCGTCT TCATACGTTT CGTACGTAGA GTTAATCAGT 2701 GCAACCAGGT GTGGAAAGTC CCCAGGCTCC CCAGCAGGCA GAAGTATGCA AAGCATGCAT
     CGTTGGTCCA CACCTTTCAG GGGTCCGAGG GGTCGTCCGT CTTCATACGT TTCGTACGTA 2761 CTCAATTAGT CAGCAACCAT AGTCCCGCCC CTAACTCCGC CCATCCCGCC CCTAACTCCG
     GAGTTAATCA GTCGTTGGTA TCAGGGCGGG GATTGAGGCG GGTAGGGCGG GGATTGAGGC NcoI
                              ~~~~~~    ?------SV40 Promoter----------
2821 CCCAGTTCCG CCCATTCTCC GCCCCATGGC TGACTAATTT TTTTTATTTA TGCAGAGGCC
     GGGTCAAGGC GGGTAAGAGG CGGGGTACCG ACTGATTAAA AAAAATAAAT ACGTCTCCGG

------------------------------------------------------------------>
```

-continued

```
2881 GAGGCCGCCT CGGCCTCTGA GCTATTCCAG AAGTAGTGAG GAGGCTTTTT TGGAGGCCTA
     CTCCGGCGGA GCCGGAGACT CGATAAGGTC TTCATCACTC CTCCGAAAAA ACCTCCGGAT

HindIII
             ~~~~~~
2941 GGCTTTTGCA AAAAGCTTGG ACAGCTGAGG GCTGCGATTT CGCGCCAAAC TTGACGGCAA
     CCGAAAACGT TTTTCGAACC TGTCGACTCC CGACGCTAAA GCGCGGTTTG AACTGCCGTT -------dhfr--------
3001 TCCTAGCGTG AAGGCTGGTA GGATTTTATC CCCGCTGCCA TCATGGTTCG ACCATTGAAC
     AGGATCGCAC TTCCGACCAT CCTAAAATAG GGGCGACGGT AGTACCAAGC TGGTAACTTG ----------------------------------------------------------------
3061 TGCATCGTCG CCGTGTCCCA AGATATGGGG ATTGGCAAGA ACGGAGACCT ACCCTGGCCT
     ACGTAGCAGC GGCACAGGGT TCTATACCCC TAACCGTTCT TGCCTCTGGA TGGGACCGGA ----------------------------------------------------------------
3121 CCGCTCAGGA ACGAGTTCAA GTACTTCCAA AGAATGACCA CAACCTCTTC AGTGGAAGGT
     GGCGAGTCCT TGCTCAAGTT CATGAAGGTT TCTTACTGGT GTTGGAGAAG TCACCTTCCA ----------------------------------------------------------------
3181 AAACAGAATC TGGTGATTAT GGGTAGGAAA ACCTGGTTCT CCATTCCTGA GAAGAATCGA
     TTTGTCTTAG ACCACTAATA CCCATCCTTT TGGACCAAGA GGTAAGGACT CTTCTTAGCT ----------------------------------------------------------------
3241 CCTTTAAAGG ACAGAATTAA TATAGTTCTC AGTAGAGAAC TCAAAGAACC ACCACGAGGA
     GGAAATTTCC TGTCTTAATT ATATCAAGAG TCATCTCTTG AGTTTCTTGG TGGTGCTCCT --------------------------- dhfr -------------------------------
3301 GCTCATTTTC TTGCCAAAAG TTTGGATGAT GCCTTAAGAC TTATTGAACA ACCGGAATTG
     CGAGTAAAAG AACGGTTTTC AAACCTACTA CGGAATTCTG AATAACTTGT TGGCCTTAAC ----------------------------------------------------------------
3361 GCAAGTAAAG TAGACATGGT TTGGATAGTC GGAGGCAGTT CTGTTTACCA GGAAGCCATG
     CGTTCATTTC ATCTGTACCA AACCTATCAG CCTCCGTCAA GACAAATGGT CCTTCGGTAC ----------------------------------------------------------------
3421 AATCAACCAG GCCACCTCAG ACTCTTTGTG ACAAGGATCA TGCAGGAATT TGAAAGTGAC
     TTAGTTGGTC CGGTGGAGTC TGAGAAACAC TGTTCCTAGT ACGTCCTTAA ACTTTCACTG ----------------------------------------------------------------
3481 ACGTTTTTCC CAGAAATTGA TTTGGGGAAA TATAAACTTC TCCCAGAATA CCCAGGCGTC
     TGCAAAAAGG GTCTTTAACT AAACCCCTTT ATATTTGAAG AGGGTCTTAT GGGTCCGCAG ----------------------------------------------------------------
3541 CTCTCTGAGG TCCAGGAGGA AAAAGGCATC AAGTATAAGT TGAAGTCTA CGAGAAGAAA
     GAGAGACTCC AGGTCCTCCT TTTTCCGTAG TTCATATTCA AACTTCAGAT GCTCTTCTTT -->
3601 GACTAACAGG AAGATGCTTT CAAGTTCTCT GCTCCCCTCC TAAAGCTATG CATTTTTATA
     CTGATTGTCC TTCTACGAAA GTTCAAGAGA CGAGGGGAGG ATTTCGATAC GTAAAAATAT NcoI                  BglII
         ~~~~~~                ~~~~~~~
3661 AGACCATGGG ACTTTTGCTG GCTTTAGATC TTTGTGAAGG AACCTTACTT CTGTGGTGTG
     TCTGGTACCC TGAAAACGAC CGAAATCTAG AAACACTTCC TTGGAATGAA GACACCACAC 3721 ACATAATTGG ACAAACTACC TACAGAGATT TAAAGCTCTA AGGTAAATAT AAAATTTTTA
     TGTATTAACC TGTTTGATGG ATGTCTCTAA ATTTCGAGAT TCCATTTATA TTTTAAAAAT 3781 AGTGTATAAT GTGTTAAACT ACTGATTCTA ATTGTTTGTG TATTTTAGAT TCCAACCTAT
     TCACATATTA CACAATTTGA TGACTAAGAT TAACAAACAC ATAAAATCTA AGGTTGGATA 3841 GGAACTGATG AATGGGAGCA GTGGTGGAAT GCCTTTAATG AGGAAAACCT GTTTTGCTCA
     CCTTGACTAC TTACCCTCGT CACCACCTTA CGGAAATTAC TCCTTTTGGA CAAAACGAGT 3901 GAAGAAATGC CATCTAGTGA TGATGAGGCT ACTGCTGACT CTCAACATTC TACTCCTCCA
     CTTCTTTACG GTAGATCACT ACTACTCCGA TGACGACTGA GAGTTGTAAG ATGAGGAGGT 3961 AAAAGAAGA GAAAGGTAGA AGACCCCAAG GACTTTCCTT CAGAATTGCT AAGTTTTTTG
     TTTTTCTTCT CTTTCCATCT TCTGGGGTTC CTGAAAGGAA GTCTTAACGA TTCAAAAAAC 4021 AGTCATGCTG TGTTTAGTAA TAGAACTCTT GCTTGCTTTG CTATTTACAC CACAAAGGAA
     TCAGTACGAC ACAAATCATT ATCTTGAGAA CGAACGAAAC GATAAATGTG GTGTTTCCTT 4081 AAAGCTGCAC TGCTATACAA GAAAATTATG GAAAAATATT CTGTAACCTT TATAAGTAGG
     TTTCGACGTG ACGATATGTT CTTTTAATAC CTTTTTATAA GACATTGGAA ATATTCATCC 4141 CATAACAGTT ATAATCATAA CATACTGTTT TTTCTTACTC CACACAGGCA TAGAGTGTCT
     GTATTGTCAA TATTAGTATT GTATGACAAA AAAGAATGAG GTGTGTCCGT ATCTCACAGA
```

```
                               -continued
4201 GCTATTAATA ACTATGCTCA AAAATTGTGT ACCTTTAGCT TTTTAATTTG TAAAGGGGTT
     CGATAATTAT TGATACGAGT TTTTAACACA TGGAAATCGA AAAATTAAAC ATTTCCCCAA 4261 AATAAGGAAT ATTTGATGTA TAGTGCCTTG ACTAGAGATC ATAATCAGCC ATACCACATT
     TTATTCCTTA TAAACTACAT ATCACGGAAC TGATCTCTAG TATTAGTCGG TATGGTGTAA 4321 TGTAGAGGTT TTACTTGCTT TAAAAAACCT CCCACACCTC CCCCTGAACC TGAAACATAA
     ACATCTCCAA AATGAACGAA ATTTTTTGGA GGGTGTGGAG GGGGACTTGG ACTTTGTATT 4381 ATTGAATGCA ATTGTTGTTG TTAACTTGTT TATTGCAGCT TATAATGGTT ACAAATAAAG
     TAACTTACGT TAACAACAAC AATTGAACAA ATAACGTCGA ATATTACCAA TGTTTATTTC 4441 CAATAGCATC ACAAATTTCA CAAATAAAGC ATTTTTTTCA CTGCATTCTA GTTGTGGTTT
     GTTATCGTAG TGTTTAAAGT GTTTATTTCG TAAAAAAAGT GACGTAAGAT CAACACCAAA 4501 GTCCAAACTC ATCAATGTAT CTTATCATGT CTGGATCGGC TGGATGATCC TCCAGCGCGG
     CAGGTTTGAG TAGTTACATA GAATAGTACA GACCTAGCCG ACCTACTAGG AGGTCGCGCC 4561 GGATCTCATG CTGGAGTTCT TCGCCCACCC CAACTTGTTT ATTGCAGCTT ATAATGGTTA
     CCTAGAGTAC GACCTCAAGA AGCGGGTGGG TTGAACAAA TAACGTCGAA TATTACCAAT 4621 CAAATAAAGC AATAGCATCA CAAATTTCAC AAATAAAGCA TTTTTTTCAC TGCATTCTAG
     GTTTATTTCG TTATCGTAGT GTTTAAAGTG TTTATTTCGT AAAAAAAGTG ACGTAAGATC 4681 TTGTGGTTTG TCCAAACTCA TCAATGTATC TTATCATGTC TGTATACCGT CGACCTCTAG
     AACACCAAAC AGGTTTGAGT AGTTACATAG AATAGTACAG ACATATGGCA GCTGGAGATC 4741 CTAGAGCTTG GCGTAATCAT GGTCATAGCT GTTTCCTGTG TGAAATTGTT ATCCGCTCAC
     GATCTCGAAC CGCATTAGTA CCAGTATCGA CAAAGGACAC ACTTTAACAA TAGGCGAGTG 4801 AATTCCACAC AACATACGAG CCGGAAGCAT AAAGTGTAAA GCCTGGGGTG CCTAATGAGT
     TTAAGGTGTG TTGTATGCTC GGCCTTCGTA TTTCACATTT CGGACCCCAC GGATTACTCA 4861 GAGCTAACTC ACATTAATTG CGTTGCGCTC ACTGCCCGCT TTCCAGTCGG GAAACCTGTC
     CTCGATTGAG TGTAATTAAC GCAACGCGAG TGACGGGCGA AAGGTCAGCC CTTTGGACAG 4921 GTGCCAGCTG CATTAATGAA TCGGCCAACG CGCGGGGAGA GGCGGTTTGC GTATTGGGCG
     CACGGTCGAC GTAATTACTT AGCCGGTTGC GCGCCCCTCT CCGCCAAACG CATAACCCGC 4981 CTCTTCCGCT TCCTCGCTCA CTGACTCGCT GCGCTCGGTC GTTCGGCTGC GGCGAGCGGT
     GAGAAGGCGA AGGAGCGAGT GACTGAGCGA CGCGAGCCAG CAAGCCGACG CCGCTCGCCA 5041 ATCAGCTCAC TCAAAGGCGG TAATACGGTT ATCCACAGAA TCAGGGGATA ACGCAGGAAA
     TAGTCGAGTG AGTTTCCGCC ATTATGCCAA TAGGTGTCTT AGTCCCCTAT TGCGTCCTTT ?------------------------ColE1 ori------------------------
5101 GAACATGTGA GCAAAAGGCC AGCAAAAGGC CAGGAACCGT AAAAAGGCCG CGTTGCTGGC
     CTTGTACACT CGTTTTCCGG TCGTTTTCCG GTCCTTGGCA TTTTTCCGGC GCAACGACCG -----------------------------------------------------------------
5161 GTTTTTCCAT AGGCTCCGCC CCCCTGACGA GCATCACAAA AATCGACGCT CAAGTCAGAG
     CAAAAAGGTA TCCGAGGCGG GGGGACTGCT CGTAGTGTTT TTAGCTGCGA GTTCAGTCTC -----------------------------------------------------------------
5221 GTGGCGAAAC CCGACAGGAC TATAAAGATA CCAGGCGTTT CCCCCTGGAA GCTCCCTCGT
     CACCGCTTTG GGCTGTCCTG ATATTTCTAT GGTCCGCAAA GGGGGACCTT CGAGGGAGCA --------------------------ColE1 ori-----------------------------
5281 GCGCTCTCCT GTTCCGACCC TGCCGCTTAC CGGATACCTG TCCGCCTTTC TCCCTTCGGG
     CGCGAGAGGA CAAGGCTGGG ACGGCGAATG GCCTATGGAC AGGCGGAAAG AGGGAAGCCC -----------------------------------------------------------------
5341 AAGCGTGGCG CTTTCTCAAT GCTCACGCTG TAGGTATCTC AGTTCGGTGT AGGTCGTTCG
     TTCGCACCGC GAAAGAGTTA CGAGTGCGAC ATCCATAGAG TCAAGCCACA TCCAGCAAGC ApaLI
                ~~~~~~~
     -----------------------------------------------------------------
5401 CTCCAAGCTG GGCTGTGTGC ACGAACCCCC CGTTCAGCCC GACCGCTGCG CCTTATCCGG
     GAGGTTCGAC CCGACACACG TGCTTGGGGG GCAAGTCGGG CTGGCGACGC GGAATAGGCC -----------------------------------------------------------------
5461 TAACTATCGT CTTGAGTCCA ACCCGGTAAG ACACGACTTA TCGCCACTGG CAGCAGCCAC
     ATTGATAGCA GAACTCAGGT TGGGCCATTC TGTGCTGAAT AGCGGTGACC GTCGTCGGTG -----------------------------------------------------------------
5521 TGGTAACAGG ATTAGCAGAG CGAGGTATGT AGGCGGTGCT ACAGAGTTCT TGAAGTGGTG
     ACCATTGTCC TAATCGTCTC GCTCCATACA TCCGCCACGA TGTCTCAAGA ACTTCACCAC
```

```
5581 GCCTAACTAC GGCTACACTA GAAGGACAGT ATTTGGTATC TGCGCTCTGC TGAAGCCAGT
     CGGATTGATG CCGATGTGAT CTTCCTGTCA TAAACCATAG ACGCGAGACG ACTTCGGTCA

5641 TACCTTCGGA AAAAGAGTTG GTAGCTCTTG ATCCGGCAAA CAAACCACCG CTGGTAGCGG
     ATGGAAGCCT TTTTCTCAAC CATCGAGAAC TAGGCCGTTT GTTTGGTGGC GACCATCGCC

5701 TGGTTTTTTT GTTTGCAAGC AGCAGATTAC GCGCAGAAAA AAAGGATCTC AAGAAGATCC
     ACCAAAAAAA CAAACGTTCG TCGTCTAATG CGCGTCTTTT TTTCCTAGAG TTCTTCTAGG

------------------?
5761 TTTGATCTTT TCTACGGGGT CTGACGCTCA GTGGAACGAA AACTCACGTT AAGGGATTTT
     AAACTAGAAA AGATGCCCCA GACTGCGAGT CACCTTGCTT TTGAGTGCAA TTCCCTAAAA

5821 GGTCATGAGA TTATCAAAAA GGATCTTCAC CTAGATCCTT TTAAATTAAA AATGAAGTTT
     CCAGTACTCT AATAGTTTTT CCTAGAAGTG GATCTAGGAA AATTTAATTT TTACTTCAAA

<-----ampR------
5881 TAAATCAATC TAAAGTATAT ATGAGTAAAC TTGGTCTGAC AGTTACCAAT GCTTAATCAG
     ATTTAGTTAG ATTTCATATA TACTCATTTG AACCAGACTG TCAATGGTTA CGAATTAGTC 5941 TGAGGCACCT ATCTCAGCGA TCTGTCTATT TCGTTCATCC ATAGTTGCCT GACTCCCCGT
     ACTCCGTGGA TAGAGTCGCT AGACAGATAA AGCAAGTAGG TATCAACGGA CTGAGGGGCA 6001 CGTGTAGATA ACTACGATAC GGGAGGGCTT ACCATCTGGC CCCAGTGCTG CAATGATACC
     GCACATCTAT TGATGCTATG CCCTCCCGAA TGGTAGACCG GGGTCACGAC GTTACTATGG 6061 GCGAGACCCA CGCTCACCGG CTCCAGATTT ATCAGCAATA AACCAGCCAG CCGGAAGGGC
     CGCTCTGGGT GCGAGTGGCC GAGGTCTAAA TAGTCGTTAT TTGGTCGGTC GGCCTTCCCG 6121 CGAGCGCAGA AGTGGTCCTG CAACTTTATC CGCCTCCATC CAGTCTATTA ATTGTTGCCG
     GCTCGCGTCT TCACCAGGAC GTTGAAATAG GCGGAGGTAG GTCAGATAAT TAACAACGGC 6181 GGAAGCTAGA GTAAGTAGTT CGCCAGTTAA TAGTTTGCGC AACGTTGTTG CCATTGCTAC
     CCTTCGATCT CATTCATCAA GCGGTCAATT ATCAAACGCG TTGCAACAAC GGTAACGATG 6241 AGGCATCGTG GTGTCACGCT CGTCGTTTGG TATGGCTTCA TTCAGCTCCG GTTCCCAACG
     TCCGTAGCAC CACAGTGCGA GCAGCAAACC ATACCGAAGT AAGTCGAGGC CAAGGGTTGC 6301 ATCAAGGCGA GTTACATGAT CCCCCATGTT GTGCAAAAAA GCGGTTAGCT CCTTCGGTCC
     TAGTTCCGCT CAATGTACTA GGGGGTACAA CACGTTTTTT CGCCAATCGA GGAAGCCAGG PvuI
          ~~~~~~
     -----------------------------ampR--------------------------------
6361 TCCGATCGTT GTCAGAAGTA AGTTGGCCGC AGTGTTATCA CTCATGGTTA TGGCAGCACT
     AGGCTAGCAA CAGTCTTCAT TCAACCGGCG TCACAATAGT GAGTACCAAT ACCGTCGTGA 6421 GCATAATTCT CTTACTGTCA TGCCATCCGT AAGATGCTTT TCTGTGACTG GTGAGTACTC
     CGTATTAAGA GAATGACAGT ACGGTAGGCA TTCTACGAAA AGACACTGAC CACTCATGAG 6481 AACCAAGTCA TTCTGAGAAT AGTGTATGCG GCGACCGAGT TGCTCTTGCC CGGCGTCAAT
     TTGGTTCAGT AAGACTCTTA TCACATACGC CGCTGGCTCA ACGAGAACGG GCCGCAGTTA 6541 ACGGGATAAT ACCGCGCCAC ATAGCAGAAC TTTAAAAGTG CTCATCATTG GAAAACGTTC
     TGCCCTATTA TGGCGCGGTG TATCGTCTTG AAATTTTCAC GAGTAGTAAC CTTTTGCAAG 6601 TTCGGGGCGA AAACTCTCAA GGATCTTACC GCTGTTGAGA TCCAGTTCGA TGTAACCCAC
     AAGCCCCGCT TTTGAGAGTT CCTAGAATGG CGACAACTCT AGGTCAAGCT ACATTGGGTG ApaLI
          ~~~~~~
6661 TCGTGCACCC AACTGATCTT CAGCATCTTT TACTTTCACC AGCGTTTCTG GGTGAGCAAA
     AGCACGTGGG TTGACTAGAA GTCGTAGAAA ATGAAAGTGG TCGCAAAGAC CCACTCGTTT
```

```
                                           -continued
6721 AACAGGAAGG CAAAATGCCG CAAAAAAGGG AATAAGGGCG ACACGGAAAT GTTGAATACT
     TTGTCCTTCC GTTTTACGGC GTTTTTTCCC TTATTCCCGC TGTGCCTTTA CAACTTATGA --?
6781 CATACTCTTC CTTTTTCAAT ATTATTGAAG CATTTATCAG GGTTATTGTC TCATGAGCGG
     GTATGAGAAG GAAAAAGTTA TAATAACTTC GTAAATAGTC CCAATAACAG AGTACTCGCC 6841 ATACATATTT GAATGTATTT AGAAAAATAA ACAAATAGGG GTTCCGCGCA CATTTCCCCG
     TATGTATAAA CTTACATAAA TCTTTTTATT TGTTTATCCC CAAGGCGCGT GTAAAGGGGC BglII
                                            ~
6901 AAAAGTGCCA CCTGACGTCG ACGGATCGGG A
     TTTTCACGGT GGACTGCAGC TGCCTAGCCC T
```

Examples 1, 2, 3, 4, 5, 6, 7, 8, 9, 10, 11, 12, 13, 14, 16, 17, 18, 21, 28, 29, 30, 31, 32, 33, 34, 42, 44, 45, 46, 47, 48, 49, 50, 51, 58, 59, 60, 61, 62, 63, 64, 65, 66, 67 above pertain in particular to the CTLA4-Ig protein having SEQ ID NO: 1, 2, 5, 6, 7, 8, 9, 10 or 18, and Examples 19, 20, 22, 23, 24, 25, 26, 27, 35, 36, 37, 38, 39, 40, 41, 52, 53, 54, 55, 56, 57 above pertain in particular to the CTLA4-Ig protein having SEQ ID NO: 4, 11, 12, 13, 14, 15 or 16. As described in this specification, the methods relating to, and uses of, these proteins in the Examples are illustrative for methods relating to, and uses of, other CTLA4-Ig proteins of the invention.

Exemplary and non-limiting compositions comprising CTLA4-Ig molecules of the invention include such compositions wherein:

(1) the CTLA4-Ig molecules comprise any one or more of SEQ ID NO: 2, 5, 6, 7, 8, 9, 10 or 18, and the CTLA4-Ig molecules are less than or equal to about 5.0 area percent CTLA4-Ig high molecular weight species (or CTLA4-Ig tetramers) as determined by size exclusion chromatography and spectrophotometric detection (a method of measurement for which is set out in Example 10). More particularly, the invention provides such compositions further having one or more of the following characteristics:

not exceeding a maximum amount of bacterial endotoxin of 0.35 EU/mg CTLA4-Ig molecules or 76.8 EU/mL (which can be an absence of bacterial endotoxin); a method for measuring this characteristic is set out in Example 48;

not exceeding a maximum bioburden of 1 CFU/10 mL or 1 CFU/mL (which can be an absence of bioburden); a method for measuring this characteristic is set out in Example 49;

providing (as CTLA4-Ig molecules or as said composition) (a) about 10 to 22 bands with a pI range of about 4.3 to about 5.6, cumulative bands intensity of 90%-110% at a pI range of about 4.3 to about 5.3, and about 3 major bands at a pI range of about 4.5 to about 5.2, or (b) dominant CTLA4-Ig isoforms having a pI that is less than or equal to 5.1, and at least 90% of the CTLA4-Ig molecules exhibit a pI less than or equal to about 5.3; a method for measuring this characteristic is set out in Example 50;

less than or equal to 3.5 area percent of the CTLA4-Ig molecules are oxidized species thereof, and less than or equal to 2.5 area percent of the CTLA4-Ig molecules are deamidated species thereof; methods for measuring these characteristics are set out in Example 47;

the CTLA4-Ig molecules are greater than or equal to 95.0 area percent CTLA4-Ig dimers as determined by size exclusion chromatography and spectrophotometric detection; a method for measuring this characteristic is set out in Example 10;

the CTLA4-Ig molecules are less than 5.0 area percent CTLA4-Ig high molecular weight species (or CTLA4-Ig tetramers) as determined by size exclusion chromatography and spectrophotometric detection; a method for measuring this characteristic is set out in Example 10;

the CTLA4-Ig molecules are less than or equal to 0.5 area percent low molecular weight species (or CTLA4-Ig monomers) as determined by size exclusion chromatography and spectrophotometric detection, or less than 0.5 area percent low molecular weight species (or CTLA4-Ig monomers) as determined by size exclusion chromatography and spectrophotometric detection; a method for measuring this characteristic is set out in Example 10;

not exceeding a maximum amount of DNA of 2.5 picogram/mg CTLA4-Ig molecules or 2.5 picogram/mg CTLA4-Ig dimer (which can be an absence of DNA); a method for measuring this characteristic is set out in Example 58;

not exceeding a maximum amount of MCP-1 of 3.0 ng/mg total CTLA4-Ig molecules, 5 ppm, or 5 ng/mg CTLA4-Ig dimer (which can be an absence of MCP-1); a method for measuring this characteristic is set out in Example 59;

not exceeding a maximum amount of host cell protein (also known as cellular protein) of 25 ng/mg CTLA4-Ig molecules or 50 ng/mg CTLA4-Ig dimer (which can be an absence of host cell protein or cellular protein); a method for measuring this characteristic is set out in Example 60;

not exceeding a maximum amount of Triton X-100 of 1.0 ng/mg CTLA4-Ig molecules (which can be an absence of Triton-X); a method for measuring this characteristic is set out in Example 61;

not exceeding a maximum amount of Protein A of 5.0 ng/mg CTLA4-Ig molecules (which can be an absence of Protein A); a method for measuring this characteristic is set out in Example 62;

the CTLA4-Ig molecules have an average molar ratio of GlcNAc to CTLA4-Ig molecules (or to CTLA4-Ig dimers), expressed as moles/mole protein, of from about 15 to about 35; a method for measuring this characteristic is set out in Example 63;

the CTLA4-Ig molecules have an average molar ratio of GalNAc to CTLA4-Ig molecules (or to CTLA4-Ig dimers), expressed as moles/mole protein, of from about 1.7 to about 3.6; a method for measuring this characteristic is set out in Example 63;

the CTLA4-Ig molecules have an average molar ratio of galactose to CTLA4-Ig molecules (or to CTLA4-Ig dimers), expressed as moles/mole protein, of from about 8.0 to about 17; a method for measuring this characteristic is set out in Example 64;

the CTLA4-Ig molecules have an average molar ratio of fucose to CTLA4-Ig molecules (or to CTLA4-Ig dimers), expressed as moles/mole protein, of from about 3.5 to about 8.3; a method for measuring this characteristic is set out in Example 64;

the CTLA4-Ig molecules have an average molar ratio of mannose to CTLA4-Ig molecules (or to CTLA4-Ig dimers), expressed as moles/mole protein, of from about 7.7 to about 22; a method for measuring this characteristic is set out in Example 64;

the CTLA4-Ig molecules have an average molar ratio of sialic acid to CTLA4-Ig molecules (or to CTLA4-Ig dimers), expressed as moles/mole protein, of greater than or equal to 8.0, such as from about 8.0 to about 12.0; a method for measuring this characteristic is set out in Example 16;

the CTLA4-Ig molecules have an average molar ratio of NANA to CTLA4-Ig molecules (or to CTLA4-Ig dimers), expressed as moles/mole protein, of greater than or equal to 8.0, such as from about 8.0 to about 12.0; a method for measuring this characteristic is set out in Example 16;

the CTLA4-Ig molecules have N-linked glycosylation such that Domain I exhibits an area percentage of about 24.5% to about 35.2%, or Domain II exhibits an area percentage of about 26.3% to about 34.1%, or Domain III exhibits an area percentage of about 21.9% to about 31.5%, or Domain IV and Domain V exhibits an area percentage of about 7.9% to about 18.6%; a method for measuring this characteristic is set out in Example 44;

the CTLA4-Ig molecules have an average molar ratio of NGNA to CTLA4-Ig molecules (or to CTLA4-Ig dimers), expressed as moles/mole protein, of less than or equal to 1.5; a method for measuring this characteristic is set out in Example 16.

The invention provides for such compositions as isolated or substantially purified. The invention provides for such compositions as pharmaceutical compositions or pharmaceutically acceptable compositions. The invention provides for compositions having any permutation or combination of these characteristics.

The invention provides for such compositions as isolated or substantially purified. The invention provides for such compositions as pharmaceutical compositions or pharmaceutically acceptable compositions. The invention provides for compositions having any permutation or combination of these characteristics:

(2) the CTLA4-Ig molecules comprise any one or more of SEQ ID NO: 4, 11, 12, 13, 14, 15, 16 or 24 (for example CTLA4$^{A29YL104E}$-Ig), the CTLA4-Ig molecules are less than or equal to 5.0 area percent CTLA4-Ig high molecular weight species (or CTLA4-Ig tetramers) as determined by size exclusion chromatography and spectrophotometric detection (a method of measurement for which is set out in Example 25). More particularly, the invention provides such compositions further having one or more of the following characteristics:

the CTLA4-Ig molecules are greater than or equal to 95.0 area percent CTLA4-Ig dimers as determined by size exclusion chromatography and spectrophotometric detection; a method for measuring this characteristic is set out in Example 25;

the CTLA4-Ig molecules are less than or equal to 1.0 area percent CTLA4-Ig low molecular weight species (or CTLA4-Ig monomers) as determined by size exclusion chromatography and spectrophotometric detection; a method for measuring this characteristic is set out in Example 25;

providing (as CTLA4-Ig molecules or as said composition) about 8-15 bands with a pI range of about 4.5 to about 5.6, and cumulative bands intensity of 95%-105% at a pI range of 4.5 to 5.6; a method for measuring this characteristic is set out in Example 22;

not exceeding a maximum amount of DNA of about 2.5 pg/mg CTLA4-Ig molecules; a method for measuring this characteristic is set out in Example 55;

not exceeding a maximum amount of Protein A of 5 ng/mg CTLA4-Ig molecules; a method for measuring this characteristic is set out in Example 53;

not exceeding a maximum amount of MCP-1 of 5 ng/mg CTLA4-Ig molecules; a method for measuring this characteristic is set out in Example 54;

not exceeding a maximum amount of host cell protein (also known as cellular protein) of 50 ng/mg CTLA4-Ig molecules; a method for measuring this characteristic is set out in Example 52;

not exceeding a maximum amount of bacterial endotoxin of 0.42 EU/mg CTLA4-Ig molecules; a method for measuring this characteristic is set out in Example 48;

not exceeding a maximum bioburden of 1 CFU/ml; a method for measuring this characteristic is set out in Example 49;

not exceeding a maximum amount of Triton X-100 of 2 ppm; a method for measuring this characteristic is set out in Example 57;

the CTLA4-Ig molecules have an average molar ratio of sialic acid to CTLA4-Ig molecules (or to CTLA4-Ig dimers), expressed as moles/mole protein, of greater than or equal to 5.0, such as from about 5.0 to about 9.0 or from about 5.0 to about 10.0; a method for measuring this characteristic is set out in Example 39;

the CTLA4-Ig molecules have an average molar ratio of NANA to CTLA4-Ig molecules (or to CTLA4-Ig dimers), expressed as moles/mole protein, of greater than or equal to 5.0, such as from about 5.0 to about 9.0 or from about 5.0 to about 10.0; a method for measuring this characteristic is set out in Example 39;

the CTLA4-Ig molecules have an average molar ratio of GalNAc to CTLA4-Ig molecules (or to CTLA4-Ig dimers), expressed as moles/mole protein, of from about 0.8 to about 4.0; a method for measuring this characteristic is set out in Example 36;

the CTLA4-Ig molecules have an average molar ratio of GlcNAc to CTLA4-Ig molecules (or to CTLA4-Ig dimers), expressed as moles/mole protein, of from about 14 to about 35; a method for measuring this characteristic is set out in Example 36;

the CTLA4-Ig molecules have an average molar ratio of galactose to CTLA4-Ig molecules (or to CTLA4-Ig dimers), expressed as moles/mole protein, of from about 8.0 to about 14; a method for measuring this characteristic is set out in Example 35;

the CTLA4-Ig molecules have an average molar ratio of fucose to CTLA4-Ig molecules (or to CTLA4-Ig dimers), expressed as moles/mole protein, of from about 1.7 to about 9.3; a method for measuring this characteristic is set out in Example 35;

the CTLA4-Ig molecules have an average molar ratio of mannose to CTLA4-Ig molecules (or to CTLA4-Ig dimers), expressed as moles/mole protein, of from about 9 to about 18; a method for measuring this characteristic is set out in Example 35;

The invention provides for such compositions to be isolated or substantially purified. The invention provides for proteins and compositions having any permutation or combination of these characteristics.

Examples 1, 2, 3, 4, 5, 6, 7, 8, 9, 10, 11, 12, 13, 14, 16, 17, 18, 21, 28, 29, 30, 31, 32, 33, 34, 42, 44, 45, 46, 47, 48, 49, 50, 51, 58, 59, 60, 61, 62, 63, 64, 65, 66, 67 above pertain in particular to the CTLA4-Ig protein of (1) above, although, as described in this specification, the methods relating to, and uses of, such protein in these Examples are illustrative for methods relating to, and uses of, other CTLA4-Ig proteins of the invention.

Examples 19, 20, 22, 23, 24, 25, 26, 27, 35, 36, 37, 38, 39, 40, 41, 52, 53, 54, 55, 56, 57 above pertain in particular to the CTLA4-Ig protein of (2) above, although, as described in this specification, the methods relating to, and uses of, such protein in these Examples are illustrative for methods relating to, and uses of, other CTLA4-Ig proteins of the invention.

What is claimed:

1. A composition comprising cytotoxic T lymphocyte antigen 4-Ig (CTLA4-Ig) molecules, wherein the CTLA4-Ig composition comprises
   (a) a N-acetyl neuraminic acid (NANA) molar ratio of from about 5.0 to about 10.0 mole of NANA/mole CTLA4-Ig molecule, and
   (b) less than or equal to 5.0 area percent high molecular weight species as determined by size exclusion chromatography and spectrophotometric detection,
   wherein the CTLA4-Ig molecules are isolated from a soluble fraction of a liquid culture medium comprising an initial population of CTLA4-Ig molecules recombinantly produced by mammalian cells, wherein
   (1) the CTLA4-Ig molecules of the initial population have one or more sialic acid residues;
   (2) the number of sialic acid residues per CTLA4-Ig molecule varies within the initial population;
   (3) the initial population comprises CTLA4-Ig dimers and high molecular weight aggregates;
   (4) the liquid culture medium contains Monocyte Chemotactic Protein-1 (MCP-1); and,
   (5) the CTLA4-Ig molecules comprise one or more polypeptides having the amino acid sequence set forth in SEQ ID NO: 4, 11, 12, 13, 14, 15, or 16,
   wherein the CTLA4-Ig composition is obtainable by a method comprising:
      (i) obtaining the soluble fraction of the liquid culture medium, wherein the liquid culture medium comprises mammalian cells that produce the initial population of CTLA4-Ig molecules; then
      (ii) subjecting the soluble fraction of the liquid culture medium to affinity chromatography to reduce MCP-1 content; then
      (iii) subjecting the composition of step (ii) to anion chromatography to separate the CTLA4-Ig molecules into two or more fractions, wherein at least one fraction has a greater molar ratio of sialic acid to CTLA4-Ig molecules compared to at least one other fraction; and then
      (iv) subjecting the composition of step (iii) to hydrophobic interaction chromatography to separate CTLA4-Ig dimers from CTLA4-Ig high molecular weight aggregates.

2. The CTLA4-Ig composition of claim 1, wherein the mammalian cells are Chinese Hamster Ovary (CHO) cells.

3. The CTLA4-Ig composition of claim 1, wherein the concentration of MCP-1 in the CTLA4-Ig composition after the method is less than about 5 ppm.

4. The CTLA4-Ig composition of claim 1, wherein the CTLA4-Ig composition comprises a N-glycolyl neuraminic acid (NGNA) molar ratio of less than 1.5 mole NGNA/mole CTLA4-Ig molecule.

5. The CTLA4-Ig composition of claim 1, wherein the CTLA4-Ig composition comprises mannose from about 10 to about 20 moles/mole CTLA4-Ig molecule.

6. The CTLA4-Ig composition of claim 1, wherein the CTLA4-Ig composition comprises fucose from about 4.2 to about 7.0 moles/mole CTLA4-Ig molecule.

7. The CTLA4-Ig composition of claim 1, wherein the CTLA4-Ig composition comprises galactose from about 9.2 to about 17 moles/mole CTLA4-Ig molecule.

8. The CTLA4-Ig composition of claim 1, wherein the CTLA4-Ig composition comprises mannose from about 10 to about 20 moles/mole CTLA4-Ig molecule, fucose from about 4.2 to about 7.0 moles/mole CTLA4-Ig molecule, and galactose from about 9.2 to about 17 moles/mole CTLA4-Ig molecule.

9. The CTLA4-Ig composition of claim 4, wherein the CTLA4-Ig composition comprises mannose from about 10 to about 20 moles/mole CTLA4-Ig molecule, fucose from about 4.2 to about 7.0 moles/mole CTLA4-Ig molecule, and galactose from about 9.2 to about 17 moles/mole CTLA4-Ig molecule.

10. The CTLA4-Ig composition of claim 9, wherein the mammalian cells are CHO cells.

11. The CTLA4-Ig composition of claim 10, wherein the CHO cells are a clonal population of CHO cells.

12. The CTLA4-Ig composition of claim 1, wherein the CTLA4-Ig composition comprises a polypeptide having the amino acid sequence set forth in SEQ ID NO: 16.

13. The CTLA4-Ig composition of claim 12, wherein the mammalian cells are CHO cells.

14. The CTLA4-Ig composition of claim 12, wherein the concentration of MCP-1 in the CTLA4-Ig composition after the method is less than about 5 ppm.

15. The CTLA4-Ig composition of claim 12, wherein the CTLA4-Ig composition comprises a NGNA molar ratio of less than 1.5 mole NGNA/mole CTLA4-Ig molecule.

16. The CTLA4-Ig composition of claim 12, wherein the CTLA4-Ig composition comprises mannose from about 10 to about 20 moles/mole CTLA4-Ig molecule.

17. The CTLA4-Ig composition of claim 12, wherein the CTLA4-Ig composition comprises fucose from about 4.2 to about 7.0 moles/mole CTLA4-Ig molecule.

18. The CTLA4-Ig composition of claim 12, wherein the CTLA4-Ig composition comprises galactose from about 9.2 to about 17 moles/mole CTLA4-Ig molecule.

19. The CTLA4-Ig composition of claim 12, wherein the CTLA4-Ig composition comprises mannose from about 10 to about 20 moles/mole CTLA4-Ig molecule, fucose from about 4.2 to about 7.0 moles/mole CTLA4-Ig molecule, and galactose from about 9.2 to about 17 moles/mole CTLA4-Ig molecule.

20. The CTLA4-Ig composition of claim 15, wherein the CTLA4-Ig composition comprises mannose from about 10 to about 20 moles/mole CTLA4-Ig molecule, fucose from about 4.2 to about 7.0 moles/mole CTLA4-Ig molecule, and galactose from about 9.2 to about 17 moles/mole CTLA4-Ig molecule.

21. The CTLA4-Ig composition of claim 20, wherein the mammalian cells are CHO cells.

22. The CTLA4-Ig composition of claim 21, wherein the CHO cells are a clonal population of CHO cells.

* * * * *

SEQUENCE LISTING

<160> NUMBER OF SEQ ID NOS: 77

<210> SEQ ID NO 1
<211> LENGTH: 1223
<212> TYPE: DNA
<213> ORGANISM: Homo sapiens
<220> FEATURE:
<221> NAME/KEY: CDS
<222> LOCATION: (11)..(1159)

<400> SEQUENCE: 1

```
agcttcacca atg ggt gta ctg ctc aca cag agg acg ctg ctc agt ctg         49
           Met Gly Val Leu Leu Thr Gln Arg Thr Leu Leu Ser Leu
            1               5                  10 gtc ctt gca ctc ctg ttt cca agc atg gcg agc atg gca atg cac gtg        97
Val Leu Ala Leu Leu Phe Pro Ser Met Ala Ser Met Ala Met His Val
 15              20                  25 gcc cag cct gct gtg gta ctg gcc agc agc cga ggc atc gcc agc ttt       145
Ala Gln Pro Ala Val Val Leu Ala Ser Ser Arg Gly Ile Ala Ser Phe
 30              35                  40                  45 gtg tgt gag tat gca tct cca ggc aaa gcc act gag gtc cgg gtg aca       193
Val Cys Glu Tyr Ala Ser Pro Gly Lys Ala Thr Glu Val Arg Val Thr
                 50                  55                  60 gtg ctt cgg cag gct gac agc cag gtg act gaa gtc tgt gcg gca acc       241
Val Leu Arg Gln Ala Asp Ser Gln Val Thr Glu Val Cys Ala Ala Thr
             65                  70                  75 tac atg atg ggg aat gag ttg acc ttc cta gat gat tcc atc tgc acg       289
Tyr Met Met Gly Asn Glu Leu Thr Phe Leu Asp Asp Ser Ile Cys Thr
         80                  85                  90 ggc acc tcc agt gga aat caa gtg aac ctc act atc caa gga ctg agg       337
Gly Thr Ser Ser Gly Asn Gln Val Asn Leu Thr Ile Gln Gly Leu Arg
     95                 100                 105 gcc atg gac acg gga ctc tac atc tgc aag gtg gag ctc atg tac cca       385
Ala Met Asp Thr Gly Leu Tyr Ile Cys Lys Val Glu Leu Met Tyr Pro
110                 115                 120                 125 ccg cca tac tac ctg ggc ata ggc aac gga acc cag att tat gta att       433
Pro Pro Tyr Tyr Leu Gly Ile Gly Asn Gly Thr Gln Ile Tyr Val Ile
                130                 135                 140 gat cca gaa ccg tgc cca gat tct gat cag gag ccc aaa tct tct gac       481
Asp Pro Glu Pro Cys Pro Asp Ser Asp Gln Glu Pro Lys Ser Ser Asp
            145                 150                 155 aaa act cac aca tcc cca ccg tcc cca gca cct gaa ctc ctg ggg gga       529
Lys Thr His Thr Ser Pro Pro Ser Pro Ala Pro Glu Leu Leu Gly Gly
        160                 165                 170 tcg tca gtc ttc ctc ttc ccc cca aaa ccc aag gac acc ctc atg atc       577
Ser Ser Val Phe Leu Phe Pro Pro Lys Pro Lys Asp Thr Leu Met Ile
    175                 180                 185 tcc cgg acc cct gag gtc aca tgc gtg gtg gtg gac gtg agc cac gaa       625
Ser Arg Thr Pro Glu Val Thr Cys Val Val Val Asp Val Ser His Glu
190                 195                 200                 205 gac cct gag gtc aag ttc aac tgg tac gtg gac ggc gtg gag gtg cat       673
Asp Pro Glu Val Lys Phe Asn Trp Tyr Val Asp Gly Val Glu Val His
                210                 215                 220 aat gcc aag aca aag ccg cgg gag gag cag tac aac agc acg tac cgt       721
Asn Ala Lys Thr Lys Pro Arg Glu Glu Gln Tyr Asn Ser Thr Tyr Arg
```

```
                        225                 230                 235
gtg gtc agc gtc ctc acc gtc ctg cac cag gac tgg ctg aat ggc aag      769
Val Val Ser Val Leu Thr Val Leu His Gln Asp Trp Leu Asn Gly Lys
            240                 245                 250 gag tac aag tgc aag gtc tcc aac aaa gcc ctc cca gcc ccc atc gag      817
Glu Tyr Lys Cys Lys Val Ser Asn Lys Ala Leu Pro Ala Pro Ile Glu
        255                 260                 265 aaa acc atc tcc aaa gcc aaa ggg cag ccc cga gaa cca cag gtg tac      865
Lys Thr Ile Ser Lys Ala Lys Gly Gln Pro Arg Glu Pro Gln Val Tyr
270                 275                 280                 285 acc ctg ccc cca tcc cgg gat gag ctg acc aag aac cag gtc agc ctg      913
Thr Leu Pro Pro Ser Arg Asp Glu Leu Thr Lys Asn Gln Val Ser Leu
                290                 295                 300 acc tgc ctg gtc aaa ggc ttc tat ccc agc gac atc gcc gtg gag tgg      961
Thr Cys Leu Val Lys Gly Phe Tyr Pro Ser Asp Ile Ala Val Glu Trp
            305                 310                 315 gag agc aat ggg cag ccg gag aac aac tac aag acc acg cct ccc gtg     1009
Glu Ser Asn Gly Gln Pro Glu Asn Asn Tyr Lys Thr Thr Pro Pro Val
        320                 325                 330 ctg gac tcc gac ggc tcc ttc ttc ctc tac agc aag ctc acc gtg gac     1057
Leu Asp Ser Asp Gly Ser Phe Phe Leu Tyr Ser Lys Leu Thr Val Asp
335                 340                 345 aag agc agg tgg cag cag ggg aac gtc ttc tca tgc tcc gtg atg cat     1105
Lys Ser Arg Trp Gln Gln Gly Asn Val Phe Ser Cys Ser Val Met His
350                 355                 360                 365 gag gct ctg cac aac cac tac acg cag aag agc ctc tcc ctg tct ccg     1153
Glu Ala Leu His Asn His Tyr Thr Gln Lys Ser Leu Ser Leu Ser Pro
                370                 375                 380 ggt aaa tgagtgcgac ggccggcaag ccccgctccc cgggctctcg cggtcgcacg     1209
Gly Lys aggatgcttc taga                                                    1223

<210> SEQ ID NO 2
<211> LENGTH: 383
<212> TYPE: PRT
<213> ORGANISM: Homo sapiens

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
```

```
             145                 150                 155                 160
        Thr Ser Pro Ser Pro Ala Pro Glu Leu Leu Gly Gly Ser Val
                        165                 170                 175

Phe Leu Phe Pro Pro Lys Pro Lys Asp Thr Leu Met Ile Ser Arg Thr
                        180                 185                 190

Pro Glu Val Thr Cys Val Val Val Asp Val Ser His Glu Asp Pro Glu
                        195                 200                 205

Val Lys Phe Asn Trp Tyr Val Asp Gly Val Glu Val His Asn Ala Lys
                210                 215                 220

Thr Lys Pro Arg Glu Glu Gln Tyr Asn Ser Thr Tyr Arg Val Val Ser
        225                 230                 235                 240

Val Leu Thr Val Leu His Gln Asp Trp Leu Asn Gly Lys Glu Tyr Lys
                        245                 250                 255

Cys Lys Val Ser Asn Lys Ala Leu Pro Ala Pro Ile Glu Lys Thr Ile
                        260                 265                 270

Ser Lys Ala Lys Gly Gln Pro Arg Glu Pro Gln Val Tyr Thr Leu Pro
                        275                 280                 285

Pro Ser Arg Asp Glu Leu Thr Lys Asn Gln Val Ser Leu Thr Cys Leu
                        290                 295                 300

Val Lys Gly Phe Tyr Pro Ser Asp Ile Ala Val Glu Trp Glu Ser Asn
        305                 310                 315                 320

Gly Gln Pro Glu Asn Asn Tyr Lys Thr Thr Pro Pro Val Leu Asp Ser
                        325                 330                 335

Asp Gly Ser Phe Phe Leu Tyr Ser Lys Leu Thr Val Asp Lys Ser Arg
                        340                 345                 350

Trp Gln Gln Gly Asn Val Phe Ser Cys Ser Val Met His Glu Ala Leu
                        355                 360                 365

His Asn His Tyr Thr Gln Lys Ser Leu Ser Leu Ser Pro Gly Lys
                        370                 375                 380

<210> SEQ ID NO 3
        <211> LENGTH: 1072
        <212> TYPE: DNA
        <213> ORGANISM: Homo sapiens

<400> SEQUENCE: 3
catgcacgtg gcccagcctg ctgtggtact ggccagcagc cgaggcatcg ctagctttgt      60
gtgtgagtat gcatctccag gcaaatatac tgaggtccgg gtgacagtgc ttcggcaggc     120
tgacagccag gtgactgaag tctgtgcggc aacctacatg atggggaatg agttgacctt     180
cctagatgat tccatctgca cgggcacctc cagtggaaat caagtgaacc tcactatcca     240
aggactgagg gccatggaca cgggactcta catctgcaag gtggagctca tgtacccacc     300
gccatactac gagggcatag caacggaac ccagatttat gtaattgatc cagaaccgtg     360
cccagattct gatcaggagc ccaaatcttc tgacaaaact cacacatccc caccgtcccc     420
agcacctgaa ctcctggggg gatcgtcagt cttcctcttc cccccaaaac ccaaggacac     480
cctcatgatc tcccggaccc ctgaggtcac atgcgtggtg gtggacgtga gccacgaaga     540
ccctgaggtc aagttcaact ggtacgtgga cggcgtggag gtgcataatg ccaagacaaa     600
gccgcgggag gagcagtaca acagcacgta ccgtgtggtc agcgtcctca ccgtcctgca     660
ccaggactgg ctgaatggca aggagtacaa gtgcaaggtc tccaacaaag ccctcccagc     720
ccccatcgag aaaaccatct ccaaagccaa agggcagccc cgagaaccac aggtgtacac     780
cctgccccca tcccgggatg agctgaccaa gaaccaggtc agcctgacct gcctggtcaa     840
```

```
aggcttctat cccagcgaca tcgccgtgga gtgggagagc aatgggcagc cggagaacaa    900
ctacaagacc acgcctcccg tgctggactc cgacggctcc ttcttcctct acagcaagct    960
caccgtggac aagagcaggt ggcagcaggg gaacgtcttc tcatgctccg tgatgcatga    1020
ggctctgcac aaccactaca cgcagaagag cctctccctg tctccgggta aa            1072
```

<210> SEQ ID NO 4
<211> LENGTH: 384
<212> TYPE: PRT
<213> ORGANISM: Homo sapiens

<400> SEQUENCE: 4

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Cys Pro Asp Ser Asp Gln Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

```
Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
            355                 360                 365

Leu His Asn His Tyr Thr Gln Lys Ser Leu Ser Leu Ser Pro Gly Lys
            370                 375                 380

<210> SEQ ID NO 5
<211> LENGTH: 359
<212> TYPE: PRT
<213> ORGANISM: Homo sapiens

<400> SEQUENCE: 5

Met Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Gln Glu
        115                 120                 125

Pro Lys Ser Ser Asp Lys Thr His Thr Ser Pro Pro Ser Pro Ala Pro
    130                 135                 140

Glu Leu Leu Gly Gly Ser Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
```

Cys Ser Val Met His Glu Ala Leu His Asn His Tyr Thr Gln Lys Ser
325                 330                 335

Leu Ser Leu Ser Pro Gly Lys
            355

<210> SEQ ID NO 6
<211> LENGTH: 358
<212> TYPE: PRT
<213> ORGANISM: Homo sapiens

<400> SEQUENCE: 6

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp Gln Glu Pro
        115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

-continued

```
Ser Val Met His Glu Ala Leu His Asn His Tyr Thr Gln Lys Ser Leu
            340                 345                 350

Ser Leu Ser Pro Gly Lys
            355

<210> SEQ ID NO 7
<211> LENGTH: 357
<212> TYPE: PRT
<213> ORGANISM: Homo sapiens

<400> SEQUENCE: 7

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350
```

Leu Ser Pro Gly Lys
        355

<210> SEQ ID NO 8
<211> LENGTH: 358
<212> TYPE: PRT
<213> ORGANISM: Homo sapiens

<400> SEQUENCE: 8

Met Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Gln Glu
        115                 120                 125

Pro Lys Ser Ser Asp Lys Thr His Thr Ser Pro Pro Ser Pro Ala Pro
    130                 135                 140

Glu Leu Leu Gly Gly Ser Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly

<210> SEQ ID NO 9
<211> LENGTH: 357
<212> TYPE: PRT
<213> ORGANISM: Homo sapiens

<400> SEQUENCE: 9

```
Ala Met His Val Ala Gln Pro Ala Val Val Leu Ala Ser Ser Arg Gly
1               5                   10                  15
Ile Ala Ser Phe Val Cys Glu Tyr Ala Ser Pro Gly Lys Ala Thr Glu
            20                  25                  30
Val Arg Val Thr Val Leu Arg Gln Ala Asp Ser Gln Val Thr Glu Val
        35                  40                  45
Cys Ala Ala Thr Tyr Met Met Gly Asn Glu Leu Thr Phe Leu Asp Asp
    50                  55                  60
Ser Ile Cys Thr Gly Thr Ser Ser Gly Asn Gln Val Asn Leu Thr Ile
65                  70                  75                  80
Gln Gly Leu Arg Ala Met Asp Thr Gly Leu Tyr Ile Cys Lys Val Glu
                85                  90                  95
Leu Met Tyr Pro Pro Pro Tyr Tyr Leu Gly Ile Gly Asn Gly Thr Gln
            100                 105                 110
Ile Tyr Val Ile Asp Pro Glu Pro Cys Pro Asp Ser Asp Gln Glu Pro
        115                 120                 125
Lys Ser Ser Asp Lys Thr His Thr Ser Pro Pro Ser Pro Ala Pro Glu
130                 135                 140
Leu Leu Gly Gly Ser Ser Val Phe Leu Phe Pro Lys Pro Lys Asp
145                 150                 155                 160
Thr Leu Met Ile Ser Arg Thr Pro Glu Val Thr Cys Val Val Val Asp
                165                 170                 175
Val Ser His Glu Asp Pro Glu Val Lys Phe Asn Trp Tyr Val Asp Gly
            180                 185                 190
Val Glu Val His Asn Ala Lys Thr Lys Pro Arg Glu Glu Gln Tyr Asn
        195                 200                 205
Ser Thr Tyr Arg Val Val Ser Val Leu Thr Val Leu His Gln Asp Trp
    210                 215                 220
Leu Asn Gly Lys Glu Tyr Lys Cys Lys Val Ser Asn Lys Ala Leu Pro
225                 230                 235                 240
Ala Pro Ile Glu Lys Thr Ile Ser Lys Ala Lys Gly Gln Pro Arg Glu
                245                 250                 255
Pro Gln Val Tyr Thr Leu Pro Pro Ser Arg Asp Glu Leu Thr Lys Asn
            260                 265                 270
Gln Val Ser Leu Thr Cys Leu Val Lys Gly Phe Tyr Pro Ser Asp Ile
        275                 280                 285
Ala Val Glu Trp Glu Ser Asn Gly Gln Pro Glu Asn Asn Tyr Lys Thr
    290                 295                 300
Thr Pro Pro Val Leu Asp Ser Asp Gly Ser Phe Phe Leu Tyr Ser Lys
305                 310                 315                 320
Leu Thr Val Asp Lys Ser Arg Trp Gln Gln Gly Asn Val Phe Ser Cys
                325                 330                 335
Ser Val Met His Glu Ala Leu His Asn His Tyr Thr Gln Lys Ser Leu
            340                 345                 350
Ser Leu Ser Pro Gly
            355
```

<210> SEQ ID NO 10
<211> LENGTH: 356
<212> TYPE: PRT
<213> ORGANISM: Homo sapiens

<400> SEQUENCE: 10

```
Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly
        355
```

<210> SEQ ID NO 11

```
<211> LENGTH: 359
<212> TYPE: PRT
<213> ORGANISM: Homo sapiens

<400> SEQUENCE: 11

Met Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Tyr Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Glu Gly Ile Gly Asn Gly Thr
            100                 105                 110

Gln Ile Tyr Val Ile Asp Pro Glu Pro Cys Pro Asp Ser Asp Gln Glu
        115                 120                 125

Pro Lys Ser Ser Asp Lys Thr His Thr Ser Pro Pro Ser Pro Ala Pro
    130                 135                 140

Glu Leu Leu Gly Gly Ser Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 12
<211> LENGTH: 358
<212> TYPE: PRT
```

<213> ORGANISM: Homo sapiens

<400> SEQUENCE: 12

```
Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Tyr Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Glu Gly Ile Gly Asn Gly Thr Gln
            100                 105                 110

Ile Tyr Val Ile Asp Pro Glu Pro Cys Pro Asp Ser Asp Gln Glu Pro
        115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 13
<211> LENGTH: 357
<212> TYPE: PRT
<213> ORGANISM: Homo sapiens
```

<400> SEQUENCE: 13

```
Met His Val Ala Gln Pro Ala Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355
```

<210> SEQ ID NO 14
<211> LENGTH: 358
<212> TYPE: PRT
<213> ORGANISM: Homo sapiens

<400> SEQUENCE: 14

| | | | | | | | | | | | | | | | |
|---|---|---|---|---|---|---|---|---|---|---|---|---|---|---|---|
|Met|Ala|Met|His|Val|Ala|Gln|Pro|Ala|Val|Val|Leu|Ala|Ser|Ser|Arg|
|1| | | |5| | | |10| | | |15| | | |

Gly Ile Ala Ser Phe Val Cys Glu Tyr Ala Ser Pro Gly Lys Tyr Thr
          20                 25                 30

Glu Val Arg Val Thr Val Leu Arg Gln Ala Asp Ser Gln Val Thr Glu
          35                 40                 45

Val Cys Ala Ala Thr Tyr Met Met Gly Asn Glu Leu Thr Phe Leu Asp
 50                  55                 60

Asp Ser Ile Cys Thr Gly Thr Ser Ser Gly Asn Gln Val Asn Leu Thr
 65                  70                 75                 80

Ile Gln Gly Leu Arg Ala Met Asp Thr Gly Leu Tyr Ile Cys Lys Val
          85                 90                 95

Glu Leu Met Tyr Pro Pro Pro Tyr Tyr Glu Gly Ile Gly Asn Gly Thr
          100               105             110

Gln Ile Tyr Val Ile Asp Pro Glu Pro Cys Pro Asp Ser Asp Gln Glu
          115               120             125

Pro Lys Ser Ser Asp Lys Thr His Thr Ser Pro Pro Ser Pro Ala Pro
          130               135             140

Glu Leu Leu Gly Gly Ser Ser Val Phe Leu Phe Pro Pro Lys Pro Lys
145                  150                 155             160

Asp Thr Leu Met Ile Ser Arg Thr Pro Glu Val Thr Cys Val Val Val
          165               170             175

Asp Val Ser His Glu Asp Pro Glu Val Lys Phe Asn Trp Tyr Val Asp
          180               185             190

Gly Val Glu Val His Asn Ala Lys Thr Lys Pro Arg Glu Glu Gln Tyr
          195               200             205

Asn Ser Thr Tyr Arg Val Val Ser Val Leu Thr Val Leu His Gln Asp
          210               215             220

Trp Leu Asn Gly Lys Glu Tyr Lys Cys Lys Val Ser Asn Lys Ala Leu
225                  230                 235             240

Pro Ala Pro Ile Glu Lys Thr Ile Ser Lys Ala Lys Gly Gln Pro Arg
          245               250             255

Glu Pro Gln Val Tyr Thr Leu Pro Pro Ser Arg Asp Glu Leu Thr Lys
          260               265             270

Asn Gln Val Ser Leu Thr Cys Leu Val Lys Gly Phe Tyr Pro Ser Asp
          275               280             285

Ile Ala Val Glu Trp Glu Ser Asn Gly Gln Pro Glu Asn Asn Tyr Lys
          290               295             300

Thr Thr Pro Pro Val Leu Asp Ser Asp Gly Ser Phe Phe Leu Tyr Ser
305                  310                 315             320

Lys Leu Thr Val Asp Lys Ser Arg Trp Gln Gln Gly Asn Val Phe Ser
          325               330             335

Cys Ser Val Met His Glu Ala Leu His Asn His Tyr Thr Gln Lys Ser
          340               345             350

Leu Ser Leu Ser Pro Gly
          355

<210> SEQ ID NO 15
<211> LENGTH: 357
<212> TYPE: PRT
<213> ORGANISM: Homo sapiens

<400> SEQUENCE: 15

Ala Met His Val Ala Gln Pro Val Val Leu Ala Ser Ser Arg Gly
1               5                 10             15

```
Ile Ala Ser Phe Val Cys Glu Tyr Ala Ser Pro Gly Lys Tyr Thr Glu
            20                  25                  30

Val Arg Val Thr Val Leu Arg Gln Ala Asp Ser Gln Val Thr Glu Val
                35                  40                  45

Cys Ala Ala Thr Tyr Met Met Gly Asn Glu Leu Thr Phe Leu Asp Asp
 50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Glu Gly Ile Gly Asn Gly Thr Gln
                100                 105                 110

Ile Tyr Val Ile Asp Pro Glu Pro Cys Pro Asp Ser Asp Gln Glu Pro
            115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
            195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
                260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
                340                 345                 350

Ser Leu Ser Pro Gly
        355

<210> SEQ ID NO 16
<211> LENGTH: 356
<212> TYPE: PRT
<213> ORGANISM: Homo sapiens

<400> SEQUENCE: 16

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
```

```
            20                  25                  30
Arg Val Thr Val Leu Arg Gln Ala Asp Ser Gln Val Thr Glu Val Cys
         35                  40                  45
Ala Ala Thr Tyr Met Met Gly Asn Glu Leu Thr Phe Leu Asp Asp Ser
 50                  55                  60
Ile Cys Thr Gly Thr Ser Ser Gly Asn Gln Val Asn Leu Thr Ile Gln
 65                  70                  75                  80
Gly Leu Arg Ala Met Asp Thr Gly Leu Tyr Ile Cys Lys Val Glu Leu
                 85                  90                  95
Met Tyr Pro Pro Pro Tyr Tyr Glu Gly Ile Gly Asn Gly Thr Gln Ile
                100                 105                 110
Tyr Val Ile Asp Pro Glu Pro Cys Pro Asp Ser Asp Gln Glu Pro Lys
                115                 120                 125
Ser Ser Asp Lys Thr His Thr Ser Pro Pro Ser Pro Ala Pro Glu Leu
            130                 135                 140
Leu Gly Gly Ser Ser Val Phe Leu Phe Pro Pro Lys Pro Lys Asp Thr
145                 150                 155                 160
Leu Met Ile Ser Arg Thr Pro Glu Val Thr Cys Val Val Asp Val
                165                 170                 175
Ser His Glu Asp Pro Glu Val Lys Phe Asn Trp Tyr Val Asp Gly Val
                180                 185                 190
Glu Val His Asn Ala Lys Thr Lys Pro Arg Glu Glu Gln Tyr Asn Ser
                195                 200                 205
Thr Tyr Arg Val Val Ser Val Leu Thr Val Leu His Gln Asp Trp Leu
            210                 215                 220
Asn Gly Lys Glu Tyr Lys Cys Lys Val Ser Asn Lys Ala Leu Pro Ala
225                 230                 235                 240
Pro Ile Glu Lys Thr Ile Ser Lys Ala Lys Gly Gln Pro Arg Glu Pro
                245                 250                 255
Gln Val Tyr Thr Leu Pro Pro Ser Arg Asp Glu Leu Thr Lys Asn Gln
                260                 265                 270
Val Ser Leu Thr Cys Leu Val Lys Gly Phe Tyr Pro Ser Asp Ile Ala
            275                 280                 285
Val Glu Trp Glu Ser Asn Gly Gln Pro Glu Asn Asn Tyr Lys Thr Thr
        290                 295                 300
Pro Pro Val Leu Asp Ser Asp Gly Ser Phe Phe Leu Tyr Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly
        355

<210> SEQ ID NO 17
<211> LENGTH: 6928
<212> TYPE: DNA
<213> ORGANISM: Homo sapiens
<220> FEATURE:
<221> NAME/KEY: CDS
<222> LOCATION: (949)..(2097)

<400> SEQUENCE: 17
gatctcccga tccccctatgg tcgactctca gtacaatctg ctctgatgcc gcatagttaa      60
gccagtatct gctccctgct tgtgtgttgg aggtcgctga gtagtgcgcg agcaaaattt     120
```

-continued

```
aagctacaac aaggcaaggc ttgaccgaca attgcatgaa gaatctgctt agggttaggc      180
gttttgcgct gcttcgcgat gtacgggcca gatatacgcg ttgacattga ttattgacta      240
gttattaata gtaatcaatt acggggtcat tagttcatag cccatatatg gagttccgcg      300
ttacataact tacggtaaat ggcccgcctg gctgaccgcc caacgacccc cgcccattga      360
cgtcaataat gacgtatgtt cccatagtaa cgccaatagg gactttccat tgacgtcaat      420
gggtggacta tttacggtaa actgcccact tggcagtaca tcaagtgtat catatgccaa      480
gtacgccccc tattgacgtc aatgacggta aatggcccgc ctggcattat gcccagtaca      540
tgaccttatg ggactttcct acttggcagt acatctacgt attagtcatc gctattacca      600
tggtgatgcg gttttggcag tacatcaatg ggcgtggata gcggtttgac tcacggggat      660
ttccaagtct ccaccccatt gacgtcaatg ggagtttgtt ttggcaccaa aatcaacggg      720
actttccaaa atgtcgtaac aactccgccc cattgacgca aatgggcggt aggcgtgtac      780
ggtgggaggt ctatataagc agagctctct ggctaactag agaacccact gcttactggc      840
ttatcgaaat taatacgact cactataggg agacccaagc ttggtaccga gctcggatcc      900
actagtaacg gccgccagtg tgctggaatt ctgcagatag cttcacca atg ggt gta      957
                                                      Met Gly Val
                                                        1 ctg ctc aca cag agg acg ctg ctc agt ctg gtc ctt gca ctc ctg ttt     1005
Leu Leu Thr Gln Arg Thr Leu Leu Ser Leu Val Leu Ala Leu Leu Phe
  5              10                  15 cca agc atg gcg agc atg gca atg cac gtg gcc cag cct gct gtg gta     1053
Pro Ser Met Ala Ser Met Ala Met His Val Ala Gln Pro Ala Val Val
 20              25                  30                  35 ctg gcc agc agc cga ggc atc gcc agc ttt gtg tgt gag tat gca tct     1101
Leu Ala Ser Ser Arg Gly Ile Ala Ser Phe Val Cys Glu Tyr Ala Ser
                 40                  45                  50 cca ggc aaa gcc act gag gtc cgg gtg aca gtg ctt cgg cag gct gac     1149
Pro Gly Lys Ala Thr Glu Val Arg Val Thr Val Leu Arg Gln Ala Asp
             55                  60                  65 agc cag gtg act gaa gtc tgt gcg gca acc tac atg atg ggg aat gag     1197
Ser Gln Val Thr Glu Val Cys Ala Ala Thr Tyr Met Met Gly Asn Glu
         70                  75                  80 ttg acc ttc cta gat gat tcc atc tgc acg ggc acc tcc agt gga aat     1245
Leu Thr Phe Leu Asp Asp Ser Ile Cys Thr Gly Thr Ser Ser Gly Asn
     85                  90                  95 caa gtg aac ctc act atc caa gga ctg agg gcc atg gac acg gga ctc     1293
Gln Val Asn Leu Thr Ile Gln Gly Leu Arg Ala Met Asp Thr Gly Leu
100                 105                 110                 115 tac atc tgc aag gtg gag ctc atg tac cca ccg cca tac tac ctg ggc     1341
Tyr Ile Cys Lys Val Glu Leu Met Tyr Pro Pro Pro Tyr Tyr Leu Gly
                120                 125                 130 ata ggc aac gga acc cag att tat gta att gat cca gaa ccg tgc cca     1389
Ile Gly Asn Gly Thr Gln Ile Tyr Val Ile Asp Pro Glu Pro Cys Pro
            135                 140                 145 gat tct gat cag gag ccc aaa tct tct gac aaa act cac aca tcc cca     1437
Asp Ser Asp Gln Glu Pro Lys Ser Ser Asp Lys Thr His Thr Ser Pro
        150                 155                 160 ccg tcc cca gca cct gaa ctc ctg ggg gga tcg tca gtc ttc ctc ttc     1485
Pro Ser Pro Ala Pro Glu Leu Leu Gly Gly Ser Ser Val Phe Leu Phe
    165                 170                 175 ccc cca aaa ccc aag gac acc ctc atg atc tcc cgg acc cct gag gtc     1533
Pro Pro Lys Pro Lys Asp Thr Leu Met Ile Ser Arg Thr Pro Glu Val
180                 185                 190                 195
```

-continued

| | | |
|---|---|---|
| aca tgc gtg gtg gtg gac gtg agc cac gaa gac cct gag gtc aag ttc<br>Thr Cys Val Val Val Asp Val Ser His Glu Asp Pro Glu Val Lys Phe<br>200 205 210 | 1581 |
| aac tgg tac gtg gac ggc gtg gag gtg cat aat gcc aag aca aag ccg<br>Asn Trp Tyr Val Asp Gly Val Glu Val His Asn Ala Lys Thr Lys Pro<br>215 220 225 | 1629 |
| cgg gag gag cag tac aac agc acg tac cgt gtg gtc agc gtc ctc acc<br>Arg Glu Glu Gln Tyr Asn Ser Thr Tyr Arg Val Val Ser Val Leu Thr<br>230 235 240 | 1677 |
| gtc ctg cac cag gac tgg ctg aat ggc aag gag tac aag tgc aag gtc<br>Val Leu His Gln Asp Trp Leu Asn Gly Lys Glu Tyr Lys Cys Lys Val<br>245 250 255 | 1725 |
| tcc aac aaa gcc ctc cca gcc ccc atc gag aaa acc atc tcc aaa gcc<br>Ser Asn Lys Ala Leu Pro Ala Pro Ile Glu Lys Thr Ile Ser Lys Ala<br>260 265 270 275 | 1773 |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>280 285 290 | 1821 |
| gat gag ctg acc aag aac cag gtc agc ctg acc tgc ctg gtc aaa ggc<br>Asp Glu Leu Thr Lys Asn Gln Val Ser Leu Thr Cys Leu Val Lys Gly<br>295 300 305 | 1869 |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>310 315 320 | 1917 |
| gag aac aac tac aag acc acg cct ccc gtg ctg gac tcc gac ggc tcc<br>Glu Asn Asn Tyr Lys Thr Thr Pro Pro Val Leu Asp Ser Asp Gly Ser<br>325 330 335 | 1965 |
| ttc ttc ctc tac agc aag ctc acc gtg gac aag agc agg tgg cag cag<br>Phe Phe Leu Tyr Ser Lys Leu Thr Val Asp Lys Ser Arg Trp Gln Gln<br>340 345 350 355 | 2013 |
| ggg aac gtc ttc tca tgc tcc gtg atg cat gag gct ctg cac aac cac<br>Gly Asn Val Phe Ser Cys Ser Val Met His Glu Ala Leu His Asn His<br>360 365 370 | 2061 |
| tac acg cag aag agc ctc tcc ctg tct ccg ggt aaa tgagtgcgac<br>Tyr Thr Gln Lys Ser Leu Ser Leu Ser Pro Gly Lys<br>375 380 | 2107 |
| ggccggcaag ccccccgctcc ccgggctctc gcggtcgcac gaggatgctt ctagagggcc | 2167 |
| ctattctata gtgtcaccta aatgctagag ctcgctgatc agcctcgact gtgccttcta | 2227 |
| gttgccagcc atctgttgtt tgcccctccc ccgtgccttc cttgaccctg gaaggtgcca | 2287 |
| ctcccactgt cctttcctaa taaaatgagg aaattgcatc gcattgtctg agtaggtgtc | 2347 |
| attctattct gggggggtggg gtggggcagg acagcaaggg ggaggattgg gaagacaata | 2407 |
| gcaggcatgc tggggatgcg gtgggctcta tggcttctga ggcggaaaga accagctggg | 2467 |
| gctctagggg gtatcccac gcgccctgta gcggcgcatt aagcgcggcg ggtgtggtgg | 2527 |
| ttacgcgcag cgtgaccgct acacttgcca gcgccctagc gcccgctcct ttcgctttct | 2587 |
| tcccttcctt tctcgccacg ttcgccctgt ggaatgtgtg tcagttaggg tgtggaaagt | 2647 |
| ccccaggctc cccagcaggc agaagtatgc aaagcatgca tctcaattag tcagcaacca | 2707 |
| ggtgtggaaa gtccccaggc tccccagcag gcagaagtat gcaaagcatg catctcaatt | 2767 |
| agtcagcaac catagtcccg cccctaactc cgcccatccc gcccctaact ccgcccagtt | 2827 |
| ccgcccattc tccgccccat ggctgactaa ttttttttat ttatgcagag gccgaggccg | 2887 |
| cctcggcctc tgagctattc cagaagtagt gaggaggctt ttttggaggc ctaggctttt | 2947 |
| gcaaaaagct tggacagctg agggctgcga tttcgcgcca aacttgacgg caatcctagc | 3007 |
| gtgaaggctg gtaggatttt atccccgctg ccatcatggt tcgaccattg aactgcatcg | 3067 |

```
tcgccgtgtc ccaagatatg gggattggca agaacggaga cctaccctgg cctccgctca   3127
ggaacgagtt caagtacttc caaagaatga ccacaacctc ttcagtggaa ggtaaacaga   3187
atctggtgat tatgggtagg aaaacctggt tctccattcc tgagaagaat cgacctttaa   3247
aggacagaat taatatagtt ctcagtagag aactcaaaga accaccacga ggagctcatt   3307
ttcttgccaa aagtttggat gatgccttaa gacttattga acaaccggaa ttggcaagta   3367
aagtagacat ggtttggata gtcggaggca gttctgttta ccaggaagcc atgaatcaac   3427
caggccacct cagactcttt gtgacaagga tcatgcagga atttgaaagt gacacgtttt   3487
tcccagaaat tgatttgggg aaatataaac ttctcccaga atacccaggc gtcctctctg   3547
aggtccagga ggaaaaaggc atcaagtata agtttgaagt ctacgagaag aaagactaac   3607
aggaagatgc tttcaagttc tctgctcccc tcctaaagct atgcattttt ataagaccat   3667
gggacttttg ctggctttag atctttgtga aggaacctta cttctgtggt gtgacataat   3727
tggacaaact acctcagaga atttaaagct ctaaggtaaa tataaaattt ttaagtgtat   3787
aatgtgttaa actactgatt ctaattgttt gtgtatttta gattccaacc tatggaactg   3847
atgaatggga gcagtggtgg aatgccttta atgaggaaaa cctgttttgc tcagaagaaa   3907
tgccatctag tgatgatgag gctactgctg actctcaaca ttctactcct ccaaaaaaga   3967
agagaaaggt agaagacccc aaggactttc cttcagaatt gctaagtttt ttgagtcatg   4027
ctgtgtttag taatagaact cttgcttgct ttgctatttta caccacaaag gaaaaagctg   4087
cactgctata caagaaaatt atggaaaaat attctgtaac ctttataagt aggcataaca   4147
gttataatca taacatactg ttttttctta ctccacacag gcatagagtg tctgctatta   4207
ataactatgc tcaaaaattg tgtacccttta gctttttaat ttgtaaaggg gttaataagg   4267
aatatttgat gtatagtgcc ttgactagag atcataatca gccataccac atttgtagag   4327
gttttacttg ctttaaaaaa cctcccacac ctcccctgaa cctgaaaaca taaaatgaat   4387
gcaattgttg ttgttaactt gtttattgca gcttataatg gttacaaata aagcaatagc   4447
atcacaaatt tcacaaataa agcatttttt tcactgcatt ctagttgtgg tttgtccaaa   4507
ctcatcaatg tatcttatca tgtctggatc ggctggatga tcctccagcg cggggatctc   4567
atgctggagt tcttcgccca ccccaacttg tttattgcag cttataatgg ttacaaataa   4627
agcaatagca tcacaaattt cacaaataaa gcatttttt cactgcattc tagttgtggt   4687
ttgtccaaac tcatcaatgt atcttatcat gtctgtatac cgtcgacctc tagctagagc   4747
ttggcgtaat catggtcata gctgtttcct gtgtgaaatt gttatccgct cacaattcca   4807
cacaacatac gagccggaag cataaagtgt aaagcctggg gtgcctaatg agtgagctaa   4867
ctcacattaa ttgcgttgcg ctcactgccc gctttccagt cgggaaacct gtcgtgccag   4927
ctgcattaat gaatcggcca acgcgcgggg agaggcggtt tgcgtattgg gcgctcttcc   4987
gcttcctcgc tcactgactc gctgcgctcg gtcgttcggc tgcggcgagc ggtatcagct   5047
cactcaaagg cggtaatacg gttatccaca gaatcagggg ataacgcagg aaagaacatg   5107
tgagcaaaag gccagcaaaa ggccaggaac cgtaaaaagg ccgcgttgct ggcgtttttc   5167
cataggctcc gcccccctga cgagcatcac aaaaatcgac gctcaagtca gaggtggcga   5227
aacccgacag gactataaag ataccaggcg tttccccctg gaagctccct cgtgcgctct   5287
cctgttccga ccctgccgct taccggatac ctgtccgcct ttctcccttc gggaagcgtg   5347
gcgctttctc aatgctcacg ctgtaggtat ctcagttcgg tgtaggtcgt tcgctccaag   5407
```

```
ctgggctgtg tgcacgaacc ccccgttcag cccgaccgct gcgccttatc cggtaactat    5467
cgtcttgagt ccaacccggt aagacacgac ttatcgccac tggcagcagc cactggtaac    5527
aggattagca gagcgaggta tgtaggcggt gctacagagt tcttgaagtg gtggcctaac    5587
tacggctaca ctagaaggac agtatttggt atctgcgctc tgctgaagcc agttaccttc    5647
ggaaaaagag ttggtagctc ttgatccggc aaacaaacca ccgctggtag cggtggtttt    5707
tttgtttgca agcagcagat tacgcgcaga aaaaaggat ctcaagaaga tcctttgatc    5767
ttttctacgg ggtctgacgc tcagtggaac gaaaactcac gttaagggat tttggtcatg    5827
agattatcaa aaaggatctt cacctagatc cttttaaatt aaaaatgaag ttttaaatca    5887
atctaaagta tatatgagta aacttggtct gacagttacc aatgcttaat cagtgaggca    5947
cctatctcag cgatctgtct atttcgttca tccatagttg cctgactccc cgtcgtgtag    6007
ataactacga tacgggaggg cttaccatct ggccccagtg ctgcaatgat accgcgagac    6067
ccacgctcac cggctccaga tttatcagca ataaaccagc cagccggaag ggccgagcgc    6127
agaagtggtc ctgcaacttt atccgcctcc atccagtcta ttaattgttg ccgggaagct    6187
agagtaagta gttcgccagt taatagtttg cgcaacgttg ttgccattgc tacaggcatc    6247
gtggtgtcac gctcgtcgtt tggtatggct tcattcagct ccggttccca acgtcaaggc    6307
gagttacatg atcccccatg ttgtgcaaaa aagcggttag ctccttcggt ccccgatcgt    6367
tgtcagaagt aagttggccg cagtgttatc actcatggtt atggcagcac tcataattct    6427
cttactgtca tgccatccgt aagatgcttt tctgtgactg gtgagtactc aaccaagtca    6487
ttctgagaat agtgtatgcg gcgaccgagt tgctcttgcc cggcgtcaat acgggataat    6547
accgcgccac atagcagaac tttaaaagtg ctcatcattg gaaaacgttc ttcggggcga    6607
aaactctcaa ggatcttacc gctgttgaga tccagttcga tgtaacccac tcgtgcaccc    6667
aactgatctt cagcatcttt tactttcacc agcgtttctg ggtgagcaaa aacaggaagg    6727
caaaatgccg caaaaaaggg aataagggcg acacggaaat gttgaatact catactcttc    6787
cttttcaat attattgaag catttatcag ggttattgtc tcatgagcgg atacatattt     6847
gaatgtattt agaaaaataa acaaataggg gttccgcgca catttccccg aaaagtgcca    6907
cctgacgtcg acggatcggg a                                             6928
```

<210> SEQ ID NO 18
<211> LENGTH: 124
<212> TYPE: PRT
<213> ORGANISM: Homo sapiens

<400> SEQUENCE: 18

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
```

```
                  100                 105                 110
Tyr Val Ile Asp Pro Glu Pro Cys Pro Asp Ser Asp
        115                 120

<210> SEQ ID NO 19
<211> LENGTH: 39
<212> TYPE: DNA
<213> ORGANISM: Homo sapiens

<400> SEQUENCE: 19
agaaaagggg ctggagagat ggctcagtgg ttaagagca                        39

<210> SEQ ID NO 20
<211> LENGTH: 9
<212> TYPE: DNA
<213> ORGANISM: Homo sapiens

<400> SEQUENCE: 20 gtactcagg                                                          9

<210> SEQ ID NO 21
<211> LENGTH: 10
<212> TYPE: DNA
<213> ORGANISM: Homo sapiens

<400> SEQUENCE: 21
agtcagagac                                                        10

<210> SEQ ID NO 22
<211> LENGTH: 48
<212> TYPE: DNA
<213> ORGANISM: Homo sapiens

<400> SEQUENCE: 22
cggcagatct ctgtgagttt gaggccagcc tggtctacaa agcaagtt              48

<210> SEQ ID NO 23
<211> LENGTH: 1152
<212> TYPE: DNA
<213> ORGANISM: Homo sapiens
<220> FEATURE:
<221> NAME/KEY: CDS
<222> LOCATION: (1)..(1149)

<400> SEQUENCE: 23 atg ggt gta ctg ctc aca cag agg acg ctg ctc agt ctg gtc ctt gca    48
Met Gly Val Leu Leu Thr Gln Arg Thr Leu Leu Ser Leu Val Leu Ala
1               5                   10                  15 ctc ctg ttt cca agc atg gcg agc atg gca atg cac gtg gcc cag cct    96
Leu Leu Phe Pro Ser Met Ala Ser Met Ala Met His Val Ala Gln Pro
            20                  25                  30 gct gtg gta ctg gcc agc agc cga ggc atc gct agc ttt gtg tgt gag   144
Ala Val Val Leu Ala Ser Ser Arg Gly Ile Ala Ser Phe Val Cys Glu
        35                  40                  45 tat gca tct cca ggc aaa tat act gag gtc cgg gtg aca gtg ctt cgg   192
Tyr Ala Ser Pro Gly Lys Tyr Thr Glu Val Arg Val Thr Val Leu Arg
    50                  55                  60 cag gct gac agc cag gtg act gaa gtc tgt gcg gca acc tac atg atg   240
Gln Ala Asp Ser Gln Val Thr Glu Val Cys Ala Ala Thr Tyr Met Met
65                  70                  75                  80 ggg aat gag ttg acc ttc cta gat gat tcc atc tgc acg ggc acc tcc   288
Gly Asn Glu Leu Thr Phe Leu Asp Asp Ser Ile Cys Thr Gly Thr Ser
                85                  90                  95
```

```
agt gga aat caa gtg aac ctc act atc caa gga ctg agg gcc atg gac      336
Ser Gly Asn Gln Val Asn Leu Thr Ile Gln Gly Leu Arg Ala Met Asp
            100                 105                 110 acg gga ctc tac atc tgc aag gtg gag ctc atg tac cca ccg cca tac      384
Thr Gly Leu Tyr Ile Cys Lys Val Glu Leu Met Tyr Pro Pro Pro Tyr
        115                 120                 125 tac gag ggc ata ggc aac gga acc cag att tat gta att gat cca gaa      432
Tyr Glu Gly Ile Gly Asn Gly Thr Gln Ile Tyr Val Ile Asp Pro Glu
    130                 135                 140 ccg tgc cca gat tct gat cag gag ccc aaa tct tct gac aaa act cac      480
Pro Cys Pro Asp Ser Asp Gln Glu Pro Lys Ser Ser Asp Lys Thr His
145                 150                 155                 160 aca tcc cca ccg tcc cca gca cct gaa ctc ctg ggg gga tcg tca gtc      528
Thr Ser Pro Pro Ser Pro Ala Pro Glu Leu Leu Gly Gly Ser Ser Val
                165                 170                 175 ttc ctc ttc ccc cca aaa ccc aag gac acc ctc atg atc tcc cgg acc      576
Phe Leu Phe Pro Pro Lys Pro Lys Asp Thr Leu Met Ile Ser Arg Thr
            180                 185                 190 cct gag gtc aca tgc gtg gtg gtg gac gtg agc cac gaa gac cct gag      624
Pro Glu Val Thr Cys Val Val Val Asp Val Ser His Glu Asp Pro Glu
        195                 200                 205 gtc aag ttc aac tgg tac gtg gac ggc gtg gag gtg cat aat gcc aag      672
Val Lys Phe Asn Trp Tyr Val Asp Gly Val Glu Val His Asn Ala Lys
    210                 215                 220 aca aag ccg cgg gag gag cag tac aac agc acg tac cgt gtg gtc agc      720
Thr Lys Pro Arg Glu Glu Gln Tyr Asn Ser Thr Tyr Arg Val Val Ser
225                 230                 235                 240 gtc ctc acc gtc ctg cac cag gac tgg ctg aat ggc aag gag tac aag      768
Val Leu Thr Val Leu His Gln Asp Trp Leu Asn Gly Lys Glu Tyr Lys
                245                 250                 255 tgc aag gtc tcc aac aaa gcc ctc cca gcc ccc atc gag aaa acc atc      816
Cys Lys Val Ser Asn Lys Ala Leu Pro Ala Pro Ile Glu Lys Thr Ile
            260                 265                 270 tcc aaa gcc aaa ggg cag ccc cga gaa cca cag gtg tac acc ctg ccc      864
Ser Lys Ala Lys Gly Gln Pro Arg Glu Pro Gln Val Tyr Thr Leu Pro
        275                 280                 285 cca tcc cgg gat gag ctg acc aag aac cag gtc agc ctg acc tgc ctg      912
Pro Ser Arg Asp Glu Leu Thr Lys Asn Gln Val Ser Leu Thr Cys Leu
    290                 295                 300 gtc aaa ggc ttc tat ccc agc gac atc gcc gtg gag tgg gag agc aat      960
Val Lys Gly Phe Tyr Pro Ser Asp Ile Ala Val Glu Trp Glu Ser Asn
305                 310                 315                 320 ggg cag ccg gag aac aac tac aag acc acg cct ccc gtg ctg gac tcc     1008
Gly Gln Pro Glu Asn Asn Tyr Lys Thr Thr Pro Pro Val Leu Asp Ser
                325                 330                 335 gac ggc tcc ttc ttc ctc tac agc aag ctc acc gtg gac aag agc agg     1056
Asp Gly Ser Phe Phe Leu Tyr Ser Lys Leu Thr Val Asp Lys Ser Arg
            340                 345                 350 tgg cag cag ggg aac gtc ttc tca tgc tcc gtg atg cat gag gct ctg     1104
Trp Gln Gln Gly Asn Val Phe Ser Cys Ser Val Met His Glu Ala Leu
        355                 360                 365 cac aac cac tac acg cag aag agc ctc tcc ctg tct ccg ggt aaa tga     1152
His Asn His Tyr Thr Gln Lys Ser Leu Ser Leu Ser Pro Gly Lys
    370                 375                 380

<210> SEQ ID NO 24
<211> LENGTH: 124
<212> TYPE: PRT
<213> ORGANISM: Homo sapiens
```

<400> SEQUENCE: 24

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 25
<211> LENGTH: 15
<212> TYPE: PRT
<213> ORGANISM: Homo sapiens

<400> SEQUENCE: 25

Ala Met His Val Ala Gln Pro Ala Val Val Leu Ala Ser Ser Arg
1               5                   10                  15

<210> SEQ ID NO 26
<211> LENGTH: 14
<212> TYPE: PRT
<213> ORGANISM: Homo sapiens

<400> SEQUENCE: 26

Met His Val Ala Gln Pro Ala Val Val Leu Ala Ser Ser Arg
1               5                   10

<210> SEQ ID NO 27
<211> LENGTH: 14
<212> TYPE: PRT
<213> ORGANISM: Homo sapiens

<400> SEQUENCE: 27

Gly Ile Ala Ser Phe Val Cys Glu Tyr Ala Ser Pro Gly Lys
1               5                   10

<210> SEQ ID NO 28
<211> LENGTH: 5
<212> TYPE: PRT
<213> ORGANISM: Homo sapiens

<400> SEQUENCE: 28

Ala Thr Glu Val Arg
1               5

<210> SEQ ID NO 29
<211> LENGTH: 5
<212> TYPE: PRT
<213> ORGANISM: Homo sapiens

<400> SEQUENCE: 29

Val Thr Val Leu Arg

-continued

<210> SEQ ID NO 30
<211> LENGTH: 45
<212> TYPE: PRT
<213> ORGANISM: Homo sapiens

<400> SEQUENCE: 30

Gln Ala Asp Ser Gln Val Thr Glu Val Cys Ala Ala Thr Tyr Met Met
1               5                   10                  15

Gly Asn Glu Leu Thr Phe Leu Asp Asp Ser Ile Cys Thr Gly Thr Ser
            20                  25                  30

Ser Gly Asn Gln Val Asn Leu Thr Ile Gln Gly Leu Arg
        35                  40                  45

<210> SEQ ID NO 31
<211> LENGTH: 10
<212> TYPE: PRT
<213> ORGANISM: Homo sapiens

<400> SEQUENCE: 31

Ala Met Asp Thr Gly Leu Tyr Ile Cys Lys
1               5                   10

<210> SEQ ID NO 32
<211> LENGTH: 35
<212> TYPE: PRT
<213> ORGANISM: Homo sapiens

<400> SEQUENCE: 32

Val Glu Leu Met Tyr Pro Pro Pro Tyr Tyr Leu Gly Ile Gly Asn Gly
1               5                   10                  15

Thr Gln Ile Tyr Val Ile Asp Pro Glu Pro Cys Pro Asp Ser Asp Gln
            20                  25                  30

Glu Pro Lys
        35

<210> SEQ ID NO 33
<211> LENGTH: 4
<212> TYPE: PRT
<213> ORGANISM: Homo sapiens

<400> SEQUENCE: 33

Ser Ser Asp Lys
1

<210> SEQ ID NO 34
<211> LENGTH: 26
<212> TYPE: PRT
<213> ORGANISM: Homo sapiens

<400> SEQUENCE: 34

Thr His Thr Ser Pro Pro Ser Pro Ala Pro Glu Leu Leu Gly Gly Ser
1               5                   10                  15

Ser Val Phe Leu Phe Pro Pro Lys Pro Lys
            20                  25

<210> SEQ ID NO 35
<211> LENGTH: 7
<212> TYPE: PRT
<213> ORGANISM: Homo sapiens

<400> SEQUENCE: 35

Asp Thr Leu Met Ile Ser Arg
1               5

<210> SEQ ID NO 36
<211> LENGTH: 19
<212> TYPE: PRT
<213> ORGANISM: Homo sapiens

<400> SEQUENCE: 36

Thr Pro Glu Val Thr Cys Val Val Val Asp Val Ser His Glu Asp Pro
1               5                   10                  15

Glu Val Lys

<210> SEQ ID NO 37
<211> LENGTH: 14
<212> TYPE: PRT
<213> ORGANISM: Homo sapiens

<400> SEQUENCE: 37

Phe Asn Trp Tyr Val Asp Gly Val Glu Val His Asn Ala Lys
1               5                   10

<210> SEQ ID NO 38
<211> LENGTH: 4
<212> TYPE: PRT
<213> ORGANISM: Homo sapiens

<400> SEQUENCE: 38

Thr Lys Pro Arg
1

<210> SEQ ID NO 39
<211> LENGTH: 9
<212> TYPE: PRT
<213> ORGANISM: Homo sapiens

<400> SEQUENCE: 39

Glu Glu Gln Tyr Asn Ser Thr Tyr Arg
1               5

<210> SEQ ID NO 40
<211> LENGTH: 16
<212> TYPE: PRT
<213> ORGANISM: Homo sapiens

<400> SEQUENCE: 40

Val Val Ser Val Leu Thr Val Leu His Gln Asp Trp Leu Asn Gly Lys
1               5                   10                  15

<210> SEQ ID NO 41
<211> LENGTH: 4
<212> TYPE: PRT
<213> ORGANISM: Homo sapiens

<400> SEQUENCE: 41

Val Ser Asn Lys
1

<210> SEQ ID NO 42
<211> LENGTH: 8
<212> TYPE: PRT
<213> ORGANISM: Homo sapiens

<400> SEQUENCE: 42

```
Ala Leu Pro Ala Pro Ile Glu Lys
1               5

<210> SEQ ID NO 43
<211> LENGTH: 4
<212> TYPE: PRT
<213> ORGANISM: Homo sapiens

<400> SEQUENCE: 43

Thr Ile Ser Lys
1

<210> SEQ ID NO 44
<211> LENGTH: 4
<212> TYPE: PRT
<213> ORGANISM: Homo sapiens

<400> SEQUENCE: 44

Gly Gln Pro Arg
1

<210> SEQ ID NO 45
<211> LENGTH: 11
<212> TYPE: PRT
<213> ORGANISM: Homo sapiens

<400> SEQUENCE: 45

Glu Pro Gln Val Tyr Thr Leu Pro Pro Ser Arg
1               5                   10

<210> SEQ ID NO 46
<211> LENGTH: 5
<212> TYPE: PRT
<213> ORGANISM: Homo sapiens

<400> SEQUENCE: 46

Asp Glu Leu Thr Lys
1               5

<210> SEQ ID NO 47
<211> LENGTH: 10
<212> TYPE: PRT
<213> ORGANISM: Homo sapiens

<400> SEQUENCE: 47

Asn Gln Val Ser Leu Thr Cys Leu Val Lys
1               5                   10

<210> SEQ ID NO 48
<211> LENGTH: 22
<212> TYPE: PRT
<213> ORGANISM: Homo sapiens

<400> SEQUENCE: 48

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 49
<211> LENGTH: 17
<212> TYPE: PRT
<213> ORGANISM: Homo sapiens
```

```
<400> SEQUENCE: 49

Thr Thr Pro Pro Val Leu Asp Ser Asp Gly Ser Phe Phe Leu Tyr Ser
1               5                   10                  15

Lys

<210> SEQ ID NO 50
<211> LENGTH: 5
<212> TYPE: PRT
<213> ORGANISM: Homo sapiens

<400> SEQUENCE: 50

Leu Thr Val Asp Lys
1               5

<210> SEQ ID NO 51
<211> LENGTH: 23
<212> TYPE: PRT
<213> ORGANISM: Homo sapiens

<400> SEQUENCE: 51

Trp Gln Gln Gly Asn Val Phe Ser Cys Ser Val Met His Glu Ala Leu
1               5                   10                  15

His Asn His Tyr Thr Gln Lys
            20

<210> SEQ ID NO 52
<211> LENGTH: 7
<212> TYPE: PRT
<213> ORGANISM: Homo sapiens

<400> SEQUENCE: 52

Ser Leu Ser Leu Ser Pro Gly
1               5

<210> SEQ ID NO 53
<211> LENGTH: 8
<212> TYPE: PRT
<213> ORGANISM: Homo sapiens

<400> SEQUENCE: 53

Ser Leu Ser Leu Ser Pro Gly Lys
1               5

<210> SEQ ID NO 54
<211> LENGTH: 9
<212> TYPE: PRT
<213> ORGANISM: Homo sapiens

<400> SEQUENCE: 54

Gly Ile Ala Ser Phe Val Cys Glu Tyr
1               5

<210> SEQ ID NO 55
<211> LENGTH: 11
<212> TYPE: PRT
<213> ORGANISM: Homo sapiens

<400> SEQUENCE: 55

Phe Asn Trp Tyr Val Asp Gly Val Glu Val His
1               5                   10

<210> SEQ ID NO 56
<211> LENGTH: 15
```

```
<212> TYPE: PRT
<213> ORGANISM: Homo sapiens

<400> SEQUENCE: 56

Thr Thr Pro Pro Val Leu Asp Ser Asp Gly Ser Phe Phe Leu Tyr
1               5                   10                  15

<210> SEQ ID NO 57
<211> LENGTH: 9
<212> TYPE: PRT
<213> ORGANISM: Homo sapiens

<400> SEQUENCE: 57

Trp Gln Gln Gly Asn Val Phe Ser Cys
1               5

<210> SEQ ID NO 58
<211> LENGTH: 7
<212> TYPE: PRT
<213> ORGANISM: Homo sapiens

<400> SEQUENCE: 58

Trp Gln Gln Gly Asn Val Phe
1               5

<210> SEQ ID NO 59
<211> LENGTH: 5
<212> TYPE: PRT
<213> ORGANISM: Homo sapiens

<400> SEQUENCE: 59

Tyr Thr Glu Val Arg
1               5

<210> SEQ ID NO 60
<211> LENGTH: 35
<212> TYPE: PRT
<213> ORGANISM: Homo sapiens

<400> SEQUENCE: 60

Val Glu Leu Met Tyr Pro Pro Tyr Tyr Glu Gly Ile Gly Asn Gly
1               5                   10                  15

Thr Gln Ile Tyr Val Ile Asp Pro Glu Pro Cys Pro Asp Ser Asp Gln
                20                  25                  30

Glu Pro Lys
        35

<210> SEQ ID NO 61
<211> LENGTH: 17
<212> TYPE: PRT
<213> ORGANISM: Homo sapiens

<400> SEQUENCE: 61

Gln Ala Asp Ser Gln Val Thr Glu Val Cys Ala Ala Thr Tyr Met Met
1               5                   10                  15

Gly

<210> SEQ ID NO 62
<211> LENGTH: 28
<212> TYPE: PRT
<213> ORGANISM: Homo sapiens

<400> SEQUENCE: 62
```

Asn Arg Leu Gly Gln Ile Thr Leu Asn Val Gln Asn Gly Ser Ser Thr
1               5                   10                  15

Gly Thr Cys Ile Ser Asp Asp Leu Phe Thr Leu Glu
            20                  25

<210> SEQ ID NO 63
<211> LENGTH: 4
<212> TYPE: PRT
<213> ORGANISM: Homo sapiens

<400> SEQUENCE: 63

Val Cys Glu Tyr
1

<210> SEQ ID NO 64
<211> LENGTH: 4
<212> TYPE: PRT
<213> ORGANISM: Homo sapiens

<400> SEQUENCE: 64

Cys Leu Val Lys
1

<210> SEQ ID NO 65
<211> LENGTH: 5
<212> TYPE: PRT
<213> ORGANISM: Homo sapiens

<400> SEQUENCE: 65

Ser Cys Ser Val Met
1               5

<210> SEQ ID NO 66
<211> LENGTH: 15
<212> TYPE: PRT
<213> ORGANISM: Homo sapiens

<400> SEQUENCE: 66

Val Ile Asp Pro Glu Pro Cys Pro Asp Ser Asp Gln Glu Pro Lys
1               5                   10                  15

<210> SEQ ID NO 67
<211> LENGTH: 26
<212> TYPE: PRT
<213> ORGANISM: Homo sapiens

<400> SEQUENCE: 67

Gln Ala Asp Ser Gln Val Thr Glu Val Cys Ala Ala Thr Tyr Met Met
1               5                   10                  15

Gly Asn Arg Leu Gly Gln Ile Thr Leu Val
            20                  25

<210> SEQ ID NO 68
<211> LENGTH: 18
<212> TYPE: PRT
<213> ORGANISM: Homo sapiens

<400> SEQUENCE: 68

Gln Asn Gly Ser Ser Thr Gly Thr Cys Ile Ser Asp Asp Leu Phe Thr
1               5                   10                  15

Leu Glu

<210> SEQ ID NO 69

```
<211> LENGTH: 8
<212> TYPE: PRT
<213> ORGANISM: Homo sapiens

<400> SEQUENCE: 69

Thr Cys Ile Ser Asp Asp Leu Phe
1               5

<210> SEQ ID NO 70
<211> LENGTH: 11
<212> TYPE: PRT
<213> ORGANISM: Homo sapiens

<400> SEQUENCE: 70

Glu Val Cys Ala Ala Thr Tyr Met Met Gly Asn
1               5                   10

<210> SEQ ID NO 71
<211> LENGTH: 6
<212> TYPE: PRT
<213> ORGANISM: Homo sapiens

<400> SEQUENCE: 71

Met Tyr Pro Pro Pro Tyr
1               5

<210> SEQ ID NO 72
<211> LENGTH: 23
<212> TYPE: PRT
<213> ORGANISM: Homo sapiens

<400> SEQUENCE: 72

Trp Gln Gln Gly Asp Val Phe Ser Cys Ser Val Met His Glu Ala Leu
1               5                   10                  15

His Asn His Tyr Thr Gln Lys
            20

<210> SEQ ID NO 73
<211> LENGTH: 22
<212> TYPE: PRT
<213> ORGANISM: Homo sapiens

<400> SEQUENCE: 73

Gly Phe Tyr Pro Ser Asp Ile Ala Val Glu Trp Glu Ser Asp Gly Gln
1               5                   10                  15

Pro Glu Asn Asn Tyr Lys
            20

<210> SEQ ID NO 74
<211> LENGTH: 15
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa can be any naturally occurring amino acid

<400> SEQUENCE: 74

Val Ile Asp Pro Glu Pro Xaa Pro Asp Ser Asp Gln Glu Pro Lys
1               5                   10                  15

<210> SEQ ID NO 75
<211> LENGTH: 6
<212> TYPE: PRT
<213> ORGANISM: Artificial Sequence
```

```
<220> FEATURE:
<223> OTHER INFORMATION: Synthetic 6x His tag

<400> SEQUENCE: 75

His His His His His His
1               5

<210> SEQ ID NO 76
<211> LENGTH: 7
<212> TYPE: PRT
<213> ORGANISM: Homo sapiens

<400> SEQUENCE: 76

Asp Gln Glu Pro Lys Ser Ser
1               5

<210> SEQ ID NO 77
<211> LENGTH: 13
<212> TYPE: PRT
<213> ORGANISM: Homo sapiens

<400> SEQUENCE: 77

Thr His Thr Ser Pro Pro Ser Pro Ala Pro Glu Leu Leu
1               5                   10
```